US011981744B2

(12) United States Patent
Schellenberger et al.

(10) Patent No.: US 11,981,744 B2
(45) Date of Patent: May 14, 2024

(54) CHIMERIC POLYPEPTIDE ASSEMBLY AND METHODS OF MAKING AND USING THE SAME

(71) Applicant: AMUNIX PHARMACEUTICALS, INC., Mountain View, CA (US)

(72) Inventors: Volker Schellenberger, Palo Alto, CA (US); Fan Yang, San Jose, CA (US); Desiree Thayer, Burlingame, CA (US); Bee-Cheng Sim, Mountain View, CA (US); Chia-Wei Wang, Santa Clara, CA (US)

(73) Assignee: AMUNIX PHARMACEUTICALS, INC., Mountain View, CA (US)

( * ) Notice: Subject to any disclaimer, the term of this patent is extended or adjusted under 35 U.S.C. 154(b) by 0 days.

(21) Appl. No.: 18/067,948

(22) Filed: Dec. 19, 2022

(65) Prior Publication Data

US 2023/0295334 A1 Sep. 21, 2023

Related U.S. Application Data

(62) Division of application No. 15/753,716, filed as application No. PCT/US2016/049137 on Aug. 26, 2016, now Pat. No. 11,713,358.

(60) Provisional application No. 62/379,673, filed on Aug. 25, 2016, provisional application No. 62/363,046, filed on Jul. 15, 2016, provisional application No. 62/338,285, filed on May 18, 2016, provisional application No. 62/278,755, filed on Jan. 14, 2016, provisional application No. 62/263,319, filed on Dec. 4, 2015, provisional application No. 62/211,532, filed on Aug. 28, 2015.

(51) Int. Cl.

| | |
|---|---|
| ***C07K 16/30*** | (2006.01) |
| ***A61P 35/00*** | (2006.01) |
| ***C07K 14/00*** | (2006.01) |
| ***C07K 16/28*** | (2006.01) |
| ***C12N 5/09*** | (2010.01) |
| *A61K 38/00* | (2006.01) |
| *A61K 39/00* | (2006.01) |

(52) U.S. Cl.

CPC .............. *C07K 16/30* (2013.01); *A61P 35/00* (2018.01); *C07K 14/00* (2013.01); *C07K 16/2809* (2013.01); *C12N 5/0693* (2013.01); *A61K 38/00* (2013.01); *A61K 2039/505* (2013.01); *A61K 2039/54* (2013.01); *A61K 2039/545* (2013.01); *A61K 2039/572* (2013.01); *C07K 2317/24* (2013.01); *C07K 2317/31* (2013.01); *C07K 2317/55* (2013.01); *C07K 2317/56* (2013.01); *C07K 2317/565* (2013.01); *C07K 2317/60* (2013.01); *C07K 2317/622* (2013.01); *C07K 2317/73* (2013.01); *C07K 2317/732* (2013.01); *C07K 2317/76* (2013.01); *C07K 2317/90* (2013.01); *C07K 2317/92* (2013.01); *C07K 2317/94* (2013.01); *C07K 2319/01* (2013.01); *C07K 2319/035* (2013.01); *C07K 2319/21* (2013.01); *C07K 2319/30* (2013.01); *C07K 2319/31* (2013.01); *C07K 2319/50* (2013.01); *C12N 2523/00* (2013.01)

(58) Field of Classification Search

None

See application file for complete search history.

(56) References Cited

U.S. PATENT DOCUMENTS

| | | | |
|---|---|---|---|
| 4,398,908 | A | 8/1983 | Siposs et al. |
| 4,435,173 | A | 3/1984 | Siposs et al. |
| 4,753,894 | A | 6/1988 | Frankel et al. |
| 4,933,185 | A | 6/1990 | Wheatley et al. |
| 4,943,533 | A | 7/1990 | Mendelsohn et al. |
| 4,976,696 | A | 12/1990 | Sanderson et al. |
| 4,988,337 | A | 1/1991 | Ito |
| 5,017,378 | A | 5/1991 | Turner et al. |
| 5,176,502 | A | 1/1993 | Becton et al. |
| 5,270,176 | A | 12/1993 | Doerschug et al. |
| 5,298,022 | A | 3/1994 | Bernardi et al. |
| 5,318,540 | A | 6/1994 | Athayde et al. |
| 5,492,534 | A | 2/1996 | Athayde et al. |
| 5,599,907 | A | 2/1997 | Anderson et al. |
| 5,677,171 | A | 10/1997 | Hudziak et al. |
| 5,736,137 | A | 4/1998 | Anderson et al. |

(Continued)

FOREIGN PATENT DOCUMENTS

| | | | |
|---|---|---|---|
| AU | 2008234019 | A1 | 10/2008 |
| EP | 0036776 | A2 | 9/1981 |

(Continued)

OTHER PUBLICATIONS

Adams, et al. High affinity restricts the localization and tumor penetration of single-chain fv antibody molecules. Cancer Res. 61(12):4750-5 (Jun. 15, 2001).

(Continued)

*Primary Examiner* — Brad Duffy

(74) *Attorney, Agent, or Firm* — LATHROP GPM LLP; James H. Velema, Esq.; Michael J. Spellberg, Esq.

(57) ABSTRACT

The present invention relates to bispecific chimeric polypeptide assembly compositions comprising bulking moieties linked to binding domains by cleavable release segments that, when cleaved are capable of concurrently binding effector T cells with targeted tumor or cancer cells and effecting cytolysis of the tumor cells or cancer cells. The invention also provides compositions and methods of making and using the cleavable chimeric polypeptide assembly compositions.

10 Claims, 60 Drawing Sheets

Specification includes a Sequence Listing.

(56) References Cited

U.S. PATENT DOCUMENTS

| | | | |
|---|---|---|---|
| 5,821,337 | A | 10/1998 | Carter et al. |
| 5,891,996 | A | 4/1999 | Mateo De Acosta Del Rio et al. |
| 6,235,883 | B1 | 5/2001 | Jakobovits et al. |
| 6,254,573 | B1 | 7/2001 | Haim et al. |
| 6,309,370 | B1 | 10/2001 | Haim et al. |
| 6,406,632 | B1 | 6/2002 | Safir et al. |
| 6,506,883 | B2 | 1/2003 | Mateo De Acosta Del Rio et al. |
| 6,572,585 | B2 | 6/2003 | Choi et al. |
| 6,899,879 | B2 | 5/2005 | De Boer et al. |
| 7,247,301 | B2 | 7/2007 | Van De Winkel et al. |
| 7,294,513 | B2 | 11/2007 | Wyatt et al. |
| 7,442,778 | B2 | 10/2008 | Gegg et al. |
| 7,452,967 | B2 | 11/2008 | Bertin |
| 7,485,302 | B2 | 2/2009 | Adams et al. |
| 7,528,242 | B2 | 5/2009 | Anderson et al. |
| 7,560,111 | B2 | 7/2009 | Kao et al. |
| 7,575,923 | B2 | 8/2009 | Dorken et al. |
| 7,595,378 | B2 | 9/2009 | Van et al. |
| 7,635,472 | B2 | 12/2009 | Kufer et al. |
| 7,709,605 | B2 | 5/2010 | Knopf et al. |
| 7,846,445 | B2 | 12/2010 | Schellenberger et al. |
| 7,855,279 | B2 | 12/2010 | Schellenberger et al. |
| 7,879,325 | B2 | 2/2011 | Kao et al. |
| 8,007,796 | B2 | 8/2011 | Baeuerle et al. |
| 8,076,459 | B2 | 12/2011 | Hofmeister et al. |
| 8,129,348 | B2 | 3/2012 | Besman et al. |
| 8,178,495 | B2 | 5/2012 | Chilkoti |
| 8,227,580 | B2 | 7/2012 | Jakobovits et al. |
| 8,236,308 | B2 | 8/2012 | Kischel et al. |
| 8,241,630 | B2 | 8/2012 | Kao et al. |
| 8,492,530 | B2 | 7/2013 | Schellenberger et al. |
| 8,513,390 | B2 | 8/2013 | Stagliano et al. |
| 8,518,404 | B2 | 8/2013 | Daugherty et al. |
| 8,529,898 | B2 | 9/2013 | Daugherty et al. |
| 8,541,203 | B2 | 9/2013 | Daugherty et al. |
| 8,563,269 | B2 | 10/2013 | Stagliano et al. |
| 8,586,041 | B2 | 11/2013 | Van De Winkel et al. |
| 8,673,860 | B2 | 3/2014 | Schellenberger et al. |
| 8,680,050 | B2 | 3/2014 | Schellenberger et al. |
| 8,703,717 | B2 | 4/2014 | Schellenberger et al. |
| 8,716,448 | B2 | 5/2014 | Schellenberger et al. |
| 8,790,645 | B2 | 7/2014 | Kufer et al. |
| 8,933,197 | B2 | 1/2015 | Stemmer et al. |
| 8,957,021 | B2 | 2/2015 | Schellenberger et al. |
| 9,062,299 | B2 | 6/2015 | Schellenberger et al. |
| 9,102,736 | B2 | 8/2015 | Hofmeister et al. |
| 9,168,312 | B2 | 10/2015 | Schellenberger et al. |
| 9,249,211 | B2 | 2/2016 | Schellenberger et al. |
| 9,371,369 | B2 | 6/2016 | Schellenberger et al. |
| 9,376,672 | B2 | 6/2016 | Schellenberger et al. |
| 9,453,078 | B2 | 9/2016 | Stagliano et al. |
| 9,493,563 | B2 | 11/2016 | Blein et al. |
| 9,540,430 | B2 | 1/2017 | Schellenberger et al. |
| 9,545,442 | B2 | 1/2017 | Lowman et al. |
| 9,562,073 | B2 | 2/2017 | Moore et al. |
| 9,758,776 | B2 | 9/2017 | Schellenberger et al. |
| 9,822,180 | B2 | 11/2017 | Cobbold et al. |
| 9,849,188 | B2 | 12/2017 | Schellenberger et al. |
| 9,850,310 | B2 | 12/2017 | Gaudet et al. |
| 9,926,351 | B2 | 3/2018 | Schellenberger et al. |
| 9,938,331 | B2 | 4/2018 | Schellenberger et al. |
| 9,976,166 | B2 | 5/2018 | Schellenberger et al. |
| 10,000,543 | B2 | 6/2018 | Schellenberger et al. |
| 10,064,957 | B2 | 9/2018 | Govindan et al. |
| 10,106,621 | B2 | 10/2018 | Cobbold et al. |
| 10,172,953 | B2 | 1/2019 | Schellenberger et al. |
| 10,179,819 | B2 | 1/2019 | Kirshner et al. |
| 10,265,414 | B2 | 4/2019 | Govindan et al. |
| 10,590,206 | B2 | 3/2020 | Labrijn et al. |
| 10,633,453 | B2 | 4/2020 | Cheng et al. |
| 10,781,264 | B2 | 9/2020 | Raum et al. |
| 10,844,122 | B2 | 11/2020 | Anderson et al. |
| 10,844,134 | B2 | 11/2020 | Baeuerle et al. |
| 10,961,287 | B2 | 3/2021 | Schellenberger et al. |
| 11,013,800 | B2 | 5/2021 | Zhou |
| 11,155,633 | B2 | 10/2021 | Kirshner et al. |
| 11,161,906 | B2 | 11/2021 | Lowman et al. |
| 11,168,139 | B2 | 11/2021 | Igawa et al. |
| 2003/0049689 | A1 | 3/2003 | Edwards et al. |
| 2003/0181381 | A1 | 9/2003 | Himmelspach et al. |
| 2003/0190740 | A1 | 10/2003 | Altman |
| 2003/0228309 | A1 | 12/2003 | Salcedo et al. |
| 2004/0043446 | A1 | 3/2004 | Defrees et al. |
| 2004/0234609 | A1 | 11/2004 | Collier et al. |
| 2004/0259780 | A1 | 12/2004 | Glasebrook et al. |
| 2005/0042721 | A1 | 2/2005 | Fang et al. |
| 2005/0118136 | A1 | 6/2005 | Leung et al. |
| 2005/0123997 | A1 | 6/2005 | Lollar |
| 2005/0287153 | A1 | 12/2005 | Dennis |
| 2006/0026719 | A1 | 2/2006 | Kieliszewski et al. |
| 2006/0275292 | A1 | 12/2006 | Delovitch |
| 2006/0287220 | A1 | 12/2006 | Li et al. |
| 2006/0293232 | A1 | 12/2006 | Levy et al. |
| 2007/0048282 | A1 | 3/2007 | Rosen et al. |
| 2007/0161087 | A1 | 7/2007 | Glaesner et al. |
| 2007/0203058 | A1 | 8/2007 | Lau et al. |
| 2007/0244301 | A1 | 10/2007 | Siekmann et al. |
| 2008/0039341 | A1 | 2/2008 | Schellenberger et al. |
| 2008/0167238 | A1 | 7/2008 | Rosen et al. |
| 2008/0176288 | A1 | 7/2008 | Leung et al. |
| 2008/0286808 | A1 | 11/2008 | Schellenberger et al. |
| 2008/0312157 | A1 | 12/2008 | Levy et al. |
| 2009/0060862 | A1 | 3/2009 | Chang et al. |
| 2009/0092582 | A1 | 4/2009 | Bogin et al. |
| 2009/0155257 | A1 | 6/2009 | Adams et al. |
| 2010/0150918 | A1 | 6/2010 | Kufer et al. |
| 2010/0189682 | A1 | 7/2010 | Schellenberger et al. |
| 2010/0239554 | A1 | 9/2010 | Schellenberger et al. |
| 2010/0292130 | A1 | 11/2010 | Skerra et al. |
| 2010/0323956 | A1 | 12/2010 | Schellenberger et al. |
| 2011/0046060 | A1 | 2/2011 | Schellenberger et al. |
| 2011/0046061 | A1 | 2/2011 | Schellenberger et al. |
| 2011/0077199 | A1 | 3/2011 | Schellenberger et al. |
| 2011/0151433 | A1 | 6/2011 | Schellenberger et al. |
| 2011/0172146 | A1 | 7/2011 | Schellenberger et al. |
| 2011/0275787 | A1 | 11/2011 | Kufer et al. |
| 2011/0293619 | A1 | 12/2011 | Kufer et al. |
| 2012/0034228 | A1 | 2/2012 | Kufer et al. |
| 2013/0052160 | A1 | 3/2013 | Zitvogel et al. |
| 2013/0129729 | A1 | 5/2013 | Kischel et al. |
| 2013/0129730 | A1* | 5/2013 | Kufer ................. C07K 16/2809<br>435/69.6 |
| 2013/0165389 | A1 | 6/2013 | Schellenberger et al. |
| 2014/0303084 | A1 | 10/2014 | Thorn |
| 2015/0037334 | A1 | 2/2015 | Kufer et al. |
| 2015/0183875 | A1 | 7/2015 | Cobbold |
| 2016/0122425 | A1 | 5/2016 | Daugherty et al. |
| 2016/0152707 | A1 | 6/2016 | Kufer et al. |
| 2016/0193332 | A1 | 7/2016 | Lowman et al. |
| 2016/0194339 | A1 | 7/2016 | Chung et al. |
| 2016/0228546 | A1 | 8/2016 | Stagliano et al. |
| 2016/0289324 | A1 | 10/2016 | Moore et al. |
| 2017/0002082 | A1 | 1/2017 | West et al. |
| 2017/0037651 | A1 | 2/2017 | Pedersen et al. |
| 2017/0081397 | A1 | 3/2017 | Stagliano et al. |
| 2017/0096489 | A1 | 4/2017 | Lowman et al. |
| 2017/0247476 | A1 | 8/2017 | Yan et al. |
| 2018/0057593 | A1 | 3/2018 | Dennis |
| 2018/0244736 | A1 | 9/2018 | Schellenberger et al. |
| 2019/0153115 | A1 | 5/2019 | Schellenberger et al. |
| 2019/0382486 | A1 | 12/2019 | Apgar et al. |
| 2020/0048349 | A1 | 2/2020 | Gaudet et al. |
| 2020/0199231 | A1 | 6/2020 | Engelberts et al. |
| 2020/0277397 | A1 | 9/2020 | Satijn et al. |
| 2021/0047406 | A1 | 2/2021 | Irving et al. |

FOREIGN PATENT DOCUMENTS

| | | | |
|---|---|---|---|
| EP | 0942968 | A2 | 9/1999 |
| EP | 1940881 | A2 | 7/2008 |
| EP | 1629011 | B1 | 1/2010 |
| EP | 2155783 | A2 | 2/2010 |
| EP | 2352765 | A2 | 8/2011 |
| EP | 2155788 | B1 | 6/2012 |

(56) References Cited

FOREIGN PATENT DOCUMENTS

| | | | |
|---|---|---|---|
| EP | 2369005 | B1 | 4/2013 |
| EP | 1400534 | B1 | 10/2015 |
| EP | 2352763 | B1 | 4/2016 |
| EP | 1940881 | B1 | 11/2016 |
| EP | 2292664 | B1 | 11/2016 |
| EP | 2542590 | B1 | 5/2017 |
| EP | 3024851 | B1 | 5/2018 |
| EP | 2904016 | B1 | 11/2018 |
| EP | 2552964 | B1 | 10/2019 |
| EP | 3049440 | B1 | 3/2020 |
| EP | 3177646 | B1 | 10/2020 |
| EP | 2819701 | B2 | 6/2021 |
| EP | 3406633 | B1 | 3/2022 |
| EP | 3387013 | B1 | 6/2022 |
| WO | WO 1993/006844 | A1 | 4/1993 |
| WO | WO 1996/040210 | A1 | 12/1996 |
| WO | WO 1997/033552 | A1 | 9/1997 |
| WO | WO 1999/049901 | A1 | 10/1999 |
| WO | WO 2002/077036 | A2 | 10/2002 |
| WO | WO 2004/106381 | A1 | 12/2004 |
| WO | WO 2005/025499 | A2 | 3/2005 |
| WO | WO 2005/025499 | A3 | 5/2005 |
| WO | WO 2005/118635 | A2 | 12/2005 |
| WO | WO 2006/081249 | A2 | 8/2006 |
| WO | WO 2006/081249 | A3 | 2/2007 |
| WO | WO 2007/033230 | A2 | 3/2007 |
| WO | WO 2007/042261 | A2 | 4/2007 |
| WO | WO 2007/073486 | A2 | 6/2007 |
| WO | WO 2007/103455 | A2 | 9/2007 |
| WO | WO 2007/103515 | A2 | 9/2007 |
| WO | WO 2007/103455 | A3 | 11/2007 |
| WO | WO 2008/049931 | A1 | 5/2008 |
| WO | WO 2008/155134 | A1 | 12/2008 |
| WO | WO 2009/023270 | A2 | 2/2009 |
| WO | WO 2010/091122 | A1 | 8/2010 |
| WO | WO 2010/144502 | A2 | 12/2010 |
| WO | WO 2010/144508 | A1 | 12/2010 |
| WO | WO 2011/028228 | A1 | 3/2011 |
| WO | WO 2011/028229 | A1 | 3/2011 |
| WO | WO 2011/028344 | A2 | 3/2011 |
| WO | WO 2011/033105 | A1 | 3/2011 |
| WO | WO 2011/084808 | A2 | 7/2011 |
| WO | WO 2011/123813 | A2 | 10/2011 |
| WO | WO 2011/123830 | A2 | 10/2011 |
| WO | WO 2011/131472 | A1 | 10/2011 |
| WO | WO 2013/040093 | A2 | 3/2013 |
| WO | WO 2013/122617 | A1 | 8/2013 |
| WO | WO 2013/130683 | A2 | 9/2013 |
| WO | WO 2013/130684 | A1 | 9/2013 |
| WO | WO 2013/184216 | A1 | 12/2013 |
| WO | WO 2014/011819 | A2 | 1/2014 |
| WO | WO 2014/164568 | A1 | 10/2014 |
| WO | WO 2014/194282 | A2 | 12/2014 |
| WO | WO 2015/023891 | A2 | 2/2015 |
| WO | WO 2016/077505 | A2 | 5/2016 |
| WO | WO 2016/081884 | A2 | 5/2016 |
| WO | WO 2016/109823 | A1 | 7/2016 |
| WO | WO 2017/040344 | A2 | 3/2017 |
| WO | WO 2017/134134 | A1 | 8/2017 |

OTHER PUBLICATIONS

Adams, et al. Increased affinity leads to improved selective tumor delivery of single-chain Fv antibodies. Cancer Res. 58(3):485-90 (Feb. 1, 1998).

Adams. The development of proteasome inhibitors as anticancer drugs. Cancer Cell 5:417-421 (May 2004).

Akagi et al. CA19-9 epitope a possible marker for MUC-1/Y protein. International Journal of Oncology 18:1085-1091 (2001).

Albright et al. Matrix metalloproteinase-activated doxorubicin prodrugs inhibit HT1080 xenograft growth better than doxorubicin with less toxicity. Mol Cancer Ther 4(5):751-760 (May 2005).

Alvarez, et al. Improving Protein Pharmacokinetics by Genetic Fusion to Simple Amino Acid Sequences. J Biol Chem. 2004; 279: 3375-81.

Amann et al. Therapeutic window of an EpCAM/CD3-speciWc BiTE antibody in mice is determined by a subpopulation of EpCAM-expressing lymphocytes that is absent in humans. Cancer Immunol Immunother (2009) 58:95-109. Published online Jul. 2, 2008.

Amler et al. HER2 as a Therapeutic Target in Ovarian Cancer. Ovarian Cancer—Clinical and Therapeutic Perspectives (Feb. 15, 2012). 25 pages. DOI: 10.5772/29064.

Annex 2: Chou Fasman (1974) and Tepitope analyses of prior art sequences. Opposition dated Aug. 18, 2015 by XL-Protein GmbH against EP2402754 Application No. 11172812.7.

Anonymous. XTEN Trademark of Amunix Operating Inc.—Registration No. 4871664—Serial No. 86395983 :: Justia Trademarks, Dec. 15, 2015.

Arcidiacono et al. Expression of matrix metalloproteinase-11 is increased under conditions of insulin resistance. World J Diabetes 8(9):422-428 (Sep. 15, 2017). DOI: 10.4239/wjd.v8.i9.422.

Armstrong. EpCAM: A New Therapeutic Target for an Old Cancer Antigen. Cancer Biology & Therapy 2(4):320-325 (Jul./Aug. 2003).

Arnau et al. Current strategies for the use of affinity tags and tag removal for the purification of recombinant proteins. Protein Expr Purif., 2006, 48(1):1-13.

Arndt, et al. Factors influencing the dimer to monomer transition of an antibody single-chain Fv fragment. Biochemistry. 1998; 37(37):12918-26.

Asano et al. Highly Effective Recombinant Format of a Humanized IgG-like Bispecific Antibody for Cancer Immunotherapy with Retargeting of Lymphocytes to Tumor Cells. The Journal of Biological Chemistry 282(38):27659-27665 (Sep. 21, 2007).

Au et al. Clinical aspects of drug delivery to tumors. Journal of Controlled Release 78:81-95 (2002).

Ayers et al. IFN-γ-related mRNA profile predicts clinical responseto PD-1 blockade. The Journal of Clinical Investigation 127(8):2930-2940 (Aug. 2017).

Babson et al. Protein transfer in tumor-bearing rats. Cancer Res 14:606-611 (1954).

Bagshawe et al. Antibody Directed Enzyme Prodrug Therapy (ADEPT): Clinical Report. Disease Markers 9:233-238 (1991).

Bagshawe et al. Antibody directed enzyme prodrug therapy: a pilot-scale clinical trial. Tumor Targeting 1:17-29 (1995).

Bagshawe et al. Antibody-directed enzyme prodrug therapy (ADEPT) for cancer. Expert Opin Biol Ther 4(11):1777-1789 (2004).

Bailon, et al. Rational design of a potent, long-lasting form of interferon: a 40 kDa branched polyethylene glycol-conjugated interferon alpha-2a for the treatment of hepatitis C. Bioconjug Chem. Mar. 2001-Apr. 12(2):195-202.

Baldus et al. Coexpression of MUC1 Mucin Peptide Core and the Thomsen-Friedenreich Antigen in Colorectal Neoplasms. Cancer 82(6):1019-1027 (Mar. 15, 1998).

Balzar et al. The biology of the 17-1A antigen (Ep-CAM), J. Mol. Med. 1999, 77:699-712.

Balzar et al. The Structural Analysis of Adhesions Mediated by Ep-CAM. Experimental Cell Research 246:108-121 (1999).

Banerjee et al. Poly(ethylene glycol)-Prodrug Conjugates: Concept, Design, and Applications. vol. 2012, Article ID 103973 (2012). 17 pages. doi:10.1155/2012/103973.

Bargou et al. Tumor Regression in Cancer Patients by Very Low Doses of a T Cell Engaging Antibody. Science 321:974-977 (Aug. 15, 2008). DOI: 10.1126/science.1158545.

Barok et al. Trastuzumab-DM1 is highly effective in preclinical models of HER2-positive gastric cancer. Cancer Letters 306:171-179 (2011).

Baxter et al. Pharmacokinetic analysis of the microscopic distribution of enzyme-conjugated antibodies and prodrugs: comparison with experimental data. British Journal of Cancer 73:447-456 (1996).

Belimezi et al. Growth inhibition of breast cancer cell lines overexpressing Her2/neu by a novel internalized fully human Fab antibody fragment. Cancer Immunol Immunother 55:1091-1099 (2006). Published online Nov. 26, 2005.

(56) References Cited

OTHER PUBLICATIONS

Bell, et al. "Differential tumor-targeting abilities of three single-domain antibody formats." Cancer Letters 289:81-90 (Mar. 1, 2010). Epub Aug. 28, 2009. doi: 10.1016/j.canlet.2009.08.003.
Bellone et al. Solitomab, an EpCAM/CD3 bispecific antibody construct(BiTE), is highly active against primary uterine serouspapillary carcinoma cell lines in vitro. American Journal of Obstetrics & Gynecology pp. 99.e2-99.e8 (Jan. 2016).
Berek et al. Catumaxomab for the Treatment of Malignant Ascites in Patients With Chemotherapy-Refractory Ovarian Cancer. Int J Gynecol Cancer 24(9):1583-1589 (Nov. 2014).
Biggers et al. VB4-845, a conjugated recombinant antibody and immunotoxin for head and neck cancer and bladder cancer. Current Opinion in Molecular Therapeutics 10(2):176-186 (2008).
Birkedal-Hansen et al. Matrix Metalloproteinases: A Review. Critical Reviews in Oral Biology & Medicine 4(2):197-250 (1993).
Blincyto Package Insert. Amgen. Issued Dec. 2014.
Borsi et al. Selective targeting of tumoral vasculature: Comparison of different formats of an antibody (L19) to the ED-B domain of fibronectin. Int J Cancer 102:75-85 (2002).
Boustany et al. EGFR-CD3 Bispecific Probody™ Therapeutic Induces Tumor Regressions and Increases Maximum Tolerated Dose 60 fold in Preclinical Studies. Poster. CytomX Therapeutics. Copyright 2017.
Boyd et al. PoPS: A Computational Tool for Modeling and Predicting Protease Specificity. Journal of Bioinformatics and Computational Biology 3(3):551-585 (2005).
Brand et al. Treatment of Colorectal Liver Metastases by Adenoviral Transfer of TissueInhibitor of Metalloproteinases-2 into the Liver Tissue. Cancer Research 60:5723-5730 (Oct. 15, 2000).
Bremer et al. In vivo molecular target assessment of matrix metalloproteinase inhibition. Nature Medicine 7(6):743-748 (Jun. 2001).
Brischwein et al. MT110: A novel bispecific single-chain antibody construct with highefficacy in eradicating established tumors. Molecular Immunology 43:1129-1143 (2006). Available online Sep. 1, 2005.
Buache et al. Functional relationship between matrixmetalloproteinase-11 and matrix metalloproteinase-14. Cancer Medicine 3(5):1197-1210 (2014). doi: 10.1002/cam4.290.
Burges et al. Effective Relief of Malignant Ascites in Patients with Advanced Ovarian Cancer by a Trifunctional Anti-EpCAM Anti-CD3 Antibody: A Phase I/II Study. Clin Cancer Res 13(13):3899-3905 (Jul. 1, 2017).
Buscaglia, et al. Tandem amino acid repeats from Trypanosoma cruzi shed antigens increase the half-life of proteins in blood. Blood. Mar. 15, 1999;93(6):2025-32.
Byrne et al. A tale of two specificities: bispecific antibodies for therapeutic and diagnostic applications. Trends in Biotechnology 31(11):621-632 (Nov. 2013).
Cai, et al. Developments in human growth hormone preparations: sustained-release, prolonged half-life, novel injection devices, and alternative delivery routes. Int J Nanomedicine. 2014; 9: 3527-3538. Published online Jul. 25, 2014. doi: 10.2147/IJN.S63507.
Cal and Obaya, eds. Proteases and Cancer: Methods and Protocols. Humana Press. Copyright 2018. DOI: https://doi.org/10.1007/978-1-4939-7595-2.
Calceti et al., 2003. Pharmacokinetic and biodistribution properties of poly(ethylene glycol)-protein conjugates. Adv Drug Deliv Rev 55:1261-1277.
Cao et al. Multiformat T-Cell-Engaging Bispecific Antibodies Targeting Human Breast Cancers. Angew Chem Int Ed 54:7022-7027 (2015). DOI: 10.1002/anie.201500799.
Cell Therapeutics Press Release. Cell Therapeutics Inc.'s Polyglutamate (PG) Technology Highlighted at International Polymer Therapeutics Meeting; Novel Recombinant Technology Extends PG Platform to G-CSF. Jan. 4, 2002. PR Newswire. Opposition by XL-Protein GmbH against EP2402754 Application No. 11172812.7.
Cesano et al. CD22 as a Target of Passive Immunotherapy. Seminars in Oncology 30(2):253-257 (Apr. 2003).
Chang et al., Phenotypic expression in *E. coli* of a DNA sequence coding for mouse dihydrofolate reductase. Nature, 275:615 (1978).
Chatenoud, CD3-specific antibody-induced active tolerance: from bench to bedside. Nat. Rev. Immunol., 3:123-132 (2003).
Chatenoud, Immunologic monitoring during OKT3 therapy. Clin Transplant 7:422-430, 1993.
Cheadle. MT-103 Micromet/MedImmune. Current Opinion in Molecular Therapeutics 8(1):62-68 (2006).
Chen et al. A Unique Substrate Recognition Profile for MatrixMetalloproteinase-2. The Journal of Biological Chemistry 277(6):4485-4491 (Feb. 8, 2002). Published, JBC Papers in Press, Nov. 2, 2001, DOI 10.1074/jbc.M109469200.
Cheng et al. Successful engineering of a highly potent single-chain variable-fragment (scFv) bispecific antibody to target disialoganglioside (GD2) positive tumors. Oncoimmunology 5(6):e1168557 (2016). 9 pages.
Chhieng et al. Expression of CEA, Tag-72, and Lewis-Y Antigen in Primary and Metastatic Lesions of Ovarian Carcinoma, pp. 1016-1021. Presented in part at the 93rd annual meeting of American Association of Cancer Research, San Francisco, CA, Apr. 6-10, 2002, and the 10th annual Specialized Program of Research Excellence (SPORE) meeting, Chantilly, VA, Jul. 13-16, 2002.
Choi et al. Bispecific antibodies engage T cells for antitumor immunotherapy. Expert Opin. Biol. Ther. [Early Online]. Copyright 2011 Informa UK, Ltd. DOI: 10.1517/14712598.2011.572874. 11 pages.
Choi et al., Predicting antibody complementarity determining region structures without classification, Molecular Biosystems, 2011, 7: 3327-3334.
Chou, et al. Conformational parameters for amino acids in helical, β-sheet, and random coil regions calculated from proteins. Biochemistry 13.2 (1974): 211-222.
Chou, et al. Empirical predictions of protein conformation. Annual review of biochemistry 47.1 (1978): 251-276.
Chou, et al. Prediction of Protein Conformation. Biochemistry. 1974; 13: 222-245.
Chou, et al. Prediction of the secondary structure of proteins from their amino acid sequence. Adv Enzymol Relat Areas Mol Biol. 1978;47:45-148.
Chou; et al., Prediction of the Secondary Structure of Proteins from Their Amino Acid Sequence, from Advances in Enzymology vol. 47, John Wiley and Sons. Published 1978, p. 60.
Chou-Fasman values for random 200mer sequences composed of the amino acids GADSTEP; Reply to notice of opposition dated Apr. 8, 2016 for EP2402754.
Clapper et al. Detection of Colorectal Adenomas Using a Bioactivatable Probe Specific for Matrix Metalloproteinase Activity. Neoplasia 13(8):685-691 (Aug. 2011).
Cleland, et al. A Monthly Dosed GLP-1 Analog for Treatment of Type 2 Diabetes Mellitus. Diabetes, 2010; 59(1):A104. 70th Annual Meeting of the American Diabetes Association, Orland, FL, USA 2010.
Cleland, et al. A novel long-acting human growth hormone fusion protein (VRS-317): enhanced in vivo potency and half-life. J Pharm Sci. Aug. 2012;101(8):2744-54. doi: 10.1002/jps.23229. Epub Jun. 7, 2012.
Cleland, et al. An extended half-life exenatide construct for weekly administration in the treatment of diabetes mellitus. In Diabetes, vol. 58, pp. A511-A512. 1701 N Beauregard St, Alexandria, VA 22311-1717 USA: Amer Diabetes Assoc, 2009. Abstract only.
Collen, et al. Polyethylene Glycol-Derivatized Cysteine-Substitution Variants of Recombinant Staphylokinase for Single-Bolus Treatment of Acute Myocardial Infarction. Circulation. 2000; 102: 1766-72.
Composition and properties of some URPs according to the invention; Reply to notice of opposition dated Apr. 8, 2016 for EP2402754.
Corrected version of "Exhibit 1" (D23) without cut and paste error; Reply to notice of opposition dated Apr. 8, 2016 for EP2402754.
Cramer et al. Conditions Associated with Antibodies Against the Tumor-Associated Antigen MUC1 and Their Relationship to Risk for Ovarian Cancer. Cancer Epidemiology, Biomarkers & Prevention 14(5):1125-1131 (May 2005).

(56) References Cited

OTHER PUBLICATIONS

Cretney et al. Cancer: Novel therapeutic strategies that exploit the TNF-related apoptosis-inducing ligand (TRAIL)/TRAIL receptor pathway. The International Journal of Biochemistry & Cell Biology 39280-286 (2007). Available online Oct. 7, 2006.
Croce et al. Expression of Tumour Associated Antigens in Normal, Benign and Malignant Human Mammary Epithelial Tissue: A Comparative Immunohistochemical Study. Anticancer Research 17:4287-7292 (1997).
Dahlberg et al. The Lymphatic System Plays a Major Role in the Intravenous and Subcutaneous Pharmacokinetics of Trastuzumab in Rats. Mol Pharmaceutics 11:496-504 (Dec. 18, 2013). DOI: dx.doi.org/10.1021/mp400464s.
Danhier et al. To exploit the tumor microenvironment: Passive and active tumor targeting of nanocarriers for anti-cancer drug delivery. Journal of Controlled Release 148:135-146 (2010). Available online Aug. 24, 2010.
D'Aquino, et al. The magnitude of the backbone conformational entropy change in protein folding. Proteins. 1996; 25: 143-56.
Davol et al. Anti-CD3 × Anti-HER2 Bispecific Antibody Effectively Redirects Armed T Cells to Inhibit Tumor Development and Growth in Hormone-Refractory Prostate Cancer-Bearing Severe Combined Immunodeficient Beige Mice. Clinical Prostate Cancer 3(2):112-121 (Sep. 2004).
De Boer et al. The tac promoter: a functional hybrid derived from the trp and lac promoters. Proc Natl Acad Sci, 1983, 80:21-25.
De Goeij et al. HER2 monoclonal antibodies that do not interfere with receptor heterodimerization-mediated signaling induce effective internalization and represent valuable components for rational antibody-drug conjugate design. mAbs 6(2):392-402 (Mar./Apr. 2014). Published online Jan. 3, 2014. DOI: 10.4161/mabs.27705.
De Lorenzo et al. Biological properties of a human compact anti-ErbB2 antibody. Carcinogenesis 26(11):1890-1895 (2005). Advance access publication Jun. 1, 2005. doi:10.1093/carcin/bgi146.
De Lorenzo et al. Intracellular route and mechanism of action of ERB-hRNase, a human anti-ErbB2 anticancer immunoagent. FEBS Letters 581:296-300 (2007). Available online Jan. 2, 2007.
De Vega et al. Multimodal laser ablation/desorption imaging analysis of Znand MMP-11 in breast tissues. Anal Bioanal Chem 410:913-922 (2018). Published online Aug. 12, 2017. DOI 10.1007/s00216-017-0537-x.
Decision revoking the European Patent dated Mar. 16, 2016 for EP1996220 Application No. 07752636.6.
Decision revoking the European Patent dated May 9, 2017 for EP2402754 Application No. 11172812.7.
Deckert, et al. Pharmacokinetics and microdistribution of polyethylene glycol-modified humanized A33 antibody targeting colon cancer xenografts. Int J Cancer. 2000; 87: 382-90.
Denton et al. Primary Sequence Determination and Molecular Modelling of the Variable Region of an AntiMUC1 Mucin Monoclonal Antibody. European Journal of Cancer 31A(2):214-221 (1995).
Deppisch et al. Efficacy and Tolerability of a GD2-Directed Trifunctional Bispecific Antibody in a Preclinical Model: Subcutaneous Administration Is Superior to Intravenous Delivery. Mol Cancer Ther 14(8):1877-1883 (Aug. 2015).
Desnoyers et al. Supplementary Materials for Tumor-Specific Activation of an EGFR-Targeting Probody Enhances Therapeutic Index. Sci Transl Med 5:207ra144 (Oct. 16, 2013). 14 pages. DOI: 10.1126/scitranslmed.3006682.
Desnoyers et al. Tumor-Specific Activation of an EGFR-Targeting Probody Enhances Therapeutic Index. Science Translational Medicine 5(207):207ra144 (Oct. 16, 2013). 12 pages.
Devy et al. Selective Inhibition of Matrix Metalloproteinase-14 Blocks TumorGrowth, Invasion, and Angiogenesis. Cancer Res 69(4):1517-1526 (Feb. 15, 2009). Published online Feb. 10, 2009. DOI: 10.1158/0008-5472.CAN-08-3255.
Dhalluin, et al. Structural and biophysical characterization of the 40 kDa PEG-interferon-alpha2a and its individual positional isomers. Bioconjug Chem. 2005; 16:504-17.
Di Paolo et al. A Recombinant Immunotoxin Derived from a Humanized Epithelial Cell Adhesion Molecule-specific Single-Chain Antibody Fragment Has Potent and Selective Antitumor Activity. Clinical Cancer Research 9:2837-2848 (Jul. 2003).
Ding et al., "Multivalent Antiviral XTEN-Peptide Conjugates with Long in Vivo Half-Life and Enhanced Solubility," Bioconjugate Chemistry, vol. 25, No. 7, pp. 1351-1359, epub Jun. 23, 2014.
Donaldson, J. M. et al., Design and development of masked therapeutic antibodies to limit off-target effects: application to anti-EGFR antibodies. Cancer Biology & Therapy 8(22):2147-2152 (Nov. 2009).
Dorvillius et al. Targeting of Human Breast Cancer by a Bispecific Antibody Directed against Two Tumour-Associated Antigens: ErbB-2 and Carcinoembryonic Antigen. Tumor Biol 23:337-347 (2002). DOI: 10.1159/000069793.
Duffy et al. uPA and PAI-1 as biomarkers in breast cancer: validated for clinical use in level-of-evidence-1 studies. Breast Cancer Research 16:428 (2014). 10 pages.
Duran-Reynals, Studies on the localization of dyes and foreign proteins in normal and malignant tissue. Am J Cancer 35:98-107 (1939).
Edwards et al., The remarkable flexibility of the human antibody repertoire; isolation of over one thousand different antibodies to a single protein, BLyS, J Mol Biol, 2003, 334:103-118.
Ellis, et al. Valid and invalid implementations of GOR secondary structure predictions. Comput Appl Biosci. Jun. 1994;10(3):341-8.
Endo-Munoz et al. Progression of Osteosarcoma from a Non-Metastatic to a Metastatic Phenotype Is Causally Associated with Activation of an Autocrine and Paracrine uPA Axis. PLOS ONE (Aug. 28, 2015). 22 pages. DOI:10.1371/journal.pone.0133592.
European Search Report for European Patent Application No. 16842718, dated Apr. 1, 2019.
Extended European Search Report for European Patent Application No. 22181008.8, dated Dec. 15, 2022.
Feldmann et al. Novel Humanized and Highly Efficient Bispecific Antibodies Mediate Killing of Prostate Stem Cell Antigen-Expressing Tumor Cells by CD8+ and CD4+ T Cells. The Journal of Immunology 189:3249-3259 (2012).
Fernandez-Garcia et al. Expression and prognostic significance of fibronectin and matrix metalloproteases in breast cancer metastasis. Histopathology 64:512-522 (2014). DOI: 10.1111/his.12300.
Ferrari et al. Solitomab, an EpCAM/CD3 bispecific antibody construct (BiTE), is highly active against primary uterine and ovarian carcinosarcoma cell lines in vitro. J Exp Clin Cancer Res. 2015, 34:123.
Filpula. Releasable PEGylation of Mesothelin Targeted Immunotoxin SS1P Achieves Single Dosage Complete Regression of a Human Carcinoma in Mice. Bioconjugate Chem 18:773-784 (2007). Published online Mar. 9, 2007. DOI: 10.1021/bc060314x.
Fortmüller et al. Effective Targeting of Prostate Cancer by Lymphocytes Redirected by a PSMA CD3 Bispecific Single-Chain Diabody. The Prostate 71:588-596 (2011).
Fousek et al. The Evolution of T-cell Therapies for Solid Malignancies. Clin Cancer Res 21(15)3384-3392 (Aug. 1, 2015).
Friberg et al. Blinatumomab (Blincyto®); lessons learned from the bispecific t-cell engager (BiTE©) in acutelymphocytic leukemia (ALL). @ The Author 2017. Published by Oxford University Press on behalf of the European Society for MedicalOncology. 8 pages.
Garber. Bispecific antibodies rise again. Nature Reviews—Drug Discovery, vol. 14, pp. 799-801 (Nov. 2014).
Garnier et al. (1996), GOR method for predicting protein scondary structure from amino acid sequence. Methods Enzymol 266:540-553.
Gastl et al., Ep-CAM overexpression in breast cancer as a predictor of survival. Lancet, 2000, 356, 1981-1982.
Geething, et al. Gcg-XTEN: an improved glucagon capable of preventing hypoglycemia without increasing baseline blood glucose. PLOS One. Apr. 14, 2010;5(4):e10175. doi: 10.1371/journal.pone.0010175.
Germain et al. Redirecting NK cells mediated tumor cell lysis by a new recombinant bifunctional protein. Protein Engineering, Design & Selection 21(11):665-672 (2008). Published online Sep. 11, 2008. doi:10.1093/protein/gzn047.

(56) References Cited

OTHER PUBLICATIONS

Goeddel et al., Direct expression in *Escherichia coli* of a DNA sequence coding for human growth hormone. Nature, 281:544-548 (1979).
Goeddel et al., Synthesis of human fibroblast interferon by *E. coli*. Nucleic Acids Res., 8:4057-4074 (1980).
Goel et al., Plasticity within the antigen-combining site may manifest as molecular mimicry in the humoral immune response, Journal of Immunology, 2004, 173(12):7358-7367.
Goitlinger et al., The epithelial cell surface antigen 17-1A, a target for antibody-mediated tumor therapy: Its biochemical nature, tissue distribution and recognition by different monoclonal antibodies. Int J Cancer. 1986; 38, 47-53.
Graves et al. Proinvasive Properties of Ovarian Cancer Ascites-Derived Membrane Vesicles. Cancer Research 64:7045-7049 (Oct. 1, 2004).
Gustafsson et al. Codon bias and heterologous protein expression. Trends in Biotechnology, 22.7 (Jul. 2004): 346-353.
Haense et al. A phase I trial of the trifunctional anti Her2 × anti CD3 antibody ertumaxomab in patients with advanced solid tumors. BMC Cancer 16:420 (2016). 10 pages. DOI 10.1186/s12885-016-2449-0.
Helfrich et al. Construction and characterization of a bispecific diabody for retargeting T cells to human carcinomas. Int. J. Cancer, 1998, 76:232-239.
Herbst. Review of Epidermal Growth Factor Receptor Biology. Int J Radiation Oncology Biol Phys vol. 59, No. 2, Supplement, pp. 21-26 (2004). doi:10.1016/j.ijrobp.2003.11.041.
Hinrichs et al. Reassessing target antigens for adoptive T-cell therapy. Nature Biotechnology 31(11):999-1008 (Nov. 2013).
Hoffmann et al. Serial killing of tumor cells by cytotoxic T cells redirected with a CD19-/CD3-bispecific single-chain antibody construct. Int J Cancer 115:98-104 (2005). Published online Feb. 1, 2005. DOI 10.1002/ijc.20908.
Hopp, et al. Prediction of protein antigenic determinants from amino acid sequences. Proc Natl Acad Sci U S A 1981; 78, 3824-3828, #3232.
Hsin et al. MMP-11 promoted the oral cancer migration and FAK/Src activation. Oncotarget 8(20):32783-32793 (Mar. 2, 2017).
Iniesta et al. Biological and clinical significance of MMP-2, MMP-9, TIMP-1 and TIMP-2 in non-small cell lung cancer. Oncology Reports 17:217-223 (2007).
International Search Report and Written Opinion for PCT International Patent Application No. PCT/US2007/005952, dated Dec. 26, 2007.
International Search Report and Written Opinion for PCT International Patent Application No. PCT/US2008/009787, dated Mar. 16, 2009.
International Search Report and Written Opinion for PCT International Patent Application No. PCT/US2010/002147, dated Dec. 20, 2010.
International Search Report and Written Opinion for PCT International Patent Application No. PCT/US2010/023106, dated Apr. 20, 2010.
International Search Report and Written Opinion for PCT International Patent Application No. PCT/US2010/061590, dated Jul. 12, 2011.
International Search Report and Written Opinion for PCT International Patent Application No. PCT/US2016/049137, dated Feb. 27, 2017.
Internet printout for Chou Fasman algorithm, 1974. Available at http://www.biogem.org/tool/chou-fasman. Opposition by XL-Protein GmbH against EP2402754 Application No. 11172812.7.
Ishiguro et al. An anti-glypican 3/CD3 bispecific T cell-redirecting antibody for treatment of solid tumors. Sci Transl Med 9:eaa14291 (Oct. 4, 2017). 13 pages. DOI: 10.1126/scitranslmed.aal4291.
Ishiguro et al. Supplementary Materials for An anti-glypican 3/CD3 bispecific T cell-redirecting antibody for treatment of solid tumors. Sci Transl Med 9:eaa14291 (Oct. 4, 2017). 25 pages. DOI: 10.1126/scitranslmed.aal4291.
Jäger et al. Immunomonitoring Results of a Phase II/III Study of Malignant Ascites Patients Treated with the Trifunctional Antibody Catumaxomab (Anti-EpCAM Anti-CD3). Cancer Res 72(1):24-32 (Jan. 1, 2012). PUblished online Nov. 1, 2011. DOI: 10.1158/0008-5472.CAN-11-2235.
James et al. Biophysical Mechanism of T Cell Receptor Triggering in a Reconstituted System. Nature 487(7405):64-69 (Jul. 5, 2012).
Jin et al. MetMAb, the one-armed 5D5 anti-c-met antibody, inhibits orthotopic pancreatic tumor growth and improves survival. Cancer Res 68(11):4360-4368 (Jun. 1, 2008).
Junttila et al. Antitumor Efficacy of a Bispecific Antibody That Targets HER2 and Activates T Cells. Cancer Res 74(19):5561-5571 (2014). doi: 10.1158/0008-5472.CAN-13-3622-T.
Kangueane, et al., T-Epitope Designer: A HLA-peptide binding prediction server. May 15, 2005, 1(1), 21-4.
Kimball et al., The OKT3 Antibody Response Study: a multicentre study of human anti-mouse antibody (HAMA) production following OKT3 use in solid organ transplantation. Transplant Immunol. 3:212-221 (1995).
Klinger. BiTE© Antibody Constructs Beyond Blinatumomab: Overview of Amgen's Early-Stage BiTE© Pipeline (slides). CHI's 6th Annual Immuno-Oncology Summit (Aug. 27-31, 2018).
Koblinski, et al. Unraveling the role of proteases in cancer. Clin Chim Acta. Feb. 15, 2000;291(2):113-35.
Kochendoerfer. Chemical and biological properties of polymer-modified proteins. Expert Opin Biol Ther. 2003; 3: 1253-61.
Kohn, et al. Random-coil behavior and the dimensions of chemically unfolded proteins. Proc Natl Acad Sci U S A. Aug. 24, 2004;101(34):12491-6.
Kornblatt, et al. Cross-linking of cytochrome oxidase subunits with difluorodinitrobenzene. Can J. Biochem. 1980; 58: 219-224.
Kridel et al. Substrate Hydrolysis by Matrix Metalloproteinase-9. J Biol Chem 276(23):20572-20578 (Jun. 8, 2001). Published, JBC Papers in Press, Mar. 14, 2001, DOI 10.1074/jbc.M100900200.
Kubetzko, et al. Protein PEGylation decreases observed target association rates via a dual blocking mechanism. Mol Pharmacol. 2005; 68: 1439-54.
Kumar et al., ATGAM versus OKT3 induction therapy in cadaveric kidney transplantation: patient and graft survival, CD3 subset, infection, and cost analysis. Transplant Proc. 30:1351-1352 (1998).
Kyngas, et al. Unreliability of the Chou-Fasman parameters in predicting protein secondary structure. Protein Eng. May 1998;11(5):345-8.
Lafky et al. Clinical implications of the ErbB/epidermal growth factor (EGF) receptor family and its ligands in ovarian cancer. Biochimica et Biophysica Acta 1785:232-265 (2008). Available online Feb. 7, 2008.
Lameris et al. Bispecific antibody platforms for cancer immunotherapy. Critical Reviews in Oncology/Hematology 92:153-165 (2014).
Lee et al. Current concepts in the diagnosis and management of cytokine release syndrome. Blood, 2014, 124(2):188-195.
Leong et al. An anti-CD3/anti-CLL-1 bispecific antibody for the treatment of acute myeloid leukemia. Blood 129(5):609-618 (2017). Published online Dec. 1, 2016. doi:10.1182/blood-2016-08-735365.
Levitt, M. A simplified representation of protein conformations for rapid simulation of protein folding. J Mol Biol. Jun. 14, 1976;104(1):59-107.
Li et al. A Novel Bispecific Antibody, S-Fab, Induces Potent Cancer Cell Killing.J Immunother 38(9):350-356 (Nov./Dec. 2015).
Li et al. IFN-γ-induced chemokines are required for CXCR3-mediated T cell recruitment and anti-tumor efficacy of anti-HER2/CD3 bispecific antibody. Author Manuscript Published Online First on Jun. 27, 2018. 29 pages. DOI: 10.1158/1078-0432.CCR-18-1139.
Li et al. Prognostic Value of MMP-9 in Ovarian Cancer: A Meta-analysis. Asian Pacific Journal of Cancer Prevention 14:4107-4113 (2013). DOI: http://dx.doi.org/10.7314/APJCP.2013.14.7.4107.
Lloyd et al., Modelling the human immune response: performance of a $10^{11}$ human antibody repertoire against a broad panel of therapeutically relevant antigens, Protein Engineering, Design & Selection, 2009, 22: 159-168.

(56) References Cited

OTHER PUBLICATIONS

Lum et al. Targeted T cell Therapy in Stage IV Breast Cancer: A Phase I Clinical Trial. Clin Cancer Res. Author Manuscript Published OnlineFirst on Feb. 16, 2015. 28 pages. DOI: 10.1158/1078-0432.CCR-14-2280.
Mack, Small bispecific antibody composition expressed as a functional single-chain molecule with high tumor cell cytotoxicity. Proc. Natl. Acad. Sci., 1995, 92:7021-7025.
Maeda, Tumoritropic and lymphotropic principles of macromolecular drugs. Crit Rev Ther Drug Carrier Syst 6:193-210 (1989).
Malia et al., Epitope mapping and structural basis for the recognition of phosphorylated tau by the anti-tau antibody AT8, Proteins, 2016, 84(4): 427-434.
Martin, Expression of the 17-1A antigen in gastric and gastro-oesophageal junction adenocarcinomas: a potential immunotherapeutic target? J Clin Pathol 1999; 52:701-704.
Mathieu et al. Substrate specificity of schistosome versus human legumain determined by P1-P3 peptide libraries. Molecular & Biochemical Parasitology 121:99-105 (2002).
Matsumura, A new concept for macromolecular therapeutics in cancer chemotherapy: mechanism of tumoritropic accumulation of proteins and the antitumor agent smancs. Cancer Res 46:6387-6392 (1986).
Mau-Sørensen et al. A phase I trial of intravenous catumaxomab: a bispecific monoclonal antibody targeting EpCAM and the T cell coreceptor CD3. Cancer Chemother Pharmacol 75:1065-1073 (2015). Published online Mar. 27, 2015. DOI 10.1007/s00280-015-2728-5.
McGowan et al. Matrix metalloproteinase expression and outcome in patients with breast cancer: analysis of a published database. Annals of Oncology 19:1566-1572 (2008). Published online May 23, 2008. doi:10.1093/annonc/mdn180.
McPherson, et al. eds. PCR 2: a practical approach. Oxford University Press. 1995.
Mehvar R. Modulation of the pharmacokinetics and pharmacodynamics of proteins by polyethylene glycol conjugation. J. Pharm Pharm Sci. 2000;3(1):125-136.
Meijer et al. Non FcR-binding murine antihuman CD3 monoclonal antibody is capable of productive TCR signalling and induces proliferation in the presence of costimulation. Clin Exp Immunol 123:511-519 (2001).
Melero et al. T-Cell and NK-Cell Infiltration into Solid Tumors: A Key Limiting Factor for Efficacious Cancer Immunotherapy. Cancer Discov 4(5):522-526 (May 2014). doi:10.1158/2159-8290.CD-13-0985.
Metz, Bispecific antibody derivatives with restricted binding functionalities that are activated by proteolytic processing, Protein Engineering, Design & Selection, 2012, 25(10): 571-580.
Miller et al. Design, Construction, and In Vitro Analyses of Multivalent Antibodies. The Journal of Immunology 170:4854-4861 (2003).
Mitraki, et al. Protein Folding Intermediates and Inclusion Body Formation. Bio/Technology. 1989; 7:690-697.
Möller et al., Bispecific-monoclonal-antibody-directed lysis of ovarian carcinoma cells by activated human T lymphocytes. Cancer Immunol. Immunother. 33:210-216, 1991.
Morgia et al. Matrix metalloproteinases as diagnostic (MMP-13) and prognostic (MMP-2, MMP-9) markers of prostate cancer. Urol Res 33:44-50 (2005). Published online Oct. 22, 2004. DOI 10.1007/s00240-004-0440-8.
Munz, Side-by-side analysis of five clinically tested anti-EpCAM monoclonal antibodies, Cancer Cell International, 10:44-56, 2010.
Myers et al. Lewis Y Antigen as Detected by the Monocolonal Antibody BR96 is Expressed Strongly in Prostatic Adenocarcinoma. The Journal of Urology 153:1572-1574 (May 1995).
Nagase et al. Substrate specificities and activation mechanisms of matrix metalloproteinases. Biochemical Society Transactions 19:715-718 (1991).
Nam et al. Robust Therapeutic Efficacy of Matrix Metalloproteinase-2-Cleavable Fas-1-RGD Peptide Complex in Chronic Inflammatory Arthritis. PLoS ONE 11(10):e0164102 (Oct. 14, 2016). 18 pages. doi:10.1371/journal.pone.0164102.
Notice of opposition dated Feb. 13, 2014 by Novo Nordisk filed Feb. 7, 2014 against EP1996220 Application No. 07752636.6.
Notice of opposition dated Feb. 17, 2014 by XL-protein GmbH filed Feb. 7, 2014 against EP1996220 Application No. 07752636.6.
Notice of opposition dated Aug. 18, 2015 by Novo Nordisk filed Aug. 13, 2015 against EP2402754 Application No. 11172812.7.
Notice of opposition dated Aug. 21, 2015 by XL-protein GmbH filed Aug. 18, 2015 against EP2402754 Application No. 11172812.7.
Oberst et al. CEA/CD3 bispecific antibody MEDI-565/AMG 211 activation of T cells and subsequent killing of human tumors is independent of mutations commonly found in colorectal adenocarcinomas. mAbs 6(6):1571-1584 (Nov./Dec. 2014).
Oberst et al. Expression of the Serine Protease Matriptase and Its Inhibitor HAI1 in Epithelial Ovarian Cancer: Correlation with Clinical Outcome and Tumor Clinicopathological Parameters. Clinical Cancer Research 8:1101-1107 (Apr. 2002).
Offner et al. Induction of regular cytolytic T cell synapses by bispecific single-chain antibody constructs on MHC class I-negative tumor cells. Molecular Immunology 43:763-771 (2006). Available online Apr. 26, 2005. doi:10.1016/j.molimm.2005.03.007.
Omidfar et al. Production of a novel camel single-domain antibody specific for the type III mutant EGFR. Tumour Biol 25(5-6):296-305 (Sep.-Dec. 2004). DOI: 10.1159/000081395.
Packeisen et al., Detection of surface antigen 17-1A in breast and colorectal cancer. Hybridoma. 1999 18(1):37-40.
Pan et al. Identification of Peptide Substrates for Human MMP-11 (Stromelysin-3) Using Phage Display. J Biol Chem 278(30):27820-27827 (Jul. 25, 2003). Published, JBC Papers in Press, May 8, 2003, DOI 10.1074/jbc.M304436200.
Passlick et al. The 17-1A antigen is expressed on primary, metastatic and disseminated nonsmall cell lung carcinoma cells. Int. J. Cancer 87(4):548-552, 2000.
Pei et al. Hydrolytic Inactivation of a Breast Carcinoma Cell-derived Serpin by Human Stromelysin-3. J Biol Chem 269 (41):25849-25855 (Oct. 14, 1994).
Pepinsky, et al. Improved pharmacokinetic properties of a polyethylene glycol-modified form of interferon-beta-1a with preserved in vitro bioactivity. J Pharmacol Exp Ther. 2001; 297: 1059-66.
Pessano et al. The T3/T cell receptor complex: antigenic distinction between the two 20-kd T3 (T3-delta and T3-epsilon) subunits. The EMBO Journal 4(2):337-344 (1985).
Podust, et al. Extension of in vivo half-life of biologically active molecules by XTEN protein polymers. J Control Release. Oct. 28, 2016;240:52-66. doi: 10.1016/j.jconrel.2015.10.038. Epub Oct. 30, 2015.
Podust, et al., Extension of in vivo half-life of biologically active peptides via chemical conjugation to XTEN protein polymer. Protein Engineering Design and Selection, vol. 26, No. 11, Oct. 16, 2013, pp. 743-753.
Ranuncolo et al. Plasma MMP-9 (92 kDa-MMP) Activity is Useful in the Follow-Up and in the Assessment of Prognosis in Breast Cancer Patients. Int J Cancer 106:745-751 (2003). DOI 10.1002/ijc.11288.
Romagnani, T-cell subsets (Thl versus Th2). Ann Allergy Asthma Immunol. 2000, 85(1):9-18.
Ross et al. Bispecific T cell engager (BiTE®) antibody constructs can mediate bystander tumor cell killing. PLoS ONE 12(8): e0183390 (Aug. 24, 2017). https://doi.org/10.1371/journal.pone.0183390.
Rossi et al. A new class of bispecific antibodies to redirect T cells for cancer immunotherapy. mabs 6(2):381-391; Mar./Apr. 2014.
Rossi et al. Differential antibody binding to the surface aβTCR . CD3 complex of CD4+ and CD8+ T lymphocytes is conserved in mammals and associated with differential glycosylation. International Immunology 20(10):1247-1258 (Oct. 2008). Advance Access publication Jul. 24, 2008. DOI: https://doi.org/10.1093/intimm/dxn081.
Rossi et al. Redirected T-Cell Killing of Solid Cancers Targeted with an Anti-CD3/Trop-2 Bispecific Antibody is Enhanced in Combination with Interferon-α. American Association for Cancer Research. Author Manuscript Published OnlineFirst on Jul. 22, 2014; DOI: 10.1158/1535-7163.MCT-14-0345. 34 pages.

(56) References Cited

OTHER PUBLICATIONS

Ruiz et al. p95HER2-T cell bispecific antibody for breast cancer treatment. Sci Transl Med 10: eaat1445 (Oct. 3, 2008). 12 pages.
Sandersjöö et al. A new prodrug form of Affibody molecules (pro-Affibody) is selectively activated by cancer-associated proteases. Cell. Mol. Life Sci. 72:1405-1415 (2015). Published online Oct. 7, 2014. DOI 10.1007/s00018-014-1751-8.
Sarin et al. Physiologic upper limit of pore size in the blood-tumor barrier of malignant solid tumors. J. Translational Medicine 2009 7:51.
Sarin, Physiologic upper limits of pore size of different blood capillary types and another perspective on the dual pore theory of microvascular permeability. J Angiogenes Res. 2010; 2:14.
Savariar et al. Real-time In Vivo Molecular Detection of Primary Tumors and Metastases with Ratiometric Activatable Cell-Penetrating Peptides. Cancer Research 73(2):855-864 (2012). Published OnlineFirst Nov. 27, 2012; DOI: 10.1158/0008-5472.CAN-12-2969.
Schellenberger et al. "Online Supplementary material: A recombinant polypeptide extends the in vivo half-life of peptides and proteins in a tunable manner", Nature Biotechnology, vol. 27, No. 12, Nov. 15, 2009 (Nov. 15, 2009), pp. 1186-1190, XP055190665, ISSN: 1087-0156, DOI: 10.1038/nb.1588.
Schellenberger, et al., A recombinant polypeptide extends the in vivo half-life of peptides and proteins in a tunable manner. Nature Biotechnology, Nature Publishing Group, US, vol. 27, No. 2, Nov. 15, 2009, pp. 1186-1190.
Schellenberger, V. Engineering of Microproteins for Pharmaceutical Applications. PowerPoint Presentation. (2006). Opposition by XL-Protein GmbH against EP2402754 Application No. 11172812.7.
Scheuer et al. Strongly Enhanced Antitumor Activity of Trastuzumab and Pertuzumab Combination Treatment on HER2-Positive Human Xenograft Tumor Models. Cancer Res 69(24):9330-9336 (Dec. 15, 2009).
Schlapschy, et al. Fusion of a recombinant antibody fragment with a homo-amino-acid polymer: effects on biophysical properties and prolonged plasma half-life. Protein Eng Des Sel. Jun. 2007;20(6):273-84. Epub Jun. 26, 2007.
Schlereth et al. Potent inhibition of local and disseminated tumor growth in immunocompetent mouse models by a bispecific antibody construct specific for Murine CD3. Cancer Immunol Immunother 55: 785-796 (2006). Published online Sep. 27, 2005. DOI 10.1007/s00262-005-0082-x.
Schlereth et al. T-cell activation and B-cell depletion in chimpanzees treated with a bispecific anti-CD19/anti-CD3 single-chain antibody construct. Cancer Immunol Immunother 55: 503-514 (2006). Published online Jul. 20, 2005. DOI 10.1007/s00262-005-0001-1.
Schmalfeldt et al. Increased Expression of Matrix Metalloproteinases (MMP)-2, MMP9, and the Urokinase-Type Plasminogen Activator Is Associated with Progression from Benign to Advanced Ovarian Cancer. Clinical Cancer Research 7:2396-2404 (Aug. 2001).
Sebastian, et al. Treatment of malignant pleural effusion with the trifunctional antibody catumaxomab (Removab) (anti-EpCAM x Anti-CD3): results of a phase 1/2 study. J Immunother. Feb.-Mar. 2009;32(2):195-202. doi: 10.1097/CJI.0b013e318195b5bb.
Senter et al. Selective activation of anticancer prodrugs by monoclonal antibody-enzyme conjugates. Advanced Drug Delivery Reviews 53:247-264 (2001).
Sgro, Side-effects of a monoclonal antibody, muromonab CD3/orthoclone OKT3: bibliographic review. Toxicology 105:23-29, 1995.
Shalaby et al. Development of humanized bispecific antibodies reactive with cytotoxic lymphocytes and tumor cells overexpressing the HER2 protooncogene. J. Exp. Med. 175, 217-225 (1992).
Shekhar. Double Whammy: Bispecific Antibodies Help Immune Cells Attack Tumors. Chemistry & Biology, vol. 15 (Sep. 22, 2008). 2 pages. DOI 10.1016/j.chembiol.2008.09.002.
Sier et al. Tissue levels of matrix metalloproteinases MMP-2 and MMP-9 are related to the overall survival of patients with gastric carcinoma. British Journal of Cancer 74:413-417 (1996).
Sim, et al. Abstract 3638: AMX-168, a long-acting, tumor protease-sensitive bispecific precursor for the treatment of solid malignancies. Cancer Res Jul. 1, 2017 (77) (13 Supplement) 3638; DOI: 10.1158/1538-7445.AM2017-3638.
Simon et al. Epithelial glycoprotein is a member of a family of epithelial cell surface antigens homologous to nidogen, a matrix adhesion protein. Proc. Natl. Acad. Sci., 1990, 87: 2755-2759.
Singh, et al. ProPred: Prediction of HLA-DR binding sites. Bioinformatics. 17 (2001): 1236-1237.
Slaga et al. Avidity-based binding to HER2 results in selective killing of HER2-overexpressing cells by anti-HER2/CD3. Sci Transl Med 10:eaat5775 (Oct. 17, 2018). 11 pages.
Smith et al. Nonmitogenic Anti-CD3 Monoclonal Antibodies Deliver a Partial T Cell Receptor Signal and Induce Clonal Anergy, J. Exp. Med. 185:1413-1422 (1997).
Smith et al., Single-Step Purification of Polypeptides Expressed in *Escherichia coli* as Fusions with Glutathione S-Transferase. Gene 67:31-40 (1988).
Smith, et al. Single-step purification of polypeptides expressed in *Escherichia coli* as fusions with glutathione S-transferase. Gene. 1988; 67(1):31-40.
Squire, Calculation of hydrodynamic parameters of random coil polymers from size exclusion chromatography and comparison with parameters by conventional methods. Joumal of Chromatography, 1981, 5, 433-442.
Stamova et al. Simultaneous engagement of the activatory receptors NKG2D and CD3 for retargeting of effector cells to CD33-positive malignant cells. Leukemia 25:1053-1056 (2011). Published online Mar. 18, 2011. doi: 10.1038/leu.2011.42.
Stickler, et al. Human population-based identification of CD4(+) T-cell peptide epitope determinants. J Immunol Methods. 2003; 281: 95-108.
Stites, et al. Empirical evaluation of the influence of side chains on the conformational entropy of the polypeptide backbone. Proteins. 1995; 22: 132-140.
Stone et al. A sensitivity scale for targeting T cells with chimeric antigen receptors (CARs) and bispecific T-cell engagers (BiTEs). OncoImmunology 1(6):863-873 (Sep. 2012). http://dx.doi.org/10.4161/onci.20592.
Sturniolo, et al. Generation of tissue-specific and promiscuous HLA ligand databases using DNA microarrays and virtual HLA class II matrices. Natural Biotechnol. 1999; 17: 555-561.
Sun, et al. Anti-CD20/CD3 T cell-dependent bispecific antibody for the treatment of B cell malignancies. Sci Transl Med. May 13, 2015;7(287):287ra70. 11 pages. doi: 10.1126/scitranslmed.aaa4802.
Suurs et al., A review of bispecific antibodies and antibody constructs in oncology and clinical challenges, Pharmacol Ther., Sep. 2019, 201: 103-119.
Taberno et al. Phase I studies of the novel carcinoembryonic antigen CD3 T-cell bispecific (CEA-TCB) antibody as a single agent and in combination with atezolizumab: preliminary efficacy and safety in patients with metastatic colorectal cancer (mCRC). Slides. 2017 American Society of Clinical Oncology (ASCO) Annual Meeting, Jun. 2-5, 2017. 19 pages.
Tanford et al., Proteins in 6 M Guanidine Hydrochride. (1966) J. Biol. Chem. 241 , 1921-1923.
Tepitope analysis for SAPA repeats of opposition cited reference D5 Buscaglia et al. (1999) Blood 93:2025-2032 by Novo Nordisk against EP2402754 Application No. 11172812.7.
Tepitope values for random 200mer sequences composed of the amino acids GADSTEP; Reply to notice of opposition dated Apr. 8, 2016 for EP2402754.
Tian, et al. Expression of CD147 and matrix metalloproteinase-11 in colorectal cancer and their relationship to clinicopathological features. J Transl Med. 2015; 13: 337. 11 pages.
Tunnacliffe, The majority of human CD3 epitopes are conferred by the epsilon chain, Int'l. Immunol., 1989, 1(5): 546-650.
Uversky, et al. Why are "natively unfolded" proteins unstructured under physiologic conditions? Proteins. Nov. 15, 2000;41(3):415-27.

(56) References Cited

OTHER PUBLICATIONS

Van Nagell, Jr et al. The Clinical Significance of Carcinoembryonic Antigen in the Plasma and Tumors of Patients with Gynecologic Malignancies. Cancer 42:1527-1532 (1978).
Venkatachalam, et al. Conformation of polypeptide chains. Annu Rev Biochem. 1969; 38: 45-82.
Voet, et al., Biochemistry (3rd Ed.). John Wiley and Sons. Published 2004, p. 230.
Walker, et al. Using protein-based motifs to stabilize peptides. J Pept Res. Nov. 2003;62(5):214-26.
Walsh G. Appendix 1—Biopharmaceuticals thus far approved in the USA or European Union. Biopharmaceuticals: Biochemistry and Biotechnology. Second Edition. John Wiley & Sons. 25 pages.
Winkler et al., Changing the antigen binding specificity by single point mutations of an anti-p24 (HIV-1) Antibody[1], Journal of Immunology, 2000, 265: 4505-4514.
Wright, et al. Intrinsically unstructured proteins: re-assessing the protein structure-function paradigm. J Mol Biol. Oct. 22, 1999;293(2):321-31.
Yankai, et al. Ten tandem repeats of beta-hCG 109-118 enhance immunogenicity and anti-tumor effects of beta-hCG C-terminal peptide carried by mycobacterial heat-shock protein HSP65. Biochem Biophys Res Commun. 2006; 345(4): 1365-71.
Yoon, Selective addition of CXCR3+CCR4-CD4+ Thl cells enhances generation of cytotoxic T cells by dendritic cells in vitro. Exp Mol Med. 2009. 41(3):161-170.
Yuen, et al., A long-acting human growth hormone with delayed clearance (VRS-317): results of a double-blind, placebo-controlled, single ascending dose study in growth hormone-deficient adults. J Clin Endocrinol Metab. Jun. 2013, 98(6), 2595-2603.
Zeidler et al. Simultaneous Activation of T Cells and Accessory Cells by a New Class of Intact Bispecific Antibody Results in Efficient Tumor Cell Killing. J. Immunol., 1999, 163: 1246-1252.
Zhang, et al. An EpCAM/CD3 bispecific antibody efficiently eliminates hepatocellular carcinoma cells with limited galectin-1 expression. Cancer Immunol Immunother. Feb. 2014;63(2):121-32. doi: 10.1007/s00262-013-1497-4. Epub Nov. 1, 2013.
Zimmerman et al. Unleashing the clinical power of T cells: CD19/CD3 bispecific T cell engager (BiTE) antibody composition blinatumomab as a potential therapy. Int. Immunol. (2015) 27(1): 31-37.

* cited by examiner

FIG. 3A
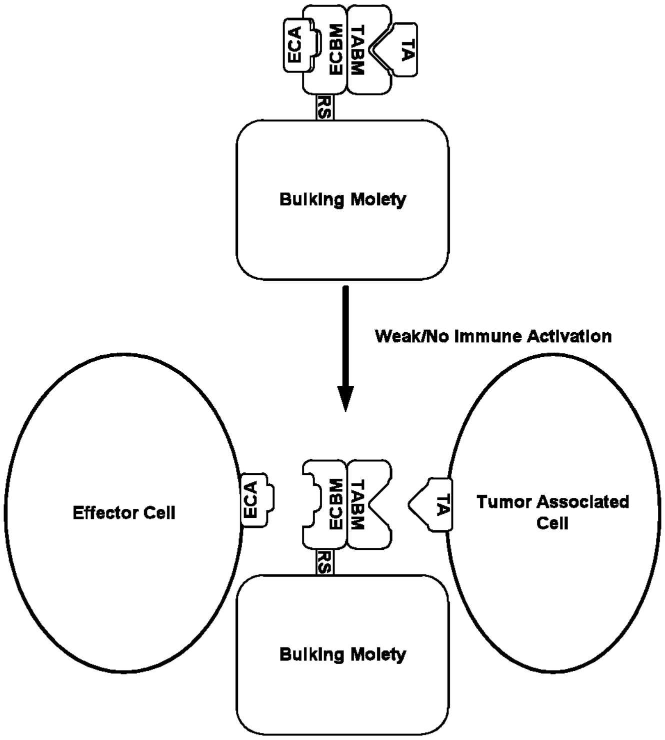
FIG. 3B
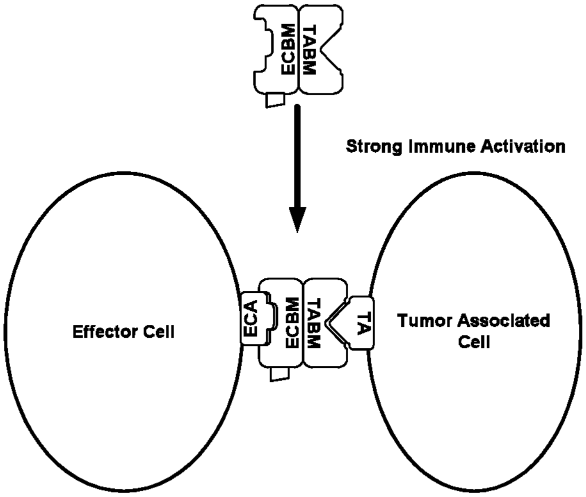
FIG. 3

Generic Construct Design

Tandem scFv Constructs

Diabody Constructs

DIQMTQSPSSLSASVGDRVTITCRSTKSLLHSNGITYLYWYQQKPGKAPKL
LIYQMSNLASGVPSRFSSSGSGTDFTLTISSLQPEDFATYYCAQNLEIPRT
FGQGTKVEIKGATPPETGAETESPGETTGGSAESEPPGEGQVQLVQSGPGL
VQPGGSVRISCAASGYTFTNYGMNWVKQAPGKGLEWMGWINTYTGESTYAD
SFKGRFTFSLDTSASAAYLQINSLRAEDTAVYYCARFAIKGDYWGQGTLLT
VSSGGGGSDIQMTQSPSSLSASVGDRVTITCRASQDIRNYLNWYQQKPGKA
PKLLIYYTSRLESGVPSRFSGSGSGTDYTLTISSLQPEDFATYYCQQGNTL
PWTFGQGTKVEIKGATPPETGAETESPGETTGGSAESEPPGEGEVQLVESG
GGLVQPGGSLRLSCAASGYSFTGYTMNWVRQAPGKGLEWVALINPYKGVST
YNQKFKDRFTISVDKSKNTAYLQMNSLRAEDTAVYYCARSGYYGDSDWYFD
VWGQGTLVTVSSGTAEAASASGLSGRSDNHSPLGLAGSPGSPAGSPTSTEE
GTSESATPESGPGTSTEPSEGSAPGSPAGSPTSTEEGTSTEPSEGSAPGTS
TEPSEGSAPGTSESATPESGPGSEPATSGSETPGSEPATSGSETPGSPAGS
PTSTEEGTSESATPESGPGTSTEPSEGSAPGTSTEPSEGSAPGSPAGSPTS
TEEGTSTEPSEGSAPGTSTEPSEGSAPGTSESATPESGPGTSTEPSEGSAP
GTSESATPESGPGSEPATSGSETPGTSTEPSEGSAPGTSTEPSEGSAPGTS
ESATPESGPGTSESATPESGPGSPAGSPTSTEEGTSESATPESGPGSEPAT
SGSETPGTSESATPESGPGTSTEPSEGSAPGTSTEPSEGSAPGTSTEPSEG
SAPGTSTEPSEGSAPGTSTEPSEGSAPGTSTEPSEGSAPGSPAGSPTSTEE
GTSTEPSEGSAPGTSESATPESGPGSEPATSGSETPGTSESATPESGPGSE
PATSGSETPGTSESATPESGPGTSTEPSEGSAPGTSESATPESGPGSPAGS
PTSTEEGSPAGSPTSTEEGSPAGSPTSTEEGTSESATPESGPGTSTEPSEG
SAPGTSESATPESGPGSEPATSGSETPGTSESATPESGPGSEPATSGSETP
GTSESATPESGPGTSTEPSEGSAPGSPAGSPTSTEEGTSESATPESGPGSE
PATSGSETPGTSESATPESGPGSPAGSPTSTEEGSPAGSPTSTEEGTSTEP
SEGSAPGTSESATPESGPGTSESATPESGPGTSESATPESGPGSEPATSGS
ETPGSEPATSGSETPGSPAGSPTSTEEGTSTEPSEGSAPGTSTEPSEGSAP
GSEPATSGSETPGTSESATPESGPGTSTEPSEGSAPGHHHHHH

FIG. 36

DIVMTQSPLSLPVTPGEPASISCRSSKNLLHSNGITYLYWYLQKPGQSPQL
LIYQMSNLASGVPDRFSSSGSGTDFTLKISRVEAEDVGVYYCAQNLEIPRT
FGQGTKVEIKGATPPETGAETESPGETTGGSAESEPPGEGQVQLVQSGPEV
KKPGASVKVSCKASGYTFTNYGMNWVRQAPGQGLEWMGWINTYTGEPTYGE
DFKGRFAFSLDTSASTAYMELSSLRSEDTAVYFCARFGNYVDYWGQGSLVT
VSSGGGGSELVVTQEPSLTVSPGGTVTLTCRSSTGAVTTSNYANWVQQKPG
QAPRGLIGGTNKRAPGTPARFSGSLLGGKAALTLSGVQPEDEAEYYCALWY
SNLWVFGGGTKLTVLGATPPETGAETESPGETTGGSAESEPPGEGEVQLLE
SGGGLVQPGGSLKLSCAASGFTFNTYAMNWVRQAPGKGLEWVARIRSKYNN
YATYYADSVKDRFTISRDDSKNTAYLQMNNLKTEDTAVYYCVRHGNFGNSY
VSWFAYWGQGTLVTVSSGTAEAASASGLSGRSDNHSPLGLAGSPGSPAGSP
TSTEEGTSESATPESGPGTSTEPSEGSAPGSPAGSPTSTEEGTSTEPSEGS
APGTSTEPSEGSAPGTSESATPESGPGSEPATSGSETPGSEPATSGSETPG
SPAGSPTSTEEGTSESATPESGPGTSTEPSEGSAPGTSTEPSEGSAPGSPA
GSPTSTEEGTSTEPSEGSAPGTSTEPSEGSAPGTSESATPESGPGTSTEPS
EGSAPGTSESATPESGPGSEPATSGSETPGTSTEPSEGSAPGTSTEPSEGS
APGTSESATPESGPGTSESATPESGPGSPAGSPTSTEEGTSESATPESGPG
SEPATSGSETPGTSESATPESGPGTSTEPSEGSAPGTSTEPSEGSAPGTST
EPSEGSAPGTSTEPSEGSAPGTSTEPSEGSAPGTSTEPSEGSAPGSPAGSP
TSTEEGTSTEPSEGSAPGTSESATPESGPGSEPATSGSETPGTSESATPES
GPGSEPATSGSETPGTSESATPESGPGTSTEPSEGSAPGTSESATPESGPG
SPAGSPTSTEEGSPAGSPTSTEEGSPAGSPTSTEEGTSESATPESGPGTST
EPSEGSAPGTSESATPESGPGSEPATSGSETPGTSESATPESGPGSEPATS
GSETPGTSESATPESGPGTSTEPSEGSAPGSPAGSPTSTEEGTSESATPES
GPGSEPATSGSETPGTSESATPESGPGSPAGSPTSTEEGSPAGSPTSTEEG
TSTEPSEGSAPGTSESATPESGPGTSESATPESGPGTSESATPESGPGSEP
ATSGSETPGSEPATSGSETPGSPAGSPTSTEEGTSTEPSEGSAPGTSTEPS
EGSAPGSEPATSGSETPGTSESATPESGPGTSTEPSEGSAPGHHHHHH

FIG. 37

■ Protease-treated aHER2 x aCD3 ProTIA on HER2 coated on plate

▲ Protease-treated aCEA x aCD3 ProTIA on CEA coated on plate

● Protease-treated aEpCAM x aCD3 ProTIA on EpCAM coated on plate

○ Protease-treated aEpCAM x aCD3 ProTIA on HER2 coated on plate

⊗ Protease-treated aEpCAM x aCD3 ProTIA on CEA coated on plate

CHIMERIC POLYPEPTIDE ASSEMBLY AND METHODS OF MAKING AND USING THE SAME

CROSS-REFERENCE TO RELATED APPLICATIONS

This application is a division of U.S. patent application Ser. No. 15/753,716, filed Feb. 20, 2018, which is a 35 U.S.C. § 371 filing of International Patent Application No. PCT/US2016/049137, filed Aug. 26, 2016, which claims the benefit of U.S. Provisional Patent Application Serial Nos. 62/211,532, filed Aug. 28, 2015; 62/263,319, filed Dec. 4, 2015; 62/278,755, filed Jan. 14, 2016; 62/338,285, filed May 18, 2016; 62/363,046, filed Jul. 15, 2016; and 62/379,673, filed Aug. 25, 2016. Each of these applications are hereby incorporated by reference in their entireties.

SEQUENCE LISTING

The instant application contains a Sequence Listing which has been submitted electronically in XML format and is hereby incorporated by reference in its entirety. Said XML copy, created on Dec. 19, 2022, is named 736794_SA9-725USDIV_ST26.xml and is 888,628 bytes in size.

BACKGROUND OF THE INVENTION

Many approved cancer therapeutics are cytotoxic drugs that kill normal cells as well as tumor cells. The therapeutic benefit of these cytotoxic drugs depends on tumor cells being more sensitive than normal cells, thereby allowing clinical responses to be achieved using doses that do not result in unacceptable side effects. However, essentially all of these non-specific drugs result in some if not severe damage to normal tissues, which often limits treatment suitability.

Bispecific antibodies offer a different approach to cytotoxic drugs in that they direct immune effector cells to kill cancer cells. Bispecific antibodies combine the benefits of different binding specificities derived from two monoclonal antibodies into a single composition, enabling approaches or combinations of coverages that are not possible with monospecific antibodies. This approach relies on binding of one arm of the bispecific antibody to a tumor-associated antigen or marker, while the other arm, upon binding the CD3 molecule on T cells, triggers their cytotoxic activity by the release of effector molecules such as such as TNF-α, IFN-γ, interleukins 2, 4 and 10, perforin, and granzymes. Advances in antibody engineering have led to the development of a number of bispecific antibody formats and compositions for redirecting effector cells to tumor targets, including Bispecific T-cell Engagers (BiTEs®) such as blinatumomab. BiTEs function by recruiting and activating polyclonal populations of T-cells at tumor sites, and do so without the need for co-stimulation or conventional MHC recognition. There remains, however, the dual problems of certain patients experiencing serious side effects referred to as "cytokine storm" or "cytokine release syndrome" (Lee D W et al. Current concepts in the diagnosis and management of cytokine release syndrome. Blood. 2014 124(2):188-195) mediated by the release of TNF-α and IFN-γ, amongst other cytokines, in addition to the fact that BiTE compositions have a very short half-life, necessitating continuous infusions of four to eight weeks in order to maintain BiTE within the therapeutic window for sufficient time to achieve a therapeutic effect.

SUMMARY OF THE INVENTION

There remains a considerable need for alternative therapeutics that offer the pharmacologic advantages of such bispecific antibody formats but with increased safety, reduced side effects, increased selectivity, and/or enhanced pharmacokinetic properties, such as requiring less frequent dosing or merely dosing by a single injection.

The present invention discloses a chimeric polypeptide assembly useful in the treatment or prevention of diseases, including but not limited to cancers, autoimmune, and inflammatory disorders. In a first aspect, the present disclosure provides a cleaveable chimeric polypeptide assembly. The cleavable chimeric polypeptide assembly compositions address an unmet need and are superior in one or more aspects including enhanced terminal half-life, targeted delivery, and reduced toxicity to healthy tissues compared to conventional bispecific antibody preparations in use.

A subject polypeptide assembly typically comprises a first portion, a second portion, and a third portion, wherein: said first portion comprises (i) a first binding domain with binding specificity to a target cell marker; and (ii) a second binding domain with binding specificity to an effector cell antigen; said second portion comprises a peptidyl release segment (RS) capable of being cleaved by one or more mammalian proteases; and said third portion comprises a bulking moiety; wherein said bulking moiety is capable of being released from said first portion by action of said mammalian protease on said second portion.

The various components in a subject chimeric polypeptide assembly can be configured in a variety of different orders. In one embodiment, the chimeric polypeptide assembly is configured, from N-terminus to C-terminus, wherein the first portion is linked to the second portion, which in turn is linked to the third portion. In another embodiment, the chimeric polypeptide assembly is configured, from N-terminus to C-terminus, wherein the third portion is linked to the second portion, which in turn is linked to the first portion. In one embodiment, the chimeric polypeptide assembly is a fusion protein. In another embodiment, the second and third portions are a fusion protein and the first portion is conjugated to the second portion. In one embodiment of the chemically conjugated polypeptide assembly composition, the C-terminus of the first portion polypeptide can be conjugated to the N-terminus of the second portion polypeptide via a cysteine or other suitable amino acids amenable for cross-linking by agents such as maleamide or other cross-linking agents known in the art. In another embodiment, the first portion and the second portion is a monomeric fusion protein and the third portion is chemically conjugated to the second portion.

Optionally, the chimeric polypeptide assembly compositions may comprise an additional bulking moiety linked to the composition by a second release segment linked to the opposite end of the composition, thereby enclosing the first and second portions.

The first and the second binding domains are generally antibody fragments derived from monoclonal antibodies. In one embodiment, the first and the second binding domains of the first portion of the chimeric polypeptide assembly compositions are scFv or configured as a diabody. In other embodiments, the first and the second binding domains of the first portion of the chimeric polypeptide assembly compositions are selected from the group consisting of Fv, Fab, Fab', Fab'-SH, F(ab')2, linear antibodies, a single domain antibody, a non-antibody scaffold, and a single domain camelid antibody. In other embodiments, the first and the second binding domains of the first portion of the chimeric polypeptide assembly compositions are selected from the group of peptides, non-antibody scaffolds such as anticalins, adnectins, fynomers, affilins, affibodies, centyrins, DARPins. In other embodiments the binding domain for the tumor cell target is a variable domain of a T cell receptor that has been engineered to bind MHC that is loaded with a peptide fragment of a protein that is overexpressed by tumor cells.

In one embodiment of the chimeric polypeptide assembly, the first binding domain of the first portion has binding affinity to a target cell marker. Target cells include any cell types of eukaryotes such as those of ectoderm, mesoderm or endoderm origin. Of particular interest are tumor cells and markers expressed by the tumor cells. Tumor cell can arise from a cell selected from the group consisting of stromal cell, fibroblasts, myofibroblasts, glial cells, epithelial cells, fat cells, lymphocytic cells, vascular cells, smooth muscle cells, mesenchymal cells, breast tissue cells, prostate cells, kidney cells, brain cells, colon cells, ovarian cells, uterine cells, bladder cells, skin cells, stomach cells, genito-urinary tract cells, cervix cells, uterine cells, small intestine cells, liver cells, pancreatic cells, gall bladder cells, bile duct cells, esophageal cells, salivary gland cells, lung cells, and thyroid cells. In some cases, the tumor specific marker include alpha 4 integrin, Ang2, B7-H3, B7-H6, CEACAM5, cMET, CTLA4, FOLR1, EpCAM, CCR5, CD19, HER2, HER2 neu, HER3, HER4, HER1 (EGFR), PD-L1, PSMA, CEA, MUC1(mucin), MUC-2, MUC3, MUC4, MUC5AC, MUC5B, MUC7, MUC16 βhCG, Lewis-Y, CD20, CD33, CD38, CD30, CD56 (NCAM), CD133, ganglioside GD3; 9-O-Acetyl-GD3, GM2, Globo H, fucosyl GM1, GD2, carbonicanhydrase IX, CD44v6, Sonic Hedgehog (Shh), Wue-1, plasma cell antigen 1, melanoma chondroitin sulfate proteoglycan (MCSP), CCR8, 6-transmembrane epithelial antigen of prostate (STEAP), mesothelin, A33 antigen, prostate stem cell antigen (PSCA), Ly-6, desmoglein 4, fetal acetylcholine receptor (fnAChR), CD25, cancer antigen 19-9 (CA19-9), cancer antigen 125 (CA-125), Muellerian inhibitory substance receptor type II (MISIIR), sialylated Tn antigen (s TN), fibroblast activation antigen (FAP), endosialin (CD248), epidermal growth factor receptor variant III (EGFRvIII), tumor-associated antigen L6 (TAL6), SAS, CD63, TAG72, Thomsen-Friedenreich antigen (TF-antigen), insulin-like growth factor I receptor (IGF-IR), Cora antigen, CD7, CD22, CD70, CD79a, CD79b, G250, MT-MMPs, F19 antigen, CA19-9, CA-125, alpha-fetoprotein (AFP), VEGFR1, VEGFR2, DLK1, SP17, ROR1, and EphA2. In another embodiment of the chimeric polypeptide assembly, the first binding domain of the first portion has binding affinity to a target cell marker that is an inflammatory marker.

In one embodiment, the first binding domain of the first portion of the chimeric polypeptide assembly compositions comprises VH and VL regions with specific binding affinity to a tumor-specific marker or an antigen of a target cell. In one embodiment of the foregoing, the first binding domain VH and VL are derived from a monoclonal antibody VH and VL selected from the group of paired sequences set forth in Table 2. The VH and VL regions of the first and second binding domains can be configured in different orders, with respect to the N-terminus to C-terminus order. In one embodiment, the first binding domain VH and VL regions are arranged in the order VH-VL. In another embodiment, the first binding domain VH and VL regions are arranged in the order VL-VH. In other cases, the first binding domain comprises a CDR-H1 region, a CDR-H2 region, a CDR-H3 region, a CDR-L1 region, a CDR-L2 region, and a CDR-H3 region, wherein each of said regions is derived from monoclonal antibody sequences selected from the group of sequences set forth in Table 2. The various configurations of VH and VL regions as well as the CDRs contained therein typically retain the desired binding specificity to an intended target cell marker.

In other embodiments of the chimeric polypeptide assembly, the second binding domain of the first portion has binding affinity to an effector cell. Where desired, the effector cell can be immune cells, including but not limited to plasma cell, T cell, B cell, cytokine induced killer cell (CIK cell), master cell, dendritic cell, regulatory T cell (RegT cell), helper T cell, myeloid cell, and NK cell. The second binding domain typically exhibits binding specificity to an antigen expressed by an effector cell. In some embodiments, the antigen is expressed on the cell surface of an effector cell. In another embodiment, the second binding domain has binding specificity to an effector cell antigen expressed on a T cell. Non-limiting exemplary effector cell antigens include CD3, CD4, CD8, ctr3 TCR, CD25, CD45RO, CD69, CD127, and CD196 (CCR6). Of particular interest is a second binding domain adopting a scFv configuration having VH and VL regions derived from a monoclonal antibody that binds specifically to human CD3. In one embodiment, the second binding domain VH and VL are derived from a monoclonal antibody VH and VL selected from the group of sequences set forth in Table 1. In another embodiment, the second binding domain comprises VH and VL regions derived from a monoclonal antibody capable of binding human CD3E.

The VH and VL of the scFv of the binding domains can be arranged in different configurations without affecting the utility of the resulting composition. In one embodiment, the second binding domain scFv comprises VH and VL regions arranged in the order VH-VL or VL-VH in the N-terminal to C-terminal direction. The binding domains can also be created from CDR regions. In one embodiment, the second binding domain comprises a CDR-H1 region, a CDR-H2 region, a CDR-H3 region, a CDR-L1 region, a CDR-L2 region, and a CDR-H3 region, wherein each is derived from a monoclonal antibody of Table 1. In the foregoing embodiments of the paragraph, the VH and VL regions and the first binding domain and the second binding domain are linked by flexible polypeptide linkers selected from the group of sequences set forth in Table 8 and Table 9. In another embodiment, the first portion of the chimeric polypeptide assembly compositions has a sequence with at least about 90%, or 91%, or 92%, or 93%, or 94%, or 95%, or 96%, or 97%, or 98%, or 99% identity to a sequence selected from the group consisting of the sequences of Table 13.

One advantage of the subject chimeric polypeptide assembly is that it is assembled in form of a prodrug, wherein the intact composition can be activated in proximity to a target tissue or a certain cellular environment in which mammalian proteases are present, releasing the first portion binding domains at the site where its activity is most desirable. For example, the first portion binding domain, when present in the intact assembly, has lower binding affinity due to the shielding effect of the bulking moiety. Upon release via cleaveage of the RS by a mammalian protease preferentially expressed in a target issue, for example, a tumor tissue, the first portion binding domain becomes "activated" without being shielded by the bulking moiety. In another embodiment, the invention provides a chimeric polypeptide assembly, wherein the mammalian protease capable of cleaving the RS is preferentially expressed in an inflammatory tissue.

In one embodiment, the chimeric polypeptide assembly comprises an RS, wherein the RS comprises an amino acid sequence selected from the group consisting of the sequences set forth in Table 4. Where desired, the RS comprises an amino acid sequence selected from the group consisting of the sequences LSGRSDNHSPLGLAGS (SEQ ID NO: 1), SPLGLAGSLSGRSDNH (SEQ ID NO: 2), SPLGLSGRSDNH (SEQ ID NO: 3), LAGRSDNHSPLGLAGS (SEQ ID NO: 4), LSGRSDNHVPLSLKMG (SEQ ID NO: 5), SPLGLAGS (SEQ ID NO: 6), GPLALARG (SEQ ID NO: 7), LSGRSDNH (SEQ ID NO: 8), VPLSLTMG (SEQ ID NO: 9), VPLSLKMG (SEQ ID NO: 10), VPLSLSMG (SEQ ID NO: 11), EPLELVAG (SEQ ID NO: 12), EPLELRAG (SEQ ID NO: 13), EPAALMAG (SEQ ID NO: 14), EPASLMAG (SEQ ID NO: 15), RIGSLRTA (SEQ ID NO: 16), RIQFLRTA (SEQ ID NO: 17), EPFHLMAG (SEQ ID NO: 18), VPLSLFMG (SEQ ID NO: 19), EPLELPAG (SEQ ID NO: 20), and EPLELAAG (SEQ ID NO: 21). Where desired, the release segment of the chimeric polypeptide assembly composition comprises the amino acid sequence the sequence LSGRSDNHSPLGLAGS (SEQ ID NO: 1). In the RS embodiments, the RS comprises an amino acid sequence capable of being cleaved by one or more proteases selected from the group consisting of the proteases set forth in Table 3.

In another aspect, the third portion of the chimeric polypeptide assembly compositions comprise a bulking moiety. Exemplary bulking moieties include but are not limited to: extended recombinant polypeptides (XTEN), albumin binding domain, albumin, IgG binding domain, polypeptides consisting of proline, serine, and alanine; fatty acid, ELP biopolymer, Fc domain, polyethylene glycol (PEG), PLGA, and hydoxylethyl starch. In one embodiment, the bulking moiety is an XTEN sequence. Where desired, the XTEN of the third portion comprises an amino acid sequence having at least about 90%, 91%, 92%, 93%, 94%, 95%, 96%, 97%, 98%, 99%, or 100% sequence identity to a sequence selected from the group of sequences set forth in Table 5.

In another aspect, the subject chimeric polypeptide assembly exhibits the ability to bind and link effector cells and target cells, thereby forming an immunological synapse such that the effector cell can mediate its biological effect in a target cell specific manner. For example, a subject chimeric polypeptide assembly possesses the ability to (1) bind specifically to a target cell marker such as a tumor-specific maker, and to (2) bind specifically to an antigen expressed on an effector cell (e.g., an antigen expressed by a T-cell). The concurrent binding of the T cell and the tumor cell mediates killing, damage, and/or lysis of the tumor cell In one embodiment, upon cleavage of the second portion by the one or more mammalian proteases and release of the first portion, the first portion is capable of concurrently binding to a T cell bearing the human CD3 antigen and to a tumor cell bearing the tumor specific marker in an in vitro assay comprising both the T cells and the tumor cells. In an exemplary design characteristic of the inventive compositions, upon cleavage of the second portion RS to release the first portion and the third portion from said chimeric polypeptide assembly, the released first portion has a molecular weight that is at least 2-fold, 3-fold, 4-fold, or 5-fold less than the third portion and has a molecular weight that is at least 20%, or at least 30%, or at least 40%, or at least 50%, or at least 60% less than the intact chimeric polypeptide assembly. In an embodiment, upon cleavage of the second portion RS, the released said first portion from said chimeric polypeptide assembly has increased binding affinity to the effector T cell bearing the CD3 antigen and/or the tumor cell marker compared to the chimeric binding assembly wherein the second portion has not been cleaved. The increased binding affinity of the released first portion to the T cell bearing the human CD3 antigen and/or the tumor cell marker is at least 2-fold, 3-fold, 4-fold, 5-fold, 6-fold, 7-fold, 8-fold, 9-fold, or 10-fold greater compared to the binding affinity of the chimeric polypeptide assembly to the T cell bearing the human CD3 antigen or the tumor cell marker wherein the RS has not been cleaved. In another embodiment, upon cleavage of the second portion RS and the release of said first portion from said chimeric polypeptide assembly, the concurrent binding of the first portion to the T cell and the tumor cell yields cytotoxic activity against the tumor cell in an in vitro assay comprising a population of T cells and tumor cells. In another embodiment, the released first portion of the chimeric polypeptide assembly is capable of effecting a greater amount of cell lysis of the tumor cell compared to an intact chimeric binding assembly in the in vitro assay. For example, the amount of cell lysis effected by the released first portion of the chimeric polypeptide assembly is at least 10-fold greater, or at least 30-fold, or at least 100-fold, or at least 300-fold, or at least 1000-fold greater compared to the intact chimeric binding assembly in the in the vitro assay. In one embodiment, the cytotoxic activity and/or cell lysis of the tumor cell is mediated by target specific activation of the T cell, wherein the amount of activation of the T cell effected by the released first portion of the chimeric polypeptide assembly is at least 10-fold greater, or at least 30-fold, or at least 100-fold, or at least 300-fold, or at least 1000-fold greater compared to the intact chimeric binding assembly. As the RS of the chimeric binding assembly may be subject to partial cleavage of the RS during an in vitro cytotoxic assay, for purposes of determining the maximum comparative difference in cytotoxicity, the RS of the assembly can be substituted with a non-cleavable peptide and assayed in comparison to a sample of the released first portion. Where desired, the in vitro assay can be assays selected from of cell membrane integrity assay, mixed cell culture assay, FACS based propidium Iodide assay, trypan Blue influx assay, photometric enzyme release assay, radiometric 51Cr release assay, fluorometric Europium release assay, CalceinAM release assay, photometric MTT assay, XTT assay, WST-1 assay, alamar blue assay, radiometric 3H-Thd incorporation assay, clonogenic assay measuring cell division activity, fluorometric rhodamine123 assay measuring mitochondrial transmembrane gradient, apoptosis assay monitored by FACS-based phosphatidylserine exposure, ELISA-based TUNEL test assay, sandwich ELISA, caspase activity assay, cell-based LDH release assay, and cell morphology assay, or any combination thereof, or by the methods described herein in the Examples, below.

In another aspect, the invention provides chimeric polypeptide assembly compositions comprising a first portion wherein said first portion comprises i) a second binding domain with binding specificity to an effector cell antigen; and ii) a first binding domain with binding specificity to a tumor-specific marker or an antigen of a target cell; a second portion wherein said second portion comprises a first release segment (RS) capable of being cleaved by a mammalian protease, a third portion comprising a first bulking moiety wherein said bulking moiety is capable of being released from said first portion by action of said mammalian protease on said second portion, a fourth portion comprising a release segment (RS) that may be the same or may be different from the second portion RS, and a fifth portion comprising a second bulking moiety that may be the same or may be different from the third portion wherein said bulking moiety is capable of being released from said first portion by action of said mammalian protease on said fourth portion. In one embodiment of the foregoing, the second release segment of the chimeric polypeptide assembly composition comprises an amino acid sequence selected from the group consisting of the sequences set forth in Table 4. In another embodiment of the foregoing, the second release segment of the chimeric polypeptide assembly composition comprises an amino acid sequence selected from the group consisting of the sequences LSGRSDNHSPLGLAGS (SEQ ID NO: 1), SPLGLAGSLSGRSDNH (SEQ ID NO: 2), SPLGLSGRSDNH (SEQ ID NO: 3), LAGRSDNHSPLGLAGS (SEQ ID NO: 4), LSGRSDNHVPLSLKMG (SEQ ID NO: 5), SPLGLAGS (SEQ ID NO: 6), GPLALARG (SEQ ID NO: 7), LSGRSDNH (SEQ ID NO: 8), VPLSLTMG (SEQ ID NO: 9), VPLSLKMG (SEQ ID NO: 10), VPLSLSMG (SEQ ID NO: 11), EPLELVAG (SEQ ID NO: 12), EPLELRAG (SEQ ID NO: 13), EPAALMAG (SEQ ID NO: 14), EPASLMAG (SEQ ID NO: 15), RIGSLRTA (SEQ ID NO: 16), RIQFLRTA (SEQ ID NO: 17), EPFHLMAG (SEQ ID NO: 18), VPLSLFMG (SEQ ID NO: 19), EPLELPAG (SEQ ID NO: 20), and EPLELAAG (SEQ ID NO: 21). In another embodiment of the foregoing, the second release segment of the chimeric polypeptide assembly composition comprises an amino acid sequence capable of being cleaved by a protease selected from the group of proteases set forth in Table 3. In another embodiment of the foregoing, the bulking moiety of the fifth portion of the composition is selected from the group consisting of: XTEN; albumin binding domain; albumin; IgG binding domain; a polypeptide of at least 350 amino acid residues consisting of proline, serine, and alanine; fatty acid; and Fc domain. In another embodiment of the foregoing, the bulking moiety of the fifth portion of the composition is XTEN. In another embodiment of the foregoing, the bulking moiety of the composition is an XTEN comprising an amino acid sequence having at least 90%, 91%, 92%, 93%, 94%, 95%, 96%, 97%, 98%, 99%, or 100% sequence identity, when optimally aligned, to a sequence selected from the group of sequences set forth in Table 5. In one embodiment, the invention provides a chimeric polypeptide assembly composition, comprising an amino acid sequence with at least 90%, 91%, 92%, 93%, 94%, 95%, 96%, 97%, 98%, 99%, or 100% sequence identity to the amino acid sequence without the signal peptide, as set forth in Table 10, when optimally aligned. In another embodiment, the invention provides a chimeric polypeptide assembly composition, comprising an amino acid sequence with at least 90%, 91%, 92%, 93%, 94%, 95%, 96%, 97%, 98%, 99%, or 100% sequence identity to the amino acid sequence, as set forth in Table 12, when optimally aligned. In another embodiment, the invention provides a chimeric polypeptide assembly composition, comprising an amino acid sequence with at least 90%, 91%, 92%, 93%, 94%, 95%, 96%, 97%, 98%, 99%, or 100% sequence identity to the amino acid sequence, as set forth in FIG. 36 or FIG. 37. In another embodiment, the invention provides chimeric polypeptide assembly consisting of an amino acid sequence having a polypeptide sequence selected from the group consisting of the sequences set forth in FIG. 36 or FIG. 37.

In an exemplary characteristic of the chimeric polypeptide assembly compositions, the ability to effect cytolysis of the target cells after release of the first portion binding domains (compared to the intact composition) is proportionally greater than the increased binding affinity to the target cell marker of released first portion as compared to that of the intact composition. In one embodiment of this characteristic, the relative cytotoxicity expressed as EC50 integer, compared to the binding affinity expressed as the log of the Kd in an in vitro assay is at least about 2:1, or at least 10:1, or at least 50:1, or at least 100:1, or at least 300:1, or at least 500:1, or at least 1000:1. In another embodiment, the ratio of cytotoxicity (e.g., expressed as the EC50 integer), to the binding affinity (e.g., expressed as the log of the $K_d$) of the released first portion of the chimeric polypeptide assembly in an in vitro assay is at least about 2-fold, at least about 3-fold, at least about 5-fold, at least about 10-fold, at least about 30-fold, at least about 50-fold, or at least about 100-fold greater.

In some embodiments, wherein in a comparison of a) the relative cytotoxicity, which is measured as a ratio between the cytotoxicity of (i) the released first portion to the target tumor cell in an in vitro assay comprising both the T cells and tumor cells bearing the target cell marker and (ii) the cytotoxicity of a composition comprising the corresponding first portion of the chimeric polypeptide assembly and the corresponding third portion of the chimeric polypeptide assembly linked by a non-cleavable peptide of 1 to about 10 amino acids; and b) the relative binding affinity to the effector cell antigen, which is measured as a ratio between the binding affinity of (i) the released first portion to the effector cell antigen and (ii) the binding affinity to the effector cell antigen of a composition comprising the corresponding first portion of the chimeric polypeptide assembly and the corresponding third portion of the chimeric polypeptide assembly linked by a non-cleavable peptide of 1 to about 10 amino acids, where the ratio between the relative cytotoxicity and the relative binding affinity is greater than at least 3:1, 10:1, or greater than at least 30:1, or greater than at least 50:1, or greater than at least 100:1, or greater than at least 300:1, or greater than at least 500:1, or greater than at least 1000:1. In one embodiment of the foregoing, the non-cleavable peptide has the sequence glycine-serine, serine-glycine, or multiple units of either dipeptide and the effector cell antigen is CD3. In one embodiment, wherein in a comparison of a) the relative cytotoxicity, which is measured as a ratio between the cytotoxicity of (i) the released first portion to the target tumor cell in an in vitro assay comprising both the T cells and tumor cells bearing the target cell marker and (ii) the cytotoxicity of a composition comprising the corresponding first portion of the chimeric polypeptide assembly and the corresponding third portion of the chimeric polypeptide assembly linked by a non-cleavable peptide of 1 to about 10 amino acids; and b) the relative binding affinity to the target cell marker, which is measured as a ratio between the binding affinity of (i) the released first portion to the target cell marker and (ii) the binding affinity to the target cell marker of a composition comprising the corresponding first portion of the chimeric polypeptide assembly and the corresponding third portion of the chimeric polypeptide assembly linked by a non-cleavable peptide of 1 to about 10 amino acids, where the ratio between the relative cytotoxicity and the relative binding affinity is greater than at least 3:1, 10:1, or greater than at least 30:1, or greater than at least 50:1, or greater than at least 100:1, or greater than at least 300:1, or greater than at least 500:1, or greater than at least 1000:1. In one embodiment of the foregoing, the non-cleavable peptide has the sequence glycine-serine, serine-glycine, or multiple units of either dipeptide and the effector cell antigen is CD3. In another embodiment, wherein in a comparison of a) the relative cytotoxicity, which is measured as a ratio between the cytotoxicity of (i)

the released first portion to the target tumor cell in an in vitro assay comprising both the T cells and tumor cells bearing the target cell marker and (ii) the cytotoxicity of a composition comprising the corresponding first portion of the chimeric polypeptide assembly and the corresponding third portion of the chimeric polypeptide assembly linked by a non-cleavable peptide of 1 to about 10 amino acids; b) the relative effector cell antigen binding affinity, which is measured as a ratio between the binding affinity of (i) the released first portion to the effector cell antigen and (ii) the binding affinity of a composition comprising the corresponding first portion of the chimeric polypeptide assembly and the corresponding third portion of the chimeric polypeptide assembly linked by a non-cleavable peptide of 1 to about 10 amino acids; and c) the relative binding affinity to the target cell marker, which is measured as a ratio between the binding affinity of (i) the released first portion to the target cell marker and (ii) the binding affinity to the target cell marker of a composition comprising the corresponding first portion of the chimeric polypeptide assembly and the corresponding third portion of the chimeric polypeptide assembly linked by a non-cleavable peptide of 1 to about 10 amino acids, where the ratio between the relative cytotoxicity and the relative effector cell antigen binding affinity multiplied with the relative binding affinity to the target cell marker is greater than at least 3:1, 10:1, or greater than at least 30:1, or greater than at least 50:1, or greater than at least 100:1, or greater than at least 300:1, or greater than at least 500:1, or greater than at least 1000:1. In one embodiment of the foregoing, the non-cleavable peptide has the sequence glycine-serine, serine-glycine, or multiple units of either dipeptide and the effector cell antigen is CD3.

In one embodiment, the invention provides chimeric polypeptide assembly compositions in which the EC50 value of the released first portion of the chimeric polypeptide assembly composition in an in vitro cytotoxicity assay comprising both the T cells and tumor cells bearing the target cell marker is ≤5000 pg/ml, even more preferably ≤1000 pg/ml, even more preferably ≤500 pg/ml, even more preferably ≤350 pg/ml, even more preferably ≤250 pg/ml, even more preferably <100 pg/ml, even more preferably ≤50 pg/ml, even more preferably <10 pg/ml, and most preferably ≤5 pg/ml. In one embodiment, the EC50 value of the released first portion of the chimeric polypeptide assembly composition in the in vitro assay is at least 10-fold, or at least 20-fold, or at least 30-fold, or at least 40-fold, or at least 50-fold, or at least 60-fold, or at least 70-fold, or at least 80-fold, or at least 90-fold, or at least 100-fold, or at least 120-fold less than the EC50 value of the intact chimeric polypeptide assembly composition.

In some cases, the binding affinity of the first binding domain of the released first portion to the tumor specific marker is greater compared to the binding affinity of the second binding domain of the released first portion to the CD3 antigen. In one embodiment, the binding affinity of the first binding domain of the released first portion to the target cell, as measured by $K_d$ constant in the in vitro assay, is at least one order of magnitude greater compared to the binding affinity of the second binding domain to the CD3 antigen. In other embodiments, the binding affinity of the first binding domain of the released first portion to the target cell, as measured by $K_d$ constant in an in vitro binding assay is between $10^{-5}$ to $10^{-9}$ M and the $K_d$ of the second binding domain is between $10^{-5}$ to $10^{-9}$ M. The binding affinity can be determined by standard cell-based assays, ELISA, assays described in the Examples, herein, or in other in vitro assays known in the art.

In another aspect, the invention relates to the enhanced properties of the chimeric polypeptide assembly when administered to a subject. It is specifically contemplated that the intact chimeric polypeptide assembly compositions comprising release segments exhibit less cytotoxicity and/or reduced capacity to elicit the production of proinflammatory cytokines compared to the released first portion component. In one embodiment, the invention provides chimeric polypeptide assembly compositions wherein upon or following administration of a composition comprising the chimeric polypeptide assembly to a subject, the second portion of the assembly is cleaved in proximity to a tumor expressing a protease capable of cleaving the RS. Upon cleavage of the second portion by said mammalian protease and release of the first portion from the assembly, the first portion is capable of concurrently binding to a T cell bearing the human CD3 antigen and to a tumor cell bearing the tumor specific marker in the subject. In one embodiment, the concurrent binding of the released first portion to a T cell bearing the CD3 antigen and the tumor cell bearing the tumor cell marker results in the release of T cell-derived effector molecules. In the foregoing, the effector molecule is selected from one or more effector molecules of the group consisting of TNF-α, IFN-γ, interleukin 2, perforin, and granzymes, or other T cell effector molecules known in the art. As a consequence of the concurrent binding of the effector cell and the target cell, an immunological synapse is created, which effects lysis of the target cell by the T cell and the effector molecules.

In another aspect, the invention relates to chimeric polypeptide assembly compositions with increased terminal half-life and other properties imparted by the bulking moiety; e.g., XTEN. In one embodiment, the invention provides chimeric polypeptide assembly compositions wherein the intact composition exhibits a half-life upon or following administration to a subject that is at least 2-fold, 3-fold, 4-fold, 5-fold, 6-fold, 7-fold, 8-fold, 9-fold, or 10-fold greater compared to the half-life of the first portion not linked to said second and third portions upon or following administration to a subject at a comparable dose. In another embodiment, upon or following administration of the chimeric polypeptide assembly to a subject and cleavage of the second portion and release of said first portion and said third portion from said chimeric polypeptide assembly, said first portion has a half-life that is at least 2-fold, 3-fold, 4-fold, 5-fold, 6-fold, 7-fold, 8-fold, 9-fold, or 10-fold less compared to the intact chimeric polypeptide assembly in the subject. In a related embodiment, the plasma Cmax concentration of the released first portion upon or following a single administration of the chimeric polypeptide composition to the subject does not exceed about 0.01 ng/ml, or about 0.1 ng/ml, or about 1 ng/ml, or about 10 ng/ml, or about 100 ng/ml. In another related embodiment, the plasma Cmax concentration of the released first portion upon or following a single administration of the intact chimeric polypeptide composition to the subject is at least 3-fold lower, or at least 10-fold lower, or at least 30-fold lower, or at least 100-fold lower than the plasma Cmax concentration of the intact chimeric polypeptide assembly in the same subject. Pharmacokinetic parameters can be measured using plasma samples from a subject being administered with the subject chimeric polypeptide assembly using methods described herein or conventional methods known in the art. In another embodiment, upon or following administration to a subject, the intact chimeric polypeptide assembly exhibits reduced extravasation from the blood circulatory system in the subject compared to the chimeric polypeptide assembly in which the RS is cleaved, releasing the first portion and the third portion. In the foregoing embodiments of this paragraph, the subject can be mouse, rat, monkey, dog, and human.

In another aspect, the invention relates to pharmaceutical compositions of the chimeric polypeptide assembly. In one embodiment, the invention provides pharmaceutical compositions comprising the chimeric polypeptide assembly of any of the chimeric polypeptide assembly disclosed herein, and one or more pharmaceutically suitable excipients and, optionally, one or more carriers or stabilizers. In another embodiment, the pharmaceutical composition is formulated for intradermal, subcutaneous, intravenous, intra-arterial, intraabdominal, intraperitoneal, intrathecal, or intramuscular administration. In another embodiment, the pharmaceutical composition is in a liquid form. In a related embodiment, the pharmaceutical composition in a liquid form is supplied in a pre-filled syringe for a single injection. In other embodiments, the pharmaceutical composition is formulated as a lyophilized powder to be reconstituted prior to administration.

In another aspect, the invention relates to methods and uses of the chimeric polypeptide assembly or a pharmaceutical composition comprising the chimeric polypeptide assembly. In one embodiment, the invention provides a chimeric polypeptide assembly or a pharmaceutical composition comprising the chimeric polypeptide assembly for the preparation of a medicament for the treatment of a disease in a subject. In a related embodiment, the medicament is used in a disease, wherein the disease is selected from the group consisting of carcinoma, Hodgkin's lymphoma, and non-Hodgkin's lymphoma, diffuse large B cell lymphoma, follicular lymphoma, mantle cell lymphoma, blastoma, breast cancer, ER/PR+ breast cancer, Her2+ breast cancer, triple-negative breast cancer, colon cancer, colon cancer with malignant ascites, mucinous tumors, prostate cancer, head and neck cancer, skin cancer, melanoma, genito-urinary tract cancer, ovarian cancer, ovarian cancer with malignant ascites, peritoneal carcinomatosis, uterine serous carcinoma, endometrial cancer, cervix cancer, colorectal, uterine cancer, mesothelioma in the peritoneum, kidney cancer, Wilm's tumor, lung cancer, small-cell lung cancer, non-small cell lung cancer, gastric cancer, stomach cancer, small intestine cancer, liver cancer, hepatocarcinoma, hepatoblastoma, liposarcoma, pancreatic cancer, gall bladder cancer, cancers of the bile duct, esophageal cancer, salivary gland carcinoma, thyroid cancer, epithelial cancer, arrhenoblastoma, adenocarcinoma, sarcoma, and B-cell derived chronic lymphatic leukemia.

In another aspect, the invention relates to chimeric polypeptide assembly or a pharmaceutical composition comprising the chimeric polypeptide assembly for use in a method of treating a disease in a subject, wherein the method comprises administering the chimeric polypeptide assembly or the pharmaceutical composition to a subject with the disease, including but not limited to cancer. Where desired, the method comprises administering to the subject in need thereof a therapeutically effective dose of a pharmaceutical composition comprising the chimeric polypeptide assembly and one or more excipients. In one embodiment of the method of treatment, the disease is selected from the group consisting of carcinomas, Hodgkin's lymphoma, non-Hodgkin's lymphoma, B cell lymphoma, T-cell lymphoma, follicular lymphoma, mantle cell lymphoma, blastoma, breast cancer, colon cancer, prostate cancer, head and neck cancer, any form of skin cancer, melanoma, genito-urinary tract cancer, ovarian cancer, ovarian cancer with malignant ascites, peritoneal carcinomatosis, uterine serous carcinoma, endometrial cancer, cervical cancer, colorectal cancer, an epithelia intraperitoneal malignancy with malignant ascites, uterine cancer, mesothelioma in the peritoneum kidney cancers, lung cancer, small-cell lung cancer, non-small cell lung cancer, gastric cancer, esophageal cancer, stomach cancer, small intestine cancer, liver cancer, hepatocarcinoma, hepatoblastoma, liposarcoma, pancreatic cancer, gall bladder cancer, cancers of the bile duct, salivary gland carcinoma, thyroid cancer, epithelial cancer, adenocarcinoma, sarcomas of any origin, primary hematologic malignancies including acute or chronic lymphocytic leukemias, acute or chronic myelogenous leukemias, myeloproliferative neoplastic disorders, or myelodysplastic disorders, myasthenia gravis, Morbus Basedow, Hashimoto thyroiditis, or Goodpasture syndrome. In another embodiment of the method of treatment, the pharmaceutical composition is administered to the subject as one or more therapeutically effective doses administered twice weekly, once a week, every two weeks, every three weeks, or monthly. In another embodiment of the method of treatment, the pharmaceutical composition is administered to the subject as one or more doses over a period of at least two weeks, or at least one month, or at least two months, or at least three months, or at least four months, or at least five months, or at least six months. In another embodiment of the method of treatment, the dose is administered intradermally, subcutaneously, intravenously, intra-arterially, intra-abdominally, intraperitoneally, intrathecally, or intramuscularly. In another embodiment of the method of treatment, the dose is administered as a bolus dose or by infusion of 5 minutes to 96 hours as tolerated for maximal safety and efficacy. In another embodiment of the method of treatment, the dose is selected from the group consisting of at least about 0.005 mg/kg, at least about 0.01 mg/kg, at least about 0.02 mg/kg, at least about 0.04 mg/kg, at least about 0.08 mg/kg, at least about 0.1 mg/kg, at least about 0.12 mg/kg, at least about 0.14 mg/kg, at least about 0.16 mg/kg, at least about 0.18 mg/kg, at least about 0.20 mg/kg, at least about 0.22 mg/kg, at least about 0.24 mg/kg, at least about 0.26 mg/kg, at least about 0.27 mg/kg, at least about 0.28 mg/kg, at least 0.3 mg/kg, at least 0.4. mg/kg, at least about 0.5 mg/kg, at least about 0.6 mg/kg, at least about 0.7 mg/kg, at least about 0.8 mg/kg, at least about 0.9 mg/kg, at least about 1.0 mg/kg, at least about 1.5 mg/kg, or at least about 2.0 mg/kg. In another embodiment of the method of treatment, the initial dose is selected from the group consisting of at least about 0.005 mg/kg, at least about 0.01 mg/kg, at least about 0.02 mg/kg, at least about 0.04 mg/kg, at least about 0.08 mg/kg, at least about 0.1 mg/kg, and a subsequent dose is selected from the group consisting of at least about 0.1 mg/kg, at least about 0.12 mg/kg, at least about 0.14 mg/kg, at least about 0.16 mg/kg, at least about 0.18 mg/kg, at least about 0.20 mg/kg, at least about 0.22 mg/kg, at least about 0.24 mg/kg, at least about 0.26 mg/kg, at least about 0.27 mg/kg, at least about 0.28 mg/kg, at least 0.3 mg/kg, at least 0.4. mg/kg, at least about 0.5 mg/kg, at least about 0.6 mg/kg, at least about 0.7 mg/kg, at least about 0.8 mg/kg, at least about 0.9 mg/kg, at least about 1.0 mg/kg, at least about 1.5 mg/kg, or at least about 2.0 mg/kg. In another embodiment of the method of treatment, the administration of the therapeutically effective dose of the pharmaceutical composition to the subject results in a plasma concentration of the chimeric polypeptide assembly of at least about 0.1 ng/mL to at least about 2 ng/mL or more in the subject for at least about 3 days, at least about 7 days, at least about 10 days, at least about 14 days, or at least about 21 days.

In another embodiments, the invention provides a pharmaceutical composition for use in a method for the treatment of a disease, the method comprising administering the pharmaceutical composition to a subject with the disease according to a treatment regimen comprising one or more consecutive doses using a therapeutically effective dose. In one embodiment of the pharmaceutical composition for the use in the method for the treatment of a disease, the disease is selected from the group consisting of carcinomas, Hodgkin's lymphoma, non-Hodgkin's lymphoma, B cell lymphoma, T-cell lymphoma, follicular lymphoma, mantle cell lymphoma, blastoma, breast cancer, colon cancer, prostate cancer, head and neck cancer, any form of skin cancer, melanoma, genito-urinary tract cancer, ovarian cancer, ovarian cancer with malignant ascites, peritoneal carcinomatosis, uterine serous carcinoma, endometrial cancer, cervical cancer, colorectal cancer, an epithelia intraperitoneal malignancy with malignant ascites, uterine cancer, mesothelioma in the peritoneum kidney cancers, lung cancer, small-cell lung cancer, non-small cell lung cancer, gastric cancer, esophageal cancer, stomach cancer, small intestine cancer, liver cancer, hepatocarcinoma, hepatoblastoma, liposarcoma, pancreatic cancer, gall bladder cancer, cancers of the bile duct, salivary gland carcinoma, thyroid cancer, epithelial cancer, adenocarcinoma, sarcomas of any origin, primary hematologic malignancies including acute or chronic lymphocytic leukemias, acute or chronic myelogenous leukemias, myeloproliferative neoplastic disorders, or myelodysplastic disorders, myasthenia gravis, Morbus Basedow, Hashimoto thyroiditis, or Goodpasture syndrome. In another embodiment of the pharmaceutical composition for the use in the treatment of a disease, the treatment regimen is part of a specified treatment cycle, wherein the specified treatment cycle comprises administration of the pharmaceutical composition twice a week, every week, every 10 days, every two weeks, every three weeks, or every month per each treatment cycle. In one embodiment, the treatment regimen results in the improvement of a clinical parameter or endpoint associated with the disease in the subject, wherein the clinical parameter or endpoint is selected from one or any combination of the group consisting of tumor shrinkage as a complete, partial or incomplete response; time-to-progression, time to treatment failure, biomarker response; progression-free survival; disease free-survival; time to recurrence; time to metastasis; time of overall survival; improvement of quality of life; and improvement of symptoms. In the foregoing embodiments of the method, the subject is selected from the group consisting of mouse, rat, monkey, and human.

In another aspect, the invention relates to kits comprising the pharmaceutical composition. In one embodiment, the invention provides a kit comprising the pharmaceutical composition of any one of embodiments disclosed herein, a container and a label or package insert on or associated with the container. In another embodiment, the invention provides a kit comprising a pre-filled syringe containing the pharmaceutical composition of any one of embodiments disclosed herein, and a label or package insert on or associated with the syringe.

In another aspect, the invention relates to the differential characteristics and effects of the intact versus the cleaved chimeric polypeptide assembly compositions. In one embodiment, the invention provides a chimeric polypeptide assembly of any of the embodiments disclosed herein, wherein the chimeric polypeptide assembly that is intact has at least a 10-fold, or at least 20-fold, or at least 30-fold, or at least 40-fold, or at least 50-fold, or at least 60-fold, or at least 70-fold, or at least 80-fold, or at least 90-fold, or at least 100-fold, or at least 1000-fold lower potential to effect production of a Th1 cytokine from an effector cell compared to the corresponding first portion of the assembly that is not linked to the assembly, when said assembly is in contact with the effector cell and a target cell. In one embodiment, the production of the Th1 cytokine is assayed in an in vitro assay comprising PBMC or CD3+ T cells and target cells having a tumor specific marker antigen selected from the group consisting of alpha 4 integrin, Ang2, B7-H3, B7-H6, CEACAM5, cMET, CTLA4, FOLR1, EpCAM, CCR5, CD19, HER2, HER2 neu, HER3, HER4, HER1 (EGFR), PD-L1, PSMA, CEA, MUC1(mucin), MUC-2, MUC3, MUC4, MUC5AC, MUC5B, MUC7, MUC16 βhCG, Lewis-Y, CD20, CD33, CD38, CD30, CD56 (NCAM), CD133, ganglioside GD3; 9-O-Acetyl-GD3, GM2, Globo H, fucosyl GM1, GD2, carbonicanhydrase IX, CD44v6, Sonic Hedgehog (Shh), Wue-1, plasma cell antigen 1, melanoma chondroitin sulfate proteoglycan (MCSP), CCR8, 6-transmembrane epithelial antigen of prostate (STEAP), mesothelin, A33 antigen, prostate stem cell antigen (PSCA), Ly-6, desmoglein 4, fetal acetylcholine receptor (fnAChR), CD25, cancer antigen 19-9 (CA19-9), cancer antigen 125 (CA-125), Muellerian inhibitory substance receptor type II (MISIIR), sialylated Tn antigen (s TN), fibroblast activation antigen (FAP), endosialin (CD248), epidermal growth factor receptor variant III (EGFRvIII), tumor-associated antigen L6 (TAL6), SAS, CD63, TAG72, Thomsen-Friedenreich antigen (TF-antigen), insulin-like growth factor I receptor (IGF-IR), Cora antigen, CD7, CD22, CD70, CD79a, CD79b, G250, MT-MMPs, F19 antigen, CA19-9, CA-125, alpha-fetoprotein (AFP), VEGFR1, VEGFR2, DLK1, SP17, ROR1, and EphA2. In the foregoing embodiment, the Th1 cytokine is selected from the group consisting of IL-2, TNF-alpha, and IFN-gamma. In another embodiment, the production of the Th1 cytokine is assayed using blood or a fluid sample from a subject administered the chimeric polypeptide assembly compared to a subject administered the corresponding first portion not linked to the chimeric polypeptide assembly, with the result that the chimeric polypeptide assembly that is intact has at least a 10-fold, or at least 20-fold, or at least 30-fold, or at least 40-fold, or at least 50-fold, or at least 60-fold, or at least 70-fold, or at least 80-fold, or at least 90-fold, or at least 100-fold, or at least 1000-fold lower potential to effect production of the Th1 cytokine. In the foregoing embodiment, the subject is selected from the group consisting of mouse, rat, monkey, and human.

In other cases, the chimeric polypeptide assembly of any of the embodiments disclosed herein exhibits the characteristic that the chimeric polypeptide assembly that is intact has at least a 10-fold, or at least 20-fold, or at least 30-fold, or at least 40-fold, or at least 50-fold, or at least 60-fold, or at least 70-fold, or at least 80-fold, or at least 90-fold, or at least 100-fold lower potential to extravasate from the circulation when administered to a subject compared to the first portion not linked to the chimeric polypeptide assembly when administered at a comparable dose to a subject.

In another aspect, the invention relates to nucleic acids encoding the subject compositions. In one embodiment, the invention provides an isolated nucleic acid comprising a polynucleotide sequence selected from (a) a polynucleotide encoding the chimeric polypeptide assembly of any one of the embodiments disclosed herein, or (b) the complement of the polynucleotide of (a). In another embodiment, the invention provides an isolated nucleic acid comprising a polynucleotide sequence with at least 90%, 91%, 92%, 93%, 94%, 95%, 96%, 97%, 98%, 99%, or 100% sequence identity to a polynucleotide sequence set forth in Table 10 or Table 14. In another embodiment, the invention provides an expression vector comprising a polynucleotide sequence of the foregoing embodiments and a recombinant regulatory sequence operably linked to the polynucleotide sequence. In another embodiment, the invention provides an isolated host cell, comprising the foregoing expression vector. In one embodiment, the host cell is *E. coli*.

In another aspect, the invention relates to T cell binding compositions and nucleic acids that encode them. In one embodiment, the invention provides a monomeric fusion protein comprising an amino acid sequence having at least 90%, 91%, 92%, 93%, 94%, 95%, 96%, 97%, 98%, 99%, or 100% sequence identity to an amino acid sequence selected from the group consisting of the amino acid sequences set forth in Table 7, wherein the monomeric fusion protein exhibits binding affinity to a CD3 antigen of a T cell. In another embodiment, the invention provides an isolated nucleic acid comprising a polynucleotide sequence selected from (a) a polynucleotide encoding the fusion protein of the foregoing T cell binding composition, (b) a polynucleotide sequence having at least 90%, 91%, 92%, 93%, 94%, 95%, 96%, 97%, 98%, 99%, or 100% sequence identity to a polynucleotide sequence selected from the group consisting of the polynucleotide sequences set forth in Table 7; or (c) the complement of the polynucleotide of (a) or (b).

In another embodiment, the invention provides a method of use of the nucleic acid encoding the fusion protein of the foregoing T cell binding composition in a method of making a polynucleotide sequence encoding the chimeric polypeptide assembly of any one of the chimeric polypeptide assembly embodiments disclosed herein, the method comprising operably linking a polynucleotide sequence encoding a scFv with binding affinity to a target cell marker disclosed herein or selected from the group of targets set forth in Table 2, in frame to a polynucleotide encoding the fusion protein of the foregoing disclosed T cell binding composition. In another embodiment, the invention provides an expression vector comprising the foregoing polynucleotide sequence and a recombinant regulatory sequence operably linked to the polynucleotide sequence. The invention also provides an isolated host cell, comprising the expression vector, wherein the host cell is *E. coli*.

In yet another aspect, the invention relates to methods of producing the chimeric polypeptide assembly embodiments disclosed herein. In one embodiment, the invention provides a method of producing a chimeric polypeptide assembly disclosed herein, the method comprising transforming a host cell with an expression vector encoding the chimeric polypeptide assembly, culturing the host cell under conditions permitting the chimeric polypeptide assembly to be expressed in the transformed host cell, and isolating the chimeric polypeptide assembly as a soluble fusion protein. In some embodiments, at least 70%, or at least 80%, or at least 90%, or at least 95%, or at least 97%, or at least 99% of the first and the second binding domains of the expressed fusion protein are correctly folded.

In other cases, the invention provides methods of inducing death of a target cell. The method typically comprises contacting said target cell with a chimeric polypeptide assembly of an embodiment disclosed herein and an effector cell. In an embodiment, the contact results in an effect in the target cell including but not limited to loss of membrane integrity, pyknosis, karyorrhexis, inducement of the intrinsic pathway of apoptosis, inducement of the extrinsic pathway of apoptosis, apoptosis, cell lysis, and cell death.

Cytotoxicity resulting in cell death (e.g., necrosis or apoptosis) can be determined by any suitable method, including, but not limited to, counting cells before and after treatment, or measuring the level of a marker associated with live or dead cells. Degree of cell death may be determined by any suitable method. In some embodiments, degree of cell death is determined with respect to a starting condition. For example, an individual may have a known starting amount of target cells, such as a starting cell mass or tumor of known size or circulating target cells at a known concentration. In another example, one can compare degree of cell death induced by one composition with respect to another (e.g. chimeric polypeptide assembly linked to a bulking moiety and a chimeric polypeptide assembly not linked to a bulking moiety). In such cases, degree of cell death may be expressed as a ratio of surviving cells after treatment to the starting cell population. In some embodiments, degree of cell death may be determined by a suitable cell death assay. In some embodiment, degree of cell death may be determined by measurement of tumor size over time. A variety of cell death assays are available, and may utilize a variety of detection methodologies. Examples of detection methodologies include, without limitation, the use of cell staining, microscopy, flow cytometry, cell sorting, and combinations of these. Further non-limiting examples of cell death assays are described in WO2011131472A1 and US20130052160, which is incorporated herein by reference.

In one embodiment of the foregoing, the method is employed in an in vitro cell-based assay comprising a mixed population of the target cells and the effector cells, and an effective amount of the chimeric polypeptide assembly having binding affinity for antigens of the target cell and the effector cell. In the assay, the target cell expresses a tumor specific marker antigen including but not limited to alpha 4 integrin, Ang2, B7-H3, B7-H6, CEACAM5, cMET, CTLA4, FOLR1, EpCAM, CCR5, CD19, HER2, HER2 neu, HER3, HER4, HER1 (EGFR), PD-L1, PSMA, CEA, MUC1(mucin), MUC-2, MUC3, MUC4, MUC5AC, MUC5B, MUC7, MUC1613hCG, Lewis-Y, CD20, CD33, CD38, CD30, CD56 (NCAM), CD133, ganglioside GD3; 9-O-Acetyl-GD3, GM2, Globo H, fucosyl GM1, GD2, carbonicanhydrase IX, CD44v6, Sonic Hedgehog (Shh), Wue-1, plasma cell antigen 1, melanoma chondroitin sulfate proteoglycan (MCSP), CCR8, 6-transmembrane epithelial antigen of prostate (STEAP), mesothelin, A33 antigen, prostate stem cell antigen (PSCA), Ly-6, desmoglein 4, fetal acetylcholine receptor (fnAChR), CD25, cancer antigen 19-9 (CA19-9), cancer antigen 125 (CA-125), Muellerian inhibitory substance receptor type II (MISIIR), sialylated Tn antigen (s TN), fibroblast activation antigen (FAP), endosialin (CD248), epidermal growth factor receptor variant III (EGFRvIII), tumor-associated antigen L6 (TAL6), SAS, CD63, TAG72, Thomsen-Friedenreich antigen (TF-antigen), insulin-like growth factor I receptor (IGF-IR), Cora antigen, CD7, CD22, CD70, CD79a, CD79b, G250, MT-MMPs, F19 antigen, CA19-9, CA-125, alpha-fetoprotein (AFP), VEGFR1, VEGFR2, DLK1, SP17, ROR1, and EphA2 and the effector cell is a is T cell wherein the effector cell antigen is CD3. In other embodiments, the method of inducing death of a target cell is employed in a subject having a cancer comprising a population of the target cell, wherein the method comprises administering a therapeutically effective amount of the chimeric polypeptide assembly to the subject. In one embodiment of the foregoing, the method comprises administering the chimeric polypeptide assembly as one or more consecutively administered therapeutically effective doses of a pharmaceutical composition comprising the chimeric polypeptide assembly and one or more excipients. In another embodiment of the foregoing, the method comprises a regimen of determining the amount of a pharmaceutical composition needed to achieve a therapeutic effect in the subject having the cancer and administering the amount as one or more consecutively doses to the subject. In the methods of inducing death of a target cell in a subject, wherein the target cell is a cancer cell, where the cancer can be carcinoma, Hodgkin's lymphoma, and non-Hodgkin's lymphoma, diffuse large B cell lymphoma, follicular lymphoma, mantle cell lymphoma, blastoma, breast cancer, ER/PR+ breast cancer, Her2+ breast cancer, triple-negative breast cancer, colon cancer, colon cancer with malignant ascites, mucinous tumors, prostate cancer, head and neck cancer, skin cancer, melanoma, genito-urinary tract cancer, ovarian cancer, ovarian cancer with malignant ascites, peritoneal carcinomatosis, uterine serous carcinoma, endometrial cancer, cervix cancer, colorectal, uterine cancer, mesothelioma in the peritoneum, kidney cancer, Wilm's tumor, lung cancer, small-cell lung cancer, non-small cell lung cancer, gastric cancer, stomach cancer, small intestine cancer, liver cancer, hepatocarcinoma, hepatoblastoma, liposarcoma, pancreatic cancer, gall bladder cancer, cancers of the bile duct, esophageal cancer, salivary gland carcinoma, thyroid cancer, epithelial cancer, arrhenoblastoma, adenocarcinoma, sarcoma, and B-cell derived chronic lymphatic leukemia. By use of the inventive method in the subject with a cancer, the method results in an improvement of a clinical parameter or endpoint wherein the clinical parameter or endpoint can be overall survival, symptom endpoints, disease-free survival, objective response rate, complete response, duration of response, progression-free survival, time to progression, time-to-treatment failure, tumor measurement, tumor size, tumor response rate, time to metastasis, and biomarker concentration. In other cases, use of the inventive method in the subject with a cancer results in a reduction in the frequency, duration, or severity in diagnostically associated side effects in the subject compared to administration of a comparable dose, in mmoles/kg, to a comparable subject of a composition comprising the first portion and an absence the second portion and third portion of the chimeric polypeptide assembly, wherein the side effects can be one or more of the following: increased plasma levels of IL-2, increased plasma levels of TNF-alpha, increased plasma levels of IFN-gamma, sepsis, febrile neutropenia, neurotoxicity, convulsions, encephalopathy, cytokine release syndrome, speech disturbance, equilibrium disturbance, fever, headache, confusion, hypotension, neutropenia, nausea, impaired consciousness, disorientation, and increased liver enzymes.

In still other cases, the invention provides methods of delivering a therapeutic agent to a tumor cell comprising a tumor specific marker, the method comprising administering to the target cell the chimeric polypeptide assembly of any one of the embodiments disclosed herein, wherein the therapeutic agent is delivered to the target cell via the first binding domain of the first portion specifically binding to the tumor specific marker. In the foregoing, the tumor specific marker is selected from the group consisting of alpha 4 integrin, Ang2, B7-H3, B7-H6, CEACAM5, cMET, CTLA4, FOLR1, EpCAM, CCR5, CD19, HER2, HER2 neu, HER3, HER4, HER1 (EGFR), PD-L1, PSMA, CEA, MUC1(mucin), MUC-2, MUC3, MUC4, MUC5AC, MUC5B, MUC7, MUC1613hCG, Lewis-Y, CD20, CD33, CD38, CD30, CD56 (NCAM), CD133, ganglioside GD3; 9-O-Acetyl-GD3, GM2, Globo H, fucosyl GM1, GD2, carbonicanhydrase IX, CD44v6, Sonic Hedgehog (Shh), Wue-1, plasma cell antigen 1, melanoma chondroitin sulfate proteoglycan (MCSP), CCR8, 6-transmembrane epithelial antigen of prostate (STEAP), mesothelin, A33 antigen, prostate stem cell antigen (PSCA), Ly-6, desmoglein 4, fetal acetylcholine receptor (fnAChR), CD25, cancer antigen 19-9 (CA19-9), cancer antigen 125 (CA-125), Muellerian inhibitory substance receptor type II (MISIIR), sialylated Tn antigen (s TN), fibroblast activation antigen (FAP), endosialin (CD248), epidermal growth factor receptor variant III (EGFRvIII), tumor-associated antigen L6 (TAL6), SAS, CD63, TAG72, Thomsen-Friedenreich antigen (TF-antigen), insulin-like growth factor I receptor (IGF-IR), Cora antigen, CD7, CD22, CD70, CD79a, CD79b, G250, MT-MMPs, F19 antigen, CA19-9, CA-125, alpha-fetoprotein (AFP), VEGFR1, VEGFR2, DLK1, SP17, ROR1, and EphA2. Where desired, the tumor specific marker is selected from the group consisting of Alpha 4 Integrin, Ang2, CEACAM5, CD19, CD20, CD33, CD38, cMET, CTLA4, EpCAM, EphA2, FOLR1, HER1(EGFR), HER2, HER3, HER1 (EGFR)/HER3, HER2/3, Mesothelin, MUC1, PD-L1, PSMA, TAG-72, VEGFR1, VEGFR2. In one embodiment of the method, the chimeric polypeptide assembly comprises an amino acid sequence having at least 90%, or at least 91%, or at least 92%, or at least 93%, or at least 94%, or at least 95%, or at least 96%, or at least 97%, or at least 98%, or at least 99%, or at least 100% sequence identity to a polypeptide sequence selected from the group consisting of the sequences of Table 12. In another embodiment of the method, the chimeric polypeptide assembly comprises an amino acid sequence having at least 90%, or at least 91%, or at least 92%, or at least 93%, or at least 94%, or at least 95%, or at least 96%, or at least 97%, or at least 98%, or at least 99%, or at least 100% sequence identity to a polypeptide sequence selected from the group consisting of the sequences set forth in FIG. 36 or FIG. 37. In an embodiment of the foregoing methods, the tumor cell resides in a tumor in a subject, wherein the subject can be mouse, rat, monkey, dog, and human.

In another aspect, the invention relates to physical characteristics of the chimeric polypeptide assembly compositions and resulting properties when administered to a subject. With respect to the chimeric polypeptide assembly embodiments disclosed herein, neither the second portion nor the third portion of the chimeric polypeptide assembly has specific binding affinity for the first portion. For each chimeric polypeptide assembly embodiments disclosed herein, the first portion accounts for less than 50% of the molecular weight of the intact chimeric polypeptide assembly. In another embodiment, the first portion of the chimeric polypeptide assembly embodiments disclosed herein accounts for less than 30%, or less than 40%, or less than 50% of the apparent molecular weight factor of the chimeric polypeptide assembly, when apparent molecular weight factor is assessed by size exclusion chromatography. Further, upon cleavage of the second portion and release of said first portion and said third portion from any of the chimeric polypeptide assembly embodiments disclosed herein, the hydrodynamic radius of the released first portion is less than about 30%, or less than about 40%, or less than about 50% of the hydrodynamic radius of the intact chimeric polypeptide assembly, when hydrodynamic radius is assessed by size exclusion chromatography. In one embodiment, the invention provides a chimeric polypeptide assembly, wherein upon cleavage of the second portion and release of said first portion and said third portion from said chimeric polypeptide assembly, the hydrodynamic radius of the released first portion is less than about 5 nm, or less than about 4 nm, or less than about 3 nm when hydrodynamic radius is determined by size exclusion chromatography. Accordingly, the released first portion has greater ability to penetrate a tumor tissue compared to an intact chimeric polypeptide assembly. In another embodiment, the hydrodynamic radius of an intact chimeric polypeptide assembly disclosed herein is greater than about 8 nm, or greater than about 9 nm, or greater than about 10 nm when hydrodynamic radius is determined by size exclusion chromatography. Accordingly, an intact chimeric polypeptide assembly administered to a subject with a tumor is less able to extravasate from vasculature of normal tissue of the subject compared to the ability to extravasate from vasculature of the tumor.

It is specifically contemplated that the chimeric polypeptide assembly composition embodiments can exhibit one or more or any combination of the properties disclosed herein. It is further specifically contemplated that the methods of treatment can exhibit one or more or any combination of the properties disclosed herein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The features and advantages of the invention may be further explained by reference to the following detailed description and accompanying drawings that sets forth illustrative embodiments

FIG. 3 shows the uncleaved "pro" form in FIG. 3A and the cleaved form in FIG. 3B in which the uncleaved form is depicted in proximity to an effector cell and a tumor associated cell, each with cell-surface antigens; however the uncleaved form in FIG. 3A is unable to concurrently bind the two cells because of the steric hindrance and shielding effects of the bulking moiety on the targeting (or binding) domains, while the cleaved form in FIG. 3B, with the released targeting domains, permits the concurrent binding of the two cells and allows and immune activation by the effector cell against the target tumor associated cell.

FIG. 8 shows schematic representations of two configurations of the ProTIA compositions in which the RS and bulking moiety is linked either to the effector cell binding moiety (on the left) or the tumor antigen binding moiety (on the right).

FIG. 9 shows schematic representations of configurations of the ProTIA compositions in which two Release Segments and two bulking moieties are linked to the binding moieties.

FIG. 14 shows the purification of uncleaved AC1278 from fermentation media, as described in Example 2.

FIG. 15 shows the lot release analytics of uncleaved AC1278, as described in Example 2.

FIG. 16 shows the preparation of cleaved ProTIA-A using uncleaved AC1278, as described in Example 2.

FIG. 17 shows the lot release analytics of cleaved AC1278, as described in Example 2.

FIG. 18 shows the purification of uncleaved AC1476 from fermentation media, as described in Example 3.

FIG. 19 shows the lot release analytics of uncleaved AC1476 as described in Example 3.

FIG. 20 shows additional lot release analytics of uncleaved AC1476 as described in Example 3.

FIG. 21 shows the preparation of cleaved ProTIA-A using uncleaved AC1476 as described in Example 3.

FIG. 22 shows the lot release analytics of cleaved AC1476 as described in Example 3.

FIG. 23 shows the additional lot release analytics of cleaved AC1476 as described in Example 3.

FIG. 29 shows schematic representations of the alternate N- to C-terminus configurations of a T-cell binding composition. FIG. 29A shows the configuration of the effector cell binding moiety (ECBM) followed by release site segment (RS) and XTEN while

FIG. 33 depicts results from an experiment to determine the cytokine profile of protease-treated and untreated anti-EpCAM x anti-CD3 ProTIA, as described in Example 12.

FIG. 34 depicts results from an experiment to determine the cytokine profile of protease-treated and untreated anti-EpCAM x anti-CD3 ProTIA, as described in Example 12.

FIG. 35 depicts results from an experiment to determine the cytokine profile of protease-treated and untreated anti- EpCAM x anti-CD3 ProTIA, as described in Example 12.

FIG. 36: The amino acid sequence of the AC1476 aEp-CAM-aCD3 ProTIA. Figure discloses SEQ ID NO: 533.

FIG. 37: The amino acid sequence of the AC1489 aEp-CAM-aCD3 ProTIA. Figure discloses SEQ ID NO: 534.

FIG. 42 depicts results from the experiment to measure activation of CD69 on CD8 and CD4 cells in co-culture of PBMC and SK-OV-3 cells with protease-treated, protease-untreated and protease noncleavable anti-EpCAM x anti-CD3 ProTIA, as described in Example 8. FIG. 42A depicts the activation of CD69 on CD8 cells, while

FIG. 43 depicts results from the experiment to measure activation of both CD69 and CD25 on CD8 and CD4 cells in co-culture of PBMC and SK-OV-3 cells with protease-treated, protease-untreated and protease noncleavable anti-EpCAM x anti-CD3 ProTIA, as described in Example 8. FIG. 43A depicts the activation of both CD69 and CD25 on CD8 cells, while

FIG. 44 depicts results from the experiment to measure activation of CD69 on CD8 and CD4 cells in co-culture of purified CD3+ cells and SK-OV-3 cells with protease-treated, protease-untreated and protease noncleavable anti-EpCAM x anti-CD3 ProTIA, as described in Example 8. FIG. 44A depicts the activation of CD69 on CD8 cells, while

FIG. 45 depicts results from the experiment to measure activation of both CD69 and CD25 on CD8 and CD4 cells in co-culture of purified CD3+ cells and SK-OV-3 cells with protease-treated, protease-untreated and protease noncleavable anti-EpCAM x anti-CD3 ProTIA, as described in Example 8. FIG. 45A depicts the activation of both CD69 and CD25 on CD8 cells, while

FIG. 46 depicts results from the experiment to measure activation of CD69 on CD8 and CD4 cells in co-culture of purified CD3+ cells and OVCAR3 cells with protease-treated, protease-untreated and protease noncleavable anti-EpCAM x anti-CD3 ProTIA, as described in Example 8. FIG. 46A depicts the activation of CD69 on CD8 cells, while

FIG. 47 depicts results from the experiment to measure activation of both CD69 and CD25 on CD8 and CD4 cells in co-culture of purified CD3+ cells and OVCAR3 cells with protease-treated, protease-untreated and protease noncleavable anti-EpCAM x anti-CD3 ProTIA, as described in Example 8. FIG. 47A depicts the activation of both CD69 and CD25 on CD8 cells, while

FIG. 48 depicts results from the experiment to measure activation of CD69 on CD8 and CD4 cells in co-culture of PBMC and OVCAR3 cells with protease-treated, protease-untreated and protease noncleavable anti-EpCAM x anti-CD3 ProTIA, as described in Example 8. FIG. 48A depicts the activation of CD69 on CD8 cells, while

FIG. 49 depicts results from the experiment to measure activation of both CD69 and granzyme B in CD8 and CD4 cells in co-culture of PBMC and OVCAR3 cells with protease-treated, protease-untreated and protease noncleavable anti-EpCAM x anti-CD3 ProTIA, as described in Example 8. FIG. 49A depicts the activation of both CD69 and granzyme B in CD8 cells, while

FIG. 50 depicts results from the experiment to measure release of cytokines IL-2 and IL-4 in co-culture of purified CD3+ cells and SK-OV-3 cells with protease-treated, protease-untreated and protease noncleavable anti-EpCAM x anti-CD3 ProTIA, as described in Example 15. FIG. 50A depicts the concentration of released IL-2, while

FIG. 51 depicts results from the experiment to measure release of cytokines IL-6 and IL-10 in co-culture of purified CD3+ cells and SK-OV-3 cells with protease-treated, protease-untreated and protease noncleavable anti-EpCAM x anti-CD3 ProTIA, as described in Example 15. FIG. 51A depicts the concentration of released IL-6, while

FIG. 52 depicts results from the experiment to measure release of cytokines TNF-alpha and IFN-gamma in co-culture of purified CD3+ cells and SK-OV-3 cells with protease-treated, protease-untreated and protease noncleavable anti-EpCAM x anti-CD3 ProTIA, as described in Example 15. FIG. 52A depicts the concentration of released TNF-alpha, while

DETAILED DESCRIPTION OF THE INVENTION

Figure 1:
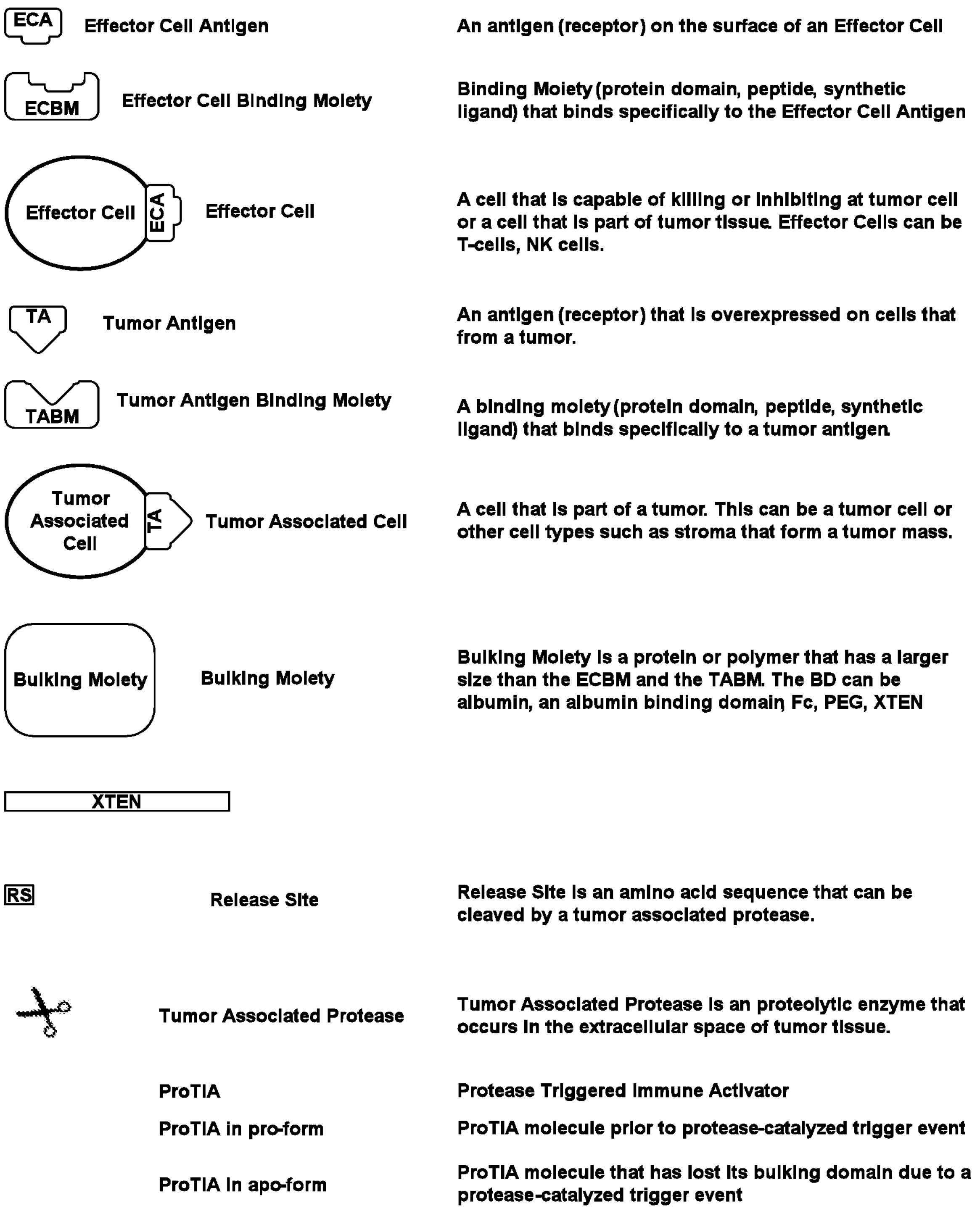
FIG. 1 depicts the various schematic figures used in various drawings, together with descriptions of what they represent.
Figure 2:
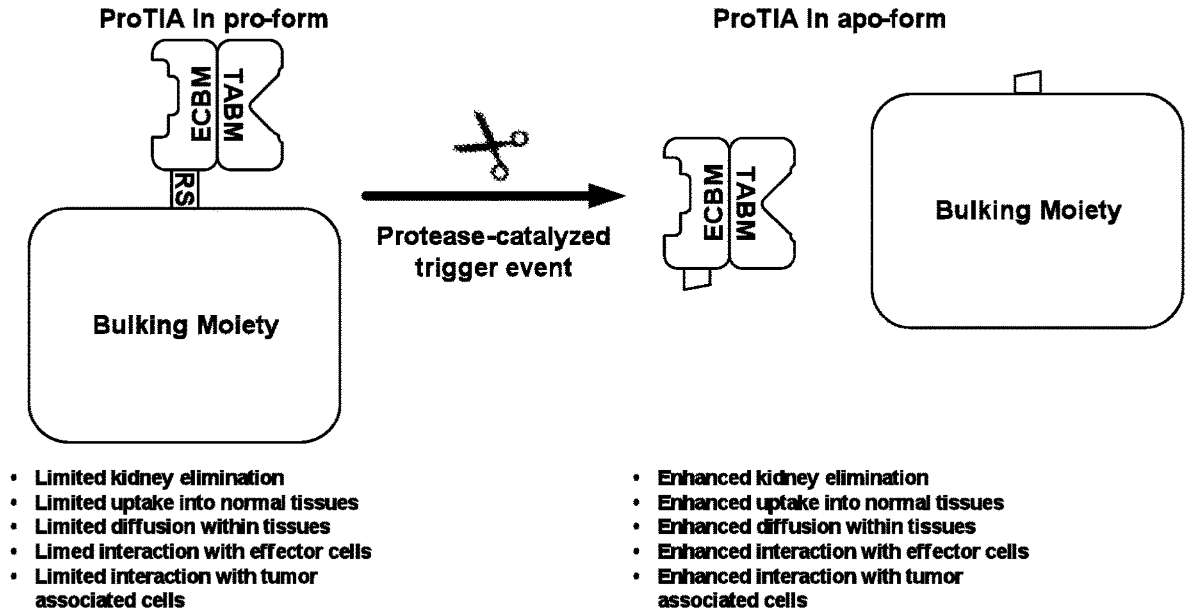
FIG. 2 depicts a ProTIA composition (also described as chimeric polypeptide assembly herein) that is in the uncleaved, "pro" form and in the cleaved state after being acted on by a tumor associated protease. The figure also describes some of the non-limiting properties of both forms of the compositions.
Figure 4:
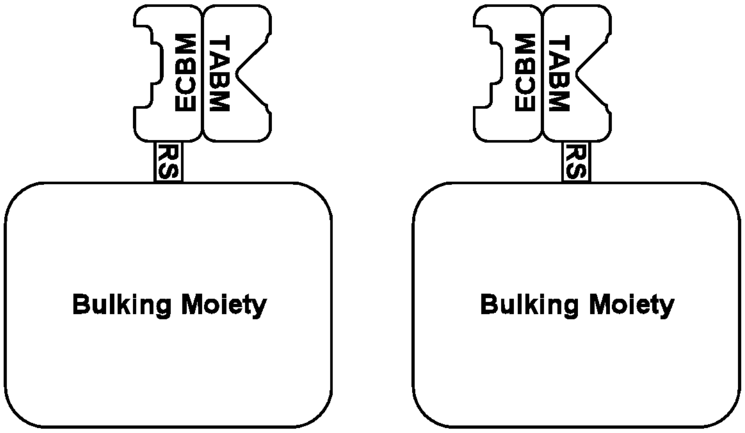
FIG. 4 shows schematic representations of two configurations of the ProTIA compositions, illustrating that the Release Segment and the bulking moiety can be attached to either the effector cell binding moiety or the tumor antigen binding moiety.
Figure 5A:
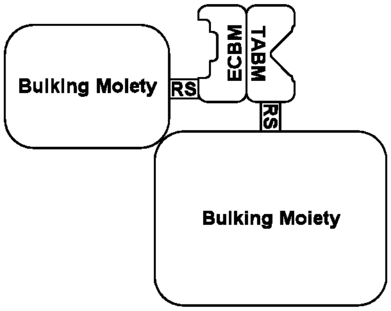
FIG. 5 shows schematic representations of two configurations of the ProTIA compositions in which two Release Segments and two bulking moieties are linked to the binding moieties. In the case of FIG. 5A, one RS and bulking moiety is linked to the effector cell binding moiety and the other RS and bulking moiety is linked to the tumor antigen binding moiety, and the composition would be in a scFv configuration. In the case of FIG. 5B, both RS and bulking moieties are attached to either the effector cell binding moiety (on the left) or the tumor antigen binding moiety (on the right), and the binding moieties would be in a diabody configuration (thus permitting the composition to be produced in recombinant form).
Figure 5B:
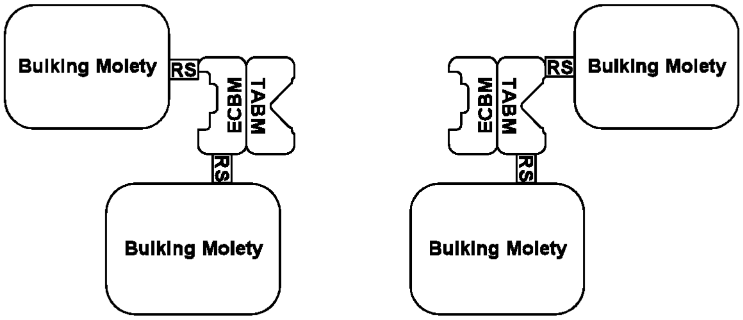
Figure 6A:
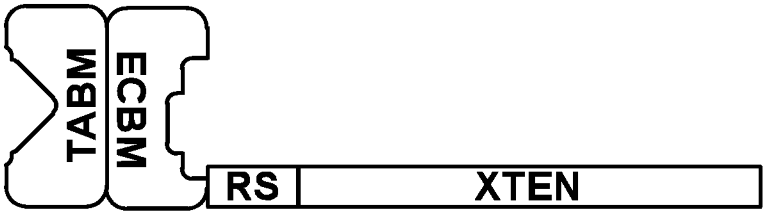
FIGS. 6A-6D shows schematic representations of two configurations of the ProTIA compositions in which the bulking moiety is an XTEN polypeptide, and the RS and bulking moiety is linked either to the effector cell binding moiety (on the left) or the RS and bulking moiety is linked to the tumor antigen binding moiety (on the right).
Figure 6B:
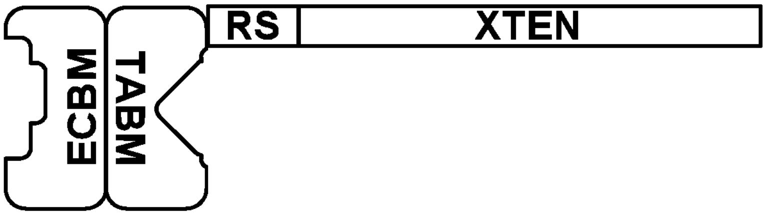
Figure 6C:
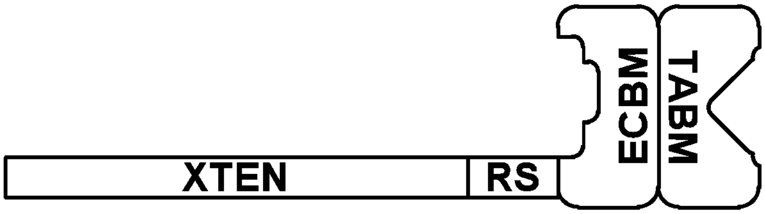
Figure 6D:
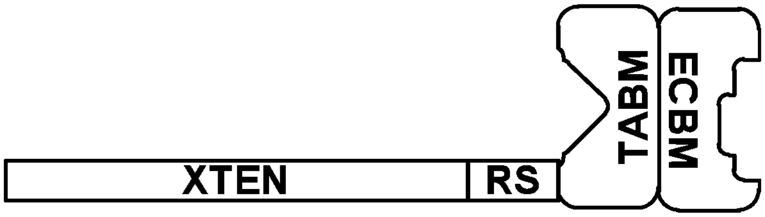
Figure 7A:
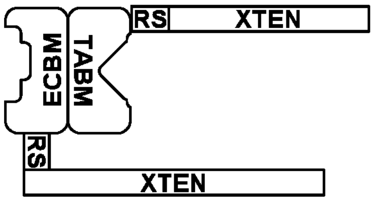
FIG. 7 shows schematic representations of two configurations of the ProTIA compositions in which two Release Segments and two XTEN are linked to the binding moieties. In the case of FIG. 7A, one RS and one XTEN is linked to the effector cell binding moiety and the other RS and bulking moiety is linked to the tumor antigen binding moiety, and the composition would be in a scFv configuration. In the case of FIG. 7B, both RS and XTEN are attached to either the effector cell binding moiety (on the right) or the tumor antigen binding moiety (on the left), and the binding moieties would be in a diabody configuration (thus permitting the composition to be produced in recombinant form).
Figure 7B:
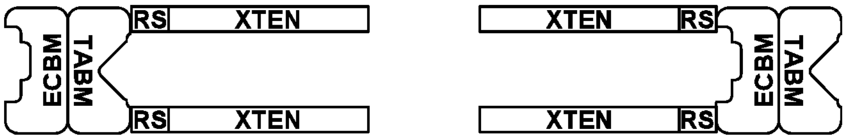
Figure 8A:
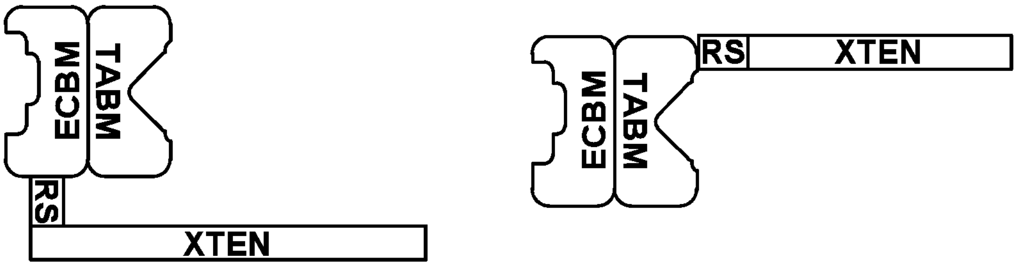
FIG. 8A depicts the binding moieties as XTEN.
Figure 8B:
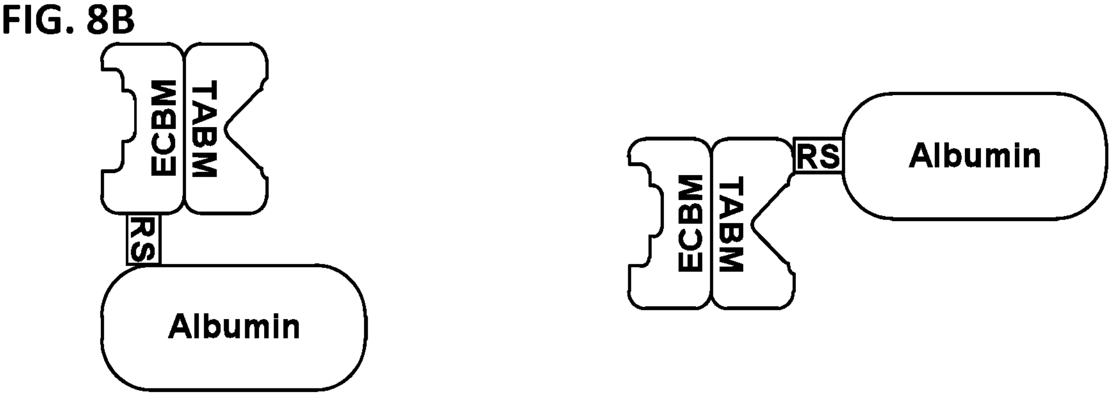
FIG. 8B depicts the binding moieties as albumin.
Figure 8C:
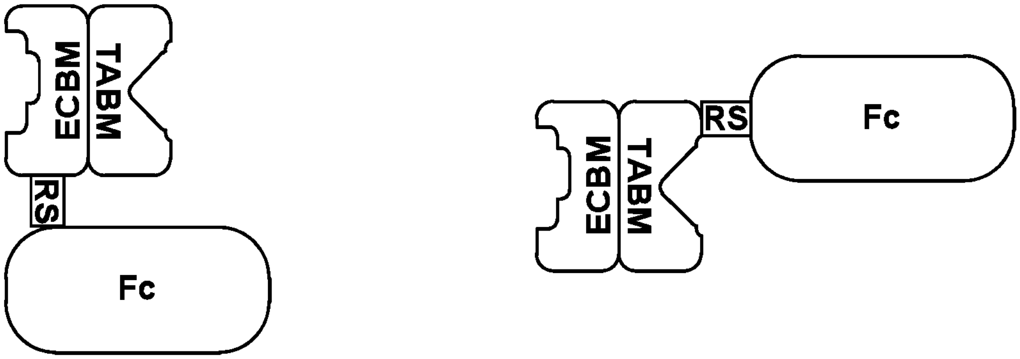
FIG. 8C depicts the binding moieties as an Fc fragment.
Figure 9A:
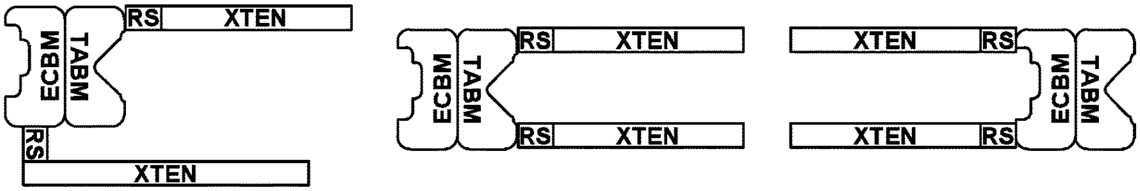
FIG. 9A depicts three configurations in which the two RS and XTEN are linked to both the effector cell binding moiety and the tumor antigen binding moiety (on the left), to the tumor antigen binding moiety (the center) or to the effector cell binding moiety (on the right).
Figure 9B:
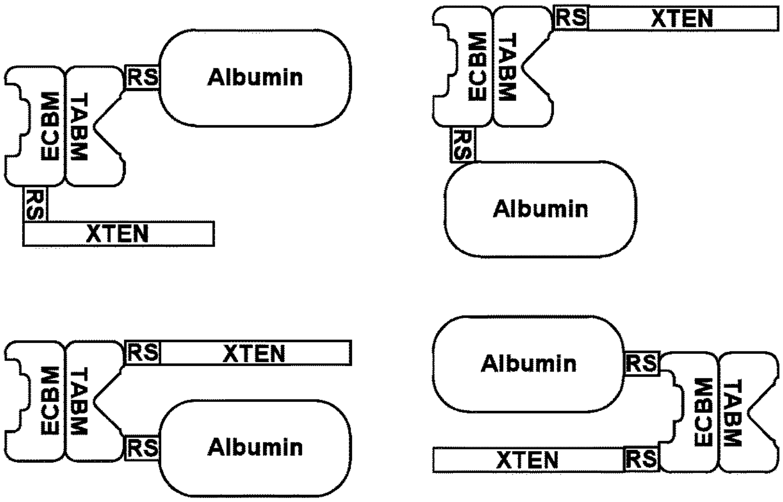
FIG. 9B depicts four configurations in which the one RS and XTEN are linked to the effector cell binding moiety and one RS and albumin are linked to the tumor antigen binding moiety (on the upper left), one RS and an XTEN are linked to the tumor antigen binding moiety and one RS and albumin are linked to the effector cell binding moiety (on the upper right), both the RS and an XTEN and the RS and albumin are linked to the tumor antigen binding moiety (on the lower left) and both the RS and an XTEN and the RS and albumin are linked to the effector cell binding moiety (on the lower right).
Figure 9C:
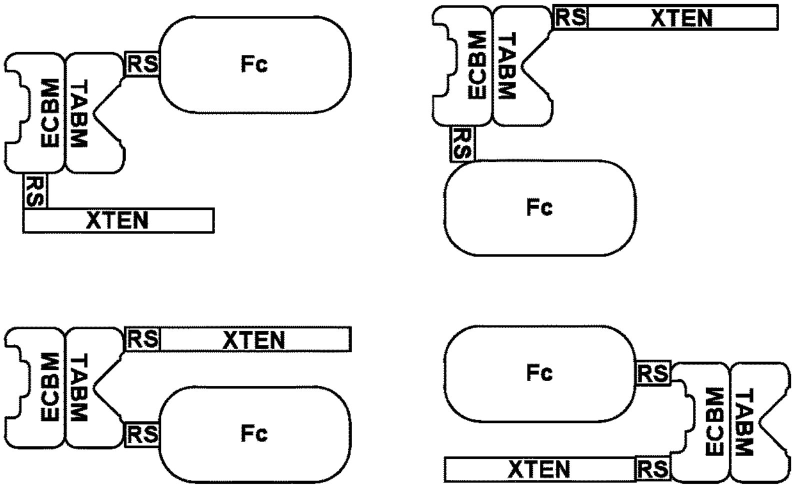
FIG. 9C depicts four configurations in which the one RS and XTEN are linked to the effector cell binding moiety and one RS and Fc are linked to the tumor antigen binding moiety (on the upper left), one RS and an XTEN are linked to the tumor antigen binding moiety and one RS and Fc are linked to the effector cell binding moiety (on the upper right), both the RS and an XTEN and the RS and Fc are linked to the tumor antigen binding moiety (on the lower left) and both the RS and an XTEN and the RS and Fc are linked to the effector cell binding moiety (on the lower right).
Figure 10:
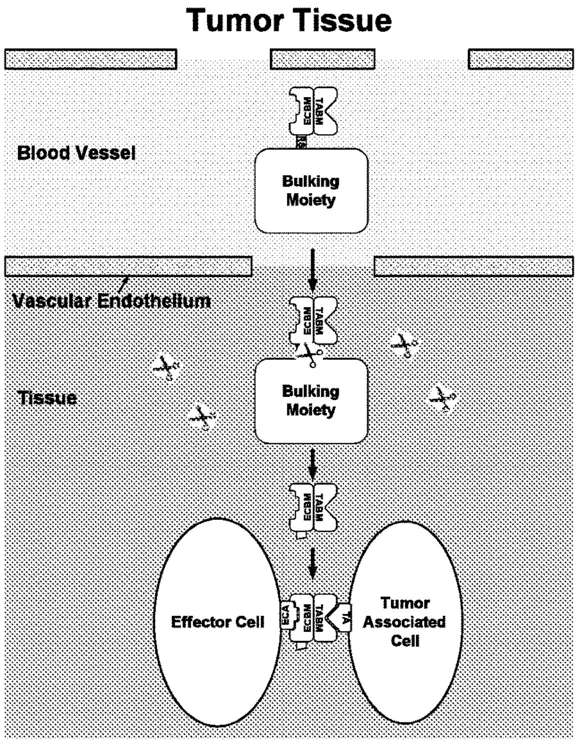
FIG. 10 shows schematic representations of a ProTIA in proximity to tumor tissue (on the left) and normal tissue (on the right) in which the more permeable vasculature in the tumor tissue permits the ProTIA to extravasate into the tissue where the tumor-associated proteases can act on the RS, cleaving it and releasing the binding moieties, which in turn can concurrently bind the effector cell and the tumor associated cell. In the case of the normal tissue, the extravasation is either blocked by the tighter vasculature barriers or, in the case where the ProTIA does extravasate, the ProTIA remains in the "pro" form and while able to bind the effector cell, no tumor cells are present or, if present, insufficient proteases are present to release the binding moieties, with the net effect that an immunological synapse is not formed.
Figure 11:
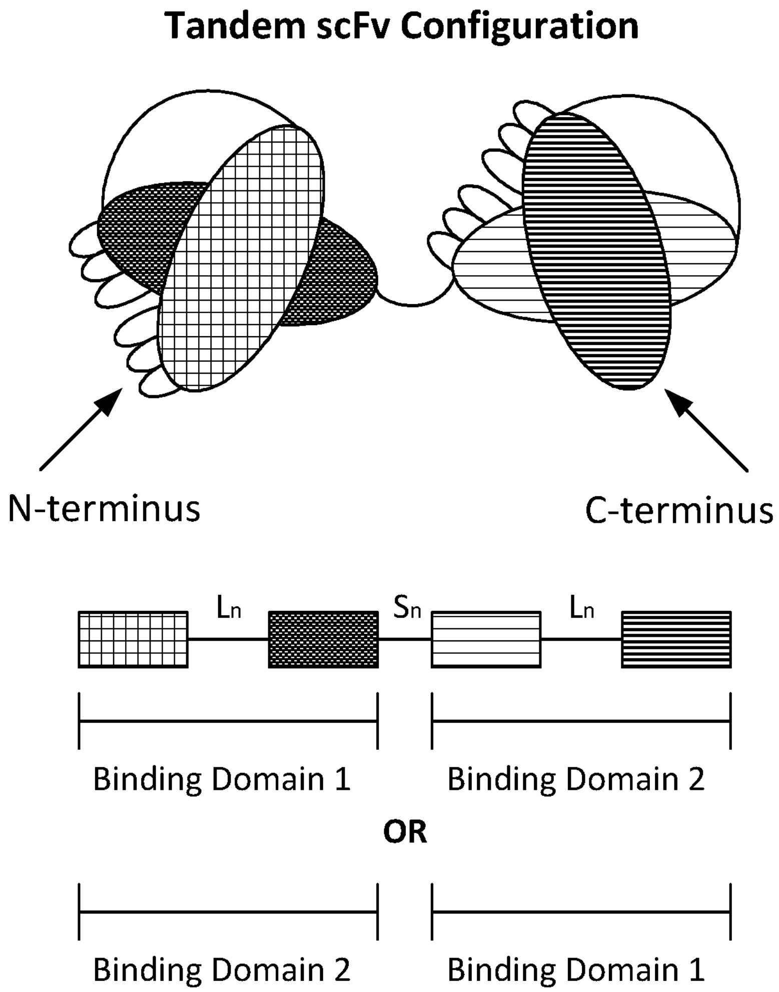
FIG. 11 shows a schematic representation of an scFv configuration of the effector cell binding moiety the tumor antigen binding moiety, each with VH/VL pairs joined by linkers, and in a tandem format.
Figure 12:
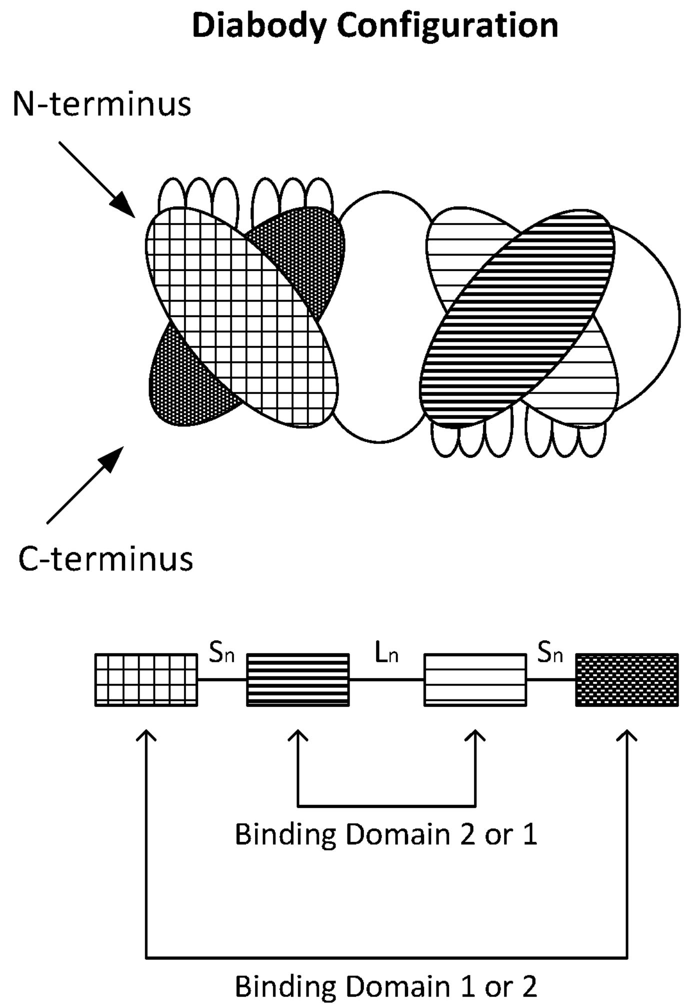
FIG. 12 shows a schematic representation of a diabody configuration of the effector cell binding moiety the tumor antigen binding moiety, each with VH/VL pairs joined by linkers.
Figure 13A:
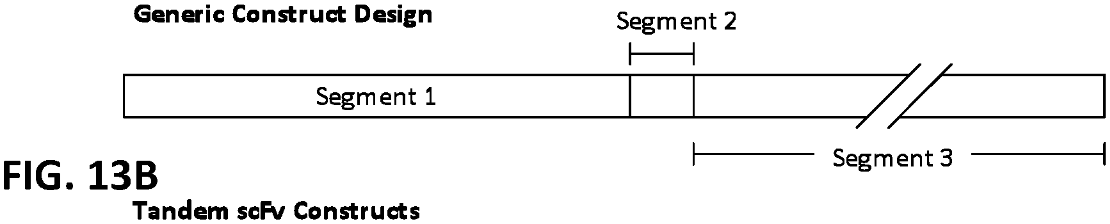
FIG. 13A shows a schematic representation of a generic construct design.
Figure 13B:
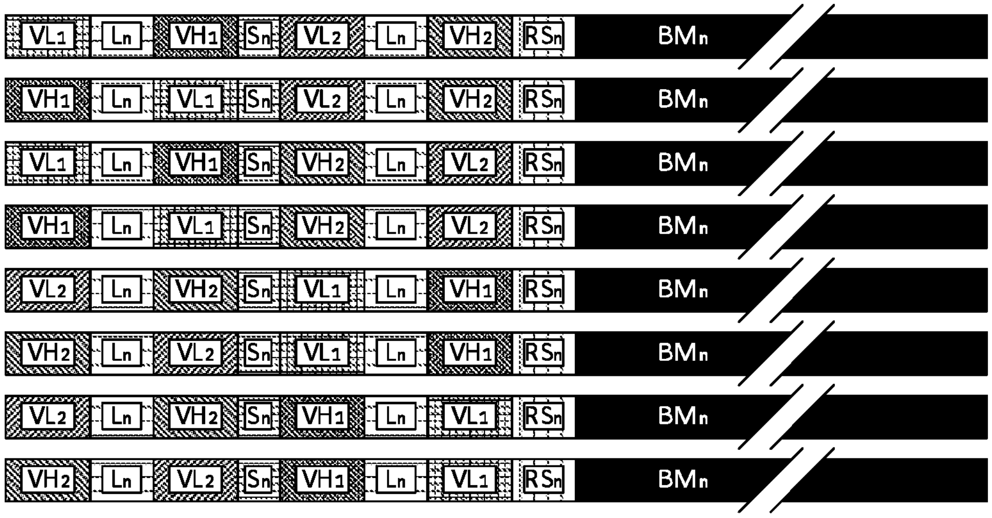
FIGS. 13B and 13C show schematic representations of ProTIA compositions in which the effector cell binding moiety and the tumor antigen binding moiety are in various permutations in scFv configurations (FIG. 13B) [with variable heavy (VH) and variable light (VL) domains linked either by intramolecular long linker (L) or intermolecular shorter linker (1)] and in diabody configurations (FIG. 13C) [with the VH and VL domains linked either by long linker (L) or intermolecular shorter linker (1).
Figure 13C:
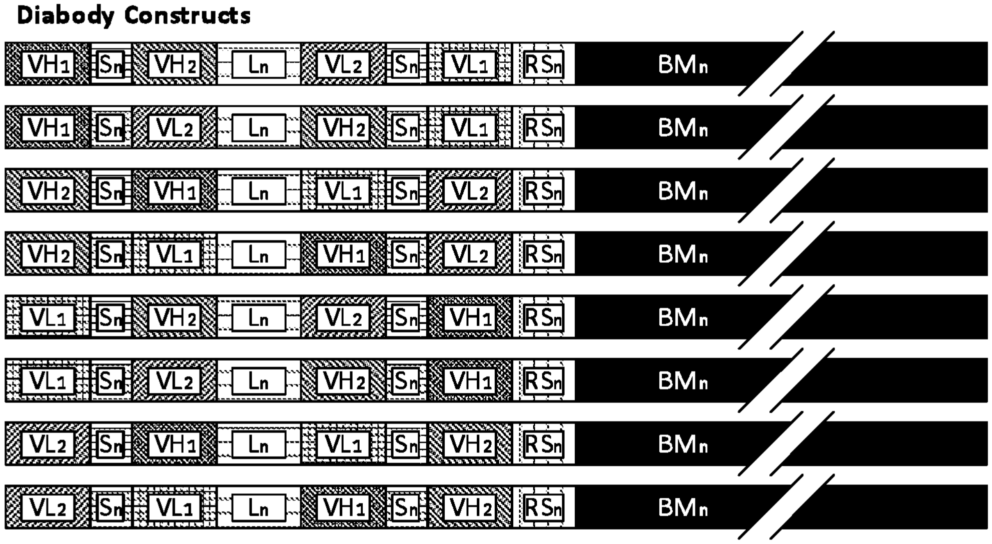

Before the embodiments of the invention are described, it is to be understood that such embodiments are provided by way of example only, and that various alternatives to the embodiments of the invention described herein may be employed in practicing the invention. Numerous variations, changes, and substitutions will now occur to those skilled in the art without departing from the invention.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting. Numerous variations, changes, and substitutions will now occur to those skilled in the art without departing from the invention.

Definitions

In the context of the present application, the following terms have the meanings ascribed to them unless specified otherwise:

As used throughout the specification and claims, the terms “a”, “an” and “the” are used in the sense that they mean “at least one”, “at least a first”, “one or more” or “a plurality” of the referenced components or steps, except in instances wherein an upper limit is thereafter specifically stated. Therefore, a “cleavage sequence”, as used herein, means “at least a first cleavage sequence” but includes a plurality of cleavage sequences. The operable limits and parameters of combinations, as with the amounts of any single agent, will be known to those of ordinary skill in the art in light of the present disclosure.

The terms “polypeptide”, “peptide”, and “protein” are used interchangeably herein to refer to polymers of amino acids of any length. The polymer may be linear or branched, it may comprise modified amino acids, and it may be interrupted by non-amino acids. The terms also encompass an amino acid polymer that has been modified, for example, by disulfide bond formation, glycosylation, lipidation, acetylation, phosphorylation, or any other manipulation, such as conjugation with a labeling component.

The term “monomeric” as applied to a polypeptide refers to the state of the polypeptide as being a single continuous amino acid sequence substantially unassociated with one or more additional polypeptide of the same or different sequence. The monomeric state of the polypeptide can be ascertained as a single proteinaceous entity of the same molecular weight by size exclusion chromatography.

As used herein, the term “amino acid” refers to either natural and/or unnatural or synthetic amino acids, including but not limited to both the D or L optical isomers, and amino acid analogs and peptidomimetics. Standard single or three letter codes may be used to designate amino acids.

The term “natural L-amino acid” or “L-amino acid” means the L optical isomer forms of glycine (G), proline (P), alanine (A), valine (V), leucine (L), isoleucine (I), methionine (M), cysteine (C), phenylalanine (F), tyrosine (Y), tryptophan (W), histidine (H), lysine (K), arginine (R), glutamine (Q), asparagine (N), glutamic acid (E), aspartic acid (D), serine (S), and threonine (T).

The term “non-naturally occurring,” as applied to sequences and as used herein, means polypeptide or polynucleotide sequences that do not have a counterpart to, are not complementary to, or do not have a high degree of homology with a wild-type or naturally-occurring sequence found in a mammal. For example, a non-naturally occurring polypeptide or fragment may share no more than 99%, 98%, 95%, 90%, 80%, 70%, 60%, 50% or even less amino acid sequence identity as compared to a natural sequence when suitably aligned.

The terms “hydrophilic” and “hydrophobic” refer to the degree of affinity that a substance has with water. A hydrophilic substance has a strong affinity for water, tending to dissolve in, mix with, or be wetted by water, while a hydrophobic substance substantially lacks affinity for water, tending to repel and not absorb water and tending not to dissolve in or mix with or be wetted by water. Amino acids can be characterized based on their hydrophobicity. A number of scales have been developed. An example is a scale developed by Levitt, M, et al., J Mol Biol (1976) 104:59, which is listed in Hopp, T P, et al., Proc Natl Acad Sci USA (1981) 78:3824. Examples of “hydrophilic amino acids” are arginine, lysine, threonine, alanine, asparagine, and glutamine. Of particular interest are the hydrophilic amino acids aspartate, glutamate, and serine, and glycine. Examples of “hydrophobic amino acids” are tryptophan, tyrosine, phenylalanine, methionine, leucine, isoleucine, and valine.

A “fragment” when applied to a biologically active protein (and not an antibody), is a truncated form of a the biologically active protein that retains at least a portion of the therapeutic and/or biological activity. A “variant,” when applied to a biologically active protein is a protein with sequence homology to the native biologically active protein that retains at least a portion of the therapeutic and/or biological activity of the biologically active protein. For example, a variant protein may share at least 70%, 75%, 80%, 85%, 90%, 95%, 96%, 97%, 98% or 99% amino acid sequence identity compared with the reference biologically active protein. As used herein, the term “biologically active protein variant” includes proteins modified deliberately, as for example, by site directed mutagenesis, synthesis of the encoding gene, insertions, or accidentally through mutations and that retain activity.

The term “sequence variant” means polypeptides that have been modified compared to their native or original sequence by one or more amino acid insertions, deletions, or substitutions. Insertions may be located at either or both termini of the protein, and/or may be positioned within internal regions of the amino acid sequence. A non-limiting example is substitution of an amino acid in an XTEN with a different amino acid. In deletion variants, one or more amino acid residues in a polypeptide as described herein are removed. Deletion variants, therefore, include all fragments of a described polypeptide sequence. In substitution variants, one or more amino acid residues of a polypeptide are removed and replaced with alternative residues. In one aspect, the substitutions are conservative in nature and conservative substitutions of this type are well known in the art.

The term "moiety" means a component of a larger composition or that is intended to be incorporated into a larger composition, such as a proteinaceous portion joined to a larger polypeptide as a contiguous or non-contiguous sequence. A moiety of a larger composition can confer a desired functionality. For example, a bulking moiety may confer the functionality of increasing molecular weight and/or half-life of a resulting larger composition with which the bulking moiety is associated.

The term "release segment" or "RS" refers to a cleavage sequence in compositions that can be recognized and cleaved by one or more proteases, effecting release of one or more portions or moieties from the composition. As used herein, "mammalian protease" means a protease that normally exists in the body fluids, cells, tissues, and may be found in higher levels in certain target tissues or cells, e.g., in diseased tissues (e.g., tumor) of a mammal. RS sequences can be engineered to be cleaved by various mammalian proteases or multiple mammalian proteases that are present in or proximal to target tissues in a subject or are introduced in an in vitro assay. Other equivalent proteases (endogenous or exogenous) that are capable of recognizing a defined cleavage site can be utilized. It is specifically contemplated that the RS sequence can be adjusted and tailored to the protease utilized and can incorporate linker amino acids to join to adjacent polypeptides The term "within", when referring to a first polypeptide being linked to a second polypeptide, encompasses linking or fusion of an additional component that connects the N-terminus of the first or second polypeptide to the C-terminus of the second or first polypeptide, respectively, as well as insertion of the first polypeptide into the sequence of the second polypeptide. For example, when an RS component is linked "within" a chimeric polypeptide assembly, the RS may be linked to the N-terminus, the C-terminus, or may be inserted between any two amino acids of an XTEN polypeptide.

"Activity" as applied to form(s) of a composition provided herein, refers to an action or effect, including but not limited to receptor binding, antagonist activity, agonist activity, a cellular or physiologic response, cell lysis, cell death, or an effect generally known in the art for the effector component of the composition, whether measured by an in vitro, ex vivo or in vivo assay or a clinical effect.

"Effector cell", as used herein, includes any eukaryotic cells capable of conferring an effect on a target cell. For example, an effect cell can induce loss of membrane integrity, pyknosis, karyorrhexis, apoptosis, lysis, and/or death of a target cell. In another example, an effector cell can induce division, growth, differentiation of a target cell or otherwise altering signal transduction of a target cell. Non-limiting examples of effector cell include plasma cell, T cell, CD4 cell, CD8 cell, B cell, cytokine induced killer cell (CIK cell), master cell, dendritic cell, regulatory T cell (RegT cell), helper T cell, myeloid cell, macrophage, and NK cell.

An "effector cell antigen" refers to molecules expressed by an effector cell, including without limitation cell surface molecules such as proteins, glycoproteins or lipoproteins. Exemplary effector cell antigens include proteins of the CD3 complex or the T cell receptor (TCR), CD4, CD8, CD25, CD38, CD69, CD45RO, CD57, CD95, CD107, and CD154, as well as effector molecules such as cytokines in association with, bound to, expressed within, or expressed and released by, an effector cell. An effector cell antigen can serve as the binding counterpart of a binding domain of the subject chimeric polypeptide assembly. Non-limiting examples of effector cell antigens to which the subject composition may bind include antigens on the cell surface such as CD3, CD4, CD8, CD25, CD38, CD69, CD45RO, CD57, CD95, CD107, and CD154 as well as Th1 cytokines selected from IL2, IL10, IL12, IFNγ, and TNFα.

As used herein, the term "ELISA" refers to an enzyme-linked immunosorbent assay as described herein or as otherwise known in the art.

A "host cell" includes an individual cell or cell culture which can be or has been a recipient for the subject vectors into which exogenous nucleic acid has been introduced, such as those described herein. Host cells include progeny of a single host cell. The progeny may not necessarily be completely identical (in morphology or in genomic of total DNA complement) to the original parent cell due to natural, accidental, or deliberate mutation. A host cell includes cells transfected in vivo with a vector of this invention.

"Isolated", when used to describe the various polypeptides disclosed herein, means polypeptide that has been identified and separated and/or recovered from a component of its natural environment or from a more complex mixture (such as during protein purification). Contaminant components of its natural environment are materials that would typically interfere with diagnostic or therapeutic uses for the polypeptide, and may include enzymes, hormones, and other proteinaceous or non-proteinaceous solutes. As is apparent to those of skill in the art, a non-naturally occurring polynucleotide, peptide, polypeptide, protein, antibody, or fragments thereof, does not require "isolation" to distinguish it from its naturally occurring counterpart. In addition, a "concentrated", "separated" or "diluted" polynucleotide, peptide, polypeptide, protein, antibody, or fragments thereof, is distinguishable from its naturally occurring counterpart in that the concentration or number of molecules per volume is generally greater than that of its naturally occurring counterpart. In general, a polypeptide made by recombinant means and expressed in a host cell is considered to be "isolated."

An "isolated nucleic acid" is a nucleic acid molecule that is identified and separated from at least one contaminant nucleic acid molecule with which it is ordinarily associated in the natural source of the polypeptide-encoding nucleic acid. For example, an isolated polypeptide-encoding nucleic acid molecule is other than in the form or setting in which it is found in nature. Isolated polypeptide-encoding nucleic acid molecules therefore are distinguished from the specific polypeptide-encoding nucleic acid molecule as it exists in natural cells. However, an isolated polypeptide-encoding nucleic acid molecule includes polypeptide-encoding nucleic acid molecules contained in cells that ordinarily express the polypeptide where, for example, the nucleic acid molecule is in a chromosomal or extra-chromosomal location different from that of natural cells.

A "chimeric" protein or polypeptide contains at least one fusion polypeptide comprising at least one region in a different position in the sequence than that which occurs in nature. The regions may normally exist in separate proteins and are brought together in the fusion polypeptide; or they may normally exist in the same protein but are placed in a new arrangement in the fusion polypeptide. A chimeric protein may be created, for example, by chemical synthesis, or by creating and translating a polynucleotide in which the peptide regions are encoded in the desired relationship.

"Fused," and "fusion" are used interchangeably herein, and refers to the joining together of two or more peptide or polypeptide sequences by recombinant means. A "fusion protein" or "chimeric protein" comprises a first amino acid sequence linked to a second amino acid sequence with which it is not naturally linked in nature.

"XTENylated" is used to denote a peptide or polypeptide that has been modified by the linking or fusion of one or more XTEN polypeptides (described, below) to the peptide or polypeptide, whether by recombinant or chemical cross-linking means.

"Operably linked" means that the DNA sequences being linked are contiguous, and in reading phase or in-frame. An "in-frame fusion" refers to the joining of two or more open reading frames (ORFs) to form a continuous longer ORF, in a manner that maintains the correct reading frame of the original ORFs. For example, a promoter or enhancer is operably linked to a coding sequence for a polypeptide if it affects the transcription of the polypeptide sequence. Thus, the resulting recombinant fusion protein is a single protein containing two or more segments that correspond to polypeptides encoded by the original ORFs (which segments are not normally so joined in nature).

"Crosslinking," "conjugating," "link," "linking" and "joined to" are used interchangeably herein, and refer to the covalent joining of two different molecules by a chemical reaction. The crosslinking can occur in one or more chemical reactions, as known in the art.

The term "conjugation partner" as used herein, refers to the individual components that can be linked or are linked in a conjugation reaction.

The term "conjugate" (used as a noun) is intended to refer to the heterogeneous molecule formed as a result of covalent linking of conjugation partners one to another, e.g., a binding domain covalently linked to a release segment.

"Cross-linker" and "cross-linking agent" are used interchangeably and in their broadest context to mean a chemical entity used to covalently join two or more entities. For example, a cross-linker joins two, three, four or more peptides, or joins a peptide to an XTEN. It will be understood by one of skill in the art that a cross-linker can refer to the covalently-bound reaction product remaining after the crosslinking of the reactants. The cross-linker can also comprise one or more reactants which have not yet reacted but which are capable to react with another entity.

In the context of polypeptides, a "linear sequence" or a "sequence" is an order of amino acids in a polypeptide in an amino to carboxyl terminus (N- to C-terminus) direction in which residues that neighbor each other in the sequence are contiguous in the primary structure of the polypeptide. A "partial sequence" is a linear sequence of part of a polypeptide that is known to comprise additional residues in one or both directions.

"Heterologous" means derived from a genotypically distinct entity from the rest of the entity to which it is being compared. For example, a glycine rich sequence removed from its native coding sequence and operatively linked to a coding sequence other than the native sequence is a heterologous glycine rich sequence. The term "heterologous" as applied to a polynucleotide, a polypeptide, means that the polynucleotide or polypeptide is derived from a genotypically distinct entity from that of the rest of the entity to which it is being compared.

The terms "polynucleotides", "nucleic acids", "nucleotides" and "oligonucleotides" are used interchangeably. They refer to nucleotides of any length, encompassing a singular nucleic acid as well as plural nucleic acids, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

The term "complement of a polynucleotide" denotes a polynucleotide molecule having a complementary base sequence and reverse orientation as compared to a reference sequence, such that it could hybridize with a reference sequence with complete fidelity.

"Recombinant" as applied to a polynucleotide means that the polynucleotide is the product of various combinations of recombination steps which may include cloning, restriction and/or ligation steps, and other procedures that result in expression of a recombinant protein in a host cell.

The terms "gene" and "gene fragment" are used interchangeably herein. They refer to a polynucleotide containing at least one open reading frame that is capable of encoding a particular protein after being transcribed and translated. A gene or gene fragment may be genomic or cDNA, as long as the polynucleotide contains at least one open reading frame, which may cover the entire coding region or a segment thereof. A "fusion gene" is a gene composed of at least two heterologous polynucleotides that are linked together.

As used herein, a "coding region" or "coding sequence" is a portion of polynucleotide which consists of codons translatable into amino acids. Although a "stop codon" (TAG, TGA, or TAA) is typically not translated into an amino acid, it may be considered to be part of a coding region, but any flanking sequences, for example promoters, ribosome binding sites, transcriptional terminators, introns, and the like, are not part of a coding region. The boundaries of a coding region are typically determined by a start codon at the 5' terminus, encoding the amino terminus of the resultant polypeptide, and a translation stop codon at the 3' terminus, encoding the carboxyl terminus of the resulting polypeptide. Two or more coding regions of the present invention can be present in a single polynucleotide construct, e.g., on a single vector, or in separate polynucleotide constructs, e.g., on separate (different) vectors. It follows, then, that a single vector can contain just a single coding region, or comprise two or more coding regions, e.g., a single vector can separately encode a binding domain-A and a binding domain-B as described below. In addition, a vector, polynucleotide, or nucleic acid of the invention can encode heterologous coding regions, either fused or unfused to a nucleic acid encoding a binding domain of the invention. Heterologous coding regions include without limitation specialized elements or motifs, such as a secretory signal peptide or a heterologous functional domain.

The term "downstream" refers to a nucleotide sequence that is located 3' to a reference nucleotide sequence. In certain embodiments, downstream nucleotide sequences relate to sequences that follow the starting point of transcription. For example, the translation initiation codon of a gene is located downstream of the start site of transcription.

The term "upstream" refers to a nucleotide sequence that is located 5' to a reference nucleotide sequence. In certain embodiments, upstream nucleotide sequences relate to sequences that are located on the 5' side of a coding region or starting point of transcription. For example, most promoters are located upstream of the start site of transcription.

"Homology" or "homologous" refers to sequence similarity or interchangeability between two or more polynucleotide sequences or between two or more polypeptide sequences. When using a program such as BestFit to determine sequence identity, similarity or homology between two different amino acid sequences, the default settings may be used, or an appropriate scoring matrix, such as blosum45 or blosum80, may be selected to optimize identity, similarity or homology scores. Preferably, polynucleotides that are homologous are those which hybridize under stringent conditions as defined herein and have at least 70%, preferably at least 80%, more preferably at least 90%, more preferably 95%, more preferably 97%, more preferably 98%, and even more preferably 99% sequence identity compared to those sequences. Polypeptides that are homologous preferably have sequence identities that are at least 70%, preferably at least 80%, even more preferably at least 90%, even more preferably at least 95-99% identical when optimally aligned over sequences of comparable length.

"Ligation" as applied to polynucleic acids refers to the process of forming phosphodiester bonds between two nucleic acid fragments or genes, linking them together. To ligate the DNA fragments or genes together, the ends of the DNA must be compatible with each other. In some cases, the ends will be directly compatible after endonuclease digestion. However, it may be necessary to first convert the staggered ends commonly produced after endonuclease digestion to blunt ends to make them compatible for ligation.

The terms "stringent conditions" or "stringent hybridization conditions" includes reference to conditions under which a polynucleotide will hybridize to its target sequence, to a detectably greater degree than other sequences (e.g., at least 2-fold over background). Generally, stringency of hybridization is expressed, in part, with reference to the temperature and salt concentration under which the wash step is carried out. Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short polynucleotides (e.g., 10 to 50 nucleotides) and at least about 60° C. for long polynucleotides (e.g., greater than 50 nucleotides)—for example, "stringent conditions" can include hybridization in 50% formamide, 1 M NaCl, 1% SDS at 37° C., and three washes for 15 min each in 0.1×SSC/1% SDS at 60° C. to 65° C. Alternatively, temperatures of about 65° C., 60° C., 55° C., or 42° C. may be used. SSC concentration may be varied from about 0.1 to 2×SSC, with SDS being present at about 0.1%. Such wash temperatures are typically selected to be about 5° C. to 20° C. lower than the thermal melting point for the specific sequence at a defined ionic strength and pH. The Tm is the temperature (under defined ionic strength and pH) at which 50% of the target sequence hybridizes to a perfectly matched probe. An equation for calculating Tm and conditions for nucleic acid hybridization are well known and can be found in Sambrook, J. et al., "Molecular Cloning: A Laboratory Manual," 3r d edition, Cold Spring Harbor Laboratory Press, 2001. Typically, blocking reagents are used to block non-specific hybridization. Such blocking reagents include, for instance, sheared and denatured salmon sperm DNA at about 100-200 μg/ml. Organic solvent, such as formamide at a concentration of about 35-50% v/v, may also be used under particular circumstances, such as for RNA:DNA hybridizations. Useful variations on these wash conditions will be readily apparent to those of ordinary skill in the art.

The terms "percent identity," percentage of sequence identity," and "% identity," as applied to polynucleotide sequences, refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. Percent identity may be measured over the length of an entire defined polynucleotide sequence, or may be measured over a shorter length, for example, over the length of a fragment taken from a larger, defined polynucleotide sequence, for instance, a fragment of at least 45, at least 60, at least 90, at least 120, at least 150, at least 210 or at least 450 contiguous residues. Such lengths are exemplary only, and it is understood that any fragment length supported by the sequences shown herein, in the tables, figures or Sequence Listing, may be used to describe a length over which percentage identity may be measured. The percentage of sequence identity is calculated by comparing two optimally aligned sequences over the window of comparison, determining the number of matched positions (at which identical residues occur in both polypeptide sequences), dividing the number of matched positions by the total number of positions in the window of comparison (i.e., the window size), and multiplying the result by 100 to yield the percentage of sequence identity. When sequences of different length are to be compared, the shortest sequence defines the length of the window of comparison. Conservative substitutions are not considered when calculating sequence identity.

"Percent (%) sequence identity," with respect to the polypeptide sequences identified herein, is defined as the percentage of amino acid residues in a query sequence that are identical with the amino acid residues of a second, reference polypeptide sequence of comparable length or a portion thereof, after aligning the sequences and introducing gaps, if necessary, to achieve the maximum percent sequence identity, and not considering any conservative substitutions as part of the sequence identity, thereby resulting in optimal alignment. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve optimal alignment over the full length of the sequences being compared. Percent identity may be measured over the length of an entire defined polypeptide sequence, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

"Repetitiveness" used in the context of polynucleotide sequences refers to the degree of internal homology in the sequence such as, for example, the frequency of identical nucleotide sequences of a given length. Repetitiveness can, for example, be measured by analyzing the frequency of identical sequences.

The term "expression" as used herein refers to a process by which a polynucleotide produces a gene product, for example, an RNA or a polypeptide. It includes without limitation transcription of the polynucleotide into messenger RNA (mRNA), transfer RNA (tRNA), small hairpin RNA (shRNA), small interfering RNA (siRNA) or any other RNA product, and the translation of an mRNA into a polypeptide. Expression produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation or splicing, or polypeptides with post translational modifications, e.g., methylation, glycosylation, the addition of lipids, association with other protein subunits, or proteolytic cleavage.

A "vector" or "expression vector" are used interchangeably and refers to a nucleic acid molecule, preferably self-replicating in an appropriate host, which transfers an inserted nucleic acid molecule into and/or between host cells. The term includes vectors that function primarily for insertion of DNA or RNA into a cell, replication of vectors that function primarily for the replication of DNA or RNA, and expression vectors that function for transcription and/or translation of the DNA or RNA. Also included are vectors that provide more than one of the above functions. An "expression vector" is a polynucleotide which, when introduced into an appropriate host cell, can be transcribed and translated into a polypeptide(s). An "expression system" usually connotes a suitable host cell comprised of an expression vector that can function to yield a desired expression product.

"Serum degradation resistance," as applied to a polypeptide, refers to the ability of the polypeptides to withstand degradation in blood or components thereof, which typically involves proteases in the serum or plasma. The serum degradation resistance can be measured by combining the protein with human (or mouse, rat, dog, monkey, as appropriate) serum or plasma, typically for a range of days (e.g. 0.25, 0.5, 1, 2, 4, 8, 16 days), typically at about 37° C. The samples for these time points can be run on a Western blot assay and the protein is detected with an antibody. The antibody can be to a tag in the protein. If the protein shows a single band on the western, where the protein's size is identical to that of the injected protein, then no degradation has occurred. In this exemplary method, the time point where 50% of the protein is degraded, as judged by Western blots or equivalent techniques, is the serum degradation half-life or "serum half-life" of the protein.

The terms "$t_{1/2}$", "half-life", "terminal half-life", "elimination half-life" and "circulating half-life" are used interchangeably herein and, as used herein means the terminal half-life calculated as $\ln(2)/K_{el}$. $K_{el}$ is the terminal elimination rate constant calculated by linear regression of the terminal linear portion of the log concentration vs. time curve. Half-life typically refers to the time required for half the quantity of an administered substance deposited in a living organism to be metabolized or eliminated by normal biological processes. When a clearance curve of a given polypeptide is constructed as a function of time, the curve is usually biphasic with a rapid α-phase and longer β-phase. The typical β-phase half-life of a human antibody in humans is 21 days. Half-life can be measured using timed samples from anybody fluid, but is most typically measured in plasma samples.

The term "molecular weight" generally refers to the sum of atomic weights of the constituent atoms in a molecule. Molecular weight can be determined theoretically by summing the atomic masses of the constituent atoms in a molecule. When applied in the context of a polypeptide, the molecular weight is calculated by adding, based on amino acid composition, the molecular weight of each type of amino acid in the composition or by estimation from comparison to molecular weight standards in an SDS electrophoresis gel. The calculated molecular weight of a molecule can differ from the "apparent molecular weight" of a molecule, which generally refers to the molecular weight of a molecule as determined by one or more analytical techniques. "Apparent molecular weight factor" and "apparent molecular weight" are related terms and when used in the context of a polypeptide, the terms refer to a measure of the relative increase or decrease in apparent molecular weight exhibited by a particular amino acid or polypeptide sequence. The apparent molecular weight can be determined, for example, using size exclusion chromatography (SEC) or similar methods by comparing to globular protein standards, as measured in "apparent kD" units. The apparent molecular weight factor is the ratio between the apparent molecular weight and the "molecular weight"; the latter is calculated by adding, based on amino acid composition as described above, or by estimation from comparison to molecular weight standards in an SDS electrophoresis gel. The determination of apparent molecular weight and apparent molecular weight factor is described in U.S. Pat. No. 8,673,860.

The terms "hydrodynamic radius" or "Stokes radius" is the effective radius (Rh in nm) of a molecule in a solution measured by assuming that it is a body moving through the solution and resisted by the solution's viscosity. In the embodiments of the invention, the hydrodynamic radius measurements of the XTEN polypeptides correlate with the "apparent molecular weight factor" which is a more intuitive measure. The "hydrodynamic radius" of a protein affects its rate of diffusion in aqueous solution as well as its ability to migrate in gels of macromolecules. The hydrodynamic radius of a protein is determined by its molecular weight as well as by its structure, including shape and compactness. Methods for determining the hydrodynamic radius are well known in the art, such as by the use of size exclusion chromatography (SEC), as described in U.S. Pat. Nos. 6,406,632 and 7,294,513. Most proteins have globular structure, which is the most compact three-dimensional structure a protein can have with the smallest hydrodynamic radius. Some proteins adopt a random and open, unstructured, or 'linear' conformation and as a result have a much larger hydrodynamic radius compared to typical globular proteins of similar molecular weight.

"Diffusion coefficient" means the magnitude of the molar flux through a surface per unit concentration gradient out-of-plane. In dilute species transport, the flux due to diffusion is given by Fick's first law, which only depends on a single property of the solute's interaction with the solvent: the diffusion coefficient.

"Physiological conditions" refers to a set of conditions in a living host as well as in vitro conditions, including temperature, salt concentration, pH, that mimic those conditions of a living subject. A host of physiologically relevant conditions for use in in vitro assays have been established.

Generally, a physiological buffer contains a physiological concentration of salt and is adjusted to a neutral pH ranging from about 6.5 to about 7.8, and preferably from about 7.0 to about 7.5. A variety of physiological buffers are listed in Sambrook et al. (2001). Physiologically relevant temperature ranges from about 25° C. to about 38° C., and preferably from about 35° C. to about 37° C.

The term "binding domain", as used herein, is specifically intended to include the categories of antibodies or antibody fragments that have specific binding affinity for a target antigen or ligand such as cell-surface receptors or antigens or glycoproteins, oligonucleotides, enzymatic substrates, antigenic determinants, or binding sites that may be present in or on the surface of a target tissue or cell.

The term "antibody" is used herein in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. The full-length antibodies may be for example monoclonal, recombinant, chimeric, deimmunized, humanized and human antibodies.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being known in the art or described herein.

An "antibody fragment" refers to a molecule other than an intact antibody that comprises a portion of an intact antibody and that binds the antigen to which the intact antibody binds. Examples of antibody fragments include but are not limited to Fv, Fab, Fab', Fab'-SH, F(ab')2, diabodies, linear antibodies, a single domain antibody, a single domain camelid antibody, single-chain antibody molecules (scFv), and multispecific antibodies formed from antibody fragments.

"scFv" or "single chain fragment variable" are used interchangeably herein to refer to an antibody fragment format comprising variable regions of heavy ("VH") and light ("VL") chains or two copies of a VH or VL chain, which are joined together by a short flexible peptide linker. The scFv is not actually a fragment of an antibody, but is a fusion protein of the variable regions of the heavy (VH) and light chains (VL) of immunoglobulins, and can be easily expressed in functional form in *E. coli.*

The terms "antigen", "target antigen" and "immunogen" are used interchangeably herein to refer to the structure or binding determinant that an antibody, antibody fragment or an antibody fragment-based molecule binds to or has specificity against.

The term "epitope" refers to the particular site on an antigen molecule to which an antibody, antibody fragment, or binding domain binds. An epitope is a ligand of an antibody or antibody fragment.

As used herein, "CD3" or "cluster of differentiation 3" means the T cell surface antigen CD3 complex, which includes in individual form or independently combined form all known CD3 subunits, for example CD3 epsilon, CD3 delta, CD3 gamma, CD3 zeta, CD3 alpha and CD3 beta. The extracellular domains of CD3 epsilon, gamma and delta contain an immunoglobulin-like domain, so are therefore considered part of the immunoglobulin superfamily.

The terms "specific binding" or "specifically bind" or "binding specificity" are used interchangeably herein to refer to the high degree of binding affinity of a binding domain to its corresponding target. Typically, specific binding as measured by one or more of the assays disclosed herein would have a dissociation constant or $K_d$ of less than about $10^{-6}$ M.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_d$). As used herein "a greater binding affinity" means a lower $K_d$ value; e.g., $1\times10^{-9}$ M is a greater binding affinity than $1\times10^{-8}$ M.

"Inhibition constant", or "Ki", are used interchangeably and mean the dissociation constant of the enzyme-inhibitor complex, or the reciprocal of the binding affinity of the inhibitor to the enzyme.

"Dissociation constant", or "$K_d$", are used interchangeably and mean the affinity between a ligand "L" and a protein "P"; i.e. how tightly a ligand binds to a particular protein. It can be calculated using the formula $K_d$=[L][P]/[LP], where [P], [L] and [LP] represent molar concentrations of the protein, ligand and complex, respectively. The term "$k_{on}$", as used herein, is intended to refer to the on rate constant for association of an antibody to the antigen to form the antibody/antigen complex as is known in the art. The term "$k_{off}$", as used herein, is intended to refer to the off rate constant for dissociation of an antibody from the antibody/antigen complex as is known in the art.

The term "antagonist", as used herein, includes any molecule that partially or fully blocks, inhibits, or neutralizes a biological activity of a native polypeptide disclosed herein. Methods for identifying antagonists of a polypeptide may comprise contacting a native polypeptide with a candidate antagonist molecule and measuring a detectable change in one or more biological activities normally associated with the native polypeptide. In the context of the present invention, antagonists may include proteins, nucleic acids, carbohydrates, antibodies or any other molecules that decrease the effect of a biologically active protein.

A "target cell marker" refers to a molecule expressed by a target cell including but not limited to cell-surface receptors, antigens, glycoproteins, oligonucleotides, enzymatic substrates, antigenic determinants, or binding sites that may be present in the on the surface of a target tissue or cell that may serve as ligands for antibodies.

A "target tissue" refers to a tissue that is the cause of or is part of a disease condition such as, but not limited to cancer or inflammatory conditions. Sources of diseased target tissue include a body organ, a tumor, a cancerous cell or population of cancerous cells or cells that form a matrix or are found in association with a population of cancerous cells, bone, skin, cells that produce cytokines or factors contributing to a disease condition.

A "defined medium" refers to a medium comprising nutritional and hormonal requirements necessary for the survival and/or growth of the cells in culture such that the components of the medium are known. Traditionally, the defined medium has been formulated by the addition of nutritional and growth factors necessary for growth and/or survival. Typically, the defined medium provides at least one component from one or more of the following categories: a) all essential amino acids, and usually the basic set of twenty amino acids plus cysteine; b) an energy source, usually in the form of a carbohydrate such as glucose; c) vitamins and/or other organic compounds required at low concentrations; d) free fatty acids; and e) trace elements, where trace elements are defined as inorganic compounds or naturally occurring elements that are typically required at very low concentrations, usually in the micromolar range. The defined medium may also optionally be supplemented with one or more components from any of the following categories: a) one or more mitogenic agents; b) salts and buffers as, for example, calcium, magnesium, and phosphate; c) nucleosides and bases such as, for example, adenosine and thymidine, hypoxanthine; and d) protein and tissue hydrolysates.

The term "agonist" is used in the broadest sense and includes any molecule that mimics a biological activity of a native polypeptide disclosed herein. Suitable agonist molecules specifically include agonist antibodies or antibody fragments, fragments or amino acid sequence variants of native polypeptides, peptides, small organic molecules, etc. Methods for identifying agonists of a native polypeptide may comprise contacting a native polypeptide with a candidate agonist molecule and measuring a detectable change in one or more biological activities normally associated with the native polypeptide.

As used herein, "treatment" or "treating," or "palliating" or "ameliorating" is used interchangeably herein. These terms refer to an approach for obtaining beneficial or desired results including but not limited to a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms or improvement in one or more clinical parameters associated with the underlying disorder such that an improvement is observed in the subject, notwithstanding that the subject may still be afflicted with the underlying disorder. For prophylactic benefit, the compositions may be administered to a subject at risk of developing a particular disease, or to a subject reporting one or more of the physiological symptoms of a disease, even though a diagnosis of this disease may not have been made.

A "therapeutic effect" or "therapeutic benefit," as used herein, refers to a physiologic effect, including but not limited to the mitigation, amelioration, or prevention of disease or an improvement in one or more clinical parameters associated with the underlying disorder in humans or other animals, or to otherwise enhance physical or mental wellbeing of humans or animals, resulting from administration of a polypeptide of the invention other than the ability to induce the production of an antibody against an antigenic epitope possessed by the biologically active protein. For prophylactic benefit, the compositions may be administered to a subject at risk of developing a particular disease, a recurrence of a former disease, condition or symptom of the disease, or to a subject reporting one or more of the physiological symptoms of a disease, even though a diagnosis of this disease may not have been made.

The terms "therapeutically effective amount" and "therapeutically effective dose", as used herein, refer to an amount of a drug or a biologically active protein, either alone or as a part of a polypeptide composition, that is capable of having any detectable, beneficial effect on any symptom, aspect, measured parameter or characteristics of a disease state or condition when administered in one or repeated doses to a subject. Such effect need not be absolute to be beneficial. Determination of a therapeutically effective amount is well within the capability of those skilled in the art, especially in light of the detailed disclosure provided herein.

The term "therapeutically effective and non-toxic dose" as used herein refers to a tolerable dose of the compositions as defined herein that is high enough to cause depletion of tumor or cancer cells, tumor elimination, tumor shrinkage or stabilization of disease without or essentially without major toxic effects in the subject. Such therapeutically effective and non-toxic doses may be determined by dose escalation studies described in the art and should be below the dose inducing severe adverse side effects.

The term "dose regimen", as used herein, refers to a schedule for consecutively administered multiple doses (i.e., at least two or more) of a composition, wherein the doses are given in therapeutically effective amounts to result in sustained beneficial effect on any symptom, aspect, measured parameter, endpoint, or characteristic of a disease state or condition.

The terms "cancer" and "cancerous" refer to or describe the physiological condition in mammals that is typically characterized by unregulated cell growth/proliferation. Examples of cancer include, but are not limited to, carcinomas, Hodgkin's lymphoma, non-Hodgkin's lymphoma, B cell lymphoma, T-cell lymphoma, follicular lymphoma, mantle cell lymphoma, blastoma, breast cancer, colon cancer, prostate cancer, head and neck cancer, any form of skin cancer, melanoma, genito-urinary tract cancer, ovarian cancer, ovarian cancer with malignant ascites, peritoneal carcinomatosis, uterine serous carcinoma, endometrial cancer, cervical cancer, colorectal cancer, an epithelia intraperitoneal malignancy with malignant ascites, uterine cancer, mesothelioma in the peritoneum kidney cancers, lung cancer, small-cell lung cancer, non-small cell lung cancer, gastric cancer, esophageal cancer, stomach cancer, small intestine cancer, liver cancer, hepatocarcinoma, hepatoblastoma, liposarcoma, pancreatic cancer, gall bladder cancer, cancers of the bile duct, salivary gland carcinoma, thyroid cancer, epithelial cancer, adenocarcinoma, sarcomas of any origin, primary hematologic malignancies including acute or chronic lymphocytic leukemias, acute or chronic myelogenous leukemias, myeloproliferative neoplastic disorders, or myelodysplastic disorders, myasthenia gravis, Morbus Basedow, Hashimoto thyroiditis, or Goodpasture syndrome.

"Tumor-specific marker" as used herein, refers to an antigen that is found on or in a cancer cell that may be, but is not necessarily, found in higher numbers in or on the cancer cell relative to normal cells or tissues.

"Target cell" refers to a cell that has the ligand of an antibody or antibody fragment of the subject compositions and is associated with or causes a disease or pathologic condition, including cancer cells, tumor cells, and inflammatory cells. The ligand of a target cell is referred to herein as a "target cell marker" or "target cell antigen" and includes, but is not limited to, cell surface receptors or antigens, cytokines, MHC proteins, and cytosol proteins or peptides that are exogenously presented. As used herein, "target cell" would not include an effector cell.

I). General Techniques

The practice of the present invention employs, unless otherwise indicated, conventional techniques of immunology, biochemistry, chemistry, molecular biology, microbiology, cell biology, genomics and recombinant DNA, which are within the skill of the art. See Sambrook, J. et al., "Molecular Cloning: A Laboratory Manual," 3rd edition, Cold Spring Harbor Laboratory Press, 2001; "Current protocols in molecular biology", F. M. Ausubel, et al. eds., 1987; the series "Methods in Enzymology," Academic Press, San Diego, CA.; "PCR 2: a practical approach", M. J. MacPherson, B. D. Hames and G. R. Taylor eds., Oxford University Press, 1995; "Antibodies, a laboratory manual" Harlow, E. and Lane, D. eds., Cold Spring Harbor Laboratory, 1988; "Goodman & Gilman's The Pharmacological Basis of Therapeutics," 11th Edition, McGraw-Hill, 2005; and Freshney, R. I., "Culture of Animal Cells: A Manual of Basic Technique," 4 th edition, John Wiley & Sons, Somerset, N J, 2000, the contents of which are incorporated in their entirety herein by reference.

Host cells can be cultured in a variety of media. Commercially available media such as Ham's F10 (Sigma), Minimal Essential Medium (MEM, Sigma), RPMI-1640 (Sigma), and Dulbecco's Modified Eagle's Medium (DMEM, Sigma) are suitable for culturing eukaryotic cells. In addition, animal cells can be grown in a defined medium that lacks serum but is supplemented with hormones, growth factors or any other factors necessary for the survival and/or growth of a particular cell type. Whereas a defined medium supporting cell survival maintains the viability, morphology, capacity to metabolize and potentially, capacity of the cell to differentiate, a defined medium promoting cell growth provides all chemicals necessary for cell proliferation or multiplication. The general parameters governing mammalian cell survival and growth in vitro are well established in the art. Physicochemical parameters which may be controlled in different cell culture systems are, e.g., pH, $pO_2$, temperature, and osmolarity. The nutritional requirements of cells are usually provided in standard media formulations developed to provide an optimal environment. Nutrients can be divided into several categories: amino acids and their derivatives, carbohydrates, sugars, fatty acids, complex lipids, nucleic acid derivatives and vitamins. Apart from nutrients for maintaining cell metabolism, most cells also require one or more hormones from at least one of the following groups: steroids, prostaglandins, growth factors, pituitary hormones, and peptide hormones to proliferate in serum-free media (Sato, G. H., et al. in "Growth of Cells in Hormonally Defined Media", Cold Spring Harbor Press, N.Y., 1982). In addition to hormones, cells may require transport proteins such as transferrin (plasma iron transport protein), ceruloplasmin (a copper transport protein), and high-density lipoprotein (a lipid carrier) for survival and growth in vitro. The set of optimal hormones or transport proteins will vary for each cell type. Most of these hormones or transport proteins have been added exogenously or, in a rare case, a mutant cell line has been found which does not require a particular factor. Those skilled in the art will know of other factors required for maintaining a cell culture without undue experimentation.

Growth media for growth of prokaryotic host cells include nutrient broths (liquid nutrient medium) or LB medium (Luria Bertani). Suitable media include defined and undefined media. In general, media contains a carbon source such as glucose needed for bacterial growth, water, and salts. Media may also include a source of amino acids and nitrogen, for example beef or yeast extract (in an undefined medium) or known quantities of amino acids (in a defined medium). In some embodiments, the growth medium is LB broth, for example LB Miller broth or LB Lennox broth. LB broth comprises peptone (enzymatic digestion product of casein), yeast extract and sodium chloride. In some embodiments, a selective medium is used which comprises an antibiotic. In this medium, only the desired cells possessing resistance to the antibiotic will grow.

II). Chimeric Polypeptide Assembly Compositions

The present invention relates, in part, to chimeric polypeptide assembly compositions (also referred to as "ProTIA") useful in the treatment, amelioration, or prevention of diseases including but not limited to cancers, autoimmune, or inflammatory disorders.

In a first aspect, the present disclosure provides a chimeric polypeptide assembly typically comprising a first portion, a second portion, and a third portion, wherein: said first portion comprises (i) a first binding domain with binding specificity to a target cell marker; and (ii) a second binding domain with binding specificity to an effector cell antigen; said second portion comprises a peptidyl release segment (RS) capable of being cleaved by one or more mammalian proteases; and said third portion comprises a bulking moiety; wherein said bulking moiety is capable of being released from said first portion by action of said mammalian protease on said second portion. Without being bound by theory, an exemplary polypeptide assembly of the present disclosure exhibits one or more of the following features: 1) the assembly comprises at least two binding domains with the capability to concurrently bind an effector cell and a target cell; 2) the assembly comprises a bulking moiety that i) shields the binding domains and reduces binding affinity for the target antigens when the composition is intact by way of, e.g., steric hindrance, ii) provides enhanced half-life of the composition when administered to a subject, and/or iii) reduces extravasation of the composition out of the vasculature in normal tissues and organs compared to diseased tissues (e.g., tumors), resulting in an increased safety profile compared to bispecific cytotoxic antibody therapeutics currently being used or evaluated in clinical trials; and 3) the assembly is capable of being cleaved by one or more mammalian proteases when in the proximity of diseased tissues, such as a tumor or inflammatory tissue, thereby releasing the binding domains of the first portion such that the binding domains can bind to the target cell marker and the effector cell antigen with a higher affinity as compared to the state when the binding domains are not cleaved from the assembly. The subject assembly can advantageously act as a "prodrug" in that the therapeutic portion (e.g., the first portion capable of bringing the target cell and effector cell together) is released at the site of a disease tissue, where the protease is preferentially expressed as compared to normal tissues. The subject assembly addresses several profound drawbacks of existing bispecific antibodies, including BiTE®. The subject assembly typically retains the known therapeutic benefits of tumor shrinkage effected by bispecific antibodies such as BiTE® while mitigating the side effects inherent in the conventional bispecific antibodies. In an embodiment, the invention provides chimeric polypeptide assembly compositions wherein the first portions comprises two binding domains in a single chain format wherein the first binding domain has binding specificity to a tumor-specific marker or an antigen of a target cell and the second binding domain has binding specificity to an effector cell antigen such as a receptor on or a ligand within the effector cell, such that the composition is bispecific.

In some embodiments, the design of the subject compositions is such that the action of the protease cleaves the release segment (RS) of the subject compositions, releasing the binding domains and the bulking moiety from the composition. Upon release from the composition, the first binding domain with binding specificity to a tumor-specific marker or an antigen of a target cell and the second binding domain with binding specificity to an effector cell antigen is capable of concurrently binding to, with greater binding affinity than the intact composition, and linking together the effector cell to the target cell, forming an immunological synapse with the result that, at very low effector to target (E:T) ratios, the target cell is acted upon by effector molecules released by the effector cell into the immunological synapse between the cells, resulting in damage, including, but not limited to perforin-mediated lysis, granzyme B-induced cell death and/or apoptosis of the target cell. In some embodiments, the released first portion of the subject composition compositions is designed with binding specificities such that it has the capability to concurrently bind effector cell cytotoxic T lymphocytes and preselected surface antigens on tumor cells in a subject, thereby effecting an immunological synapse and a selective, directed, and localized effect of released cytokines and effector molecules against the target tumor, with the result that tumor cells are damaged or destroyed, resulting in antitumor activity and therapeutic benefit to a subject. In other embodiments, the effector cell bound by the released first portion is a cell selected from the group consisting of plasma cell, B cell, cytokine induced killer cell (CIK cell), master cell, dendritic cell, regulatory T cell (RegT cell), helper T cell, myeloid cell, and NK cell.

In another aspect, the invention provides chimeric polypeptide assembly compositions comprising a first portion, a second portion, a third portion, a fourth portion, and a fifth portion, wherein the first portion comprises a first and a second binding domain (described more fully below), the second portion comprises a release segment (RS), the third portion comprises a bulking moiety (described more fully below), the fourth portion comprises a release segment (RS) that may be the same or may be different from the second portion RS, and the fifth portion comprises a bulking moiety that may be the same or may be different from the third portion bulking moiety; the composition being essentially in a prodrug form until acted upon by a protease.

The compositions address the long-felt need to provide bispecific therapeutics that have more selectivity, greater half-life, and result in less toxicity and fewer side effects once they are cleaved by proteases found in associated with the target tissues or tissues rendered unhealthy by a disease, such that the subject compositions have improved therapeutic index compared to bispecific antibody compositions known in the art. Such compositions are useful in the treatment of certain diseases, including, but not limited to cancer.

1. Binding Domains

It is an object of the invention to provide chimeric polypeptide assembly compositions comprising a first portion comprising at least a first binding domain with binding specificity to a target cell marker (e.g., a tumor-specific marker) and a second binding domain with binding specificity to an effector cell antigen. In some embodiments, the binding domains are linked as a single chain exhibiting bispecific binding specificity to a target cell marker and an effector cell antigen.

In another aspect, it is an object of the invention to provide cleavable chimeric polypeptide assembly compositions designed with configurations wherein the first portion binding domains are linked to the bulking moiety by a short peptide release segment comprising a cleavage sequence. In this exemplary configuration, the binding domains are shielded by the proximal bulking moiety component(s) in order to reduce or eliminate non-specific interactions and binding with non-diseased tissues or cells that are not the intended targets of the compositions, thereby reducing undesirable toxicity or side effects. In addition, the shielding bulking moiety is released at a target site (e.g., a disease tissue) upon cleavage of the release segment by a protease (described more fully below) that is preferentially expressed at the disease tissue. The released first portion then regains its ability to more freely or more avidly bind to the respective ligands, including a target cell marker and an effector cell marker. Not wishing to be bound by any particular theory, the subject chimeric polypeptide assembly confers manifold advantages as a therapeutic in terms of reduced frequency of administration, increased duration of therapeutic effect, and reduced severity in diagnostically associated side effects in the subject compared to the side effects upon or following administration of a comparable dose, in mmoles/kg, to a composition having only the first portion bispecific binding domains. Non-limiting examples of side effects that are avoided or reduced by use of the subject compositions include undesired increases in plasma levels of IL-2, TNF-alpha, IFN-gamma, liver enzymes, and/or incidences of sepsis, febrile neutropenia, neurotoxicity, convulsions, encephalopathy, cytokine release syndrome, speech disturbance, equilibrium disturbance, fever, headache, confusion, hypotension, neutropenia, nausea, impaired consciousness, and disorientation, The invention contemplates use of single chain binding domains for use in the subject compositions, such as but not limited to Fv, Fab, Fab', Fab'-SH, F(ab')2, linear antibodies, single domain antibody, single domain camelid antibody, single-chain antibody molecules (scFv), and diabodies capable of binding ligands or receptors associated with effector cells and antigens of diseased tissues or cells that are cancers, tumors, or other malignant tissues. In other embodiments, the first and the second binding domains of the first portion of the chimeric polypeptide assembly compositions can be non-antibody scaffolds such as anticalins, adnectins, fynomers, affilins, affibodies, centyrins, DARPins. In other embodiments the binding domain for the tumor cell target is a variable domain of a T cell receptor that has been engineered to bind MHC that is loaded with a peptide fragment of a protein that is overexpressed by tumor cells. The compositions of the instant invention are designed with considerations of the location of the target tissue protease as well as the presence of the same protease in healthy tissues not intended to be targeted, as well as the presence of the target ligand in healthy tissue but a greater presence of the ligand in unhealthy target tissue, in order to provide a wide therapeutic window. A "therapeutic window" refers to the largest difference between the minimal effective dose and the maximal tolerated dose for a given therapeutic composition. To help achieve a wide therapeutic window, the binding domains of the first portion of the compositions are shielded by the proximity of the bulking moiety (e.g., XTEN) such that the binding affinity of the intact composition for one or both of the ligands is reduced compared to the composition that has been cleaved by a mammalian protease, thereby releasing the first portion from the shielding effects of the bulking moiety.

With respect to single chain binding domains, as is well established, Fv is the minimum antibody fragment which contains a complete antigen recognition and binding site; consisting of a dimer of one heavy (VH) and one light chain variable domain (VL) in non-covalent association. Within each VH and VL chain are three complementarity determining regions (CDRs) that interact to define an antigen binding site on the surface of the VH-VL dimer; the six CDRs of a binding domain confer antigen binding specificity to the antibody or single chain binding domain. In some cases, scFv are created in which each has 3, 4, or 5 CHRs within each binding domain. Framework sequences flanking the CDRs have a tertiary structure that is essentially conserved in native immunoglobulins across species, and the framework residues (FR) serve to hold the CDRs in their appropriate orientation. The constant domains are not required for binding function, but may aid in stabilizing VH-VL interaction. The domain of the binding site of the polypeptide of the invention can be a pair of VH-VL, VH-VH or VL-VL domains either of the same or of different immunoglobulins, however it is generally preferred to make single chain binding domains using the respective VH and VL chains from the parental antibody. The order of VH and VL domains within the polypeptide chain is not limiting for the present invention; the order of domains given may be reversed usually without any loss of function, but it is understood that the VH and VL domains are arranged so that the antigen binding site can properly fold. Thus, the single chain binding domains of the bispecific scFv embodiments of the subject compositions can be in the order (VL-VH)1-(VL-VH)2, wherein "1" and "2" represent the first and second binding domains, respectively, or (VL-VH)1-(VH-VL)2, or (VH-VL)1-(VL-VH)2, or (VH-VL)1-(VH-VL)2, wherein the paired binding domains are linked by a polypeptide linker as described herein, below.

The arrangement of the binding domains in an exemplary bispecific single chain antibody disclosed herein may therefore be one in which the first binding domain is located C-terminally to the second binding domain. The arrangement of the V chains may be VH (target cell surface antigen)-VL(target cell surface antigen)-VL(effector cell antigen)-VH(effector cell antigen), VH(target cell surface antigen)-VL(target cell surface antigen)-VH(effector cell antigen)-VL(effector cell antigen), VL(target cell surface antigen)-VH(target cell surface antigen)-VL(effector cell antigen)-VH(effector cell antigen) or VL(target cell surface antigen)-VH(target cell surface antigen)-VH(effector cell antigen)-VL(effector cell antigen). For an arrangement, in which the second binding domain is located N-terminally to the first binding domain, the following orders are possible: VH (effector cell antigen)-VL(effector cell antigen)-VL(target cell surface antigen)-VH(target cell surface antigen), VH(effector cell antigen)-VL(effector cell antigen)-VH(target cell surface antigen)-VL(target cell surface antigen), VL(effector cell antigen)-VH(effector cell antigen)-VL(target cell surface antigen)-VH(target cell surface antigen) or VL(effector cell antigen)-VH(effector cell antigen)-VH(target cell surface antigen)-VL(target cell surface antigen). As used herein, "N-terminally to" or "C-terminally to" and grammatical variants thereof denote relative location within the primary amino acid sequence rather than placement at the absolute N- or C-terminus of the bispecific single chain antibody. Hence, as a non-limiting example, a first binding domain which is "located C-terminally to the second binding domain" denotes that the first binding is located on the carboxyl side of the second binding domain within the bispecific single chain antibody, and does not exclude the possibility that an additional sequence, for example a His-tag, or another compound such as a radioisotope, is located at the C-terminus of the bispecific single chain antibody.

In one embodiment, the chimeric polypeptide assembly compositions comprise a first portion comprising a first binding domain and a second binding domain wherein each of said binding domains is an scFv and wherein each scFv comprises one VL and one VH. In another embodiment, the chimeric polypeptide assembly compositions comprise a first portion comprising a first binding domain and a second binding domain wherein said binding domains are in a diabody configuration and wherein each domain comprises one VL domain and one VH. In the foregoing embodiments, the first domain has binding specificity to a tumor-specific marker or an antigen of a target cell and the second binding domain has binding specificity to an effector cell antigen. In one embodiment of the foregoing, the effector cell antigen is expressed on or within an effector cell. In one embodiment, the effector cell antigen is expressed on a T cell, such as a CD4+, CD8+, or natural killer (NK) cell. In another embodiment, the effector cell antigen is expressed on a B cell, master cell, dendritic cell, or myeloid cell. In one embodiment, the effector cell antigen is CD3, the cluster of differentiation 3 antigen of a cytotoxic T cell. In some embodiments of the foregoing, the first binding domain exhibits binding specificity to a tumor-specific marker associated with a tumor cell. In one embodiment, the binding domain has binding affinity to a tumor-specific marker wherein the tumor cell can include without limitation cells fromstroma cell tumor, fibroblast tumor, myofibroblast tumor, glial cell tumor, epithelial cell tumor, fat cell tumor, immune cell tumor, vascular cell tumor, and smooth muscle cell tumor. In one embodiment, the tumor-specific marker or an antigen of a target cell is selected from the group consisting of alpha 4 integrin, Ang2, B7-H3, B7-H6, CEACAM5, cMET, CTLA4, FOLR1, EpCAM, CCR5, CD19, HER2, HER2 neu, HER3, HER4, HER1 (EGFR), PD-L1, PSMA, CEA, MUC1(mucin), MUC-2, MUC3, MUC4, MUC5AC, MUC5B, MUC7, MUC16 βhCG, Lewis-Y, CD20, CD33, CD38, CD30, CD56 (NCAM), CD133, ganglioside GD3; 9-O-Acetyl-GD3, GM2, Globo H, fucosyl GM1, GD2, carbonicanhydrase IX, CD44v6, Sonic Hedgehog (Shh), Wue-1, plasma cell antigen 1, melanoma chondroitin sulfate proteoglycan (MCSP), CCR8, 6-transmembrane epithelial antigen of prostate (STEAP), mesothelin, A33 antigen, prostate stem cell antigen (PSCA), Ly-6, desmoglein 4, fetal acetylcholine receptor (fnAChR), CD25, cancer antigen 19-9 (CA19-9), cancer antigen 125 (CA-125), Muellerian inhibitory substance receptor type II (MISIIR), sialylated Tn antigen (s TN), fibroblast activation antigen (FAP), endosialin (CD248), epidermal growth factor receptor variant III (EGFRvIII), tumor-associated antigen L6 (TAL6), SAS, CD63, TAG72, Thomsen-Friedenreich antigen (TF-antigen), insulin-like growth factor I receptor (IGF-IR), Cora antigen, CD7, CD22, CD70, CD79a, CD79b, G250, MT-MMPs, F19 antigen, CA19-9, CA-125, alpha-fetoprotein (AFP), VEGFR1, VEGFR2, DLK1, SP17, ROR1, and EphA2. In one embodiment, the first binding domain that exhibits binding affinity to CD70 is its natural ligand, CD27 rather than an antibody fragment. In another embodiment, the first binding domain that exhibits binding affinity to B7-H6 is its natural ligand Nkp30 rather than an antibody fragment.

It is envisaged that the scFv embodiments of the subject compositions of the invention comprise a first binding domain and a second binding domain wherein the VL and VH domains are derived from monoclonal antibodies with binding specificity to the tumor-specific marker or an antigen of a target cell and effector cell antigens, respectively. In other cases, the first and second binding domains each comprise six CDRs derived from monoclonal antibodies with binding specificity to the a target cell marker, such as a tumor-specific marker and effector cell antigens, respectively. In other embodiments, the first and second binding domains of the first portion of the subject compositions can have 3, 4, or 5 CHRs within each binding domain. In other embodiments, the embodiments of the invention comprise a first binding domain and a second binding domain wherein each comprises a CDR-H1 region, a CDR-H2 region, a CDR-H3 region, a CDR-L1 region, a CDR-L2 region, and a CDR-H3 region, wherein each of said regions is derived from a monoclonal antibody capable of binding the tumor-specific marker or an antigen of a target cell, and effector cell antigens, respectively. In one embodiment, the invention provides a chimeric polypeptide assembly composition wherein the second binding domain comprises VH and VL regions derived from a monoclonal antibody capable of binding human CD3. In another embodiment, the invention provides a chimeric polypeptide assembly composition, wherein the scFv second binding domain comprises VH and VL regions wherein each VH and VL regions exhibit at least about 90%, or 91%, or 92%, or 93%, or 94%, or 95%, or 96%, or 97%, or 98%, or 99% identity to or is identical to paired VL and VH sequences of an anti-CD3 antibody selected from Table 1. In another aspect, the second domain embodiments of the invention comprise a CDR-H1 region, a CDR-H2 region, a CDR-H3 region, a CDR-L1 region, a CDR-L2 region, and a CDR-H3 region, wherein each of said regions is derived from a monoclonal antibody selected from the group of antibodies set forth in Table 1. In the foregoing embodiments, the VH and/or VL domains can be configured as scFv, diabodies, a single domain antibody, or a single domain camelid antibody.

In other embodiments, the second domains of the subject compositions are derived from an anti-CD3 antibody selected from the group of antibodies set forth in Table 1. In one embodiment of the foregoing, the second domain of the subject composition comprises the paired VL and the VH region sequences of the anti-CD3 antibody selected from the group of antibodies set forth in Table 1. In another embodiment, the invention provides a chimeric polypeptide assembly composition, wherein the second binding domain comprises VH and VL regions wherein each VH and VL regions exhibit at least about 90%, or 91%, or 92%, or 93%, or 94%, or 95%, or 96%, or 97%, or 98%, or 99% identity to or is identical to paired VL and VH sequences of the huUCHT1 anti-CD3 antibody of Table 1. In the foregoing embodiments, the VH and/or VL domains can be configured as scFv, a portion of a diabody, a single domain antibody, or a single domain camelid antibody.

In other embodiments, the scFv of the first domain of the composition are derived from an anti-tumor cell antibody selected from the group of antibodies set forth in Table 2. In another embodiment, the invention provides a chimeric polypeptide assembly composition, wherein the first binding domain comprises VH and VL regions wherein each VH and VL regions exhibit at least about 90%, or 91%, or 92%, or 93%, or 94%, or 95%, or 96%, or 97%, or 98%, or 99% identity to or is identical to paired VL and VH sequences of an anti-tumor cell antibody selected from Table 2. In one embodiment of the foregoing, the first domain of the recited compositions comprises the paired VL and the VH region sequences of an anti-tumor cell antibody disclosed herein. In the foregoing embodiments, the VH and/or VL domains can be configured as scFv, a portion of a diabody, a single domain antibody, or a single domain camelid antibody.

In another embodiment, the first portion of the chimeric polypeptide assembly compositions has a sequence with at least about 90%, or 91%, or 92%, or 93%, or 94%, or 95%, or 96%, or 97%, or 98%, or 99% identity to a sequence selected from the group consisting of the sequences of Table 13.

In another embodiment, the chimeric polypeptide assembly compositions comprise a first portion comprising a first binding domain and a second binding domain wherein said binding domains are in a diabody configuration and each of said binding domains comprises one VL domain and one VH domain. In one embodiment, the diabody embodiments of the invention comprise a first binding domain and a second binding domain wherein the VL and VH domains are derived from monoclonal antibodies with binding specificity to a tumor-specific marker or an antigen of a target cell, and the effector cell antigen, respectively. In another embodiment, the diabody embodiments of the invention comprise a first binding domain and a second binding domain wherein each comprises a CDR-H1 region, a CDR-H2 region, a CDR-H3 region, a CDR-L1 region, a CDR-L2 region, and a CDR-H3 region, wherein each of said regions is derived from a monoclonal antibody capable of binding the tumor-specific marker or target cell antigen, and the effector cell antigen, respectively. It is envisaged that the diabody embodiments of the invention comprise a first binding domain and a second binding domain wherein the VL and VH domains are derived from monoclonal antibodies with binding specificity to the tumor-specific marker or target cell antigen, and the effector cell antigen, respectively. In another aspect, the diabody embodiments of the invention comprise a first binding domain and a second binding domain wherein each comprises a CDR-H1 region, a CDR-H2 region, a CDR-H3 region, a CDR-L1 region, a CDR-L2 region, and a CDR-H3 region, wherein each of said regions is derived from a monoclonal antibody capable of binding the tumor-specific marker or target cell antigen, and the effector cell antigen, respectively. In one embodiment, the invention provides a chimeric polypeptide assembly composition wherein the diabody second binding domain comprises the paired VH and VL regions derived from a monoclonal antibody capable of binding human CD3. In another embodiment, the invention provides a chimeric polypeptide assembly composition, wherein the diabody second binding domain comprises VH and VL regions wherein each VH and VL regions exhibit at least about 90%, or 91%, or 92%, or 93%, or 94%, or 95%, or 96%, or 97%, or 98%, or 99% identity to or is identical to paired VL and VH sequences of an anti-CD3 antibody selected from Table 1. In another embodiment, the invention provides a chimeric polypeptide assembly composition, wherein the diabody second binding domain comprises VH and VL regions wherein each VH and VL regions exhibit at least about 90%, or 91%, or 92%, or 93%, or 94%, or 95%, or 96%, or 97%, or 98%, or 99% identity to or is identical to the VL and a VH sequence of the huUCHT1 antibody selected of Table 1. In other embodiments, the diabody second domain of the composition is derived from an anti-CD3 antibody described herein. In another embodiment, the invention provides a chimeric polypeptide assembly composition, wherein the diabody first binding domain comprises VH and VL regions wherein each VH and VL regions exhibit at least about 90%, or 91%, or 92%, or 93%, or 94%, or 95%, or 96%, or 97%, or 98%, or 99% identity to or is identical to VL and VH sequences of an anti-tumor cell antibody selected from Table 2. In other embodiments, the diabody first domain of the composition is derived from an anti-tumor cell antibody described herein.

Therapeutic monoclonal antibodies from which VL and VH and CDR domains can be derived for the subject compositions are known in the art. Such therapeutic antibodies include, but are not limited to, rituximab, IDEC/Genentech/Roche (see for example U.S. Pat. No. 5,736,137), a chimeric anti-CD20 antibody used in the treatment of many lymphomas, leukemias, and some autoimmune disorders; ofatumumab, an anti-CD20 antibody approved for use for chronic lymphocytic leukemia, and under development for follicular non-Hodgkin's lymphoma, diffuse large B cell lymphoma, rheumatoid arthritis and relapsing remitting multiple sclerosis, being developed by GlaxoSmithKline; lucatumumab (HCD122), an anti-CD40 antibody developed by Novartis for Non-Hodgkin's or Hodgkin's Lymphoma (see, for example, U.S. Pat. No. 6,899,879), AME-133, an antibody developed by Applied Molecular Evolution which binds to cells expressing CD20 to treat non-Hodgkin's lymphoma, veltuzumab (hA20), an antibody developed by Immunomedics, Inc. which binds to cells expressing CD20 to treat immune thrombocytopenic purpura, HumaLYM developed by Intracel for the treatment of low-grade B-cell lymphoma, and ocrelizumab, developed by Genentech which is an anti-CD20 monoclonal antibody for treatment of rheumatoid arthritis (see for example U.S. Patent Application 20090155257), trastuzumab (see for example U.S. Pat. No. 5,677,171), a humanized anti-Her2/neu antibody approved to treat breast cancer developed by Genentech; pertuzumab, an anti-HER2 dimerization inhibitor antibody developed by Genentech in treatment of in prostate, breast, and ovarian cancers; (see for example U.S. Pat. No. 4,753,894); cetuximab, an anti-EGFR antibody used to treat epidermal growth factor receptor (EGFR)-expressing, KRAS wild-type metastatic colorectal cancer and head and neck cancer, developed by Imclone and BMS (see U.S. Pat. No. 4,943,533; PCT WO 96/40210); panitumumab, a fully human monoclonal antibody specific to the epidermal growth factor receptor (also known as EGF receptor, EGFR, ErbB-1 and HER1, currently marketed by Amgen for treatment of metastatic colorectal cancer (see U.S. Pat. No. 6,235,883); zalutumumab, a fully human IgG1 monoclonal antibody developed by Genmab that is directed towards the epidermal growth factor receptor (EGFR) for the treatment of squamous cell carcinoma of the head and neck (see for example U.S. Pat. No. 7,247,301); nimotuzumab, a chimeric antibody to EGFR developed by Biocon, YM Biosciences, Cuba, and Oncosciences, Europe) in the treatment of squamous cell carcinomas of the head and neck, nasopharyngeal cancer and glioma (see for example U.S. Pat. Nos. 5,891,996; 6,506,883); alemtuzumab, a humanized monoclonal antibody to CD52 marketed by Bayer Schering Pharma for the treatment of chronic lymphocytic leukemia (CLL), cutaneous T-cell lymphoma (CTCL) and T-cell lymphoma; muromonab-CD3, an anti-CD3 antibody developed by Ortho Biotech/Johnson & Johnson used as an immunosuppressant biologic given to reduce acute rejection in patients with organ transplants; ibritumomab tiuxetan, an anti-CD20 monoclonal antibody developed by IDEC/Schering AG as treatment for some forms of B cell non-Hodgkin's lymphoma; gemtuzumab ozogamicin, an anti-CD33 (p67 protein) antibody linked to a cytotoxic chelator tiuxetan, to which a radioactive isotope is attached, developed by Celltech/Wyeth used to treat acute myelogenous leukemia; ABX-CBL, an anti-CD147 antibody developed by Abgenix; ABX-IL8, an anti-IL8 antibody developed by Abgenix, ABX-MA1, an anti-MUC18 antibody developed by Abgenix, Pemtumomab (R1549, 90Y-muHMFG1), an anti-MUC1 in development by Antisoma, Therex (R1550), an anti-MUC1 antibody developed by Antisoma, AngioMab (AS1405), developed by Antisoma, HuBC-1, developed by Antisoma, Thioplatin (AS1407) developed by Antisoma, ANTEGREN (natalizumab), an anti-alpha-4-beta-1 (VLA4) and alpha-4-beta-7 antibody developed by Biogen, VLA-1 mAb, an anti-VLA-1 integrin antibody developed by Biogen, LTBR mAb, an anti-lymphotoxin beta receptor (LTBR) antibody developed by Biogen, CAT-152, an anti-TGF-02 antibody developed by Cambridge Antibody Technology, J695, an anti-IL-12 antibody developed by Cambridge Antibody Technology and Abbott, CAT-192, an anti-TGF431 antibody developed by Cambridge Antibody Technology and Genzyme, CAT-213, an anti-Eotaxin1 antibody developed by Cambridge Antibody Technology, LYMPHOSTAT-B, an anti-Blys antibody developed by Cambridge Antibody Technology and Human Genome Sciences Inc., TRAIL-R1mAb, an anti-TRAIL-R1 antibody developed by Cambridge Antibody Technology and Human Genome Sciences, Inc.; HERCEPTIN, an anti-HER receptor family antibody developed by Genentech; Anti-Tissue Factor (ATF), an anti-Tissue Factor antibody developed by Genentech; XOLAIR (Omalizumab), an anti-IgE antibody developed by Genentech, MLN-02 Antibody (formerly LDP-02), developed by Genentech and Millennium Pharmaceuticals; HUMAX CD4®, an anti-CD4 antibody developed by Genmab; tocilizuma, and anti-IL6R antibody developed by Chugai; HUMAX-IL15, an anti-IL15 antibody developed by Genmab and Amgen, HUMAX-Inflam, developed by Genmab and Medarex; HUMAX-Cancer, an anti-Heparanase I antibody developed by Genmab and Medarex and Oxford GlycoSciences; HUMAX-Lymphoma, developed by Genmab and Amgen, HUMAX-TAC, developed by Genmab; IDEC-131, an anti-CD40L antibody developed by IDEC Pharmaceuticals; IDEC-151 (Clenoliximab), an anti-CD4 antibody developed by IDEC Pharmaceuticals; IDEC-114, an anti-CD80 antibody developed by IDEC Pharmaceuticals; IDEC-152, an anti-CD23 developed by IDEC Pharmaceuticals; an anti-KDR antibody developed by Imclone, DC101, an anti-flk-1 antibody developed by Imclone; anti-VE cadherin antibodies developed by Imclone; CEA-CIDE (labetuzumab), an anti-carcinoembryonic antigen (CEA) antibody developed by Immunomedics; Yervoy (ipilimumab), an anti-CTLA4 antibody developed by Bristol-Myers Squibb in the treatment of melanoma; Lumphocide® (Epratuzumab), an anti-CD22 antibody developed by Immunomedics, AFP-Cide, developed by Immunomedics; MyelomaCide, developed by Immunomedics; LkoCide, developed by Immunomedics; ProstaCide, developed by Immunomedics; MDX-010, an anti-CTLA4 antibody developed by Medarex; MDX-060, an anti-CD30 antibody developed by Medarex; MDX-070 developed by Medarex; MDX-018 developed by Medarex; OSIDEM (IDM-1), an anti-HER2 antibody developed by Medarex and Immuno-Designed Molecules; HUMAX®-CD4, an anti-CD4 antibody developed by Medarex and Genmab; HuMax-IL15, an anti-IL15 antibody developed by Medarex and Genmab; anti-intercellular adhesion molecule-1 (ICAM-1) (CD54) antibodies developed by MorphoSys, MOR201; tremelimumab, an anti-CTLA-4 antibody developed by Pfizer; visilizumab, an anti-CD3 antibody developed by Protein Design Labs; Anti-a 5(31 Integrin, developed by Protein Design Labs; anti-IL-12, developed by Protein Design Labs; ING-1, an anti-Ep-CAM antibody developed by Xoma; and MLN01, an anti-Beta2 integrin antibody developed by Xoma; all of the above-cited antibody references in this paragraph are expressly incorporated herein by reference. The sequences for the above antibodies can be obtained from publicly available databases, patents, or literature references. In addition, non-limiting examples of monoclonal antibodies and VH and VL sequences from anti-CD3 antibodies are presented in Table 1 and non-limiting examples of monoclonal antibodies and VH and VL sequences to cancer, tumor, or target cell markers are presented in Table 2.

TABLE 1

Anti-CD3 Monoclonal Antibodies and Sequences

| Clone Name | Antibody Name | Target | VH Sequence | SEQ ID NO: | VL Sequence | SEQ ID NO: |
|---|---|---|---|---|---|---|
| huOKT3 | | CD3 | QVQLVQSGGGVVQPGRSLRLSCKAS**GYTFTRYTMH**WVRQAPGKGLEWIG**YINPSRGYTNYNQKVKD**RFTISRDNSKNTAFLQMDSLRPEDTGVYFCAR**YYDDHYCLDY**WGQGTPVTVSS | 22 | DIQMTQSPSSLSASVGDRVTITC**SASSSVSYMN**WYQQTPGKAPKRWIY**DTSKLAS**GVPSRFSGSGSGTDYTFTISSLQPEDIATYYC**QQWSSNPFT**FGQGTKLQITR | 32 |
| huUCHT1 | | CD3 | EVQLVESGGGLVQPGGSLRLSCAAS**GYSFTGYTMN**WVRQAPGKGLEWVA**LINPYKGVST**YNQKFKDRFTISVDKSKNTAYLQMNSLRAEDTAVYYCAR**SGYYGDSDWYFDV**WGQGTLVTVSS | 23 | DIQMTQSPSSLSASVGDRVTITC**RASQDIRNYLN**WYQQKPGKAPKLLIY**YTSRLES**GVPSRFSGSGSGTDYTLTISSLQPEDFATYYC**QQGNTLPWT**FGQGTKVEIK | 33 |
| hu12F6 | | CD3 | QVQLVQSGGGVVQPGRSLRLSCKAS**GYTFTSYTMH**WVRQAPGKGLEWIG**YINPSSGYTKYNQKFKD**RFTISADKSKSTAFLQMDSLRPEDTGVYFCAR**WQDYDVYFDY**WGQGTPVTVSS | 24 | DIQMTQSPSSLSASVGDRVTMTC**RASSSVSYMH**WYQQTPGKAPKPWIY**ATSNLAS**GVPSRFSGSGSGTDYTLTISSLQPEDIATYYC**QQWSSNPPT**FGQGTKLQITR | 34 |
| mOKT3 | | CD3 | QVQLQQSGAELARPGASVKMSCKAS**GYTFTRYTMH**WVKQRPGQGLEWIG**YINPSRGYTNYNQKFKD**KATLTTDKSSSTAYMQLSSLTSEDSAVYYCAR**YYDDHYCLDY**WGQGTTLTVSS | 25 | QIVLTQSPAIMSASPGEKVTMTC**SASSSVSYMN**WYQQKSGTSPKRWIY**DTSKLAS**GVPAHFRGSGSGTSYSLTISGMEAEDAATYYC**QQWSSNPFT**FGSGTKLEINR | 35 |
| MT103 | blinatumomab | CD3 | DIKLQQSGAELARPGASVKMSCKTS**GYTFTRYTMH**WVKQRPGQGLEWIG**YINPSRGYTNYNQKFKD**KATLTTDKSSSTAYMQLSSLTSEDSAVYYCAR**YYDDHYCLDY**WGQGTTLTVSS | 26 | DIQLTQSPAIMSASPGEKVTMTC**RASSSVSYMN**WYQQKSGTSPKRWIY**DTSKVAS**GVPYRFSGSGSGTSYSLTISSMEAEDAATYYC**QQWSSNPLT**FGAGTKLELK | 36 |
| MT110 | solitomab | CD3 | DVQLVQSGAEVKKPGASVKVSCKAS**GYTFTRYTMH**WVRQAPGQGLEWIG**YINPSRGYTNYADSVKG**RFTITTDKSTSTAYMELSSLRSEDTATYYCAR**YYDDHYCLDY**WGQGTTVTVSS | 27 | DIVLTQSPATLSLSPGERATLSC**RASQSVSYMN**WYQQKPGKAPKRWIY**DTSKVAS**GVPARFSGSGSGTDYSLTINSLEAEDAATYYC**QQWSSNPLT**FGGGTKVEIK | 37 |

TABLE 1-continued

Anti-CD3 Monoclonal Antibodies and Sequences

| Clone Name | Antibody Name | Target | VH Sequence | SEQ ID NO: | VL Sequence | SEQ ID NO: |
|---|---|---|---|---|---|---|
| CD3.7 | | CD3 | EVQLVESGGGLVQPGGSLKLSCAASGFTENKYAMNWVRQAPGKGLEWVARIRSKYNNYATYYADSVKDRFTISRDDSKNTAYLQMNNLKTEDTAVYYCVRHGNEGNSYISYWAYWGQGTLVTVSS | 28 | QTVVTQEPSLTVSPGGTVTLTCGSSTGAVTSGYYPNWVQQKPGQAPRGLIGGTKFLAPGTPARFSGSLLGGKAALTLSGVQPEDEAEYYCALWYSNRWVEGGGTKLTVL | 38 |
| CD3.8 | | CD3 | EVQLVESGGGLVQPGGSLRLSCAASGFTENTYAMNWVRQAPGKGLEWVGRIRSKYNNYATYYADSVKGRFTISRDDS KNTLYLQMNSLRAEDTAVYYCVRHGNFGNSYVSWFAYWGQGTLVTVSS | 29 | QAVVTQEPSLTVSPGGTVTLTCGSSTGAVTTSNYANWVQQKPGQAPRGLIGGTNKRAPGVPARFSGSLLGGKAALTLSGAQPEDEAEYYCALWYSNLWVFGGGTKLTVL | 39 |
| CD3.9 | | CD3 | EVQLLESGGGLVQPGGSLKLSCAASGFTENTYAMNWVRQAPGKGLEWVARIRSKYNNYATYYADSVKDRFTISRDDSKNTAYLQMNNLKTEDTAVYYCVRHGNEGNSYVSWFAYWGQGTLVTVSS | 30 | ELVVTQEPSLTVSPGGTVTLTCRSSTGAVTTSNYANWVQQKPGQAPRGLIGGTNKRAPGTPARFSGSLLGGKAALTLSGVQPEDEAEYYCALWYSNLWVEGGGTKLTVL | 40 |
| CD3.10 | | CD3 | EVKLLESGGGLVQPKGSLKLSCAASGFTENTYAMNWVRQAPGKGLEWVARIRSKYNNYATYYADSVKDRFTISRDDSQSILYLQMNNLKTEDTAMYYCVRHGNEGNSYVSWFAYWGQGTLVTVSS | 31 | QAVVTQESALTTSPGETVTLTCRSSTGAVTTSNYANWVQEKPDHLFTGLIGGTNKRAPGVPARFSGSLIGDKAALTITGAQTEDEAIYFCALWYSNLWVEGGGTKLTVL | 41 |

* underlined sequences, if present, are CDRs within the VL and VH

TABLE 2

Anti-target Cell Monoclonal Antibodies and Sequences

| Trade Name | Antibody Name | Target | VH Sequence | SEQ ID NO: | VL Sequence | SEQ ID NO: |
|---|---|---|---|---|---|---|
| Tysabri™ | natalizumab | Alpha 4 Integrin | QVQLVQSGAEVKKPGASVKVSCKASGENIK**DTYIH**WVRQAPGQRLEWMG**RIDPANGYTKYDPKFQG**RVTITADTSASTAYMELSSLRSEDTAVYYCAR**EGYYGNYGVYAMDY**WGQGTLVTVSS | 42 | DIQMTQSPSSLSASVGDRVTITC**KTSQDINKYMA**WYQQTPGKAPRLLIH**YTSALQ**PGIPSRFSGSGSGRDYTFTISSLQPEDIATYYC**LQYDNLWT**FGQGTKVEIK | 141 |
| REGN910 | nesvacumab | Ang2 | EVQLVESGGGLVQPGGSLRLSCAAS**GFTFSSYDIH**WVRQATGKGLEWVSAI**GPAGDTYYPGSV**KGRFTISRENAKNSLYLQMNSLRAGDTAVYYCAR**GLITFGGLIAPFD**YWGQGTLVTVSS | 43 | EIVLTQSPGTLSLSPGERATLSCRA**SQSVSSTYLA**WYQQKPGQAPRLLIY**GASSRAT**GIPDRESGSGSGTDFTLTISRLEPEDEAVYYC**QHYDNSQ**TFGQGTKVEIK | 142 |

TABLE 2-continued

Anti-target Cell Monoclonal Antibodies and Sequences

| Trade Name | Antibody Name | Target | VH Sequence | SEQ ID NO: | VL Sequence | SEQ ID NO: |
|---|---|---|---|---|---|---|
| hMFE23 | | CEA | QVKLEQSGAEVVKPGASVKLSCKAS**GFNIKDS**YMHWLRQGPGQRLEWIGWI**DPENGD**TEYAPKFQGKATFTTDTSANTAYLGLSSLRPEDTAVYYCNEG**TPTGPYYFD**YWGQGTLVTVSS | 44 | ENVLTQSPSSMSASVGDRVNIACSA**SSSVS**YMHWFQQKPGKSPKLWIYSTSN**LAS**GVPSRFSGSGSGTDYSLTISSMQPEDAATYYCQQ**RSSYPL**TFGGGTKLEIK | 143 |
| M5A (humanized T84.66) | | CEA | EVQLVESGGGLVQPGGSLRLSCAASGENIK**DTYMH**WVRQAPGKGLEWVA**RIDPANGNSKYADSVKG**RFTISADTSKNTAYLQMNSLRAEDTAVYYCAP**FGYYVSDYAMAY**WGQGTLVTVSS | 45 | DIQLTQSPSSLSASVGDRVTITC**RAGESVDIFGVGFLH**WYQQKPGKAPKLLIY**RASNLES**GVPSRFSGSGSRTDFTLTISSLQPEDFATYYC**QQTNEDPYT**FGQGTKVEIK | 144 |
| M5B (humanized T84.66) | | CEA | EVQLVESGGGLVQPGGSLRLSCAASGENIK**DTYMH**WVRQAPGKGLEWVA**RIDPANGNSKYVPKFQG**RATISADTSKNTAYLQMNSLRAEDTAVYYCAP**FGYYVSDYAMAY**WGQGTLVTVSS | 46 | DIQLTQSPSSLSASVGDRVTITC**RAGESVDIFGVGELH**WYQQKPGKAPKLLIY**RASNLES**GVPSRESGSGSRTDFTLTISSLQPEDFATYYC**QQTNEDPYT**FGQGTKVEIK | 144 |
| CEA-Cide | Labetuzumab (MN-14) | CEACAM5 | EVQLVESGGGVVQPGRSLRLSCSASGEDFT**TYWMS**WVRQAPGKGLEWIG**EIHPDSSTINYAPSLKD**RFTISRDNAKNTLFLQMDSLRPEDTGVYFCAS**LYFGFPWFAY**WGQGTPVTVSS | 47 | DIQLTQSPSSLSASVGDRVTITC**KASQDVGTSVA**WYQQKPGKAPKLLIY**WTSTRHT**GVPSRFSGSGSGTDFTFTISSLQPEDIATYYC**QQYSLYRS**FGQGTKVEIK | 145 |
| CEA-Scan | arcitumomab | CEACAM5 | EVKLVESGGGLVQPGGSLRLSCATSG**FTFTDYYMN**WVRQPPGKALEWLG**FIGNKANGYTTEYSAS**VKGRFTISRDKSQSILYLQMNTLRAEDSA**TYYCTRDR**GLRFYFDYWGQGTTLTVSS | 48 | QTVLSQSPAILSASPGEKVTMTC**RASSSVTYIHW**YQQKPGSSPKSWIYA**TSNLAS**GVPARFSGSGSGTSYSLTISRVEAEDAATYYC**QHWSSKPPT**FGGGTKLEIKR | 146 |
| MT110 | | CEACAM5 | EVQLVESGGGLVQPGRSLRLSCAASGFTVS**SYWMH**WVRQAPGKGLEWVG**FIRNKANGGTTEYAASVKG**RFTISRDDSKNTLYLQMNSLRAEDTAVYYCAR**DRGLRFYFDY**WGQGTTVTVSS | 49 | QAVLTQPASLSASPGASASLTC**TLRRGINVGAYSIY**WYQQKPGSPPQYLLR**YKSDSDKQQGS**GVSSRFSASKDASANAGILLISGLQSEDEADYYC**MIWHSGASAV**FGGGTKLTVL | 147 |
| MT103 | blinatumomab | CD19 | QVQLQQSGAELVRPGSSVKISCKASGYAFS**SYWMN**WVKQRPGQGLEWIG**QIWPGDGDTNYNGKFKG**KATLTADESSSTAYMQLSSLASEDSAVYFCAR**RETTTVGRYYYAMDY**WGQGTTVTVSS | 50 | DIQLTQSPASLAVSLGQRATISC**KASQSVDYDGDSYL**NWYQQIPGQPPKLLI**YDASNLVS**GIPPRESGSGSGTDETLNIHPVEKVDAATYHC**QQSTEDPWT**FGGGTKLEIK | 148 |
| Arzerra | ofatumumab | CD20 | EVQLVESGGGLVQPGRSLRLSCAASGFTFN**DYAMH**WVRQAPGKGLEWVS**TISWNSG** | 51 | EIVLTQSPATLSLSPGERATLSC**RASQSVSSYLA**WYQQKPGQAPRLLIY**DASNRAT** | 149 |

TABLE 2-continued

Anti-target Cell Monoclonal Antibodies and Sequences

| Trade Name | Antibody Name | Target | VH Sequence | SEQ ID NO: | VL Sequence | SEQ ID NO: |
|---|---|---|---|---|---|---|
| | | | **SIGYADSVKG**RFTISRDNAKKSLYLQMNSLRAEDTALYYCAK**DIQYGNYYYGMDV**WGQGTTVTVSS | | GIPARFSGSGSGTDFTLTISSLEPEDFAVYYC**QQRSNWPIT**FGQGTRLEIK | |
| Bexxar™ | tositumomab | CD20 | QAYLQQSGAELVRPGASVKMSCKASGYTFT**SYNMH**WVKQTPRQGLEWIG**AIYPGNGDTSYNQKFKG**KATLTVDKSSSTAYMQLSSLTSEDSAVYFCAR**VVYYSNSYWYFDV**WGTGTTVTVSG | 52 | QIVLSQSPAILSASPGEKVTMTC**RASSSVSYMH**WYQQKPGSSPKPWIY**APSNLAS**GVPARFSGSGSGTSYSLTISRVEAEDAATYYC**QQWSFNPPT**FGAGTKLELK | 150 |
| GAZYVA | Obinutuzumab | CD20 | QVQLVQSGAEVKKPGSSVKVSCKASGYAFS**YSWIN**WVRQAPGQGLEWMG**RIFPGDGDTDYNGKFKG**RVTITADKSTSTAYMELSSLRSEDTAVYYCAR**NVFDGYWLVY**WGQGTLVTVSS | 53 | DIVMTQTPLSLPVTPGEPASISC**RSSKSLLHSNGITYLY**WYLQKPGQSPQLLIY**QMSNLVS**GVPDRFSGSGSGTDFTLKISRVEAEDVGVYYC**AQNLELPYT**FGGGTKVEIK | 151 |
| | Ocrelizumab/ 2H7v16 | CD20 | EVQLVESGGGLVQPGGSLRLSCAAS**GYTFTSYN**MHWVRQAPGKGLEWVGA**IYPGNGDT**SYNQKFKGRFTISVDKSKNTLYLQMNSLRAEDTAVYYCAR**VVYYSNSYWYFDV**WGQGTLVTVSS | 54 | DIQMTQSPSSLSASVGDRVTITC**RASSSVSYMH**WYQQKPGKAPKPLIY**APSNLAS**GVPSRFSGSGSGTDFTLTISSLQPEDFATYYC**QQWSFNPPT**FGQGTKVEIK | 152 |
| Rituxan™ | rituximab | CD20 | QVQLQQPGAELVKPGASVKMSCKAS**GYTFTSYN**MHWVKQTPGRGLEWIGA**IYPGNGDT**SYNQKFKGKATLTADKSSSTAYMQLSSLTSEDSAVYYC**ARSTYYGGDWYFNV**WGAGTTVTVSA | 55 | QIVLSQSPAILSASPGEKVTMTCRAS**SSVSY**IHWFQQKPGSSPKPWIY**ATS**NLASGVPVRFSGSGSGTSYSLTISRVEAEDAATYYC**QQWTSNPPT**FGGGTKLEIK | 153 |
| Zevalin™ | ibritumomab tieuxetan | CD20 | QAYLQQSGAELVRPGASVKMSCKAS**GYTFTSYN**MHWVKQTPRQGLEWIG**AIYPGNGDTSYNQKF**KGKATLTVDKSSSTAYMQLSSLTSEDSAVYFCAR**VVYYSNSYWYFDV**WGTGTTVTVSA | 56 | QIVLSQSPAILSASPGEKVTMTC**RASSSVSYMH**WYQQKPGSSPKPWIY**APSNLAS**GVPARFSGSGSGTSYSLTISRVEAEDAATYYC**QQWSFNPPT**FGAGTKLELK | 150 |
| Mylotarg | Gemtuzumab (hP67.6) | CD33 | QLVQSGAEVKKPGSSVKVSCKAS**GYTITDSNIH**WVRQAPGQSLEWIG**YIYPYNGGTDYNQKFKN**RATLTVDNPTNTAYMELSSLRSEDTDFYYCVN**GNPWLAY**WGQGTLVTVSS | 57 | DIQLTQSPSTLSASVGDRVTITC**RASESLDNYGIRFLT**WFQQKPGKAPKLLMY**AASNQGS**GVPSRFSGSGSGTEFTLTISSLQPDDFATYYC**QQTKEVPWS**FGQGTKVEVK | 154 |

TABLE 2-continued

Anti-target Cell Monoclonal Antibodies and Sequences

| Trade Name | Antibody Name | Target | VH Sequence | SEQ ID NO: | VL Sequence | SEQ ID NO: |
|---|---|---|---|---|---|---|
| Daratumumab | | CD38 | EVQLLESGGGLVQPGGSLRLSCAVSGFTFNSFAMSWVRQAPGKGLEWVSAISGSGGGTYYADSVKGRFTISRDNSKNTLYLQMNSLRAEDTAVYFCAKDKILWFGEPVFDYWGQGTLVTVSS | 58 | EIVLTQSPATLSLSPGERATLSCRASQSVSSYLAWYQQKPGQAPRLLIYDASNRATGIPARFSGSGSGTDFTLTISSLEPEDFAVYYCQQRSNWPPTFGQGTKVEIK | 155 |
| | 1F6 | CD70 | QIQLVQSGPEVKKPGETVKISCKASGYTFTNYGMNWVKQAPGKGLKWMGWINTYTGEPTYADAFKGRFAFSLETSASTAYLQINNLKNEDTATYFCARDYGDYGMDYWGQGTSVTVSS | 59 | DIVLTQSPASLAVSLGQRATISCRASKSVSTSGYSFMHWYQQKPGQPPKLLIYLASNLESGVPARFSGSGSGTDFTLNIHPVEEEDAATYYCQHSREVPWTFGGGTKLEIK | 156 |
| | 2F2 | CD70 | QVQLQQSGTELMTPGASVTMSCKTSGYTFSTYWIEWVKQRPGHGLEWIGEILGPSGYTDYNEKFKAKATETADTSSNTAYMQLSSLASEDSAVYYCARWDRLYAMDYWGGGTSVTVSS | 60 | DIVLTQSPASLTVSLGQKTTISCRASKSVSTSGYSFMHWYQLKPGQSPKLLIYLASDLPSGVPARFSGSGSGTDFTLKIHPVEEEDAATYYCQHSREIPYTFGGGTKLEIT | 157 |
| | 2H5 | CD70 | QVQLVESGGGVVQPGRSLRLSCAASGFTFSSYIMHWVRQAPGKGLEWVAVISYDGRNKYYADSVKGRFTISRDNSKNTLYLQMNSLRAEDTAVYYCARDTDGYDFDYWGQGTLVTVSS | 61 | EIVLTQSPATLSLSPGERATLSCRASQSVSSYLAWYQQKPGQAPRLLIYDASNRATGIPARFSGSGSGTDFTLTISSLEPEDFAVYYCQQRTNWPLTFGGGTKVEIK | 158 |
| | 10B4 | CD70 | QIQLVESGGGVVQPGRSLRLSCAASGFTFGYYAMHWVRQAPGKGLEWVAVISYDGSIKYYADSVKGRFTISRDNSKNTLYLQMNSLRAEDTAVYYCAREGPYSNYLDYWGQGTLVTVSS | 62 | AIQLTQSPSSLSASVGDRVTITCRASQGISSALAWYQQKPGKAPKFLIYDASSLESGVPSRFSGSGSGTDFTLTISSLQPEDFATYYCQQFNSYPFTFGPGTKVDIK | 159 |
| | 8B5 | CD70 | QVQLVESGGGVVQPGRSLRLSCATSGFTFSDYGMHWVRQAPGKGLEWVAVIWYDGSNKYYADSVKGRFTISRDNSKKTLSLQMNSLRAEDTAVYYCARDSIMVRGDYWGQGTLVTVSS | 63 | DIQMTQSPSSLSASVGDRVTITCRASQGISSWLAWYQQKPEKAPKSLIYAASSLQSGVPSRFSGSGSGTDFTLTISSLQPEDFATYYCQQYNSYPLTFGGGTKVEIK | 160 |
| | 18E7 | CD70 | QVQLVESGGGVVQPGRSLRLSCAASGFTFSDHGMHWVRQAPGKGLEWVAVIWYDGSNKYYADSVKGRFTISRDNSKNTLYLQMNSLRAEDTAVYYCARDSIMVRGDYWGQGTLVTVSS | 64 | DIQMTQSPSSLSASVGDRVTITCRASQGISSWLAWYQQKPEKAPKSLIYAASSLQSGVPSRFSGSGSGTDFTLTISSLQPEDFATYYCQQYNSYPLTFGGGTKVEIK | 160 |
| | 69A7 | CD70 | QVQLQESGPGLVKPSETLSLTCTVSGGSVSSDYYYWSWIRQP | 65 | EIVLTQSPATLSLSPGERATLSCRASQSVSSYLAWYQQKPGQ | 161 |

TABLE 2-continued

Anti-target Cell Monoclonal Antibodies and Sequences

| Trade Name | Antibody Name | Target | VH Sequence | SEQ ID NO: | VL Sequence | SEQ ID NO: |
|---|---|---|---|---|---|---|
| | | | PGKGLEWLGYIYYSGSTNYNPSLKSRVTISVDTSKNQFSLKLRSVTTADTAVYYCARGDGDYGGNCFDYWGQGTLVTVSS | | APRLLIFDASNRATGIPARFSGSGSGTDFTLTISSLEPEDFAVYYCQQRSNWPLTFGGGTKVEIK | |
| CE-355621 | | cMET | QVQLVQSGAEVKKPGASVKVSCKASGYTFTSYGFSWVRQAPGQGLEWMGWISASNGNTYYAQKLQGRVTMTTDTSTSTAYMELRSLRSDDTAVYYCARVYADYADYWGQGTLVTVSS | 66 | DIQMTQSPSSVSASVGDRVTITCRASQGINTWLAWYQQKPGKAPKLLIYAASSLKSGVPSRFSGSGSGTDFTLTISSLQPEDFATYYCQQANSFPLTFGGGTKVEIK | 162 |
| LY2875358 | emibetuzumab | cMET | QVQLVQSGAEVKKPGASVKVSCKASGYTFTDYYMHWVRQAPGQGLEWMGRVNPNRRGTTYNQKFEGRVTMTTDTSTSTAYMELRSLRSDDTAVYYCARANWLDYWGQGTTVTVSS | 67 | DIQMTQSPSSLSASVGDRVTITCSVSSSVSSIYLHWYQQKPGKAPKLLIYSTSNLASGVPSRFSGSGSGTDFTLTISSLQPEDEATYYCQVYSGYPLTFGGGTKVEIK | 163 |
| MetMAb | onartuzumab | cMET | EVQLVESGGGLVQPGGSLRLSCAASGYTFTSYWLHWVRQAPGKGLEWVGMIDPSNSDTRFNPNFKDRFTISADTSKNTAYLQMNSLRAEDTAVYYCATYRSYVTPLDYWGQGTLVTVSS | 68 | DIQMTQSPSSLSASVGDRVTITCKSSQSLLYTSSQKNYLAWYQQKPGKAPKLLIYWASTRESGVPSRFSGSGSGTDFTLTISSLQPEDFATYYCQQYYAYPWTFGQGTKVEIK | 164 |
| | tremelimumab (CP-675206, or 11.2.1) | CTLA4 | QVQLVESGGGVVQPGRSLRLSCAASGFTFSSYGMHWVRQAPGKGLEWVAVIWYDGSNKYYADSVKGRFTISRDNSKNTLYLQMNSLRAEDTAVYYCARDPRGATLYYYYYGMDVWGQGTTVTVSS | 69 | DIQMTQSPSSLSASVGDRVTITCRASQSINSYLDWYQQKPGKAPKLLIYAASSLQSGVPSRFSGSGSGTDFTLTISSLQPEDFATYYCQQYYSTPFTFGPGTKVEIK | 165 |
| Yervoy | Ipilimumab 10D1 | CTLA4 | QVQLVESGGGVVQPGRSLRLSCAASGFTFSSYTMHWVRQAPGKGLEWVTFISYDGNNKYYADSVKGRFTISRDNSKNTLYLQMNSLRAEDTAIYYCARTGWLGPFDYWGQGTLVTVSS | 70 | EIVLTQSPGTLSLSPGERATLSCRASQSVGSSYLAWYQQKPGQAPRLLIYGAFSRATGIPDRFSGSGSGTDFTLTISRLEPEDFAVYYCQQYGSSPWTFGQGTKVEIK | 166 |
| AGS16F | H16-7.8 | ENPP3 | QVQLQESGPGLVKPSQTLSLTCTVSGGSISSGGYYWSWIRQHPGKGLEWIGIIYYSGSTYYNPSLKSRVTISVDTSKNQFSLKLNSVTAADTAVFYCARVAIVTTIPGGMDVWGQGTTVTVSS | 71 | EIVLTQSPDFQSVTPKEKVTITCRASQSIGISLHWYQQKPDQSPKLLIKYASQSFSGVPSRFSGSGSGTDFTLTINSLEAEDAATYYCHQSRSFPWTFGQGTKVEIK | 167 |
| MT110 | solitomab | EpCAM | EVQLLEQSGAELVRPGTSVKISCKASGYAFTNYWLGWVKQRPGHGLEWIGDIFPGSGNIHYNEKFKGKATLTADKSSSTAYMQL | 72 | ELVMTQSPSSLTVTAGEKVTMSCKSSQSLLNSGNQKNYLTWYQQKPGQPPKLLIYWASTRESGVPDRFTGSGSGTDFTLTISSV | 168 |

TABLE 2-continued

Anti-target Cell Monoclonal Antibodies and Sequences

| Trade Name | Antibody Name | Target | VH Sequence | SEQ ID NO: | VL Sequence | SEQ ID NO: |
|---|---|---|---|---|---|---|
| | | | SSLTFEDSAVYFCARLRNWDEPMDYWGQGTTVTVSS | | QAEDLAVYYCQNDYSYPLTFGAGTKLEIK | |
| MT201 | Adecatumumab | EpCAM | EVQLLESGGGVVQPGRSLRLSCAASGFTFSSYGMHWVRQAPGKGLEWVAVISYDGSNKYYADSVKGRFTISRDNSKNTLYLQMNSLRAEDTAVYYCAKDMGWGSGWRPYYYYGMDVWGQGTTVTVSS | 73 | ELQMTQSPSSLSASVGDRVTITCRTSQSISSYLNWYQQKPGQPPKLLIYWASTRESGVPDRFSGSGSGTDFTLTISSLQPEDSATYYCQQSYDIPYTFGQGTKLEIK | 169 |
| Panorex | Edrecolomab Mab CO17-1A | EpCAM | QVQLQQSGAELVRPGTSVKVSCKASGYAFTNYLIEWVKQRPGQGLEWIGVINPGSGGTNYNEKFKGKATLTADKSSSTAYMQLSSLTSDDSAVYFCARDGPWFAYWGQGTLVTVSA | 74 | NIVMTQSPKSMSMSVGERVTLTCKASENVVTYVSWYQQKPEQSPKLLIYGASNRYTGVPDRFTGSGSATDFTLTISSVQAEDLADYHCGQGYSYPYTFGGGTKLEIK | 170 |
| | tucotuzumab | EpCAM | QIQLVQSGPELKKPGETVKISCKASGYTFTNYGMNWVRQAPGKGLKWMGWINTYTGEPTYADDFKGREVESLETSASTAFLQLNNLRSEDTATYFCVRFISKGDYWGQGTSVTVSS | 75 | QILLTQSPAIMSASPGEKVTMTCSASSSVSYMLWYQQKPGSSPKPWIFDTSNLASGFPARFSGSGSGTSYSLIISSMEAEDAATYYCHQRSGYPYTFGGGTKLEIK | 171 |
| UBS-54 | | EpCAM | VQLQQSDAELVKPGASVKISCKASGYTFTDHAIHWVKQNPEQGLEWIGYFSPGNDDFKYNERFKGKATLTADKSSSTAYVQLNSLTSEDSAVYFCTRSLNMAYWGQGTSVTVSS | 76 | DIVMTQSPDSLAVSLGERATINCKSSQSVLYSSNNKNYLAWYQQKPGQPPKLLIYWASTRESGVPDRESGSGSGTDFTLTISSLQAEDVAVYYCQQYYSYPLTFGGGTKVKES | 172 |
| 3622W94 | 323/A3 | EpCAM | EVQLVQSGPEVKKPGASVKVSCKASGYTFTNYGMNWVRQAPGQGLEWMGWINTYTGEPTYGEDFKGRFAFSLDTSASTAYMELSSLRSEDTAVYFCARFGNYVDYWGQGSLVTVSS | 77 | DIVMTQSPLSLPVTPGEPASISCRSSINKKGSNGITYLYWYLQKPGQSPQLLIYQMSNLASGVPDRESGSGSGTDFTLKISRVEAEDVGVYYCAQNLEIPRTFGQGTKVEIK | 173 |
| 4D5MOCBv2 | | EpCAM | EVQLVQSGPGLVQPGGSVRISCAASGYTFTNYGMNWVKQAPGKGLEWMGWINTYTGESTYADSFKGRFTFSLDTSASAAYLQINSLRAEDTAVYYCARFAIKGDYWGQGTLLTVSS | 78 | DIQMTQSPSSLSASVGDRVTITCRSTKSLLHSNGITYLYWYQQKPGKAPKLLIYQMSNLASGVPSRESSSGSGTDFTLTISSLQPEDFATYYCAQNLEIPRTFGQGTKVEIK | 174 |
| 4D5MOCB | | EpCAM | EVQLVQSGPGLVQPGGSVRISCAASGYTFTNYGMNWVKQAPGKGLEWMGWINTYTGESTYADSFKGRFTFSLDTSASAAYLQINSLRAEDTAVYYCARFAIKGDYWGQGTLLTVSS | 78 | DIQMTQSPSSLSASVGDRVTITCRSTKSLLHSNGITYLYWYQQKPGKAPKLLIYQMSNLASGVPSRFSSSGSGTDFTLTISSLQPEDFATYYCAQNLEIPRTFGQGTKVELK | 175 |

TABLE 2-continued

Anti-target Cell Monoclonal Antibodies and Sequences

| Trade Name | Antibody Name | Target | VH Sequence | SEQ ID NO: | VL Sequence | SEQ ID NO: |
|---|---|---|---|---|---|---|
| MEDI-547 | 1C1 | EphA2 | EVQLLESGGGLVQP GGSLRLSCAASGFT FS**HYMMA**WVRQAPG KGLEWVS**RIGPSGG PTHYADSVK**GRFTI SRDNSKNTLYLQMN SLRAEDTAVYYCAG YDSG**YDYVAVAGPA EYFQH**WGQGTLVTV SS | 79 | DIQMTQSPSSLSAS VGDRVTITC**RASQS ISTWLA**WYQQKPGK APKLLIY**KASNLHT** GVPSRFSGSGSGTE FSLTISGLQPDDFA TYYC**QQYNSYSRTF** GQGTKVEIK | 176 |
| MORAb-003 | farletuzumab | FOLR1 | EVQLVESGGGVVQP GRSLRLSCSAS**GFT FSGYGL**SWVRQAPG KGLEWVAM**ISSGGS YT**YYADSVKGRFAI SRDNAKNTLFLQMD SLRPEDTGVYFC**AR HGDDPAWF**AYWGQG TPVTVSS | 80 | DIQLTQSPSSLSAS VGDRVTITCSVS**SS ISSNN**LHWYQQKPG KAPKPWIY**GTSNLA** SGVPSRESGSGSGT DYTFTISSLQPEDI ATYYC**QQWSSYPYM YT**FGQGTKVEIK | 177 |
| M9346A | huMOV19 (vLCv1.00) | FOLR1 | QVQLVQSGAEVVKP GASVKISCKASGYT FT**GYFMN**WVKQSPG QSLEWIG**RIHPYDG DTFYNQKFQ**GKATL TVDKSSNTAHMELL SLTSEDFAVYYCTR **YDGSRAMDY**WGQGT TVTVSS | 81 | DIVLTQSPLSLAVS LGQPAIISC**KASQS VSFAGTSLMH**WYHQ KPGQQPRLLIY**RAS NLEA**GVPDRESGSG SKTDFTLNISPVEA EDAATYYC**QQSREY PYT**FGGGTKLEIK | 178 |
| M9346A | huMOV19 (vLCv1.60) | FOLR1 | QVQLVQSGAEVVKP GASVKISCKASGYT FT**GYFMN**WVKQSPG QSLEWIG**RIHPYDG DTFYNQKFQ**GKATL TVDKSSNTAHMELL SLTSEDFAVYYCTR **YDGSRAMDY**WGQGT TVTVSS | 82 | DIVLTQSPLSLAVS LGQPAIISC**KASQS VSFAGTSLMH**WYHQ KPGQQPRLLIY**RAS NLEA**GVPDRESGSG SKTDFTLTISPVEA EDAATYYC**QQSREY PYT**FGGGTKLEIK | 179 |
| 26B3.F2 | | FOLR1 | GPELVKPGASVKIS CKASDYSFT**GYFMN** WVMQSHGKSLEWIG **RIFPYNGDTFYNQK FK**GRATLTVDKSSS TAHMELRSLASEDS AVYFCAR**GTHYFDY** WGQGTTLTVSS | 83 | PASLSASVGETVTI TC**RTSENIFSYLAW** YQQKQGISPQLLVY **NAKTLAE**GVPSRES GSGSGTQFSLKINS LQPEDEGSYYC**QHH YAFPWT**FGGGSKLE IK | 180 |
| RG7686 | GC33 | GPC3 | QVQLVQSGAEVKKP GASVKVSCKASGYT FT**DYEMH**WVRQAPG QGLEWMG**ALDPKTG DTAYSQKFK**GRVTL TADKSTSTAYMELS SLTSED TAVYYCTR**FYSYTY** WGQGTLVTVSS | 84 | DVVMTQSPLSLPVT PGEPASISC**RSSQS LVHSNGNTYLH**WYL QKPGQSPQLLIY**KV SNRFS**GVPDRESGS GSGTDFTLKISRVE AEDVG VYYC**SQNTHVPPT**FG QGTKLEIK | 181 |
| | 4A6 | GPC3 | EVQLVQSGAEVKKP GESLKISCKGSGYS FT**SYWIA**WVRQMPG KGLEWMG**IIFPGDS DTRYSPSFQ**GQVTI SADRSIRTAYLQWS SLKASD TALYYCAR**TREGYF DY**WGQGTLVTVSS | 85 | EIVLTQSPGTLSLS PGERATLSC**RAVQS VSSSYLA**WYQQKPG QAPRLLIY**GASSRA T**GIPDRESGSGSGT DFTLTISRLEPEDF AVYYC**Q QYGSSPT**FGGGTKV EIK | 182 |
| | 11E7 | GPC3 | EVQLVQSGAEVKKP GESLKISCKGSGYS FT**NYWIA**WVRQMPG | 86 | EIVLTQSPGTLSLS PGERATLSC**RASQS VSSSYLA**WYQQKPG | 183 |

TABLE 2-continued

Anti-target Cell Monoclonal Antibodies and Sequences

| Trade Name | Antibody Name | Target | VH Sequence | SEQ ID NO: | VL Sequence | SEQ ID NO: |
|---|---|---|---|---|---|---|
| | | | KGLEWMG**IIYPGDS**<br>**DTRYSPSFQG**QVTI<br>SADKSIRTAYLQWS<br>SLKASD<br>TAMYYCAR**TREGYF**<br>**DY**WGQGTLVTVSS | | QAPRLLIY**GASSRA**<br>**T**GIPDRFSGSGSGT<br>DFTLTISRLEPEDF<br>AVYYC**Q**<br>**QYGSSPT**FGGGTKV<br>EIK | |
| | 16D10 | GPC3 | EVQLVQSGADVTKP<br>GESLKISCKVSGYR<br>FT**NYWIG**WMRQMSG<br>KGLEWMG**IIYPGDS**<br>**DTRYSPSFQG**HVTI<br>SADKSINTAYLRWS<br>SLKASD<br>TAIYYCAR**TREGFF**<br>**DY**WGQGTPVTVSS | 87 | EILLTQSPGTLSLS<br>PGERATLSC**RASQS**<br>**VSSSYLA**WYQQKPG<br>QAPRLLIY**GASSRA**<br>**T**GIPDRESGSGSGT<br>DFTLTISRLEPEDF<br>AVYYC**Q**<br>**QYGSSPT**FGQGTKV<br>EIK | 184 |
| AMG-595 | | HER1 (EGFR) | QVQLVESGGGVVQS<br>GRSLRLSCAAS**GFT**<br>**FRNYGMH**WVRQAPG<br>KGLEW**VAVIWYDGS**<br>**DKYYADSVRG**RFTI<br>SRDNSKNTLYLQMN<br>SLRAEDTAVYYCAR<br>DGY**DILTGNPRDFD**<br>**Y**WGQGTLVTVSS | 88 | DTVMTQTPLSSHVT<br>LGQPASISC**RSSQS**<br>**LVHSDGNTYLS**WLQ<br>QRPGQPPRLLIY**RI**<br>**SRRFS**GVPDRESGS<br>GAGTDFTLEISRVE<br>AEDVGVYYC**MQSTH**<br>**VPRT**FGQGTKVEIK | 185 |
| Erubitux™ | cetutximab | HER1 (EGFR) | QVQLKQSGPGLVQP<br>SQSLSITCTVS**GFS**<br>**LTNYG**VHWVRQSPG<br>KGLEWLGV**IWSGGN**<br>**T**DYNTPFTSRLSIN<br>KDNSKSQVFFKMNS<br>LQSNDTAIYYC**ARA**<br>**LTYYDYEFAY**WGQG<br>TLVTVSA | 89 | DILLTQSPVILSVS<br>PGERVSFSCRAS**QS**<br>**IGTN**IHWYQQRTNG<br>SPRLLIK**YAS**ESIS<br>GIPSRFSGSGSGTD<br>FTLSINSVESEDIA<br>DYYC**QQNNNWPTT**F<br>GAGTKLELK | 186 |
| GA201 | Imgatuzumab | HER1 (EGFR) | QVQLVQSGAEVKKP<br>GSSVKVSCKASGFT<br>FT**DYKIH**WVRQAPG<br>QGLEWMG**YFNPNSG**<br>**YSTYAQKFQG**RVTI<br>TADKSTSTAYMELS<br>SLRSEDTAVYYCAR<br>**LSPGGYYVMDA**WGQ<br>GTTVTVSS | 90 | DIQMTQSPSSLSAS<br>VGDRVTITC**RASQG**<br>**INNYLN**WYQQKPGK<br>APKRLIY**NTNNLQT**<br>GVPSRESGSGSGTE<br>FTLTISSLQPEDFA<br>TYYC**LQHNSFPT**FG<br>QGTKLEIK | 187 |
| Humax | zalutumumab | HER1 (EGFR) | QVQLVESGGGVVQP<br>GRSLRLSCAASGFT<br>FS**TYGMH**WVRQAPG<br>KGLEWVA**VIWDDGS**<br>**YKYYGDSVKG**RFTI<br>SRDNSKNTLYLQMN<br>SLRAEDTAVYYCAR<br>**DGITMVRGVMKDYF**<br>**DY**WGQGTLVTVSS | 91 | AIQLTQSPSSLSAS<br>VGDRVTITC**RASQD**<br>**ISSALV**WYQQKPGK<br>APKLLIY**DASSLES**<br>GVPSRFSGSESGTD<br>FTLTISSLQPEDFA<br>TYYC**QQFNSYPLT**F<br>GGGTKVEIK | 188 |
| IMC-11F8 | necitumumab | HER1 (EGFR) | QVQLQESGPGLVKP<br>SQTLSLTCTVSGGS<br>IS**SGDYYWS**WIRQP<br>PGKGLEWIG**YIYYS**<br>**GSTDYNPSLKS**RVT<br>MSVDTSKNQFSLKV<br>NSVTAADTAVYYCA<br>R**VSIFGVGTEDY**WG<br>QGTLVTVSS | 92 | EIVMTQSPATLSLS<br>PGERATLSC**RASQS**<br>**VSSYLA**WYQQKPGQ<br>APRLLIY**DASNRAT**<br>GIPARFSGSGSGTD<br>FTLTISSLEPEDFA<br>VYYC**HQYGSTPLT**F<br>GGGTKAEIK | 189 |

TABLE 2-continued

Anti-target Cell Monoclonal Antibodies and Sequences

| Trade Name | Antibody Name | Target | VH Sequence | SEQ ID NO: | VL Sequence | SEQ ID NO: |
|---|---|---|---|---|---|---|
| MM-151 | P1X | HER1 (EGFR) | QVQLVQSGAEVKKPGSSVKVSCKASGGTFS**SYAIS**WVRQAPGQGLEWMG**SIIPIFGTVNYAQKFQ**GRVTITADESTSTAYMELSSLRSEDTAVYYCAR**DPSVNLYWYFDL**WGRGTLVTVSS | 93 | DIQMTQSPSTLSASVGDRVTITC**RASQSISSWWA**WYQQKPGKAPKLLIY**DASSLES**GVPSRFSGSGSGTEFTLTISSLQPDDFATYYC**QQYHAHPTTF**GGGTKVEIK | 190 |
| MM-151 | P2X | HER1 (EGFR) | QVQLVQSGAEVKKPGSSVKVSCKASGGTFG**SYAIS**WVRQAPGQGLEWMG**SIIPIFGAANPAQKSQ**GRVTITADESTSTAYMELSSLRSEDTAVYYCAK**MGRGKVAFDI**WGQGTMVTVSS | 94 | DIVMTQSPDSLAVSLGERATINC**KSSQSVLYSPNNKNYLA**WYQQKPGQPPKLLIY**WASTRES**GVPDRESGSGSGTDFTLTISSLQAEDVAVYYC**QQYYGSPIT**FGGGTKVEIK | 191 |
| MM-151 | P3X | HER1 (EGFR) | QVQLVQSGAEVKKPGASVKVSCKASGYAFT**SYGIN**WVRQAPGQGLEWMG**WISAYNGNTYYAQKLR**GRVTMTTDTSTSTAYMELRSLRSDDTAVYYCAR**DLGGYGSGSVPFDP**WGQGTLVTVSS | 95 | EIVMTQSPATLSVSPGERATLSC**RASQSVSSNLA**WYQQKPGQAPRLLIY**GASTRAT**GIPARFSGSGSGTEFTLTISSLQSEDFAVYYC**QDYRTWPRRV**FGGGTKVEIK | 192 |
| TheraCIM | nimotuzumab | HER1 (EGFR) | QVQLQQSGAEVKKPGSSVKVSCKASGYTFT**NYYIY**WVRQAPGQGLEWIG**GINPTSGGSNFNEKFK**TRVTITADESSTTAYMELSSLRSEDTAFYFCTR**QGLWFDSDRGFDF**WGQGTTVTVSS | 96 | DIQMTQSPSSLSASVGDRVTITC**RSSQNIVHSNGNTYLD**WYQQTPGKAPKLLIY**KVSNRFS**GVPSRESGSGSGTDFTFTISSLQPEDIATYYC**FQYSHVPWT**FGQGTKLQIT | 193 |
| Vectibix™ | panitumimab | HER1 (EGFR) | QVQLQESGPGLVKPSETLSLTCTVS**GGSVSSGDYY**WTWIRQSPGKGLEWIG**HIYYSGNT**NYNPSLKSRLTISIDTSKTQFSLKLSSVTAADTAIYYC**VRDRVTGAFDI**WGQGTMVTVSS | 97 | DIQMTQSPSSLSASVGDRVTITCQAS**QDISNY**LNWYQQKPGKAPKLLIY**DASNLET**GVPSRFSGSGSGTDFTFTISSLQPEDIATYFC**QHFDHLPLAF**GGGTKVEIK | 194 |
| 07D06 | | HER1 (EGFR) | QIQLVQSGPELKKPGETVKISCKAS**GYTFTEYP**IHWVKQAPGKGFKWMG**MIYTDIGKPT**YAEEFKGRFAFSLETSASTAYLQINNLKNEDTATYFC**VRDRYDSLFDY**WGQGTTLTVSS | 98 | DVVMTQTPLSLPVSLGDQASISCRSS**QSLVHSNGNTY**LHWYLQKPGQSPKLLIY**KVSNRFS**GVPDRESGSGSGTDFTLKISRVEAEDLGVYFC**SQSTHVPWT**FGGGTKLEIK | 195 |
| 12D03 | | HER1 (EGFR) | EMQLVESGGGFVKPGGSLKLSCAASGFAFS**HYDMS**WVRQTPKQRLEWVA**YIASGGDITYY**ADTVKGRFTISRDNAQNTLYLQMSSLKSEDTAMFYCSR**SSYGNNGDALDF**WGQGTSVTVSS | 99 | DVVMTQTPLSLPVSLGDQASISC**RSSQSLVHSNGNTYLH**WYLQKPGQSPKLLIY**KVSNRFS**GVPDRESGSGSGTDFTLKISRVEAEDLGVYFC**SQSTHVLT**FGSGTKLEIK | 196 |
| | C1 | HER2 | QVQLVESGGGLVQPGGSLRLSCAASGFTFS**SYAMG**WVRQAPGKGLEWVS**SISGSSR** | 100 | QSPSFLSAFVGDRITITC**RASPGIRNYL**AWYQQKPGKAPKLLIY**AASTLQS**GVPSR | 197 |

TABLE 2-continued

Anti-target Cell Monoclonal Antibodies and Sequences

| Trade Name | Antibody Name | Target | VH Sequence | SEQ ID NO: | VL Sequence | SEQ ID NO: |
|---|---|---|---|---|---|---|
| | | | **YIYYADSVKG**RFTISRDNSKNTLYLQMNSLRAEDTAVYYCAK**MDASGSYFNF**WGQGTLVTVSS | | FSGSGSGTDFTLTISSLQPEDFATYYC**QQYNSYPLS**FGGTKVEIK | |
| Erbicin | | HER2 | QVQLLQSAAEVKKPGESLKISCKGSGYSFT**SYWIG**WVRQMPGKGLEWMG**IIYPGDSDTRYSPSFQG**QVTISADKSISTAYLQWSSLKASDTAVYYCAR**WRDSPL**WGQGTLVTVSS | 101 | QAVVTQEPSFSVSPGGTVTLTC**GLSSGSVSTSYYPS**WYQQTPGQAPRTLIY**STNTRSS**GVPDRESGSILGNKAALTITGAQADDESDYYC**VLYMGSGQYV**FGGGTKLTVL | 198 |
| Herceptin | trastuzumab | HER2 | EVQLVESGGGLVQPGGSLRLSCAAS**GFNIKDTY**IHWVRQAPGKGLEWVAR**IYPTNGYT**RYADSVKGRFTISADTSKNTAYLQMNSLRAEDTAVYYC**SRWGGDGFYAMDY**WGQGTLVTVSS | 102 | DIQMTQSPSSLSASVGDRVTITCRAS**QDVNTA**VAWYQQKPGKAPKLLIY**SAS**FLYSGVPSRFSGSRSGTDFTLTISSLQPEDFATYYC**QQHYTTPPT**FGQGTKVEIK | 199 |
| MAGH22 | margetuximab | HER2 | QVQLQQSGPELVKPGASLKLSCTAS**GFNIKDTY**IHWVKQRPEQGLEWIGR**IYPTNGYT**RYDPKFQDKATITADTSSNTAYLQVSRLTSEDTAVYYC**SRWGGDGFYAMDY**WGQGASVTVSS | 103 | DIVMTQSHKFMSTSVGDRVSITCKAS**QDVNTA**VAWYQQKPGHSPKLLIY**SAS**FRYTGVPDRFTGSRSGTDFTFTISSVQAEDLAVYYC**QQHYTTPPT**FGGGTKVEIK | 200 |
| MM-302 | F5 | HER2 | QVQLVESGGGLVQPGGSLRLSCAASGFTFR**SYAMS**WVRQAPGKGLEWVS**AISGRGDNTYYADSVKG**RFTISRDNSKNTLYLQMNSLRAEDTAVYYC**AKMTSNAFAFDY**WGQGTLVTVSS | 104 | QSVLTQPPSVSGAPGQRVTISC**TGSSSNIGAGYGVH**WYQQLPGTAPKLLIY**GNTNRPS**GVPDRESGFKSGTSASLAITGLQAEDEADYYC**QFYDSSLSGWV**FGGGTKLTVL | 201 |
| Perjeta | pertuzumab | HER2 | EVQLVESGGGLVQPGGSLRLSCAAS**GFTFTDYT**MDWVRQAPGKGLEWVAD**VNPNSGGS**IYNQRFKGRFTLSVDRSKNTLYLQMNSLRAEDTAVYYC**ARNLGPSFYFDY**WGQGTLVTVSS | 105 | DIQMTQSPSSLSASVGDRVTITCKASQ**DVSIG**VAWYQQKPGKAPKLLIY**SAS**YRYTGVPSRFSGSGSGTDFTLTISSLQPEDFATYYC**QQYYTYPYT**FGQGTKVEIK | 202 |
| MM-121/ SAR256212 | | HER3 | EVQLLESGGGLVQPGGSLRLSCAASGFTFS**HYVMA**WVRQAPGKGLEWVS**SISSSGGWTLYADSVKG**RFTISRDNSKNTLYLQMNSLRAEDTAVYYCTR**GLKMATIFDY**WGQGTLVTVSS | 106 | QSALTQPASVSGSPGQSITISC**TGTSSDVGSYNVVS**WYQQHPGKAPKLIIY**EVSQRPS**GVSNRFSGSKSGNTASLTISGLQTEDEADYYC**CSYAGSSIFVI**FGGGTKVTVL | 203 |

TABLE 2-continued

Anti-target Cell Monoclonal Antibodies and Sequences

| Trade Name | Antibody Name | Target | VH Sequence | SEQ ID NO: | VL Sequence | SEQ ID NO: |
|---|---|---|---|---|---|---|
| MEHD7945A | Duligotumab | HER1 (EGFR)/ HER3 | EVQLVESGGGLVQPGGSLRLSCAASGFTLS**GDWIH**WVRQAPGKGLEWVG**EISAAGGYTDYADSVKG**RFTISADTSKNTAYLQMNSLRAEDTAVYYCAR**ESRVSFEAAMDY**WGQGTLVTVSS | 107 | DIQMTQSPSSLSASVGDRVTITC**RASQNIATDVA**WYQQKPGKAPKLLIY**SASFLYS**GVPSRFSGSGSGTDFTLTISSLQPEDFATYYC**QQSEPEPYT**FGQGTKVEIK | 204 |
| MM-111 | | HER2/3 | QVQLQESGGGLVKPGGSLRLSCAASGFTFS**SYWMS**WVRQAPGKGLEWVA**NINRDGSASYYVDSVKG**RFTISRDDAKNSLYLQMNSLRAEDTAVYYCAR**DRGVGYFDL**WGRGTLVTVSS | 108 | QSALTQPASVSGSPGQSITISC**TGTSSDVGGYNFVS**WYQQHPGKAPKLMIY**DVSDRPS**GVSDRESGSKSGNTASLIISGLQADDEADYYC**SSYGSSSTHVI**FGGGTKVTVL | 205 |
| MM-111 | | HER2/3 | QVQLVQSGAEVKKPGESLKISCKGSGYSFT**SYWIA**WVRQMPGKGLEYMG**LIYPGDSDTKYSPSFQG**QVTISVDKSVSTAYLQWSSLKPSDSAVYFCAR**HDVGYCTDRTCAKWPEWLGV**WGQGTLVTVSS | 109 | QSVLTQPPSVSAAPGQKVTISC**SGSSSNIGNNYVS**WYQQLPGTAPKLLIY**DHTNRPA**GVPDRESGSKSGTSASLAISGFRSEDEADYYC**ASWDYTLSGWV**FGGGTKLTVL | 206 |
| | Hu3S193 | Lewis-Y | EVQLVESGGGVVQPGRSLRLSCSTSGFTFS**DYYMY**WVRQAPGKGLEWVA**YMSNVGAITDYPDTVKG**RFTISRDNSKNTLFLQMDSLRPEDTGVYFCAR**GTRDGSWFAY**WGQGTPVTVSS | 110 | DIQMTQSPSSLSASVGDRVTITC**RSSQRIVHSNGNTYLE**WYQQTPGKAPKLLIY**KVSNRFS**GVPSRESGSGSGTDFTFTISSLQPEDIATYYC**FQGSHVPFT**FGQGTKLQIT | 207 |
| BAY 94-9343 | anetumab-ravtansine | Mesothelin | QVELVQSGAEVKKPGESLKISCKGS**GYSFTSYW**IGWVRQAPGKGLEWMGI**IDPGDSRT**RYSPSFQGQVTISADKSISTAYLQWSSLKASDTAMYYC**ARGQLYGGTYMDG**WGQGTLVTVSS | 111 | DIALTQPASVSGSPGQSITISCTGT**SSDIGGYNS**VSWYQQHPGKAPKLMIY**GVN**NRPSGVSNRFSGSKSGNTASLTISGLQAEDEADYYC**SSYDIESATPV**FGGGTKLTVL | 208 |
| | SS1 | Mesothelin | QVQLQQSGPELEKPGASVKISCKASGYSFTGYTMNWVKQSHGKSLEWIGLITPYNGASSYNQKFRGKATLTVDKSSSTAYMDLLSLTSEDSAVYFCARGGYDGRGFDYWGQGTTVTVSS | 112 | DIELTQSPAIMSASPGEKVTMTCSASSSVSYMHWYQQKSGTSPKRWIYDTSKLASGVPGRESGSGSGNSYSLTISSVEAEDDATYYCQQWSGYPLTFGAGTKLEIK | 209 |
| | | Mesothelin | QVYLVESGGGVVQPGRSLRLSCAASGITFS**IYGMH**WVRQAPGKGLEWVA**VIWYDGSHEYYADSVKG**RFTISRDNSKNTLYLLMNSLRAEDTAVYYCAR**DGDYYDSGSPLDY**WGQGTLVTVSS | 113 | EIVLTQSPATLSLSPGERATLSC**RASQSVSSYLA**WYQQKPGQAPRLLIY**DASNRAT**GIPARFSGSGSGTDFTLTISSLEPEDFAVYYC**QQRSNWPLT**FGGGTKVEIK | 210 |

TABLE 2-continued

Anti-target Cell Monoclonal Antibodies and Sequences

| Trade Name | Antibody Name | Target | VH Sequence | SEQ ID NO: | VL Sequence | SEQ ID NO: |
|---|---|---|---|---|---|---|
| | | Mesothelin | QVHLVESGGGVVQPGRSLRLSCVASGITFRIYGMHWVRQAPGKGLEWVAVLWYDGSHEYYADSVKGRFTISRDNSKNTLYLQMNSLRAEDTAIYYCARDGDYYDSGSPLDYWGQGTLVTVSS | 114 | EIVLTQSPATLSLSPGERATLSCRASQSVSSYLAWYQQKPGQAPRLLIYDASNRATGIPARFSGSGSGTDFTLTISSLEPEDFAVYYCQQRSNWPLTFGGGTKVEIK | 210 |
| | | Mesothelin | EVHLVESGGGLVQPGGSLRLSCAASGFTFSRYWMSWVRQAQGKGLEWVASIKQAGSEKTYVDSVKGRFTISRDNAKNSLSLQMNSLRAEDTAVYYCAREGAYYYDSASYYPYYYYYSMDVWGQGTTVTVSS | 115 | EIVLTQSPGTLSLSPGERATLSCRASQSVSSSYLAWYQQKPGQAPRLLIYGASSRATGIPDRFSGSGSGTDFTLTISRLEPEDFAVYYCQQYGSSQYTFGQGTKLEIK | 211 |
| MORAb-009 | amatuximab | Mesothelin | QVQLQQSGPELEKPGASVKISCKASGYSFTGYTMNWVKQSHGKSLEWIGLITPYNGASSYNQKFRGKATLTVDKSSSTAYMDLLSLTSEDSAVYFCARGGYDGRGFDYWGSGTPVTVSS | 116 | DIELTQSPAIMSASPGEKVTMTCSASSSVSYMHWYQQKSGTSPKRWIYDTSKLASGVPGRFSGSGSGNSYSLTISSVEAEDDATYYCQQWSKHPLTFGSGTKVEIK | 212 |
| hPAM4 | | MUC-1 | EVQLQESGPELVKPGASVKMSCKASGYTFPSYVLHWVKQKPGQGLEWIGYINPYNDGTQYNEKFKGKATLTSDKSSSTAYMELSRLTSEDSAVYYCARGFGGSYGFAYWGQGTLITVSA | 117 | DIVMTQSPAIMSASPGEKVTMTCSASSSVSSSYLYWYQQKPGSSPKLWIYSTSNLASGVPARFSGSGSGTSYSLTISSMEAEDAASYFCHQWNRYPYTFGGGTKLEIK | 213 |
| hPAM4-Cide | clivatuzumab | MUC1 | QVQLQQSGAEVKKEGASVKVSCEASGYTFPSYVLHWVKQAPGQGLEWIGYINPYNDGTQTNKKFKGKATLTRDTSINTAYMELSRLRSDDTAVYYCARGFGGSYGFAYNGQGTLVTVSS | 118 | DIQLTQSPSSLSASVGDRVTMTCSASSSVSSSYLYWYQQKPGKAPKLWIYSTSNLASGVPARFSGSGSGTDFTLTISSLQPEDSASYFCHQWNRYPYTFGGGTRLEIK | 214 |
| SAR566658 | huDS6v1.01 | MUC1 | QAQLVQSGAEVVKPGASVKMSCKASGYTFTSYNMHWVKQTPGQGLEWIGYIYPGNGATNYNQKFQGKATLTADTSSSTAYMQISSLTSEDSAVYFCARGDSVPFAYWGQGTLVTVSA | 119 | EIVLTQSPATMSASPGERVTITCSAHSSVSFMHWFQQKPGTSPKLWIYSTSSLASGVPARFGGSGSGTSYSLTISSMEAEDAATYYCQQRSSFPLTFGAGTKLELK | 215 |
| Theragyn | Pemtumomab muHMFG1 | MUC1 | QVQLQQSGAELMKPGASVKISCKATGYTFSAYWIEWVKQRPGHGLEWIGEILPGSNNSRYNEKFKGKATFTADTSSNTAYMQLSSLTSEDSAVYYCSRSYDFAWFAYWGQGTPVTVSA | 120 | DIVMSQSPSSLAVSVGEKVTMSCKSSQSLLYSSNQKIYLAWYQQKPGQSPKLLIYWASTRESGVPDRFTGGGSGTDFTLTISSVKAEDLAVYYCQQYYRYPRTFGGGTKLEIK | 216 |

TABLE 2-continued

Anti-target Cell Monoclonal Antibodies and Sequences

| Trade Name | Antibody Name | Target | VH Sequence | SEQ ID NO: | VL Sequence | SEQ ID NO: |
|---|---|---|---|---|---|---|
| Therex | Sontuzumab huHMFG1 AS1402 R1150 | MUC1 | QVQLVQSGAEVKKP GASVKVSCKASGYT FS**AYWIE**WVRQAPG KGLEWVG**EILPGSN NSRYNEKFKG**RVTV TRDTSTNTAYMELS SLRSEDTAVYYCAR **SYDFAWFAY**WGQGT LVTVSS | 121 | DIQMTQSPSSLSAS VGDRVTITCK**SSQS LLYSSNQKIYLA**WY QQKPGKAPKLLIYW **ASTRES**GVPSRFSG SGSGTDFTFTISSL QPEDIATYYC**QQYY RYPRT**FGQGTKVEI K | 217 |
| MDX-1105 or BMS-936559 | | PD-L1 | QVQLVQSGAEVKKP GSSVKVSCKTSGDT FS**TYAIS**WVRQAPG QGLEWMG**GIIPIFG KAHYAQKFQ**GRVTI TADESTSTAYMELS SLRSEDTAVYFCAR **KFHFVSGSPFGMDV** WGQGTTVTVSS | 122 | EIVLTQSPATLSLS PGERATLSC**RASQS VSSYLA**WYQQKPGQ APRLLIY**DASNRAT** GIPARFSGSGSGTD FTLTISSLEPEDFA VYYC**QQRSNWPT**FG QGTKVEIK | 218 |
| MEDI-4736 | durvalumab | PD-L1 | EVQLVESGGGLVQP GGSLRLSCAAS**GFT FSRYW**MSWVRQAPG KGLEWVAN**IKQDGS EK**YYVDSVKGRFTI SRDNAKNSLYLQMN SLRAEDTAVYYCAR **EGGWFGELAFDY**WG QGTLVTVSS | 123 | EIVLTQSPGTLSLS PGERATLSCRAS**QR VSSSYLA**WYQQKPG QAPRLLIY**DAS**SRA TGIPDRFSGSGSGT DFTLTISRLEPEDE AVYYC**QQYGSLPWT** FGQGTKVEIK | 219 |
| MPDL3280A | atezolizumab | PD-L1 | EVQLVESGGGLVQP GGSLRLSCAAS**GFT FSDSW**IHWVRQAPG KGLEWVAW**ISPYGG ST**YYADSVKGRFTI SADTSKNTAYLQMN SLRAEDTAVYYCAR **RHWPGGFDY**WGQGT LVTVSS | 124 | DIQMTQSPSSLSAS VGDRVTITCRAS**QD VSTA**VAWYQQKPGK APKLLIY**SASFLYS** GVPSRFSGSGSGTD FTLTISSLQPEDFA TYYC**QQYLYHPAT**F GQGTKVEIK | 220 |
| MSB0010718C | avelumab | PD-L1 | EVQLLESGGGLVQP GGSLRLSCAAS**GFT FSSYI**MMWVRQAPG KGLEWVSS**IYPSGG ITF**YADTVKGRFTI SRDNSKNTLYLQMN SLRAEDTAVYYCAR **IKLGTVTTVDY**WGQ GTLVTVSS | 125 | QSALTQPASVSGSP GQSITISCTGT**SSD VGGYNY**VSWYQQHP GKAPKLMIY**DVSNR** PSGVSNRFSGSKSG NTASLTISGLQAED EADYC**SSYTSSST RV**FGTGTKVTVL | 221 |
| MLN591 | | PSMA | EVQLVQSGPEVKKP GATVKISCKTS**GYT FTEYTIH**WVKQAPG KGLEWIG**NINPNNG GTTYNQKFED**KATL TVDKSTDTAYMELS SLRSEDTAVYYCAA **GWNFDY**WGQGTLLT VSS | 126 | DIQMTQSPSSLSTS VGDRVTLTC**KASQD VGTAVD**WYQQKPGP SPKLLIY**WASTRHT** GIPSRFSGSGSGTD FTLTISSLQPEDFA DYYC**QQYNSYPLT**F GPGTKVDIK | 222 |
| MT112 | pasotuxizumab | PSMA | QVQLVESGGGLVKP GESLRLSCAAS**GFT FSDYY**MYWVRQAPG KGLEWVAI**ISDGGY YT**YYSDIIKGRFTI SRDNAKNSLYLQMN SLKAEDTAVYYCAR **GFPLLRHGAMDY**WG QGTLVTVSS | 127 | DIQMTQSPSSLSAS VGDRVTITCKAS**QN VDTN**VAWYQQKPGQ APKSLIY**SAS**YRYS DVPSRESGSASGTD FTLTISSVQSEDFA TYYC**QQYDSYPYT**F GGGTKLEIK | 223 |
| | | ROR1 | QEQLVESGGRLVTP GGSLTLSCKASGED FS**AYYMS**WVRQAPG KGLEWIA**TIYPSSG | 128 | ELVLTQSPSVSAAL GSPAKITC**TLSSAH KTDTID**WYQQLQGE APRYLMQVQSD**GSY | 224 |

TABLE 2-continued

Anti-target Cell Monoclonal Antibodies and Sequences

| Trade Name | Antibody Name | Target | VH Sequence | SEQ ID NO: | VL Sequence | SEQ ID NO: |
|---|---|---|---|---|---|---|
| | | | KTYYATWVNGRFTISSDNAQNTVDLQMNSLTAADRATYFCARDSYADDGALFNIWGPGTLVTISS | | TKRPGVPDRESGSSSGADRYLIIPSVQADDEADYYCGADYIGGYVEGGGTQLTVTG | |
| | | ROR1 | EVKLVESGGGLVKPGGSLKLSCAASGFTFSSYAMSWVRQIPEKRLEWVASISRGGTTYYPDSVKGRFTISRDNVRNILYLQMSSLRSEDTAMYYCGRYDYDGYYAMDYWGQGTSVTVSS | 129 | DIKMTQSPSSMYASLGERVTITCKASPDINSYLSWFQQKPGKSPKTLIYRANRLVDGVPSRFSGGGSGQDYSLTINSLEYEDMGIYYCLQYDEFPYTFGGGTKLEMK | 225 |
| | | ROR1 | QSLEESGGRLVTPGTPLTLTCTVSGIDLNSHWMSWVRQAPGKGLEWIGIIAASGSTYYANWAKGRFTISKTSTTVDLRIASPTTEDTATYFCARDYGDYRLVTFNIWGPGTLVTVSS | 130 | ELVMTQTPSSVSAAVGGTVTINCQASQSIGSYLAWYQQKPGQPPKLLIYYASNLASGVPSRFSGSGSGTEYTLTISGVQREDAATYYCLGSLSNSDNVFGGGTELEIL | 226 |
| | | ROR1 | QSVKESEGDLVTPAGNLTLTCTASGSDINDYPISWVRQAPGKGLEWIGFINSGGSTWYASWVKGRFTISRTSTTVDLKMTSLTTDDTATYFCARGYSTYYCDFNIWGPGTLVTISS | 131 | ELVMTQTPSSTSGAVGGTVTINCQASQSIDSNLAWFQQKPGQPPTLLIYRASNLASGVPSRFSGSRSGTEYTLTISGVQREDAATYYCLGGVGNVSYRTSFGGGTEVVVK | 227 |
| CC49 (Humanized) | | TAG-72 | QVQLVQSGAEVVKPGASVKISCKASGYTFTDHAIHWVKQNPGQRLEWIGYFSPGNDDFKYNERFKGKATLTADTSASTAYVELSSLRSEDTAVYFCTRSLNMAYWGQGTLVTVSS | 132 | DIVMSQSPDSLAVSLGERVTLNCKSSQSLLYSGNQKNYLAWYQQKPGQSPKLLIYWASARESGVPDRESGSGSGTDFTLTISSVQAEDVAVYYCQQYYSYPLTFGAGTKLELK | 228 |
| | Murine A1 | TPBG/5T4 | QIQLVQSGPELKKPGETVKISCKASGYTFTNFGMNWVKQGPGEGLKWMGWINTNTGEPRYAEEFKGRXAFSLETTASTAYLQINNLKNEDTATYFCARDWDGAYFFDYWGQGTTLTVSS | 133 | SIVMTQTPKFLLVSAGDRVTITCKASQSVSNDVAWYQQKPGQSPKLLINFATNRYTGVPNRFTGSGYGTDFTFTISTVQAEDLALYFCQQDYSSPWTFGGGTKLEIK | 229 |
| | Murine A2 | TPBG/5T4 | QVQLQQSRPELVKPGASVKMSCKASGYTFTDYVISWVKQRTGQGLEWIGEIYPGSNSIYYNEKFKGRATLTADKSSSTAYMQLSSLTSEDSAVYFCAMGGNYGFDYWGQGTTLTVSS | 134 | SVIMSRGQIVLTQSPAIMSASLGERVTLTCTASSSVNSNYLHWYQQKPGSSPKLWIYSTSNLASGVPARFSGSGSGTSYSLTISSMEAEDAATYYCHQYHRSPLTFGAGTKLELK | 230 |
| | Murine A3 | TPBG/5T4 | EVQLVESGGGLVQPKGSLKLSCAASGFTFNTYAMNWVRQAPGKGLEWVARIRSKSNNYATYYADSVKDRF | 135 | DIVMTQSHIFMSTSVGDRVSITCKASQDVDTAVAWYQQKPGQSPKLLIYWASTRLTGVPDRFTGSGSGTD | 231 |

TABLE 2-continued

Anti-target Cell Monoclonal Antibodies and Sequences

| Trade Name | Antibody Name | Target | VH Sequence | SEQ ID NO: | VL Sequence | SEQ ID NO: |
|---|---|---|---|---|---|---|
| | | | TISRDDSQSMLYLQ MNNLKTEDTAMYXC VR**QWDYDVRAMNY**W GQGTSVTVSS | | FTLTISNVQSEDLA DYFC**QQ** **YSSYPYT**FGGGTKL EIK | |
| IMMU-132 | hRS-7 | TROP-2 | QVQLQQSGSELKKP GASVKVSCKASGYT FT**NYGMN**WVKQAPG QGLKWMG**WINTYTG** **EPTYTDDFKG**RFAF SLDTSVSTAYLQIS SLKADDTAVYFCAR **GGFGSSYWYFDV**WG QGSLVTVSS | 136 | DIQLTQSPSSLSAS VGDRVSITC**KASQD** **VSIAVA**WYQQKPGK APKLLIY**SASYRYT** GVPDRFSGSGSGTD FTLTISSLQPEDFA VYYC**QQHYITPLTF** GAGTKVEIK | 232 |
| IMC-18F1 | icrucumab | VEGFR1 | QAQVVESGGGVVQS GRSLRLSCAASG**FA** **FSSYGMH**WVRQAPG KGLEWVA**VIWYDGS** **NKYYADSVR**GRFTI SRDNSENTLYLQMN SLRAEDTAVYYCAR **DHYGSGVHHYFYYG** **LDV**WGQGTTVTVSS | 137 | EIVLTQSPGTLSLS PGERATLSC**RASQS** **VSSSYLA**WYQQKPG QAPRLLIY**GASSRA** TGIPDRESGSGSGT DFTLTISRLEPEDF AVYYC**QQYGSSPLT** FGGGTKVEIK | 233 |
| Cyramza | ramucirumab | VEGFR2 | EVQLVQSGGGLVKP GGSLRLSCAASG**FT** **FSSYSMN**WVRQAPG KGLEWVS**SISSSSS** **YIYYADSVK**GRFTI SRDNAKNSLYLQMN SLRAEDTAVYYCAR **VTDAFDI**WGQGTMV TVSSA | 138 | DIQMTQSPSSVSAS IGDRVTITC**RASQG** **IDN**WLGWYQQKPGK APKLLIY**DASNLDT** GVPSRFSGSGSGTY FTLTISSLQAEDFA VYFC**QQAKAFPPTF** GGGTKVDIK | 234 |
| g165DFM-PEG | alacizumabpegol | VEGFR2 | EVQLVESGGGLVQP GGSLRLSCAASG**FT** **FSSYGM**SWVRQAPG KGLEWVA**TITSGGS** **YT**YYVDSVKGRFTI SRDNAKNTLYLQMN SLRAEDTAVYYC**VR** **IGEDALDY**WGQGTL VTVSS | 139 | DIQMTQSPSSLSAS VGDRVTITCRAS**QD** **IAGS**LNWLQQKPGK AIKRLIY**ATS**SLDS GVPKRFSGSRSGSD YTLTISSLQPEDFA TYYC**LQYGSFPPTF** GQGTKVEIK | 235 |
| Imclone6.64 | | VEGFR2 | KVQLQQSGTELVKP GASVKVSCKASGYI FTEYIIHWVKQRSG QGLEWIGWLYPESN IIKYNEKFKDKATL TADKSSSTVYMELS RLTSEDSAVYFCTR HDGTNFDYWGQGTT LTVSSA | 140 | DIVLTQSPASLAVS LGQRATISCRASES VDSYGNSFMHWYQQ KPGQPPKLLIYRAS NLESGIPARFSGSG SRTDFTLTINPVEA DDVATYYCQQSNED PLTFGAGTKLELK | 236 |

*underlined & bolded sequences, if present, are CDRs within the VL and VH

Methods to measure binding affinity and/or other biologic activity of the subject compositions of the invention can be those disclosed herein or methods generally known in the art. For example, the binding affinity of a binding pair (e.g., antibody and antigen), denoted as $K_d$, can be determined using various suitable assays including, but not limited to, radioactive binding assays, non-radioactive binding assays such as fluorescence resonance energy transfer and surface plasmon resonance (SPR, Biacore), and enzyme-linked immunosorbent assays (ELISA), kinetic exclusion assay (KinExA®) or as described in the Examples. An increase or decrease in binding affinity, for example of a chimeric polypeptide assembly which has been cleaved to remove a bulking moiety compared to the chimeric polypeptide assembly with the bulking moiety attached, can be determined by measuring the binding affinity of the chimeric polypeptide assembly to its target binding partner with and without the bulking moiety.

Measurement of half-life of a subject chimeric assembly can be performed by various suitable methods. For example, the half-life of a substance can be determined by administering the substance to a subject and periodically sampling a biological sample (e.g., biological fluid such as blood or plasma or ascites) to determine the concentration and/or amount of that substance in the sample over time. The concentration of a substance in a biological sample can be determined using various suitable methods, including enzyme-linked immunosorbent assays (ELISA), immunoblots, and chromatography techniques including high-pressure liquid chromatography and fast protein liquid chromatography. In some cases, the substance may be labeled with a detectable tag, such as a radioactive tag or a fluorescence tag, which can be used to determine the concentration of the substance in the sample (e.g., a blood sample or a plasma sample. The various pharmacokinetic parameters are then determined from the results, which can be done using software packages such as SoftMax Pro software, or by manual calculations known in the art.

In addition, the physicochemical properties of the chimeric polypeptide assembly compositions may be measured to ascertain the degree of solubility, structure and retention of stability. Assays of the subject compositions are conducted that allow determination of binding characteristics of the binding domains towards a ligand, including binding dissociation constant ($K_d$, $K_{on}$ and $K_{off}$), the half-life of dissociation of the ligand-receptor complex, as well as the activity of the binding domain to inhibit the biologic activity of the sequestered ligand compared to free ligand ($IC_{50}$ values). The term "$IC_{50}$" refers to the concentration needed to inhibit half of the maximum biological response of the ligand agonist, and is generally determined by competition binding assays. The term "$EC_{50}$" refers to the concentration needed to achieve half of the maximum biological response of the active substance, and is generally determined by ELISA or cell-based assays, including the methods of the Examples described herein.

(i) Anti-CD3 Binding Domains

In some embodiments, the invention provides chimeric polypeptide assembly compositions comprising a binding domain of the first portion with binding affinity to T cells. In one embodiment, the binding domain of the second portion comprises VL and VH derived from a monoclonal antibody to an antigen of the CD3. In another embodiment, the binding domain comprises VL and VH derived from a monoclonal antibody to CD3epsilon and CD3delta. Monoclonal antibodies to CD3 neu are known in the art. Exemplary, non-limiting examples of VL and VH sequences of monoclonal antibodies to CD3 are presented in Table 1. In one embodiment, the invention provides a chimeric polypeptide assembly comprising a binding domain with binding affinity to CD3 comprising anti-CD3 VL and VH sequences set forth in Table 1. In another embodiment, the invention provides a chimeric polypeptide assembly comprising a binding domain of the first portion with binding affinity to CD3epsilon comprising anti-CD3epsilon VL and VH sequences set forth in Table 1. In another embodiment, the invention provides a chimeric polypeptide assembly composition, wherein the scFv second binding domain of the first portion comprises VH and VL regions wherein each VH and VL regions exhibit at least about 90%, or 91%, or 92%, or 93%, or 94%, or 95%, or 96%, or 97%, or 98%, or 99% identity to or is identical to paired VL and VH sequences of the huUCHT1 anti-CD3 antibody of Table 1. In another embodiment, the invention provides a chimeric polypeptide assembly composition comprising a binding domain with binding affinity to CD3 comprising the CDR-L1 region, the CDR-L2 region, the CDR-L3 region, the CDR-H1 region, the CDR-H2 region, and the CDR-H3 region, wherein each is derived from the respective anti-CD3 VL and VH sequences set forth in Table 1. In another embodiment, the invention provides a chimeric polypeptide assembly composition comprising a binding domain with binding affinity to CD3 comprising the CDR-L1 region, the CDR-L2 region, the CDR-L3 region, the CDR-H1 region, the CDR-H2 region, and the CDR-H3 region, wherein the CDR sequences are RASQDIRNYLN (SEQ ID NO: 237), YTSRLES (SEQ ID NO: 238), QQGNTLPWT (SEQ ID NO: 239), GYSFTGYTMN (SEQ ID NO: 240), LINPYKGVST (SEQ ID NO: 241), and SGYYGDSDWYFDV (SEQ ID NO: 242)

The CD3 complex is a group of cell surface molecules that associates with the T-cell antigen receptor (TCR) and functions in the cell surface expression of TCR and in the signaling transduction cascade that originates when a peptide:MHC ligand binds to the TCR. Typically, when an antigen binds to the T-cell receptor, the CD3 sends signals through the cell membrane to the cytoplasm inside the T cell. This causes activation of the T cell that rapidly divide to produce new T cells sensitized to attack the particular antigen to which the TCR were exposed. The CD3 complex is comprised of the CD3epsilon molecule, along with four other membrane-bound polypeptides (CD3-gamma, -delta, -zeta, and -beta). In humans, CD3-epsilon is encoded by the CD3E gene on Chromosome 11. The intracellular domains of each of the CD3 chains contain immunoreceptor tyrosine-based activation motifs (ITAMs) that serve as the nucleating point for the intracellular signal transduction machinery upon T cell receptor engagement.

A number of therapeutic strategies modulate T cell immunity by targeting TCR signalling, particularly the anti-human CD3 monoclonal antibodies (mAbs) that are widely used clinically in immunosuppressive regimes. The CD3-specific mouse mAb OKT3 was the first mAb licensed for use in humans (Sgro, C. Side-effects of a monoclonal antibody, muromonab CD3/orthoclone OKT3: bibliographic review. Toxicology 105:23-29, 1995) and is widely used clinically as an immunosuppressive agent in transplantation (Chatenoud, Clin. Transplant 7:422-430, (1993); Chatenoud, Nat. Rev. Immunol. 3:123-132 (2003); Kumar, Transplant. Proc. 30:1351-1352 (1998)), type 1 diabetes, and psoriasis. Importantly, anti-CD3 mAbs can induce partial T cell signalling and clonal anergy (Smith, JA, Nonmitogenic Anti-CD3 Monoclonal Antibodies Deliver a Partial T Cell Receptor Signal and Induce Clonal Anergy J. Exp. Med. 185:1413-1422 (1997)). OKT3 has been described in the literature as a T cell mitogen as well as a potent T cell killer (Wong, JT. The mechanism of anti-CD3 monoclonal antibodies. Mediation of cytolysis by inter-T cell bridging. Transplantation 50:683-689 (1990)). In particular, the studies of Wong demonstrated that by bridging CD3 T cells and target cells, one could achieve killing of the target and that neither FcR-mediated ADCC nor complement fixation was necessary for bivalent anti-CD3 MAB to lyse the target cells.

OKT3 exhibits both a mitogenic and T-cell killing activity in a time-dependent fashion; following early activation of T cells leading to cytokine release, upon further administration OKT3 later blocks all known T-cell functions. It is due to this later blocking of T cell function that OKT3 has found such wide application as an immunosuppressant in therapy regimens for reduction or even abolition of allograft tissue rejection. Other antibodies specific for the CD3 molecule are disclosed in Tunnacliffe, Int. Immunol. 1 (1989), 546-50, WO2005/118635 and WO2007/033230 describe anti-human monoclonal CD3 epsilon antibodies, U.S. Pat. No. 5,821,337 describes the VL and VH sequences of murine anti-CD3 monoclonal Ab UCHT1 (muxCD3, Shalaby et al., J. Exp. Med. 175, 217-225 (1992) and a humanized variant of this antibody (hu UCHT1), and United States Patent Application 20120034228 discloses binding domains capable of binding to an epitope of human and non-chimpanzee primate CD3 epsilon chain.

(ii) Anti-EpCAM Binding Domains

In some embodiments, the invention provides chimeric polypeptide assembly compositions comprising a binding domain with binding affinity to the tumor-specific marker EpCAM. In one embodiment, the binding domain comprises VL and VH derived form a monoclonal antibody to EpCAM. Monoclonal antibodies to EpCAM are known in the art. Exemplary, non-limiting examples of EpCAM monoclonal antibodies and the VL and VH sequences thereof are presented in Table 2. In one embodiment, the invention provides a chimeric polypeptide assembly composition comprising a binding domain with binding affinity to the tumor-specific marker EpCAM comprising anti-EpCAM VL and VH sequences set forth in Table 2. In another embodiment, the invention provides a chimeric polypeptide assembly composition, wherein the first portion first binding domain comprises VH and VL regions wherein each VH and VL regions exhibit at least about 90%, or 91%, or 92%, or 93%, or 94%, or 95%, or 96%, or 97%, or 98%, or 99% identity to or is identical to paired VL and VH sequences of the 4D5MUCB anti-EpCAM antibody of Table 2. In another embodiment, the invention provides a chimeric polypeptide assembly composition comprising a binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences set forth in Table 2.

Epithelial cell adhesion molecule (EpCAM, also known as 17-1A antigen) is a 40-kDa membrane-integrated glycoprotein composed of 314 amino acids expressed in certain epithelia and on many human carcinomas (see, Balzar, The biology of the 17-1A antigen (Ep-CAM), J. Mol. Med. 1999, 77:699-712). EpCAM was initially discovered by use of the murine monoclonal antibody 17-1A/edrecolomab that was generated by immunization of mice with colon carcinoma cells (Goettlinger, Int J Cancer. 1986; 38, 47-53 and Simon, Proc. Natl. Acad. Sci. USA. 1990; 87, 2755-2759). Because of their epithelial cell origin, tumor cells from most carcinomas express EpCAM on their surface (more so than normal, healthy cells), including the majority of primary, metastatic, and disseminated non-small cell lung carcinoma cells (Passlick, B., et al. The 17-1A antigen is expressed on primary, metastatic and disseminated non-small cell lung carcinoma cells. Int. J. Cancer 87(4):548-552, 2000), gastric and gastro-oesophageal junction adenocarcinomas (Martin, I. G., Expression of the 17-1A antigen in gastric and gastro-oesophageal junction adenocarcinomas: a potential immunotherapeutic target? J Clin Pathol 1999; 52:701-704), and breast and colorectal cancer (Packeisen J, et al. Detection of surface antigen 17-1A in breast and colorectal cancer. Hybridoma. 1999 18(1):37-40) and, therefore, are an attractive target for immunotherapy approaches. Indeed, increased expression of EpCAM correlates to increased epithelial proliferation; in breast cancer, overexpression of EpCAM on tumor cells is a predictor of survival (Gastl, Lancet. 2000, 356, 1981-1982). Due to their epithelial cell origin, tumor cells from most carcinomas still express EpCAM on their surface, and the bispecific solitomab single-chain antibody composition that targets EpCAM on tumor cells and also contains a CD3 binding region has been proposed for use against primary uterine and ovarian CS cell lines (Ferrari F, et al., Solitomab, an EpCAM/CD3 bispecific antibody construct (BiTE®), is highly active against primary uterine and ovarian carcinosarcoma cell lines in vitro. J Exp Clin Cancer Res. 2015 34:123).

Monoclonal antibodies to EpCAM are known in the art. The EpCAM monclonals ING-1, 3622W94, adecatumumab and edrecolomab have been described as having been tested in human patients (Mtinz, M. Side-by-side analysis of five clinically tested anti-EpCAM monoclonal antibodies Cancer Cell International, 10:44-56, 2010). Bispecific antibodies directed against EpCAM and against CD3 have also been described, including construction of two different bispecific antibodies by fusing a hybridoma producing monoclonal antibody against EpCAM with either of the two hybridomas OKT3 and 9.3 (Möller, S A, Reisfeld, R A, Bispecific-monoclonal-antibody-directed lysis of ovarian carcinoma cells by activated human T lymphocytes. Cancer Immunol. Immunother. 33:210-216, 1991). Other examples of bispecific antibodies against EpCAM include BiUII, (anti-CD3 (rat) x anti-EpCAM (mouse)) (Zeidler, J. Immunol., 1999, 163:1247-1252), a scFv CD3/17-1A-bispecific (Mack, M. A small bispecific antibody composition expressed as a functional single-chain molecule with high tumor cell cytotoxicity. Proc. Natl. Acad. Sci., 1995, 92:7021-7025), and a partially humanized bispecific diabody having anti-CD3 and antiEpCAM specificity (Helfrich, W. Construction and characterization of a bispecific diabody for retargeting T cells to human carcinomas. Int. J. Cancer, 1998, 76:232-239).

In one embodiment provided herein are bispecific chimeric polypeptide assembly compositions with a first portion having a binding domain specific for EpCAM and a binding domain specific for CD3. The technical problem to be solved was to provide means and methods for the generation of improved compositions exhibiting the properties of being well-tolerated and more convenient medicaments (less frequent dosing) for the effective treatment and or amelioration of tumorous diseases. The solution to said technical problem is achieved by the embodiments disclosed herein and characterized in the claims.

Accordingly, in some embodiments, the present invention relates to chimeric polypeptide assembly compositions whereby said composition comprises a first portion comprising a bispecific single chain antibody composition comprising at least two binding domains, whereby one of said domains binds to an effector cell antigen, such as CD3 antigen and a second domain binds to EpCAM antigen, wherein said binding domains comprise VL and VH specific for EpCAM and VL and VH specific for human CD3 antigen. Preferably, in the embodiment, said binding domain specific for EpCAM has a $K_d$ value of greater than $10^{-7}$ to $10^{-10}$ M, as determined in an vitro binding assay. In one embodiment of the foregoing, the binding domains are in a scFv format. In another embodiment of the foregoing, the binding domains are in a single chain diabody format.

(iii) Anti-CCR5 Binding Domains

In some embodiments, the invention provides chimeric polypeptide assembly compositions comprising a first portion binding domain with binding affinity to the tumor-specific marker CCR5 and a second binding domain binds to an effector cell antigen, such as CD3 antigen. In one embodiment, the binding domain comprises VL and VH derived form a monoclonal antibody to CCR5. Monoclonal antibodies to CCR5 are known in the art. In one embodiment, the invention provides a chimeric polypeptide assembly composition comprising a first portion binding domain with binding affinity to the tumor-specific marker CCR5 comprising anti-CCR5 VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

(iv) Anti-CD19 Binding Domains

In some embodiments, the invention provides chimeric polypeptide assembly compositions comprising a first portion binding domain with binding affinity to the tumor-specific marker CD19 and a second binding domain binds to an effector cell antigen, such as CD3 antigen. In one embodiment, the binding domain comprises VL and VH derived form a monoclonal antibody to CD19. Monoclonal antibodies to CD19 are known in the art. Exemplary, non-limiting examples of VL and VH sequences are presented in Table 2. In one embodiment, the invention provides a chimeric polypeptide assembly composition comprising a first portion binding domain with binding affinity to the tumor-specific marker CD19 comprising anti-CD19 VL and VH sequences set forth in Table 2. In another embodiment, the invention provides a chimeric polypeptide assembly composition, wherein the scFv second binding domain comprises VH and VL regions wherein each VH and VL regions exhibit at least about 90%, or 91%, or 92%, or 93%, or 94%, or 95%, or 96%, or 97%, or 98%, or 99% identity to or is identical to paired VL and VH sequences of the MT103 anti-CD19 antibody of Table 2. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences set forth in Table 2. Preferably, in the embodiments, said binding has a $K_d$ value of greater than $10^{-7}$ to $10^{-10}$ M, as determined in an vitro binding assay.

(v) Anti-HER-2 Binding Domains

In some embodiments, the invention provides chimeric polypeptide assembly compositions comprising a first portion binding domain with binding affinity to the tumor-specific marker HER-2 and a second binding domain binds to an effector cell antigen, such as CD3 antigen. In one embodiment, the binding domain comprises VL and VH derived form a monoclonal antibody to HER-2. Monoclonal antibodies to HER-2 are known in the art. Exemplary, non-limiting examples of VL and VH sequences are presented in Table 2. In one embodiment, the invention provides a chimeric polypeptide assembly composition comprising a first portion binding domain with binding affinity to the tumor-specific marker HER-2 comprising anti-HER-2 VL and VH sequences set forth in Table 2. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences set forth in Table 2. Preferably, in the embodiments, said binding has a $K_d$ value of greater than $10^{-7}$ to $10^{-10}$ M, as determined in an vitro binding assay.

(vi) Anti-HER-3 Binding Domains

In some embodiments, the invention provides chimeric polypeptide assembly compositions comprising a first portion binding domain with binding affinity to the tumor-specific marker HER-3 and a second binding domain binds to an effector cell antigen, such as CD3 antigen. In one embodiment, the binding domain comprises VL and VH derived form a monoclonal antibody to HER-3. Monoclonal antibodies to HER-3 are known in the art. Exemplary, non-limiting examples of VL and VH sequences are presented in Table 2. In one embodiment, the invention provides a chimeric polypeptide assembly composition comprising a first portion binding domain with binding affinity to the tumor-specific marker HER-3 comprising anti-HER-3 VL and VH sequences set forth in Table 2. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences set forth in Table 2. Preferably, in the embodiments, said binding has a $K_d$ value of greater than $10^{-7}$ to $10^{-10}$ M, as determined in an vitro binding assay.

(vii) Anti-HER-4 Binding Domains

In some embodiments, the invention provides chimeric polypeptide assembly compositions comprising a first portion binding domain with binding affinity to the tumor-specific marker HER-4 and a second binding domain binds to an effector cell antigen, such as CD3 antigen. In one embodiment, the binding domain comprises VL and VH derived form a monoclonal antibody to HER-4. Monoclonal antibodies to HER-4 are known in the art. In one embodiment, the invention provides a chimeric polypeptide assembly composition comprising a first portion binding domain with binding affinity to the tumor-specific marker HER-4 comprising anti-HER-4 VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

(viii) Anti-EGFR Binding Domains

In some embodiments, the invention provides chimeric polypeptide assembly compositions comprising a first portion binding domain with binding affinity to the tumor-specific marker EGFR and a second binding domain binds to an effector cell antigen, such as CD3 antigen. In one embodiment, the binding domain comprises VL and VH derived form a monoclonal antibody to EGFR. Monoclonal antibodies to EGFR are known in the art. Exemplary, non-limiting examples of VL and VH sequences are presented in Table 2. In one embodiment, the invention provides a chimeric polypeptide assembly composition comprising a first portion binding domain with binding affinity to the tumor-specific marker EGFR comprising anti-EGFR VL and VH sequences set forth in Table 2. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences set forth in Table 2. Preferably, in the embodiments, said binding has a $K_d$ value of greater than $10^{-7}$ to $10^{-10}$ M, as determined in an vitro binding assay.

(ix) Anti-PSMA Binding Domains

In some embodiments, the invention provides chimeric polypeptide assembly compositions comprising a first portion binding domain with binding affinity to the tumor-specific marker PSMA and a second binding domain binds to an effector cell antigen, such as CD3 antigen. In one embodiment, the binding domain comprises VL and VH derived form a monoclonal antibody to PSMA. Monoclonal antibodies to PSMA are known in the art. Exemplary, non-limiting examples of VL and VH sequences are presented in Table 2. In one embodiment, the invention provides a chimeric polypeptide assembly composition comprising a first portion binding domain with binding affinity to the tumor-specific marker PSMA comprising anti-PSMA VL and VH sequences set forth in Table 2. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences set forth in Table 2. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences set forth in Table 2. Preferably, in the embodiments, said binding has a $K_d$ value of greater than $10^{-7}$ to $10^{-10}$ M, as determined in an vitro binding assay.

(x) Anti-CEA Binding Domains

In some embodiments, the invention provides chimeric polypeptide assembly compositions comprising a first portion binding domain with binding affinity to the tumor-specific marker CEA and a second binding domain binds to an effector cell antigen, such as CD3 antigen. In one embodiment, the binding domain comprises VL and VH derived form a monoclonal antibody to CEA. Monoclonal antibodies to CEA are known in the art. Exemplary, non-limiting examples of VL and VH sequences are presented in Table 2. In one embodiment, the invention provides a chimeric polypeptide assembly composition comprising a first portion binding domain with binding affinity to the tumor-specific marker CEA comprising anti-CEA VL and VH sequences set forth in Table 2. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences set forth in Table 2. Preferably, in the embodiments, said binding has a $K_d$ value of greater than $10^{-7}$ to $10^{-10}$ M, as determined in an vitro binding assay.

(xi) Anti-MUC1 Binding Domains

In some embodiments, the invention provides chimeric polypeptide assembly compositions comprising a first portion binding domain with binding affinity to the tumor-specific marker MUC1 and a second binding domain binds to an effector cell antigen, such as CD3 antigen. In one embodiment, the binding domain comprises VL and VH derived form a monoclonal antibody to MUC1. Monoclonal antibodies to MUC1 are known in the art. Exemplary, non-limiting examples of VL and VH sequences are presented in Table 2. In one embodiment, the invention provides a chimeric polypeptide assembly composition comprising a first portion binding domain with binding affinity to the tumor-specific marker MUC1 comprising anti-MUC1 VL and VH sequences set forth in Table 2. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences set forth in Table 2. Preferably, in the embodiments, said binding has a $K_d$ value of greater than $10^{-7}$ to $10^{-10}$ M, as determined in an vitro binding assay.

(xii) Anti-MUC2 Binding Domains

In some embodiments, the invention provides chimeric polypeptide assembly compositions comprising a first portion binding domain with binding affinity to the tumor-specific marker MUC2 and a second binding domain binds to an effector cell antigen, such as CD3 antigen. In one embodiment, the binding domain comprises VL and VH derived form a monoclonal antibody to MUC2. Monoclonal antibodies to MUC2 are known in the art. In one embodiment, the invention provides a chimeric polypeptide assembly composition comprising a first portion binding domain with binding affinity to the tumor-specific marker MUC2 comprising anti-MUC2 VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

(xiii) Anti-MUC3 Binding Domains

In some embodiments, the invention provides chimeric polypeptide assembly compositions comprising a first portion binding domain with binding affinity to the tumor-specific marker MUC3 and a second binding domain binds to an effector cell antigen, such as CD3 antigen. In one embodiment, the binding domain comprises VL and VH derived form a monoclonal antibody to MUC3. Monoclonal antibodies to MUC3 are known in the art. In one embodiment, the invention provides a chimeric polypeptide assembly composition comprising a first portion binding domain with binding affinity to the tumor-specific marker MUC3 comprising the anti-MUC3 VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

(xiv) Anti-MUC4 Binding Domains

In some embodiments, the invention provides chimeric polypeptide assembly compositions comprising a first portion binding domain with binding affinity to the tumor-specific marker MUC4 and a second binding domain binds to an effector cell antigen, such as CD3 antigen. In one embodiment, the binding domain comprises VL and VH derived form a monoclonal antibody to MUC4. Monoclonal antibodies to MUC4 are known in the art. In one embodiment, the invention provides a chimeric polypeptide assembly composition comprising a first portion binding domain with binding affinity to the tumor-specific marker MUC4 comprising anti-MUC4 VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

(xv) Anti-MUC5AC Binding Domains

In some embodiments, the invention provides chimeric polypeptide assembly compositions comprising a first portion binding domain with binding affinity to the tumor-specific marker MUC5AC and a second binding domain binds to an effector cell antigen, such as CD3 antigen. In one embodiment, the binding domain comprises VL and VH derived form a monoclonal antibody to MUC5AC. Monoclonal antibodies to MUC5AC are known in the art. In one embodiment, the invention provides a chimeric polypeptide assembly composition comprising a first portion binding domain with binding affinity to the tumor-specific marker MUC5AC comprising anti-MUC5AC VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

(xvi) Anti-MUC5B Binding Domains

In some embodiments, the invention provides chimeric polypeptide assembly compositions comprising a first portion binding domain with binding affinity to the tumor-specific marker MUC5B and a second binding domain binds to an effector cell antigen, such as CD3 antigen. In one embodiment, the binding domain comprises VL and VH derived form a monoclonal antibody to MUC5B. Monoclonal antibodies to MUC5B are known in the art. In one embodiment, the invention provides a chimeric polypeptide assembly composition comprising a first portion binding domain with binding affinity to the tumor-specific marker MUC5B comprising anti-MUC5B VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

(xvii) Anti-MUC7 Binding Domains

In some embodiments, the invention provides chimeric polypeptide assembly compositions comprising a first portion binding domain with binding affinity to the tumor-specific marker MUC7 and a second binding domain binds to an effector cell antigen, such as CD3 antigen. In one embodiment, the binding domain comprises VL and VH derived form a monoclonal antibody to MUC7. Monoclonal antibodies to MUC7 are known in the art. In one embodiment, the invention provides a chimeric polypeptide assembly composition comprising a first portion binding domain with binding affinity to the tumor-specific marker MUC7 comprising anti-MUC7 VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

(xviii) Anti-βhCG Binding Domains

In some embodiments, the invention provides chimeric polypeptide assembly compositions comprising a first portion binding domain with binding affinity to the tumor-specific marker βhCG and a second binding domain binds to an effector cell antigen, such as CD3 antigen. In one embodiment, the binding domain comprises VL and VH derived form a monoclonal antibody to βhCG. Monoclonal antibodies to βhCG are known in the art. In one embodiment, the invention provides a chimeric polypeptide assembly composition comprising a first portion binding domain with binding affinity to the tumor-specific marker βhCG comprising anti-βhCG VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

(xix) Anti-Lewis-Y Binding Domains

In some embodiments, the invention provides chimeric polypeptide assembly compositions comprising a first portion binding domain with binding affinity to the tumor-specific marker Lewis-Y and a second binding domain binds to an effector cell antigen, such as CD3 antigen. In one embodiment, the binding domain comprises VL and VH derived form a monoclonal antibody to Lewis-Y. Monoclonal antibodies to Lewis-Y are known in the art. In one embodiment, the invention provides a chimeric polypeptide assembly composition comprising a first portion binding domain with binding affinity to the tumor-specific marker Lewis-Y comprising the anti-Lewis-Y VL and VH sequences set forth in Table 2. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from respective VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

(xx) Anti-CD20 Binding Domains

In some embodiments, the invention provides chimeric polypeptide assembly compositions comprising a first portion binding domain with binding affinity to the tumor-specific marker CD20 and a second binding domain binds to an effector cell antigen, such as CD3 antigen. In one embodiment, the binding domain comprises VL and VH derived form a monoclonal antibody to CD20. Monoclonal antibodies to CD20 are known in the art. Exemplary, non-limiting examples of VL and VH sequences are presented in Table 2. In one embodiment, the invention provides a chimeric polypeptide assembly composition comprising a first portion binding domain with binding affinity to the tumor-specific marker CD20 comprising anti-CD20 VL and VH sequences set forth in Table 2. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences set forth in Table 2. Preferably, in the embodiments, said binding has a $K_d$ value of greater than $10^{-7}$ to $10^{-10}$ M, as determined in an vitro binding assay.

(xxi) Anti-CD33 Binding Domains

In some embodiments, the invention provides chimeric polypeptide assembly compositions comprising a first portion binding domain with binding affinity to the tumor-specific marker CD33 and a second binding domain binds to an effector cell antigen, such as CD3 antigen. In one embodiment, the binding domain comprises VL and VH derived form a monoclonal antibody to CD33. Monoclonal antibodies to CD33 are known in the art. Exemplary, non-limiting examples of VL and VH sequences are presented in Table 2. In one embodiment, the invention provides a chimeric polypeptide assembly composition comprising a first portion binding domain with binding affinity to the tumor-specific marker CD33 comprising anti-CD33 VL and VH sequences set forth in Table 2. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences set forth in Table 2. Preferably, in the embodiments, said binding has a $K_d$ value of greater than $10^{-7}$ to $10^{-10}$ M, as determined in an vitro binding assay.

(xxii) Anti-CD30 Binding Domains

In some embodiments, the invention provides chimeric polypeptide assembly compositions comprising a first portion binding domain with binding affinity to the tumor-specific marker CD30 and a second binding domain binds to an effector cell antigen, such as CD3 antigen. In one embodiment, the binding domain comprises VL and VH derived form a monoclonal antibody to CD30. Monoclonal antibodies to CD30 are known in the art. Exemplary, non-limiting examples of VL and VH sequences are presented in Table 2. In one embodiment, the invention provides a chimeric polypeptide assembly composition comprising a first portion binding domain with binding affinity to the tumor-specific marker CD30 comprising anti-CD30 VL and VH sequences set forth in Table 2. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences set forth in Table 2. Preferably, in the embodiments, said binding has a $K_d$ value of greater than $10^{-7}$ to $10^{-10}$ M, as determined in an vitro binding assay.

(xxiii) Anti-ganglioside GD3 Binding Domains

In some embodiments, the invention provides chimeric polypeptide assembly compositions comprising a first portion binding domain with binding affinity to the tumor-specific marker ganglioside GD3 and a second binding domain binds to an effector cell antigen, such as CD3 antigen. In one embodiment, the binding domain comprises VL and VH derived form a monoclonal antibody to ganglioside GD3. Monoclonal antibodies to ganglioside GD3 are known in the art. In one embodiment, the invention provides a chimeric polypeptide assembly composition comprising a first portion binding domain with binding affinity to the tumor-specific marker ganglioside GD3 comprising anti-ganglioside GD3 VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

(xxiv) Anti-9-O-Acetyl-GD3 Binding Domains

In some embodiments, the invention provides chimeric polypeptide assembly compositions comprising a first portion binding domain with binding affinity to the tumor-specific marker 9-O-Acetyl-GD3 and a second binding domain binds to an effector cell antigen, such as CD3 antigen. In one embodiment, the binding domain comprises VL and VH derived form a monoclonal antibody to 9-O-Acetyl-GD3. Monoclonal antibodies to 9-O-Acetyl-GD3 are known in the art. In one embodiment, the invention provides a chimeric polypeptide assembly composition comprising a first portion binding domain with binding affinity to the tumor-specific marker 9-O-Acetyl-GD3 comprising the anti-9-O-Acetyl-GD3 VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

(xxv) Anti-Globo H Binding Domains

In some embodiments, the invention provides chimeric polypeptide assembly compositions comprising a first portion binding domain with binding affinity to the tumor-specific marker Globo H and a second binding domain binds to an effector cell antigen, such as CD3 antigen. In one embodiment, the binding domain comprises VL and VH derived form a monoclonal antibody to Globo H. Monoclonal antibodies to Globo H are known in the art. In one embodiment, the invention provides a chimeric polypeptide assembly composition comprising a first portion binding domain with binding affinity to the tumor-specific marker Globo H comprising anti-Globo H VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

(xxvi) Anti-fucosyl GM1 Binding Domains

In some embodiments, the invention provides chimeric polypeptide assembly compositions comprising a first portion binding domain with binding affinity to the tumor-specific marker fucosyl GM1 and a second binding domain binds to an effector cell antigen, such as CD3 antigen. In one embodiment, the binding domain comprises VL and VH derived form a monoclonal antibody to fucosyl GM1. Monoclonal antibodies to fucosyl GM1 are known in the art. In one embodiment, the invention provides a chimeric polypeptide assembly composition comprising a first portion binding domain with binding affinity to the tumor-specific marker fucosyl GM1 comprising anti-fucosyl GM1 VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

(xxvii) Anti-GD2 Binding Domains

In some embodiments, the invention provides chimeric polypeptide assembly compositions comprising a first portion binding domain with binding affinity to the tumor-specific marker GD2 and a second binding domain binds to an effector cell antigen, such as CD3 antigen. In one embodiment, the binding domain comprises VL and VH derived form a monoclonal antibody to GD2. Monoclonal antibodies to GD2 are known in the art. In one embodiment, the invention provides a chimeric polypeptide assembly composition comprising a first portion binding domain with binding affinity to the tumor-specific marker GD2 comprising anti-GD2 VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

(xxviii) Anti-carbonicanhydrase IX Binding Domains

In some embodiments, the invention provides chimeric polypeptide assembly compositions comprising a first portion binding domain with binding affinity to the tumor-specific marker carbonicanhydrase IX and a second binding domain binds to an effector cell antigen, such as CD3 antigen. In one embodiment, the binding domain comprises VL and VH derived form a monoclonal antibody to carbonicanhydrase IX. Monoclonal antibodies to carbonicanhydrase IX are known in the art. In one embodiment, the invention provides a chimeric polypeptide assembly composition comprising a first portion binding domain with binding affinity to the tumor-specific marker carbonicanhydrase IX comprising anti-carbonicanhydrase IX VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

(xxix) Anti-CD44v6 Binding Domains

In some embodiments, the invention provides chimeric polypeptide assembly compositions comprising a first portion binding domain with binding affinity to the tumor-specific marker CD44v6 and a second binding domain binds to an effector cell antigen, such as CD3 antigen. In one embodiment, the binding domain comprises VL and VH derived form a monoclonal antibody to CD44v6. Monoclonal antibodies to CD44v6 are known in the art. In one embodiment, the invention provides a chimeric polypeptide assembly composition comprising a first portion binding domain with binding affinity to the tumor-specific marker CD44v6 comprising anti-CD44v6 VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

(xxx) Anti-Sonic Hedgehog Binding Domains

In some embodiments, the invention provides chimeric polypeptide assembly compositions comprising a first portion binding domain with binding affinity to the tumor-specific marker Sonic Hedgehog and a second binding domain binds to an effector cell antigen, such as CD3 antigen. In one embodiment, the binding domain comprises VL and VH derived form a monoclonal antibody to Sonic Hedgehog. Monoclonal antibodies to Sonic Hedgehog are known in the art. In one embodiment, the invention provides a chimeric polypeptide assembly composition comprising a first portion binding domain with binding affinity to the tumor-specific marker Sonic Hedgehog comprising anti-Sonic Hedgehog VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

(xxxi) Anti-Wue-1 Binding Domains

In some embodiments, the invention provides chimeric polypeptide assembly compositions comprising a first portion binding domain with binding affinity to the tumor-specific marker Wue-1 and a second binding domain binds to an effector cell antigen, such as CD3 antigen. In one embodiment, the binding domain comprises VL and VH derived form a monoclonal antibody to Wue-1. Monoclonal antibodies to Wue-1 are known in the art. In one embodiment, the invention provides a chimeric polypeptide assembly composition comprising a first portion binding domain with binding affinity to the tumor-specific marker Wue-1 comprising anti-Wue-1 VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

(xxxii) Anti-Plasma Cell Antigen 1 Binding Domains

In some embodiments, the invention provides chimeric polypeptide assembly compositions comprising a first portion binding domain with binding affinity to the tumor-specific marker plasma cell antigen 1 and a second binding domain binds to an effector cell antigen, such as CD3 antigen. In one embodiment, the binding domain comprises VL and VH derived form a monoclonal antibody to plasma cell antigen 1. Monoclonal antibodies to plasma cell antigen 1 are known in the art. In one embodiment, the invention provides a chimeric polypeptide assembly composition comprising a first portion binding domain with binding affinity to the tumor-specific marker plasma cell antigen 1 comprising anti-plasma cell antigen 1 VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

(xxxiii) Anti-Melanoma Chondroitin Sulfate Proteoglycan Binding Domains

In some embodiments, the invention provides chimeric polypeptide assembly compositions comprising a first portion binding domain with binding affinity to the tumor-specific marker melanoma chondroitin sulfate proteoglycan and a second binding domain binds to an effector cell antigen, such as CD3 antigen. In one embodiment, the binding domain comprises VL and VH derived form a monoclonal antibody to melanoma chondroitin sulfate proteoglycan. Monoclonal antibodies to melanoma chondroitin sulfate proteoglycan are known in the art. In one embodiment, the invention provides a chimeric polypeptide assembly composition comprising a first portion binding domain with binding affinity to the tumor-specific marker melanoma chondroitin sulfate proteoglycan comprising anti-melanoma chondroitin sulfate proteoglycan VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

(xxxiv) Anti-CCR8 Binding Domains

In some embodiments, the invention provides chimeric polypeptide assembly compositions comprising a first portion binding domain with binding affinity to the tumor-specific marker CCR8 and a second binding domain binds to an effector cell antigen, such as CD3 antigen. In one embodiment, the binding domain comprises VL and VH derived form a monoclonal antibody to CCR8. Monoclonal antibodies to CCR8 are known in the art. In one embodiment, the invention provides a chimeric polypeptide assembly composition comprising a first portion binding domain with binding affinity to the tumor-specific marker CCR8 comprising anti-CCR8 VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

(xxxv) Anti-STEAP Binding Domains

In some embodiments, the invention provides chimeric polypeptide assembly compositions comprising a first portion binding domain with binding affinity to the tumor-specific marker 6-transmembrane epithelial antigen of prostate (STEAP) and a second binding domain binds to an effector cell antigen, such as CD3 antigen. In one embodiment, the binding domain comprises VL and VH derived form a monoclonal antibody to STEAP. Monoclonal antibodies to STEAP are known in the art. In one embodiment, the invention provides a chimeric polypeptide assembly composition comprising a first portion binding domain with binding affinity to the tumor-specific marker STEAP comprising anti-STEAP VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

(xxxvi) Anti-Mesothelin Binding Domains

In some embodiments, the invention provides chimeric polypeptide assembly compositions comprising a first portion binding domain with binding affinity to the tumor-specific marker mesothelin and a second binding domain binds to an effector cell antigen, such as CD3 antigen. In one embodiment, the binding domain comprises VL and VH derived form a monoclonal antibody to mesothelin. Monoclonal antibodies to mesothelin are known in the art. In one embodiment, the invention provides a chimeric polypeptide assembly composition comprising a first portion binding domain with binding affinity to the tumor-specific marker mesothelin comprising anti-mesothelin VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

(xxxvii) Anti-A33 Antigen Binding Domains

In some embodiments, the invention provides chimeric polypeptide assembly compositions comprising a first portion binding domain with binding affinity to the tumor-specific marker A33 antigen and a second binding domain binds to an effector cell antigen, such as CD3 antigen. In one embodiment, the binding domain comprises VL and VH derived form a monoclonal antibody to A33 antigen. Monoclonal antibodies to A33 antigen are known in the art. In one embodiment, the invention provides a chimeric polypeptide assembly composition comprising a first portion binding domain with binding affinity to the tumor-specific marker A33 antigen comprising anti-A33 antigen VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

(xxxviii) Anti-PSCA Binding Domains

In some embodiments, the invention provides chimeric polypeptide assembly compositions comprising a first portion binding domain with binding affinity to the tumor-specific marker prostate stem cell antigen (PSCA) and a second binding domain binds to an effector cell antigen, such as CD3 antigen. In one embodiment, the binding domain comprises VL and VH derived form a monoclonal antibody to PSCA. Monoclonal antibodies to PSCA are known in the art. In one embodiment, the invention provides a chimeric polypeptide assembly composition comprising a first portion binding domain with binding affinity to the tumor-specific marker PSCA comprising anti-PSCA VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

(xxxix) Anti-Ly-6 Binding Domains

In some embodiments, the invention provides chimeric polypeptide assembly compositions comprising a first portion binding domain with binding affinity to the tumor-specific marker Ly-6 and a second binding domain binds to an effector cell antigen, such as CD3 antigen. In one embodiment, the binding domain comprises VL and VH derived form a monoclonal antibody to LY-6. Monoclonal antibodies to LY-6 are known in the art. In one embodiment, the invention provides a chimeric polypeptide assembly composition comprising a first portion binding domain with binding affinity to the tumor-specific marker LY-6 comprising anti-LY-6 VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

(xl) Anti-SAS Binding Domains

In some embodiments, the invention provides chimeric polypeptide assembly compositions comprising a first portion binding domain with binding affinity to the tumor-specific marker SAS and a second binding domain binds to an effector cell antigen, such as CD3 antigen. In one embodiment, the binding domain comprises VL and VH derived form a monoclonal antibody to SAS. Monoclonal antibodies to SAS are known in the art. In one embodiment, the invention provides a chimeric polypeptide assembly composition comprising a first portion binding domain with binding affinity to the tumor-specific marker SAS comprising anti-SAS VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

(xli) Anti-Desmoglein 4 Binding Domains

In some embodiments, the invention provides chimeric polypeptide assembly compositions comprising a first portion binding domain with binding affinity to the tumor-specific marker desmoglein 4 and a second binding domain binds to an effector cell antigen, such as CD3 antigen. In one embodiment, the binding domain comprises VL and VH derived form a monoclonal antibody to desmoglein 4. Monoclonal antibodies to desmoglein 4 are known in the art. In one embodiment, the invention provides a chimeric polypeptide assembly composition comprising a first portion binding domain with binding affinity to the tumor-specific marker desmoglein 4 comprising anti-desmoglein 4 VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

(xlii) Anti-Fetal Acetylcholine Receptor Binding Domains

In some embodiments, the invention provides chimeric polypeptide assembly compositions comprising a first portion binding domain with binding affinity to the tumor-specific marker fetal acetylcholine receptor and a second binding domain binds to an effector cell antigen, such as CD3 antigen. In one embodiment, the binding domain comprises VL and VH derived form a monoclonal antibody to fetal acetylcholine receptor. Monoclonal antibodies to fetal acetylcholine receptor are known in the art. In one embodiment, the invention provides a chimeric polypeptide assembly composition comprising a first portion binding domain with binding affinity to the tumor-specific marker fetal acetylcholine receptor comprising anti-fetal acetylcholine receptor VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

(xliii) Anti-CD25 Binding Domains

In some embodiments, the invention provides chimeric polypeptide assembly compositions comprising a first portion binding domain with binding affinity to the tumor-specific marker CD25 and a second binding domain binds to an effector cell antigen, such as CD3 antigen. In one embodiment, the binding domain comprises VL and VH derived form a monoclonal antibody to CD25. Monoclonal antibodies to CD25 are known in the art; e.g., daclizumab. In one embodiment, the invention provides a chimeric polypeptide assembly composition comprising a first portion binding domain with binding affinity to the tumor-specific marker CD25 comprising anti-CD25 VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

(xliv) Anti-Cancer Antigen 19-9 Binding Domains

In some embodiments, the invention provides chimeric polypeptide assembly compositions comprising a first portion binding domain with binding affinity to the tumor-specific marker cancer antigen 19-9 (CA 19-9) and a second binding domain binds to an effector cell antigen, such as CD3 antigen. In one embodiment, the binding domain comprises VL and VH derived form a monoclonal antibody to CA 19-9. Monoclonal antibodies to CA 19-9 are known in the art. In one embodiment, the invention provides a chimeric polypeptide assembly composition comprising a first portion binding domain with binding affinity to the tumor-specific marker CA 19-9 comprising anti-cancer antigen 19-9 VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

(xlv) Anti-CA-125 Binding Domains

In some embodiments, the invention provides chimeric polypeptide assembly compositions comprising a first portion binding domain with binding affinity to the tumor-specific marker cancer antigen 125 (CA-125) and a second binding domain binds to an effector cell antigen, such as CD3 antigen. In one embodiment, the binding domain comprises VL and VH derived form a monoclonal antibody to CA-125. Monoclonal antibodies to CA-125 are known in the art. In one embodiment, the invention provides a chimeric polypeptide assembly composition comprising a first portion binding domain with binding affinity to the tumor-specific marker CA-125 comprising anti-CA-125 VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

(xlvi) Anti-MISIIR Binding Domains

In some embodiments, the invention provides chimeric polypeptide assembly compositions comprising a first portion binding domain with binding affinity to the tumor-specific marker Muellerian inhibitory substance type II receptor (MISIIR) and a second binding domain binds to an effector cell antigen, such as CD3 antigen. In one embodiment, the binding domain comprises VL and VH derived form a monoclonal antibody to MIS. Monoclonal antibodies to MISIIR are known in the art. In one embodiment, the invention provides a chimeric polypeptide assembly composition comprising a first portion binding domain with binding affinity to the tumor-specific marker MISIIR comprising anti-MISIIR VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

(xlvii) Anti-Sialylated Tn Antigen Binding Domains

In some embodiments, the invention provides chimeric polypeptide assembly compositions comprising a first portion binding domain with binding affinity to the tumor-specific marker sialylated Tn antigen and a second binding domain binds to an effector cell antigen, such as CD3 antigen. In one embodiment, the binding domain comprises VL and VH derived form a monoclonal antibody to sialylated Tn antigen. Monoclonal antibodies to sialylated Tn antigen are known in the art. In one embodiment, the invention provides a chimeric polypeptide assembly composition comprising a first portion binding domain with binding affinity to the tumor-specific marker sialylated Tn antigen comprising anti-sialylated Tn antigen VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

(xlviii) Anti-FAP Binding Domains

In some embodiments, the invention provides chimeric polypeptide assembly compositions comprising a first portion binding domain with binding affinity to the tumor-specific marker fibroblast activation antigen (FAP) and a second binding domain binds to an effector cell antigen, such as CD3 antigen. In one embodiment, the binding domain comprises VL and VH derived form a monoclonal antibody to FAP. Monoclonal antibodies to FAP are known in the art. In one embodiment, the invention provides a chimeric polypeptide assembly composition comprising a first portion binding domain with binding affinity to the tumor-specific marker FAP comprising anti-FAP VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

(xlix) Anti-CD248 Binding Domains

In some embodiments, the invention provides chimeric polypeptide assembly compositions comprising a first portion binding domain with binding affinity to the tumor-specific marker endosialin (CD248) and a second binding domain binds to an effector cell antigen, such as CD3 antigen. In one embodiment, the binding domain comprises VL and VH derived form a monoclonal antibody to CD248. Monoclonal antibodies to CD248 are known in the art. In one embodiment, the invention provides a chimeric polypeptide assembly composition comprising a first portion binding domain with binding affinity to the tumor-specific marker CD248 comprising anti-CD248 VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

(l) Anti-EGFRvIII Binding Domains

In some embodiments, the invention provides chimeric polypeptide assembly compositions comprising a first portion binding domain with binding affinity to the tumor-specific marker epidermal growth factor receptor variant III (EGFRvIII) and a second binding domain binds to an effector cell antigen, such as CD3 antigen. In one embodiment, the binding domain comprises VL and VH derived form a monoclonal antibody to EGFRvIII. Monoclonal antibodies to EGFRvIII are known in the art. Exemplary, non-limiting examples of VL and VH sequences are presented in Table 2. In one embodiment, the invention provides a chimeric polypeptide assembly composition comprising a first portion binding domain with binding affinity to the tumor-specific marker EGFRvIII comprising the anti-EGFRvIII VL and VH sequences set forth in Table 2. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences set forth in Table 2. Preferably, in the embodiments, said binding has a $K_d$ value of greater than $10^{-7}$ to $10^{-10}$ M, as determined in an vitro binding assay.

(li) Anti-TAL6 Binding Domains

In some embodiments, the invention provides chimeric polypeptide assembly compositions comprising a first portion binding domain with binding affinity to the tumor-specific marker tumor-associated antigen L6 (TAL6) and a second binding domain binds to an effector cell antigen, such as CD3 antigen. In one embodiment, the binding domain comprises VL and VH derived form a monoclonal antibody to TAL6. Monoclonal antibodies to TAL6 are known in the art. In one embodiment, the invention provides a chimeric polypeptide assembly composition comprising a first portion binding domain with binding affinity to the tumor-specific marker TAL6 comprising anti-TAL6 VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

(lii) Anti-SAS Binding Domains

In some embodiments, the invention provides chimeric polypeptide assembly compositions comprising a first portion binding domain with binding affinity to the tumor-specific marker tumor-associated antigen SAS and a second binding domain binds to an effector cell antigen, such as CD3 antigen. In one embodiment, the binding domain comprises VL and VH derived form a monoclonal antibody to SAS. Monoclonal antibodies to SAS are known in the art. In one embodiment, the invention provides a chimeric polypeptide assembly composition comprising a first portion binding domain with binding affinity to the tumor-specific marker SAS comprising anti-SAS VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

(liii) Anti-CD63 Binding Domains

In some embodiments, the invention provides chimeric polypeptide assembly compositions comprising a first portion binding domain with binding affinity to the tumor-specific marker tumor-associated antigen CD63 and a second binding domain binds to an effector cell antigen, such as CD3 antigen. In one embodiment, the binding domain comprises VL and VH derived form a monoclonal antibody to CD63. Monoclonal antibodies to CD63 are known in the art. In one embodiment, the invention provides a chimeric polypeptide assembly composition comprising a first portion binding domain with binding affinity to the tumor-specific marker CD63 comprising anti-CD63 VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

(liv) Anti-TAG72 Binding Domains

In some embodiments, the invention provides chimeric polypeptide assembly compositions comprising a first portion binding domain with binding affinity to the tumor-specific marker tumor-associated antigen TAG72 and a second binding domain binds to an effector cell antigen, such as CD3 antigen. In one embodiment, the binding domain comprises VL and VH derived form a monoclonal antibody to TAG72. Monoclonal antibodies to TAG72 are known in the art. Exemplary, non-limiting examples of VL and VH sequences are presented in Table 2. In one embodiment, the invention provides a chimeric polypeptide assembly composition comprising a first portion binding domain with binding affinity to the tumor-specific marker TAG72 comprising the anti-TAG72 VL and VH sequences set forth in Table 2. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences set forth in Table 2. Preferably, in the embodiments, said binding has a $K_d$ value of greater than $10^{-7}$ to $10^{-10}$ M, as determined in an vitro binding assay.

(lv) Anti-TF-ANTIGEN Binding Domains

In some embodiments, the invention provides chimeric polypeptide assembly compositions comprising a first portion binding domain with binding affinity to the tumor-specific marker tumor-associated antigen Thomsen-Friedenreich antigen (TF-antigen) and a second binding domain binds to an effector cell antigen, such as CD3 antigen. In one embodiment, the binding domain comprises VL and VH derived form a monoclonal antibody to TF-antigen. Monoclonal antibodies to TF-antigen are known in the art. In one embodiment, the invention provides a chimeric polypeptide assembly composition comprising a first portion binding domain with binding affinity to the tumor-specific marker TF-antigen comprising anti-TF-antigen VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

(lvi) Anti-IGF-IR Binding Domains

In some embodiments, the invention provides chimeric polypeptide assembly compositions comprising a first portion binding domain with binding affinity to the tumor-specific marker tumor-associated antigen insulin-like growth factor I receptor (IGF-IR) and a second binding domain binds to an effector cell antigen, such as CD3 antigen. In one embodiment, the binding domain comprises VL and VH derived form a monoclonal antibody to IGF-IR. Monoclonal antibodies to IGF-IR are known in the art. In one embodiment, the invention provides a chimeric polypeptide assembly composition comprising a first portion binding domain with binding affinity to the tumor-specific marker IGF-IR comprising anti-IGF-IR VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

(lvii) Anti-Cora Antigen Binding Domains

In some embodiments, the invention provides chimeric polypeptide assembly compositions comprising a first portion binding domain with binding affinity to the tumor-specific marker tumor-associated antigen Cora antigen and a second binding domain binds to an effector cell antigen, such as CD3 antigen. In one embodiment, the binding domain comprises VL and VH derived form a monoclonal antibody to Cora antigen. Monoclonal antibodies to Cora antigen are known in the art. In one embodiment, the invention provides a chimeric polypeptide assembly composition comprising a first portion binding domain with binding affinity to the tumor-specific marker Cora antigen comprising anti-Cora antigen VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

(lviii) Anti-CD7 Binding Domains

In some embodiments, the invention provides chimeric polypeptide assembly compositions comprising a first portion binding domain with binding affinity to the tumor-specific marker tumor-associated antigen CD7 and a second binding domain binds to an effector cell antigen, such as CD3 antigen. In one embodiment, the binding domain comprises VL and VH derived form a monoclonal antibody to CD7. Monoclonal antibodies to CD7 are known in the art. In one embodiment, the invention provides a chimeric polypeptide assembly composition comprising a first portion binding domain with binding affinity to the tumor-specific marker CD7 comprising anti-CD7 VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

(lix) Anti-CD22 Binding Domains

In some embodiments, the invention provides chimeric polypeptide assembly compositions comprising a first portion binding domain with binding affinity to the tumor-specific marker tumor-associated antigen CD22 and a second binding domain binds to an effector cell antigen, such as CD3 antigen. In one embodiment, the binding domain comprises VL and VH derived form a monoclonal antibody to CD22. Monoclonal antibodies to CD22 are known in the art. In one embodiment, the invention provides a chimeric polypeptide assembly composition comprising a first portion binding domain with binding affinity to the tumor-specific marker CD22 comprising anti-CD22 VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

(lx) Anti-CD79a Binding Domains

In some embodiments, the invention provides chimeric polypeptide assembly compositions comprising a first portion binding domain with binding affinity to the tumor-specific marker tumor-associated antigen CD79a and a second binding domain binds to an effector cell antigen, such as CD3 antigen. In one embodiment, the binding domain comprises VL and VH derived form a monoclonal antibody to CD79a. Monoclonal antibodies to CD79a are known in the art. In one embodiment, the invention provides a chimeric polypeptide assembly composition comprising a first portion binding domain with binding affinity to the tumor-specific marker CD79a comprising anti-CD79a VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

(lxi) Anti-CD79b Binding Domains

In some embodiments, the invention provides chimeric polypeptide assembly compositions comprising a first portion binding domain with binding affinity to the tumor-specific marker tumor-associated antigen CD79b and a second binding domain binds to an effector cell antigen, such as CD3 antigen. In one embodiment, the binding domain comprises VL and VH derived form a monoclonal antibody to CD79b. Monoclonal antibodies to CD79b are known in the art. In one embodiment, the invention provides a chimeric polypeptide assembly composition comprising a first portion binding domain with binding affinity to the tumor-specific marker CD79b comprising anti-CD79b VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

(lxii) Anti-G250 Binding Domains

In some embodiments, the invention provides chimeric polypeptide assembly compositions comprising a first portion binding domain with binding affinity to the tumor-specific marker tumor-associated antigen G250 and a second binding domain binds to an effector cell antigen, such as CD3 antigen. In one embodiment, the binding domain comprises VL and VH derived form a monoclonal antibody to G250. Monoclonal antibodies to G250 are known in the art. In one embodiment, the invention provides a chimeric polypeptide assembly composition comprising a first portion binding domain with binding affinity to the tumor-specific marker G250 comprising anti-G250 VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

(lxiii) Anti-MT-MMPs Binding Domains

In some embodiments, the invention provides chimeric polypeptide assembly compositions comprising a first portion binding domain with binding affinity to the tumor-specific marker tumor-associated antigen MT-MMPs and a second binding domain binds to an effector cell antigen, such as CD3 antigen. In one embodiment, the binding domain comprises VL and VH derived form a monoclonal antibody to MT-MMPs. Monoclonal antibodies to MT-MMPs are known in the art. In one embodiment, the invention provides a chimeric polypeptide assembly composition comprising a first portion binding domain with binding affinity to the tumor-specific marker MT-MMPs comprising anti-MT-MMPs VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

(lxiv) Anti-F19 Antigen Binding Domains

In some embodiments, the invention provides chimeric polypeptide assembly compositions comprising a first portion binding domain with binding affinity to the tumor-specific marker tumor-associated antigen F19 antigen and a second binding domain binds to an effector cell antigen, such as CD3 antigen. In one embodiment, the binding domain comprises VL and VH derived form a monoclonal antibody to F19 antigen. Monoclonal antibodies to F19 antigen are known in the art. In one embodiment, the invention provides a chimeric polypeptide assembly composition comprising a first portion binding domain with binding affinity to the tumor-specific marker F19 antigen comprising anti-F19 antigen VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

(lxv) Anti-EphA2 Receptor Binding Domains

In some embodiments, the invention provides chimeric polypeptide assembly compositions comprising a first portion binding domain with binding affinity to the tumor-specific marker tumor-associated antigen EphA2 receptor and a second binding domain binds to an effector cell antigen, such as CD3 antigen. In one embodiment, the binding domain comprises VL and VH derived form a monoclonal antibody to EphA2 receptor. Monoclonal antibodies to EphA2 receptor are known in the art. In one embodiment, the invention provides a chimeric polypeptide assembly composition comprising a first portion binding domain with binding affinity to the tumor-specific marker EphA2 receptor comprising anti-EphA2 receptor VL and VH sequences. In another embodiment, the invention provides a chimeric polypeptide assembly composition comprising a first portion binding domain with binding affinity to the tumor-specific marker comprising the CDR-L1 region, the CDR-L2 region, the CDR-L3 region, the CDR-H1 region, the CDR-H2 region, and the CDR-H3 region, wherein each is derived from the respective VL and VH sequences. Preferably, in the embodiments, said binding has a $K_d$ value of greater than $10^{-7}$ to $10^{-10}$ M, as determined in an vitro binding assay.

It is specifically contemplated that the chimeric polypeptide assembly composition can comprise any one of the foregoing binding domains or sequence variants thereof so long as the variants exhibit binding specificity for the described antigen. In one embodiment, a sequence variant would be created by substitution of an amino acid in the VL or VH sequence with a different amino acid. In deletion variants, one or more amino acid residues in a VL or VH sequence as described herein are removed. Deletion variants, therefore, include all fragments of a binding domain polypeptide sequence. In substitution variants, one or more amino acid residues of a VL or VH (or CDR) polypeptide are removed and replaced with alternative residues. In one aspect, the substitutions are conservative in nature and conservative substitutions of this type are well known in the art. In addition, it is specifically contemplated that the compositions comprising the first and the second binding domains disclosed herein can be utilized in any of the methods disclosed herein.

2. Release Segment

In another aspect, the invention relates to chimeric polypeptide assembly compositions incorporating release segment (RS) peptide sequences capable of being cleaved by one or more mammalian proteases, wherein upon exposure of the RS to the protease (or proteases) the RS is cleaved and the bispecific binding domains are released from the composition. Upon release of the bispecific binding domains and the shielding bulking moiety of the subject chimeric polypeptide assembly compositions, the binding domains regain, due to the loss of the shielding effect of the bulking moiety, their full capacity to concurrently bind to an effector T cell and a cancer, tumor or target cell, resulting in damage or cytolysis of the cancer, tumor or target cell.

In certain embodiments, the invention provides chimeric polypeptide assembly composition compositions comprising a single fusion protein comprising a bifunctional binding domain portion, a binding moiety such as an XTEN, and an incorporated peptidic RS that is a substrate for one or more proteases associated with a target tissue, wherein the RS is recombinantly linked to the terminus of a bulking moiety, and the RS is recombinantly linked to a first portion comprising the first and the second binding domains; thus, the RS is located between the first portion and the XTEN or other bulking moiety.

In the embodiments the invention provides chimeric polypeptide assembly composition comprising one or more RS that are a substrate for a protease associated with a diseased target tissue in a subject; non-limiting examples of which are a cancer, tumor, or tissues or organs involved in a proliferative disorder or inflammatory disease. It is an object of the invention to provide RS specifically configured for use in chimeric polypeptide assembly compositions comprising bispecific binding domains such that the binding domains are released from the composition when the composition comprising the RS is in proximity with the targeted tissue-associated protease. The design of the chimeric polypeptide assembly compositions is such that the resulting released component comprising the binding domains have an enhanced ability to extravasate and to attach to or to penetrate into the target tissue; whether by the reduced molecular mass of the resulting fragment or by reduced steric hindrance by the flanking bulking moiety (e.g., XTEN) that is cleaved away.

Stroma in human carcinomas consists of extracellular matrix and various types of non-carcinoma cells such as leukocytes, endothelial cells, fibroblasts, and myofibroblasts. The tumor-associated stroma actively supports tumor growth by stimulating neo-angiogenesis, as well as proliferation and invasion of apposed carcinoma cells. Stromal fibroblasts, often referred to as cancer-associated fibroblasts (CAF), have a particularly important role in tumor progression due to their ability to dynamically modify the composition of the extracellular matrix (ECM), thereby facilitating tumor cell invasion and subsequent metastatic colonization. In particular, it is known in the art that proteases are important components that contribute to malignant progression, including tumor angiogenesis, invasion, extracellular matrix remodeling, and metastasis, where proteases function as part of an extensive multidirectional network of proteolytic interactions. As a requirement of malignant tumours is their ability to acquire a vasculature system in order to penetrate into surrounding normal tissues and disseminate to distant sites, the tumor relies heavily upon the increased expression of extracellular endoproteases from multiple enzymatic classes; e.g., the metalloproteases (MMP) and serine, threonine, cysteine and aspartic proteases. The role of proteases are not limited to tissue invasion and angiogenesis, however; these enzymes also have major roles in growth factor activation, cellular adhesion, cellular survival and immune surveillance. For example, MMPs are able to impact tumour cell behaviour as a consequence of their ability to cleave growth factors, cell surface receptors, cell adhesion molecules, or chemokines. Collectively, the actions of tumor-associated proteases represent a significant force in the phenotypic evolution of cancer.

As there is considerable evidence demonstrating differential expression of many such proteolytic enzymes between normal and tumour tissue, it is specifically contemplated that this differential expression can be utilized as a means to activate the subject compositions that are in proximity of a tumor. In this respect, the serine and metalloproteases, in particular, are candidates for targeted, differential drug delivery of the subject composition due to both their elevated activity in the extracellular tumour environment and their ability to selectively and specifically cleave the short peptide sequences of the RS, resulting in high levels of the active first portion of the subject composition at the tumour and low levels of intact chimeric polypeptide assembly composition in normal healthy tissues. As a consequence of the selective delivery of the chimeric polypeptide assembly composition, there is both a concomitant reduction in the required activity or dose of these agents and reduced toxicity against normal tissues, including liver, heart and bone marrow, thereby greatly improving the therapeutic index of the chimeric polypeptide assembly compositions. It is specifically contemplated that the disclosed compositions have the beneficial properties of this prodrug concept in that, amongst other properties, in the uncleaved state they exhibit reduced binding affinity for their respective ligands and they exhibit reduced extravasation in normal, healthy tissues, but upon cleavage are able to better extravasate, penetrate a tumor, and have higher binding affinity for their respective ligands; all of which contribute to an enhanced therapeutic index and reduced side effects of the subject compositions.

In some embodiments, the invention comprises chimeric polypeptide assembly compositions comprising RS wherein when the composition is cleaved by the targeted tissue-associated protease(s), releasing a fragment comprising the first portion binding domains, wherein the fragment is capable of penetrating within said targeted tissue, such as a tumor, to a concentration that is at least 2-fold, or at least 3-fold, or at least 4-fold, or at least 5-fold greater compared to the composition that is not cleaved. In other embodiments, the invention comprises chimeric polypeptide assembly compositions comprising RS wherein when the composition is cleaved by the targeted tissue-associated protease, releasing a fragment comprising the first portion binding domains, the fragment comprising the first portion binding domains is capable of penetrating within said tissue at a rate that is at least 2-fold, or at least 3-fold, or at least 4-fold, or at least 5-fold faster compared to the composition not comprising the RS. In one embodiment, the invention comprises a chimeric polypeptide assembly composition comprising RS wherein when the composition is cleaved by the targeted tissue-associated protease, releasing a fragment comprising the first portion binding domains, the cleaved first portion fragment has a resulting molecular weight that is at least 20% less, or at least 30% less, or at least 40% less, or at least 50% less, or at least 60% less, or at least 70% less, or at least 80% less than the intact chimeric polypeptide assembly composition that is not cleaved by the protease. In another embodiment, the invention comprises a chimeric polypeptide assembly composition comprising RS wherein when the composition is cleaved by the targeted tissue-associated protease, releasing a fragment comprising the first portion binding domains, the cleaved first portion fragment has a resulting hydrodynamic radius that is at least 20% less, or 30% less, or at least 40% less, or at least 50% less, or at least 60% less, or at least 70% less, or at least 80% less than the intact chimeric polypeptide assembly composition that is not cleaved by the protease. It is specifically contemplated that in the subject chimeric polypeptide assembly composition embodiments, the cleavage by the tissue-associated protease results in a fragment comprising the first portion binding domains that is able to more effectively penetrate the tissue, such as a tumor, because of the reduced size of the fragment relative to the intact composition, resulting in a pharmacologic effect known in the art for the combined binding domains within said tissue or cell, which may include damage to the membrane, induction of apoptosis, cytolysis or death of the target cell. It is also specifically contemplated that the RS of the chimeric polypeptide assembly compositions are designed for use in compositions intended to target specific tissues with a specific protease known to be produced by that target tissue or cell. In one embodiment, the RS comprises an amino acid sequence that is a substrate for a protease associated with a tissue that is a cancer. In another embodiment, the RS comprises an amino acid sequence that is a substrate for a protease associated with a cancerous tumor. In another embodiment, the RS comprises an amino acid sequence that is a substrate for a protease associated with a cancer such as a leukemia. In another embodiment, the RS comprises an amino acid sequence that is a substrate for a protease associated with a proliferative disorder. In another embodiment, the RS of the chimeric polypeptide assembly composition comprises an amino acid sequence that is a substrate for a protease associated with an inflammatory disease.

In some embodiments, the RS is a substrate for at least one protease selected from the group consisting of metalloproteinases, cysteine proteases, aspartate proteases, and serine proteases. In another embodiment, the RS is a substrate for one or more proteases selected from the group consisting of meprin, neprilysin (CD10), PSMA, BMP-1, A disintegrin and metalloproteinases (ADAMs), ADAMS, ADAMS, ADAM10, ADAM12, ADAM15, ADAM17 (TACE), ADAM19, ADAM28 (MDC-L), ADAM with thrombospondin motifs (ADAMTS), ADAMTS1, ADAMTS4, ADAMTS5, MMP-1 (Collagenase 1), MMP-2 (Gelatinase A), MMP-3 (Stromelysin 1), MMP-7 (Matrilysin 1), MMP-8 (Collagenase 2), MMP-9 (Gelatinase B), MMP-10 (Stromelysin 2), MMP-11(Stromelysin 3), MMP-12 (Macrophage elastase), MMP-13 (Collagenase 3), MMP-14 (MT1-MMP), MMP-15 (MT2-MMP), MMP-19, MMP-23 (CA-MMP), MMP-24 (MT5-MMP), MMP-26 (Matrilysin 2), MMP-27 (CMMP), Legumain, Cathepsin B, Cathepsin C, Cathepsin K, Cathepsin L, Cathepsin S, Cathespin X, Cathepsin D, Cathepsin E, Secretase, urokinase (uPA), Tissue-type plasminogen activator (tPA), plasmin, thrombin, prostate-specific antigen (PSA, KLK3), human neutrophil elastase (HNE), Elastase, Tryptase, Type II transmembrane serine proteases (TTSPs), DESC1, Hepsin (HPN), Matriptase, Matriptase-2, TMPRSS2, TMPRSS3, TMPRSS4 (CAP2), Fibroblast Activation Protein (FAP), kallikrein-related peptidase (KLK family), KLK4, KLK5, KLK6, KLK7, KLK8, KLK10, KLK11, KLK13, and KLK14. In some embodiments, the RS is a substrate for an ADAM17. In some embodiments, the RS is a substrate for a BMP-1. In some embodiments, the RS is a substrate for a cathepsin. In some embodiments, the RS is a substrate for a cysteine protease. In some embodiments, the RS is a substrate for a HtrA1. In some embodiments, the RS is a substrate for a legumain. In some embodiments, the RS is a substrate for a MT-SP1. In some embodiments, the RS is a substrate for a metalloproteinase. In some embodiments, the RS is a substrate for a neutrophil elastase. In some embodiments, the RS is a substrate for thrombin. In some embodiments, the RS is a substrate for a Type II transmembrane serine protease (TTSP). In some embodiments, the RS is a substrate for TMPRSS3. In some embodiments, the RS is a substrate for TMPRSS4. In some embodiments, the RS is a substrate for uPA. In one embodiment, the RS of the chimeric polypeptide assembly composition is a substrate for at least two proteases selected from the group consisting of MMP-2, MMP-9, uPA, and matriptase. In another embodiment, the RS of the chimeric polypeptide assembly composition is a substrate for MMP-2, MMP-9, uPA, and matriptase proteases.

In one embodiment, the RS of the chimeric polypeptide assembly composition comprises an amino acid sequence that is a substrate for an extracellular protease secreted by the target tissue, including but not limited to the proteases of Table 3. In another embodiment, the RS of the chimeric polypeptide assembly composition comprises an amino acid sequence that is a substrate for a cellular protease located within a cell, including but not limited to the proteases of Table 3.

In certain embodiments, the invention provides RS compositions intended for use in the subject chimeric polypeptide assembly compositions comprising at least a first cleavage sequence selected from the group of sequences set forth in Table 4. In some embodiments, the RS sequence of the subject compositions is selected from the group of sequences consisting of LSGRSDNHSPLGLAGS (SEQ ID NO: 1), SPLGLAGSLSGRSDNH (SEQ ID NO: 2), SPLGLSGRSDNH (SEQ ID NO: 3), LAGRSDNHSPLGLAGS (SEQ ID NO: 4), LSGRSDNHVPLSLKMG (SEQ ID NO: 5), SPLGLAGS (SEQ ID NO: 6), GPLALARG (SEQ ID NO: 7), LSGRSDNH (SEQ ID NO: 8), VPLSLTMG (SEQ ID NO: 9), VPLSLKMG (SEQ ID NO: 10), VPLSLSMG (SEQ ID NO: 11), EPLELVAG (SEQ ID NO: 12), EPLELRAG (SEQ ID NO: 13), EPAALMAG (SEQ ID NO: 14), EPASLMAG (SEQ ID NO: 15), RIGSLRTA (SEQ ID NO: 16), RIQFLRTA (SEQ ID NO: 17), EPFHLMAG (SEQ ID NO: 18), VPLSLFMG (SEQ ID NO: 19), EPLELPAG (SEQ ID NO: 20), and EPLELAAG (SEQ ID NO: 21). Where desired, the RS sequence of the subject chimeric polypeptide assembly composition is LSGRSDNHSPLGLAGS (SEQ ID NO: 1). In one embodiment, the RS of the chimeric polypeptide assembly composition comprises the sequence of BSRS1 of Table 4. In another embodiment, the RS of the chimeric polypeptide assembly composition consists of the sequence of BSRS1 of Table 4.

In another embodiment, the RS of the cleavage conjugate composition comprises a first cleavage sequence and a second cleavage sequence different from said first cleavage sequence wherein each sequence is selected from the group of sequences set forth in Table 4 and the first and the second cleavage sequences are linked to each other by 1 to 6 amino acids selected from glycine, serine, alanine, and threonine. In another embodiment, the RS of the cleavage conjugate composition comprises a first cleavage sequence, a second cleavage sequence different from said first cleavage sequence, and a third cleavage sequence wherein each sequence is selected from the group of sequences set forth in Table 4 and the first and the second and the third cleavage sequences are linked to each other by 1 to 6 amino acids selected from glycine, serine, alanine, and threonine. In other embodiments, the invention provides chimeric polypeptide assembly compositions comprising one, two, or three RS It is specifically intended that the multiple RS of the chimeric polypeptide assembly compositions can be concatenated to form a universal sequence that can be cleaved by multiple proteases. It is contemplated that such compositions would be more readily cleaved by diseased target tissues that express multiple proteases, with the result that the resulting fragments bearing the binding domains would more readily penetrate the target tissue and exert the pharmacologic effect of the binding domains.

TABLE 3

Proteases of Target Tissues.

| Class of Proteases | Protease |
|---|---|
| Metalloproteinases | Meprin |
| | Neprilysin (CD10) |
| | PSMA |
| | BMP-1 |
| | A disintegrin and metalloproteinases (ADAMs) |
| | ADAM8 |
| | ADAM9 |
| | ADAM10 |
| | ADAM12 |
| | ADAM15 |
| | ADAM17 (TACE) |
| | ADAM19 |
| | ADAM28 (MDC-L) |
| | ADAM with thrombospondin motifs (ADAMTS) |
| | ADAMTS1 |
| | ADAMTS4 |
| | ADAMTS5 |
| | Matrix Metalloproteinases (MMPs) |
| | MMP-1 (Collagenase 1) |
| | MMP-2 (Gelatinase A) |
| | MMP-3 (Stromelysin 1) |
| | MMP-7 (Matrilysin 1) |
| | MMP-8 (Collagenase 2) |
| | MMP-9 (Gelatinase B) |
| | MMP-10 (Stromelysin 2) |
| | MMP-11(Stromelysin 3) |
| | MMP-12 (Macrophage elastase) |
| | MMP-13 (Collagenase 3) |
| | MMP-14 (MT1-MMP) |
| | MMP-15 (MT2-MMP) |

TABLE 3-continued

Proteases of Target Tissues.

| Class of Proteases | Protease |
|---|---|
| | MMP-19 |
| | MMP-23 (CA-MMP) |
| | MMP-24 (MT5-MMP) |
| | MMP-26 (Matrilysin 2) |
| | MMP-27 (CMMP) |
| Cysteine Proteases | Legumain |
| | Cysteine Cathepsins |
| | Cathepsin B |
| | Cathepsin C |
| | Cathepsin K |
| | Cathepsin L |
| | Cathepsin S |
| | Cathespin X |
| Aspartate Proteases | Cathepsin D |
| | Cathepsin E |
| | Secretase |
| Serine Proteases | Urokinase (uPA) |
| | Tissue-type plasminogen activator (tPA) |
| | Plasmin |
| | Thrombin |
| | Prostate-specific antigen (PSA, KLK3) |
| | Human neutrophil elastase (HNE) |
| | Elastase |
| | Tryptase |
| | Type II transmembrane serine proteases (TTSPs) |
| | DESC1 |
| | Hepsin (HPN) |
| | Matriptase |
| | Matriptase-2 |
| | TMPRSS2 |
| | TMPRSS3 |
| | TMPRSS4 (CAP2) |
| | Fibroblast Activation Protein (FAP) |
| | kallikrein-related peptidase (KLK family) |
| | KLK4 |
| | KLK5 |
| | KLK6 |
| | KLK7 |
| | KLK8 |
| | KLK10 |
| | KLK11 |
| | KLK13 |
| | KLK14 |

TABLE 4

Sequences of Release Segments (RS)

| RS Designation | Protease Acting Upon Sequence | Exemplary Cleavage Sequence | SEQ ID NO: | Cleavage Sequences* | SEQ ID NO: |
|---|---|---|---|---|---|
| BSRS1 | MMP-2, 7, 9, 14, matriptase, uPA, legumain | LSGR↓SDN↓HSPLG↓LAGS | 243 | | |
| BSRS2 | MMP-2, 7, 9, 14, matriptase, uPA, legumain | SPLG↓LAGSLSGR↓SDN↓H | 244 | | |
| BSRS3 | MMP-2, 7, 9, 14, matriptase, uPA, legumain | SPLG↓LSGR↓SDN↓H | 245 | | |
| BSRS4 | MMP-2, 7, 9, 14, matriptase, uPA, legumain | LAGR↓SDN↓HSPLG↓LAGS | 246 | | |
| BSRS5 | MMP-2, 7, 9, 14, matriptase, uPA, legumain | LAGR↓SDN↓HVPLS↓LSMG | 247 | | |

TABLE 4-continued

| Sequences of Release Segments (RS) | | | | | |
|---|---|---|---|---|---|
| RS Designation | Protease Acting Upon Sequence | Exemplary Cleavage Sequence | SEQ ID NO: | Cleavage Sequences* | SEQ ID NO: |
| BSRS6 | MMP-2, 7, 9, 14, matriptase, uPA, legumain | LAGR↓SDN↓HEPLE↓LVAG | 248 | | |
| BRSS7 | MMP-2, 7, 9, 14, matriptase, uPA, legumain | LSGR↓SDN↓HVPLS↓LK↓MG | 249 | | |
| RS1 | MMP-2, 7, 9, 14 | SPLG↓LAGS | 250 | | |
| RS2 | MMP-2, 7, 9, 14, matriptase, uPA, legumain | GPLG↓LAR↓G | 251 | | |
| RS3 | Matriptase, uPA, legumain | LSGRVSDNVH | 252 | | |
| RS4 | MMP-2,14 | GTAH↓LMGG | 253 | | |
| RS5 | MMP-14 | RIGS↓LRTA | 254 | | |
| RS6 | MMP-14 | RIGA↓LRTA | 255 | | |
| RS7 | MMP-14 | RIGW↓LRTA | 256 | | |
| RS8 | MMP-14 | RIGN↓LRTA | 257 | | |
| RS9 | MMP-14 | RIGF↓LRTA | 258 | | |
| RS10 | MMP-14 | RIFF↓LRTA | 259 | | |
| RS11 | MMP-14 | RILF↓LRTA | 260 | | |
| RS12 | MMP-14 | RIYF↓LRTA | 261 | | |
| RS13 | MMP-14 | RIQF↓LRTA | 262 | | |
| RS14 | MMP-14 | EPAA↓LMAG | 263 | | |
| RS15 | MMP-14 | EPAN↓LMAG | 264 | | |
| RS16 | MMP-14 | EPAS↓LMAG | 265 | | |
| RS17 | MMP-14 | EPFH↓LMAG | 266 | | |
| RS18 | MMP-14 | EPWH↓LMAG | 267 | | |
| RS19 | MMP-14 | EPRH↓LMAG | 268 | | |
| RS20 | MMP-7 | VPLS↓LFMG | 269 | | |
| RS21 | MMP-7 | VPLS↓LHMG | 270 | | |
| RS22 | MMP-7 | VPLS↓LQAG | 271 | | |
| RS23 | MMP-2, 7, 9, 14 | VPLS↓LTMG | 272 | | |
| RS24 | MMP-2, 7, 9, 14, matriptase | VPLS↓LKMG | 273 | | |
| RS25 | MMP-2, 7, 9, 14 | VPLS↓LSMG | 274 | | |
| RS26 | MMP-7 | VPLS↓LNAG | 275 | | |
| RS27 | MMP-7 | VPLS↓LLMG | 276 | | |
| RS28 | MMP-7 | EPLE↓LPAG | 277 | | |
| RS29 | MMP-2, 7, 9, 14 | EPLE↓LAAG | 278 | | |
| RS30 | MMP-2, 7, 9 | EPLE↓LVAG | 279 | | |
| RS31 | MMP-7 | EPLE↓LSAG | 280 | | |

TABLE 4-continued

Sequences of Release Segments (RS)

| RS Designation | Protease Acting Upon Sequence | Exemplary Cleavage Sequence | SEQ ID NO: | Cleavage Sequences* | SEQ ID NO: |
|---|---|---|---|---|---|
| RS32 | MMP-7 | EPLE↓LDAG | 281 | | |
| RS33 | MMP-7 | EPLE↓LQAG | 282 | | |
| RS34 | MMP-2, 7, 9, 14, matriptase | EPLE↓LRAG | 283 | | |
| RS35 | MMP-7 | EPLE↓LKAG | 284 | | |
| RS36 | MMP-2,7, 9, 14 | EPLE↓LIAG | 285 | | |
| RS37 | Elastase-2 | LGPV↓SGVP | 286 | —/—/—/VIAT/—/—/—/— | |
| RS38 | Granzyme-B | VAGD↓SLEE | 287 | V/—/—/D/—/—/—/— | |
| RS39 | MMP-12 | GPAG↓LGGA | 288 | G/PA/—/G/L/—/G/— | 359 |
| RS40 | MMP-13 | GPAG↓LRGA | 289 | G/P/—/G/L/—/GA/— | 360 |
| RS41 | MMP-17 | APLG↓LRLR | 290 | —/PS/—/—/LQ/—/LT/— | |
| RS42 | MMP-20 | PALP↓LVAQ | 291 | | |
| RS43 | TEV | ENLYFQ↓G | 292 | E/N/L/Y/F/Q/GS | 361 |
| RS44 | Enterokinase | DDDK↓IVGG | 293 | | |
| RS45 | Protease 3C (PreScission™) | LEVLFQ↓GP | 294 | | |
| RS46 | Sortase A | LPKT↓GSES | 295 | L/P/KEAD/T/G/—/ EKS/S | 362 |
| RS47 | Trypsin | K↓VX** or R↓X | | K/X or R/X | |
| RS48 | Trypsin | R↓X** | | SASRSA | 363 |
| RS49 | uPA | SGR↓SA | 296 | S/G/R/SRKA/AG SVR | 364 |
| RS50 | tPA | YGR↓SA | 297 | RYFLI/GA/R/RV AS/AG | |
| RS51 | PSA | SSYY↓SG | 298 | S/S/FY/Y/S/G | 365 |
| RS52 | DESC1 | RRAR↓VVGG | 299 | R/RAL/ALY/R/A V/V/G/G | 366 |
| RS53 | Hepsin | RQLR↓VVGG | 300 | R/RQ/YL/R/V/V/ G/G | 367 |
| RS54 | Matriptase-2 | RRAR↓VVGG | 299 | R/R/A/R/AV/V/G/ G | 368 |
| RS55 | MT-SP1/Matriptase | RQAR↓VVGG | 301 | R/QR/A/R/AVY/ V/G/G | 369 |
| RS56 | PSMA | N↓γN | | NγN | |
| RS57 | Cathepsin C | GF↓FY | 302 | GP/FWR/X/- | |
| RS58 | Cathepsin D | F↓IK | | FL/IV/KE | |
| RS59 | Cathepsin E | F↓IK | | FL/IV/KE | |
| RS60 | Cathepsin F | WLR↓ | | WYRNle/L/RKQ | |
| RS61 | Cathepsin K | KPR↓ | | KMGH/ILPNle/RKQ | |
| RS62 | Cathepsin L | KFR↓ | | RKLnL/FYW/RKQ | |
| RS63 | Cathepsin S | RVK↓ | | RPI/VLMnL/RKQ | |

TABLE 4-continued

Sequences of Release Segments (RS)

| RS Designation | Protease Acting Upon Sequence | Exemplary Cleavage Sequence | SEQ ID NO: | Cleavage Sequences* | SEQ ID NO: |
|---|---|---|---|---|---|
| RS64 | Cathepsin V/L2 | PWR↓ | | PNleR/WYF/RKQ | |
| RS65 | MMP | PLG↓HofOrnL | 303 | | |
| RS66 | MMP | EPCitFHofYL | 304 | | |
| RS67 | MMP-2 | PQG↓IAGQ | 305 | | |
| RS68 | MMP-2 | PQG↓IMelG | 306 | | |
| RS69 | MMP-9 | AALG↓NvaP | 307 | | |
| RS70 | MMP-9 | GPQG↓IAGQR | 308 | | |
| RS71 | MMP-9 | SGKIPRT↓ATA | 309 | S/G/K/I/P/R/PSTRA/ Hy/ST/A | 370 |
| RS72 | MMP-9 | SGPLF↓YSVTA | 310 | | |
| RS73 | MMP-9 | PLR↓LSW | 311 | | |
| RS74 | MMP-9 | GKGPRQ↓ITA | 312 | | |
| RS75 | MMP-9 | SGRR↓LIHHT | 313 | S/G/R/R/L/IL/H/H/T | 371 |
| RS76 | MMP-9 | SGQPHY↓LTTA | 314 | | |
| RS77 | MMP-9 | SG↓LKALM | 315 | | |
| RS78 | MMP-9 | SGFGSRY↓LTA | 316 | | |
| RS79 | MMP-9 | SGLRPAK↓STA | 317 | | |
| RS80 | MMP-9 | LGP↓STST | 318 | | |
| RS81 | MMP-9 | PQG↓VR | 319 | | |
| RS82 | MMP-9 | PSG↓LP | 320 | P/S/G/L/HyP | 372 |
| RS83 | MMP-9 | PAG↓VQ | 321 | | |
| RS84 | MMP-9 | PSG↓RD | 322 | | |
| RS85 | MMP-9 | PPG↓IV | 323 | P/PG/G/Hy/HyR | |
| RS86 | MMP-9 | PEN↓FF | 324 | | |
| RS87 | MMP-9 | PLK↓LM | 325 | | |
| RS88 | MMP-9 | PGA↓YH | 326 | | |
| RS89 | MMP-9 | AIH↓IQ | 327 | | |
| RS90 | MMP-9 | HFF↓KN | 328 | | |
| RS91 | MMP-9 | GLS↓LS | 329 | | |
| RS92 | MMP-9 | ASD↓YK | 330 | | |
| RS93 | MMP-2, MMP-9 | GPLG↓MLSQ | 331 | | |
| RS94 | MMP-2, MMP-9 | CG↓LDD | 332 | | |
| RS95 | MMP-2, MMP-9, MT1-MMP | GPQG↓VIWGQ | 333 | | |
| RS96 | MMP-7 | RPLA↓LWRS | 334 | | |
| RS97 | MMP-7 | GPLG↓LARK | 335 | | |
| RS98 | Hk2 | GKAFR↓RL | 336 | | |
| RS99 | MMP-9, uPA | RPSA↓SRSA | 337 | | |

TABLE 4-continued

| Sequences of Release Segments (RS) | | | | | |
|---|---|---|---|---|---|
| RS Designation | Protease Acting Upon Sequence | Exemplary Cleavage Sequence | SEQ ID NO: | Cleavage Sequences* | SEQ ID NO: |
| RS100 | MMP-2 | PLGLDpaAR | 338 | | |
| RS101 | MMP-9 | PMG↓IST | 339 | P/LMVQChaHofNva/ G/LIYSFC/ST | |
| RS102 | MMP-9 | PChaG↓SmcHA | 340 | P/LCha/G/LSmc/ HW/A | |
| RS103 | MMP-13, MMP-8 | PChaGNvaHADpa | 341 | | |
| RS104 | ADAM10 | PTASA↓LKG | 342 | P/T/A/AS/A/LFYQ/ KRTI/GAS | 373 |
| RS105 | ADAM17 | PRPAA↓VKGT | 343 | P/HR/P/AS/A/VIL/ KRTVI/GST/TP | |
| RS106 | Cathepsin B | V↓Cit | | | |
| RS107 | Cathepsin B | F↓K | | | |
| RS108 | Elastase | AA↓PV | 344 | | |
| RS109 | Cathepsin D | GPIC↓FRLG | 345 | | |
| RS110 | Plasmin | A↓FK | | | |
| RS111 | Legumain | AAN↓L | 346 | | |
| RS112 | Legumain | PTN↓ | | PTAWS/TPASI/N | |
| RS113 | Meprin | ↓DGP | | ED/GTAV/— | |
| RS114 | Meprin A | F↓SPFR | 347 | SFAMTY/SFAMTY/P/ PVIGA/— | |
| RS115 | Meprin B | E↓EEAY | 348 | DE/DE/YEFDG/ PVIGA/— | |
| RS116 | Neprilysin | $_{\beta}$-AIA↓L | 349 | $_{\beta}$—A/LI/A/L | |
| RS117 | ADAMTS4 | E↓VQRKTGT | 350 | E/AFVLMY/(—)/ RK/——(—)/ST | |
| RS118 | ADAMTS4 | DVQE↓FRGVTAVIR | 351 | | |
| RS119 | ADAMTS4 | HNE↓FRQRETYMVF | 352 | | |
| RS120 | ADAMTS5 | KEEE↓GLGS | 353 | | |
| RS121 | ADAMTS5 | GELE↓GRGT | 354 | | |
| RS122 | ADAMTS5 | NITEGE↓ARGS | 355 | | |
| RS123 | ADAMTS5 | TAQE↓AGEG | 356 | | |

TABLE 4-continued

| Sequences of Release Segments (RS) | | | | | |
|---|---|---|---|---|---|
| RS Designation | Protease Acting Upon Sequence | Exemplary Cleavage Sequence | SEQ ID NO: | Cleavage Sequences* | SEQ ID NO: |
| RS124 | ADAMTS5 | VSQE↓LGQR | 357 | | |
| RS125 | ADAMTS5 | PTAQE↓AGE | 358 | | |

↓indicates cleavage site
Special amino acid abbreviation:
Cit: Citrilline;
Cha: β-cyclohexylalanine;
Hof: homophenylalanine;
Nva: aminosuberic acid;
Dpa: D-phenylalanine;
Nle: Norleucine;
Smc: S-methylcysteine;
MnL: methylnorleucine;
Mel: Melphalan.
*the listing of multiple amino acids before, between, or after a slash indicate alternative amino acids that can be substituted at the position; "–" indicates that any amino acid may be substituted for the corresponding amino acid indicated in the middle column
**x is any L-amino acid other than proline
Hy is any hydrophobic L-amino acid
γ indicates that bond is a gamma carboxy linkage

3. Bulking Moiety

In another aspect, the instant invention relates to chimeric polypeptide assembly compositions comprising at least a first bulking moiety. In some embodiments, the invention provides a chimeric polypeptide assembly compositions comprising a bulking moiety. Non-limiting examples of bulking moieties include extended recombinant polypeptide (XTEN, as described herein, below); albumin binding domain; albumin; IgG binding domain; polypeptides of at least 350 amino acid residues consisting of proline, serine, and alanine; fatty acid; elastin-like protein (ELP) (the individual subunit or building blocks of ELPs are derived from a five amino acid motif found in human protein elastin that is repeated multiple times to form the ELP biopolymer, as described in WO2016081884), Fc domain, polyethylene glycol (PEG), PLGA, and hydoxylethyl starch. In another embodiment, the bulking moiety comprises two different bulking moieties selected from the group consisting of XTEN; albumin binding domain; albumin; IgG binding domain; polypeptides consisting of proline, serine, and alanine; fatty acid; Fc domain, polyethylene glycol (PEG), PLGA, and hydoxylethyl starch, wherein the two bulking moieties are linked to each other and, in turn, to the release segment of the composition. In a preferred embodiment, the bulking moiety of the subject compositions is one or more molecules of XTEN. In another preferred embodiment, the chimeric polypeptide assembly compositions comprise a bulking moiety sequence having at least 90%, 91%, 92%, 93%, 94%, 95%, 96%, 97%, 98%, 99%, or 100% sequence identity to an XTEN sequence of comparable length selected from the group of sequences set forth in Table 5. In the embodiments, the XTEN polypeptides linked recombinantly to the second portion release segment(s) (RS) of the compositions.

Without being bound by theory, the incorporation of the bulking moiety was incorporated into the design of the subject compositions to confer certain important properties; 1) provide chimeric polypeptide assembly compositions with a bulking moiety that shields the binding domains and reduces binding affinity for the target antigens and effector cell antigens when the composition is intact, ii) provide chimeric polypeptide assembly compositions with a bulking moiety that provides enhanced half-life when administered to a subject, iii) provide chimeric polypeptide assembly compositions with a bulking moiety that reduces extravasation in normal tissues and organs yet permits a degree of extravasation in diseased tissues (e.g., a tumor) with larger pore sizes in the vasculature, yet could be released from the composition by action of certain mammalian proteases, thereby permitting the binding domains of the composition to more readily penetrate into the diseased tissues and to concurrently bind the target antigens on the effector cell and tumor cell. To meet these needs, the invention provides chimeric polypeptide assembly compositions in which the bulking moiety provides increased mass and hydrodynamic radius to the resulting composition. In preferred embodiments, the bulking moiety is an XTEN polypeptide, which provides certain advantages in the design of the subject compositions in that is provides not only provides increased mass and hydrodynamic radius, but its flexible, unstructured characteristics provides a shielding effect over the binding domains of first portion of the composition, thereby reducing the likelihood of binding to antigens in normal tissues or the vasculature of normal tissues that don't express or express reduced levels of target antigens and/or effector cell antigens, and enhances solubility and proper folding of the scFv.

(i) XTEN

In certain embodiments, the invention provides chimeric polypeptide assembly compositions comprising one or more molecules of an XTEN linked recombinantly to the composition.

"XTEN" as used herein, are polypeptides with non-naturally occurring, substantially non-repetitive sequences having a low degree or no secondary or tertiary structure under physiologic conditions, as well as additional properties described in the paragraphs that follow. XTEN typically have from at least about 100 to at least about 1000 or more amino acids, and more preferably at least about 200 to at least about 900 amino acids, and more preferably at least about 400 to about 866 amino acids of which the majority or the entirety are small hydrophilic amino acids. As used herein, XTEN specifically excludes whole antibodies or antibody fragments (e.g. single-chain antibodies and Fc fragments). XTEN polypeptides have utility as fusion partners in that they serve in various roles, conferring certain desirable properties when linked to a composition comprising, for example, the first portion bispecific binding domains of the subject chimeric polypeptide assembly compositions described herein. The resulting compositions have enhanced properties, such as enhanced pharmacokinetic, physicochemical, pharmacologic, and improved toxicological and pharmaceutical properties compared to the corresponding binding domains not linked to XTEN, making them useful in the treatment of certain conditions for which the binding domains are known in the art to be used.

The unstructured characteristic and physicochemical properties of the XTEN result, in part, from the overall amino acid composition that is disproportionately limited to 4-6 types of hydrophilic amino acids, the linking of the amino acids in a quantifiable, substantially non-repetitive design, and from the resulting length and/or configuration of the XTEN polypeptide. In an advantageous feature common to XTEN but uncommon to native polypeptides, the properties of XTEN disclosed herein are not tied to absolute primary amino acid sequences, as evidenced by the diversity of the exemplary sequences of Table 5 that, within varying ranges of length, possess similar properties and confer enhanced properties on the compositions to which they are linked, many of which are documented in the Examples. Indeed, it is specifically contemplated that the compositions of the invention not be limited to those XTEN specifically enumerated in Table 5, but, rather, the embodiments include sequences having at least 90%, 91%, 92%, 93%, 94%, 95%, 96%, 97%, 98%, or 99% sequence identity to the sequences of Table 5 as they exhibit the properties of XTEN described below. It has been established that such XTEN have properties more like non-proteinaceous, hydrophilic polymers (such as polyethylene glycol, or "PEG") than they do proteins. The XTEN of the present invention exhibit one or more of the following advantageous properties: defined and uniform length (for a given sequence), conformational flexibility, reduced or lack of secondary structure, high degree of random coil formation, high degree of aqueous solubility, high degree of protease resistance, low immunogenicity, low binding to mammalian receptors, a defined degree of charge, and increased hydrodynamic (or Stokes) radii; properties that are similar to certain hydrophilic polymers (e.g., polyethylene glycol) that make them particularly useful as fusion partners.

The XTEN component(s) of the subject fusion proteins are designed to behave like denatured peptide sequences under physiological conditions, despite the extended length of the polymer. "Denatured" describes the state of a peptide in solution that is characterized by a large conformational freedom of the peptide backbone. Most peptides and proteins adopt a denatured conformation in the presence of high concentrations of denaturants or at elevated temperature. Peptides in denatured conformation have, for example, characteristic circular dichroism (CD) spectra and are characterized by a lack of long-range interactions as determined by NMR. "Denatured conformation" and "unstructured conformation" are used synonymously herein. In some embodiments, the invention provides chimeric polypeptide assembly compositions that comprise XTEN sequences that, under physiologic conditions, resemble denatured sequences that are substantially devoid of secondary structure under physiologic conditions. "Substantially devoid," as used in this context, means that at least about 80%, or about 90%, or about 95%, or about 97%, or at least about 99% of the XTEN amino acid residues of the XTEN sequence do not contribute to secondary structure, as measured or determined by the methods described herein, including algorithms or spectrophotometric assays.

A variety of well-established methods and assays are known in the art for determining and confirming the physicochemical properties of the subject XTEN. Such properties include but are not limited to secondary or tertiary structure, solubility, protein aggregation, stability, absolute and apparent molecular weight, purity and uniformity, melting properties, contamination and water content. The methods to measure such properties include analytical centrifugation, EPR, HPLC-ion exchange, HPLC-size exclusion chromatography (SEC), HPLC-reverse phase, light scattering, capillary electrophoresis, circular dichroism, differential scanning calorimetry, fluorescence, HPLC-ion exchange, HPLC-size exclusion, IR, NMR, Raman spectroscopy, refractometry, and UV/Visible spectroscopy. In particular, secondary structure can be measured spectrophotometrically, e.g., by circular dichroism spectroscopy in the "far-UV" spectral region (190-250 nm). Secondary structure elements, such as alpha-helix and beta-sheet, each give rise to a characteristic shape and magnitude of CD spectra, as does the lack of these structure elements. Secondary structure can also be predicted for a polypeptide sequence via certain computer programs or algorithms, such as the well-known Chou-Fasman algorithm (Chou, P. Y., et al. (1974) Biochemistry, 13: 222-45) and the Garnier-Osguthorpe-Robson algorithm ("Gor algorithm") (Gamier J, Gibrat J F, Robson B. (1996), GOR method for predicting protein secondary structure from amino acid sequence. Methods Enzymol 266:540-553), as described in US Patent Application Publication No. 20030228309A1. For a given sequence, the algorithms can predict whether there exists some or no secondary structure at all, expressed as the total and/or percentage of residues of the sequence that form, for example, alpha-helices or beta-sheets or the percentage of residues of the sequence predicted to result in random coil formation (which lacks secondary structure). Polypeptide sequences can be analyzed using the Chou-Fasman algorithm using sites on the world wide web at, for example, fasta.bioch.virginia.edu/fasta_www2/fasta_www.cgi?rm=misc1 and the Gor algorithm at npsa-pbil.ibcp.fr/cgi-bin/npsa_automat.pl?page=npsa_gor4.html (both accessed on Sep. 5, 2012). Random coil can be determined by a variety of methods, including by using intrinsic viscosity measurements, which scale with chain length in a conformation-dependent way (Tanford, C., Kawahara, K. & Lapanje, S. (1966) J. Biol. Chem. 241, 1921-1923), as well as by size-exclusion chromatography (Squire, P. G., Calculation of hydrodynamic parameters of random coil polymers from size exclusion chromatography and comparison with parameters by conventional methods. Journal of Chromatography, 1981, 5, 433-442). Additional methods are disclosed in Arnau, et al., Prot Expr and Purif (2006) 48, 1-13.

In one embodiment, the XTEN sequences of the chimeric polypeptide assembly compositions have an alpha-helix percentage ranging from 0% to less than about 5% and a beta-sheet percentage ranging from 0% to less than about 5% as determined by the Chou-Fasman algorithm and at least about 90% random coil formation as determined by the GOR algorithm. In another embodiment, the XTEN sequences of the disclosed compositions have an alpha-helix percentage less than about 2% and a beta-sheet percentage less than about 2% as determined by the Chou-Fasman algorithm and at least about 90% random coil formation as determined by the GOR algorithm. In another embodiment, the XTEN sequences of the compositions are substantially lacking secondary structure as measured by circular dichroism.

It has been established that the non-repetitive characteristic of XTEN employed in the subject compositions of the present invention together with the particular types of amino acids that predominate in the XTEN, rather than the absolute primary sequence, confers one or more of the enhanced physicochemical and biological properties of the XTEN and the resulting chimeric polypeptide assembly compositions. Accordingly, while the sequences of Table 5 are exemplary, they are not intended to be limiting as sequences having at least 90%, 91%, 92%, 93%, 94%, 95%, 96%, 97%, 98%, or 99% sequence identity to the sequences of Table 5 exhibit the enhanced properties of XTEN. These enhanced properties include a high degree of expression of the chimeric polypeptide assembly compositions fusion protein in the host cell, greater genetic stability of the gene encoding the XTEN portion of the subject compositions, XTEN confers a greater degree of solubility on the resulting chimeric polypeptide assembly compositions with less tendency to aggregate, and enhanced pharmacokinetics of the resulting chimeric polypeptide assembly compositions compared to binding domains not linked to XTEN. These enhanced properties permit more efficient manufacturing, greater uniformity of the final product, lower cost of goods, and/or facilitate the formulation of pharmaceutical preparations containing extremely high protein concentrations of chimeric polypeptide assembly composition, in some cases exceeding 100 mg/ml, as well as an improved safety profile and reduced dosing interval, described more fully below, of the resulting compositions.

In some embodiments, the XTEN sequence used in the chimeric polypeptide assembly compositions of the invention is at least 90%, 91%, 92%, 93%, 94%, 95%, 96%, 97%, 98%, 99%, or 100% identical to a sequence selected from the group consisting of AE144, AE144_1A, AE144_2A, AE144_2B, AE144_3A, AE144_3B, AE144_4A, AE144_4B, AE144_5A, AE144_6B, AE288_1, AE288_2, AE144A, AE144B, AE180A, AE216A, AE252A, AE288A, AE324A, AE360A, AE396A, AE432A, AE468A, AE504A, AE540A, AE576A, AE612A, AE648A, AE684A, AE720A, AE756A, AE792A, AE828A, AE869, AE144_R1, AE288_R1, AE432_R1, AE576_R1, AE864_R1, AE712, AE864_R2, AE912, AM923, AE948, AE1044, AE1140, AE1236, AE1332, AE1428, AE1524, AE1620, AE1716, AE1812, AE1908, AE2004A, and any combination thereof. See US 2010-0239554 A1. In one particular embodiment, the XTEN comprises a sequence selected from AE144, AE288, AE576, AE864, AE865, or AE866, or any combination thereof.

In some embodiments, wherein less than 100% of amino acids of an XTEN in the chimeric polypeptide assembly compositions are selected from glycine (G), alanine (A), serine (S), threonine (T), glutamate (E) and proline (P), or wherein less than 100% of the sequence consists of the XTEN sequences of Table 5, the remaining amino acid residues of the XTEN are selected from any of the other 14 natural L-amino acids, but are preferentially selected from hydrophilic amino acids such that the XTEN sequence contains at least about 90%, 91%, 92%, 93%, 94%, 95%, 96%, 97%, 98%, or at least about 99% hydrophilic amino acids. The content of hydrophobic amino acids in the XTEN utilized in the chimeric polypeptide assembly compositions can be less than 5%, or less than 2%, or less than 1% hydrophobic amino acid content. Hydrophobic residues that are less favored in construction of XTEN include tryptophan, phenylalanine, tyrosine, leucine, isoleucine, valine, and methionine. Additionally, XTEN sequences can contain less than 5% or less than 4% or less than 3% or less than 2% or less than 1% or none of the following amino acids: methionine (for example, to avoid oxidation), or asparagine and glutamine (to avoid desamidation).

The amino acid sequences for certain XTEN sequences utilized in the chimeric polypeptide assembly embodiments of the invention are shown in Table 5.

TABLE 5

XTEN Polypeptides

| XTEN Name | Amino Acid Sequence | SEQ ID NO: |
|---|---|---|
| AE144 | GSEPATSGSETPGTSESATPESGPGSEPATSGSETPGSPAGSPTSTEEGT STEPSEGSAPGSEPATSGSETPGSEPATSGSETPGSEPATSGSETPGTST EPSEGSAPGTSESATPESGPGSEPATSGSETPGTSTEPSEGSAP | 374 |
| AE144_1A | SPAGSPTSTEEGTSESATPESGPGTSTEPSEGSAPGSPAGSPTSTEEGTS TEPSEGSAPGTSTEPSEGSAPGTSESATPESGPGSEPATSGSETPGSEPA TSGSETPGSPAGSPTSTEEGTSESATPESGPGTSTEPSEGSAPG | 375 |
| AE144_2A | TSTEPSEGSAPGSPAGSPTSTEEGTSTEPSEGSAPGTSTEPSEGSAPGTS ESATPESGPGTSTEPSEGSAPGTSESATPESGPGSEPATSGSETPGTSTE PSEGSAPGTSTEPSEGSAPGTSESATPESGPGTSESATPESGPG | 376 |
| AE144_2B | TSTEPSEGSAPGSPAGSPTSTEEGTSTEPSEGSAPGTSTEPSEGSAPGTS ESATPESGPGTSTEPSEGSAPGTSESATPESGPGSEPATSGSETPGTSTE PSEGSAPGTSTEPSEGSAPGTS ESATPESGPGTSESATPESGPG | 376 |
| AE144_3A | SPAGSPTSTEEGTSESATPESGPGSEPATSGSETPGTSESATPESGPGTS TEPSEGSAPGTSTEPSEGSAPGTSTEPSEGSAPGTSTEPSEGSAPGTSTE PSEGSAPGTSTEPSEGSAPGSPAGSPTSTEEGTSTEPSEGSAPG | 377 |

TABLE 5-continued

| XTEN Polypeptides | | |
|---|---|---|
| XTEN Name | Amino Acid Sequence | SEQ ID NO: |
| AE144_3B | SPAGSPTSTEEGTSESATPESGPGSEPATSGSETPGTSESATPESGPGTS<br>TEPSEGSAPGTSTEPSEGSAPGTSTEPSEGSAPGTSTEPSEGSAPGTSTE<br>PSEGSAPGTSTEPSEGSAPGSPAGSPTSTEEGTSTEPSEGSAPG | 377 |
| AE144_4A | TSESATPESGPGSEPATSGSETPGTSESATPESGPGSEPATSGSETPGTS<br>ESATPESGPGTSTEPSEGSAPGTSESATPESGPGSPAGSPTSTEEGSPAG<br>SPTSTEEGSPAGSPTSTEEGTSESATPESGPGTSTEPSEGSAPG | 378 |
| AE144_4B | TSESATPESGPGSEPATSGSETPGTSESATPESGPGSEPATSGSETPGTS<br>ESATPESGPGTSTEPSEGSAPGTSESATPESGPGSPAGSPTSTEEGSPAG<br>SPTSTEEGSPAGSPTSTEEGTSESATPESGPGTSTEPSEGSAPG | 378 |
| AE144_5A | TSESATPESGPGSEPATSGSETPGTSESATPESGPGSEPATSGSETPGTS<br>ESATPESGPGTSTEPSEGSAPGSPAGSPTSTEEGTSESATPESGPGSEPA<br>TSGSETPGTSESATPESGPGSPAGSPTSTEEGSPAGSPTSTEEG | 379 |
| AE144_6B | TSTEPSEGSAPGTSESATPESGPGTSESATPESGPGTSESATPESGPGSEP<br>ATSGSETPGSEPATSGSETPGSPAGSPTSTEEGTSTEPSEGSAPGTSTEP<br>SEGSAPGSEPATSGSETPGTSESATPESGPGTSTEPSEGSAPG | 380 |
| AE288_1 | GTSESATPESGPGSEPATSGSETPGTSESATPESGPGSEPATSGSETPGT<br>SESATPESGPGTSTEPSEGSAPGSPAGSPTSTEEGTSESATPESGPGSEP<br>ATSGSETPGTSESATPESGPGSPAGSPTSTEEGSPAGSPTSTEEGTSTEP<br>SEGSAPGTSESATPESGPGTSESATPESGPGTSESATPESGPGSEPATSG<br>SETPGSEPATSGSETPGSPAGSPTSTEEGTSTEPSEGSAPGTSTEPSEGS<br>APGSEPATSGSETPGTSESATPESGPGTSTEPSEGSAP | 381 |
| AE288_2 | GSPAGSPTSTEEGTSESATPESGPGSEPATSGSETPGTSESATPESGPGT<br>STEPSEGSAPGTSTEPSEGSAPGTSTEPSEGSAPGTSTEPSEGSAPGTST<br>EPSEGSAPGTSTEPSEGSAPGSPAGSPTSTEEGTSTEPSEGSAPGTSESA<br>TPESGPGSEPATSGSETPGTSESATPESGPGSEPATSGSETPGTSESATP<br>ESGPGTSTEPSEGSAPGTSESATPESGPGSPAGSPTSTEEGSPAGSPTST<br>EEGSPAGSPTSTEEGTSESATPESGPGTSTEPSEGSAP | 382 |
| AE576 | GSPAGSPTSTEEGTSESATPESGPGTSTEPSEGSAPGSPAGSPTSTEEGT<br>STEPSEGSAPGTSTEPSEGSAPGTSESATPESGPGSEPATSGSETPGSEP<br>ATSGSETPGSPAGSPTSTEEGTSESATPESGPGTSTEPSEGSAPGTSTEP<br>SEGSAPGSPAGSPTSTEEGTSTEPSEGSAPGTSTEPSEGSAPGTSESATP<br>ESGPGTSTEPSEGSAPGTSESATPESGPGSEPATSGSETPGTSTEPSEGS<br>APGTSTEPSEGSAPGTSESATPESGPGTSESATPESGPGSPAGSPTSTEE<br>GTSESATPESGPGSEPATSGSETPGTSESATPESGPGTSTEPSEGSAPGT<br>STEPSEGSAPGTSTEPSEGSAPGTSTEPSEGSAPGTSTEPSEGSAPGTST<br>EPSEGSAPGSPAGSPTSTEEGTSTEPSEGSAPGTSESATPESGPGSEPAT<br>SGSETPGTSESATPESGPGSEPATSGSETPGTSESATPESGPGTSTEPSE<br>GSAPGTSESATPESGPGSPAGSPTSTEEGSPAGSPTSTEEGSPAGSPTST<br>EEGTSESATPESGPGTSTEPSEGSAP | 383 |
| AE624 | MAEPAGSPTSTEEGTPGSGTASSSPGSSTPSGATGSPGASPGTSSTGSP<br>GSPAGSPTSTEEGTSESATPESGPGTSTEPSEGSAPGSPAGSPTSTEEGT<br>STEPSEGSAPGTSTEPSEGSAPGTSESATPESGPGSEPATSGSETPGSEP<br>ATSGSETPGSPAGSPTSTEEGTSESATPESGPGTSTEPSEGSAPGTSTEP<br>SEGSAPGSPAGSPTSTEEGTSTEPSEGSAPGTSTEPSEGSAPGTSESATP<br>ESGPGTSTEPSEGSAPGTSESATPESGPGSEPATSGSETPGTSTEPSEGS<br>APGTSTEPSEGSAPGTSESATPESGPGTSESATPESGPGSPAGSPTSTEE<br>GTSESATPESGPGSEPATSGSETPGTSESATPESGPGTSTEPSEGSAPGT<br>STEPSEGSAPGTSTEPSEGSAPGTSTEPSEGSAPGTSTEPSEGSAPGTST<br>EPSEGSAPGSPAGSPTSTEEGTSTEPSEGSAPGTSESATPESGPGSEPAT<br>SGSETPGTSESATPESGPGSEPATSGSETPGTSESATPESGPGTSTEPSE<br>GSAPGTSESATPESGPGSPAGSPTSTEEGSPAGSPTSTEEGSPAGSPTST<br>EEGTSESATPESGPGTSTEPSEGSAP | 384 |
| AE864 | GSPAGSPTSTEEGTSESATPESGPGTSTEPSEGSAPGSPAGSPTSTEEGT<br>STEPSEGSAPGTSTEPSEGSAPGTSESATPESGPGSEPATSGSETPGSEP<br>ATSGSETPGSPAGSPTSTEEGTSESATPESGPGTSTEPSEGSAPGTSTEP<br>SEGSAPGSPAGSPTSTEEGTSTEPSEGSAPGTSTEPSEGSAPGTSESATP<br>ESGPGTSTEPSEGSAPGTSESATPESGPGSEPATSGSETPGTSTEPSEGS<br>APGTSTEPSEGSAPGTSESATPESGPGTSESATPESGPGSPAGSPTSTEE<br>GTSESATPESGPGSEPATSGSETPGTSESATPESGPGTSTEPSEGSAPGT<br>STEPSEGSAPGTSTEPSEGSAPGTSTEPSEGSAPGTSTEPSEGSAPGTST<br>EPSEGSAPGSPAGSPTSTEEGTSTEPSEGSAPGTSESATPESGPGSEPAT<br>SGSETPGTSESATPESGPGSEPATSGSETPGTSESATPESGPGTSTEPSE<br>GSAPGTSESATPESGPGSPAGSPTSTEEGSPAGSPTSTEEGSPAGSPTST<br>EEGTSESATPESGPGTSTEPSEGSAPGTSESATPESGPGSEPATSGSETP<br>GTSESATPESGPGSEPATSGSETPGTSESATPESGPGTSTEPSEGSAPGS | 385 |

TABLE 5-continued

| XTEN Polypeptides | | |
|---|---|---|
| XTEN Name | Amino Acid Sequence | SEQ ID NO: |
| | PAGSPTSTEEGTSESATPESGPGSEPATSGSETPGTSESATPESGPGSPA GSPTSTEEGSPAGSPTSTEEGTSTEPSEGSAPGTSESATPESGPGTSESA TPESGPGTSESATPESGPGSEPATSGSETPGSEPATSGSETPGSPAGSPT STEEGTSTEPSEGSAPGTSTEPSEGSAPGSEPATSGSETPGTSESATPES GPGTSTEPSEGSAP | |
| AE865 | GGSPAGSPTSTEEGTSESATPESGPGTSTEPSEGSAPGSPAGSPTSTEEG TSTEPSEGSAPGTSTEPSEGSAPGTSESATPESGPGSEPATSGSETPGSEP ATSGSETPGSPAGSPTSTEEGTSESATPESGPGTSTEPSEGSAPGTSTEP SEGSAPGSPAGSPTSTEEGTSTEPSEGSAPGTSTEPSEGSAPGTSESATP ESGPGTSTEPSEGSAPGTSESATPESGPGSEPATSGSETPGTSTEPSEGS APGTSTEPSEGSAPGTSESATPESGPGTSESATPESGPGSPAGSPTSTEE GTSESATPESGPGSEPATSGSETPGTSESATPESGPGTSTEPSEGSAPGT STEPSEGSAPGTSTEPSEGSAPGTSTEPSEGSAPGTSTEPSEGSAPGTST EPSEGSAPGSPAGSPTSTEEGTSTEPSEGSAPGTSESATPESGPGSEPAT SGSETPGTSESATPESGPGSEPATSGSETPGTSESATPESGPGTSTEPSE GSAPGTSESATPESGPGSPAGSPTSTEEGSPAGSPTSTEEGSPAGSPTST EEGTSESATPESGPGTSTEPSEGSAPGTSESATPESGPGSEPATSGSETP GTSESATPESGPGSEPATSGSETPGTSESATPESGPGTSTEPSEGSAPGS PAGSPTSTEEGTSESATPESGPGSEPATSGSETPGTSESATPESGPGSPA GSPTSTEEGSPAGSPTSTEEGTSTEPSEGSAPGTSESATPESGPGTSESA TPESGPGTSESATPESGPGSEPATSGSETPGSEPATSGSETPGSPAGSPT STEEGTSTEPSEGSAPGTSTEPSEGSAPGSEPATSGSETPGTSESATPES GPGTSTEPSEGSAP | 386 |
| AE866 | PGSPAGSPTSTEEGTSESATPESGPGTSTEPSEGSAPGSPAGSPTSTEEG TSTEPSEGSAPGTSTEPSEGSAPGTSESATPESGPGSEPATSGSETPGSEP ATSGSETPGSPAGSPTSTEEGTSESATPESGPGTSTEPSEGSAPGTSTEP SEGSAPGSPAGSPTSTEEGTSTEPSEGSAPGTSTEPSEGSAPGTSESATP ESGPGTSTEPSEGSAPGTSESATPESGPGSEPATSGSETPGTSTEPSEGS APGTSTEPSEGSAPGTSESATPESGPGTSESATPESGPGSPAGSPTSTEE GTSESATPESGPGSEPATSGSETPGTSESATPESGPGTSTEPSEGSAPGT STEPSEGSAPGTSTEPSEGSAPGTSTEPSEGSAPGTSTEPSEGSAPGTST EPSEGSAPGSPAGSPTSTEEGTSTEPSEGSAPGTSESATPESGPGSEPAT SGSETPGTSESATPESGPGSEPATSGSETPGTSESATPESGPGTSTEPSE GSAPGTSESATPESGPGSPAGSPTSTEEGSPAGSPTSTEEGSPAGSPTST EEGTSESATPESGPGTSTEPSEGSAPGTSESATPESGPGSEPATSGSETP GTSESATPESGPGSEPATSGSETPGTSESATPESGPGTSTEPSEGSAPGS PAGSPTSTEEGTSESATPESGPGSEPATSGSETPGTSESATPESGPGSPA GSPTSTEEGSPAGSPTSTEEGTSTEPSEGSAPGTSESATPESGPGTSESA TPESGPGTSESATPESGPGSEPATSGSETPGSEPATSGSETPGSPAGSPT STEEGTSTEPSEGSAPGTSTEPSEGSAPGSEPATSGSETPGTSESATPES GPGTSTEPSEGSAPG | 387 |
| AE1152 | GSPAGSPTSTEEGTSESATPESGPGTSTEPSEGSAPGSPAGSPTSTEEGT STEPSEGSAPGTSTEPSEGSAPGTSESATPESGPGSEPATSGSETPGSEP ATSGSETPGSPAGSPTSTEEGTSESATPESGPGTSTEPSEGSAPGTSTEP SEGSAPGSPAGSPTSTEEGTSTEPSEGSAPGTSTEPSEGSAPGTSESATP ESGPGTSTEPSEGSAPGTSESATPESGPGSEPATSGSETPGTSTEPSEGS APGTSTEPSEGSAPGTSESATPESGPGTSESATPESGPGSPAGSPTSTEE GTSESATPESGPGSEPATSGSETPGTSESATPESGPGTSTEPSEGSAPGT STEPSEGSAPGTSTEPSEGSAPGTSTEPSEGSAPGTSTEPSEGSAPGTST EPSEGSAPGSPAGSPTSTEEGTSTEPSEGSAPGTSESATPESGPGSEPAT SGSETPGTSESATPESGPGSEPATSGSETPGTSESATPESGPGTSTEPSE GSAPGTSESATPESGPGSPAGSPTSTEEGSPAGSPTSTEEGSPAGSPTST EEGTSESATPESGPGTSTEPSEGSAPGTSESATPESGPGSEPATSGSETP GTSESATPESGPGSEPATSGSETPGTSESATPESGPGTSTEPSEGSAPGS PAGSPTSTEEGTSESATPESGPGSEPATSGSETPGTSESATPESGPGSPA GSPTSTEEGSPAGSPTSTEEGTSTEPSEGSAPGTSESATPESGPGTSESA TPESGPGTSESATPESGPGSEPATSGSETPGSEPATSGSETPGSPAGSPT STEEGTSTEPSEGSAPGTSTEPSEGSAPGSEPATSGSETPGTSESATPES GPGTSTEPSEGSAPGTSESATPESGPGSEPATSGSETPGTSESATPESGP GSEPATSGSETPGTSESATPESGPGTSTEPSEGSAPGSPAGSPTSTEEGT SESATPESGPGSEPATSGSETPGTSESATPESGPGSPAGSPTSTEEGSPA GSPTSTEEGTSTEPSEGSAPGTSESATPESGPGTSESATPESGPGTSESA TPESGPGSEPATSGSETPGSEPATSGSETPGSPAGSPTSTEEGTSTEPSE GSAPGTSTEPSEGSAPGSEPATSGSETPGTSESATPESGPGTSTEPSEGS AP | 388 |

TABLE 5-continued

XTEN Polypeptides

| XTEN Name | Amino Acid Sequence | SEQ ID NO: |
|---|---|---|
| AE144A | STEPSEGSAPGSPAGSPTSTEEGTSTEPSEGSAPGTSESATPESGPGSEP ATSGSETPGTSESATPESGPGSEPATSGSETPGTSESATPESGPGTSTEP SEGSAPGTSESATPESGPGSPAGSPTSTEEGSPAGSPTSTEEGS | 389 |
| AE144B | SEPATSGSETPGTSESATPESGPGSEPATSGSETPGTSESATPESGPGTS TEPSEGSAPGSPAGSPTSTEEGTSESATPESGPGSEPATSGSETPGTSES ATPESGPGSPAGSPTSTEEGSPAGSPTSTEEGTSTEPSEGSAPG | 390 |
| AE180A | TSTEEGTSESATPESGPGSEPATSGSETPGTSESATPESGPGSPAGSPTS TEEGSPAGSPTSTEEGTSTEPSEGSAPGTSESATPESGPGTSESATPESG PGTSESATPESGPGSEPATSGSETPGSEPATSGSETPGSPAGSPTSTEEG TSTEPSEGSAPGTSTEPSEGSAPGSEPATS | 391 |
| AE216A | PESGPGTSTEPSEGSAPGSPAGSPTSTEEGTSESATPESGPGSEPATSGS ETPGTSESATPESGPGSPAGSPTSTEEGSPAGSPTSTEEGTSTEPSEGSA PGTSESATPESGPGTSESATPESGPGTSESATPESGPGSEPATSGSETPG SEPATSGSETPGSPAGSPTSTEEGTSTEPSEGSAPGTSTEPSEGSAPGSEP ATSGSETPGTSESAT | 392 |
| AE252A | ESGPGSEPATSGSETPGTSESATPESGPGTSTEPSEGSAPGSPAGSPTST EEGTSESATPESGPGSEPATSGSETPGTSESATPESGPGSPAGSPTSTEE GSPAGSPTSTEEGTSTEPSEGSAPGTSESATPESGPGTSESATPESGPGT SESATPESGPGSEPATSGSETPGSEPATSGSETPGSPAGSPTSTEEGTST EPSEGSAPGTSTEPSEGSAPGSEPATSGSETPGTSESATPESGPGTSTEPS E | 393 |
| AE288A | TPESGPGTSTEPSEGSAPGTSESATPESGPGSEPATSGSETPGTSESATP ESGPGSEPATSGSETPGTSESATPESGPGTSTEPSEGSAPGSPAGSPTST EEGTSESATPESGPGSEPATSGSETPGTSESATPESGPGSPAGSPTSTEE GSPAGSPTSTEEGTSTEPSEGSAPGTSESATPESGPGTSESATPESGPGT SESATPESGPGSEPATSGSETPGSEPATSGSETPGSPAGSPTSTEEGTST EPSEGSAPGTSTEPSEGSAPGSEPATSGSETPGTSESA | 394 |
| AE324A | PESGPGSPAGSPTSTEEGSPAGSPTSTEEGSPAGSPTSTEEGTSESATPES GPGTSTEPSEGSAPGTSESATPESGPGSEPATSGSETPGTSESATPESGP GSEPATSGSETPGTSESATPESGPGTSTEPSEGSAPGSPAGSPTSTEEGT SESATPESGPGSEPATSGSETPGTSESATPESGPGSPAGSPTSTEEGSPA GSPTSTEEGTSTEPSEGSAPGTSESATPESGPGTSESATPESGPGTSESA TPESGPGSEPATSGSETPGSEPATSGSETPGSPAGSPTSTEEGTSTEPSE GSAPGTSTEPSEGSAPGSEPATS | 395 |
| AE360A | PESGPGTSTEPSEGSAPGTSESATPESGPGSPAGSPTSTEEGSPAGSPTS TEEGSPAGSPTSTEEGTSESATPESGPGTSTEPSEGSAPGTSESATPESG PGSEPATSGSETPGTSESATPESGPGSEPATSGSETPGTSESATPESGPG TSTEPSEGSAPGSPAGSPTSTEEGTSESATPESGPGSEPATSGSETPGTS ESATPESGPGSPAGSPTSTEEGSPAGSPTSTEEGTSTEPSEGSAPGTSES ATPESGPGTSESATPESGPGTSESATPESGPGSEPATSGSETPGSEPATS GSETPGSPAGSPTSTEEGTSTEPSEGSAPGTSTEPSEGSAPGSEPATSGS ETPGTSESAT | 396 |
| AE396A | PESGPGSEPATSGSETPGTSESATPESGPGTSTEPSEGSAPGTSESATPES GPGSPAGSPTSTEEGSPAGSPTSTEEGSPAGSPTSTEEGTSESATPESGP GTSTEPSEGSAPGTSESATPESGPGSEPATSGSETPGTSESATPESGPGS EPATSGSETPGTSESATPESGPGTSTEPSEGSAPGSPAGSPTSTEEGTSE SATPESGPGSEPATSGSETPGTSESATPESGPGSPAGSPTSTEEGSPAGS PTSTEEGTSTEPSEGSAPGTSESATPESGPGTSESATPESGPGTSESATPE SGPGSEPATSGSETPGSEP ATSGSETPGSPAGSPTSTEEGTSTEPSEGSA PGTSTEPS | 397 |
| AE432A | EGSAPGSPAGSPTSTEEGTSTEPSEGSAPGTSESATPESGPGSEPATSGS ETPGTSESATPESGPGSEPATSGSETPGTSESATPESGPGTSTEPSEGSA PGTSESATPESGPGSPAGSPTSTEEGSPAGSPTSTEEGSPAGSPTSTEEG TSESATPESGPGTSTEPSEGSAPGTSESATPESGPGSEPATSGSETPGTS ESATPESGPGSEPATSGSETPGTSESATPESGPGTSTEPSEGSAPGSPAG SPTSTEEGTSESATPESGPGSEPATSGSETPGTSESATPESGPGSPAGSPT STEEGSPAGSPTSTEEGTSTEPSEGSAPGTSESATPESGPGTSESATPES GPGTSESATPESGPGSEPATSGSETPGSEPATSGSETPGSPAGSPTSTEE GTSTEPSEGSAPGTSTEPSEGSAPGSEPATS | 398 |
| AE468A | EGSAPGTSTEPSEGSAPGTSTEPSEGSAPGSPAGSPTSTEEGTSTEPSEG SAPGTSESATPESGPGSEPATSGSETPGTSESATPESGPGSEPATSGSET PGTSESATPESGPGTSTEPSEGSAPGTSESATPESGPGSPAGSPTSTEEG SPAGSPTSTEEGSPAGSPTSTEEGTSESATPESGPGTSTEPSEGSAPGTS ESATPESGPGSEPATSGSETPGTSESATPESGPGSEPATSGSETPGTSES | 399 |

TABLE 5-continued

XTEN Polypeptides

| XTEN Name | Amino Acid Sequence | SEQ ID NO: |
|---|---|---|
| | ATPESGPGTSTEPSEGSAPGSPAGSPTSTEEGTSESATPESGPGSEPATS<br>GSETPGTSESATPESGPGSPAGSPTSTEEGSPAGSPTSTEEGTSTEPSEG<br>SAPGTSESATPESGPGTSESATPESGPGTSESATPESGPGSEPATSGSET<br>PGSEPATSGSETPGSPAGSPTSTEEGTSTEPSEGSAPGTSTEPSEGSAPG<br>SEPATSGSETPGTSESAT | |
| AE504A | EGSAPGTSTEPSEGSAPGTSTEPSEGSAPGTSTEPSEGSAPGTSTEPSEG<br>SAPGSPAGSPTSTEEGTSTEPSEGSAPGTSESATPESGPGSEPATSGSET<br>PGTSESATPESGPGSEPATSGSETPGTSESATPESGPGTSTEPSEGSAPG<br>TSESATPESGPGSPAGSPTSTEEGSPAGSPTSTEEGSPAGSPTSTEEGTS<br>ESATPESGPGTSTEPSEGSAPGTSESATPESGPGSEPATSGSETPGTSES<br>ATPESGPGSEPATSGSETPGTSESATPESGPGTSTEPSEGSAPGSPAGSP<br>TSTEEGTSESATPESGPGSEPATSGSETPGTSESATPESGPGSPAGSPTS<br>TEEGSPAGSPTSTEEGTSTEPSEGSAPGTSESATPESGPGTSESATPESG<br>PGTSESATPESGPGSEPATSGSETPGSEPATSGSETPGSPAGSPTSTEEG<br>TSTEPSEGSAPGTSTEPSEGSAPGSEPATSGSETPGTSESATPESGPGTS<br>TEPS | 400 |
| AE540A | TPESGPGSPAGSPTSTEEGTSESATPESGPGSEPATSGSETPGTSESATP<br>ESGPGTSTEPSEGSAPGTSTEPSEGSAPGTSTEPSEGSAPGTSTEPSEGS<br>APGTSTEPSEGSAPGTSTEPSEGSAPGSPAGSPTSTEEGTSTEPSEGSAP<br>GTSESATPESGPGSEPATSGSETPGTSESATPESGPGSEPATSGSETPGT<br>SESATPESGPGTSTEPSEGSAPGTSESATPESGPGSPAGSPTSTEEGSPA<br>GSPTSTEEGSPAGSPTSTEEGTSESATPESGPGTSTEPSEGSAPGTSESA<br>TPESGPGSEPATSGSETPGTSESATPESGPGSEPATSGSETPGTSESATP<br>ESGPGTSTEPSEGSAPGSPAGSPTSTEEGTSESATPESGPGSEPATSGSE<br>TPGTSESATPESGPGSPAGSPTSTEEGSPAGSPTSTEEGTSTEPSEGSAP<br>GTSESATPESGPGTSESATPESGPGTSESATPESGPGSEPATSGSETPGS<br>EPATSGSETPGSPAGSPTSTEEGTSTEPSEGSAPGTSTEP | 401 |
| AE576A | TPESGPGTSESATPESGPGSPAGSPTSTEEGTSESATPESGPGSEPATSG<br>SETPGTSESATPESGPGTSTEPSEGSAPGTSTEPSEGSAPGTSTEPSEGS<br>APGTSTEPSEGSAPGTSTEPSEGSAPGTSTEPSEGSAPGSPAGSPTSTEE<br>GTSTEPSEGSAPGTSESATPESGPGSEPATSGSETPGTSESATPESGPGS<br>EPATSGSETPGTSESATPESGPGTSTEPSEGSAPGTSESATPESGPGSPA<br>GSPTSTEEGSPAGSPTSTEEGSPAGSPTSTEEGTSESATPESGPGTSTEPS<br>EGSAPGTSESATPESGPGSEPATSGSETPGTSESATPESGPGSEPATSGS<br>ETPGTSESATPESGPGTSTEPSEGSAPGSPAGSPTSTEEGTSESATPESG<br>PGSEPATSGSETPGTSESATPESGPGSPAGSPTSTEEGSPAGSPTSTEEG<br>TSTEPSEGSAPGTSESATPESGPGTSESATPESGPGTSESATPESGPGSEP<br>ATSGSETPGSEPATSGSETPGSPAGSPTSTEEGTSTEPSEGSAPGTSTEP<br>SEGSAPGSEPATSGSETPGTSESA | 402 |
| AE612A | GSETPGTSTEPSEGSAPGTSTEPSEGSAPGTSESATPESGPGTSESATPE<br>SGPGSPAGSPTSTEEGTSESATPESGPGSEPATSGSETPGTSESATPESG<br>PGTSTEPSEGSAPGTSTEPSEGSAPGTSTEPSEGSAPGTSTEPSEGSAPG<br>TSTEPSEGSAPGTSTEPSEGSAPGSPAGSPTSTEEGTSTEPSEGSAPGTS<br>ESATPESGPGSEPATSGSETPGTSESATPESGPGSEPATSGSETPGTSES<br>ATPESGPGTSTEPSEGSAPGTSESATPESGPGSPAGSPTSTEEGSPAGSP<br>TSTEEGSPAGSPTSTEEGTSESATPESGPGTSTEPSEGSAPGTSESATPES<br>GPGSEPATSGSETPGTSESATPESGPGSEPATSGSETPGTSESATPESGP<br>GTSTEPSEGSAPGSPAGSPTSTEEGTSESATPESGPGSEPATSGSETPGT<br>SESATPESGPGSPAGSPTSTEEGSPAGSPTSTEEGTSTEPSEGSAPGTSES<br>ATPESGPGTSESATPESGPGTSESATPESGPGSEPATSGSETPGSEPATS<br>GSETPGSPAGSPTSTEEGTSTEPSEGSAPGTSTEPSEGSAPGSEPATSGS<br>ETPGTSESAT | 403 |
| AE648A | PESGPGTSTEPSEGSAPGTSESATPESGPGSEPATSGSETPGTSTEPSEGS<br>APGTSTEPSEGSAPGTSESATPESGPGTSESATPESGPGSPAGSPTSTEE<br>GTSESATPESGPGSEPATSGSETPGTSESATPESGPGTSTEPSEGSAPGT<br>STEPSEGSAPGTSTEPSEGSAPGTSTEPSEGSAPGTSTEPSEGSAPGTST<br>EPSEGSAPGSPAGSPTSTEEGTSTEPSEGSAPGTSESATPESGPGSEPAT<br>SGSETPGTSESATPESGPGSEPATSGSETPGTSESATPESGPGTSTEPSE<br>GSAPGTSESATPESGPGSPAGSPTSTEEGSPAGSPTSTEEGSPAGSPTST<br>EEGTSESATPESGPGTSTEPSEGSAPGTSESATPESGPGSEPATSGSETP<br>GTSESATPESGPGSEPATSGSETPGTSESATPESGPGTSTEPSEGSAPGS<br>PAGSPTSTEEGTSESATPESGPGSEPATSGSETPGTSESATPESGPGSPA<br>GSPTSTEEGSPAGSPTSTEEGTSTEPSEGSAPGTSESATPESGPGTSESA<br>TPESGPGTSESATPESGPGSEPATSGSETPGSEPATSGSETPGSPAGSPT<br>STEEGTSTEPSEGSAPGTSTEPSEGSAPGSEPATSGSETPGTSESAT | 404 |
| AE684A | EGSAPGSPAGSPTSTEEGTSTEPSEGSAPGTSTEPSEGSAPGTSESATPE<br>SGPGTSTEPSEGSAPGTSESATPESGPGSEPATSGSETPGTSTEPSEGSA<br>PGTSTEPSEGSAPGTSESATPESGPGTSESATPESGPGSPAGSPTSTEEG | 405 |

TABLE 5-continued

XTEN Polypeptides

| XTEN Name | Amino Acid Sequence | SEQ ID NO: |
|---|---|---|
| | TSESATPESGPGSEPATSGSETPGTSESATPESGPGTSTEPSEGSAPGTS TEPSEGSAPGTSTEPSEGSAPGTSTEPSEGSAPGTSTEPSEGSAPGTSTE PSEGSAPGSPAGSPTSTEEGTSTEPSEGSAPGTSESATPESGPGSEPATS GSETPGTSESATPESGPGSEPATSGSETPGTSESATPESGPGTSTEPSEG SAPGTSESATPESGPGSPAGSPTSTEEGSPAGSPTSTEEGSPAGSPTSTE EGTSESATPESGPGTSTEPSEGSAPGTSESATPESGPGSEPATSGSETPG TSESATPESGPGSEPATSGSETPGTSESATPESGPGTSTEPSEGSAPGSP AGSPTSTEEGTSESATPESGPGSEPATSGSETPGTSESATPESGPGSPAG SPTSTEEGSPAGSPTSTEEGTSTEPSEGSAPGTSESATPESGPGTSESATP ESGPGTSESATPESGPGSEPATSGSETPGSEPATSGSETPGSPAGSPTST EEGTSTEPSEGSAPGTSTEPSEGSAPGSEPATS | |
| AE720A | TSGSETPGSEPATSGSETPGSPAGSPTSTEEGTSESATPESGPGTSTEPSE GSAPGTSTEPSEGSAPGSPAGSPTSTEEGTSTEPSEGSAPGTSTEPSEGS APGTSESATPESGPGTSTEPSEGSAPGTSESATPESGPGSEPATSGSETP GTSTEPSEGSAPGTSTEPSEGSAPGTSESATPESGPGTSESATPESGPGS PAGSPTSTEEGTSESATPESGPGSEPATSGSETPGTSESATPESGPGTST EPSEGSAPGTSTEPSEGSAPGTSTEPSEGSAPGTSTEPSEGSAPGTSTEPS EGSAPGTSTEPSEGSAPGSPAGSPTSTEEGTSTEPSEGSAPGTSESATPE SGPGSEPATSGSETPGTSESATPESGPGSEPATSGSETPGTSESATPESG PGTSTEPSEGSAPGTSESATPESGPGSPAGSPTSTEEGSPAGSPTSTEEG SPAGSPTSTEEGTSESATPESGPGTSTEPSEGSAPGTSESATPESGPGSEP ATSGSETPGTSESATPESGPGSEPATSGSETPGTSESATPESGPGTSTEP SEGSAPGSPAGSPTSTEEGTSESATPESGPGSEPATSGSETPGTSESATP ESGPGSPAGSPTSTEEGSPAGSPTSTEEGTSTEPSEGSAPGTSESATPES GPGTSESATPESGPGTSESATPESGPGSEPATSGSETPGSEPATSGSETP GSPAGSPTSTEEGTSTE | 406 |
| AE756A | TSGSETPGSEPATSGSETPGSPAGSPTSTEEGTSESATPESGPGTSTEPSE GSAPGTSTEPSEGSAPGSPAGSPTSTEEGTSTEPSEGSAPGTSTEPSEGS APGTSESATPESGPGTSTEPSEGSAPGTSESATPESGPGSEPATSGSETP GTSTEPSEGSAPGTSTEPSEGSAPGTSESATPESGPGTSESATPESGPGS PAGSPTSTEEGTSESATPESGPGSEPATSGSETPGTSESATPESGPGTST EPSEGSAPGTSTEPSEGSAPGTSTEPSEGSAPGTSTEPSEGSAPGTSTEPS EGSAPGTSTEPSEGSAPGSPAGSPTSTEEGTSTEPSEGSAPGTSESATPE SGPGSEPATSGSETPGTSESATPESGPGSEPATSGSETPGTSESATPESG PGTSTEPSEGSAPGTSESATPESGPGSPAGSPTSTEEGSPAGSPTSTEEG SPAGSPTSTEEGTSESATPESGPGTSTEPSEGSAPGTSESATPESGPGSEP ATSGSETPGTSESATPESGPGSEPATSGSETPGTSESATPESGPGTSTEP SEGSAPGSPAGSPTSTEEGTSESATPESGPGSEPATSGSETPGTSESATP ESGPGSPAGSPTSTEEGSPAGSPTSTEEGTSTEPSEGSAPGTSESATPES GPGTSESATPESGPGTSESATPESGPGSEPATSGSETPGSEPATSGSETP GSPAGSPTSTEEGTSTEPSEGSAPGTSTEPSEGSAPGSEPATSGSETPGT SES | 407 |
| AE792A | EGSAPGTSESATPESGPGSEPATSGSETPGSEPATSGSETPGSPAGSPTS TEEGTSESATPESGPGTSTEPSEGSAPGTSTEPSEGSAPGSPAGSPTSTE EGTSTEPSEGSAPGTSTEPSEGSAPGTSESATPESGPGTSTEPSEGSAPG TSESATPESGPGSEPATSGSETPGTSTEPSEGSAPGTSTEPSEGSAPGTS ESATPESGPGTSESATPESGPGSPAGSPTSTEEGTSESATPESGPGSEPA TSGSETPGTSESATPESGPGTSTEPSEGSAPGTSTEPSEGSAPGTSTEPSE GSAPGTSTEPSEGSAPGTSTEPSEGSAPGTSTEPSEGSAPGSPAGSPTST EEGTSTEPSEGSAPGTSESATPESGPGSEPATSGSETPGTSESATPESGP GSEPATSGSETPGTSESATPESGPGTSTEPSEGSAPGTSESATPESGPGS PAGSPTSTEEGSPAGSPTSTEEGSPAGSPTSTEEGTSESATPESGPGTST EPSEGSAPGTSESATPESGPGSEPATSGSETPGTSESATPESGPGSEPAT SGSETPGTSESATPESGPGTSTEPSEGSAPGSPAGSPTSTEEGTSESATP ESGPGSEPATSGSETPGTSESATPESGPGSPAGSPTSTEEGSPAGSPTST EEGTSTEPSEGSAPGTSESATPESGPGTSESATPESGPGTSESATPESGP GSEPATSGSETPGSEPATSGSETPGSPAGSPTSTEEGTSTEPSEGSAPGT STEPSEGSAPGSEPATSGSETPGTSESATPESGPGTSTEPS | 408 |
| AE828A | PESGPGTSTEPSEGSAPGSPAGSPTSTEEGTSTEPSEGSAPGTSTEPSEGS APGTSESATPESGPGSEPATSGSETPGSEPATSGSETPGSPAGSPTSTEE GTSESATPESGPGTSTEPSEGSAPGTSTEPSEGSAPGSPAGSPTSTEEGT STEPSEGSAPGTSTEPSEGSAPGTSESATPESGPGTSTEPSEGSAPGTSES ATPESGPGSEPATSGSETPGTSTEPSEGSAPGTSTEPSEGSAPGTSESAT PESGPGTSESATPESGPGSPAGSPTSTEEGTSESATPESGPGSEPATSGS ETPGTSESATPESGPGTSTEPSEGSAPGTSTEPSEGSAPGTSTEPSEGSA PGTSTEPSEGSAPGTSTEPSEGSAPGTSTEPSEGSAPGSPAGSPTSTEEG TSTEPSEGSAPGTSESATPESGPGSEPATSGSETPGTSESATPESGPGSEP ATSGSETPGTSESATPESGPGTSTEPSEGSAPGTSESATPESGPGSPAGS PTSTEEGSPAGSPTSTEEGSPAGSPTSTEEGTSESATPESGPGTSTEPSEG SAPGTSESATPESGPGSEPATSGSETPGTSESATPESGPGSEPATSGSET | 409 |

TABLE 5-continued

| XTEN Polypeptides | | |
|---|---|---|
| XTEN Name | Amino Acid Sequence | SEQ ID NO: |
| | PGTSESATPESGPGTSTEPSEGSAPGSPAGSPTSTEEGTSESATPESGPG SEPATSGSETPGTSESATPESGPGSPAGSPTSTEEGSPAGSPTSTEEGTS TEPSEGSAPGTSESATPESGPGTSESATPESGPGTSESATPESGPGSEPA TSGSETPGSEPATSGSETPGSPAGSPTSTEEGTSTEPSEGSAPGTSTEPSE GSAPGSEPATSGSETPGTSESAT | |
| AE869 | GSPGSPAGSPTSTEEGTSESATPESGPGTSTEPSEGSAPGSPAGSPTSTE EGTSTEPSEGSAPGTSTEPSEGSAPGTSESATPESGPGSEPATSGSETPG SEPATSGSETPGSPAGSPTSTEEGTSESATPESGPGTSTEPSEGSAPGTS TEPSEGSAPGSPAGSPTSTEEGTSTEPSEGSAPGTSTEPSEGSAPGTSES ATPESGPGTSTEPSEGSAPGTSESATPESGPGSEPATSGSETPGTSTEPS EGSAPGTSTEPSEGSAPGTSESATPESGPGTSESATPESGPGSPAGSPTS TEEGTSESATPESGPGSEPATSGSETPGTSESATPESGPGTSTEPSEGSA PGTSTEPSEGSAPGTSTEPSEGSAPGTSTEPSEGSAPGTSTEPSEGSAPG TSTEPSEGSAPGSPAGSPTSTEEGTSTEPSEGSAPGTSESATPESGPGSEP ATSGSETPGTSESATPESGPGSEPATSGSETPGTSESATPESGPGTSTEP SEGSAPGTSESATPESGPGSPAGSPTSTEEGSPAGSPTSTEEGSPAGSPT STEEGTSESATPESGPGTSTEPSEGSAPGTSESATPESGPGSEPATSGSE TPGTSESATPESGPGSEPATSGSETPGTSESATPESGPGTSTEPSEGSAP GSPAGSPTSTEEGTSESATPESGPGSEPATSGSETPGTSESATPESGPGS PAGSPTSTEEGSPAGSPTSTEEGTSTEPSEGSAPGTSESATPESGPGTSE SATPESGPGTSESATPESGPGSEPATSGSETPGSEPATSGSETPGSPAGS PTSTEEGTSTEPSEGSAPGTSTEPSEGSAPGSEPATSGSETPGTSESATPE SGPGTSTEPSEGSAPGR | 410 |
| AE144_R1 | SAGSPGSPAGSPTSTEEGTSESATPESGPGTSTEPSEGSAPGSPAGSPTS TEEGTSTEPSEGSAPGTSTEPSEGSAPGTSESATPESGPGSEPATSGSET PGSEPATSGSETPGSPAGSPTSTEEGTSESATPESGPGTESASR | 411 |
| AE288_R1 | SAGSPTGPGSEPATSGSETPGTSESATPESGPGSEPATSGSETPGTSESA TPESGPGTSTEPSEGSAPGSPAGSPTSTEEGTSESATPESGPGSEPATSG SETPGTSESATPESGPGSPAGSPTSTEEGSPAGSPTSTEEGTSTEPSEGS APGTSESATPESGPGTSESATPESGPGTSESATPESGPGSEPATSGSETP GSEPATSGSETPGSPAGSPTSTEEGTSTEPSEGSAPGTSTEPSEGSAPGS EPATSGSETPGTSESATPESGPGTSTEPSEGSAPSASR | 412 |
| AE432_R1 | SAGSPGSPAGSPTSTEEGTSESATPESGPGTSTEPSEGSAPGSPAGSPTS TEEGTSTEPSEGSAPGTSTEPSEGSAPGTSESATPESGPGSEPATSGSET PGSEPATSGSETPGSPAGSPTSTEEGTSESATPESGPGTSTEPSEGSAPG TSTEPSEGSAPGSPAGSPTSTEEGTSTEPSEGSAPGTSTEPSEGSAPGTS ESATPESGPGTSTEPSEGSAPGTSESATPESGPGSEPATSGSETPGTSTE PSEGSAPGTSTEPSEGSAPGTSESATPESGPGTSESATPESGPGSPAGSP TSTEEGTSESATPESGPGSEPATSGSETPGTSESATPESGPGTSTEPSEGS APGTSTEPSEGSAPGTSTEPSEGSAPGTSTEPSEGSAPGTSTEPSEGSAP GTSTEPSEGSAPGSPAGSPTSTEEGTESASR | 413 |
| AE576_R1 | SAGSPTEEGTSESATPESGPGSEPATSGSETPGTSESATPESGPGTSTEP SEGSAPGTSTEPSEGSAPGTSTEPSEGSAPGTSTEPSEGSAPGTSTEPSE GSAPGTSTEPSEGSAPGSPAGSPTSTEEGTSTEPSEGSAPGTSESATPES GPGSEPATSGSETPGTSESATPESGPGSEPATSGSETPGTSESATPESGP GTSTEPSEGSAPGTSESATPESGPGSPAGSPTSTEEGSPAGSPTSTEEGS PAGSPTSTEEGTSESATPESGPGTSTEPSEGSAPGTSESATPESGPGSEP ATSGSETPGTSESATPESGPGSEPATSGSETPGTSESATPESGPGTSTEP SEGSAPGSPAGSPTSTEEGTSESATPESGPGSEPATSGSETPGTSESATP ESGPGSPAGSPTSTEEGSPAGSPTSTEEGTSTEPSEGSAPGTSESATPES GPGTSESATPESGPGTSESATPESGPGSEPATSGSETPGSEPATSGSETP GSPAGSPTSTEEGTSTEPSEGSAPGTSTEPSEGSAPGSEPATSGSETPGT SESATPESGPGTSTEPSEGSAPSASR | 414 |
| AE864_R1 | SAGSPGSPAGSPTSTEEGTSESATPESGPGTSTEPSEGSAPGSPAGSPTS TEEGTSTEPSEGSAPGTSTEPSEGSAPGTSESATPESGPGSEPATSGSET PGSEPATSGSETPGSPAGSPTSTEEGTSESATPESGPGTSTEPSEGSAPG TSTEPSEGSAPGSPAGSPTSTEEGTSTEPSEGSAPGTSTEPSEGSAPGTS ESATPESGPGTSTEPSEGSAPGTSESATPESGPGSEPATSGSETPGTSTE PSEGSAPGTSTEPSEGSAPGTSESATPESGPGTSESATPESGPGSPAGSP TSTEEGTSESATPESGPGSEPATSGSETPGTSESATPESGPGTSTEPSEGS APGTSTEPSEGSAPGTSTEPSEGSAPGTSTEPSEGSAPGTSTEPSEGSAP GTSTEPSEGSAPGSPAGSPTSTEEGTSTEPSEGSAPGTSESATPESGPGS EPATSGSETPGTSESATPESGPGSEPATSGSETPGTSESATPESGPGTST EPSEGSAPGTSESATPESGPGSPAGSPTSTEEGSPAGSPTSTEEGSPAGS PTSTEEGTSESATPESGPGTSTEPSEGSAPGTSESATPESGPGSEPATSG SETPGTSESATPESGPGSEPATSGSETPGTSESATPESGPGTSTEPSEGS APGSPAGSPTSTEEGTSESATPESGPGSEPATSGSETPGTSESATPESGP GSPAGSPTSTEEGSPAGSPTSTEEGTSTEPSEGSAPGTSESATPESGPGT | 415 |

TABLE 5-continued

| XTEN Polypeptides | | |
|---|---|---|
| XTEN Name | Amino Acid Sequence | SEQ ID NO: |
| | SESATPESGPGTSESATPESGPGSEPATSGSETPGSEPATSGSETPGSPA GSPTSTEEGTSTEPSEGSAPGTSTEPSEGSAPGSEPATSGSETPGTSESA TPESGPGTESASR | |
| AE712 | PGSPAGSPTSTEEGTSESATPESGPGTSTEPSEGSAPGSPAGSPTSTEEG TSTEPSEGSAPGTSTEPSEGSAPGTSESATPESGPGSEPATSGSETPGSEP ATSGSETPGSPAGSPTSTEEGTSESATPESGPGTSTEPSEGSAPGTSTEP SEGSAPGSPAGSPTSTEEGTSTEPSEGSAPGTSTEPSEGSAPGTSESATP ESGPGTSTEPSEGSAPGTSESATPESGPGSEPATSGSETPGTSTEPSEGS APGTSTEPSEGSAPGTSESATPESGPGTSESATPESGPGSPAGSPTSTEE GTSESATPESGPGSEPATSGSETPGTSESATPESGPGTSTEPSEGSAPGT STEPSEGSAPGTSTEPSEGSAPGTSTEPSEGSAPGTSTEPSEGSAPGTST EPSEGSAPGSPAGSPTSTEEGTSTEPSEGSAPGTSESATPESGPGSEPAT SGSETPGTSESATPESGPGSEPATSGSETPGTSESATPESGPGTSTEPSE GSAPGTSESATPESGPGSPAGSPTSTEEGSPAGSPTSTEEGSPAGSPTST EEGTSESATPESGPGTSTEPSEGSAPGTSESATPESGPGSEPATSGSETP GTSESATPESGPGSEPATSGSETPGTSESATPESGPGTSTEPSEGSAPGS PAGSPTSTEEGTSESATPESGPGSEPATSGSETPGTSESATPESGPGSPA GSPTSTEAHHH | 416 |
| AE864_R2 | GSPGAGSPAGSPTSTEEGTSESATPESGPGTSTEPSEGSAPGSPAGSPTS TEEGTSTEPSEGSAPGTSTEPSEGSAPGTSESATPESGPGSEPATSGSET PGSEPATSGSETPGSPAGSPTSTEEGTSESATPESGPGTSTEPSEGSAPG TSTEPSEGSAPGSPAGSPTSTEEGTSTEPSEGSAPGTSTEPSEGSAPGTS ESATPESGPGTSTEPSEGSAPGTSESATPESGPGSEPATSGSETPGTSTE PSEGSAPGTSTEPSEGSAPGTSESATPESGPGTSESATPESGPGSPAGSP TSTEEGTSESATPESGPGSEPATSGSETPGTSESATPESGPGTSTEPSEGS APGTSTEPSEGSAPGTSTEPSEGSAPGTSTEPSEGSAPGTSTEPSEGSAP GTSTEPSEGSAPGSPAGSPTSTEEGTSTEPSEGSAPGTSESATPESGPGS EPATSGSETPGTSESATPESGPGSEPATSGSETPGTSESATPESGPGTST EPSEGSAPGTSESATPESGPGSPAGSPTSTEEGSPAGSPTSTEEGSPAGS PTSTEEGTSESATPESGPGTSTEPSEGSAPGTSESATPESGPGSEPATSG SETPGTSESATPESGPGSEPATSGSETPGTSESATPESGPGTSTEPSEGS APGSPAGSPTSTEEGTSESATPESGPGSEPATSGSETPGTSESATPESGP GSPAGSPTSTEEGSPAGSPTSTEEGTSTEPSEGSAPGTSESATPESGPGT SESATPESGPGTSESATPESGPGSEPATSGSETPGSEPATSGSETPGSPA GSPTSTEEGTSTEPSEGSAPGTSTEPSEGSAPGSEPATSGSETPGTSESA TPESGPGTESASR | 417 |

The invention contemplates chimeric polypeptide assembly compositions comprising XTEN of intermediate lengths to those of Table 5, as well as XTEN of longer lengths in which motifs of 12 amino acids are added to the N- or C-terminus of an XTEN of Table 5 incorporated into the chimeric polypeptide assembly. In one embodiment, the chimeric polypeptide assembly composition comprises an XTEN of Table 5 with the addition of one or more copies of one or more motifs selected from the group of motifs set forth in Table 6.

TABLE 6

| XTEN Sequence Motifs of 12 Amino Acids and Motif Families | | |
|---|---|---|
| Motif Family* | MOTIF SEQUENCE | SEQ ID NO: |
| AD | GESPGGSSGSES | 418 |
| AD | GSEGSSGPGESS | 419 |
| AD | GSSESGSSEGGP | 420 |
| AD | GSGGEPSESGSS | 421 |
| AE | GSPAGSPTSTEE | 422 |
| AE | GSEPATSGSETP | 423 |

TABLE 6-continued

| XTEN Sequence Motifs of 12 Amino Acids and Motif Families | | |
|---|---|---|
| Motif Family* | MOTIF SEQUENCE | SEQ ID NO: |
| AE | GTSESATPESGP | 424 |
| AE | GTSTEPSEGSAP | 425 |
| AF | GSTSESPSGTAP | 426 |
| AF | GTSTPESGSASP | 427 |
| AF | GTSPSGESSTAP | 428 |
| AF | GSTSSTAESPGP | 429 |

*Denotes individual motif sequences that, when used together in various permutations, results in a "family sequence"

Additional examples of XTEN sequences that can be used according to the present invention and are disclosed in US Patent Publication Nos. 2010/0239554 A1, 2010/0323956 A1, 2011/0046060 A1, 2011/0046061 A1, 2011/0077199 A1, or 2011/0172146 A1, or International Patent Publication Nos. WO 2010091122 A1, WO 2010144502 A2, WO 2010144508 A1, WO 2011028228 A1, WO 2011028229 A1, WO 2011028344 A2, WO 2014/011819 A2, or WO 2015/023891.

4. T Cell Binding Compositions

Figure 29A:
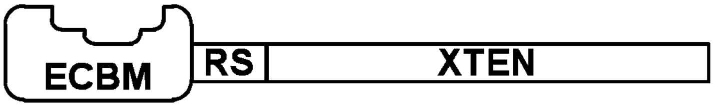
Figure 29B:
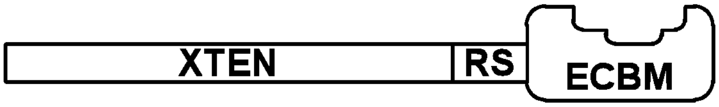
FIG. 29B shows the configuration of XTEN followed by the RS segment and then ECBM.

In another aspect, the present invention provides monomeric fusion proteins comprising a first portion, a second portion, and a third portion wherein said first portion comprises VL and VH sequences of an anti-CD3 binding domain, joined by a flexible linker; the said second portion comprises a first release segment (RS) capable of being cleaved by a mammalian protease; and the third portion comprises a first bulking moiety comprising an XTEN sequence wherein said bulking moiety and first portions are capable of being released from the composition by action of said mammalian protease on said second portion. In some embodiments of the foregoing, the first portion VL and VH sequences of the subject composition are derived from a monoclonal antibody VL and VH selected from the group of sequences set forth in Table 1. Where desired, the VL and VH of the subject compositions are derived from the huUCHT1 monoclonal antibody of Table 1. It is specifically contemplated that the compositions can be configured in different orders, with respect to the N-terminus to C-terminus order, as shown schematically in FIG. 29. In one embodiment, the compositions are configured, in an N- to C-terminus orientation of binding domains-RS-XTEN and in another embodiment the portions are configured in the order XTEN-RS-binding domains.

In some embodiments of the T-cell binding compositions, the anti-CD3 binding domains comprise a VH and a VL sequence of Table 1, the RS of the second portion is selected from the group consisting of the sequences set forth in Table 4 and the XTEN of the third portion is selected from the group consisting of the sequences set forth in Table 5.

In other embodiments, the invention provides T-cell binding composition fusion proteins having at least about 90% sequence identity, or at least about 91%, 92%, 93%, 94%, 95%, 96%, 97%, 98%, 99% identity, or is 100% identical to a sequence, when optimally aligned, selected from the group consisting of the amino acid sequences set forth in Table 7. In one embodiment, the T-cell binding composition has the amino acid sequence of TCB-1 of Table 7. In another embodiment, the T-cell binding composition has the amino acid sequence of TCB-2 of Table 7. In another embodiment, the T-cell binding composition has the amino acid sequence of TCB-3 of Table 7. In another embodiment, the T-cell binding composition has the amino acid sequence of TCB-4 of Table 7. In another embodiment, the T-cell binding composition has the amino acid sequence of TCB-5 of Table 7. In another embodiment, the T-cell binding composition has the amino acid sequence of TCB-6 of Table 7. In another embodiment, the T-cell binding composition has the amino acid sequence of TCB7 of Table 7. In another embodiment, the T-cell binding composition has the amino acid sequence of TCB-8 of Table 7. In another embodiment, the T-cell binding composition has the amino acid sequence of TCB-9 of Table 7. In another embodiment, the T-cell binding composition has the amino acid sequence of TCB-10 of Table 7. In another embodiment, the T-cell binding composition has the amino acid sequence of TCB11 of Table 7. In another embodiment, the T-cell binding composition has the amino acid sequence of TCB-12 of Table 7. In another embodiment, the T-cell binding composition has the amino acid sequence of TCB-13 of Table 7. In another embodiment, the T-cell binding composition has the amino acid sequence of TCB-14 of Table 7. In another embodiment, the T-cell binding composition has the amino acid sequence of TCB-15 of Table 7. In another embodiment, the T-cell binding composition has the amino acid sequence of TCB-16 of Table 7. In still other embodiments, the invention provides pharmaceutical compositions comprising T-cell binding composition fusion proteins with at least about 90% sequence identity, or at least about 91%, 92%, 93%, 94%, 95%, 96%, 97%, 98%, 99% identity, or is 100% identical to a sequence set forth in Table 7 and, optionally, suitable formulations of carrier, stabilizers and/or excipients.

In another aspect, the invention relates to polynucleotides encoding the T-cell binding composition fusion proteins of Table 7. In one embodiment, the invention provides polynucleotide sequences encoding T-cell binding fusion proteins, wherein the polynucleotide sequences have at least about 90% sequence identity, or at least about 91%, 92%, 93%, 94%, 95%, 96%, 97%, 98%, 99% identity, or is 100% identical to a sequence, when optimally aligned, selected from the group consisting of the polynucleotide sequences set forth in Table 7, or the complement thereof.

In a related aspect, the invention relates to a method of making chimeric polypeptide assembly compositions utilizing a polynucleotide encoding a T-cell binding contract composition and ligating a polynucleotide sequence encoding a binding domain with affinity to a target cell antigen. In one embodiment, the invention provides a method of making chimeric polypeptide assembly compositions, the method comprising utilizing a polynucleotide of Table 7 encoding T-cell binding contract compositions followed by the recombinant addition of a gene encoding the second binding domain and a linker wherein the second binding domain has binding specificity to a tumor-specific marker or an antigen of a target cell, with the resulting gene introduced into a suitable expression vector under the control of a promoter and linker; the resulting expression vector is then used to transform a suitable *E. coli* host cell, which is then grown under conditions suitable for the expression of the chimeric polypeptide assembly fusion protein, which is then isolated by purification methods described herein or known in the art. Examples 1 and 2, below, provide exemplary methods for the implementation of the foregoing method. In some embodiments of the foregoing, the second binding domain is a scFv wherein the second binding domain VH and VL are selected from the group of paired monoclonal antibody VH and VL sequences set forth in Table 2. The foregoing embodiments take advantage of the modular nature of the genes encoding the T-cell binding compositions that can be readily utilized with polynucleotides encoding the variety of second binding domains described herein by recombinantly fusing the encoding sequences of the anti-CD3 variable sequence and the encoding sequence of the second binding domain to the encoding sequences of the T-cell binding composition, resulting in the ability to create multiple individual genes that can be utilized to express the desired fusion protein product of a chimeric polypeptide assembly. It is specifically contemplated that the use of a gene encoding a T-cell binding composition to prepare chimeric polypeptide assembly compositions is not limited to the polynucleotides encoding the chimeric polypeptide assembly compositions described herein, but could be utilized in conjunction with a gene encoding a binding domain with affinity to any target tissue or cell of interest that would be susceptible to the cytotoxic effects of the resulting expressed fusion protein.

In another aspect, the T-cell binding compositions of Table 7 are useful as therapeutic immunosuppressive agents in the treatment of certain diseases or conditions in a subject for which anti-CD3 antibody preparations have been demonstrated to result in clinical benefits such as, but not limited to organ transplant and acute graft rejection, Crohn's disease, ulcerative colitis and type 1 diabetes, and for inducing immune tolerance.

TABLE 7

T-cell binding compositions

| Construct Name | Amino Acid Sequence | SEQ ID NO: | DNA Sequence | SEQ ID NO: |
|---|---|---|---|---|
| TBP-1 | DIQMTQSPSSLSA | 430 | GACATCCAAATGACCCAGAGCCCGAGCAGCCTGA | 446 |
| | SVGDRVTITCRAS | | GCGCGAGCGTGGGCGACCGTGTTACCATCACCTG | |
| | QDIRNYLNWYQQK | | CCGTGCGAGCCAAGACATCCGTAACTACCTGAAC | |
| | PGKAPKLLIYYTS | | TGGTATCAGCAAAAGCCGGGTAAAGCGCCGAAGC | |
| | RLESGVPSRFSGS | | TGCTGATCTACTATACCAGCCGTCTGGAGAGCGG | |
| | GSGTDYTLTISSL | | CGTGCCGAGCCGTTTCAGCGGTAGCGGTAGCGGT | |
| | QPEDFATYYCQQG | | ACCGACTACACCCTGACCATTAGCAGCCTGCAGC | |
| | NTLPWTFGQGTKV | | CGGAAGATTTCGCGACCTACTATTGCCAGCAGGG | |
| | EIKGATPPETGAE | | TAACACCCTGCCGTGGACCTTTGGTCAAGGCACC | |
| | TESPGETTGGSAE | | AAAGTTGAGATTAAAGGCGCCACGCCTCCGGAAA | |
| | SEPPGEGEVOLVE | | CTGGTGCTGAGACGGAATCCCCTGGTGAAACCAC | |
| | SGGGLVQPGGSLR | | TGGCGGTTCTGCCGAATCTGAACCGCCTGGTGAA | |
| | LSCAASGYSFTGY | | GGCGAGGTGCAGCTGGTTGAAAGCGGTGGCGGTC | |
| | TMNWVRQAPGKGL | | TGGTGCAACCAGGCGGTAGCCTGCGTCTGAGCTG | |
| | EWVALINPYKGVS | | CGCGGCGAGCGGTTACAGCTTTACCGGTTATACC | |
| | TYNQKFKDRFTIS | | ATGAACTGGGTTCGTCAAGCGCCAGGTAAAGGTC | |
| | VDKSKNTAYLQMN | | TGGAGTGGGTGGCGCTGATCAACCCGTACAAGGG | |
| | SLRAEDTAVYYCA | | TGTTAGCACCTATAACCAGAAGTTCAAAGACCGT | |
| | RSGYYGDSDWYFD | | TTTACCATTAGCGTGGATAAGAGCAAAAACACCG | |
| | VWGQGTLVTVSSG | | CGTACCTGCAAATGAACAGCCTGCGTGCGGAGGA | |
| | TAEAASASGLSGR | | CACCGCTGTGTACTATTGCGCGCGTAGCGGTTAC | |
| | SDNHSPLGLAGSP | | TATGGCGACAGCGACTGGTATTTTGATGTGTGGG | |
| | GSPAGSPTSTEEG | | GCCAAGGCACCCTGGTTACCGTGAGCTCCGGCAC | |
| | TSESATPESGPGT | | CGCCGAAGCAGCTagcgcctctGGCctgTCAggt | |
| | STEPSEGSAPGSP | | CGTtctGATaacCATtccCCActgGGTctgGCTG | |
| | AGSPTSTEEGTST | | GGTCTCCAGGTAGCCCAGCTGGTAGCCCAACCTC | |
| | EPSEGSAPGTSTE | | TACCGAAGAAGGTACCTCTGAATCCGCTACTCCA | |
| | PSEGSAPGTSESA | | GAATCCGGTCCTGGTACTAGCACTGAGCCAAGCG | |
| | TPESGPGSEPATS | | AAGGTTCTGCTCCAGGCTCCCCGGCAGGTAGCCC | |
| | GSETPGSEPATSG | | TACCTCTACCGAAGAGGGCACTAGCACCGAACCA | |
| | SETPGSPAGSPTS | | TCTGAGGGTTCCGCTCCTGGCACCTCCACTGAAC | |
| | TEEGTSESATPES | | CGTCCGAAGGCAGTGCTCCGGGTACTTCCGAAAG | |
| | GPGTSTEPSEGSA | | CGCAACTCCGGAATCCGGCCCTGGTTCTGAGCCT | |
| | PGTSTEPSEGSAP | | GCTACTTCCGGCTCTGAAACTCCAGGTAGCGAGC | |
| | GSPAGSPTSTEEG | | CAGCGACTTCTGGTTCTGAAACTCCAGGTTCACC | |
| | TSTEPSEGSAPGT | | GGCGGGTAGCCCGACGAGCACGGAGGAAGGTACC | |
| | STEPSEGSAPGTS | | TCTGAGTCGGCCACTCCTGAGTCCGGTCCGGGCA | |
| | ESATPESGPGTST | | CGAGCACCGAGCCGAGCGAGGGTTCAGCCCCGGG | |
| | EPSEGSAPGTSES | | TACCAGCACGGAGCCGTCCGAGGGTAGCGCACCG | |
| | ATPESGPGSEPAT | | GGTTCTCCGGCGGGCTCCCCTACGTCTACGGAAG | |
| | SGSETPGTSTEPS | | AGGGTACGTCCACTGAACCTAGCGAGGGCAGCGC | |
| | EGSAPGTSTEPSE | | GCCAGGCACCAGCACTGAACCGAGCGAAGGCAGC | |
| | GSAPGTSESATPE | | GCACCTGGCACTAGCGAGTCTGCGACTCCGGAGA | |
| | SGPGTSESATPES | | GCGGTCCGGGTACGAGCACGGAACCAAGCGAAGG | |
| | GPGSPAGSPTSTE | | CAGCGCCCCAGGTACCTCTGAATCTGCTACCCCA | |
| | EGTSESATPESGP | | GAATCTGGCCCGGGTTCCGAGCCAGCTACCTCTG | |
| | GSEPATSGSETPG | | GTTCTGAAACCCCAGGTACTTCCACTGAACCAAG | |
| | TSESATPESGPGT | | CGAAGGTAGCGCTCCTGGCACTTCTACTGAACCA | |
| | STEPSEGSAPGTS | | TCCGAAGGTTCCGCTCCTGGTACGTCTGAAAGCG | |
| | TEPSEGSAPGTST | | CTACCCCTGAAAGCGGCCCAGGCACCTCTGAAAG | |
| | EPSEGSAPGTSTE | | CGCTACTCCTGAGAGCGGTCCAGGCTCTCCAGCA | |
| | PSEGSAPGTSTEP | | GGTTCTCCAACCTCCACTGAAGAAGGCACCTCTG | |
| | SEGSAPGTSTEPS | | AGTCTGCTACCCCTGAATCTGGTCCTGGCTCCGA | |
| | EGSAPGSPAGSPT | | ACCTGCTACCTCTGGTTCCGAAACTCCAGGTACC | |
| | STEEGTSTEPSEG | | TCGGAATCTGCGACTCCGGAATCTGGCCCGGGCA | |
| | SAPGTSESATPES | | CGAGCACGGAGCCGTCTGAGGGTAGCGCACCAGG | |
| | GPGSEPATSGSET | | TACCAGCACTGAGCCTTCTGAGGGCTCTGCACCG | |
| | PGTSESATPESGP | | GGTACCTCCACGGAACCTTCGGAAGGTTCTGCGC | |
| | GSEPATSGSETPG | | CGGGTACCTCCACTGAGCCATCCGAGGGTTCAGC | |
| | TSESATPESGPGT | | ACCAGGTACTAGCACGGAACCGTCCGAGGGCTCT | |
| | STEPSEGSAPGTS | | GCACCAGGTACGAGCACCGAACCGTCGGAGGGTA | |
| | ESATPESGPGSPA | | GCGCTCCAGGTAGCCCAGCGGGCTCTCCGACAAG | |
| | GSPTSTEEGSPAG | | CACCGAAGAAGGCACCAGCACCGAGCCGTCCGAA | |
| | SPTSTEEGSPAGS | | GGTTCCGCACCAGGTACAAGCGAGAGCGCGACTC | |
| | PTSTEEGTSESAT | | CTGAATCTGGTCCGGGTAGCGAGCCTGCAACCAG | |
| | PESGPGTSTEPSE | | CGGTTCTGAGACGCCGGGCACTTCCGAATCTGCG | |
| | GSAPGTSESATPE | | ACCCCGGAGTCCGGTCCAGGTTCAGAGCCGGCGA | |
| | SGPGSEPATSGSE | | CGAGCGGTTCGGAAACGCCGGGTACGTCTGAATC | |
| | TPGTSESATPESG | | AGCCACGCCGGAGTCTGGTCCGGGTACCTCGACC | |
| | PGSEPATSGSETP | | GAACCAAGCGAAGGTTCGGCACCGGGTACTAGCG | |
| | GTSESATPESGPG | | AGAGCGCAACCCCTGAAAGCGGTCCGGGCAGCCC | |
| | TSTEPSEGSAPGS | | GGCAGGTTCTCCAACCAGCACCGAAGAAGGTTCC | |
| | PAGSPTSTEEGTS | | CCTGCTGGTAGCCCGACCTCTACGGAGGAAGGTA | |
| | ESATPESGPGSEP | | GCCCTGCAGGTTCCCCAACTTCTACTGAGGAAGG | |

TABLE 7-continued

T-cell binding compositions

| Construct Name | Amino Acid Sequence | SEQ ID NO: | DNA Sequence | SEQ ID NO: |
|---|---|---|---|---|
| | ATSGSETPGTSES | | TACTTCTGAGTCCGCTACCCCAGAAAGCGGTCCT | |
| | ATPESGPGSPAGS | | GGTACCTCCACTGAACCGTCTGAAGGCTCTGCAC | |
| | PTSTEEGSPAGSP | | CAGGCACTTCTGAGTCTGCTACTCCAGAAAGCGG | |
| | TSTEEGTSTEPSE | | CCCAGGTTCTGAACCAGCAACTTCTGGCTCTGAG | |
| | GSAPGTSESATPE | | ACTCCAGGCACTTCTGAGTCCGCAACGCCTGAAT | |
| | SGPGTSESATPES | | CCGGTCCTGGTTCTGAACCAGCTACTTCCGGCAG | |
| | GPGTSESATPESG | | CGAAACCCCAGGTACCTCTGAGTCTGCGACTCCA | |
| | PGSEPATSGSETP | | GAGTCTGGTCCTGGTACTTCCACTGAGCCTAGCG | |
| | GSEPATSGSETPG | | AGGGTTCCGCACCAGGTTCTCCGGCTGGTAGCCC | |
| | SPAGSPTSTEEGT | | GACCAGCACGGAGGAGGGTACGTCTGAATCTGCA | |
| | STEPSEGSAPGTS | | ACGCCGGAATCGGGCCCAGGTTCGGAGCCTGCAA | |
| | TEPSEGSAPGSEP | | CGTCTGGCAGCGAAACCCCGGGTACCTCCGAATC | |
| | ATSGSETPGTSES | | TGCTACACCGGAAAGCGGTCCTGGCAGCCCTGCT | |
| | ATPESGPGTSTEP | | GGTTCTCCAACCTCTACCGAGGAGGGTTCACCGG | |
| | SEGSAPGHHHHHH | | CAGGTAGCCCGACTAGCACTGAAGAAGGTACTAG | |
| | | | CACGGAGCCGAGCGAGGGTAGTGCTCCGGGTACG | |
| | | | AGCGAGAGCGCAACGCCAGAGAGCGGTCCAGGCA | |
| | | | CCAGCGAATCGGCCACCCCTGAGAGCGGCCCAGG | |
| | | | TACTTCTGAGAGCGCCACTCCTGAATCCGGCCCT | |
| | | | GGTAGCGAGCCGGCAACCTCCGGCTCAGAAACTC | |
| | | | CTGGTTCGGAACCAGCGACCAGCGGTTCTGAAAC | |
| | | | TCCGGGTAGCCCGGCAGGCAGCCCAACGAGCACC | |
| | | | GAAGAGGGTACCAGCACGGAACCGAGCGAGGGTT | |
| | | | CTGCCCCGGGTACTTCCACCGAACCATCGGAGGG | |
| | | | CTCTGCACCTGGTAGCGAACCTGCGACGTCTGGT | |
| | | | TCTGAAACGCCGGGTACCAGCGAAAGCGCTACCC | |
| | | | CAGAATCCGGTCCGGGCACTAGCACCGAGCCATC | |
| | | | GGAGGGCTCCGCACCAGGTCACCATCATCACCAT | |
| | | | CAC | |
| TBP-2 | DIQMTQSPSSLSA | 431 | GACATCCAAATGACCCAGAGCCCGAGCAGCCTGA | 447 |
| | SVGDRVTITCRAS | | GCGCGAGCGTGGGCGACCGTGTTACCATCACCTG | |
| | QDIRNYLNWYQQK | | CCGTGCGAGCCAAGACATCCGTAACTACCTGAAC | |
| | PGKAPKLLIYYTS | | TGGTATCAGCAAAAGCCGGGTAAAGCGCCGAAGC | |
| | RLESGVPSRFSGS | | TGCTGATCTACTATACCAGCCGTCTGGAGAGCGG | |
| | GSGTDYTLTISSL | | CGTGCCGAGCCGTTTCAGCGGTAGCGGTAGCGGT | |
| | QPEDFATYYCQOG | | ACCGACTACACCCTGACCATTAGCAGCCTGCAGC | |
| | NTLPWTFGQGTKV | | CGGAAGATTTCGCGACCTACTATTGCCAGCAGGG | |
| | EIKGATPPETGAE | | TAACACCCTGCCGTGGACCTTTGGTCAAGGCACC | |
| | TESPGETTGGSAE | | AAAGTTGAGATTAAAGGCGCCACGCCTCCGGAAA | |
| | SEPPGEGEVOLVE | | CTGGTGCTGAGACGGAATCCCCTGGTGAAACCAC | |
| | SGGGLVQPGGSLR | | TGGCGGTTCTGCCGAATCTGAACCGCCTGGTGAA | |
| | LSCAASGYSFTGY | | GGCGAGGTGCAGCTGGTTGAAAGCGGTGGCGGTC | |
| | TMNWVRQAPGKGL | | TGGTGCAACCAGGCGGTAGCCTGCGTCTGAGCTG | |
| | EWVALINPYKGVS | | CGCGGCGAGCGGTTACAGCTTTACCGGTTATACC | |
| | TYNQKFKDRFTIS | | ATGAACTGGGTTCGTCAAGCGCCAGGTAAAGGTC | |
| | VDKSKNTAYLQMN | | TGGAGTGGGTGGCGCTGATCAACCCGTACAAGGG | |
| | SLRAEDTAVYYCA | | TGTTAGCACCTATAACCAGAAGTTCAAAGACCGT | |
| | RSGYYGDSDWYFD | | TTTACCATTAGCGTGGATAAGAGCAAAAACACCG | |
| | VWGQGTLVTVSSG | | CGTACCTGCAAATGAACAGCCTGCGTGCGGAGGA | |
| | TAEAASASGLSGR | | CACCGCTGTGTACTATTGCGCGCGTAGCGGTTAC | |
| | SDNHVPLSLKMGP | | TATGGCGACAGCGACTGGTATTTTGATGTGTGGG | |
| | GSPAGSPTSTEEG | | GCCAAGGCACCCTGGTTACCGTGAGCTCCGGCAC | |
| | TSESATPESGPGT | | CGCCGAAGCAGCTagcgcctctGGCctgTCAggt | |
| | STEPSEGSAPGSP | | CGTtctGATaacCATgttCCActgTCTctgAAAa | |
| | AGSPTSTEEGTST | | tgGGTCCAGGTAGCCCAGCTGGTAGCCCAACCTC | |
| | EPSEGSAPGTSTE | | TACCGAAGAAGGTACCTCTGAATCCGCTACTCCA | |
| | PSEGSAPGTSESA | | GAATCCGGTCCTGGTACTAGCACTGAGCCAAGCG | |
| | TPESGPGSEPATS | | AAGGTTCTGCTCCAGGCTCCCCGGCAGGTAGCCC | |
| | GSETPGSEPATSG | | TACCTCTACCGAAGAGGGCACTAGCACCGAACCA | |
| | SETPGSPAGSPTS | | TCTGAGGGTTCCGCTCCTGGCACCTCCACTGAAC | |
| | TEEGTSESATPES | | CGTCCGAAGGCAGTGCTCCGGGTACTTCCGAAAG | |
| | GPGTSTEPSEGSA | | CGCAACTCCGGAATCCGGCCCTGGTTCTGAGCCT | |
| | PGTSTEPSEGSAP | | GCTACTTCCGGCTCTGAAACTCCAGGTAGCGAGC | |
| | GSPAGSPTSTEEG | | CAGCGACTTCTGGTTCTGAAACTCCAGGTTCACC | |
| | TSTEPSEGSAPGT | | GGCGGGTAGCCCGACGAGCACGGAGGAAGGTACC | |
| | STEPSEGSAPGTS | | TCTGAGTCGGCCACTCCTGAGTCCGGTCCGGGCA | |
| | ESATPESGPGTST | | CGAGCACCGAGCCGAGCGAGGGTTCAGCCCCGGG | |
| | EPSEGSAPGTSES | | TACCAGCACGGAGCCGTCCGAGGGTAGCGCACCG | |
| | ATPESGPGSEPAT | | GGTTCTCCGGCGGGCTCCCCTACGTCTACGGAAG | |
| | SGSETPGTSTEPS | | AGGGTACGTCCACTGAACCTAGCGAGGGCAGCGC | |
| | EGSAPGTSTEPSE | | GCCAGGCACCAGCACTGAACCGAGCGAAGGCAGC | |
| | GSAPGTSESATPE | | GCACCTGGCACTAGCGAGTCTGCGACTCCGGAGA | |
| | SGPGTSESATPES | | GCGGTCCGGGTACGAGCACGGAACCAAGCGAAGG | |

TABLE 7-continued

T-cell binding compositions

| Construct Name | Amino Acid Sequence | SEQ ID NO: | DNA Sequence | SEQ ID NO: |
|---|---|---|---|---|
| | GPGSPAGSPTSTE | | CAGCGCCCCAGGTACCTCTGAATCTGCTACCCCA | |
| | EGTSESATPESGP | | GAATCTGGCCCGGGTTCCGAGCCAGCTACCTCTG | |
| | GSEPATSGSETPG | | GTTCTGAAACCCCAGGTACTTCCACTGAACCAAG | |
| | TSESATPESGPGT | | CGAAGGTAGCGCTCCTGGCACTTCTACTGAACCA | |
| | STEPSEGSAPGTS | | TCCGAAGGTTCCGCTCCTGGTACGTCTGAAAGCG | |
| | TEPSEGSAPGTST | | CTACCCCTGAAAGCGGCCCAGGCACCTCTGAAAG | |
| | EPSEGSAPGTSTE | | CGCTACTCCTGAGAGCGGTCCAGGCTCTCCAGCA | |
| | PSEGSAPGTSTEP | | GGTTCTCCAACCTCCACTGAAGAAGGCACCTCTG | |
| | SEGSAPGTSTEPS | | AGTCTGCTACCCCTGAATCTGGTCCTGGCTCCGA | |
| | EGSAPGSPAGSPT | | ACCTGCTACCTCTGGTTCCGAAACTCCAGGTACC | |
| | STEEGTSTEPSEG | | TCGGAATCTGCGACTCCGGAATCTGGCCCGGGCA | |
| | SAPGTSESATPES | | CGAGCACGGAGCCGTCTGAGGGTAGCGCACCAGG | |
| | GPGSEPATSGSET | | TACCAGCACTGAGCCTTCTGAGGGCTCTGCACCG | |
| | PGTSESATPESGP | | GGTACCTCCACGGAACCTTCGGAAGGTTCTGCGC | |
| | GSEPATSGSETPG | | CGGGTACCTCCACTGAGCCATCCGAGGGTTCAGC | |
| | TSESATPESGPGT | | ACCAGGTACTAGCACGGAACCGTCCGAGGGCTCT | |
| | STEPSEGSAPGTS | | GCACCAGGTACGAGCACCGAACCGTCGGAGGGTA | |
| | ESATPESGPGSPA | | GCGCTCCAGGTAGCCCAGCGGGCTCTCCGACAAG | |
| | GSPTSTEEGSPAG | | CACCGAAGAAGGCACCAGCACCGAGCCGTCCGAA | |
| | SPTSTEEGSPAGS | | GGTTCCGCACCAGGTACAAGCGAGAGCGCGACTC | |
| | PTSTEEGTSESAT | | CTGAATCTGGTCCGGGTAGCGAGCCTGCAACCAG | |
| | PESGPGTSTEPSE | | CGGTTCTGAGACGCCGGGCACTTCCGAATCTGCG | |
| | GSAPGTSESATPE | | ACCCCGGAGTCCGGTCCAGGTTCAGAGCCGGCGA | |
| | SGPGSEPATSGSE | | CGAGCGGTTCGGAAACGCCGGGTACGTCTGAATC | |
| | TPGTSESATPESG | | AGCCACGCCGGAGTCTGGTCCGGGTACCTCGACC | |
| | PGSEPATSGSETP | | GAACCAAGCGAAGGTTCGGCACCGGGTACTAGCG | |
| | GTSESATPESGPG | | AGAGCGCAACCCCTGAAAGCGGTCCGGGCAGCCC | |
| | TSTEPSEGSAPGS | | GGCAGGTTCTCCAACCAGCACCGAAGAAGGTTCC | |
| | PAGSPTSTEEGTS | | CCTGCTGGTAGCCCGACCTCTACGGAGGAAGGTA | |
| | ESATPESGPGSEP | | GCCCTGCAGGTTCCCCAACTTCTACTGAGGAAGG | |
| | ATSGSETPGTSES | | TACTTCTGAGTCCGCTACCCCAGAAAGCGGTCCT | |
| | ATPESGPGSPAGS | | GGTACCTCCACTGAACCGTCTGAAGGCTCTGCAC | |
| | PTSTEEGSPAGSP | | CAGGCACTTCTGAGTCTGCTACTCCAGAAAGCGG | |
| | TSTEEGTSTEPSE | | CCCAGGTTCTGAACCAGCAACTTCTGGCTCTGAG | |
| | GSAPGTSESATPE | | ACTCCAGGCACTTCTGAGTCCGCAACGCCTGAAT | |
| | SGPGTSESATPES | | CCGGTCCTGGTTCTGAACCAGCTACTTCCGGCAG | |
| | GPGTSESATPESG | | CGAAACCCCAGGTACCTCTGAGTCTGCGACTCCA | |
| | PGSEPATSGSETP | | GAGTCTGGTCCTGGTACTTCCACTGAGCCTAGCG | |
| | GSEPATSGSETPG | | AGGGTTCCGCACCAGGTTCTCCGGCTGGTAGCCC | |
| | SPAGSPTSTEEGT | | GACCAGCACGGAGGAGGGTACGTCTGAATCTGCA | |
| | STEPSEGSAPGTS | | ACGCCGGAATCGGGCCCAGGTTCGGAGCCTGCAA | |
| | TEPSEGSAPGSEP | | CGTCTGGCAGCGAAACCCCGGGTACCTCCGAATC | |
| | ATSGSETPGTSES | | TGCTACACCGGAAAGCGGTCCTGGCAGCCCTGCT | |
| | ATPESGPGTSTEP | | GGTTCTCCAACCTCTACCGAGGAGGGTTCACCGG | |
| | SEGSAPGHHHHHH | | CAGGTAGCCCGACTAGCACTGAAGAAGGTACTAG | |
| | | | CACGGAGCCGAGCGAGGGTAGTGCTCCGGGTACG | |
| | | | AGCGAGAGCGCAACGCCAGAGAGCGGTCCAGGCA | |
| | | | CCAGCGAATCGGCCACCCCTGAGAGCGGCCCAGG | |
| | | | TACTTCTGAGAGCGCCACTCCTGAATCCGGCCCT | |
| | | | GGTAGCGAGCCGGCAACCTCCGGCTCAGAAACTC | |
| | | | CTGGTTCGGAACCAGCGACCAGCGGTTCTGAAAC | |
| | | | TCCGGGTAGCCCGGCAGGCAGCCCAACGAGCACC | |
| | | | GAAGAGGGTACCAGCACGGAACCGAGCGAGGGTT | |
| | | | CTGCCCCGGGTACTTCCACCGAACCATCGGAGGG | |
| | | | CTCTGCACCTGGTAGCGAACCTGCGACGTCTGGT | |
| | | | TCTGAAACGCCGGGTACCAGCGAAAGCGCTACCC | |
| | | | CAGAATCCGGTCCGGGCACTAGCACCGAGCCATC | |
| | | | GGAGGGCTCCGCACCAGGTCACCATCATCACCAT | |
| | | | CAC | |
| TBP-3 | EVOLVESGGGLVQ | 432 | GAGGTGCAGCTGGTTGAAAGCGGTGGCGGTCTGG | 448 |
| | PGGSLRLSCAASG | | TGCAACCAGGCGGTAGCCTGCGTCTGAGCTGCGC | |
| | YSFTGYTMNWVRQ | | GGCGAGCGGTTACAGCTTTACCGGTTATACCATG | |
| | APGKGLEWVALIN | | AACTGGGTTCGTCAAGCGCCAGGTAAAGGTCTGG | |
| | PYKGVSTYNQKFK | | AGTGGGTGGCGCTGATCAACCCGTACAAGGGTGT | |
| | DRFTISVDKSKNT | | TAGCACCTATAACCAGAAGTTCAAAGACCGTTTT | |
| | AYLQMNSLRAEDT | | ACCATTAGCGTGGATAAGAGCAAAAACACCGCGT | |
| | AVYYCARSGYYGD | | ACCTGCAAATGAACAGCCTGCGTGCGGAGGACAC | |
| | SDWYFDVWGQGTL | | CGCTGTGTACTATTGCGCGCGTAGCGGTTACTAT | |
| | VTVSSGATPPETG | | GGCGACAGCGACTGGTATTTTGATGTGTGGGGCC | |
| | AETESPGETTGGS | | AAGGCACCCTGGTTACCGTGAGCTCCGGCGCCAC | |
| | AESEPPGEGDIQM | | GCCTCCGGAAACTGGTGCTGAGACGGAATCCCCT | |
| | TQSPSSLSASVGD | | GGTGAAACCACTGGCGGTTCTGCCGAATCTGAAC | |
| | RVTITCRASQDIR | | CGCCTGGTGAAGGCGACATCCAAATGACCCAGAG | |

TABLE 7-continued

T-cell binding compositions

| Construct Name | Amino Acid Sequence | SEQ ID NO: | DNA Sequence | SEQ ID NO: |
|---|---|---|---|---|
| | NYLNWYQQKPGKA | | CCCGAGCAGCCTGAGCGCGAGCGTGGGCGACCGT | |
| | PKLLIYYTSRLES | | GTTACCATCACCTGCCGTGCGAGCCAAGACATCC | |
| | GVPSRFSGSGSGT | | GTAACTACCTGAACTGGTATCAGCAAAAGCCGGG | |
| | DYTLTISSLOPED | | TAAAGCGCCGAAGCTGCTGATCTACTATACCAGC | |
| | FATYYCQQGNTLP | | CGTCTGGAGAGCGGCGTGCCGAGCCGTTTCAGCG | |
| | WTFGQGTKVEIKG | | GTAGCGGTAGCGGTACCGACTACACCCTGACCAT | |
| | TAEAASASGLSGR | | TAGCAGCCTGCAGCCGGAAGATTTCGCGACCTAC | |
| | SDNHSPLGLAGSP | | TATTGCCAGCAGGGTAACACCCTGCCGTGGACCT | |
| | GSPAGSPTSTEEG | | TTGGTCAAGGCACCAAAGTTGAGATTAAAGGCAC | |
| | TSESATPESGPGT | | CGCCGAAGCAGCTagcgcctctGGCctgTCAggt | |
| | STEPSEGSAPGSP | | CGTtctGATaacCATtccCCActgGGTctgGCTG | |
| | AGSPTSTEEGTST | | GGTCTCCAGGTAGCCCAGCTGGTAGCCCAACCTC | |
| | EPSEGSAPGTSTE | | TACCGAAGAAGGTACCTCTGAATCCGCTACTCCA | |
| | PSEGSAPGTSESA | | GAATCCGGTCCTGGTACTAGCACTGAGCCAAGCG | |
| | TPESGPGSEPATS | | AAGGTTCTGCTCCAGGCTCCCCGGCAGGTAGCCC | |
| | GSETPGSEPATSG | | TACCTCTACCGAAGAGGGCACTAGCACCGAACCA | |
| | SETPGSPAGSPTS | | TCTGAGGGTTCCGCTCCTGGCACCTCCACTGAAC | |
| | TEEGTSESATPES | | CGTCCGAAGGCAGTGCTCCGGGTACTTCCGAAAG | |
| | GPGTSTEPSEGSA | | CGCAACTCCGGAATCCGGCCCTGGTTCTGAGCCT | |
| | PGTSTEPSEGSAP | | GCTACTTCCGGCTCTGAAACTCCAGGTAGCGAGC | |
| | GSPAGSPTSTEEG | | CAGCGACTTCTGGTTCTGAAACTCCAGGTTCACC | |
| | TSTEPSEGSAPGT | | GGCGGGTAGCCCGACGAGCACGGAGGAAGGTACC | |
| | STEPSEGSAPGTS | | TCTGAGTCGGCCACTCCTGAGTCCGGTCCGGGCA | |
| | ESATPESGPGTST | | CGAGCACCGAGCCGAGCGAGGGTTCAGCCCCGGG | |
| | EPSEGSAPGTSES | | TACCAGCACGGAGCCGTCCGAGGGTAGCGCACCG | |
| | ATPESGPGSEPAT | | GGTTCTCCGGCGGGCTCCCCTACGTCTACGGAAG | |
| | SGSETPGTSTEPS | | AGGGTACGTCCACTGAACCTAGCGAGGGCAGCGC | |
| | EGSAPGTSTEPSE | | GCCAGGCACCAGCACTGAACCGAGCGAAGGCAGC | |
| | GSAPGTSESATPE | | GCACCTGGCACTAGCGAGTCTGCGACTCCGGAGA | |
| | SGPGTSESATPES | | GCGGTCCGGGTACGAGCACGGAACCAAGCGAAGG | |
| | GPGSPAGSPTSTE | | CAGCGCCCCAGGTACCTCTGAATCTGCTACCCCA | |
| | EGTSESATPESGP | | GAATCTGGCCCGGGTTCCGAGCCAGCTACCTCTG | |
| | GSEPATSGSETPG | | GTTCTGAAACCCCAGGTACTTCCACTGAACCAAG | |
| | TSESATPESGPGT | | CGAAGGTAGCGCTCCTGGCACTTCTACTGAACCA | |
| | STEPSEGSAPGTS | | TCCGAAGGTTCCGCTCCTGGTACGTCTGAAAGCG | |
| | TEPSEGSAPGTST | | CTACCCCTGAAAGCGGCCCAGGCACCTCTGAAAG | |
| | EPSEGSAPGTSTE | | CGCTACTCCTGAGAGCGGTCCAGGCTCTCCAGCA | |
| | PSEGSAPGTSTEP | | GGTTCTCCAACCTCCACTGAAGAAGGCACCTCTG | |
| | SEGSAPGTSTEPS | | AGTCTGCTACCCCTGAATCTGGTCCTGGCTCCGA | |
| | EGSAPGSPAGSPT | | ACCTGCTACCTCTGGTTCCGAAACTCCAGGTACC | |
| | STEEGTSTEPSEG | | TCGGAATCTGCGACTCCGGAATCTGGCCCGGGCA | |
| | SAPGTSESATPES | | CGAGCACGGAGCCGTCTGAGGGTAGCGCACCAGG | |
| | GPGSEPATSGSET | | TACCAGCACTGAGCCTTCTGAGGGCTCTGCACCG | |
| | PGTSESATPESGP | | GGTACCTCCACGGAACCTTCGGAAGGTTCTGCGC | |
| | GSEPATSGSETPG | | CGGGTACCTCCACTGAGCCATCCGAGGGTTCAGC | |
| | TSESATPESGPGT | | ACCAGGTACTAGCACGGAACCGTCCGAGGGCTCT | |
| | STEPSEGSAPGTS | | GCACCAGGTACGAGCACCGAACCGTCGGAGGGTA | |
| | ESATPESGPGSPA | | GCGCTCCAGGTAGCCCAGCGGGCTCTCCGACAAG | |
| | GSPTSTEEGSPAG | | CACCGAAGAAGGCACCAGCACCGAGCCGTCCGAA | |
| | SPTSTEEGSPAGS | | GGTTCCGCACCAGGTACAAGCGAGAGCGCGACTC | |
| | PTSTEEGTSESAT | | CTGAATCTGGTCCGGGTAGCGAGCCTGCAACCAG | |
| | PESGPGTSTEPSE | | CGGTTCTGAGACGCCGGGCACTTCCGAATCTGCG | |
| | GSAPGTSESATPE | | ACCCCGGAGTCCGGTCCAGGTTCAGAGCCGGCGA | |
| | SGPGSEPATSGSE | | CGAGCGGTTCGGAAACGCCGGGTACGTCTGAATC | |
| | TPGTSESATPESG | | AGCCACGCCGGAGTCTGGTCCGGGTACCTCGACC | |
| | PGSEPATSGSETP | | GAACCAAGCGAAGGTTCGGCACCGGGTACTAGCG | |
| | GTSESATPESGPG | | AGAGCGCAACCCCTGAAAGCGGTCCGGGCAGCCC | |
| | TSTEPSEGSAPGS | | GGCAGGTTCTCCAACCAGCACCGAAGAAGGTTCC | |
| | PAGSPTSTEEGTS | | CCTGCTGGTAGCCCGACCTCTACGGAGGAAGGTA | |
| | ESATPESGPGSEP | | GCCCTGCAGGTTCCCCAACTTCTACTGAGGAAGG | |
| | ATSGSETPGTSES | | TACTTCTGAGTCCGCTACCCCAGAAAGCGGTCCT | |
| | ATPESGPGSPAGS | | GGTACCTCCACTGAACCGTCTGAAGGCTCTGCAC | |
| | PTSTEEGSPAGSP | | CAGGCACTTCTGAGTCTGCTACTCCAGAAAGCGG | |
| | TSTEEGTSTEPSE | | CCCAGGTTCTGAACCAGCAACTTCTGGCTCTGAG | |
| | GSAPGTSESATPE | | ACTCCAGGCACTTCTGAGTCCGCAACGCCTGAAT | |
| | SGPGTSESATPES | | CCGGTCCTGGTTCTGAACCAGCTACTTCCGGCAG | |
| | GPGTSESATPESG | | CGAAACCCCAGGTACCTCTGAGTCTGCGACTCCA | |
| | PGSEPATSGSETP | | GAGTCTGGTCCTGGTACTTCCACTGAGCCTAGCG | |

TABLE 7-continued

T-cell binding compositions

| Construct Name | Amino Acid Sequence | SEQ ID NO: | DNA Sequence | SEQ ID NO: |
|---|---|---|---|---|
| | GSEPATSGSETPG | | AGGGTTCCGCACCAGGTTCTCCGGCTGGTAGCCC | |
| | SPAGSPTSTEEGT | | GACCAGCACGGAGGAGGGTACGTCTGAATCTGCA | |
| | STEPSEGSAPGTS | | ACGCCGGAATCGGGCCCAGGTTCGGAGCCTGCAA | |
| | TEPSEGSAPGSEP | | CGTCTGGCAGCGAAACCCCGGGTACCTCCGAATC | |
| | ATSGSETPGTSES | | TGCTACACCGGAAAGCGGTCCTGGCAGCCCTGCT | |
| | ATPESGPGTSTEP | | GGTTCTCCAACCTCTACCGAGGAGGGTTCACCGG | |
| | SEGSAPGHHHHHH | | CAGGTAGCCCGACTAGCACTGAAGAAGGTACTAG | |
| | | | CACGGAGCCGAGCGAGGGTAGTGCTCCGGGTACG | |
| | | | AGCGAGAGCGCAACGCCAGAGAGCGGTCCAGGCA | |
| | | | CCAGCGAATCGGCCACCCCTGAGAGCGGCCCAGG | |
| | | | TACTTCTGAGAGCGCCACTCCTGAATCCGGCCCT | |
| | | | GGTAGCGAGCCGGCAACCTCCGGCTCAGAAACTC | |
| | | | CTGGTTCGGAACCAGCGACCAGCGGTTCTGAAAC | |
| | | | TCCGGGTAGCCCGGCAGGCAGCCCAACGAGCACC | |
| | | | GAAGAGGGTACCAGCACGGAACCGAGCGAGGGTT | |
| | | | CTGCCCCGGGTACTTCCACCGAACCATCGGAGGG | |
| | | | CTCTGCACCTGGTAGCGAACCTGCGACGTCTGGT | |
| | | | TCTGAAACGCCGGGTACCAGCGAAAGCGCTACCC | |
| | | | CAGAATCCGGTCCGGGCACTAGCACCGAGCCATC | |
| | | | GGAGGGCTCCGCACCAGGTCACCATCATCACCAT | |
| | | | CAC | |
| TBP-4 | EVOLVESGGGLVQ | 433 | GAGGTGCAGCTGGTTGAAAGCGGTGGCGGTCTGG | 449 |
| | PGGSLRLSCAASG | | TGCAACCAGGCGGTAGCCTGCGTCTGAGCTGCGC | |
| | YSFTGYTMNWVRQ | | GGCGAGCGGTTACAGCTTTACCGGTTATACCATG | |
| | APGKGLEWVALIN | | AACTGGGTTCGTCAAGCGCCAGGTAAAGGTCTGG | |
| | PYKGVSTYNQKFK | | AGTGGGTGGCGCTGATCAACCCGTACAAGGGTGT | |
| | DRFTISVDKSKNT | | TAGCACCTATAACCAGAAGTTCAAAGACCGTTTT | |
| | AYLQMNSLRAEDT | | ACCATTAGCGTGGATAAGAGCAAAAACACCGCGT | |
| | AVYYCARSGYYGD | | ACCTGCAAATGAACAGCCTGCGTGCGGAGGACAC | |
| | SDWYFDVWGQGTL | | CGCTGTGTACTATTGCGCGCGTAGCGGTTACTAT | |
| | VTVSSGATPPETG | | GGCGACAGCGACTGGTATTTTGATGTGTGGGGCC | |
| | AETESPGETTGGS | | AAGGCACCCTGGTTACCGTGAGCTCCGGCGCCAC | |
| | AESEPPGEGDIQM | | GCCTCCGGAAACTGGTGCTGAGACGGAATCCCCT | |
| | TQSPSSLSASVGD | | GGTGAAACCACTGGCGGTTCTGCCGAATCTGAAC | |
| | RVTITCRASQDIR | | CGCCTGGTGAAGGCGACATCCAAATGACCCAGAG | |
| | NYLNWYQQKPGKA | | CCCGAGCAGCCTGAGCGCGAGCGTGGGCGACCGT | |
| | PKLLIYYTSRLES | | GTTACCATCACCTGCCGTGCGAGCCAAGACATCC | |
| | GVPSRFSGSGSGT | | GTAACTACCTGAACTGGTATCAGCAAAAGCCGGG | |
| | DYTLTISSLOPED | | TAAAGCGCCGAAGCTGCTGATCTACTATACCAGC | |
| | FATYYCQQGNTLP | | CGTCTGGAGAGCGGCGTGCCGAGCCGTTTCAGCG | |
| | WTFGQGTKVEIKG | | GTAGCGGTAGCGGTACCGACTACACCCTGACCAT | |
| | TAEAASASGLSGR | | TAGCAGCCTGCAGCCGGAAGATTTCGCGACCTAC | |
| | SDNHVPLSLKMGP | | TATTGCCAGCAGGGTAACACCCTGCCGTGGACCT | |
| | GSPAGSPTSTEEG | | TTGGTCAAGGCACCAAAGTTGAGATTAAAGGCAC | |
| | TSESATPESGPGT | | CGCCGAAGCAGCTagcgcctctGGCctgTCAggt | |
| | STEPSEGSAPGSP | | CGTtctGATaacCATgttCCActgTCTctgAAAa | |
| | AGSPTSTEEGTST | | tgGGTCCAGGTAGCCCAGCTGGTAGCCCAACCTC | |
| | EPSEGSAPGTSTE | | TACCGAAGAAGGTACCTCTGAATCCGCTACTCCA | |
| | PSEGSAPGTSESA | | GAATCCGGTCCTGGTACTAGCACTGAGCCAAGCG | |
| | TPESGPGSEPATS | | AAGGTTCTGCTCCAGGCTCCCCGGCAGGTAGCCC | |
| | GSETPGSEPATSG | | TACCTCTACCGAAGAGGGCACTAGCACCGAACCA | |
| | SETPGSPAGSPTS | | TCTGAGGGTTCCGCTCCTGGCACCTCCACTGAAC | |
| | TEEGTSESATPES | | CGTCCGAAGGCAGTGCTCCGGGTACTTCCGAAAG | |
| | GPGTSTEPSEGSA | | CGCAACTCCGGAATCCGGCCCTGGTTCTGAGCCT | |
| | PGTSTEPSEGSAP | | GCTACTTCCGGCTCTGAAACTCCAGGTAGCGAGC | |
| | GSPAGSPTSTEEG | | CAGCGACTTCTGGTTCTGAAACTCCAGGTTCACC | |
| | TSTEPSEGSAPGT | | GGCGGGTAGCCCGACGAGCACGGAGGAAGGTACC | |
| | STEPSEGSAPGTS | | TCTGAGTCGGCCACTCCTGAGTCCGGTCCGGGCA | |
| | ESATPESGPGTST | | CGAGCACCGAGCCGAGCGAGGGTTCAGCCCCGGG | |
| | EPSEGSAPGTSES | | TACCAGCACGGAGCCGTCCGAGGGTAGCGCACCG | |
| | ATPESGPGSEPAT | | GGTTCTCCGGCGGGCTCCCCTACGTCTACGGAAG | |
| | SGSETPGTSTEPS | | AGGGTACGTCCACTGAACCTAGCGAGGGCAGCGC | |
| | EGSAPGTSTEPSE | | GCCAGGCACCAGCACTGAACCGAGCGAAGGCAGC | |
| | GSAPGTSESATPE | | GCACCTGGCACTAGCGAGTCTGCGACTCCGGAGA | |
| | SGPGTSESATPES | | GCGGTCCGGGTACGAGCACGGAACCAAGCGAAGG | |
| | GPGSPAGSPTSTE | | CAGCGCCCCAGGTACCTCTGAATCTGCTACCCCA | |
| | EGTSESATPESGP | | GAATCTGGCCCGGGTTCCGAGCCAGCTACCTCTG | |
| | GSEPATSGSETPG | | GTTCTGAAACCCCAGGTACTTCCACTGAACCAAG | |
| | TSESATPESGPGT | | CGAAGGTAGCGCTCCTGGCACTTCTACTGAACCA | |
| | STEPSEGSAPGTS | | TCCGAAGGTTCCGCTCCTGGTACGTCTGAAAGCG | |
| | TEPSEGSAPGTST | | CTACCCCTGAAAGCGGCCCAGGCACCTCTGAAAG | |
| | EPSEGSAPGTSTE | | CGCTACTCCTGAGAGCGGTCCAGGCTCTCCAGCA | |
| | PSEGSAPGTSTEP | | GGTTCTCCAACCTCCACTGAAGAAGGCACCTCTG | |

TABLE 7-continued

| T-cell binding compositions | | | | |
|---|---|---|---|---|
| Construct Name | Amino Acid Sequence | SEQ ID NO: | DNA Sequence | SEQ ID NO: |
| | SEGSAPGTSTEPS | | AGTCTGCTACCCCTGAATCTGGTCCTGGCTCCGA | |
| | EGSAPGSPAGSPT | | ACCTGCTACCTCTGGTTCCGAAACTCCAGGTACC | |
| | STEEGTSTEPSEG | | TCGGAATCTGCGACTCCGGAATCTGGCCCGGGCA | |
| | SAPGTSESATPES | | CGAGCACGGAGCCGTCTGAGGGTAGCGCACCAGG | |
| | GPGSEPATSGSET | | TACCAGCACTGAGCCTTCTGAGGGCTCTGCACCG | |
| | PGTSESATPESGP | | GGTACCTCCACGGAACCTTCGGAAGGTTCTGCGC | |
| | GSEPATSGSETPG | | CGGGTACCTCCACTGAGCCATCCGAGGGTTCAGC | |
| | TSESATPESGPGT | | ACCAGGTACTAGCACGGAACCGTCCGAGGGCTCT | |
| | STEPSEGSAPGTS | | GCACCAGGTACGAGCACCGAACCGTCGGAGGGTA | |
| | ESATPESGPGSPA | | GCGCTCCAGGTAGCCCAGCGGGCTCTCCGACAAG | |
| | GSPTSTEEGSPAG | | CACCGAAGAAGGCACCAGCACCGAGCCGTCCGAA | |
| | SPTSTEEGSPAGS | | GGTTCCGCACCAGGTACAAGCGAGAGCGCGACTC | |
| | PTSTEEGTSESAT | | CTGAATCTGGTCCGGGTAGCGAGCCTGCAACCAG | |
| | PESGPGTSTEPSE | | CGGTTCTGAGACGCCGGGCACTTCCGAATCTGCG | |
| | GSAPGTSESATPE | | ACCCCGGAGTCCGGTCCAGGTTCAGAGCCGGCGA | |
| | SGPGSEPATSGSE | | CGAGCGGTTCGGAAACGCCGGGTACGTCTGAATC | |
| | TPGTSESATPESG | | AGCCACGCCGGAGTCTGGTCCGGGTACCTCGACC | |
| | PGSEPATSGSETP | | GAACCAAGCGAAGGTTCGGCACCGGGTACTAGCG | |
| | GTSESATPESGPG | | AGAGCGCAACCCCTGAAAGCGGTCCGGGCAGCCC | |
| | TSTEPSEGSAPGS | | GGCAGGTTCTCCAACCAGCACCGAAGAAGGTTCC | |
| | PAGSPTSTEEGTS | | CCTGCTGGTAGCCCGACCTCTACGGAGGAAGGTA | |
| | ESATPESGPGSEP | | GCCCTGCAGGTTCCCCAACTTCTACTGAGGAAGG | |
| | ATSGSETPGTSES | | TACTTCTGAGTCCGCTACCCCAGAAAGCGGTCCT | |
| | ATPESGPGSPAGS | | GGTACCTCCACTGAACCGTCTGAAGGCTCTGCAC | |
| | PTSTEEGSPAGSP | | CAGGCACTTCTGAGTCTGCTACTCCAGAAAGCGG | |
| | TSTEEGTSTEPSE | | CCCAGGTTCTGAACCAGCAACTTCTGGCTCTGAG | |
| | GSAPGTSESATPE | | ACTCCAGGCACTTCTGAGTCCGCAACGCCTGAAT | |
| | SGPGTSESATPES | | CCGGTCCTGGTTCTGAACCAGCTACTTCCGGCAG | |
| | GPGTSESATPESG | | CGAAACCCCAGGTACCTCTGAGTCTGCGACTCCA | |
| | PGSEPATSGSETP | | GAGTCTGGTCCTGGTACTTCCACTGAGCCTAGCG | |
| | GSEPATSGSETPG | | AGGGTTCCGCACCAGGTTCTCCGGCTGGTAGCCC | |
| | SPAGSPTSTEEGT | | GACCAGCACGGAGGAGGGTACGTCTGAATCTGCA | |
| | STEPSEGSAPGTS | | ACGCCGGAATCGGGCCCAGGTTCGGAGCCTGCAA | |
| | TEPSEGSAPGSEP | | CGTCTGGCAGCGAAACCCCGGGTACCTCCGAATC | |
| | ATSGSETPGTSES | | TGCTACACCGGAAAGCGGTCCTGGCAGCCCTGCT | |
| | ATPESGPGTSTEP | | GGTTCTCCAACCTCTACCGAGGAGGGTTCACCGG | |
| | SEGSAPGHHHHHH | | CAGGTAGCCCGACTAGCACTGAAGAAGGTACTAG | |
| | | | CACGGAGCCGAGCGAGGGTAGTGCTCCGGGTACG | |
| | | | AGCGAGAGCGCAACGCCAGAGAGCGGTCCAGGCA | |
| | | | CCAGCGAATCGGCCACCCCTGAGAGCGGCCCAGG | |
| | | | TACTTCTGAGAGCGCCACTCCTGAATCCGGCCCT | |
| | | | GGTAGCGAGCCGGCAACCTCCGGCTCAGAAACTC | |
| | | | CTGGTTCGGAACCAGCGACCAGCGGTTCTGAAAC | |
| | | | TCCGGGTAGCCCGGCAGGCAGCCCAACGAGCACC | |
| | | | GAAGAGGGTACCAGCACGGAACCGAGCGAGGGTT | |
| | | | CTGCCCCGGGTACTTCCACCGAACCATCGGAGGG | |
| | | | CTCTGCACCTGGTAGCGAACCTGCGACGTCTGGT | |
| | | | TCTGAAACGCCGGGTACCAGCGAAAGCGCTACCC | |
| | | | CAGAATCCGGTCCGGGCACTAGCACCGAGCCATC | |
| | | | GGAGGGCTCCGCACCAGGTCACCATCATCACCAT | |
| | | | CAC | |
| TBP-5 | ELVVTQEPSLTVS | 434 | GAACTGGTCGTCACGCAGGAGCCGTCCCTTACCG | 450 |
| | PGGTVTLTCRSST | | TTTCACCAGGTGGAACAGTGACTCTGACGTGTCG | |
| | GAVTTSNYANWVQ | | CTCCTCCACTGGGGCGGTTACAACTTCCAATTAT | |
| | QKPGQAPRGLIGG | | GCTAATTGGGTCCAGCAGAAGCCGGGCCAAGCCC | |
| | TNKRAPGTPARES | | CTCGCGGGTTGATTGGCGGCACCAACAAACGTGC | |
| | GSLLGGKAALTLS | | TCCAGGGACACCTGCCCGTTTTTCGGGCTCCTTA | |
| | GVQPEDEAEYYCA | | TTGGGGGGCAAAGCTGCACTGACGTTGTCTGGAG | |
| | LWYSNLWVFGGGT | | TTCAGCCGGAGGATGAGGCAGAGTATTACTGCGC | |
| | KLTVLGATPPETG | | ATTGTGGTATTCTAATTTATGGGTTTTTGGAGGC | |
| | AETESPGETTGGS | | GGCACAAAGCTGACCGTCCTGggtgcgaccccgc | |
| | AESEPPGEGEVQL | | cggaaaccggtgcggaaaccgaaagcccgggtga | |
| | LESGGGLVQPGGS | | aaccaccggtggcagcgcggagagcgaaccgccg | |
| | LKLSCAASGFTEN | | ggtgaaggtGAGGTTCAGTTGTTGGAAAGCGGGG | |
| | TYAMNWVRQAPGK | | GCGGGCTTGTCCAACCTGGAGGTTCATTAAAATT | |
| | GLEWVARIRSKYN | | GAGCTGTGCAGCCTCCGGATTCACCTTTAACACG | |
| | NYATYYADSVKDR | | TATGCAATGAACTGGGTCCGTCAAGCGCCCGGTA | |
| | FTISRDDSKNTAY | | AGGGGCTGGAGTGGGTAGCTCGCATCCGCTCGAA | |
| | LQMNNLKTEDTAV | | GTATAATAATTACGCAACCTACTACGCAGACAGT | |
| | YYCVRHGNFGNSY | | GTCAAAGATCGCTTCACTATCTCACGCGACGACA | |
| | VSWFAYWGQGTLV | | GTAAGAACACGGCCTACTTACAGATGAACAATCT | |
| | TVSSGTAEAASAS | | TAAAACGGAGGACACCGCTGTCTACTACTGCGTG | |
| | GLSGRSDNHSPLG | | CGCCACGGGAATTTCGGTAACTCTTATGTAAGTT | |

TABLE 7-continued

T-cell binding compositions

| Construct Name | Amino Acid Sequence | SEQ ID NO: | DNA Sequence | SEQ ID NO: |
|---|---|---|---|---|
| | LAGSPGSPAGSPT | | GGTTCGCATATTGGGGACAAGGTACGTTGGTAAC | |
| | STEEGTSESATPE | | CGTATCCAGCGGCACCGCCGAAGCAGCTagcgcc | |
| | SGPGTSTEPSEGS | | tctGGCctgTCAggtCGTtctGATaacCATtccC | |
| | APGSPAGSPTSTE | | CActgGGTctgGCTGGGTCTCCAGGTAGCCCAGC | |
| | EGTSTEPSEGSAP | | TGGTAGCCCAACCTCTACCGAAGAAGGTACCTCT | |
| | GTSTEPSEGSAPG | | GAATCCGCTACTCCAGAATCCGGTCCTGGTACTA | |
| | TSESATPESGPGS | | GCACTGAGCCAAGCGAAGGTTCTGCTCCAGGCTC | |
| | EPATSGSETPGSE | | CCCGGCAGGTAGCCCTACCTCTACCGAAGAGGGC | |
| | PATSGSETPGSPA | | ACTAGCACCGAACCATCTGAGGGTTCCGCTCCTG | |
| | GSPTSTEEGTSES | | GCACCTCCACTGAACCGTCCGAAGGCAGTGCTCC | |
| | ATPESGPGTSTEP | | GGGTACTTCCGAAAGCGCAACTCCGGAATCCGGC | |
| | SEGSAPGTSTEPS | | CCTGGTTCTGAGCCTGCTACTTCCGGCTCTGAAA | |
| | EGSAPGSPAGSPT | | CTCCAGGTAGCGAGCCAGCGACTTCTGGTTCTGA | |
| | STEEGTSTEPSEG | | AACTCCAGGTTCACCGGCGGGTAGCCCGACGAGC | |
| | SAPGTSTEPSEGS | | ACGGAGGAAGGTACCTCTGAGTCGGCCACTCCTG | |
| | APGTSESATPESG | | AGTCCGGTCCGGGCACGAGCACCGAGCCGAGCGA | |
| | PGTSTEPSEGSAP | | GGGTTCAGCCCCGGGTACCAGCACGGAGCCGTCC | |
| | GTSESATPESGPG | | GAGGGTAGCGCACCGGGTTCTCCGGCGGGCTCCC | |
| | SEPATSGSETPGT | | CTACGTCTACGGAAGAGGGTACGTCCACTGAACC | |
| | STEPSEGSAPGTS | | TAGCGAGGGCAGCGCGCCAGGCACCAGCACTGAA | |
| | TEPSEGSAPGTSE | | CCGAGCGAAGGCAGCGCACCTGGCACTAGCGAGT | |
| | SATPESGPGTSES | | CTGCGACTCCGGAGAGCGGTCCGGGTACGAGCAC | |
| | ATPESGPGSPAGS | | GGAACCAAGCGAAGGCAGCGCCCCAGGTACCTCT | |
| | PTSTEEGTSESAT | | GAATCTGCTACCCCAGAATCTGGCCCGGGTTCCG | |
| | PESGPGSEPATSG | | AGCCAGCTACCTCTGGTTCTGAAACCCCAGGTAC | |
| | SETPGTSESATPE | | TTCCACTGAACCAAGCGAAGGTAGCGCTCCTGGC | |
| | SGPGTSTEPSEGS | | ACTTCTACTGAACCATCCGAAGGTTCCGCTCCTG | |
| | APGTSTEPSEGSA | | GTACGTCTGAAAGCGCTACCCCTGAAAGCGGCCC | |
| | PGTSTEPSEGSAP | | AGGCACCTCTGAAAGCGCTACTCCTGAGAGCGGT | |
| | GTSTEPSEGSAPG | | CCAGGCTCTCCAGCAGGTTCTCCAACCTCCACTG | |
| | TSTEPSEGSAPGT | | AAGAAGGCACCTCTGAGTCTGCTACCCCTGAATC | |
| | STEPSEGSAPGSP | | TGGTCCTGGCTCCGAACCTGCTACCTCTGGTTCC | |
| | AGSPTSTEEGTST | | GAAACTCCAGGTACCTCGGAATCTGCGACTCCGG | |
| | EPSEGSAPGTSES | | AATCTGGCCCGGGCACGAGCACGGAGCCGTCTGA | |
| | ATPESGPGSEPAT | | GGGTAGCGCACCAGGTACCAGCACTGAGCCTTCT | |
| | SGSETPGTSESAT | | GAGGGCTCTGCACCGGGTACCTCCACGGAACCTT | |
| | PESGPGSEPATSG | | CGGAAGGTTCTGCGCCGGGTACCTCCACTGAGCC | |
| | SETPGTSESATPE | | ATCCGAGGGTTCAGCACCAGGTACTAGCACGGAA | |
| | SGPGTSTEPSEGS | | CCGTCCGAGGGCTCTGCACCAGGTACGAGCACCG | |
| | APGTSESATPESG | | AACCGTCGGAGGGTAGCGCTCCAGGTAGCCCAGC | |
| | PGSPAGSPTSTEE | | GGGCTCTCCGACAAGCACCGAAGAAGGCACCAGC | |
| | GSPAGSPTSTEEG | | ACCGAGCCGTCCGAAGGTTCCGCACCAGGTACAA | |
| | SPAGSPTSTEEGT | | GCGAGAGCGCGACTCCTGAATCTGGTCCGGGTAG | |
| | SESATPESGPGTS | | CGAGCCTGCAACCAGCGGTTCTGAGACGCCGGGC | |
| | TEPSEGSAPGTSE | | ACTTCCGAATCTGCGACCCCGGAGTCCGGTCCAG | |
| | SATPESGPGSEPA | | GTTCAGAGCCGGCGACGAGCGGTTCGGAAACGCC | |
| | TSGSETPGTSESA | | GGGTACGTCTGAATCAGCCACGCCGGAGTCTGGT | |
| | TPESGPGSEPATS | | CCGGGTACCTCGACCGAACCAAGCGAAGGTTCGG | |
| | GSETPGTSESATP | | CACCGGGTACTAGCGAGAGCGCAACCCCTGAAAG | |
| | ESGPGTSTEPSEG | | CGGTCCGGGCAGCCCGGCAGGTTCTCCAACCAGC | |
| | SAPGSPAGSPTST | | ACCGAAGAAGGTTCCCCTGCTGGTAGCCCGACCT | |
| | EEGTSESATPESG | | CTACGGAGGAAGGTAGCCCTGCAGGTTCCCCAAC | |
| | PGSEPATSGSETP | | TTCTACTGAGGAAGGTACTTCTGAGTCCGCTACC | |
| | GTSESATPESGPG | | CCAGAAAGCGGTCCTGGTACCTCCACTGAACCGT | |
| | SPAGSPTSTEEGS | | CTGAAGGCTCTGCACCAGGCACTTCTGAGTCTGC | |
| | PAGSPTSTEEGTS | | TACTCCAGAAAGCGGCCCAGGTTCTGAACCAGCA | |
| | TEPSEGSAPGTSE | | ACTTCTGGCTCTGAGACTCCAGGCACTTCTGAGT | |
| | SATPESGPGTSES | | CCGCAACGCCTGAATCCGGTCCTGGTTCTGAACC | |
| | ATPESGPGTSESA | | AGCTACTTCCGGCAGCGAAACCCCAGGTACCTCT | |
| | TPESGPGSEPATS | | GAGTCTGCGACTCCAGAGTCTGGTCCTGGTACTT | |
| | GSETPGSEPATSG | | CCACTGAGCCTAGCGAGGGTTCCGCACCAGGTTC | |
| | SETPGSPAGSPTS | | TCCGGCTGGTAGCCCGACCAGCACGGAGGAGGGT | |
| | TEEGTSTEPSEGS | | ACGTCTGAATCTGCAACGCCGGAATCGGGCCCAG | |
| | APGTSTEPSEGSA | | GTTCGGAGCCTGCAACGTCTGGCAGCGAAACCCC | |
| | PGSEPATSGSETP | | GGGTACCTCCGAATCTGCTACACCGGAAAGCGGT | |
| | GTSESATPESGPG | | CCTGGCAGCCCTGCTGGTTCTCCAACCTCTACCG | |
| | TSTEPSEGSAPGH | | AGGAGGGTTCACCGGCAGGTAGCCCGACTAGCAC | |
| | HHHHH | | TGAAGAAGGTACTAGCACGGAGCCGAGCGAGGGT | |
| | | | AGTGCTCCGGGTACGAGCGAGAGCGCAACGCCAG | |
| | | | AGAGCGGTCCAGGCACCAGCGAATCGGCCACCCC | |
| | | | TGAGAGCGGCCCAGGTACTTCTGAGAGCGCCACT | |
| | | | CCTGAATCCGGCCCTGGTAGCGAGCCGGCAACCT | |
| | | | CCGGCTCAGAAACTCCTGGTTCGGAACCAGCGAC | |
| | | | CAGCGGTTCTGAAACTCCGGGTAGCCCGGCAGGC | |

TABLE 7-continued

T-cell binding compositions

| Construct Name | Amino Acid Sequence | SEQ ID NO: | DNA Sequence | SEQ ID NO: |
|---|---|---|---|---|
| | | | AGCCCAACGAGCACCGAAGAGGGTACCAGCACGG | |
| | | | AACCGAGCGAGGGTTCTGCCCCGGGTACTTCCAC | |
| | | | CGAACCATCGGAGGGCTCTGCACCTGGTAGCGAA | |
| | | | CCTGCGACGTCTGGTTCTGAAACGCCGGGTACCA | |
| | | | GCGAAAGCGCTACCCCAGAATCCGGTCCGGGCAC | |
| | | | TAGCACCGAGCCATCGGAGGGCTCCGCACCAGGT | |
| | | | CACCATCATCACCATCAC | |
| TBP-6 | ELVVTQEPSLTVS | 435 | GAACTGGTCGTCACGCAGGAGCCGTCCCTTACCG | 451 |
| | PGGTVTLTCRSST | | TTTCACCAGGTGGAACAGTGACTCTGACGTGTCG | |
| | GAVTTSNYANWVQ | | CTCCTCCACTGGGGCGGTTACAACTTCCAATTAT | |
| | QKPGQAPRGLIGG | | GCTAATTGGGTCCAGCAGAAGCCGGGCCAAGCCC | |
| | TNKRAPGTPARES | | CTCGCGGGTTGATTGGCGGCACCAACAAACGTGC | |
| | GSLLGGKAALTLS | | TCCAGGGACACCTGCCCGTTTTTCGGGCTCCTTA | |
| | GVQPEDEAEYYCA | | TTGGGGGGCAAAGCTGCACTGACGTTGTCTGGAG | |
| | LWYSNLWVFGGGT | | TTCAGCCGGAGGATGAGGCAGAGTATTACTGCGC | |
| | KLTVLGATPPETG | | ATTGTGGTATTCTAATTTATGGGTTTTTGGAGGC | |
| | AETESPGETTGGS | | GGCACAAAGCTGACCGTCCTGggtgcgaccccgc | |
| | AESEPPGEGEVQL | | cggaaaccggtgcggaaaccgaaagcccgggtga | |
| | LESGGGLVQPGGS | | aaccaccggtggcagcgcggagagcgaaccgccg | |
| | LKLSCAASGFTEN | | ggtgaaggtGAGGTTCAGTTGTTGGAAAGCGGGG | |
| | TYAMNWVRQAPGK | | GCGGGCTTGTCCAACCTGGAGGTTCATTAAAATT | |
| | GLEWVARIRSKYN | | GAGCTGTGCAGCCTCCGGATTCACCTTTAACACG | |
| | NYATYYADSVKDR | | TATGCAATGAACTGGGTCCGTCAAGCGCCCGGTA | |
| | FTISRDDSKNTAY | | AGGGGCTGGAGTGGGTAGCTCGCATCCGCTCGAA | |
| | LQMNNLKTEDTAV | | GTATAATAATTACGCAACCTACTACGCAGACAGT | |
| | YYCVRHGNFGNSY | | GTCAAAGATCGCTTCACTATCTCACGCGACGACA | |
| | VSWFAYWGQGTLV | | GTAAGAACACGGCCTACTTACAGATGAACAATCT | |
| | TVSSGTAEAASAS | | TAAAACGGAGGACACCGCTGTCTACTACTGCGTG | |
| | GLSGRSDNHVPLS | | CGCCACGGGAATTTCGGTAACTCTTATGTAAGTT | |
| | LKMGPGSPAGSPT | | GGTTCGCATATTGGGGACAAGGTACGTTGGTAAC | |
| | STEEGTSESATPE | | CGTATCCAGCGGCACCGCCGAAGCAGCTagcgcc | |
| | SGPGTSTEPSEGS | | tctGGCctgTCAggtCGTtctGATaacCATgttC | |
| | APGSPAGSPTSTE | | CActgTCTctgAAAatgGGTCCAGGTAGCCCAGC | |
| | EGTSTEPSEGSAP | | TGGTAGCCCAACCTCTACCGAAGAAGGTACCTCT | |
| | GTSTEPSEGSAPG | | GAATCCGCTACTCCAGAATCCGGTCCTGGTACTA | |
| | TSESATPESGPGS | | GCACTGAGCCAAGCGAAGGTTCTGCTCCAGGCTC | |
| | EPATSGSETPGSE | | CCCGGCAGGTAGCCCTACCTCTACCGAAGAGGGC | |
| | PATSGSETPGSPA | | ACTAGCACCGAACCATCTGAGGGTTCCGCTCCTG | |
| | GSPTSTEEGTSES | | GCACCTCCACTGAACCGTCCGAAGGCAGTGCTCC | |
| | ATPESGPGTSTEP | | GGGTACTTCCGAAAGCGCAACTCCGGAATCCGGC | |
| | SEGSAPGTSTEPS | | CCTGGTTCTGAGCCTGCTACTTCCGGCTCTGAAA | |
| | EGSAPGSPAGSPT | | CTCCAGGTAGCGAGCCAGCGACTTCTGGTTCTGA | |
| | STEEGTSTEPSEG | | AACTCCAGGTTCACCGGCGGGTAGCCCGACGAGC | |
| | SAPGTSTEPSEGS | | ACGGAGGAAGGTACCTCTGAGTCGGCCACTCCTG | |
| | APGTSESATPESG | | AGTCCGGTCCGGGCACGAGCACCGAGCCGAGCGA | |
| | PGTSTEPSEGSAP | | GGGTTCAGCCCCGGGTACCAGCACGGAGCCGTCC | |
| | GTSESATPESGPG | | GAGGGTAGCGCACCGGGTTCTCCGGCGGGCTCCC | |
| | SEPATSGSETPGT | | CTACGTCTACGGAAGAGGGTACGTCCACTGAACC | |
| | STEPSEGSAPGTS | | TAGCGAGGGCAGCGCGCCAGGCACCAGCACTGAA | |
| | TEPSEGSAPGTSE | | CCGAGCGAAGGCAGCGCACCTGGCACTAGCGAGT | |
| | SATPESGPGTSES | | CTGCGACTCCGGAGAGCGGTCCGGGTACGAGCAC | |
| | ATPESGPGSPAGS | | GGAACCAAGCGAAGGCAGCGCCCCAGGTACCTCT | |
| | PTSTEEGTSESAT | | GAATCTGCTACCCCAGAATCTGGCCCGGGTTCCG | |
| | PESGPGSEPATSG | | AGCCAGCTACCTCTGGTTCTGAAACCCCAGGTAC | |
| | SETPGTSESATPE | | TTCCACTGAACCAAGCGAAGGTAGCGCTCCTGGC | |
| | SGPGTSTEPSEGS | | ACTTCTACTGAACCATCCGAAGGTTCCGCTCCTG | |
| | APGTSTEPSEGSA | | GTACGTCTGAAAGCGCTACCCCTGAAAGCGGCCC | |
| | PGTSTEPSEGSAP | | AGGCACCTCTGAAAGCGCTACTCCTGAGAGCGGT | |
| | GTSTEPSEGSAPG | | CCAGGCTCTCCAGCAGGTTCTCCAACCTCCACTG | |
| | TSTEPSEGSAPGT | | AAGAAGGCACCTCTGAGTCTGCTACCCCTGAATC | |
| | STEPSEGSAPGSP | | TGGTCCTGGCTCCGAACCTGCTACCTCTGGTTCC | |
| | AGSPTSTEEGTST | | GAAACTCCAGGTACCTCGGAATCTGCGACTCCGG | |
| | EPSEGSAPGTSES | | AATCTGGCCCGGGCACGAGCACGGAGCCGTCTGA | |
| | ATPESGPGSEPAT | | GGGTAGCGCACCAGGTACCAGCACTGAGCCTTCT | |
| | SGSETPGTSESAT | | GAGGGCTCTGCACCGGGTACCTCCACGGAACCTT | |
| | PESGPGSEPATSG | | CGGAAGGTTCTGCGCCGGGTACCTCCACTGAGCC | |
| | SETPGTSESATPE | | ATCCGAGGGTTCAGCACCAGGTACTAGCACGGAA | |
| | SGPGTSTEPSEGS | | CCGTCCGAGGGCTCTGCACCAGGTACGAGCACCG | |
| | APGTSESATPESG | | AACCGTCGGAGGGTAGCGCTCCAGGTAGCCCAGC | |
| | PGSPAGSPTSTEE | | GGGCTCTCCGACAAGCACCGAAGAAGGCACCAGC | |
| | GSPAGSPTSTEEG | | ACCGAGCCGTCCGAAGGTTCCGCACCAGGTACAA | |
| | SPAGSPTSTEEGT | | GCGAGAGCGCGACTCCTGAATCTGGTCCGGGTAG | |
| | SESATPESGPGTS | | CGAGCCTGCAACCAGCGGTTCTGAGACGCCGGGC | |

TABLE 7-continued

T-cell binding compositions

| Construct Name | Amino Acid Sequence | SEQ ID NO: | DNA Sequence | SEQ ID NO: |
|---|---|---|---|---|
| | TEPSEGSAPGTSE | | ACTTCCGAATCTGCGACCCCGGAGTCCGGTCCAG | |
| | SATPESGPGSEPA | | GTTCAGAGCCGGCGACGAGCGGTTCGGAAACGCC | |
| | TSGSETPGTSESA | | GGGTACGTCTGAATCAGCCACGCCGGAGTCTGGT | |
| | TPESGPGSEPATS | | CCGGGTACCTCGACCGAACCAAGCGAAGGTTCGG | |
| | GSETPGTSESATP | | CACCGGGTACTAGCGAGAGCGCAACCCCTGAAAG | |
| | ESGPGTSTEPSEG | | CGGTCCGGGCAGCCCGGCAGGTTCTCCAACCAGC | |
| | SAPGSPAGSPTST | | ACCGAAGAAGGTTCCCCTGCTGGTAGCCCGACCT | |
| | EEGTSESATPESG | | CTACGGAGGAAGGTAGCCCTGCAGGTTCCCCAAC | |
| | PGSEPATSGSETP | | TTCTACTGAGGAAGGTACTTCTGAGTCCGCTACC | |
| | GTSESATPESGPG | | CCAGAAAGCGGTCCTGGTACCTCCACTGAACCGT | |
| | SPAGSPTSTEEGS | | CTGAAGGCTCTGCACCAGGCACTTCTGAGTCTGC | |
| | PAGSPTSTEEGTS | | TACTCCAGAAAGCGGCCCAGGTTCTGAACCAGCA | |
| | TEPSEGSAPGTSE | | ACTTCTGGCTCTGAGACTCCAGGCACTTCTGAGT | |
| | SATPESGPGTSES | | CCGCAACGCCTGAATCCGGTCCTGGTTCTGAACC | |
| | ATPESGPGTSESA | | AGCTACTTCCGGCAGCGAAACCCCAGGTACCTCT | |
| | TPESGPGSEPATS | | GAGTCTGCGACTCCAGAGTCTGGTCCTGGTACTT | |
| | GSETPGSEPATSG | | CCACTGAGCCTAGCGAGGGTTCCGCACCAGGTTC | |
| | SETPGSPAGSPTS | | TCCGGCTGGTAGCCCGACCAGCACGGAGGAGGGT | |
| | TEEGTSTEPSEGS | | ACGTCTGAATCTGCAACGCCGGAATCGGGCCCAG | |
| | APGTSTEPSEGSA | | GTTCGGAGCCTGCAACGTCTGGCAGCGAAACCCC | |
| | PGSEPATSGSETP | | GGGTACCTCCGAATCTGCTACACCGGAAAGCGGT | |
| | GTSESATPESGPG | | CCTGGCAGCCCTGCTGGTTCTCCAACCTCTACCG | |
| | TSTEPSEGSAPGH | | AGGAGGGTTCACCGGCAGGTAGCCCGACTAGCAC | |
| | HHHHH | | TGAAGAAGGTACTAGCACGGAGCCGAGCGAGGGT | |
| | | | AGTGCTCCGGGTACGAGCGAGAGCGCAACGCCAG | |
| | | | AGAGCGGTCCAGGCACCAGCGAATCGGCCACCCC | |
| | | | TGAGAGCGGCCCAGGTACTTCTGAGAGCGCCACT | |
| | | | CCTGAATCCGGCCCTGGTAGCGAGCCGGCAACCT | |
| | | | CCGGCTCAGAAACTCCTGGTTCGGAACCAGCGAC | |
| | | | CAGCGGTTCTGAAACTCCGGGTAGCCCGGCAGGC | |
| | | | AGCCCAACGAGCACCGAAGAGGGTACCAGCACGG | |
| | | | AACCGAGCGAGGGTTCTGCCCCGGGTACTTCCAC | |
| | | | CGAACCATCGGAGGGCTCTGCACCTGGTAGCGAA | |
| | | | CCTGCGACGTCTGGTTCTGAAACGCCGGGTACCA | |
| | | | GCGAAAGCGCTACCCCAGAATCCGGTCCGGGCAC | |
| | | | TAGCACCGAGCCATCGGAGGGCTCCGCACCAGGT | |
| | | | CACCATCATCACCATCAC | |
| TBP-7 | EVQLLESGGGLVQ | 436 | GAGGTTCAGTTGTTGGAAAGCGGGGGCGGGCTTG | 452 |
| | PGGSLKLSCAASG | | TCCAACCTGGAGGTTCATTAAAATTGAGCTGTGC | |
| | FTFNTYAMNWVRQ | | AGCCTCCGGATTCACCTTTAACACGTATGCAATG | |
| | APGKGLEWVARIR | | AACTGGGTCCGTCAAGCGCCCGGTAAGGGGCTGG | |
| | SKYNNYATYYADS | | AGTGGGTAGCTCGCATCCGCTCGAAGTATAATAA | |
| | VKDRFTISRDDSK | | TTACGCAACCTACTACGCAGACAGTGTCAAAGAT | |
| | NTAYLQMNNLKTE | | CGCTTCACTATCTCACGCGACGACAGTAAGAACA | |
| | DTAVYYCVRHGNF | | CGGCCTACTTACAGATGAACAATCTTAAAACGGA | |
| | GNSYVSWFAYWGQ | | GGACACCGCTGTCTACTACTGCGTGCGCCACGGG | |
| | GTLVTVSSGATPP | | AATTTCGGTAACTCTTATGTAAGTTGGTTCGCAT | |
| | ETGAETESPGETT | | ATTGGGGACAAGGTACGTTGGTAACCGTATCCAG | |
| | GGSAESEPPGEGE | | Cggtgcgaccccgccggaaaccggtgcggaaacc | |
| | LVVTQEPSLTVSP | | gaaagcccgggtgaaaccaccggtggcagcgcgg | |
| | GGTVTLTCRSSTG | | agagcgaaccgccgggtgaaggtGAACTGGTCGT | |
| | AVTTSNYANWVQQ | | CACGCAGGAGCCGTCCCTTACCGTTTCACCAGGT | |
| | KPGQAPRGLIGGT | | GGAACAGTGACTCTGACGTGTCGCTCCTCCACTG | |
| | NKRAPGTPARFSG | | GGGCGGTTACAACTTCCAATTATGCTAATTGGGT | |
| | SLLGGKAALTLSG | | CCAGCAGAAGCCGGGCCAAGCCCCTCGCGGGTTG | |
| | VQPEDEAEYYCAL | | ATTGGCGGCACCAACAAACGTGCTCCAGGGACAC | |
| | WYSNLWVFGGGTK | | CTGCCCGTTTTTCGGGCTCCTTATTGGGGGGCAA | |
| | LTVLGTAEAASAS | | AGCTGCACTGACGTTGTCTGGAGTTCAGCCGGAG | |
| | GLSGRSDNHSPLG | | GATGAGGCAGAGTATTACTGCGCATTGTGGTATT | |
| | LAGSPGSPAGSPT | | CTAATTTATGGGTTTTTGGAGGCGGCACAAAGCT | |
| | STEEGTSESATPE | | GACCGTCCTGGGCACCGCCGAAGCAGCTagcgcc | |
| | SGPGTSTEPSEGS | | tctGGCctgTCAggtCGTtctGATaacCATtccC | |
| | APGSPAGSPTSTE | | CActgGGTctgGCTGGGTCTCCAGGTAGCCCAGC | |
| | EGTSTEPSEGSAP | | TGGTAGCCCAACCTCTACCGAAGAAGGTACCTCT | |
| | GTSTEPSEGSAPG | | GAATCCGCTACTCCAGAATCCGGTCCTGGTACTA | |
| | TSESATPESGPGS | | GCACTGAGCCAAGCGAAGGTTCTGCTCCAGGCTC | |
| | EPATSGSETPGSE | | CCCGGCAGGTAGCCCTACCTCTACCGAAGAGGGC | |
| | PATSGSETPGSPA | | ACTAGCACCGAACCATCTGAGGGTTCCGCTCCTG | |
| | GSPTSTEEGTSES | | GCACCTCCACTGAACCGTCCGAAGGCAGTGCTCC | |
| | ATPESGPGTSTEP | | GGGTACTTCCGAAAGCGCAACTCCGGAATCCGGC | |
| | SEGSAPGTSTEPS | | CCTGGTTCTGAGCCTGCTACTTCCGGCTCTGAAA | |
| | EGSAPGSPAGSPT | | CTCCAGGTAGCGAGCCAGCGACTTCTGGTTCTGA | |
| | STEEGTSTEPSEG | | AACTCCAGGTTCACCGGCGGGTAGCCCGACGAGC | |

TABLE 7-continued

T-cell binding compositions

| Construct Name | Amino Acid Sequence | SEQ ID NO: | DNA Sequence | SEQ ID NO: |
|---|---|---|---|---|
| | SAPGTSTEPSEGS<br>APGTSESATPESG<br>PGTSTEPSEGSAP<br>GTSESATPESGPG<br>SEPATSGSETPGT<br>STEPSEGSAPGTS<br>TEPSEGSAPGTSE<br>SATPESGPGTSES<br>ATPESGPGSPAGS<br>PTSTEEGTSESAT<br>PESGPGSEPATSG<br>SETPGTSESATPE<br>SGPGTSTEPSEGS<br>APGTSTEPSEGSA<br>PGTSTEPSEGSAP<br>GTSTEPSEGSAPG<br>TSTEPSEGSAPGT<br>STEPSEGSAPGSP<br>AGSPTSTEEGTST<br>EPSEGSAPGTSES<br>ATPESGPGSEPAT<br>SGSETPGTSESAT<br>PESGPGSEPATSG<br>SETPGTSESATPE<br>SGPGTSTEPSEGS<br>APGTSESATPESG<br>PGSPAGSPTSTEE<br>GSPAGSPTSTEEG<br>SPAGSPTSTEEGT<br>SESATPESGPGTS<br>TEPSEGSAPGTSE<br>SATPESGPGSEPA<br>TSGSETPGTSESA<br>TPESGPGSEPATS<br>GSETPGTSESATP<br>ESGPGTSTEPSEG<br>SAPGSPAGSPTST<br>EEGTSESATPESG<br>PGSEPATSGSETP<br>GTSESATPESGPG<br>SPAGSPTSTEEGS<br>PAGSPTSTEEGTS<br>TEPSEGSAPGTSE<br>SATPESGPGTSES<br>ATPESGPGTSESA<br>TPESGPGSEPATS<br>GSETPGSEPATSG<br>SETPGSPAGSPTS<br>TEEGTSTEPSEGS<br>APGTSTEPSEGSA<br>PGSEPATSGSETP<br>GTSESATPESGPG<br>TSTEPSEGSAPGH<br>HHHHH | | ACGGAGGAAGGTACCTCTGAGTCGGCCACTCCTG<br>AGTCCGGTCCGGGCACGAGCACCGAGCCGAGCGA<br>GGGTTCAGCCCCGGGTACCAGCACGGAGCCGTCC<br>GAGGGTAGCGCACCGGGTTCTCCGGCGGGCTCCC<br>CTACGTCTACGGAAGAGGGTACGTCCACTGAACC<br>TAGCGAGGGCAGCGCGCCAGGCACCAGCACTGAA<br>CCGAGCGAAGGCAGCGCACCTGGCACTAGCGAGT<br>CTGCGACTCCGGAGAGCGGTCCGGGTACGAGCAC<br>GGAACCAAGCGAAGGCAGCGCCCCAGGTACCTCT<br>GAATCTGCTACCCCAGAATCTGGCCCGGGTTCCG<br>AGCCAGCTACCTCTGGTTCTGAAACCCCAGGTAC<br>TTCCACTGAACCAAGCGAAGGTAGCGCTCCTGGC<br>ACTTCTACTGAACCATCCGAAGGTTCCGCTCCTG<br>GTACGTCTGAAAGCGCTACCCCTGAAAGCGGCCC<br>AGGCACCTCTGAAAGCGCTACTCCTGAGAGCGGT<br>CCAGGCTCTCCAGCAGGTTCTCCAACCTCCACTG<br>AAGAAGGCACCTCTGAGTCTGCTACCCCTGAATC<br>TGGTCCTGGCTCCGAACCTGCTACCTCTGGTTCC<br>GAAACTCCAGGTACCTCGGAATCTGCGACTCCGG<br>AATCTGGCCCGGGCACGAGCACGGAGCCGTCTGA<br>GGGTAGCGCACCAGGTACCAGCACTGAGCCTTCT<br>GAGGGCTCTGCACCGGGTACCTCCACGGAACCTT<br>CGGAAGGTTCTGCGCCGGGTACCTCCACTGAGCC<br>ATCCGAGGGTTCAGCACCAGGTACTAGCACGGAA<br>CCGTCCGAGGGCTCTGCACCAGGTACGAGCACCG<br>AACCGTCGGAGGGTAGCGCTCCAGGTAGCCCAGC<br>GGGCTCTCCGACAAGCACCGAAGAAGGCACCAGC<br>ACCGAGCCGTCCGAAGGTTCCGCACCAGGTACAA<br>GCGAGAGCGCGACTCCTGAATCTGGTCCGGGTAG<br>CGAGCCTGCAACCAGCGGTTCTGAGACGCCGGGC<br>ACTTCCGAATCTGCGACCCCGGAGTCCGGTCCAG<br>GTTCAGAGCCGGCGACGAGCGGTTCGGAAACGCC<br>GGGTACGTCTGAATCAGCCACGCCGGAGTCTGGT<br>CCGGGTACCTCGACCGAACCAAGCGAAGGTTCGG<br>CACCGGGTACTAGCGAGAGCGCAACCCCTGAAAG<br>CGGTCCGGGCAGCCCGGCAGGTTCTCCAACCAGC<br>ACCGAAGAAGGTTCCCCTGCTGGTAGCCCGACCT<br>CTACGGAGGAAGGTAGCCCTGCAGGTTCCCCAAC<br>TTCTACTGAGGAAGGTACTTCTGAGTCCGCTACC<br>CCAGAAAGCGGTCCTGGTACCTCCACTGAACCGT<br>CTGAAGGCTCTGCACCAGGCACTTCTGAGTCTGC<br>TACTCCAGAAAGCGGCCCAGGTTCTGAACCAGCA<br>ACTTCTGGCTCTGAGACTCCAGGCACTTCTGAGT<br>CCGCAACGCCTGAATCCGGTCCTGGTTCTGAACC<br>AGCTACTTCCGGCAGCGAAACCCCAGGTACCTCT<br>GAGTCTGCGACTCCAGAGTCTGGTCCTGGTACTT<br>CCACTGAGCCTAGCGAGGGTTCCGCACCAGGTTC<br>TCCGGCTGGTAGCCCGACCAGCACGGAGGAGGGT<br>ACGTCTGAATCTGCAACGCCGGAATCGGGCCCAG<br>GTTCGGAGCCTGCAACGTCTGGCAGCGAAACCCC<br>GGGTACCTCCGAATCTGCTACACCGGAAAGCGGT<br>CCTGGCAGCCCTGCTGGTTCTCCAACCTCTACCG<br>AGGAGGGTTCACCGGCAGGTAGCCCGACTAGCAC<br>TGAAGAAGGTACTAGCACGGAGCCGAGCGAGGGT<br>AGTGCTCCGGGTACGAGCGAGAGCGCAACGCCAG<br>AGAGCGGTCCAGGCACCAGCGAATCGGCCACCCC<br>TGAGAGCGGCCCAGGTACTTCTGAGAGCGCCACT<br>CCTGAATCCGGCCCTGGTAGCGAGCCGGCAACCT<br>CCGGCTCAGAAACTCCTGGTTCGGAACCAGCGAC<br>CAGCGGTTCTGAAACTCCGGGTAGCCCGGCAGGC<br>AGCCCAACGAGCACCGAAGAGGGTACCAGCACGG<br>AACCGAGCGAGGGTTCTGCCCCGGGTACTTCCAC<br>CGAACCATCGGAGGGCTCTGCACCTGGTAGCGAA<br>CCTGCGACGTCTGGTTCTGAAACGCCGGGTACCA<br>GCGAAAGCGCTACCCCAGAATCCGGTCCGGGCAC<br>TAGCACCGAGCCATCGGAGGGCTCCGCACCAGGT<br>CACCATCATCACCATCAC | |
| TBP-8 | EVQLLESGGGLVQ<br>PGGSLKLSCAASG<br>FTFNTYAMNWVRQ<br>APGKGLEWVARIR<br>SKYNNYATYYADS<br>VKDRFTISRDDSK | 437 | GAGGTTCAGTTGTTGGAAAGCGGGGGCGGGCTTG<br>TCCAACCTGGAGGTTCATTAAAATTGAGCTGTGC<br>AGCCTCCGGATTCACCTTTAACACGTATGCAATG<br>AACTGGGTCCGTCAAGCGCCCGGTAAGGGGCTGG<br>AGTGGGTAGCTCGCATCCGCTCGAAGTATAATAA<br>TTACGCAACCTACTACGCAGACAGTGTCAAAGAT | 453 |

TABLE 7-continued

T-cell binding compositions

| Construct Name | Amino Acid Sequence | SEQ ID NO: | DNA Sequence | SEQ ID NO: |
|---|---|---|---|---|
| | NTAYLQMNNLKTE | | CGCTTCACTATCTCACGCGACGACAGTAAGAACA | |
| | DTAVYYCVRHGNF | | CGGCCTACTTACAGATGAACAATCTTAAAACGGA | |
| | GNSYVSWFAYWGQ | | GGACACCGCTGTCTACTACTGCGTGCGCCACGGG | |
| | GTLVTVSSGATPP | | AATTTCGGTAACTCTTATGTAAGTTGGTTCGCAT | |
| | ETGAETESPGETT | | ATTGGGGACAAGGTACGTTGGTAACCGTATCCAG | |
| | GGSAESEPPGEGE | | Cggtgcgaccccgccggaaaccggtgcggaaacc | |
| | LVVTQEPSLTVSP | | gaaagcccgggtgaaaccaccggtggcagcgcgg | |
| | GGTVTLTCRSSTG | | agagcgaaccgccgggtgaaggtGAACTGGTCGT | |
| | AVTTSNYANWVQQ | | CACGCAGGAGCCGTCCCTTACCGTTTCACCAGGT | |
| | KPGQAPRGLIGGT | | GGAACAGTGACTCTGACGTGTCGCTCCTCCACTG | |
| | NKRAPGTPARFSG | | GGGCGGTTACAACTTCCAATTATGCTAATTGGGT | |
| | SLLGGKAALTLSG | | CCAGCAGAAGCCGGGCCAAGCCCCTCGCGGGTTG | |
| | VQPEDEAEYYCAL | | ATTGGCGGCACCAACAAACGTGCTCCAGGGACAC | |
| | WYSNLWVFGGGTK | | CTGCCCGTTTTTCGGGCTCCTTATTGGGGGGCAA | |
| | LTVLGTAEAASAS | | AGCTGCACTGACGTTGTCTGGAGTTCAGCCGGAG | |
| | GLSGRSDNHVPLS | | GATGAGGCAGAGTATTACTGCGCATTGTGGTATT | |
| | LKMGPGSPAGSPT | | CTAATTTATGGGTTTTTGGAGGCGGCACAAAGCT | |
| | STEEGTSESATPE | | GACCGTCCTGGGCACCGCCGAAGCAGCTagcgcc | |
| | SGPGTSTEPSEGS | | tctGGCctgTCAggtCGTtctGATaacCATgttC | |
| | APGSPAGSPTSTE | | CActgTCTctgAAAatgGGTCCAGGTAGCCCAGC | |
| | EGTSTEPSEGSAP | | TGGTAGCCCAACCTCTACCGAAGAAGGTACCTCT | |
| | GTSTEPSEGSAPG | | GAATCCGCTACTCCAGAATCCGGTCCTGGTACTA | |
| | TSESATPESGPGS | | GCACTGAGCCAAGCGAAGGTTCTGCTCCAGGCTC | |
| | EPATSGSETPGSE | | CCCGGCAGGTAGCCCTACCTCTACCGAAGAGGGC | |
| | PATSGSETPGSPA | | ACTAGCACCGAACCATCTGAGGGTTCCGCTCCTG | |
| | GSPTSTEEGTSES | | GCACCTCCACTGAACCGTCCGAAGGCAGTGCTCC | |
| | ATPESGPGTSTEP | | GGGTACTTCCGAAAGCGCAACTCCGGAATCCGGC | |
| | SEGSAPGTSTEPS | | CCTGGTTCTGAGCCTGCTACTTCCGGCTCTGAAA | |
| | EGSAPGSPAGSPT | | CTCCAGGTAGCGAGCCAGCGACTTCTGGTTCTGA | |
| | STEEGTSTEPSEG | | AACTCCAGGTTCACCGGCGGGTAGCCCGACGAGC | |
| | SAPGTSTEPSEGS | | ACGGAGGAAGGTACCTCTGAGTCGGCCACTCCTG | |
| | APGTSESATPESG | | AGTCCGGTCCGGGCACGAGCACCGAGCCGAGCGA | |
| | PGTSTEPSEGSAP | | GGGTTCAGCCCCGGGTACCAGCACGGAGCCGTCC | |
| | GTSESATPESGPG | | GAGGGTAGCGCACCGGGTTCTCCGGCGGGCTCCC | |
| | SEPATSGSETPGT | | CTACGTCTACGGAAGAGGGTACGTCCACTGAACC | |
| | STEPSEGSAPGTS | | TAGCGAGGGCAGCGCGCCAGGCACCAGCACTGAA | |
| | TEPSEGSAPGTSE | | CCGAGCGAAGGCAGCGCACCTGGCACTAGCGAGT | |
| | SATPESGPGTSES | | CTGCGACTCCGGAGAGCGGTCCGGGTACGAGCAC | |
| | ATPESGPGSPAGS | | GGAACCAAGCGAAGGCAGCGCCCCAGGTACCTCT | |
| | PTSTEEGTSESAT | | GAATCTGCTACCCCAGAATCTGGCCCGGGTTCCG | |
| | PESGPGSEPATSG | | AGCCAGCTACCTCTGGTTCTGAAACCCCAGGTAC | |
| | SETPGTSESATPE | | TTCCACTGAACCAAGCGAAGGTAGCGCTCCTGGC | |
| | SGPGTSTEPSEGS | | ACTTCTACTGAACCATCCGAAGGTTCCGCTCCTG | |
| | APGTSTEPSEGSA | | GTACGTCTGAAAGCGCTACCCCTGAAAGCGGCCC | |
| | PGTSTEPSEGSAP | | AGGCACCTCTGAAAGCGCTACTCCTGAGAGCGGT | |
| | GTSTEPSEGSAPG | | CCAGGCTCTCCAGCAGGTTCTCCAACCTCCACTG | |
| | TSTEPSEGSAPGT | | AAGAAGGCACCTCTGAGTCTGCTACCCCTGAATC | |
| | STEPSEGSAPGSP | | TGGTCCTGGCTCCGAACCTGCTACCTCTGGTTCC | |
| | AGSPTSTEEGTST | | GAAACTCCAGGTACCTCGGAATCTGCGACTCCGG | |
| | EPSEGSAPGTSES | | AATCTGGCCCGGGCACGAGCACGGAGCCGTCTGA | |
| | ATPESGPGSEPAT | | GGGTAGCGCACCAGGTACCAGCACTGAGCCTTCT | |
| | SGSETPGTSESAT | | GAGGGCTCTGCACCGGGTACCTCCACGGAACCTT | |
| | PESGPGSEPATSG | | CGGAAGGTTCTGCGCCGGGTACCTCCACTGAGCC | |
| | SETPGTSESATPE | | ATCCGAGGGTTCAGCACCAGGTACTAGCACGGAA | |
| | SGPGTSTEPSEGS | | CCGTCCGAGGGCTCTGCACCAGGTACGAGCACCG | |
| | APGTSESATPESG | | AACCGTCGGAGGGTAGCGCTCCAGGTAGCCCAGC | |
| | PGSPAGSPTSTEE | | GGGCTCTCCGACAAGCACCGAAGAAGGCACCAGC | |
| | GSPAGSPTSTEEG | | ACCGAGCCGTCCGAAGGTTCCGCACCAGGTACAA | |
| | SPAGSPTSTEEGT | | GCGAGAGCGCGACTCCTGAATCTGGTCCGGGTAG | |
| | SESATPESGPGTS | | CGAGCCTGCAACCAGCGGTTCTGAGACGCCGGGC | |
| | TEPSEGSAPGTSE | | ACTTCCGAATCTGCGACCCCGGAGTCCGGTCCAG | |
| | SATPESGPGSEPA | | GTTCAGAGCCGGCGACGAGCGGTTCGGAAACGCC | |
| | TSGSETPGTSESA | | GGGTACGTCTGAATCAGCCACGCCGGAGTCTGGT | |
| | TPESGPGSEPATS | | CCGGGTACCTCGACCGAACCAAGCGAAGGTTCGG | |
| | GSETPGTSESATP | | CACCGGGTACTAGCGAGAGCGCAACCCCTGAAAG | |
| | ESGPGTSTEPSEG | | CGGTCCGGGCAGCCCGGCAGGTTCTCCAACCAGC | |
| | SAPGSPAGSPTST | | ACCGAAGAAGGTTCCCCTGCTGGTAGCCCGACCT | |
| | EEGTSESATPESG | | CTACGGAGGAAGGTAGCCCTGCAGGTTCCCCAAC | |
| | PGSEPATSGSETP | | TTCTACTGAGGAAGGTACTTCTGAGTCCGCTACC | |
| | GTSESATPESGPG | | CCAGAAAGCGGTCCTGGTACCTCCACTGAACCGT | |
| | SPAGSPTSTEEGS | | CTGAAGGCTCTGCACCAGGCACTTCTGAGTCTGC | |
| | PAGSPTSTEEGTS | | TACTCCAGAAAGCGGCCCAGGTTCTGAACCAGCA | |
| | TEPSEGSAPGTSE | | ACTTCTGGCTCTGAGACTCCAGGCACTTCTGAGT | |
| | SATPESGPGTSES | | CCGCAACGCCTGAATCCGGTCCTGGTTCTGAACC | |

TABLE 7-continued

T-cell binding compositions

| Construct Name | Amino Acid Sequence | SEQ ID NO: | DNA Sequence | SEQ ID NO: |
|---|---|---|---|---|
| | ATPESGPGTSESA | | AGCTACTTCCGGCAGCGAAACCCCAGGTACCTCT | |
| | TPESGPGSEPATS | | GAGTCTGCGACTCCAGAGTCTGGTCCTGGTACTT | |
| | GSETPGSEPATSG | | CCACTGAGCCTAGCGAGGGTTCCGCACCAGGTTC | |
| | SETPGSPAGSPTS | | TCCGGCTGGTAGCCCGACCAGCACGGAGGAGGGT | |
| | TEEGTSTEPSEGS | | ACGTCTGAATCTGCAACGCCGGAATCGGGCCCAG | |
| | APGTSTEPSEGSA | | GTTCGGAGCCTGCAACGTCTGGCAGCGAAACCCC | |
| | PGSEPATSGSETP | | GGGTACCTCCGAATCTGCTACACCGGAAAGCGGT | |
| | GTSESATPESGPG | | CCTGGCAGCCCTGCTGGTTCTCCAACCTCTACCG | |
| | TSTEPSEGSAPGH | | AGGAGGGTTCACCGGCAGGTAGCCCGACTAGCAC | |
| | HHHHH | | TGAAGAAGGTACTAGCACGGAGCCGAGCGAGGGT | |
| | | | AGTGCTCCGGGTACGAGCGAGAGCGCAACGCCAG | |
| | | | AGAGCGGTCCAGGCACCAGCGAATCGGCCACCCC | |
| | | | TGAGAGCGGCCCAGGTACTTCTGAGAGCGCCACT | |
| | | | CCTGAATCCGGCCCTGGTAGCGAGCCGGCAACCT | |
| | | | CCGGCTCAGAAACTCCTGGTTCGGAACCAGCGAC | |
| | | | CAGCGGTTCTGAAACTCCGGGTAGCCCGGCAGGC | |
| | | | AGCCCAACGAGCACCGAAGAGGGTACCAGCACGG | |
| | | | AACCGAGCGAGGGTTCTGCCCCGGGTACTTCCAC | |
| | | | CGAACCATCGGAGGGCTCTGCACCTGGTAGCGAA | |
| | | | CCTGCGACGTCTGGTTCTGAAACGCCGGGTACCA | |
| | | | GCGAAAGCGCTACCCCAGAATCCGGTCCGGGCAC | |
| | | | TAGCACCGAGCCATCGGAGGGCTCCGCACCAGGT | |
| | | | CACCATCATCACCATCAC | |
| TBP-9 | HHHHHHGGSPAGS | 438 | CATCACCACCATCATCACggAGGTAGCCCAGCTG | 454 |
| | PTSTEEGTSESAT | | GTAGCCCAACCTCTACCGAAGAAGGTACCTCTGA | |
| | PESGPGTSTEPSE | | ATCCGCTACTCCAGAATCCGGTCCTGGTACTAGC | |
| | GSAPGSPAGSPTS | | ACTGAGCCAAGCGAAGGTTCTGCTCCAGGCTCCC | |
| | TEEGTSTEPSEGS | | CGGCAGGTAGCCCTACCTCTACCGAAGAGGGCAC | |
| | APGTSTEPSEGSA | | TAGCACCGAACCATCTGAGGGTTCCGCTCCTGGC | |
| | PGTSESATPESGP | | ACCTCCACTGAACCGTCCGAAGGCAGTGCTCCGG | |
| | GSEPATSGSETPG | | GTACTTCCGAAAGCGCAACTCCGGAATCCGGCCC | |
| | SEPATSGSETPGS | | TGGTTCTGAGCCTGCTACTTCCGGCTCTGAAACT | |
| | PAGSPTSTEEGTS | | CCAGGTAGCGAGCCAGCGACTTCTGGTTCTGAAA | |
| | ESATPESGPGTST | | CTCCAGGTTCACCGGCGGGTAGCCCGACGAGCAC | |
| | EPSEGSAPGTSTE | | GGAGGAAGGTACCTCTGAGTCGGCCACTCCTGAG | |
| | PSEGSAPGSPAGS | | TCCGGTCCGGGCACGAGCACCGAGCCGAGCGAGG | |
| | PTSTEEGTSTEPS | | GTTCAGCCCCGGGTACCAGCACGGAGCCGTCCGA | |
| | EGSAPGTSTEPSE | | GGGTAGCGCACCGGGTTCTCCGGCGGGCTCCCCT | |
| | GSAPGTSESATPE | | ACGTCTACGGAAGAGGGTACGTCCACTGAACCTA | |
| | SGPGTSTEPSEGS | | GCGAGGGCAGCGCGCCAGGCACCAGCACTGAACC | |
| | APGTSESATPESG | | GAGCGAAGGCAGCGCACCTGGCACTAGCGAGTCT | |
| | PGSEPATSGSETP | | GCGACTCCGGAGAGCGGTCCGGGTACGAGCACGG | |
| | GTSTEPSEGSAPG | | AACCAAGCGAAGGCAGCGCCCCAGGTACCTCTGA | |
| | TSTEPSEGSAPGT | | ATCTGCTACCCCAGAATCTGGCCCGGGTTCCGAG | |
| | SESATPESGPGTS | | CCAGCTACCTCTGGTTCTGAAACCCCAGGTACTT | |
| | ESATPESGPGSPA | | CCACTGAACCAAGCGAAGGTAGCGCTCCTGGCAC | |
| | GSPTSTEEGTSES | | TTCTACTGAACCATCCGAAGGTTCCGCTCCTGGT | |
| | ATPESGPGSEPAT | | ACGTCTGAAAGCGCTACCCCTGAAAGCGGCCCAG | |
| | SGSETPGTSESAT | | GCACCTCTGAAAGCGCTACTCCTGAGAGCGGTCC | |
| | PESGPGTSTEPSE | | AGGCTCTCCAGCAGGTTCTCCAACCTCCACTGAA | |
| | GSAPGTSTEPSEG | | GAAGGCACCTCTGAGTCTGCTACCCCTGAATCTG | |
| | SAPGTSTEPSEGS | | GTCCTGGCTCCGAACCTGCTACCTCTGGTTCCGA | |
| | APGTSTEPSEGSA | | AACTCCAGGTACCTCGGAATCTGCGACTCCGGAA | |
| | PGTSTEPSEGSAP | | TCTGGCCCGGGCACGAGCACGGAGCCGTCTGAGG | |
| | GTSTEPSEGSAPG | | GTAGCGCACCAGGTACCAGCACTGAGCCTTCTGA | |
| | SPAGSPTSTEEGT | | GGGCTCTGCACCGGGTACCTCCACGGAACCTTCG | |
| | STEPSEGSAPGTS | | GAAGGTTCTGCGCCGGGTACCTCCACTGAGCCAT | |
| | ESATPESGPGSEP | | CCGAGGGTTCAGCACCAGGTACTAGCACGGAACC | |
| | ATSGSETPGTSES | | GTCCGAGGGCTCTGCACCAGGTACGAGCACCGAA | |
| | ATPESGPGSEPAT | | CCGTCGGAGGGTAGCGCTCCAGGTAGCCCAGCGG | |
| | SGSETPGTSESAT | | GCTCTCCGACAAGCACCGAAGAAGGCACCAGCAC | |
| | PESGPGTSTEPSE | | CGAGCCGTCCGAAGGTTCCGCACCAGGTACAAGC | |
| | GSAPGTSESATPE | | GAGAGCGCGACTCCTGAATCTGGTCCGGGTAGCG | |
| | SGPGSPAGSPTST | | AGCCTGCAACCAGCGGTTCTGAGACGCCGGGCAC | |
| | EEGSPAGSPTSTE | | TTCCGAATCTGCGACCCCGGAGTCCGGTCCAGGT | |
| | EGSPAGSPTSTEE | | TCAGAGCCGGCGACGAGCGGTTCGGAAACGCCGG | |
| | GTSESATPESGPG | | GTACGTCTGAATCAGCCACGCCGGAGTCTGGTCC | |
| | TSTEPSEGSAPGT | | GGGTACCTCGACCGAACCAAGCGAAGGTTCGGCA | |
| | SESATPESGPGSE | | CCGGGTACTAGCGAGAGCGCAACCCCTGAAAGCG | |
| | PATSGSETPGTSE | | GTCCGGGCAGCCCGGCAGGTTCTCCAACCAGCAC | |
| | SATPESGPGSEPA | | CGAAGAAGGTTCCCCTGCTGGTAGCCCGACCTCT | |
| | TSGSETPGTSESA | | ACGGAGGAAGGTAGCCCTGCAGGTTCCCCAACTT | |
| | TPESGPGTSTEPS | | CTACTGAGGAAGGTACTTCTGAGTCCGCTACCCC | |

TABLE 7-continued

T-cell binding compositions

| Construct Name | Amino Acid Sequence | SEQ ID NO: | DNA Sequence | SEQ ID NO: |
|---|---|---|---|---|
| | EGSAPGSPAGSPT | | AGAAAGCGGTCCTGGTACCTCCACTGAACCGTCT | |
| | STEEGTSESATPE | | GAAGGCTCTGCACCAGGCACTTCTGAGTCTGCTA | |
| | SGPGSEPATSGSE | | CTCCAGAAAGCGGCCCAGGTTCTGAACCAGCAAC | |
| | TPGTSESATPESG | | TTCTGGCTCTGAGACTCCAGGCACTTCTGAGTCC | |
| | PGSPAGSPTSTEE | | GCAACGCCTGAATCCGGTCCTGGTTCTGAACCAG | |
| | GSPAGSPTSTEEG | | CTACTTCCGGCAGCGAAACCCCAGGTACCTCTGA | |
| | TSTEPSEGSAPGT | | GTCTGCGACTCCAGAGTCTGGTCCTGGTACTTCC | |
| | SESATPESGPGTS | | ACTGAGCCTAGCGAGGGTTCCGCACCAGGTTCTC | |
| | ESATPESGPGTSE | | CGGCTGGTAGCCCGACCAGCACGGAGGAGGGTAC | |
| | SATPESGPGSEPA | | GTCTGAATCTGCAACGCCGGAATCGGGCCCAGGT | |
| | TSGSETPGSEPAT | | TCGGAGCCTGCAACGTCTGGCAGCGAAACCCCGG | |
| | SGSETPGSPAGSP | | GTACCTCCGAATCTGCTACACCGGAAAGCGGTCC | |
| | TSTEEGTSTEPSE | | TGGCAGCCCTGCTGGTTCTCCAACCTCTACCGAG | |
| | GSAPGTSTEPSEG | | GAGGGTTCACCGGCAGGTAGCCCGACTAGCACTG | |
| | SAPGSEPATSGSE | | AAGAAGGTACTAGCACGGAGCCGAGCGAGGGTAG | |
| | TPGTSESATPESG | | TGCTCCGGGTACGAGCGAGAGCGCAACGCCAGAG | |
| | PGTSTEPSEGSAP | | AGCGGTCCAGGCACCAGCGAATCGGCCACCCCTG | |
| | LSGRSDNHSPLGL | | AGAGCGGCCCAGGTACTTCTGAGAGCGCCACTCC | |
| | AGSGTAEAASASG | | TGAATCCGGCCCTGGTAGCGAGCCGGCAACCTCC | |
| | DIQMTQSPSSLSA | | GGCTCAGAAACTCCTGGTTCGGAACCAGCGACCA | |
| | SVGDRVTITCRAS | | GCGGTTCTGAAACTCCGGGTAGCCCGGCAGGCAG | |
| | QDIRNYLNWYQQK | | CCCAACGAGCACCGAAGAGGGTACCAGCACGGAA | |
| | PGKAPKLLIYYTS | | CCGAGCGAGGGTTCTGCCCCGGGTACTTCCACCG | |
| | RLESGVPSRFSGS | | AACCATCGGAGGGCTCTGCACCTGGTAGCGAACC | |
| | GSGTDYTLTISSL | | TGCGACGTCTGGTTCTGAAACGCCGGGTACCAGC | |
| | QPEDFATYYCQQG | | GAAAGCGCTACCCCAGAATCCGGTCCGGGCACTA | |
| | NTLPWTFGQGTKV | | GCACCGAGCCATCGGAGGGCTCCGCACCActgTC | |
| | EIKGATPPETGAE | | AggtCGTtctGATaacCATtccCCActgGGTctg | |
| | TESPGETTGGSAE | | GCTGGGTCTGGCACCGCCGAAGCAGCTagcgcct | |
| | SEPPGEGEVQLVE | | ctGGCGACATCCAAATGACCCAATCACCGTCATC | |
| | SGGGLVQPGGSLR | | CCTGAGCGCCTCTGTTGGAGATCGTGTAACAATT | |
| | LSCAASGYSFTGY | | ACCTGCCGCGCCTCCCAAGACATCCGCAATTACT | |
| | TMNWVRQAPGKGL | | TAAACTGGTATCAGCAAAAACCCGGTAAGGCACC | |
| | EWVALINPYKGVS | | GAAATTGCTGATTTATTATACTTCACGCTTAGAG | |
| | TYNQKFKDRFTIS | | AGTGGGGTGCCGTCGCGCTTCAGTGGCTCGGGTA | |
| | VDKSKNTAYLQMN | | GTGGGACCGATTACACATTGACAATTTCATCACT | |
| | SLRAEDTAVYYCA | | GCAGCCAGAGGATTTTGCGACTTATTACTGTCAA | |
| | RSGYYGDSDWYFD | | CAGGGTAACACGCTTCCCTGGACCTTCGGGCAAG | |
| | VWGQGTLVTVSS | | GCACGAAAGTTGAGATCAAGGGCGCTACTCCCCC | |
| | | | TGAGACAGGAGCGGAAACGGAATCCCCTGGCGAG | |
| | | | ACGACGGGTGGTTCCGCAGAGTCGGAACCTCCTG | |
| | | | GTGAGGGCGAGGTGCAGCTGGTTGAAAGCGGTGG | |
| | | | CGGTCTGGTGCAACCAGGCGGTAGCCTGCGTCTG | |
| | | | AGCTGCGCGGCGAGCGGTTACAGCTTTACCGGTT | |
| | | | ATACCATGAACTGGGTTCGTCAAGCGCCAGGTAA | |
| | | | AGGTCTGGAGTGGGTGGCGCTGATCAACCCGTAC | |
| | | | AAGGGTGTTAGCACCTATAACCAGAAGTTCAAAG | |
| | | | ACCGTTTTACCATTAGCGTGGATAAGAGCAAAAA | |
| | | | CACCGCGTACCTGCAAATGAACAGCCTGCGTGCG | |
| | | | GAGGACACCGCTGTGTACTATTGCGCGCGTAGCG | |
| | | | GTTACTATGGCGACAGCGACTGGTATTTTGATGT | |
| | | | GTGGGGCCAAGGCACCCTGGTTACCGTGAGCTCC | |
| TBP-10 | HHHHHHGGSPAGS | 439 | CATCACCACCATCATCACggAGGTAGCCCAGCTG | 455 |
| | PTSTEEGTSESAT | | GTAGCCCAACCTCTACCGAAGAAGGTACCTCTGA | |
| | PESGPGTSTEPSE | | ATCCGCTACTCCAGAATCCGGTCCTGGTACTAGC | |
| | GSAPGSPAGSPTS | | ACTGAGCCAAGCGAAGGTTCTGCTCCAGGCTCCC | |
| | TEEGTSTEPSEGS | | CGGCAGGTAGCCCTACCTCTACCGAAGAGGGCAC | |
| | APGTSTEPSEGSA | | TAGCACCGAACCATCTGAGGGTTCCGCTCCTGGC | |
| | PGTSESATPESGP | | ACCTCCACTGAACCGTCCGAAGGCAGTGCTCCGG | |
| | GSEPATSGSETPG | | GTACTTCCGAAAGCGCAACTCCGGAATCCGGCCC | |
| | SEPATSGSETPGS | | TGGTTCTGAGCCTGCTACTTCCGGCTCTGAAACT | |
| | PAGSPTSTEEGTS | | CCAGGTAGCGAGCCAGCGACTTCTGGTTCTGAAA | |
| | ESATPESGPGTST | | CTCCAGGTTCACCGGCGGGTAGCCCGACGAGCAC | |
| | EPSEGSAPGTSTE | | GGAGGAAGGTACCTCTGAGTCGGCCACTCCTGAG | |
| | PSEGSAPGSPAGS | | TCCGGTCCGGGCACGAGCACCGAGCCGAGCGAGG | |
| | PTSTEEGTSTEPS | | GTTCAGCCCCGGGTACCAGCACGGAGCCGTCCGA | |
| | EGSAPGTSTEPSE | | GGGTAGCGCACCGGGTTCTCCGGCGGGCTCCCCT | |
| | GSAPGTSESATPE | | ACGTCTACGGAAGAGGGTACGTCCACTGAACCTA | |
| | SGPGTSTEPSEGS | | GCGAGGGCAGCGCGCCAGGCACCAGCACTGAACC | |
| | APGTSESATPESG | | GAGCGAAGGCAGCGCACCTGGCACTAGCGAGTCT | |
| | PGSEPATSGSETP | | GCGACTCCGGAGAGCGGTCCGGGTACGAGCACGG | |
| | GTSTEPSEGSAPG | | AACCAAGCGAAGGCAGCGCCCCAGGTACCTCTGA | |
| | TSTEPSEGSAPGT | | ATCTGCTACCCCAGAATCTGGCCCGGGTTCCGAG | |

TABLE 7-continued

T-cell binding compositions

| Construct Name | Amino Acid Sequence | SEQ ID NO: | DNA Sequence | SEQ ID NO: |
|---|---|---|---|---|
| | SESATPESGPGTS | | CCAGCTACCTCTGGTTCTGAAACCCCAGGTACTT | |
| | ESATPESGPGSPA | | CCACTGAACCAAGCGAAGGTAGCGCTCCTGGCAC | |
| | GSPTSTEEGTSES | | TTCTACTGAACCATCCGAAGGTTCCGCTCCTGGT | |
| | ATPESGPGSEPAT | | ACGTCTGAAAGCGCTACCCCTGAAAGCGGCCCAG | |
| | SGSETPGTSESAT | | GCACCTCTGAAAGCGCTACTCCTGAGAGCGGTCC | |
| | PESGPGTSTEPSE | | AGGCTCTCCAGCAGGTTCTCCAACCTCCACTGAA | |
| | GSAPGTSTEPSEG | | GAAGGCACCTCTGAGTCTGCTACCCCTGAATCTG | |
| | SAPGTSTEPSEGS | | GTCCTGGCTCCGAACCTGCTACCTCTGGTTCCGA | |
| | APGTSTEPSEGSA | | AACTCCAGGTACCTCGGAATCTGCGACTCCGGAA | |
| | PGTSTEPSEGSAP | | TCTGGCCCGGGCACGAGCACGGAGCCGTCTGAGG | |
| | GTSTEPSEGSAPG | | GTAGCGCACCAGGTACCAGCACTGAGCCTTCTGA | |
| | SPAGSPTSTEEGT | | GGGCTCTGCACCGGGTACCTCCACGGAACCTTCG | |
| | STEPSEGSAPGTS | | GAAGGTTCTGCGCCGGGTACCTCCACTGAGCCAT | |
| | ESATPESGPGSEP | | CCGAGGGTTCAGCACCAGGTACTAGCACGGAACC | |
| | ATSGSETPGTSES | | GTCCGAGGGCTCTGCACCAGGTACGAGCACCGAA | |
| | ATPESGPGSEPAT | | CCGTCGGAGGGTAGCGCTCCAGGTAGCCCAGCGG | |
| | SGSETPGTSESAT | | GCTCTCCGACAAGCACCGAAGAAGGCACCAGCAC | |
| | PESGPGTSTEPSE | | CGAGCCGTCCGAAGGTTCCGCACCAGGTACAAGC | |
| | GSAPGTSESATPE | | GAGAGCGCGACTCCTGAATCTGGTCCGGGTAGCG | |
| | SGPGSPAGSPTST | | AGCCTGCAACCAGCGGTTCTGAGACGCCGGGCAC | |
| | EEGSPAGSPTSTE | | TTCCGAATCTGCGACCCCGGAGTCCGGTCCAGGT | |
| | EGSPAGSPTSTEE | | TCAGAGCCGGCGACGAGCGGTTCGGAAACGCCGG | |
| | GTSESATPESGPG | | GTACGTCTGAATCAGCCACGCCGGAGTCTGGTCC | |
| | TSTEPSEGSAPGT | | GGGTACCTCGACCGAACCAAGCGAAGGTTCGGCA | |
| | SESATPESGPGSE | | CCGGGTACTAGCGAGAGCGCAACCCCTGAAAGCG | |
| | PATSGSETPGTSE | | GTCCGGGCAGCCCGGCAGGTTCTCCAACCAGCAC | |
| | SATPESGPGSEPA | | CGAAGAAGGTTCCCCTGCTGGTAGCCCGACCTCT | |
| | TSGSETPGTSESA | | ACGGAGGAAGGTAGCCCTGCAGGTTCCCCAACTT | |
| | TPESGPGTSTEPS | | CTACTGAGGAAGGTACTTCTGAGTCCGCTACCCC | |
| | EGSAPGSPAGSPT | | AGAAAGCGGTCCTGGTACCTCCACTGAACCGTCT | |
| | STEEGTSESATPE | | GAAGGCTCTGCACCAGGCACTTCTGAGTCTGCTA | |
| | SGPGSEPATSGSE | | CTCCAGAAAGCGGCCCAGGTTCTGAACCAGCAAC | |
| | TPGTSESATPESG | | TTCTGGCTCTGAGACTCCAGGCACTTCTGAGTCC | |
| | PGSPAGSPTSTEE | | GCAACGCCTGAATCCGGTCCTGGTTCTGAACCAG | |
| | GSPAGSPTSTEEG | | CTACTTCCGGCAGCGAAACCCCAGGTACCTCTGA | |
| | TSTEPSEGSAPGT | | GTCTGCGACTCCAGAGTCTGGTCCTGGTACTTCC | |
| | SESATPESGPGTS | | ACTGAGCCTAGCGAGGGTTCCGCACCAGGTTCTC | |
| | ESATPESGPGTSE | | CGGCTGGTAGCCCGACCAGCACGGAGGAGGGTAC | |
| | SATPESGPGSEPA | | GTCTGAATCTGCAACGCCGGAATCGGGCCCAGGT | |
| | TSGSETPGSEPAT | | TCGGAGCCTGCAACGTCTGGCAGCGAAACCCCGG | |
| | SGSETPGSPAGSP | | GTACCTCCGAATCTGCTACACCGGAAAGCGGTCC | |
| | TSTEEGTSTEPSE | | TGGCAGCCCTGCTGGTTCTCCAACCTCTACCGAG | |
| | GSAPGTSTEPSEG | | GAGGGTTCACCGGCAGGTAGCCCGACTAGCACTG | |
| | SAPGSEPATSGSE | | AAGAAGGTACTAGCACGGAGCCGAGCGAGGGTAG | |
| | TPGTSESATPESG | | TGCTCCGGGTACGAGCGAGAGCGCAACGCCAGAG | |
| | PGTSTEPSEGSAP | | AGCGGTCCAGGCACCAGCGAATCGGCCACCCCTG | |
| | LSGRSDNHVPLSL | | AGAGCGGCCCAGGTACTTCTGAGAGCGCCACTCC | |
| | KMGGTAEAASASG | | TGAATCCGGCCCTGGTAGCGAGCCGGCAACCTCC | |
| | DIQMTQSPSSLSA | | GGCTCAGAAACTCCTGGTTCGGAACCAGCGACCA | |
| | SVGDRVTITCRAS | | GCGGTTCTGAAACTCCGGGTAGCCCGGCAGGCAG | |
| | QDIRNYLNWYQQK | | CCCAACGAGCACCGAAGAGGGTACCAGCACGGAA | |
| | PGKAPKLLIYYTS | | CCGAGCGAGGGTTCTGCCCCGGGTACTTCCACCG | |
| | RLESGVPSRFSGS | | AACCATCGGAGGGCTCTGCACCTGGTAGCGAACC | |
| | GSGTDYTLTISSL | | TGCGACGTCTGGTTCTGAAACGCCGGGTACCAGC | |
| | QPEDFATYYCQQG | | GAAAGCGCTACCCCAGAATCCGGTCCGGGCACTA | |
| | NTLPWTFGQGTKV | | GCACCGAGCCATCGGAGGGCTCCGCACCActgTC | |
| | EIKGATPPETGAE | | AggtCGTtctGATaacCATgttCCActgTCTctg | |
| | TESPGETTGGSAE | | AAAatgGGTGGCACCGCCGAAGCAGCTagcgcct | |
| | SEPPGEGEVOLVE | | ctGGCGACATCCAAATGACCCAATCACCGTCATC | |
| | SGGGLVQPGGSLR | | CCTGAGCGCCTCTGTTGGAGATCGTGTAACAATT | |
| | LSCAASGYSFTGY | | ACCTGCCGCGCCTCCCAAGACATCCGCAATTACT | |
| | TMNWVRQAPGKGL | | TAAACTGGTATCAGCAAAAACCCGGTAAGGCACC | |
| | EWVALINPYKGVS | | GAAATTGCTGATTTATTATACTTCACGCTTAGAG | |
| | TYNQKFKDRFTIS | | AGTGGGGTGCCGTCGCGCTTCAGTGGCTCGGGTA | |
| | VDKSKNTAYLQMN | | GTGGGACCGATTACACATTGACAATTTCATCACT | |
| | SLRAEDTAVYYCA | | GCAGCCAGAGGATTTTGCGACTTATTACTGTCAA | |
| | RSGYYGDSDWYFD | | CAGGGTAACACGCTTCCCTGGACCTTCGGGCAAG | |
| | VWGQGTLVTVSS | | GCACGAAAGTTGAGATCAAGGGCGCTACTCCCCC | |
| | | | TGAGACAGGAGCGGAAACGGAATCCCCTGGCGAG | |
| | | | ACGACGGGTGGTTCCGCAGAGTCGGAACCTCCTG | |
| | | | GTGAGGGCGAGGTGCAGCTGGTTGAAAGCGGTGG | |
| | | | CGGTCTGGTGCAACCAGGCGGTAGCCTGCGTCTG | |
| | | | AGCTGCGCGGCGAGCGGTTACAGCTTTACCGGTT | |
| | | | ATACCATGAACTGGGTTCGTCAAGCGCCAGGTAA | |

TABLE 7-continued

| T-cell binding compositions | | | | |
|---|---|---|---|---|
| Construct Name | Amino Acid Sequence | SEQ ID NO: | DNA Sequence | SEQ ID NO: |
| | | | AGGTCTGGAGTGGGTGGCGCTGATCAACCCGTAC<br>AAGGGTGTTAGCACCTATAACCAGAAGTTCAAAG<br>ACCGTTTTACCATTAGCGTGGATAAGAGCAAAAA<br>CACCGCGTACCTGCAAATGAACAGCCTGCGTGCG<br>GAGGACACCGCTGTGTACTATTGCGCGCGTAGCG<br>GTTACTATGGCGACAGCGACTGGTATTTTGATGT<br>GTGGGGCCAAGGCACCCTGGTTACCGTGAGCTCC | |
| TBP-11 | HHHHHHGGSPAGS<br>PTSTEEGTSESAT<br>PESGPGTSTEPSE<br>GSAPGSPAGSPTS<br>TEEGTSTEPSEGS<br>APGTSTEPSEGSA<br>PGTSESATPESGP<br>GSEPATSGSETPG<br>SEPATSGSETPGS<br>PAGSPTSTEEGTS<br>ESATPESGPGTST<br>EPSEGSAPGTSTE<br>PSEGSAPGSPAGS<br>PTSTEEGTSTEPS<br>EGSAPGTSTEPSE<br>GSAPGTSESATPE<br>SGPGTSTEPSEGS<br>APGTSESATPESG<br>PGSEPATSGSETP<br>GTSTEPSEGSAPG<br>TSTEPSEGSAPGT<br>SESATPESGPGTS<br>ESATPESGPGSPA<br>GSPTSTEEGTSES<br>ATPESGPGSEPAT<br>SGSETPGTSESAT<br>PESGPGTSTEPSE<br>GSAPGTSTEPSEG<br>SAPGTSTEPSEGS<br>APGTSTEPSEGSA<br>PGTSTEPSEGSAP<br>GTSTEPSEGSAPG<br>SPAGSPTSTEEGT<br>STEPSEGSAPGTS<br>ESATPESGPGSEP<br>ATSGSETPGTSES<br>ATPESGPGSEPAT<br>SGSETPGTSESAT<br>PESGPGTSTEPSE<br>GSAPGTSESATPE<br>SGPGSPAGSPTST<br>EEGSPAGSPTSTE<br>EGSPAGSPTSTEE<br>GTSESATPESGPG<br>TSTEPSEGSAPGT<br>SESATPESGPGSE<br>PATSGSETPGTSE<br>SATPESGPGSEPA<br>TSGSETPGTSESA<br>TPESGPGTSTEPS<br>EGSAPGSPAGSPT<br>STEEGTSESATPE<br>SGPGSEPATSGSE<br>TPGTSESATPESG<br>PGSPAGSPTSTEE<br>GSPAGSPTSTEEG<br>TSTEPSEGSAPGT<br>SESATPESGPGTS<br>ESATPESGPGTSE<br>SATPESGPGSEPA<br>TSGSETPGSEPAT<br>SGSETPGSPAGSP<br>TSTEEGTSTEPSE<br>GSAPGTSTEPSEG<br>SAPGSEPATSGSE<br>TPGTSESATPESG | 440 | CATCACCACCATCATCACggAGGTAGCCCAGCTG<br>GTAGCCCAACCTCTACCGAAGAAGGTACCTCTGA<br>ATCCGCTACTCCAGAATCCGGTCCTGGTACTAGC<br>ACTGAGCCAAGCGAAGGTTCTGCTCCAGGCTCCC<br>CGGCAGGTAGCCCTACCTCTACCGAAGAGGGCAC<br>TAGCACCGAACCATCTGAGGGTTCCGCTCCTGGC<br>ACCTCCACTGAACCGTCCGAAGGCAGTGCTCCGG<br>GTACTTCCGAAAGCGCAACTCCGGAATCCGGCCC<br>TGGTTCTGAGCCTGCTACTTCCGGCTCTGAAACT<br>CCAGGTAGCGAGCCAGCGACTTCTGGTTCTGAAA<br>CTCCAGGTTCACCGGCGGGTAGCCCGACGAGCAC<br>GGAGGAAGGTACCTCTGAGTCGGCCACTCCTGAG<br>TCCGGTCCGGGCACGAGCACCGAGCCGAGCGAGG<br>GTTCAGCCCCGGGTACCAGCACGGAGCCGTCCGA<br>GGGTAGCGCACCGGGTTCTCCGGCGGGCTCCCCT<br>ACGTCTACGGAAGAGGGTACGTCCACTGAACCTA<br>GCGAGGGCAGCGCGCCAGGCACCAGCACTGAACC<br>GAGCGAAGGCAGCGCACCTGGCACTAGCGAGTCT<br>GCGACTCCGGAGAGCGGTCCGGGTACGAGCACGG<br>AACCAAGCGAAGGCAGCGCCCCAGGTACCTCTGA<br>ATCTGCTACCCCAGAATCTGGCCCGGGTTCCGAG<br>CCAGCTACCTCTGGTTCTGAAACCCCAGGTACTT<br>CCACTGAACCAAGCGAAGGTAGCGCTCCTGGCAC<br>TTCTACTGAACCATCCGAAGGTTCCGCTCCTGGT<br>ACGTCTGAAAGCGCTACCCCTGAAAGCGGCCCAG<br>GCACCTCTGAAAGCGCTACTCCTGAGAGCGGTCC<br>AGGCTCTCCAGCAGGTTCTCCAACCTCCACTGAA<br>GAAGGCACCTCTGAGTCTGCTACCCCTGAATCTG<br>GTCCTGGCTCCGAACCTGCTACCTCTGGTTCCGA<br>AACTCCAGGTACCTCGGAATCTGCGACTCCGGAA<br>TCTGGCCCGGGCACGAGCACGGAGCCGTCTGAGG<br>GTAGCGCACCAGGTACCAGCACTGAGCCTTCTGA<br>GGGCTCTGCACCGGGTACCTCCACGGAACCTTCG<br>GAAGGTTCTGCGCCGGGTACCTCCACTGAGCCAT<br>CCGAGGGTTCAGCACCAGGTACTAGCACGGAACC<br>GTCCGAGGGCTCTGCACCAGGTACGAGCACCGAA<br>CCGTCGGAGGGTAGCGCTCCAGGTAGCCCAGCGG<br>GCTCTCCGACAAGCACCGAAGAAGGCACCAGCAC<br>CGAGCCGTCCGAAGGTTCCGCACCAGGTACAAGC<br>GAGAGCGCGACTCCTGAATCTGGTCCGGGTAGCG<br>AGCCTGCAACCAGCGGTTCTGAGACGCCGGGCAC<br>TTCCGAATCTGCGACCCCGGAGTCCGGTCCAGGT<br>TCAGAGCCGGCGACGAGCGGTTCGGAAACGCCGG<br>GTACGTCTGAATCAGCCACGCCGGAGTCTGGTCC<br>GGGTACCTCGACCGAACCAAGCGAAGGTTCGGCA<br>CCGGGTACTAGCGAGAGCGCAACCCCTGAAAGCG<br>GTCCGGGCAGCCCGGCAGGTTCTCCAACCAGCAC<br>CGAAGAAGGTTCCCCTGCTGGTAGCCCGACCTCT<br>ACGGAGGAAGGTAGCCCTGCAGGTTCCCCAACTT<br>CTACTGAGGAAGGTACTTCTGAGTCCGCTACCCC<br>AGAAAGCGGTCCTGGTACCTCCACTGAACCGTCT<br>GAAGGCTCTGCACCAGGCACTTCTGAGTCTGCTA<br>CTCCAGAAAGCGGCCCAGGTTCTGAACCAGCAAC<br>TTCTGGCTCTGAGACTCCAGGCACTTCTGAGTCC<br>GCAACGCCTGAATCCGGTCCTGGTTCTGAACCAG<br>CTACTTCCGGCAGCGAAACCCCAGGTACCTCTGA<br>GTCTGCGACTCCAGAGTCTGGTCCTGGTACTTCC<br>ACTGAGCCTAGCGAGGGTTCCGCACCAGGTTCTC<br>CGGCTGGTAGCCCGACCAGCACGGAGGAGGGTAC<br>GTCTGAATCTGCAACGCCGGAATCGGGCCCAGGT<br>TCGGAGCCTGCAACGTCTGGCAGCGAAACCCCGG<br>GTACCTCCGAATCTGCTACACCGGAAAGCGGTCC<br>TGGCAGCCCTGCTGGTTCTCCAACCTCTACCGAG<br>GAGGGTTCACCGGCAGGTAGCCCGACTAGCACTG<br>AAGAAGGTACTAGCACGGAGCCGAGCGAGGGTAG<br>TGCTCCGGGTACGAGCGAGAGCGCAACGCCAGAG | 456 |

TABLE 7-continued

T-cell binding compositions

| Construct Name | Amino Acid Sequence | SEQ ID NO: | DNA Sequence | SEQ ID NO: |
|---|---|---|---|---|
| | PGTSTEPSEGSAP | | AGCGGTCCAGGCACCAGCGAATCGGCCACCCCTG | |
| | LSGRSDNHSPLGL | | AGAGCGGCCCAGGTACTTCTGAGAGCGCCACTCC | |
| | AGSGTAEAASASG | | TGAATCCGGCCCTGGTAGCGAGCCGGCAACCTCC | |
| | EVOLVESGGGLVQ | | GGCTCAGAAACTCCTGGTTCGGAACCAGCGACCA | |
| | PGGSLRLSCAASG | | GCGGTTCTGAAACTCCGGGTAGCCCGGCAGGCAG | |
| | YSFTGYTMNWVRQ | | CCCAACGAGCACCGAAGAGGGTACCAGCACGGAA | |
| | APGKGLEWVALIN | | CCGAGCGAGGGTTCTGCCCCGGGTACTTCCACCG | |
| | PYKGVSTYNQKFK | | AACCATCGGAGGGCTCTGCACCTGGTAGCGAACC | |
| | DRFTISVDKSKNT | | TGCGACGTCTGGTTCTGAAACGCCGGGTACCAGC | |
| | AYLQMNSLRAEDT | | GAAAGCGCTACCCCAGAATCCGGTCCGGGCACTA | |
| | AVYYCARSGYYGD | | GCACCGAGCCATCGGAGGGCTCCGCACCActgTC | |
| | SDWYFDVWGQGTL | | AggtCGTtctGATaacCATtccCCActgGGTctg | |
| | VTVSSGATPPETG | | GCTGGGTCTGGCACCGCCGAAGCAGCTagcgcct | |
| | AETESPGETTGGS | | ctGGCGAGGTGCAGCTGGTTGAAAGCGGTGGCGG | |
| | AESEPPGEGDIQM | | TCTGGTGCAACCAGGCGGTAGCCTGCGTCTGAGC | |
| | TQSPSSLSASVGD | | TGCGCGGCGAGCGGTTACAGCTTTACCGGTTATA | |
| | RVTITCRASQDIR | | CCATGAACTGGGTTCGTCAAGCGCCAGGTAAAGG | |
| | NYLNWYQQKPGKA | | TCTGGAGTGGGTGGCGCTGATCAACCCGTACAAG | |
| | PKLLIYYTSRLES | | GGTGTTAGCACCTATAACCAGAAGTTCAAAGACC | |
| | GVPSRFSGSGSGT | | GTTTTACCATTAGCGTGGATAAGAGCAAAAACAC | |
| | DYTLTISSLOPED | | CGCGTACCTGCAAATGAACAGCCTGCGTGCGGAG | |
| | FATYYCQQGNTLP | | GACACCGCTGTGTACTATTGCGCGCGTAGCGGTT | |
| | WTFGQGTKVEIK | | ACTATGGCGACAGCGACTGGTATTTTGATGTGTG | |
| | | | GGGCCAAGGCACCCTGGTTACCGTGAGCTCCGGC | |
| | | | GCTACTCCCCCTGAGACAGGAGCGGAAACGGAAT | |
| | | | CCCCTGGCGAGACGACGGGTGGTTCCGCAGAGTC | |
| | | | GGAACCTCCTGGTGAGGGCGACATCCAAATGACC | |
| | | | CAATCACCGTCATCCCTGAGCGCCTCTGTTGGAG | |
| | | | ATCGTGTAACAATTACCTGCCGCGCCTCCCAAGA | |
| | | | CATCCGCAATTACTTAAACTGGTATCAGCAAAAA | |
| | | | CCCGGTAAGGCACCGAAATTGCTGATTTATTATA | |
| | | | CTTCACGCTTAGAGAGTGGGGTGCCGTCGCGCTT | |
| | | | CAGTGGCTCGGGTAGTGGGACCGATTACACATTG | |
| | | | ACAATTTCATCACTGCAGCCAGAGGATTTTGCGA | |
| | | | CTTATTACTGTCAACAGGGTAACACGCTTCCCTG | |
| | | | GACCTTCGGGCAAGGCACGAAAGTTGAGATCAAG | |
| TBP-12 | HHHHHHGGSPAGS | 441 | CATCACCACCATCATCACggAGGTAGCCCAGCTG | 457 |
| | PTSTEEGTSESAT | | GTAGCCCAACCTCTACCGAAGAAGGTACCTCTGA | |
| | PESGPGTSTEPSE | | ATCCGCTACTCCAGAATCCGGTCCTGGTACTAGC | |
| | GSAPGSPAGSPTS | | ACTGAGCCAAGCGAAGGTTCTGCTCCAGGCTCCC | |
| | TEEGTSTEPSEGS | | CGGCAGGTAGCCCTACCTCTACCGAAGAGGGCAC | |
| | APGTSTEPSEGSA | | TAGCACCGAACCATCTGAGGGTTCCGCTCCTGGC | |
| | PGTSESATPESGP | | ACCTCCACTGAACCGTCCGAAGGCAGTGCTCCGG | |
| | GSEPATSGSETPG | | GTACTTCCGAAAGCGCAACTCCGGAATCCGGCCC | |
| | SEPATSGSETPGS | | TGGTTCTGAGCCTGCTACTTCCGGCTCTGAAACT | |
| | PAGSPTSTEEGTS | | CCAGGTAGCGAGCCAGCGACTTCTGGTTCTGAAA | |
| | ESATPESGPGTST | | CTCCAGGTTCACCGGCGGGTAGCCCGACGAGCAC | |
| | EPSEGSAPGTSTE | | GGAGGAAGGTACCTCTGAGTCGGCCACTCCTGAG | |
| | PSEGSAPGSPAGS | | TCCGGTCCGGGCACGAGCACCGAGCCGAGCGAGG | |
| | PTSTEEGTSTEPS | | GTTCAGCCCCGGGTACCAGCACGGAGCCGTCCGA | |
| | EGSAPGTSTEPSE | | GGGTAGCGCACCGGGTTCTCCGGCGGGCTCCCCT | |
| | GSAPGTSESATPE | | ACGTCTACGGAAGAGGGTACGTCCACTGAACCTA | |
| | SGPGTSTEPSEGS | | GCGAGGGCAGCGCGCCAGGCACCAGCACTGAACC | |
| | APGTSESATPESG | | GAGCGAAGGCAGCGCACCTGGCACTAGCGAGTCT | |
| | PGSEPATSGSETP | | GCGACTCCGGAGAGCGGTCCGGGTACGAGCACGG | |
| | GTSTEPSEGSAPG | | AACCAAGCGAAGGCAGCGCCCCAGGTACCTCTGA | |
| | TSTEPSEGSAPGT | | ATCTGCTACCCCAGAATCTGGCCCGGGTTCCGAG | |
| | SESATPESGPGTS | | CCAGCTACCTCTGGTTCTGAAACCCCAGGTACTT | |
| | ESATPESGPGSPA | | CCACTGAACCAAGCGAAGGTAGCGCTCCTGGCAC | |
| | GSPTSTEEGTSES | | TTCTACTGAACCATCCGAAGGTTCCGCTCCTGGT | |
| | ATPESGPGSEPAT | | ACGTCTGAAAGCGCTACCCCTGAAAGCGGCCCAG | |
| | SGSETPGTSESAT | | GCACCTCTGAAAGCGCTACTCCTGAGAGCGGTCC | |
| | PESGPGTSTEPSE | | AGGCTCTCCAGCAGGTTCTCCAACCTCCACTGAA | |
| | GSAPGTSTEPSEG | | GAAGGCACCTCTGAGTCTGCTACCCCTGAATCTG | |
| | SAPGTSTEPSEGS | | GTCCTGGCTCCGAACCTGCTACCTCTGGTTCCGA | |
| | APGTSTEPSEGSA | | AACTCCAGGTACCTCGGAATCTGCGACTCCGGAA | |
| | PGTSTEPSEGSAP | | TCTGGCCCGGGCACGAGCACGGAGCCGTCTGAGG | |
| | GTSTEPSEGSAPG | | GTAGCGCACCAGGTACCAGCACTGAGCCTTCTGA | |
| | SPAGSPTSTEEGT | | GGGCTCTGCACCGGGTACCTCCACGGAACCTTCG | |
| | STEPSEGSAPGTS | | GAAGGTTCTGCGCCGGGTACCTCCACTGAGCCAT | |
| | ESATPESGPGSEP | | CCGAGGGTTCAGCACCAGGTACTAGCACGGAACC | |
| | ATSGSETPGTSES | | GTCCGAGGGCTCTGCACCAGGTACGAGCACCGAA | |
| | ATPESGPGSEPAT | | CCGTCGGAGGGTAGCGCTCCAGGTAGCCCAGCGG | |

TABLE 7-continued

T-cell binding compositions

| Construct Name | Amino Acid Sequence | SEQ ID NO: | DNA Sequence | SEQ ID NO: |
|---|---|---|---|---|
| | SGSETPGTSESAT | | GCTCTCCGACAAGCACCGAAGAAGGCACCAGCAC | |
| | PESGPGTSTEPSE | | CGAGCCGTCCGAAGGTTCCGCACCAGGTACAAGC | |
| | GSAPGTSESATPE | | GAGAGCGCGACTCCTGAATCTGGTCCGGGTAGCG | |
| | SGPGSPAGSPTST | | AGCCTGCAACCAGCGGTTCTGAGACGCCGGGCAC | |
| | EEGSPAGSPTSTE | | TTCCGAATCTGCGACCCCGGAGTCCGGTCCAGGT | |
| | EGSPAGSPTSTEE | | TCAGAGCCGGCGACGAGCGGTTCGGAAACGCCGG | |
| | GTSESATPESGPG | | GTACGTCTGAATCAGCCACGCCGGAGTCTGGTCC | |
| | TSTEPSEGSAPGT | | GGGTACCTCGACCGAACCAAGCGAAGGTTCGGCA | |
| | SESATPESGPGSE | | CCGGGTACTAGCGAGAGCGCAACCCCTGAAAGCG | |
| | PATSGSETPGTSE | | GTCCGGGCAGCCCGGCAGGTTCTCCAACCAGCAC | |
| | SATPESGPGSEPA | | CGAAGAAGGTTCCCCTGCTGGTAGCCCGACCTCT | |
| | TSGSETPGTSESA | | ACGGAGGAAGGTAGCCCTGCAGGTTCCCCAACTT | |
| | TPESGPGTSTEPS | | CTACTGAGGAAGGTACTTCTGAGTCCGCTACCCC | |
| | EGSAPGSPAGSPT | | AGAAAGCGGTCCTGGTACCTCCACTGAACCGTCT | |
| | STEEGTSESATPE | | GAAGGCTCTGCACCAGGCACTTCTGAGTCTGCTA | |
| | SGPGSEPATSGSE | | CTCCAGAAAGCGGCCCAGGTTCTGAACCAGCAAC | |
| | TPGTSESATPESG | | TTCTGGCTCTGAGACTCCAGGCACTTCTGAGTCC | |
| | PGSPAGSPTSTEE | | GCAACGCCTGAATCCGGTCCTGGTTCTGAACCAG | |
| | GSPAGSPTSTEEG | | CTACTTCCGGCAGCGAAACCCCAGGTACCTCTGA | |
| | TSTEPSEGSAPGT | | GTCTGCGACTCCAGAGTCTGGTCCTGGTACTTCC | |
| | SESATPESGPGTS | | ACTGAGCCTAGCGAGGGTTCCGCACCAGGTTCTC | |
| | ESATPESGPGTSE | | CGGCTGGTAGCCCGACCAGCACGGAGGAGGGTAC | |
| | SATPESGPGSEPA | | GTCTGAATCTGCAACGCCGGAATCGGGCCCAGGT | |
| | TSGSETPGSEPAT | | TCGGAGCCTGCAACGTCTGGCAGCGAAACCCCGG | |
| | SGSETPGSPAGSP | | GTACCTCCGAATCTGCTACACCGGAAAGCGGTCC | |
| | TSTEEGTSTEPSE | | TGGCAGCCCTGCTGGTTCTCCAACCTCTACCGAG | |
| | GSAPGTSTEPSEG | | GAGGGTTCACCGGCAGGTAGCCCGACTAGCACTG | |
| | SAPGSEPATSGSE | | AAGAAGGTACTAGCACGGAGCCGAGCGAGGGTAG | |
| | TPGTSESATPESG | | TGCTCCGGGTACGAGCGAGAGCGCAACGCCAGAG | |
| | PGTSTEPSEGSAP | | AGCGGTCCAGGCACCAGCGAATCGGCCACCCCTG | |
| | LSGRSDNHVPLSL | | AGAGCGGCCCAGGTACTTCTGAGAGCGCCACTCC | |
| | KMGGTAEAASASG | | TGAATCCGGCCCTGGTAGCGAGCCGGCAACCTCC | |
| | EVOLVESGGGLVQ | | GGCTCAGAAACTCCTGGTTCGGAACCAGCGACCA | |
| | PGGSLRLSCAASG | | GCGGTTCTGAAACTCCGGGTAGCCCGGCAGGCAG | |
| | YSFTGYTMNWVRQ | | CCCAACGAGCACCGAAGAGGGTACCAGCACGGAA | |
| | APGKGLEWVALIN | | CCGAGCGAGGGTTCTGCCCCGGGTACTTCCACCG | |
| | PYKGVSTYNQKFK | | AACCATCGGAGGGCTCTGCACCTGGTAGCGAACC | |
| | DRFTISVDKSKNT | | TGCGACGTCTGGTTCTGAAACGCCGGGTACCAGC | |
| | AYLOMNSLRAEDT | | GAAAGCGCTACCCCAGAATCCGGTCCGGGCACTA | |
| | AVYYCARSGYYGD | | GCACCGAGCCATCGGAGGGCTCCGCACCActgTC | |
| | SDWYFDVWGQGTL | | AggtCGTtctGATaacCATgttCCActgTCTctg | |
| | VTVSSGATPPETG | | AAAatgGGTGGCACCGCCGAAGCAGCTagcgcct | |
| | AETESPGETTGGS | | ctGGCGAGGTGCAGCTGGTTGAAAGCGGTGGCGG | |
| | AESEPPGEGDIQM | | TCTGGTGCAACCAGGCGGTAGCCTGCGTCTGAGC | |
| | TQSPSSLSASVGD | | TGCGCGGCGAGCGGTTACAGCTTTACCGGTTATA | |
| | RVTITCRASQDIR | | CCATGAACTGGGTTCGTCAAGCGCCAGGTAAAGG | |
| | NYLNWYQQKPGKA | | TCTGGAGTGGGTGGCGCTGATCAACCCGTACAAG | |
| | PKLLIYYTSRLES | | GGTGTTAGCACCTATAACCAGAAGTTCAAAGACC | |
| | GVPSRFSGSGSGT | | GTTTTACCATTAGCGTGGATAAGAGCAAAAACAC | |
| | DYTLTISSLOPED | | CGCGTACCTGCAAATGAACAGCCTGCGTGCGGAG | |
| | FATYYCQQGNTLP | | GACACCGCTGTGTACTATTGCGCGCGTAGCGGTT | |
| | WTFGQGTKVEIK | | ACTATGGCGACAGCGACTGGTATTTTGATGTGTG | |
| | | | GGGCCAAGGCACCCTGGTTACCGTGAGCTCCGGC | |
| | | | GCTACTCCCCCTGAGACAGGAGCGGAAACGGAAT | |
| | | | CCCCTGGCGAGACGACGGGTGGTTCCGCAGAGTC | |
| | | | GGAACCTCCTGGTGAGGGCGACATCCAAATGACC | |
| | | | CAATCACCGTCATCCCTGAGCGCCTCTGTTGGAG | |
| | | | ATCGTGTAACAATTACCTGCCGCGCCTCCCAAGA | |
| | | | CATCCGCAATTACTTAAACTGGTATCAGCAAAAA | |
| | | | CCCGGTAAGGCACCGAAATTGCTGATTTATTATA | |
| | | | CTTCACGCTTAGAGAGTGGGGTGCCGTCGCGCTT | |
| | | | CAGTGGCTCGGGTAGTGGGACCGATTACACATTG | |
| | | | ACAATTTCATCACTGCAGCCAGAGGATTTTGCGA | |
| | | | CTTATTACTGTCAACAGGGTAACACGCTTCCCTG | |
| | | | GACCTTCGGGCAAGGCACGAAAGTTGAGATCAAG | |
| TBP-13 | HHHHHHGGSPAGS | 442 | CATCACCACCATCATCACggAGGTAGCCCAGCTG | 458 |
| | PTSTEEGTSESAT | | GTAGCCCAACCTCTACCGAAGAAGGTACCTCTGA | |
| | PESGPGTSTEPSE | | ATCCGCTACTCCAGAATCCGGTCCTGGTACTAGC | |
| | GSAPGSPAGSPTS | | ACTGAGCCAAGCGAAGGTTCTGCTCCAGGCTCCC | |
| | TEEGTSTEPSEGS | | CGGCAGGTAGCCCTACCTCTACCGAAGAGGGCAC | |
| | APGTSTEPSEGSA | | TAGCACCGAACCATCTGAGGGTTCCGCTCCTGGC | |
| | PGTSESATPESGP | | ACCTCCACTGAACCGTCCGAAGGCAGTGCTCCGG | |
| | GSEPATSGSETPG | | GTACTTCCGAAAGCGCAACTCCGGAATCCGGCCC | |

TABLE 7-continued

T-cell binding compositions

| Construct Name | Amino Acid Sequence | SEQ ID NO: | DNA Sequence | SEQ ID NO: |
|---|---|---|---|---|
| | SEPATSGSETPGS | | TGGTTCTGAGCCTGCTACTTCCGGCTCTGAAACT | |
| | PAGSPTSTEEGTS | | CCAGGTAGCGAGCCAGCGACTTCTGGTTCTGAAA | |
| | ESATPESGPGTST | | CTCCAGGTTCACCGGCGGGTAGCCCGACGAGCAC | |
| | EPSEGSAPGTSTE | | GGAGGAAGGTACCTCTGAGTCGGCCACTCCTGAG | |
| | PSEGSAPGSPAGS | | TCCGGTCCGGGCACGAGCACCGAGCCGAGCGAGG | |
| | PTSTEEGTSTEPS | | GTTCAGCCCCGGGTACCAGCACGGAGCCGTCCGA | |
| | EGSAPGTSTEPSE | | GGGTAGCGCACCGGGTTCTCCGGCGGGCTCCCCT | |
| | GSAPGTSESATPE | | ACGTCTACGGAAGAGGGTACGTCCACTGAACCTA | |
| | SGPGTSTEPSEGS | | GCGAGGGCAGCGCGCCAGGCACCAGCACTGAACC | |
| | APGTSESATPESG | | GAGCGAAGGCAGCGCACCTGGCACTAGCGAGTCT | |
| | PGSEPATSGSETP | | GCGACTCCGGAGAGCGGTCCGGGTACGAGCACGG | |
| | GTSTEPSEGSAPG | | AACCAAGCGAAGGCAGCGCCCCAGGTACCTCTGA | |
| | TSTEPSEGSAPGT | | ATCTGCTACCCCAGAATCTGGCCCGGGTTCCGAG | |
| | SESATPESGPGTS | | CCAGCTACCTCTGGTTCTGAAACCCCAGGTACTT | |
| | ESATPESGPGSPA | | CCACTGAACCAAGCGAAGGTAGCGCTCCTGGCAC | |
| | GSPTSTEEGTSES | | TTCTACTGAACCATCCGAAGGTTCCGCTCCTGGT | |
| | ATPESGPGSEPAT | | ACGTCTGAAAGCGCTACCCCTGAAAGCGGCCCAG | |
| | SGSETPGTSESAT | | GCACCTCTGAAAGCGCTACTCCTGAGAGCGGTCC | |
| | PESGPGTSTEPSE | | AGGCTCTCCAGCAGGTTCTCCAACCTCCACTGAA | |
| | GSAPGTSTEPSEG | | GAAGGCACCTCTGAGTCTGCTACCCCTGAATCTG | |
| | SAPGTSTEPSEGS | | GTCCTGGCTCCGAACCTGCTACCTCTGGTTCCGA | |
| | APGTSTEPSEGSA | | AACTCCAGGTACCTCGGAATCTGCGACTCCGGAA | |
| | PGTSTEPSEGSAP | | TCTGGCCCGGGCACGAGCACGGAGCCGTCTGAGG | |
| | GTSTEPSEGSAPG | | GTAGCGCACCAGGTACCAGCACTGAGCCTTCTGA | |
| | SPAGSPTSTEEGT | | GGGCTCTGCACCGGGTACCTCCACGGAACCTTCG | |
| | STEPSEGSAPGTS | | GAAGGTTCTGCGCCGGGTACCTCCACTGAGCCAT | |
| | ESATPESGPGSEP | | CCGAGGGTTCAGCACCAGGTACTAGCACGGAACC | |
| | ATSGSETPGTSES | | GTCCGAGGGCTCTGCACCAGGTACGAGCACCGAA | |
| | ATPESGPGSEPAT | | CCGTCGGAGGGTAGCGCTCCAGGTAGCCCAGCGG | |
| | SGSETPGTSESAT | | GCTCTCCGACAAGCACCGAAGAAGGCACCAGCAC | |
| | PESGPGTSTEPSE | | CGAGCCGTCCGAAGGTTCCGCACCAGGTACAAGC | |
| | GSAPGTSESATPE | | GAGAGCGCGACTCCTGAATCTGGTCCGGGTAGCG | |
| | SGPGSPAGSPTST | | AGCCTGCAACCAGCGGTTCTGAGACGCCGGGCAC | |
| | EEGSPAGSPTSTE | | TTCCGAATCTGCGACCCCGGAGTCCGGTCCAGGT | |
| | EGSPAGSPTSTEE | | TCAGAGCCGGCGACGAGCGGTTCGGAAACGCCGG | |
| | GTSESATPESGPG | | GTACGTCTGAATCAGCCACGCCGGAGTCTGGTCC | |
| | TSTEPSEGSAPGT | | GGGTACCTCGACCGAACCAAGCGAAGGTTCGGCA | |
| | SESATPESGPGSE | | CCGGGTACTAGCGAGAGCGCAACCCCTGAAAGCG | |
| | PATSGSETPGTSE | | GTCCGGGCAGCCCGGCAGGTTCTCCAACCAGCAC | |
| | SATPESGPGSEPA | | CGAAGAAGGTTCCCCTGCTGGTAGCCCGACCTCT | |
| | TSGSETPGTSESA | | ACGGAGGAAGGTAGCCCTGCAGGTTCCCCAACTT | |
| | TPESGPGTSTEPS | | CTACTGAGGAAGGTACTTCTGAGTCCGCTACCCC | |
| | EGSAPGSPAGSPT | | AGAAAGCGGTCCTGGTACCTCCACTGAACCGTCT | |
| | STEEGTSESATPE | | GAAGGCTCTGCACCAGGCACTTCTGAGTCTGCTA | |
| | SGPGSEPATSGSE | | CTCCAGAAAGCGGCCCAGGTTCTGAACCAGCAAC | |
| | TPGTSESATPESG | | TTCTGGCTCTGAGACTCCAGGCACTTCTGAGTCC | |
| | PGSPAGSPTSTEE | | GCAACGCCTGAATCCGGTCCTGGTTCTGAACCAG | |
| | GSPAGSPTSTEEG | | CTACTTCCGGCAGCGAAACCCCAGGTACCTCTGA | |
| | TSTEPSEGSAPGT | | GTCTGCGACTCCAGAGTCTGGTCCTGGTACTTCC | |
| | SESATPESGPGTS | | ACTGAGCCTAGCGAGGGTTCCGCACCAGGTTCTC | |
| | ESATPESGPGTSE | | CGGCTGGTAGCCCGACCAGCACGGAGGAGGGTAC | |
| | SATPESGPGSEPA | | GTCTGAATCTGCAACGCCGGAATCGGGCCCAGGT | |
| | TSGSETPGSEPAT | | TCGGAGCCTGCAACGTCTGGCAGCGAAACCCCGG | |
| | SGSETPGSPAGSP | | GTACCTCCGAATCTGCTACACCGGAAAGCGGTCC | |
| | TSTEEGTSTEPSE | | TGGCAGCCCTGCTGGTTCTCCAACCTCTACCGAG | |
| | GSAPGTSTEPSEG | | GAGGGTTCACCGGCAGGTAGCCCGACTAGCACTG | |
| | SAPGSEPATSGSE | | AAGAAGGTACTAGCACGGAGCCGAGCGAGGGTAG | |
| | TPGTSESATPESG | | TGCTCCGGGTACGAGCGAGAGCGCAACGCCAGAG | |
| | PGTSTEPSEGSAP | | AGCGGTCCAGGCACCAGCGAATCGGCCACCCCTG | |
| | LSGRSDNHSPLGL | | AGAGCGGCCCAGGTACTTCTGAGAGCGCCACTCC | |
| | AGSGTAEAASASG | | TGAATCCGGCCCTGGTAGCGAGCCGGCAACCTCC | |
| | ELVVTQEPSLTVS | | GGCTCAGAAACTCCTGGTTCGGAACCAGCGACCA | |
| | PGGTVTLTCRSST | | GCGGTTCTGAAACTCCGGGTAGCCCGGCAGGCAG | |
| | GAVTTSNYANWVQ | | CCCAACGAGCACCGAAGAGGGTACCAGCACGGAA | |
| | QKPGQAPRGLIGG | | CCGAGCGAGGGTTCTGCCCCGGGTACTTCCACCG | |
| | TNKRAPGTPARES | | AACCATCGGAGGGCTCTGCACCTGGTAGCGAACC | |
| | GSLLGGKAALTLS | | TGCGACGTCTGGTTCTGAAACGCCGGGTACCAGC | |
| | GVQPEDEAEYYCA | | GAAAGCGCTACCCCAGAATCCGGTCCGGGCACTA | |
| | LWYSNLWVFGGGT | | GCACCGAGCCATCGGAGGGCTCCGCACCACtgTC | |
| | KLTVLGATPPETG | | AggtCGTtctGATaacCATtccCCActgGGTctg | |
| | AETESPGETTGGS | | GCTGGGTCTGGCACCGCCGAAGCAGCTagcgcct | |
| | AESEPPGEGEVQL | | ctGGCGAACTGGTCGTCACGCAGGAGCCGTCCCT | |
| | LESGGGLVQPGGS | | TACCGTTTCACCAGGTGGAACAGTGACTCTGACG | |
| | LKLSCAASGFTEN | | TGTCGCTCCTCCACTGGGGCGGTTACAACTTCCA | |

TABLE 7-continued

| T-cell binding compositions | | | | |
|---|---|---|---|---|
| Construct Name | Amino Acid Sequence | SEQ ID NO: | DNA Sequence | SEQ ID NO: |
| | TYAMNWVRQAPGK | | ATTATGCTAATTGGGTCCAGCAGAAGCCGGGCCA | |
| | GLEWVARIRSKYN | | AGCCCCTCGCGGGTTGATTGGCGGCACCAACAAA | |
| | NYATYYADSVKDR | | CGTGCTCCAGGGACACCTGCCCGTTTTTCGGGCT | |
| | FTISRDDSKNTAY | | CCTTATTGGGGGGCAAAGCTGCACTGACGTTGTC | |
| | LQMNNLKTEDTAV | | TGGAGTTCAGCCGGAGGATGAGGCAGAGTATTAC | |
| | YYCVRHGNFGNSY | | TGCGCATTGTGGTATTCTAATTTATGGGTTTTTG | |
| | VSWFAYWGQGTLV | | GAGGCGGCACAAAGCTGACCGTCCTGggtgcgac | |
| | TVSS | | cccgccggaaaccggtgcggaaaccgaaagcccg | |
| | | | ggtgaaaccaccggtggcagcgcggagagcgaac | |
| | | | cgccgggtgaaggtGAGGTTCAGTTGTTGGAAAG | |
| | | | CGGGGGCGGGCTTGTCCAACCTGGAGGTTCATTA | |
| | | | AAATTGAGCTGTGCAGCCTCCGGATTCACCTTTA | |
| | | | ACACGTATGCAATGAACTGGGTCCGTCAAGCGCC | |
| | | | CGGTAAGGGGCTGGAGTGGGTAGCTCGCATCCGC | |
| | | | TCGAAGTATAATAATTACGCAACCTACTACGCAG | |
| | | | ACAGTGTCAAAGATCGCTTCACTATCTCACGCGA | |
| | | | CGACAGTAAGAACACGGCCTACTTACAGATGAAC | |
| | | | AATCTTAAAACGGAGGACACCGCTGTCTACTACT | |
| | | | GCGTGCGCCACGGGAATTTCGGTAACTCTTATGT | |
| | | | AAGTTGGTTCGCATATTGGGGACAAGGTACGTTG | |
| | | | GTAACCGTATCCAGC | |
| TBP-14 | HHHHHHGGSPAGS | 443 | CATCACCACCATCATCACggAGGTAGCCCAGCTG | 459 |
| | PTSTEEGTSESAT | | GTAGCCCAACCTCTACCGAAGAAGGTACCTCTGA | |
| | PESGPGTSTEPSE | | ATCCGCTACTCCAGAATCCGGTCCTGGTACTAGC | |
| | GSAPGSPAGSPTS | | ACTGAGCCAAGCGAAGGTTCTGCTCCAGGCTCCC | |
| | TEEGTSTEPSEGS | | CGGCAGGTAGCCCTACCTCTACCGAAGAGGGCAC | |
| | APGTSTEPSEGSA | | TAGCACCGAACCATCTGAGGGTTCCGCTCCTGGC | |
| | PGTSESATPESGP | | ACCTCCACTGAACCGTCCGAAGGCAGTGCTCCGG | |
| | GSEPATSGSETPG | | GTACTTCCGAAAGCGCAACTCCGGAATCCGGCCC | |
| | SEPATSGSETPGS | | TGGTTCTGAGCCTGCTACTTCCGGCTCTGAAACT | |
| | PAGSPTSTEEGTS | | CCAGGTAGCGAGCCAGCGACTTCTGGTTCTGAAA | |
| | ESATPESGPGTST | | CTCCAGGTTCACCGGCGGGTAGCCCGACGAGCAC | |
| | EPSEGSAPGTSTE | | GGAGGAAGGTACCTCTGAGTCGGCCACTCCTGAG | |
| | PSEGSAPGSPAGS | | TCCGGTCCGGGCACGAGCACCGAGCCGAGCGAGG | |
| | PTSTEEGTSTEPS | | GTTCAGCCCCGGGTACCAGCACGGAGCCGTCCGA | |
| | EGSAPGTSTEPSE | | GGGTAGCGCACCGGGTTCTCCGGCGGGCTCCCCT | |
| | GSAPGTSESATPE | | ACGTCTACGGAAGAGGGTACGTCCACTGAACCTA | |
| | SGPGTSTEPSEGS | | GCGAGGGCAGCGCGCCAGGCACCAGCACTGAACC | |
| | APGTSESATPESG | | GAGCGAAGGCAGCGCACCTGGCACTAGCGAGTCT | |
| | PGSEPATSGSETP | | GCGACTCCGGAGAGCGGTCCGGGTACGAGCACGG | |
| | GTSTEPSEGSAPG | | AACCAAGCGAAGGCAGCGCCCCAGGTACCTCTGA | |
| | TSTEPSEGSAPGT | | ATCTGCTACCCCAGAATCTGGCCCGGGTTCCGAG | |
| | SESATPESGPGTS | | CCAGCTACCTCTGGTTCTGAAACCCCAGGTACTT | |
| | ESATPESGPGSPA | | CCACTGAACCAAGCGAAGGTAGCGCTCCTGGCAC | |
| | GSPTSTEEGTSES | | TTCTACTGAACCATCCGAAGGTTCCGCTCCTGGT | |
| | ATPESGPGSEPAT | | ACGTCTGAAAGCGCTACCCCTGAAAGCGGCCCAG | |
| | SGSETPGTSESAT | | GCACCTCTGAAAGCGCTACTCCTGAGAGCGGTCC | |
| | PESGPGTSTEPSE | | AGGCTCTCCAGCAGGTTCTCCAACCTCCACTGAA | |
| | GSAPGTSTEPSEG | | GAAGGCACCTCTGAGTCTGCTACCCCTGAATCTG | |
| | SAPGTSTEPSEGS | | GTCCTGGCTCCGAACCTGCTACCTCTGGTTCCGA | |
| | APGTSTEPSEGSA | | AACTCCAGGTACCTCGGAATCTGCGACTCCGGAA | |
| | PGTSTEPSEGSAP | | TCTGGCCCGGGCACGAGCACGGAGCCGTCTGAGG | |
| | GTSTEPSEGSAPG | | GTAGCGCACCAGGTACCAGCACTGAGCCTTCTGA | |
| | SPAGSPTSTEEGT | | GGGCTCTGCACCGGGTACCTCCACGGAACCTTCG | |
| | STEPSEGSAPGTS | | GAAGGTTCTGCGCCGGGTACCTCCACTGAGCCAT | |
| | ESATPESGPGSEP | | CCGAGGGTTCAGCACCAGGTACTAGCACGGAACC | |
| | ATSGSETPGTSES | | GTCCGAGGGCTCTGCACCAGGTACGAGCACCGAA | |
| | ATPESGPGSEPAT | | CCGTCGGAGGGTAGCGCTCCAGGTAGCCCAGCGG | |
| | SGSETPGTSESAT | | GCTCTCCGACAAGCACCGAAGAAGGCACCAGCAC | |
| | PESGPGTSTEPSE | | CGAGCCGTCCGAAGGTTCCGCACCAGGTACAAGC | |
| | GSAPGTSESATPE | | GAGAGCGCGACTCCTGAATCTGGTCCGGGTAGCG | |
| | SGPGSPAGSPTST | | AGCCTGCAACCAGCGGTTCTGAGACGCCGGGCAC | |
| | EEGSPAGSPTSTE | | TTCCGAATCTGCGACCCCGGAGTCCGGTCCAGGT | |
| | EGSPAGSPTSTEE | | TCAGAGCCGGCGACGAGCGGTTCGGAAACGCCGG | |
| | GTSESATPESGPG | | GTACGTCTGAATCAGCCACGCCGGAGTCTGGTCC | |
| | TSTEPSEGSAPGT | | GGGTACCTCGACCGAACCAAGCGAAGGTTCGGCA | |
| | SESATPESGPGSE | | CCGGGTACTAGCGAGAGCGCAACCCCTGAAAGCG | |
| | PATSGSETPGTSE | | GTCCGGGCAGCCCGGCAGGTTCTCCAACCAGCAC | |
| | SATPESGPGSEPA | | CGAAGAAGGTTCCCCTGCTGGTAGCCCGACCTCT | |
| | TSGSETPGTSESA | | ACGGAGGAAGGTAGCCCTGCAGGTTCCCCAACTT | |
| | TPESGPGTSTEPS | | CTACTGAGGAAGGTACTTCTGAGTCCGCTACCCC | |
| | EGSAPGSPAGSPT | | AGAAAGCGGTCCTGGTACCTCCACTGAACCGTCT | |
| | STEEGTSESATPE | | GAAGGCTCTGCACCAGGCACTTCTGAGTCTGCTA | |

TABLE 7-continued

T-cell binding compositions

| Construct Name | Amino Acid Sequence | SEQ ID NO: | DNA Sequence | SEQ ID NO: |
|---|---|---|---|---|
| | SGPGSEPATSGSE | | CTCCAGAAAGCGGCCCAGGTTCTGAACCAGCAAC | |
| | TPGTSESATPESG | | TTCTGGCTCTGAGACTCCAGGCACTTCTGAGTCC | |
| | PGSPAGSPTSTEE | | GCAACGCCTGAATCCGGTCCTGGTTCTGAACCAG | |
| | GSPAGSPTSTEEG | | CTACTTCCGGCAGCGAAACCCCAGGTACCTCTGA | |
| | TSTEPSEGSAPGT | | GTCTGCGACTCCAGAGTCTGGTCCTGGTACTTCC | |
| | SESATPESGPGTS | | ACTGAGCCTAGCGAGGGTTCCGCACCAGGTTCTC | |
| | ESATPESGPGTSE | | CGGCTGGTAGCCCGACCAGCACGGAGGAGGGTAC | |
| | SATPESGPGSEPA | | GTCTGAATCTGCAACGCCGGAATCGGGCCCAGGT | |
| | TSGSETPGSEPAT | | TCGGAGCCTGCAACGTCTGGCAGCGAAACCCCGG | |
| | SGSETPGSPAGSP | | GTACCTCCGAATCTGCTACACCGGAAAGCGGTCC | |
| | TSTEEGTSTEPSE | | TGGCAGCCCTGCTGGTTCTCCAACCTCTACCGAG | |
| | GSAPGTSTEPSEG | | GAGGGTTCACCGGCAGGTAGCCCGACTAGCACTG | |
| | SAPGSEPATSGSE | | AAGAAGGTACTAGCACGGAGCCGAGCGAGGGTAG | |
| | TPGTSESATPESG | | TGCTCCGGGTACGAGCGAGAGCGCAACGCCAGAG | |
| | PGTSTEPSEGSAP | | AGCGGTCCAGGCACCAGCGAATCGGCCACCCCTG | |
| | LSGRSDNHVPLSL | | AGAGCGGCCCAGGTACTTCTGAGAGCGCCACTCC | |
| | KMGGTAEAASASG | | TGAATCCGGCCCTGGTAGCGAGCCGGCAACCTCC | |
| | ELVVTQEPSLTVS | | GGCTCAGAAACTCCTGGTTCGGAACCAGCGACCA | |
| | PGGTVTLTCRSST | | GCGGTTCTGAAACTCCGGGTAGCCCGGCAGGCAG | |
| | GAVTTSNYANWVQ | | CCCAACGAGCACCGAAGAGGGTACCAGCACGGAA | |
| | QKPGQAPRGLIGG | | CCGAGCGAGGGTTCTGCCCCGGGTACTTCCACCG | |
| | TNKRAPGTPARES | | AACCATCGGAGGGCTCTGCACCTGGTAGCGAACC | |
| | GSLLGGKAALTLS | | TGCGACGTCTGGTTCTGAAACGCCGGGTACCAGC | |
| | GVQPEDEAEYYCA | | GAAAGCGCTACCCCAGAATCCGGTCCGGGCACTA | |
| | LWYSNLWVFGGGT | | GCACCGAGCCATCGGAGGGCTCCGCACCActgTC | |
| | KLTVLGATPPETG | | AggtCGTtctGATaacCATgttCCActgTCTctg | |
| | AETESPGETTGGS | | AAAatgGGTGGCACCGCCGAAGCAGCTagcgcct | |
| | AESEPPGEGEVOL | | ctGGCGAACTGGTCGTCACGCAGGAGCCGTCCCT | |
| | LESGGGLVQPGGS | | TACCGTTTCACCAGGTGGAACAGTGACTCTGACG | |
| | LKLSCAASGFTEN | | TGTCGCTCCTCCACTGGGGCGGTTACAACTTCCA | |
| | TYAMNWVRQAPGK | | ATTATGCTAATTGGGTCCAGCAGAAGCCGGGCCA | |
| | GLEWVARIRSKYN | | AGCCCCTCGCGGGTTGATTGGCGGCACCAACAAA | |
| | NYATYYADSVKDR | | CGTGCTCCAGGGACACCTGCCCGTTTTTCGGGCT | |
| | FTISRDDSKNTAY | | CCTTATTGGGGGGCAAAGCTGCACTGACGTTGTC | |
| | LQMNNLKTEDTAV | | TGGAGTTCAGCCGGAGGATGAGGCAGAGTATTAC | |
| | YYCVRHGNFGNSY | | TGCGCATTGTGGTATTCTAATTTATGGGTTTTTG | |
| | VSWFAYWGQGTLV | | GAGGCGGCACAAAGCTGACCGTCCTGggtgcgac | |
| | TVSS | | cccgccggaaaccggtgcggaaaccgaaagcccg | |
| | | | ggtgaaaccaccggtggcagcgcggagagcgaac | |
| | | | cgccgggtgaaggtGAGGTTCAGTTGTTGGAAAG | |
| | | | CGGGGGCGGGCTTGTCCAACCTGGAGGTTCATTA | |
| | | | AAATTGAGCTGTGCAGCCTCCGGATTCACCTTTA | |
| | | | ACACGTATGCAATGAACTGGGTCCGTCAAGCGCC | |
| | | | CGGTAAGGGGCTGGAGTGGGTAGCTCGCATCCGC | |
| | | | TCGAAGTATAATAATTACGCAACCTACTACGCAG | |
| | | | ACAGTGTCAAAGATCGCTTCACTATCTCACGCGA | |
| | | | CGACAGTAAGAACACGGCCTACTTACAGATGAAC | |
| | | | AATCTTAAAACGGAGGACACCGCTGTCTACTACT | |
| | | | GCGTGCGCCACGGGAATTTCGGTAACTCTTATGT | |
| | | | AAGTTGGTTCGCATATTGGGGACAAGGTACGTTG | |
| | | | GTAACCGTATCCAGC | |
| TBP-15 | HHHHHHGGSPAGS | 444 | CATCACCACCATCATCACggAGGTAGCCCAGCTG | 460 |
| | PTSTEEGTSESAT | | GTAGCCCAACCTCTACCGAAGAAGGTACCTCTGA | |
| | PESGPGTSTEPSE | | ATCCGCTACTCCAGAATCCGGTCCTGGTACTAGC | |
| | GSAPGSPAGSPTS | | ACTGAGCCAAGCGAAGGTTCTGCTCCAGGCTCCC | |
| | TEEGTSTEPSEGS | | CGGCAGGTAGCCCTACCTCTACCGAAGAGGGCAC | |
| | APGTSTEPSEGSA | | TAGCACCGAACCATCTGAGGGTTCCGCTCCTGGC | |
| | PGTSESATPESGP | | ACCTCCACTGAACCGTCCGAAGGCAGTGCTCCGG | |
| | GSEPATSGSETPG | | GTACTTCCGAAAGCGCAACTCCGGAATCCGGCCC | |
| | SEPATSGSETPGS | | TGGTTCTGAGCCTGCTACTTCCGGCTCTGAAACT | |
| | PAGSPTSTEEGTS | | CCAGGTAGCGAGCCAGCGACTTCTGGTTCTGAAA | |
| | ESATPESGPGTST | | CTCCAGGTTCACCGGCGGGTAGCCCGACGAGCAC | |
| | EPSEGSAPGTSTE | | GGAGGAAGGTACCTCTGAGTCGGCCACTCCTGAG | |
| | PSEGSAPGSPAGS | | TCCGGTCCGGGCACGAGCACCGAGCCGAGCGAGG | |
| | PTSTEEGTSTEPS | | GTTCAGCCCCGGGTACCAGCACGGAGCCGTCCGA | |
| | EGSAPGTSTEPSE | | GGGTAGCGCACCGGGTTCTCCGGCGGGCTCCCCT | |
| | GSAPGTSESATPE | | ACGTCTACGGAAGAGGGTACGTCCACTGAACCTA | |
| | SGPGTSTEPSEGS | | GCGAGGGCAGCGCGCCAGGCACCAGCACTGAACC | |
| | APGTSESATPESG | | GAGCGAAGGCAGCGCACCTGGCACTAGCGAGTCT | |
| | PGSEPATSGSETP | | GCGACTCCGGAGAGCGGTCCGGGTACGAGCACGG | |
| | GTSTEPSEGSAPG | | AACCAAGCGAAGGCAGCGCCCCAGGTACCTCTGA | |
| | TSTEPSEGSAPGT | | ATCTGCTACCCCAGAATCTGGCCCGGGTTCCGAG | |
| | SESATPESGPGTS | | CCAGCTACCTCTGGTTCTGAAACCCCAGGTACTT | |

TABLE 7-continued

T-cell binding compositions

| Construct Name | Amino Acid Sequence | SEQ ID NO: | DNA Sequence | SEQ ID NO: |
|---|---|---|---|---|
| | ESATPESGPGSPA | | CCACTGAACCAAGCGAAGGTAGCGCTCCTGGCAC | |
| | GSPTSTEEGTSES | | TTCTACTGAACCATCCGAAGGTTCCGCTCCTGGT | |
| | ATPESGPGSEPAT | | ACGTCTGAAAGCGCTACCCCTGAAAGCGGCCCAG | |
| | SGSETPGTSESAT | | GCACCTCTGAAAGCGCTACTCCTGAGAGCGGTCC | |
| | PESGPGTSTEPSE | | AGGCTCTCCAGCAGGTTCTCCAACCTCCACTGAA | |
| | GSAPGTSTEPSEG | | GAAGGCACCTCTGAGTCTGCTACCCCTGAATCTG | |
| | SAPGTSTEPSEGS | | GTCCTGGCTCCGAACCTGCTACCTCTGGTTCCGA | |
| | APGTSTEPSEGSA | | AACTCCAGGTACCTCGGAATCTGCGACTCCGGAA | |
| | PGTSTEPSEGSAP | | TCTGGCCCGGGCACGAGCACGGAGCCGTCTGAGG | |
| | GTSTEPSEGSAPG | | GTAGCGCACCAGGTACCAGCACTGAGCCTTCTGA | |
| | SPAGSPTSTEEGT | | GGGCTCTGCACCGGGTACCTCCACGGAACCTTCG | |
| | STEPSEGSAPGTS | | GAAGGTTCTGCGCCGGGTACCTCCACTGAGCCAT | |
| | ESATPESGPGSEP | | CCGAGGGTTCAGCACCAGGTACTAGCACGGAACC | |
| | ATSGSETPGTSES | | GTCCGAGGGCTCTGCACCAGGTACGAGCACCGAA | |
| | ATPESGPGSEPAT | | CCGTCGGAGGGTAGCGCTCCAGGTAGCCCAGCGG | |
| | SGSETPGTSESAT | | GCTCTCCGACAAGCACCGAAGAAGGCACCAGCAC | |
| | PESGPGTSTEPSE | | CGAGCCGTCCGAAGGTTCCGCACCAGGTACAAGC | |
| | GSAPGTSESATPE | | GAGAGCGCGACTCCTGAATCTGGTCCGGGTAGCG | |
| | SGPGSPAGSPTST | | AGCCTGCAACCAGCGGTTCTGAGACGCCGGGCAC | |
| | EEGSPAGSPTSTE | | TTCCGAATCTGCGACCCCGGAGTCCGGTCCAGGT | |
| | EGSPAGSPTSTEE | | TCAGAGCCGGCGACGAGCGGTTCGGAAACGCCGG | |
| | GTSESATPESGPG | | GTACGTCTGAATCAGCCACGCCGGAGTCTGGTCC | |
| | TSTEPSEGSAPGT | | GGGTACCTCGACCGAACCAAGCGAAGGTTCGGCA | |
| | SESATPESGPGSE | | CCGGGTACTAGCGAGAGCGCAACCCCTGAAAGCG | |
| | PATSGSETPGTSE | | GTCCGGGCAGCCCGGCAGGTTCTCCAACCAGCAC | |
| | SATPESGPGSEPA | | CGAAGAAGGTTCCCCTGCTGGTAGCCCGACCTCT | |
| | TSGSETPGTSESA | | ACGGAGGAAGGTAGCCCTGCAGGTTCCCCAACTT | |
| | TPESGPGTSTEPS | | CTACTGAGGAAGGTACTTCTGAGTCCGCTACCCC | |
| | EGSAPGSPAGSPT | | AGAAAGCGGTCCTGGTACCTCCACTGAACCGTCT | |
| | STEEGTSESATPE | | GAAGGCTCTGCACCAGGCACTTCTGAGTCTGCTA | |
| | SGPGSEPATSGSE | | CTCCAGAAAGCGGCCCAGGTTCTGAACCAGCAAC | |
| | TPGTSESATPESG | | TTCTGGCTCTGAGACTCCAGGCACTTCTGAGTCC | |
| | PGSPAGSPTSTEE | | GCAACGCCTGAATCCGGTCCTGGTTCTGAACCAG | |
| | GSPAGSPTSTEEG | | CTACTTCCGGCAGCGAAACCCCAGGTACCTCTGA | |
| | TSTEPSEGSAPGT | | GTCTGCGACTCCAGAGTCTGGTCCTGGTACTTCC | |
| | SESATPESGPGTS | | ACTGAGCCTAGCGAGGGTTCCGCACCAGGTTCTC | |
| | ESATPESGPGTSE | | CGGCTGGTAGCCCGACCAGCACGGAGGAGGGTAC | |
| | SATPESGPGSEPA | | GTCTGAATCTGCAACGCCGGAATCGGGCCCAGGT | |
| | TSGSETPGSEPAT | | TCGGAGCCTGCAACGTCTGGCAGCGAAACCCCGG | |
| | SGSETPGSPAGSP | | GTACCTCCGAATCTGCTACACCGGAAAGCGGTCC | |
| | TSTEEGTSTEPSE | | TGGCAGCCCTGCTGGTTCTCCAACCTCTACCGAG | |
| | GSAPGTSTEPSEG | | GAGGGTTCACCGGCAGGTAGCCCGACTAGCACTG | |
| | SAPGSEPATSGSE | | AAGAAGGTACTAGCACGGAGCCGAGCGAGGGTAG | |
| | TPGTSESATPESG | | TGCTCCGGGTACGAGCGAGAGCGCAACGCCAGAG | |
| | PGTSTEPSEGSAP | | AGCGGTCCAGGCACCAGCGAATCGGCCACCCCTG | |
| | LSGRSDNHSPLGL | | AGAGCGGCCCAGGTACTTCTGAGAGCGCCACTCC | |
| | AGSGTAEAASASG | | TGAATCCGGCCCTGGTAGCGAGCCGGCAACCTCC | |
| | EVQLLESGGGLVQ | | GGCTCAGAAACTCCTGGTTCGGAACCAGCGACCA | |
| | PGGSLKLSCAASG | | GCGGTTCTGAAACTCCGGGTAGCCCGGCAGGCAG | |
| | FTENTYAMNWVRQ | | CCCAACGAGCACCGAAGAGGGTACCAGCACGGAA | |
| | APGKGLEWVARIR | | CCGAGCGAGGGTTCTGCCCCGGGTACTTCCACCG | |
| | SKYNNYATYYADS | | AACCATCGGAGGGCTCTGCACCTGGTAGCGAACC | |
| | VKDRFTISRDDSK | | TGCGACGTCTGGTTCTGAAACGCCGGGTACCAGC | |
| | NTAYLQMNNLKTE | | GAAAGCGCTACCCCAGAATCCGGTCCGGGCACTA | |
| | DTAVYYCVRHGNF | | GCACCGAGCCATCGGAGGGCTCCGCACCActgTC | |
| | GNSYVSWFAYWGQ | | AggtCGTtctGATaacCATtccCCActgGGTctg | |
| | GTLVTVSSGATPP | | GCTGGGTCTGGCACCGCCGAAGCAGCTagcgcct | |
| | ETGAETESPGETT | | ctGGCGAGGTTCAGTTGTTGGAAAGCGGGGGCGG | |
| | GGSAESEPPGEGE | | GCTTGTCCAACCTGGAGGTTCATTAAAATTGAGC | |
| | LVVTQEPSLTVSP | | TGTGCAGCCTCCGGATTCACCTTTAACACGTATG | |
| | GGTVTLTCRSSTG | | CAATGAACTGGGTCCGTCAAGCGCCCGGTAAGGG | |
| | AVTTSNYANWVQQ | | GCTGGAGTGGGTAGCTCGCATCCGCTCGAAGTAT | |
| | KPGQAPRGLIGGT | | AATAATTACGCAACCTACTACGCAGACAGTGTCA | |
| | NKRAPGTPARFSG | | AAGATCGCTTCACTATCTCACGCGACGACAGTAA | |
| | SLLGGKAALTLSG | | GAACACGGCCTACTTACAGATGAACAATCTTAAA | |
| | VQPEDEAEYYCAL | | ACGGAGGACACCGCTGTCTACTACTGCGTGCGCC | |
| | WYSNLWVFGGGTK | | ACGGGAATTTCGGTAACTCTTATGTAAGTTGGTT | |
| | LTVL | | CGCATATTGGGGACAAGGTACGTTGGTAACCGTA | |
| | | | TCCAGCggtgcgaccccgccggaaaccggtgcgg | |
| | | | aaaccgaaagcccgggtgaaaccaccggtggcag | |
| | | | cgcggagagcgaaccgccgggtgaaggtGAACTG | |
| | | | GTCGTCACGCAGGAGCCGTCCCTTACCGTTTCAC | |
| | | | CAGGTGGAACAGTGACTCTGACGTGTCGCTCCTC | |
| | | | CACTGGGGCGGTTACAACTTCCAATTATGCTAAT | |

TABLE 7-continued

T-cell binding compositions

| Construct Name | Amino Acid Sequence | SEQ ID NO: | DNA Sequence | SEQ ID NO: |
|---|---|---|---|---|
| | | | TGGGTCCAGCAGAAGCCGGGCCAAGCCCCTCGCG | |
| | | | GGTTGATTGGCGGCACCAACAAACGTGCTCCAGG | |
| | | | GACACCTGCCCGTTTTTCGGGCTCCTTATTGGGG | |
| | | | GGCAAAGCTGCACTGACGTTGTCTGGAGTTCAGC | |
| | | | CGGAGGATGAGGCAGAGTATTACTGCGCATTGTG | |
| | | | GTATTCTAATTTATGGGTTTTTGGAGGCGGCACA | |
| | | | AAGCTGACCGTCCTG | |
| TBP-16 | HHHHHHGGSPAGS | 445 | CATCACCACCATCATCACggAGGTAGCCCAGCTG | 461 |
| | PTSTEEGTSESAT | | GTAGCCCAACCTCTACCGAAGAAGGTACCTCTGA | |
| | PESGPGTSTEPSE | | ATCCGCTACTCCAGAATCCGGTCCTGGTACTAGC | |
| | GSAPGSPAGSPTS | | ACTGAGCCAAGCGAAGGTTCTGCTCCAGGCTCCC | |
| | TEEGTSTEPSEGS | | CGGCAGGTAGCCCTACCTCTACCGAAGAGGGCAC | |
| | APGTSTEPSEGSA | | TAGCACCGAACCATCTGAGGGTTCCGCTCCTGGC | |
| | PGTSESATPESGP | | ACCTCCACTGAACCGTCCGAAGGCAGTGCTCCGG | |
| | GSEPATSGSETPG | | GTACTTCCGAAAGCGCAACTCCGGAATCCGGCCC | |
| | SEPATSGSETPGS | | TGGTTCTGAGCCTGCTACTTCCGGCTCTGAAACT | |
| | PAGSPTSTEEGTS | | CCAGGTAGCGAGCCAGCGACTTCTGGTTCTGAAA | |
| | ESATPESGPGTST | | CTCCAGGTTCACCGGCGGGTAGCCCGACGAGCAC | |
| | EPSEGSAPGTSTE | | GGAGGAAGGTACCTCTGAGTCGGCCACTCCTGAG | |
| | PSEGSAPGSPAGS | | TCCGGTCCGGGCACGAGCACCGAGCCGAGCGAGG | |
| | PTSTEEGTSTEPS | | GTTCAGCCCCGGGTACCAGCACGGAGCCGTCCGA | |
| | EGSAPGTSTEPSE | | GGGTAGCGCACCGGGTTCTCCGGCGGGCTCCCCT | |
| | GSAPGTSESATPE | | ACGTCTACGGAAGAGGGTACGTCCACTGAACCTA | |
| | SGPGTSTEPSEGS | | GCGAGGGCAGCGCGCCAGGCACCAGCACTGAACC | |
| | APGTSESATPESG | | GAGCGAAGGCAGCGCACCTGGCACTAGCGAGTCT | |
| | PGSEPATSGSETP | | GCGACTCCGGAGAGCGGTCCGGGTACGAGCACGG | |
| | GTSTEPSEGSAPG | | AACCAAGCGAAGGCAGCGCCCCAGGTACCTCTGA | |
| | TSTEPSEGSAPGT | | ATCTGCTACCCCAGAATCTGGCCCGGGTTCCGAG | |
| | SESATPESGPGTS | | CCAGCTACCTCTGGTTCTGAAACCCCAGGTACTT | |
| | ESATPESGPGSPA | | CCACTGAACCAAGCGAAGGTAGCGCTCCTGGCAC | |
| | GSPTSTEEGTSES | | TTCTACTGAACCATCCGAAGGTTCCGCTCCTGGT | |
| | ATPESGPGSEPAT | | ACGTCTGAAAGCGCTACCCCTGAAAGCGGCCCAG | |
| | SGSETPGTSESAT | | GCACCTCTGAAAGCGCTACTCCTGAGAGCGGTCC | |
| | PESGPGTSTEPSE | | AGGCTCTCCAGCAGGTTCTCCAACCTCCACTGAA | |
| | GSAPGTSTEPSEG | | GAAGGCACCTCTGAGTCTGCTACCCCTGAATCTG | |
| | SAPGTSTEPSEGS | | GTCCTGGCTCCGAACCTGCTACCTCTGGTTCCGA | |
| | APGTSTEPSEGSA | | AACTCCAGGTACCTCGGAATCTGCGACTCCGGAA | |
| | PGTSTEPSEGSAP | | TCTGGCCCGGGCACGAGCACGGAGCCGTCTGAGG | |
| | GTSTEPSEGSAPG | | GTAGCGCACCAGGTACCAGCACTGAGCCTTCTGA | |
| | SPAGSPTSTEEGT | | GGGCTCTGCACCGGGTACCTCCACGGAACCTTCG | |
| | STEPSEGSAPGTS | | GAAGGTTCTGCGCCGGGTACCTCCACTGAGCCAT | |
| | ESATPESGPGSEP | | CCGAGGGTTCAGCACCAGGTACTAGCACGGAACC | |
| | ATSGSETPGTSES | | GTCCGAGGGCTCTGCACCAGGTACGAGCACCGAA | |
| | ATPESGPGSEPAT | | CCGTCGGAGGGTAGCGCTCCAGGTAGCCCAGCGG | |
| | SGSETPGTSESAT | | GCTCTCCGACAAGCACCGAAGAAGGCACCAGCAC | |
| | PESGPGTSTEPSE | | CGAGCCGTCCGAAGGTTCCGCACCAGGTACAAGC | |
| | GSAPGTSESATPE | | GAGAGCGCGACTCCTGAATCTGGTCCGGGTAGCG | |
| | SGPGSPAGSPTST | | AGCCTGCAACCAGCGGTTCTGAGACGCCGGGCAC | |
| | EEGSPAGSPTSTE | | TTCCGAATCTGCGACCCCGGAGTCCGGTCCAGGT | |
| | EGSPAGSPTSTEE | | TCAGAGCCGGCGACGAGCGGTTCGGAAACGCCGG | |
| | GTSESATPESGPG | | GTACGTCTGAATCAGCCACGCCGGAGTCTGGTCC | |
| | TSTEPSEGSAPGT | | GGGTACCTCGACCGAACCAAGCGAAGGTTCGGCA | |
| | SESATPESGPGSE | | CCGGGTACTAGCGAGAGCGCAACCCCTGAAAGCG | |
| | PATSGSETPGTSE | | GTCCGGGCAGCCCGGCAGGTTCTCCAACCAGCAC | |
| | SATPESGPGSEPA | | CGAAGAAGGTTCCCCTGCTGGTAGCCCGACCTCT | |
| | TSGSETPGTSESA | | ACGGAGGAAGGTAGCCCTGCAGGTTCCCCAACTT | |
| | TPESGPGTSTEPS | | CTACTGAGGAAGGTACTTCTGAGTCCGCTACCCC | |
| | EGSAPGSPAGSPT | | AGAAAGCGGTCCTGGTACCTCCACTGAACCGTCT | |
| | STEEGTSESATPE | | GAAGGCTCTGCACCAGGCACTTCTGAGTCTGCTA | |
| | SGPGSEPATSGSE | | CTCCAGAAAGCGGCCCAGGTTCTGAACCAGCAAC | |
| | TPGTSESATPESG | | TTCTGGCTCTGAGACTCCAGGCACTTCTGAGTCC | |
| | PGSPAGSPTSTEE | | GCAACGCCTGAATCCGGTCCTGGTTCTGAACCAG | |
| | GSPAGSPTSTEEG | | CTACTTCCGGCAGCGAAACCCCAGGTACCTCTGA | |
| | TSTEPSEGSAPGT | | GTCTGCGACTCCAGAGTCTGGTCCTGGTACTTCC | |
| | SESATPESGPGTS | | ACTGAGCCTAGCGAGGGTTCCGCACCAGGTTCTC | |
| | ESATPESGPGTSE | | CGGCTGGTAGCCCGACCAGCACGGAGGAGGGTAC | |
| | SATPESGPGSEPA | | GTCTGAATCTGCAACGCCGGAATCGGGCCCAGGT | |
| | TSGSETPGSEPAT | | TCGGAGCCTGCAACGTCTGGCAGCGAAACCCCGG | |
| | SGSETPGSPAGSP | | GTACCTCCGAATCTGCTACACCGGAAAGCGGTCC | |
| | TSTEEGTSTEPSE | | TGGCAGCCCTGCTGGTTCTCCAACCTCTACCGAG | |
| | GSAPGTSTEPSEG | | GAGGGTTCACCGGCAGGTAGCCCGACTAGCACTG | |
| | SAPGSEPATSGSE | | AAGAAGGTACTAGCACGGAGCCGAGCGAGGGTAG | |
| | TPGTSESATPESG | | TGCTCCGGGTACGAGCGAGAGCGCAACGCCAGAG | |

TABLE 7-continued

T-cell binding compositions

| Construct Name | Amino Acid Sequence | SEQ ID NO: | DNA Sequence | SEQ ID NO: |
|---|---|---|---|---|
| | PGTSTEPSEGSAP<br>LSGRSDNHVPLSL<br>KMGGTAEAASASG<br>EVQLLESGGGLVQ<br>PGGSLKLSCAASG<br>FTFNTYAMNWVRQ<br>APGKGLEWVARIR<br>SKYNNYATYYADS<br>VKDRFTISRDDSK<br>NTAYLQMNNLKTE<br>DTAVYYCVRHGNF<br>GNSYVSWFAYWGQ<br>GTLVTVSSGATPP<br>ETGAETESPGETT<br>GGSAESEPPGEGE<br>LVVTQEPSLTVSP<br>GGTVTLTCRSSTG<br>AVTTSNYANWVQQ<br>KPGQAPRGLIGGT<br>NKRAPGTPARFSG<br>SLLGGKAALTLSG<br>VQPEDEAEYYCAL<br>WYSNLWVEGGGTK<br>LTVL | | AGCGGTCCAGGCACCAGCGAATCGGCCACCCCTG<br>AGAGCGGCCCAGGTACTTCTGAGAGCGCCACTCC<br>TGAATCCGGCCCTGGTAGCGAGCCGGCAACCTCC<br>GGCTCAGAAACTCCTGGTTCGGAACCAGCGACCA<br>GCGGTTCTGAAACTCCGGGTAGCCCGGCAGGCAG<br>CCCAACGAGCACCGAAGAGGGTACCAGCACGGAA<br>CCGAGCGAGGGTTCTGCCCCGGGTACTTCCACCG<br>AACCATCGGAGGGCTCTGCACCTGGTAGCGAACC<br>TGCGACGTCTGGTTCTGAAACGCCGGGTACCAGC<br>GAAAGCGCTACCCCAGAATCCGGTCCGGGCACTA<br>GCACCGAGCCATCGGAGGGCTCCGCACCActgTC<br>AggtCGTtctGATaacCATgttCCActgTCTctg<br>AAAatgGGTGGCACCGCCGAAGCAGCTagcgcct<br>ctGGCGAGGTTCAGTTGTTGGAAAGCGGGGGCGG<br>GCTTGTCCAACCTGGAGGTTCATTAAAATTGAGC<br>TGTGCAGCCTCCGGATTCACCTTTAACACGTATG<br>CAATGAACTGGGTCCGTCAAGCGCCCGGTAAGGG<br>GCTGGAGTGGGTAGCTCGCATCCGCTCGAAGTAT<br>AATAATTACGCAACCTACTACGCAGACAGTGTCA<br>AAGATCGCTTCACTATCTCACGCGACGACAGTAA<br>GAACACGGCCTACTTACAGATGAACAATCTTAAA<br>ACGGAGGACACCGCTGTCTACTACTGCGTGCGCC<br>ACGGGAATTTCGGTAACTCTTATGTAAGTTGGTT<br>CGCATATTGGGGACAAGGTACGTTGGTAACCGTA<br>TCCAGCggtgcgaccccgccggaaaccggtgcgg<br>aaaccgaaagcccgggtgaaaccaccggtggcag<br>cgcggagagcgaaccgccgggtgaaggtGAACTG<br>GTCGTCACGCAGGAGCCGTCCCTTACCGTTTCAC<br>CAGGTGGAACAGTGACTCTGACGTGTCGCTCCTC<br>CACTGGGGCGGTTACAACTTCCAATTATGCTAAT<br>TGGGTCCAGCAGAAGCCGGGCCAAGCCCCTCGCG<br>GGTTGATTGGCGGCACCAACAAACGTGCTCCAGG<br>GACACCTGCCCGTTTTTCGGGCTCCTTATTGGGG<br>GGCAAAGCTGCACTGACGTTGTCTGGAGTTCAGC<br>CGGAGGATGAGGCAGAGTATTACTGCGCATTGTG<br>GTATTCTAATTTATGGGTTTTTGGAGGCGGCACA<br>AAGCTGACCGTCCTG | |

5. Flexible Linkers

In another aspect, the present invention provides flexible linkers to join the respective binding domains of the subject compositions. In some embodiments, the invention provides chimeric polypeptide assembly compositions comprising a first scFv and a second scFv in which the VL and VH of each scFv are linked together by a long linker of hydrophilic amino acids selected from the sequences set forth in Table 8 and the scFv are linked together by a short linker of hydrophilic amino acids selected from the group of sequences set forth in Table 9. In one embodiment, the long linker used to link the VL and VH is L7 of Table 8 and the intermolecular linker that links the two scFv is S-1 of Table 9. In another embodiment, the invention provides chimeric polypeptide assembly compositions comprising a single chain diabody in which after folding, the first domain (VL or VH) is paired with the last domain (VH or VL) to form one scFv and the two domains in the middle are paired to form the other scFv in which the first and second domains, as well as the third and last domains, are linked together by a short linker of hydrophilic amino acids selected from the sequences set forth in Table 9 and the second and the third variable domains are linked by a long linker selected from Table 8. As will be appreciated by one of skill in the art, the selection of the short linker and long linker is to prevent the incorrect pairing of adjacent variable domains, thereby facilitating the formation of the diabody configuration.

TABLE 8

Intramolecular Long Linkers

| Linker # | Name | Amino Acid Sequence | SEQ ID NO: |
|---|---|---|---|
| L1 | (G4S)3 | GGGGSGGGGSGGGGS | 462 |
| L2 | MT110_18 | GEGTSTGSGGSGGSGGAD | 463 |
| L3 | MT103_18 | VEGGSGGSGGSGGSGGVD | 464 |

TABLE 8-continued

| Intramolecular Long Linkers | | | |
|---|---|---|---|
| Linker # | Name | Amino Acid Sequence | SEQ ID NO: |
| L4 | UCHT1_29 | RTSGPGDGGKGGPGKGPGGEGTKGTGPGG | 465 |
| L5 | Y30 | GSGEGSEGEGGGEGSEGEGSGEGGEGEGSG | 466 |
| L6 | Y32 | TGSGEGSEGEGGGEGSEGEGSGEGGEGEGSGT | 467 |
| L7 | G1_30_3 | GATPPETGAETESPGETTGGSAESEPPGEG | 468 |
| L8 | G9_30_1 | GSAAPTAGTTPSASPAPPTGGSSAAGSPST | 469 |
| L9 | Y30_modified | GEGGESGGSEGEGSGEGEGGSGGEGESEGG | 470 |
| L10 | G1_30_1 | STETSPSTPTESPEAGSGSGSPESPSGTEA | 471 |
| L11 | G1_30_2 | PTGTTGEPSGEGSEPEGSAPTSSTSEATPS | 472 |
| L12 | G1_30_4 | SESESEGEAPTGPGASTTPEPSESPTPETS | 473 |
| L13 | UCHT1_modified | PEGGESGEGTGPGTGGEPEGEGGPGGEGGT | 474 |

TABLE 9

| Intermolecular Short Linkers | | |
|---|---|---|
| Name | Amino Acid Sequence | SEQ ID NO: |
| S-1 | SGGGGS | 475 |
| S-2 | GGGGS | 476 |
| S-3 | GGS | |
| S-4 | GSP | |

6. Chimeric Polypeptide Assembly Configurations

It is an object of the invention to provide chimeric polypeptide assembly compositions that are designed and created in prodrug form in order to confer certain structural, activity, pharmaceutical and pharmacologic properties. The design of the subject compositions was driven by at least three important properties; 1) providing compositions having bispecific binding domains with the capability to concurrently bind an effector cell to a target cell with the resultant formation of an immunological synapse; 2) providing compositions with a bulking moiety that i) shields the binding domains and reduces binding affinity for the target antigens when the composition is in an intact prodrug form, ii) provides enhanced half-life when administered to a subject, iii) reduces extravasation in normal tissues and organs compared to diseased tissues (e.g., tumor), and iv) has an increased safety profile compared to conventional bispecific cytotoxic antibody therapeutics; and 3) is capable of being activated when cleaved by one or more mammalian proteases when in proximity of diseased tissues, thereby releasing the bispecific binding domain such that it regains its full binding affinity potential for the target antigens. The design of the subject compositions takes advantage of the properties of XTEN and the peptidic release segment (RS) components, and their positioning relative to the first portion bispecific binding domains achieves the foregoing properties.

Without being bound to a particular theory, it is believed that using the bispecific binding domain format as described above, the released binding domains are capable of killing target cells by recruitment of cytotoxic effector cells without any need for pre- and/or co-stimulation. Further, the independence from pre- and/or co-stimulation of the effector cell may substantially contribute to the exceptionally high cytotoxicity mediated by the released binding domains. In some embodiments, the released second binding domain is designed with binding specificities such that it has the capability to target cytotoxic effector cells (e.g., T cells, NK cells, cytokine induced killer cell (CIK cell)), to preselected surface antigens on tumor cells in a subject while the first binding domain is designed with binding specificities to tumor marker antigens associated with tumor cells, thereby effecting an immunological synapse and a selective, directed, and localized effect of released cytokines and effector molecules against the target tumor, with the result that tumor cells are damaged or destroyed, resulting in antitumor activity and therapeutic benefit to a subject. In one embodiment, the released second binding domain binds to an effector cell antigen that is capable of modulating one or more functions of an effector cell, resulting in or contributed to the cytolytic effect on the target tumor cell. The effector cell antigen can by expressed by the effector cell or other cells. In some embodiments, the effector cell antigen is expressed on cell surface of the effector cell. Non-limiting examples are CD3, CD4, CD8, CD25, CD38, CD69, CD45RO, CD57, CD95, CD107, and CD154. In other embodiments, the effector cell antigen is a Th1 cytokine selected from IL2, IL10, IL12, IFNγ, and TNFα. Thus, it will be understood by one of skill in the art that the configurations of the subject compositions are intended to selectively or disproportionately deliver the active form of the composition to the target tumor tissue or cancer cell, compared to healthy tissue or healthy cells in a subject in which the composition is administered, with resultant therapeutic benefit. As is evident from the foregoing, the invention provides a large family of polypeptides in designed configurations to effect the desired properties.

In the case of XTEN as a bulking moiety, several unique and beneficial physicochemical and pharmacologic properties are conferred to the subject compositions that are XTENylated. Non-limiting examples of the enhanced properties of the subject compositions include increases in the overall solubility and metabolic stability, reduced susceptibility to proteolysis in circulation, reduced immunogenicity, reduced rate of absorption when administered subcutaneously or intramuscularly, reduced clearance by the kidney, reduced toxicity, the shielding effect of XTEN on the first portion binding moieties until released by cleavage of the RS, and enhanced pharmacokinetic properties. In particular, it is specifically contemplated that the subject compositions are designed such that they have an enhanced therapeutic index and reduced toxicity or side effects, achieved by a combination of the shielding effect and steric hindrance of XTEN on binding affinity over the first portion binding domains in the prodrug form, yet are able to release the bispecific binding domains (achieved by inclusion of a peptidyl cleavage sequence in the RS composition) in proximity to or within a target tissue (e.g., a tumor) that produces a protease for which the RS is a substrate.

In one aspect, XTEN are used as a carrier in the compositions, the invention taking advantage of the discovery that increasing the length of the non-repetitive, unstructured polypeptides enhances the unstructured nature of the XTENs and correspondingly enhances the physicochemical and pharmacokinetic properties of compositions comprising the XTEN carrier. In general, XTEN with cumulative lengths longer that about 400 residues incorporated into the composition results in longer half-life compared to shorter cumulative lengths, e.g., shorter than about 290 residues. Not to be bound by a particular theory, the XTEN can adopt open conformations due to the electrostatic repulsion between individual charges of incorporated charged residues in the XTEN as well as because of the inherent flexibility imparted by the particular hydrophilic amino acids in the sequence that lack potential to confer secondary structure. The result is that the subject XTEN are useful, in part, because they impart a high hydrodynamic radius to the resulting composition; a property that confers a corresponding increased apparent molecular weight to the XTENylated composition compared to the composition without the XTEN. The XTENylation results in compositions that have increased hydrodynamic radii, increased apparent molecular weight, and increased apparent molecular weight factor compared to a protein not linked to an XTEN. For example, the XTEN can effectively enlarge the hydrodynamic radius of the composition beyond the glomerular pore size of approximately 3-5 nm (corresponding to an apparent molecular weight of about 70 kDa) (Caliceti. 2003. Pharmacokinetic and biodistribution properties of poly(ethylene glycol)-protein conjugates. Adv Drug Deliv Rev 55:1261-1277), resulting in reduced renal clearance of circulating proteins with a corresponding increase in terminal half-life. The increased hydrodynamic radius imparted by XTEN also reduces the extravasation of intact prodrug form of the chimeric polypeptide assembly compositions from the circulatory system in areas of normal, healthy tissue with average pore sizes of 5-12 nm, but permits the exit of the intact composition molecules in blood vessels that permeate tumors, where the epithelial cell junctions are more porous. It is long been known that various functions of tumor vasculature are impaired, such as a higher vascular permeability than normal vessels (Duran-Reynals, F. Studies on the localization of dyes and foreign proteins in normal and malignant tissue. Am J Cancer 35:98-107 (1939); Babson A L, Winnick T. Protein transfer in tumor-bearing rats. Cancer Res 14:606-611 (1954)). These impaired functions contributed to the higher concentration of plasma proteins detected in tumor tissues than in normal tissues; a phenomenon was elucidated by Maeda and colleagues (Matsumura Y, Maeda H. A new concept for macromolecular therapeutics in cancer chemotherapy: mechanism of tumoritropic accumulation of proteins and the antitumor agent smancs. Cancer Res 46:6387-6392 (1986); Maeda H, Matsumura Y. Tumoritropic and lymphotropic principles of macromolecular drugs. Crit Rev Ther Drug Carrier Syst 6:193-210 (1989), who described it as the enhanced permeability and retention effect, resultings from a combination of the increased permeability of tumor blood vessels and the decreased rate of clearance of functional lymphatic vessels in the tumor, with the net result that macromolecules accumulate in tumors. It is generally known that the physiologic upper limit of pore size in the capillary walls of most non-sinusoidal blood capillaries to the passage of non-endogenous macromolecules ranges between 5 and 12 nm (Hemant Sarin. Physiologic upper limits of pore size of different blood capillary types and another perspective on the dual pore theory of microvascular permeability. J Angiogenes Res. 2010; 2:14), while inter-endothelial cell gaps in the blood-tumor barrier of both brain tumors and peripheral tumors have been reported to range between 40 nm and 200 nm or greater in diameter (Sarin, H. et al. Physiologic upper limit of pore size in the blood-tumor barrier of malignant solid tumors. J. Translational Medicine 2009 7:51). In an object of the invention, the subject chimeric polypeptide assembly compositions were designed to take advantage of this differential in pore size by the addition of the bulking moiety, e.g., XTEN, such that extravasation of the intact chimeric polypeptide assembly in normal tissue is reduced, but in the leaky environment of the tumor vasculature or other areas of inflammation, the intact assembly can extravasate and be activated by the proteases in the tumor environment, releasing the first portion comprising the binding domains to the effector and target cells. In the case of the RS of the chimeric polypeptide assembly, the design takes advantage of the circumstance that when a chimeric polypeptide assembly is in proximity to diseased tissues; e.g., a tumor, that elaborates one or more proteases, the RS sequences that are susceptible to the one or more proteases expressed by the tumor are capable of being cleaved by the proteases (described more fully, above). The action of the protease cleaves the release segment (RS) of the composition, releasing the first portion binding domains from the composition, decreasing the molecular weight and hydrodynamic radius of the released first portion bispecific binding domains. As will be appreciated, the decrease in molecular weight and hydrodynamic radius of the composition also confers the property that the released first portion bispecific binding domains are able to more freely move in solution, move through smaller pore spaces in tissue and tumors, and extraysate more readily from the larger pores of the tumor vasculature into the tumor, resulting in the attachment and linkage of the effector cell and the tumor cell. Such property can be measured by different assays. In one embodiment, wherein the RS of the chimeric polypeptide assembly is cleaved by a mammalian protease, upon cleavage and release of the first portion bispecific binding domains and the third portion from said composition, said first portion has a diffusion coefficient in phosphate buffered saline that is at least 2-fold, 3-fold, 4-fold, 5-fold, 6-fold, 7-fold, 8-fold, 9-fold, 10-fold, 20-fold, 50-fold, or 100-fold greater compared to the intact chimeric polypeptide assembly composition. In another embodiment, the apparent molecular weight of the intact composition is at least 2-fold, at least 3-fold, at least 4-fold, or at least 5-fold, or at least 10-fold greater than the first portion released by cleavage of the RS by a mammalian protease, when the apparent molecular weight is determined by size exclusion chromatography (SEC). In another embodiment, the hydrodynamic radius of the intact chimeric polypeptide assembly composition is at least 2-fold, or at least 3-fold, or at least 4-fold, or at least 5-fold, or at least 10-fold greater than the first portion released by cleavage of the RS by a mammalian protease, when the hydrodynamic radius is determined by size exclusion chromatography (SEC). In another embodiment, the invention provides a chimeric polypeptide assembly, wherein upon cleavage of the second portion to release said first portion and said third portion from said chimeric polypeptide assembly, the hydrodynamic radius of the released first portion is less than about 30%, or less than about 40%, or less than about 50% of the hydrodynamic radius of the intact chimeric polypeptide assembly, when hydrodynamic radius is assessed by size exclusion chromatography. In another embodiment, the invention provides a chimeric polypeptide assembly, wherein upon cleavage of the second portion to release said first portion and said third portion from said chimeric polypeptide assembly, the hydrodynamic radius of the released first portion is less than about 5 nm, or less than about 4 nm, or less than about 3 nm when hydrodynamic radius is determined by size exclusion chromatography. In another embodiment, the invention provides a chimeric polypeptide assembly, wherein the released first portion having a hydrodynamic radius of less than about 5 nm, or less than about 4 nm, or less than about 3 nm, when hydrodynamic radius is determined by size exclusion chromatography, has greater ability to penetrate a tumor tissue compared to an intact chimeric polypeptide assembly. In another embodiment, the invention provides a chimeric polypeptide assembly, wherein the hydrodynamic radius of the intact chimeric polypeptide assembly is greater than about 8 nm, or greater than about 9 nm, or greater than about 10 nm when hydrodynamic radius is determined by size exclusion chromatography, and wherein the intact chimeric polypeptide assembly is less able to extravasate from vasculature of normal tissue of a subject compared to vasculature of a tumor tissue.

It is contemplated that the subject compositions will, by their design and linkage to XTEN, have enhanced pharmacokinetic properties when administer to a subject compared to the corresponding first portion binding domains not linked to XTEN. In one embodiment, a chimeric polypeptide assembly composition exhibits a terminal half-life in a subject that is increased, upon or following administration to a subject, in comparison to the corresponding first portion not linked to the composition, by at least about 2-fold, 3-fold, 4-fold, 5-fold, 6-fold, 7-fold, 8-fold, 9-fold, 10-fold, 20-fold, 30-fold, 40-fold, or 100-fold greater. In another embodiment, a chimeric polypeptide assembly composition exhibits increased area under the curve (AUC), upon or following administration to a subject, in comparison to the corresponding first portion not linked to the composition, of at least 25%, 50%, 100%, 200%, or at least 300% or more. In another embodiment, a chimeric polypeptide assembly composition exhibits a lower volume of distribution, upon or following administration to a subject, in comparison to the corresponding first portion not linked to the composition, of at least 25% lower, or 50%, or 100%, or 200%, or at least 300% lower. In one embodiment, a chimeric polypeptide assembly composition exhibits a terminal half-life of at least about 20 h, or at least about 30 h, or at least about 32 h, or at least about 48 h, or at least about 72 h, or at least about 96 h, or at least about 120 h, or at least about 144 h, or at least about 7 days, or at least about 10 days, or at least about 14 days following administration to a subject. In another aspect, it is specifically contemplated that because of the design of the subject chimeric polypeptide assembly compositions that are preferentially activated by protease(s) in association with a diseased tissue such as, but not limited to, a tumor, the concentration of the released first portion in the circulation of a subject will be low, thereby contributing to the improved safety profile and lower incidence of side effects compared to bispecific compositions not having the protective bulking moiety and release segment. In one embodiment, the invention provides a chimeric polypeptide assembly, wherein the plasma Cmax concentration of the released first portion upon or following a single administration of the chimeric polypeptide composition to a subject does not exceed about 0.01 ng/ml, or about 0.03 ng/ml, or about 0.1 ng/ml, or about 0.3 ng/ml, or about 1 ng/ml, or about 10 ng/ml, or about 100 ng/ml. In another embodiment, the invention provides a chimeric polypeptide assembly, wherein the plasma Cmax concentration of the released first portion upon or following a single administration of the chimeric polypeptide composition to a subject is a least 3-fold lower, or at least 10-fold lower, or at least 30-fold lower, or at least 100-fold lower than the plasma levels of the intact chimeric polypeptide assembly in the same subject. In the foregoing embodiments of the paragraph, the subject is a mouse, or a rat, or a dog, or a monkey, or a human.

In another embodiment, a chimeric polypeptide assembly composition exhibits slower absorption after subcutaneous or intramuscular injection in a subject, in comparison to the corresponding first portion not linked to the composition, such that the Cmax is at least 25%, 50%, 100%, 200%, or at least 300% lower, which, in turn, results in reductions in adverse effects of the chimeric polypeptide assembly compositions that, collectively, results in an increased period of time that a conjugation composition administered to a subject provides or retains therapeutic activity.

In another aspect, it is specifically contemplated that the XTEN of the subject chimeric polypeptide chimeric polypeptide assembly compositions provides both steric hindrance and a shielding effect for the binding domains of the first portion of the compositions such that both the effector cell binding component and the target cell binding component of the intact prodrug form have a reduced ability to interact with their respective ligands, but that upon cleavage of the RS by a protease and release of the XTEN and the conversion of the prodrug form of the assembly to the activated form, the optimal binding capacity of the released bispecific binding components is restored. Thus, the XTEN of the intact chimeric polypeptide assembly composition inhibits the binding of the binding domains to the tumor-specific marker or an antigen of a target cell antigen (e.g., EpCAM or HER2) and/or the effector cell antigen (e.g., CD3 T-cell antigen) compared to the binding domains released by the cleavage of the RS by the protease. Conversely, the binding domains of the released first portion from the composition by the action of the protease have a higher binding affinity for their respective ligands compared to the binding domains of the intact chimeric polypeptide assembly composition. It is an object of the invention that the binding affinity of each binding domain of the released first portion from the chimeric polypeptide assembly composition is greater for the respective target ligands compared to the binding domains of the intact composition, such as when assayed in an in vitro binding assay as described herein. In one embodiment, the binding affinity of the effector cell binding domain released from the composition by cleavage of the RS by a protease is at least 2-fold, or at least 3-fold, or at least 4-fold, or at least 5-fold, or at least 6-fold, or at least 7-fold, or at least 8-fold, or at least 9-fold, or at least 10-fold, or at least 20-fold greater for the effector cell antigen compared to the effector cell binding domain of the intact chimeric polypeptide assembly composition, as measured in an in vitro cell assay with an effector cell having said effector cell antigen on the cell surface of said cell or in an ELISA with bound effector cell antigen. In one embodiment, the effector cell antigen is CD3. In other embodiments, the binding affinity of the tumor cell binding domain released from the composition by cleavage of the RS by a protease is at least 2-fold, or at least 3-fold, or at least 4-fold, or at least 5-fold, or at least 6-fold, or at least 7-fold, or at least 8-fold, or at least 9-fold, or at least 10-fold, or at least 20-fold greater for the tumor-specific marker or target cell antigen compared to the tumor cell binding domain of the intact chimeric polypeptide assembly composition, as measured in an in vitro cell assay with an tumor cell having said antigen on the cell surface of said cell or in an ELISA with bound effector cell antigen. In one embodiment of the foregoing, the tumor-specific marker or an antigen of a target cell is selected from the group consisting of alpha 4 integrin, Ang2, B7-H3, B7-H6, CEACAM5, cMET, CTLA4, FOLR1, EpCAM, CCR5, CD19, HER2, HER2 neu, HER3, HER4, HER1 (EGFR), PD-L1, PSMA, CEA, MUC1(mucin), MUC-2, MUC3, MUC4, MUC5AC, MUC5B, MUC7, MUC16 βhCG, Lewis-Y, CD20, CD33, CD38, CD30, CD56 (NCAM), CD133, ganglioside GD3; 9-O-Acetyl-GD3, GM2, Globo H, fucosyl GM1, GD2, carbonicanhydrase IX, CD44v6, Sonic Hedgehog (Shh), Wue-1, plasma cell antigen 1, melanoma chondroitin sulfate proteoglycan (MCSP), CCR8, 6-transmembrane epithelial antigen of prostate (STEAP), mesothelin, A33 antigen, prostate stem cell antigen (PSCA), Ly-6, desmoglein 4, fetal acetylcholine receptor (fnAChR), CD25, cancer antigen 19-9 (CA19-9), cancer antigen 125 (CA-125), Muellerian inhibitory substance receptor type II (MISIIR), sialylated Tn antigen (s TN), fibroblast activation antigen (FAP), endosialin (CD248), epidermal growth factor receptor variant III (EGFRvIII), tumor-associated antigen L6 (TAL6), SAS, CD63, TAG72, Thomsen-Friedenreich antigen (TF-antigen), insulin-like growth factor I receptor (IGF-IR), Cora antigen, CD7, CD22, CD70, CD79a, CD79b, G250, MT-MMPs, F19 antigen, CA19-9, CA-125, alpha-fetoprotein (AFP), VEGFR1, VEGFR2, DLK1, SP17, ROR1, and EphA2. It is specifically contemplated in the embodiments of the paragraph that the shielding effect of the XTEN applies to both binding domains of the foregoing embodiments of the intact, prodrug form of the chimeric polypeptide assembly, and that upon release of the XTEN from the chimeric polypeptide assembly composition by cleavage of the RS, the full binding capacity of the respective binding domains is restored.

It is an object of the invention that the addition of the bulking moiety to the composition results in a shielding effect in the intact chimeric polypeptide assembly composition and the concomitant reduction in binding to T cells and target tissues results in reduced production of Th1 T-cell associated cytokines or other proinflammatory mediators during systemic exposure when administered to a subject such that the overall side-effect and safety profile is improved compared to bispecific binding compositions not linked to a binding moiety such as XTEN. As an important component of cellular immunity, the production of IL-2, TNF-alpha, and IFN-gamma are hallmarks of a Th1 response (Romagnani S. T-cell subsets (Th1 versus Th2). Ann Allergy Asthma Immunol. 2000. 85(1):9-18), particularly in T cells stimulated by anti-CD3 (Yoon, S. H. Selective addition of CXCR3+CCR4−CD4+ Th1 cells enhances generation of cytotoxic T cells by dendritic cells in vitro. Exp Mol Med. 2009. 41(3):161-170), and 11-4, IL-6, and IL-10 are also proinflammatory cytokines important in a cytotoxic response for bispecific antibody composition (Zimmerman, Z., et al. Unleashing the clinical power of T cells: CD19/CD3 bi-specific T cell engager (BiTE®) antibody composition blinatumomab as a potential therapy. Int. Immunol. (2015) 27(1): 31-37). In some embodiments, an intact, uncleaved chimeric polypeptide assembly composition exhibits at least 2-fold, or at least 3-fold, or at least 4-fold, or at least 5-fold, or at least 6-fold, or at least 7-fold, or at least 8-fold, or at least 9-fold, or at least 10-fold, or at least 20-fold, or at least 30-fold, or at least 50-fold, or at least 100-fold, or at least 1000-fold reduced potential to result in the production of Th1 and/or proinflammatory cytokines when said assembly is in contact with the effector cell and a target cell in an in vitro cell-based cytokine stimulation assay (such as described in the Examples, below) compared to the cytokine levels stimulated by the corresponding released first portion binding domains of a protease-treated chimeric polypeptide assembly composition in the in vitro cell-based stimulation cytokine assay, wherein the cytokines are selected from the group consisting of IL-2, IL-4, IL-6, IL-10, TNF-alpha and IFN-gamma. In one embodiment of the foregoing, the production of the Th1 cytokine is assayed in an in vitro assay comprising effector cells such as PBMC or CD3+ T cells and target cells having a tumor specific marker antigen selected from the group consisting of alpha 4 integrin, Ang2, B7-H3, B7-H6, CEACAM5, cMET, CTLA4, FOLR1, EpCAM, CCR5, CD19, HER2, HER2 neu, HER3, HER4, HER1 (EGFR), PD-L1, PSMA, CEA, MUC1(mucin), MUC-2, MUC3, MUC4, MUC5AC, MUC5B, MUC7, MUC16 βhCG, Lewis-Y, CD20, CD33, CD38, CD30, CD56 (NCAM), CD133, ganglioside GD3; 9-O-Acetyl-GD3, GM2, Globo H, fucosyl GM1, GD2, carbonicanhydrase IX, CD44v6, Sonic Hedgehog (Shh), Wue-1, plasma cell antigen 1, melanoma chondroitin sulfate proteoglycan (MCSP), CCR8, 6-transmembrane epithelial antigen of prostate (STEAP), mesothelin, A33 antigen, prostate stem cell antigen (PSCA), Ly-6, desmoglein 4, fetal acetylcholine receptor (fnAChR), CD25, cancer antigen 19-9 (CA19-9), cancer antigen 125 (CA-125), Muellerian inhibitory substance receptor type II (MISIIR), sialylated Tn antigen (s TN), fibroblast activation antigen (FAP), endosialin (CD248), epidermal growth factor receptor variant III (EGFRvIII), tumor-associated antigen L6 (TAL6), SAS, CD63, TAG72, Thomsen-Friedenreich antigen (TF-antigen), insulin-like growth factor I receptor (IGF-IR), Cora antigen, CD7, CD22, CD70, CD79a, CD79b, G250, MT-MMPs, F19 antigen, CA19-9, CA-125, alpha-fetoprotein (AFP), VEGFR1, VEGFR2, DLK1, SP17, ROR1, and EphA2. In another embodiment of the foregoing, the cytokine is IL-2. In another embodiment of the foregoing, the cytokine is TNFalpha. In another embodiment of the foregoing, the cytokine is IFN-gamma. In another embodiment, an intact, uncleaved chimeric polypeptide assembly composition administered to a subject having a tumor with an antigen that can be bound by the binding domain of the released first portion of the assembly exhibits at least 2-fold, at least 3-fold, at least 4-fold, at least 5-fold, at least 6-fold, at least 7-fold, at least 8-fold, at least 9-fold, at least 10-fold, at least 20-fold, at least 30-fold, at least 50-fold, at least 100-fold, or at least 1000-fold reduced potential to result in the production of Th1 and/or proinflammatory cytokines in the subject compared to the cytokine levels produced by the corresponding released binding domains of a protease-treated chimeric polypeptide assembly composition in a comparable subject with a tumor. In the foregoing embodiment, the cytokines can be assessed from a blood, fluid, or tissue sample removed from the subject. In the foregoing embodiment, the subject can be mouse, rat, monkey, and human. In an advantage of the subject chimeric polypeptide assembly compositions, however, it has been discovered that the cytolytic properties of the compositions do not require prestimulation by cytokines; that formation of the immunological synapse of the effector cell bound to the target cell by the first portion binding domains is sufficient to effect cytolysis or apoptosis in the target cell. Nevertheless, the production of proinflammatory cytokines are useful markers to assess the potency or the effects of the subject chimeric polypeptide assembly compositions; whether by in vitro assay or in the monitoring of treatment of a subject with a tumor.

In accordance with the binding domain embodiments referred to above, it is advantageous if the binding site recognizing the tumor cell marker antigen has a high binding affinity in order to capture the target cells to be destroyed with high efficiency. The chimeric polypeptide assembly compositions of the invention have the advantage that they may be used a number of times for killing tumour cells since, in preferred embodiments, the target cell binding domain has an affinity with a $K_d$ value in the range of $10^{-7}$ to $10^{-10}$ M, as determined in an vitro binding assay. If the affinity of a bispecific binding domain for binding a target tumor antigen is too high, the composition binds the expressing tumour cell and remains on its surface, making it unable to release and bind to another cell. In one embodiment, the effector cell binding domain of a subject chimeric polypeptide assembly composition has a binding constant of between $10^{-5}$ and $10^{-7}$ M, as determined in an vitro binding assay, detailed examples of which are described in the Examples, below. In another embodiment, the effector cell binding domain of a subject chimeric polypeptide assembly composition has a binding constant of between $10^{-5}$ and $10^{-10}$ M, as determined in an vitro binding assay.

In one aspect, it is a feature of the designed composition that when the RS of the chimeric polypeptide assembly is cleaved by a mammalian protease in the environment of the target cell and is converted from the prodrug form to the activated form, upon cleavage and release of the first portion bispecific binding domains and the third portion from said composition, said first portion concurrently binds to a T cell bearing the effector cell antigen, e.g., CD3, and to a tumor cell bearing the tumor-specific marker or an antigen of a target cell targeted by the first binding domain, whereupon the effector cell is activated. In some embodiments, wherein the assembly is activated by the cleavage of the RS, the subsequent concurrent binding of the effector cell and the target cell results in at least a 3-fold, or a 10-fold, or a 30-fold, or a 100-fold, or a 300-fold, or a 1000-fold activation of the effector cell, wherein the activation is assessed by the production of cytokines, cytolytic proteins, or lysis of the target cell, assessed in an in vitro cell-based assay. In another embodiment, the concurrent binding of a T cell bearing the human CD3 antigen and a tumor cell bearing the tumor-specific marker or an antigen of a target cell by the released first portion binding domains forms an immunologic synapse, wherein the binding results in the release of T cell-derived effector molecules capable of lysing the tumor cell. Non-limiting examples of the in vitro assay for measuring effector cell activation and/or cytolysis include cell membrane integrity assay, mixed cell culture assay, FACS based propidium Iodide assay, trypan Blue influx assay, photometric enzyme release assay, ELISA, radiometric 51Cr release assay, fluorometric Europium release assay, CalceinAM release assay, photometric MTT assay, XTT assay, WST-1 assay, alamarBlue assay, radiometric 3H-Thd incorporation assay, clonogenic assay measuring cell division activity, fluorometric Rhodamine123 assay measuring mitochondrial transmembrane gradient, apoptosis assay monitored by FACS-based phosphatidylserine exposure, ELISA-based TUNEL test assay, caspase activity assay, and cell morphology assay, or other assays known in the art for the assay of cytokines, cytolytic proteins, or lysis of cells, or the methods of the Examples, below.

It will be appreciated by one of skill in the art that in the context of treatment of a subject using the subject compositions, the chimeric polypeptide assembly are present in a prodrug form and are converted to a more active form when entering a certain cellular environment by the action of proteases colocalized with the cellular environment. Upon release from the composition by the action of the protease(s) in the target tissue, the second binding domain with binding specificity to an effector cell antigen and the first binding domain with binding specificity to a tumor-specific marker or an antigen of a target cell regain their full capability to concurrently bind to and link together the effector cell to the target cell, forming an immunological synapse. The formation of the immuological synapse causes the effector cell to become activated, with various signal pathways turning on new gene transcription and the release, by exocytosis, the effector molecule contents of its vesicles. Depending on the type of effector cell, different cytokines and lymphokines are released; e.g., Type 1 helper T cells (Th1) release cytokines like IFN-γ and TNF-β while Type 2 helper T cells (Th2) release cytokines like IL-4, IL-5, IL-10, and IL-13 that stimulate B cells, and cytotoxic T Lymphocytes (CTLs) release cytotoxic molecules like perforin and granzymes that kill the target (collectively, "effector molecules"). It is specifically contemplated that upon the concurrent binding to and linking together the effector cell to the target tumor cell by the released bispecific binding domains of the first portion of the chimeric polypeptide assembly, at very low effector to target (E:T) ratios the tumor cell is acted upon by the effector molecules released by the effector cell into the immunological synapse between the cells, resulting in damage, perforin-mediated lysis, granzyme B-induced cell death and/or apoptosis of the tumor cell. Thus, in another aspect, it is a feature of the designed composition that when the chimeric polypeptide assembly is administered to a subject with a tumor, the prodrug form remains in the circulatory system in normal tissue but is able to extravasate in the more permeable vasculature of the tumor such that the prodrug form of the assembly is activated by the proteases co-localized with the tumor and that the released first portion second binding domain concurrently binds an effector cell (e.g., CD3 antigen of a T cell) and a tumor cell expressing the tumor-specific market targeted by the first binding domain of the composition, whereupon the effector cell is activated and lysis of the tumor cell is effected. In one embodiment of the foregoing, the released first portion in the tumor of the subject concurrently bound to a tumor cell and an effector cell exhibits an increased ability to activate effector cells of at least 10-fold, or at least 30-fold, or at least 100-fold, or at least 200-fold, or at least 300-fold, or at least 400-fold, or at least 500-fold, or at least 1000-fold compared to the corresponding intact chimeric polypeptide assembly composition. In another embodiment of the foregoing, the released first portion in the tumor of the subject concurrently bound to a tumor cell and an effector cell exhibits an increased ability to lyse the tumor cell of at least 10-fold, or at least 30-fold, or at least 100-fold, or at least 200-fold, or at least 300-fold, or at least 400-fold, or at least 500-fold, or at least 1000-fold compared to the corresponding intact chimeric polypeptide assembly composition. In the foregoing embodiments, the effector cell activation and/or the cytotoxicity is assayed by conventional methods known in the art, such as cytometric measurement of activated effector cells, assay of cytokines, measurement of tumor size, or by histopathology. In the foregoing embodiments, the subject can be mouse, rat, dog, monkey, and human.

As is evident from the foregoing, the invention provides a large family of polypeptides in designed configurations to effect the desired properties; specific formulae of which are provided herein. In one embodiment, the invention provides a chimeric polypeptide assembly composition with a first portion comprising the first binding domain and the second binding domain, a second portion comprising the release segment, and a third portion comprising the bulking moiety. In the embodiment, the invention provides a composition having the configuration of formula I (depicted N-terminus to C-terminus):

(first portion)-(second portion)-(third portion)  I wherein first portion is a bispecific comprising two scFv wherein the first binding domain has specific binding affinity to a tumor-specific marker or an antigen of a target cell and the second binding domain has specific binding affinity to an effector cell; the second portion comprises a release segment (RS) capable of being cleaved by a mammalian protease; and the third portion is a bulking moiety. In the foregoing embodiment, the first portion binding domains can be in the order (VL-VH)1-(VL-VH)2, wherein "1" and "2" represent the first and second binding domains, respectively, or (VL-VH)1-(VH-VL)2, or (VH-VL)1-(VL-VH)2, or (VH-VL)1-(VH-VL)2, wherein the paired binding domains are linked by a polypeptide linker as described herein, below. In one embodiment, the first portion VL and VH are selected from Tables 1 and 2; RS is selected from the group of sequences set forth in Table 4; and the bulking moiety is selected from the group consisting of: XTEN; albumin binding domain; albumin; IgG binding domain; polypeptides consisting of proline, serine, and alanine; fatty acid; Fc domain; polyethylene glycol (PEG), PLGA; and hydoxylethyl starch. Where desired, the bulking moiety is an XTEN having at least about 90%, 91%, 92%, 93%, 94%, 95%, 96%, 97%, 98%, 99%, or 100% sequence identity to a sequence selected from the group of sequences set forth in Table 5. In the foregoing embodiments, the composition is a recombinant fusion protein. In another embodiment, the portions are linked by chemical conjugation. A schematic of the composition configuration of formula I is presented in FIG. 6.

In another embodiment, the invention provides a composition having the configuration of formula II (depicted N-terminus to C-terminus):

(third portion)-(second portion)-(first portion)  II wherein first portion is a bispecific comprising two scFv wherein the first binding domain has specific binding affinity to a tumor-specific marker or an antigen of a target cell and the second binding domain has specific binding affinity to an effector cell; the second portion comprises a release segment (RS) capable of being cleaved by a mammalian protease; and the third portion is a bulking moiety. In the foregoing embodiment, the first portion binding domains can be in the order (VL-VH)1-(VL-VH)2, wherein "1" and "2" represent the first and second binding domains, respectively, or (VL-VH)1-(VH-VL)2, or (VH-VL)1-(VL-VH)2, or (VH-VL)1-(VH-VL)2, wherein the paired binding domains are linked by a polypeptide linker as described herein, below. In one embodiment, the first portion VL and VH are selected from Tables 1 and 2; RS is selected from the group of sequences set forth in Table 4; and the bulking moiety is selected from the group consisting of: XTEN; albumin binding domain; albumin; IgG binding domain; polypeptides consisting of proline, serine, and alanine; fatty acid; and Fc domain. Where desired, the bulking moiety is an XTEN having at least about 90%, 91%, 92%, 93%, 94%, 95%, 96%, 97%, 98%, 99%, or 100% sequence identity to a sequence selected from the group of sequences set forth in Table 5. In the foregoing embodiments, the composition is a recombinant fusion protein. In another embodiment, the portions are linked by chemical conjugation. A schematic of the composition configuration of formula I is presented in FIG. 6.

In another embodiment, the invention provides a composition having the configuration of formula III (depicted N-terminus to C-terminus):

(fifth portion)-(fourth portion)-(first portion)-(second portion)-(third portion)  III wherein first portion is a bispecific comprising two scFv wherein the first binding domain has specific binding affinity to a tumor-specific marker or an antigen of a target cell and the second binding domain has specific binding affinity to an effector cell; the second portion comprises a release segment (RS) capable of being cleaved by a mammalian protease; the third portion is a bulking moiety; the fourth portion comprises a release segment (RS) capable of being cleaved by a mammalian protease which may be identical or different from the second portion; and the fifth portion is a bulking moiety that may be identical or may be different from the third portion. In the foregoing embodiment, the first portion binding domains can be in the order (VL-VH)1-(VL-VH)2, wherein "1" and "2" represent the first and second binding domains, respectively, or (VL-VH)1-(VH-VL)2, or (VH-VL)1-(VL-VH)2, or (VH-VL)1-(VH-VL)2, wherein the paired binding domains are linked by a polypeptide linker as described herein, below. In the foregoing embodiments, the RS is selected from the group of sequences set forth in Table 4. In the foregoing embodiments, the bulking moiety is selected from the group consisting of: XTEN; albumin binding domain; albumin; IgG binding domain; polypeptides consisting of proline, serine, and alanine; fatty acid; and Fc domain. Where desired, the bulking moiety is an XTEN having at least about 90%, 91%, 92%, 93%, 94%, 95%, 96%, 97%, 98%, 99%, or 100% sequence identity to a sequence selected from the group of sequences set forth in Table 5. In the foregoing embodiments, the composition is a recombinant fusion protein. In another embodiment, the portions are linked by chemical conjugation.

The subject compositions, based on their design and specific components, address the long-felt need to provide bispecific therapeutics that have more selectivity, greater half-life, and result in less toxicity and fewer side effects once they are cleaved by proteases found in associated with the target tissues or tissues rendered unhealthy by a disease, such that the subject compositions have improved therapeutic index compared to bispecific antibody compositions known in the art. Such compositions are useful in the treatment of certain diseases, including, but not limited to cancer. It will be appreciated by those of skill in the art that the compositions of the instant invention achieve this reduction in non-specific interactions by a combination of mechanism, which include steric hindrance by locating the binding domains to the bulky XTEN molecules, steric hindrance in that the flexible, unstructured characteristic of the long flexible XTEN polypeptides, by being tethered to the composition, are able to oscillate and move around the binding domains, providing blocking between the composition and tissues or cells, as well as a reduction in the ability of the intact composition to penetrate a cell or tissue due to the large molecular mass (contributed to by both the actual molecular weight of the XTEN and due to the large hydrodynamic radius of the unstructured XTEN) compared to the size of the individual binding domains. However, the compositions are designed such that when in proximity to a target tissue or cell bearing or secreting a protease capable of cleaving the RS, or when internalized into a target cell or tissue when a binding domain has bound the ligand, the bispecific binding domains are liberated from the bulk of the XTEN by the action of the protease(s), removing the steric hindrance barrier, and is freer to exert its pharmacologic effect. The subject compositions find use in the treatment of a variety of conditions where selective delivery of a therapeutic bispecific antibody composition to a cell, tissue or organ is desired. In one embodiment, the target tissue is a cancer, which may be a leukemia, a lymphoma, or a tumor of an organ or system.

III). PHARMACEUTICAL COMPOSITIONS

The present invention provides pharmaceutical compositions comprising chimeric polypeptide assembly compositions. In one embodiment, the pharmaceutical composition comprises the chimeric polypeptide assembly and one or more pharmaceutically acceptable carriers. In another embodiment, the pharmaceutical composition comprises the chimeric polypeptide assembly of any one of the embodiments described herein and optionally, suitable formulations of carrier, stabilizers and/or excipients. In another embodiment, the pharmaceutical composition comprises the T cell binding composition of any one of the embodiments described herein and optionally, suitable formulations of carrier, stabilizers and/or excipients. Suitable excipients and acceptable carriers or include: buffering agents such as sodium citrate, dicalcium phosphate, or sodium phosphate; preservatives; co-solvents; antioxidants, including ascorbic acid and methionine; chelating agents such as EDTA; metal complexes (e.g., Zn-protein complexes); polymers, such as polyesters, polyoxyethylene-stearates, polyoxyethylene alkyl ethers, e.g. polyoxyethylene monolauryl ether, alkylphenylpolyoxyethylene ethers (Triton-X), polyoxyethylene-polyoxypropylene copolymer, and polethylene glycols; salt-forming counter-ions, such as sodium, polyhydric sugar alcohols; amino acids, such as alanine, glycine, asparagine, 2-phenylalanine, and threonine; sugars or sugar alcohols, such as trehalose, sucrose, octasulfate, sorbitol or xylitol stachyose, mannose, sorbose, xylose, ribose, myoinisitose, galactose, lactitol, ribitol, myoinisitol, polysorbate, galactitol, glycerol, cyclitols (e.g., inositol); sulfur containing reducing agents, such as glutathione, thioctic acid, sodium thioglycolate, thioglycerol, [alpha]-monothioglycerol, and sodium thio sulfate; low molecular weight proteins, such as human serum albumin, bovine serum albumin, gelatin; and hydrophilic polymers, such as polyvinylpyrrolidone.

The pharmaceutical compositions of the present invention can be formulated according to known methods to prepare pharmaceutically useful compositions, whereby the polypeptide is combined in admixture with a pharmaceutically acceptable carrier vehicle, such as aqueous solutions or buffers, pharmaceutically acceptable suspensions and emulsions. Examples of non-aqueous solvents include propyl ethylene glycol, polyethylene glycol and vegetable oils. Therapeutic formulations of the pharmaceutical compositions are prepared for storage by mixing the active ingredient having the desired degree of purity with optional physiologically acceptable carriers, excipients or stabilizers, as described in Remington's Pharmaceutical Sciences 16th edition, Osol, A. Ed. (1980), in the form of lyophilized formulations or aqueous solutions. In addition, the pharmaceutical compositions can also contain other pharmaceutically active compounds or a plurality of compositions of the invention.

The compositions of the invention may be formulated using a variety of excipients. Suitable excipients include microcrystalline cellulose (e.g. Avicel PH102, Avicel PH101), polymethacrylate, poly(ethyl acrylate, methyl methacrylate, trimethylammonioethyl methacrylate chloride) (such as Eudragit RS-30D), hydroxypropyl methylcellulose (Methocel K100M, Premium CR Methocel K100M, Methocel E5, Opadry®), magnesium stearate, talc, triethyl citrate, aqueous ethylcellulose dispersion (Surelease®), and protamine sulfate. The slow release agent may also comprise a carrier, which can comprise, for example, solvents, dispersion media, coatings, antibacterial and antifungal agents, isotonic and absorption delaying agents. Pharmaceutically acceptable salts can also be used in these slow release agents, for example, mineral salts such as hydrochlorides, hydrobromides, phosphates, or sulfates, as well as the salts of organic acids such as acetates, proprionates, malonates, or benzoates. The composition may also contain liquids, such as water, saline, glycerol, and ethanol, as well as substances such as wetting agents, emulsifying agents, or pH buffering agents. Liposomes may also be used as a carrier.

The pharmaceutical compositions may be administered for therapy by any suitable route including parenteral (including subcutaneous, subcutaneous by infusion pump, intramuscular, intravenous, intra-arterial, and intradermal), intravitreally, intrathecally, intraperitoneally, intraabdominally, and pulmonary. It will also be appreciated that the preferred route will vary with the condition and age of the recipient, and the disease being treated.

In some embodiments, the pharmaceutical composition comprising a chimeric polypeptide assembly of the embodiments described herein are used in a method for treatment of a disease, the method comprising administering the pharmaceutical composition to a subject with the disease according to a treatment regimen comprising one or more consecutive doses using a therapeutically effective dose. treatment regimen is part of a specified treatment cycle. In one embodiment, the specified treatment cycle comprises administration of the pharmaceutical composition twice a week, every week, every 10 days, every two weeks, every three weeks, or every month per each treatment cycle. In another embodiment, the treatment regimen results in the improvement of a clinical parameter or endpoint associated with the disease in the subject wherein the clinical parameter or endpoint is selected from one or any combination of the group consisting of tumor shrinkage as a complete, partial or incomplete response; time-to-progression, time to treatment failure, biomarker response; progression-free survival; disease free-survival; time to recurrence; time to metastasis; time of overall survival; improvement of quality of life; and improvement of symptoms. In other embodiments, the pharmaceutical composition comprising a chimeric polypeptide assembly of the embodiments described herein is prepared as a medicament for the treatment of a disease in a subject. In the foregoing embodiments of this paragraph, the disease can be carcinoma, Hodgkin's lymphoma, and non-Hodgkin's lymphoma, diffuse large B cell lymphoma, follicular lymphoma, mantle cell lymphoma, blastoma, breast cancer, ER/PR+ breast cancer, Her2+ breast cancer, triple-negative breast cancer, colon cancer, colon cancer with malignant ascites, mucinous tumors, prostate cancer, head and neck cancer, skin cancer, melanoma, genito-urinary tract cancer, ovarian cancer, ovarian cancer with malignant ascites, peritoneal carcinomatosis, uterine serous carcinoma, endometrial cancer, cervix cancer, colorectal, uterine cancer, mesothelioma in the peritoneum, kidney cancer, Wilm's tumor, lung cancer, small-cell lung cancer, non-small cell lung cancer, gastric cancer, stomach cancer, small intestine cancer, liver cancer, hepatocarcinoma, hepatoblastoma, liposarcoma, pancreatic cancer, gall bladder cancer, cancers of the bile duct, esophageal cancer, salivary gland carcinoma, thyroid cancer, epithelial cancer, arrhenoblastoma, adenocarcinoma, sarcoma, and B-cell derived chronic lymphatic leukemia. In one embodiment, the medicament is prepared for administration to the subject by the parenteral route (by intra-arterial or intravenous routes). In another embodiment, the medicament is prepared for administration to a subject by the subcutaneous route. In another embodiment, the medicament is prepared for the treatment of a disease in a subject for administration to the subject by the intradermal route. Where desired, the pharmaceutical composition comprising a chimeric polypeptide assembly of the embodiments described herein is prepared as a medicament for treatment of a disease in a subject wherein administration is by the intraabdominal or intraperitoneal route for the treatment of tumors and/or ascites in the abdominal cavity.

In another aspect, the invention relates to formulations of the pharmaceutical compositions. In one embodiment, the pharmaceutical composition may be supplied as a lyophilized powder to be reconstituted prior to administration. In one embodiment, the pharmaceutical composition may be supplied as a lyophilized powder to be reconstituted using normal saline, D5 water, lactated Ringer's, and the like, for administration. In another embodiment, the composition may also be supplied in a liquid form, which can be administered directly to a patient. In one embodiment, the pharmaceutical composition is supplied as a liquid in a pre-filled syringe for a single injection. In one embodiment, the pharmaceutical composition is supplied as a liquid in a vial. In another embodiment, the pharmaceutical composition is supplied as a lyophilized powder in a vial. For liquid formulations of the pharmaceutical composition embodiments, a desired property is that the formulation be supplied in a form that can pass through a needle for intravenous, intramuscular, intraarticular, or subcutaneous administration. In one embodiment, the pharmaceutical composition is in a liquid form. In another embodiment, the pharmaceutical composition is in a pre-filled syringe for use as a single injection. In one embodiment, the pharmaceutical composition is formulated in a saline buffer solution at a concentration of at least at least 11.04, or at least 101.04, or at least 1001.04, or at least 1 mM, or at least 2 mM, or at least 3 mM, or at least 4 mM, or at least 5 mM, or at least 6 mM, or at least 7 mM, or at least 8 mM, or at least 9 mM, or at least 10 mM, wherein such solution can be passed through a 25, 26, 27, 28, 29, 30, 31, or 32 gauge needle for intradermal, subcutaneous, intravenous, intra-arterial, intraabdominal, intraperitoneal, intrathecal, or intramuscular administration. Syringe pumps may also be used to deliver the pharmaceutical compositions of the invention. Such devices are described in U.S. Pat. Nos. 4,976,696; 4,933,185; 5,017,378; 6,309,370; 6,254,573; 4,435,173; 4,398,908; 6,572,585; 5,298,022; 5,176,502; 5,492,534; 5,318,540; and 4,988,337, the contents of which are incorporated herein by reference. One skilled in the art, considering both the disclosure of this invention and the disclosures of these other patents could produce a syringe pump for the extended release of the compositions of the present invention.

IV). METHODS AND USES OF CHIMERIC POLYPEPTIDE ASSEMBLY COMPOSITIONS

The present invention provides cleavable chimeric polypeptide assembly compositions, or ProTIA (Protease Triggered Immune Activator), and pharmaceutical compositions comprising a chimeric polypeptide assembly that are particularly useful in medical settings; for example in the prevention, treatment and/or the amelioration of certain cancers, tumors or inflammatory diseases.

A number of therapeutic strategies have been used to design the chimeric polypeptide assembly compositions for use in methods of treatment of a subject with a cancerous disease, including the modulation of T cell responses by targeting TcR signalling, particularly using VL and VH portions of the anti-human CD3 monoclonal antibodies that are widely used clinically in immunosuppressive regimes. The CD3-specific monoclonal OKT3 was the first such monoclonal approved for use in humans (Sgro, Toxicology 105 (1995), 23-29) and is widely used clinically as an immunosuppressive agent in transplantation (Chatenoud L: Immunologic monitoring during OKT3 therapy. Clin Transplant 7:422-430, 1993). Moreover, anti-CD3 monoclonals can induce partial T cell signalling and clonal anergy (Smith, J. Exp. Med. 185 (1997), 1413-1422). OKT3 reverses allograft tissue rejection most probably by blocking the function of all T cells, which play a major role in acute rejection. The OKT3 reacts with and blocks the function of the CD3 complex in the membrane of T cells; the CD3 complex being associated with the antigen recognition structure of T cells (TCR), which is essential for signal transduction. These and other such CD3 specific antibodies are able to induce various T cell responses, including cytokine production (Von Wussow, Human gamma interferon production by leukocytes induced with monoclonal antibodies recognizing T cells. J. Immunol. 127:1197-1200 (1981), proliferation and suppressor T-cell induction. Depending on the conditions, CD3 specific monoclonal antibody can either inhibit or induce cytotoxicity (Kimball J A, et al. The OKT3 Antibody Response Study: a multicentre study of human anti-mouse antibody (HAMA) production following OKT3 use in solid organ transplantation. Transplant Immunol. 3:212-221 (1995). In cancer, attempts have been made to utilize cytotoxic T cells to lyse cancer cells. To effect target cell lysis, cytotoxic T cells require direct cell-to-cell contact; the TCR on the cytotoxic T cell must recognize and engage the appropriate antigen on the target cell. This creates the immulogic synapse that, in turn initiates a signaling cascade within the cytotoxic T cell, causing T-cell activation and the production of a variety of cytotoxic cytokines and effector molecules. Perforin and granzymes are highly toxic molecules that are stored in preformed granules that reside in activated cytotoxic T cells. After recognition of the target cell, the cytoplasmic granules of the engaged cytotoxic T cells migrate toward the cytotoxic T-cell membrane, ultimately fusing with it and releasing their contents in directed fashion into the immunolgical synapse to form a pore within the membrane of the target cell, disrupting the tumor cell plasma membrane. The created pore acts as a point of entry for granzymes; a family of serine proteases that that induce apoptosis of the tumor cells. These and other effector molecules are described more fully, above. The invention contemplates methods of use of bispecific compositions that are engineered to target a range of malignant cells, such as tumors, in addition to the effector cells, in order to initiate target cell lysis and to effect a beneficial therapeutic outcome by the mechanisms described, above. The compositions are designed such that one binding domain binds and engages CD3 to activate the cytotoxic T cell while the second binding domain can be designed to target a variety of different target cell antigens that are characteristic of specific malignancies; bridging them together for the creation of the immunological synapse. In a particular advantage of the design, the physical binding of the cytotoxic effector cell and the cancer cell eliminates the need for antigen processing, MHCI/ß2-microglobulin, as well as co-stimulatory molecules. Examples of important tumor cell markers include the epithelial cell adhesion molecule (Ep-CAM); a cell surface glycoprotein expressed in multiple solid tumors. Another example is HER2/neu, also expressed in several solid tumors, such as breast cancer. Other cancer cell markers and representative VL and VH sequences that can be utilized to create binding domains of the inventive chimeric polypeptide assembly compositions are listed in Table 2 or described herein. Because of the range of tumor-specific markers (more extensively described, above) that can be engineered into the various embodiments of the subject compositions antibodies, it will be appreciated that the resulting compositions will have utility against a variety of cancers, including solid and hematological tumors. In one embodiment, the invention provides a method of treatment of a subject with a tumor. The tumor being treated can comprise tumor cells arising from a cell selected from the group consisting of stromal cell, fibroblasts, myofibroblasts, glial cells, epithelial cells, fat cells, lymphocytic cells, vascular cells, smooth muscle cells, mesenchymal cells, breast tissue cells, prostate cells, kidney cells, brain cells, colon cells, ovarian cells, uterine cells, bladder cells, skin cells, stomach cells, genito-urinary tract cells, cervix cells, uterine cells, small intestine cells, liver cells, pancreatic cells, gall bladder cells, bile duct cells, esophageal cells, salivary gland cells, lung cells, and thyroid cells. In a further advantage of the compositions, as the cytotoxic effector cells are not consumed during the damage/destruction of the bridged target cancer cell, after causing lysis of one target cell, an activated effector cell can release and move on through the local tissue towards other target cancer cells, bind the target antigen, and initiate additional cell lysis. In addition, it is contemplated that in a localized environment like a solid tumor, the release of effector cell molecules such as perforin and granzymes will result in damage to tumor cells that are adjacent but not bound by a given molecule of the bispecific binding domains, resulting in stasis of growth or regression of the tumor.

Accordingly, the utility of the invention will be understood; that after administration of a therapeutically effective dose of pharmaceutical composition comprising a chimeric polypeptide assembly described herein to a subject with a cancer or tumor having the target cell marker, the composition can be acted upon by proteases in association with the cancer or tumor cells, releasing the bispecific first portion binding domains such that an immunological synapse can be created by the linking of the target cell and a effector cell, with the result that effector cell-derived effector molecules capable of lysing the target cell are released into the synapse, leading to apoptosis, cytolysis, or death of the target cancer or tumor cell. Furthermore, it will be appreciated by one of skill in the art that use of the chimeric polypeptide assembly compositions can result in a sustained and more generalized beneficial therapeutic effect than a "single kill" once the immunological synapse is formed by the binding of the released binding domains to the effector cell and target cancer cell.

In one aspect, the invention relates to methods of treating a disease in a subject, such as a cancer or an inflammatory disorder. In some embodiments, the invention provides a method of treating a disease in a subject, comprising administering to the subject in need thereof a therapeutically effective amount of a pharmaceutical composition comprising a chimeric polypeptide assembly described herein. A therapeutically effective amount of the pharmaceutical composition may vary according to factors such as the disease state, age, sex, and weight of the individual, and the ability of the antibody or antibody portion to elicit a desired response in the individual. A therapeutically effective amount is also one in which any toxic or detrimental effects of the subject compositions are outweighed by the therapeutically beneficial effects. A prophylactically effective amount refers to an amount of pharmaceutical composition required for the period of time necessary to achieve the desired prophylactic result.

In one embodiment of the method of treating a disease in a subject, the disease for treatment can be carcinomas, Hodgkin's lymphoma, non-Hodgkin's lymphoma, B cell lymphoma, T-cell lymphoma, follicular lymphoma, mantle cell lymphoma, blastoma, breast cancer, colon cancer, prostate cancer, head and neck cancer, any form of skin cancer, melanoma, genito-urinary tract cancer, ovarian cancer, ovarian cancer with malignant ascites, peritoneal carcinomatosis, uterine serous carcinoma, endometrial cancer, cervical cancer, colorectal cancer, an epithelia intraperitoneal malignancy with malignant ascites, uterine cancer, mesothelioma in the peritoneum kidney cancers, lung cancer, small-cell lung cancer, non-small cell lung cancer, gastric cancer, esophageal cancer, stomach cancer, small intestine cancer, liver cancer, hepatocarcinoma, hepatoblastoma, liposarcoma, pancreatic cancer, gall bladder cancer, cancers of the bile duct, salivary gland carcinoma, thyroid cancer, epithelial cancer, adenocarcinoma, sarcomas of any origin, primary hematologic malignancies including acute or chronic lymphocytic leukemias, acute or chronic myelogenous leukemias, myeloproliferative neoplastic disorders, or myelodysplastic disorders, myasthenia gravis, Morbus Basedow, Hashimoto thyroiditis, or Goodpasture syndrome. The therapeutically effective amount can produce a beneficial effect in helping to treat (e.g., cure or reduce the severity) or prevent (e.g., reduce the likelihood of recurrence) of a cancer or a tumor. In another embodiment of the method of treating the disease in a subject, the pharmaceutical composition is administered to the subject as one or more therapeutically effective doses administered twice weekly, once a week, every two weeks, every three weeks, or monthly. In another embodiment of the method, the pharmaceutical composition is administered to the subject as one or more doses over a period of at least two weeks, or at least one month, or at least two months, or at least three months, or at least four months, or at least five months, or at least six months. In another embodiment of the method, a first low priming dose is administered to the subject, followed by one or more higher maintenance doses over the dosing schedule of at least two weeks, or at least one month, or at least two months, or at least three months, or at least four months, or at least five months, or at least six months. The initial priming dose administered is selected from the group consisting of at least about 0.005 mg/kg, at least about 0.01 mg/kg, at least about 0.02 mg/kg, at least about 0.04 mg/kg, at least about 0.08 mg/kg, at least about 0.1 mg/kg, and one or more subsequent maintenance dose(s) administered is selected from the group consisting of at least about 0.1 mg/kg, at least about 0.12 mg/kg, at least about 0.14 mg/kg, at least about 0.16 mg/kg, at least about 0.18 mg/kg, at least about 0.20 mg/kg, at least about 0.22 mg/kg, at least about 0.24 mg/kg, at least about 0.26 mg/kg, at least about 0.27 mg/kg, at least about 0.28 mg/kg, at least 0.3 mg/kg, at least 0.4. mg/kg, at least about 0.5 mg/kg, at least about 0.6 mg/kg, at least about 0.7 mg/kg, at least about 0.8 mg/kg, at least about 0.9 mg/kg, at least about 1.0 mg/kg, at least about 1.5 mg/kg, or at least about 2.0 mg/kg. In another embodiment of the method, the pharmaceutical composition is administered to the subject intradermally, subcutaneously, intravenously, intra-arterially, intra-abdominally, intraperitoneally, intrathecally, or intramuscularly. In another embodiment of the method, the pharmaceutical composition is administered to the subject as one or more therapeutically effective bolus doses or by infusion of 5 minutes to 96 hours as tolerated for maximal safety and efficacy. In another embodiment of the method, the pharmaceutical composition is administered to the subject as one or more therapeutically effective bolus doses or by infusion of 5 minutes to 96 hours, wherein the dose is selected from the group consisting of at least about 0.005 mg/kg, at least about 0.01 mg/kg, at least about 0.02 mg/kg, at least about 0.04 mg/kg, at least about 0.08 mg/kg, at least about 0.1 mg/kg, at least about 0.12 mg/kg, at least about 0.14 mg/kg, at least about 0.16 mg/kg, at least about 0.18 mg/kg, at least about 0.20 mg/kg, at least about 0.22 mg/kg, at least about 0.24 mg/kg, at least about 0.26 mg/kg, at least about 0.27 mg/kg, at least about 0.28 mg/kg, at least 0.3 mg/kg, at least 0.4. mg/kg, at least about 0.5 mg/kg, at least about 0.6 mg/kg, at least about 0.7 mg/kg, at least about 0.8 mg/kg, at least about 0.9 mg/kg, at least about 1.0 mg/kg, at least about 1.5 mg/kg, or at least about 2.0 mg/kg. In another embodiment of the method, the pharmaceutical composition is administered to the subject as one or more therapeutically effective bolus doses or by infusion over a period of 5 minutes to 96 hours, wherein the administration to the subject results in a plasma concentration of the chimeric polypeptide assembly of at least about 0.1 ng/mL to at least about 2 μg/mL or more in the subject that is maintained for at least about 3 days, at least about 7 days, at least about 10 days, at least about 14 days, or at least about 21 days. In the foregoing embodiments of the method, the subject can be mouse, rat, monkey, and human.

In particular, the pharmaceutical compositions comprising a chimeric polypeptide assembly can be used for the treatment of epithelial cancer, preferably adenocarcinomas, or minimal residual disease, more preferably early solid tumor, advanced solid tumor or metastatic solid tumor. In addition, the pharmaceutical compositions comprising a chimeric polypeptide assembly provided in this invention are useful in the treatment of sarcomas. In addition, the pharmaceutical compositions comprising a chimeric polypeptide assembly provided in this invention are useful in the treatment of lymphomas and leukemias, including primary hematologic malignancies including acute or chronic lymphocytic leukemias, acute or chronic myelogenous leukemias, myeloproliferative neoplastic disorders, or myelodysplastic disorders, B-cell disorders such as B-cell lymphoma, Hodgkin's lymphoma, and non-Hodgkin's lymphoma, diffuse large B cell lymphoma, follicular lymphoma, mantle cell lymphoma, blastoma, B-cell derived chronic lymphatic leukemia (B-CLL) and/or having a B-cell related autoimmune disease such as myasthenia gravis, Morbus Basedow, Hashimoto thyroiditis, or Goodpasture syndrome. In addition, the pharmaceutical compositions comprising a chimeric polypeptide assembly provided in this invention are useful in the treatment of cancers leading to ascites, including genito-urinary tract cancer, ovarian cancer, ovarian cancer with malignant ascites, peritoneal carcinomatosis, uterine serous carcinoma, endometrial cancer, cervix cancer, colorectal, uterine cancer, mesothelioma in the peritoneum, pancreatic cancer, colon cancer, colon cancer with malignant ascites, and gastric cancer.

In one aspect, the invention provides a method of for achieving a beneficial effect in a cancer or tumor mediated by administration of pharmaceutical compositions comprising chimeric polypeptide assembly compositions. In one embodiment of the method, the invention provides the use of a pharmaceutical composition comprising a chimeric polypeptide assembly in a method of treatment of a cancer or tumor in a subject in need thereof by administration of a therapeutically effective amount of the pharmaceutical composition in which one binding domain of the chimeric polypeptide assembly composition is derived from a parental antibody that binds to an effector cell CD3 antigen and a second binding domain is derived from a parental antibody that binds to an effector cell target antigen selected from the group consisting of alpha 4 integrin, Ang2, B7-H3, B7-H6, CEACAM5, cMET, CTLA4, FOLR1, EpCAM, CCR5, CD19, HER2, HER2 neu, HER3, HER4, HER1 (EGFR), PD-L1, PSMA, CEA, MUC1(mucin), MUC-2, MUC3, MUC4, MUC5AC, MUC5B, MUC7, MUC16 βhCG, Lewis-Y, CD20, CD33, CD38, CD30, CD56 (NCAM), CD133, ganglioside GD3; 9-O-Acetyl-GD3, GM2, Globo H, fucosyl GM1, GD2, carbonicanhydrase IX, CD44v6, Sonic Hedgehog (Shh), Wue-1, plasma cell antigen 1, melanoma chondroitin sulfate proteoglycan (MCSP), CCR8, 6-transmembrane epithelial antigen of prostate (STEAP), mesothelin, A33 antigen, prostate stem cell antigen (PSCA), Ly-6, desmoglein 4, fetal acetylcholine receptor (fnAChR), CD25, cancer antigen 19-9 (CA19-9), cancer antigen 125 (CA-125), Muellerian inhibitory substance receptor type II (MISIIR), sialylated Tn antigen (s TN), fibroblast activation antigen (FAP), endosialin (CD248), epidermal growth factor receptor variant III (EGFRvIII), tumor-associated antigen L6 (TAL6), SAS, CD63, TAG72, Thomsen-Friedenreich antigen (TF-antigen), insulin-like growth factor I receptor (IGF-IR), Cora antigen, CD7, CD22, CD70, CD79a, CD79b, G250, MT-MMPs, F19 antigen, CA19-9, CA-125, alpha-fetoprotein (AFP), VEGFR1, VEGFR2, DLK1, SP17, ROR1, and EphA2. In one embodiment of the method, the administration of the therapeutically effective amount of the pharmaceutical composition leads to the eradication or amelioration of the underlying cancer or tumor disorder such that an improvement is observed in the subject, notwithstanding that the subject may still be afflicted with the underlying disorder.

In another embodiment, the invention provides use of a pharmaceutical composition comprising a chimeric polypeptide assembly in a method of treatment of a cancer or tumor in a subject by administration of a therapeutically effective amount of the pharmaceutical composition in which one binding domain of the chimeric polypeptide assembly composition is derived from a parental antibody directed to an effector cell selected from the group consisting of the antibodies of Table 1 and a second binding domain is derived from a parental antibody that binds to an target cell target antigen selected from the group consisting of the antibodies of Table 2. In another embodiment, the invention provides use of a pharmaceutical composition comprising a chimeric polypeptide assembly in a method of treatment of a cancer or tumor in a subject by administration of a therapeutically effective amount of the pharmaceutical composition in which one binding domain of the chimeric polypeptide assembly composition comprises VL and VH sequences derived from a parental antibody directed to an effector cell selected from the group of sequences set forth in Table 1 and a second binding domain comprises paired VL and VH sequences derived from a parental antibody directed to a target cell antigen selected from the group consisting of the antibodies of Table 2. In another embodiment, the invention provides use of a pharmaceutical composition comprising a chimeric polypeptide assembly in a method of treatment of a cancer or tumor in a subject by administration of a therapeutically effective amount of the pharmaceutical composition in which one binding domain of the chimeric polypeptide assembly composition comprises VL and VH sequences derived from a parental antibody directed to an effector cell linked to a second binding domain comprises paired VL and VH sequences derived from a parental antibody directed to a target cell antigen wherein the linked binding domains have an amino acid sequence with at least 90%, 91%, 92%, 93%, 94%, 95%, 96%, 97%, 98%, 99%, or 100% sequence identity to an amino acid sequence set forth in Table 13. In another embodiment, the invention provides use of a pharmaceutical composition comprising a chimeric polypeptide assembly in a method of treatment of a cancer or tumor in a subject by administration of a therapeutically effective amount of the pharmaceutical composition comprising a chimeric polypeptide assembly comprising an amino acid sequence with at least 90%, 91%, 92%, 93%, 94%, 95%, 96%, 97%, 98%, 99%, or 100% sequence identity to an amino acid sequence set forth in Table 10 or Table 12. In one embodiment, the pharmaceutical composition doses of the method are administered as a bolus dose. In another embodiment, the pharmaceutical composition doses of the method are each administered by intravenous infusion. In another embodiment, the pharmaceutical composition doses of the method are each administered by intraabdominal infusion. In another embodiment, the pharmaceutical composition doses of the method are each administered by intra-arterial infusion. In another embodiment, the pharmaceutical composition doses of the method are each administered by subcutaneous injection. In another embodiment, the pharmaceutical composition doses of the method are each administered by intramuscular injection. In another embodiment, the pharmaceutical composition doses of the method are each administered by intraabdominal infusion. In the foregoing embodiments of this paragraph, the subject is selected from the group consisting of mouse, rat, dog, monkey, and human.

In another aspect, the invention relates to a method of treating a cancer or a tumor in a subject according to a treatment regimen. In one embodiment, the invention provides a method of treating a cancer or a tumor in a subject comprising administering to the subject with the disease according to a treatment regimen comprising one or more consecutive doses of a therapeutically effective amount of a pharmaceutical composition comprising a chimeric polypeptide assembly composition disclosed herein. In one embodiment, the invention provides a method of treating a cancer or a tumor in a subject comprising administering to the subject with the disease according to a treatment regimen comprising one or more consecutive doses of a therapeutically effective amount of a pharmaceutical composition comprising a chimeric polypeptide assembly wherein the administration of the therapeutically effective amount of a pharmaceutical composition to the subject achieves a beneficial therapeutic effect. In another embodiment, the invention provides a method of treating a cancer or a tumor in a subject comprising administering to the subject with the disease according to a treatment regimen comprising one or more consecutive doses of a therapeutically effective amount of a pharmaceutical composition comprising a chimeric polypeptide assembly wherein the treatment regimen results in the improvement of a clinical parameter or endpoint associated with the disease in the subject. In the foregoing, the clinical parameter or endpoint is selected from one or any combination of the group consisting of tumor shrinkage as a complete, partial or incomplete response; time-to-progression; time to treatment failure; biomarker response; progression-free survival; disease free-survival; time to recurrence; time to metastasis; time of overall survival; improvement of quality of life; and improvement of symptoms.

In another aspect, the invention relates to a method of use in which the treatment regimen is part of a specified treatment cycle. In one embodiment of the method, the specified treatment cycle of the treatment regimen comprises administration of a pharmaceutical composition comprising a chimeric polypeptide assembly twice a week, every week, every 10 days, every two weeks, every three weeks, or every month per each treatment cycle. In another embodiment of the method, the treatment regimen is used in treatment of a disease, wherein the disease is selected from the group consisting of carcinomas, Hodgkin's lymphoma, non-Hodgkin's lymphoma, B cell lymphoma, T-cell lymphoma, follicular lymphoma, mantle cell lymphoma, blastoma, breast cancer, colon cancer, prostate cancer, head and neck cancer, any form of skin cancer, melanoma, genito-urinary tract cancer, ovarian cancer, ovarian cancer with malignant ascites, peritoneal carcinomatosis, uterine serous carcinoma, endometrial cancer, cervical cancer, colorectal cancer, an epithelia intraperitoneal malignancy with malignant ascites, uterine cancer, mesothelioma in the peritoneum kidney cancers, lung cancer, small-cell lung cancer, non-small cell lung cancer, gastric cancer, esophageal cancer, stomach cancer, small intestine cancer, liver cancer, hepatocarcinoma, hepatoblastoma, liposarcoma, pancreatic cancer, gall bladder cancer, cancers of the bile duct, salivary gland carcinoma, thyroid cancer, epithelial cancer, adenocarcinoma, sarcomas of any origin, primary hematologic malignancies including acute or chronic lymphocytic leukemias, acute or chronic myelogenous leukemias, myeloproliferative neoplastic disorders, or myelodysplastic disorders, myasthenia gravis, Morbus Basedow, Hashimoto thyroiditis, or Goodpasture syndrome.

In another aspect, the invention relates to improved methods of inducing death of a target cell, such as a cancer cell, utilizing the chimeric polypeptide assembly compositions, wherein the method effects death or induces apoptosis in the target cell or tissue, but with reduced toxicity and side effects. In a particular advantage of the inventive methods, the enhanced properties of the chimeric polypeptide assembly compositions permit lower-dose pharmaceutical formulations or treatment methods using a reduced dosage, reduced dosing frequency and a superior dose regimen, both because of targeted delivery to tissues and cells and because of enhanced pharmacokinetic properties, resulting in a superior therapeutic index; i.e., improved efficacy with reduced toxicity. Consequently, the subject compositions can have superior efficacy and safety compared to the corresponding first portion binding domains not linked to the RS and bulking moiety because of the ability of the attached bulking moiety to reduce the non-specific binding to healthy tissues and to prevent extravasation from the circulatory system in healthy tissue, while permitting enhanced penetration and binding into the cancer or tumor tissue upon the cleavage of the RS and release of the bispecific first portion binding domains; thus resulting in a differential compartmentalization of the prodrug form versus the released first portion upon cleavage of the composition. In one embodiment, the invention provides a method of inducing death of a target cell, the method comprising contacting the target cell and an effector cell with a chimeric polypeptide assembly described herein, wherein the contact results in an effect in the target cell selected from the group consisting of loss of membrane integrity, pyknosis, karyorrhexis, inducement of the intrinsic pathway of apoptosis, inducement of the extrinsic pathway of apoptosis, apoptosis, cell lysis, and cell death. The effect can be determined in an in vitro cell-based assay comprising a mixed population of the target cells and the effector cells, and an effective amount of the chimeric polypeptide assembly having binding affinity for antigens of the target cell and the effector cell. Non-limiting examples of target cell antigens include, but are not limited to a tumor specific marker antigen selected from the group consisting of alpha 4 integrin, Ang2, B7-H3, B7-H6, CEACAM5, cMET, CTLA4, FOLR1, EpCAM, CCR5, CD19, HER2, HER2 neu, HER3, HER4, HER1 (EGFR), PD-L1, PSMA, CEA, MUC1(mucin), MUC-2, MUC3, MUC4, MUC5AC, MUC5B, MUC7, MUC16 βhCG, Lewis-Y, CD20, CD33, CD38, CD30, CD56 (NCAM), CD133, ganglioside GD3; 9-O-Acetyl-GD3, GM2, Globo H, fucosyl GM1, GD2, carbonicanhydrase IX, CD44v6, Sonic Hedgehog (Shh), Wue-1, plasma cell antigen 1, melanoma chondroitin sulfate proteoglycan (MCSP), CCR8, 6-transmembrane epithelial antigen of prostate (STEAP), mesothelin, A33 antigen, prostate stem cell antigen (PSCA), Ly-6, desmoglein 4, fetal acetylcholine receptor (fnAChR), CD25, cancer antigen 19-9 (CA19-9), cancer antigen 125 (CA-125), Muellerian inhibitory substance receptor type II (MISIIR), sialylated Tn antigen (s TN), fibroblast activation antigen (FAP), endosialin (CD248), epidermal growth factor receptor variant III (EGFRvIII), tumor-associated antigen L6 (TAL6), SAS, CD63, TAG72, Thomsen-Friedenreich antigen (TF-antigen), insulin-like growth factor I receptor (IGF-IR), Cora antigen, CD7, CD22, CD70, CD79a, CD79b, G250, MT-MMPs, F19 antigen, CA19-9, CA-125, alpha-fetoprotein (AFP), VEGFR1, VEGFR2, DLK1, SP17, ROR1, and EphA2 and the effector cell is a is T cell wherein the effector cell antigen is CD3.

In other embodiments, the invention provides methods of inducing death of a target cell in a subject having a cancer comprising a population of the target cell. In one embodiment of the method, the method comprises administering a therapeutically effective amount of a pharmaceutical composition comprising the chimeric polypeptide assembly to the subject. In another embodiment of the method, the method comprises administering the chimeric polypeptide assembly as one or more consecutively administered therapeutically effective doses of the pharmaceutical composition. In another embodiment of the method, the method comprises determining the amount of a pharmaceutical composition comprising the chimeric polypeptide assembly needed to achieve a therapeutic effect in the subject having the cancer and administering the amount as one or more consecutively doses to the subject. In the foregoing methods, the cancer is selected from the group consisting of carcinoma, Hodgkin's lymphoma, and non-Hodgkin's lymphoma, diffuse large B cell lymphoma, follicular lymphoma, mantle cell lymphoma, blastoma, breast cancer, ER/PR+ breast cancer, Her2+ breast cancer, triple-negative breast cancer, colon cancer, colon cancer with malignant ascites, mucinous tumors, prostate cancer, head and neck cancer, skin cancer, melanoma, genito-urinary tract cancer, ovarian cancer, ovarian cancer with malignant ascites, peritoneal carcinomatosis, uterine serous carcinoma, endometrial cancer, cervix cancer, colorectal, uterine cancer, mesothelioma in the peritoneum, kidney cancer, Wilm's tumor, lung cancer, small-cell lung cancer, non-small cell lung cancer, gastric cancer, stomach cancer, small intestine cancer, liver cancer, hepatocarcinoma, hepatoblastoma, liposarcoma, pancreatic cancer, gall bladder cancer, cancers of the bile duct, esophageal cancer, salivary gland carcinoma, thyroid cancer, epithelial cancer, arrhenoblastoma, adenocarcinoma, sarcoma, and B-cell derived chronic lymphatic leukemia. In another embodiment of the method, the method comprises administering a therapeutically effective amount of a pharmaceutical composition comprising the chimeric polypeptide assembly to the subject wherein the method results in an improvement of a clinical parameter or endpoint. Exemplary clinical parameters or endpoints can be overall survival, symptom endpoints, disease-free survival, objective response rate, complete response, duration of response, progression-free survival, time to progression, time-to-treatment failure, tumor measurement, tumor size, tumor response rate, time to metastasis, and biomarker concentration. In another embodiment of the method, the method comprises administering a therapeutically effective amount of a pharmaceutical composition comprising the chimeric polypeptide assembly to the subject wherein the method results in a reduction in the frequency, duration, or severity in diagnostically associated side effects in the subject compared to administration of a comparable dose, in mmoles/kg, to a comparable subject of a composition comprising the first portion and an absence the second portion and third portion of the chimeric polypeptide assembly, wherein the side effects are selected from the group consisting of increased plasma levels of IL-2, increased plasma levels of TNF-alpha, increased plasma levels of IFN-gamma, sepsis, febrile neutropenia, neurotoxicity, convulsions, encephalopathy, cytokine release syndrome, speech disturbance, equilibrium disturbance, fever, headache, confusion, hypotension, neutropenia, nausea, impaired consciousness, disorientation, and increased liver enzymes.

In one embodiment, the method comprises administering a therapeutically-effective amount of a pharmaceutical composition comprising a chimeric polypeptide assembly to a subject in need thereof that results in an improvement in at least one parameter, endpoint, physiologic condition, or clinical outcome mediated by the bispecific first portion binding domains. The methods contemplate administration of the pharmaceutical composition by any route appropriate for the disease, disorder or condition being treated, including intradermally, subcutaneously, intramuscularly, intra-abdominally, or intravenously.

The methods of the invention may include administration of consecutive doses of a therapeutically effective amount of the pharmaceutical composition for a period of time sufficient to achieve and/or maintain the desired parameter or clinical effect, and such consecutive doses of a therapeutically effective amount establishes the therapeutically effective dose regimen for the pharmaceutical composition; i.e., the schedule for consecutively administered doses, wherein the doses are given in therapeutically effective amounts to result in a sustained beneficial effect on any clinical sign or symptom, aspect, measured parameter or characteristic of a cancer disease state or condition, including, but not limited to, those cancers and tumors described herein.

For the inventive methods, longer acting chimeric polypeptide assembly compositions or pharmaceutical compositions comprising the chimeric polypeptide assembly compositions are preferred, so as to improve patient convenience, to increase the interval between doses and to reduce the amount of drug required to achieve a sustained effect. In one embodiment, a method of treatment comprises administration of a therapeutically effective dose of a pharmaceutical composition comprising the chimeric polypeptide assembly to a subject in need thereof that results in a gain in time spent within a therapeutic window established for the targeting components of the pharmaceutical composition compared to the corresponding targeting components not linked to the fusion protein and administered at a comparable dose to a subject. In some cases, the gain in time spent within the therapeutic window is at least about three-fold, or at least about four-fold, or at least about five-fold, or at least about six-fold, or at least about eight-fold, or at least about 10-fold, or at least about 20-fold, or at least about 40-fold, or at least about 50-fold, or at least about 100-fold greater compared to the corresponding targeting components not linked to the fusion protein and administered at a comparable dose to a subject. The methods further provide that administration of multiple consecutive doses of a pharmaceutical composition administered using a therapeutically effective dose regimen to a subject in need thereof can result in a gain in time between consecutive $C_{max}$ peaks and/or $C_{min}$ troughs for blood levels of the composition compared to the corresponding targeting components not linked to the fusion protein. In the foregoing embodiment, the gain in time spent between consecutive $C_{max}$ peaks and/or $C_{min}$ troughs can be at least about three-fold, or at least about four-fold, or at least about five-fold, or at least about six-fold, or at least about eight-fold, or at least about 10-fold, or at least about 20-fold, or at least about 40-fold, or at least about 50-fold, or at least about 100-fold longer compared to the corresponding targeting component(s) not linked to the fusion protein and administered using a comparable dose regimen established for the targeting components. In the embodiments hereinabove described in this paragraph the administration of the fusion protein or pharmaceutical composition can result in an improvement in at least one parameter known to be useful for assessing the subject cancer or tumor using a lower unit dose in moles of fusion protein compared to the corresponding targeting components not linked to the fusion protein and administered at a comparable unit dose or dose regimen to a subject.

In one embodiment, the administration of a pharmaceutical composition comprising a subject chimeric polypeptide assembly composition can result in an improvement in one of the clinical, biochemical or physiologic parameters that is greater than that achieved by administration of the first portion not linked to the second and third portions of the composition, determined using the same assay or based on a measured clinical parameter or endpoint. In another embodiment, administration of the pharmaceutical composition can result in improvement two or more clinical or metabolic-related parameters or endpoints, each mediated by one of the different targeting moieties that collectively result in an enhanced effect compared the targeting moiety component not linked to XTEN, determined using the same assays or based on measured clinical parameters. In one embodiment, administration of the pharmaceutical composition to the subject results in improvement of a clinical parameter or endpoint wherein the clinical parameter or endpoint is selected from one or any combination of the group consisting of tumor shrinkage as a complete, partial or incomplete response; time-to-progression, time to treatment failure, biomarker response; progression-free survival; disease free-survival; time to recurrence; time of overall survival; improvement of quality of life; improvement of symptoms; and time to metastasis. In another embodiment, administration of the pharmaceutical composition can result in improvement of one or more of the foregoing clinical parameters that is at least 20% longer duration, or at least 30%, or at least 40%, or at least 50%, or at least 60%, or at least 70%, or at least 80%, or at least 90%, or at least 100% longer than the activity of the first portion not linked to the second and third portions of the composition.

In another aspect, the invention relates to a method of delivering a therapeutic agent to a tumor cell. In one embodiment, the invention provides a method of delivering a therapeutic agent to a tumor cell comprising a tumor specific marker, the method comprising administering to the target cell the chimeric polypeptide assembly of any of the embodiments described herein, wherein the therapeutic agent is delivered to the target cell via the first binding domain of the first portion specifically binding to the tumor specific marker. In one embodiment of the method, the tumor specific marker is selected from the group consisting of alpha 4 integrin, Ang2, B7-H3, B7-H6, CEACAM5, cMET, CTLA4, FOLR1, EpCAM, CCR5, CD19, HER2, HER2 neu, HER3, HER4, HER1 (EGFR), PD-L1, PSMA, CEA, MUC1(mucin), MUC-2, MUC3, MUC4, MUC5AC, MUC5B, MUC7, MUC1613hCG, Lewis-Y, CD20, CD33, CD38, CD30, CD56 (NCAM), CD133, ganglioside GD3; 9-O-Acetyl-GD3, GM2, Globo H, fucosyl GM1, GD2, carbonicanhydrase IX, CD44v6, Sonic Hedgehog (Shh), Wue-1, plasma cell antigen 1, melanoma chondroitin sulfate proteoglycan (MCSP), CCR8, 6-transmembrane epithelial antigen of prostate (STEAP), mesothelin, A33 antigen, prostate stem cell antigen (PSCA), Ly-6, desmoglein 4, fetal acetylcholine receptor (fnAChR), CD25, cancer antigen 19-9 (CA19-9), cancer antigen 125 (CA-125), Muellerian inhibitory substance receptor type II (MISIIR), sialylated Tn antigen (s TN), fibroblast activation antigen (FAP), endosialin (CD248), epidermal growth factor receptor variant III (EGFRvIII), tumor-associated antigen L6 (TAL6), SAS, CD63, TAG72, Thomsen-Friedenreich antigen (TF-antigen), insulin-like growth factor I receptor (IGF-IR), Cora antigen, CD7, CD22, CD70, CD79a, CD79b, G250, MT-MMPs, F19 antigen, CA19-9, CA-125, alpha-fetoprotein (AFP), VEGFR1, VEGFR2, DLK1, SP17, ROR1, and EphA2. In another embodiment of the method of delivering a therapeutic agent to a tumor cell comprising administering to the target cell the chimeric polypeptide assembly, the chimeric polypeptide assembly comprises an amino acid sequence having at least 90%, or at least 91%, or at least 92%, or at least 93%, or at least 94%, or at least 95%, or at least 96%, or at least 97%, or at least 98%, or at least 99%, or at least 100% sequence identity to a polypeptide sequence selected from the group consisting of the sequences of Table 12. In another embodiment of the method of delivering a therapeutic agent to a tumor cell comprising administering to the target cell the chimeric polypeptide assembly, the chimeric polypeptide assembly comprises an amino acid sequence having at least 90%, or at least 91%, or at least 92%, or at least 93%, or at least 94%, or at least 95%, or at least 96%, or at least 97%, or at least 98%, or at least 99%, or at least 100% sequence identity to the polypeptide sequence set forth in FIG. 36 or FIG. 37. In another embodiment of the method of delivering a therapeutic agent to a tumor cell, wherein the tumor cell resides in a tumor in a subject, wherein the subject is selected from the group consisting of mouse, rat, monkey, dog, and human.

V). THE NUCLEIC ACIDS SEQUENCES OF THE INVENTION

In another aspect, the present invention relates to isolated polynucleotide sequences encoding the polypeptide chimeric polypeptide assembly compositions and sequences complementary to polynucleotide molecules encoding the polypeptide chimeric polypeptide assembly compositions.

In some embodiments, the invention provides polynucleotides encoding the chimeric polypeptide assembly compositions embodiments described herein, or the complement of the polynucleotide sequence. In other embodiments, the invention provides isolated polynucleotide sequences encoding the first portion, or the second portion, or the third portion of any of the embodiments described herein, or the complement of the polynucleotide sequences. In one embodiment, the invention provides an isolated polynucleotide sequence encoding a chimeric polypeptide assembly fusion protein consisting of an amino acid sequence with at least 90%, 91%, 92%, 93%, 94%, 95%, 96%, 97%, 98%, 99%, or 100% sequence identity to an amino acid sequence set forth in Table 10 or Table 12, or the complement of the polynucleotide sequence. In one embodiment, the invention provides an isolated polynucleotide sequence encoding a chimeric polypeptide assembly composition wherein the polynucleotide sequence has at least 90%, 91%, 92%, 93%, 94%, 95%, 96%, 97%, 98%, 99%, or 100% sequence identity to a polynucleotide sequence set forth in Table 10 or Table 14.

In another embodiment, the invention provides an isolated polynucleotide sequence encoding a T cell binding composition comprising of a sequence with at least 90%, 91%, 92%, 93%, 94%, 95%, 96%, 97%, 98%, 99%, or 100% sequence identity to a polynucleotide sequence set forth in Table 7, or the complement of the polynucleotide sequence.

In another aspect, the invention relates to methods to produce polynucleotide sequences encoding the chimeric polypeptide assembly composition embodiments, or sequences complementary to the polynucleotide sequences, including homologous variants thereof, as well as methods to express the fusion proteins expressed by the polynucleotide sequences. In general, the methods include producing a polynucleotide sequence coding for the proteinaceous chimeric polypeptide assembly composition components and expressing the resulting gene product and assembling nucleotides encoding the components, ligating the components in frame, and incorporating the encoding gene into an expression vector appropriate for a host cell. For production of the encoded fusion protein of the chimeric polypeptide assembly, the method includes transforming an appropriate host cell with the expression vector, and culturing the host cell under conditions causing or permitting the resulting fusion protein to be expressed in the transformed host cell, thereby producing the fusion protein polypeptide, which is recovered by methods described herein or by standard protein purification methods known in the art. Standard recombinant techniques in molecular biology are used to make the polynucleotides and expression vectors of the present invention.

In accordance with the invention, nucleic acid sequences that encode chimeric polypeptide assembly compositions (or its complement) are used to generate recombinant DNA molecules that direct the expression in appropriate host cells. Several cloning strategies are suitable for performing the present invention, many of which are used to generate a construct that comprises a gene coding for a composition of the present invention, or its complement. In one embodiment, the cloning strategy is used to create a gene that encodes a chimeric polypeptide assembly construct that comprises nucleotides encoding the chimeric polypeptide assembly that is used to transform a host cell for expression of the composition. In the foregoing embodiments hereinabove described in this paragraph, the genes can comprise nucleotides encoding the binding moieties, release segments, and the bulking moieties in the configurations disclosed herein.

In one approach, a construct is first prepared containing the DNA sequence corresponding to chimeric polypeptide assembly construct. Exemplary methods for the preparation of such constructs are described in the Examples. The construct is then used to create an expression vector suitable for transforming a host cell, such as a prokaryotic host cell for the expression and recovery of the chimeric polypeptide assembly construct. Where desired, the host cell is an *E. coli*. Exemplary methods for the creation of expression vectors, the transformation of host cells and the expression and recovery of XTEN are described in the Examples.

The gene encoding for the chimeric polypeptide assembly construct can be made in one or more steps, either fully synthetically or by synthesis combined with enzymatic processes, such as restriction enzyme-mediated cloning, PCR and overlap extension, including methods more fully described in the Examples. The methods disclosed herein can be used, for example, to ligate sequences of polynucleotides encoding the various components (e.g., binding domains, linkers, release segments, and XTEN) genes of a desired length and sequence. Genes encoding chimeric polypeptide assembly compositions are assembled from oligonucleotides using standard techniques of gene synthesis. The gene design can be performed using algorithms that optimize codon usage and amino acid composition appropriate for the *E. coli* host cell utilized in the production of the chimeric polypeptide assembly. In one method of the invention, a library of polynucleotides encoding the components of the constructs is created and then assembled, as described above. The resulting genes are then assembled and the resulting genes used to transform a host cell and produce and recover the chimeric polypeptide assembly compositions for evaluation of its properties, as described herein.

The resulting polynucleotides encoding the chimeric polypeptide assembly sequences can then be individually cloned into an expression vector. The nucleic acid sequence is inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan. Such techniques are well known in the art and well described in the scientific and patent literature. Various vectors are publicly available. The vector may, for example, be in the form of a plasmid, cosmid, viral particle, or phage that may conveniently be subjected to recombinant DNA procedures, and the choice of vector will often depend on the host cell into which it is to be introduced. Thus, the vector may be an autonomously replicating vector, i.e., a vector, which exists as an extrachromosomal entity, the replication of which is independent of chromosomal replication, e.g., a plasmid. Alternatively, the vector may be one which, when introduced into a host cell, is integrated into the host cell genome and replicated together with the chromosome(s) into which it has been integrated.

The invention provides for the use of plasmid expression vectors containing replication and control sequences that are compatible with and recognized by the host cell, and are operably linked to the gene encoding the polypeptide for controlled expression of the polypeptide. The vector ordinarily carries a replication site, as well as sequences that encode proteins that are capable of providing phenotypic selection in transformed cells. Such vector sequences are well known for a variety of bacteria, yeast, and viruses. Useful expression vectors that can be used include, for example, segments of chromosomal, non-chromosomal and synthetic DNA sequences. "Expression vector" refers to a DNA construct containing a DNA sequence that is operably linked to a suitable control sequence capable of effecting the expression of the DNA encoding the polypeptide in a suitable host. The requirements are that the vectors are replicable and viable in the host cell of choice. Low- or high-copy number vectors may be used as desired.

Suitable vectors include, but are not limited to, derivatives of SV40 and pcDNA and known bacterial plasmids such as col EI, pCRl, pBR322, pMal-C2, pET, pGEX as described by Smith, et al., Gene 57:31-40 (1988), pMB9 and derivatives thereof, plasmids such as RP4, phage DNAs such as the numerous derivatives of phage I such as NM98 9, as well as other phage DNA such as M13 and filamentous single stranded phage DNA; yeast plasmids such as the 2 micron plasmid or derivatives of the 2m plasmid, as well as centomeric and integrative yeast shuttle vectors; vectors useful in eukaryotic cells such as vectors useful in insect or mammalian cells; vectors derived from combinations of plasmids and phage DNAs, such as plasmids that have been modified to employ phage DNA or the expression control sequences; and the like. Yeast expression systems that can also be used in the present invention include, but are not limited to, the non-fusion pYES2 vector (Invitrogen), the fusion pYESHisA, B, C (Invitrogen), pRS vectors and the like. The control sequences of the vector include a promoter to effect transcription, an optional operator sequence to control such transcription, a sequence encoding suitable mRNA ribosome binding sites, and sequences that control termination of transcription and translation. The promoter may be any DNA sequence, which shows transcriptional activity in the host cell of choice and may be derived from genes encoding proteins either homologous or heterologous to the host cell. Promoters suitable for use in expression vectors with prokaryotic hosts include the β-lactamase and lactose promoter systems [Chang et al., Nature, 275:615 (1978); Goeddel et al., Nature, 281:544 (1979)], alkaline phosphatase, a tryptophan (trp) promoter system [Goeddel, Nucleic Acids Res., 8:4057 (1980); EP 36,776], and hybrid promoters such as the tac promoter [deBoer et al., Proc. Natl. Acad. Sci. USA, 80:21-25 (1983)], all is operably linked to the DNA encoding CFXTEN polypeptides. Promoters for use in bacterial systems can also contain a Shine-Dalgarno (S.D.) sequence, operably linked to the DNA encoding chimeric polypeptide assembly polypeptides.

VI). METHODS OF MAKING THE COMPOSITIONS OF THE INVENTION

In another aspect, the invention relates to methods of making the chimeric polypeptide assembly compositions at high fermentation expression levels of functional protein using an *E. coli* host cell, as well as providing expression vectors encoding the constructs useful in methods to produce the cytotoxically active polypeptide construct compositions at high expression levels.

In one embodiment, the method comprises the steps of 1) preparing the polynucleotide encoding the chimeric polypeptide assembly fusion protein of any of the embodiments disclosed herein, 2) cloning the polynucleotide into an expression vector, which can be a plasmid or other vector under control of appropriate transcription and translation sequences for high level protein expression in a biological system, 3) transforming an appropriate *E. coli* host cell with the expression vector, and 4) culturing the host cell in conventional nutrient media under conditions suitable for the expression of the chimeric polypeptide assembly composition. Where desired, the *E. coli* host cell is BL21 Gold. By the method, the expression of the chimeric polypeptide assembly fusion protein the results in fermentation titers of at least 0.1 g/L, or at least 0.2 g/L, or at least 0.3 g/L, or at least 0.5 g/L, or at least 0.6 g/L, or at least 0.7 g/L, or at least 0.8 g/L, or at least 0.9 g/L, or at least 1 g/L of the expressed fusion protein as a component of a crude expression product of the host cell and wherein at least 70%, or at least 80%, or at least 90%, or at least 95%, or at least 97%, or at least 99% of the first and the second binding domains of the expressed fusion protein are correctly folded. As used herein, the term "correctly folded" means that the binding domain protein has the ability to specifically bind its target ligand. In another embodiment, the invention provides a method for producing a chimeric polypeptide assembly composition, the method comprising culturing in a fermentation reaction a host cell that comprises a vector encoding a polypeptide comprising the chimeric polypeptide assembly compositions under conditions effective to express the polypeptide product at a concentration of more than about 10 milligrams/gram of dry weight host cell (mg/g), or at least about 250 mg/g, or about 300 mg/g, or about 350 mg/g, or about 400 mg/g, or about 450 mg/g, or about 500 mg/g of said polypeptide when the fermentation reaction reaches an optical density of at least 130 at a wavelength of 600 nm, and wherein the first and the second binding domains of the expressed fusion protein are correctly folded. In another embodiment, the invention provides a method for producing a chimeric polypeptide assembly composition, the method comprising culturing in a fermentation reaction a host cell that comprises a vector encoding a polypeptide comprising the chimeric polypeptide assembly compositions under conditions effective to express the polypeptide product at a concentration of more than about 10 milligrams/gram of dry weight host cell (mg/g), or at least about 250 mg/g, or about 300 mg/g, or about 350 mg/g, or about 400 mg/g, or about 450 mg/g, or about 500 mg/g of said polypeptide when the fermentation reaction reaches an optical density of at least 130 at a wavelength of 600 nm, and wherein the expressed polypeptide product is soluble.

The following are examples of compositions, methods, and treatment regimens of the invention. It is understood that various other embodiments may be practiced, given the general description provided above.

EXAMPLES

Example 1: Construction of ProTIA Construct with Anti-EpCAM-Anti-CD3-XTEN with Release Segment and XTEN The gene encoding anti-EpCAM/anti-CD3 tandem scFv followed with one of the multi-specific release segment sequences (BSRS-1, amino acid sequence LSGRSDNHSPLGLAGS (SEQ ID NO: 1)) was synthesized at Genescript, which introduced NdeI and BsaI restriction sites that are compatible with the NdeI and BsaI sites in the pBR322-XTEN864 destination vector. Restriction digested gene fragments containing anti-EpCAM/anti-CD3 tandem scFv and the BSRS-1 were ligated into the pBR322-XTEN864 vector using T4 DNA ligase and transformed into BL21 Gold cells (New England Biolabs). Transformants were screened by DNA miniprep and the desired construct was confirmed by DNA sequencing. The final vector encodes the ProTIA molecule with the components (in the N- to C-terminus) of anti-EpCAM-anti-CD3 bispecific tandem scFv with BSRS-1 as release segment fused to XTEN_864 gene under the control of a PhoA promoter and STII secretion leader. The resulting construct is AC1278, with the DNA sequence and encoded amino acid sequence provided in Table 10.

Another anti-EpCAM anti-CD3-XTEN with Release Segment, designated AC1476 and with the DNA sequence and encoded amino acid sequence provided in Table 10 as well, was constructed in a similar manner into base vector pYS0044-XTEN864-H6 base vector.

The underscored sequence represents signal peptide, which is cleaved off during secretion and is absent in the final mature protein.

TABLE 10

DNA and amino acid sequence of AC1278 and AC1476 anti-EpCAM-anti-CD3-XTEN with Release Segment

| Construct Name | DNA Sequence | SEQ ID NO: | Amino Acid Sequence* | SEQ ID NO: |
|---|---|---|---|---|
| AC1278 | ATGAAGAAAAACATCGCTTTTCTTCTTGCATC | 477 | MKKNIAFLLASMFV | 479 |
| | TATGTTCGTTTTTTCTATTGCTACAAACGCGT | | FSIATNAYAHHHHH | |
| | ACGCTCATCACCACCATCATCACCATCACGAA | | HHHELVMTQSPSSL | |
| | CTGGTTATGACCCAAAGCCCGAGCAGCCTGAC | | TVTAGEKVTMSCKS | |
| | CGTTACCGCGGGCGAAAAGGTTACCATGAGCT | | SQSLLNSGNQKNYL | |
| | GCAAAAGCAGCCAAAGCCTGCTGAACAGCGGC | | TWYQQKPGQPPKLL | |
| | AACCAAAAGAACTACCTGACCTGGTACCAACA | | IYWASTRESGVPDR | |
| | GAAGCCGGGTCAGCCGCCGAAACTGCTGATCT | | FTGSGSGTDFTLTI | |
| | ACTGGGCGAGCACCCGTGAGAGCGGCGTTCCG | | SSVQAEDLAVYYCQ | |
| | GACCGTTTTACCGGCAGCGGCAGCGGTACCGA | | NDYSYPLTFGAGTK | |
| | CTTTACCCTGACCATTAGCAGCGTGCAGGCGG | | LEIKGGGGSGGGGS | |
| | AAGATCTGGCGGTGTACTATTGCCAAAACGAC | | GGGGSEVQLLEQSG | |
| | TACAGCTACCCGCTGACCTTTGGTGCGGGCAC | | AELVRPGTSVKISC | |
| | CAAACTGGAGATCAAGGGTGGCGGTGGCAGCG | | KASGYAFTNYWLGW | |
| | GCGGTGGTGGCAGCGGCGGCGGTGGCAGCGAG | | VKQRPGHGLEWIGD | |
| | GTTCAGCTGCTGGAACAGAGCGGCGCGGAGCT | | IFPGSGNIHYNEKF | |
| | GGTGCGTCCGGGTACCAGCGTTAAGATCAGCT | | KGKATLTADKSSST | |
| | GCAAGGCGAGCGGTTATGCGTTCACCAACTAC | | AYMQLSSLTFEDSA | |
| | TGGCTGGGTTGGGTGAAGCAACGTCCGGGTCA | | VYFCARLRNWDEPM | |
| | CGGTCTGGAGTGGATCGGCGACATTTTCCCGG | | DYWGQGTTVTVSSG | |
| | GCAGCGGTAACATCCACTACAACGAGAAATTC | | GGGSDVQLVQSGAE | |
| | AAGGGTAAAGCGACCCTGACCGCGGATAAAAG | | VKKPGASVKVSCKA | |
| | CAGCAGCACCGCGTATATGCAGCTGAGCAGCC | | SGYTFTRYTMHWVR | |
| | TGACCTTCGAAGATAGCGCGGTTTACTTCTGC | | QAPGQGLEWIGYIN | |
| | GCGCGTCTGCGTAACTGGGATGAACCGATGGA | | PSRGYTNYADSVKG | |
| | TTACTGGGGTCAGGGCACCACCGTGACCGTTA | | RFTITTDKSTSTAY | |
| | GCAGCGGTGGTGGCGGCAGCGATGTTCAGCTG | | MELSSLRSEDTATY | |
| | GTGCAAAGCGGTGCGGAAGTGAAAAAGCCGGG | | YCARYYDDHYCLDY | |
| | TGCGAGCGTGAAAGTTAGCTGCAAAGCGAGCG | | WGQGTTVTVSSGEG | |
| | GCTATACCTTCACCCGTTACACCATGCACTGG | | TSTGSGGSGGSGGA | |
| | GTTCGTCAGGCGCCGGGTCAGGGCCTGGAATG | | DDIVLTQSPATLSL | |
| | GATCGGCTACATCAACCCGAGCCGTGGCTATA | | SPGERATLSCRASQ | |
| | CCAACTACGCGGATAGCGTGAAAGGTCGTTTC | | SVSYMNWYQQKPGK | |
| | ACCATTACCACCGACAAAAGCACCAGCACCGC | | APKRWIYDTSKVAS | |
| | GTACATGGAACTGAGCAGCCTGCGTAGCGAGG | | GVPARFSGSGSGTD | |
| | ATACCGCGACCTACTATTGCGCGCGTTACTAT | | YSLTINSLEAEDAA | |
| | GATGACCACTACTGCCTGGACTATTGGGGCCA | | TYYCQQWSSNPLTF | |
| | AGGTACCACCGTTACCGTGAGCAGCGGTGAAG | | GGGTKVEIKGTAEA | |
| | GCACCAGCACCGGCAGCGGTGGTAGCGGTGGT | | ASASGLSGRSDNHS | |
| | AGCGGCGGTGCGGATGACATCGTTCTGACCCA | | PLGLAGSPGSPAGS | |
| | AAGCCCGGCGACCCTGAGCCTGAGCCCGGGCG | | PTSTEEGTSESATP | |
| | AGCGTGCGACCCTGAGCTGCCGTGCGAGCCAG | | ESGPGTSTEPSEGS | |
| | AGCGTTAGCTACATGAACTGGTACCAGCAAAA | | APGSPAGSPTSTEE | |
| | GCCGGGCAAAGCGCCGAAGCGTTGGATTTATG | | GTSTEPSEGSAPGT | |
| | ATACCAGCAAGGTTGCGAGCGGTGTTCCGGCG | | STEPSEGSAPGTSE | |
| | CGTTTCAGCGGTAGCGGTAGCGGCACCGATTA | | SATPESGPGSEPAT | |
| | TAGCCTGACCATTAACAGCCTGGAGGCGGAAG | | SGSETPGSEPATSG | |
| | ATGCGGCGACCTACTACTGCCAACAATGGAGC | | SETPGSPAGSPTST | |
| | AGCAATCCGCTGACCTTCGGTGGTGGTACCAA | | EEGTSESATPESGP | |
| | AGTTGAAATTAAGGGCACCGCCGAAGCAGCTA | | GTSTEPSEGSAPGT | |
| | GCGCCTCTGGCCTGTCAGGTCGTTCTGATAAC | | STEPSEGSAPGSPA | |

TABLE 10-continued

DNA and amino acid sequence of AC1278 and AC1476 anti-EpCAM-anti-CD3-XTEN with Release Segment

| Construct Name | DNA Sequence | SEQ ID NO: | Amino Acid Sequence* | SEQ ID NO: |
|---|---|---|---|---|
| | CATTCCCCACTGGGTCTGGCTGGGTCTCCAGG<br>TAGCCCAGCTGGTAGCCCAACCTCTACCGAAG<br>AAGGTACCTCTGAATCCGCTACTCCAGAATCC<br>GGTCCTGGTACTAGCACTGAGCCAAGCGAAGG<br>TTCTGCTCCAGGCTCCCCGGCAGGTAGCCCTA<br>CCTCTACCGAAGAGGGCACTAGCACCGAACCA<br>TCTGAGGGTTCCGCTCCTGGCACCTCCACTGA<br>ACCGTCCGAAGGCAGTGCTCCGGGTACTTCCG<br>AAAGCGCAACTCCGGAATCCGGCCCTGGTTCT<br>GAGCCTGCTACTTCCGGCTCTGAAACTCCAGG<br>TAGCGAGCCAGCGACTTCTGGTTCTGAAACTC<br>CAGGTTCACCGGCGGGTAGCCCGACGAGCACG<br>GAGGAAGGTACCTCTGAGTCGGCCACTCCTGA<br>GTCCGGTCCGGGCACGAGCACCGAGCCGAGCG<br>AGGGTTCAGCCCCGGGTACCAGCACGGAGCCG<br>TCCGAGGGTAGCGCACCGGGTTCTCCGGCGGG<br>CTCCCCTACGTCTACGGAAGAGGGTACGTCCA<br>CTGAACCTAGCGAGGGCAGCGCGCCAGGCACC<br>AGCACTGAACCGAGCGAAGGCAGCGCACCTGG<br>CACTAGCGAGTCTGCGACTCCGGAGAGCGGTC<br>CGGGTACGAGCACGGAACCAAGCGAAGGCAGC<br>GCCCCAGGTACCTCTGAATCTGCTACCCCAGA<br>ATCTGGCCCGGGTTCCGAGCCAGCTACCTCTG<br>GTTCTGAAACCCCAGGTACTTCCACTGAACCA<br>AGCGAAGGTAGCGCTCCTGGCACTTCTACTGA<br>ACCATCCGAAGGTTCCGCTCCTGGTACGTCTG<br>AAAGCGCTACCCCTGAAAGCGGCCCAGGCACC<br>TCTGAAAGCGCTACTCCTGAGAGCGGTCCAGG<br>CTCTCCAGCAGGTTCTCCAACCTCCACTGAAG<br>AAGGCACCTCTGAGTCTGCTACCCCTGAATCT<br>GGTCCTGGCTCCGAACCTGCTACCTCTGGTTC<br>CGAAACTCCAGGTACCTCGGAATCTGCGACTC<br>CGGAATCTGGCCCGGGCACGAGCACGGAGCCG<br>TCTGAGGGTAGCGCACCAGGTACCAGCACTGA<br>GCCTTCTGAGGGCTCTGCACCGGGTACCTCCA<br>CGGAACCTTCGGAAGGTTCTGCGCCGGGTACC<br>TCCACTGAGCCATCCGAGGGTTCAGCACCAGG<br>TACTAGCACGGAACCGTCCGAGGGCTCTGCAC<br>CAGGTACGAGCACCGAACCGTCGGAGGGTAGC<br>GCTCCAGGTAGCCCAGCGGGCTCTCCGACAAG<br>CACCGAAGAAGGCACCAGCACCGAGCCGTCCG<br>AAGGTTCCGCACCAGGTACAAGCGAGAGCGCG<br>ACTCCTGAATCTGGTCCGGGTAGCGAGCCTGC<br>AACCAGCGGTTCTGAGACGCCGGGCACTTCCG<br>AATCTGCGACCCCGGAGTCCGGTCCAGGTTCA<br>GAGCCGGCGACGAGCGGTTCGGAAACGCCGGG<br>TACGTCTGAATCAGCCACGCCGGAGTCTGGTC<br>CGGGTACCTCGACCGAACCAAGCGAAGGTTCG<br>GCACCGGGTACTAGCGAGAGCGCAACCCCTGA<br>AAGCGGTCCGGGCAGCCCGGCAGGTTCTCCAA<br>CCAGCACCGAAGAAGGTTCCCCTGCTGGTAGC<br>CCGACCTCTACGGAGGAAGGTAGCCCTGCAGG<br>TTCCCCAACTTCTACTGAGGAAGGTACTTCTG<br>AGTCCGCTACCCCAGAAAGCGGTCCTGGTACC<br>TCCACTGAACCGTCTGAAGGCTCTGCACCAGG<br>CACTTCTGAGTCTGCTACTCCAGAAAGCGGCC<br>CAGGTTCTGAACCAGCAACTTCTGGCTCTGAG<br>ACTCCAGGCACTTCTGAGTCCGCAACGCCTGA<br>ATCCGGTCCTGGTTCTGAACCAGCTACTTCCG<br>GCAGCGAAACCCCAGGTACCTCTGAGTCTGCG<br>ACTCCAGAGTCTGGTCCTGGTACTTCCACTGA<br>GCCTAGCGAGGGTTCCGCACCAGGTTCTCCGG<br>CTGGTAGCCCGACCAGCACGGAGGAGGGTACG<br>TCTGAATCTGCAACGCCGGAATCGGGCCCAGG<br>TTCGGAGCCTGCAACGTCTGGCAGCGAAACCC<br>CGGGTACCTCCGAATCTGCTACACCGGAAAGC<br>GGTCCTGGCAGCCCTGCTGGTTCTCCAACCTC<br>TACCGAGGAGGGTTCACCGGCAGGTAGCCCGA<br>CTAGCACTGAAGAAGGTACTAGCACGGAGCCG<br>AGCGAGGGTAGTGCTCCGGGTACGAGCGAGAG<br>CGCAACGCCAGAGAGCGGTCCAGGCACCAGCG<br>AATCGGCCACCCCTGAGAGCGGCCCAGGTACT<br>TCTGAGAGCGCCACTCCTGAATCCGGCCCTGG | | GSPTSTEEGTSTEP<br>SEGSAPGTSTEPSE<br>GSAPGTSESATPES<br>GPGTSTEPSEGSAP<br>GTSESATPESGPGS<br>EPATSGSETPGTST<br>EPSEGSAPGTSTEP<br>SEGSAPGTSESATP<br>ESGPGTSESATPES<br>GPGSPAGSPTSTEE<br>GTSESATPESGPGS<br>EPATSGSETPGTSE<br>SATPESGPGTSTEP<br>SEGSAPGTSTEPSE<br>GSAPGTSTEPSEGS<br>APGTSTEPSEGSAP<br>GTSTEPSEGSAPGT<br>STEPSEGSAPGSPA<br>GSPTSTEEGTSTEP<br>SEGSAPGTSESATP<br>ESGPGSEPATSGSE<br>TPGTSESATPESGP<br>GSEPATSGSETPGT<br>SESATPESGPGTST<br>EPSEGSAPGTSESA<br>TPESGPGSPAGSPT<br>STEEGSPAGSPTST<br>EEGSPAGSPTSTEE<br>GTSESATPESGPGT<br>STEPSEGSAPGTSE<br>SATPESGPGSEPAT<br>SGSETPGTSESATP<br>ESGPGSEPATSGSE<br>TPGTSESATPESGP<br>GTSTEPSEGSAPGS<br>PAGSPTSTEEGTSE<br>SATPESGPGSEPAT<br>SGSETPGTSESATP<br>ESGPGSPAGSPTST<br>EEGSPAGSPTSTEE<br>GTSTEPSEGSAPGT<br>SESATPESGPGTSE<br>SATPESGPGTSESA<br>TPESGPGSEPATSG<br>SETPGSEPATSGSE<br>TPGSPAGSPTSTEE<br>GTSTEPSEGSAPGT<br>STEPSEGSAPGSEP<br>ATSGSETPGTSESA<br>TPESGPGTSTEPSE<br>GSAPG | |

TABLE 10-continued

DNA and amino acid sequence of AC1278 and AC1476 anti-EpCAM-anti-CD3-XTEN with Release Segment

| Construct Name | DNA Sequence | SEQ ID NO: | Amino Acid Sequence* | SEQ ID NO: |
|---|---|---|---|---|
| | TAGCGAGCCGGCAACCTCCGGCTCAGAAACTC<br>CTGGTTCGGAACCAGCGACCAGCGGTTCTGAA<br>ACTCCGGGTAGCCCGGCAGGCAGCCCAACGAG<br>CACCGAAGAGGGTACCAGCACGGAACCGAGCG<br>AGGGTTCTGCCCCGGGTACTTCCACCGAACCA<br>TCGGAGGGCTCTGCACCTGGTAGCGAACCTGC<br>GACGTCTGGTTCTGAAACGCCGGGTACCAGCG<br>AAAGCGCTACCCCAGAATCCGGTCCGGGCACT<br>AGCACCGAGCCATCGGAGGGCTCCGCACCAGG<br>T | | | |
| AC1476 | ATGAAGAAAAACATCGCTTTTCTTCTTGCATC<br>TATGTTCGTTTTTTCTATTGCTACAAACGCGT<br>ACGCTGATATTCAGATGACCCAATCGCCGTCG<br>TCCCTGTCAGCTTCAGTCGGTGATCGTGTTAC<br>CATTACCTGTCGCTCAACGAAATCCCTGCTGC<br>ATTCAAACGGTATTACCTATCTGTACTGGTAT<br>CAGCAAAAACCGGGCAAAGCGCCGAAACTGCT<br>GATCTACCAGATGTCGAATCTGGCCAGCGGTG<br>TTCCGTCTCGTTTTAGCTCTAGTGGTTCTGGC<br>ACCGATTTCACCCTGACGATTTCCTCACTGCA<br>ACCGGAAGACTTTGCAACGTATTACTGCGCTC<br>AGAACCTGGAAATCCCGCGTACCTTCGGTCAA<br>GGCACGAAAGTCGAAATTAAAGGTGCAACGCC<br>TCCGGAGACTGGTGCTGAAACTGAGTCCCCGG<br>GCGAGACGACCGGTGGCTCTGCTGAATCCGAA<br>CCACCGGGCGAAGGCCAAGTGCAACTGGTTCA<br>GAGCGGTCCGGGTCTGGTCCAACCGGGTGGCA<br>GTGTGCGTATTTCCTGCGCGGCCTCAGGTTAC<br>ACCTTTACGAACTATGGCATGAATTGGGTGAA<br>ACAGGCCCCGGGTAAAGGCCTGGAATGGATGG<br>GTTGGATCAACACCTACACGGGCGAATCTACC<br>TATGCAGATAGTTTCAAAGGCCGCTTTACCTT<br>CAGCCTGGACACGTCTGCTAGTGCAGCTTATC<br>TGCAGATTAATAGCCTGCGTGCGGAAGATACG<br>GCCGTTTATTACTGTGCGCGCTTTGCAATCAA<br>AGGCGACTACTGGGGCCAAGGCACCCTGCTGA<br>CCGTGTCCTCCGGTGGTGGCGGCAGCGACATC<br>CAAATGACCCAGAGCCCGAGCAGCCTGAGCGC<br>GAGCGTGGGCGACCGTGTTACCATCACCTGCC<br>GTGCGAGCCAAGACATCCGTAACTACCTGAAC<br>TGGTATCAGCAAAAGCCGGGTAAAGCGCCGAA<br>GCTGCTGATCTACTATACCAGCCGTCTGGAGA<br>GCGGCGTGCCGAGCCGTTTCAGCGGTAGCGGT<br>AGCGGTACCGACTACACCCTGACCATTAGCAG<br>CCTGCAGCCGGAAGATTTCGCGACCTACTATT<br>GCCAGCAGGGTAACACCCTGCCGTGGACCTTT<br>GGTCAAGGCACCAAAGTTGAGATTAAAGGCGC<br>CACGCCTCCGGAAACTGGTGCTGAGACGGAAT<br>CCCCTGGTGAAACCACTGGCGGTTCTGCCGAA<br>TCTGAACCGCCTGGTGAAGGCGAGGTGCAGCT<br>GGTTGAAAGCGGTGGCGGTCTGGTGCAACCAG<br>GCGGTAGCCTGCGTCTGAGCTGCGCGGCGAGC<br>GGTTACAGCTTTACCGGTTATACCATGAACTG<br>GGTTCGTCAAGCGCCAGGTAAAGGTCTGGAGT<br>GGGTGGCGCTGATCAACCCGTACAAGGGTGTT<br>AGCACCTATAACCAGAAGTTCAAAGACCGTTT<br>TACCATTAGCGTGGATAAGAGCAAAAACACCG<br>CGTACCTGCAAATGAACAGCCTGCGTGCGGAG<br>GACACCGCTGTGTACTATTGCGCGCGTAGCGG<br>TTACTATGGCGACAGCGACTGGTATTTTGATG<br>TGTGGGGCCAAGGCACCCTGGTTACCGTGAGC<br>TCCGGCACCGCCGAAGCAGCTAGCGCCTCTGG<br>CCTGTCAGGTCGTTCTGATAACCATTCCCCAC<br>TGGGTCTGGCTGGGTCTCCAGGTAGCCCAGCT<br>GGTAGCCCAACCTCTACCGAAGAAGGTACCTC<br>TGAATCCGCTACTCCAGAATCCGGTCCTGGTA<br>CTAGCACTGAGCCAAGCGAAGGTTCTGCTCCA<br>GGCTCCCCGGCAGGTAGCCCTACCTCTACCGA<br>AGAGGGCACTAGCACCGAACCATCTGAGGGTT<br>CCGCTCCTGGCACCTCCACTGAACCGTCCGAA<br>GGCAGTGCTCCGGGTACTTCCGAAAGCGCAAC<br>TCCGGAATCCGGCCCTGGTTCTGAGCCTGCTA | 478 | MKKNIAFLLASMFV<br>FSIATNAYADIQMT<br>QSPSSLSASVGDRV<br>TITCRSTKSLLHSN<br>GITYLYWYQQKPGK<br>APKLLIYQMSNLAS<br>GVPSRFSSSGSGTD<br>FTLTISSLQPEDFA<br>TYYCAQNLEIPRTF<br>GQGTKVEIKGATPP<br>ETGAETESPGETTG<br>GSAESEPPGEGQVQ<br>LVQSGPGLVQPGGS<br>VRISCAASGYTFTN<br>YGMNWVKQAPGKGL<br>EWMGWINTYTGEST<br>YADSFKGRFTFSLD<br>TSASAAYLQINSLR<br>AEDTAVYYCARFAI<br>KGDYWGQGTLLTVS<br>SGGGGSDIQMTQSP<br>SSLSASVGDRVTIT<br>CRASQDIRNYLNWY<br>QQKPGKAPKLLIYY<br>TSRLESGVPSRESG<br>SGSGTDYTLTISSL<br>QPEDFATYYCQQGN<br>TLPWTFGQGTKVEI<br>KGATPPETGAETES<br>PGETTGGSAESEPP<br>GEGEVQLVESGGGL<br>VQPGGSLRLSCAAS<br>GYSFTGYTMNWVRQ<br>APGKGLEWVALINP<br>YKGVSTYNQKFKDR<br>FTISVDKSKNTAYL<br>QMNSLRAEDTAVYY<br>CARSGYYGDSDWYF<br>DVWGQGTLVTVSSG<br>TAEAASASGLSGRS<br>DNESPLGLAGSPGS<br>PAGSPTSTEEGTSE<br>SATPESGPGTSTEP<br>SEGSAPGSPAGSPT<br>STEEGTSTEPSEGS<br>APGTSTEPSEGSAP<br>GTSESATPESGPGS<br>EPATSGSETPGSEP<br>ATSGSETPGSPAGS<br>PTSTEEGTSESATP<br>ESGPGTSTEPSEGS<br>APGTSTEPSEGSAP<br>GSPAGSPTSTEEGT<br>STEPSEGSAPGTST<br>EPSEGSAPGTSESA<br>TPESGPGTSTEPSE<br>GSAPGTSESATPES<br>GPGSEPATSGSETP<br>GTSTEPSEGSAPGT<br>STEPSEGSAPGTSE<br>SATPESGPGTSESA<br>TPESGPGSPAGSPT | 480 |

TABLE 10-continued

DNA and amino acid sequence of AC1278 and AC1476 anti-EpCAM-anti-CD3-XTEN with Release Segment

| Construct Name | DNA Sequence | SEQ ID NO: | Amino Acid Sequence* | SEQ ID NO: |
|---|---|---|---|---|
| | CTTCCGGCTCTGAAACTCCAGGTAGCGAGCCA<br>GCGACTTCTGGTTCTGAAACTCCAGGTTCACC<br>GGCGGGTAGCCCGACGAGCACGGAGGAAGGTA<br>CCTCTGAGTCGGCCACTCCTGAGTCCGGTCCG<br>GGCACGAGCACCGAGCCGAGCGAGGGTTCAGC<br>CCCGGGTACCAGCACGGAGCCGTCCGAGGGTA<br>GCGCACCGGGTTCTCCGGCGGGCTCCCCTACG<br>TCTACGGAAGAGGGTACGTCCACTGAACCTAG<br>CGAGGGCAGCGCGCCAGGCACCAGCACTGAAC<br>CGAGCGAAGGCAGCGCACCTGGCACTAGCGAG<br>TCTGCGACTCCGGAGAGCGGTCCGGGTACGAG<br>CACGGAACCAAGCGAAGGCAGCGCCCCAGGTA<br>CCTCTGAATCTGCTACCCCAGAATCTGGCCCG<br>GGTTCCGAGCCAGCTACCTCTGGTTCTGAAAC<br>CCCAGGTACTTCCACTGAACCAAGCGAAGGTA<br>GCGCTCCTGGCACTTCTACTGAACCATCCGAA<br>GGTTCCGCTCCTGGTACGTCTGAAAGCGCTAC<br>CCCTGAAAGCGGCCCAGGCACCTCTGAAAGCG<br>CTACTCCTGAGAGCGGTCCAGGCTCTCCAGCA<br>GGTTCTCCAACCTCCACTGAAGAAGGCACCTC<br>TGAGTCTGCTACCCCTGAATCTGGTCCTGGCT<br>CCGAACCTGCTACCTCTGGTTCCGAAACTCCA<br>GGTACCTCGGAATCTGCGACTCCGGAATCTGG<br>CCCGGGCACGAGCACGGAGCCGTCTGAGGGTA<br>GCGCACCAGGTACCAGCACTGAGCCTTCTGAG<br>GGCTCTGCACCGGGTACCTCCACGGAACCTTC<br>GGAAGGTTCTGCGCCGGGTACCTCCACTGAGC<br>CATCCGAGGGTTCAGCACCAGGTACTAGCACG<br>GAACCGTCCGAGGGCTCTGCACCAGGTACGAG<br>CACCGAACCGTCGGAGGGTAGCGCTCCAGGTA<br>GCCCAGCGGGCTCTCCGACAAGCACCGAAGAA<br>GGCACCAGCACCGAGCCGTCCGAAGGTTCCGC<br>ACCAGGTACAAGCGAGAGCGCGACTCCTGAAT<br>CTGGTCCGGGTAGCGAGCCTGCAACCAGCGGT<br>TCTGAGACGCCGGGCACTTCCGAATCTGCGAC<br>CCCGGAGTCCGGTCCAGGTTCAGAGCCGGCGA<br>CGAGCGGTTCGGAAACGCCGGGTACGTCTGAA<br>TCAGCCACGCCGGAGTCTGGTCCGGGTACCTC<br>GACCGAACCAAGCGAAGGTTCGGCACCGGGTA<br>CTAGCGAGAGCGCAACCCCTGAAAGCGGTCCG<br>GGCAGCCCGGCAGGTTCTCCAACCAGCACCGA<br>AGAAGGTTCCCCTGCTGGTAGCCCGACCTCTA<br>CGGAGGAAGGTAGCCCTGCAGGTTCCCCAACT<br>TCTACTGAGGAAGGTACTTCTGAGTCCGCTAC<br>CCCAGAAAGCGGTCCTGGTACCTCCACTGAAC<br>CGTCTGAAGGCTCTGCACCAGGCACTTCTGAG<br>TCTGCTACTCCAGAAAGCGGCCCAGGTTCTGA<br>ACCAGCAACTTCTGGCTCTGAGACTCCAGGCA<br>CTTCTGAGTCCGCAACGCCTGAATCCGGTCCT<br>GGTTCTGAACCAGCTACTTCCGGCAGCGAAAC<br>CCCAGGTACCTCTGAGTCTGCGACTCCAGAGT<br>CTGGTCCTGGTACTTCCACTGAGCCTAGCGAG<br>GGTTCCGCACCAGGTTCTCCGGCTGGTAGCCC<br>GACCAGCACGGAGGAGGGTACGTCTGAATCTG<br>CAACGCCGGAATCGGGCCCAGGTTCGGAGCCT<br>GCAACGTCTGGCAGCGAAACCCCGGGTACCTC<br>CGAATCTGCTACACCGGAAAGCGGTCCTGGCA<br>GCCCTGCTGGTTCTCCAACCTCTACCGAGGAG<br>GGTTCACCGGCAGGTAGCCCGACTAGCACTGA<br>AGAAGGTACTAGCACGGAGCCGAGCGAGGGTA<br>GTGCTCCGGGTACGAGCGAGAGCGCAACGCCA | | STEEGTSESATPES<br>GPGSEPATSGSETP<br>GTSESATPESGPGT<br>STEPSEGSAPGTST<br>EPSEGSAPGTSTEP<br>SEGSAPGTSTEPSE<br>GSAPGTSTEPSEGS<br>APGTSTEPSEGSAP<br>GSPAGSPTSTEEGT<br>STEPSEGSAPGTSE<br>SATPESGPGSEPAT<br>SGSETPGTSESATP<br>ESGPGSEPATSGSE<br>TPGTSESATPESGP<br>GTSTEPSEGSAPGT<br>SESATPESGPGSPA<br>GSPTSTEEGSPAGS<br>PTSTEEGSPAGSPT<br>STEEGTSESATPES<br>GPGTSTEPSEGSAP<br>GTSESATPESGPGS<br>EPATSGSETPGTSE<br>SATPESGPGSEPAT<br>SGSETPGTSESATP<br>ESGPGTSTEPSEGS<br>APGSPAGSPTSTEE<br>GTSESATPESGPGS<br>EPATSGSETPGTSE<br>SATPESGPGSPAGS<br>PTSTEEGSPAGSPT<br>STEEGTSTEPSEGS<br>APGTSESATPESGP<br>GTSESATPESGPGT<br>SESATPESGPGSEP<br>ATSGSETPGSEPAT<br>SGSETPGSPAGSPT<br>STEEGTSTEPSEGS<br>APGTSTEPSEGSAP<br>GSEPATSGSETPGT<br>SESATPESGPGTST<br>EPSEGSAPGHHHHH<br>H | |

TABLE 10-continued

DNA and amino acid sequence of AC1278 and AC1476 anti-EpCAM-anti-CD3-XTEN with Release Segment

| Construct Name | DNA Sequence | SEQ ID NO: | Amino Acid Sequence* | SEQ ID NO: |
|---|---|---|---|---|
| | GAGAGCGGTCCAGGCACCAGCGAATCGGCCAC CCCTGAGAGCGGCCCAGGTACTTCTGAGAGCG CCACTCCTGAATCCGGCCCTGGTAGCGAGCCG GCAACCTCCGGCTCAGAAACTCCTGGTTCGGA ACCAGCGACCAGCGGTTCTGAAACTCCGGGTA GCCCGGCAGGCAGCCCAACGAGCACCGAAGAG GGTACCAGCACGGAACCGAGCGAGGGTTCTGC CCCGGGTACTTCCACCGAACCATCGGAGGGCT CTGCACCTGGTAGCGAACCTGCGACGTCTGGT TCTGAAACGCCGGGTACCAGCGAAAGCGCTAC CCCAGAATCCGGTCCGGGCACTAGCACCGAGC CATCGGAGGGCTCCGCACCAGGTCACCATCAT CACCATCAC | | | |

*underlined peptide represents the signal peptide

Example 2: Production of Uncleaved and Cleaved His8-aEpCAM-aCD3-BSRS1-XTEN864 ("His8" Disclosed as SEQ ID NO: 481) from *E. coli* Fermentation Culture 1) Expression and Purification of His(8)-aEpCAM-aCD3-BSRS1-XTEN_AE864 ("His8" disclosed as SEQ ID NO: 481) from *E. coli* fermentation culture The fusion protein AC1278 (MKKNIAFLLASMFVFSI-ATNAYA-His(8)-aEpCAM-aCD3-BSRS1-XTEN_AE864 (SEQ ID NO: 482)) was expressed in Amunix's proprietary *E. coli* AmE098 strain A 10 L fermentation culture was grown at 37° C. and temperature shifted to 26° C. following depletion of the salt feed. During harvest, fermentation whole broth was centrifuged to pellet the cells. The supernatant was collected, and acid flocculation was then used to reduce endotoxin and host cell protein contamination. Using 1 M acetic acid, the supernatant pH was gradually lowered to pH 4.5 and left to incubate at room temperature for 30 minutes. The pH was then raised back to pH 7.5 using 2M NaOH and held overnight at 4° C. On the following day, the supernatant was 0.20 μm filtered using a 3M LifeAssure filter capsule.

Figure 14A:
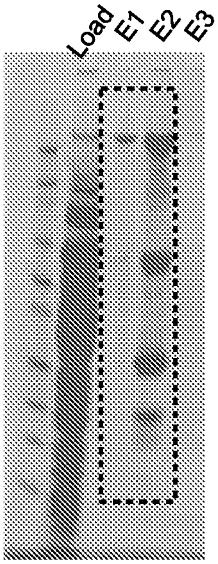
FIG. 14A shows exemplary SDS-PAGE of IMAC capture of AC1278 from fermentation media.

To ensure N-terminal integrity at the His affinity tag, immobilized-metal affinity chromatography was used as the first capture step. Five 10-mL RedisepRf 25G column housings (Teledyne Isco) were packed with 10 mL of ToyoPearl-AF-Chelate 650M resin (TOSOH Biosciences). The columns were sanitized with 0.5M NaOH, thoroughly rinsed with distilled water, and then charged with 0.1M $Ni_2SO_4$, and equilibrated with 5 column volumes (CVs) of equilibration buffer (20 mM Tris, 250 mM NaCl, pH 7.5). Due to Triton X-114's cloud point of 23° C., Triton Wash buffer (20 mM Tris, 100 mM NaCl, 0.1% Triton X-114, pH 7.5) and Wash 2 buffer (20 mM Tris, 100 mM NaCl, pH 7.5) were prepared in advance, stored at 4° C., and kept on ice during use. After column equilibration, the supernatant was loaded to the column. Following 3 CVs of equilibration buffer as chase, the column was washed with 10CVs of cold Triton Wash buffer to lower endotoxin, followed by 10 CVs of cold Wash 2 buffer to remove Triton X-114. Protein was then eluted from the column with 3 CVs of elution buffer (20 mM Tris, 100 mM NaCl, 150 mM imidazole, pH 7.5), and 1 CV fractions (10 mL) were collected. To reduced protein oxidation, 5 mM EDTA was added to each elution. The load, flowthrough, and elution's were analyzed by non-reducing 4-12% Bis-Tris SDS-PAGE and Coomassie staining. Based on the gel, elution CV1 and CV2 were saved for further processing. (FIG. 14A)

Figure 14B:
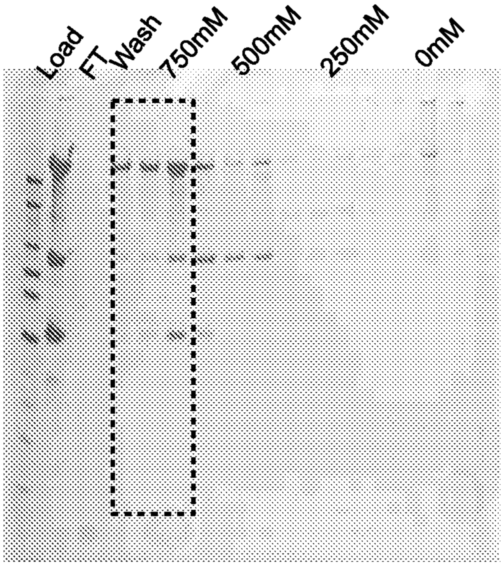
FIG. 14B shows SDS-PAGE analysis of fractions in HIC polishing step.

Hydrophobic interaction chromatography (HIC) was chosen as the subsequent polishing step. Two 20-mL RedisepRf 25G column housings (Teledyne Isco) were packed with 20 mL of Toyopearl-Phenyl-650M resin (TOSOH Biosciences). The columns were sanitized with 0.5M NaOH, thoroughly rinsed with distilled water, and equilibrated with 5 CVs of Buffer A (20 mM Tris, 1M $(NH4)_2SO_4$, pH 7.5). Elution buffers at 75% Buffer A, 50% Buffer A, and 25% Buffer A were prepared in advance by mixing appropriate volumes of Buffer A and Buffer B (20 mM Tris, pH 7.5). IMAC elutions CV1 and 2 were pooled together from the previous column step, and ammonium sulfate was added to a final concentration of 1M before loading to the pre-equilibrated Phenyl columns. After loading and chasing with 3 CVs of Buffer A, the column was eluted with 3 CVs each of 75% Buffer A, 50% Buffer A, 25% Buffer A, and 0% Buffer A. The load, flowthrough, and elutions were analyzed by non-reducing 4-12% Bis-Tris SDS-PAGE and Coomassie staining. Based on the gel, wash and elutions CV1-2 at 750 mM $(NH4)_2SO_4$ (boxed) were pooled for further processing (FIG. 14B).

Figure 14C:
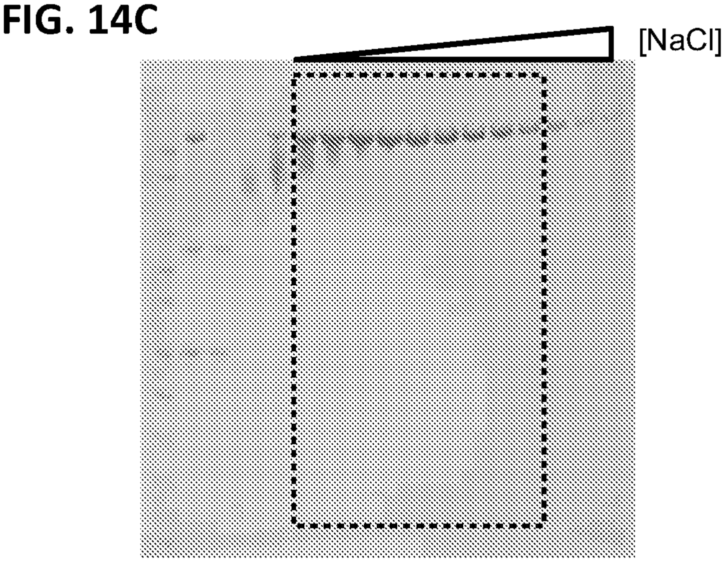
FIG. 14C shows SDS-PAGE analysis of fractions in ImpRes-Q polishing step.

To ensure C-terminal integrity of XTEN and to further lower endotoxin, anion exchange chromatography was chosen as the final polishing step. A XK16 column housing on AKTApurifier was packed with 5 mL of Capto Q Impress resin (GE Healthcare), sanitized with 0.5M NaOH, thoroughly rinsed with distilled water, stripped with 2 CVs of Buffer B (20 mM Tris, 500 mM NaCl, pH 7.5), and equilibrated with 5 CVs of Buffer A (20 mM Tris pH 7.5). The HIC elution pool was diluted 4 fold before loading to the column. The column was then washed with 3 CVs of 30% Buffer B and eluted in a gradient of 30% to 70% Buffer B over 15 CVs. Elutions were collected in ½ CV (2.5 mL) fractions. The load, flowthrough, and elutions were then analyzed by non-reducing SDS-PAGE and Coomassie staining to determine fractions to pool for formulation (FIG. 14C).

2) Formulation and Characterization

Figure 15A:
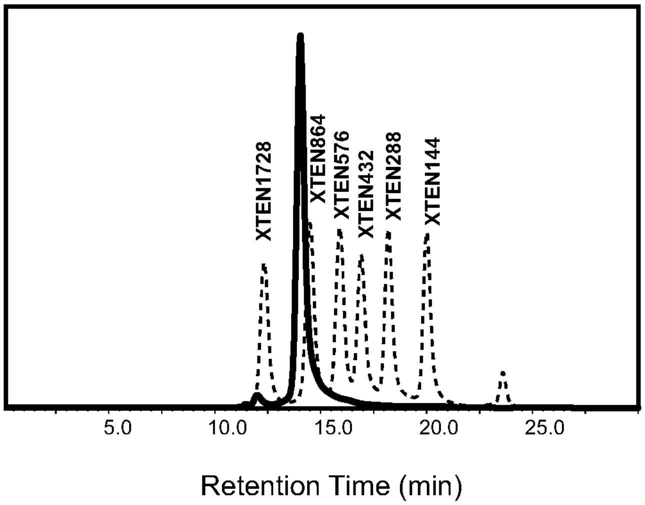
FIG. 15A shows the lot release analytical SEC chromatography of uncleaved AC1278 (in solid line) against XTEN length standard (in dashed line)
Figure 15B:
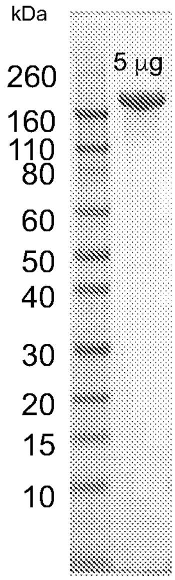
FIG. 15B shows the lot release SDS-PAGE of uncleaved AC1278.

Desired elution fractions (boxed in FIG. 14C) were concentrated and buffer exchanged into 50 mM Tris, 150 mM NaCl, pH 7.5. Formulated product was 0.2 μm sterile filtered. Lot release to determine product quality involved size exclusion chromatography analysis and SDS-PAGE analysis. For SEC analysis, 10 μg of formulated product was injected to an analytical SEC column, confirming >95% monomeric product. (FIG. 15A). SDS-PAGE analysis was conducted by loading 5 μg of formulated product to a 4-12% Bis-Tris gel and staining with Coomassie Blue. The product purity was >90% (FIG. 15B).

3) Enzyme Activation and Storage

Recombinant mouse MMP-9 was supplied as zymogen from R&D Systems and required activation by 4-aminophenylmercuric acetate (APMA). APMA was first dissolved in 0.1M NaOH to a final concentration of 10 mM before the pH was readjusted to neutral using 0.1N HCl. Further dilution of the APMA stock to 2.5 mM was done in 50 mM Tris, 150 mM NaCl, 10 mM $CaCl_2$, pH 7.5. To activate pro-MMP, 1 mM APMA and 100 ug/mL of pro-MMP-9 were incubated at 37° C. for 3 hours. Activated enzyme added to a final concentration of 50% glycerol could then be stored at −20° C. for several weeks.

4) MMP-9 Digestion of his(8)-aEpCAM-aCD3-BSRS1-XTEN864 ("his(8)" Disclosed as SEQ ID NO: 481)

Figure 16A:
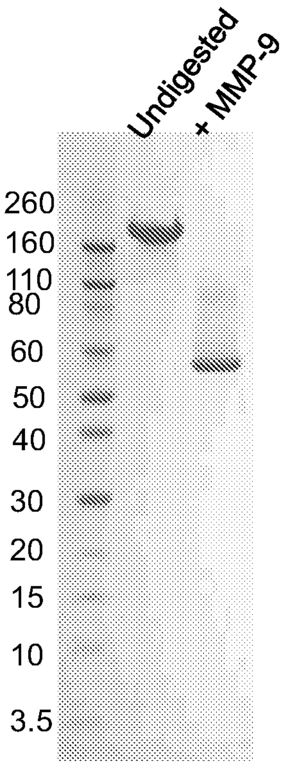
FIG. 16A shows SDS-PAGE analysis of MMP-9 digestion reaction mixture.

To produce cleaved aEpCAM-aCD3 ProTIA-A, 9.12 mg of formulated His(8)-aEpCAM-aCD3-BSRS1-XTEN864 (ProTIA-X) ("His(8)" disclosed as SEQ ID NO: 481) was incubated for 2 hours at 37° C. in a reaction mixture containing 10 mM $CaCl_2$ and a 1:2237 enzyme-to-substrate molar ratio of active recombinant mouse MMP-9 (R&D Systems). To confirm specific digestion at BSRS1, 5 μg of undigested and MMP-9 digested product were run on 4-12% Bis-Tris SDS-PAGE, followed by staining by Coomasie Blue. Use of Coomassie Blue staining allowed visualization of the full-length His8-aEpCAM-aCD3-BSRS1-XTEN864 (ProTIA-X) ("His8" disclosed as SEQ ID NO: 481) before MMP-9 digestion and the His8-aEpCAM-aCD3 cleaved fragment (ProTIA-A) ("His8" disclosed as SEQ ID NO: 481) after MMP-9 digestion (FIG. 16A).

Figure 16B:
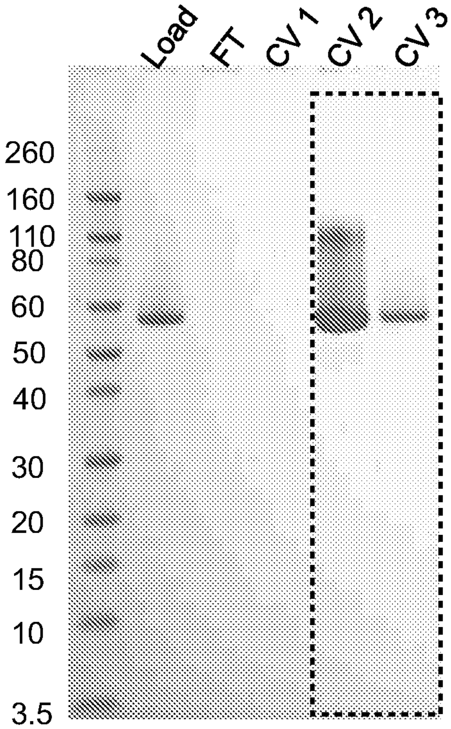
FIG. 16B show SDS-PAGE analysis of IMAC purification of MMP-9 digestion mixture to remove cleaved XTEN segment.

5) Purification of Cleaved his(8)-aEpCAM-aCD3 ProTIA-A ("his(8)" Disclosed as SEQ ID NO: 481) Following MMP-9 Digestion Following confirmation of MMP-9 digestion at BSRS1, immobilized-metal affinity chromatography was used to remove MMP-9. A 5-mL polypropylene column housing (ThermoScientific) was packed with 2 mL of ToyoPearl-AF-Chelate 650M resin (TOSOH Biosciences). The column was equilibrated with 5 CVs of equilibration buffer (20 mM Tris, 250 mM NaCl, pH 7.5). The digestion mixture was then loaded to the column. After loading and chasing with 1 CV of equilibration buffer, the column was washed with 3 CVs of equilibration buffer. Protein was eluted from the column with 3 CVs of elution buffer (20 mM Tris, 100 mM NaCl, 150 mM imidazole, pH 7.5), and 1 CV fractions (2 mL) were collected. The load, flow-through, and elutions were analyzed by non-reducing 4-12% Bis-Tris SDS-PAGE and Coomassie straining to determine elutions containing ProTIA-A (FIG. 16B).

6) Formulation and Characterization of Cleaved his(8)-aEpCAM-aCD3 ("his(8)" Disclosed as SEQ ID NO: 481)

Figure 17A:
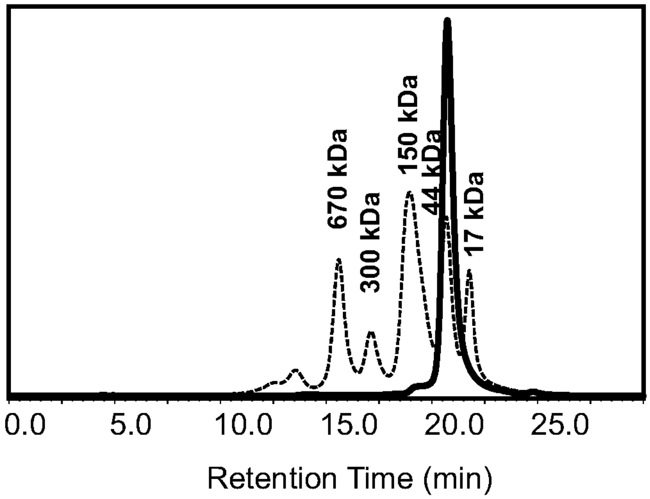
FIG. 17A shows the lot release analytical SEC chromatography of cleaved AC1278 (in solid line) against globular protein standard (in dashed line)
Figure 17B:
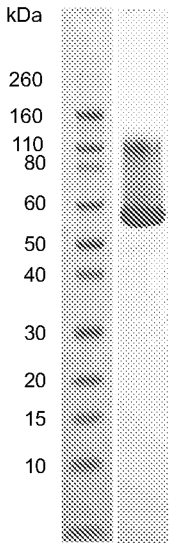
FIG. 17B shows the lot release SDS-PAGE of cleaved AC1278.

Desired elutions (boxed in FIG. 16B) were concentrated and buffer exchanged into 50 mM Tris, 150 mM NaCl, pH 7.5. Lot release to determine product quality involved size exclusion chromatography analysis and SDS-PAGE analysis. For SEC analysis, 10 μg of product was injected to an analytical SEC column, confirming >95% monomeric product (FIG. 17A). For SDS-PAGE analysis, 5 μg of product was run on a 4-12% Bis-Tris gel, confirming >90% product purity (FIG. 17B).

Figure 18A:
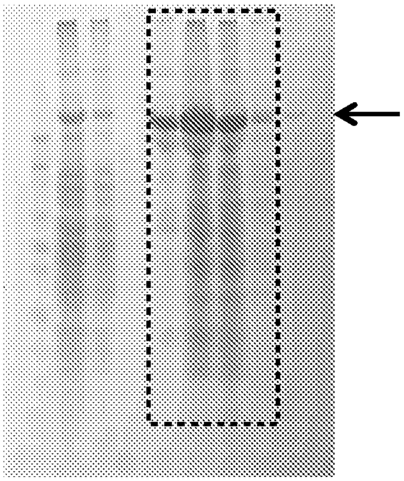
FIG. 18A shows exemplary SDS-PAGE of IMAC capture of AC1476 from fermentation media.

Example 3: Production of Uncleaved and Cleaved AC1476 aEpCAM-aCD3-BSRS1-XTEN_AE864-his(6) ("his(6)" Disclosed as SEQ ID NO: 483) from *E. coli* Fermentation Culture 1) Expression and Purification of AC1476 aEpCAM-aCD3-BSRS1-XTEN_AE864-his(6) ("his(6)" Disclosed as SEQ ID NO: 483) from *E. coli* Fermentation Culture The fusion protein AC1476 (MKKNIAFLLASMFVFSIATNAYA-aEpCAM-aCD3-BSRS1-XTEN_AE864-His(6) (SEQ ID NO: 484; "His(6)" disclosed as SEQ ID NO: 483)) was expressed in Amunix's proprietary *E. coli* AmE097 strain. A 10 L fermentation culture was grown at 37° C. and temperature shifted to 28° C. after depletion of the salt feed. During harvest, fermentation whole broth was centrifuged to pellet the cells. The supernatant was 0.20 μm filtered using a 3M LifeAssure filter capsule. A XK50 housing column was packed with 100 mL of Toyopearl-AF-Chelate-650M resin (TOSOH Biosciences) and connected to a peristaltic pump at 4° C. The column was sanitized with 0.5M NaOH, thoroughly rinsed with distilled water, charged with 0.1M $NiSO_4$, and equilibrated with 5 CVs of equilibration buffer (20 mM Tris, 250 mM NaCl, pH 7.5). After column equilibration, the supernatant was loaded to the column, followed by Triton Wash, Wash 2, and elution similar to the process described above in Example 2-1. Elutions were collected in ¼ CV (25 mL) fractions and EDTA was added to a final concentration of 5 mM to chelate free nickel. The load, flowthrough, and elutions were analyzed by non-reducing 4-12% Bis-Tris SDS-PAGE and Coomassie staining. Based on the gel, elutions 2-5 (boxed) were saved for further processing. (FIG. 18A)

Figure 18B:
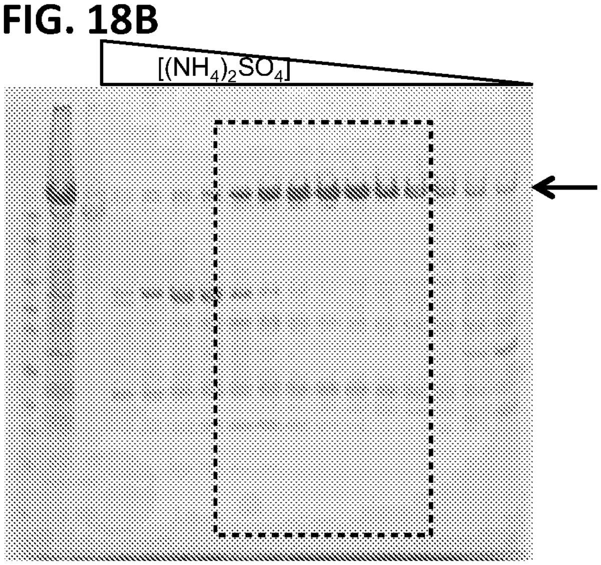
FIG. 18B shows SDS-PAGE analysis of fractions in HIC polishing step.

Hydrophobic interaction chromatography (HIC) was chosen as the subsequent polishing step. A XK24 housing column on AKTApurifier was packed with 50 mL of Toyopearl-Phenyl-650M resin (TOSOH Biosciences). The column was sanitized with 0.5M NaOH, thoroughly rinsed with distilled water, and equilibrated with 5 CVs of Buffer A (20 mM Tris, 1M (NH4)2504, pH 7.5). Desired IMAC elutions were pooled together from the previous column step, and ammonium sulfate was added to a final concentration of 1M before loading to the column. Elutions were collected in ½ CV (25 mL) fractions in a gradient from 100% to 50% Buffer A over 10 CVs. The load, flowthrough, and elutions were analyzed by non-reducing 4-12% Bis-Tris SDS-PAGE and Coomassie staining. Based on the gel, elutions boxed were pooled for further processing (FIG. 18B).

Figure 18C:
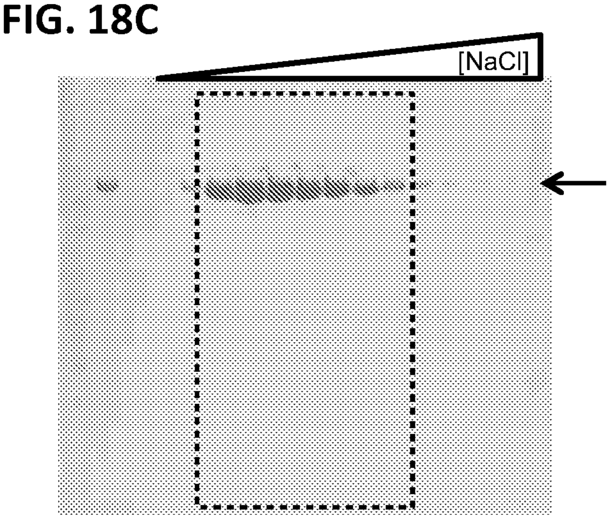
FIG. 18C shows SDS-PAGE analysis of fractions in ImpRes-Q polishing step.

Anion exchange chromatography was chosen as the final polishing step. A XK24 housing column was packed with 30 mL Capto Q Impress resin (GE Healthcare), sanitized with 0.5M NaOH, thoroughly rinsed with distilled water, stripped with 2 CVs of Buffer B (20 mM Tris, 500 mM NaCl, pH 7.5), and equilibrated with 5 CVs of Buffer A (20 mM Tris, pH 7.5). The elution pool was buffer exchanged through a Pellicon XL Ultrafiltration module Biomax 10 kDa into 20 mM Tris pH 7.5 until the permeate had a conductivity of 8 ms/cm. The permeate was loaded to the Capto Q Impress column, and the column was then washed with 3 CVs of 10% and 20% Buffer B. Elutions were collected in ¼ CV (7.5 mL) fractions in a gradient from 20% to 70% Buffer B over 10 CVs. The load, flowthrough, and elutions were analyzed by non-reducing 4-12% Bis-Tris SDS-PAGE and Coomassie staining. Based on the gel, selected elutions (boxed) were pooled for formulation (FIG. 18C).

2) Formulation and Characterization of aEpCAM-aCD3-BSRS1-XTEN864-his(6) ("his(6)" Disclosed as SEQ ID NO: 483)

Figure 19A:
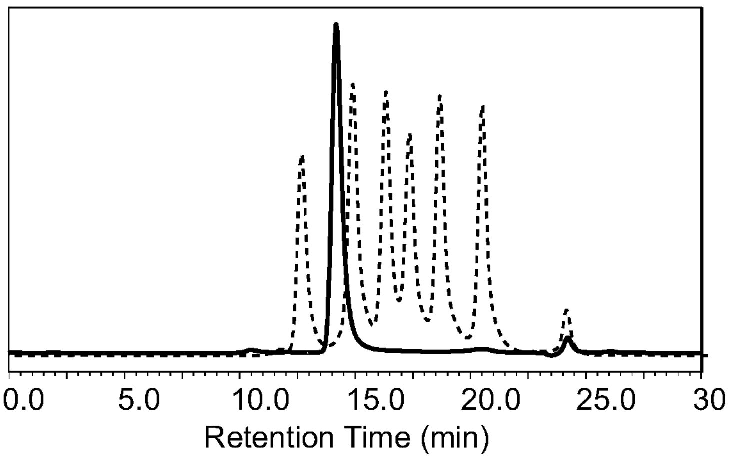
FIG. 19A shows the lot release analytical SEC chromatography of uncleaved AC1476 (in solid line) against XTEN length standard (in dashed line)
Figure 19B:
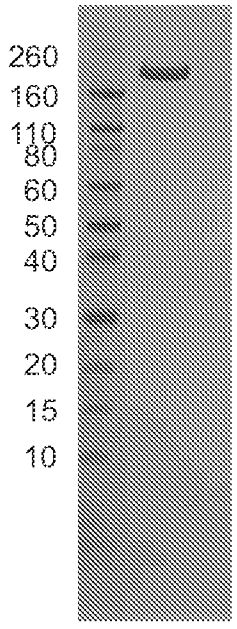
FIG. 19B shows the lot release SDS-PAGE of uncleaved AC1476 with Coomassie staining.
Figure 19C:
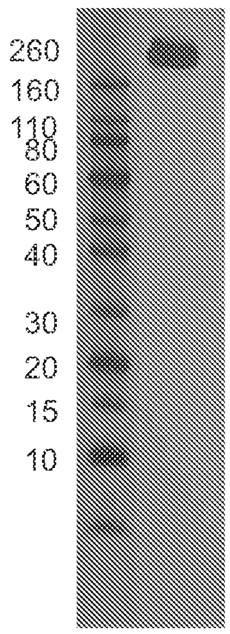
FIG. 19C shows the lot release SDS-PAGE of uncleaved AC1476 with silver staining.

Desired elutions were concentrated and buffer exchanged into 50 mM Tris, 150 mM NaCl, pH 7.5. Lot release to determine product quality was performed following protocol established in Example 2 for SEC analysis (FIG. 19A) and SDS-PAGE (FIG. 19B). Additionally, 2 μg was loaded to a 4-12% Bis-Tris non-reducing SDS-PAGE gel, with subsequent silver staining (FIG. 19C). The results of SEC were also used to determine the apparent molecular weight and apparent molecular weight factor (relative to actual molecular weight) and the hydrodynamic radius of the aEpCAM-aCD3-BSRS1-XTEN864-His(6) ("His(6)" disclosed as SEQ ID NO: 483). The apparent molecular weight determined was 1.7 MDa, which would result in an apparent molecular weight factor of 12.3 and a calculated hydrodynamic radius of 10.8 nm.

Figure 20A:
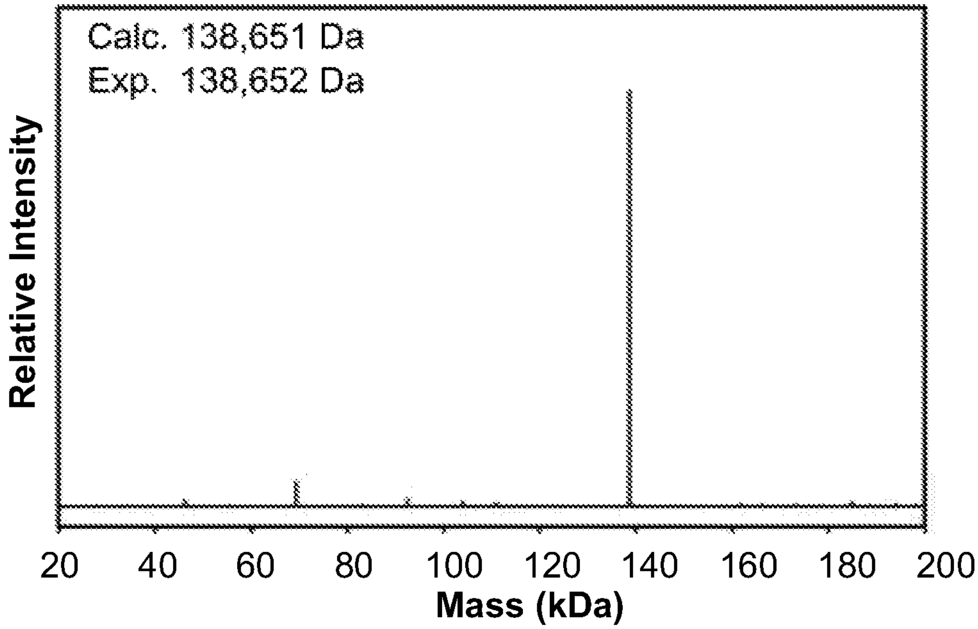
FIG. 20A shows the lot release ESI-MS of uncleaved AC1476.
Figure 20B:
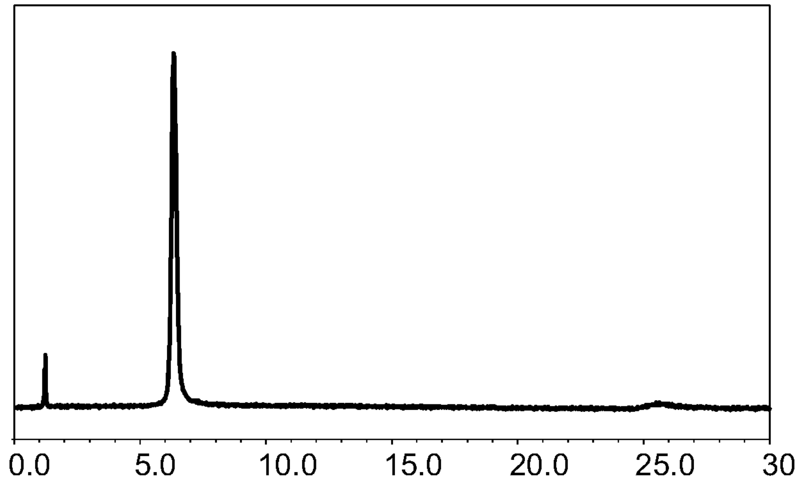
FIG. 20B shows the lot release cation exchange chromatography of uncleaved AC1476.

To further prove the identity of the molecule, electrospray ionization mass spectrometry (ESI-MS) was performed and the experimental mass was determined to be 138,652 Da, with ΔMass of +1 Da when compared to theoretical molecular weight of 138,651 Da (FIG. 20A). For analytical cation exchange chromatography, 10 μg of sample was loaded onto Agilent Bio SCX NP3 with mobile phase A 20 mM sodium acetate, pH 4.5 and mobile phase B 20 mM sodium acetate, 1 M sodium chloride, pH 4.5. A linear gradient of 0-100% B was applied during the course of 20 minutes and only one single major peak was detected (FIG. 20B).

4) MMP-9 Digestion of aEpCAM-aCD3-BSRS1-XTEN864-his(6) ("his(6)" Disclosed as SEQ ID NO: 483)

Figure 21A:
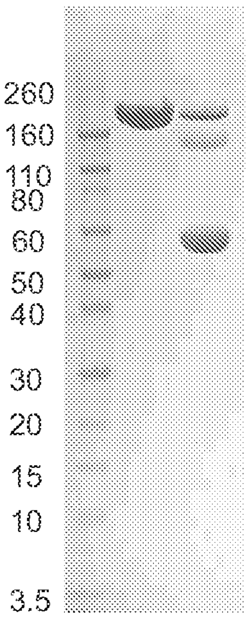
FIG. 21A shows the SDS-PAGE analysis of MMP-9 digestion reaction mixture.

Following MMP-9 activation and digestion protocol described in Example 2, 20 mg of aEpCAM-aCD3-BSRS1-XTEN864-His(6) (ProTIA-X) ("His(6)" disclosed as SEQ ID NO: 483) was digested, however using only 1:6000 molar enzyme-to-substrate molar ratio of active recombinant mouse MMP-9. Undigested and digested products were analyzed by SDS-PAGE (FIG. 21A).

Figure 21B:
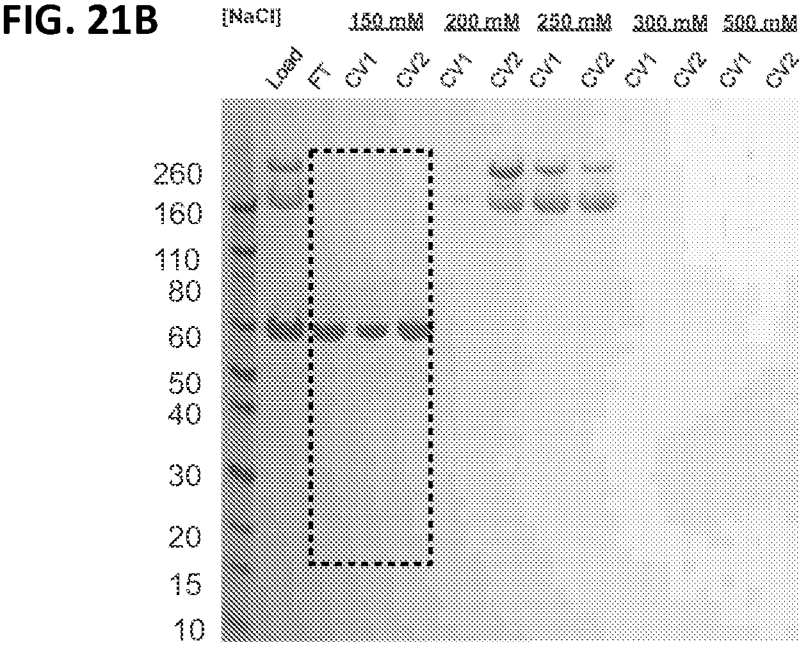
FIG. 21B shows the SDS-PAGE analysis of anion exchange fractions of MMP-9 digestion mixture to remove uncleaved substrate, as well as cleaved XTEN segment.

5) Purification of Cleaved aEpCAM-aCD3-BSRS1-XTEN864-his(6) ("his(6)" Disclosed as SEQ ID NO: 483) Following MMP-9 Digestion Following confirmation of MMP-9 digestion at BSRS1, anion exchange chromatography was used to remove cleaved free XTEN and uncleaved ProTIA-X. Two 5-ml polypropylene column housings (ThermoScientific) were packed with 3 mL each of MacroCap Q resin (GE Healthcare), sanitized with CIP (0.5M NaOH, 1M NaCl), thoroughly rinsed with distilled water, stripped with 2 CVs of Buffer B (20 mM Tris, 500 mM NaCl, PH 7.5), and equilibrated with 5 CVs of Buffer A (20 mM Tris, pH 7.5). The digestion mixture was loaded to the column. After loading and chasing with 1 CV of Buffer A, the column was eluted with 2 CVs each of 150 mM, 200 mM, 250 mM, 300 mM, and 500 mM NaCl. The load, flowthrough, and elutions were analyzed by 4-12% Bis-Tris SDS-PAGE and Coomassie straining to determine fractions containing ProTIA-A (FIG. 21B).

Figure 22A:
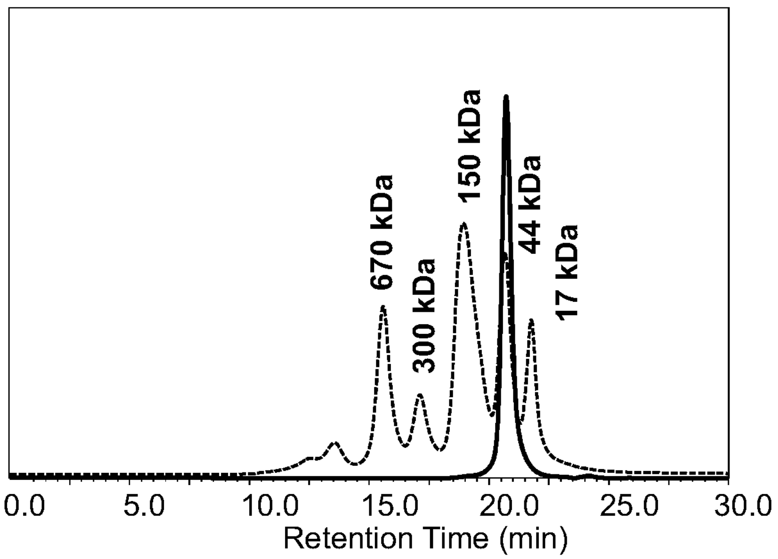
FIG. 22A shows the lot release analytical SEC of cleaved AC1476 (in solid line) against globular protein standard (in dashed line)
Figure 22B:
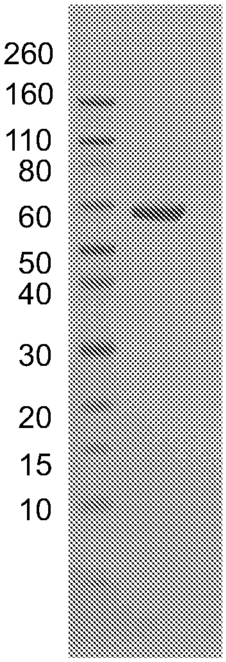
FIG. 22B shows the lot release SDS-PAGE of cleaved AC1476 with Coomassie staining.
Figure 22C:
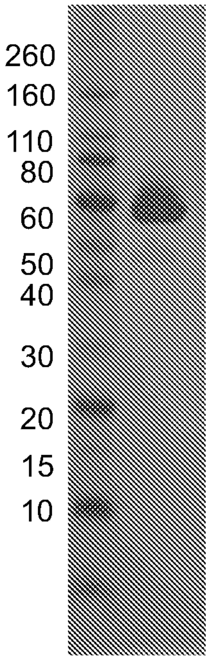
FIG. 22C shows the lot release SDS-PAGE of cleaved AC1476 with silver staining.

6) Formulation and characterization of cleaved aEpCAM-aCD3 Desired ProTIA-A fractions were concentrated and buffer exchanged into 50 mM Tris, 150 mM NaCl, pH 7.5. Lot release to determine product quality was performed following protocol established in Example 2 for SEC analysis (FIG. 22A) and SDS-PAGE (FIG. 22B). Additionally, 2 μg was loaded to a 4-12% Bis-Tris non-reducing SDS-PAGE gel, with subsequent silver staining (FIG. 22C). The results of SEC were also used to determine the apparent molecular weight and apparent molecular weight factor (relative to actual molecular weight) and the calculated hydrodynamic radius of the aEpCAM-aCD3. The apparent molecular weight determined was 39.8 kDa (the latter being about 23-fold less than that of the intact construct, above), which would give apparent molecular weight factor of 0.7 (the latter being about 17-fold less than that of the intact construct, above) and a hydrodynamic radius of 2.3 nm (the latter being about 5-fold less than that of the intact construct, above).

Figure 23A:
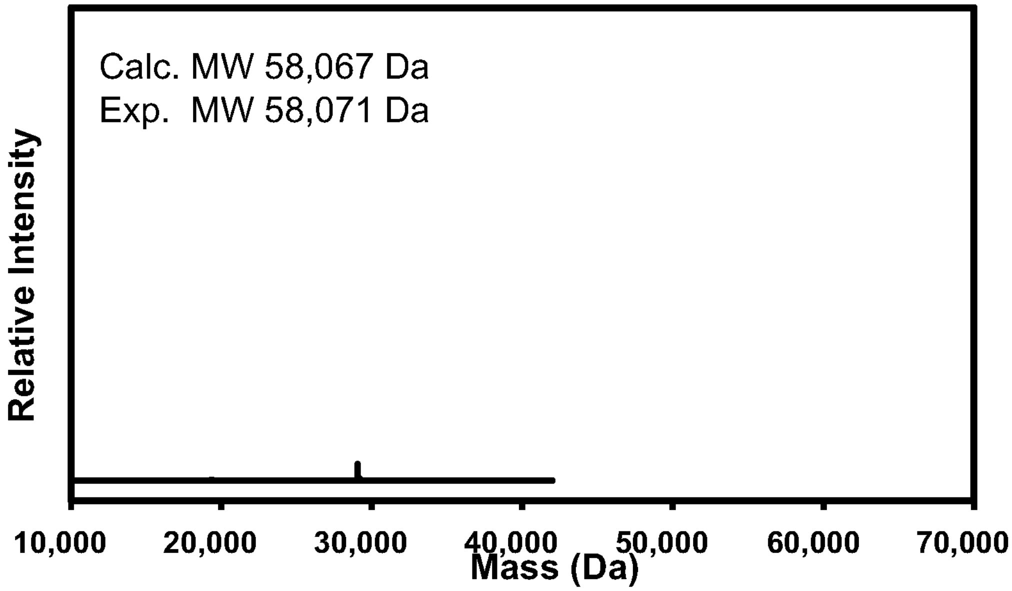
FIG. 23A shows the lot release ESI-MS of cleaved AC1476.
Figure 23B:
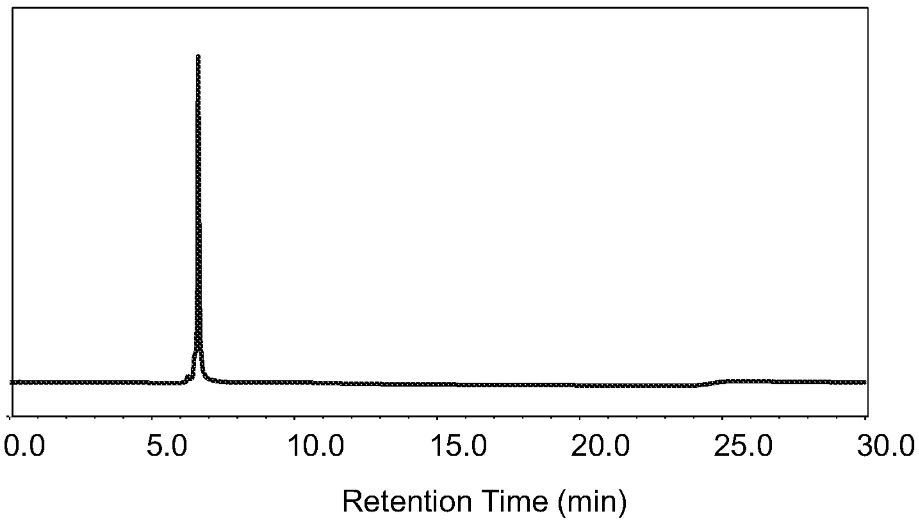
FIG. 23B shows the lot release cation exchange chromatography of cleaved AC1476.

To further prove the identity of the molecule, electrospray ionization mass spectrometry (ESI-MS) was performed and the experimental mass was determined to be 58,071 Da, with ΔMass of +4 Da when compared to theoretical molecular weight of 58,067 Da (FIG. 23A). Analytical cation exchange chromatography (FIG. 23B) using a protocol previously described in 2) also confirmed the homogeneity of the sample.

Example 4: Epcam Binding Assays of Anti-EpCAM x Anti-CD3 Protease Triggered Immune Activator (ProTIA) Composition The binding capability of anti-EpCAM x anti-CD3 ProTIA composition was verified with an EpCAM/peroxidase-conjugated protein-L sandwich ELISA. In the ELISA binding assay, recombinant human EpCAM (rhEpCAM) (Sino BiologicalR&D Systems cat #10694-H08H960-EP-50) was coated on a 96-well, flat-bottomed plate at a concentration of 0.1 microg/100 microL. After overnight incubation at 4° C., the assay plate was washed and blocked with 3% bovine serum albumin (BSA) for 1 h at room temperature. The plate was washed again followed by the introduction of a dose range of non-cleavable anti-EpCAM x anti-CD3 ProTIA (i.e., a ProTIA without the release segment cleavage sequence and AC1484, a ProTIA chimeric polypeptide assembly composition) and protease-treated and protease-untreated anti-EpCAM x anti-CD3 ProTIA (e.g. AC1476). The dose range utilized for non-cleavable and protease-treated and untreated ProTIA was 0.0006 to 5 nM, achieved with a 1:6 fold serial dilution scheme from a starting concentration of 5 nM. The plate was allowed to incubate with shaking for 1 h at room temperature to allow the non-cleavable, protease-cleaved and uncleaved ProTIA to bind to the rhEpCAM coated on the plate. Unbound components were removed with a wash step and a peroxidase-conjugated protein L (PierceThermoFisher Scientific cat #32420) was added. After an appropriate incubation period that allowed protein-L to bind to the kappa light of the scFvs, any unbound reagent was removed by a wash step followed by the addition of tetramethylbenzidine (TMB) substrate to each well. TMB is a chromogenic substrate of peroxidase. After desired color intensity was reached, 0.2 N sulfuric acid was added to stop the reaction and absorbance (OD) was measured at 450 nm using a spectrophotometer. The intensity of the color is proportional to the concentration of non-cleavable, protease-treated and untreated anti-EpCAM x anti-CD3 ProTIA captured by the rhEpCAM/protein-L sandwich ELISA. The intensity of the color produced (measured OD) was plotted against protein concentration; and the concentration of non-cleavable, protease-cleaved and uncleaved anti-EpCAM x anti-CD3 ProTIA that gave half-maximal response ($EC_{50}$) was derived with a 4-parameter logistic regression equation using GraphPad prism software.

Figure 24:
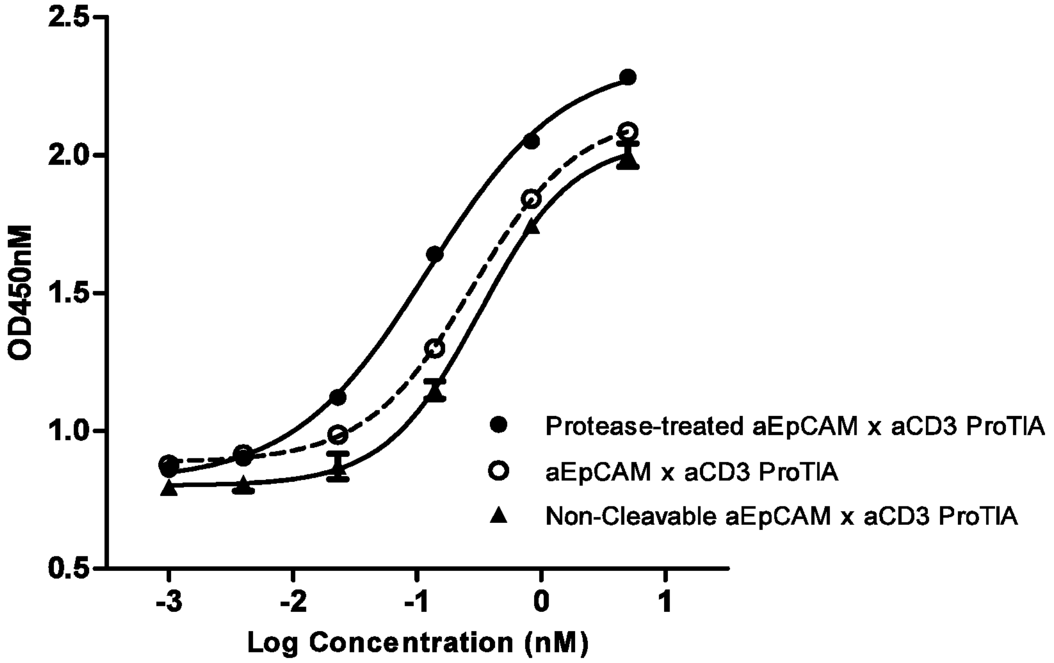
FIG. 24 shows binding of protease-treated and untreated anti-EpCAM x anti-CD3 ProTIA for its ligand, as described in Example 4.

As shown in FIG. 24, the non-cleavable anti-EpCAM x anti-CD3 ProTIA has a binding activity similar to that of protease-untreated anti-EpCAM x anti-CD3 bispecific ProTIA molecule each bearing an $EC_{50}$ of 320 nMpM and 280 nMpM respectively. The protease-treated ProTIA has the strongest binding activity at $EC_{50}$ of 120 nMpM for the rhEpCAM ligand compared to the intact protease-untreated bispecific molecule or the non-cleavable ProTIA molecule. The data suggest that the presence of XTEN864 hindered the binding of the anti-EpCAM moiety for its ligand by at least 2.3-fold.

Example 5: Cell Binding Assessed by Flow Cytometry

Bispecific binding of the anti-EpCAM x anti-CD3 ProTIA composition is also evaluated by fluorescence-activated cell sorting (FACS)-based assays utilizing CD3 positive human Jurkat cells and EpCAM positive human cells selected from SW480, HCT-116, Kato III, MDA-MB-453, MCF-7, MT3, SK-Br-3, SK-OV-3, OVCAR-3 and PC3. $CD3^+$ and $EpCAM^+$ cells are incubated with a dose range of untreated anti-EpCAM x anti-CD3 ProTIA, protease-treated anti-EpCAM x anti-CD3 ProTIA, and anti-CD3 scFv and anti-EpCAM scFv positive controls for 30 min at 4° C. in FACS buffer containing PBS with 1% BSA and 0.05% sodium azide. After several washes in FACS buffer to remove unbound test material, cells are incubated with FITC-conjugated anti-His tag antibody (Abcam cat #ab1206) for 30 min at 4° C. Unbound FITC-conjugated antibody is removed by several washes with FACS buffer and cells resuspended in FACS buffer for acquisition on a FACS Calibur flow cytometer (Becton Dickerson) or equivalent instrument. All flow cytometry data are analyzed with FlowJo software (FlowJo LLC) or equivalent.

While anti-EpCAM scFv is not expected to bind to Jurkat cells, anti-CD3 scFv, untreated anti-EpCAM x anti-CD3 ProTIA and protease-treated anti-EpCAM x anti-CD3 ProTIA are all expected to bind to Jurkat cells as indicated by an increase in fluorescence intensity when compared to Jurkat cells incubated with FITC-conjugated anti-His tag antibody alone. Similarly, anti-EpCAM scFv, protease-treated and untreated anti-EpCAM x anti-CD3 ProTIA are all expected to bind to EpCAM positive cells, while anti-CD3 scFv is not expected to bind to EpCAM positive cells. It is expected that these data will reflect the bispecific binding ability of the anti-EpCAM x anti-CD3 ProTIA composition to recognize both the CD3 and EpCAM antigen expressed respectively on Jurkat and the panel of EpCAM expressing human cell lines. Furthermore, due to the XTEN polymer providing some interference in surface binding, the untreated anti-EpCAM x anti-CD3 ProTIA is expected to bind at a lower affinity than the protease-treated ProTIA for both the CD3 and EpCAM antigens.

Example 6: Cytotoxicity Assays of Anti-EpCAM x Anti-CD3 Protease Triggered Immune Activator (ProTIA) Composition Redirected cellular cytotoxicity of anti-EpCAM x anti-CD3 ProTIA compositions were assessed by using human peripheral blood mononuclear cells (PBMC) as effectors and EpCAM positive human carcinoma cells such as SW480 colon cells (or selected from HCT-116, Kato III, NCI-N87, MKN45, MDA-MB-231, MDA-MB-453, MCF-7, MT3, SK-Br-3, SK-OV-3, OVCAR3 and PC3) as targets. PBMC were isolated from screened, healthy donors by ficoll density gradient centrifugation from either whole blood or from lymphocyte-enriched buffy coat preparations obtained from local blood banks or Bioreclamation IVT. PBMC were resuspended and cultured at appropriate cell density as discussed below in RPMI-1640/10% FCS/25 mmol/mL HEPES at 37° C. in a 5% $CO_2$ humidified incubator until use. Three different types of cytotoxicity assays are used for the determination of the cytolytic activity of non-cleavable anti-EpCAM x anti-CD3 composition (e.g. AC1484), protease-treated and untreated anti-EpCAM x anti-CD3 cleavable ProTIA compositions (e.g. AC1278 & AC1476), namely lactate dehydrogenase (LDH) release assay, caspase 3/7 assay and FACS-based analysis.

As a non-radioactive alternative to 51 Cr release cytotoxicity assay, the LDH release assay quantitatively measures the stable cytosolic enzyme LDH that is released upon cell lysis in much the same way as 51 Cr is released in radioactive assays. Released LDH in culture supernatants is measured by an enzymatic assay that converts a tetrazolium salt into a red formazan product; the amount of color formed being proportional to the number of lysed cells.

The cytotoxic performance of the protease-treated and untreated anti-EpCAM x anti-CD3 ProTIA compositions in SW480 were thus analyzed as follows: cell density of SW480 and PBMC was first adjusted to $2.5\times10^5$ cells/mL and $1\times10^6$ cells/mL respectively in assay medium comprised of phenol red-free RPMI and 5% FCS. (Phenol red-free medium and 5% FCS were used to minimize background absorbance with the use of Promega CytoTox 96 Non-radioactive Cytotoxicity Assay kit (cat #G1780)). To achieve an effector to target ratio of 5:1, 100 microL aliquots of PBMC were co-cultured with 80 microL aliquots of SW480 cells per assay well in a 96-well round-bottom plate. Protease-treated and untreated anti-EpCAM x anti-CD3 composition samples were diluted in assay medium to the desired dose concentration and added in 20 microL to the respective experimental wells bringing the total assay volume to 200 microL. The protease-cleaved ProTIA was evaluated as a 12-point, 5× serial diluted dose concentration starting at 440 nM to obtain a final dose range of 0.000005 to 44 nM. The untreated non-cleaved ProTIA composition was analyzed as a 12 point, 5× serial diluted dose concentration starting at 184 nM to derive at a final dose range of 0.000002 to 18.4 nM. Assay controls that included spontaneous LDH released by effector and target cells; target cell maximum LDH released; volume correction control due to the addition of lysis solution and culture medium background were also set up at this time. For target spontaneous LDH released, SW480 cells were incubated in 200 microL of assay medium in the absence of any protease-treated or untreated composition. For effector spontaneous LDH released, PBMC were incubated in 200 microL of assay medium in the absence of any protease-treated or untreated composition. Target cell maximum LDH released was determined by the addition of 20 microL of 10× lysis solution to SW480 (220 microL total volume) and incubating the target cells in the presence of lysis solution for 45 min prior to harvesting the supernatant for LDH measurement. Volume correction control was achieved by adding 20 microL of 10× lysis solution to 200 microL of assay media, while culture medium background was obtained by incubating 200 microL of assay medium. The plate containing experimental wells of protease-treated and untreated anti-EpCAM x anti-CD3 ProTIA compositions and all the respective assay controls, all tested in duplicates, was then allowed to incubate overnight in a 37° C., 5% $CO_2$ humidified incubator.

The amount of LDH released into the supernatant as a result of cell lysis was measured using the Promega CytoTox Assay kit and following manufacturer's instructions. Briefly, 50 microL of the supernatant from each well of the assay plate was transferred to the corresponding well of a flat-bottomed enzymatic plate. To each well in the enzymatic plate, 50 microL of the reconstituted substrate was added. The plate was then covered, protected from light and allowed to incubate at room temperature for 30 min. After the desired incubation period, 50 microL of stop solution was added to each well and absorbance recorded at 490 nm.

Data analysis was then performed as followed:

1. Experimental, E:T ratio of 5:1 (average)–culture medium background (average) SW480 target spontaneous (average)–culture medium background (average) PBMC effector spontaneous (average)–culture medium background (average)
2. SW480 target maximum (average)–volume correction control (average)
3. % specific lysis=[(Experimental–SW480 target spontaneous–PBMC effector spontaneous)/(SW480 target maximum–SW480 target spontaneous)]×100
4. Dose concentration of protease-treated and untreated anti-EpCAM x anti-CD3 ProTIA was then plotted against % specific lysis; and the concentration of protein that gave half maximal response ($EC_{50}$) was derived with a 4-parameter logistic regression equation using GraphPad prism software.

Figure 25:
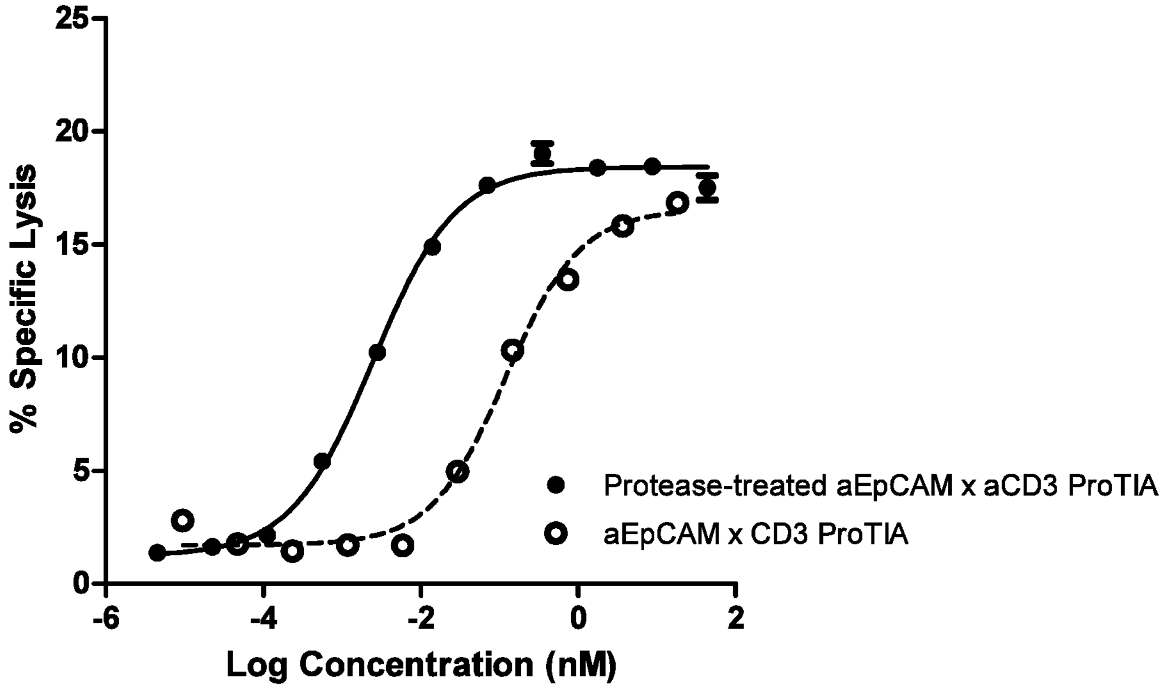
FIG. 25 depicts results from the experiment to determine the in vitro activity of protease-treated and untreated anti-EpCAM x anti-CD3 ProTIA, as described in Example 6.

As shown in FIG. 25, exposure of SW480 cells to protease-treated ProTIA and the untreated anti-EpCAM x anti-CD3 ProTIA compositions in the presence of PBMC yielded concentration-dependent cytotoxic dose curves; with the protease-treated ProTIA being 48-fold more active than the intact, untreated ProTIA ($EC_{50}$ of 2.5 pM vs. 120 pM respectively).

The specificity of the anti-EpCAM x anti-CD3 ProTIA was further evaluated by comparing the cytotoxic activity of protease-treated and protease-untreated ProTIA to that of unconjugated monospecific anti-EpCAM scFv and monospecific anti-CD3 scFv in the LDH assay. Briefly, PBMC and SW480 cells were co-cultured in an effector to target ratio of 5:1 in assay medium in a 96-well round-bottom plate as described above. Protease-treated anti-EpCAM x anti-CD3 ProTIA, protease-untreated anti-EpCAM x anti-CD3 ProTIA, and unconjugated monospecific anti-EpCAM scFv plus monospecific anti-CD3 scFv samples were all evaluated as a 12-point, 5× serial dilution of a final dose range of 0.00005 to 45 nM in a total assay volume to 200 microL. Together with experimental wells, all relevant assay controls as described above were also included in the assay plate and the plate was incubated overnight in a 37° C., 5% $CO_2$ humidified incubator.

The amount of LDH released into the supernatant as a result of cell lysis was measured using the Promega CytoTox Assay kit and results analyzed as described above.

Figure 26:
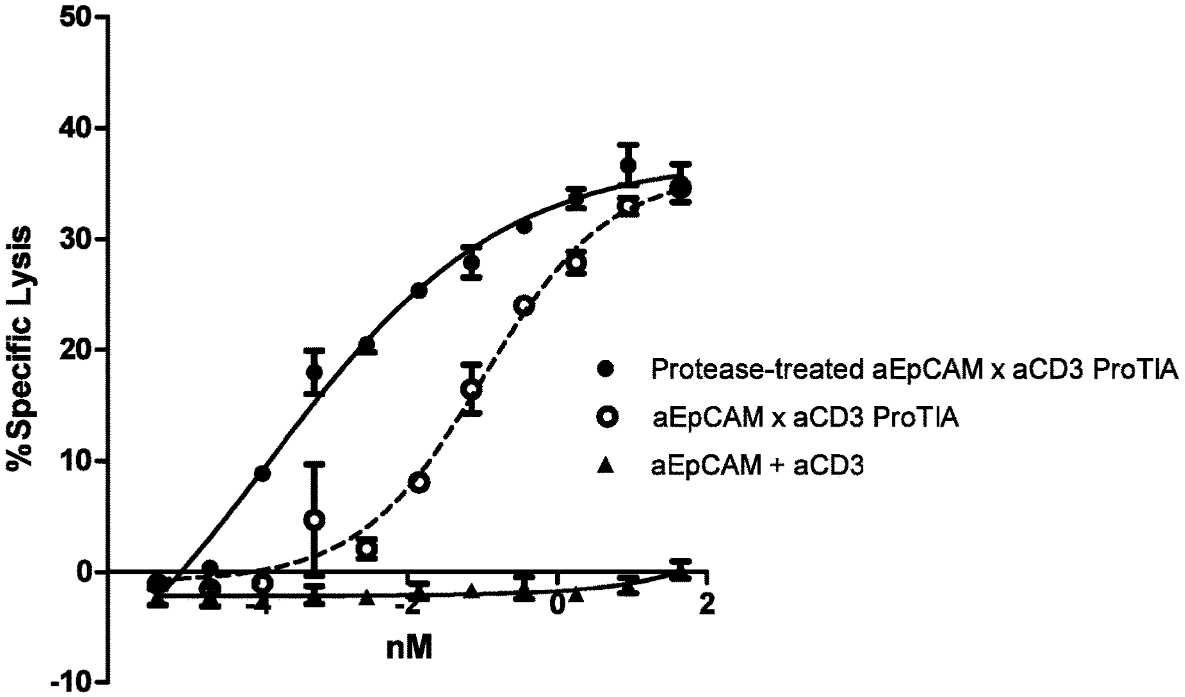
FIG. 26 depicts results from the experiment to determine the in vitro specificity of anti-EpCAM x anti-CD3 ProTIA, as described in Example 6.

As expected, exposure of SW480 cells to protease-treated anti-EpCAM x anti-CD3 ProTIA in the presence of PBMC show enhanced cytotoxicity as compared to untreated ProTIA. Significantly, combining monospecific anti-EpCAM scFv and monospecific anti-CD3 scFv in the presence of SW480 target cells and PBMC did not result in any cytotoxic activity (FIG. 26). The data indicate that linking the targeting aEpCAM moiety to the aCD3 effector moiety in the form of a bispecific molecule is required for the active recruitment of CD3 positive cells to the vicinity of the target cells for induced cytotoxicity.

We also hypothesized that the release segment cleavage sequence present in the anti-EpCAM x anti-CD3 ProTIA may by itself be susceptible to cleavage by proteases released by the tumor cells or by activated CD3 positive T cells (e.g. granzymes). To address this hypothesis, a non-cleavable anti-EpCAM x anti-CD3 ProTIA without the release segment (e.g. AC1357) was constructed and evaluated in conjugation with the protease-treated and untreated anti-EpCAM x anti-CD3 ProTIA (e.g. AC1278). All three ProTIA were analyzed in the LDH assay using a 5:1 PBMC to SW480 ratio and tested in a 12-point dose concentration range of 0.00005 to 45 nM achieved with a 5× serial dilution scheme.

Figure 27:
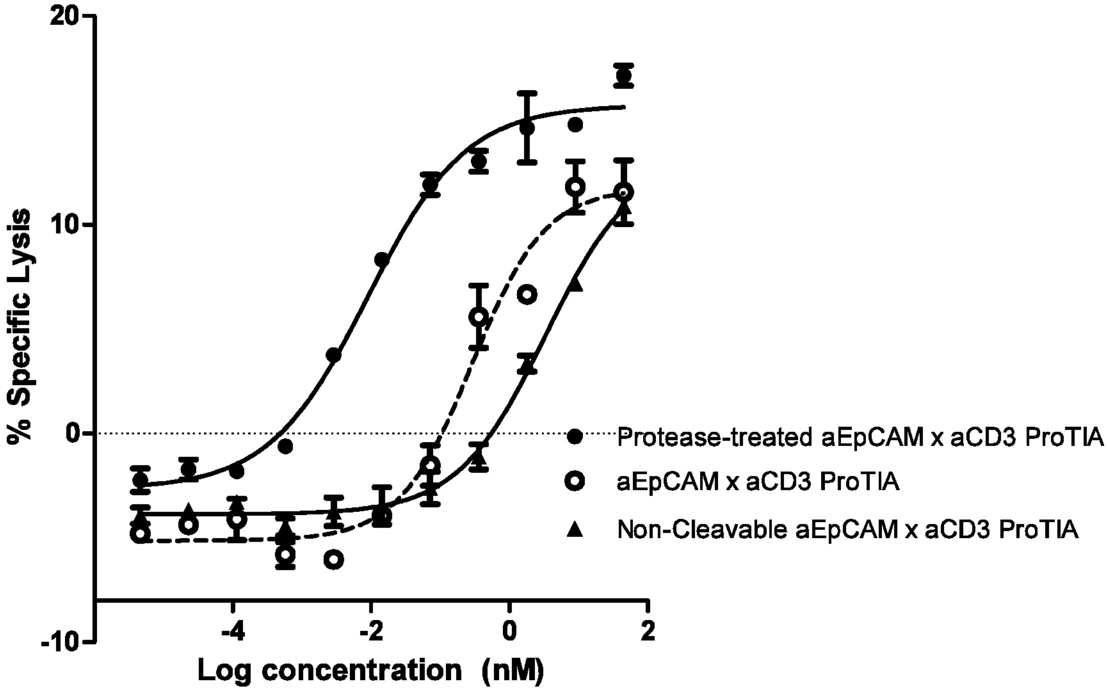
FIG. 27 depicts results from the experiment to determine the in vitro activity of protease-treated, protease-untreated and protease-uncleavable anti-EpCAM x anti-CD3 ProTIA, as described in Example 6.

As shown in FIG. 27, untreated anti-EpCAM x anti-CD3 ProTIA is 32-fold less active than protease-treated ProTIA ($EC_{50}$ of 288 pM vs. 8.9 pM). Interestingly, the non-cleavable anti-EpCAM x anti-CD3 ProTIA (i.e., ProTIA without the release segment cleavage sequence) is 371-fold less active than the protease-cleaved ProTIA ($EC_{50}$ of 3300 pM vs. 8.9 pM). The results suggest that the release segment contained within the cleavable anti-EpCAM x anti-CD3 ProTIA molecule is susceptible to some cleavage by proteases likely released from the tumor cells and/or activated CD3 positive T cells.

Figure 30:
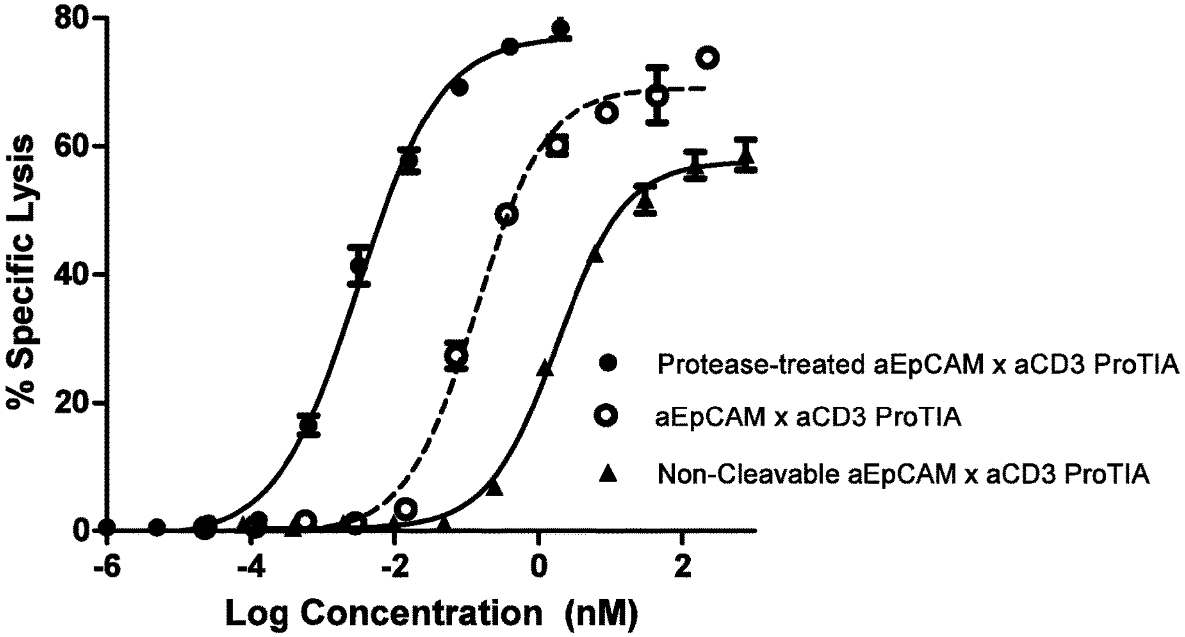
FIG. 30 depicts results from the experiment to determine the in vitro activity of protease-treated, protease-untreated and protease-noncleavable anti-EpCAM x anti-CD3 ProTIA in SK-OV-3 as described in Example 6.

The non-cleavable anti-EpCAM x anti-CD3 ProTIA without the release segment (e.g. AC1484) and protease-treated and untreated anti-EpCAM x anti-CD3 ProTIA (e.g. AC1476) were also evaluated in human cell line of ovarian origin. In this experiment, PBMC was mixed with SK-OV-3 ovarian cells in a ratio of 5:1 and all three ProTIA molecules were tested as a 12-point, 5× serial dilution dose curve in the LDH assay as described above. As expected, the activity trend of the three ProTIA molecules profiled in SK-OV-3 ovarian cell line was found to be similar to that observed in the SW480 colorectal cell line. In SK-OV-3 cells, untreated anti-EpCAM x anti-CD3 ProTIA was 45-fold less active than protease-treated ProTIA ($EC_{50}$ of 136 pM vs. 3 pM); and the non-cleavable anti-EpCAM x anti-CD3 ProTIA was 600-fold less active than the protease-cleaved ProTIA ($EC_{50}$ of 1793 pM vs. 3 pM) (FIG. 30).

Example 7: Cell Lysis Assessed by Flow Cytometry

For analysis of cell lysis after 24 h by flow cytometer, EpCAM positive SK-OV-3 target cells (or target cells selected from HCT-116, Kato III, MDA-MB-453, MCF-7, MKN45, MT3, NCI-N87, SK-Br-3, SW480, OVCAR3 and PC3 cell lines) are labeled with the fluorescent membrane dye CellVue Maroon dye (Affymetrix/eBioscience, cat #88-0870-16) according to manufacturer's instructions. Alternatively PKH26 (Sigma, cat #MINI26 and PKH26GL) can also be used. In brief, SK-OV-3 cells are washed twice with PBS followed by resuspension of $2\times10^6$ cells in 0.1 mL diluent C provided with the CellVue Maroon labeling kit. In a separate tube, 2 mircoL of CellVue Maroon dye is mixed with 0.5 mL diluent C, and then 0.1 mL added to the SK-OV-3 cell suspension. The cell suspension and CellVue Maroon dye are mixed and incubated for 2 min at room temperature. The labeling reaction is then quenched by the addition of 0.2 mL of FCS. Labeled cells are washed twice with complete cell culture medium (RPMI-1640 containing 10% FCS) and total number of viable cells determined by trypan blue exclusion. For an effector to target ratio of 5:1 in a total volume of 200 microL per well, $1\times10^5$ PBMC are co-cultured with $2\times10^4$ CellVue Maroon-labeled SK-OV-3 cells per well in a 96-well round-bottom plate in the absence or presence of the indicated dose range concentration of protease-treated and untreated anti-EpCAM x anti-CD3 ProTIA samples. After 24 h, cells are harvested with Accutase (Innovative Cell Technologies, cat #AT104) and washed with 2% FCS/PBS. Before cell acquisition on a Guava easyCyte flow cytometer (Millipore), cells are resuspended in 100 microL 2% FCS/PBS supplemented with 2.5 micrograms/mL 7-AAD (Affymetrix/eBioscience, cat #00-6993-50) to discriminate between alive (7-AAD-negative) and dead (7-AAD-positive) cells. FACS data are analyzed with guavaSoft software (Millipore); and percentage of dead target cells is calculated by the number of 7-AAD-positive/CellVue Maroon-positive cells divided by the total number of CellVue Maroon-positive cells.

Dose response kill curves of percent cytotoxicity against ProTIA concentration are analyzed by 4 parameter-logistic regression equation using GraphPad Prism; and the concentration of ProTIA that induced half maximal percent cell cytotoxicity is thus determined.

Cytotoxicity results utilizing flow cytometry are expected to be in line with results obtained with the LDH assay. Exposure of SK-OV-3 cells to protease-cleaved and uncleaved anti-EpCAM x anti-CD3 ProTIA compositions in the absence of PBMC are expected to have no effect. Similarly, PBMC are not expected to be activated in the presence of ProTIA without target cells. These results are expected to indicate that ProTIA compositions need to be clustered on the surface of target cells in order to stimulate PBMC for cytotoxicity activity. In the presence of PBMC and target cells, there would be a concentration-dependent cytotoxic effect due to ProTIA pretreated or untreated with protease. Further, results are expected to show that exposure of SK-OV-3 cells to untreated ProTIA (no protease) in the presence of PBMC would show reduced cytotoxicity as compared to protease-cleaved ProTIA composition.

The above set of cytotoxicity experiments is performed for other bispecific ProTIA compositions such as anti-CD19 x anti-CD3 ProTIA composition and anti-HER2 x anti-CD3 ProTIA composition. In these instances, CD19 and HER2 positive target cells will be used instead of EpCAM positive cells. Example cell lines for CD19 expressing cells will include but not limited to NAML-6, Blin-1, SKW6.4, Raji, Daudi and BJAB. For anti-HER2 targeting, HER2 positive cell lines such as SK-BR-3, BT474, HCC-1954, MDA-MB-453, SK-OV-3, NCI-N87, JIMT-1, HCT-116 will be used.

Example 8: T-Cell Activation Marker Assays of Anti-EpCAM x Anti-CD3 Protease Triggered Immune Activator (ProTIA) Composition To measure the anti-EpCAM x anti-CD3 ProTIA induced activation markers (CD69 and CD25), $1\times10^5$ PBMC or purified CD3+ cells were co-cultured in RPMI-1640 containing 10% FCS with 2×10 4 SK-OV-3 or OVCAR3 cells per assay well (i.e., effector to target ratio of 5:1) in the presence of anti-EpCAM x anti-CD3 ProTIA in a 96-well round-bottom plate with total final volume of 200 microL. After 20 h incubation in a 37° C., 5% $CO_2$ humidified incubator, cells were stained with PECy5-conjugated anti-CD4, APC-conjugated anti-CD8, PE-conjugated anti-CD25, and FITC-conjugated anti-CD69 (all antibodies from BioLegend) in FACS buffer (1% BSA/PBS) at 4° C., washed twice with FACS buffer, and then resuspended in FACS buffer for acquisition on a Guava easyCyte flow cytometer (Millipore).

Figure 42A:
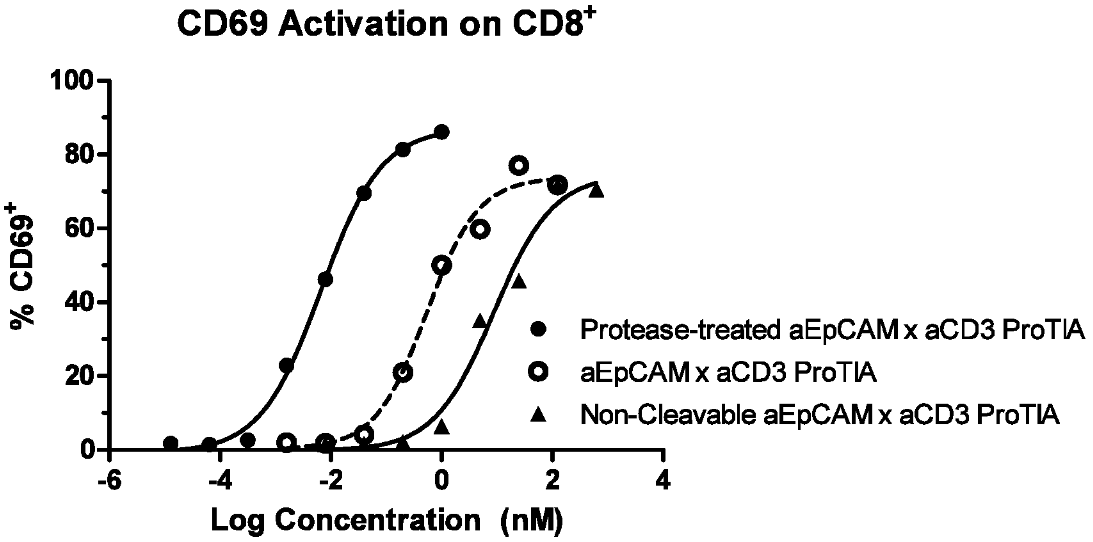
Figure 42B:
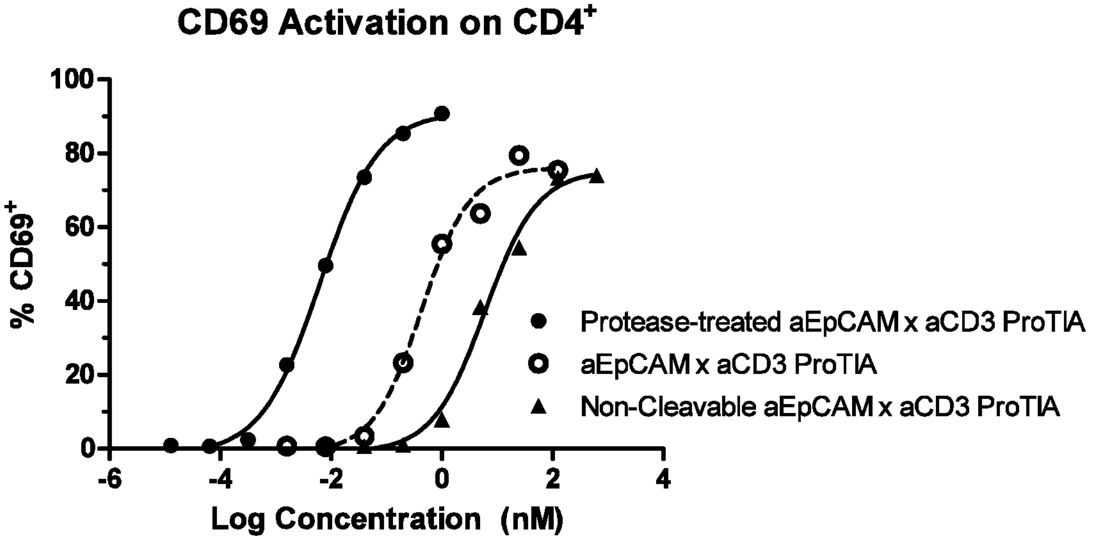
FIG. 42B depicts the activation of CD69 on CD4 cells.

As expected, the T-cell activation marker expression trend of the three ProTIA molecules profiled in SK-OV-3 ovarian cell line was found to be similar to that observed by LDH cytotoxicity assay. Using SK-OV-3 cells, activation of CD69 on CD8 and CD4 populations of PBMC by untreated anti-EpCAM x anti-CD3 ProTIA was ~70-fold less active than protease-treated ProTIA ($EC_{50}$ of 540 pM vs. 6.7 pM for CD8+, $EC_{50}$ of 430 pM vs. 6.3 pM for CD4+); and the non-cleavable anti-EpCAM x anti-CD3 ProTIA was 1000-fold less active than the protease-cleaved ProTIA ($EC_{50}$ of 8700 pM vs. 6.7 pM for CD8+, $EC_{50}$ of 6000 pM vs. 6.3 pM for CD4+) (FIG. 42).

Figure 43A:
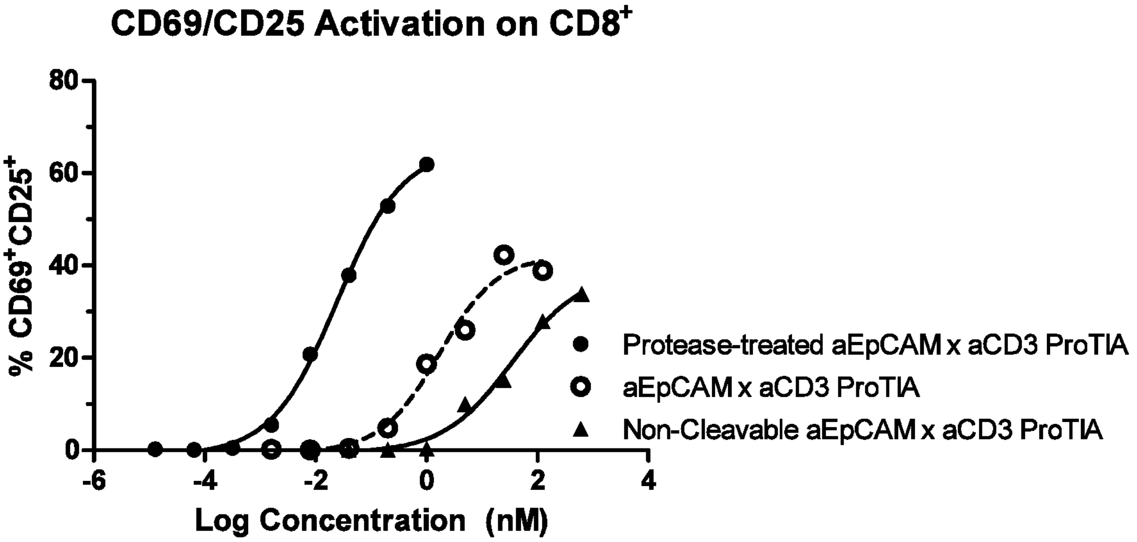
Figure 43B:
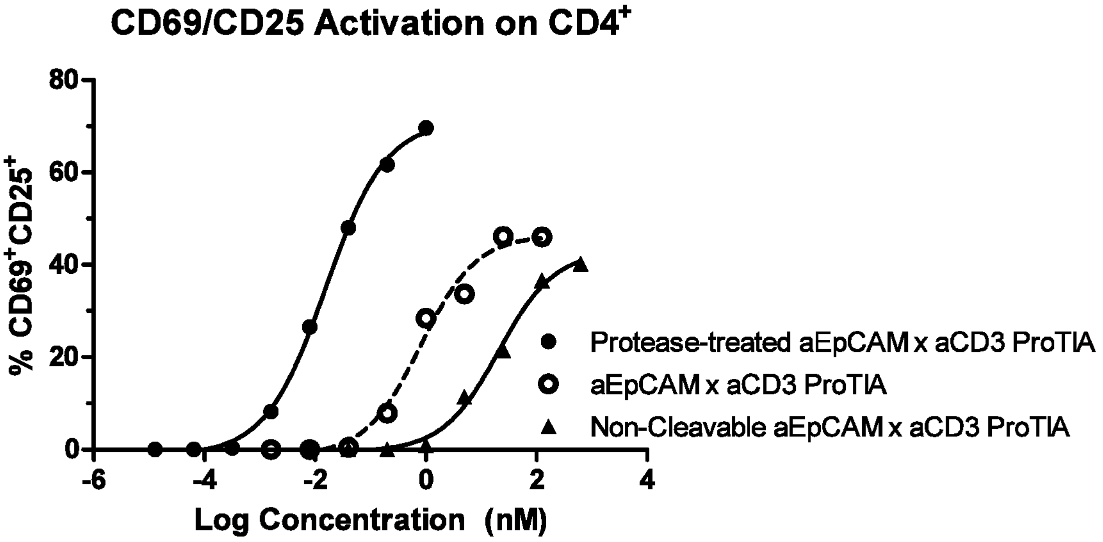
FIG. 43B depicts the activation of both CD69 and CD25 on CD4 cells.

Similarly, activation of both CD69 and CD25 on CD8 and CD4 populations of PBMC cells by untreated anti-EpCAM x anti-CD3 ProTIA was ~60-fold less active than protease-treated ProTIA, and the non-cleavable anti-EpCAM x anti-CD3 ProTIA was ~1300-fold less active than the protease-cleaved ProTIA (FIG. 43).

Figure 44A:
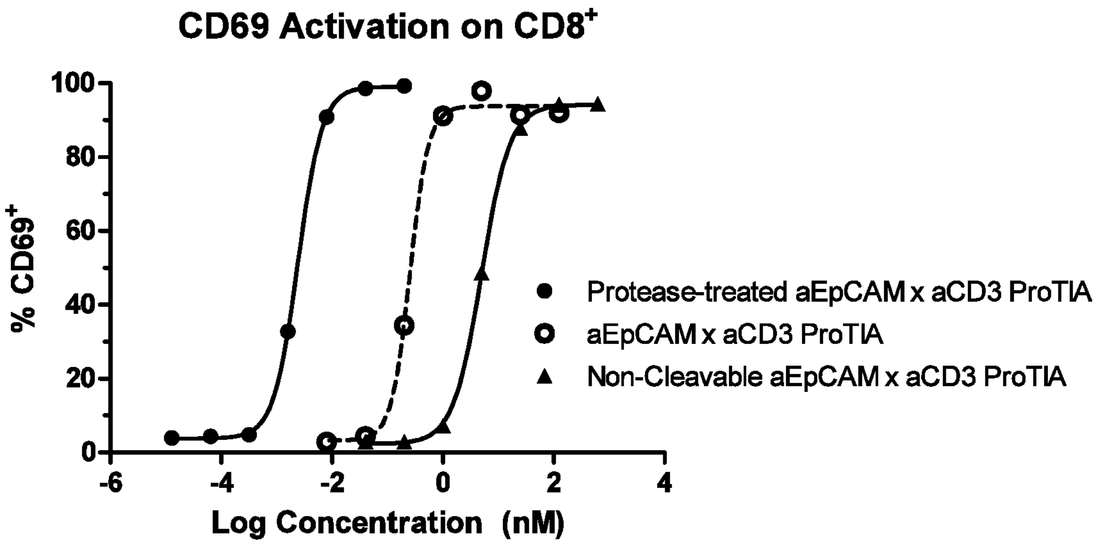
Figure 44B:
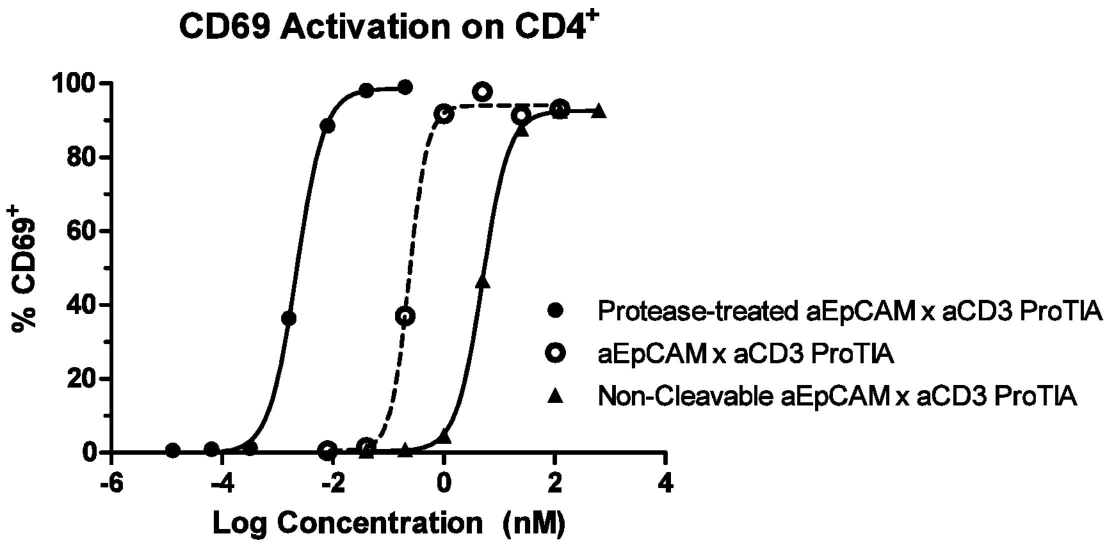
FIG. 44B depicts the activation of CD69 on CD4 cells.
Figure 45A:
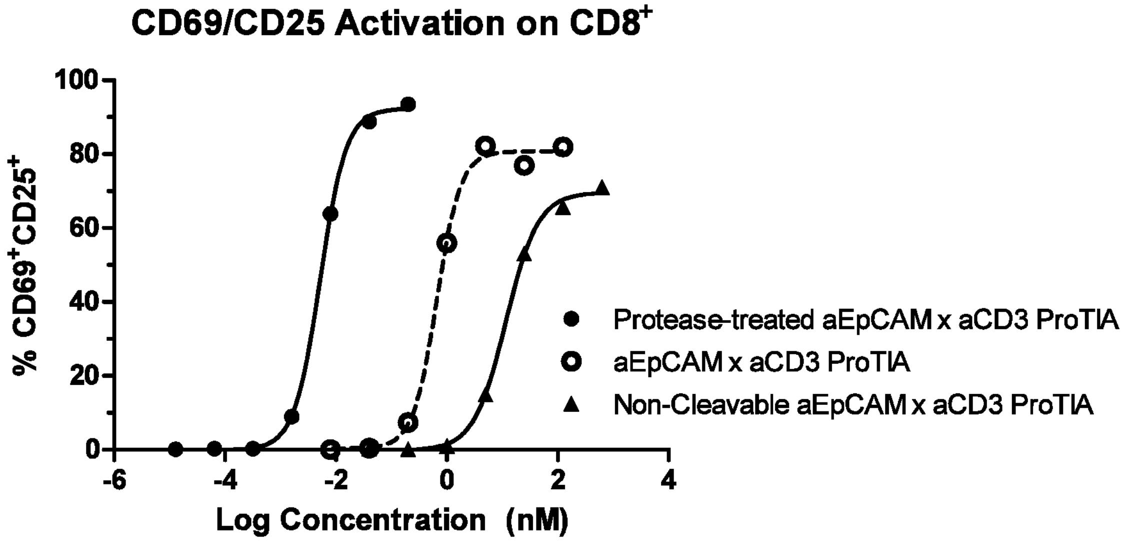
Figure 45B:
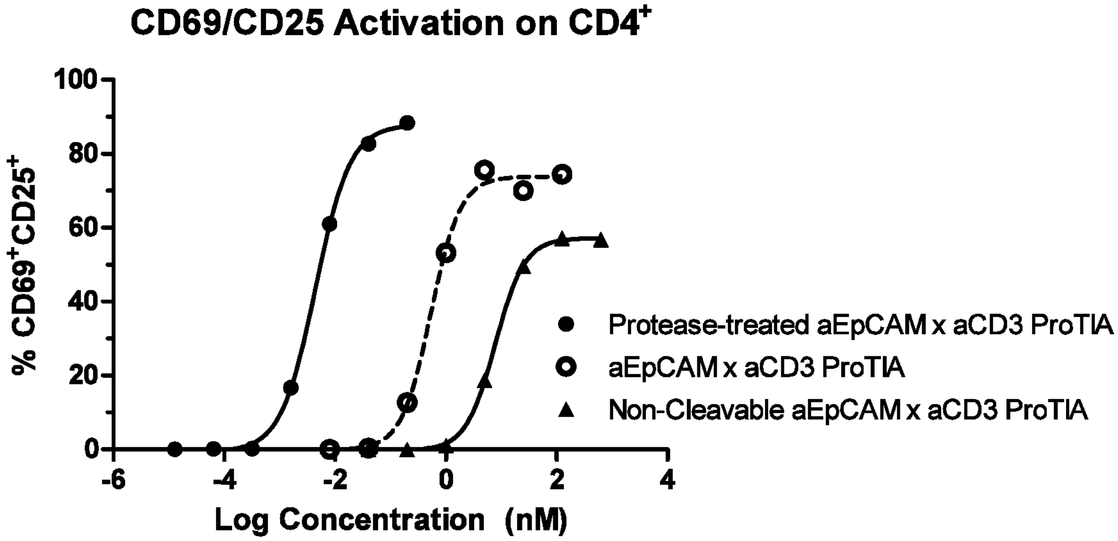
FIG. 45B depicts the activation of both CD69 and CD25 on CD4 cells.

To confirm the mechanism of action is through CD3+ cells, SK-OV-3 cells were used as target cells, and activation of CD69 on CD8 and CD4 populations of purified CD3+ cells by untreated anti-EpCAM x anti-CD3 ProTIA was ~100-fold less active than protease-treated ProTIA ($EC_{50}$ of 260 pM vs. 2.4 pM for CD8+, $EC_{50}$ of 240 pM vs. 2.2 pM for CD4+); and the non-cleavable anti-EpCAM x anti-CD3 ProTIA was 2000-fold less active than the protease-cleaved ProTIA ($EC_{50}$ of 5000 pM vs. 2.4 pM for CD8+, $EC_{50}$ of 5000 pM vs. 2.2 pM for CD4+) (FIG. 44). Activation of both CD69 and CD25 on CD8 and CD4 populations of purified CD3+ cells by untreated anti-EpCAM x anti-CD3 ProTIA was ~100-fold less active than protease-treated ProTIA, and the non-cleavable anti-EpCAM x anti-CD3 ProTIA was 2000-fold less active than the protease-cleaved ProTIA (FIG. 45).

Figure 46A:
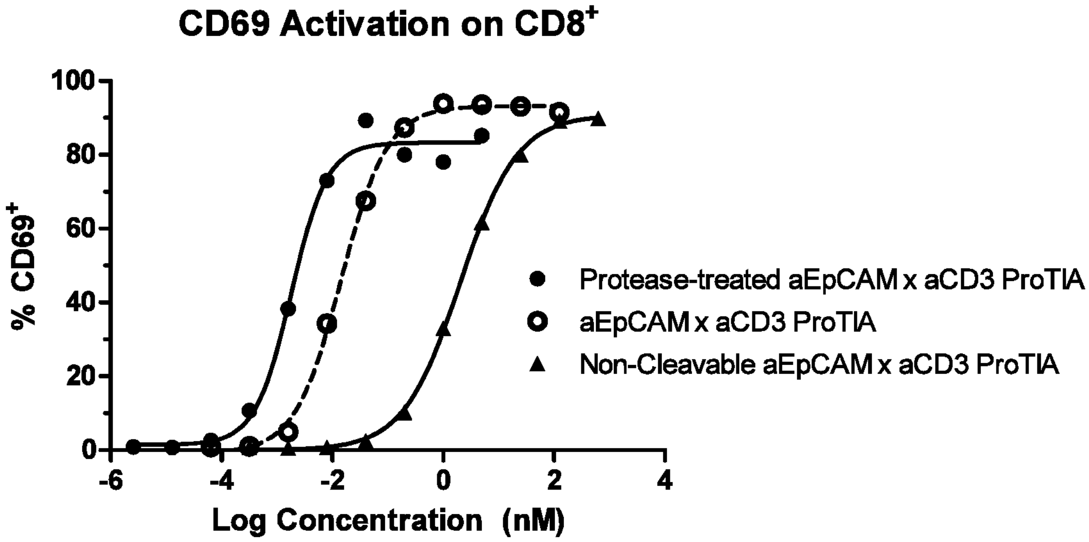
Figure 46B:
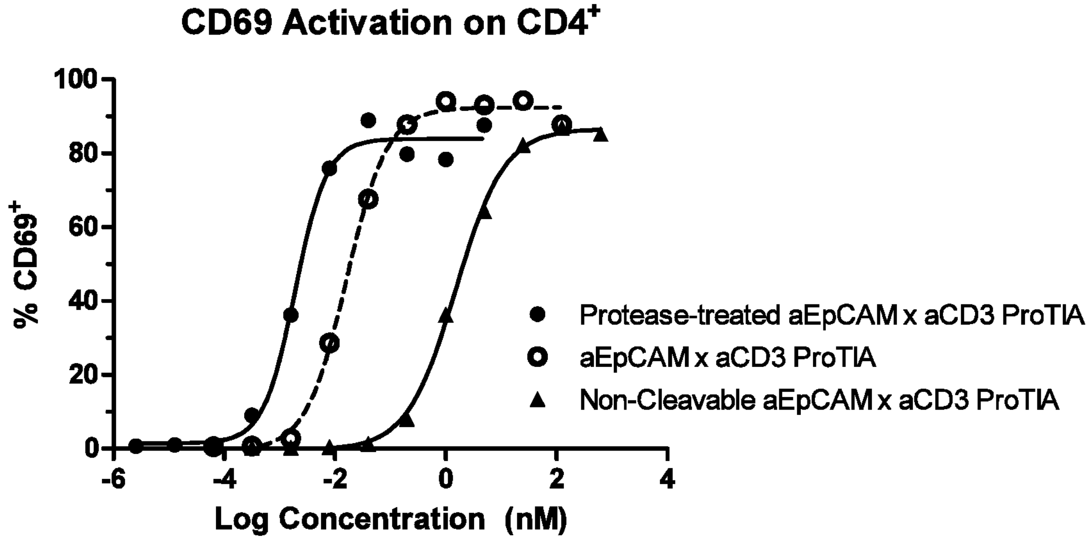
FIG. 46B depicts the activation of CD69 on CD4 cells.
Figure 47A:
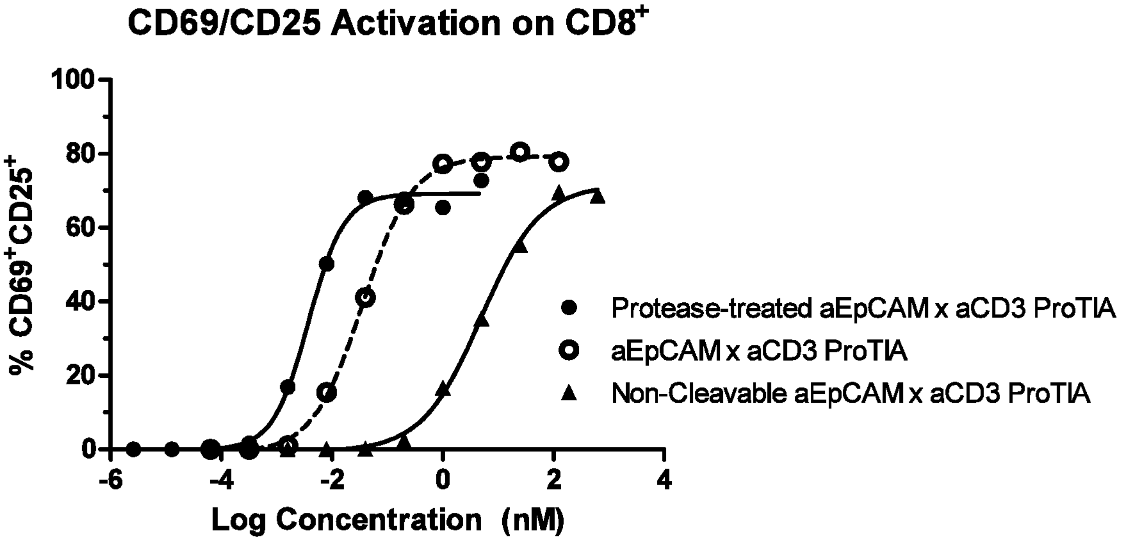
Figure 47B:
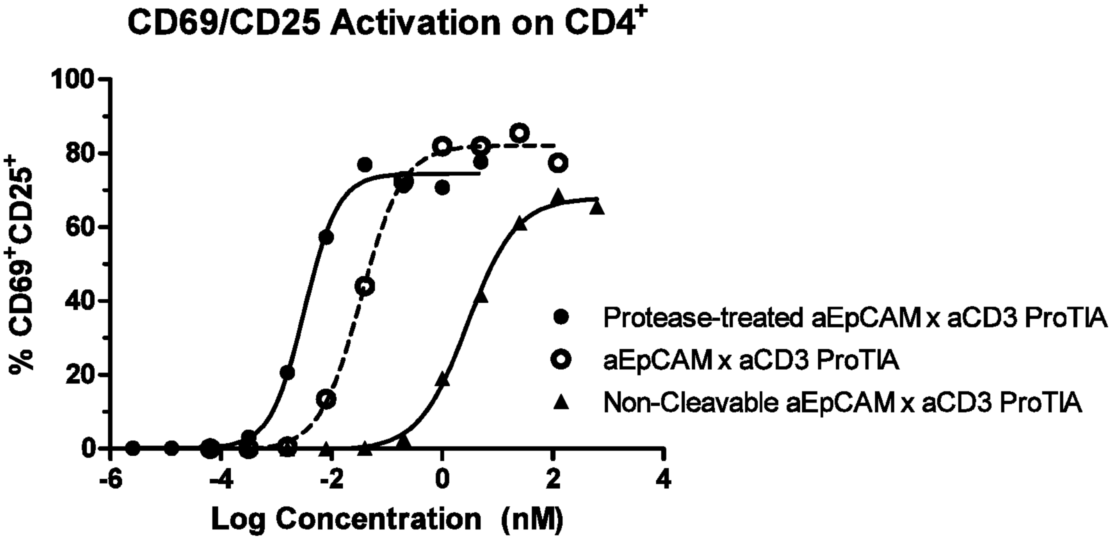
FIG. 47B depicts the activation of both CD69 and CD25 on CD4 cells.

Using OVCAR3 cells, activation of CD69 on CD8 and CD4 populations of purified CD3+ cells by untreated anti-EpCAM x anti-CD3 ProTIA was ~10-fold less active than protease-treated ProTIA ($EC_{50}$ of 14 pM vs. 1.8 pM for CD8+, $EC_{50}$ of 16 pM vs. 1.9 pM for CD4+); and the non-cleavable anti-EpCAM x anti-CD3 ProTIA was 1000-fold less active than the protease-cleaved ProTIA ($EC_{50}$ of 2000 pM vs. 1.8 pM for CD8+, $EC_{50}$ of 1500 pM vs. 1.9 pM for CD4+) (FIG. 46). Activation of both CD69 and CD25 on CD8 and CD4 populations of purified CD3+ cells by untreated anti-EpCAM x anti-CD3 ProTIA was also ~10-fold less active than protease-treated ProTIA, and the non-cleavable anti-EpCAM x anti-CD3 ProTIA was also 1000-fold less active than the protease-cleaved ProTIA. These results suggest the untreated anti-EpCAM x anti-CD3 ProTIA was cleaved during the assay to a greater extent in the presence of OVCAR3 cells compared to SK-OV-3 cells (FIG. 47).

As further evidence of activation of T cells by anti-EpCAM x anti-CD3 ProTIA in the presence of target cells, induction of CD69 and granzyme B were measured. PBMC ($1\times10^5$) were co-cultured with $2\times10^4$ OVCAR3 cells per assay well (i.e., effector to target ratio of 5:1) in the presence of anti-EpCAM x anti-CD3 ProTIA in a 96-well round-bottom plate with total final volume of 200 microL. After 20 h incubation in a 37° C., 5% $CO_2$ humidified incubator, cells were stained with PECy5-conjugated anti-CD4, APC-conjugated anti-CD8, and FITC-conjugated anti-CD69 (all antibodies from BioLegend) in FACS buffer (1% BSA/PBS) at 4° C. Cells were then fixed and permeabilized with 0.1% Triton X-100/PBS before staining with PE-conjugated anti-granzyme B (ThermoFisher, cat #MHGB04) in FACS buffer. Cells were washed with FACS buffer and then resuspended in FACS buffer for acquisition on a Guava easyCyte flow cytometer.

Figure 48A:
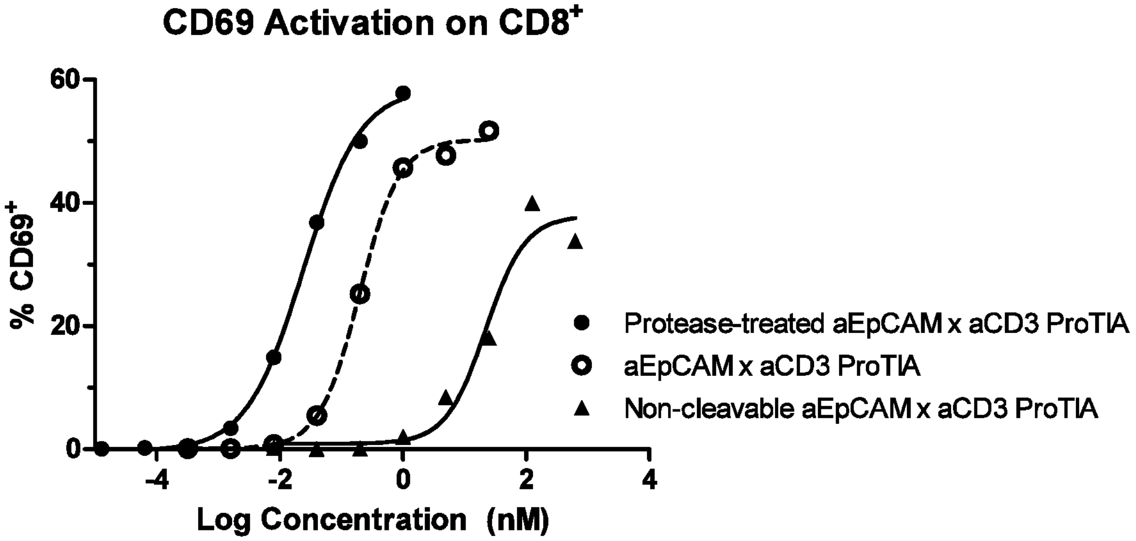
Figure 48B:
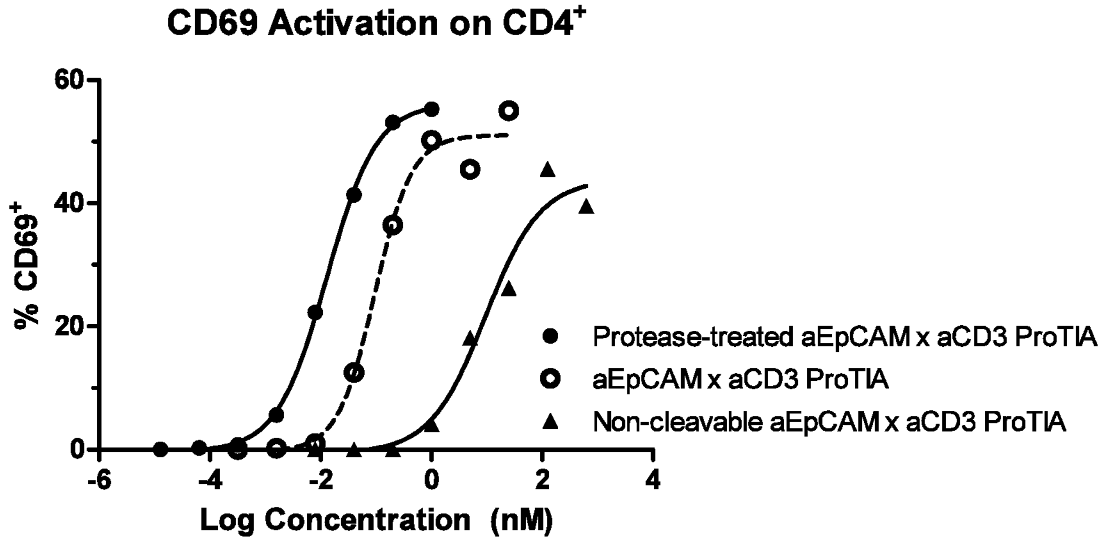
FIG. 48B depicts the activation of CD69 on CD4 cells.
Figure 49A:
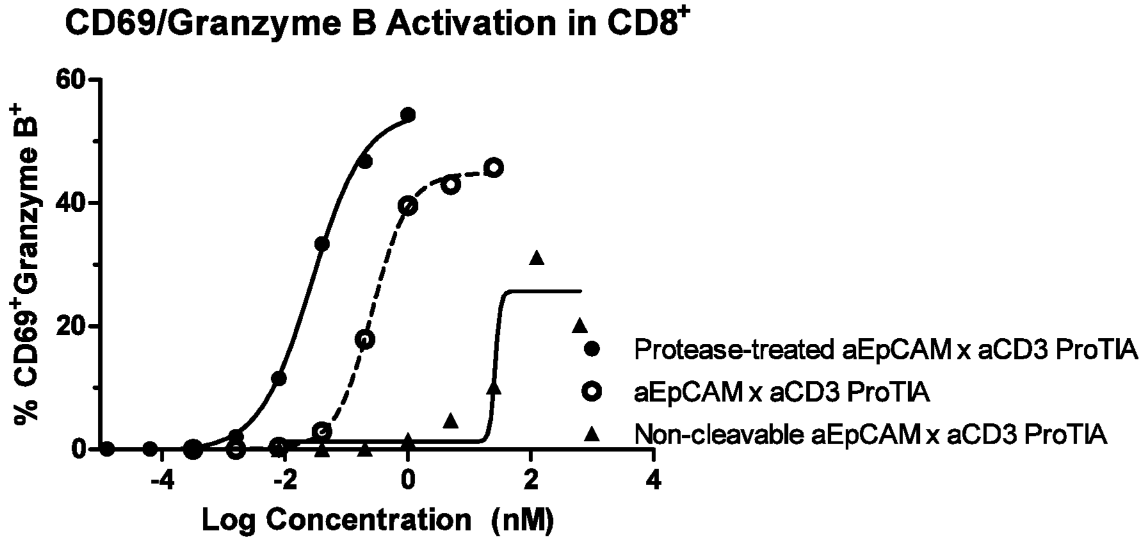
Figure 49B:
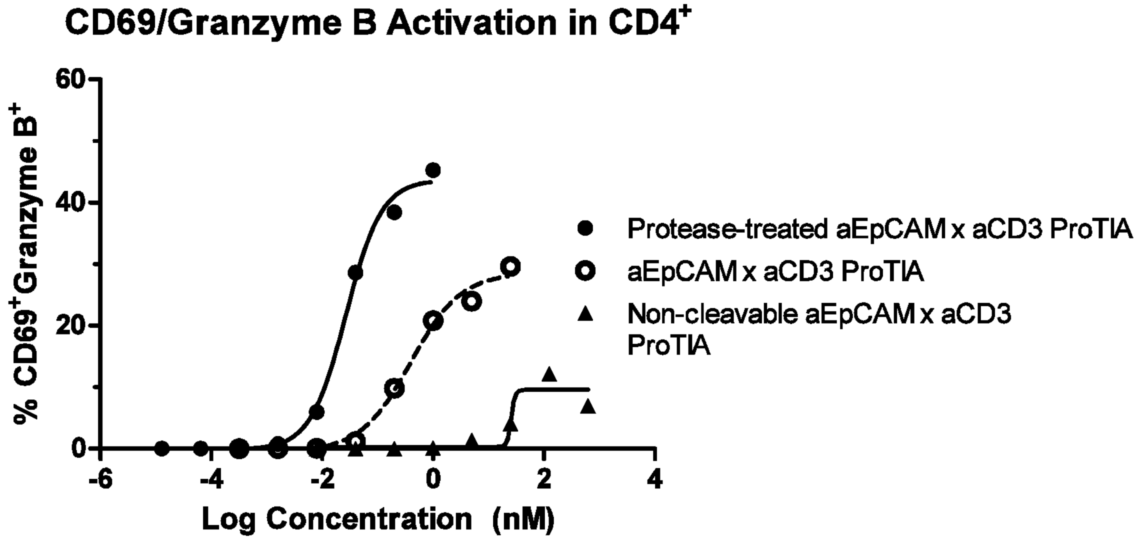
FIG. 49B depicts the activation of both CD69 and granzyme B in CD4 cells.

As expected, both CD69 and granzyme B are expressed in ProTIA-activated T cells in the presence of OVCAR3 cells. Additionally, a greater fraction of CD8+ cells express granzyme B compared to CD4+ cells (FIGS. 48 and 49).

Example 9: Pharmacokinetic Properties of Anti-EpCAM x Anti-CD3 Protease Triggered Immune Activator (ProTIA) Composition The pharmacokinetic properties of anti-EpCAM x anti-CD3 ProTIA were analyzed in C57BL/6 mice. Three mice in group 1 were injected intravenously with 4 mg/kg of protease-treated anti-EpCAM x anti-CD3 ProTIA (e.g. AC1278), and 3 mice in group 2 were injected intravenously with untreated anti-EpCAM x anti-CD3 ProTIA (e.g. AC1278). At appropriate time points, blood was collected into lithium heparinized tubes and processed into plasma. For the protease-treated anti-EpCAM x anti-CD3 ProTIA animals, plasma collection time points were pre-dose, 2 min, 15 min, 30 min, 2 h, 4 h, 8 h and 24 h. For the untreated ProTIA mice, plasma collection time points were pre-dose, 4 h, 8 h, 24 h, 2 d, 4 d, 6 d and 7 d. Plasma concentration of protease-treated ProTIA was quantified by a rhEpCAM/biotinylated-anti-His tag sandwich ELISA with the protease-cleaved ProTIA as standard; while plasma concentration of untreated ProTIA was quantified by a rhEpCAM/biotinylated-anti-XTEN sandwich ELISA with the uncleaved ProTIA as standard.

Briefly, ELISA plate (Nunc Maxisorp cat #442404) was coated with 0.1 mircog/100 microL per well of rhEpCAM (R&D Systems, cat #EHH104111). After overnight incubation at 4° C., the ELISA plate was washed and blocked with 3% BSA for 1 h at room temperature. The plate was washed again followed by the appropriate addition of a dose range of protease-treated and untreated anti-EpCAM x anti-CD3 ProTIA standards, appropriate quality controls and plasma test samples. The plate was allowed to incubate with shaking for 1 h at room temperature to allow the ProTIA standards, quality controls and test samples to bind to rhEpCAM coated on the plate. Unbound components were removed with several washes. For the detection of protease-cleaved ProTIA, biotinylated anti-His tag antibody (R&D Systems, cat #BAM050) was added at 0.2 microg/100 microL and plate allowed to incubate at room temperature for 1 h. For the detection of the protease-untreated ProTIA, biotinylated anti-XTEN antibody (Amunix proprietary antibody) was added at 0.1 microg/100 microL and the plate allowed to incubate at room temperature for 1 h. After washing away unbound biotinylated reagent, streptavidin-HRP (Thermo Scientific cat #21130) was added at 1:30,000 dilution and plate incubated at room temperature for 1 h. After several washes, TMB substrate was added to each well. Once desired color intensity was reached, 0.2 N sulfuric acid was added to stop the reaction and absorbance (OD) was measured at 450 nm using a spectrophotometer. The intensity of the color is proportional to the concentration of protease-treated and untreated ProTIA captured by the respective rhEpCAM/biotinylated-anti-His tag and rhEpCAM/biotinylated-anti-XTEN sandwich ELISA. The concentration of ProTIA present in the plasma samples was determined against the appropriate protease-treated or untreated ProTIA standard curve using SoftMax Pro software. Pharmacokinetic calculations of terminal half-life (T112) of the protease-cleaved and uncleaved anti-EpCAM x anti-CD3 ProTIA were performed with GraphPad Prism.

Figure 28:
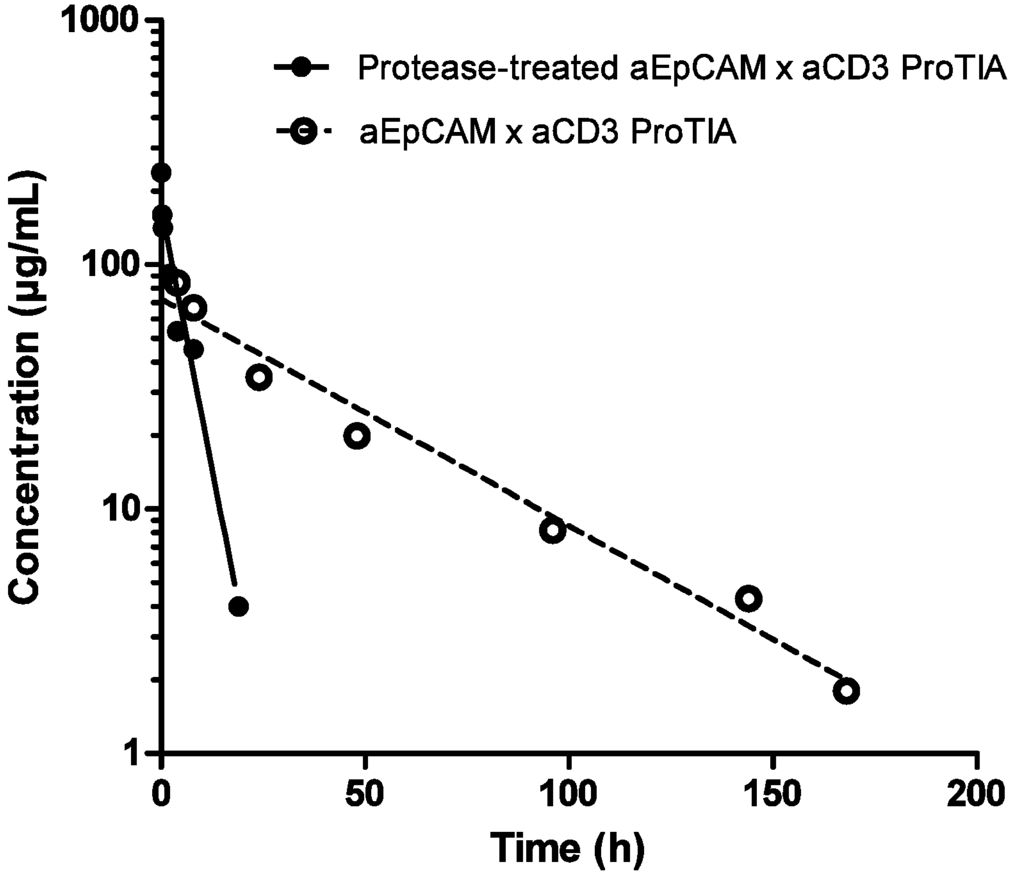
FIG. 28 depicts results from the experiment to determine the PK of protease-treated and untreated anti-EpCAM x anti-CD3 ProTIA, as described in Example 9.

In line with expectation, the protease-treated anti-EpCAM x anti-CD3 ProTIA has a short terminal elimination half-life (T112) of about 3.5 h, whereas the protease-untreated ProTIA (with attached XTEN) has an extended T112 of 32 h (FIG. 28), confirming that the intact ProTIA molecule has significantly longer half-life (at least 9-fold longer) than the cleaved molecule.

Example 10: Anti-Tumor Properties of Anti-EpCAM x Anti-CD3 Protease Triggered Immune Activator (ProTIA) Composition in Early Treatment SW40 Model An in vivo efficacy experiment—was performed in immunodeficient NOD/SCID mice, characterized by the deficiency of T and B cells, and impaired natural killer cells. Mice were maintained in sterile, standardized environmental conditions and experiment performed in accordance to US Institutional Animal Care Association for Assessment and Use Committee (IACUCAccreditation of Laboratory Animal Care (AAALAC) guidelines. The efficacy of protease-treated and protease-untreated anti-EpCAM x anti-CD3 ProTIA (e.g. AC1278) was evaluated using the human SW480 carcinoma xenograft model. Briefly, on day 0, six cohorts of 5 NOD/SCID mice per group were subcutaneously injected in the right flank with $1\times10^7$ human PBMC mixed with $1\times10^7$ SW480 cells. An hour after SW480/PBMC inoculation, cohort 1 was injected with vehicle (PBS+0.05% Tween 80), cohort 2 and 3 with 0.04 mg/kg and 0.4 mg/kg protease-treated anti-EpCAM x anti-CD3 ProTIA respectively, cohort 4 and 5 with 0.1 mg/kg and 1 mg/kg protease-untreated anti-EpCAM x anti-CD3 ProTIA and cohort 6 with 1 mg/kg protease-untreated anti-EpCAM x anti-CD3 ProTIA. Cohort 1 to 5, but not cohort 6, were further subjected to four additional doses administered daily from day 1 to day 4.

Tumors were measured twice per week for a projected 35 days with a caliper in two perpendicular dimensions and tumor volumes were calculated by applying the (width 2 X length)/2 formula. Body weight, general appearance and clinical observations such as seizures, tremors, lethargy, hyper-reactivity, pilo-erection, labored/rapid breathing, coloration and ulceration of tumor and death were also closely monitored as a measure of treatment related toxicity. Study endpoint was defined as a tumor volume of 12002000 $mm^3$ or survival to 3536 days, whichever comes first. Percent tumor growth inhibition index (% TGI) was calculated for each of the treatment group by applying the formula: ((Mean tumor volume of PBSvehicle control−Mean tumor volume of ProTIA treatment)/mean tumor volume of PBSvehicle control)×100. Treatment group with % TGI 60% is considered therapeutically active.

Figure 31:
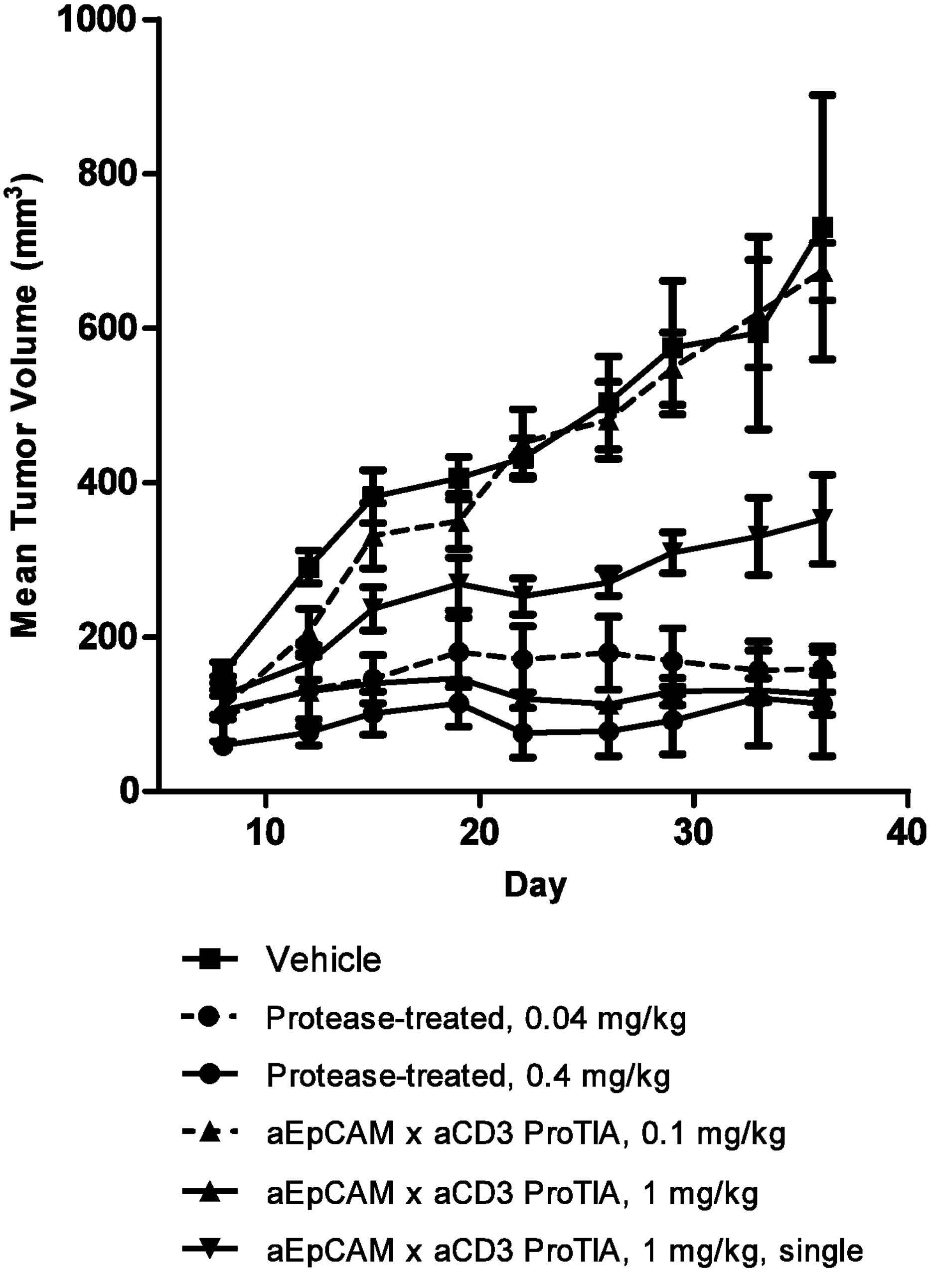
FIG. 31 depicts tumor volume results from experiment to determine the anti-tumor effect of protease-treated and untreated anti-EpCAM x anti-CD3 ProTIA, as described in Example 10.

At day 26, cohort 1 mice treated with PBSvehicle in the presence of human effector cells did not inhibit tumor progression, demonstrating that human effector cells alone as such could not elicit an anti-tumor effect. Treatment with the protease-treated anti-EpCAM x anti-CD3 ProTIA at 0.04 mg/kg and 0.4 mg/kg (cohort 2 and 3 respectively) in the presence of human effector cells exhibited clear dose-dependent response for suppression of tumor growth with the 0.4 mg/kg dose group providing more protection (% TGI=8584%) than the 0.04 mg/kg dose group (% TGI=6478%). Significantly, treatment with anti-EpCAM x anti-CD3 ProTIA at 1 mg/kg (cohort 5) in the presence of human effector cells also inhibited tumor growth (% TGI=7883%) to almost the same extend as molar-equivalent 0.4 mg/kg protease-treated ProTIA (cohort 3). Data suggest that at 1 mg/kg, sufficient anti-EpCAM x anti-CD3 ProTIA was effectively cleaved by proteases in the in vivo tumor environment to the more active, unXTENylated anti-EpCAM x anti-CD3 moiety to yield the observed efficacy. The lack of tumor regression in the 0.1 mg/kg protease-untreated anti-EpCAM x anti-CD3 ProTIA cohort 4 (% TGI=58%) suggested that at this dose, insufficient unXTENylated anti-EpCAM x anti-CD3 moiety was released to induced noticeable tumor regression. Cohort 6, subjected to a single 1 mg/kg dose of anti-EpCAM x anti-CD3 ProTIA, did not attained the threshold for therapeutic activity (% TGI=4652%) despite exhibiting suppressed tumor growth as compared to control group (FIG. 31). Results suggest that anti-EpCAM x anti-CD3 ProTIA can be effectively cleaved in the SW480 tumor environment to inhibit tumor progression and drug concentration plus exposure are important factors in determining drug efficacy.

Figure 32:
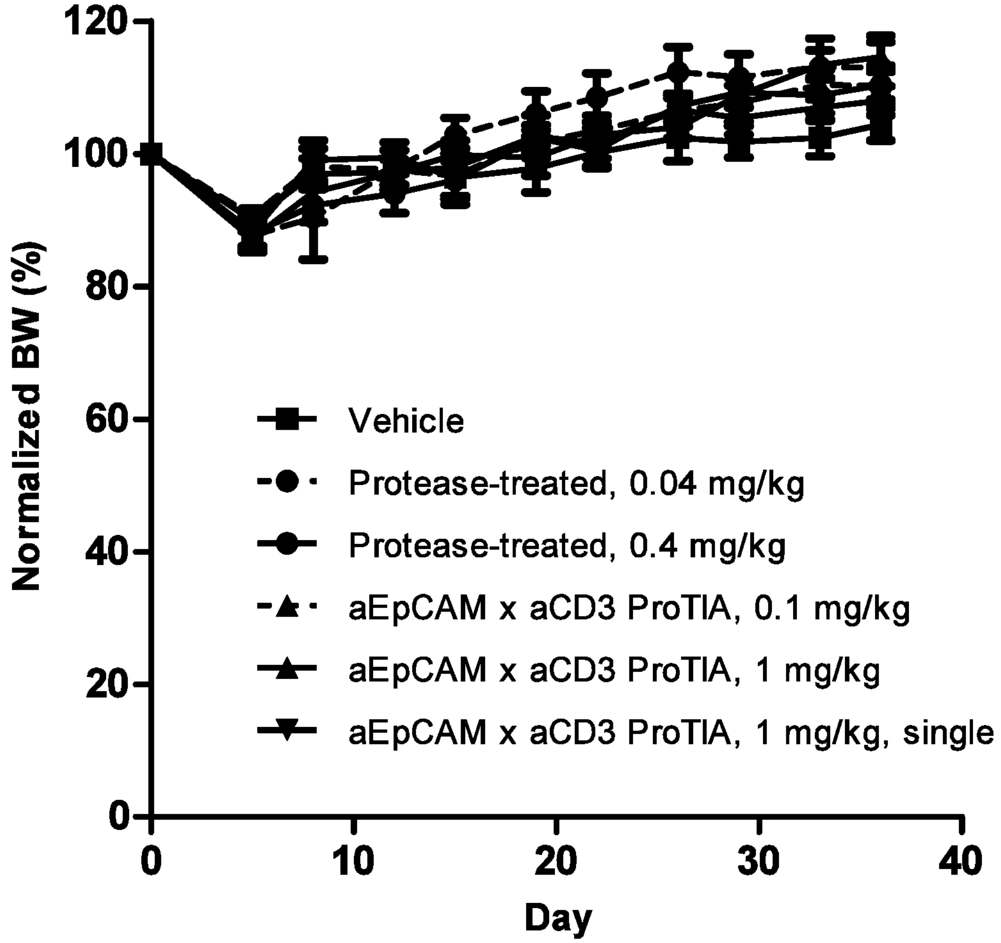
FIG. 32 depicts body weight results from an experiment to determine the anti-tumor effect of protease-treated and untreated anti-EpCAM x anti-CD3 ProTIA, as described in Example 10.

Of note, no significant body weight loss was observed in all ProTIA treatment groups and vehicle control indicating that all treatments were well tolerated (FIG. 32).

The specificity of the antitumor activity of anti-EpCAM x anti-CD3 ProTIA is performed in SW480/PBMC inoculated NOD/SCID mice much like the study described above but with eight mice per treatment group. In this study, early treatment with PBS vehicle control, non-cleavable anti-EpCAM x anti-CD3 ProTIA (e.g. AC1357 or AC1484), a bispecific negative control ProTIA (having the binding activity for CD3 but not for EpCAM), anti-EpCAM x anti-CD3 ProTIA or protease-treated anti-EpCAM x anti-CD3 ProTIA is initiated an hour after SW480/PBMC inoculation. The 1 mg/kg dose concentration of protease-untreated anti-EpCAM x anti-CD3 ProTIA as determined in the above study is used in this study and the bispecific negative control ProTIA, non-cleavable and protease-treated anti-EpCAM x anti-CD3 ProTIA test articles are all intravenously administered at equimolar concentration. Tumor volume, body weight and clinical observations are monitored two times per week for 35 days.

Treatment with PBS vehicle and the bispecific control ProTIA in the presence of human effector cells are not expected to induce anti-tumor effects, demonstrating that neither human effector cells alone nor a non-EpCAM targeting moiety could elicit an anti-tumor effect. Mice in both these treatment groups are expected to meet the study endpoint (day 35 or tumor volume of 2000 $mm^3$). Five daily doses of protease-treated and untreated anti-EpCAM x anti-CD3 ProTIA, in the presence of human effector are expected to induce suppression of tumor growth. Treatment with equimolar concentration of the non-cleavable ProTIA is expected to retard tumor growth but to a much lesser degree than that exhibited by the release segment bearing untreated ProTIA as it does not contain the substrate for protease cleavage.

Example 11: Anti-Tumor Properties of Anti-EpCAM x Anti-CD3 Protease Triggered Immune Activator (ProTIA) Composition in Established Colorectal Tumor Model In the established colorectal tumor model, SW480 and HCT-116 tumor cells are independently implanted into NOG (NOD/Shi-scid/IL-2R$\gamma^{null}$) or NSG (NOD.Cg-Prkdc$^{scid}$.IL2$^{tm1Wjl}$/SzJ) mice on day 0. (The NOG or NSG mice are NOD/SCID mice bearing IL-2Ry mutation resulting in the mice lacking T, B and NK cells, dysfunctional macrophage, dysfunctional dendritic cells and reduced complement activity.) Human PBMC are then intravenously or intraperitoneally introduced sometime between days 3 to 10. When the SW480 and HCT-116 tumor have reached a volume of 150 $mm^3$, treatment with protease-treated anti-EpCAM x anti-CD3 ProTIA, intact protease-untreated anti-EpCAM x anti-CD3 ProTIA and a non-cleavable form of anti-EpCAM x anti-CD3 ProTIA is initiated as five daily doses or as a single dose. It is expected that both protease-cleaved and protease-untreated ProTIA (e.g. AC1476) will lead to reduction or eradication of established SW480 and HCT-116 tumors, with the protease-untreated ProTIA imparting better therapeutic exposure over time resulting in a more efficacious anti-tumor effect and better safety profile than protease-treated ProTIA.

The non-cleavable anti-EpCAM x anti-CD3 ProTIA (e.g. AC1484) is expected to retard tumor growth, but to a much lesser degree than that exhibited by the release segment bearing protease-untreated ProTIA as it does not contain the substrate sequence for protease cleavage within the tumor environment.

Example 12: Cytometric Bead Array Analysis for Human Th1/Th2 Cytokines Using Stimulated Normal Healthy Human PBMCs and Intact and Protease-Treated Anti-EpCAM x Anti-CD3 ProTIA As a safety assessment of the ability of intact versus cleaved anti-EpCAM x anti-CD3 ProTIA to stimulate release of T-cell related cytokines in a cell-based in vitro assay, a panel of cytokines including IL-2, IL-4, IL-6, IL-10, TNF-alpha, IFN-gamma were analyzed using the cytometric bead array (CBA) on supernatants from cultured human PBMC stimulated with protease-treated and untreated anti-EpCAM x anti-CD3 ProTIA samples. The anti-human CD3 antibody, OKT3, was used as positive control and untreated wells served as negative control.

Briefly, OKT3 (0, 10 nM, 100 nM and 1000 nM) and protease-treated and untreated anti-EpCAM x anti-CD3 ProTIA (e.g. AC1278 at 10 nM, 100 nM, 1000 nM and 2000 nM) were dry coated onto a 96-well flat bottomed plate by allowing the wells to evaporate overnight in the biosafety hood. Wells were then washed once gently with PBS and $1\times10^6$ PBMC in 200 microL were added to each well. The plate was then incubated at 37° C., 5% $CO_2$ for 24 h, after which tissue culture supernatant was collected from each well and analyzed for cytokine released using the validated commercial CBA kit (BD CBA human Th1/Th2 cytokine kit, cat #551809) by flow cytometry following manufacturer's instructions.

Figure 33A:
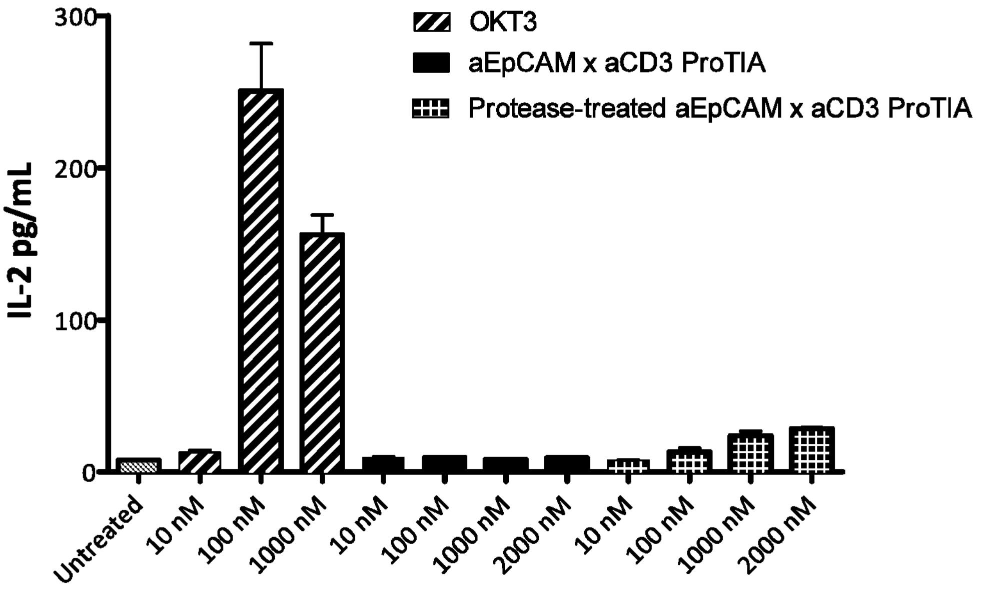
FIG. 33A shows the results of the assay to detect IL-2 and FIG. 33B shows the results to detect IL-4.
Figure 33B:
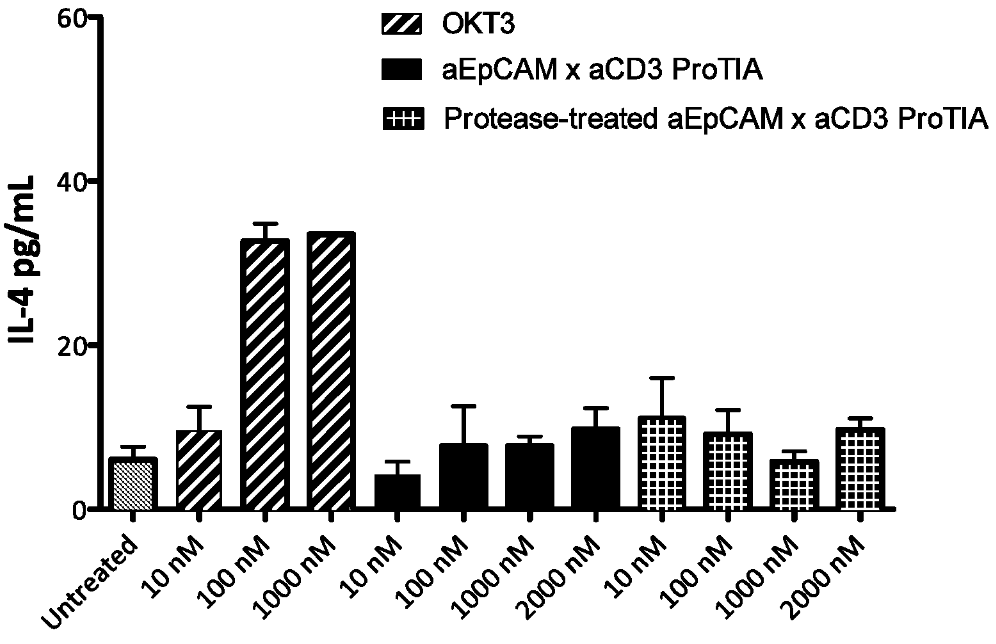

Results:

The raw data for detected levels of cytokines are presented in Table 11, and are depicted graphically in FIGS. 33-3.

TABLE 11

Cytokine levels in response to test compound

| Cytokine | Compound (nM) | Detected Cytokine (pg/ml) Untreated | OKT3 | ProTIA-X | ProTIA-A |
|---|---|---|---|---|---|
| IL-2 | 0 | 7.8 | | | |
| IL-4 | | 6.1 | | | |
| IL-6 | | 33.4 | | | |
| IL-10 | | 20.7 | | | |
| TNFa | | 2.1 | | | |
| IFNg | | 0.0 | | | |
| IL-2 | | | 12.8 | 9.0 | 7.5 |
| IL-4 | | | 9.5 | 4.1 | 11.2 |
| IL-6 | 10 | | 130.2 | 26.3 | 25.2 |
| IL-10 | | | 23.8 | 20.8 | 16.8 |
| TNFa | | | 6.1 | 4.8 | 2.1 |
| IFNg | | | 47.4 | 1.5 | 1.1 |
| IL-2 | | | 250.6 | 9.4 | 13.1 |
| IL-4 | | | 32.7 | 7.7 | 9.2 |
| IL-6 | 100 | | 6658.1 | 22.9 | 56.4 |
| IL-10 | | | 486.3 | 18.3 | 20.7 |
| TNFa | | | 6120.1 | 2.8 | 10.0 |
| IFNg | | | 15512.9 | 3.5 | 106.5 |
| IL-2 | | | 156.0 | 8.1 | 23.8 |

TABLE 11-continued

Cytokine levels in response to test compound

| Cytokine | Compound (nM) | Detected Cytokine (pg/ml) Untreated | OKT3 | ProTIA-X | ProTIA-A |
|---|---|---|---|---|---|
| IL-4 | | | 33.5 | 7.7 | 5.8 |
| IL-6 | 1000 | | 7962.1 | 32.7 | 3683.7 |
| IL-10 | | | 206.0 | 16.4 | 88.0 |
| TNFa | | | 10118.1 | 4.6 | 91.5 |
| IFNg | | | 14060.9 | 0.0 | 1371.5 |
| IL-2 | | | | 9.2 | 28.5 |
| IL-4 | 2000 | | | 9.8 | 9.7 |
| IL-6 | | | | 35.2 | 589.3 |
| IL-10 | | | | 16.9 | 163.9 |
| TNFa | | | | 3.1 | 250.4 |
| IFNg | | | | 0.4 | 3330.0 |

Figure 34A:
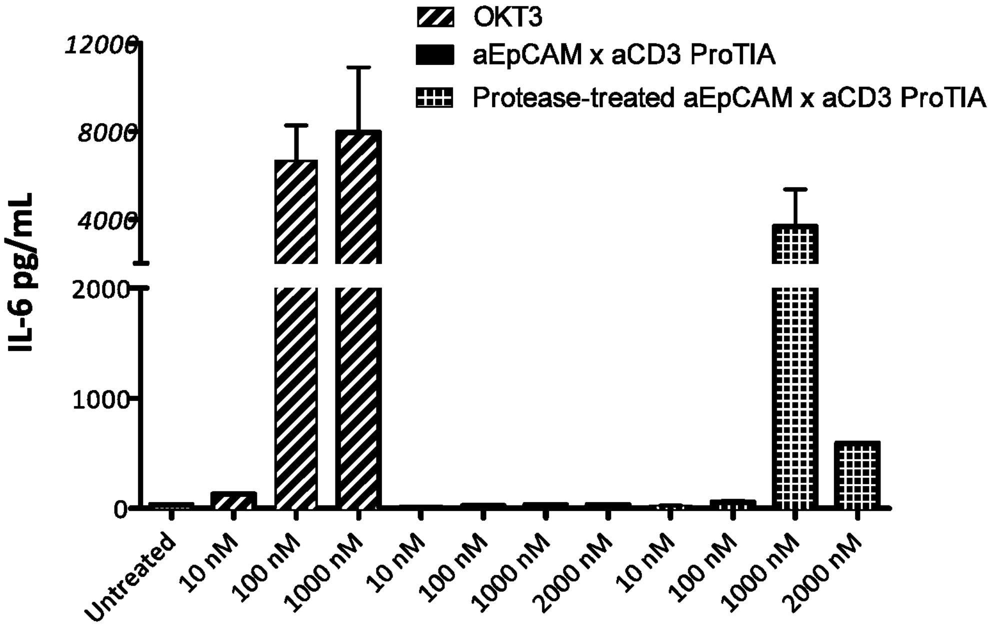
FIG. 34A shows the results of the assay to detect IL-6 and FIG. 34B shows the results to detect IL-10.
Figure 34B:
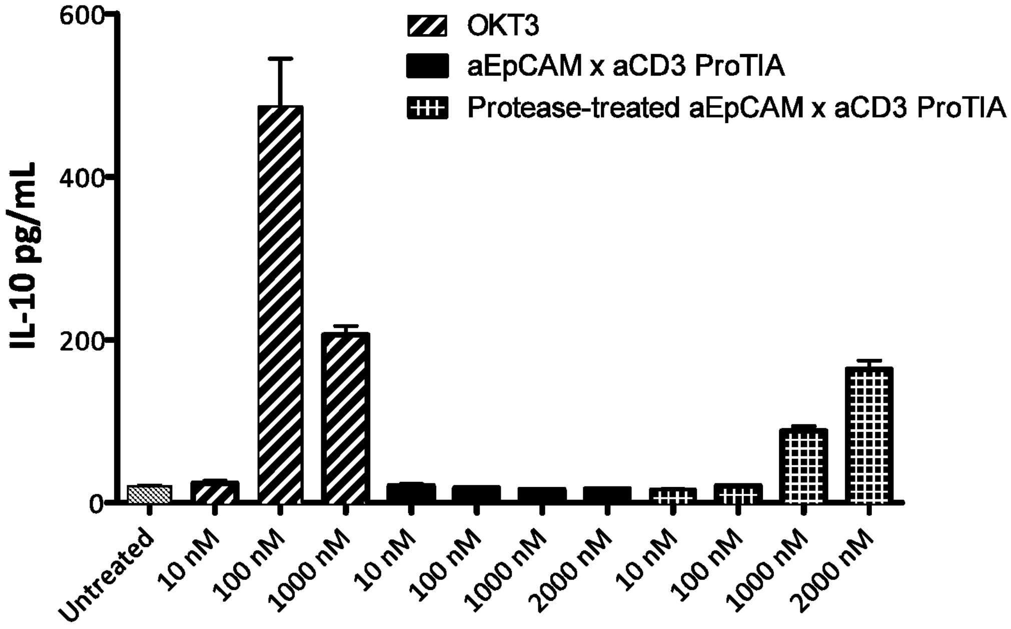
Figure 35A:
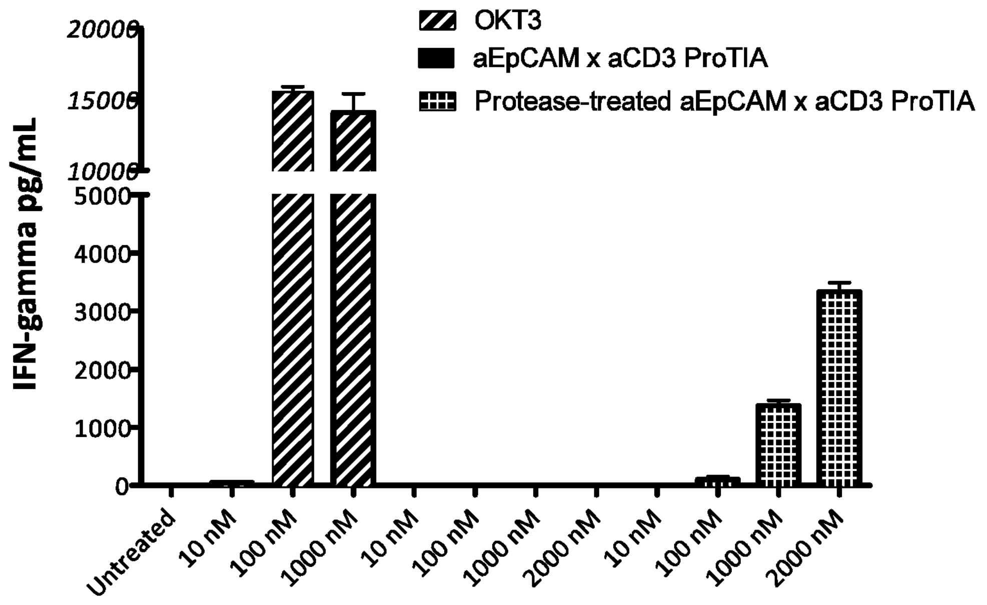
FIG. 35A shows the results of the assay to detect IFN-gamma and FIG. 35B shows the results to detect TNF-alpha.
Figure 35B:
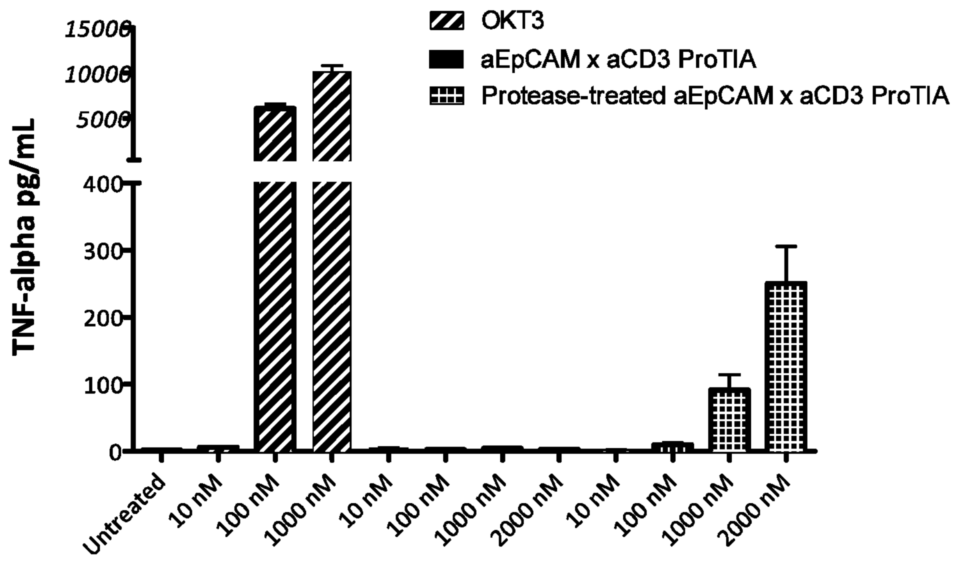

As expected, OKT3, but not untreated wells, induced robust secretion of all cytokines (IL-2, IL-4, IL-6, IL-10, TNF-alpha, IFN-gamma) evaluated, thereby confirming the performance of the CBA cytokine assay. Stimulation with protease-treated anti-EpCAM x anti-CD3 ProTIA triggered significant cytokine expression, especially at concentrations higher than 100 nM for all of the cytokines tested. In contrast, baseline levels of IL-2, IL-6, IL-10, TNF-alpha and IFN-gamma were detected when the intact non-cleaved anti-EpCAM x anti-CD3 ProTIA molecule was the stimulant at a concentration range of 10 to 2000 nM. While an appreciable level of IL-4 was detected when induced with the protease-untreated ProTIA, the level of IL-4 was, however, not higher than that observed with the protease-treated ProTIA (FIGS. 33-35). These data suggest that the XTEN polymer of the intact ProTIA composition provides considerable shielding effect and hinders PBMC stimulated cytokine responses compared to the protease-treated ProTIA in which the EpCAM x anti-CD3 portion is released from the composition.

Example 13: Anti-Tumor Properties of Anti-EpCAM x Anti-CD3 Protease Triggered Immune Activator (ProTIA) Composition in Early Treatment HCT-116 Model In vivo efficacy experiment was performed in immunodeficient NOD/SCID mice, characterized by the deficiency of T and B cells, and impaired natural killer cells. Mice were maintained in sterile, standardized environmental conditions and experiment performed in accordance with the Association for Assessment and Accreditation of Laboratory Animal Care (AAALAC) guidelines. The efficacy of protease-treated and protease-untreated anti-EpCAM x anti-CD3 ProTIA (e.g. AC1476) together with non-cleavable anti-EpCAM x anti-CD3 ProTIA (i.e. ProTIA without the release segment cleavage sequence and an example of which being AC1484) was evaluated using the human HCT-116 colorectal carcinoma xenograft model. Briefly, on day 0, four cohorts of 5 NOD/SCID mice per group were subcutaneously injected in the right flank with $5\times10^6$ human PBMC mixed with $5\times10^6$ HCT-116 cells. An hour after HCT-116/PBMC inoculation and based on equimolar dosing, cohort 1 was injected with vehicle (PBS+0.05% Tween 80), cohort 2 with 0.21 mg/kg protease-treated anti-EpCAM x anti-CD3 ProTIA, cohort 3 with 0.5 mg/kg protease-untreated anti-EpCAM x anti-CD3 ProTIA and cohort 4 with 0.49 mg/kg non-cleavable anti-EpCAM x anti-CD3 ProTIA. Cohort 1 to 4 were all subjected to four additional doses administered daily from day 1 to 4.

Tumors were measured twice per week for a projected 35 days with a caliper in two perpendicular dimensions and tumor volumes were calculated by applying the ($width^2\times length$)/2 formula. Body weight, general appearance and clinical observations such as seizures, tremors, lethargy, hyper-reactivity, pilo-erection, labored/rapid breathing, coloration and ulceration of tumor and death were also closely monitored as a measure of treatment related toxicity. Study endpoint was defined as a tumor volume of 12002000 $mm^3$ or survival to 35 days, whichever comes first. Percent tumor growth inhibition index (% TGI) was calculated for each of the treatment group by applying the formula: ((Mean tumor volume of PBS control−Mean tumor volume of ProTIA treatment)/mean tumor volume of PBS control)×100. Treatment group with % TGI 60% is considered therapeutically active.

Figure 38:
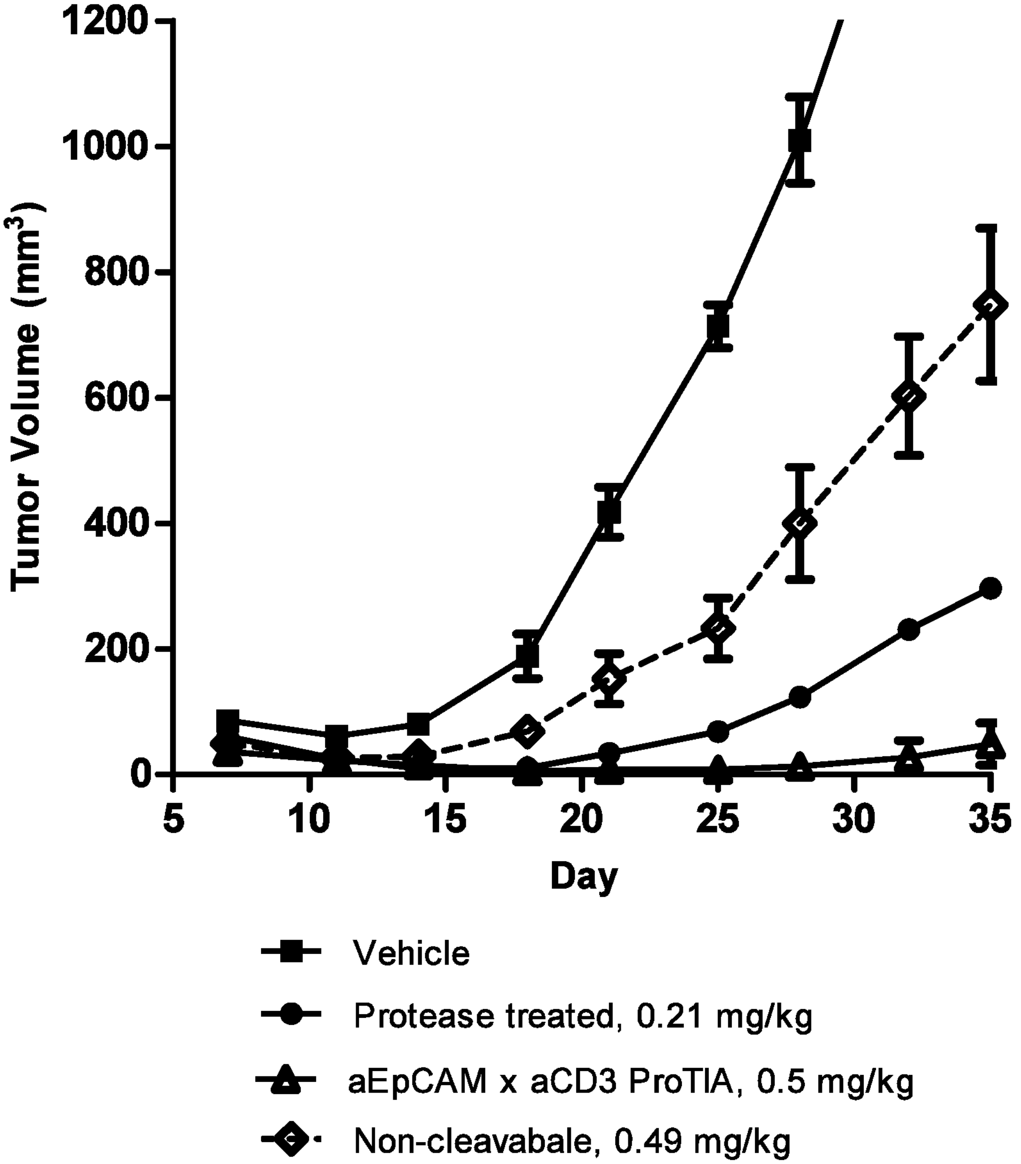
FIG. 38 depicts HCT-116 tumor volume results from experiment to determine the anti-tumor effect of anti-Ep-CAM x anti-CD3 ProTIA, protease-treated anti-EpCAM x anti-CD3 ProTIA and non-cleavable anti-EpCAM x anti-CD3 ProTIA, as described in Example 13.

At day 1835, cohort 1 mice treated with vehicle in the presence of human effector cells did not inhibit tumor progression and exiting the study with a group mean tumor volume of 1823 $mm^3$, demonstrating that human effector cells alone as such could not elicit an anti-tumor effect. Treatment with the protease-treated anti-EpCAM x anti-CD3 ProTIA at 0.21 mg/kg (cohort 2) in the presence of human effector cells exhibited robust suppression of tumor growth; with 2/5 mice exhibiting complete tumor regression by displaying no measureable tumor volume at day 18. However, tumor regrowth and progression was observed from day 25 onwards in this cohort resulting in all 5 mice bearing a tumor burden exiting the study with a mean tumor volume of 296 $mm^3$. Significantly, treatment with intact anti-EpCAM x anti-CD3 ProTIA at 0.5 mg/kg (cohort 3) in the presence of human effector cells also imparted strong inhibition of tumor growth. In fact 4/5 mice in cohort 3 exhibited complete tumor regression by day 18. On the other hand; with 2 mice still retaining complete regression on day 35 ensuing a cohort mean tumor volume of 48 $mm^3$ exiting the study. Importantly, Cohort 4 subjected to 0.49 mg/kg dose of non-cleavable anti-EpCAM x anti-CD3 ProTIA, did not induce any sustained inhibition of tumor progression as effectively as cohort 2 and 3, leaving 5/5 mice in this cohort with significant tumor burden by. Cohort 4 exited study at day 18.35 with a group mean tumor volume of 748 $mm^3$. Both protease-treated anti-EpCAM x anti-CD3 ProTIA at 0.21 mg/kg (cohort 2) and intact anti-EpCAM x anti-CD3 ProTIA at 0.5 mg/kg (cohort 3) are considered therapeutically active with a TGI of 84% and 97% respectively. With a TGI of 59%, the non-cleavable anti-EpCAM x anti-CD3 ProTIA is considered therapeutically inactive. As expected, the group mean tumor volume of intact anti-EpCAM x anti-CD3 ProTIA is found to be significantly different from that of non-cleavable anti-EpCAM x anti-CD3 ProTIA cohort (student's t-test, p=0.0016). Appreciably, the group mean tumor volume of intact anti-EpCAM x anti-CD3 ProTIA cohort is also found to be significantly different from that of protease-treated anti-EpCAM x anti-CD3 ProTIA cohort (p=0.002). Results suggest that at 0.5 mg/kg, significant amount of anti-EpCAM x anti-CD3 ProTIA was effectively cleaved by proteases present in the in vivo HCT-116 tumor environment to the highly active, unXTENylated anti-EpCAM x anti-CD3 moiety to impart the remarkable observed tumor regression. This hypothesis is very much supported by the non-cleavable anti-EpCAM x anti-CD3 ProTIA molecule lacking the release segment substrate that resulted in the lack of sustained tumor regression property (FIG. 38). Importantly, data also suggest that the anti-EpCAM x anti-CD3 ProTIA levied better therapeutic exposure than protease-treated anti-EpCAM x anti-CD3 ProTIA therefore reporting a more sustained tumor regression effect.

Figure 39:
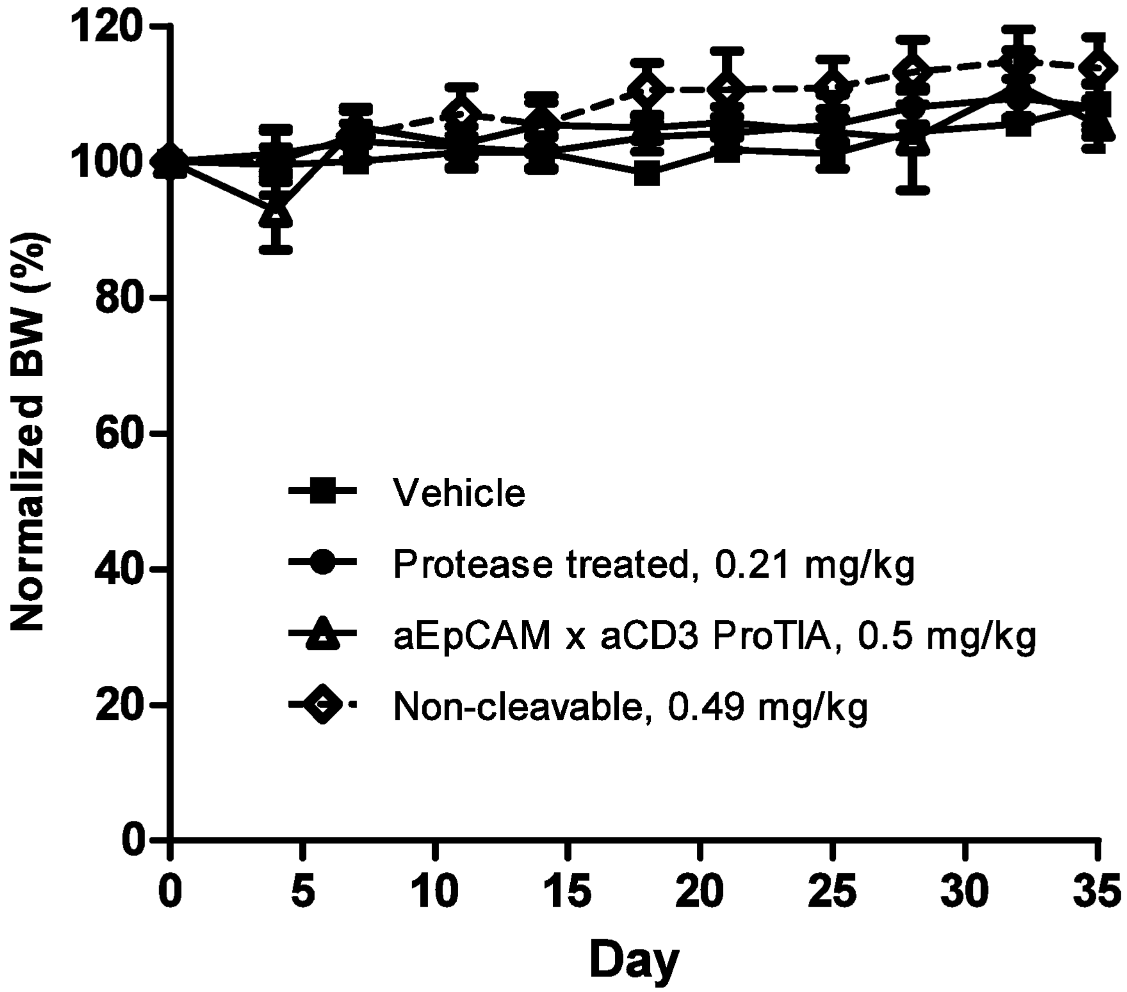
FIG. 39 depicts body weight results from experiment to determine the anti-HCT-116 tumor effect of anti-EpCAM x anti-CD3 ProTIA, protease-treated anti-EpCAM x anti-CD3 ProTIA and non-cleavable anti-EpCAM x anti-CD3 ProTIA, as described in Example 13.

Of note, no significant body weight loss was observed in all ProTIA treatment groups and vehicle control indicating that all treatments were generally well tolerated (FIG. 39).

Figure 40:
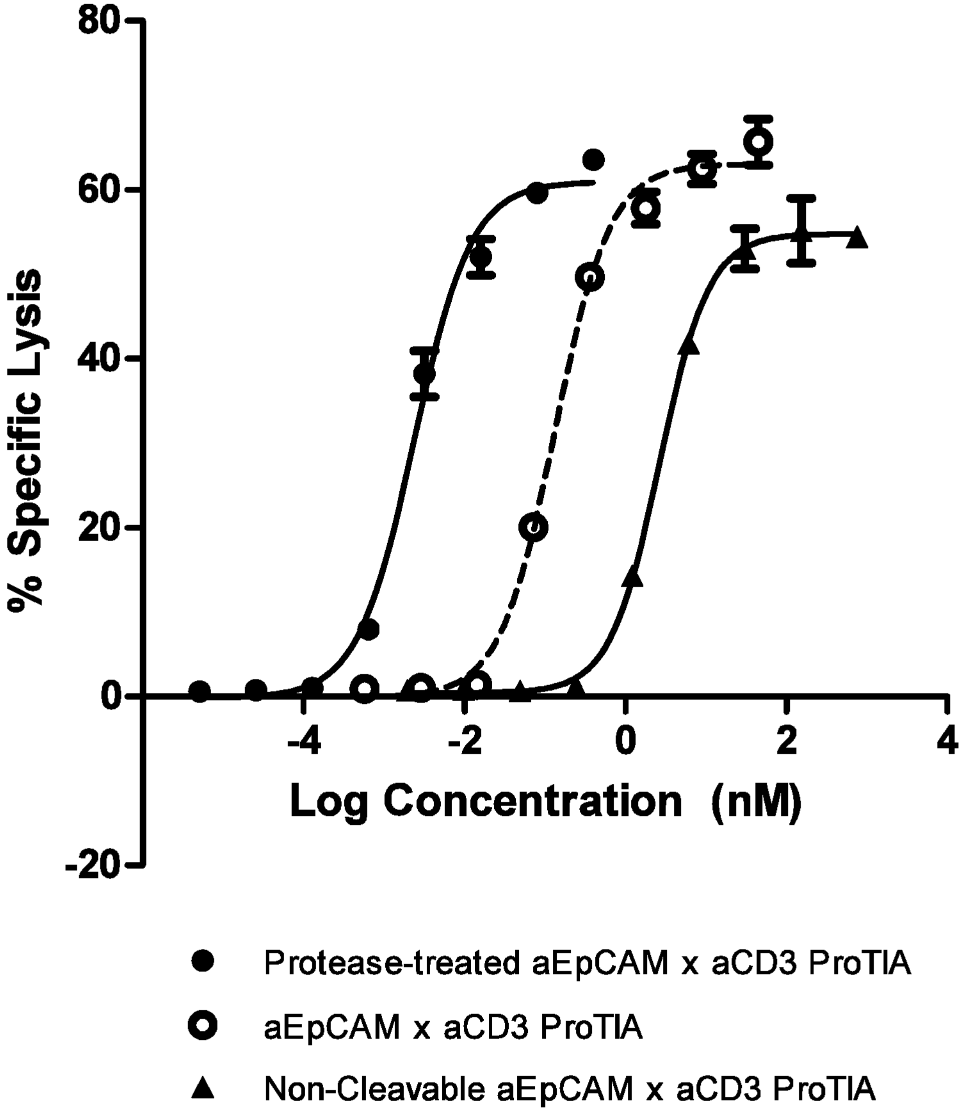
FIG. 40 depicts results from the experiment to determine the in vitro activity of protease-treated, protease-untreated and protease-non cleavable anti-EpCAM x anti-CD3 Pro-TIA in SK-OV-3 with human purified CD3 positive T cells as described in Example 14.
Figure 41:
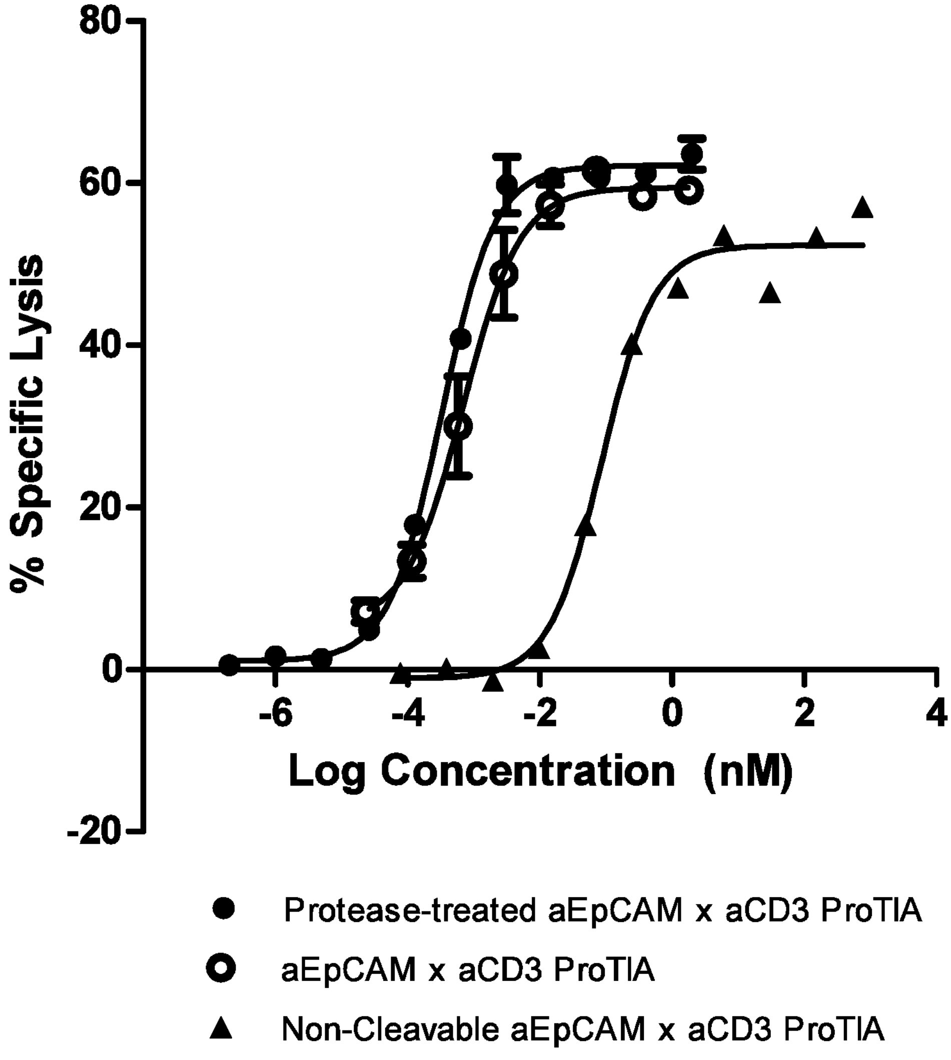
FIG. 41 depicts results from the experiment to determine the in vitro activity of protease-treated, protease-untreated and protease-non cleavable anti-EpCAM x anti-CD3 Pro-TIA in OVCAR-3 with human purified CD3 positive T cells as described in Example 14.

Example 14: Cytotoxicity Assays of Anti-EpCAM x Anti-CD3 Protease Triggered Immune Activator (ProTIA) Composition in the Presence of Purified CD3 Positive T Cells To demonstrate that cytotoxic activity of ProTIA molecules is mediated by CD3 positive T cells, non-cleavable anti-EpCAM x anti-CD3 ProTIA without the release segment (e.g. AC1484) and protease-treated and untreated anti-EpCAM x anti-CD3 ProTIA (e.g. AC1476) were further evaluated in SK-OV-3 and OVCAR-3 human ovarian cell lines in the presence of purified human CD3 positive T cells. Purified human CD3 positive T cells were purchased from BioreclamationlVT and isolated by negative selection using MagCellect Human CD3+ T cell isolation kit from whole blood of healthy donors. In this experiment, purified human CD3 positive T cells were mixed with SK-OV-3 or OVAR-3 ovarian cells in a ratio of 5:1 and all three ProTIA molecules were tested as a 12-point, 5× serial dilution dose curve in the LDH assay as described above. As expected, the activity trend of the three ProTIA molecules profiled in SK-OV-3 was found to be similar to that observed in the SK-OV-3 with PBMC analysis (FIG. 30). In the cytotoxic killing of SK-OV-3 ovarian cells by human CD3 positive T cells, untreated anti-EpCAM x anti-CD3 ProTIA is 56-fold less active than protease-treated ProTIA ($EC_{50}$ of 134 pM vs. 2.4 pM); and the non-cleavable anti-EpCAM x anti-CD3 ProTIA is >1000-fold less active than the protease-cleaved ProTIA ($EC_{50}$ of 2660 pM vs. 2.4 pM) (FIG. 40). In the cytotoxic killing of OVCAR-3 ovarian cells by human CD3 positive T cells, untreated anti-EpCAM x anti-CD3 ProTIA is only 2-fold less active than protease-treated ProTIA ($EC_{50}$ of 0.7 pM vs. 0.3 pM); and the non-cleavable anti-EpCAM x anti-CD3 ProTIA is 287-fold less active than the protease-cleaved ProTIA ($EC_{50}$ of 86 pM vs. 0.3 pM) (FIG. 41). Results demonstrated that cytotoxic activity of ProTIA molecules is indeed mediated by CD3 positive T cells; and that the susceptibility of the release segment contained within the cleavable anti-EpCAM x anti-CD3 ProTIA molecule to proteases postulated to be released from the tumor cells and/or activated CD3 positive T cells in the assay mixture is likely to differ between cell lines.

Example 15: T-Cell Activation Marker and Cytokine Release Assays of Anti-EpCAM x Anti-CD3 Protease Triggered Immune Activator (ProTIA) Composition To measure the anti-EpCAM x anti-CD3 ProTIA induced expression of cytokines, $1\times10^5$ purified CD3+ cells were co-cultured with 2×10 4 SK-OV-3 cells per assay well (i.e., effector to target ratio of 5:1) in the presence of anti-EpCAM x anti-CD3 ProTIA in a 96-well round-bottom plate with total final volume of 200 microL. After 20 h incubation in a 37° C., 5% $CO_2$ humidified incubator, cell supernatant was harvested for cytokine measurements. This assay can also be performed with other target cells selected from HCT-116, Kato III, MDA-MB-453, MCF-7, MKN45, MT3, NCI-N87, SK-Br-3, SW480, OVCAR3 and PC3 cell lines as well as PBMC in place of purified CD3+ cells.

Cytokine analysis of interleukin (IL)-2, IL-4, IL-6, IL-10, tumor necrosis factor (TNF)-alpha and interferon (IFN)-gamma secreted into the cell culture supernatant was quantitated using the Human Th1/Th2 Cytokine Cytometric Bead Array (CBA) kit (BD Biosciences cat #550749) following manufacturer's instruction. In the absence of ProTIA, no cytokine secretion above background is expected from purified CD3+ cells. ProTIA in the presence of EpCAM-positive target cells and purified CD3+ cells is expected to activate T cells and secrete a pattern of T cell cytokines with a high proportion of Th1 cytokines such as IFN-gamma and TNF-alpha.

Figure 50A:
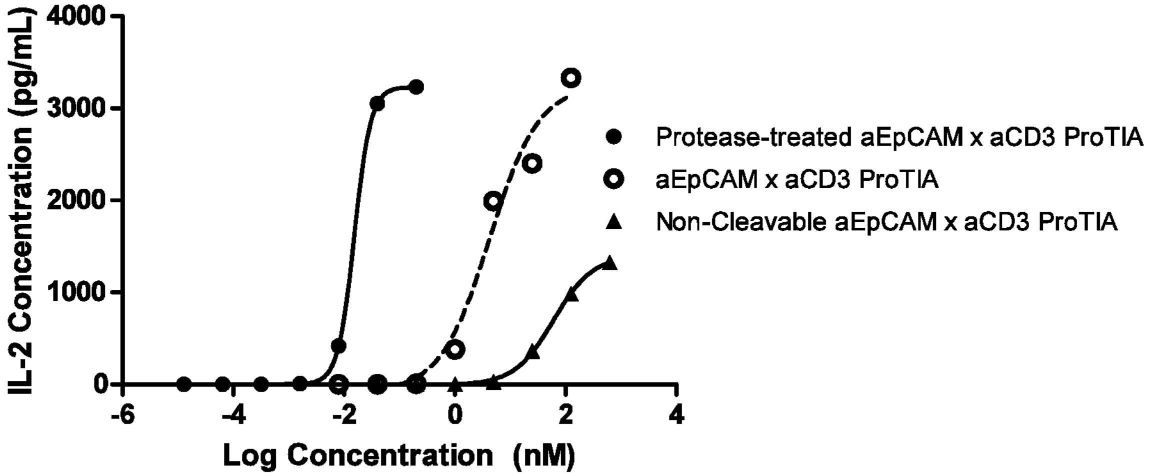
Figure 50B:
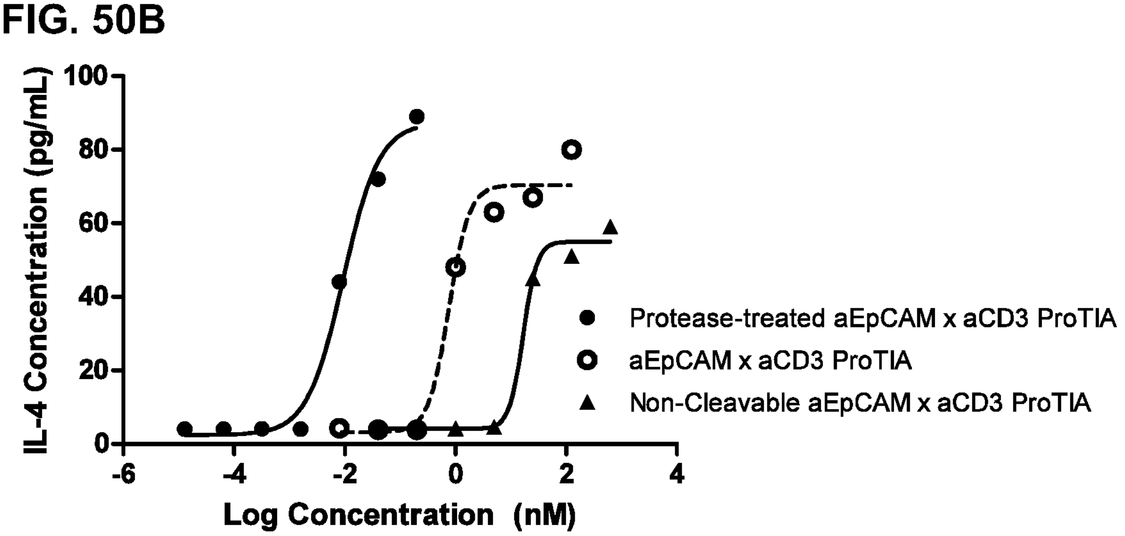
FIG. 50B depicts the concentration of released IL-4.
Figure 51A:
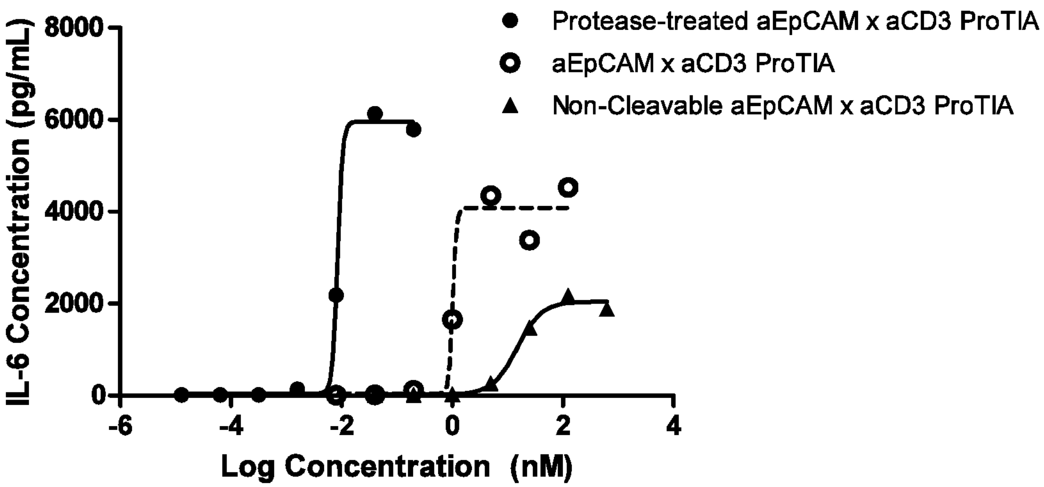
Figure 51B:
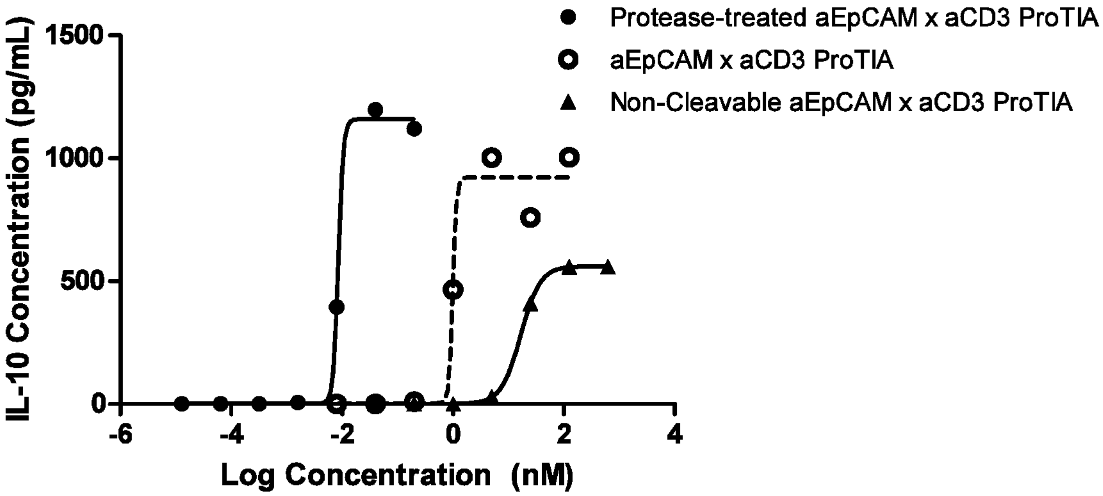
FIG. 51B depicts the concentration of released IL-10.
Figure 52A:
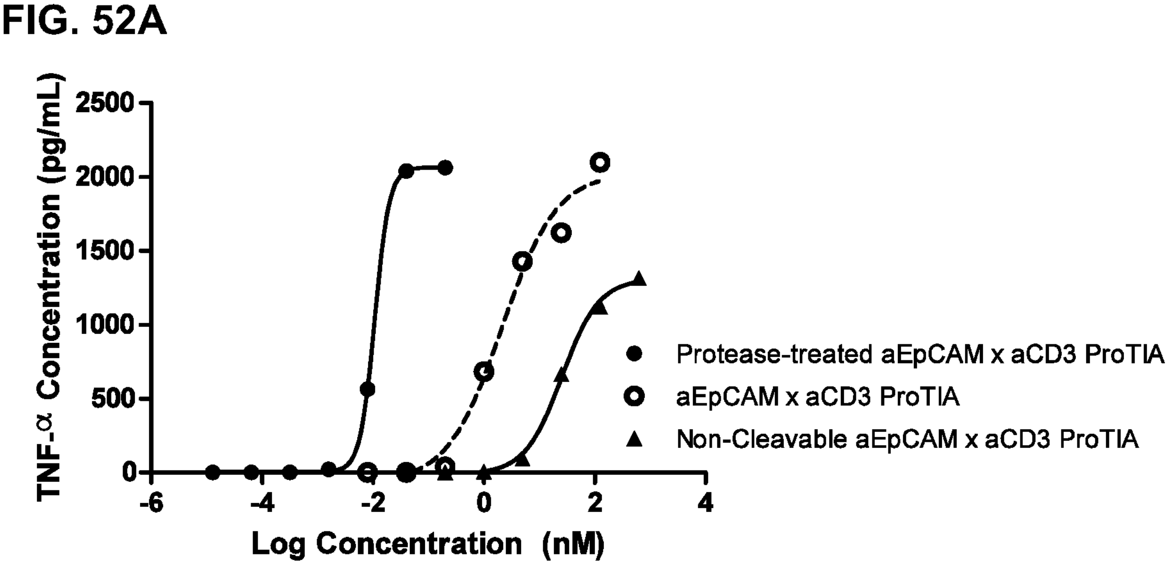
Figure 52B:
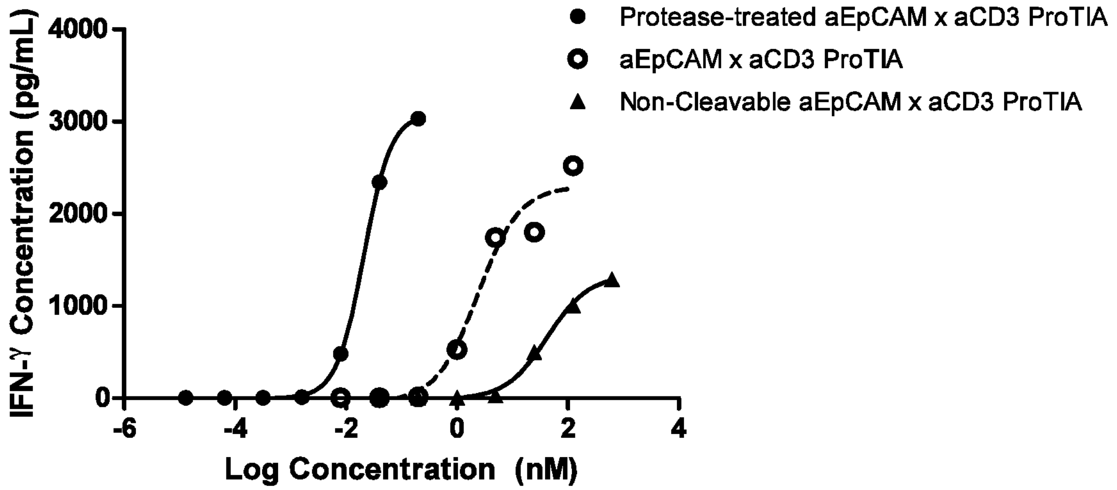
FIG. 52B depicts the concentration of released IFN-gamma.

As expected, anti-EpCAM x anti-CD3 ProTIA induced robust secretion of all cytokines (IL-2, IL-4, IL-6, IL-10, TNF-alpha, IFN-gamma) evaluated (see FIGS. 50-52). Stimulation of purified CD3+ cells with SK-OV-3 cells and protease-treated anti-EpCAM x anti-CD3 ProTIA triggered significant cytokine expression, especially at concentrations higher than 20 pM for all of the cytokines tested. In contrast, baseline levels of IL-2, IL-4, IL-6, IL-10, TNF-alpha and IFN-gamma were detected when the intact non-cleaved anti-EpCAM x anti-CD3 ProTIA molecule was used at a concentration range of 8 to 200 pM ($EC_{50}$ of 4.3 nM). Additionally, baseline levels of all cytokines tested were detected when the non-cleavable anti-EpCAM x anti-CD3 ProTIA molecule was used at a concentration range of 40 pM to 1 nM. These data suggest that the XTEN polymer of the intact ProTIA composition provides considerable shielding effect and hinders CD3+ T-cell stimulated cytokine responses compared to the protease-treated ProTIA in which the EpCAM x anti-CD3 portion is released from the composition.

Example 16: CD3 Binding Specificity of Anti-EpCAM x Anti-CD3 Protease Triggered Immune Activator (ProTIA) Composition As ProTIA is a bispecific-targeting composition, the binding capability of anti-EpCAM x anti-CD3 ProTIA composition was also evaluated for binding affinity to human CD3. This was determined with a CD368/peroxidase-conjugated protein-L sandwich ELISA. In this ELISA, recombinant human CD3 (rhCD368) (Creative BioMart cat #CD3E&CD3D-219H) was coated on a 96-well, flat-bottomed plate at a concentration of 0.025 microg/100 microL. After overnight incubation at 4° C., the assay plate was washed and blocked with 3% bovine serum albumin (BSA) for 1 h at room temperature. The plate was washed again followed by the introduction of dose ranges of non-cleavable anti-EpCAM x anti-CD3 ProTIA (e.g. AC1484), protease-treated and protease-untreated anti-EpCAM x anti-CD3 ProTIA (e.g. AC1476). The dose range utilized for all three versions of ProTIA was 0.002 to 100 nM, achieved with a 1:6 fold serial dilution scheme from a starting concentration of 100 nM. The plate was allowed to incubate with shaking for 1 h at room temperature to allow the non-cleavable, protease-cleaved and protease-untreated ProTIA to bind to the rhCD368 coated on the plate. Unbound components were removed with a wash step and a peroxidase-conjugated protein L (ThermoFisher Scientific cat #32420) at 0.05 microg/100 microL was added. After an appropriate incubation period, any unbound reagent was removed by a wash step followed by the addition of tetramethylbenzidine (TMB) substrate to each well. After desired color intensity was reached, 0.2 N sulfuric acid was added to stop the reaction and absorbance (OD) was measured at 450 nm using a spectrophotometer. The intensity of the color is proportional to the concentration of non-cleavable, protease-treated and untreated anti-EpCAM x anti-CD3 ProTIA captured by the rhCD368/protein-L sandwich ELISA. The intensity of the color produced (measured OD) was plotted against protein concentration; and the concentration of non-cleavable, protease-cleaved and uncleaved anti-EpCAM x anti-CD3 ProTIA that gave half-maximal response ($EC_{50}$) was derived with a 4-parameter logistic regression equation using GraphPad prism software.

Figure 53:
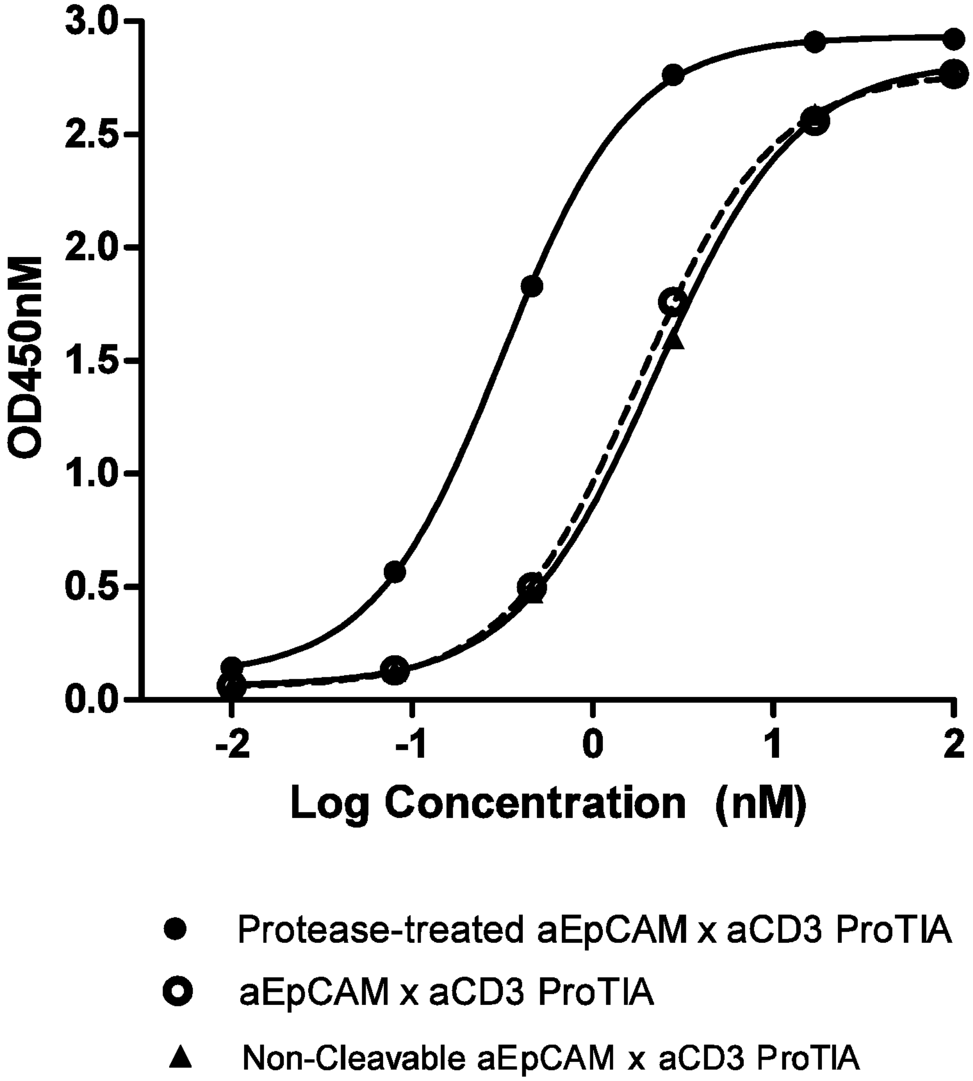
FIG. 53 shows the binding curves of protease-treated, protease-untreated and noncleavable antiEpCAM x antiCD3 ProTIA for CD368 ligands, as described in Example 16.

Results: As shown in FIG. 53, the protease-untreated anti-EpCAM x anti-CD3 ProTIA had a binding activity similar to that of non-cleavable anti-EpCAM x anti-CD3 bispecific ProTIA molecule each bearing an $EC_{50}$ of 1800 pM and 2200 pM respectively. The protease-treated ProTIA had the strongest binding activity at $EC_{50}$ of 310 pM for the rhCD368 ligand compared to the intact protease-untreated bispecific molecule or the non-cleavable ProTIA molecule. As the XTEN864 blocking moiety is located right after the anti-CD3scFv moiety, the XTEN864 results in hindrance in the binding of the non-cleaved anti-CD3 entity for its ligand by ~5.8 fold as compared to the cleaved and released anti-CD3scFv portion of the ProTIA binding to the CD3 ligand.

Example 17: Binding Specificity of Anti-EpCAM x Anti-CD3 Protease Triggered Immune Activator (ProTIA) Composition The binding specificity of an anti-EpCAM x anti-CD3 ProTIA (e.g. AC1476) was evaluated in conjunction with the control ProTIA compositions anti-CEA x anti-CD3 ProTIA (e.g. AC1432) and anti-HER2 x anti-CD3 ProTIA (e.g. AC1408), in a target antigen/biotin-conjugated protein-L sandwich ELISA. Both the anti-CEA x anti-CD3 ProTIA (AC1432) and the anti-HER2 x anti-CD3 ProTIA (AC1408) bear the same anti-CD3 scFv component as the anti-EpCAM x anti-CD3 ProTIA (AC1476) albeit with different targeting component. In the ELISA binding assay, recombinant human EpCAM (rhEpCAM) (R&D Systems cat #960-EP-50), recombinant human CEA (Abcam cat #ab742) and recombinant human HER2 (AcroBiosystems cat #HE2-H525) were coated on a 96-well, flat-bottomed plate at a concentration of 0.1 microg/100 microL. After overnight incubation at 4° C., the assay plate was washed and blocked with 3% bovine serum albumin (BSA) for 1 h at room temperature. The plate was washed again followed by the introduction of a dose range (0.0007 to 0.5 nM, achieved with a 1:3 fold serial dilution scheme from a starting concentration of 0.5 nM) of protease-treated anti-EpCAM x anti-CD3 ProTIA (e.g. AC1476) to EpCAM-coated wells, CEA-coated wells and HER2-coated wells. Serving as controls, protease-treated anti-CEA x anti-CD3 ProTIA (AC1432) was introduced at a similar dose range onto CEA-coated wells, and protease-treated anti-HER2 x anti-CD3 ProTIA (AC1408) was also introduced at a similar dose range onto HER2-coated wells. The plate was allowed to incubate with shaking for 1 h at room temperature to allow the various protease-cleaved ProTIAs to bind to the respective antigen coated on the plate. Unbound components were removed with a wash step and a biotin-conjugated protein L (ThermoFisher Scientific cat #29997) was added at 0.05 microg/100 microL. After an appropriate incubation period, any unbound reagent was removed by a wash step followed by the addition of tetramethylbenzidine (TMB) substrate to each well. After desired color intensity was reached, 0.2 N sulfuric acid was added to stop the reaction and absorbance (OD) was measured at 450 nm using a spectrophotometer. The intensity of the color is proportional to the concentration of the respective protease-treated ProTIAs captured by the appropriate antigen coated on the plate. The intensity of the color produced (measured OD) was plotted against ProTIA concentration; and the respective dose curve derived with a 4-parameter logistic regression equation using GraphPad prism software.

Figure 54:
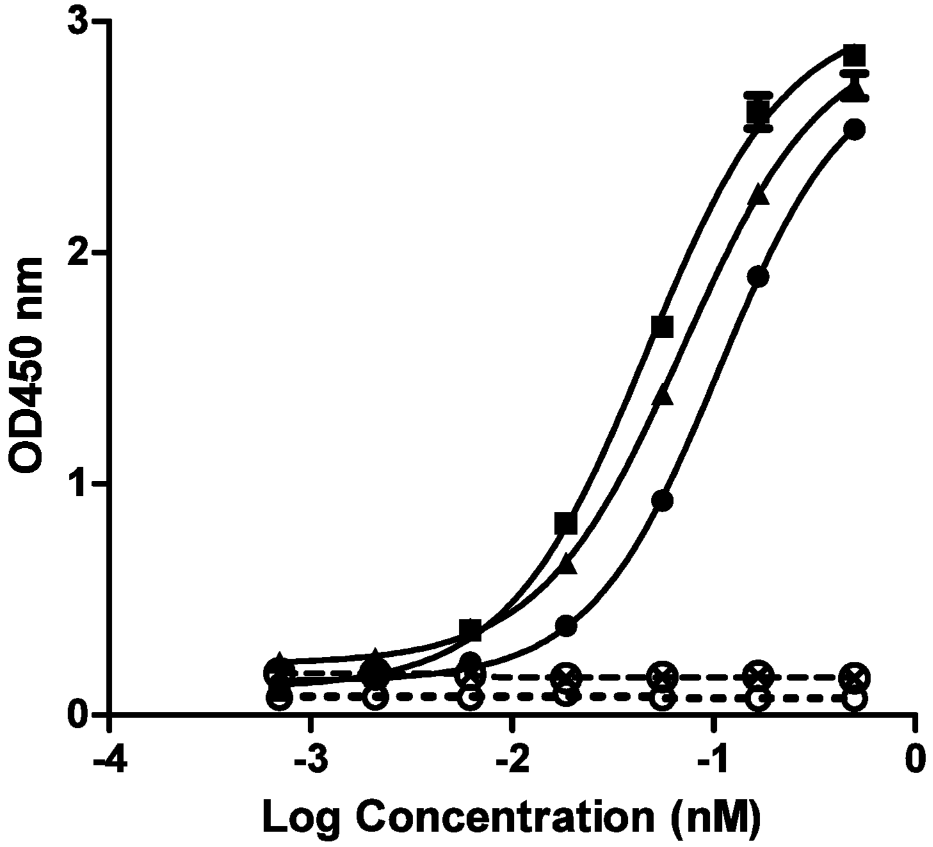
FIG. 54 shows binding specificity of protease treated antiEpCAM x antiCD3 ProTIA for rhEpCAM ligand, as described in Example 17.

Results: As shown in FIG. 54 (and comparable with the results of FIG. 24), protease-treated anti-EpCAM x anti-CD3 ProTIA binds to rhEpCAM coated on the plate in a dose-dependent manner to yield an $EC_{50}$ of 110 pM. Similarly, protease-treated anti-CEA x anti-CD3 ProTIA binds to the CEA antigen coated on the plate in a dose-dependent manner to yield an $EC_{50}$ of 70 pM; and protease-treated anti-HER2 x anti-CD3 ProTIA binds to the HER2 antigen coated on the plate in a dose-dependent manner to yield an $EC_{50}$ of 47 pM. Significantly, no dose-dependent binding was observed for protease-treated anti-EpCAM x anti-CD3 ProTIA binding to both CEA- and HER2-antigen coated on the plate indicating that protease-treated anti-EpCAM x anti-CD3 ProTIA binds specifically to EpCAM but not to CEA or HER2 antigen. Thus, the compositions exhibited specific binding affinity to their target ligands and no non-specific binding.

Example 18: Anti-Tumor Properties of Intact Anti-EpCAM x Anti-CD3 ProTIA Versus Non-Cleavable Anti-EpCAM x Anti-CD3 ProTIA in Early Treatment SW480 Model The protease susceptibility of the release segment (RS) as engineered into the anti-EpCAM x anti-CD3 ProTIA molecule (e.g. AC1476) in tumor environment was also evaluated in vivo together with non-cleavable anti-EpCAM x anti-CD3 ProTIA (e.g. AC1484), protease-treated and protease-untreated anti-EpCAM x anti-CD3 ProTIA (e.g. AC1476) in the SW480/PBMC inoculated NOD/SCID xenograft model. Much like the study described in Examples 10 and 13, an hour after SW480/PBMC inoculation (denoted as day 0), cohort 1 mice was injected with vehicle (PBS 0.05% Tween 80), cohort 2 with 0.21 mg/kg protease-treated anti-EpCAM x anti-CD3 ProTIA, cohort 3 with 0.5 mg/kg intact anti-EpCAM x anti-CD3 ProTIA and cohort 4 with 0.49 mg/kg non-cleavable anti-EpCAM x anti-CD3 ProTIA. All cohorts (i.e. 1 to 4) were further treated with four additional doses administered daily from day 1 to day 4. Tumor volume, body weight and clinical observations are monitored two times per week for a targeted 35 days.

Figure 55:
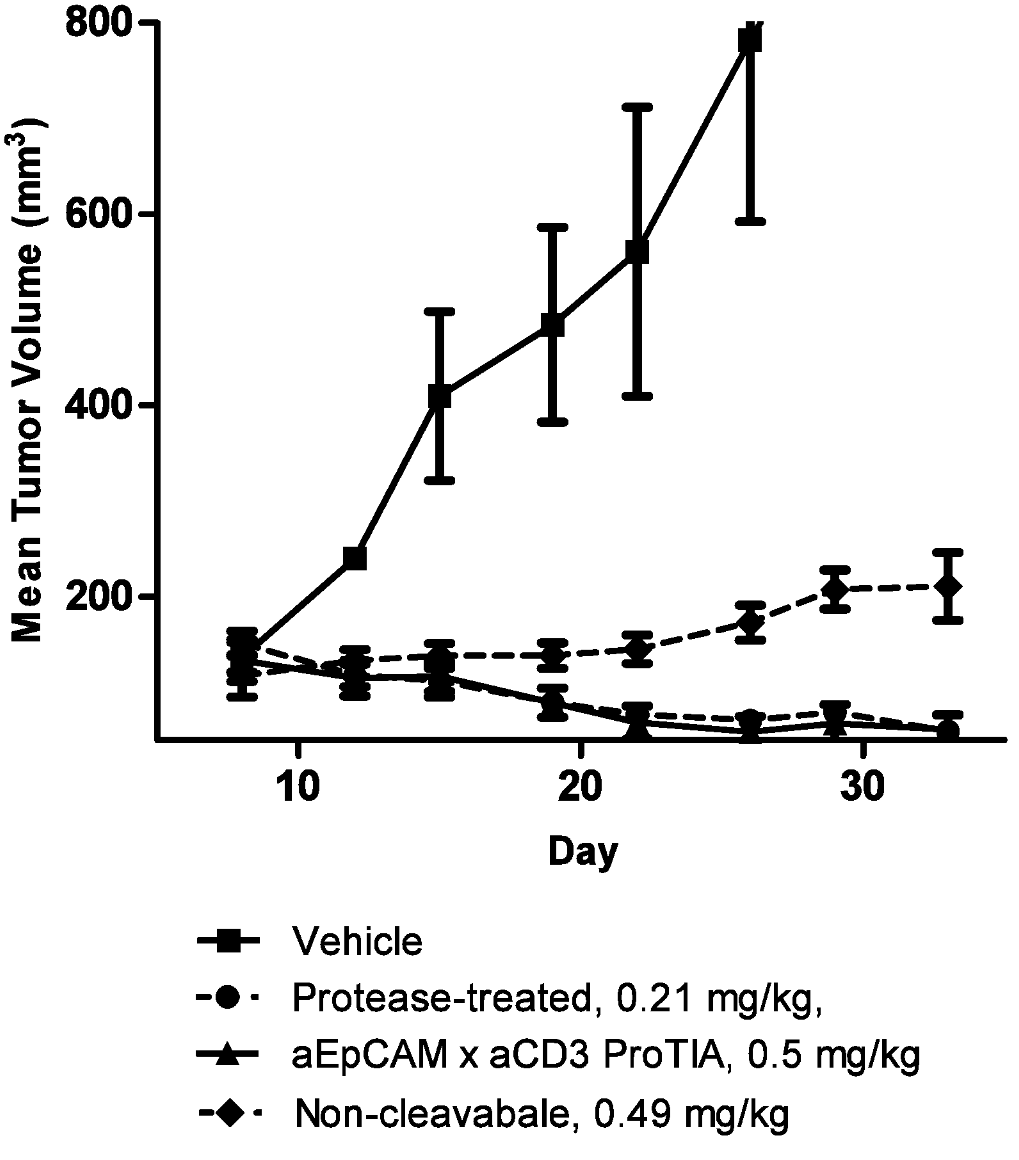
FIG. 55 depicts SW480 tumor volume results from the experiment to determine the antitumor effect of antiEpCAM x antiCD3 ProTIA, protease treated antiEpCAM x antiCD3 ProTIA and noncleavable antiEpCAM x antiCD3 ProTIA, as described in Example 18.

As shown in FIG. 55, protease-treated anti-EpCAM x anti-CD3 ProTIA at 0.21 mg/kg (cohort 2), intact anti-EpCAM x anti-CD3 ProTIA at 0.5 mg/kg (cohort 3) and non-cleavable anti-EpCAM x anti-CD3 ProTIA at 0.49 mg/kg (cohort 4) are all determined to be therapeutically active with a tumor growth inhibition index (% TGI) of 93%, 95% and 80% respectively. Thus, dosed at equimolar, intact anti-EpCAM x anti-CD3 ProTIA is effectively cleaved by tumor-enriched proteases to the highly active released anti-EpCAM x anti-CD3 (not linked to the XTEN moiety) to display equivalent tumor regression efficacy as protease-treated anti-EpCAM x anti-CD3 ProTIA. As expected, though efficacious in inhibiting tumor progression, the non-cleavable anti-EpCAM x anti-CD3 ProTIA is less effective than intact anti-EpCAM x anti-CD3 ProTIA indicating that the presence of the release segment improved therapeutic efficacy of the composition by permitting the release of the anti-EpCAM x anti-CD3 binding domains.

Figure 56:
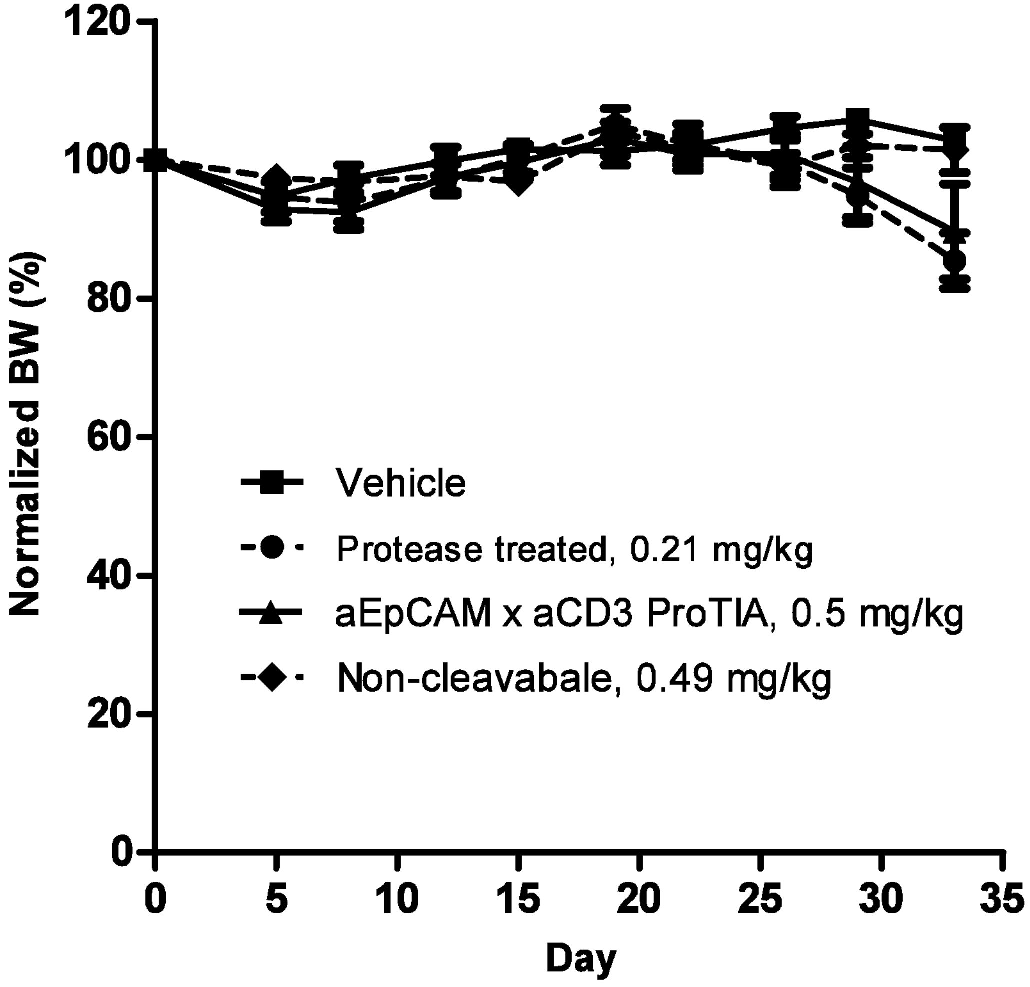
FIG. 56 depicts body weight results from the experiment to determine the antiSW480 tumor effect of antiEpCAM x antiCD3 ProTIA, protease-treated antiEpCAM x antiCD3 ProTIA and noncleavable antiEpCAM x antiCD3 ProTIA, as described in Example 18.

As shown in FIG. 56, some body weight loss was observed in cohort 2 and 3 in the SW480 xenograft model, suggesting some possible toxicity. Additional experiments evaluating minimum effective dose, reduced number of dosing and evaluation in established tumor model will shed more light on this initial observation.

Example 19: Anti-Tumor Properties of Anti-EpCAM x Anti-CD3 Protease Triggered Immune Activator (ProTIA) Composition in OVCAR-3 Ovarian Model The in vivo efficacy of anti-EpCAM x anti-CD3 ProTIA is also evaluated using the human ovarian OVCAR-3 cell line implanted intraperitoneally into the severely immunodeficient NSG (NOD.Cg-Prkdc$^{scid}$.IL2rg$^{tm1Wjl}$/SzJ) or NOG (NOD/Shi-scid/IL-2Rγ$^{null}$) mice. NOG and NSG mice are characterized by the deficiency of T, B and NK cells, as well as the dysfunction of macrophages, dendritic cell and complement system. Briefly, on day 0, seven cohorts of 5 NOG or NSG mice per group are implanted intraperitoneally with 5-10×10$^6$ OVCAR-3 cells, followed by the intravenous introduction of 5-10×10$^6$ of PBMC on day 14. On day 16, treatment is initiated with cohort 1 injected with vehicle (PBS+0.05% Tween 80) daily for 5 doses (qdx5), cohort 2 with 0.21 mg/kg protease-treated anti-EpCAM x anti-CD3 ProTIA qdx5, cohort 3 with 1.05 mg/kg protease-treated anti-EpCAM x anti-CD3 ProTIA once per week (qw), cohort 4 with 0.5 mg/kg with protease-untreated anti-EpCAM x anti-CD3 ProTIA qdx5, cohort 5 with 2.5 mg/kg with protease-untreated anti-EpCAM x anti-CD3 ProTIA qw, cohort 6 with 0.49 mg/kg non-cleavable anti-EpCAM x anti-CD3 ProTIA qdx5 and cohort 7 with 2.45 mg/kg non-cleavable anti-EpCAM x anti-CD3 ProTIA qw. All cohorts are subjected to another cycle of treatment the following week. Mice are monitored daily for behavior and survival, and twice weekly for body weight and abdomen distention. Blood are collected on day 30, day 40, day 50 and day 60 for CA125 determination as sign of tumor development. When weight of animals has increased by 30% from day 0, the animal is defined as having met study endpoint and is sacrificed and autopsied.

Growth of OVCAR-3 tumor is evidenced by the development of intraperitoneal ascites as monitored by increase in body weight, increase in abdomen diameter and an increase in circulating CA125 levels. It is expected that both protease-cleaved and protease-untreated anti-EpCAM x anti-CD3 ProTIA (e.g. AC1476) will lead to improve survival and an absence or delay of ascites formation. It is also expected that the protease-untreated ProTIA will have a better therapeutic exposure leading to a more efficacious anti-tumor effect and better safety profile than protease-treated ProTIA. The non-cleavable anti-EpCAM x anti-CD3 ProTIA is also expected to retard tumor growth but to a much lesser extent than that demonstrated by the release segment bearing protease-untreated and the protease-treated ProTIA.

Example 20: PK Properties of Anti-EpCAM x Anti-CD3 Protease Triggered Immune Activator (ProTIA) Composition in OVCAR-3 Ovarian Model Protease-cleaved, protease-untreated and non-cleavable anti-EpCAM x anti-CD3 ProTIAs' PK and bio-distribution profile is evaluated as a mixture of independently metal-labeled molecules in the OVCAR-3 tumor bearing BALB/c nude mice. To each irradiated BALB/c nude mice, ten million OVCAR-3 cells are injected intraperitoneally on day 0. Treatment is initiated when abdominal distention is visibly observed and/or when animal body weight has increased by 10$^{-15}$% over day 0. Out of twenty OVCAR-3 tumor bearing mice, 18 are selected and randomized according to their individual body weight into 2 groups of 9 animals per group. One group of 9 mice is intravenously injected with 1.5 mg/kg of the mixture comprising of equimolar concentration of metal 1-labeled protease-cleaved anti-EpCAM x anti-CD3 ProTIA, metal 2-labeled protease-untreated anti-EpCAM x anti-CD3 ProTIA and metal 3-labeled non-cleavable anti-EpCAM x anti-CD3 ProTIA. The other group of 9 animals is administered intraperitoneally with 1.5 mg/kg of the same ProTIA mixture.

By alternating between animals in the same group (i.e. intravenously and intraperitoneal administered groups), blood is collected by jugular/mandibular vein puncture into lithium heparin tubes at 0.5 h, 4 h, 8 h, 24 h, 48 h, day 3, day 5 and day 7 post-test article administration. Blood is processed into plasma by centrifugation at 1300 g for 10 minutes at 4° C. and stored at −80° C. till analysis.

Ascites is collected from both intravenously and intraperitoneal administered groups at 4 h, 8 h, 24 h, 48 h, day 3, day 5 and day 7 post-test article administrations by alternating between animals in the same group. Ascites samples are immediately centrifuged at 300 g for 10 minutes at 4° C. and fluid component frozen down at −80° C. until analysis.

Three mice from each group will be terminated on day 3, day 5 and day 7. Organs (brain, heart, liver, lung, spleen, and pancreas) and tumor nodules in the peritoneal cavity are harvested, weighed, flash frozen and stored at −80° C. until analysis is performed.

All samples (blood, ascites, normal organs and tumor tissues) are analyzed by ICP-MS (inductively coupled plasma mass spectrometry). In the intravenous arm, low amount of all 3 ProTIAs are expected to be detected in the ascites. In the plasma component, metal 2-labeled protease-untreated anti-EpCAM x anti-CD3 ProTIA and metal 3-labeled non-cleavable anti-EpCAM x anti-CD3 ProTIA are expected to demonstrate a longer systemic half-life than metal 1-labeled protease-cleaved anti-EpCAM x anti-CD3 ProTIA. In the intraperitoneal arm, all 3 ProTIA versions are expected to be detectable in the ascites with metal 2-labeled protease-untreated anti-EpCAM x anti-CD3 ProTIA and metal 3-labeled non-cleavable anti-EpCAM x anti-CD3 ProTIA having a longer retention time in the peritoneal cavity as compared to metal 1-labeled protease-cleaved anti-EpCAM x anti-CD3 ProTIA. It is also expected that metal 2-labeled protease-untreated anti-EpCAM x anti-CD3 ProTIA will have a shorter intraperitoneal half-life than metal 3-labeled non-cleavable anti-EpCAM x anti-CD3 ProTIA due to cleavage by proteases found in the tumor-loaded intraperitoneal environment. Metal 2-labeled protease-untreated anti-EpCAM x anti-CD3 ProTIA and metal 3-labeled non-cleavable anti-EpCAM x anti-CD3 ProTIA will be minimally detected in plasma at early time points indicating little leakage of intraperitoneally administered molecules into systemic circulation. All 3 ProTIA versions are expected to be present in tumor nodules extracted from the peritoneal cavity but not in normal organs.

Example 21: Anti-Tumor Properties of Anti-EpCAM x Anti-CD3 Protease Triggered Immune Activator (ProTIA) Composition in SK-OV-3 Ovarian Model The in vivo efficacy of anti-EpCAM x anti-CD3 ProTIA is also evaluated using the human ovarian SK-OV-3 cell line implanted intraperitoneally into the severely immunodeficient NSG (NOD.Cg-Prkdc$^{scid}$.IL2rg$^{tm1Wjl}$/SzJ) or NOG (NOD/Shi-scid/IL-2Rγ$^{null}$) mice. NOG and NSG mice are characterized by the deficiency of T, B and NK cells, as well as the dysfunction of macrophages, dendritic cell and complement system. Briefly, on day 0, seven cohorts of 5 NOG or NSG mice per group are implanted intraperitoneally with 5-10×10 6 SK-OV-3 cells, followed by the intraperitoneal introduction of 5-10×10 6 of PBMC on day 5. On day 7, treatment is initiated with cohort 1 injected with vehicle (PBS+0.05% Tween 80) daily for 5 doses (qdx5), cohort 2 with 0.21 mg/kg protease-treated anti-EpCAM x anti-CD3 ProTIA qdx5, cohort 3 with 1.05 mg/kg protease-treated anti-EpCAM x anti-CD3 ProTIA once per week (qw), cohort 4 with 0.5 mg/kg with protease-untreated anti-EpCAM x anti-CD3 ProTIA qdx5, cohort 5 with 2.5 mg/kg with protease-untreated anti-EpCAM x anti-CD3 ProTIA qw, cohort 6 with 0.49 mg/kg non-cleavable anti-EpCAM x anti-CD3 ProTIA qdx5 and cohort 7 with 2.45 mg/kg non-cleavable anti-EpCAM x anti-CD3 ProTIA qw. Mice are monitored daily for behavior and survival, and twice weekly for body weight and abdomen distention. When weight of animals has increased by 30% from day 0, animal is defined as having met study endpoint and are sacrificed and autopsied.

Growth of SK-OV-3 is evidenced by the development of intraperitoneally ascites monitored by increase in body weight and increase in abdomen diameter. It is expected that both protease-cleaved and protease-untreated anti-EpCAM x anti-CD3 ProTIA (e.g. AC1476) will lead to improve survival and absence or delay of ascites formation. It is also expected that the protease-untreated ProTIA will impart better therapeutic exposure, a more efficacious anti-tumor effect and better safety profile than protease-treated ProTIA. The non-cleavable anti-EpCAM x anti-CD3 ProTIA is also expected to retard tumor growth but to a much lesser magnitude than that exhibited by the release segment bearing protease-untreated ProTIA and the protease-treated ProTIA.

Example 22: Performance of Anti-EpCAM x Anti-CD3 Protease Triggered Immune Activator (ProTIA) Composition in Human Malignant Ascites Samples Human malignant ascites are collected from patients with primary intraperitoneal EpCAM positive epithelial malignancies which includes but not limited to advanced, relapsed and refractory ovarian (adenocarcinoma and mucinous), colorectal, gastric, bile duct/cholangiocarcinoma, Ampulla of Vater, pancreatic and non-clear renal cell carcinoma patients. Patients who are receiving chemotherapy, immunological therapy, biologics and/or corticosteroid therapy within the last 30 days prior to sample collection are excluded. Malignant ascites are centrifuged at 300-400 g for 10 min at room temperature and the fluid and pellet component harvested. The concentration of human proteases including but not limited to MMP-9, MMP-2, matriptase and uPA are quantitated in the fluid component using commercially available ELISA kits (human MMP-9, Invitrogen cat #KHC3061 or equivalent; human MMP-2, Invitrogen cat #KHC3081 or equivalent; human matriptase, Enzo cat #ADI-900-221; and human uPA, Abcam cat #119611) following manufacturer's instructions. The rate of intact anti-EpCAM x anti-CD3 (e.g. AC1476) cleavage by protease found in the ascites fluid is determined by spiking a known concentration of the ProTIA into the ascites fluid component and incubating mixture at 37° C., with an aliquot withdrawn at indicated time points of 0.5 h, 2 h, 4 h, 8 h, 24 h, 48 h, 3 day, 4 day, 5 day and 7 day. The amount of intact anti-EpCAM x anti-CD3 ProTIA present at the respective time points are then analyzed on a rhEpCAM/biotinylated-anti-XTEN sandwich ELISA with intact anti-EpCAM x anti-CD3 as standard.

Briefly, ELISA plate (Nunc Maxisorp cat #442404) is coated with 0.1 mircog/100 microL per well of rhEpCAM (R&D Systems, cat #EHH104111). After overnight incubation at 4° C., the ELISA plate is washed and blocked with 3% BSA for 1 h at room temperature. The plate is washed again followed by the appropriate addition of a dose range of intact, protease-untreated anti-EpCAM x anti-CD3 ProTIA standards, appropriate quality controls and ProTIA-spiked ascites test samples. The plate is allowed to incubate with shaking for 1 h at room temperature to allow the ProTIA standards, quality controls and test samples to bind to rhEpCAM coated on the plate. Unbound components are removed with several washes. Biotinylated anti-XTEN antibody (Amunix proprietary antibody) is added at 0.1 microg/100 microL and the plate allowed to incubate at room temperature for 1 h. After washing away unbound biotinylated reagent, streptavidin-HRP (ThermoFisher Scientific cat #21130) is added at 1:30,000 dilution and plate incubated at room temperature for 1 h. After several washes, TMB substrate is added to each well. Once desired color intensity is reached, 0.2 N sulfuric acid is added to stop the reaction and absorbance (OD) is measured at 450 nm using a spectrophotometer. The intensity of the color is proportional to the concentration of intact ProTIA captured by the rhEpCAM/biotinylated-anti-XTEN sandwich ELISA. The concentration of intact ProTIA present in the ascites test samples is determined against the intact ProTIA standard curve using the SoftMax Pro software. The rate of decrease of intact ProTIA as detected in the rhEpCAM/biotinylated-anti-XTEN sandwich ELISA (i.e. half-life) is determined using GraphPad Prism.

The ascites pellet is phenotyped for EpCAM, CD3, CD4, CD8, CA125 and CD56 expression. Malignant ascites samples tested positive for EpCAM and CD3 are used for cytotoxic analysis with protease-treated and protease-untreated ProTIA. Briefly, $1\times10^5$ ascites cells are reconstituted with appropriate amount of ascites fluid and allowed to adhere on a 24-well plate for 24 h in triplicate. Cells are treated with dose concentrations of protease-treated and intact anti-EpCAM x anti-CD3 ProTIA for 48 h, followed by quantitation of caspase 3/7 using a luminogenic caspase 3/7 substrate as instructed by manufacturer (Promega Caspase-Glo 3/7 cat #G8091). With luminescence signal being proportional to caspase-3/7 activity, dose concentration of protease-treated and untreated anti-EpCAM x anti-CD3 ProTIA is then plotted against luminescence signal and the concentration of protein that give half maximal response ($EC_{50}$) is derived with a 4-parameter logistic regression equation using GraphPad prism software. It is expected that the human malignant ascites derived from advanced, relapsed and refractory EpCAM positive cancer patients will contain all necessary components for the cleavage and subsequent activation of intact anti-EpCAM x anti-CD3 ProTIA to the unXTENylated anti-EpCAM x anti-CD3 moiety that exert strong cytotoxic activity. A decrease in number of EpCAM positive cells as a sign of tumor elimination; and an increase in T cell activation markers such as CD69 and granzymes as reflective of T cell activation are also expected,

Example 23: Caspase 3/7 Assay of Anti-EpCAM x Anti-CD3 Protease Triggered Immune Activator (ProTIA) Composition Redirected cellular cytotoxicity of anti-EpCAM x anti-CD3 ProTIA compositions was also assessed via caspase 3/7 activities of apoptotic cells. Similar to the LDH cytotoxicity assay described above, PBMC or purified CD3 positive T cells were mixed with EpCAM positive tumor target cells such as SW480, SK-OV-3 and OVAR-3 cells in a ratio of 5 effectors to 1 target, HCT-116 at a ratio of 10:1; and all three ProTIA versions were tested as a 12-point, 5× serial dilution dose concentrations as in the LDH assay described above.

Upon cell lysis, released caspase 3/7 in culture supernatants was measured by the amount of luminogenic caspase 3/7 substrate cleavage by caspase 3/7 to generate the "glow-type" luminescent signal (Promega Caspase-Glo 3/7 cat #G8091). The amount of luminescence is proportional to the amount of caspase activities.

Figure 57:
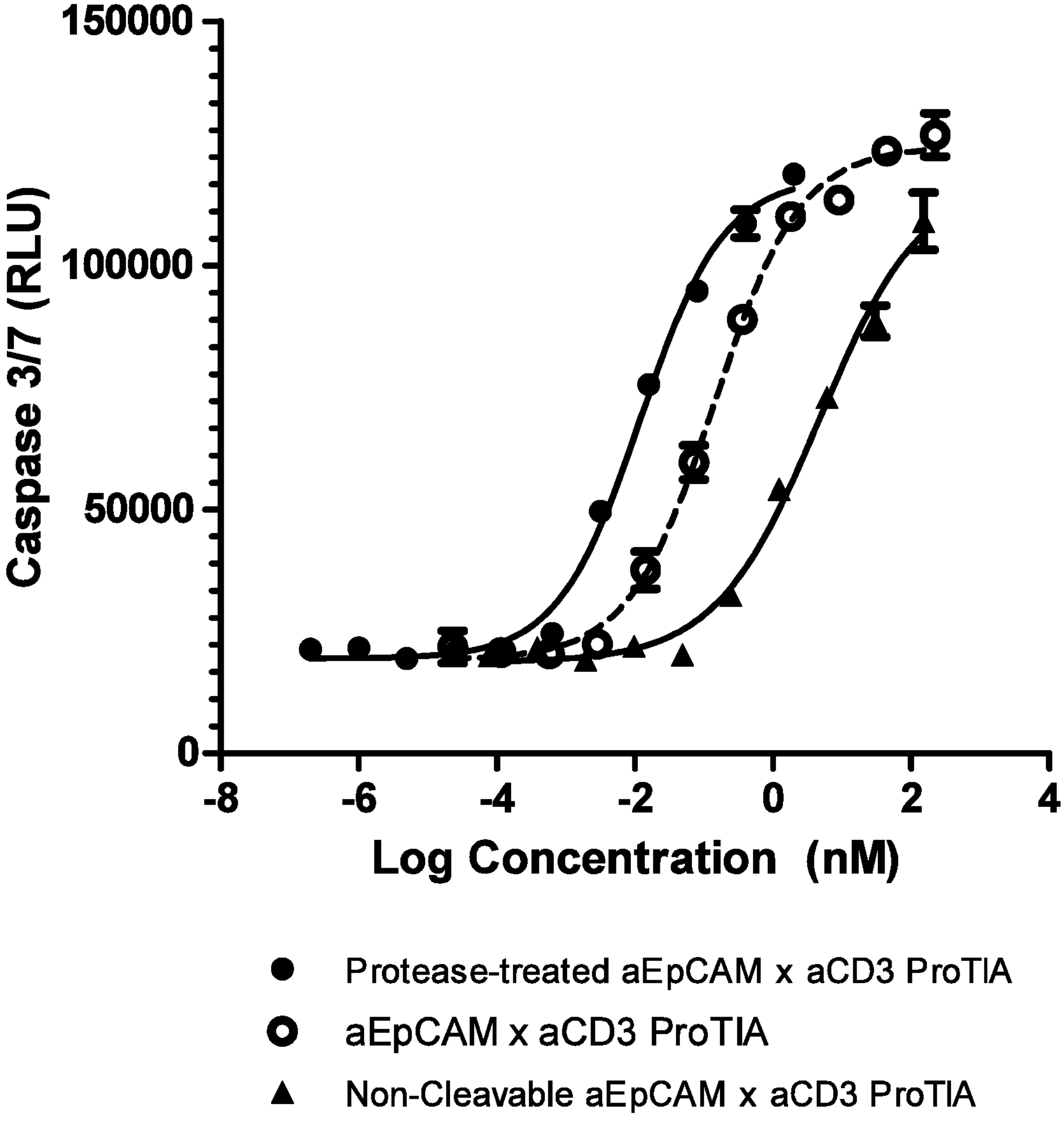
FIG. 57 depicts results from the experiment to determine the in vitro activity of protease-treated, protease-untreated and protease-noncleavable antiEpCAM x antiCD3 ProTIA in SKOV3 with human PBMC as described in Example 23.
Figure 58:
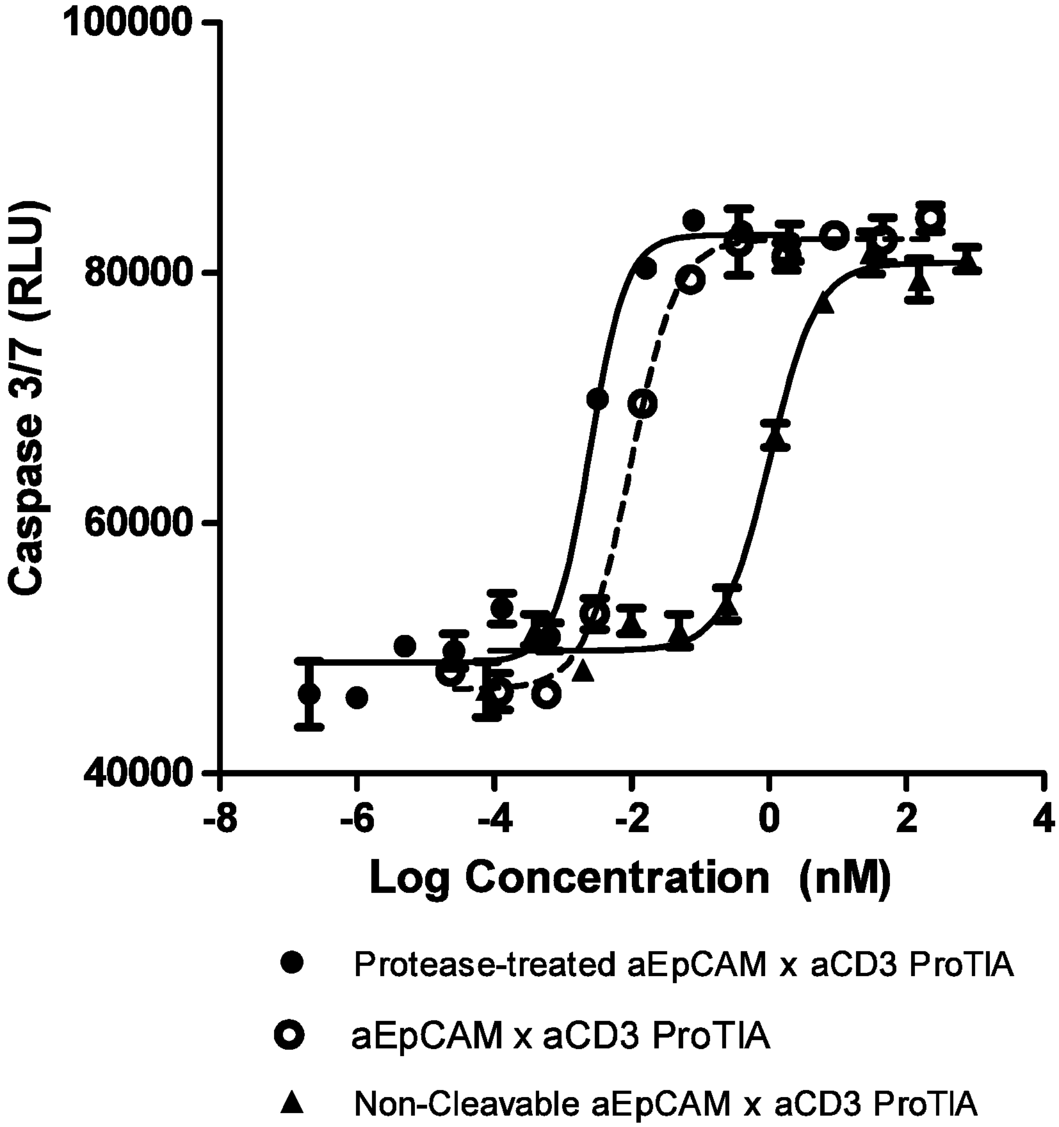
FIG. 58 depicts results from the experiment to determine the in vitro activity of protease-treated, protease-untreated and protease-noncleavable antiEpCAM x antiCD3 ProTIA in OVCAR3 with human PBMC as described in Example 23.
Figure 59:
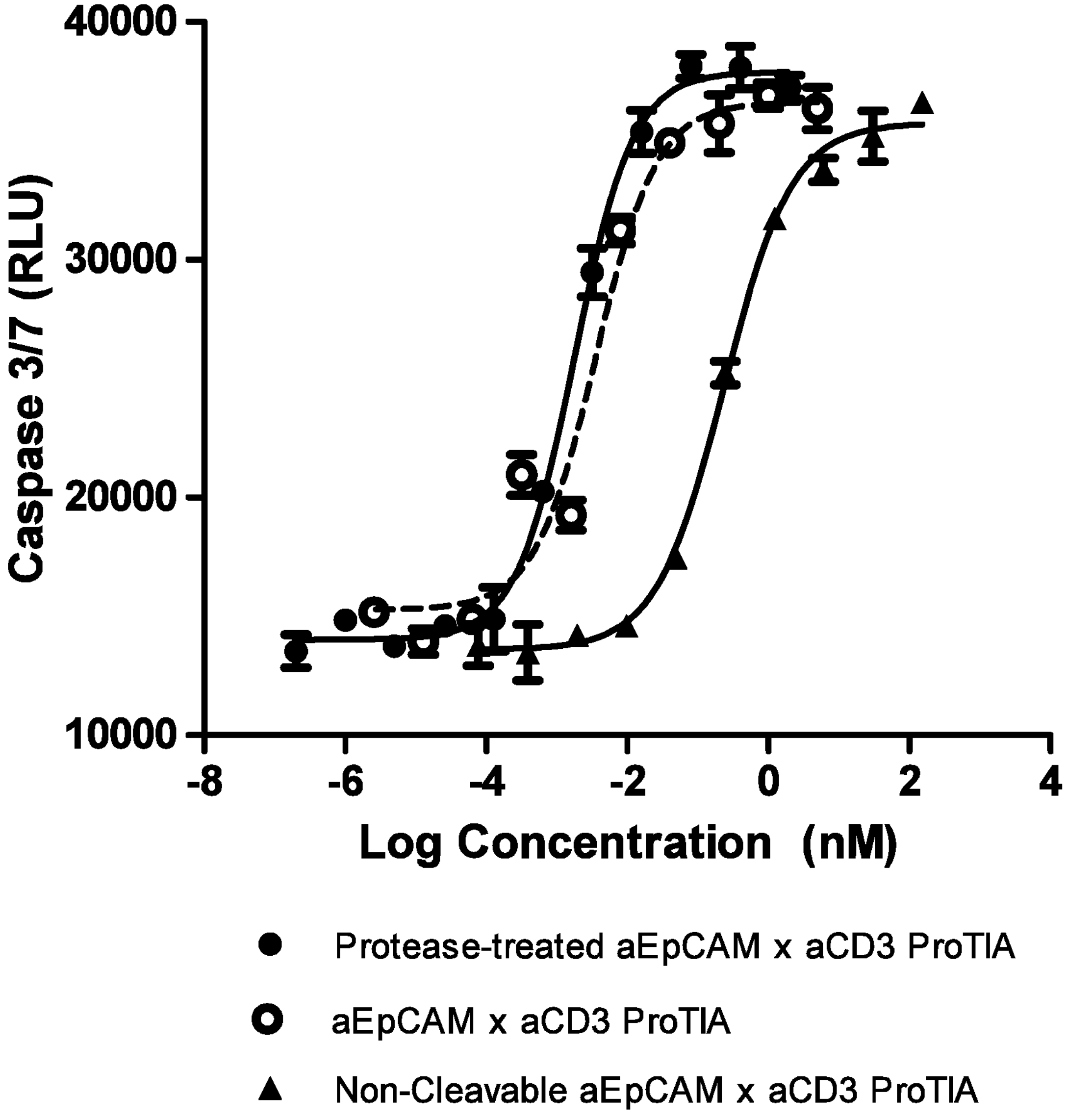
FIG. 59 depicts results from the experiment to determine the in vitro activity of protease-treated, protease-untreated and protease-noncleavable antiEpCAM x antiCD3 ProTIA in HCT116 with human PBMC as described in Example 23.
Figure 60:
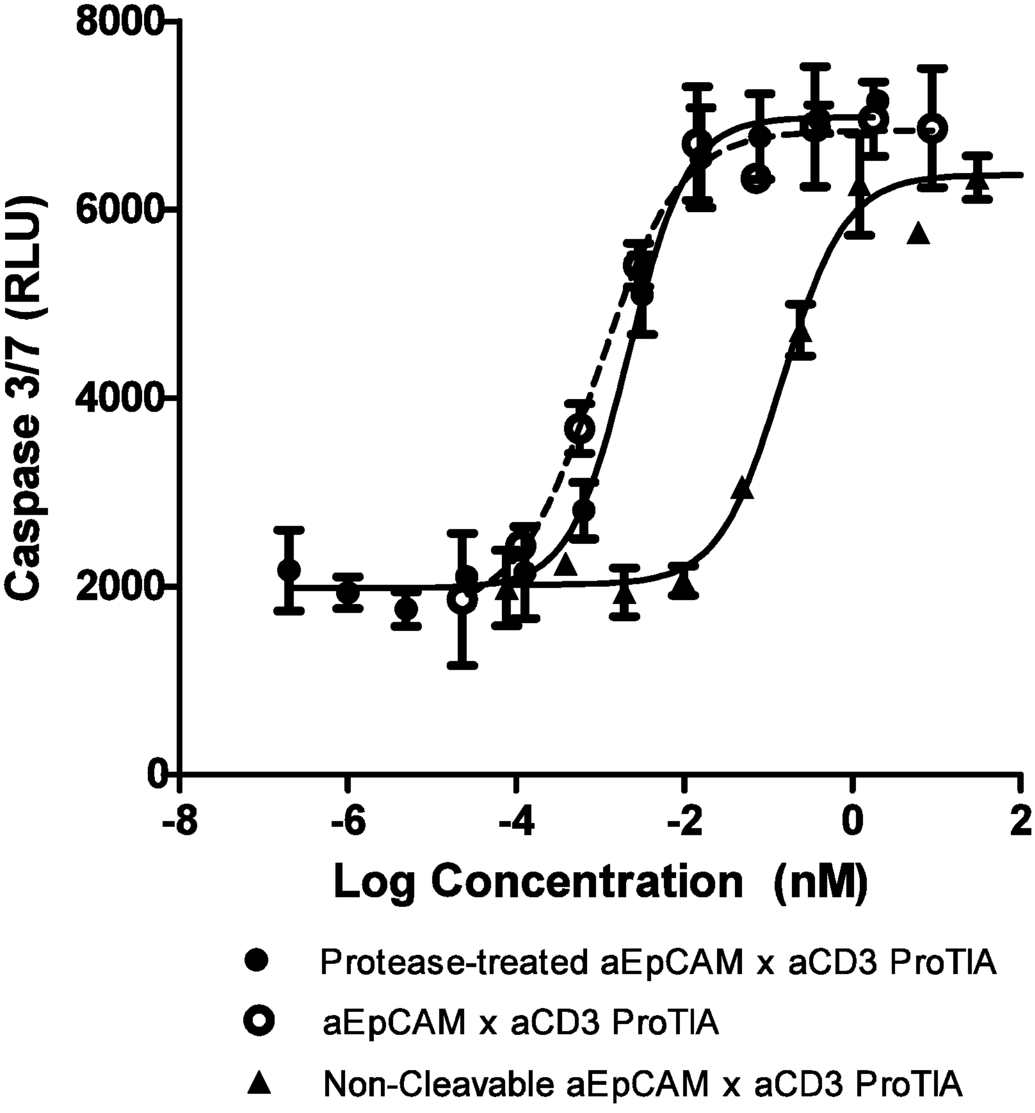
FIG. 60 depicts results from the experiment to determine the in vitro activity of protease-treated, protease-untreated and protease-noncleavable antiEpCAM x antiCD3 ProTIA in SW480 with human PBMC as described in Example 23.

As expected, the activity trend of the protease-treated, protease-untreated and non-cleavable anti-EpCAM x anti-CD3 ProTIA profiled in SK-OV-3, OVCAR-3, HCT-116 and SW480 tumor cell lines was found to be in agreement with the activities observed in the LDH assay analysis. In the cytotoxic killing of SK-OV-3 ovarian cells by human PBMC, untreated anti-EpCAM x anti-CD3 ProTIA is 12-fold less active than protease-treated ProTIA ($EC_{50}$ of 140 pM vs. 12 pM); and the non-cleavable anti-EpCAM x anti-CD3 ProTIA is 390-fold less active than the protease-cleaved ProTIA ($EC_{50}$ of 4700 pM vs. 12 pM) (FIG. 57). In the cytotoxic killing of OVCAR-3 ovarian cells by PBMC, protease-uncleaved anti-EpCAM x anti-CD3 ProTIA is 4-fold less active than protease-treated ProTIA ($EC_{50}$ of 9.8 pM vs. 2.5 pM); and the non-cleavable anti-EpCAM x anti-CD3 ProTIA is 420-fold less active than the protease-cleaved ProTIA ($EC_{50}$ of 1043 pM vs. 2.5 pM) (FIG. 58). In the cytotoxic killing of HCT-116 colorectal cells by PBMC, protease-treated and intact protease-untreated anti-EpCAM x anti-CD3 ProTIA have almost similar activity ($EC_{50}$ of 1.8 pM vs. 3.6 pM); and the non-cleavable anti-EpCAM x anti-CD3 ProTIA is 130-fold less active than the protease-cleaved ProTIA ($EC_{50}$ of 240 pM vs. 1.8 pM) (FIG. 59). In the cytotoxic killing of SW480 colorectal cells by PBMC, protease-treated and protease-uncleaved anti-EpCAM x anti-CD3 ProTIA also demonstrated similar activity ($EC_{50}$ of 2 pM vs. 1 pM); and the non-cleavable anti-EpCAM x anti-CD3 ProTIA is 70-fold less active than the protease-cleaved ProTIA ($EC_{50}$ of 148 pM vs. 2 pM) (FIG. 60). Results demonstrated that non-cleavable ProTIA is consistently less active than the unXTENylated anti-EpCAM x anti-CD3 moiety. Depending on cell lines used, the activity of intact, protease-untreated ProTIA ranged from similar to 12-fold less active as compared to protease-cleaved ProTIA, suggesting a difference in degree of susceptibility of the release segment to proteases postulated to be released from the tumor cells and/or activated CD3 positive T cells in the assay mixture.

Example 24: Proteolytic Cleavage of AC1476 aEpCAM-aCD3-BSRS1-XTEN_AE864-his(6) Using Various Proteases ("his(6)" Disclosed as SEQ ID NO: 483)

The experiment was conducted to demonstrate that the aEpCAM-aCD3-BSRS1-XTEN_AE864-His(6) AC1476 ("His(6)" disclosed as SEQ ID NO: 483), previously described in Example 3, can be cleaved in vitro by multiple tumor-associated proteases, including MMP-2, MMP-9, and neutrophil elastase.

1. Enzyme Activation

All enzymes used were obtained from R&D Systems. Recombinant neutrophil elastase and recombinant human matriptase were provided as activated enzymes and stored at −80° C. until use. Recombinant mouse MMP-2 and recombinant mouse MMP-9 were supplied as zymogens and required activation by 4-aminophenylmercuric acetate (APMA). APMA was first dissolved in 0.1M NaOH to a final concentration of 10 mM before the pH was readjusted to neutral using 0.1N HCl. Further dilution of the APMA stock to 2.5 mM was done in 50 mM Tris, 150 mM NaCl, 10 mM $CaCl_2$, pH 7.5. To activate pro-MMP, 1 mM APMA and 100 μg/mL of pro-MMP were incubated at 37° C. for 1 hour (MMP-2) or 3 hours (MMP-9). Glycerol was added to activated enzymes to a final concentration of 50% and then each was stored at −20° C.

2. Enzymatic Digestion

A panel of enzymes was used to digest the AC1476 aEpCAM-aCD3-BSRS1-XTEN_AE864-His(6) ProTIA ("His(6)" disclosed as SEQ ID NO: 483) composition. 10 μM of the substrate composition was incubated individually with each enzyme in the following enzyme-to-substrate molar ratios: MMP-2 (1:200), MMP-9 (1:2000), matriptase (1:12.5), and neutrophil elastase (1:1000). Reactions were incubated at 37° C. for two hours before stopping digestion by gel loading dye and heating at 80° C.

3. Analysis of Cleavage.

Analysis of the samples was performed by loading 5 μg of undigested and digested material on SDS-PAGE and staining with Coomassie Blue. Upon treatment by each protease at the BSRS-1 release segment, the substrate yielded two fragments detectable in the SDS-PAGE gel, with the small fragment containing aEpCAM-aCD3 (the activated first portion form with the binding domains) and the other containing released XTEN bulking moiety, which migrates at a slightly lower apparent molecular weight on SDS-PAGE than the intact form. For neutrophil elastase, which also digests released XTEN, the activated form was observed in the gel as well as other smaller fragments; the latter due to the cleavage of XTEN at various locations along the sequence. The results confirm that all proteases tested cleaved the construct as intended, with the release of the binding domains.

TABLE 12

Chimeric Polypeptide Assembly Sequences

| Construct ID | Tumor Targets | Amino Acid Sequences | SEQ ID NO: |
|---|---|---|---|
| AC1277 | CD19 | HHHHHHHHDIQLTQSPASLAVSLGQRATISCKASQSVDYDGDSYL NWYQQIPGQPPKLLIYDASNLVSGIPPRESGSGSGTDETLNIHPV | 485 |

TABLE 12-continued

Chimeric Polypeptide Assembly Sequences

| Construct ID | Tumor Targets | Amino Acid Sequences | SEQ ID NO: |
|---|---|---|---|
| | | EKVDAATYHCQQSTEDPWTFGGGTKLEIKGGGGSGGGGSGGGGSQVQLQQSGAELVRPGSSVKISCKASGYAFSSYWMNWVKQRPGQGLEWIGQIWPGDGDTNYNGKFKGKATLTADESSSTAYMQLSSLASEDSAVYFCARRETTTVGRYYYAMDYWGQGTTVTVSSGGGGSDIKLQQSGAELARPGASVKMSCKTSGYTFTRYTMHWVKQRPGQGLEWIGYINPSRGYTNYNQKFKDKATLTTDKSSSTAYMQLSSLTSEDSAVYYCARYYDDHYCLDYWGQGTTLTVSSVEGGSGGSGGSGGSGGVDDIQLTQSPAIMSASPGEKVTMTCRASSSVSYMNWYQQKSGTSPKRWIYDTSKVASGVPYRFSGSGSGTSYSLTISSMEAEDAATYYCQQWSSNPLTFGAGTKLELKGTAEAASASGLSGRSDNHSPLGLAGSPGSPAGSPTSTEEGTSESATPESGPGTSTEPSEGSAPGSPAGSPTSTEEGTSTEPSEGSAPGTSTEPSEGSAPGTSESATPESGPGSEPATSGSETPGSEPATSGSETPGSPAGSPTSTEEGTSESATPESGPGTSTEPSEGSAPGTSTEPSEGSAPGSPAGSPTSTEEGTSTEPSEGSAPGTSTEPSEGSAPGTSESATPESGPGTSTEPSEGSAPGTSESATPESGPGSEPATSGSETPGTSTEPSEGSAPGTSTEPSEGSAPGTSESATPESGPGTSESATPESGPGSPAGSPTSTEEGTSESATPESGPGSEPATSGSETPGTSESATPESGPGTSTEPSEGSAPGTSTEPSEGSAPGTSTEPSEGSAPGTSTEPSEGSAPGTSTEPSEGSAPGTSTEPSEGSAPGSPAGSPTSTEEGTSTEPSEGSAPGTSESATPESGPGSEPATSGSETPGTSESATPESGPGSEPATSGSETPGTSESATPESGPGTSTEPSEGSAPGTSESATPESGPGSPAGSPTSTEEGSPAGSPTSTEEGSPAGSPTSTEEGTSESATPESGPGTSTEPSEGSAPGTSESATPESGPGSEPATSGSETPGTSESATPESGPGSEPATSGSETPGTSESATPESGPGTSTEPSEGSAPGSPAGSPTSTEEGTSESATPESGPGSEPATSGSETPGTSESATPESGPGSPAGSPTSTEEGSPAGSPTSTEEGTSTEPSEGSAPGTSESATPESGPGTSESATPESGPGTSESATPESGPGSEPATSGSETPGSEPATSGSETPGSPAGSPTSTEEGTSTEPSEGSAPGTSTEPSEGSAPGSEPATSGSETPGTSESATPESGPGTSTEPSEGSAPG | |
| AC1278 | EpCAM | HHHHHHHHELVMTQSPSSLTVTAGEKVTMSCKSSQSLLNSGNQKNYLTWYQQKPGQPPKLLIYWASTRESGVPDRFTGSGSGTDFTLTISSVQAEDLAVYYCQNDYSYPLTFGAGTKLEIKGGGGSGGGGSGGGGSEVQLLEQSGAELVRPGTSVKISCKASGYAFTNYWLGWVKQRPGHGLEWIGDIFPGSGNIHYNEKFKGKATLTADKSSSTAYMQLSSLTFEDSAVYFCARLRNWDEPMDYWGQGTTVTVSSGGGGSDVQLVQSGAEVKKPGASVKVSCKASGYTFTRYTMHWVRQAPGQGLEWIGYINPSRGYTNYADSVKGRFTITTDKSTSTAYMELSSLRSEDTATYYCARYYDDHYCLDYWGQGTTVTVSSGEGTSTGSGGSGGSGGADDIVLTQSPATLSLSPGERATLSCRASQSVSYMNWYQQKPGKAPKRWIYDTSKVASGVPARFSGSGSGTDYSLTINSLEAEDAATYYCQQWSSNPLTFGGGTKVEIKGTAEAASASGLSGRSDNHSPLGLAGSPGSPAGSPTSTEEGTSESATPESGPGTSTEPSEGSAPGSPAGSPTSTEEGTSTEPSEGSAPGTSTEPSEGSAPGTSESATPESGPGSEPATSGSETPGSEPATSGSETPGSPAGSPTSTEEGTSESATPESGPGTSTEPSEGSAPGTSTEPSEGSAPGSPAGSPTSTEEGTSTEPSEGSAPGTSTEPSEGSAPGTSESATPESGPGTSTEPSEGSAPGTSESATPESGPGSEPATSGSETPGTSTEPSEGSAPGTSTEPSEGSAPGTSESATPESGPGTSESATPESGPGSPAGSPTSTEEGTSESATPESGPGSEPATSGSETPGTSESATPESGPGTSTEPSEGSAPGTSTEPSEGSAPGTSTEPSEGSAPGTSTEPSEGSAPGTSTEPSEGSAPGTSTEPSEGSAPGSPAGSPTSTEEGTSTEPSEGSAPGTSESATPESGPGSEPATSGSETPGTSESATPESGPGSEPATSGSETPGTSESATPESGPGTSTEPSEGSAPGTSESATPESGPGSPAGSPTSTEEGSPAGSPTSTEEGSPAGSPTSTEEGTSESATPESGPGTSTEPSEGSAPGTSESATPESGPGSEPATSGSETPGTSESATPESGPGSEPATSGSETPGTSESATPESGPGTSTEPSEGSAPGSPAGSPTSTEEGTSESATPESGPGSEPATSGSETPGTSESATPESGPGSPAGSPTSTEEGSPAGSPTSTEEGTSTEPSEGSAPGTSESATPESGPGTSESATPESGPGTSESATPESGPGSEPATSGSETPGSEPATSGSETPGSPAGSPTSTEEGTSTEPSEGSAPGTSTEPSEGSAPGSEPATSGSETPGTSESATPESGPGTSTEPSEGSAPG | 486 |
| AC1345 | EpCAM | HHHHHHHHEVQLLEQSGAELVRPGTSVKISCKASGYAFTNYWLGWVKQRPGHGLEWIGDIFPGSGNIHYNEKFKGKATLTADKSSSTAYMQLSSLTFEDSAVYFCARLRNWDEPMDYWGQGTTVTVSSGGGGSDVQLVQSGAEVKKPGASVKVSCKASGYTFTRYTMHWVRQAPGQGLEWIGYINPSRGYTNYADSVKGRFTITTDKSTSTAYMELSSLRSEDTATYYCARYYDDHYCLDYWGQGTTVTVSSGEGTSTGSGGSGGSGGADDIVLTQSPATLSLSPGERATLSCRASQSVSYMNWYQQKPGKAPKRWIYDTSKVASGVPARFSGSGSGTDYSLTINSLEAEDAATYYCQQWSSNPLTFGGGTKVEIKGGGGSELVMTQSPSSLTVTAGEKVTMSCKSSQSLLNSGNQKNYLTWYQQKPGQPPKLLIYWASTRESGVPDRFT | 487 |

TABLE 12-continued

Chimeric Polypeptide Assembly Sequences

| Construct ID | Tumor Targets | Amino Acid Sequences | SEQ ID NO: |
|---|---|---|---|
| | | GSGSGTDFTLTISSVQAEDLAVYYCQNDYSYPLTFGAGTKLEIKG TAEAASASGLSGRSDNHSPLGLAGSPGSPAGSPTSTEEGTSESAT PESGPGTSTEPSEGSAPGSPAGSPTSTEEGTSTEPSEGSAPGTST EPSEGSAPGTSESATPESGPGSEPATSGSETPGSEPATSGSETPG SPAGSPTSTEEGTSESATPESGPGTSTEPSEGSAPGTSTEPSEGS APGSPAGSPTSTEEGTSTEPSEGSAPGTSTEPSEGSAPGTSESAT PESGPGTSTEPSEGSAPGTSESATPESGPGSEPATSGSETPGTST EPSEGSAPGTSTEPSEGSAPGTSESATPESGPGTSESATPESGPG SPAGSPTSTEEGTSESATPESGPGSEPATSGSETPGTSESATPES GPGTSTEPSEGSAPGTSTEPSEGSAPGTSTEPSEGSAPGTSTEPS EGSAPGTSTEPSEGSAPGTSTEPSEGSAPGSPAGSPTSTEEGTST EPSEGSAPGTSESATPESGPGSEPATSGSETPGTSESATPESGPG SEPATSGSETPGTSESATPESGPGTSTEPSEGSAPGTSESATPES GPGSPAGSPTSTEEGSPAGSPTSTEEGSPAGSPTSTEEGTSESAT PESGPGTSTEPSEGSAPGTSESATPESGPGSEPATSGSETPGTSE SATPESGPGSEPATSGSETPGTSESATPESGPGTSTEPSEGSAPG SPAGSPTSTEEGTSESATPESGPGSEPATSGSETPGTSESATPES GPGSPAGSPTSTEEGSPAGSPTSTEEGTSTEPSEGSAPGTSESAT PESGPGTSESATPESGPGTSESATPESGPGSEPATSGSETPGSEP ATSGSETPGSPAGSPTSTEEGTSTEPSEGSAPGTSTEPSEGSAPG SEPATSGSETPGTSESATPESGPGTSTEPSEGSAPG | |
| AC1346 | EpCAM | HHHHHHHHDVQLVQSGAEVKKPGASVKVSCKASGYTFTRYTMHWV RQAPGQGLEWIGYINPSRGYTNYADSVKGRFTITTDKSTSTAYME LSSLRSEDTATYYCARYYDDHYCLDYWGQGTTVTVSSGGSELVMT QSPSSLTVTAGEKVTMSCKSSQSLLNSGNQKNYLTWYQQKPGQPP KLLIYWASTRESGVPDRFTGSGSGTDFTLTISSVQAEDLAVYYCQ NDYSYPLTFGAGTKLEIKGGGGSGGGGSGGGGSEVQLLEQSGAEL VRPGTSVKISCKASGYAFTNYWLGWVKQRPGHGLEWIGDIFPGSG NIHYNEKFKGKATLTADKSSSTAYMQLSSLTFEDSAVYFCARLRN WDEPMDYWGQGTTVTVSSGGGSDIVLTQSPATLSLSPGERATLSC RASQSVSYMNWYQQKPGKAPKRWIYDTSKVASGVPARFSGSGSGT DYSLTINSLEAEDAATYYCQQWSSNPLTFGGGTKVEIKGTAEAAS ASGLSGRSDNHSPLGLAGSPGSPAGSPTSTEEGTSESATPESGPG TSTEPSEGSAPGSPAGSPTSTEEGTSTEPSEGSAPGTSTEPSEGS APGTSESATPESGPGSEPATSGSETPGSEPATSGSETPGSPAGSP TSTEEGTSESATPESGPGTSTEPSEGSAPGTSTEPSEGSAPGSPA GSPTSTEEGTSTEPSEGSAPGTSTEPSEGSAPGTSESATPESGPG TSTEPSEGSAPGTSESATPESGPGSEPATSGSETPGTSTEPSEGS APGTSTEPSEGSAPGTSESATPESGPGTSESATPESGPGSPAGSP TSTEEGTSESATPESGPGSEPATSGSETPGTSESATPESGPGTST EPSEGSAPGTSTEPSEGSAPGTSTEPSEGSAPGTSTEPSEGSAPG TSTEPSEGSAPGTSTEPSEGSAPGSPAGSPTSTEEGTSTEPSEGS APGTSESATPESGPGSEPATSGSETPGTSESATPESGPGSEPATS GSETPGTSESATPESGPGTSTEPSEGSAPGTSESATPESGPGSPA GSPTSTEEGSPAGSPTSTEEGSPAGSPTSTEEGTSESATPESGPG TSTEPSEGSAPGTSESATPESGPGSEPATSGSETPGTSESATPES GPGSEPATSGSETPGTSESATPESGPGTSTEPSEGSAPGSPAGSP TSTEEGTSESATPESGPGSEPATSGSETPGTSESATPESGPGSPA GSPTSTEEGSPAGSPTSTEEGTSTEPSEGSAPGTSESATPESGPG TSESATPESGPGTSESATPESGPGSEPATSGSETPGSEPATSGSE TPGSPAGSPTSTEEGTSTEPSEGSAPGTSTEPSEGSAPGSEPATS GSETPGTSESATPESGPGTSTEPSEGSAPG | 488 |
| AC1357 | EpCAM | HHHHHHHHELVMTQSPSSLTVTAGEKVTMSCKSSQSLLNSGNQKN YLTWYQQKPGQPPKLLIYWASTRESGVPDRFTGSGSGTDFTLTIS SVQAEDLAVYYCQNDYSYPLTFGAGTKLEIKGGGGSGGGGSGGGG SEVQLLEQSGAELVRPGTSVKISCKASGYAFTNYWLGWVKQRPGH GLEWIGDIFPGSGNIHYNEKFKGKATLTADKSSSTAYMQLSSLTF EDSAVYFCARLRNWDEPMDYWGQGTTVTVSSGGGGSDVQLVQSGA EVKKPGASVKVSCKASGYTFTRYTMHWVRQAPGQGLEWIGYINPS RGYTNYADSVKGRFTITTDKSTSTAYMELSSLRSEDTATYYCARY YDDHYCLDYWGQGTTVTVSSGEGTSTGSGGSGGSGGADDIVLTQS PATLSLSPGERATLSCRASQSVSYMNWYQQKPGKAPKRWIYDTSK VASGVPARFSGSGSGTDYSLTINSLEAEDAATYYCQQWSSNPLTF GGGTKVEIKGSPGSPAGSPTSTEEGTSESATPESGPGTSTEPSEG SAPGSPAGSPTSTEEGTSTEPSEGSAPGTSTEPSEGSAPGTSESA TPESGPGSEPATSGSETPGSEPATSGSETPGSPAGSPTSTEEGTS ESATPESGPGTSTEPSEGSAPGTSTEPSEGSAPGSPAGSPTSTEE GTSTEPSEGSAPGTSTEPSEGSAPGTSESATPESGPGTSTEPSEG SAPGTSESATPESGPGSEPATSGSETPGTSTEPSEGSAPGTSTEP SEGSAPGTSESATPESGPGTSESATPESGPGSPAGSPTSTEEGTS ESATPESGPGSEPATSGSETPGTSESATPESGPGTSTEPSEGSAP GTSTEPSEGSAPGTSTEPSEGSAPGTSTEPSEGSAPGTSTEPSEG | 489 |

TABLE 12-continued

Chimeric Polypeptide Assembly Sequences

| Construct ID | Tumor Targets | Amino Acid Sequences | SEQ ID NO: |
|---|---|---|---|
| | | SAPGTSTEPSEGSAPGSPAGSPTSTEEGTSTEPSEGSAPGTSESA<br>TPESGPGSEPATSGSETPGTSESATPESGPGSEPATSGSETPGTS<br>ESATPESGPGTSTEPSEGSAPGTSESATPESGPGSPAGSPTSTEE<br>GSPAGSPTSTEEGSPAGSPTSTEEGTSESATPESGPGTSTEPSEG<br>SAPGTSESATPESGPGSEPATSGSETPGTSESATPESGPGSEPAT<br>SGSETPGTSESATPESGPGTSTEPSEGSAPGSPAGSPTSTEEGTS<br>ESATPESGPGSEPATSGSETPGTSESATPESGPGSPAGSPTSTEE<br>GSPAGSPTSTEEGTSTEPSEGSAPGTSESATPESGPGTSESATPE<br>SGPGTSESATPESGPGSEPATSGSETPGSEPATSGSETPGSPAGS<br>PTSTEEGTSTEPSEGSAPGTSTEPSEGSAPGSEPATSGSETPGTS<br>ESATPESGPGTSTEPSEGSAPG | |
| AC1358 | EpCAM | HHHHHHHHELVMTQSPSSLTVTAGEKVTMSCKSSQSLLNSGNQKN<br>YLTWYQQKPGQPPKLLIYWASTRESGVPDRFTGSGSGTDFTLTIS<br>SVQAEDLAVYYCQNDYSYPLTFGAGTKLEIKGGGGSGGGGSGGGG<br>SEVQLLEQSGAELVRPGTSVKISCKASGYAFTNYWLGWVKQRPGH<br>GLEWIGDIFPGSGNIHYNEKFKGKATLTADKSSSTAYMQLSSLTF<br>EDSAVYFCARLRNWDEPMDYWGQGTTVTVSSGGGGSDIQMTQSPS<br>SLSASVGDRVTITCRASQDIRNYLNWYQQKPGKAPKLLIYYTSRL<br>ESGVPSRFSGSGSGTDYTLTISSLQPEDFATYYCQQGNTLPWTFG<br>QGTKVEIKRTSGPGDGGKGGPGKGPGGEGTKGTGPGGEVQLVESG<br>GGLVQPGGSLRLSCAASGYSFTGYTMNWVRQAPGKGLEWVALINP<br>YKGVSTYNQKFKDRFTISVDKSKNTAYLQMNSLRAEDTAVYYCAR<br>SGYYGDSDWYFDVWGQGTLVTVSSGTAEAASASGLSGRSDNHSPL<br>GLAGSPGSPAGSPTSTEEGTSESATPESGPGTSTEPSEGSAPGSP<br>AGSPTSTEEGTSTEPSEGSAPGTSTEPSEGSAPGTSESATPESGP<br>GSEPATSGSETPGSEPATSGSETPGSPAGSPTSTEEGTSESATPE<br>SGPGTSTEPSEGSAPGTSTEPSEGSAPGSPAGSPTSTEEGTSTEP<br>SEGSAPGTSTEPSEGSAPGTSESATPESGPGTSTEPSEGSAPGTS<br>ESATPESGPGSEPATSGSETPGTSTEPSEGSAPGTSTEPSEGSAP<br>GTSESATPESGPGTSESATPESGPGSPAGSPTSTEEGTSESATPE<br>SGPGSEPATSGSETPGTSESATPESGPGTSTEPSEGSAPGTSTEP<br>SEGSAPGTSTEPSEGSAPGTSTEPSEGSAPGTSTEPSEGSAPGTS<br>TEPSEGSAPGSPAGSPTSTEEGTSTEPSEGSAPGTSESATPESGP<br>GSEPATSGSETPGTSESATPESGPGSEPATSGSETPGTSESATPE<br>SGPGTSTEPSEGSAPGTSESATPESGPGSPAGSPTSTEEGSPAGS<br>PTSTEEGSPAGSPTSTEEGTSESATPESGPGTSTEPSEGSAPGTS<br>ESATPESGPGSEPATSGSETPGTSESATPESGPGSEPATSGSETP<br>GTSESATPESGPGTSTEPSEGSAPGSPAGSPTSTEEGTSESATPE<br>SGPGSEPATSGSETPGTSESATPESGPGSPAGSPTSTEEGSPAGS<br>PTSTEEGTSTEPSEGSAPGTSESATPESGPGTSESATPESGPGTS<br>ESATPESGPGSEPATSGSETPGSEPATSGSETPGSPAGSPTSTEE<br>GTSTEPSEGSAPGTSTEPSEGSAPGSEPATSGSETPGTSESATPE<br>SGPGTSTEPSEGSAPG | 490 |
| AC1359 | EpCAM | HHHHHHHHELVMTQSPSSLTVTAGEKVTMSCKSSQSLLNSGNQKN<br>YLTWYQQKPGQPPKLLIYWASTRESGVPDRFTGSGSGTDFTLTIS<br>SVQAEDLAVYYCQNDYSYPLTFGAGTKLEIKGGGGSGGGGSGGGG<br>SEVQLLEQSGAELVRPGTSVKISCKASGYAFTNYWLGWVKQRPGH<br>GLEWIGDIFPGSGNIHYNEKFKGKATLTADKSSSTAYMQLSSLTF<br>EDSAVYFCARLRNWDEPMDYWGQGTTVTVSSGGGGSEVQLVESGG<br>GLVQPGGSLRLSCAASGYSFTGYTMNWVRQAPGKGLEWVALINPY<br>KGVSTYNQKFKDRFTISVDKSKNTAYLQMNSLRAEDTAVYYCARS<br>GYYGDSDWYFDVWGQGTLVTVSSRTSGPGDGGKGGPGKGPGGEGT<br>KGTGPGGDIQMTQSPSSLSASVGDRVTITCRASQDIRNYLNWYQQ<br>KPGKAPKLLIYYTSRLESGVPSRFSGSGSGTDYTLTISSLQPEDE<br>ATYYCQQGNTLPWTFGQGTKVEIKGTAEAASASGLSGRSDNHSPL<br>GLAGSPGSPAGSPTSTEEGTSESATPESGPGTSTEPSEGSAPGSP<br>AGSPTSTEEGTSTEPSEGSAPGTSTEPSEGSAPGTSESATPESGP<br>GSEPATSGSETPGSEPATSGSETPGSPAGSPTSTEEGTSESATPE<br>SGPGTSTEPSEGSAPGTSTEPSEGSAPGSPAGSPTSTEEGTSTEP<br>SEGSAPGTSTEPSEGSAPGTSESATPESGPGTSTEPSEGSAPGTS<br>ESATPESGPGSEPATSGSETPGTSTEPSEGSAPGTSTEPSEGSAP<br>GTSESATPESGPGTSESATPESGPGSPAGSPTSTEEGTSESATPE<br>SGPGSEPATSGSETPGTSESATPESGPGTSTEPSEGSAPGTSTEP<br>SEGSAPGTSTEPSEGSAPGTSTEPSEGSAPGTSTEPSEGSAPGTS<br>TEPSEGSAPGSPAGSPTSTEEGTSTEPSEGSAPGTSESATPESGP<br>GSEPATSGSETPGTSESATPESGPGSEPATSGSETPGTSESATPE<br>SGPGTSTEPSEGSAPGTSESATPESGPGSPAGSPTSTEEGSPAGS<br>PTSTEEGSPAGSPTSTEEGTSESATPESGPGTSTEPSEGSAPGTS<br>ESATPESGPGSEPATSGSETPGTSESATPESGPGSEPATSGSETP<br>GTSESATPESGPGTSTEPSEGSAPGSPAGSPTSTEEGTSESATPE<br>SGPGSEPATSGSETPGTSESATPESGPGSPAGSPTSTEEGSPAGS<br>PTSTEEGTSTEPSEGSAPGTSESATPESGPGTSESATPESGPGTS | 491 |

TABLE 12-continued

Chimeric Polypeptide Assembly Sequences

| Construct ID | Tumor Targets | Amino Acid Sequences | SEQ ID NO: |
|---|---|---|---|
| | | ESATPESGPGSEPATSGSETPGSEPATSGSETPGSPAGSPTSTEE<br>GTSTEPSEGSAPGTSTEPSEGSAPGSEPATSGSETPGTSESATPE<br>SGPGTSTEPSEGSAPG | |
| AC1409 | EpCAM | HHHHHHHHGTSESATPESGPGSEPATSGSETPGTSESATPESGPG<br>SEPATSGSETPGTSESATPESGPGTSTEPSEGSAPGSPAGSPTST<br>EEGTSESATPESGPGSEPATSGSETPGTSESATPESGPGSPAGSP<br>TSTEEGSPAGSPTSTEEGTSTEPSEGSAPGTSESATPESGPGTSE<br>SATPESGPGTSESATPESGPGSEPATSGSETPGSEPATSGSETPG<br>SPAGSPTSTEEGTSTEPSEGSAPGTSTEPSEGSAPGSEPATSGSE<br>TPGTSESATPESGPGTSTEPSEGSAPGLSGRSDNHSPLGLAGSGT<br>AEAASASGELVMTQSPSSLTVTAGEKVTMSCKSSQSLLNSGNQKN<br>YLTWYQQKPGQPPKLLIYWASTRESGVPDRFTGSGSGTDFTLTIS<br>SVQAEDLAVYYCQNDYSYPLTFGAGTKLEIKGGGGSGGGGSGGGG<br>SEVQLLEQSGAELVRPGTSVKISCKASGYAFTNYWLGWVKQRPGH<br>GLEWIGDIFPGSGNIHYNEKFKGKATLTADKSSSTAYMQLSSLTF<br>EDSAVYFCARLRNWDEPMDYWGQGTTVTVSSGGGGSDVQLVQSGA<br>EVKKPGASVKVSCKASGYTFTRYTMHWVRQAPGQGLEWIGYINPS<br>RGYTNYADSVKGRFTITTDKSTSTAYMELSSLRSEDTATYYCARY<br>YDDHYCLDYWGQGTTVTVSSGEGTSTGSGGSGGSGGADDIVLTQS<br>PATLSLSPGERATLSCRASQSVSYMNWYQQKPGKAPKRWIYDTSK<br>VASGVPARFSGSGSGTDYSLTINSLEAEDAATYYCQQWSSNPLTE<br>GGGTKVEIKGTAEAASASGLSGRSDNHSPLGLAGSPGSPAGSPTS<br>TEEGTSESATPESGPGTSTEPSEGSAPGSPAGSPTSTEEGTSTEP<br>SEGSAPGTSTEPSEGSAPGTSESATPESGPGSEPATSGSETPGSE<br>PATSGSETPGSPAGSPTSTEEGTSESATPESGPGTSTEPSEGSAP<br>GTSTEPSEGSAPGSPAGSPTSTEEGTSTEPSEGSAPGTSTEPSEG<br>SAPGTSESATPESGPGTSTEPSEGSAPGTSESATPESGPGSEPAT<br>SGSETPGTSTEPSEGSAPGTSTEPSEGSAPGTSESATPESGPGTS<br>ESATPESGPGSPAGSPTSTEEGTSESATPESGPGSEPATSGSETP<br>GTSESATPESGPGTSTEPSEGSAPGTSTEPSEGSAPGTSTEPSEG<br>SAPGTSTEPSEGSAPGTSTEPSEGSAPGTSTEPSEGSAPGSPAGS<br>PTSTEEGTSTEPSEGSAPGTSESATPESGPGSEPATSGSETPGTS<br>ESATPESGPGSEPATSGSETPGTSESATPESGPGTSTEPSEGSAP<br>GTSESATPESGPGSPAGSPTSTEEGSPAGSPTSTEEGSPAGSPTS<br>TEEGTSESATPESGPGTSTEPSEGSAPG | 492 |
| AC1410 | EpCAM | GSPGSPAGSPTSTEEGTSESATPESGPGTSTEPSEGSAPGSPAGS<br>PTSTEEGTSTEPSEGSAPGTSTEPSEGSAPGTSESATPESGPGSE<br>PATSGSETPGSEPATSGSETPGSPAGSPTSTEEGTSESATPESGP<br>GTSTEPSEGSAPGTSTEPSEGSAPGSPAGSPTSTEEGTSTEPSEG<br>SAPGTSTEPSEGSAPGTSESATPESGPGTSTEPSEGSAPGTSESA<br>TPESGPGSEPATSGSETPGTSTEPSEGSAPGTSTEPSEGSAPGTS<br>ESATPESGPGTSESATPESGPGSPAGSPTSTEEGTSESATPESGP<br>GSEPATSGSETPGTSESATPESGPGTSTEPSEGSAPGTSTEPSEG<br>SAPGTSTEPSEGSAPGTSTEPSEGSAPGTSTEPSEGSAPGTSTEP<br>SEGSAPGSPAGSPTSTEEGTSTEPSEGSAPGTSESATPESGPGSE<br>PATSGSETPGTSESATPESGPGSEPATSGSETPGTSESATPESGP<br>GTSTEPSEGSAPGTSESATPESGPGSPAGSPTSTEEGSPAGSPTS<br>TEEGSPAGSPTSTEEGTSESATPESGPGTSTEPSEGSAPGTSESA<br>TPESGPGSEPATSGSETPGTSESATPESGPGSEPATSGSETPGTS<br>ESATPESGPGTSTEPSEGSAPGSPAGSPTSTEEGTSESATPESGP<br>GSEPATSGSETPGTSESATPESGPGSPAGSPTSTEEGSPAGSPTS<br>TEEGTSTEPSEGSAPGTSESATPESGPGTSESATPESGPGTSESA<br>TPESGPGSEPATSGSETPGSEPATSGSETPGSPAGSPTSTEEGTS<br>TEPSEGSAPGTSTEPSEGSAPGSEPATSGSETPGTSESATPESGP<br>GTSTEPSEGSAPGLSGRSDNHSPLGLAGSGTAEAASASGELVMTQ<br>SPSSLTVTAGEKVTMSCKSSQSLLNSGNQKNYLTWYQQKPGQPPK<br>LLIYWASTRESGVPDRFTGSGSGTDFTLTISSVQAEDLAVYYCQN<br>DYSYPLTFGAGTKLEIKGGGGSGGGGSGGGGSEVQLLEQSGAELV<br>RPGTSVKISCKASGYAFTNYWLGWVKQRPGHGLEWIGDIFPGSGN<br>IHYNEKFKGKATLTADKSSSTAYMQLSSLTFEDSAVYFCARLRNW<br>DEPMDYWGQGTTVTVSSGGGGSDVQLVQSGAEVKKPGASVKVSCK<br>ASGYTFTRYTMHWVRQAPGQGLEWIGYINPSRGYTNYADSVKGRF<br>TITTDKSTSTAYMELSSLRSEDTATYYCARYYDDHYCLDYWGQGT<br>TVTVSSGEGTSTGSGGSGGSGGADDIVLTQSPATLSLSPGERATL<br>SCRASQSVSYMNWYQQKPGKAPKRWIYDTSKVASGVPARFSGSGS<br>GTDYSLTINSLEAEDAATYYCQQWSSNPLTFGGGTKVEIKHHHHH<br>HHH | 493 |
| AC1411 | EpCAM | HHHHHHHHELVMTQSPSSLTVTAGEKVTMSCKSSQSLLNSGNQKN<br>YLTWYQQKPGQPPKLLIYWASTRESGVPDRFTGSGSGTDFTLTIS<br>SVQAEDLAVYYCQNDYSYPLTFGAGTKLEIKGGGGSGGGGSGGGG<br>SEVQLLEQSGAELVRPGTSVKISCKASGYAFTNYWLGWVKQRPGH | 494 |

TABLE 12-continued

Chimeric Polypeptide Assembly Sequences

| Construct ID | Tumor Targets | Amino Acid Sequences | SEQ ID NO: |
|---|---|---|---|
| | | GLEWIGDIFPGSGNIHYNEKFKGKATLTADKSSSTAYMQLSSLTFEDSAVYFCARLRNWDEPMDYWGQGTTVTVSSGGGGSDIVLTQSPATLSLSPGERATLSCRASQSVSYMNWYQQKPGKAPKRWIYDTSKVASGVPARFSGSGSGTDYSLTINSLEAEDAATYYCQQWSSNPLTEGGGTKVEIKGEGTSTGSGGSGGSGGADDVQLVQSGAEVKKPGASVKVSCKASGYTFTRYTMHWVRQAPGQGLEWIGYINPSRGYTNYADSVKGRFTITTDKSTSTAYMELSSLRSEDTATYYCARYYDDHYCLDYWGQGTTVTVSSGTAEAASASGLSGRSDNHSPLGLAGSPGSPAGSPTSTEEGTSESATPESGPGTSTEPSEGSAPGSPAGSPTSTEEGTSTEPSEGSAPGTSTEPSEGSAPGTSESATPESGPGSEPATSGSETPGSEPATSGSETPGSPAGSPTSTEEGTSESATPESGPGTSTEPSEGSAPGTSTEPSEGSAPGSPAGSPTSTEEGTSTEPSEGSAPGTSTEPSEGSAPGTSESATPESGPGTSTEPSEGSAPGTSESATPESGPGSEPATSGSETPGTSTEPSEGSAPGTSTEPSEGSAPGTSESATPESGPGTSESATPESGPGSPAGSPTSTEEGTSESATPESGPGSEPATSGSETPGTSESATPESGPGTSTEPSEGSAPGTSTEPSEGSAPGTSTEPSEGSAPGTSTEPSEGSAPGTSTEPSEGSAPGTSTEPSEGSAPGSPAGSPTSTEEGTSTEPSEGSAPGTSESATPESGPGSEPATSGSETPGTSESATPESGPGSEPATSGSETPGTSESATPESGPGTSTEPSEGSAPGTSESATPESGPGSPAGSPTSTEEGSPAGSPTSTEEGSPAGSPTSTEEGTSESATPESGPGTSTEPSEGSAPGTSESATPESGPGSEPATSGSETPGTSESATPESGPGSEPATSGSETPGTSESATPESGPGTSTEPSEGSAPGSPAGSPTSTEEGTSESATPESGPGSEPATSGSETPGTSESATPESGPGSPAGSPTSTEEGSPAGSPTSTEEGTSTEPSEGSAPGTSESATPESGPGTSESATPESGPGTSESATPESGPGSEPATSGSETPGSEPATSGSETPGSPAGSPTSTEEGTSTEPSEGSAPGTSTEPSEGSAPGSEPATSGSETPGTSESATPESGPGTSTEPSEGSAPG | |
| AC1412 | EpCAM | HHHHHHHHEVQLLEQSGAELVRPGTSVKISCKASGYAFTNYWLGWVKQRPGHGLEWIGDIFPGSGNIHYNEKFKGKATLTADKSSSTAYMQLSSLTFEDSAVYFCARLRNWDEPMDYWGQGTTVTVSSGGGGSGGGGSGGGGSELVMTQSPSSLTVTAGEKVTMSCKSSQSLLNSGNQKNYLTWYQQKPGQPPKLLIYWASTRESGVPDRFTGSGSGTDFTLTISSVQAEDLAVYYCQNDYSYPLTFGAGTKLEIKGGGGSDVQLVQSGAEVKKPGASVKVSCKASGYTFTRYTMHWVRQAPGQGLEWIGYINPSRGYTNYADSVKGRFTITTDKSTSTAYMELSSLRSEDTATYYCARYYDDHYCLDYWGQGTTVTVSSGEGTSTGSGGSGGSGGADDIVLTQSPATLSLSPGERATLSCRASQSVSYMNWYQQKPGKAPKRWIYDTSKVASGVPARFSGSGSGTDYSLTINSLEAEDAATYYCQQWSSNPLTFGGGTKVEIKGTAEAASASGLSGRSDNHSPLGLAGSPGSPAGSPTSTEEGTSESATPESGPGTSTEPSEGSAPGSPAGSPTSTEEGTSTEPSEGSAPGTSTEPSEGSAPGTSESATPESGPGSEPATSGSETPGSEPATSGSETPGSPAGSPTSTEEGTSESATPESGPGTSTEPSEGSAPGTSTEPSEGSAPGSPAGSPTSTEEGTSTEPSEGSAPGTSTEPSEGSAPGTSESATPESGPGTSTEPSEGSAPGTSESATPESGPGSEPATSGSETPGTSTEPSEGSAPGTSTEPSEGSAPGTSESATPESGPGTSESATPESGPGSPAGSPTSTEEGTSESATPESGPGSEPATSGSETPGTSESATPESGPGTSTEPSEGSAPGTSTEPSEGSAPGTSTEPSEGSAPGTSTEPSEGSAPGTSTEPSEGSAPGTSTEPSEGSAPGSPAGSPTSTEEGTSTEPSEGSAPGTSESATPESGPGSEPATSGSETPGTSESATPESGPGSEPATSGSETPGTSESATPESGPGTSTEPSEGSAPGTSESATPESGPGSPAGSPTSTEEGSPAGSPTSTEEGSPAGSPTSTEEGTSESATPESGPGTSTEPSEGSAPGTSESATPESGPGSEPATSGSETPGTSESATPESGPGSEPATSGSETPGTSESATPESGPGTSTEPSEGSAPGSPAGSPTSTEEGTSESATPESGPGSEPATSGSETPGTSESATPESGPGSPAGSPTSTEEGSPAGSPTSTEEGTSTEPSEGSAPGTSESATPESGPGTSESATPESGPGTSESATPESGPGSEPATSGSETPGSEPATSGSETPGSPAGSPTSTEEGTSTEPSEGSAPGTSTEPSEGSAPGSEPATSGSETPGTSESATPESGPGTSTEPSEGSAPG | 495 |
| AC1413 | EpCAM | HHHHHHHHDVQLVQSGAEVKKPGASVKVSCKASGYTFTRYTMHWVRQAPGQGLEWIGYINPSRGYTNYADSVKGRFTITTDKSTSTAYMELSSLRSEDTATYYCARYYDDHYCLDYWGQGTTVTVSSGEGTSTGSGGSGGSGGADDIVLTQSPATLSLSPGERATLSCRASQSVSYMNWYQQKPGKAPKRWIYDTSKVASGVPARFSGSGSGTDYSLTINSLEAEDAATYYCQQWSSNPLTFGGGTKVEIKGGGGSELVMTQSPSSLTVTAGEKVTMSCKSSQSLLNSGNQKNYLTWYQQKPGQPPKLLIYWASTRESGVPDRFTGSGSGTDFTLTISSVQAEDLAVYYCQNDYSYPLTFGAGTKLEIKGGGGSGGGGSGGGGSEVQLLEQSGAELVRPGTSVKISCKASGYAFTNYWLGWVKQRPGHGLEWIGDIFPGSGNIHYNEKFKGKATLTADKSSSTAYMQLSSLTFEDSAVYFCARLRNWDEPMDYWGQGTTVTVSSGTAEAASASGLSGRSDNHSPLGLAGSPGSPAGSPTS | 496 |

TABLE 12-continued

Chimeric Polypeptide Assembly Sequences

| Construct ID | Tumor Targets | Amino Acid Sequences | SEQ ID NO: |
|---|---|---|---|
| | | TEEGTSESATPESGPGTSTEPSEGSAPGSPAGSPTSTEEGTSTEP<br>SEGSAPGTSTEPSEGSAPGTSESATPESGPGSEPATSGSETPGSE<br>PATSGSETPGSPAGSPTSTEEGTSESATPESGPGTSTEPSEGSAP<br>GTSTEPSEGSAPGSPAGSPTSTEEGTSTEPSEGSAPGTSTEPSEG<br>SAPGTSESATPESGPGTSTEPSEGSAPGTSESATPESGPGSEPAT<br>SGSETPGTSTEPSEGSAPGTSTEPSEGSAPGTSESATPESGPGTS<br>ESATPESGPGSPAGSPTSTEEGTSESATPESGPGSEPATSGSETP<br>GTSESATPESGPGTSTEPSEGSAPGTSTEPSEGSAPGTSTEPSEG<br>SAPGTSTEPSEGSAPGTSTEPSEGSAPGTSTEPSEGSAPGSPAGS<br>PTSTEEGTSTEPSEGSAPGTSESATPESGPGSEPATSGSETPGTS<br>ESATPESGPGSEPATSGSETPGTSESATPESGPGTSTEPSEGSAP<br>GTSESATPESGPGSPAGSPTSTEEGSPAGSPTSTEEGSPAGSPTS<br>TEEGTSESATPESGPGTSTEPSEGSAPGTSESATPESGPGSEPAT<br>SGSETPGTSESATPESGPGSEPATSGSETPGTSESATPESGPGTS<br>TEPSEGSAPGSPAGSPTSTEEGTSESATPESGPGSEPATSGSETP<br>GTSESATPESGPGSPAGSPTSTEEGSPAGSPTSTEEGTSTEPSEG<br>SAPGTSESATPESGPGTSESATPESGPGTSESATPESGPGSEPAT<br>SGSETPGSEPATSGSETPGSPAGSPTSTEEGTSTEPSEGSAPGTS<br>TEPSEGSAPGSEPATSGSETPGTSESATPESGPGTSTEPSEGSAP<br>G | |
| AC1414 | EpCAM | HHHHHHHHDIVLTQSPATLSLSPGERATLSCRASQSVSYMNWYQQ<br>KPGKAPKRWIYDTSKVASGVPARFSGSGSGTDYSLTINSLEAEDA<br>ATYYCQQWSSNPLTFGGGTKVEIKGEGTSTGSGGSGGSGGADDVQ<br>LVQSGAEVKKPGASVKVSCKASGYTFTRYTMHWVRQAPGQGLEWI<br>GYINPSRGYTNYADSVKGRFTITTDKSTSTAYMELSSLRSEDTAT<br>YYCARYYDDHYCLDYWGQGTTVTVSSGGGGSELVMTQSPSSLTVT<br>AGEKVTMSCKSSQSLLNSGNQKNYLTWYQQKPGQPPKLLIYWAST<br>RESGVPDRFTGSGSGTDFTLTISSVQAEDLAVYYCQNDYSYPLTF<br>GAGTKLEIKGGGGSGGGGSGGGGSEVQLLEQSGAELVRPGTSVKI<br>SCKASGYAFTNYWLGWVKQRPGHGLEWIGDIFPGSGNIHYNEKFK<br>GKATLTADKSSSTAYMQLSSLTFEDSAVYFCARLRNWDEPMDYWG<br>QGTTVTVSSGTAEAASASGLSGRSDNHSPLGLAGSPGSPAGSPTS<br>TEEGTSESATPESGPGTSTEPSEGSAPGSPAGSPTSTEEGTSTEP<br>SEGSAPGTSTEPSEGSAPGTSESATPESGPGSEPATSGSETPGSE<br>PATSGSETPGSPAGSPTSTEEGTSESATPESGPGTSTEPSEGSAP<br>GTSTEPSEGSAPGSPAGSPTSTEEGTSTEPSEGSAPGTSTEPSEG<br>SAPGTSESATPESGPGTSTEPSEGSAPGTSESATPESGPGSEPAT<br>SGSETPGTSTEPSEGSAPGTSTEPSEGSAPGTSESATPESGPGTS<br>ESATPESGPGSPAGSPTSTEEGTSESATPESGPGSEPATSGSETP<br>GTSESATPESGPGTSTEPSEGSAPGTSTEPSEGSAPGTSTEPSEG<br>SAPGTSTEPSEGSAPGTSTEPSEGSAPGTSTEPSEGSAPGSPAGS<br>PTSTEEGTSTEPSEGSAPGTSESATPESGPGSEPATSGSETPGTS<br>ESATPESGPGSEPATSGSETPGTSESATPESGPGTSTEPSEGSAP<br>GTSESATPESGPGSPAGSPTSTEEGSPAGSPTSTEEGSPAGSPTS<br>TEEGTSESATPESGPGTSTEPSEGSAPGTSESATPESGPGSEPAT<br>SGSETPGTSESATPESGPGSEPATSGSETPGTSESATPESGPGTS<br>TEPSEGSAPGSPAGSPTSTEEGTSESATPESGPGSEPATSGSETP<br>GTSESATPESGPGSPAGSPTSTEEGSPAGSPTSTEEGTSTEPSEG<br>SAPGTSESATPESGPGTSESATPESGPGTSESATPESGPGSEPAT<br>SGSETPGSEPATSGSETPGSPAGSPTSTEEGTSTEPSEGSAPGTS<br>TEPSEGSAPGSEPATSGSETPGTSESATPESGPGTSTEPSEGSAP<br>G | 497 |
| AC1476 | EpCAM | DIQMTQSPSSLSASVGDRVTITCRSTKSLLHSNGITYLYWYQQKP<br>GKAPKLLIYQMSNLASGVPSRESSSGSGTDFTLTISSLQPEDFAT<br>YYCAQNLEIPRTFGQGTKVEIKGATPPETGAETESPGETTGGSAE<br>SEPPGEGQVQLVQSGPGLVQPGGSVRISCAASGYTFTNYGMNWVK<br>QAPGKGLEWMGWINTYTGESTYADSFKGRFTESLDTSASAAYLQI<br>NSLRAEDTAVYYCARFAIKGDYWGQGTLLTVSSGGGGSDIQMTQS<br>PSSLSASVGDRVTITCRASQDIRNYLNWYQQKPGKAPKLLIYYTS<br>RLESGVPSRESGSGSGTDYTLTISSLQPEDFATYYCQQGNTLPWT<br>FGQGTKVEIKGATPPETGAETESPGETTGGSAESEPPGEGEVQLV<br>ESGGGLVQPGGSLRLSCAASGYSFTGYTMNWVRQAPGKGLEWVAL<br>INPYKGVSTYNQKFKDRFTISVDKSKNTAYLQMNSLRAEDTAVYY<br>CARSGYYGDSDWYFDVWGQGTLVTVSSGTAEAASASGLSGRSDNH<br>SPLGLAGSPGSPAGSPTSTEEGTSESATPESGPGTSTEPSEGSAP<br>GSPAGSPTSTEEGTSTEPSEGSAPGTSTEPSEGSAPGTSESATPE<br>SGPGSEPATSGSETPGSEPATSGSETPGSPAGSPTSTEEGTSESA<br>TPESGPGTSTEPSEGSAPGTSTEPSEGSAPGSPAGSPTSTEEGTS<br>TEPSEGSAPGTSTEPSEGSAPGTSESATPESGPGTSTEPSEGSAP<br>GTSESATPESGPGSEPATSGSETPGTSTEPSEGSAPGTSTEPSEG<br>SAPGTSESATPESGPGTSESATPESGPGSPAGSPTSTEEGTSESA<br>TPESGPGSEPATSGSETPGTSESATPESGPGTSTEPSEGSAPGTS | 498 |

TABLE 12-continued

Chimeric Polypeptide Assembly Sequences

| Construct ID | Tumor Targets | Amino Acid Sequences | SEQ ID NO: |
|---|---|---|---|
| | | TEPSEGSAPGTSTEPSEGSAPGTSTEPSEGSAPGTSTEPSEGSAP GTSTEPSEGSAPGSPAGSPTSTEEGTSTEPSEGSAPGTSESATPE SGPGSEPATSGSETPGTSESATPESGPGSEPATSGSETPGTSESA TPESGPGTSTEPSEGSAPGTSESATPESGPGSPAGSPTSTEEGSP AGSPTSTEEGSPAGSPTSTEEGTSESATPESGPGTSTEPSEGSAP GTSESATPESGPGSEPATSGSETPGTSESATPESGPGSEPATSGS ETPGTSESATPESGPGTSTEPSEGSAPGSPAGSPTSTEEGTSESA TPESGPGSEPATSGSETPGTSESATPESGPGSPAGSPTSTEEGSP AGSPTSTEEGTSTEPSEGSAPGTSESATPESGPGTSESATPESGP GTSESATPESGPGSEPATSGSETPGSEPATSGSETPGSPAGSPTS TEEGTSTEPSEGSAPGTSTEPSEGSAPGSEPATSGSETPGTSESA TPESGPGTSTEPSEGSAPGHHHHHH | |
| AC1484 | EpCAM | DIQMTQSPSSLSASVGDRVTITCRSTKSLLHSNGITYLYWYQQKP GKAPKLLIYQMSNLASGVPSRESSSGSGTDFTLTISSLQPEDFAT YYCAQNLEIPRTFGQGTKVEIKGATPPETGAETESPGETTGGSAE SEPPGEGQVQLVQSGPGLVQPGGSVRISCAASGYTFTNYGMNWVK QAPGKGLEWMGWINTYTGESTYADSFKGRFTFSLDTSASAAYLQI NSLRAEDTAVYYCARFAIKGDYWGQGTLLTVSSGGGGSDIQMTQS PSSLSASVGDRVTITCRASQDIRNYLNWYQQKPGKAPKLLIYYTS RLESGVPSRFSGSGSGTDYTLTISSLQPEDFATYYCQQGNTLPWT FGQGTKVEIKGATPPETGAETESPGETTGGSAESEPPGEGEVQLV ESGGGLVQPGGSLRLSCAASGYSFTGYTMNWVRQAPGKGLEWVAL INPYKGVSTYNQKFKDRFTISVDKSKNTAYLQMNSLRAEDTAVYY CARSGYYGDSDWYFDVWGQGTLVTVSSGSPGSPAGSPTSTEEGTS ESATPESGPGTSTEPSEGSAPGSPAGSPTSTEEGTSTEPSEGSAP GTSTEPSEGSAPGTSESATPESGPGSEPATSGSETPGSEPATSGS ETPGSPAGSPTSTEEGTSESATPESGPGTSTEPSEGSAPGTSTEP SEGSAPGSPAGSPTSTEEGTSTEPSEGSAPGTSTEPSEGSAPGTS ESATPESGPGTSTEPSEGSAPGTSESATPESGPGSEPATSGSETP GTSTEPSEGSAPGTSTEPSEGSAPGTSESATPESGPGTSESATPE SGPGSPAGSPTSTEEGTSESATPESGPGSEPATSGSETPGTSESA TPESGPGTSTEPSEGSAPGTSTEPSEGSAPGTSTEPSEGSAPGTS TEPSEGSAPGTSTEPSEGSAPGTSTEPSEGSAPGSPAGSPTSTEE GTSTEPSEGSAPGTSESATPESGPGSEPATSGSETPGTSESATPE SGPGSEPATSGSETPGTSESATPESGPGTSTEPSEGSAPGTSESA TPESGPGSPAGSPTSTEEGSPAGSPTSTEEGSPAGSPTSTEEGTS ESATPESGPGTSTEPSEGSAPGTSESATPESGPGSEPATSGSETP GTSESATPESGPGSEPATSGSETPGTSESATPESGPGTSTEPSEG SAPGSPAGSPTSTEEGTSESATPESGPGSEPATSGSETPGTSESA TPESGPGSPAGSPTSTEEGSPAGSPTSTEEGTSTEPSEGSAPGTS ESATPESGPGTSESATPESGPGTSESATPESGPGSEPATSGSETP GSEPATSGSETPGSPAGSPTSTEEGTSTEPSEGSAPGTSTEPSEG SAPGSEPATSGSETPGTSESATPESGPGTSTEPSEGSAPGHHHHH H | 499 |
| AC1489 | EpCAM | DIVMTQSPLSLPVTPGEPASISCRSSKNLLHSNGITYLYWYLQKP GQSPQLLIYQMSNLASGVPDRESSSGSGTDFTLKISRVEAEDVGV YYCAQNLEIPRTFGQGTKVEIKGATPPETGAETESPGETTGGSAE SEPPGEGQVQLVQSGPEVKKPGASVKVSCKASGYTFTNYGMNWVR QAPGQGLEWMGWINTYTGEPTYGEDFKGRFAFSLDTSASTAYMEL SSLRSEDTAVYFCARFGNYVDYWGQGSLVTVSSGGGGSELVVTQE PSLTVSPGGTVTLTCRSSTGAVTTSNYANWVQQKPGQAPRGLIGG TNKRAPGTPARFSGSLLGGKAALTLSGVQPEDEAEYYCALWYSNL WVFGGGTKLTVLGATPPETGAETESPGETTGGSAESEPPGEGEVQ LLESGGGLVQPGGSLKLSCAASGFTENTYAMNWVRQAPGKGLEWV ARIRSKYNNYATYYADSVKDRFTISRDDSKNTAYLQMNNLKTEDT AVYYCVRHGNFGNSYVSWFAYWGQGTLVTVSSGTAEAASASGLSG RSDNHSPLGLAGSPGSPAGSPTSTEEGTSESATPESGPGTSTEPS EGSAPGSPAGSPTSTEEGTSTEPSEGSAPGTSTEPSEGSAPGTSE SATPESGPGSEPATSGSETPGSEPATSGSETPGSPAGSPTSTEEG TSESATPESGPGTSTEPSEGSAPGTSTEPSEGSAPGSPAGSPTST EEGTSTEPSEGSAPGTSTEPSEGSAPGTSESATPESGPGTSTEPS EGSAPGTSESATPESGPGSEPATSGSETPGTSTEPSEGSAPGTST EPSEGSAPGTSESATPESGPGTSESATPESGPGSPAGSPTSTEEG TSESATPESGPGSEPATSGSETPGTSESATPESGPGTSTEPSEGS APGTSTEPSEGSAPGTSTEPSEGSAPGTSTEPSEGSAPGTSTEPS EGSAPGTSTEPSEGSAPGSPAGSPTSTEEGTSTEPSEGSAPGTSE SATPESGPGSEPATSGSETPGTSESATPESGPGSEPATSGSETPG TSESATPESGPGTSTEPSEGSAPGTSESATPESGPGSPAGSPTST EEGSPAGSPTSTEEGSPAGSPTSTEEGTSESATPESGPGTSTEPS EGSAPGTSESATPESGPGSEPATSGSETPGTSESATPESGPGSEP ATSGSETPGTSESATPESGPGTSTEPSEGSAPGSPAGSPTSTEEG TSESATPESGPGSEPATSGSETPGTSESATPESGPGSPAGSPTST | 500 |

TABLE 12-continued

Chimeric Polypeptide Assembly Sequences

| Construct ID | Tumor Targets | Amino Acid Sequences | SEQ ID NO: |
| --- | --- | --- | --- |
| | | EEGSPAGSPTSTEEGTSTEPSEGSAPGTSESATPESGPGTSESATPESGPGTSESATPESGPGSEPATSGSETPGSEPATSGSETPGSPAGSPTSTEEGTSTEPSEGSAPGTSTEPSEGSAPGSEPATSGSETPGTSESATPESGPGTSTEPSEGSAPGHHHHHH | |
| AC1490 | EpCAM | DIVMTQSPLSLPVTPGEPASISCRSSKNLLHSNGITYLYWYLQKPGQSPQLLIYQMSNLASGVPDRFSSSGSGTDFTLKISRVEAEDVGVYYCAQNLEIPRTFGQGTKVEIKGATPPETGAETESPGETTGGSAESEPPGEGQVQLVQSGPEVKKPGASVKVSCKASGYTFTNYGMNWVRQAPGQGLEWMGWINTYTGEPTYGEDFKGRFAFSLDTSASTAYMELSSLRSEDTAVYFCARFGNYVDYWGQGSLVTVSSGGGGSELVVTQEPSLTVSPGGTVTLTCRSSTGAVTTSNYANWVQQKPGQAPRGLIGGTNKRAPGTPARFSGSLLGGKAALTLSGVQPEDEAEYYCALWYSNLWVFGGGTKLTVLGATPPETGAETESPGETTGGSAESEPPGEGEVQLLESGGGLVQPGGSLKLSCAASGFTFNTYAMNWVRQAPGKGLEWVARIRSKYNNYATYYADSVKDRFTISRDDSKNTAYLQMNNLKTEDTAVYYCVRHGNFGNSYVSWFAYWGQGTLVTVSSGSPGSPAGSPTSTEEGTSESATPESGPGTSTEPSEGSAPGSPAGSPTSTEEGTSTEPSEGSAPGTSTEPSEGSAPGTSESATPESGPGSEPATSGSETPGSEPATSGSETPGSPAGSPTSTEEGTSESATPESGPGTSTEPSEGSAPGTSTEPSEGSAPGSPAGSPTSTEEGTSTEPSEGSAPGTSTEPSEGSAPGTSESATPESGPGTSTEPSEGSAPGTSESATPESGPGSEPATSGSETPGTSTEPSEGSAPGTSTEPSEGSAPGTSESATPESGPGTSESATPESGPGSPAGSPTSTEEGTSESATPESGPGSEPATSGSETPGTSESATPESGPGTSTEPSEGSAPGTSTEPSEGSAPGTSTEPSEGSAPGTSTEPSEGSAPGTSTEPSEGSAPGTSTEPSEGSAPGSPAGSPTSTEEGTSTEPSEGSAPGTSESATPESGPGSEPATSGSETPGTSESATPESGPGSEPATSGSETPGTSESATPESGPGTSTEPSEGSAPGTSESATPESGPGSPAGSPTSTEEGSPAGSPTSTEEGSPAGSPTSTEEGTSESATPESGPGTSTEPSEGSAPGTSESATPESGPGSEPATSGSETPGTSESATPESGPGSEPATSGSETPGTSESATPESGPGTSTEPSEGSAPGSPAGSPTSTEEGTSESATPESGPGSEPATSGSETPGTSESATPESGPGSPAGSPTSTEEGSPAGSPTSTEEGTSTEPSEGSAPGTSESATPESGPGTSESATPESGPGTSESATPESGPGSEPATSGSETPGSEPATSGSETPGSPAGSPTSTEEGTSTEPSEGSAPGTSTEPSEGSAPGSEPATSGSETPGTSESATPESGPGTSTEPSEGSAPGHHHHHH | 501 |
| AC1507 | EpCAM | HHHHHHGGSPAGSPTSTEEGTSESATPESGPGTSTEPSEGSAPGSPAGSPTSTEEGTSTEPSEGSAPGTSTEPSEGSAPGTSESATPESGPGSEPATSGSETPGSEPATSGSETPGSPAGSPTSTEEGTSESATPESGPGTSTEPSEGSAPGTSTEPSEGSAPGSPAGSPTSTEEGTSTEPSEGSAPGTSTEPSEGSAPGTSESATPESGPGTSTEPSEGSAPGTSESATPESGPGSEPATSGSETPGTSTEPSEGSAPGTSTEPSEGSAPGTSESATPESGPGTSESATPESGPGSPAGSPTSTEEGTSESATPESGPGSEPATSGSETPGTSESATPESGPGTSTEPSEGSAPGTSTEPSEGSAPGTSTEPSEGSAPGTSTEPSEGSAPGTSTEPSEGSAPGTSTEPSEGSAPGSPAGSPTSTEEGTSTEPSEGSAPGTSESATPESGPGSEPATSGSETPGTSESATPESGPGSEPATSGSETPGTSESATPESGPGTSTEPSEGSAPGTSESATPESGPGSPAGSPTSTEEGSPAGSPTSTEEGSPAGSPTSTEEGTSESATPESGPGTSTEPSEGSAPGTSESATPESGPGSEPATSGSETPGTSESATPESGPGSEPATSGSETPGTSESATPESGPGTSTEPSEGSAPGSPAGSPTSTEEGTSESATPESGPGSEPATSGSETPGTSESATPESGPGSPAGSPTSTEEGSPAGSPTSTEEGTSTEPSEGSAPGTSESATPESGPGTSESATPESGPGTSESATPESGPGSEPATSGSETPGSEPATSGSETPGSPAGSPTSTEEGTSTEPSEGSAPGTSTEPSEGSAPGSEPATSGSETPGTSESATPESGPGTSTEPSEGSAPLSGRSDNHSPLGLAGSGTAEAASASGDIQMTQSPSSLSASVGDRVTITCRASQDIRNYLNWYQQKPGKAPKLLIYYTSRLESGVPSRFSGSGSGTDYTLTISSLQPEDFATYYCQQGNTLPWTFGQGTKVEIKGATPPETGAETESPGETTGGSAESEPPGEGEVQLVESGGGLVQPGGSLRLSCAASGYSFTGYTMNWVRQAPGKGLEWVALINPYKGVSTYNQKFKDRFTISVDKSKNTAYLQMNSLRAEDTAVYYCARSGYYGDSDWYFDVWGQGTLVTVSSGGGGSDIQMTQSPSSLSASVGDRVTITCRSTKSLLHSNGITYLYWYQQKPGKAPKLLIYQMSNLASGVPSRFSSSGSGTDFTLTISSLQPEDFATYYCAQNLEIPRTFGQGTKVEIKGATPPETGAETESPGETTGGSAESEPPGEGQVQLVQSGPGLVQPGGSVRISCAASGYTFTNYGMNWVKQAPGKGLEWMGWINTYTGESTYADSFKGRFTFSLDTSASAAYLQINSLRAEDTAVYYCARFAIKGDYWGQGTLLTVSS | 502 |
| AC1510 | EpCAM | HHHHHHGGSPAGSPTSTEEGTSESATPESGPGTSTEPSEGSAPGSPAGSPTSTEEGTSTEPSEGSAPGTSTEPSEGSAPGTSESATPESGPGSEPATSGSETPGSEPATSGSETPGSPAGSPTSTEEGTSESATP | 503 |

TABLE 12-continued

Chimeric Polypeptide Assembly Sequences

| Construct ID | Tumor Targets | Amino Acid Sequences | SEQ ID NO: |
|---|---|---|---|
| | | ESGPGTSTEPSEGSAPGTSTEPSEGSAPGSPAGSPTSTEEGTSTE<br>PSEGSAPGTSTEPSEGSAPGTSESATPESGPGTSTEPSEGSAPGT<br>SESATPESGPGSEPATSGSETPGTSTEPSEGSAPGTSTEPSEGSA<br>PGTSESATPESGPGTSESATPESGPGSPAGSPTSTEEGTSESATP<br>ESGPGSEPATSGSETPGTSESATPESGPGTSTEPSEGSAPGTSTE<br>PSEGSAPGTSTEPSEGSAPGTSTEPSEGSAPGTSTEPSEGSAPGT<br>STEPSEGSAPGSPAGSPTSTEEGTSTEPSEGSAPGTSESATPESG<br>PGSEPATSGSETPGTSESATPESGPGSEPATSGSETPGTSESATP<br>ESGPGTSTEPSEGSAPGTSESATPESGPGSPAGSPTSTEEGSPAG<br>SPTSTEEGSPAGSPTSTEEGTSESATPESGPGTSTEPSEGSAPGT<br>SESATPESGPGSEPATSGSETPGTSESATPESGPGSEPATSGSET<br>PGTSESATPESGPGTSTEPSEGSAPGSPAGSPTSTEEGTSESATP<br>ESGPGSEPATSGSETPGTSESATPESGPGSPAGSPTSTEEGSPAG<br>SPTSTEEGTSTEPSEGSAPGTSESATPESGPGTSESATPESGPGT<br>SESATPESGPGSEPATSGSETPGSEPATSGSETPGSPAGSPTSTE<br>EGTSTEPSEGSAPGTSTEPSEGSAPGSEPATSGSETPGTSESATP<br>ESGPGTSTEPSEGSAPGSPDIQMTQSPSSLSASVGDRVTITCRAS<br>QDIRNYLNWYQQKPGKAPKLLIYYTSRLESGVPSRFSGSGSGTDY<br>TLTISSLQPEDFATYYCQQGNTLPWTFGQGTKVEIKGATPPETGA<br>ETESPGETTGGSAESEPPGEGEVQLVESGGGLVQPGGSLRLSCAA<br>SGYSFTGYTMNWVRQAPGKGLEWVALINPYKGVSTYNQKFKDRET<br>ISVDKSKNTAYLQMNSLRAEDTAVYYCARSGYYGDSDWYFDVWGQ<br>GTLVTVSSGGGGSDIQMTQSPSSLSASVGDRVTITCRSTKSLLHS<br>NGITYLYWYQQKPGKAPKLLIYQMSNLASGVPSRESSSGSGTDFT<br>LTISSLQPEDFATYYCAQNLEIPRTFGQGTKVEIKGATPPETGAE<br>TESPGETTGGSAESEPPGEGQVQLVQSGPGLVQPGGSVRISCAAS<br>GYTFTNYGMNWVKQAPGKGLEWMGWINTYTGESTYADSFKGRFTF<br>SLDTSASAAYLQINSLRAEDTAVYYCARFAIKGDYWGQGTLLTVS<br>S | |
| AC1501 | HER2 | DIQMTQSPSSLSASVGDRVTITCRASQDVNTAVAWYQQKPGKAPK<br>LLIYSASFLYSGVPSRFSGSRSGTDFTLTISSLQPEDFATYYCQQ<br>HYTTPPTFGQGTKVEIKGATPPETGAETESPGETTGGSAESEPPG<br>EGEVQLVESGGGLVQPGGSLRLSCAASGENIKDTYIHWVRQAPGK<br>GLEWVARIYPTNGYTRYADSVKGRFTISADTSKNTAYLQMNSLRA<br>EDTAVYYCSRWGGDGFYAMDYWGQGTLVTVSSGGGGSDIQMTQSP<br>SSLSASVGDRVTITCRASQDIRNYLNWYQQKPGKAPKLLIYYTSR<br>LESGVPSRFSGSGSGTDYTLTISSLQPEDFATYYCQQGNTLPWTF<br>GQGTKVEIKGATPPETGAETESPGETTGGSAESEPPGEGEVQLVE<br>SGGGLVQPGGSLRLSCAASGYSFTGYTMNWVRQAPGKGLEWVALI<br>NPYKGVSTYNQKFKDRFTISVDKSKNTAYLQMNSLRAEDTAVYYC<br>ARSGYYGDSDWYFDVWGQGTLVTVSSGTAEAASASGLSGRSDNHS<br>PLGLAGSPGSPAGSPTSTEEGTSESATPESGPGTSTEPSEGSAPG<br>SPAGSPTSTEEGTSTEPSEGSAPGTSTEPSEGSAPGTSESATPES<br>GPGSEPATSGSETPGSEPATSGSETPGSPAGSPTSTEEGTSESAT<br>PESGPGTSTEPSEGSAPGTSTEPSEGSAPGSPAGSPTSTEEGTST<br>EPSEGSAPGTSTEPSEGSAPGTSESATPESGPGTSTEPSEGSAPG<br>TSESATPESGPGSEPATSGSETPGTSTEPSEGSAPGTSTEPSEGS<br>APGTSESATPESGPGTSESATPESGPGSPAGSPTSTEEGTSESAT<br>PESGPGSEPATSGSETPGTSESATPESGPGTSTEPSEGSAPGTST<br>EPSEGSAPGTSTEPSEGSAPGTSTEPSEGSAPGTSTEPSEGSAPG<br>TSTEPSEGSAPGSPAGSPTSTEEGTSTEPSEGSAPGTSESATPES<br>GPGSEPATSGSETPGTSESATPESGPGSEPATSGSETPGTSESAT<br>PESGPGTSTEPSEGSAPGTSESATPESGPGSPAGSPTSTEEGSPA<br>GSPTSTEEGSPAGSPTSTEEGTSESATPESGPGTSTEPSEGSAPG<br>TSESATPESGPGSEPATSGSETPGTSESATPESGPGSEPATSGSE<br>TPGTSESATPESGPGTSTEPSEGSAPGSPAGSPTSTEEGTSESAT<br>PESGPGSEPATSGSETPGTSESATPESGPGSPAGSPTSTEEGSPA<br>GSPTSTEEGTSTEPSEGSAPGTSESATPESGPGTSESATPESGPG<br>TSESATPESGPGSEPATSGSETPGSEPATSGSETPGSPAGSPTST<br>EEGTSTEPSEGSAPGTSTEPSEGSAPGSEPATSGSETPGTSESAT<br>PESGPGTSTEPSEGSAPGHHHHHH | 504 |
| AC1502 | HER2 | DIQMTQSPSSLSASVGDRVTITCRASQDVNTAVAWYQQKPGKAPK<br>LLIYSASFLYSGVPSRFSGSRSGTDFTLTISSLQPEDFATYYCQQ<br>HYTTPPTFGQGTKVEIKGATPPETGAETESPGETTGGSAESEPPG<br>EGEVQLVESGGGLVQPGGSLRLSCAASGENIKDTYIHWVRQAPGK<br>GLEWVARIYPTNGYTRYADSVKGRFTISADTSKNTAYLQMNSLRA<br>EDTAVYYCSRWGGDGFYAMDYWGQGTLVTVSSGGGGSDIQMTQSP<br>SSLSASVGDRVTITCRASQDIRNYLNWYQQKPGKAPKLLIYYTSR<br>LESGVPSRFSGSGSGTDYTLTISSLQPEDFATYYCQQGNTLPWTF<br>GQGTKVEIKGATPPETGAETESPGETTGGSAESEPPGEGEVQLVE<br>SGGGLVQPGGSLRLSCAASGYSFTGYTMNWVRQAPGKGLEWVALI<br>NPYKGVSTYNQKFKDRFTISVDKSKNTAYLQMNSLRAEDTAVYYC | 505 |

TABLE 12-continued

Chimeric Polypeptide Assembly Sequences

| Construct ID | Tumor Targets | Amino Acid Sequences | SEQ ID NO: |
|---|---|---|---|
| | | ARSGYYGDSDWYFDVWGQGTLVTVSSGSPGSPAGSPTSTEEGTSE SATPESGPGTSTEPSEGSAPGSPAGSPTSTEEGTSTEPSEGSAPG TSTEPSEGSAPGTSESATPESGPGSEPATSGSETPGSEPATSGSE TPGSPAGSPTSTEEGTSESATPESGPGTSTEPSEGSAPGTSTEPS EGSAPGSPAGSPTSTEEGTSTEPSEGSAPGTSTEPSEGSAPGTSE SATPESGPGTSTEPSEGSAPGTSESATPESGPGSEPATSGSETPG TSTEPSEGSAPGTSTEPSEGSAPGTSESATPESGPGTSESATPES GPGSPAGSPTSTEEGTSESATPESGPGSEPATSGSETPGTSESAT PESGPGTSTEPSEGSAPGTSTEPSEGSAPGTSTEPSEGSAPGTST EPSEGSAPGTSTEPSEGSAPGTSTEPSEGSAPGSPAGSPTSTEEG TSTEPSEGSAPGTSESATPESGPGSEPATSGSETPGTSESATPES GPGSEPATSGSETPGTSESATPESGPGTSTEPSEGSAPGTSESAT PESGPGSPAGSPTSTEEGSPAGSPTSTEEGSPAGSPTSTEEGTSE SATPESGPGTSTEPSEGSAPGTSESATPESGPGSEPATSGSETPG TSESATPESGPGSEPATSGSETPGTSESATPESGPGTSTEPSEGS APGSPAGSPTSTEEGTSESATPESGPGSEPATSGSETPGTSESAT PESGPGSPAGSPTSTEEGSPAGSPTSTEEGTSTEPSEGSAPGTSE SATPESGPGTSESATPESGPGTSESATPESGPGSEPATSGSETPG SEPATSGSETPGSPAGSPTSTEEGTSTEPSEGSAPGTSTEPSEGS APGSEPATSGSETPGTSESATPESGPGTSTEPSEGSAPGHHHHHH | |
| AC1503 | HER2 | DIQMTQSPSSLSASVGDRVTITCRASQDVNTAVAWYQQKPGKAPK LLIYSASFLYSGVPSRFSGSRSGTDFTLTISSLQPEDFATYYCQQ HYTTPPTFGQGTKVEIKGATPPETGAETESPGETTGGSAESEPPG EGEVQLVESGGGLVQPGGSLRLSCAASGENIKDTYIHWVRQAPGK GLEWVARIYPTNGYTRYADSVKGRFTISADTSKNTAYLQMNSLRA EDTAVYYCSRWGGDGFYAMDYWGQGTLVTVSSGGGGSELVVTQEP SLTVSPGGTVTLTCRSSTGAVTTSNYANWVQQKPGQAPRGLIGGT NKRAPGTPARFSGSLLGGKAALTLSGVQPEDEAEYYCALWYSNLW VFGGGTKLTVLGATPPETGAETESPGETTGGSAESEPPGEGEVQL LESGGGLVQPGGSLKLSCAASGFTFNTYAMNWVRQAPGKGLEWVA RIRSKYNNYATYYADSVKDRFTISRDDSKNTAYLQMNNLKTEDTA VYYCVRHGNFGNSYVSWFAYWGQGTLVTVSSGTAEAASASGLSGR SDNHSPLGLAGSPGSPAGSPTSTEEGTSESATPESGPGTSTEPSE GSAPGSPAGSPTSTEEGTSTEPSEGSAPGTSTEPSEGSAPGTSES ATPESGPGSEPATSGSETPGSEPATSGSETPGSPAGSPTSTEEGT SESATPESGPGTSTEPSEGSAPGTSTEPSEGSAPGSPAGSPTSTE EGTSTEPSEGSAPGTSTEPSEGSAPGTSESATPESGPGTSTEPSE GSAPGTSESATPESGPGSEPATSGSETPGTSTEPSEGSAPGTSTE PSEGSAPGTSESATPESGPGTSESATPESGPGSPAGSPTSTEEGT SESATPESGPGSEPATSGSETPGTSESATPESGPGTSTEPSEGSA PGTSTEPSEGSAPGTSTEPSEGSAPGTSTEPSEGSAPGTSTEPSE GSAPGTSTEPSEGSAPGSPAGSPTSTEEGTSTEPSEGSAPGTSES ATPESGPGSEPATSGSETPGTSESATPESGPGSEPATSGSETPGT SESATPESGPGTSTEPSEGSAPGTSESATPESGPGSPAGSPTSTE EGSPAGSPTSTEEGSPAGSPTSTEEGTSESATPESGPGTSTEPSE GSAPGTSESATPESGPGSEPATSGSETPGTSESATPESGPGSEPA TSGSETPGTSESATPESGPGTSTEPSEGSAPGSPAGSPTSTEEGT SESATPESGPGSEPATSGSETPGTSESATPESGPGSPAGSPTSTE EGSPAGSPTSTEEGTSTEPSEGSAPGTSESATPESGPGTSESATP ESGPGTSESATPESGPGSEPATSGSETPGSEPATSGSETPGSPAG SPTSTEEGTSTEPSEGSAPGTSTEPSEGSAPGSEPATSGSETPGT SESATPESGPGTSTEPSEGSAPGHHHHHH | 506 |
| AC1504 | HER2 | DIQMTQSPSSLSASVGDRVTITCRASQDVNTAVAWYQQKPGKAPK LLIYSASFLYSGVPSRFSGSRSGTDFTLTISSLQPEDFATYYCQQ HYTTPPTFGQGTKVEIKGATPPETGAETESPGETTGGSAESEPPG EGEVQLVESGGGLVQPGGSLRLSCAASGENIKDTYIHWVRQAPGK GLEWVARIYPTNGYTRYADSVKGRFTISADTSKNTAYLQMNSLRA EDTAVYYCSRWGGDGFYAMDYWGQGTLVTVSSGGGGSELVVTQEP SLTVSPGGTVTLTCRSSTGAVTTSNYANWVQQKPGQAPRGLIGGT NKRAPGTPARFSGSLLGGKAALTLSGVQPEDEAEYYCALWYSNLW VFGGGTKLTVLGATPPETGAETESPGETTGGSAESEPPGEGEVQL LESGGGLVQPGGSLKLSCAASGFTENTYAMNWVRQAPGKGLEWVA RIRSKYNNYATYYADSVKDRFTISRDDSKNTAYLQMNNLKTEDTA VYYCVRHGNFGNSYVSWFAYWGQGTLVTVSSGSPGSPAGSPTSTE EGTSESATPESGPGTSTEPSEGSAPGSPAGSPTSTEEGTSTEPSE GSAPGTSTEPSEGSAPGTSESATPESGPGSEPATSGSETPGSEPA TSGSETPGSPAGSPTSTEEGTSESATPESGPGTSTEPSEGSAPGT STEPSEGSAPGSPAGSPTSTEEGTSTEPSEGSAPGTSTEPSEGSA PGTSESATPESGPGTSTEPSEGSAPGTSESATPESGPGSEPATSG SETPGTSTEPSEGSAPGTSTEPSEGSAPGTSESATPESGPGTSES ATPESGPGSPAGSPTSTEEGTSESATPESGPGSEPATSGSETPGT SESATPESGPGTSTEPSEGSAPGTSTEPSEGSAPGTSTEPSEGSA | 507 |

TABLE 12-continued

Chimeric Polypeptide Assembly Sequences

| Construct ID | Tumor Targets | Amino Acid Sequences | SEQ ID NO: |
|---|---|---|---|
| | | PGTSTEPSEGSAPGTSTEPSEGSAPGTSTEPSEGSAPGSPAGSPT | |
| | | STEEGTSTEPSEGSAPGTSESATPESGPGSEPATSGSETPGTSES | |
| | | ATPESGPGSEPATSGSETPGTSESATPESGPGTSTEPSEGSAPGT | |
| | | SESATPESGPGSPAGSPTSTEEGSPAGSPTSTEEGSPAGSPTSTE | |
| | | EGTSESATPESGPGTSTEPSEGSAPGTSESATPESGPGSEPATSG | |
| | | SETPGTSESATPESGPGSEPATSGSETPGTSESATPESGPGTSTE | |
| | | PSEGSAPGSPAGSPTSTEEGTSESATPESGPGSEPATSGSETPGT | |
| | | SESATPESGPGSPAGSPTSTEEGSPAGSPTSTEEGTSTEPSEGSA | |
| | | PGTSESATPESGPGTSESATPESGPGTSESATPESGPGSEPATSG | |
| | | SETPGSEPATSGSETPGSPAGSPTSTEEGTSTEPSEGSAPGTSTE | |
| | | PSEGSAPGSEPATSGSETPGTSESATPESGPGTSTEPSEGSAPGH | |
| | | HHHHH | |
| AC1505 | HER2 | DIQMTQSPSSLSASVGDRVTITCKASQDVSIGVAWYQQKPGKAPK | 508 |
| | | LLIYSASYRYTGVPSRFSGSGSGTDFTLTISSLQPEDFATYYCQQ | |
| | | YYIYPYTFGQGTKVEIKGATPPETGAETESPGETTGGSAESEPPG | |
| | | EGEVQLVESGGGLVQPGGSLRLSCAASGFTFTDYTMDWVRQAPGK | |
| | | GLEWVADVNPNSGGSIYNQRFKGRFTLSVDRSKNTLYLQMNSLRA | |
| | | EDTAVYYCARNLGPSFYFDYWGQGTLVTVSSGGGGSDIQMTQSPS | |
| | | SLSASVGDRVTITCRASQDIRNYLNWYQQKPGKAPKLLIYYTSRL | |
| | | ESGVPSRESGSGSGTDYTLTISSLQPEDFATYYCQQGNTLPWTFG | |
| | | QGTKVEIKGATPPETGAETESPGETTGGSAESEPPGEGEVQLVES | |
| | | GGGLVQPGGSLRLSCAASGYSFTGYTMNWVRQAPGKGLEWVALIN | |
| | | PYKGVSTYNQKFKDRFTISVDKSKNTAYLQMNSLRAEDTAVYYCA | |
| | | RSGYYGDSDWYFDVWGQGTLVTVSSGTAEAASASGLSGRSDNHSP | |
| | | LGLAGSPGSPAGSPTSTEEGTSESATPESGPGTSTEPSEGSAPGS | |
| | | PAGSPTSTEEGTSTEPSEGSAPGTSTEPSEGSAPGTSESATPESG | |
| | | PGSEPATSGSETPGSEPATSGSETPGSPAGSPTSTEEGTSESATP | |
| | | ESGPGTSTEPSEGSAPGTSTEPSEGSAPGSPAGSPTSTEEGTSTE | |
| | | PSEGSAPGTSTEPSEGSAPGTSESATPESGPGTSTEPSEGSAPGT | |
| | | SESATPESGPGSEPATSGSETPGTSTEPSEGSAPGTSTEPSEGSA | |
| | | PGTSESATPESGPGTSESATPESGPGSPAGSPTSTEEGTSESATP | |
| | | ESGPGSEPATSGSETPGTSESATPESGPGTSTEPSEGSAPGTSTE | |
| | | PSEGSAPGTSTEPSEGSAPGTSTEPSEGSAPGTSTEPSEGSAPGT | |
| | | STEPSEGSAPGSPAGSPTSTEEGTSTEPSEGSAPGTSESATPESG | |
| | | PGSEPATSGSETPGTSESATPESGPGSEPATSGSETPGTSESATP | |
| | | ESGPGTSTEPSEGSAPGTSESATPESGPGSPAGSPTSTEEGSPAG | |
| | | SPTSTEEGSPAGSPTSTEEGTSESATPESGPGTSTEPSEGSAPGT | |
| | | SESATPESGPGSEPATSGSETPGTSESATPESGPGSEPATSGSET | |
| | | PGTSESATPESGPGTSTEPSEGSAPGSPAGSPTSTEEGTSESATP | |
| | | ESGPGSEPATSGSETPGTSESATPESGPGSPAGSPTSTEEGSPAG | |
| | | SPTSTEEGTSTEPSEGSAPGTSESATPESGPGTSESATPESGPGT | |
| | | SESATPESGPGSEPATSGSETPGSEPATSGSETPGSPAGSPTSTE | |
| | | EGTSTEPSEGSAPGTSTEPSEGSAPGSEPATSGSETPGTSESATP | |
| | | ESGPGTSTEPSEGSAPGHHHHHH | |
| AC1506 | HER2 | DIQMTQSPSSLSASVGDRVTITCKASQDVSIGVAWYQQKPGKAPK | 509 |
| | | LLIYSASYRYTGVPSRFSGSGSGTDFTLTISSLQPEDFATYYCQQ | |
| | | YYIYPYTFGQGTKVEIKGATPPETGAETESPGETTGGSAESEPPG | |
| | | EGEVQLVESGGGLVQPGGSLRLSCAASGFTFTDYTMDWVRQAPGK | |
| | | GLEWVADVNPNSGGSIYNQRFKGRFTLSVDRSKNTLYLQMNSLRA | |
| | | EDTAVYYCARNLGPSFYFDYWGQGTLVTVSSGGGGSDIQMTQSPS | |
| | | SLSASVGDRVTITCRASQDIRNYLNWYQQKPGKAPKLLIYYTSRL | |
| | | ESGVPSRFSGSGSGTDYTLTISSLQPEDFATYYCQQGNTLPWTFG | |
| | | QGTKVEIKGATPPETGAETESPGETTGGSAESEPPGEGEVQLVES | |
| | | GGGLVQPGGSLRLSCAASGYSFTGYTMNWVRQAPGKGLEWVALIN | |
| | | PYKGVSTYNQKFKDRFTISVDKSKNTAYLQMNSLRAEDTAVYYCA | |
| | | RSGYYGDSDWYFDVWGQGTLVTVSSGSPGSPAGSPTSTEEGTSES | |
| | | ATPESGPGTSTEPSEGSAPGSPAGSPTSTEEGTSTEPSEGSAPGT | |
| | | STEPSEGSAPGTSESATPESGPGSEPATSGSETPGSEPATSGSET | |
| | | PGSPAGSPTSTEEGTSESATPESGPGTSTEPSEGSAPGTSTEPSE | |
| | | GSAPGSPAGSPTSTEEGTSTEPSEGSAPGTSTEPSEGSAPGTSES | |
| | | ATPESGPGTSTEPSEGSAPGTSESATPESGPGSEPATSGSETPGT | |
| | | STEPSEGSAPGTSTEPSEGSAPGTSESATPESGPGTSESATPESG | |
| | | PGSPAGSPTSTEEGTSESATPESGPGSEPATSGSETPGTSESATP | |
| | | ESGPGTSTEPSEGSAPGTSTEPSEGSAPGTSTEPSEGSAPGTSTE | |
| | | PSEGSAPGTSTEPSEGSAPGTSTEPSEGSAPGSPAGSPTSTEEGT | |
| | | STEPSEGSAPGTSESATPESGPGSEPATSGSETPGTSESATPESG | |
| | | PGSEPATSGSETPGTSESATPESGPGTSTEPSEGSAPGTSESATP | |
| | | ESGPGSPAGSPTSTEEGSPAGSPTSTEEGSPAGSPTSTEEGTSES | |
| | | ATPESGPGTSTEPSEGSAPGTSESATPESGPGSEPATSGSETPGT | |
| | | SESATPESGPGSEPATSGSETPGTSESATPESGPGTSTEPSEGSA | |
| | | PGSPAGSPTSTEEGTSESATPESGPGSEPATSGSETPGTSESATP | |
| | | ESGPGSPAGSPTSTEEGSPAGSPTSTEEGTSTEPSEGSAPGTSES | |

TABLE 12-continued

| Chimeric Polypeptide Assembly Sequences | | | |
|---|---|---|---|
| Construct ID | Tumor Targets | Amino Acid Sequences | SEQ ID NO: |
| | | ATPESGPGTSESATPESGPGTSESATPESGPGSEPATSGSETPGS<br>EPATSGSETPGSPAGSPTSTEEGTSTEPSEGSAPGTSTEPSEGSA<br>PGSEPATSGSETPGTSESATPESGPGTSTEPSEGSAPGHHHHHH | |

TABLE 13

| Sequences of First Portion Binding Domains | | | |
|---|---|---|---|
| Construct ID | Tumor Targets | Amino Acid Sequences | SEQ ID NO: |
| AC1277 | CD19 | HHHHHHHHDIQLTQSPASLAVSLGQRATISCKASQSVDYDGDSYL<br>NWYQQIPGQPPKLLIYDASNLVSGIPPRESGSGSGTDFTLNIHPV<br>EKVDAATYHCQQSTEDPWTFGGGTKLEIKGGGGSGGGGSGGGGSQ<br>VQLQQSGAELVRPGSSVKISCKASGYAFSSYWMNWVKQRPGQGLE<br>WIGQIWPGDGDTNYNGKFKGKATLTADESSSTAYMQLSSLASEDS<br>AVYFCARRETTTVGRYYYAMDYWGQGTTVTVSSGGGGSDIKLQQS<br>GAELARPGASVKMSCKTSGYTFTRYTMHWVKQRPGQGLEWIGYIN<br>PSRGYTNYNQKFKDKATLTTDKSSSTAYMQLSSLTSEDSAVYYCA<br>RYYDDHYCLDYWGQGTTLTVSSVEGGSGGSGGSGGSGGVDDIQLT<br>QSPAIMSASPGEKVTMTCRASSSVSYMNWYQQKSGTSPKRWIYDT<br>SKVASGVPYRFSGSGSGTSYSLTISSMEAEDAATYYCQQWSSNPL<br>TFGAGTKLELKGTAEAASASGLSGRSDNHSPLG | 510 |
| AC1278 | EpCAM | HHHHHHHHELVMTQSPSSLTVTAGEKVTMSCKSSQSLLNSGNQKN<br>YLTWYQQKPGQPPKLLIYWASTRESGVPDRFTGSGSGTDFTLTIS<br>SVQAEDLAVYYCQNDYSYPLTFGAGTKLEIKGGGGSGGGGSGGGG<br>SEVQLLEQSGAELVRPGTSVKISCKASGYAFTNYWLGWVKQRPGH<br>GLEWIGDIFPGSGNIHYNEKFKGKATLTADKSSSTAYMQLSSLTF<br>EDSAVYFCARLRNWDEPMDYWGQGTTVTVSSGGGGSDVQLVQSGA<br>EVKKPGASVKVSCKASGYTFTRYTMHWVRQAPGQGLEWIGYINPS<br>RGYTNYADSVKGRFTITTDKSTSTAYMELSSLRSEDTATYYCARY<br>YDDHYCLDYWGQGTTVTVSSGEGTSTGSGGSGGSGGADDIVLTQS<br>PATLSLSPGERATLSCRASQSVSYMNWYQQKPGKAPKRWIYDTSK<br>VASGVPARFSGSGSGTDYSLTINSLEAEDAATYYCQQWSSNPLTF<br>GGGTKVEIKGTAEAASASGLSGRSDNHSPLG | 511 |
| AC1345 | EpCAM | HHHHHHHHEVQLLEQSGAELVRPGTSVKISCKASGYAFTNYWLGW<br>VKQRPGHGLEWIGDIFPGSGNIHYNEKFKGKATLTADKSSSTAYM<br>QLSSLTFEDSAVYFCARLRNWDEPMDYWGQGTTVTVSSGGGGSDV<br>QLVQSGAEVKKPGASVKVSCKASGYTFTRYTMHWVRQAPGQGLEW<br>IGYINPSRGYTNYADSVKGRFTITTDKSTSTAYMELSSLRSEDTA<br>TYYCARYYDDHYCLDYWGQGTTVTVSSGEGTSTGSGGSGGSGGAD<br>DIVLTQSPATLSLSPGERATLSCRASQSVSYMNWYQQKPGKAPKR<br>WIYDTSKVASGVPARFSGSGSGTDYSLTINSLEAEDAATYYCQQW<br>SSNPLTFGGGTKVEIKGGGGSELVMTQSPSSLTVTAGEKVTMSCK<br>SSQSLLNSGNQKNYLTWYQQKPGQPPKLLIYWASTRESGVPDRET<br>GSGSGTDFTLTISSVQAEDLAVYYCQNDYSYPLTFGAGTKLEIKG<br>TAEAASASGLSGRSDNHSPLG | 512 |
| AC1346 | EpCAM | HHHHHHHHDVQLVQSGAEVKKPGASVKVSCKASGYTFTRYTMHWV<br>RQAPGQGLEWIGYINPSRGYTNYADSVKGRFTITTDKSTSTAYME<br>LSSLRSEDTATYYCARYYDDHYCLDYWGQGTTVTVSSGGSELVMT<br>QSPSSLTVTAGEKVTMSCKSSQSLLNSGNQKNYLTWYQQKPGQPP<br>KLLIYWASTRESGVPDRFTGSGSGTDFTLTISSVQAEDLAVYYCQ<br>NDYSYPLTFGAGTKLEIKGGGGSGGGGSGGGGSEVQLLEQSGAEL<br>VRPGTSVKISCKASGYAFTNYWLGWVKQRPGHGLEWIGDIFPGSG<br>NIHYNEKFKGKATLTADKSSSTAYMQLSSLTFEDSAVYFCARLRN<br>WDEPMDYWGQGTTVTVSSGGGSDIVLTQSPATLSLSPGERATLSC<br>RASQSVSYMNWYQQKPGKAPKRWIYDTSKVASGVPARFSGSGSGT<br>DYSLTINSLEAEDAATYYCQQWSSNPLTFGGGTKVEIKGTAEAAS<br>ASGLSGRSDNHSPLG | 513 |
| AC1358 | EpCAM | HHHHHHHHELVMTQSPSSLTVTAGEKVTMSCKSSQSLLNSGNQKN<br>YLTWYQQKPGQPPKLLIYWASTRESGVPDRFTGSGSGTDFTLTIS<br>SVQAEDLAVYYCQNDYSYPLTFGAGTKLEIKGGGGSGGGGSGGGG<br>SEVQLLEQSGAELVRPGTSVKISCKASGYAFTNYWLGWVKQRPGH<br>GLEWIGDIFPGSGNIHYNEKFKGKATLTADKSSSTAYMQLSSLTF<br>EDSAVYFCARLRNWDEPMDYWGQGTTVTVSSGGGGSDIQMTQSPS<br>SLSASVGDRVTITCRASQDIRNYLNWYQQKPGKAPKLLIYYTSRL | 514 |

TABLE 13-continued

Sequences of First Portion Binding Domains

| Construct ID | Tumor Targets | Amino Acid Sequences | SEQ ID NO: |
|---|---|---|---|
| | | ESGVPSRFSGSGSGTDYTLTISSLQPEDFATYYCQQGNTLPWTFGQGTKVEIKRTSGPGDGGKGGPGKGPGGEGTKGTGPGGEVQLVESGGGLVQPGGSLRLSCAASGYSFTGYTMNWVRQAPGKGLEWVALINPYKGVSTYNQKFKDRFTISVDKSKNTAYLQMNSLRAEDTAVYYCARSGYYGDSDWYFDVWGQGTLVTVSSGTAEAASASGLSGRSDNHSPLG | |
| AC1359 | EpCAM | HHHHHHHHELVMTQSPSSLTVTAGEKVTMSCKSSQSLLNSGNQKNYLTWYQQKPGQPPKLLIYWASTRESGVPDRFTGSGSGTDFTLTISSVQAEDLAVYYCQNDYSYPLTFGAGTKLEIKGGGGSGGGGSGGGGSEVQLLEQSGAELVRPGTSVKISCKASGYAFTNYWLGWVKQRPGHGLEWIGDIFPGSGNIHYNEKFKGKATLTADKSSSTAYMQLSSLTFEDSAVYFCARLRNWDEPMDYWGQGTTVTVSSGGGGSEVQLVESGGGLVQPGGSLRLSCAASGYSFTGYTMNWVRQAPGKGLEWVALINPYKGVSTYNQKFKDRFTISVDKSKNTAYLQMNSLRAEDTAVYYCARSGYYGDSDWYFDVWGQGTLVTVSSRTSGPGDGGKGGPGKGPGGEGTKGTGPGGDIQMTQSPSSLSASVGDRVTITCRASQDIRNYLNWYQQKPGKAPKLLIYYTSRLESGVPSRESGSGSGTDYTLTISSLQPEDEATYYCQQGNTLPWTFGQGTKVEIKGTAEAASASGLSGRSDNHSPLG | 515 |
| AC1409 | EpCAM | LAGSGTAEAASASGELVMTQSPSSLTVTAGEKVTMSCKSSQSLLNSGNQKNYLTWYQQKPGQPPKLLIYWASTRESGVPDRFTGSGSGTDFTLTISSVQAEDLAVYYCQNDYSYPLTFGAGTKLEIKGGGGSGGGGSGGGGSEVQLLEQSGAELVRPGTSVKISCKASGYAFTNYWLGWVKQRPGHGLEWIGDIFPGSGNIHYNEKFKGKATLTADKSSSTAYMQLSSLTFEDSAVYFCARLRNWDEPMDYWGQGTTVTVSSGGGGSDVQLVQSGAEVKKPGASVKVSCKASGYTFTRYTMHWVRQAPGQGLEWIGYINPSRGYTNYADSVKGRFTITTDKSTSTAYMELSSLRSEDTATYYCARYYDDHYCLDYWGQGTTVTVSSGEGTSTGSGGSGGSGGADDIVLTQSPATLSLSPGERATLSCRASQSVSYMNWYQQKPGKAPKRWIYDTSKVASGVPARFSGSGSGTDYSLTINSLEAEDAATYYCQQWSSNPLTFGGGTKVEIKGTAEAASASGLSGRSDNHSPLG | 516 |
| AC1410 | EpCAM | LAGSGTAEAASASGELVMTQSPSSLTVTAGEKVTMSCKSSQSLLNSGNQKNYLTWYQQKPGQPPKLLIYWASTRESGVPDRFTGSGSGTDFTLTISSVQAEDLAVYYCQNDYSYPLTFGAGTKLEIKGGGGSGGGGSGGGGSEVQLLEQSGAELVRPGTSVKISCKASGYAFTNYWLGWVKQRPGHGLEWIGDIFPGSGNIHYNEKFKGKATLTADKSSSTAYMQLSSLTFEDSAVYFCARLRNWDEPMDYWGQGTTVTVSSGGGGSDVQLVQSGAEVKKPGASVKVSCKASGYTFTRYTMHWVRQAPGQGLEWIGYINPSRGYTNYADSVKGRFTITTDKSTSTAYMELSSLRSEDTATYYCARYYDDHYCLDYWGQGTTVTVSSGEGTSTGSGGSGGSGGADDIVLTQSPATLSLSPGERATLSCRASQSVSYMNWYQQKPGKAPKRWIYDTSKVASGVPARFSGSGSGTDYSLTINSLEAEDAATYYCQQWSSNPLTFGGGTKVEIKHHHHHHHH | 517 |
| AC1411 | EpCAM | HHHHHHHHELVMTQSPSSLTVTAGEKVTMSCKSSQSLLNSGNQKNYLTWYQQKPGQPPKLLIYWASTRESGVPDRFTGSGSGTDFTLTISSVQAEDLAVYYCQNDYSYPLTFGAGTKLEIKGGGGSGGGGSGGGGSEVQLLEQSGAELVRPGTSVKISCKASGYAFTNYWLGWVKQRPGHGLEWIGDIFPGSGNIHYNEKFKGKATLTADKSSSTAYMQLSSLTFEDSAVYFCARLRNWDEPMDYWGQGTTVTVSSGGGGSDIVLTQSPATLSLSPGERATLSCRASQSVSYMNWYQQKPGKAPKRWIYDTSKVASGVPARFSGSGSGTDYSLTINSLEAEDAATYYCQQWSSNPLTFGGGTKVEIKGEGTSTGSGGSGGSGGADDVQLVQSGAEVKKPGASVKVSCKASGYTFTRYTMHWVRQAPGQGLEWIGYINPSRGYTNYADSVKGRFTITTDKSTSTAYMELSSLRSEDTATYYCARYYDDHYCLDYWGQGTTVTVSSGTAEAASASGLSGRSDNHSPLG | 518 |
| AC1412 | EpCAM | HHHHHHHHEVQLLEQSGAELVRPGTSVKISCKASGYAFTNYWLGWVKQRPGHGLEWIGDIFPGSGNIHYNEKFKGKATLTADKSSSTAYMQLSSLTFEDSAVYFCARLRNWDEPMDYWGQGTTVTVSSGGGGSGGGGSGGGGSELVMTQSPSSLTVTAGEKVTMSCKSSQSLLNSGNQKNYLTWYQQKPGQPPKLLIYWASTRESGVPDRFTGSGSGTDETLTISSVQAEDLAVYYCQNDYSYPLTFGAGTKLEIKGGGGSDVQLVQSGAEVKKPGASVKVSCKASGYTFTRYTMHWVRQAPGQGLEWIGYINPSRGYTNYADSVKGRFTITTDKSTSTAYMELSSLRSEDTATYYCARYYDDHYCLDYWGQGTTVTVSSGEGTSTGSGGSGGSGGADDIVLTQSPATLSLSPGERATLSCRASQSVSYMNWYQQKPGKAPKRWIYDTSKVASGVPARFSGSGSGTDYSLTINSLEAEDAATYYCQQWSSNPLTFGGGTKVEIKGTAEAASASGLSGRSDNHSPLG | 519 |

TABLE 13-continued

| Sequences of First Portion Binding Domains | | | |
|---|---|---|---|
| Construct ID | Tumor Targets | Amino Acid Sequences | SEQ ID NO: |
| AC1413 | EpCAM | HHHHHHHHDVQLVQSGAEVKKPGASVKVSCKASGYTFTRYTMHWV RQAPGQGLEWIGYINPSRGYTNYADSVKGRFTITTDKSTSTAYME LSSLRSEDTATYYCARYYDDHYCLDYWGQGTTVTVSSGEGTSTGS GGSGGSGGADDIVLTQSPATLSLSPGERATLSCRASQSVSYMNWY QQKPGKAPKRWIYDTSKVASGVPARFSGSGSGTDYSLTINSLEAE DAATYYCQQWSSNPLTFGGGTKVEIKGGGGSELVMTQSPSSLTVT AGEKVTMSCKSSQSLLNSGNQKNYLTWYQQKPGQPPKLLIYWAST RESGVPDRFTGSGSGTDFTLTISSVQAEDLAVYYCQNDYSYPLTF GAGTKLEIKGGGGSGGGGSGGGGSEVQLLEQSGAELVRPGTSVKI SCKASGYAFTNYWLGWVKQRPGHGLEWIGDIFPGSGNIHYNEKFK GKATLTADKSSSTAYMQLSSLTFEDSAVYFCARLRNWDEPMDYWG QGTTVTVSSGTAEAASASGLSGRSDNHSPLG | 520 |
| AC1414 | EpCAM | HHHHHHHHDIVLTQSPATLSLSPGERATLSCRASQSVSYMNWYQQ KPGKAPKRWIYDTSKVASGVPARFSGSGSGTDYSLTINSLEAEDA ATYYCQQWSSNPLTFGGGTKVEIKGEGTSTGSGGSGGSGGADDVQ LVQSGAEVKKPGASVKVSCKASGYTFTRYTMHWVRQAPGQGLEWI GYINPSRGYTNYADSVKGRFTITTDKSTSTAYMELSSLRSEDTAT YYCARYYDDHYCLDYWGQGTTVTVSSGGGGSELVMTQSPSSLTVT AGEKVTMSCKSSQSLLNSGNQKNYLTWYQQKPGQPPKLLIYWAST RESGVPDRFTGSGSGTDFTLTISSVQAEDLAVYYCQNDYSYPLTF GAGTKLEIKGGGGSGGGGSGGGGSEVQLLEQSGAELVRPGTSVKI SCKASGYAFTNYWLGWVKQRPGHGLEWIGDIFPGSGNIHYNEKFK GKATLTADKSSSTAYMQLSSLTFEDSAVYFCARLRNWDEPMDYWG QGTTVTVSSGTAEAASASGLSGRSDNHSPLG | 521 |
| AC1476 | EpCAM | DIQMTQSPSSLSASVGDRVTITCRSTKSLLHSNGITYLYWYQQKP GKAPKLLIYQMSNLASGVPSRESSSGSGTDFTLTISSLQPEDFAT YYCAQNLEIPRTFGQGTKVEIKGATPPETGAETESPGETTGGSAE SEPPGEGQVQLVQSGPGLVQPGGSVRISCAASGYTFTNYGMNWVK QAPGKGLEWMGWINTYTGESTYADSFKGRFTFSLDTSASAAYLQI NSLRAEDTAVYYCARFAIKGDYWGQGTLLTVSSGGGGSDIQMTQS PSSLSASVGDRVTITCRASQDIRNYLNWYQQKPGKAPKLLIYYTS RLESGVPSRESGSGSGTDYTLTISSLQPEDFATYYCQQGNTLPWT FGQGTKVEIKGATPPETGAETESPGETTGGSAESEPPGEGEVQLV ESGGGLVQPGGSLRLSCAASGYSFTGYTMNWVRQAPGKGLEWVAL INPYKGVSTYNQKFKDRFTISVDKSKNTAYLQMNSLRAEDTAVYY CARSGYYGDSDWYFDVWGQGTLVTVSSGTAEAASASGLSGRSDNH SPLG | 522 |
| AC1489 | EpCAM | DIVMTQSPLSLPVTPGEPASISCRSSKNLLHSNGITYLYWYLQKP GQSPQLLIYQMSNLASGVPDRESSSGSGTDFTLKISRVEAEDVGV YYCAQNLEIPRTFGQGTKVEIKGATPPETGAETESPGETTGGSAE SEPPGEGQVQLVQSGPEVKKPGASVKVSCKASGYTFTNYGMNWVR QAPGQGLEWMGWINTYTGEPTYGEDFKGRFAFSLDTSASTAYMEL SSLRSEDTAVYFCARFGNYVDYWGQGSLVTVSSGGGGSELVVTQE PSLTVSPGGTVTLTCRSSTGAVTTSNYANWVQQKPGQAPRGLIGG TNKRAPGTPARFSGSLLGGKAALTLSGVQPEDEAEYYCALWYSNL WVFGGGTKLTVLGATPPETGAETESPGETTGGSAESEPPGEGEVQ LLESGGGLVQPGGSLKLSCAASGFTFNTYAMNWVRQAPGKGLEWV ARIRSKYNNYATYYADSVKDRFTISRDDSKNTAYLQMNNLKTEDT AVYYCVRHGNFGNSYVSWFAYWGQGTLVTVSSGTAEAASASGLSG RSDNHSPLG | 523 |
| AC1507 | EpCAM | LAGSGTAEAASASGDIQMTQSPSSLSASVGDRVTITCRASQDIRN YLNWYQQKPGKAPKLLIYYTSRLESGVPSRESGSGSGTDYTLTIS SLQPEDFATYYCQQGNTLPWTFGQGTKVEIKGATPPETGAETESP GETTGGSAESEPPGEGEVQLVESGGGLVQPGGSLRLSCAASGYSF TGYTMNWVRQAPGKGLEWVALINPYKGVSTYNQKFKDRFTISVDK SKNTAYLQMNSLRAEDTAVYYCARSGYYGDSDWYFDVWGQGTLVT VSSGGGGSDIQMTQSPSSLSASVGDRVTITCRSTKSLLHSNGITY LYWYQQKPGKAPKLLIYQMSNLASGVPSRESSSGSGTDFTLTISS LQPEDFATYYCAQNLEIPRTFGQGTKVEIKGATPPETGAETESPG ETTGGSAESEPPGEGQVQLVQSGPGLVQPGGSVRISCAASGYTFT NYGMNWVKQAPGKGLEWMGWINTYTGESTYADSFKGRFTESLDTS ASAAYLQINSLRAEDTAVYYCARFAIKGDYWGQGTLLTVSS | 524 |
| AC1501 | HER2 | DIQMTQSPSSLSASVGDRVTITCRASQDVNTAVAWYQQKPGKAPK LLIYSASFLYSGVPSRFSGSRSGTDFTLTISSLQPEDFATYYCQQ HYTTPPTFGQGTKVEIKGATPPETGAETESPGETTGGSAESEPPG EGEVQLVESGGGLVQPGGSLRLSCAASGENIKDTYIHWVRQAPGK GLEWVARIYPTNGYTRYADSVKGRFTISADTSKNTAYLQMNSLRA EDTAVYYCSRWGGDGFYAMDYWGQGTLVTVSSGGGGSDIQMTQSP SSLSASVGDRVTITCRASQDIRNYLNWYQQKPGKAPKLLIYYTSR | 525 |

TABLE 13-continued

| Sequences of First Portion Binding Domains | | | |
|---|---|---|---|
| Construct ID | Tumor Targets | Amino Acid Sequences | SEQ ID NO: |
| | | LESGVPSRFSGSGSGTDYTLTISSLQPEDFATYYCQQGNTLPWTF<br>GQGTKVEIKGATPPETGAETESPGETTGGSAESEPPGEGEVQLVE<br>SGGGLVQPGGSLRLSCAASGYSFTGYTMNWVRQAPGKGLEWVALI<br>NPYKGVSTYNQKFKDRFTISVDKSKNTAYLQMNSLRAEDTAVYYC<br>ARSGYYGDSDWYFDVWGQGTLVTVSSGTAEAASASGLSGRSDNHS<br>PLG | |
| AC1503 | HER2 | DIQMTQSPSSLSASVGDRVTITCRASQDVNTAVAWYQQKPGKAPK<br>LLIYSASFLYSGVPSRESGSRSGTDFTLTISSLQPEDFATYYCQQ<br>HYTTPPTFGQGTKVEIKGATPPETGAETESPGETTGGSAESEPPG<br>EGEVQLVESGGGLVQPGGSLRLSCAASGENIKDTYIHWVRQAPGK<br>GLEWVARIYPTNGYTRYADSVKGRFTISADTSKNTAYLQMNSLRA<br>EDTAVYYCSRWGGDGFYAMDYWGQGTLVTVSSGGGGSELVVTQEP<br>SLTVSPGGTVTLTCRSSTGAVTTSNYANWVQQKPGQAPRGLIGGT<br>NKRAPGTPARFSGSLLGGKAALTLSGVQPEDEAEYYCALWYSNLW<br>VFGGGTKLTVLGATPPETGAETESPGETTGGSAESEPPGEGEVQL<br>LESGGGLVQPGGSLKLSCAASGFTFNTYAMNWVRQAPGKGLEWVA<br>RIRSKYNNYATYYADSVKDRFTISRDDSKNTAYLQMNNLKTEDTA<br>VYYCVRHGNFGNSYVSWFAYWGQGTLVTVSSGTAEAASASGLSGR<br>SDNHSPLG | 526 |
| AC1505 | HER2 | DIQMTQSPSSLSASVGDRVTITCKASQDVSIGVAWYQQKPGKAPK<br>LLIYSASYRYTGVPSRFSGSGSGTDFTLTISSLQPEDFATYYCQQ<br>YYIYPYTFGQGTKVEIKGATPPETGAETESPGETTGGSAESEPPG<br>EGEVQLVESGGGLVQPGGSLRLSCAASGFTFTDYTMDWVRQAPGK<br>GLEWVADVNPNSGGSIYNQRFKGRFTLSVDRSKNTLYLQMNSLRA<br>EDTAVYYCARNLGPSFYFDYWGQGTLVTVSSGGGGSDIQMTQSPS<br>SLSASVGDRVTITCRASQDIRNYLNWYQQKPGKAPKLLIYYTSRL<br>ESGVPSRESGSGSGTDYTLTISSLQPEDFATYYCQQGNTLPWTFG<br>QGTKVEIKGATPPETGAETESPGETTGGSAESEPPGEGEVQLVES<br>GGGLVQPGGSLRLSCAASGYSFTGYTMNWVRQAPGKGLEWVALIN<br>PYKGVSTYNQKFKDRFTISVDKSKNTAYLQMNSLRAEDTAVYYCA<br>RSGYYGDSDWYFDVWGQGTLVTVSSGTAEAASASGLSGRSDNHSP<br>LG | 527 |
| AC1518 | HER2 | DIQMTQSPSSLSASVGDRVTITCKASQDVSIGVAWYQQKPGKAPK<br>LLIYSASYRYTGVPSRFSGSGSGTDFTLTISSLQPEDFATYYCQQ<br>YYIYPYTFGQGTKVEIKGATPPETGAETESPGETTGGSAESEPPG<br>EGEVQLVESGGGLVQPGGSLRLSCAASGFTFTDYTMDWVRQAPGK<br>GLEWVADVNPNSGGSIYNQRFKGRFTLSVDRSKNTLYLQMNSLRA<br>EDTAVYYCARNLGPSFYFDYWGQGTLVTVSSGGGGSELVVTQEPS<br>LTVSPGGTVTLTCRSSTGAVTTSNYANWVQQKPGQAPRGLIGGTN<br>KRAPGTPARFSGSLLGGKAALTLSGVQPEDEAEYYCALWYSNLWV<br>FGGGTKLTVLGATPPETGAETESPGETTGGSAESEPPGEGEVQLL<br>ESGGGLVQPGGSLKLSCAASGFTENTYAMNWVRQAPGKGLEWVAR<br>IRSKYNNYATYYADSVKDRFTISRDDSKNTAYLQMNNLKTEDTAV<br>YYCVRHGNFGNSYVSWFAYWGQGTLVTVSSGTAEAASASGLSGRS<br>DNHSPLG | 528 |
| AC1521 | CEA | DIQLTQSPSSLSASVGDRVTITCKASQDVGTSVAWYQQKPGKAPK<br>LLIYWTSTRHTGVPSRFSGSGSGTDFTFTISSLQPEDIATYYCQQ<br>YSLYRSFGQGTKVEIKGATPPETGAETESPGETTGGSAESEPPGE<br>GEVQLVESGGGVVQPGRSLRLSCSASGFDFTTYWMSWVRQAPGKG<br>LEWIGEIHPDSSTINYAPSLKDRFTISRDNAKNTLFLQMDSLRPE<br>DTGVYFCASLYFGFPWFAYWGQGTPVTVSSGGGGSDIQMTQSPSS<br>LSASVGDRVTITCRASQDIRNYLNWYQQKPGKAPKLLIYYTSRLE<br>SGVPSRFSGSGSGTDYTLTISSLQPEDFATYYCQQGNTLPWTFGQ<br>GTKVEIKGATPPETGAETESPGETTGGSAESEPPGEGEVQLVESG<br>GGLVQPGGSLRLSCAASGYSFTGYTMNWVRQAPGKGLEWVALINP<br>YKGVSTYNQKFKDRFTISVDKSKNTAYLQMNSLRAEDTAVYYCAR<br>SGYYGDSDWYFDVWGQGTLVTVSSGTAEAASASGLSGRSDNHSPL<br>G | 529 |

TABLE 13-continued

Sequences of First Portion Binding Domains

| Construct ID | Tumor Targets | Amino Acid Sequences | SEQ ID NO: |
|---|---|---|---|
| AC1522 | PSMA | DIQMTQSPSSLSTSVGDRVTLTCKASQDVGTAVDWYQQKPGPSPK<br>LLIYWASTRHTGIPSRFSGSGSGTDFTLTISSLQPEDFADYYCQQ<br>YNSYPLTFGPGTKVDIKGATPPETGAETESPGETTGGSAESEPPG<br>EGEVQLVQSGPEVKKPGATVKISCKTSGYTFTEYTIHWVKQAPGK<br>GLEWIGNINPNNGGTTYNQKFEDKATLTVDKSTDTAYMELSSLRS<br>EDTAVYYCAAGWNFDYWGQGTLLTVSSGGGGSDIQMTQSPSSLSA<br>SVGDRVTITCRASQDIRNYLNWYQQKPGKAPKLLIYYTSRLESGV<br>PSRFSGSGSGTDYTLTISSLQPEDFATYYCQQGNTLPWTFGQGTK<br>VEIKGATPPETGAETESPGETTGGSAESEPPGEGEVQLVESGGGL<br>VQPGGSLRLSCAASGYSFTGYTMNWVRQAPGKGLEWVALINPYKG<br>VSTYNQKFKDRFTISVDKSKNTAYLQMNSLRAEDTAVYYCARSGY<br>YGDSDWYFDVWGQGTLVTVSSGTAEAASASGLSGRSDNHSPLG | 530 |

TABLE 14

Chimeric Polypeptide Assembly Encoding-construct Sequences

| Construct ID | Tumor Targets | DNA Sequences | SEQ ID NO: |
|---|---|---|---|
| AC1476 | EpCAM | gatattcagatgacccaatcgccgtcgtccctgtcagcttcagtc<br>ggtgatcgtgttaccattacctgtcgctcaacgaaatccctgctg<br>cattcaaacggtattacctatctgtactggtatcagcaaaaaccg<br>ggcaaagcgccgaaactgctgatctaccagatgtcgaatctggcc<br>agcggtgttccgtctcgttttagctctagtggttctggcaccgat<br>ttcaccctgacgatttcctcactgcaaccggaagactttgcaacg<br>tattactgcgctcagaacctggaaatcccgcgtaccttcggtcaa<br>ggcacgaaagtcgaaattaaaGGTGCAACGCCTCCGGAGACTGGT<br>GCTGAAACTGAGTCCCCGGGCGAGACGACCGGTGGCTCTGCTGAA<br>TCCGAACCACCGGGCGAAGGCcaagtgcaactggttcagagcggt<br>ccgggtctggtccaaccgggtggcagtgtgcgtatttcctgcgcg<br>gcctcaggttacacctttacgaactatggcatgaattgggtgaaa<br>caggccccgggtaaaggcctggaatggatgggttggatcaacacc<br>tacacgggcgaatctacctatgcagatagtttcaaaggccgcttt<br>accttcagcctggacacgtctgctagtgcagcttatctgcagatt<br>aatagcctgcgtgcggaagatacggccgtttattactgtgcgcgc<br>tttgcaatcaaaggcgactactggggccaaggcaccctgctgacc<br>gtgtcctccGGTGGTGGCGGCAGCGACATCCAAATGACCCAGAGC<br>CCGAGCAGCCTGAGCGCGAGCGTGGGCGACCGTGTTACCATCACC<br>TGCCGTGCGAGCCAAGACATCCGTAACTACCTGAACTGGTATCAG<br>CAAAAGCCGGGTAAAGCGCCGAAGCTGCTGATCTACTATACCAGC<br>CGTCTGGAGAGCGGCGTGCCGAGCCGTTTCAGCGGTAGCGGTAGC<br>GGTACCGACTACACCCTGACCATTAGCAGCCTGCAGCCGGAAGAT<br>TTCGCGACCTACTATTGCCAGCAGGGTAACACCCTGCCGTGGACC<br>TTTGGTCAAGGCACCAAAGTTGAGATTAAAGGCGCCACGCCTCCG<br>GAAACTGGTGCTGAGACGGAATCCCCTGGTGAAACCACTGGCGGT<br>TCTGCCGAATCTGAACCGCCTGGTGAAGGCGAGGTGCAGCTGGTT<br>GAAAGCGGTGGCGGTCTGGTGCAACCAGGCGGTAGCCTGCGTCTG<br>AGCTGCGCGGCGAGCGGTTACAGCTTTACCGGTTATACCATGAAC<br>TGGGTTCGTCAAGCGCCAGGTAAAGGTCTGGAGTGGGTGGCGCTG<br>ATCAACCCGTACAAGGGTGTTAGCACCTATAACCAGAAGTTCAAA<br>GACCGTTTTACCATTAGCGTGGATAAGAGCAAAAACACCGCGTAC<br>CTGCAAATGAACAGCCTGCGTGCGGAGGACACCGCTGTGTACTAT<br>TGCGCGCGTAGCGGTTACTATGGCGACAGCGACTGGTATTTTGAT<br>GTGTGGGGCCAAGGCACCCTGGTTACCGTGAGCTCCGGCACCGCC<br>GAAGCAGCTagcgcctctGGCctgTCAggtCGTtctGATaacCAT<br>tccCCActgGGTctgGCTGGGTCTCCAGGTAGCCCAGCTGGTAGC<br>CCAACCTCTACCGAAGAAGGTACCTCTGAATCCGCTACTCCAGAA<br>TCCGGTCCTGGTACTAGCACTGAGCCAAGCGAAGGTTCTGCTCCA<br>GGCTCCCCGGCAGGTAGCCCTACCTCTACCGAAGAGGGCACTAGC<br>ACCGAACCATCTGAGGGTTCCGCTCCTGGCACCTCCACTGAACCG<br>TCCGAAGGCAGTGCTCCGGGTACTTCCGAAAGCGCAACTCCGGAA<br>TCCGGCCCTGGTTCTGAGCCTGCTACTTCCGGCTCTGAAACTCCA<br>GGTAGCGAGCCAGCGACTTCTGGTTCTGAAACTCCAGGTTCACCG<br>GCGGGTAGCCCGACGAGCACGGAGGAAGGTACCTCTGAGTCGGCC<br>ACTCCTGAGTCCGGTCCGGGCACGAGCACCGAGCCGAGCGAGGGT<br>TCAGCCCCGGGTACCAGCACGGAGCCGTCCGAGGGTAGCGCACCG<br>GGTTCTCCGGCGGGCTCCCCTACGTCTACGGAAGAGGGTACGTCC<br>ACTGAACCTAGCGAGGGCAGCGCGCCAGGCACCAGCACTGAACCG<br>AGCGAAGGCAGCGCACCTGGCACTAGCGAGTCTGCGACTCCGGAG | 531 |

TABLE 14-continued

Chimeric Polypeptide Assembly Encoding-construct Sequences

| Construct ID | Tumor Targets | DNA Sequences | SEQ ID NO: |
|---|---|---|---|
| | | AGCGGTCCGGGTACGAGCACGGAACCAAGCGAAGGCAGCGCCCCA | |
| | | GGTACCTCTGAATCTGCTACCCCAGAATCTGGCCCGGGTTCCGAG | |
| | | CCAGCTACCTCTGGTTCTGAAACCCCAGGTACTTCCACTGAACCA | |
| | | AGCGAAGGTAGCGCTCCTGGCACTTCTACTGAACCATCCGAAGGT | |
| | | TCCGCTCCTGGTACGTCTGAAAGCGCTACCCCTGAAAGCGGCCCA | |
| | | GGCACCTCTGAAAGCGCTACTCCTGAGAGCGGTCCAGGCTCTCCA | |
| | | GCAGGTTCTCCAACCTCCACTGAAGAAGGCACCTCTGAGTCTGCT | |
| | | ACCCCTGAATCTGGTCCTGGCTCCGAACCTGCTACCTCTGGTTCC | |
| | | GAAACTCCAGGTACCTCGGAATCTGCGACTCCGGAATCTGGCCCG | |
| | | GGCACGAGCACGGAGCCGTCTGAGGGTAGCGCACCAGGTACCAGC | |
| | | ACTGAGCCTTCTGAGGGCTCTGCACCGGGTACCTCCACGGAACCT | |
| | | TCGGAAGGTTCTGCGCCGGGTACCTCCACTGAGCCATCCGAGGGT | |
| | | TCAGCACCAGGTACTAGCACGGAACCGTCCGAGGGCTCTGCACCA | |
| | | GGTACGAGCACCGAACCGTCGGAGGGTAGCGCTCCAGGTAGCCCA | |
| | | GCGGGCTCTCCGACAAGCACCGAAGAAGGCACCAGCACCGAGCCG | |
| | | TCCGAAGGTTCCGCACCAGGTACAAGCGAGAGCGCGACTCCTGAA | |
| | | TCTGGTCCGGGTAGCGAGCCTGCAACCAGCGGTTCTGAGACGCCG | |
| | | GGCACTTCCGAATCTGCGACCCCGGAGTCCGGTCCAGGTTCAGAG | |
| | | CCGGCGACGAGCGGTTCGGAAACGCCGGGTACGTCTGAATCAGCC | |
| | | ACGCCGGAGTCTGGTCCGGGTACCTCGACCGAACCAAGCGAAGGT | |
| | | TCGGCACCGGGTACTAGCGAGAGCGCAACCCCTGAAAGCGGTCCG | |
| | | GGCAGCCCGGCAGGTTCTCCAACCAGCACCGAAGAAGGTTCCCCT | |
| | | GCTGGTAGCCCGACCTCTACGGAGGAAGGTAGCCCTGCAGGTTCC | |
| | | CCAACTTCTACTGAGGAAGGTACTTCTGAGTCCGCTACCCCAGAA | |
| | | AGCGGTCCTGGTACCTCCACTGAACCGTCTGAAGGCTCTGCACCA | |
| | | GGCACTTCTGAGTCTGCTACTCCAGAAAGCGGCCCAGGTTCTGAA | |
| | | CCAGCAACTTCTGGCTCTGAGACTCCAGGCACTTCTGAGTCCGCA | |
| | | ACGCCTGAATCCGGTCCTGGTTCTGAACCAGCTACTTCCGGCAGC | |
| | | GAAACCCCAGGTACCTCTGAGTCTGCGACTCCAGAGTCTGGTCCT | |
| | | GGTACTTCCACTGAGCCTAGCGAGGGTTCCGCACCAGGTTCTCCG | |
| | | GCTGGTAGCCCGACCAGCACGGAGGAGGGTACGTCTGAATCTGCA | |
| | | ACGCCGGAATCGGGCCCAGGTTCGGAGCCTGCAACGTCTGGCAGC | |
| | | GAAACCCCGGGTACCTCCGAATCTGCTACACCGGAAAGCGGTCCT | |
| | | GGCAGCCCTGCTGGTTCTCCAACCTCTACCGAGGAGGGTTCACCG | |
| | | GCAGGTAGCCCGACTAGCACTGAAGAAGGTACTAGCACGGAGCCG | |
| | | AGCGAGGGTAGTGCTCCGGGTACGAGCGAGAGCGCAACGCCAGAG | |
| | | AGCGGTCCAGGCACCAGCGAATCGGCCACCCCTGAGAGCGGCCCA | |
| | | GGTACTTCTGAGAGCGCCACTCCTGAATCCGGCCCTGGTAGCGAG | |
| | | CCGGCAACCTCCGGCTCAGAAACTCCTGGTTCGGAACCAGCGACC | |
| | | AGCGGTTCTGAAACTCCGGGTAGCCCGGCAGGCAGCCCAACGAGC | |
| | | ACCGAAGAGGGTACCAGCACGGAACCGAGCGAGGGTTCTGCCCCG | |
| | | GGTACTTCCACCGAACCATCGGAGGGCTCTGCACCTGGTAGCGAA | |
| | | CCTGCGACGTCTGGTTCTGAAACGCCGGGTACCAGCGAAAGCGCT | |
| | | ACCCCAGAATCCGGTCCGGGCACTAGCACCGAGCCATCGGAGGGC | |
| | | TCCGCACCAGGTCACCATCATCACCATCAC | |
| AC1516 | EpCAM | GATATCCAGATGACCCAGAGCCCTTCTTCCCTGTCCGCATCCGTC | 532 |
| (codon | | GGCGATCGTGTCACGATTACCTGTCGCAGCACTAAGAGCCTGCTG | |
| optimized | | CACTCAAACGGTATCACGTACCTGTACTGGTACCAGCAGAAGCCG | |
| by | | GGCAAAGCGCCGAAGCTGCTGATTTATCAGATGAGCAACCTGGCA | |
| DNA2.0) | | TCGGGCGTGCCGAGCCGTTTCAGCAGCAGCGGTAGCGGTACCGAC | |
| | | TTCACGCTGACCATCAGCTCGTTGCAGCCAGAGGACTTTGCGACG | |
| | | TACTATTGTGCGCAAAACTTGGAAATTCCGCGCACCTTCGGCCAG | |
| | | GGTACGAAAGTTGAGATTAAAGGTGCCACCCCACCGGAGACTGGT | |
| | | GCAGAAACCGAGTCTCCGGGCGAAACCACGGGCGGTAGCGCGGAG | |
| | | AGCGAACCGCCTGGTGAGGGTCAAGTTCAATTGGTTCAGAGCGGT | |
| | | CCGGGTCTGGTTCAACCGGGCGGCAGCGTGCGCATTTCTTGTGCG | |
| | | GCCAGCGGTTACACCTTTACGAACTACGGTATGAATTGGGTGAAA | |
| | | CAAGCTCCGGGCAAAGGTCTGGAGTGGATGGGTTGGATCAATACC | |
| | | TATACCGGTGAATCCACTTACGCGGATTCCTTTAAGGGCCGTTTC | |
| | | ACCTTCAGCCTGGACACGAGCGCGAGCGCTGCATATCTGCAAATC | |
| | | AATAGCCTGCGTGCCGAAGATACCGCGGTGTACTATTGCGCGCGT | |
| | | TTTGCAATCAAGGGCGACTATTGGGGTCAAGGCACGCTGCTGACC | |
| | | GTGAGCAGCGGTGGTGGCGGCAGCGATATCCAAATGACCCAATCC | |
| | | CCATCCTCCCTGTCTGCAAGCGTTGGTGATCGTGTGACGATTACG | |
| | | TGCCGTGCCTCCCAAGATATCCGTAACTACCTGAATTGGTATCAG | |
| | | CAGAAACCGGGCAAGGCTCCGAAATTGCTGATCTACTACACCAGC | |
| | | CGCCTGGAGTCGGGTGTGCCTAGCCGCTTCAGCGGCAGCGGTTCG | |
| | | GGTACCGACTATACCTTGACCATTAGCAGCCTGCAGCCGGAAGAT | |
| | | TTCGCGACGTATTACTGCCAACAGGGTAACACGCTGCCGTGGACC | |
| | | TTTGGCCAAGGTACCAAAGTCGAGATTAAGGGTGCGACCCCGCCG | |
| | | GAAACCGGTGCGGAAACCGAGAGCCCGGGTGAAACGACTGGCGGC | |
| | | TCTGCAGAGAGCGAGCCGCCAGGTGAGGGCGAAGTCCAACTGGTC | |
| | | GAGTCTGGTGGCGGCCTGGTGCAACCGGGTGGCAGCCTGCGTCTG | |

TABLE 14-continued

Chimeric Polypeptide Assembly Encoding-construct Sequences

| Construct ID | Tumor Targets | DNA Sequences | SEQ ID NO: |
|---|---|---|---|
| | | AGCTGCGCTGCGAGCGGCTATAGCTTTACCGGTTATACCATGAAC<br>TGGGTTCGCCAGGCACCGGGTAAGGGTCTGGAATGGGTGGCGCTG<br>ATCAATCCGTACAAAGGTGTGAGCACTTACAATCAGAAATTCAAA<br>GACCGTTTCACCATTAGCGTTGACAAGAGCAAGAATACCGCGTAT<br>CTGCAGATGAACAGCTTGCGCGCCGAGGATACGGCCGTTTACTAC<br>TGTGCACGTAGCGGCTATTACGGTGACAGCGACTGGTACTTTGAC<br>GTCTGGGGTCAGGGCACGCTGGTCACCGTTAGCAGCGGCACCGCC<br>GAAGCAGCTagcgcctctGGCctgTCAggtCGTtctGATaacCAT<br>tccCCActgGGTctgGCTGGGTCTCCAGGTAGCCCAGCTGGTAGC<br>CCAACCTCTACCGAAGAAGGTACCTCTGAATCCGCTACTCCAGAA<br>TCCGGTCCTGGTACTAGCACTGAGCCAAGCGAAGGTTCTGCTCCA<br>GGCTCCCCGGCAGGTAGCCCTACCTCTACCGAAGAGGGCACTAGC<br>ACCGAACCATCTGAGGGTTCCGCTCCTGGCACCTCCACTGAACCG<br>TCCGAAGGCAGTGCTCCGGGTACTTCCGAAAGCGCAACTCCGGAA<br>TCCGGCCCTGGTTCTGAGCCTGCTACTTCCGGCTCTGAAACTCCA<br>GGTAGCGAGCCAGCGACTTCTGGTTCTGAAACTCCAGGTTCACCG<br>GCGGGTAGCCCGACGAGCACGGAGGAAGGTACCTCTGAGTCGGCC<br>ACTCCTGAGTCCGGTCCGGGCACGAGCACCGAGCCGAGCGAGGGT<br>TCAGCCCCGGGTACCAGCACGGAGCCGTCCGAGGGTAGCGCACCG<br>GGTTCTCCGGCGGGCTCCCCTACGTCTACGGAAGAGGGTACGTCC<br>ACTGAACCTAGCGAGGGCAGCGCGCCAGGCACCAGCACTGAACCG<br>AGCGAAGGCAGCGCACCTGGCACTAGCGAGTCTGCGACTCCGGAG<br>AGCGGTCCGGGTACGAGCACGGAACCAAGCGAAGGCAGCGCCCCA<br>GGTACCTCTGAATCTGCTACCCCAGAATCTGGCCCGGGTTCCGAG<br>CCAGCTACCTCTGGTTCTGAAACCCCAGGTACTTCCACTGAACCA<br>AGCGAAGGTAGCGCTCCTGGCACTTCTACTGAACCATCCGAAGGT<br>TCCGCTCCTGGTACGTCTGAAAGCGCTACCCCTGAAAGCGGCCCA<br>GGCACCTCTGAAAGCGCTACTCCTGAGAGCGGTCCAGGCTCTCCA<br>GCAGGTTCTCCAACCTCCACTGAAGAAGGCACCTCTGAGTCTGCT<br>ACCCCTGAATCTGGTCCTGGCTCCGAACCTGCTACCTCTGGTTCC<br>GAAACTCCAGGTACCTCGGAATCTGCGACTCCGGAATCTGGCCCG<br>GGCACGAGCACGGAGCCGTCTGAGGGTAGCGCACCAGGTACCAGC<br>ACTGAGCCTTCTGAGGGCTCTGCACCGGGTACCTCCACGGAACCT<br>TCGGAAGGTTCTGCGCCGGGTACCTCCACTGAGCCATCCGAGGGT<br>TCAGCACCAGGTACTAGCACGGAACCGTCCGAGGGCTCTGCACCA<br>GGTACGAGCACCGAACCGTCGGAGGGTAGCGCTCCAGGTAGCCCA<br>GCGGGCTCTCCGACAAGCACCGAAGAAGGCACCAGCACCGAGCCG<br>TCCGAAGGTTCCGCACCAGGTACAAGCGAGAGCGCGACTCCTGAA<br>TCTGGTCCGGGTAGCGAGCCTGCAACCAGCGGTTCTGAGACGCCG<br>GGCACTTCCGAATCTGCGACCCCGGAGTCCGGTCCAGGTTCAGAG<br>CCGGCGACGAGCGGTTCGGAAACGCCGGGTACGTCTGAATCAGCC<br>ACGCCGGAGTCTGGTCCGGGTACCTCGACCGAACCAAGCGAAGGT<br>TCGGCACCGGGTACTAGCGAGAGCGCAACCCCTGAAAGCGGTCCG<br>GGCAGCCCGGCAGGTTCTCCAACCAGCACCGAAGAAGGTTCCCCT<br>GCTGGTAGCCCGACCTCTACGGAGGAAGGTAGCCCTGCAGGTTCC<br>CCAACTTCTACTGAGGAAGGTACTTCTGAGTCCGCTACCCCAGAA<br>AGCGGTCCTGGTACCTCCACTGAACCGTCTGAAGGCTCTGCACCA<br>GGCACTTCTGAGTCTGCTACTCCAGAAAGCGGCCCAGGTTCTGAA<br>CCAGCAACTTCTGGCTCTGAGACTCCAGGCACTTCTGAGTCCGCA<br>ACGCCTGAATCCGGTCCTGGTTCTGAACCAGCTACTTCCGGCAGC<br>GAAACCCCAGGTACCTCTGAGTCTGCGACTCCAGAGTCTGGTCCT<br>GGTACTTCCACTGAGCCTAGCGAGGGTTCCGCACCAGGTTCTCCG<br>GCTGGTAGCCCGACCAGCACGGAGGAGGGTACGTCTGAATCTGCA<br>ACGCCGGAATCGGGCCCAGGTTCGGAGCCTGCAACGTCTGGCAGC<br>GAAACCCCGGGTACCTCCGAATCTGCTACACCGGAAAGCGGTCCT<br>GGCAGCCCTGCTGGTTCTCCAACCTCTACCGAGGAGGGTTCACCG<br>GCAGGTAGCCCGACTAGCACTGAAGAAGGTACTAGCACGGAGCCG<br>AGCGAGGGTAGTGCTCCGGGTACGAGCGAGAGCGCAACGCCAGAG<br>AGCGGTCCAGGCACCAGCGAATCGGCCACCCCTGAGAGCGGCCCA<br>GGTACTTCTGAGAGCGCCACTCCTGAATCCGGCCCTGGTAGCGAG<br>CCGGCAACCTCCGGCTCAGAAACTCCTGGTTCGGAACCAGCGACC<br>AGCGGTTCTGAAACTCCGGGTAGCCCGGCAGGCAGCCCAACGAGC<br>ACCGAAGAGGGTACCAGCACGGAACCGAGCGAGGGTTCTGCCCCG<br>GGTACTTCCACCGAACCATCGGAGGGCTCTGCACCTGGTAGCGAA<br>CCTGCGACGTCTGGTTCTGAAACGCCGGGTACCAGCGAAAGCGCT<br>ACCCCAGAATCCGGTCCGGGCACTAGCACCGAGCCATCGGAGGGC<br>TCCGCACCAGGTCACCATCATCACCATCAC | |

What is claimed is:

1. A method of treating prostate cancer in a subject in need thereof, comprising intravenously administering to the subject a therapeutically effective amount of a chimeric polypeptide assembly, wherein the chimeric polypeptide assembly comprises a bispecific antibody comprising i. a first antibody binding domain having binding specificity to PSMA, wherein the first antibody binding domain is a Fab, and ii. a second antibody binding domain having binding specificity to CD3, wherein the second binding domain comprises an scFv, wherein the second antibody binding domain is attached to a bulking moiety via a linker comprising a peptidyl release segment that is capable of being cleaved by at least one mammalian protease, and wherein the bulking moiety (i) reduces the ability of the second antibody binding domain to bind CD3 and (ii) comprises an albumin binding domain;

wherein cleavage of the peptidyl release segment by the at least one mammalian protease converts the chimeric polypeptide assembly into an activated bispecific antibody, wherein the activated bispecific antibody is capable of effecting at least a 10-fold greater amount of cell lysis of tumor cells compared to the chimeric polypeptide assembly, when cell lysis is measured in an in vitro assay comprising the tumor cells and a population of human peripheral blood mononuclear cells (PBMCs) comprising T cells.

2. The method of claim 1, wherein, in the in vitro assay:

(a) the PBMCs are isolated from one or more healthy donors by ficoll density gradient centrifugation from either whole blood or from a lymphocyte-enriched buffy coat preparation;

(b) the PBMCs are resuspended and cultured in RPMI-1640/10% FCS/25 mmol/mL HEPES at 37° C. in a 5% $CO_2$ humidified incubator until use in the in vitro assay;

(c) the cell density of the tumor cells is $2.5\times10^5$ cells/mL and the cell density of the PBMCs is $1\times10^6$ cells/mL in the in vitro assay;

(d) the tumor cells and the PBMCs are co-cultured in assay medium comprised of phenol red-free RPMI and 5% FCS; and/or (e) cell lysis is measured by a lactate dehydrogenase (LDH) release assay, a caspase 3/7 assay, or FACS-based analysis.

3. The method of claim 2, wherein, in the in vitro assay, an effector cell to tumor cell ratio of 5:1 is present in the assay medium.

4. The method of claim 1, wherein the tumor cells have arisen from prostate cells.

5. The method of claim 3, wherein the tumor cells have arisen from prostate cells.

6. The method of claim 1, wherein the CD3 is CD3 epsilon.

7. The method of claim 1, wherein binding affinity of the first antibody binding domain to PSMA, if measured by a $K_d$ constant in an in vitro assay, is at least one order of magnitude greater compared to lower binding affinity of the second antibody binding domain to CD3.

8. The method of claim 1, wherein the prostate cancer is metastatic.

9. The method of claim 1, wherein the chimeric polypeptide assembly has been produced by a process comprising expression of the chimeric polypeptide assembly by a cultured mammalian host cell followed by purification of the chimeric polypeptide assembly.

10. The method of claim 1, wherein the at least one mammalian protease comprises MMP-2, MMP-7, MMP-9, MMP-13, MMP-14, Urokinase (uPA), or matriptase.

* * * * *

SEQUENCE LISTING

```
Sequence total quantity: 534
SEQ ID NO: 1            moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 1
LSGRSDNHSP LGLAGS                                                   16

SEQ ID NO: 2            moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 2
SPLGLAGSLS GRSDNH                                                   16

SEQ ID NO: 3            moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 3
SPLGLSGRSD NH                                                       12

SEQ ID NO: 4            moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 4
LAGRSDNHSP LGLAGS                                                   16

SEQ ID NO: 5            moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 5
LSGRSDNHVP LSLKMG                                                   16

SEQ ID NO: 6            moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 6
SPLGLAGS                                                            8

SEQ ID NO: 7            moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 7
GPLALARG                                                            8

SEQ ID NO: 8            moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
```

```
SEQUENCE: 8
LSGRSDNH                                                                  8

SEQ ID NO: 9            moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 9
VPLSLTMG                                                                  8

SEQ ID NO: 10           moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 10
VPLSLKMG                                                                  8

SEQ ID NO: 11           moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 11
VPLSLSMG                                                                  8

SEQ ID NO: 12           moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 12
EPLELVAG                                                                  8

SEQ ID NO: 13           moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 13
EPLELRAG                                                                  8

SEQ ID NO: 14           moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 14
EPAALMAG                                                                  8

SEQ ID NO: 15           moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 15
EPASLMAG                                                                  8

SEQ ID NO: 16           moltype = AA  length = 8
FEATURE                 Location/Qualifiers
REGION                  1..8
                        note = Description of Artificial Sequence: Synthetic peptide
source                  1..8
                        mol_type = protein
```

```
                         organism = synthetic construct
SEQUENCE: 16
RIGSLRTA                                                                 8

SEQ ID NO: 17            moltype = AA  length = 8
FEATURE                  Location/Qualifiers
REGION                   1..8
                         note = Description of Artificial Sequence: Synthetic peptide
source                   1..8
                         mol_type = protein
                         organism = synthetic construct
SEQUENCE: 17
RIQFLRTA                                                                 8

SEQ ID NO: 18            moltype = AA  length = 8
FEATURE                  Location/Qualifiers
REGION                   1..8
                         note = Description of Artificial Sequence: Synthetic peptide
source                   1..8
                         mol_type = protein
                         organism = synthetic construct
SEQUENCE: 18
EPFHLMAG                                                                 8

SEQ ID NO: 19            moltype = AA  length = 8
FEATURE                  Location/Qualifiers
REGION                   1..8
                         note = Description of Artificial Sequence: Synthetic peptide
source                   1..8
                         mol_type = protein
                         organism = synthetic construct
SEQUENCE: 19
VPLSLFMG                                                                 8

SEQ ID NO: 20            moltype = AA  length = 8
FEATURE                  Location/Qualifiers
REGION                   1..8
                         note = Description of Artificial Sequence: Synthetic peptide
source                   1..8
                         mol_type = protein
                         organism = synthetic construct
SEQUENCE: 20
EPLELPAG                                                                 8

SEQ ID NO: 21            moltype = AA  length = 8
FEATURE                  Location/Qualifiers
REGION                   1..8
                         note = Description of Artificial Sequence: Synthetic peptide
source                   1..8
                         mol_type = protein
                         organism = synthetic construct
SEQUENCE: 21
EPLELAAG                                                                 8

SEQ ID NO: 22            moltype = AA  length = 119
FEATURE                  Location/Qualifiers
REGION                   1..119
                         note = Description of Artificial Sequence: Synthetic
                          polypeptide
source                   1..119
                         mol_type = protein
                         organism = synthetic construct
SEQUENCE: 22
QVQLVQSGGG VVQPGRSLRL SCKASGYTFT RYTMHWVRQA PGKGLEWIGY INPSRGYTNY  60
NQKVKDRFTI SRDNSKNTAF LQMDSLRPED TGVYFCARYY DDHYCLDYWG QGTPVTVSS   119

SEQ ID NO: 23            moltype = AA  length = 122
FEATURE                  Location/Qualifiers
REGION                   1..122
                         note = Description of Artificial Sequence: Synthetic
                          polypeptide
source                   1..122
                         mol_type = protein
                         organism = synthetic construct
SEQUENCE: 23
EVQLVESGGG LVQPGGSLRL SCAASGYSFT GYTMNWVRQA PGKGLEWVAL INPYKGVSTY  60
NQKFKDRFTI SVDKSKNTAY LQMNSLRAED TAVYYCARSG YYGDSDWYFD VWGQGTLVTV  120
SS                                                                 122
```

```
SEQ ID NO: 24          moltype = AA  length = 119
FEATURE                Location/Qualifiers
REGION                 1..119
                       note = Description of Artificial Sequence: Synthetic
                        polypeptide
source                 1..119
                       mol_type = protein
                       organism = synthetic construct
SEQUENCE: 24
QVQLVQSGGG VVQPGRSLRL SCKASGYTFT SYTMHWVRQA PGKGLEWIGY INPSSGYTKY  60
NQKFKDRFTI SADKSKSTAF LQMDSLRPED TGVYFCARWQ DYDVYFDYWG QGTPVTVSS   119

SEQ ID NO: 25          moltype = AA  length = 119
FEATURE                Location/Qualifiers
REGION                 1..119
                       note = Description of Artificial Sequence: Synthetic
                        polypeptide
source                 1..119
                       mol_type = protein
                       organism = synthetic construct
SEQUENCE: 25
QVQLQQSGAE LARPGASVKM SCKASGYTFT RYTMHWVKQR PGQGLEWIGY INPSRGYTNY  60
NQKFKDKATL TTDKSSSTAY MQLSSLTSED SAVYYCARYY DDHYCLDYWG QGTTLTVSS   119

SEQ ID NO: 26          moltype = AA  length = 119
FEATURE                Location/Qualifiers
REGION                 1..119
                       note = Description of Artificial Sequence: Synthetic
                        polypeptide
source                 1..119
                       mol_type = protein
                       organism = synthetic construct
SEQUENCE: 26
DIKLQQSGAE LARPGASVKM SCKTSGYTFT RYTMHWVKQR PGQGLEWIGY INPSRGYTNY  60
NQKFKDKATL TTDKSSSTAY MQLSSLTSED SAVYYCARYY DDHYCLDYWG QGTTLTVSS   119

SEQ ID NO: 27          moltype = AA  length = 119
FEATURE                Location/Qualifiers
REGION                 1..119
                       note = Description of Artificial Sequence: Synthetic
                        polypeptide
source                 1..119
                       mol_type = protein
                       organism = synthetic construct
SEQUENCE: 27
DVQLVQSGAE VKKPGASVKV SCKASGYTFT RYTMHWVRQA PGQGLEWIGY INPSRGYTNY  60
ADSVKGRFTI TTDKSTSTAY MELSSLRSED TATYYCARYY DDHYCLDYWG QGTTVTVSS   119

SEQ ID NO: 28          moltype = AA  length = 125
FEATURE                Location/Qualifiers
REGION                 1..125
                       note = Description of Artificial Sequence: Synthetic
                        polypeptide
source                 1..125
                       mol_type = protein
                       organism = synthetic construct
SEQUENCE: 28
EVQLVESGGG LVQPGGSLKL SCAASGFTFN KYAMNWVRQA PGKGLEWVAR IRSKYNNYAT  60
YYADSVKDRF TISRDDSKNT AYLQMNNLKT EDTAVYYCVR HGNFGNSYIS YWAYWGQGTL  120
VTVSS                                                              125

SEQ ID NO: 29          moltype = AA  length = 125
FEATURE                Location/Qualifiers
REGION                 1..125
                       note = Description of Artificial Sequence: Synthetic
                        polypeptide
source                 1..125
                       mol_type = protein
                       organism = synthetic construct
SEQUENCE: 29
EVQLVESGGG LVQPGGSLRL SCAASGFTFN TYAMNWVRQA PGKGLEWVGR IRSKYNNYAT  60
YYADSVKGRF TISRDDSKNT LYLQMNSLRA EDTAVYYCVR HGNFGNSYVS WFAYWGQGTL  120
VTVSS                                                              125

SEQ ID NO: 30          moltype = AA  length = 125
FEATURE                Location/Qualifiers
REGION                 1..125
                       note = Description of Artificial Sequence: Synthetic
                        polypeptide
```

-continued

```
source                  1..125
                        mol_type = protein
                        organism = synthetic construct
SEQUENCE: 30
EVQLLESGGG LVQPGGSLKL SCAASGFTFN TYAMNWVRQA PGKGLEWVAR IRSKYNNYAT  60
YYADSVKDRF TISRDDSKNT AYLQMNNLKT EDTAVYYCVR HGNFGNSYVS WFAYWGQGTL  120
VTVSS                                                              125

SEQ ID NO: 31           moltype = AA  length = 125
FEATURE                 Location/Qualifiers
REGION                  1..125
                        note = Description of Artificial Sequence: Synthetic
                         polypeptide
source                  1..125
                        mol_type = protein
                        organism = synthetic construct
SEQUENCE: 31
EVKLLESGGG LVQPKGSLKL SCAASGFTFN TYAMNWVRQA PGKGLEWVAR IRSKYNNYAT  60
YYADSVKDRF TISRDDSQSI LYLQMNNLKT EDTAMYYCVR HGNFGNSYVS WFAYWGQGTL  120
VTVSS                                                              125

SEQ ID NO: 32           moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 32
DIQMTQSPSS LSASVGDRVT ITCSASSSVS YMNWYQQTPG KAPKRWIYDT SKLASGVPSR  60
FSGSGSGTDY TFTISSLQPE DIATYYCQQW SSNPFTFGQG TKLQITR                107

SEQ ID NO: 33           moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 33
DIQMTQSPSS LSASVGDRVT ITCRASQDIR NYLNWYQQKP GKAPKLLIYY TSRLESGVPS  60
RFSGSGSGTD YTLTISSLQP EDFATYYCQQ GNTLPWTFGQ GTKVEIK                107

SEQ ID NO: 34           moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 34
DIQMTQSPSS LSASVGDRVT MTCRASSSVS YMHWYQQTPG KAPKPWIYAT SNLASGVPSR  60
FSGSGSGTDY TLTISSLQPE DIATYYCQQW SSNPPTFGQG TKLQITR                107

SEQ ID NO: 35           moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 35
QIVLTQSPAI MSASPGEKVT MTCSASSSVS YMNWYQQKSG TSPKRWIYDT SKLASGVPAH  60
FRGSGSGTSY SLTISGMEAE DAATYYCQQW SSNPFTFGSG TKLEINR                107

SEQ ID NO: 36           moltype = AA  length = 106
FEATURE                 Location/Qualifiers
REGION                  1..106
                        note = Description of Artificial Sequence: Synthetic
                         polypeptide
source                  1..106
                        mol_type = protein
                        organism = synthetic construct
SEQUENCE: 36
DIQLTQSPAI MSASPGEKVT MTCRASSSVS YMNWYQQKSG TSPKRWIYDT SKVASGVPYR  60
```

```
FSGSGSGTSY SLTISSMEAE DAATYYCQQW SSNPLTFGAG TKLELK                106

SEQ ID NO: 37          moltype = AA  length = 106
FEATURE                Location/Qualifiers
REGION                 1..106
                       note = Description of Artificial Sequence: Synthetic
                        polypeptide
source                 1..106
                       mol_type = protein
                       organism = synthetic construct
SEQUENCE: 37
DIVLTQSPAT LSLSPGERAT LSCRASQSVS YMNWYQQKPG KAPKRWIYDT SKVASGVPAR  60
FSGSGSGTDY SLTINSLEAE DAATYYCQQW SSNPLTFGGG TKVEIK                106

SEQ ID NO: 38          moltype = AA  length = 109
FEATURE                Location/Qualifiers
REGION                 1..109
                       note = Description of Artificial Sequence: Synthetic
                        polypeptide
source                 1..109
                       mol_type = protein
                       organism = synthetic construct
SEQUENCE: 38
QTVVTQEPSL TVSPGGTVTL TCGSSTGAVT SGYYPNWVQQ KPGQAPRGLI GGTKFLAPGT  60
PARFSGSLLG GKAALTLSGV QPEDEAEYYC ALWYSNRWVF GGGTKLTVL             109

SEQ ID NO: 39          moltype = AA  length = 109
FEATURE                Location/Qualifiers
REGION                 1..109
                       note = Description of Artificial Sequence: Synthetic
                        polypeptide
source                 1..109
                       mol_type = protein
                       organism = synthetic construct
SEQUENCE: 39
QAVVTQEPSL TVSPGGTVTL TCGSSTGAVT TSNYANWVQQ KPGQAPRGLI GGTNKRAPGV  60
PARFSGSLLG GKAALTLSGA QPEDEAEYYC ALWYSNLWVF GGGTKLTVL             109

SEQ ID NO: 40          moltype = AA  length = 109
FEATURE                Location/Qualifiers
REGION                 1..109
                       note = Description of Artificial Sequence: Synthetic
                        polypeptide
source                 1..109
                       mol_type = protein
                       organism = synthetic construct
SEQUENCE: 40
ELVVTQEPSL TVSPGGTVTL TCRSSTGAVT TSNYANWVQQ KPGQAPRGLI GGTNKRAPGT  60
PARFSGSLLG GKAALTLSGV QPEDEAEYYC ALWYSNLWVF GGGTKLTVL             109

SEQ ID NO: 41          moltype = AA  length = 109
FEATURE                Location/Qualifiers
REGION                 1..109
                       note = Description of Artificial Sequence: Synthetic
                        polypeptide
source                 1..109
                       mol_type = protein
                       organism = synthetic construct
SEQUENCE: 41
QAVVTQESAL TTSPGETVTL TCRSSTGAVT TSNYANWVQE KPDHLFTGLI GGTNKRAPGV  60
PARFSGSLIG DKAALTITGA QTEDEAIYFC ALWYSNLWVF GGGTKLTVL             109

SEQ ID NO: 42          moltype = AA  length = 123
FEATURE                Location/Qualifiers
REGION                 1..123
                       note = Description of Artificial Sequence: Synthetic
                        polypeptide
source                 1..123
                       mol_type = protein
                       organism = synthetic construct
SEQUENCE: 42
QVQLVQSGAE VKKPGASVKV SCKASGFNIK DTYIHWVRQA PGQRLEWMGR IDPANGYTKY  60
DPKFQGRVTI TADTSASTAY MELSSLRSED TAVYYCAREG YYGNYGVYAM DYWGQGTLVT  120
VSS                                                               123

SEQ ID NO: 43          moltype = AA  length = 122
FEATURE                Location/Qualifiers
REGION                 1..122
                       note = Description of Artificial Sequence: Synthetic
```

```
                          polypeptide
source                   1..122
                         mol_type = protein
                         organism = synthetic construct
SEQUENCE: 43
EVQLVESGGG LVQPGGSLRL SCAASGFTFS SYDIHWVRQA TGKGLEWVSA IGPAGDTYYP  60
GSVKGRFTIS RENAKNSLYL QMNSLRAGDT AVYYCARGLI TFGGLIAPFD YWGQGTLVTV  120
SS                                                                122

SEQ ID NO: 44            moltype = AA  length = 120
FEATURE                  Location/Qualifiers
REGION                   1..120
                         note = Description of Artificial Sequence: Synthetic
                          polypeptide
source                   1..120
                         mol_type = protein
                         organism = synthetic construct
SEQUENCE: 44
QVKLEQSGAE VVKPGASVKL SCKASGFNIK DSYMHWLRQG PGQRLEWIGW IDPENGDTEY  60
APKFQGKATF TTDTSANTAY LGLSSLRPED TAVYYCNEGT PTGPYYFDYW GQGTLVTVSS  120

SEQ ID NO: 45            moltype = AA  length = 121
FEATURE                  Location/Qualifiers
REGION                   1..121
                         note = Description of Artificial Sequence: Synthetic
                          polypeptide
source                   1..121
                         mol_type = protein
                         organism = synthetic construct
SEQUENCE: 45
EVQLVESGGG LVQPGGSLRL SCAASGFNIK DTYMHWVRQA PGKGLEWVAR IDPANGNSKY  60
ADSVKGRFTI SADTSKNTAY LQMNSLRAED TAVYYCAPFG YYVSDYAMAY WGQGTLVTVS  120
S                                                                 121

SEQ ID NO: 46            moltype = AA  length = 121
FEATURE                  Location/Qualifiers
REGION                   1..121
                         note = Description of Artificial Sequence: Synthetic
                          polypeptide
source                   1..121
                         mol_type = protein
                         organism = synthetic construct
SEQUENCE: 46
EVQLVESGGG LVQPGGSLRL SCAASGFNIK DTYMHWVRQA PGKGLEWVAR IDPANGNSKY  60
VPKFQGRATI SADTSKNTAY LQMNSLRAED TAVYYCAPFG YYVSDYAMAY WGQGTLVTVS  120
S                                                                 121

SEQ ID NO: 47            moltype = AA  length = 119
FEATURE                  Location/Qualifiers
REGION                   1..119
                         note = Description of Artificial Sequence: Synthetic
                          polypeptide
source                   1..119
                         mol_type = protein
                         organism = synthetic construct
SEQUENCE: 47
EVQLVESGGG VVQPGRSLRL SCSASGFDFT TYWMSWVRQA PGKGLEWIGE IHPDSSTINY  60
APSLKDRFTI SRDNAKNTLF LQMDSLRPED TGVYFCASLY FGFPWFAYWG QGTPVTVSS   119

SEQ ID NO: 48            moltype = AA  length = 121
FEATURE                  Location/Qualifiers
REGION                   1..121
                         note = Description of Artificial Sequence: Synthetic
                          polypeptide
source                   1..121
                         mol_type = protein
                         organism = synthetic construct
SEQUENCE: 48
EVKLVESGGG LVQPGGSLRL SCATSGFTFT DYYMNWVRQP PGKALEWLGF IGNKANGYTT  60
EYSASVKGRF TISRDKSQSI LYLQMNTLRA EDSATYYCTR DRGLRFYFDY WGQGTTLTVS  120
S                                                                 121

SEQ ID NO: 49            moltype = AA  length = 121
FEATURE                  Location/Qualifiers
REGION                   1..121
                         note = Description of Artificial Sequence: Synthetic
                          polypeptide
source                   1..121
                         mol_type = protein
```

```
                       organism = synthetic construct
SEQUENCE: 49
EVQLVESGGG LVQPGRSLRL SCAASGFTVS SYWMHWVRQA PGKGLEWVGF IRNKANGGTT  60
EYAASVKGRF TISRDDSKNT LYLQMNSLRA EDTAVYYCAR DRGLRFYFDY WGQGTTVTVS  120
S                                                                  121

SEQ ID NO: 50          moltype = AA  length = 124
FEATURE                Location/Qualifiers
REGION                 1..124
                       note = Description of Artificial Sequence: Synthetic
                        polypeptide
source                 1..124
                       mol_type = protein
                       organism = synthetic construct
SEQUENCE: 50
QVQLQQSGAE LVRPGSSVKI SCKASGYAFS SYWMNWVKQR PGQGLEWIGQ IWPGDGDTNY  60
NGKFKGKATL TADESSSTAY MQLSSLASED SAVYFCARRE TTTVGRYYYA MDYWGQGTTV  120
TVSS                                                               124

SEQ ID NO: 51          moltype = AA  length = 122
FEATURE                Location/Qualifiers
REGION                 1..122
                       note = Description of Artificial Sequence: Synthetic
                        polypeptide
source                 1..122
                       mol_type = protein
                       organism = synthetic construct
SEQUENCE: 51
EVQLVESGGG LVQPGRSLRL SCAASGFTFN DYAMHWVRQA PGKGLEWVST ISWNSGSIGY  60
ADSVKGRFTI SRDNAKKSLY LQMNSLRAED TALYYCAKDI QYGNYYYGMD VWGQGTTVTV  120
SS                                                                 122

SEQ ID NO: 52          moltype = AA  length = 122
FEATURE                Location/Qualifiers
REGION                 1..122
                       note = Description of Artificial Sequence: Synthetic
                        polypeptide
source                 1..122
                       mol_type = protein
                       organism = synthetic construct
SEQUENCE: 52
QAYLQQSGAE LVRPGASVKM SCKASGYTFT SYNMHWVKQT PRQGLEWIGA IYPGNGDTSY  60
NQKFKGKATL TVDKSSSTAY MQLSSLTSED SAVYFCARVV YYSNSYWYFD VWGTGTTVTV  120
SG                                                                 122

SEQ ID NO: 53          moltype = AA  length = 119
FEATURE                Location/Qualifiers
REGION                 1..119
                       note = Description of Artificial Sequence: Synthetic
                        polypeptide
source                 1..119
                       mol_type = protein
                       organism = synthetic construct
SEQUENCE: 53
QVQLVQSGAE VKKPGSSVKV SCKASGYAFS YSWINWVRQA PGQGLEWMGR IFPGDGDTDY  60
NGKFKGRVTI TADKSTSTAY MELSSLRSED TAVYYCARNV FDGYWLVYWG QGTLVTVSS   119

SEQ ID NO: 54          moltype = AA  length = 122
FEATURE                Location/Qualifiers
REGION                 1..122
                       note = Description of Artificial Sequence: Synthetic
                        polypeptide
source                 1..122
                       mol_type = protein
                       organism = synthetic construct
SEQUENCE: 54
EVQLVESGGG LVQPGGSLRL SCAASGYTFT SYNMHWVRQA PGKGLEWVGA IYPGNGDTSY  60
NQKFKGRFTI SVDKSKNTLY LQMNSLRAED TAVYYCARVV YYSNSYWYFD VWGQGTLVTV  120
SS                                                                 122

SEQ ID NO: 55          moltype = AA  length = 121
FEATURE                Location/Qualifiers
REGION                 1..121
                       note = Description of Artificial Sequence: Synthetic
                        polypeptide
source                 1..121
                       mol_type = protein
                       organism = synthetic construct
SEQUENCE: 55
```

-continued

```
QVQLQQPGAE LVKPGASVKM SCKASGYTFT SYNMHWVKQT PGRGLEWIGA IYPGNGDTSY  60
NQKFKGKATL TADKSSSTAY MQLSSLTSED SAVYYCARST YYGGDWYFNV WGAGTTVTVS  120
A                                                                  121

SEQ ID NO: 56          moltype = AA  length = 122
FEATURE                Location/Qualifiers
REGION                 1..122
                       note = Description of Artificial Sequence: Synthetic
                        polypeptide
source                 1..122
                       mol_type = protein
                       organism = synthetic construct
SEQUENCE: 56
QAYLQQSGAE LVRPGASVKM SCKASGYTFT SYNMHWVKQT PRQGLEWIGA IYPGNGDTSY  60
NQKFKGKATL TVDKSSSTAY MQLSSLTSED SAVYFCARVV YYSNSYWYFD VWGTGTTVTV  120
SA                                                                 122

SEQ ID NO: 57          moltype = AA  length = 114
FEATURE                Location/Qualifiers
REGION                 1..114
                       note = Description of Artificial Sequence: Synthetic
                        polypeptide
source                 1..114
                       mol_type = protein
                       organism = synthetic construct
SEQUENCE: 57
QLVQSGAEVK KPGSSVKVSC KASGYTITDS NIHWVRQAPG QSLEWIGYIY PYNGGTDYNQ  60
KFKNRATLTV DNPTNTAYME LSSLRSEDTD FYYCVNGNPW LAYWGQGTLV TVSS        114

SEQ ID NO: 58          moltype = AA  length = 122
FEATURE                Location/Qualifiers
REGION                 1..122
                       note = Description of Artificial Sequence: Synthetic
                        polypeptide
source                 1..122
                       mol_type = protein
                       organism = synthetic construct
SEQUENCE: 58
EVQLLESGGG LVQPGGSLRL SCAVSGFTFN SFAMSWVRQA PGKGLEWVSA ISGSGGGTYY  60
ADSVKGRFTI SRDNSKNTLY LQMNSLRAED TAVYFCAKDK ILWFGEPVFD YWGQGTLVTV  120
SS                                                                 122

SEQ ID NO: 59          moltype = AA  length = 118
FEATURE                Location/Qualifiers
REGION                 1..118
                       note = Description of Artificial Sequence: Synthetic
                        polypeptide
source                 1..118
                       mol_type = protein
                       organism = synthetic construct
SEQUENCE: 59
QIQLVQSGPE VKKPGETVKI SCKASGYTFT NYGMNWVKQA PGKGLKWMGW INTYTGEPTY  60
ADAFKGRFAF SLETSASTAY LQINNLKNED TATYFCARDY GDYGMDYWGQ GTSVTVSS    118

SEQ ID NO: 60          moltype = AA  length = 118
FEATURE                Location/Qualifiers
REGION                 1..118
                       note = Description of Artificial Sequence: Synthetic
                        polypeptide
source                 1..118
                       mol_type = protein
                       organism = synthetic construct
SEQUENCE: 60
QVQLQQSGTE LMTPGASVTM SCKTSGYTFS TYWIEWVKQR PGHGLEWIGE ILGPSGYTDY  60
NEKFKAKATF TADTSSNTAY MQLSSLASED SAVYYCARWD RLYAMDYWGG GTSVTVSS    118

SEQ ID NO: 61          moltype = AA  length = 118
FEATURE                Location/Qualifiers
REGION                 1..118
                       note = Description of Artificial Sequence: Synthetic
                        polypeptide
source                 1..118
                       mol_type = protein
                       organism = synthetic construct
SEQUENCE: 61
QVQLVESGGG VVQPGRSLRL SCAASGFTFS SYIMHWVRQA PGKGLEWVAV ISYDGRNKYY  60
ADSVKGRFTI SRDNSKNTLY LQMNSLRAED TAVYYCARDT DGYDFDYWGQ GTLVTVSS    118

SEQ ID NO: 62          moltype = AA  length = 119
```

-continued

```
FEATURE                Location/Qualifiers
REGION                 1..119
                       note = Description of Artificial Sequence: Synthetic
                        polypeptide
source                 1..119
                       mol_type = protein
                       organism = synthetic construct
SEQUENCE: 62
QIQLVESGGG VVQPGRSLRL SCAASGFTFG YYAMHWVRQA PGKGLEWVAV ISYDGSIKYY  60
ADSVKGRFTI SRDNSKNTLY LQMNSLRAED TAVYYCAREG PYSNYLDYWG QGTLVTVSS   119

SEQ ID NO: 63          moltype = AA  length = 118
FEATURE                Location/Qualifiers
REGION                 1..118
                       note = Description of Artificial Sequence: Synthetic
                        polypeptide
source                 1..118
                       mol_type = protein
                       organism = synthetic construct
SEQUENCE: 63
QVQLVESGGG VVQPGRSLRL SCATSGFTFS DYGMHWVRQA PGKGLEWVAV IWYDGSNKYY  60
ADSVKGRFTI SRDNSKKTLS LQMNSLRAED TAVYYCARDS IMVRGDYWGQ GTLVTVSS    118

SEQ ID NO: 64          moltype = AA  length = 118
FEATURE                Location/Qualifiers
REGION                 1..118
                       note = Description of Artificial Sequence: Synthetic
                        polypeptide
source                 1..118
                       mol_type = protein
                       organism = synthetic construct
SEQUENCE: 64
QVQLVESGGG VVQPGRSLRL SCAASGFTFS DHGMHWVRQA PGKGLEWVAV IWYDGSNKYY  60
ADSVKGRFTI SRDNSKNTLY LQMNSLRAED TAVYYCARDS IMVRGDYWGQ GTLVTVSS    118

SEQ ID NO: 65          moltype = AA  length = 122
FEATURE                Location/Qualifiers
REGION                 1..122
                       note = Description of Artificial Sequence: Synthetic
                        polypeptide
source                 1..122
                       mol_type = protein
                       organism = synthetic construct
SEQUENCE: 65
QVQLQESGPG LVKPSETLSL TCTVSGGSVS SDYYYWSWIR QPPGKGLEWL GYIYYSGSTN  60
YNPSLKSRVT ISVDTSKNQF SLKLRSVTTA DTAVYYCARG DGDYGGNCFD YWGQGTLVTV  120
SS                                                                 122

SEQ ID NO: 66          moltype = AA  length = 117
FEATURE                Location/Qualifiers
REGION                 1..117
                       note = Description of Artificial Sequence: Synthetic
                        polypeptide
source                 1..117
                       mol_type = protein
                       organism = synthetic construct
SEQUENCE: 66
QVQLVQSGAE VKKPGASVKV SCKASGYTFT SYGFSWVRQA PGQGLEWMGW ISASNGNTYY  60
AQKLQGRVTM TTDTSTSTAY MELRSLRSDD TAVYYCARVY ADYADYWGQG TLVTVSS     117

SEQ ID NO: 67          moltype = AA  length = 115
FEATURE                Location/Qualifiers
REGION                 1..115
                       note = Description of Artificial Sequence: Synthetic
                        polypeptide
source                 1..115
                       mol_type = protein
                       organism = synthetic construct
SEQUENCE: 67
QVQLVQSGAE VKKPGASVKV SCKASGYTFT DYYMHWVRQA PGQGLEWMGR VNPNRRGTTY  60
NQKFEGRVTM TTDTSTSTAY MELRSLRSDD TAVYYCARAN WLDYWGQGTT VTVSS       115

SEQ ID NO: 68          moltype = AA  length = 119
FEATURE                Location/Qualifiers
REGION                 1..119
                       note = Description of Artificial Sequence: Synthetic
                        polypeptide
source                 1..119
                       mol_type = protein
```

```
                       organism = synthetic construct
SEQUENCE: 68
EVQLVESGGG LVQPGGSLRL SCAASGYTFT SYWLHWVRQA PGKGLEWVGM IDPSNSDTRF  60
NPNFKDRFTI SADTSKNTAY LQMNSLRAED TAVYYCATYR SYVTPLDYWG QGTLVTVSS   119

SEQ ID NO: 69          moltype = AA  length = 125
FEATURE                Location/Qualifiers
REGION                 1..125
                       note = Description of Artificial Sequence: Synthetic
                        polypeptide
source                 1..125
                       mol_type = protein
                       organism = synthetic construct
SEQUENCE: 69
QVQLVESGGG VVQPGRSLRL SCAASGFTFS SYGMHWVRQA PGKGLEWVAV IWYDGSNKYY  60
ADSVKGRFTI SRDNSKNTLY LQMNSLRAED TAVYYCARDP RGATLYYYYY GMDVWGQGTT  120
VTVSS                                                             125

SEQ ID NO: 70          moltype = AA  length = 118
FEATURE                Location/Qualifiers
REGION                 1..118
                       note = Description of Artificial Sequence: Synthetic
                        polypeptide
source                 1..118
                       mol_type = protein
                       organism = synthetic construct
SEQUENCE: 70
QVQLVESGGG VVQPGRSLRL SCAASGFTFS SYTMHWVRQA PGKGLEWVTF ISYDGNNKYY  60
ADSVKGRFTI SRDNSKNTLY LQMNSLRAED TAIYYCARTG WLGPFDYWGQ GTLVTVSS    118

SEQ ID NO: 71          moltype = AA  length = 123
FEATURE                Location/Qualifiers
REGION                 1..123
                       note = Description of Artificial Sequence: Synthetic
                        polypeptide
source                 1..123
                       mol_type = protein
                       organism = synthetic construct
SEQUENCE: 71
QVQLQESGPG LVKPSQTLSL TCTVSGGSIS SGGYYWSWIR QHPGKGLEWI GIIYYSGSTY  60
YNPSLKSRVT ISVDTSKNQF SLKLNSVTAA DTAVFYCARV AIVTTIPGGM DVWGQGTTVT  120
VSS                                                               123

SEQ ID NO: 72          moltype = AA  length = 120
FEATURE                Location/Qualifiers
REGION                 1..120
                       note = Description of Artificial Sequence: Synthetic
                        polypeptide
source                 1..120
                       mol_type = protein
                       organism = synthetic construct
SEQUENCE: 72
EVQLLEQSGA ELVRPGTSVK ISCKASGYAF TNYWLGWVKQ RPGHGLEWIG DIFPGSGNIH  60
YNEKFKGKAT LTADKSSSTA YMQLSSLTFE DSAVYFCARL RNWDEPMDYW GQGTTVTVSS  120

SEQ ID NO: 73          moltype = AA  length = 127
FEATURE                Location/Qualifiers
REGION                 1..127
                       note = Description of Artificial Sequence: Synthetic
                        polypeptide
source                 1..127
                       mol_type = protein
                       organism = synthetic construct
SEQUENCE: 73
EVQLLESGGG VVQPGRSLRL SCAASGFTFS SYGMHWVRQA PGKGLEWVAV ISYDGSNKYY  60
ADSVKGRFTI SRDNSKNTLY LQMNSLRAED TAVYYCAKDM GWGSGWRPYY YYGMDVWGQG  120
TTVTVSS                                                           127

SEQ ID NO: 74          moltype = AA  length = 116
FEATURE                Location/Qualifiers
REGION                 1..116
                       note = Description of Artificial Sequence: Synthetic
                        polypeptide
source                 1..116
                       mol_type = protein
                       organism = synthetic construct
SEQUENCE: 74
QVQLQQSGAE LVRPGTSVKV SCKASGYAFT NYLIEWVKQR PGQGLEWIGV INPGSGGTNY  60
NEKFKGKATL TADKSSSTAY MQLSSLTSDD SAVYFCARDG PWFAYWGQGT LVTVSA      116
```

```
SEQ ID NO: 75           moltype = AA  length = 116
FEATURE                 Location/Qualifiers
REGION                  1..116
                        note = Description of Artificial Sequence: Synthetic
                         polypeptide
source                  1..116
                        mol_type = protein
                        organism = synthetic construct
SEQUENCE: 75
QIQLVQSGPE LKKPGETVKI SCKASGYTFT NYGMNWVRQA PGKGLKWMGW INTYTGEPTY  60
ADDFKGRFVF SLETSASTAF LQLNNLRSED TATYFCVRFI SKGDYWGQGT SVTVSS      116

SEQ ID NO: 76           moltype = AA  length = 114
FEATURE                 Location/Qualifiers
REGION                  1..114
                        note = Description of Artificial Sequence: Synthetic
                         polypeptide
source                  1..114
                        mol_type = protein
                        organism = synthetic construct
SEQUENCE: 76
VQLQQSDAEL VKPGASVKIS CKASGYTFTD HAIHWVKQNP EQGLEWIGYF SPGNDDFKYN  60
ERFKGKATLT ADKSSSTAYV QLNSLTSEDS AVYFCTRSLN MAYWGQGTSV TVSS        114

SEQ ID NO: 77           moltype = AA  length = 116
FEATURE                 Location/Qualifiers
REGION                  1..116
                        note = Description of Artificial Sequence: Synthetic
                         polypeptide
source                  1..116
                        mol_type = protein
                        organism = synthetic construct
SEQUENCE: 77
EVQLVQSGPE VKKPGASVKV SCKASGYTFT NYGMNWVRQA PGQGLEWMGW INTYTGEPTY  60
GEDFKGRFAF SLDTSASTAY MELSSLRSED TAVYFCARFG NYVDYWGQGS LVTVSS      116

SEQ ID NO: 78           moltype = AA  length = 116
FEATURE                 Location/Qualifiers
REGION                  1..116
                        note = Description of Artificial Sequence: Synthetic
                         polypeptide
source                  1..116
                        mol_type = protein
                        organism = synthetic construct
SEQUENCE: 78
EVQLVQSGPG LVQPGGSVRI SCAASGYTFT NYGMNWVKQA PGKGLEWMGW INTYTGESTY  60
ADSFKGRFTF SLDTSASAAY LQINSLRAED TAVYYCARFA IKGDYWGQGT LLTVSS      116

SEQ ID NO: 79           moltype = AA  length = 128
FEATURE                 Location/Qualifiers
REGION                  1..128
                        note = Description of Artificial Sequence: Synthetic
                         polypeptide
source                  1..128
                        mol_type = protein
                        organism = synthetic construct
SEQUENCE: 79
EVQLLESGGG LVQPGGSLRL SCAASGFTFS HYMMAWVRQA PGKGLEWVSR IGPSGGPTHY  60
ADSVKGRFTI SRDNSKNTLY LQMNSLRAED TAVYYCAGYD SGYDYVAVAG PAEYFQHWGQ  120
GTLVTVSS                                                           128

SEQ ID NO: 80           moltype = AA  length = 119
FEATURE                 Location/Qualifiers
REGION                  1..119
                        note = Description of Artificial Sequence: Synthetic
                         polypeptide
source                  1..119
                        mol_type = protein
                        organism = synthetic construct
SEQUENCE: 80
EVQLVESGGG VVQPGRSLRL SCSASGFTFS GYGLSWVRQA PGKGLEWVAM ISSGGSYTYY  60
ADSVKGRFAI SRDNAKNTLF LQMDSLRPED TGVYFCARHG DDPAWFAYWG QGTPVTVSS   119

SEQ ID NO: 81           moltype = AA  length = 118
FEATURE                 Location/Qualifiers
REGION                  1..118
                        note = Description of Artificial Sequence: Synthetic
                         polypeptide
```

```
source                  1..118
                        mol_type = protein
                        organism = synthetic construct
SEQUENCE: 81
QVQLVQSGAE VVKPGASVKI SCKASGYTFT GYFMNWVKQS PGQSLEWIGR IHPYDGDTFY  60
NQKFQGKATL TVDKSSNTAH MELLSLTSED FAVYYCTRYD GSRAMDYWGQ GTTVTVSS    118

SEQ ID NO: 82           moltype = AA  length = 118
FEATURE                 Location/Qualifiers
REGION                  1..118
                        note = Description of Artificial Sequence: Synthetic
                         polypeptide
source                  1..118
                        mol_type = protein
                        organism = synthetic construct
SEQUENCE: 82
QVQLVQSGAE VVKPGASVKI SCKASGYTFT GYFMNWVKQS PGQSLEWIGR IHPYDGDTFY  60
NQKFQGKATL TVDKSSNTAH MELLSLTSED FAVYYCTRYD GSRAMDYWGQ GTTVTVSS    118

SEQ ID NO: 83           moltype = AA  length = 109
FEATURE                 Location/Qualifiers
REGION                  1..109
                        note = Description of Artificial Sequence: Synthetic
                         polypeptide
source                  1..109
                        mol_type = protein
                        organism = synthetic construct
SEQUENCE: 83
GPELVKPGAS VKISCKASDY SFTGYFMNWV MQSHGKSLEW IGRIFPYNGD TFYNQKFKGR  60
ATLTVDKSSS TAHMELRSLA SEDSAVYFCA RGTHYFDYWG QGTTLTVSS              109

SEQ ID NO: 84           moltype = AA  length = 115
FEATURE                 Location/Qualifiers
REGION                  1..115
                        note = Description of Artificial Sequence: Synthetic
                         polypeptide
source                  1..115
                        mol_type = protein
                        organism = synthetic construct
SEQUENCE: 84
QVQLVQSGAE VKKPGASVKV SCKASGYTFT DYEMHWVRQA PGQGLEWMGA LDPKTGDTAY  60
SQKFKGRVTL TADKSTSTAY MELSSLTSED TAVYYCTRFY SYTYWGQGTL VTVSS       115

SEQ ID NO: 85           moltype = AA  length = 117
FEATURE                 Location/Qualifiers
REGION                  1..117
                        note = Description of Artificial Sequence: Synthetic
                         polypeptide
source                  1..117
                        mol_type = protein
                        organism = synthetic construct
SEQUENCE: 85
EVQLVQSGAE VKKPGESLKI SCKGSGYSFT SYWIAWVRQM PGKGLEWMGI IFPGDSDTRY  60
SPSFQGQVTI SADRSIRTAY LQWSSLKASD TALYYCARTR EGYFDYWGQG TLVTVSS     117

SEQ ID NO: 86           moltype = AA  length = 117
FEATURE                 Location/Qualifiers
REGION                  1..117
                        note = Description of Artificial Sequence: Synthetic
                         polypeptide
source                  1..117
                        mol_type = protein
                        organism = synthetic construct
SEQUENCE: 86
EVQLVQSGAE VKKPGESLKI SCKGSGYSFT NYWIAWVRQM PGKGLEWMGI IYPGDSDTRY  60
SPSFQGQVTI SADKSIRTAY LQWSSLKASD TAMYYCARTR EGYFDYWGQG TLVTVSS     117

SEQ ID NO: 87           moltype = AA  length = 117
FEATURE                 Location/Qualifiers
REGION                  1..117
                        note = Description of Artificial Sequence: Synthetic
                         polypeptide
source                  1..117
                        mol_type = protein
                        organism = synthetic construct
SEQUENCE: 87
EVQLVQSGAD VTKPGESLKI SCKVSGYRFT NYWIGWMRQM SGKGLEWMGI IYPGDSDTRY  60
SPSFQGHVTI SADKSINTAY LRWSSLKASD TAIYYCARTR EGFFDYWGQG TPVTVSS     117
```

```
SEQ ID NO: 88          moltype = AA  length = 124
FEATURE                Location/Qualifiers
REGION                 1..124
                       note = Description of Artificial Sequence: Synthetic
                        polypeptide
source                 1..124
                       mol_type = protein
                       organism = synthetic construct
SEQUENCE: 88
QVQLVESGGG VVQSGRSLRL SCAASGFTFR NYGMHWVRQA PGKGLEWVAV IWYDGSDKYY  60
ADSVRGRFTI SRDNSKNTLY LQMNSLRAED TAVYYCARDG YDILTGNPRD FDYWGQGTLV  120
TVSS                                                               124

SEQ ID NO: 89          moltype = AA  length = 119
FEATURE                Location/Qualifiers
REGION                 1..119
                       note = Description of Artificial Sequence: Synthetic
                        polypeptide
source                 1..119
                       mol_type = protein
                       organism = synthetic construct
SEQUENCE: 89
QVQLKQSGPG LVQPSQSLSI TCTVSGFSLT NYGVHWVRQS PGKGLEWLGV IWSGGNTDYN  60
TPFTSRLSIN KDNSKSQVFF KMNSLQSNDT AIYYCARALT YYDYEFAYWG QGTLVTVSA   119

SEQ ID NO: 90          moltype = AA  length = 120
FEATURE                Location/Qualifiers
REGION                 1..120
                       note = Description of Artificial Sequence: Synthetic
                        polypeptide
source                 1..120
                       mol_type = protein
                       organism = synthetic construct
SEQUENCE: 90
QVQLVQSGAE VKKPGSSVKV SCKASGFTFT DYKIHWVRQA PGQGLEWMGY FNPNSGYSTY  60
AQKFQGRVTI TADKSTSTAY MELSSLRSED TAVYYCARLS PGGYYVMDAW GQGTTVTVSS  120

SEQ ID NO: 91          moltype = AA  length = 125
FEATURE                Location/Qualifiers
REGION                 1..125
                       note = Description of Artificial Sequence: Synthetic
                        polypeptide
source                 1..125
                       mol_type = protein
                       organism = synthetic construct
SEQUENCE: 91
QVQLVESGGG VVQPGRSLRL SCAASGFTFS TYGMHWVRQA PGKGLEWVAV IWDDGSYKYY  60
GDSVKGRFTI SRDNSKNTLY LQMNSLRAED TAVYYCARDG ITMVRGVMKD YFDYWGQGTL  120
VTVSS                                                              125

SEQ ID NO: 92          moltype = AA  length = 121
FEATURE                Location/Qualifiers
REGION                 1..121
                       note = Description of Artificial Sequence: Synthetic
                        polypeptide
source                 1..121
                       mol_type = protein
                       organism = synthetic construct
SEQUENCE: 92
QVQLQESGPG LVKPSQTLSL TCTVSGGSIS SGDYYWSWIR QPPGKGLEWI GYIYYSGSTD  60
YNPSLKSRVT MSVDTSKNQF SLKVNSVTAA DTAVYYCARV SIFGVGTFDY WGQGTLVTVS  120
S                                                                  121

SEQ ID NO: 93          moltype = AA  length = 121
FEATURE                Location/Qualifiers
REGION                 1..121
                       note = Description of Artificial Sequence: Synthetic
                        polypeptide
source                 1..121
                       mol_type = protein
                       organism = synthetic construct
SEQUENCE: 93
QVQLVQSGAE VKKPGSSVKV SCKASGGTFS SYAISWVRQA PGQGLEWMGS IIPIFGTVNY  60
AQKFQGRVTI TADESTSTAY MELSSLRSED TAVYYCARDP SVNLYWYFDL WGRGTLVTVS  120
S                                                                  121

SEQ ID NO: 94          moltype = AA  length = 119
FEATURE                Location/Qualifiers
REGION                 1..119
```

```
                          note = Description of Artificial Sequence: Synthetic
                           polypeptide
source                    1..119
                          mol_type = protein
                          organism = synthetic construct
SEQUENCE: 94
QVQLVQSGAE VKKPGSSVKV SCKASGGTFG SYAISWVRQA PGQGLEWMGS IIPIFGAANP  60
AQKSQGRVTI TADESTSTAY MELSSLRSED TAVYYCAKMG RGKVAFDIWG QGTMVTVSS   119

SEQ ID NO: 95             moltype = AA  length = 123
FEATURE                   Location/Qualifiers
REGION                    1..123
                          note = Description of Artificial Sequence: Synthetic
                           polypeptide
source                    1..123
                          mol_type = protein
                          organism = synthetic construct
SEQUENCE: 95
QVQLVQSGAE VKKPGASVKV SCKASGYAFT SYGINWVRQA PGQGLEWMGW ISAYNGNTYY  60
AQKLRGRVTM TTDTSTSTAY MELRSLRSDD TAVYYCARDL GGYGSGSVPF DPWGQGTLVT  120
VSS                                                                123

SEQ ID NO: 96             moltype = AA  length = 123
FEATURE                   Location/Qualifiers
REGION                    1..123
                          note = Description of Artificial Sequence: Synthetic
                           polypeptide
source                    1..123
                          mol_type = protein
                          organism = synthetic construct
SEQUENCE: 96
QVQLQQSGAE VKKPGSSVKV SCKASGYTFT NYYIYWVRQA PGQGLEWIGG INPTSGGSNF  60
NEKFKTRVTI TADESSTTAY MELSSLRSED TAFYFCTRQG LWFDSDGRGF DFWGQGTTVT  120
VSS                                                                123

SEQ ID NO: 97             moltype = AA  length = 119
FEATURE                   Location/Qualifiers
REGION                    1..119
                          note = Description of Artificial Sequence: Synthetic
                           polypeptide
source                    1..119
                          mol_type = protein
                          organism = synthetic construct
SEQUENCE: 97
QVQLQESGPG LVKPSETLSL TCTVSGGSVS SGDYYWTWIR QSPGKGLEWI GHIYYSGNTN  60
YNPSLKSRLT ISIDTSKTQF SLKLSSVTAA DTAIYYCVRD RVTGAFDIWG QGTMVTVSS   119

SEQ ID NO: 98             moltype = AA  length = 118
FEATURE                   Location/Qualifiers
REGION                    1..118
                          note = Description of Artificial Sequence: Synthetic
                           polypeptide
source                    1..118
                          mol_type = protein
                          organism = synthetic construct
SEQUENCE: 98
QIQLVQSGPE LKKPGETVKI SCKASGYTFT EYPIHWVKQA PGKGFKWMGM IYTDIGKPTY  60
AEEFKGRFAF SLETSASTAY LQINNLKNED TATYFCVRDR YDSLFDYWGQ GTTLTVSS    118

SEQ ID NO: 99             moltype = AA  length = 121
FEATURE                   Location/Qualifiers
REGION                    1..121
                          note = Description of Artificial Sequence: Synthetic
                           polypeptide
source                    1..121
                          mol_type = protein
                          organism = synthetic construct
SEQUENCE: 99
EMQLVESGGG FVKPGGSLKL SCAASGFAFS HYDMSWVRQT PKQRLEWVAY IASGGDITYY  60
ADTVKGRFTI SRDNAQNTLY LQMSSLKSED TAMFYCSRSS YGNNGDALDF WGQGTSVTVS  120
S                                                                  121

SEQ ID NO: 100            moltype = AA  length = 119
FEATURE                   Location/Qualifiers
REGION                    1..119
                          note = Description of Artificial Sequence: Synthetic
                           polypeptide
source                    1..119
                          mol_type = protein
```

```
                         organism = synthetic construct
SEQUENCE: 100
QVQLVESGGG LVQPGGSLRL SCAASGFTFS SYAMGWVRQA PGKGLEWVSS ISGSSRYIYY  60
ADSVKGRFTI SRDNSKNTLY LQMNSLRAED TAVYYCAKMD ASGSYFNFWG QGTLVTVSS   119

SEQ ID NO: 101           moltype = AA  length = 115
FEATURE                  Location/Qualifiers
REGION                   1..115
                         note = Description of Artificial Sequence: Synthetic
                          polypeptide
source                   1..115
                         mol_type = protein
                         organism = synthetic construct
SEQUENCE: 101
QVQLLQSAAE VKKPGESLKI SCKGSGYSFT SYWIGWVRQM PGKGLEWMGI IYPGDSDTRY  60
SPSFQGQVTI SADKSISTAY LQWSSLKASD TAVYYCARWR DSPLWGQGTL VTVSS       115

SEQ ID NO: 102           moltype = AA  length = 120
FEATURE                  Location/Qualifiers
REGION                   1..120
                         note = Description of Artificial Sequence: Synthetic
                          polypeptide
source                   1..120
                         mol_type = protein
                         organism = synthetic construct
SEQUENCE: 102
EVQLVESGGG LVQPGGSLRL SCAASGFNIK DTYIHWVRQA PGKGLEWVAR IYPTNGYTRY  60
ADSVKGRFTI SADTSKNTAY LQMNSLRAED TAVYYCSRWG GDGFYAMDYW GQGTLVTVSS  120

SEQ ID NO: 103           moltype = AA  length = 120
FEATURE                  Location/Qualifiers
REGION                   1..120
                         note = Description of Artificial Sequence: Synthetic
                          polypeptide
source                   1..120
                         mol_type = protein
                         organism = synthetic construct
SEQUENCE: 103
QVQLQQSGPE LVKPGASLKL SCTASGFNIK DTYIHWVKQR PEQGLEWIGR IYPTNGYTRY  60
DPKFQDKATI TADTSSNTAY LQVSRLTSED TAVYYCSRWG GDGFYAMDYW GQGASVTVSS  120

SEQ ID NO: 104           moltype = AA  length = 119
FEATURE                  Location/Qualifiers
REGION                   1..119
                         note = Description of Artificial Sequence: Synthetic
                          polypeptide
source                   1..119
                         mol_type = protein
                         organism = synthetic construct
SEQUENCE: 104
QVQLVESGGG LVQPGGSLRL SCAASGFTFR SYAMSWVRQA PGKGLEWVSA ISGRGDNTYY  60
ADSVKGRFTI SRDNSKNTLY LQMNSLRAED TAVYYCAKMT SNAFAFDYWG QGTLVTVSS   119

SEQ ID NO: 105           moltype = AA  length = 119
FEATURE                  Location/Qualifiers
REGION                   1..119
                         note = Description of Artificial Sequence: Synthetic
                          polypeptide
source                   1..119
                         mol_type = protein
                         organism = synthetic construct
SEQUENCE: 105
EVQLVESGGG LVQPGGSLRL SCAASGFTFT DYTMDWVRQA PGKGLEWVAD VNPNSGGSIY  60
NQRFKGRFTL SVDRSKNTLY LQMNSLRAED TAVYYCARNL GPSFYFDYWG QGTLVTVSS   119

SEQ ID NO: 106           moltype = AA  length = 119
FEATURE                  Location/Qualifiers
REGION                   1..119
                         note = Description of Artificial Sequence: Synthetic
                          polypeptide
source                   1..119
                         mol_type = protein
                         organism = synthetic construct
SEQUENCE: 106
EVQLLESGGG LVQPGGSLRL SCAASGFTFS HYVMAWVRQA PGKGLEWVSS ISSSGGWTLY  60
ADSVKGRFTI SRDNSKNTLY LQMNSLRAED TAVYYCTRGL KMATIFDYWG QGTLVTVSS   119

SEQ ID NO: 107           moltype = AA  length = 121
FEATURE                  Location/Qualifiers
```

```
REGION                  1..121
                        note = Description of Artificial Sequence: Synthetic
                         polypeptide
source                  1..121
                        mol_type = protein
                        organism = synthetic construct
SEQUENCE: 107
EVQLVESGGG LVQPGGSLRL SCAASGFTLS GDWIHWVRQA PGKGLEWVGE ISAAGGYTDY  60
ADSVKGRFTI SADTSKNTAY LQMNSLRAED TAVYYCARES RVSFEAAMDY WGQGTLVTVS  120
S                                                                  121

SEQ ID NO: 108          moltype = AA  length = 118
FEATURE                 Location/Qualifiers
REGION                  1..118
                        note = Description of Artificial Sequence: Synthetic
                         polypeptide
source                  1..118
                        mol_type = protein
                        organism = synthetic construct
SEQUENCE: 108
QVQLQESGGG LVKPGGSLRL SCAASGFTFS SYWMSWVRQA PGKGLEWVAN INRDGSASYY  60
VDSVKGRFTI SRDDAKNSLY LQMNSLRAED TAVYYCARDR GVGYFDLWGR GTLVTVSS    118

SEQ ID NO: 109          moltype = AA  length = 129
FEATURE                 Location/Qualifiers
REGION                  1..129
                        note = Description of Artificial Sequence: Synthetic
                         polypeptide
source                  1..129
                        mol_type = protein
                        organism = synthetic construct
SEQUENCE: 109
QVQLVQSGAE VKKPGESLKI SCKGSGYSFT SYWIAWVRQM PGKGLEYMGL IYPGDSDTKY  60
SPSFQGQVTI SVDKSVSTAY LQWSSLKPSD SAVYFCARHD VGYCTDRTCA KWPEWLGVWG  120
QGTLVTVSS                                                          129

SEQ ID NO: 110          moltype = AA  length = 119
FEATURE                 Location/Qualifiers
REGION                  1..119
                        note = Description of Artificial Sequence: Synthetic
                         polypeptide
source                  1..119
                        mol_type = protein
                        organism = synthetic construct
SEQUENCE: 110
EVQLVESGGG VVQPGRSLRL SCSTSGFTFS DYYMYWVRQA PGKGLEWVAY MSNVGAITDY  60
PDTVKGRFTI SRDNSKNTLF LQMDSLRPED TGVYFCARGT RDGSWFAYWG QGTPVTVSS   119

SEQ ID NO: 111          moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 111
QVELVQSGAE VKKPGESLKI SCKGSGYSFT SYWIGWVRQA PGKGLEWMGI IDPGDSRTRY  60
SPSFQGQVTI SADKSISTAY LQWSSLKASD TAMYYCARGQ LYGGTYMDGW GQGTLVTVSS  120

SEQ ID NO: 112          moltype = AA  length = 119
FEATURE                 Location/Qualifiers
REGION                  1..119
                        note = Description of Artificial Sequence: Synthetic
                         polypeptide
source                  1..119
                        mol_type = protein
                        organism = synthetic construct
SEQUENCE: 112
QVQLQQSGPE LEKPGASVKI SCKASGYSFT GYTMNWVKQS HGKSLEWIGL ITPYNGASSY  60
NQKFRGKATL TVDKSSSTAY MDLLSLTSED SAVYFCARGG YDGRGFDYWG QGTTVTVSS   119

SEQ ID NO: 113          moltype = AA  length = 122
FEATURE                 Location/Qualifiers
REGION                  1..122
                        note = Description of Artificial Sequence: Synthetic
                         polypeptide
source                  1..122
                        mol_type = protein
```

```
                         organism = synthetic construct
SEQUENCE: 113
QVYLVESGGG VVQPGRSLRL SCAASGITFS IYGMHWVRQA PGKGLEWVAV IWYDGSHEYY  60
ADSVKGRFTI SRDNSKNTLY LLMNSLRAED TAVYYCARDG DYYDSGSPLD YWGQGTLVTV  120
SS                                                                 122

SEQ ID NO: 114           moltype = AA  length = 122
FEATURE                  Location/Qualifiers
REGION                   1..122
                         note = Description of Artificial Sequence: Synthetic
                          polypeptide
source                   1..122
                         mol_type = protein
                         organism = synthetic construct
SEQUENCE: 114
QVHLVESGGG VVQPGRSLRL SCVASGITFR IYGMHWVRQA PGKGLEWVAV LWYDGSHEYY  60
ADSVKGRFTI SRDNSKNTLY LQMNSLRAED TAIYYCARDG DYYDSGSPLD YWGQGTLVTV  120
SS                                                                 122

SEQ ID NO: 115           moltype = AA  length = 131
FEATURE                  Location/Qualifiers
REGION                   1..131
                         note = Description of Artificial Sequence: Synthetic
                          polypeptide
source                   1..131
                         mol_type = protein
                         organism = synthetic construct
SEQUENCE: 115
EVHLVESGGG LVQPGGSLRL SCAASGFTFS RYWMSWVRQA QGKGLEWVAS IKQAGSEKTY  60
VDSVKGRFTI SRDNAKNSLS LQMNSLRAED TAVYYCAREG AYYYDSASYY PYYYYYSMDV  120
WGQGTTVTVS S                                                       131

SEQ ID NO: 116           moltype = AA  length = 119
FEATURE                  Location/Qualifiers
REGION                   1..119
                         note = Description of Artificial Sequence: Synthetic
                          polypeptide
source                   1..119
                         mol_type = protein
                         organism = synthetic construct
SEQUENCE: 116
QVQLQQSGPE LEKPGASVKI SCKASGYSFT GYTMNWVKQS HGKSLEWIGL ITPYNGASSY  60
NQKFRGKATL TVDKSSSTAY MDLLSLTSED SAVYFCARGG YDGRGFDYWG SGTPVTVSS   119

SEQ ID NO: 117           moltype = AA  length = 119
FEATURE                  Location/Qualifiers
REGION                   1..119
                         note = Description of Artificial Sequence: Synthetic
                          polypeptide
source                   1..119
                         mol_type = protein
                         organism = synthetic construct
SEQUENCE: 117
EVQLQESGPE LVKPGASVKM SCKASGYTFP SYVLHWVKQK PGQGLEWIGY INPYNDGTQY  60
NEKFKGKATL TSDKSSSTAY MELSRLTSED SAVYYCARGF GGSYGFAYWG QGTLITVSA   119

SEQ ID NO: 118           moltype = AA  length = 119
FEATURE                  Location/Qualifiers
REGION                   1..119
                         note = Description of Artificial Sequence: Synthetic
                          polypeptide
source                   1..119
                         mol_type = protein
                         organism = synthetic construct
SEQUENCE: 118
QVQLQQSGAE VKKFGASVKV SCEASGYTFP SYVLHWVKQA PGQGLEWIGY INPYNDGTQT  60
NKKFKGKATL TRDTSINTAY MELSRLRSDD TAVYYCARGF GGSYGFAYNG QGTLVTVSS   119

SEQ ID NO: 119           moltype = AA  length = 117
FEATURE                  Location/Qualifiers
REGION                   1..117
                         note = Description of Artificial Sequence: Synthetic
                          polypeptide
source                   1..117
                         mol_type = protein
                         organism = synthetic construct
SEQUENCE: 119
QAQLQVSGAE VVKPGASVKM SCKASGYTFT SYNMHWVKQT PGQGLEWIGY IYPGNGATNY  60
NQKFQGKATL TADTSSSTAY MQISSLTSED SAVYFCARGD SVPFAYWGQG TLVTVSA     117
```

```
SEQ ID NO: 120          moltype = AA  length = 118
FEATURE                 Location/Qualifiers
REGION                  1..118
                        note = Description of Artificial Sequence: Synthetic
                         polypeptide
source                  1..118
                        mol_type = protein
                        organism = synthetic construct
SEQUENCE: 120
QVQLQQSGAE LMKPGASVKI SCKATGYTFS AYWIEWVKQR PGHGLEWIGE ILPGSNNSRY  60
NEKFKGKATF TADTSSNTAY MQLSSLTSED SAVYYCSRSY DFAWFAYWGQ GTPVTVSA    118

SEQ ID NO: 121          moltype = AA  length = 118
FEATURE                 Location/Qualifiers
REGION                  1..118
                        note = Description of Artificial Sequence: Synthetic
                         polypeptide
source                  1..118
                        mol_type = protein
                        organism = synthetic construct
SEQUENCE: 121
QVQLVQSGAE VKKPGASVKV SCKASGYTFS AYWIEWVRQA PGKGLEWVGE ILPGSNNSRY  60
NEKFKGRVTV TRDTSTNTAY MELSSLRSED TAVYYCARSY DFAWFAYWGQ GTLVTVSS    118

SEQ ID NO: 122          moltype = AA  length = 123
FEATURE                 Location/Qualifiers
REGION                  1..123
                        note = Description of Artificial Sequence: Synthetic
                         polypeptide
source                  1..123
                        mol_type = protein
                        organism = synthetic construct
SEQUENCE: 122
QVQLVQSGAE VKKPGSSVKV SCKTSGDTFS TYAISWVRQA PGQGLEWMGG IIPIFGKAHY  60
AQKFQGRVTI TADESTSTAY MELSSLRSED TAVYFCARKF HFVSGSPFGM DVWGQGTTVT  120
VSS                                                                123

SEQ ID NO: 123          moltype = AA  length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 123
EVQLVESGGG LVQPGGSLRL SCAASGFTFS RYWMSWVRQA PGKGLEWVAN IKQDGSEKYY  60
VDSVKGRFTI SRDNAKNSLY LQMNSLRAED TAVYYCAREG GWFGELAFDY WGQGTLVTVS  120
S                                                                  121

SEQ ID NO: 124          moltype = AA  length = 118
FEATURE                 Location/Qualifiers
REGION                  1..118
                        note = Description of Artificial Sequence: Synthetic
                         polypeptide
source                  1..118
                        mol_type = protein
                        organism = synthetic construct
SEQUENCE: 124
EVQLVESGGG LVQPGGSLRL SCAASGFTFS DSWIHWVRQA PGKGLEWVAW ISPYGGSTYY  60
ADSVKGRFTI SADTSKNTAY LQMNSLRAED TAVYYCARRH WPGGFDYWGQ GTLVTVSS    118

SEQ ID NO: 125          moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 125
EVQLLESGGG LVQPGGSLRL SCAASGFTFS SYIMMWVRQA PGKGLEWVSS IYPSGGITFY  60
ADTVKGRFTI SRDNSKNTLY LQMNSLRAED TAVYYCARIK LGTVTTVDYW GQGTLVTVSS  120

SEQ ID NO: 126          moltype = AA  length = 115
FEATURE                 Location/Qualifiers
REGION                  1..115
                        note = Description of Artificial Sequence: Synthetic
```

```
                         polypeptide
source                  1..115
                        mol_type = protein
                        organism = synthetic construct
SEQUENCE: 126
EVQLVQSGPE VKKPGATVKI SCKTSGYTFT EYTIHWVKQA PGKGLEWIGN INPNNGGTTY  60
NQKFEDKATL TVDKSTDTAY MELSSLRSED TAVYYCAAGW NFDYWGQGTL LTVSS       115

SEQ ID NO: 127          moltype = AA  length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 127
QVQLVESGGG LVKPGESLRL SCAASGFTFS DYYMYWVRQA PGKGLEWVAI ISDGGYYTYY  60
SDIIKGRFTI SRDNAKNSLY LQMNSLKAED TAVYYCARGF PLLRHGAMDY WGQGTLVTVS  120
S                                                                  121

SEQ ID NO: 128          moltype = AA  length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 128
QEQLVESGGR LVTPGGSLTL SCKASGFDFS AYYMSWVRQA PGKGLEWIAT IYPSSGKTYY  60
ATWVNGRFTI SSDNAQNTVD LQMNSLTAAD RATYFCARDS YADDGALFNI WGPGTLVTIS  120
S                                                                  121

SEQ ID NO: 129          moltype = AA  length = 119
FEATURE                 Location/Qualifiers
REGION                  1..119
                        note = Description of Artificial Sequence: Synthetic
                         polypeptide
source                  1..119
                        mol_type = protein
                        organism = synthetic construct
SEQUENCE: 129
EVKLVESGGG LVKPGGSLKL SCAASGFTFS SYAMSWVRQI PEKRLEWVAS ISRGGTTYYP  60
DSVKGRFTIS RDNVRNILYL QMSSLRSEDT AMYYCGRYDY DGYYAMDYWG QGTSVTVSS   119

SEQ ID NO: 130          moltype = AA  length = 117
FEATURE                 Location/Qualifiers
REGION                  1..117
                        note = Description of Artificial Sequence: Synthetic
                         polypeptide
source                  1..117
                        mol_type = protein
                        organism = synthetic construct
SEQUENCE: 130
QSLEESGGRL VTPGTPLTLT CTVSGIDLNS HWMSWVRQAP GKGLEWIGII AASGSTYYAN  60
WAKGRFTISK TSTTVDLRIA SPTTEDTATY FCARDYGDYR LVTFNIWGPG TLVTVSS     117

SEQ ID NO: 131          moltype = AA  length = 116
FEATURE                 Location/Qualifiers
REGION                  1..116
                        note = Description of Artificial Sequence: Synthetic
                         polypeptide
source                  1..116
                        mol_type = protein
                        organism = synthetic construct
SEQUENCE: 131
QSVKESEGDL VTPAGNLTLT CTASGSDIND YPISWVRQAP GKGLEWIGFI NSGGSTWYAS  60
WVKGRFTISR TSTTVDLKMT SLTTDDTATY FCARGYSTYY CDFNIWGPGT LVTISS      116

SEQ ID NO: 132          moltype = AA  length = 115
FEATURE                 Location/Qualifiers
REGION                  1..115
                        note = Description of Artificial Sequence: Synthetic
                         polypeptide
source                  1..115
                        mol_type = protein
                        organism = synthetic construct
SEQUENCE: 132
```

-continued

```
QVQLVQSGAE VVKPGASVKI SCKASGYTFT DHAIHWVKQN PGQRLEWIGY FSPGNDDFKY  60
NERFKGKATL TADTSASTAY VELSSLRSED TAVYFCTRSL NMAYWGQGTL VTVSS       115

SEQ ID NO: 133          moltype = AA  length = 119
FEATURE                 Location/Qualifiers
REGION                  1..119
                        note = Description of Artificial Sequence: Synthetic
                         polypeptide
MOD_RES                 68
                        note = Any amino acid
source                  1..119
                        mol_type = protein
                        organism = synthetic construct
SEQUENCE: 133
QIQLVQSGPE LKKPGETVKI SCKASGYTFT NFGMNWVKQG PGEGLKWMGW INTNTGEPRY  60
AEEFKGRXAF SLETTASTAY LQINNLKNED TATYFCARDW DGAYFFDYWG QGTTLTVSS   119

SEQ ID NO: 134          moltype = AA  length = 117
FEATURE                 Location/Qualifiers
REGION                  1..117
                        note = Description of Artificial Sequence: Synthetic
                         polypeptide
source                  1..117
                        mol_type = protein
                        organism = synthetic construct
SEQUENCE: 134
QVQLQQSRPE LVKPGASVKM SCKASGYTFT DYVISWVKQR TGQGLEWIGE IYPGSNSIYY  60
NEKFKGRATL TADKSSSTAY MQLSSLTSED SAVYFCAMGG NYGFDYWGQG TTLTVSS     117

SEQ ID NO: 135          moltype = AA  length = 122
FEATURE                 Location/Qualifiers
REGION                  1..122
                        note = Description of Artificial Sequence: Synthetic
                         polypeptide
MOD_RES                 97
                        note = Any amino acid
source                  1..122
                        mol_type = protein
                        organism = synthetic construct
SEQUENCE: 135
EVQLVESGGG LVQPKGSLKL SCAASGFTFN TYAMNWVRQA PGKGLEWVAR IRSKSNNYAT  60
YYADSVKDRF TISRDDSQSM LYLQMNNLKT EDTAMYXCVR QWDYDVRAMN YWGQGTSVTV  120
SS                                                                 122

SEQ ID NO: 136          moltype = AA  length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 136
QVQLQQSGSE LKKPGASVKV SCKASGYTFT NYGMNWVKQA PGQGLKWMGW INTYTGEPTY  60
TDDFKGRFAF SLDTSVSTAY LQISSLKADD TAVYFCARGG FGSSYWYFDV WGQGSLVTVS  120
S                                                                  121

SEQ ID NO: 137          moltype = AA  length = 126
FEATURE                 Location/Qualifiers
REGION                  1..126
                        note = Description of Artificial Sequence: Synthetic
                         polypeptide
source                  1..126
                        mol_type = protein
                        organism = synthetic construct
SEQUENCE: 137
QAQVVESGGG VVQSGRSLRL SCAASGFAFS SYGMHWVRQA PGKGLEWVAV IWYDGSNKYY  60
ADSVRGRFTI SRDNSENTLY LQMNSLRAED TAVYYCARDH YGSGVHHYFY YGLDVWGQGT  120
TVTVSS                                                             126

SEQ ID NO: 138          moltype = AA  length = 117
FEATURE                 Location/Qualifiers
REGION                  1..117
                        note = Description of Artificial Sequence: Synthetic
                         polypeptide
source                  1..117
                        mol_type = protein
                        organism = synthetic construct
SEQUENCE: 138
```

-continued

```
EVQLVQSGGG LVKPGGSLRL SCAASGFTFS SYSMNWVRQA PGKGLEWVSS ISSSSSYIYY  60
ADSVKGRFTI SRDNAKNSLY LQMNSLRAED TAVYYCARVT DAFDIWGQGT MVTVSSA     117

SEQ ID NO: 139          moltype = AA  length = 117
FEATURE                 Location/Qualifiers
REGION                  1..117
                        note = Description of Artificial Sequence: Synthetic
                         polypeptide
source                  1..117
                        mol_type = protein
                        organism = synthetic construct
SEQUENCE: 139
EVQLVESGGG LVQPGGSLRL SCAASGFTFS SYGMSWVRQA PGKGLEWVAT ITSGGSYTYY  60
VDSVKGRFTI SRDNAKNTLY LQMNSLRAED TAVYYCVRIG EDALDYWGQG TLVTVSS     117

SEQ ID NO: 140          moltype = AA  length = 118
FEATURE                 Location/Qualifiers
REGION                  1..118
                        note = Description of Artificial Sequence: Synthetic
                         polypeptide
source                  1..118
                        mol_type = protein
                        organism = synthetic construct
SEQUENCE: 140
KVQLQQSGTE LVKPGASVKV SCKASGYIFT EYIIHWVKQR SGQGLEWIGW LYPESNIIKY  60
NEKFKDKATL TADKSSSTVY MELSRLTSED SAVYFCTRHD GTNFDYWGQG TTLTVSSA    118

SEQ ID NO: 141          moltype = AA  length = 106
FEATURE                 Location/Qualifiers
REGION                  1..106
                        note = Description of Artificial Sequence: Synthetic
                         polypeptide
source                  1..106
                        mol_type = protein
                        organism = synthetic construct
SEQUENCE: 141
DIQMTQSPSS LSASVGDRVT ITCKTSQDIN KYMAWYQQTP GKAPRLLIHY TSALQPGIPS  60
RFSGSGSGRD YTFTISSLQP EDIATYYCLQ YDNLWTFGQG TKVEIK                 106

SEQ ID NO: 142          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 142
EIVLTQSPGT LSLSPGERAT LSCRASQSVS STYLAWYQQK PGQAPRLLIY GASSRATGIP  60
DRFSGSGSGT DFTLTISRLE PEDFAVYYCQ HYDNSQTFGQ GTKVEIK                107

SEQ ID NO: 143          moltype = AA  length = 106
FEATURE                 Location/Qualifiers
REGION                  1..106
                        note = Description of Artificial Sequence: Synthetic
                         polypeptide
source                  1..106
                        mol_type = protein
                        organism = synthetic construct
SEQUENCE: 143
ENVLTQSPSS MSASVGDRVN IACSASSSVS YMHWFQQKPG KSPKLWIYST SNLASGVPSR  60
FSGSGSGTDY SLTISSMQPE DAATYYCQQR SSYPLTFGGG TKLEIK                 106

SEQ ID NO: 144          moltype = AA  length = 111
FEATURE                 Location/Qualifiers
REGION                  1..111
                        note = Description of Artificial Sequence: Synthetic
                         polypeptide
source                  1..111
                        mol_type = protein
                        organism = synthetic construct
SEQUENCE: 144
DIQLTQSPSS LSASVGDRVT ITCRAGESVD IFGVGFLHWY QQKPGKAPKL LIYRASNLES  60
GVPSRFSGSG SRTDFTLTIS SLQPEDFATY YCQQTNEDPY TFGQGTKVEI K           111

SEQ ID NO: 145          moltype = AA  length = 106
FEATURE                 Location/Qualifiers
REGION                  1..106
                        note = Description of Artificial Sequence: Synthetic
```

```
                         polypeptide
source                  1..106
                        mol_type = protein
                        organism = synthetic construct
SEQUENCE: 145
DIQLTQSPSS LSASVGDRVT ITCKASQDVG TSVAWYQQKP GKAPKLLIYW TSTRHTGVPS  60
RFSGSGSGTD FTFTISSLQP EDIATYYCQQ YSLYRSFGQG TKVEIK                106

SEQ ID NO: 146          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 146
QTVLSQSPAI LSASPGEKVT MTCRASSSVT YIHWYQQKPG SSPKSWIYAT SNLASGVPAR  60
FSGSGSGTSY SLTISRVEAE DAATYYCQHW SSKPPTFGGG TKLEIKR               107

SEQ ID NO: 147          moltype = AA  length = 116
FEATURE                 Location/Qualifiers
REGION                  1..116
                        note = Description of Artificial Sequence: Synthetic
                         polypeptide
source                  1..116
                        mol_type = protein
                        organism = synthetic construct
SEQUENCE: 147
QAVLTQPASL SASPGASASL TCTLRRGINV GAYSIYWYQQ KPGSPPQYLL RYKSDSDKQQ  60
GSGVSSRFSA SKDASANAGI LLISGLQSED EADYYCMIWH SGASAVFGGG TKLTVL      116

SEQ ID NO: 148          moltype = AA  length = 111
FEATURE                 Location/Qualifiers
REGION                  1..111
                        note = Description of Artificial Sequence: Synthetic
                         polypeptide
source                  1..111
                        mol_type = protein
                        organism = synthetic construct
SEQUENCE: 148
DIQLTQSPAS LAVSLGQRAT ISCKASQSVD YDGDSYLNWY QQIPGQPPKL LIYDASNLVS  60
GIPPRFSGSG SGTDFTLNIH PVEKVDAATY HCQQSTEDPW TFGGGTKLEI K           111

SEQ ID NO: 149          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 149
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPITFGQ GTRLEIK               107

SEQ ID NO: 150          moltype = AA  length = 106
FEATURE                 Location/Qualifiers
REGION                  1..106
                        note = Description of Artificial Sequence: Synthetic
                         polypeptide
source                  1..106
                        mol_type = protein
                        organism = synthetic construct
SEQUENCE: 150
QIVLSQSPAI LSASPGEKVT MTCRASSSVS YMHWYQQKPG SSPKPWIYAP SNLASGVPAR  60
FSGSGSGTSY SLTISRVEAE DAATYYCQQW SFNPPTFGAG TKLELK                106

SEQ ID NO: 151          moltype = AA  length = 112
FEATURE                 Location/Qualifiers
REGION                  1..112
                        note = Description of Artificial Sequence: Synthetic
                         polypeptide
source                  1..112
                        mol_type = protein
                        organism = synthetic construct
SEQUENCE: 151
DIVMTQTPLS LPVTPGEPAS ISCRSSKSLL HSNGITYLYW YLQKPGQSPQ LLIYQMSNLV  60
SGVPDRFSGS GSGTDFTLKI SRVEAEDVGV YYCAQNLELP YTFGGGTKVE IK         112
```

```
SEQ ID NO: 152          moltype = AA  length = 106
FEATURE                 Location/Qualifiers
REGION                  1..106
                        note = Description of Artificial Sequence: Synthetic
                         polypeptide
source                  1..106
                        mol_type = protein
                        organism = synthetic construct
SEQUENCE: 152
DIQMTQSPSS LSASVGDRVT ITCRASSSVS YMHWYQQKPG KAPKPLIYAP SNLASGVPSR  60
FSGSGSGTDF TLTISSLQPE DFATYYCQQW SFNPPTFGQG TKVEIK                 106

SEQ ID NO: 153          moltype = AA  length = 106
FEATURE                 Location/Qualifiers
REGION                  1..106
                        note = Description of Artificial Sequence: Synthetic
                         polypeptide
source                  1..106
                        mol_type = protein
                        organism = synthetic construct
SEQUENCE: 153
QIVLSQSPAI LSASPGEKVT MTCRASSSVS YIHWFQQKPG SSPKPWIYAT SNLASGVPVR  60
FSGSGSGTSY SLTISRVEAE DAATYYCQQW TSNPPTFGGG TKLEIK                 106

SEQ ID NO: 154          moltype = AA  length = 111
FEATURE                 Location/Qualifiers
REGION                  1..111
                        note = Description of Artificial Sequence: Synthetic
                         polypeptide
source                  1..111
                        mol_type = protein
                        organism = synthetic construct
SEQUENCE: 154
DIQLTQSPST LSASVGDRVT ITCRASESLD NYGIRFLTWF QQKPGKAPKL LMYAASNQGS  60
GVPSRFSGSG SGTEFTLTIS SLQPDDFATY YCQQTKEVPW SFGQGTKVEV K           111

SEQ ID NO: 155          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 155
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPPTFGQ GTKVEIK                107

SEQ ID NO: 156          moltype = AA  length = 111
FEATURE                 Location/Qualifiers
REGION                  1..111
                        note = Description of Artificial Sequence: Synthetic
                         polypeptide
source                  1..111
                        mol_type = protein
                        organism = synthetic construct
SEQUENCE: 156
DIVLTQSPAS LAVSLGQRAT ISCRASKSVS TSGYSFMHWY QQKPGQPPKL LIYLASNLES  60
GVPARFSGSG SGTDFTLNIH PVEEEDAATY YCQHSREVPW TFGGGTKLEI K           111

SEQ ID NO: 157          moltype = AA  length = 111
FEATURE                 Location/Qualifiers
REGION                  1..111
                        note = Description of Artificial Sequence: Synthetic
                         polypeptide
source                  1..111
                        mol_type = protein
                        organism = synthetic construct
SEQUENCE: 157
DIVLTQSPAS LTVSLGQKTT ISCRASKSVS TSGYSFMHWY QLKPGQSPKL LIYLASDLPS  60
GVPARFSGSG SGTDFTLKIH PVEEEDAATY YCQHSREIPY TFGGGTKLEI T           111

SEQ ID NO: 158          moltype = AA  length = 107
FEATURE                 Location/Qualifiers
REGION                  1..107
                        note = Description of Artificial Sequence: Synthetic
                         polypeptide
source                  1..107
```

```
                        mol_type = protein
                        organism = synthetic construct
SEQUENCE: 158
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RTNWPLTFGG GTKVEIK                107

SEQ ID NO: 159          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 159
AIQLTQSPSS LSASVGDRVT ITCRASQGIS SALAWYQQKP GKAPKFLIYD ASSLESGVPS  60
RFSGSGSGTD FTLTISSLQP EDFATYYCQQ FNSYPFTFGP GTKVDIK                107

SEQ ID NO: 160          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 160
DIQMTQSPSS LSASVGDRVT ITCRASQGIS SWLAWYQQKP EKAPKSLIYA ASSLQSGVPS  60
RFSGSGSGTD FTLTISSLQP EDFATYYCQQ YNSYPLTFGG GTKVEIK                107

SEQ ID NO: 161          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 161
EIVLTQSPAT LSLSPGERAT LSCRASQSVS SYLAWYQQKP GQAPRLLIFD ASNRATGIPA  60
RFSGSGSGTD FTLTISSLEP EDFAVYYCQQ RSNWPLTFGG GTKVEIK                107

SEQ ID NO: 162          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 162
DIQMTQSPSS VSASVGDRVT ITCRASQGIN TWLAWYQQKP GKAPKLLIYA ASSLKSGVPS  60
RFSGSGSGTD FTLTISSLQP EDFATYYCQQ ANSFPLTFGG GTKVEIK                107

SEQ ID NO: 163          moltype = AA  length = 108
FEATURE                 Location/Qualifiers
REGION                  1..108
                        note = Description of Artificial Sequence: Synthetic
                         polypeptide
source                  1..108
                        mol_type = protein
                        organism = synthetic construct
SEQUENCE: 163
DIQMTQSPSS LSASVGDRVT ITCSVSSSVS SIYLHWYQQK PGKAPKLLIY STSNLASGVP  60
SRFSGSGSGT DFTLTISSLQ PEDFATYYCQ VYSGYPLTFG GGTKVEIK               108

SEQ ID NO: 164          moltype = AA  length = 113
FEATURE                 Location/Qualifiers
REGION                  1..113
                        note = Description of Artificial Sequence: Synthetic
                         polypeptide
source                  1..113
                        mol_type = protein
                        organism = synthetic construct
SEQUENCE: 164
DIQMTQSPSS LSASVGDRVT ITCKSSQSLL YTSSQKNYLA WYQQKPGKAP KLLIYWASTR  60
ESGVPSRFSG SGSGTDFTLT ISSLQPEDFA TYYCQQYYAY PWTFGQGTKV EIK         113

SEQ ID NO: 165          moltype = AA  length = 107
```

```
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 165
DIQMTQSPSS LSASVGDRVT ITCRASQSIN SYLDWYQQKP GKAPKLLIYA ASSLQSGVPS  60
RFSGSGSGTD FTLTISSLQP EDFATYYCQQ YYSTPFTFGP GTKVEIK               107

SEQ ID NO: 166         moltype = AA  length = 108
FEATURE                Location/Qualifiers
REGION                 1..108
                       note = Description of Artificial Sequence: Synthetic
                        polypeptide
source                 1..108
                       mol_type = protein
                       organism = synthetic construct
SEQUENCE: 166
EIVLTQSPGT LSLSPGERAT LSCRASQSVG SSYLAWYQQK PGQAPRLLIY GAFSRATGIP  60
DRFSGSGSGT DFTLTISRLE PEDFAVYYCQ QYGSSPWTFG QGTKVEIK              108

SEQ ID NO: 167         moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 167
EIVLTQSPDF QSVTPKEKVT ITCRASQSIG ISLHWYQQKP DQSPKLLIKY ASQSFSGVPS  60
RFSGSGSGTD FTLTINSLEA EDAATYYCHQ SRSFPWTFGQ GTKVEIK               107

SEQ ID NO: 168         moltype = AA  length = 113
FEATURE                Location/Qualifiers
REGION                 1..113
                       note = Description of Artificial Sequence: Synthetic
                        polypeptide
source                 1..113
                       mol_type = protein
                       organism = synthetic construct
SEQUENCE: 168
ELVMTQSPSS LTVTAGEKVT MSCKSSQSLL NSGNQKNYLT WYQQKPGQPP KLLIYWASTR  60
ESGVPDRFTG SGSGTDFTLT ISSVQAEDLA VYYCQNDYSY PLTFGAGTKL EIK        113

SEQ ID NO: 169         moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 169
ELQMTQSPSS LSASVGDRVT ITCRTSQSIS SYLNWYQQKP GQPPKLLIYW ASTRESGVPD  60
RFSGSGSGTD FTLTISSLQP EDSATYYCQQ SYDIPYTFGQ GTKLEIK               107

SEQ ID NO: 170         moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 170
NIVMTQSPKS MSMSVGERVT LTCKASENVV TYVSWYQQKP EQSPKLLIYG ASNRYTGVPD  60
RFTGSGSATD FTLTISSVQA EDLADYHCGQ GYSYPYTFGG GTKLEIK               107

SEQ ID NO: 171         moltype = AA  length = 106
FEATURE                Location/Qualifiers
REGION                 1..106
                       note = Description of Artificial Sequence: Synthetic
                        polypeptide
source                 1..106
                       mol_type = protein
                       organism = synthetic construct
```

```
SEQUENCE: 171
QILLTQSPAI MSASPGEKVT MTCSASSSVS YMLWYQQKPG SSPKPWIFDT SNLASGFPAR  60
FSGSGSGTSY SLIISSMEAE DAATYYCHQR SGYPYTFGGG TKLEIK                106

SEQ ID NO: 172         moltype = AA  length = 113
FEATURE                Location/Qualifiers
REGION                 1..113
                       note = Description of Artificial Sequence: Synthetic
                        polypeptide
source                 1..113
                       mol_type = protein
                       organism = synthetic construct
SEQUENCE: 172
DIVMTQSPDS LAVSLGERAT INCKSSQSVL YSSNNKNYLA WYQQKPGQPP KLLIYWASTR  60
ESGVPDRFSG SGSGTDFTLT ISSLQAEDVA VYYCQQYYSY PLTFGGGTKV KES         113

SEQ ID NO: 173         moltype = AA  length = 112
FEATURE                Location/Qualifiers
REGION                 1..112
                       note = Description of Artificial Sequence: Synthetic
                        polypeptide
source                 1..112
                       mol_type = protein
                       organism = synthetic construct
SEQUENCE: 173
DIVMTQSPLS LPVTPGEPAS ISCRSSINKK GSNGITYLYW YLQKPGQSPQ LLIYQMSNLA  60
SGVPDRFSGS GSGTDFTLKI SRVEAEDVGV YYCAQNLEIP RTFGQGTKVE IK          112

SEQ ID NO: 174         moltype = AA  length = 112
FEATURE                Location/Qualifiers
REGION                 1..112
                       note = Description of Artificial Sequence: Synthetic
                        polypeptide
source                 1..112
                       mol_type = protein
                       organism = synthetic construct
SEQUENCE: 174
DIQMTQSPSS LSASVGDRVT ITCRSTKSLL HSNGITYLYW YQQKPGKAPK LLIYQMSNLA  60
SGVPSRFSSS GSGTDFTLTI SSLQPEDFAT YYCAQNLEIP RTFGQGTKVE IK          112

SEQ ID NO: 175         moltype = AA  length = 112
FEATURE                Location/Qualifiers
REGION                 1..112
                       note = Description of Artificial Sequence: Synthetic
                        polypeptide
source                 1..112
                       mol_type = protein
                       organism = synthetic construct
SEQUENCE: 175
DIQMTQSPSS LSASVGDRVT ITCRSTKSLL HSNGITYLYW YQQKPGKAPK LLIYQMSNLA  60
SGVPSRFSSS GSGTDFTLTI SSLQPEDFAT YYCAQNLEIP RTFGQGTKVE LK          112

SEQ ID NO: 176         moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 176
DIQMTQSPSS LSASVGDRVT ITCRASQSIS TWLAWYQQKP GKAPKLLIYK ASNLHTGVPS  60
RFSGSGSGTE FSLTISGLQP DDFATYYCQQ YNSYSRTFGQ GTKVEIK                107

SEQ ID NO: 177         moltype = AA  length = 110
FEATURE                Location/Qualifiers
REGION                 1..110
                       note = Description of Artificial Sequence: Synthetic
                        polypeptide
source                 1..110
                       mol_type = protein
                       organism = synthetic construct
SEQUENCE: 177
DIQLTQSPSS LSASVGDRVT ITCSVSSSIS SNNLHWYQQK PGKAPKPWIY GTSNLASGVP  60
SRFSGSGSGT DYTFTISSLQ PEDIATYYCQ QWSSYPYMYT FGQGTKVEIK             110

SEQ ID NO: 178         moltype = AA  length = 111
FEATURE                Location/Qualifiers
REGION                 1..111
```

```
                        note = Description of Artificial Sequence: Synthetic
                         polypeptide
source                  1..111
                        mol_type = protein
                        organism = synthetic construct
SEQUENCE: 178
DIVLTQSPLS LAVSLGQPAI ISCKASQSVS FAGTSLMHWY HQKPGQQPRL LIYRASNLEA  60
GVPDRFSGSG SKTDFTLNIS PVEAEDAATY YCQQSREYPY TFGGGTKLEI K           111

SEQ ID NO: 179          moltype = AA  length = 111
FEATURE                 Location/Qualifiers
REGION                  1..111
                        note = Description of Artificial Sequence: Synthetic
                         polypeptide
source                  1..111
                        mol_type = protein
                        organism = synthetic construct
SEQUENCE: 179
DIVLTQSPLS LAVSLGQPAI ISCKASQSVS FAGTSLMHWY HQKPGQQPRL LIYRASNLEA  60
GVPDRFSGSG SKTDFTLTIS PVEAEDAATY YCQQSREYPY TFGGGTKLEI K           111

SEQ ID NO: 180          moltype = AA  length = 100
FEATURE                 Location/Qualifiers
REGION                  1..100
                        note = Description of Artificial Sequence: Synthetic
                         polypeptide
source                  1..100
                        mol_type = protein
                        organism = synthetic construct
SEQUENCE: 180
PASLSASVGE TVTITCRTSE NIFSYLAWYQ QKQGISPQLL VYNAKTLAEG VPSRFSGSGS  60
GTQFSLKINS LQPEDFGSYY CQHHYAFPWT FGGGSKLEIK                        100

SEQ ID NO: 181          moltype = AA  length = 112
FEATURE                 Location/Qualifiers
REGION                  1..112
                        note = Description of Artificial Sequence: Synthetic
                         polypeptide
source                  1..112
                        mol_type = protein
                        organism = synthetic construct
SEQUENCE: 181
DVVMTQSPLS LPVTPGEPAS ISCRSSQSLV HSNGNTYLHW YLQKPGQSPQ LLIYKVSNRF  60
SGVPDRFSGS GSGTDFTLKI SRVEAEDVGV YYCSQNTHVP PTFGQGTKLE IK          112

SEQ ID NO: 182          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 182
EIVLTQSPGT LSLSPGERAT LSCRAVQSVS SSYLAWYQQK PGQAPRLLIY GASSRATGIP  60
DRFSGSGSGT DFTLTISRLE PEDFAVYYCQ QYGSSPTFGG GTKVEIK                107

SEQ ID NO: 183          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 183
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QYGSSPTFGG GTKVEIK                107

SEQ ID NO: 184          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 184
EILLTQSPGT LSLSPGERAT LSCRASQSVS SSYLAWYQQK PGQAPRLLIY GASSRATGIP  60
```

```
DRFSGSGSGT DFTLTISRLE PEDFAVYYCQ QYGSSPTFGQ GTKVEIK                107

SEQ ID NO: 185          moltype = AA  length = 112
FEATURE                 Location/Qualifiers
REGION                  1..112
                        note = Description of Artificial Sequence: Synthetic
                         polypeptide
source                  1..112
                        mol_type = protein
                        organism = synthetic construct
SEQUENCE: 185
DTVMTQTPLS SHVTLGQPAS ISCRSSQSLV HSDGNTYLSW LQQRPGQPPR LLIYRISRRF  60
SGVPDRFSGS GAGTDFTLEI SRVEAEDVGV YYCMQSTHVP RTFGQGTKVE IK          112

SEQ ID NO: 186          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 186
DILLTQSPVI LSVSPGERVS FSCRASQSIG TNIHWYQQRT NGSPRLLIKY ASESISGIPS  60
RFSGSGSGTD FTLSINSVES EDIADYYCQQ NNNWPTTFGA GTKLELK                107

SEQ ID NO: 187          moltype = AA  length = 106
FEATURE                 Location/Qualifiers
REGION                  1..106
                        note = Description of Artificial Sequence: Synthetic
                         polypeptide
source                  1..106
                        mol_type = protein
                        organism = synthetic construct
SEQUENCE: 187
DIQMTQSPSS LSASVGDRVT ITCRASQGIN NYLNWYQQKP GKAPKRLIYN TNNLQTGVPS  60
RFSGSGSGTE FTLTISSLQP EDFATYYCLQ HNSFPTFGQG TKLEIK                 106

SEQ ID NO: 188          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 188
AIQLTQSPSS LSASVGDRVT ITCRASQDIS SALVWYQQKP GKAPKLLIYD ASSLESGVPS  60
RFSGSESGTD FTLTISSLQP EDFATYYCQQ FNSYPLTFGG GTKVEIK                107

SEQ ID NO: 189          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 189
EIVMTQSPAT LSLSPGERAT LSCRASQSVS SYLAWYQQKP GQAPRLLIYD ASNRATGIPA  60
RFSGSGSGTD FTLTISSLEP EDFAVYYCHQ YGSTPLTFGG GTKAEIK                107

SEQ ID NO: 190          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 190
DIQMTQSPST LSASVGDRVT ITCRASQSIS SWWAWYQQKP GKAPKLLIYD ASSLESGVPS  60
RFSGSGSGTE FTLTISSLQP DDFATYYCQQ YHAHPTTFGG GTKVEIK                107

SEQ ID NO: 191          moltype = AA  length = 113
FEATURE                 Location/Qualifiers
REGION                  1..113
                        note = Description of Artificial Sequence: Synthetic
                         polypeptide
```

```
source                  1..113
                        mol_type = protein
                        organism = synthetic construct
SEQUENCE: 191
DIVMTQSPDS LAVSLGERAT INCKSSQSVL YSPNNKNYLA WYQQKPGQPP KLLIYWASTR  60
ESGVPDRFSG SGSGTDFTLT ISSLQAEDVA VYYCQQYYGS PITFGGGTKV EIK         113

SEQ ID NO: 192          moltype = AA  length = 108
FEATURE                 Location/Qualifiers
REGION                  1..108
                        note = Description of Artificial Sequence: Synthetic
                         polypeptide
source                  1..108
                        mol_type = protein
                        organism = synthetic construct
SEQUENCE: 192
EIVMTQSPAT LSVSPGERAT LSCRASQSVS SNLAWYQQKP GQAPRLLIYG ASTRATGIPA  60
RFSGSGSGTE FTLTISSLQS EDFAVYYCQD YRTWPRRVFG GGTKVEIK               108

SEQ ID NO: 193          moltype = AA  length = 112
FEATURE                 Location/Qualifiers
REGION                  1..112
                        note = Description of Artificial Sequence: Synthetic
                         polypeptide
source                  1..112
                        mol_type = protein
                        organism = synthetic construct
SEQUENCE: 193
DIQMTQSPSS LSASVGDRVT ITCRSSQNIV HSNGNTYLDW YQQTPGKAPK LLIYKVSNRF  60
SGVPSRFSGS GSGTDFTFTI SSLQPEDIAT YYCFQYSHVP WTFGQGTKLQ IT          112

SEQ ID NO: 194          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 194
DIQMTQSPSS LSASVGDRVT ITCQASQDIS NYLNWYQQKP GKAPKLLIYD ASNLETGVPS  60
RFSGSGSGTD FTFTISSLQP EDIATYFCQH FDHLPLAFGG GTKVEIK                107

SEQ ID NO: 195          moltype = AA  length = 112
FEATURE                 Location/Qualifiers
REGION                  1..112
                        note = Description of Artificial Sequence: Synthetic
                         polypeptide
source                  1..112
                        mol_type = protein
                        organism = synthetic construct
SEQUENCE: 195
DVVMTQTPLS LPVSLGDQAS ISCRSSQSLV HSNGNTYLHW YLQKPGQSPK LLIYKVSNRF  60
SGVPDRFSGS GSGTDFTLKI SRVEAEDLGV YFCSQSTHVP WTFGGGTKLE IK          112

SEQ ID NO: 196          moltype = AA  length = 111
FEATURE                 Location/Qualifiers
REGION                  1..111
                        note = Description of Artificial Sequence: Synthetic
                         polypeptide
source                  1..111
                        mol_type = protein
                        organism = synthetic construct
SEQUENCE: 196
DVVMTQTPLS LPVSLGDQAS ISCRSSQSLV HSNGNTYLHW YLQKPGQSPK LLIYKVSNRF  60
SGVPDRFSGS GSGTDFTLKI SRVEAEDLGV YFCSQSTHVL TFGSGTKLEI K           111

SEQ ID NO: 197          moltype = AA  length = 102
FEATURE                 Location/Qualifiers
REGION                  1..102
                        note = Description of Artificial Sequence: Synthetic
                         polypeptide
source                  1..102
                        mol_type = protein
                        organism = synthetic construct
SEQUENCE: 197
QSPSFLSAFV GDRITITCRA SPGIRNYLAW YQQKPGKAPK LLIYAASTLQ SGVPSRFSGS  60
GSGTDFTLTI SSLQPEDFAT YYCQQYNSYP LSFGGGTKVE IK                     102
```

```
SEQ ID NO: 198          moltype = AA  length = 110
FEATURE                 Location/Qualifiers
REGION                  1..110
                        note = Description of Artificial Sequence: Synthetic
                         polypeptide
source                  1..110
                        mol_type = protein
                        organism = synthetic construct
SEQUENCE: 198
QAVVTQEPSF SVSPGGTVTL TCGLSSGSVS TSYYPSWYQQ TPGQAPRTLI YSTNTRSSGV  60
PDRFSGSILG NKAALTITGA QADDESDYYC VLYMGSGQYV FGGGTKLTVL             110

SEQ ID NO: 199          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 199
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ HYTTPPTFGQ GTKVEIK                107

SEQ ID NO: 200          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 200
DIVMTQSHKF MSTSVGDRVS ITCKASQDVN TAVAWYQQKP GHSPKLLIYS ASFRYTGVPD  60
RFTGSRSGTD FTFTISSVQA EDLAVYYCQQ HYTTPPTFGG GTKVEIK                107

SEQ ID NO: 201          moltype = AA  length = 111
FEATURE                 Location/Qualifiers
REGION                  1..111
                        note = Description of Artificial Sequence: Synthetic
                         polypeptide
source                  1..111
                        mol_type = protein
                        organism = synthetic construct
SEQUENCE: 201
QSVLTQPPSV SGAPGQRVTI SCTGSSSNIG AGYGVHWYQQ LPGTAPKLLI YGNTNRPSGV  60
PDRFSGFKSG TSASLAITGL QAEDEADYYC QFYDSSLSGW VFGGGTKLTV L           111

SEQ ID NO: 202          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 202
DIQMTQSPSS LSASVGDRVT ITCKASQDVS IGVAWYQQKP GKAPKLLIYS ASYRYTGVPS  60
RFSGSGSGTD FTLTISSLQP EDFATYYCQQ YYIYPYTFGQ GTKVEIK                107

SEQ ID NO: 203          moltype = AA  length = 111
FEATURE                 Location/Qualifiers
REGION                  1..111
                        note = Description of Artificial Sequence: Synthetic
                         polypeptide
source                  1..111
                        mol_type = protein
                        organism = synthetic construct
SEQUENCE: 203
QSALTQPASV SGSPGQSITI SCTGTSSDVG SYNVVSWYQQ HPGKAPKLII YEVSQRPSGV  60
SNRFSGSKSG NTASLTISGL QTEDEADYYC CSYAGSSIFV IFGGGTKVTV L           111

SEQ ID NO: 204          moltype = AA  length = 107
FEATURE                 Location/Qualifiers
REGION                  1..107
                        note = Description of Artificial Sequence: Synthetic
                         polypeptide
source                  1..107
                        mol_type = protein
```

```
                         organism = synthetic construct
SEQUENCE: 204
DIQMTQSPSS LSASVGDRVT ITCRASQNIA TDVAWYQQKP GKAPKLLIYS ASFLYSGVPS  60
RFSGSGSGTD FTLTISSLQP EDFATYYCQQ SEPEPYTFGQ GTKVEIK               107

SEQ ID NO: 205           moltype = AA  length = 111
FEATURE                  Location/Qualifiers
REGION                   1..111
                         note = Description of Artificial Sequence: Synthetic
                          polypeptide
source                   1..111
                         mol_type = protein
                         organism = synthetic construct
SEQUENCE: 205
QSALTQPASV SGSPGQSITI SCTGTSSDVG GYNFVSWYQQ HPGKAPKLMI YDVSDRPSGV  60
SDRFSGSKSG NTASLIISGL QADDEADYYC SSYGSSSTHV IFGGGTKVTV L           111

SEQ ID NO: 206           moltype = AA  length = 110
FEATURE                  Location/Qualifiers
REGION                   1..110
                         note = Description of Artificial Sequence: Synthetic
                          polypeptide
source                   1..110
                         mol_type = protein
                         organism = synthetic construct
SEQUENCE: 206
QSVLTQPPSV SAAPGQKVTI SCSGSSSNIG NNYVSWYQQL PGTAPKLLIY DHTNRPAGVP  60
DRFSGSKSGT SASLAISGFR SEDEADYYCA SWDYTLSGWV FGGGTKLTVL            110

SEQ ID NO: 207           moltype = AA  length = 112
FEATURE                  Location/Qualifiers
REGION                   1..112
                         note = Description of Artificial Sequence: Synthetic
                          polypeptide
source                   1..112
                         mol_type = protein
                         organism = synthetic construct
SEQUENCE: 207
DIQMTQSPSS LSASVGDRVT ITCRSSQRIV HSNGNTYLEW YQQTPGKAPK LLIYKVSNRF  60
SGVPSRFSGS GSGTDFTFTI SSLQPEDIAT YYCFQGSHVP FTFGQGTKLQ IT          112

SEQ ID NO: 208           moltype = AA  length = 111
FEATURE                  Location/Qualifiers
REGION                   1..111
                         note = Description of Artificial Sequence: Synthetic
                          polypeptide
source                   1..111
                         mol_type = protein
                         organism = synthetic construct
SEQUENCE: 208
DIALTQPASV SGSPGQSITI SCTGTSSDIG GYNSVSWYQQ HPGKAPKLMI YGVNNRPSGV  60
SNRFSGSKSG NTASLTISGL QAEDEADYYC SSYDIESATP VFGGGTKLTV L           111

SEQ ID NO: 209           moltype = AA  length = 106
FEATURE                  Location/Qualifiers
REGION                   1..106
                         note = Description of Artificial Sequence: Synthetic
                          polypeptide
source                   1..106
                         mol_type = protein
                         organism = synthetic construct
SEQUENCE: 209
DIELTQSPAI MSASPGEKVT MTCSASSSVS YMHWYQQKSG TSPKRWIYDT SKLASGVPGR  60
FSGSGSGNSY SLTISSVEAE DDATYYCQQW SGYPLTFGAG TKLEIK                106

SEQ ID NO: 210           moltype = AA  length = 107
FEATURE                  Location/Qualifiers
REGION                   1..107
                         note = Description of Artificial Sequence: Synthetic
                          polypeptide
source                   1..107
                         mol_type = protein
                         organism = synthetic construct
SEQUENCE: 210
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPLTFGG GTKVEIK               107

SEQ ID NO: 211           moltype = AA  length = 108
FEATURE                  Location/Qualifiers
```

```
REGION                 1..108
                       note = Description of Artificial Sequence: Synthetic
                        polypeptide
source                 1..108
                       mol_type = protein
                       organism = synthetic construct
SEQUENCE: 211
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QYGSSQYTFG QGTKLEIK               108

SEQ ID NO: 212         moltype = AA  length = 106
FEATURE                Location/Qualifiers
REGION                 1..106
                       note = Description of Artificial Sequence: Synthetic
                        polypeptide
source                 1..106
                       mol_type = protein
                       organism = synthetic construct
SEQUENCE: 212
DIELTQSPAI MSASPGEKVT MTCSASSSVS YMHWYQQKSG TSPKRWIYDT SKLASGVPGR  60
FSGSGSGNSY SLTISSVEAE DDATYYCQQW SKHPLTFGSG TKVEIK                 106

SEQ ID NO: 213         moltype = AA  length = 108
FEATURE                Location/Qualifiers
REGION                 1..108
                       note = Description of Artificial Sequence: Synthetic
                        polypeptide
source                 1..108
                       mol_type = protein
                       organism = synthetic construct
SEQUENCE: 213
DIVMTQSPAI MSASPGEKVT MTCSASSSVS SSYLYWYQQK PGSSPKLWIY STSNLASGVP  60
ARFSGSGSGT SYSLTISSME AEDAASYFCH QWNRYPYTFG GGTKLEIK               108

SEQ ID NO: 214         moltype = AA  length = 108
FEATURE                Location/Qualifiers
REGION                 1..108
                       note = Description of Artificial Sequence: Synthetic
                        polypeptide
source                 1..108
                       mol_type = protein
                       organism = synthetic construct
SEQUENCE: 214
DIQLTQSPSS LSASVGDRVT MTCSASSSVS SSYLYWYQQK PGKAPKLWIY STSNLASGVP  60
ARFSGSGSGT DFTLTISSLQ PEDSASYFCH QWNRYPYTFG GGTRLEIK               108

SEQ ID NO: 215         moltype = AA  length = 106
FEATURE                Location/Qualifiers
REGION                 1..106
                       note = Description of Artificial Sequence: Synthetic
                        polypeptide
source                 1..106
                       mol_type = protein
                       organism = synthetic construct
SEQUENCE: 215
EIVLTQSPAT MSASPGERVT ITCSAHSSVS FMHWFQQKPG TSPKLWIYST SSLASGVPAR  60
FGGSGSGTSY SLTISSMEAE DAATYYCQQR SSFPLTFGAG TKLELK                 106

SEQ ID NO: 216         moltype = AA  length = 113
FEATURE                Location/Qualifiers
REGION                 1..113
                       note = Description of Artificial Sequence: Synthetic
                        polypeptide
source                 1..113
                       mol_type = protein
                       organism = synthetic construct
SEQUENCE: 216
DIVMSQSPSS LAVSVGEKVT MSCKSSQSLL YSSNQKIYLA WYQQKPGQSP KLLIYWASTR  60
ESGVPDRFTG GGSGTDFTLT ISSVKAEDLA VYYCQQYYRY PRTFGGGTKL EIK         113

SEQ ID NO: 217         moltype = AA  length = 113
FEATURE                Location/Qualifiers
REGION                 1..113
                       note = Description of Artificial Sequence: Synthetic
                        polypeptide
source                 1..113
                       mol_type = protein
                       organism = synthetic construct
SEQUENCE: 217
```

```
DIQMTQSPSS LSASVGDRVT ITCKSSQSLL YSSNQKIYLA WYQQKPGKAP KLLIYWASTR  60
ESGVPSRFSG SGSGTDFTFT ISSLQPEDIA TYYCQQYYRY PRTFGQGTKV EIK         113

SEQ ID NO: 218         moltype = AA  length = 106
FEATURE                Location/Qualifiers
REGION                 1..106
                       note = Description of Artificial Sequence: Synthetic
                        polypeptide
source                 1..106
                       mol_type = protein
                       organism = synthetic construct
SEQUENCE: 218
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPTFGQG TKVEIK                106

SEQ ID NO: 219         moltype = AA  length = 108
FEATURE                Location/Qualifiers
REGION                 1..108
                       note = Description of Artificial Sequence: Synthetic
                        polypeptide
source                 1..108
                       mol_type = protein
                       organism = synthetic construct
SEQUENCE: 219
EIVLTQSPGT LSLSPGERAT LSCRASQRVS SSYLAWYQQK PGQAPRLLIY DASSRATGIP  60
DRFSGSGSGT DFTLTISRLE PEDFAVYYCQ QYGSLPWTFG QGTKVEIK              108

SEQ ID NO: 220         moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 220
DIQMTQSPSS LSASVGDRVT ITCRASQDVS TAVAWYQQKP GKAPKLLIYS ASFLYSGVPS  60
RFSGSGSGTD FTLTISSLQP EDFATYYCQQ YLYHPATFGQ GTKVEIK               107

SEQ ID NO: 221         moltype = AA  length = 110
FEATURE                Location/Qualifiers
REGION                 1..110
                       note = Description of Artificial Sequence: Synthetic
                        polypeptide
source                 1..110
                       mol_type = protein
                       organism = synthetic construct
SEQUENCE: 221
QSALTQPASV SGSPGQSITI SCTGTSSDVG GYNYVSWYQQ HPGKAPKLMI YDVSNRPSGV  60
SNRFSGSKSG NTASLTISGL QAEDEADYYC SSYTSSSTRV FGTGTKVTVL            110

SEQ ID NO: 222         moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 222
DIQMTQSPSS LSTSVGDRVT LTCKASQDVG TAVDWYQQKP GPSPKLLIYW ASTRHTGIPS  60
RFSGSGSGTD FTLTISSLQP EDFADYYCQQ YNSYPLTFGP GTKVDIK               107

SEQ ID NO: 223         moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 223
DIQMTQSPSS LSASVGDRVT ITCKASQNVD TNVAWYQQKP GQAPKSLIYS ASYRYSDVPS  60
RFSGSASGTD FTLTISSVQS EDFATYYCQQ YDSYPYTFGG GTKLEIK               107

SEQ ID NO: 224         moltype = AA  length = 112
FEATURE                Location/Qualifiers
REGION                 1..112
                       note = Description of Artificial Sequence: Synthetic
```

```
                         polypeptide
source                  1..112
                        mol_type = protein
                        organism = synthetic construct
SEQUENCE: 224
ELVLTQSPSV SAALGSPAKI TCTLSSAHKT DTIDWYQQLQ GEAPRYLMQV QSDGSYTKRP  60
GVPDRFSGSS SGADRYLIIP SVQADDEADY YCGADYIGGY VFGGGTQLTV TG          112

SEQ ID NO: 225          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 225
DIKMTQSPSS MYASLGERVT ITCKASPDIN SYLSWFQQKP GKSPKTLIYR ANRLVDGVPS  60
RFSGGGSGQD YSLTINSLEY EDMGIYYCLQ YDEFPYTFGG GTKLEMK                107

SEQ ID NO: 226          moltype = AA  length = 108
FEATURE                 Location/Qualifiers
REGION                  1..108
                        note = Description of Artificial Sequence: Synthetic
                         polypeptide
source                  1..108
                        mol_type = protein
                        organism = synthetic construct
SEQUENCE: 226
ELVMTQTPSS VSAAVGGTVT INCQASQSIG SYLAWYQQKP GQPPKLLIYY ASNLASGVPS  60
RFSGSGSGTE YTLTISGVQR EDAATYYCLG SLSNSDNVFG GGTELEIL               108

SEQ ID NO: 227          moltype = AA  length = 110
FEATURE                 Location/Qualifiers
REGION                  1..110
                        note = Description of Artificial Sequence: Synthetic
                         polypeptide
source                  1..110
                        mol_type = protein
                        organism = synthetic construct
SEQUENCE: 227
ELVMTQTPSS TSGAVGGTVT INCQASQSID SNLAWFQQKP GQPPTLLIYR ASNLASGVPS  60
RFSGSRSGTE YTLTISGVQR EDAATYYCLG GVGNVSYRTS FGGGTEVVVK             110

SEQ ID NO: 228          moltype = AA  length = 113
FEATURE                 Location/Qualifiers
REGION                  1..113
                        note = Description of Artificial Sequence: Synthetic
                         polypeptide
source                  1..113
                        mol_type = protein
                        organism = synthetic construct
SEQUENCE: 228
DIVMSQSPDS LAVSLGERVT LNCKSSQSLL YSGNQKNYLA WYQQKPGQSP KLLIYWASAR  60
ESGVPDRFSG SGSGTDFTLT ISSVQAEDVA VYYCQQYYSY PLTFGAGTKL ELK         113

SEQ ID NO: 229          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 229
SIVMTQTPKF LLVSAGDRVT ITCKASQSVS NDVAWYQQKP GQSPKLLINF ATNRYTGVPN  60
RFTGSGYGTD FTFTISTVQA EDLALYFCQQ DYSSPWTFGG GTKLEIK                107

SEQ ID NO: 230          moltype = AA  length = 115
FEATURE                 Location/Qualifiers
REGION                  1..115
                        note = Description of Artificial Sequence: Synthetic
                         polypeptide
source                  1..115
                        mol_type = protein
                        organism = synthetic construct
SEQUENCE: 230
SVIMSRGQIV LTQSPAIMSA SLGERVTLTC TASSSVNSNY LHWYQQKPGS SPKLWIYSTS  60
NLASGVPARF SGSGSGTSYS LTISSMEAED AATYYCHQYH RSPLTFGAGT KLELK       115
```

```
SEQ ID NO: 231         moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 231
DIVMTQSHIF MSTSVGDRVS ITCKASQDVD TAVAWYQQKP GQSPKLLIYW ASTRLTGVPD  60
RFTGSGSGTD FTLTISNVQS EDLADYFCQQ YSSYPYTFGG GTKLEIK                107

SEQ ID NO: 232         moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 232
DIQLTQSPSS LSASVGDRVS ITCKASQDVS IAVAWYQQKP GKAPKLLIYS ASYRYTGVPD  60
RFSGSGSGTD FTLTISSLQP EDFAVYYCQQ HYITPLTFGA GTKVEIK                107

SEQ ID NO: 233         moltype = AA  length = 108
FEATURE                Location/Qualifiers
REGION                 1..108
                       note = Description of Artificial Sequence: Synthetic
                        polypeptide
source                 1..108
                       mol_type = protein
                       organism = synthetic construct
SEQUENCE: 233
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QYGSSPLTFG GGTKVEIK               108

SEQ ID NO: 234         moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 234
DIQMTQSPSS VSASIGDRVT ITCRASQGID NWLGWYQQKP GKAPKLLIYD ASNLDTGVPS  60
RFSGSGSGTY FTLTISSLQA EDFAVYFCQQ AKAFPPTFGG GTKVDIK                107

SEQ ID NO: 235         moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 235
DIQMTQSPSS LSASVGDRVT ITCRASQDIA GSLNWLQQKP GKAIKRLIYA TSSLDSGVPK  60
RFSGSRSGSD YTLTISSLQP EDFATYYCLQ YGSFPPTFGQ GTKVEIK                107

SEQ ID NO: 236         moltype = AA  length = 111
FEATURE                Location/Qualifiers
REGION                 1..111
                       note = Description of Artificial Sequence: Synthetic
                        polypeptide
source                 1..111
                       mol_type = protein
                       organism = synthetic construct
SEQUENCE: 236
DIVLTQSPAS LAVSLGQRAT ISCRASESVD SYGNSFMHWY QQKPGQPPKL LIYRASNLES  60
GIPARFSGSG SRTDFTLTIN PVEADDVATY YCQQSNEDPL TFGAGTKLEL K           111

SEQ ID NO: 237         moltype = AA  length = 11
FEATURE                Location/Qualifiers
REGION                 1..11
                       note = Description of Artificial Sequence: Synthetic peptide
source                 1..11
                       mol_type = protein
```

```
                        organism = synthetic construct
SEQUENCE: 237
RASQDIRNYL N                                                            11

SEQ ID NO: 238          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 238
YTSRLES                                                                 7

SEQ ID NO: 239          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 239
QQGNTLPWT                                                               9

SEQ ID NO: 240          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 240
GYSFTGYTMN                                                              10

SEQ ID NO: 241          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 241
LINPYKGVST                                                              10

SEQ ID NO: 242          moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 242
SGYYGDSDWY FDV                                                          13

SEQ ID NO: 243          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 243
LSGRSDNHSP LGLAGS                                                       16

SEQ ID NO: 244          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 244
SPLGLAGSLS GRSDNH                                                       16

SEQ ID NO: 245          moltype = AA  length = 12
FEATURE                 Location/Qualifiers
REGION                  1..12
                        note = Description of Artificial Sequence: Synthetic peptide
source                  1..12
```

```
                        mol_type = protein
                        organism = synthetic construct
SEQUENCE: 245
SPLGLSGRSD NH                                                12

SEQ ID NO: 246          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 246
LAGRSDNHSP LGLAGS                                            16

SEQ ID NO: 247          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 247
LAGRSDNHVP LSLSMG                                            16

SEQ ID NO: 248          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 248
LAGRSDNHEP LELVAG                                            16

SEQ ID NO: 249          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 249
LSGRSDNHVP LSLKMG                                            16

SEQ ID NO: 250          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 250
SPLGLAGS                                                     8

SEQ ID NO: 251          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 251
GPLGLARG                                                     8

SEQ ID NO: 252          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 252
LSGRSDNH                                                     8

SEQ ID NO: 253          moltype = AA  length = 8
FEATURE                 Location/Qualifiers
REGION                  1..8
                        note = Description of Artificial Sequence: Synthetic peptide
```

```
source                  1..8
                        mol_type = protein
                        organism = synthetic construct
SEQUENCE: 253
GTAHLMGG                                                                   8

SEQ ID NO: 254          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 254
RIGSLRTA                                                                   8

SEQ ID NO: 255          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 255
RIGALRTA                                                                   8

SEQ ID NO: 256          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 256
RIGWLRTA                                                                   8

SEQ ID NO: 257          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 257
RIGNLRTA                                                                   8

SEQ ID NO: 258          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 258
RIGFLRTA                                                                   8

SEQ ID NO: 259          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 259
RIFFLRTA                                                                   8

SEQ ID NO: 260          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 260
RILFLRTA                                                                   8

SEQ ID NO: 261          moltype = AA  length = 8
FEATURE                 Location/Qualifiers
REGION                  1..8
```

```
                        note = Description of Artificial Sequence: Synthetic peptide
source                  1..8
                        mol_type = protein
                        organism = synthetic construct
SEQUENCE: 261
RIYFLRTA                                                                    8

SEQ ID NO: 262          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 262
RIQFLRTA                                                                    8

SEQ ID NO: 263          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 263
EPAALMAG                                                                    8

SEQ ID NO: 264          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 264
EPANLMAG                                                                    8

SEQ ID NO: 265          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 265
EPASLMAG                                                                    8

SEQ ID NO: 266          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 266
EPFHLMAG                                                                    8

SEQ ID NO: 267          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 267
EPWHLMAG                                                                    8

SEQ ID NO: 268          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 268
EPRHLMAG                                                                    8

SEQ ID NO: 269          moltype = AA  length = 8
FEATURE                 Location/Qualifiers
```

```
REGION                  1..8
                        note = Description of Artificial Sequence: Synthetic peptide
source                  1..8
                        mol_type = protein
                        organism = synthetic construct
SEQUENCE: 269
VPLSLFMG                                                                      8

SEQ ID NO: 270          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 270
VPLSLHMG                                                                      8

SEQ ID NO: 271          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 271
VPLSLQAG                                                                      8

SEQ ID NO: 272          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 272
VPLSLTMG                                                                      8

SEQ ID NO: 273          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 273
VPLSLKMG                                                                      8

SEQ ID NO: 274          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 274
VPLSLSMG                                                                      8

SEQ ID NO: 275          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 275
VPLSLNAG                                                                      8

SEQ ID NO: 276          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 276
VPLSLLMG                                                                      8

SEQ ID NO: 277          moltype = AA  length = 8
```

```
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 277
EPLELPAG                                                                    8

SEQ ID NO: 278          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 278
EPLELAAG                                                                    8

SEQ ID NO: 279          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 279
EPLELVAG                                                                    8

SEQ ID NO: 280          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 280
EPLELSAG                                                                    8

SEQ ID NO: 281          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 281
EPLELDAG                                                                    8

SEQ ID NO: 282          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 282
EPLELQAG                                                                    8

SEQ ID NO: 283          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 283
EPLELRAG                                                                    8

SEQ ID NO: 284          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 284
EPLELKAG                                                                    8
```

```
SEQ ID NO: 285          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 285
EPLELIAG                                                                  8

SEQ ID NO: 286          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 286
LGPVSGVP                                                                  8

SEQ ID NO: 287          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 287
VAGDSLEE                                                                  8

SEQ ID NO: 288          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 288
GPAGLGGA                                                                  8

SEQ ID NO: 289          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 289
GPAGLRGA                                                                  8

SEQ ID NO: 290          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 290
APLGLRLR                                                                  8

SEQ ID NO: 291          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 291
PALPLVAQ                                                                  8

SEQ ID NO: 292          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 292
ENLYFQG                                                                   7
```

```
SEQ ID NO: 293          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 293
DDDKIVGG                                                                  8

SEQ ID NO: 294          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 294
LEVLFQGP                                                                  8

SEQ ID NO: 295          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 295
LPKTGSES                                                                  8

SEQ ID NO: 296          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 296
SGRSA                                                                     5

SEQ ID NO: 297          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 297
YGRSA                                                                     5

SEQ ID NO: 298          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 298
SSYYSG                                                                    6

SEQ ID NO: 299          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 299
RRARVVGG                                                                  8

SEQ ID NO: 300          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 300
```

```
RQLRVVGG                                                       8

SEQ ID NO: 301          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 301
RQARVVGG                                                       8

SEQ ID NO: 302          moltype = AA  length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 302
GFFY                                                           4

SEQ ID NO: 303          moltype = AA  length = 6
FEATURE                 Location/Qualifiers
REGION                  1..6
                        note = Description of Artificial Sequence: Synthetic peptide
MOD_RES                 4
                        note = Homophenylalanine
MOD_RES                 5
                        note = Orn
source                  1..6
                        mol_type = protein
                        organism = synthetic construct
SEQUENCE: 303
PLGXXL                                                         6

SEQ ID NO: 304          moltype = AA  length = 7
FEATURE                 Location/Qualifiers
REGION                  1..7
                        note = Description of Artificial Sequence: Synthetic peptide
MOD_RES                 3
                        note = Citrulline
MOD_RES                 5
                        note = Homophenylalanine
source                  1..7
                        mol_type = protein
                        organism = synthetic construct
SEQUENCE: 304
EPXFXYL                                                        7

SEQ ID NO: 305          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 305
PQGIAGQ                                                        7

SEQ ID NO: 306          moltype = AA  length = 6
FEATURE                 Location/Qualifiers
REGION                  1..6
                        note = Description of Artificial Sequence: Synthetic peptide
MOD_RES                 5
                        note = Melphalan
source                  1..6
                        mol_type = protein
                        organism = synthetic construct
SEQUENCE: 306
PQGIXG                                                         6

SEQ ID NO: 307          moltype = AA  length = 6
FEATURE                 Location/Qualifiers
REGION                  1..6
                        note = Description of Artificial Sequence: Synthetic peptide
MOD_RES                 5
                        note = Aminosuberic acid
source                  1..6
```

```
                        mol_type = protein
                        organism = synthetic construct
SEQUENCE: 307
AALGXP                                                                 6

SEQ ID NO: 308          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 308
GPQGIAGQR                                                              9

SEQ ID NO: 309          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 309
SGKIPRTATA                                                             10

SEQ ID NO: 310          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 310
SGPLFYSVTA                                                             10

SEQ ID NO: 311          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 311
PLRLSW                                                                 6

SEQ ID NO: 312          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 312
GKGPRQITA                                                              9

SEQ ID NO: 313          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 313
SGRRLIHHT                                                              9

SEQ ID NO: 314          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 314
SGQPHYLTTA                                                             10

SEQ ID NO: 315          moltype = AA  length = 7
FEATURE                 Location/Qualifiers
REGION                  1..7
                        note = Description of Artificial Sequence: Synthetic peptide
```

```
source                  1..7
                        mol_type = protein
                        organism = synthetic construct
SEQUENCE: 315
SGLKALM                                                                    7

SEQ ID NO: 316          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 316
SGFGSRYLTA                                                                 10

SEQ ID NO: 317          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 317
SGLRPAKSTA                                                                 10

SEQ ID NO: 318          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 318
LGPSTST                                                                    7

SEQ ID NO: 319          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 319
PQGVR                                                                      5

SEQ ID NO: 320          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 320
PSGLP                                                                      5

SEQ ID NO: 321          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 321
PAGVQ                                                                      5

SEQ ID NO: 322          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 322
PSGRD                                                                      5

SEQ ID NO: 323          moltype = AA  length = 5
FEATURE                 Location/Qualifiers
REGION                  1..5
```

```
                        note = Description of Artificial Sequence: Synthetic peptide
source                  1..5
                        mol_type = protein
                        organism = synthetic construct
SEQUENCE: 323
PPGIV                                                                       5

SEQ ID NO: 324          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 324
PENFF                                                                       5

SEQ ID NO: 325          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 325
PLKLM                                                                       5

SEQ ID NO: 326          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 326
PGAYH                                                                       5

SEQ ID NO: 327          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 327
AIHIQ                                                                       5

SEQ ID NO: 328          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 328
HFFKN                                                                       5

SEQ ID NO: 329          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 329
GLSLS                                                                       5

SEQ ID NO: 330          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 330
ASDYK                                                                       5

SEQ ID NO: 331          moltype = AA  length = 8
FEATURE                 Location/Qualifiers
```

```
REGION                  1..8
                        note = Description of Artificial Sequence: Synthetic peptide
source                  1..8
                        mol_type = protein
                        organism = synthetic construct
SEQUENCE: 331
GPLGMLSQ                                                                    8

SEQ ID NO: 332          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 332
CGLDD                                                                       5

SEQ ID NO: 333          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 333
GPQGIWGQ                                                                    8

SEQ ID NO: 334          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 334
RPLALWRS                                                                    8

SEQ ID NO: 335          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 335
GPLGLARK                                                                    8

SEQ ID NO: 336          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 336
GKAFRRL                                                                     7

SEQ ID NO: 337          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 337
RPSASRSA                                                                    8

SEQ ID NO: 338          moltype = AA  length = 7
FEATURE                 Location/Qualifiers
REGION                  1..7
                        note = Description of Artificial Sequence: Synthetic peptide
MOD_RES                 5
                        note = D-phenylalanine
source                  1..7
                        mol_type = protein
                        organism = synthetic construct
SEQUENCE: 338
PLGLXAR                                                                     7
```

```
SEQ ID NO: 339          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 339
PMGIST                                                                      6

SEQ ID NO: 340          moltype = AA  length = 6
FEATURE                 Location/Qualifiers
REGION                  1..6
                        note = Description of Artificial Sequence: Synthetic peptide
MOD_RES                 2
                        note = Beta-cyclohexylalanine
MOD_RES                 4
                        note = S-methylcysteine
source                  1..6
                        mol_type = protein
                        organism = synthetic construct
SEQUENCE: 340
PXGXHA                                                                      6

SEQ ID NO: 341          moltype = AA  length = 7
FEATURE                 Location/Qualifiers
REGION                  1..7
                        note = Description of Artificial Sequence: Synthetic peptide
MOD_RES                 2
                        note = Beta-cyclohexylalanine
MOD_RES                 4
                        note = Aminosuberic acid
MOD_RES                 7
                        note = D-phenylalanine
source                  1..7
                        mol_type = protein
                        organism = synthetic construct
SEQUENCE: 341
PXGXHAX                                                                     7

SEQ ID NO: 342          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 342
PTASALKG                                                                    8

SEQ ID NO: 343          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 343
PRPAAVKGT                                                                   9

SEQ ID NO: 344          moltype = AA  length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 344
AAPV                                                                        4

SEQ ID NO: 345          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 345
```

```
GPICFRLG                                                    8

SEQ ID NO: 346          moltype = AA  length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 346
AANL                                                        4

SEQ ID NO: 347          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 347
FSPFR                                                       5

SEQ ID NO: 348          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 348
EEEAY                                                       5

SEQ ID NO: 349          moltype = AA  length = 4
FEATURE                 Location/Qualifiers
REGION                  1..4
                        note = Description of Artificial Sequence: Synthetic peptide
MOD_RES                 1
                        note = Beta-Ala
source                  1..4
                        mol_type = protein
                        organism = synthetic construct
SEQUENCE: 349
AIAL                                                        4

SEQ ID NO: 350          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 350
EVQRKTGT                                                    8

SEQ ID NO: 351          moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 351
DVQEFRGVTA VIR                                              13

SEQ ID NO: 352          moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 352
HNEFRQRETY MVF                                              13

SEQ ID NO: 353          moltype = AA  length = 8
FEATURE                 Location/Qualifiers
REGION                  1..8
                        note = Description of Artificial Sequence: Synthetic peptide
source                  1..8
```

```
                        mol_type = protein
                        organism = synthetic construct
SEQUENCE: 353
KEEEGLGS                                                                8

SEQ ID NO: 354          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 354
GELEGRGT                                                                8

SEQ ID NO: 355          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 355
NITEGEARGS                                                              10

SEQ ID NO: 356          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 356
TAQEAGEG                                                                8

SEQ ID NO: 357          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 357
VSQELGQR                                                                8

SEQ ID NO: 358          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 358
PTAQEAGE                                                                8

SEQ ID NO: 359          moltype = AA  length = 8
FEATURE                 Location/Qualifiers
REGION                  1..8
                        note = Description of Artificial Sequence: Synthetic peptide
MOD_RES                 2
                        note = Pro or Ala
MOD_RES                 3
                        note = Any amino acid
MOD_RES                 6
                        note = Any amino acid
MOD_RES                 8
                        note = Any amino acid
source                  1..8
                        mol_type = protein
                        organism = synthetic construct
SEQUENCE: 359
GXXGLXGX                                                                8

SEQ ID NO: 360          moltype = AA  length = 8
FEATURE                 Location/Qualifiers
REGION                  1..8
                        note = Description of Artificial Sequence: Synthetic peptide
MOD_RES                 3
                        note = Any amino acid
```

```
MOD_RES                 6
                        note = Any amino acid
MOD_RES                 7
                        note = Gly or Ala
MOD_RES                 8
                        note = Any amino acid
source                  1..8
                        mol_type = protein
                        organism = synthetic construct
SEQUENCE: 360
GPXGLXXX                                                                    8

SEQ ID NO: 361          moltype = AA  length = 7
FEATURE                 Location/Qualifiers
REGION                  1..7
                        note = Description of Artificial Sequence: Synthetic peptide
MOD_RES                 7
                        note = Gly or Ser
source                  1..7
                        mol_type = protein
                        organism = synthetic construct
SEQUENCE: 361
ENLYFQX                                                                     7

SEQ ID NO: 362          moltype = AA  length = 8
FEATURE                 Location/Qualifiers
REGION                  1..8
                        note = Description of Artificial Sequence: Synthetic peptide
MOD_RES                 3
                        note = Lys, Glu, Ala or Asp
MOD_RES                 6
                        note = Any amino acid
MOD_RES                 7
                        note = Glu, Lys or Ser
source                  1..8
                        mol_type = protein
                        organism = synthetic construct
SEQUENCE: 362
LPXTGXXS                                                                    8

SEQ ID NO: 363          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 363
SASRSA                                                                      6

SEQ ID NO: 364          moltype =   length =
SEQUENCE: 364
000

SEQ ID NO: 365          moltype = AA  length = 6
FEATURE                 Location/Qualifiers
REGION                  1..6
                        note = Description of Artificial Sequence: Synthetic peptide
MOD_RES                 3
                        note = Phe or Tyr
source                  1..6
                        mol_type = protein
                        organism = synthetic construct
SEQUENCE: 365
SSXYSG                                                                      6

SEQ ID NO: 366          moltype = AA  length = 8
FEATURE                 Location/Qualifiers
REGION                  1..8
                        note = Description of Artificial Sequence: Synthetic peptide
MOD_RES                 2
                        note = Arg, Ala or Leu
MOD_RES                 3
                        note = Ala, Leu or Tyr
MOD_RES                 5
                        note = Ala or Val
source                  1..8
                        mol_type = protein
                        organism = synthetic construct
```

```
SEQUENCE: 366
RXXRXVGG                                                  8

SEQ ID NO: 367          moltype = AA  length = 8
FEATURE                 Location/Qualifiers
REGION                  1..8
                        note = Description of Artificial Sequence: Synthetic peptide
MOD_RES                 2
                        note = Arg or Gln
MOD_RES                 3
                        note = Tyr or Leu
source                  1..8
                        mol_type = protein
                        organism = synthetic construct
SEQUENCE: 367
RXXRVVGG                                                  8

SEQ ID NO: 368          moltype = AA  length = 8
FEATURE                 Location/Qualifiers
REGION                  1..8
                        note = Description of Artificial Sequence: Synthetic peptide
MOD_RES                 5
                        note = Ala or Val
source                  1..8
                        mol_type = protein
                        organism = synthetic construct
SEQUENCE: 368
RRARXVGG                                                  8

SEQ ID NO: 369          moltype = AA  length = 8
FEATURE                 Location/Qualifiers
REGION                  1..8
                        note = Description of Artificial Sequence: Synthetic peptide
MOD_RES                 2
                        note = Gln or Arg
MOD_RES                 5
                        note = Ala, Val or Tyr
source                  1..8
                        mol_type = protein
                        organism = synthetic construct
SEQUENCE: 369
RXARXVGG                                                  8

SEQ ID NO: 370          moltype = AA  length = 10
FEATURE                 Location/Qualifiers
REGION                  1..10
                        note = Description of Artificial Sequence: Synthetic peptide
MOD_RES                 7
                        note = Pro, Ser, Thr, Arg or Ala
MOD_RES                 8
                        note = Any hydrophobic L-amino acid
MOD_RES                 9
                        note = Ser or Thr
source                  1..10
                        mol_type = protein
                        organism = synthetic construct
SEQUENCE: 370
SGKIPRXXXA                                                10

SEQ ID NO: 371          moltype = AA  length = 9
FEATURE                 Location/Qualifiers
REGION                  1..9
                        note = Description of Artificial Sequence: Synthetic peptide
MOD_RES                 6
                        note = Ile or Leu
source                  1..9
                        mol_type = protein
                        organism = synthetic construct
SEQUENCE: 371
SGRRLXHHT                                                 9

SEQ ID NO: 372          moltype = AA  length = 5
FEATURE                 Location/Qualifiers
REGION                  1..5
                        note = Description of Artificial Sequence: Synthetic peptide
MOD_RES                 5
                        note = Pro or any hydrophobic L-amino acid
source                  1..5
                        mol_type = protein
```

```
                        organism = synthetic construct
SEQUENCE: 372
PSGLX                                                               5

SEQ ID NO: 373          moltype = AA  length = 8
FEATURE                 Location/Qualifiers
REGION                  1..8
                        note = Description of Artificial Sequence: Synthetic peptide
MOD_RES                 4
                        note = Ala or Ser
MOD_RES                 6
                        note = Leu, Phe, Tyr or Gln
MOD_RES                 7
                        note = Lys, Arg, Thr or Ile
MOD_RES                 8
                        note = Gly, Ala or Ser
source                  1..8
                        mol_type = protein
                        organism = synthetic construct
SEQUENCE: 373
PTAXAXXX                                                            8

SEQ ID NO: 374          moltype = AA  length = 144
FEATURE                 Location/Qualifiers
REGION                  1..144
                        note = Description of Artificial Sequence: Synthetic
                         polypeptide
source                  1..144
                        mol_type = protein
                        organism = synthetic construct
SEQUENCE: 374
GSEPATSGSE TPGTSESATP ESGPGSEPAT SGSETPGSPA GSPTSTEEGT STEPSEGSAP  60
GSEPATSGSE TPGSEPATSG SETPGSEPAT SGSETPGTST EPSEGSAPGT SESATPESGP  120
GSEPATSGSE TPGTSTEPSE GSAP                                          144

SEQ ID NO: 375          moltype = AA  length = 144
FEATURE                 Location/Qualifiers
REGION                  1..144
                        note = Description of Artificial Sequence: Synthetic
                         polypeptide
source                  1..144
                        mol_type = protein
                        organism = synthetic construct
SEQUENCE: 375
SPAGSPTSTE EGTSESATPE SGPGTSTEPS EGSAPGSPAG SPTSTEEGTS TEPSEGSAPG  60
TSTEPSEGSA PGTSESATPE SGPGSEPATS GSETPGSEPA TSGSETPGSP AGSPTSTEEG  120
TSESATPESG PGTSTEPSEG SAPG                                          144

SEQ ID NO: 376          moltype = AA  length = 144
FEATURE                 Location/Qualifiers
REGION                  1..144
                        note = Description of Artificial Sequence: Synthetic
                         polypeptide
source                  1..144
                        mol_type = protein
                        organism = synthetic construct
SEQUENCE: 376
TSTEPSEGSA PGSPAGSPTS TEEGTSTEPS EGSAPGTSTE PSEGSAPGTS ESATPESGPG  60
TSTEPSEGSA PGTSESATPE SGPGSEPATS GSETPGTSTE PSEGSAPGTS TEPSEGSAPG  120
TSESATPESG PGTSESATPE SGPG                                          144

SEQ ID NO: 377          moltype = AA  length = 144
FEATURE                 Location/Qualifiers
REGION                  1..144
                        note = Description of Artificial Sequence: Synthetic
                         polypeptide
source                  1..144
                        mol_type = protein
                        organism = synthetic construct
SEQUENCE: 377
SPAGSPTSTE EGTSESATPE SGPGSEPATS GSETPGTSES ATPESGPGTS TEPSEGSAPG  60
TSTEPSEGSA PGTSTEPSEG SAPGTSTEPS EGSAPGTSTE PSEGSAPGTS TEPSEGSAPG  120
SPAGSPTSTE EGTSTEPSEG SAPG                                          144

SEQ ID NO: 378          moltype = AA  length = 144
FEATURE                 Location/Qualifiers
REGION                  1..144
                        note = Description of Artificial Sequence: Synthetic
                         polypeptide
```

```
source                  1..144
                        mol_type = protein
                        organism = synthetic construct
SEQUENCE: 378
TSESATPESG PGSEPATSGS ETPGTSESAT PESGPGSEPA TSGSETPGTS ESATPESGPG  60
TSTEPSEGSA PGTSESATPE SGPGSPAGSP TSTEEGSPAG SPTSTEEGSP AGSPTSTEEG  120
TSESATPESG PGTSTEPSEG SAPG                                         144

SEQ ID NO: 379          moltype = AA  length = 144
FEATURE                 Location/Qualifiers
REGION                  1..144
                        note = Description of Artificial Sequence: Synthetic
                         polypeptide
source                  1..144
                        mol_type = protein
                        organism = synthetic construct
SEQUENCE: 379
TSESATPESG PGSEPATSGS ETPGTSESAT PESGPGSEPA TSGSETPGTS ESATPESGPG  60
TSTEPSEGSA PGSPAGSPTS TEEGTSESAT PESGPGSEPA TSGSETPGTS ESATPESGPG  120
SPAGSPTSTE EGSPAGSPTS TEEG                                         144

SEQ ID NO: 380          moltype = AA  length = 144
FEATURE                 Location/Qualifiers
REGION                  1..144
                        note = Description of Artificial Sequence: Synthetic
                         polypeptide
source                  1..144
                        mol_type = protein
                        organism = synthetic construct
SEQUENCE: 380
TSTEPSEGSA PGTSESATPE SGPGTSESAT PESGPGTSES ATPESGPGSE PATSGSETPG  60
SEPATSGSET PGSPAGSPTS TEEGTSTEPS EGSAPGTSTE PSEGSAPGSE PATSGSETPG  120
TSESATPESG PGTSTEPSEG SAPG                                         144

SEQ ID NO: 381          moltype = AA  length = 288
FEATURE                 Location/Qualifiers
REGION                  1..288
                        note = Description of Artificial Sequence: Synthetic
                         polypeptide
source                  1..288
                        mol_type = protein
                        organism = synthetic construct
SEQUENCE: 381
GTSESATPES GPGSEPATSG SETPGTSESA TPESGPGSEP ATSGSETPGT SESATPESGP  60
GTSTEPSEGS APGSPAGSPT STEEGTSESA TPESGPGSEP ATSGSETPGT SESATPESGP  120
GSPAGSPTST EEGSPAGSPT STEEGTSTEP SEGSAPGTSE SATPESGPGT SESATPESGP  180
GTSESATPES GPGSEPATSG SETPGSEPAT SGSETPGSPA GSPTSTEEGT STEPSEGSAP  240
GTSTEPSEGS APGSEPATSG SETPGTSESA TPESGPGTST EPSEGSAP               288

SEQ ID NO: 382          moltype = AA  length = 288
FEATURE                 Location/Qualifiers
REGION                  1..288
                        note = Description of Artificial Sequence: Synthetic
                         polypeptide
source                  1..288
                        mol_type = protein
                        organism = synthetic construct
SEQUENCE: 382
GSPAGSPTST EEGTSESATP ESGPGSEPAT SGSETPGTSE SATPESGPGT STEPSEGSAP  60
GTSTEPSEGS APGTSTEPSE GSAPGTSTEP SEGSAPGTST EPSEGSAPGT STEPSEGSAP  120
GSPAGSPTST EEGTSTEPSE GSAPGTSESA TPESGPGSEP ATSGSETPGT SESATPESGP  180
GSEPATSGSE TPGTSESATP ESGPGTSTEP SEGSAPGTSE SATPESGPGS PAGSPTSTEE  240
GSPAGSPTST EEGSPAGSPT STEEGTSESA TPESGPGTST EPSEGSAP               288

SEQ ID NO: 383          moltype = AA  length = 576
FEATURE                 Location/Qualifiers
REGION                  1..576
                        note = Description of Artificial Sequence: Synthetic
                         polypeptide
source                  1..576
                        mol_type = protein
                        organism = synthetic construct
SEQUENCE: 383
GSPAGSPTST EEGTSESATP ESGPGTSTEP SEGSAPGSPA GSPTSTEEGT STEPSEGSAP  60
GTSTEPSEGS APGTSESATP ESGPGSEPAT SGSETPGSEP ATSGSETPGS PAGSPTSTEE  120
GTSESATPES GPGTSTEPSE GSAPGTSTEP SEGSAPGSPA GSPTSTEEGT STEPSEGSAP  180
GTSTEPSEGS APGTSESATP ESGPGTSTEP SEGSAPGTSE SATPESGPGS EPATSGSETP  240
GTSTEPSEGS APGTSTEPSE GSAPGTSESA TPESGPGTSE SATPESGPGS PAGSPTSTEE  300
GTSESATPES GPGSEPATSG SETPGTSESA TPESGPGTST EPSEGSAPGT STEPSEGSAP  360
```

```
GTSTEPSEGS APGTSTEPSE GSAPGTSTEP SEGSAPGTST EPSEGSAPGS PAGSPTSTEE  420
GTSTEPSEGS APGTSESATP ESGPGSEPAT SGSETPGTSE SATPESGPGS EPATSGSETP  480
GTSESATPES GPGTSTEPSE GSAPGTSESA TPESGPGSPA GSPTSTEEGS PAGSPTSTEE  540
GSPAGSPTST EEGTSESATP ESGPGTSTEP SEGSAP                            576

SEQ ID NO: 384         moltype = AA  length = 625
FEATURE                Location/Qualifiers
REGION                 1..625
                       note = Description of Artificial Sequence: Synthetic
                        polypeptide
source                 1..625
                       mol_type = protein
                       organism = synthetic construct
SEQUENCE: 384
MAEPAGSPTS TEEGTPGSGT ASSSPGSSTP SGATGSPGAS PGTSSTGSPG SPAGSPTSTE  60
EGTSESATPE SGPGTSTEPS EGSAPGSPAG SPTSTEEGTS TEPSEGSAPG TSTEPSEGSA  120
PGTSESATPE SGPGSEPATS GSETPGSEPA TSGSETPGSP AGSPTSTEEG TSESATPESG  180
PGTSTEPSEG SAPGTSTEPS EGSAPGSPAG SPTSTEEGTS TEPSEGSAPG TSTEPSEGSA  240
PGTSESATPE SGPGTSTEPS EGSAPGTSES ATPESGPGSE PATSGSETPG TSTEPSEGSA  300
PGTSTEPSEG SAPGTSESAT PESGPGTSES ATPESGPGSP AGSPTSTEEG TSESATPESG  360
PGSEPATSGS ETPGTSESAT PESGPGTSTE PSEGSAPGTS TEPSEGSAPG TSTEPSEGSA  420
PGTSTEPSEG SAPGTSTEPS EGSAPGTSTE PSEGSAPGSP AGSPTSTEEG TSTEPSEGSA  480
PGTSESATPE SGPGSEPATS GSETPGTSES ATPESGPGSE PATSGSETPG TSESATPESG  540
PGTSTEPSEG SAPGTSESAT PESGPGSPAG SPTSTEEGSP AGSPTSTEEG SPAGSPTSTE  600
EGTSESATPE SGPGTSTEPS EGSAP                                        625

SEQ ID NO: 385         moltype = AA  length = 864
FEATURE                Location/Qualifiers
REGION                 1..864
                       note = Description of Artificial Sequence: Synthetic
                        polypeptide
source                 1..864
                       mol_type = protein
                       organism = synthetic construct
SEQUENCE: 385
GSPAGSPTST EEGTSESATP ESGPGTSTEP SEGSAPGSPA GSPTSTEEGT STEPSEGSAP  60
GTSTEPSEGS APGTSESATP ESGPGSEPAT SGSETPGSEP ATSGSETPGS PAGSPTSTEE  120
GTSESATPES GPGTSTEPSE GSAPGTSTEP SEGSAPGSPA GSPTSTEEGT STEPSEGSAP  180
GTSTEPSEGS APGTSESATP ESGPGTSTEP SEGSAPGTSE SATPESGPGS EPATSGSETP  240
GTSTEPSEGS APGTSTEPSE GSAPGTSESA TPESGPGTSE SATPESGPGS PAGSPTSTEE  300
GTSESATPES GPGSEPATSG SETPGTSESA TPESGPGTST EPSEGSAPGT STEPSEGSAP  360
GTSTEPSEGS APGTSTEPSE GSAPGTSTEP SEGSAPGTST EPSEGSAPGS PAGSPTSTEE  420
GTSTEPSEGS APGTSESATP ESGPGSEPAT SGSETPGTSE SATPESGPGS EPATSGSETP  480
GTSESATPES GPGTSTEPSE GSAPGTSESA TPESGPGSPA GSPTSTEEGS PAGSPTSTEE  540
GSPAGSPTST EEGTSESATP ESGPGTSTEP SEGSAPGTSE SATPESGPGS EPATSGSETP  600
GTSESATPES GPGSEPATSG SETPGTSESA TPESGPGTST EPSEGSAPGS PAGSPTSTEE  660
GTSESATPES GPGSEPATSG SETPGTSESA TPESGPGSPA GSPTSTEEGS PAGSPTSTEE  720
GTSTEPSEGS APGTSESATP ESGPGTSESA TPESGPGTSE SATPESGPGS EPATSGSETP  780
GSEPATSGSE TPGSPAGSPT STEEGTSTEP SEGSAPGTST EPSEGSAPGS EPATSGSETP  840
GTSESATPES GPGTSTEPSE GSAP                                         864

SEQ ID NO: 386         moltype = AA  length = 865
FEATURE                Location/Qualifiers
REGION                 1..865
                       note = Description of Artificial Sequence: Synthetic
                        polypeptide
source                 1..865
                       mol_type = protein
                       organism = synthetic construct
SEQUENCE: 386
GGSPAGSPTS TEEGTSESAT PESGPGTSTE PSEGSAPGSP AGSPTSTEEG TSTEPSEGSA  60
PGTSTEPSEG SAPGTSESAT PESGPGSEPA TSGSETPGSE PATSGSETPG SPAGSPTSTE  120
EGTSESATPE SGPGTSTEPS EGSAPGTSTE PSEGSAPGSP AGSPTSTEEG TSTEPSEGSA  180
PGTSTEPSEG SAPGTSESAT PESGPGTSTE PSEGSAPGTS ESATPESGPG SEPATSGSET  240
PGTSTEPSEG SAPGTSTEPS EGSAPGTSES ATPESGPGTS ESATPESGPG SPAGSPTSTE  300
EGTSESATPE SGPGSEPATS GSETPGTSES ATPESGPGTS TEPSEGSAPG TSTEPSEGSA  360
PGTSTEPSEG SAPGTSTEPS EGSAPGTSTE PSEGSAPGTS TEPSEGSAPG SPAGSPTSTE  420
EGTSTEPSEG SAPGTSESAT PESGPGSEPA TSGSETPGTS ESATPESGPG SEPATSGSET  480
PGTSESATPE SGPGTSTEPS EGSAPGTSES ATPESGPGSP AGSPTSTEEG SPAGSPTSTE  540
EGSPAGSPTS TEEGTSESAT PESGPGTSTE PSEGSAPGTS ESATPESGPG SEPATSGSET  600
PGTSESATPE SGPGSEPATS GSETPGTSES ATPESGPGTS TEPSEGSAPG SPAGSPTSTE  660
EGTSESATPE SGPGSEPATS GSETPGTSES ATPESGPGSP AGSPTSTEEG SPAGSPTSTE  720
EGTSTEPSEG SAPGTSESAT PESGPGTSES ATPESGPGTS ESATPESGPG SEPATSGSET  780
PGSEPATSGS ETPGSPAGSP TSTEEGTSTE PSEGSAPGTS TEPSEGSAPG SEPATSGSET  840
PGTSESATPE SGPGTSTEPS EGSAP                                        865

SEQ ID NO: 387         moltype = AA  length = 866
FEATURE                Location/Qualifiers
REGION                 1..866
```

```
                        note = Description of Artificial Sequence: Synthetic
                         polypeptide
source                  1..866
                        mol_type = protein
                        organism = synthetic construct
SEQUENCE: 387
PGSPAGSPTS TEEGTSESAT PESGPGTSTE PSEGSAPGSP AGSPTSTEEG TSTEPSEGSA  60
PGTSTEPSEG SAPGTSESAT PESGPGSEPA TSGSETPGSE PATSGSETPG SPAGSPTSTE  120
EGTSESATPE SGPGTSTEPS EGSAPGTSTE PSEGSAPGSP AGSPTSTEEG TSTEPSEGSA  180
PGTSTEPSEG SAPGTSESAT PESGPGTSTE PSEGSAPGTS ESATPESGPG SEPATSGSET  240
PGTSTEPSEG SAPGTSTEPS EGSAPGTSES ATPESGPGTS ESATPESGPG SPAGSPTSTE  300
EGTSESATPE SGPGSEPATS GSETPGTSES ATPESGPGTS TEPSEGSAPG TSTEPSEGSA  360
PGTSTEPSEG SAPGTSTEPS EGSAPGTSTE PSEGSAPGTS TEPSEGSAPG SPAGSPTSTE  420
EGTSTEPSEG SAPGTSESAT PESGPGSEPA TSGSETPGTS ESATPESGPG SEPATSGSET  480
PGTSESATPE SGPGTSTEPS EGSAPGTSES ATPESGPGSP AGSPTSTEEG SPAGSPTSTE  540
EGSPAGSPTS TEEGTSESAT PESGPGTSTE PSEGSAPGTS ESATPESGPG SEPATSGSET  600
PGTSESATPE SGPGSEPATS GSETPGTSES ATPESGPGTS TEPSEGSAPG SPAGSPTSTE  660
EGTSESATPE SGPGSEPATS GSETPGTSES ATPESGPGSP AGSPTSTEEG SPAGSPTSTE  720
EGTSTEPSEG SAPGTSESAT PESGPGTSES ATPESGPGTS ESATPESGPG SEPATSGSET  780
PGSEPATSGS ETPGSPAGSP TSTEEGTSTE PSEGSAPGTS TEPSEGSAPG SEPATSGSET  840
PGTSESATPE SGPGTSTEPS EGSAPG                                       866

SEQ ID NO: 388          moltype = AA  length = 1152
FEATURE                 Location/Qualifiers
REGION                  1..1152
                        note = Description of Artificial Sequence: Synthetic
                         polypeptide
source                  1..1152
                        mol_type = protein
                        organism = synthetic construct
SEQUENCE: 388
GSPAGSPTST EEGTSESATP ESGPGTSTEP SEGSAPGSPA GSPTSTEEGT STEPSEGSAP  60
GTSTEPSEGS APGTSESATP ESGPGSEPAT SGSETPGSEP ATSGSETPGS PAGSPTSTEE  120
GTSESATPES GPGTSTEPSE GSAPGTSTEP SEGSAPGSPA GSPTSTEEGT STEPSEGSAP  180
GTSTEPSEGS APGTSESATP ESGPGTSTEP SEGSAPGTSE SATPESGPGS EPATSGSETP  240
GTSTEPSEGS APGTSTEPSE GSAPGTSESA TPESGPGTSE SATPESGPGS PAGSPTSTEE  300
GTSESATPES GPGSEPATSG SETPGTSESA TPESGPGTST EPSEGSAPGT STEPSEGSAP  360
GTSTEPSEGS APGTSTEPSE GSAPGTSTEP SEGSAPGTST EPSEGSAPGS PAGSPTSTEE  420
GTSTEPSEGS APGTSESATP ESGPGSEPAT SGSETPGTSE SATPESGPGS EPATSGSETP  480
GTSESATPES GPGTSTEPSE GSAPGTSESA TPESGPGSPA GSPTSTEEGS PAGSPTSTEE  540
GSPAGSPTST EEGTSESATP ESGPGTSTEP SEGSAPGTSE SATPESGPGS EPATSGSETP  600
GTSESATPES GPGSEPATSG SETPGTSESA TPESGPGTST EPSEGSAPGS PAGSPTSTEE  660
GTSESATPES GPGSEPATSG SETPGTSESA TPESGPGSPA GSPTSTEEGS PAGSPTSTEE  720
GTSTEPSEGS APGTSESATP ESGPGTSESA TPESGPGTSE SATPESGPGS EPATSGSETP  780
GSEPATSGSE TPGSPAGSPT STEEGTSTEP SEGSAPGTST EPSEGSAPGS EPATSGSETP  840
GTSESATPES GPGTSTEPSE GSAPGTSESA TPESGPGSEP ATSGSETPGT SESATPESGP  900
GSEPATSGSE TPGTSESATP ESGPGTSTEP SEGSAPGSPA GSPTSTEEGT SESATPESGP  960
GSEPATSGSE TPGTSESATP ESGPGSPAGS PTSTEEGSPA GSPTSTEEGT STEPSEGSAP  1020
GTSESATPES GPGTSESATP ESGPGTSESA TPESGPGSEP ATSGSETPGS EPATSGSETP  1080
GSPAGSPTST EEGTSTEPSE GSAPGTSTEP SEGSAPGSEP ATSGSETPGT SESATPESGP  1140
GTSTEPSEGS AP                                                      1152

SEQ ID NO: 389          moltype = AA  length = 144
FEATURE                 Location/Qualifiers
REGION                  1..144
                        note = Description of Artificial Sequence: Synthetic
                         polypeptide
source                  1..144
                        mol_type = protein
                        organism = synthetic construct
SEQUENCE: 389
STEPSEGSAP GSPAGSPTST EEGTSTEPSE GSAPGTSESA TPESGPGSEP ATSGSETPGT  60
SESATPESGP GSEPATSGSE TPGTSESATP ESGPGTSTEP SEGSAPGTSE SATPESGPGS  120
PAGSPTSTEE GSPAGSPTST EEGS                                         144

SEQ ID NO: 390          moltype = AA  length = 144
FEATURE                 Location/Qualifiers
REGION                  1..144
                        note = Description of Artificial Sequence: Synthetic
                         polypeptide
source                  1..144
                        mol_type = protein
                        organism = synthetic construct
SEQUENCE: 390
SEPATSGSET PGTSESATPE SGPGSEPATS GSETPGTSES ATPESGPGTS TEPSEGSAPG  60
SPAGSPTSTE EGTSESATPE SGPGSEPATS GSETPGTSES ATPESGPGSP AGSPTSTEEG  120
SPAGSPTSTE EGTSTEPSEG SAPG                                         144

SEQ ID NO: 391          moltype = AA  length = 180
```

```
FEATURE                 Location/Qualifiers
REGION                  1..180
                        note = Description of Artificial Sequence: Synthetic
                         polypeptide
source                  1..180
                        mol_type = protein
                        organism = synthetic construct
SEQUENCE: 391
TSTEEGTSES ATPESGPGSE PATSGSETPG TSESATPESG PGSPAGSPTS TEEGSPAGSP  60
TSTEEGTSTE PSEGSAPGTS ESATPESGPG TSESATPESG PGTSESATPE SGPGSEPATS  120
GSETPGSEPA TSGSETPGSP AGSPTSTEEG TSTEPSEGSA PGTSTEPSEG SAPGSEPATS  180

SEQ ID NO: 392          moltype = AA  length = 216
FEATURE                 Location/Qualifiers
REGION                  1..216
                        note = Description of Artificial Sequence: Synthetic
                         polypeptide
source                  1..216
                        mol_type = protein
                        organism = synthetic construct
SEQUENCE: 392
PESGPGTSTE PSEGSAPGSP AGSPTSTEEG TSESATPESG PGSEPATSGS ETPGTSESAT  60
PESGPGSPAG SPTSTEEGSP AGSPTSTEEG TSTEPSEGSA PGTSESATPE SGPGTSESAT  120
PESGPGTSES ATPESGPGSE PATSGSETPG SEPATSGSET PGSPAGSPTS TEEGTSTEPS  180
EGSAPGTSTE PSEGSAPGSE PATSGSETPG TSESAT                            216

SEQ ID NO: 393          moltype = AA  length = 252
FEATURE                 Location/Qualifiers
REGION                  1..252
                        note = Description of Artificial Sequence: Synthetic
                         polypeptide
source                  1..252
                        mol_type = protein
                        organism = synthetic construct
SEQUENCE: 393
ESGPGSEPAT SGSETPGTSE SATPESGPGT STEPSEGSAP GSPAGSPTST EEGTSESATP  60
ESGPGSEPAT SGSETPGTSE SATPESGPGS PAGSPTSTEE GSPAGSPTST EEGTSTEPSE  120
GSAPGTSESA TPESGPGTSE SATPESGPGT SESATPESGP GSEPATSGSE TPGSEPATSG  180
SETPGSPAGS PTSTEEGTST EPSEGSAPGT STEPSEGSAP GSEPATSGSE TPGTSESATP  240
ESGPGTSTEP SE                                                      252

SEQ ID NO: 394          moltype = AA  length = 288
FEATURE                 Location/Qualifiers
REGION                  1..288
                        note = Description of Artificial Sequence: Synthetic
                         polypeptide
source                  1..288
                        mol_type = protein
                        organism = synthetic construct
SEQUENCE: 394
TPESGPGTST EPSEGSAPGT SESATPESGP GSEPATSGSE TPGTSESATP ESGPGSEPAT  60
SGSETPGTSE SATPESGPGT STEPSEGSAP GSPAGSPTST EEGTSESATP ESGPGSEPAT  120
SGSETPGTSE SATPESGPGS PAGSPTSTEE GSPAGSPTST EEGTSTEPSE GSAPGTSESA  180
TPESGPGTSE SATPESGPGT SESATPESGP GSEPATSGSE TPGSEPATSG SETPGSPAGS  240
PTSTEEGTST EPSEGSAPGT STEPSEGSAP GSEPATSGSE TPGTSESA               288

SEQ ID NO: 395          moltype = AA  length = 324
FEATURE                 Location/Qualifiers
REGION                  1..324
                        note = Description of Artificial Sequence: Synthetic
                         polypeptide
source                  1..324
                        mol_type = protein
                        organism = synthetic construct
SEQUENCE: 395
PESGPGSPAG SPTSTEEGSP AGSPTSTEEG SPAGSPTSTE EGTSESATPE SGPGTSTEPS  60
EGSAPGTSES ATPESGPGSE PATSGSETPG TSESATPESG PGSEPATSGS ETPGTSESAT  120
PESGPGTSTE PSEGSAPGSP AGSPTSTEEG TSESATPESG PGSEPATSGS ETPGTSESAT  180
PESGPGSPAG SPTSTEEGSP AGSPTSTEEG TSTEPSEGSA PGTSESATPE SGPGTSESAT  240
PESGPGTSES ATPESGPGSE PATSGSETPG SEPATSGSET PGSPAGSPTS TEEGTSTEPS  300
EGSAPGTSTE PSEGSAPGSE PATS                                         324

SEQ ID NO: 396          moltype = AA  length = 360
FEATURE                 Location/Qualifiers
REGION                  1..360
                        note = Description of Artificial Sequence: Synthetic
                         polypeptide
source                  1..360
                        mol_type = protein
```

```
                         organism = synthetic construct
SEQUENCE: 396
PESGPGTSTE PSEGSAPGTS ESATPESGPG SPAGSPTSTE EGSPAGSPTS TEEGSPAGSP  60
TSTEEGTSES ATPESGPGTS TEPSEGSAPG TSESATPESG PGSEPATSGS ETPGTSESAT  120
PESGPGSEPA TSGSETPGTS ESATPESGPG TSTEPSEGSA PGSPAGSPTS TEEGTSESAT  180
PESGPGSEPA TSGSETPGTS ESATPESGPG SPAGSPTSTE EGSPAGSPTS TEEGTSTEPS  240
EGSAPGTSES ATPESGPGTS ESATPESGPG TSESATPESG PGSEPATSGS ETPGSEPATS  300
GSETPGSPAG SPTSTEEGTS TEPSEGSAPG TSTEPSEGSA PGSEPATSGS ETPGTSESAT  360

SEQ ID NO: 397           moltype = AA  length = 360
FEATURE                  Location/Qualifiers
REGION                   1..360
                         note = Description of Artificial Sequence: Synthetic
                          polypeptide
source                   1..360
                         mol_type = protein
                         organism = synthetic construct
SEQUENCE: 397
PESGPGSEPA TSGSETPGTS ESATPESGPG TSTEPSEGSA PGTSESATPE SGPGSPAGSP  60
TSTEEGSPAG SPTSTEEGSP AGSPTSTEEG TSESATPESG PGTSTEPSEG SAPGTSESAT  120
PESGPGSEPA TSGSETPGTS ESATPESGPG SEPATSGSET PGTSESATPE SGPGTSTEPS  180
EGSAPGSPAG SPTSTEEGTS ESATPESGPG SEPATSGSET PGTSESATPE SGPGSPAGSP  240
TSTEEGSPAG SPTSTEEGTS TEPSEGSAPG TSESATPESG PGTSESATPE SGPGTSESAT  300
PESGPGSEPA TSGSETPGSE PATSGSETPG SPAGSPTSTE EGTSTEPSEG SAPGTSTEPS  360

SEQ ID NO: 398           moltype = AA  length = 432
FEATURE                  Location/Qualifiers
REGION                   1..432
                         note = Description of Artificial Sequence: Synthetic
                          polypeptide
source                   1..432
                         mol_type = protein
                         organism = synthetic construct
SEQUENCE: 398
EGSAPGSPAG SPTSTEEGTS TEPSEGSAPG TSESATPESG PGSEPATSGS ETPGTSESAT  60
PESGPGSEPA TSGSETPGTS ESATPESGPG TSTEPSEGSA PGTSESATPE SGPGSPAGSP  120
TSTEEGSPAG SPTSTEEGSP AGSPTSTEEG TSESATPESG PGTSTEPSEG SAPGTSESAT  180
PESGPGSEPA TSGSETPGTS ESATPESGPG SEPATSGSET PGTSESATPE SGPGTSTEPS  240
EGSAPGSPAG SPTSTEEGTS ESATPESGPG SEPATSGSET PGTSESATPE SGPGSPAGSP  300
TSTEEGSPAG SPTSTEEGTS TEPSEGSAPG TSESATPESG PGTSESATPE SGPGTSESAT  360
PESGPGSEPA TSGSETPGSE PATSGSETPG SPAGSPTSTE EGTSTEPSEG SAPGTSTEPS  420
EGSAPGSEPA TS                                                      432

SEQ ID NO: 399           moltype = AA  length = 468
FEATURE                  Location/Qualifiers
REGION                   1..468
                         note = Description of Artificial Sequence: Synthetic
                          polypeptide
source                   1..468
                         mol_type = protein
                         organism = synthetic construct
SEQUENCE: 399
EGSAPGTSTE PSEGSAPGTS TEPSEGSAPG SPAGSPTSTE EGTSTEPSEG SAPGTSESAT  60
PESGPGSEPA TSGSETPGTS ESATPESGPG SEPATSGSET PGTSESATPE SGPGTSTEPS  120
EGSAPGTSES ATPESGPGSP AGSPTSTEEG SPAGSPTSTE EGSPAGSPTS TEEGTSESAT  180
PESGPGTSTE PSEGSAPGTS ESATPESGPG SEPATSGSET PGTSESATPE SGPGSEPATS  240
GSETPGTSES ATPESGPGTS TEPSEGSAPG SPAGSPTSTE EGTSESATPE SGPGSEPATS  300
GSETPGTSES ATPESGPGSP AGSPTSTEEG SPAGSPTSTE EGTSTEPSEG SAPGTSESAT  360
PESGPGTSES ATPESGPGTS ESATPESGPG SEPATSGSET PGSEPATSGS ETPGSPAGSP  420
TSTEEGTSTE PSEGSAPGTS TEPSEGSAPG SEPATSGSET PGTSESAT               468

SEQ ID NO: 400           moltype = AA  length = 504
FEATURE                  Location/Qualifiers
REGION                   1..504
                         note = Description of Artificial Sequence: Synthetic
                          polypeptide
source                   1..504
                         mol_type = protein
                         organism = synthetic construct
SEQUENCE: 400
EGSAPGTSTE PSEGSAPGTS TEPSEGSAPG TSTEPSEGSA PGTSTEPSEG SAPGSPAGSP  60
TSTEEGTSTE PSEGSAPGTS ESATPESGPG SEPATSGSET PGTSESATPE SGPGSEPATS  120
GSETPGTSES ATPESGPGTS TEPSEGSAPG TSESATPESG PGSPAGSPTS TEEGSPAGSP  180
TSTEEGSPAG SPTSTEEGTS ESATPESGPG TSTEPSEGSA PGTSESATPE SGPGSEPATS  240
GSETPGTSES ATPESGPGSE PATSGSETPG TSESATPESG PGTSTEPSEG SAPGSPAGSP  300
TSTEEGTSES ATPESGPGSE PATSGSETPG TSESATPESG PGSPAGSPTS TEEGSPAGSP  360
TSTEEGTSTE PSEGSAPGTS ESATPESGPG TSESATPESG PGTSESATPE SGPGSEPATS  420
GSETPGSEPA TSGSETPGSP AGSPTSTEEG TSTEPSEGSA PGTSTEPSEG SAPGSEPATS  480
GSETPGTSES ATPESGPGTS TEPS                                         504
```

```
SEQ ID NO: 401          moltype = AA  length = 540
FEATURE                 Location/Qualifiers
REGION                  1..540
                        note = Description of Artificial Sequence: Synthetic
                         polypeptide
source                  1..540
                        mol_type = protein
                        organism = synthetic construct
SEQUENCE: 401
TPESGPGSPA GSPTSTEEGT SESATPESGP GSEPATSGSE TPGTSESATP ESGPGTSTEP  60
SEGSAPGTST EPSEGSAPGT STEPSEGSAP GTSTEPSEGS APGTSTEPSE GSAPGTSTEP  120
SEGSAPGSPA GSPTSTEEGT STEPSEGSAP GTSESATPES GPGSEPATSG SETPGTSESA  180
TPESGPGSEP ATSGSETPGT SESATPESGP GTSTEPSEGS APGTSESATP ESGPGSPAGS  240
PTSTEEGSPA GSPTSTEEGS PAGSPTSTEE GTSESATPES GPGTSTEPSE GSAPGTSESA  300
TPESGPGSEP ATSGSETPGT SESATPESGP GSEPATSGSE TPGTSESATP ESGPGTSTEP  360
SEGSAPGSPA GSPTSTEEGT SESATPESGP GSEPATSGSE TPGTSESATP ESGPGSPAGS  420
PTSTEEGSPA GSPTSTEEGT STEPSEGSAP GTSESATPES GPGTSESATP ESGPGTSESA  480
TPESGPGSEP ATSGSETPGS EPATSGSETP GSPAGSPTST EEGTSTEPSE GSAPGTSTEP  540

SEQ ID NO: 402          moltype = AA  length = 576
FEATURE                 Location/Qualifiers
REGION                  1..576
                        note = Description of Artificial Sequence: Synthetic
                         polypeptide
source                  1..576
                        mol_type = protein
                        organism = synthetic construct
SEQUENCE: 402
TPESGPGTSE SATPESGPGS PAGSPTSTEE GTSESATPES GPGSEPATSG SETPGTSESA  60
TPESGPGTST EPSEGSAPGT STEPSEGSAP GTSTEPSEGS APGTSTEPSE GSAPGTSTEP  120
SEGSAPGTST EPSEGSAPGS PAGSPTSTEE GTSTEPSEGS APGTSESATP ESGPGSEPAT  180
SGSETPGTSE SATPESGPGS EPATSGSETP GTSESATPES GPGTSTEPSE GSAPGTSESA  240
TPESGPGSPA GSPTSTEEGS PAGSPTSTEE GSPAGSPTST EEGTSESATP ESGPGTSTEP  300
SEGSAPGTSE SATPESGPGS EPATSGSETP GTSESATPES GPGSEPATSG SETPGTSESA  360
TPESGPGTST EPSEGSAPGS PAGSPTSTEE GTSESATPES GPGSEPATSG SETPGTSESA  420
TPESGPGSPA GSPTSTEEGS PAGSPTSTEE GTSTEPSEGS APGTSESATP ESGPGTSESA  480
TPESGPGTSE SATPESGPGS EPATSGSETP GSEPATSGSE TPGSPAGSPT STEEGTSTEP  540
SEGSAPGTST EPSEGSAPGS EPATSGSETP GTSESA                            576

SEQ ID NO: 403          moltype = AA  length = 612
FEATURE                 Location/Qualifiers
REGION                  1..612
                        note = Description of Artificial Sequence: Synthetic
                         polypeptide
source                  1..612
                        mol_type = protein
                        organism = synthetic construct
SEQUENCE: 403
GSETPGTSTE PSEGSAPGTS TEPSEGSAPG TSESATPESG PGTSESATPE SGPGSPAGSP  60
TSTEEGTSES ATPESGPGSE PATSGSETPG TSESATPESG PGTSTEPSEG SAPGTSTEPS  120
EGSAPGTSTE PSEGSAPGTS TEPSEGSAPG TSTEPSEGSA PGTSTEPSEG SAPGSPAGSP  180
TSTEEGTSTE PSEGSAPGTS ESATPESGPG SEPATSGSET PGTSESATPE SGPGSEPATS  240
GSETPGTSES ATPESGPGTS TEPSEGSAPG TSESATPESG PGSPAGSPTS TEEGSPAGSP  300
TSTEEGSPAG SPTSTEEGTS ESATPESGPG TSTEPSEGSA PGTSESATPE SGPGSEPATS  360
GSETPGTSES ATPESGPGSE PATSGSETPG TSESATPESG PGTSTEPSEG SAPGSPAGSP  420
TSTEEGTSES ATPESGPGSE PATSGSETPG TSESATPESG PGSPAGSPTS TEEGSPAGSP  480
TSTEEGTSTE PSEGSAPGTS ESATPESGPG TSESATPESG PGTSESATPE SGPGSEPATS  540
GSETPGSEPA TSGSETPGSP AGSPTSTEEG TSTEPSEGSA PGTSTEPSEG SAPGSEPATS  600
GSETPGTSES AT                                                      612

SEQ ID NO: 404          moltype = AA  length = 648
FEATURE                 Location/Qualifiers
REGION                  1..648
                        note = Description of Artificial Sequence: Synthetic
                         polypeptide
source                  1..648
                        mol_type = protein
                        organism = synthetic construct
SEQUENCE: 404
PESGPGTSTE PSEGSAPGTS ESATPESGPG SEPATSGSET PGTSTEPSEG SAPGTSTEPS  60
EGSAPGTSES ATPESGPGTS ESATPESGPG SPAGSPTSTE EGTSESATPE SGPGSEPATS  120
GSETPGTSES ATPESGPGTS TEPSEGSAPG TSTEPSEGSA PGTSTEPSEG SAPGTSTEPS  180
EGSAPGTSTE PSEGSAPGTS TEPSEGSAPG SPAGSPTSTE EGTSTEPSEG SAPGTSESAT  240
PESGPGSEPA TSGSETPGTS ESATPESGPG SEPATSGSET PGTSESATPE SGPGTSTEPS  300
EGSAPGTSES ATPESGPGSP AGSPTSTEEG SPAGSPTSTE EGSPAGSPTS TEEGTSESAT  360
PESGPGTSTE PSEGSAPGTS ESATPESGPG SEPATSGSET PGTSESATPE SGPGSEPATS  420
GSETPGTSES ATPESGPGTS TEPSEGSAPG SPAGSPTSTE EGTSESATPE SGPGSEPATS  480
GSETPGTSES ATPESGPGSP AGSPTSTEEG SPAGSPTSTE EGTSTEPSEG SAPGTSESAT  540
```

```
PESGPGTSES ATPESGPGTS ESATPESGPG SEPATSGSET PGSEPATSGS ETPGSPAGSP  600
TSTEEGTSTE PSEGSAPGTS TEPSEGSAPG SEPATSGSET PGTSESAT               648

SEQ ID NO: 405         moltype = AA  length = 684
FEATURE                Location/Qualifiers
REGION                 1..684
                       note = Description of Artificial Sequence: Synthetic
                        polypeptide
source                 1..684
                       mol_type = protein
                       organism = synthetic construct
SEQUENCE: 405
EGSAPGSPAG SPTSTEEGTS TEPSEGSAPG TSTEPSEGSA PGTSESATPE SGPGTSTEPS  60
EGSAPGTSES ATPESGPGSE PATSGSETPG TSTEPSEGSA PGTSTEPSEG SAPGTSESAT  120
PESGPGTSES ATPESGPGSP AGSPTSTEEG TSESATPESG PGSEPATSGS ETPGTSESAT  180
PESGPGTSTE PSEGSAPGTS TEPSEGSAPG TSTEPSEGSA PGTSTEPSEG SAPGTSTEPS  240
EGSAPGTSTE PSEGSAPGSP AGSPTSTEEG TSTEPSEGSA PGTSESATPE SGPGSEPATS  300
GSETPGTSES ATPESGPGSE PATSGSETPG TSESATPESG PGTSTEPSEG SAPGTSESAT  360
PESGPGSPAG SPTSTEEGSP AGSPTSTEEG SPAGSPTSTE EGTSESATPE SGPGTSTEPS  420
EGSAPGTSES ATPESGPGSE PATSGSETPG TSESATPESG PGSEPATSGS ETPGTSESAT  480
PESGPGTSTE PSEGSAPGSP AGSPTSTEEG TSESATPESG PGSEPATSGS ETPGTSESAT  540
PESGPGSPAG SPTSTEEGSP AGSPTSTEEG TSTEPSEGSA PGTSESATPE SGPGTSESAT  600
PESGPGTSES ATPESGPGSE PATSGSETPG SEPATSGSET PGSPAGSPTS TEEGTSTEPS  660
EGSAPGTSTE PSEGSAPGSE PATS                                         684

SEQ ID NO: 406         moltype = AA  length = 720
FEATURE                Location/Qualifiers
REGION                 1..720
                       note = Description of Artificial Sequence: Synthetic
                        polypeptide
source                 1..720
                       mol_type = protein
                       organism = synthetic construct
SEQUENCE: 406
TSGSETPGSE PATSGSETPG SPAGSPTSTE EGTSESATPE SGPGTSTEPS EGSAPGTSTE  60
PSEGSAPGSP AGSPTSTEEG TSTEPSEGSA PGTSTEPSEG SAPGTSESAT PESGPGTSTE  120
PSEGSAPGTS ESATPESGPG SEPATSGSET PGTSTEPSEG SAPGTSTEPS EGSAPGTSES  180
ATPESGPGTS ESATPESGPG SPAGSPTSTE EGTSESATPE SGPGSEPATS GSETPGTSES  240
ATPESGPGTS TEPSEGSAPG TSTEPSEGSA PGTSTEPSEG SAPGTSTEPS EGSAPGTSTE  300
PSEGSAPGTS TEPSEGSAPG SPAGSPTSTE EGTSTEPSEG SAPGTSESAT PESGPGSEPA  360
TSGSETPGTS ESATPESGPG SEPATSGSET PGTSESATPE SGPGTSTEPS EGSAPGTSES  420
ATPESGPGSP AGSPTSTEEG SPAGSPTSTE EGSPAGSPTS TEEGTSESAT PESGPGTSTE  480
PSEGSAPGTS ESATPESGPG SEPATSGSET PGTSESATPE SGPGSEPATS GSETPGTSES  540
ATPESGPGTS TEPSEGSAPG SPAGSPTSTE EGTSESATPE SGPGSEPATS GSETPGTSES  600
ATPESGPGSP AGSPTSTEEG SPAGSPTSTE EGTSTEPSEG SAPGTSESAT PESGPGTSES  660
ATPESGPGTS ESATPESGPG SEPATSGSET PGSEPATSGS ETPGSPAGSP TSTEEGTSTE  720

SEQ ID NO: 407         moltype = AA  length = 756
FEATURE                Location/Qualifiers
REGION                 1..756
                       note = Description of Artificial Sequence: Synthetic
                        polypeptide
source                 1..756
                       mol_type = protein
                       organism = synthetic construct
SEQUENCE: 407
TSGSETPGSE PATSGSETPG SPAGSPTSTE EGTSESATPE SGPGTSTEPS EGSAPGTSTE  60
PSEGSAPGSP AGSPTSTEEG TSTEPSEGSA PGTSTEPSEG SAPGTSESAT PESGPGTSTE  120
PSEGSAPGTS ESATPESGPG SEPATSGSET PGTSTEPSEG SAPGTSTEPS EGSAPGTSES  180
ATPESGPGTS ESATPESGPG SPAGSPTSTE EGTSESATPE SGPGSEPATS GSETPGTSES  240
ATPESGPGTS TEPSEGSAPG TSTEPSEGSA PGTSTEPSEG SAPGTSTEPS EGSAPGTSTE  300
PSEGSAPGTS TEPSEGSAPG SPAGSPTSTE EGTSTEPSEG SAPGTSESAT PESGPGSEPA  360
TSGSETPGTS ESATPESGPG SEPATSGSET PGTSESATPE SGPGTSTEPS EGSAPGTSES  420
ATPESGPGSP AGSPTSTEEG SPAGSPTSTE EGSPAGSPTS TEEGTSESAT PESGPGTSTE  480
PSEGSAPGTS ESATPESGPG SEPATSGSET PGTSESATPE SGPGSEPATS GSETPGTSES  540
ATPESGPGTS TEPSEGSAPG SPAGSPTSTE EGTSESATPE SGPGSEPATS GSETPGTSES  600
ATPESGPGSP AGSPTSTEEG SPAGSPTSTE EGTSTEPSEG SAPGTSESAT PESGPGTSES  660
ATPESGPGTS ESATPESGPG SEPATSGSET PGSEPATSGS ETPGSPAGSP TSTEEGTSTE  720
PSEGSAPGTS TEPSEGSAPG SEPATSGSET PGTSES                             756

SEQ ID NO: 408         moltype = AA  length = 792
FEATURE                Location/Qualifiers
REGION                 1..792
                       note = Description of Artificial Sequence: Synthetic
                        polypeptide
source                 1..792
                       mol_type = protein
                       organism = synthetic construct
SEQUENCE: 408
```

```
EGSAPGTSES ATPESGPGSE PATSGSETPG SEPATSGSET PGSPAGSPTS TEEGTSESAT  60
PESGPGTSTE PSEGSAPGTS TEPSEGSAPG SPAGSPTSTE EGTSTEPSEG SAPGTSTEPS  120
EGSAPGTSES ATPESGPGTS TEPSEGSAPG TSESATPESG PGSEPATSGS ETPGTSTEPS  180
EGSAPGTSTE PSEGSAPGTS ESATPESGPG TSESATPESG PGSPAGSPTS TEEGTSESAT  240
PESGPGSEPA TSGSETPGTS ESATPESGPG TSTEPSEGSA PGTSTEPSEG SAPGTSTEPS  300
EGSAPGTSTE PSEGSAPGTS TEPSEGSAPG TSTEPSEGSA PGSPAGSPTS TEEGTSTEPS  360
EGSAPGTSES ATPESGPGSE PATSGSETPG TSESATPESG PGSEPATSGS ETPGTSESAT  420
PESGPGTSTE PSEGSAPGTS ESATPESGPG SPAGSPTSTE EGSPAGSPTS TEEGSPAGSP  480
TSTEEGTSES ATPESGPGTS TEPSEGSAPG TSESATPESG PGSEPATSGS ETPGTSESAT  540
PESGPGSEPA TSGSETPGTS ESATPESGPG TSTEPSEGSA PGSPAGSPTS TEEGTSESAT  600
PESGPGSEPA TSGSETPGTS ESATPESGPG SPAGSPTSTE EGSPAGSPTS TEEGTSTEPS  660
EGSAPGTSES ATPESGPGTS ESATPESGPG TSESATPESG PGSEPATSGS ETPGSEPATS  720
GSETPGSPAG SPTSTEEGTS TEPSEGSAPG TSTEPSEGSA PGSEPATSGS ETPGTSESAT  780
PESGPGTSTE PS                                                      792
```

```
SEQ ID NO: 409         moltype = AA  length = 828
FEATURE                Location/Qualifiers
REGION                 1..828
                       note = Description of Artificial Sequence: Synthetic
                        polypeptide
source                 1..828
                       mol_type = protein
                       organism = synthetic construct
SEQUENCE: 409
PESGPGTSTE PSEGSAPGSP AGSPTSTEEG TSTEPSEGSA PGTSTEPSEG SAPGTSESAT  60
PESGPGSEPA TSGSETPGSE PATSGSETPG SPAGSPTSTE EGTSESATPE SGPGTSTEPS  120
EGSAPGTSTE PSEGSAPGSP AGSPTSTEEG TSTEPSEGSA PGTSTEPSEG SAPGTSESAT  180
PESGPGTSTE PSEGSAPGTS ESATPESGPG SEPATSGSET PGTSTEPSEG SAPGTSTEPS  240
EGSAPGTSES ATPESGPGTS ESATPESGPG SPAGSPTSTE EGTSESATPE SGPGSEPATS  300
GSETPGTSES ATPESGPGTS TEPSEGSAPG TSTEPSEGSA PGTSTEPSEG SAPGTSTEPS  360
EGSAPGTSTE PSEGSAPGTS TEPSEGSAPG SPAGSPTSTE EGTSTEPSEG SAPGTSESAT  420
PESGPGSEPA TSGSETPGTS ESATPESGPG SEPATSGSET PGTSESATPE SGPGTSTEPS  480
EGSAPGTSES ATPESGPGSP AGSPTSTEEG SPAGSPTSTE EGSPAGSPTS TEEGTSESAT  540
PESGPGTSTE PSEGSAPGTS ESATPESGPG SEPATSGSET PGTSESATPE SGPGSEPATS  600
GSETPGTSES ATPESGPGTS TEPSEGSAPG SPAGSPTSTE EGTSESATPE SGPGSEPATS  660
GSETPGTSES ATPESGPGSP AGSPTSTEEG SPAGSPTSTE EGTSTEPSEG SAPGTSESAT  720
PESGPGTSES ATPESGPGTS ESATPESGPG SEPATSGSET PGSEPATSGS ETPGSPAGSP  780
TSTEEGTSTE PSEGSAPGTS TEPSEGSAPG SEPATSGSET PGTSESAT            828
```

```
SEQ ID NO: 410         moltype = AA  length = 869
FEATURE                Location/Qualifiers
REGION                 1..869
                       note = Description of Artificial Sequence: Synthetic
                        polypeptide
source                 1..869
                       mol_type = protein
                       organism = synthetic construct
SEQUENCE: 410
GSPGSPAGSP TSTEEGTSES ATPESGPGTS TEPSEGSAPG SPAGSPTSTE EGTSTEPSEG  60
SAPGTSTEPS EGSAPGTSES ATPESGPGSE PATSGSETPG SEPATSGSET PGSPAGSPTS  120
TEEGTSESAT PESGPGTSTE PSEGSAPGTS TEPSEGSAPG SPAGSPTSTE EGTSTEPSEG  180
SAPGTSTEPS EGSAPGTSES ATPESGPGTS TEPSEGSAPG TSESATPESG PGSEPATSGS  240
ETPGTSTEPS EGSAPGTSTE PSEGSAPGTS ESATPESGPG TSESATPESG PGSPAGSPTS  300
TEEGTSESAT PESGPGSEPA TSGSETPGTS ESATPESGPG TSTEPSEGSA PGTSTEPSEG  360
SAPGTSTEPS EGSAPGTSTE PSEGSAPGTS TEPSEGSAPG TSTEPSEGSA PGSPAGSPTS  420
TEEGTSTEPS EGSAPGTSES ATPESGPGSE PATSGSETPG TSESATPESG PGSEPATSGS  480
ETPGTSESAT PESGPGTSTE PSEGSAPGTS ESATPESGPG SPAGSPTSTE EGSPAGSPTS  540
TEEGSPAGSP TSTEEGTSES ATPESGPGTS TEPSEGSAPG TSESATPESG PGSEPATSGS  600
ETPGTSESAT PESGPGSEPA TSGSETPGTS ESATPESGPG TSTEPSEGSA PGSPAGSPTS  660
TEEGTSESAT PESGPGSEPA TSGSETPGTS ESATPESGPG SPAGSPTSTE EGSPAGSPTS  720
TEEGTSTEPS EGSAPGTSES ATPESGPGTS ESATPESGPG TSESATPESG PGSEPATSGS  780
ETPGSEPATS GSETPGSPAG SPTSTEEGTS TEPSEGSAPG TSTEPSEGSA PGSEPATSGS  840
ETPGTSESAT PESGPGTSTE PSEGSAPGR                                    869
```

```
SEQ ID NO: 411         moltype = AA  length = 144
FEATURE                Location/Qualifiers
REGION                 1..144
                       note = Description of Artificial Sequence: Synthetic
                        polypeptide
source                 1..144
                       mol_type = protein
                       organism = synthetic construct
SEQUENCE: 411
SAGSPGSPAG SPTSTEEGTS ESATPESGPG TSTEPSEGSA PGSPAGSPTS TEEGTSTEPS  60
EGSAPGTSTE PSEGSAPGTS ESATPESGPG SEPATSGSET PGSEPATSGS ETPGSPAGSP  120
TSTEEGTSES ATPESGPGTE SASR                                         144
```

```
SEQ ID NO: 412         moltype = AA  length = 288
FEATURE                Location/Qualifiers
```

```
REGION                  1..288
                        note = Description of Artificial Sequence: Synthetic
                         polypeptide
source                  1..288
                        mol_type = protein
                        organism = synthetic construct
SEQUENCE: 412
SAGSPTGPGS EPATSGSETP GTSESATPES GPGSEPATSG SETPGTSESA TPESGPGTST  60
EPSEGSAPGS PAGSPTSTEE GTSESATPES GPGSEPATSG SETPGTSESA TPESGPGSPA  120
GSPTSTEEGS PAGSPTSTEE GTSTEPSEGS APGTSESATP ESGPGTSESA TPESGPGTSE  180
SATPESGPGS EPATSGSETP GSEPATSGSE TPGSPAGSPT STEEGTSTEP SEGSAPGTST  240
EPSEGSAPGS EPATSGSETP GTSESATPES GPGTSTEPSE GSAPSASR              288

SEQ ID NO: 413          moltype = AA  length = 432
FEATURE                 Location/Qualifiers
REGION                  1..432
                        note = Description of Artificial Sequence: Synthetic
                         polypeptide
source                  1..432
                        mol_type = protein
                        organism = synthetic construct
SEQUENCE: 413
SAGSPGSPAG SPTSTEEGTS ESATPESGPG TSTEPSEGSA PGSPAGSPTS TEEGTSTEPS  60
EGSAPGTSTE PSEGSAPGTS ESATPESGPG SEPATSGSET PGSEPATSGS ETPGSPAGSP  120
TSTEEGTSES ATPESGPGTS TEPSEGSAPG TSTEPSEGSA PGSPAGSPTS TEEGTSTEPS  180
EGSAPGTSTE PSEGSAPGTS ESATPESGPG TSTEPSEGSA PGTSESATPE SGPGSEPATS  240
GSETPGTSTE PSEGSAPGTS TEPSEGSAPG TSESATPESG PGTSESATPE SGPGSPAGSP  300
TSTEEGTSES ATPESGPGSE PATSGSETPG TSESATPESG PGTSTEPSEG SAPGTSTEPS  360
EGSAPGTSTE PSEGSAPGTS TEPSEGSAPG TSTEPSEGSA PGTSTEPSEG SAPGSPAGSP  420
TSTEEGTESA SR                                                      432

SEQ ID NO: 414          moltype = AA  length = 576
FEATURE                 Location/Qualifiers
REGION                  1..576
                        note = Description of Artificial Sequence: Synthetic
                         polypeptide
source                  1..576
                        mol_type = protein
                        organism = synthetic construct
SEQUENCE: 414
SAGSPTEEGT SESATPESGP GSEPATSGSE TPGTSESATP ESGPGTSTEP SEGSAPGTST  60
EPSEGSAPGT STEPSEGSAP GTSTEPSEGS APGTSTEPSE GSAPGTSTEP SEGSAPGSPA  120
GSPTSTEEGT STEPSEGSAP GTSESATPES GPGSEPATSG SETPGTSESA TPESGPGSEP  180
ATSGSETPGT SESATPESGP GTSTEPSEGS APGTSESATP ESGPGSPAGS PTSTEEGSPA  240
GSPTSTEEGS PAGSPTSTEE GTSESATPES GPGTSTEPSE GSAPGTSESA TPESGPGSEP  300
ATSGSETPGT SESATPESGP GSEPATSGSE TPGTSESATP ESGPGTSTEP SEGSAPGSPA  360
GSPTSTEEGT SESATPESGP GSEPATSGSE TPGTSESATP ESGPGSPAGS PTSTEEGSPA  420
GSPTSTEEGT STEPSEGSAP GTSESATPES GPGTSESATP ESGPGTSESA TPESGPGSEP  480
ATSGSETPGS EPATSGSETP GSPAGSPTST EEGTSTEPSE GSAPGTSTEP SEGSAPGSEP  540
ATSGSETPGT SESATPESGP GTSTEPSEGS APSASR                            576

SEQ ID NO: 415          moltype = AA  length = 864
FEATURE                 Location/Qualifiers
REGION                  1..864
                        note = Description of Artificial Sequence: Synthetic
                         polypeptide
source                  1..864
                        mol_type = protein
                        organism = synthetic construct
SEQUENCE: 415
SAGSPGSPAG SPTSTEEGTS ESATPESGPG TSTEPSEGSA PGSPAGSPTS TEEGTSTEPS  60
EGSAPGTSTE PSEGSAPGTS ESATPESGPG SEPATSGSET PGSEPATSGS ETPGSPAGSP  120
TSTEEGTSES ATPESGPGTS TEPSEGSAPG TSTEPSEGSA PGSPAGSPTS TEEGTSTEPS  180
EGSAPGTSTE PSEGSAPGTS ESATPESGPG TSTEPSEGSA PGTSESATPE SGPGSEPATS  240
GSETPGTSTE PSEGSAPGTS TEPSEGSAPG TSESATPESG PGTSESATPE SGPGSPAGSP  300
TSTEEGTSES ATPESGPGSE PATSGSETPG TSESATPESG PGTSTEPSEG SAPGTSTEPS  360
EGSAPGTSTE PSEGSAPGTS TEPSEGSAPG TSTEPSEGSA PGTSTEPSEG SAPGSPAGSP  420
TSTEEGTSTE PSEGSAPGTS ESATPESGPG SEPATSGSET PGTSESATPE SGPGSEPATS  480
GSETPGTSES ATPESGPGTS TEPSEGSAPG TSESATPESG PGSPAGSPTS TEEGSPAGSP  540
TSTEEGSPAG SPTSTEEGTS ESATPESGPG TSTEPSEGSA PGTSESATPE SGPGSEPATS  600
GSETPGTSES ATPESGPGSE PATSGSETPG TSESATPESG PGTSTEPSEG SAPGSPAGSP  660
TSTEEGTSES ATPESGPGSE PATSGSETPG TSESATPESG PGSPAGSPTS TEEGSPAGSP  720
TSTEEGTSTE PSEGSAPGTS ESATPESGPG TSESATPESG PGTSESATPE SGPGSEPATS  780
GSETPGSEPA TSGSETPGSP AGSPTSTEEG TSTEPSEGSA PGTSTEPSEG SAPGSEPATS  840
GSETPGTSES ATPESGPGTE SASR                                         864

SEQ ID NO: 416          moltype = AA  length = 712
FEATURE                 Location/Qualifiers
REGION                  1..712
```

-continued

```
                        note = Description of Artificial Sequence: Synthetic
                         polypeptide
source                  1..712
                        mol_type = protein
                        organism = synthetic construct
SEQUENCE: 416
PGSPAGSPTS TEEGTSESAT PESGPGTSTE PSEGSAPGSP AGSPTSTEEG TSTEPSEGSA  60
PGTSTEPSEG SAPGTSESAT PESGPGSEPA TSGSETPGSE PATSGSETPG SPAGSPTSTE  120
EGTSESATPE SGPGTSTEPS EGSAPGTSTE PSEGSAPGSP AGSPTSTEEG TSTEPSEGSA  180
PGTSTEPSEG SAPGTSESAT PESGPGTSTE PSEGSAPGTS ESATPESGPG SEPATSGSET  240
PGTSTEPSEG SAPGTSTEPS EGSAPGTSES ATPESGPGTS ESATPESGPG SPAGSPTSTE  300
EGTSESATPE SGPGSEPATS GSETPGTSES ATPESGPGTS TEPSEGSAPG TSTEPSEGSA  360
PGTSTEPSEG SAPGTSTEPS EGSAPGTSTE PSEGSAPGTS TEPSEGSAPG SPAGSPTSTE  420
EGTSTEPSEG SAPGTSESAT PESGPGSEPA TSGSETPGTS ESATPESGPG SEPATSGSET  480
PGTSESATPE SGPGTSTEPS EGSAPGTSES ATPESGPGSP AGSPTSTEEG SPAGSPTSTE  540
EGSPAGSPTS TEEGTSESAT PESGPGTSTE PSEGSAPGTS ESATPESGPG SEPATSGSET  600
PGTSESATPE SGPGSEPATS GSETPGTSES ATPESGPGTS TEPSEGSAPG SPAGSPTSTE  660
EGTSESATPE SGPGSEPATS GSETPGTSES ATPESGPGSP AGSPTSTEAH HH          712

SEQ ID NO: 417          moltype = AA  length = 864
FEATURE                 Location/Qualifiers
REGION                  1..864
                        note = Description of Artificial Sequence: Synthetic
                         polypeptide
source                  1..864
                        mol_type = protein
                        organism = synthetic construct
SEQUENCE: 417
GSPGAGSPAG SPTSTEEGTS ESATPESGPG TSTEPSEGSA PGSPAGSPTS TEEGTSTEPS  60
EGSAPGTSTE PSEGSAPGTS ESATPESGPG SEPATSGSET PGSEPATSGS ETPGSPAGSP  120
TSTEEGTSES ATPESGPGTS TEPSEGSAPG TSTEPSEGSA PGSPAGSPTS TEEGTSTEPS  180
EGSAPGTSTE PSEGSAPGTS ESATPESGPG TSTEPSEGSA PGTSESATPE SGPGSEPATS  240
GSETPGTSTE PSEGSAPGTS TEPSEGSAPG TSESATPESG PGTSESATPE SGPGSPAGSP  300
TSTEEGTSES ATPESGPGSE PATSGSETPG TSESATPESG PGTSTEPSEG SAPGTSTEPS  360
EGSAPGTSTE PSEGSAPGTS TEPSEGSAPG TSTEPSEGSA PGTSTEPSEG SAPGSPAGSP  420
TSTEEGTSTE PSEGSAPGTS ESATPESGPG SEPATSGSET PGTSESATPE SGPGSEPATS  480
GSETPGTSES ATPESGPGTS TEPSEGSAPG TSESATPESG PGSPAGSPTS TEEGSPAGSP  540
TSTEEGSPAG SPTSTEEGTS ESATPESGPG TSTEPSEGSA PGTSESATPE SGPGSEPATS  600
GSETPGTSES ATPESGPGSE PATSGSETPG TSESATPESG PGTSTEPSEG SAPGSPAGSP  660
TSTEEGTSES ATPESGPGSE PATSGSETPG TSESATPESG PGSPAGSPTS TEEGSPAGSP  720
TSTEEGTSTE PSEGSAPGTS ESATPESGPG TSESATPESG PGTSESATPE SGPGSEPATS  780
GSETPGSEPA TSGSETPGSP AGSPTSTEEG TSTEPSEGSA PGTSTEPSEG SAPGSEPATS  840
GSETPGTSES ATPESGPGTE SASR                                         864

SEQ ID NO: 418          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 418
GESPGGSSGS ES                                                      12

SEQ ID NO: 419          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 419
GSEGSSGPGE SS                                                      12

SEQ ID NO: 420          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 420
GSSESGSSEG GP                                                      12

SEQ ID NO: 421          moltype = AA  length = 12
FEATURE                 Location/Qualifiers
REGION                  1..12
                        note = Description of Artificial Sequence: Synthetic peptide
source                  1..12
```

```
                        mol_type = protein
                        organism = synthetic construct
SEQUENCE: 421
GSGGEPSESG SS                                                      12

SEQ ID NO: 422          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 422
GSPAGSPTST EE                                                      12

SEQ ID NO: 423          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 423
GSEPATSGSE TP                                                      12

SEQ ID NO: 424          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 424
GTSESATPES GP                                                      12

SEQ ID NO: 425          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 425
GTSTEPSEGS AP                                                      12

SEQ ID NO: 426          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 426
GSTSESPSGT AP                                                      12

SEQ ID NO: 427          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 427
GTSTPESGSA SP                                                      12

SEQ ID NO: 428          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 428
GTSPSGESST AP                                                      12

SEQ ID NO: 429          moltype = AA  length = 12
FEATURE                 Location/Qualifiers
REGION                  1..12
                        note = Description of Artificial Sequence: Synthetic peptide
```

```
source                  1..12
                        mol_type = protein
                        organism = synthetic construct
SEQUENCE: 429
GSTSSTAESP GP                                                      12

SEQ ID NO: 430          moltype = AA  length = 1157
FEATURE                 Location/Qualifiers
REGION                  1..1157
                        note = Description of Artificial Sequence: Synthetic
                         polypeptide
source                  1..1157
                        mol_type = protein
                        organism = synthetic construct
SEQUENCE: 430
DIQMTQSPSS LSASVGDRVT ITCRASQDIR NYLNWYQQKP GKAPKLLIYY TSRLESGVPS  60
RFSGSGSGTD YTLTISSLQP EDFATYYCQQ GNTLPWTFGQ GTKVEIKGAT PPETGAETES  120
PGETTGGSAE SEPPGEGEVQ LVESGGGLVQ PGGSLRLSCA ASGYSFTGYT MNWVRQAPGK  180
GLEWVALINP YKGVSTYNQK FKDRFTISVD KSKNTAYLQM NSLRAEDTAV YYCARSGYYG  240
DSDWYFDVWG QGTLVTVSSG TAEAASASGL SGRSDNHSPL GLAGSPGSPA GSPTSTEEGT  300
SESATPESGP GTSTEPSEGS APGSPAGSPT STEEGTSTEP SEGSAPGTST EPSEGSAPGT  360
SESATPESGP GSEPATSGSE TPGSEPATSG SETPGSPAGS PTSTEEGTSE SATPESGPGT  420
STEPSEGSAP GTSTEPSEGS APGSPAGSPT STEEGTSTEP SEGSAPGTST EPSEGSAPGT  480
SESATPESGP GTSTEPSEGS APGTSESATP ESGPGSEPAT SGSETPGTST EPSEGSAPGT  540
STEPSEGSAP GTSESATPES GPGTSESATP ESGPGSPAGS PTSTEEGTSE SATPESGPGS  600
EPATSGSETP GTSESATPES GPGTSTEPSE GSAPGTSTEP SEGSAPGTST EPSEGSAPGT  660
STEPSEGSAP GTSTEPSEGS APGTSTEPSE GSAPGSPAGS PTSTEEGTST EPSEGSAPGT  720
SESATPESGP GSEPATSGSE TPGTSESATP ESGPGSEPAT SGSETPGTSE SATPESGPGT  780
STEPSEGSAP GTSESATPES GPGSPAGSPT STEEGSPAGS PTSTEEGSPA GSPTSTEEGT  840
SESATPESGP GTSTEPSEGS APGTSESATP ESGPGSEPAT SGSETPGTSE SATPESGPGS  900
EPATSGSETP GTSESATPES GPGTSTEPSE GSAPGSPAGS PTSTEEGTSE SATPESGPGS  960
EPATSGSETP GTSESATPES GPGSPAGSPT STEEGSPAGS PTSTEEGTST EPSEGSAPGT  1020
SESATPESGP GTSESATPES GPGTSESATP ESGPGSEPAT SGSETPGSEP ATSGSETPGS  1080
PAGSPTSTEE GTSTEPSEGS APGTSTEPSE GSAPGSEPAT SGSETPGTSE SATPESGPGT  1140
STEPSEGSAP GHHHHHH                                                 1157

SEQ ID NO: 431          moltype = AA  length = 1157
FEATURE                 Location/Qualifiers
REGION                  1..1157
                        note = Description of Artificial Sequence: Synthetic
                         polypeptide
source                  1..1157
                        mol_type = protein
                        organism = synthetic construct
SEQUENCE: 431
DIQMTQSPSS LSASVGDRVT ITCRASQDIR NYLNWYQQKP GKAPKLLIYY TSRLESGVPS  60
RFSGSGSGTD YTLTISSLQP EDFATYYCQQ GNTLPWTFGQ GTKVEIKGAT PPETGAETES  120
PGETTGGSAE SEPPGEGEVQ LVESGGGLVQ PGGSLRLSCA ASGYSFTGYT MNWVRQAPGK  180
GLEWVALINP YKGVSTYNQK FKDRFTISVD KSKNTAYLQM NSLRAEDTAV YYCARSGYYG  240
DSDWYFDVWG QGTLVTVSSG TAEAASASGL SGRSDNHVPL SLKMGPGSPA GSPTSTEEGT  300
SESATPESGP GTSTEPSEGS APGSPAGSPT STEEGTSTEP SEGSAPGTST EPSEGSAPGT  360
SESATPESGP GSEPATSGSE TPGSEPATSG SETPGSPAGS PTSTEEGTSE SATPESGPGT  420
STEPSEGSAP GTSTEPSEGS APGSPAGSPT STEEGTSTEP SEGSAPGTST EPSEGSAPGT  480
SESATPESGP GTSTEPSEGS APGTSESATP ESGPGSEPAT SGSETPGTST EPSEGSAPGT  540
STEPSEGSAP GTSESATPES GPGTSESATP ESGPGSPAGS PTSTEEGTSE SATPESGPGS  600
EPATSGSETP GTSESATPES GPGTSTEPSE GSAPGTSTEP SEGSAPGTST EPSEGSAPGT  660
STEPSEGSAP GTSTEPSEGS APGTSTEPSE GSAPGSPAGS PTSTEEGTST EPSEGSAPGT  720
SESATPESGP GSEPATSGSE TPGTSESATP ESGPGSEPAT SGSETPGTSE SATPESGPGT  780
STEPSEGSAP GTSESATPES GPGSPAGSPT STEEGSPAGS PTSTEEGSPA GSPTSTEEGT  840
SESATPESGP GTSTEPSEGS APGTSESATP ESGPGSEPAT SGSETPGTSE SATPESGPGS  900
EPATSGSETP GTSESATPES GPGTSTEPSE GSAPGSPAGS PTSTEEGTSE SATPESGPGS  960
EPATSGSETP GTSESATPES GPGSPAGSPT STEEGSPAGS PTSTEEGTST EPSEGSAPGT  1020
SESATPESGP GTSESATPES GPGTSESATP ESGPGSEPAT SGSETPGSEP ATSGSETPGS  1080
PAGSPTSTEE GTSTEPSEGS APGTSTEPSE GSAPGSEPAT SGSETPGTSE SATPESGPGT  1140
STEPSEGSAP GHHHHHH                                                 1157

SEQ ID NO: 432          moltype = AA  length = 1157
FEATURE                 Location/Qualifiers
REGION                  1..1157
                        note = Description of Artificial Sequence: Synthetic
                         polypeptide
source                  1..1157
                        mol_type = protein
                        organism = synthetic construct
SEQUENCE: 432
EVQLVESGGG LVQPGGSLRL SCAASGYSFT GYTMNWVRQA PGKGLEWVAL INPYKGVSTY  60
NQKFKDRFTI SVDKSKNTAY LQMNSLRAED TAVYYCARSG YYGDSDWYFD VWGQGTLVTV  120
SSGATPPETG AETESPGETT GGSAESEPPG EGDIQMTQSP SSLSASVGDR VTITCRASQD  180
IRNYLNWYQQ KPGKAPKLLI YYTSRLESGV PSRFSGSGSG TDYTLTISSL QPEDFATYYC  240
```

-continued

```
QQGNTLPWTF GQGTKVEIKG TAEAASASGL SGRSDNHSPL GLAGSPGSPA GSPTSTEEGT  300
SESATPESGP GTSTEPSEGS APGSPAGSPT STEEGTSTEP SEGSAPGTST EPSEGSAPGT  360
SESATPESGP GSEPATSGSE TPGSEPATSG SETPGSPAGS PTSTEEGTSE SATPESGPGT  420
STEPSEGSAP GTSTEPSEGS APGSPAGSPT STEEGTSTEP SEGSAPGTST EPSEGSAPGT  480
SESATPESGP GTSTEPSEGS APGTSESATP ESGPGSEPAT SGSETPGTST EPSEGSAPGT  540
STEPSEGSAP GTSESATPES GPGTSESATP ESGPGSPAGS PTSTEEGTSE SATPESGPGS  600
EPATSGSETP GTSESATPES GPGTSTEPSE GSAPGTSTEP SEGSAPGTST EPSEGSAPGT  660
STEPSEGSAP GTSTEPSEGS APGTSTEPSE GSAPGSPAGS PTSTEEGTST EPSEGSAPGT  720
SESATPESGP GSEPATSGSE TPGTSESATP ESGPGSEPAT SGSETPGTSE SATPESGPGT  780
STEPSEGSAP GTSESATPES GPGSPAGSPT STEEGSPAGS PTSTEEGSPA GSPTSTEEGT  840
SESATPESGP GTSTEPSEGS APGTSESATP ESGPGSEPAT SGSETPGTSE SATPESGPGS  900
EPATSGSETP GTSESATPES GPGTSTEPSE GSAPGSPAGS PTSTEEGTSE SATPESGPGS  960
EPATSGSETP GTSESATPES GPGSPAGSPT STEEGSPAGS PTSTEEGTST EPSEGSAPGT  1020
SESATPESGP GTSESATPES GPGTSESATP ESGPGSEPAT SGSETPGSEP ATSGSETPGS  1080
PAGSPTSTEE GTSTEPSEGS APGTSTEPSE GSAPGSEPAT SGSETPGTSE SATPESGPGT  1140
STEPSEGSAP GHHHHHH                                                 1157

SEQ ID NO: 433          moltype = AA  length = 1157
FEATURE                 Location/Qualifiers
REGION                  1..1157
                        note = Description of Artificial Sequence: Synthetic
                         polypeptide
source                  1..1157
                        mol_type = protein
                        organism = synthetic construct
SEQUENCE: 433
EVQLVESGGG LVQPGGSLRL SCAASGYSFT GYTMNWVRQA PGKGLEWVAL INPYKGVSTY  60
NQKFKDRFTI SVDKSKNTAY LQMNSLRAED TAVYYCARSG YYGDSDWYFD VWGQGTLVTV  120
SSGATPPETG AETESPGETT GGSAESEPPG EGDIQMTQSP SSLSASVGDR VTITCRASQD  180
IRNYLNWYQQ KPGKAPKLLI YYTSRLESGV PSRFSGSGSG TDYTLTISSL QPEDFATYYC  240
QQGNTLPWTF GQGTKVEIKG TAEAASASGL SGRSDNHVPL SLKMGPGSPA GSPTSTEEGT  300
SESATPESGP GTSTEPSEGS APGSPAGSPT STEEGTSTEP SEGSAPGTST EPSEGSAPGT  360
SESATPESGP GSEPATSGSE TPGSEPATSG SETPGSPAGS PTSTEEGTSE SATPESGPGT  420
STEPSEGSAP GTSTEPSEGS APGSPAGSPT STEEGTSTEP SEGSAPGTST EPSEGSAPGT  480
SESATPESGP GTSTEPSEGS APGTSESATP ESGPGSEPAT SGSETPGTST EPSEGSAPGT  540
STEPSEGSAP GTSESATPES GPGTSESATP ESGPGSPAGS PTSTEEGTSE SATPESGPGS  600
EPATSGSETP GTSESATPES GPGTSTEPSE GSAPGTSTEP SEGSAPGTST EPSEGSAPGT  660
STEPSEGSAP GTSTEPSEGS APGTSTEPSE GSAPGSPAGS PTSTEEGTST EPSEGSAPGT  720
SESATPESGP GSEPATSGSE TPGTSESATP ESGPGSEPAT SGSETPGTSE SATPESGPGT  780
STEPSEGSAP GTSESATPES GPGSPAGSPT STEEGSPAGS PTSTEEGSPA GSPTSTEEGT  840
SESATPESGP GTSTEPSEGS APGTSESATP ESGPGSEPAT SGSETPGTSE SATPESGPGS  900
EPATSGSETP GTSESATPES GPGTSTEPSE GSAPGSPAGS PTSTEEGTSE SATPESGPGS  960
EPATSGSETP GTSESATPES GPGSPAGSPT STEEGSPAGS PTSTEEGTST EPSEGSAPGT  1020
SESATPESGP GTSESATPES GPGTSESATP ESGPGSEPAT SGSETPGSEP ATSGSETPGS  1080
PAGSPTSTEE GTSTEPSEGS APGTSTEPSE GSAPGSEPAT SGSETPGTSE SATPESGPGT  1140
STEPSEGSAP GHHHHHH                                                 1157

SEQ ID NO: 434          moltype = AA  length = 1162
FEATURE                 Location/Qualifiers
REGION                  1..1162
                        note = Description of Artificial Sequence: Synthetic
                         polypeptide
source                  1..1162
                        mol_type = protein
                        organism = synthetic construct
SEQUENCE: 434
ELVVTQEPSL TVSPGGTVTL TCRSSTGAVT TSNYANWVQQ KPGQAPRGLI GGTNKRAPGT  60
PARFSGSLLG GKAALTLSGV QPEDEAEYYC ALWYSNLWVF GGGTKLTVLG ATPPETGAET  120
ESPGETTGGS AESEPPGEGE VQLLESGGGL VQPGGSLKLS CAASGFTFNT YAMNWVRQAP  180
GKGLEWVARI RSKYNNYATY YADSVKDRFT ISRDDSKNTA YLQMNNLKTE DTAVYYCVRH  240
GNFGNSYVSW FAYWGQGTLV TVSSGTAEAA SASGLSGRSD NHSPLGLAGS PGSPAGSPTS  300
TEEGTSESAT PESGPGTSTE PSEGSAPGSP AGSPTSTEEG TSTEPSEGSA PGTSTEPSEG  360
SAPGTSESAT PESGPGSEPA TSGSETPGSE PATSGSETPG SPAGSPTSTE EGTSESATPE  420
SGPGTSTEPS EGSAPGTSTE PSEGSAPGSP AGSPTSTEEG TSTEPSEGSA PGTSTEPSEG  480
SAPGTSESAT PESGPGTSTE PSEGSAPGTS ESATPESGPG SEPATSGSET PGTSTEPSEG  540
SAPGTSTEPS EGSAPGTSES ATPESGPGTS ESATPESGPG SPAGSPTSTE EGTSESATPE  600
SGPGSEPATS GSETPGTSES ATPESGPGTS TEPSEGSAPG TSTEPSEGSA PGTSTEPSEG  660
SAPGTSTEPS EGSAPGTSTE PSEGSAPGTS TEPSEGSAPG SPAGSPTSTE EGTSTEPSEG  720
SAPGTSESAT PESGPGSEPA TSGSETPGTS ESATPESGPG SEPATSGSET PGTSESATPE  780
SGPGTSTEPS EGSAPGTSES ATPESGPGSP AGSPTSTEEG SPAGSPTSTE EGSPAGSPTS  840
TEEGTSESAT PESGPGTSTE PSEGSAPGTS ESATPESGPG SEPATSGSET PGTSESATPE  900
SGPGSEPATS GSETPGTSES ATPESGPGTS TEPSEGSAPG SPAGSPTSTE EGTSESATPE  960
SGPGSEPATS GSETPGTSES ATPESGPGSP AGSPTSTEEG SPAGSPTSTE EGTSTEPSEG  1020
SAPGTSESAT PESGPGTSES ATPESGPGTS ESATPESGPG SEPATSGSET PGSEPATSGS  1080
ETPGSPAGSP TSTEEGTSTE PSEGSAPGTS TEPSEGSAPG SEPATSGSET PGTSESATPE  1140
SGPGTSTEPS EGSAPGHHHH HH                                           1162

SEQ ID NO: 435          moltype = AA  length = 1162
FEATURE                 Location/Qualifiers
```

-continued

```
REGION                  1..1162
                        note = Description of Artificial Sequence: Synthetic
                         polypeptide
source                  1..1162
                        mol_type = protein
                        organism = synthetic construct
SEQUENCE: 435
ELVVTQEPSL TVSPGGTVTL TCRSSTGAVT TSNYANWVQQ KPGQAPRGLI GGTNKRAPGT  60
PARFSGSLLG GKAALTLSGV QPEDEAEYYC ALWYSNLWVF GGGTKLTVLG ATPPETGAET  120
ESPGETTGGS AESEPPGEGE VQLLESGGGL VQPGGSLKLS CAASGFTFNT YAMNWVRQAP  180
GKGLEWVARI RSKYNNYATY YADSVKDRFT ISRDDSKNTA YLQMNNLKTE DTAVYYCVRH  240
GNFGNSYVSW FAYWGQGTLV TVSSGTAEAA SASGLSGRSD NHVPLSLKMG PGSPAGSPTS  300
TEEGTSESAT PESGPGTSTE PSEGSAPGSP AGSPTSTEEG TSTEPSEGSA PGTSTEPSEG  360
SAPGTSESAT PESGPGSEPA TSGSETPGSE PATSGSETPG SPAGSPTSTE EGTSESATPE  420
SGPGTSTEPS EGSAPGTSTE PSEGSAPGSP AGSPTSTEEG TSTEPSEGSA PGTSTEPSEG  480
SAPGTSESAT PESGPGTSTE PSEGSAPGTS ESATPESGPG SEPATSGSET PGTSTEPSEG  540
SAPGTSTEPS EGSAPGTSES ATPESGPGTS ESATPESGPG SPAGSPTSTE EGTSESATPE  600
SGPGSEPATS GSETPGTSES ATPESGPGTS TEPSEGSAPG TSTEPSEGSA PGTSTEPSEG  660
SAPGTSTEPS EGSAPGTSTE PSEGSAPGTS TEPSEGSAPG SPAGSPTSTE EGTSTEPSEG  720
SAPGTSESAT PESGPGSEPA TSGSETPGTS ESATPESGPG SEPATSGSET PGTSESATPE  780
SGPGTSTEPS EGSAPGTSES ATPESGPGSP AGSPTSTEEG SPAGSPTSTE EGSPAGSPTS  840
TEEGTSESAT PESGPGTSTE PSEGSAPGTS ESATPESGPG SEPATSGSET PGTSESATPE  900
SGPGSEPATS GSETPGTSES ATPESGPGTS TEPSEGSAPG SPAGSPTSTE EGTSESATPE  960
SGPGSEPATS GSETPGTSES ATPESGPGSP AGSPTSTEEG SPAGSPTSTE EGTSTEPSEG  1020
SAPGTSESAT PESGPGTSES ATPESGPGTS ESATPESGPG SEPATSGSET PGSEPATSGS  1080
ETPGSPAGSP TSTEEGTSTE PSEGSAPGTS TEPSEGSAPG SEPATSGSET PGTSESATPE  1140
SGPGTSTEPS EGSAPGHHHH HH                                         1162

SEQ ID NO: 436          moltype = AA  length = 1162
FEATURE                 Location/Qualifiers
REGION                  1..1162
                        note = Description of Artificial Sequence: Synthetic
                         polypeptide
source                  1..1162
                        mol_type = protein
                        organism = synthetic construct
SEQUENCE: 436
EVQLLESGGG LVQPGGSLKL SCAASGFTFN TYAMNWVRQA PGKGLEWVAR IRSKYNNYAT  60
YYADSVKDRF TISRDDSKNT AYLQMNNLKT EDTAVYYCVR HGNFGNSYVS WFAYWGQGTL  120
VTVSSGATPP ETGAETESPG ETTGGSAESE PPGEGELVVT QEPSLTVSPG GTVTLTCRSS  180
TGAVTTSNYA NWVQQKPGQA PRGLIGGTNK RAPGTPARFS GSLLGGKAAL TLSGVQPEDE  240
AEYYCALWYS NLWVFGGGTK LTVLGTAEAA SASGLSGRSD NHSPLGLAGS PGSPAGSPTS  300
TEEGTSESAT PESGPGTSTE PSEGSAPGSP AGSPTSTEEG TSTEPSEGSA PGTSTEPSEG  360
SAPGTSESAT PESGPGSEPA TSGSETPGSE PATSGSETPG SPAGSPTSTE EGTSESATPE  420
SGPGTSTEPS EGSAPGTSTE PSEGSAPGSP AGSPTSTEEG TSTEPSEGSA PGTSTEPSEG  480
SAPGTSESAT PESGPGTSTE PSEGSAPGTS ESATPESGPG SEPATSGSET PGTSTEPSEG  540
SAPGTSTEPS EGSAPGTSES ATPESGPGTS ESATPESGPG SPAGSPTSTE EGTSESATPE  600
SGPGSEPATS GSETPGTSES ATPESGPGTS TEPSEGSAPG TSTEPSEGSA PGTSTEPSEG  660
SAPGTSTEPS EGSAPGTSTE PSEGSAPGTS TEPSEGSAPG SPAGSPTSTE EGTSTEPSEG  720
SAPGTSESAT PESGPGSEPA TSGSETPGTS ESATPESGPG SEPATSGSET PGTSESATPE  780
SGPGTSTEPS EGSAPGTSES ATPESGPGSP AGSPTSTEEG SPAGSPTSTE EGSPAGSPTS  840
TEEGTSESAT PESGPGTSTE PSEGSAPGTS ESATPESGPG SEPATSGSET PGTSESATPE  900
SGPGSEPATS GSETPGTSES ATPESGPGTS TEPSEGSAPG SPAGSPTSTE EGTSESATPE  960
SGPGSEPATS GSETPGTSES ATPESGPGSP AGSPTSTEEG SPAGSPTSTE EGTSTEPSEG  1020
SAPGTSESAT PESGPGTSES ATPESGPGTS ESATPESGPG SEPATSGSET PGSEPATSGS  1080
ETPGSPAGSP TSTEEGTSTE PSEGSAPGTS TEPSEGSAPG SEPATSGSET PGTSESATPE  1140
SGPGTSTEPS EGSAPGHHHH HH                                         1162

SEQ ID NO: 437          moltype = AA  length = 1162
FEATURE                 Location/Qualifiers
REGION                  1..1162
                        note = Description of Artificial Sequence: Synthetic
                         polypeptide
source                  1..1162
                        mol_type = protein
                        organism = synthetic construct
SEQUENCE: 437
EVQLLESGGG LVQPGGSLKL SCAASGFTFN TYAMNWVRQA PGKGLEWVAR IRSKYNNYAT  60
YYADSVKDRF TISRDDSKNT AYLQMNNLKT EDTAVYYCVR HGNFGNSYVS WFAYWGQGTL  120
VTVSSGATPP ETGAETESPG ETTGGSAESE PPGEGELVVT QEPSLTVSPG GTVTLTCRSS  180
TGAVTTSNYA NWVQQKPGQA PRGLIGGTNK RAPGTPARFS GSLLGGKAAL TLSGVQPEDE  240
AEYYCALWYS NLWVFGGGTK LTVLGTAEAA SASGLSGRSD NHVPLSLKMG PGSPAGSPTS  300
TEEGTSESAT PESGPGTSTE PSEGSAPGSP AGSPTSTEEG TSTEPSEGSA PGTSTEPSEG  360
SAPGTSESAT PESGPGSEPA TSGSETPGSE PATSGSETPG SPAGSPTSTE EGTSESATPE  420
SGPGTSTEPS EGSAPGTSTE PSEGSAPGSP AGSPTSTEEG TSTEPSEGSA PGTSTEPSEG  480
SAPGTSESAT PESGPGTSTE PSEGSAPGTS ESATPESGPG SEPATSGSET PGTSTEPSEG  540
SAPGTSTEPS EGSAPGTSES ATPESGPGTS ESATPESGPG SPAGSPTSTE EGTSESATPE  600
SGPGSEPATS GSETPGTSES ATPESGPGTS TEPSEGSAPG TSTEPSEGSA PGTSTEPSEG  660
SAPGTSTEPS EGSAPGTSTE PSEGSAPGTS TEPSEGSAPG SPAGSPTSTE EGTSTEPSEG  720
```

```
SAPGTSESAT PESGPGSEPA TSGSETPGTS ESATPESGPG SEPATSGSET PGTSESATPE  780
SGPGTSTEPS EGSAPGTSES ATPESGPGSP AGSPTSTEEG SPAGSPTSTE EGSPAGSPTS  840
TEEGTSESAT PESGPGTSTE PSEGSAPGTS ESATPESGPG SEPATSGSET PGTSESATPE  900
SGPGSEPATS GSETPGTSES ATPESGPGTS TEPSEGSAPG SPAGSPTSTE EGTSESATPE  960
SGPGSEPATS GSETPGTSES ATPESGPGSP AGSPTSTEEG SPAGSPTSTE EGTSTEPSEG  1020
SAPGTSESAT PESGPGTSES ATPESGPGTS ESATPESGPG SEPATSGSET PGSEPATSGS  1080
ETPGSPAGSP TSTEEGTSTE PSEGSAPGTS TEPSEGSAPG SEPATSGSET PGTSESATPE  1140
SGPGTSTEPS EGSAPGHHHH HH                                           1162

SEQ ID NO: 438         moltype = AA  length = 1156
FEATURE                Location/Qualifiers
REGION                 1..1156
                       note = Description of Artificial Sequence: Synthetic
                        polypeptide
source                 1..1156
                       mol_type = protein
                       organism = synthetic construct
SEQUENCE: 438
HHHHHHGGSP AGSPTSTEEG TSESATPESG PGTSTEPSEG SAPGSPAGSP TSTEEGTSTE  60
PSEGSAPGTS TEPSEGSAPG TSESATPESG PGSEPATSGS ETPGSEPATS GSETPGSPAG  120
SPTSTEEGTS ESATPESGPG TSTEPSEGSA PGTSTEPSEG SAPGSPAGSP TSTEEGTSTE  180
PSEGSAPGTS TEPSEGSAPG TSESATPESG PGTSTEPSEG SAPGTSESAT PESGPGSEPA  240
TSGSETPGTS TEPSEGSAPG TSTEPSEGSA PGTSESATPE SGPGTSESAT PESGPGSPAG  300
SPTSTEEGTS ESATPESGPG SEPATSGSET PGTSESATPE SGPGTSTEPS EGSAPGTSTE  360
PSEGSAPGTS TEPSEGSAPG TSTEPSEGSA PGTSTEPSEG SAPGTSTEPS EGSAPGSPAG  420
SPTSTEEGTS TEPSEGSAPG TSESATPESG PGSEPATSGS ETPGTSESAT PESGPGSEPA  480
TSGSETPGTS ESATPESGPG TSTEPSEGSA PGTSESATPE SGPGSPAGSP TSTEEGSPAG  540
SPTSTEEGSP AGSPTSTEEG TSESATPESG PGTSTEPSEG SAPGTSESAT PESGPGSEPA  600
TSGSETPGTS ESATPESGPG SEPATSGSET PGTSESATPE SGPGTSTEPS EGSAPGSPAG  660
SPTSTEEGTS ESATPESGPG SEPATSGSET PGTSESATPE SGPGSPAGSP TSTEEGSPAG  720
SPTSTEEGTS TEPSEGSAPG TSESATPESG PGTSESATPE SGPGTSESAT PESGPGSEPA  780
TSGSETPGSE PATSGSETPG SPAGSPTSTE EGTSTEPSEG SAPGTSTEPS EGSAPGSEPA  840
TSGSETPGTS ESATPESGPG TSTEPSEGSA PLSGRSDNHS PLGLAGSGTA EAASASGDIQ  900
MTQSPSSLSA SVGDRVTITC RASQDIRNYL NWYQQKPGKA PKLLIYYTSR LESGVPSRFS  960
GSGSGTDYTL TISSLQPEDF ATYYCQQGNT LPWTFGQGTK VEIKGATPPE TGAETESPGE  1020
TTGGSAESEP PGEGEVQLVE SGGGLVQPGG SLRLSCAASG YSFTGYTMNW VRQAPGKGLE  1080
WVALINPYKG VSTYNQKFKD RFTISVDKSK NTAYLQMNSL RAEDTAVYYC ARSGYYGDSD  1140
WYFDVWGQGT LVTVSS                                                  1156

SEQ ID NO: 439         moltype = AA  length = 1156
FEATURE                Location/Qualifiers
REGION                 1..1156
                       note = Description of Artificial Sequence: Synthetic
                        polypeptide
source                 1..1156
                       mol_type = protein
                       organism = synthetic construct
SEQUENCE: 439
HHHHHHGGSP AGSPTSTEEG TSESATPESG PGTSTEPSEG SAPGSPAGSP TSTEEGTSTE  60
PSEGSAPGTS TEPSEGSAPG TSESATPESG PGSEPATSGS ETPGSEPATS GSETPGSPAG  120
SPTSTEEGTS ESATPESGPG TSTEPSEGSA PGTSTEPSEG SAPGSPAGSP TSTEEGTSTE  180
PSEGSAPGTS TEPSEGSAPG TSESATPESG PGTSTEPSEG SAPGTSESAT PESGPGSEPA  240
TSGSETPGTS TEPSEGSAPG TSTEPSEGSA PGTSESATPE SGPGTSESAT PESGPGSPAG  300
SPTSTEEGTS ESATPESGPG SEPATSGSET PGTSESATPE SGPGTSTEPS EGSAPGTSTE  360
PSEGSAPGTS TEPSEGSAPG TSTEPSEGSA PGTSTEPSEG SAPGTSTEPS EGSAPGSPAG  420
SPTSTEEGTS TEPSEGSAPG TSESATPESG PGSEPATSGS ETPGTSESAT PESGPGSEPA  480
TSGSETPGTS ESATPESGPG TSTEPSEGSA PGTSESATPE SGPGSPAGSP TSTEEGSPAG  540
SPTSTEEGSP AGSPTSTEEG TSESATPESG PGTSTEPSEG SAPGTSESAT PESGPGSEPA  600
TSGSETPGTS ESATPESGPG SEPATSGSET PGTSESATPE SGPGTSTEPS EGSAPGSPAG  660
SPTSTEEGTS ESATPESGPG SEPATSGSET PGTSESATPE SGPGSPAGSP TSTEEGSPAG  720
SPTSTEEGTS TEPSEGSAPG TSESATPESG PGTSESATPE SGPGTSESAT PESGPGSEPA  780
TSGSETPGSE PATSGSETPG SPAGSPTSTE EGTSTEPSEG SAPGTSTEPS EGSAPGSEPA  840
TSGSETPGTS ESATPESGPG TSTEPSEGSA PLSGRSDNHV PLSLKMGGTA EAASASGDIQ  900
MTQSPSSLSA SVGDRVTITC RASQDIRNYL NWYQQKPGKA PKLLIYYTSR LESGVPSRFS  960
GSGSGTDYTL TISSLQPEDF ATYYCQQGNT LPWTFGQGTK VEIKGATPPE TGAETESPGE  1020
TTGGSAESEP PGEGEVQLVE SGGGLVQPGG SLRLSCAASG YSFTGYTMNW VRQAPGKGLE  1080
WVALINPYKG VSTYNQKFKD RFTISVDKSK NTAYLQMNSL RAEDTAVYYC ARSGYYGDSD  1140
WYFDVWGQGT LVTVSS                                                  1156

SEQ ID NO: 440         moltype = AA  length = 1156
FEATURE                Location/Qualifiers
REGION                 1..1156
                       note = Description of Artificial Sequence: Synthetic
                        polypeptide
source                 1..1156
                       mol_type = protein
                       organism = synthetic construct
SEQUENCE: 440
HHHHHHGGSP AGSPTSTEEG TSESATPESG PGTSTEPSEG SAPGSPAGSP TSTEEGTSTE  60
```

-continued

```
PSEGSAPGTS TEPSEGSAPG TSESATPESG PGSEPATSGS ETPGSEPATS GSETPGSPAG  120
SPTSTEEGTS ESATPESGPG TSTEPSEGSA PGTSTEPSEG SAPGSPAGSP TSTEEGTSTE  180
PSEGSAPGTS TEPSEGSAPG TSESATPESG PGTSTEPSEG SAPGTSESAT PESGPGSEPA  240
TSGSETPGTS TEPSEGSAPG TSTEPSEGSA PGTSESATPE SGPGTSESAT PESGPGSPAG  300
SPTSTEEGTS ESATPESGPG SEPATSGSET PGTSESATPE SGPGTSTEPS EGSAPGTSTE  360
PSEGSAPGTS TEPSEGSAPG TSTEPSEGSA PGTSTEPSEG SAPGTSTEPS EGSAPGSPAG  420
SPTSTEEGTS TEPSEGSAPG TSESATPESG PGSEPATSGS ETPGTSESAT PESGPGSEPA  480
TSGSETPGTS ESATPESGPG TSTEPSEGSA PGTSESATPE SGPGSPAGSP TSTEEGSPAG  540
SPTSTEEGSP AGSPTSTEEG TSESATPESG PGTSTEPSEG SAPGTSESAT PESGPGSEPA  600
TSGSETPGTS ESATPESGPG SEPATSGSET PGTSESATPE SGPGTSTEPS EGSAPGSPAG  660
SPTSTEEGTS ESATPESGPG SEPATSGSET PGTSESATPE SGPGSPAGSP TSTEEGSPAG  720
SPTSTEEGTS TEPSEGSAPG TSESATPESG PGTSESATPE SGPGTSESAT PESGPGSEPA  780
TSGSETPGSE PATSGSETPG SPAGSPTSTE EGTSTEPSEG SAPGTSTEPS EGSAPGSEPA  840
TSGSETPGTS ESATPESGPG TSTEPSEGSA PLSGRSDNHS PLGLAGSGTA EAASASGEVQ  900
LVESGGGLVQ PGGSLRLSCA ASGYSFTGYT MNWVRQAPGK GLEWVALINP YKGVSTYNQK  960
FKDRFTISVD KSKNTAYLQM NSLRAEDTAV YYCARSGYYG DSDWYFDVWG QGTLVTVSSG  1020
ATPPETGAET ESPGETTGGS AESEPPGEGD IQMTQSPSSL SASVGDRVTI TCRASQDIRN  1080
YLNWYQQKPG KAPKLLIYYT SRLESGVPSR FSGSGSGTDY TLTISSLQPE DFATYYCQQG  1140
NTLPWTFGQG TKVEIK                                                  1156

SEQ ID NO: 441         moltype = AA  length = 1156
FEATURE                Location/Qualifiers
REGION                 1..1156
                       note = Description of Artificial Sequence: Synthetic
                        polypeptide
source                 1..1156
                       mol_type = protein
                       organism = synthetic construct
SEQUENCE: 441
HHHHHHGGSP AGSPTSTEEG TSESATPESG PGTSTEPSEG SAPGSPAGSP TSTEEGTSTE  60
PSEGSAPGTS TEPSEGSAPG TSESATPESG PGSEPATSGS ETPGSEPATS GSETPGSPAG  120
SPTSTEEGTS ESATPESGPG TSTEPSEGSA PGTSTEPSEG SAPGSPAGSP TSTEEGTSTE  180
PSEGSAPGTS TEPSEGSAPG TSESATPESG PGTSTEPSEG SAPGTSESAT PESGPGSEPA  240
TSGSETPGTS TEPSEGSAPG TSTEPSEGSA PGTSESATPE SGPGTSESAT PESGPGSPAG  300
SPTSTEEGTS ESATPESGPG SEPATSGSET PGTSESATPE SGPGTSTEPS EGSAPGTSTE  360
PSEGSAPGTS TEPSEGSAPG TSTEPSEGSA PGTSTEPSEG SAPGTSTEPS EGSAPGSPAG  420
SPTSTEEGTS TEPSEGSAPG TSESATPESG PGSEPATSGS ETPGTSESAT PESGPGSEPA  480
TSGSETPGTS ESATPESGPG TSTEPSEGSA PGTSESATPE SGPGSPAGSP TSTEEGSPAG  540
SPTSTEEGSP AGSPTSTEEG TSESATPESG PGTSTEPSEG SAPGTSESAT PESGPGSEPA  600
TSGSETPGTS ESATPESGPG SEPATSGSET PGTSESATPE SGPGTSTEPS EGSAPGSPAG  660
SPTSTEEGTS ESATPESGPG SEPATSGSET PGTSESATPE SGPGSPAGSP TSTEEGSPAG  720
SPTSTEEGTS TEPSEGSAPG TSESATPESG PGTSESATPE SGPGTSESAT PESGPGSEPA  780
TSGSETPGSE PATSGSETPG SPAGSPTSTE EGTSTEPSEG SAPGTSTEPS EGSAPGSEPA  840
TSGSETPGTS ESATPESGPG TSTEPSEGSA PLSGRSDNHV PLSLKMGGTA EAASASGEVQ  900
LVESGGGLVQ PGGSLRLSCA ASGYSFTGYT MNWVRQAPGK GLEWVALINP YKGVSTYNQK  960
FKDRFTISVD KSKNTAYLQM NSLRAEDTAV YYCARSGYYG DSDWYFDVWG QGTLVTVSSG  1020
ATPPETGAET ESPGETTGGS AESEPPGEGD IQMTQSPSSL SASVGDRVTI TCRASQDIRN  1080
YLNWYQQKPG KAPKLLIYYT SRLESGVPSR FSGSGSGTDY TLTISSLQPE DFATYYCQQG  1140
NTLPWTFGQG TKVEIK                                                  1156

SEQ ID NO: 442         moltype = AA  length = 1161
FEATURE                Location/Qualifiers
REGION                 1..1161
                       note = Description of Artificial Sequence: Synthetic
                        polypeptide
source                 1..1161
                       mol_type = protein
                       organism = synthetic construct
SEQUENCE: 442
HHHHHHGGSP AGSPTSTEEG TSESATPESG PGTSTEPSEG SAPGSPAGSP TSTEEGTSTE  60
PSEGSAPGTS TEPSEGSAPG TSESATPESG PGSEPATSGS ETPGSEPATS GSETPGSPAG  120
SPTSTEEGTS ESATPESGPG TSTEPSEGSA PGTSTEPSEG SAPGSPAGSP TSTEEGTSTE  180
PSEGSAPGTS TEPSEGSAPG TSESATPESG PGTSTEPSEG SAPGTSESAT PESGPGSEPA  240
TSGSETPGTS TEPSEGSAPG TSTEPSEGSA PGTSESATPE SGPGTSESAT PESGPGSPAG  300
SPTSTEEGTS ESATPESGPG SEPATSGSET PGTSESATPE SGPGTSTEPS EGSAPGTSTE  360
PSEGSAPGTS TEPSEGSAPG TSTEPSEGSA PGTSTEPSEG SAPGTSTEPS EGSAPGSPAG  420
SPTSTEEGTS TEPSEGSAPG TSESATPESG PGSEPATSGS ETPGTSESAT PESGPGSEPA  480
TSGSETPGTS ESATPESGPG TSTEPSEGSA PGTSESATPE SGPGSPAGSP TSTEEGSPAG  540
SPTSTEEGSP AGSPTSTEEG TSESATPESG PGTSTEPSEG SAPGTSESAT PESGPGSEPA  600
TSGSETPGTS ESATPESGPG SEPATSGSET PGTSESATPE SGPGTSTEPS EGSAPGSPAG  660
SPTSTEEGTS ESATPESGPG SEPATSGSET PGTSESATPE SGPGSPAGSP TSTEEGSPAG  720
SPTSTEEGTS TEPSEGSAPG TSESATPESG PGTSESATPE SGPGTSESAT PESGPGSEPA  780
TSGSETPGSE PATSGSETPG SPAGSPTSTE EGTSTEPSEG SAPGTSTEPS EGSAPGSEPA  840
TSGSETPGTS ESATPESGPG TSTEPSEGSA PLSGRSDNHS PLGLAGSGTA EAASASGELV  900
VTQEPSLTVS PGGTVTLTCR SSTGAVTTSN YANWVQQKPG QAPRGLIGGT NKRAPGTPAR  960
FSGSLLGGKA ALTLSGVQPE DEAEYYCALW YSNLWVFGGG TKLTVLGATP PETGAETESP  1020
GETTGGSAES EPPGEGEVQL LESGGGLVQP GGSLKLSCAA SGFTFNTYAM NWVRQAPGKG  1080
LEWVARIRSK YNNYATYYAD SVKDRFTISR DDSKNTAYLQ MNNLKTEDTA VYYCVRHGNF  1140
GNSYVSWFAY WGQGTLVTVS S                                            1161
```

```
SEQ ID NO: 443         moltype = AA  length = 1161
FEATURE                Location/Qualifiers
REGION                 1..1161
                       note = Description of Artificial Sequence: Synthetic
                        polypeptide
source                 1..1161
                       mol_type = protein
                       organism = synthetic construct
SEQUENCE: 443
HHHHHHGGSP AGSPTSTEEG TSESATPESG PGTSTEPSEG SAPGSPAGSP TSTEEGTSTE  60
PSEGSAPGTS TEPSEGSAPG TSESATPESG PGSEPATSGS ETPGSEPATS GSETPGSPAG  120
SPTSTEEGTS ESATPESGPG TSTEPSEGSA PGTSTEPSEG SAPGSPAGSP TSTEEGTSTE  180
PSEGSAPGTS TEPSEGSAPG TSESATPESG PGTSTEPSEG SAPGTSESAT PESGPGSEPA  240
TSGSETPGTS TEPSEGSAPG TSTEPSEGSA PGTSESATPE SGPGTSESAT PESGPGSPAG  300
SPTSTEEGTS ESATPESGPG SEPATSGSET PGTSESATPE SGPGTSTEPS EGSAPGTSTE  360
PSEGSAPGTS TEPSEGSAPG TSTEPSEGSA PGTSTEPSEG SAPGTSTEPS EGSAPGSPAG  420
SPTSTEEGTS TEPSEGSAPG TSESATPESG PGSEPATSGS ETPGTSESAT PESGPGSEPA  480
TSGSETPGTS ESATPESGPG TSTEPSEGSA PGTSESATPE SGPGSPAGSP TSTEEGSPAG  540
SPTSTEEGSP AGSPTSTEEG TSESATPESG PGTSTEPSEG SAPGTSESAT PESGPGSEPA  600
TSGSETPGTS ESATPESGPG SEPATSGSET PGTSESATPE SGPGTSTEPS EGSAPGSPAG  660
SPTSTEEGTS ESATPESGPG SEPATSGSET PGTSESATPE SGPGSPAGSP TSTEEGSPAG  720
SPTSTEEGTS TEPSEGSAPG TSESATPESG PGTSESATPE SGPGTSESAT PESGPGSEPA  780
TSGSETPGSE PATSGSETPG SPAGSPTSTE EGTSTEPSEG SAPGTSTEPS EGSAPGSEPA  840
TSGSETPGTS ESATPESGPG TSTEPSEGSA PLSGRSDNHV PLSLKMGGTA EAASASGELV  900
VTQEPSLTVS PGGTVTLTCR SSTGAVTTSN YANWVQQKPG QAPRGLIGGT NKRAPGTPAR  960
FSGSLLGGKA ALTLSGVQPE DEAEYYCALW YSNLWVFGGG TKLTVLGATP PETGAETESP  1020
GETTGGSAES EPPGEGEVQL LESGGGLVQP GGSLKLSCAA SGFTFNTYAM NWVRQAPGKG  1080
LEWVARIRSK YNNYATYYAD SVKDRFTISR DDSKNTAYLQ MNNLKTEDTA VYYCVRHGNF  1140
GNSYVSWFAY WGQGTLVTVS S                                            1161

SEQ ID NO: 444         moltype = AA  length = 1161
FEATURE                Location/Qualifiers
REGION                 1..1161
                       note = Description of Artificial Sequence: Synthetic
                        polypeptide
source                 1..1161
                       mol_type = protein
                       organism = synthetic construct
SEQUENCE: 444
HHHHHHGGSP AGSPTSTEEG TSESATPESG PGTSTEPSEG SAPGSPAGSP TSTEEGTSTE  60
PSEGSAPGTS TEPSEGSAPG TSESATPESG PGSEPATSGS ETPGSEPATS GSETPGSPAG  120
SPTSTEEGTS ESATPESGPG TSTEPSEGSA PGTSTEPSEG SAPGSPAGSP TSTEEGTSTE  180
PSEGSAPGTS TEPSEGSAPG TSESATPESG PGTSTEPSEG SAPGTSESAT PESGPGSEPA  240
TSGSETPGTS TEPSEGSAPG TSTEPSEGSA PGTSESATPE SGPGTSESAT PESGPGSPAG  300
SPTSTEEGTS ESATPESGPG SEPATSGSET PGTSESATPE SGPGTSTEPS EGSAPGTSTE  360
PSEGSAPGTS TEPSEGSAPG TSTEPSEGSA PGTSTEPSEG SAPGTSTEPS EGSAPGSPAG  420
SPTSTEEGTS TEPSEGSAPG TSESATPESG PGSEPATSGS ETPGTSESAT PESGPGSEPA  480
TSGSETPGTS ESATPESGPG TSTEPSEGSA PGTSESATPE SGPGSPAGSP TSTEEGSPAG  540
SPTSTEEGSP AGSPTSTEEG TSESATPESG PGTSTEPSEG SAPGTSESAT PESGPGSEPA  600
TSGSETPGTS ESATPESGPG SEPATSGSET PGTSESATPE SGPGTSTEPS EGSAPGSPAG  660
SPTSTEEGTS ESATPESGPG SEPATSGSET PGTSESATPE SGPGSPAGSP TSTEEGSPAG  720
SPTSTEEGTS TEPSEGSAPG TSESATPESG PGTSESATPE SGPGTSESAT PESGPGSEPA  780
TSGSETPGSE PATSGSETPG SPAGSPTSTE EGTSTEPSEG SAPGTSTEPS EGSAPGSEPA  840
TSGSETPGTS ESATPESGPG TSTEPSEGSA PLSGRSDNHS PLGLAGSGTA EAASASGEVQ  900
LLESGGGLVQ PGGSLKLSCA ASGFTFNTYA MNWVRQAPGK GLEWVARIRS KYNNYATYYA  960
DSVKDRFTIS RDDSKNTAYL QMNNLKTEDT AVYYCVRHGN FGNSYVSWFA YWGQGTLVTV  1020
SSGATPPETG AETESPGETT GGSAESEPPG EGELVVTQEP SLTVSPGGTV TLTCRSSTGA  1080
VTTSNYANWV QQKPGQAPRG LIGGTNKRAP GTPARFSGSL LGGKAALTLS GVQPEDEAEY  1140
YCALWYSNLW VFGGGTKLTV L                                            1161

SEQ ID NO: 445         moltype = AA  length = 1161
FEATURE                Location/Qualifiers
REGION                 1..1161
                       note = Description of Artificial Sequence: Synthetic
                        polypeptide
source                 1..1161
                       mol_type = protein
                       organism = synthetic construct
SEQUENCE: 445
HHHHHHGGSP AGSPTSTEEG TSESATPESG PGTSTEPSEG SAPGSPAGSP TSTEEGTSTE  60
PSEGSAPGTS TEPSEGSAPG TSESATPESG PGSEPATSGS ETPGSEPATS GSETPGSPAG  120
SPTSTEEGTS ESATPESGPG TSTEPSEGSA PGTSTEPSEG SAPGSPAGSP TSTEEGTSTE  180
PSEGSAPGTS TEPSEGSAPG TSESATPESG PGTSTEPSEG SAPGTSESAT PESGPGSEPA  240
TSGSETPGTS TEPSEGSAPG TSTEPSEGSA PGTSESATPE SGPGTSESAT PESGPGSPAG  300
SPTSTEEGTS ESATPESGPG SEPATSGSET PGTSESATPE SGPGTSTEPS EGSAPGTSTE  360
PSEGSAPGTS TEPSEGSAPG TSTEPSEGSA PGTSTEPSEG SAPGTSTEPS EGSAPGSPAG  420
SPTSTEEGTS TEPSEGSAPG TSESATPESG PGSEPATSGS ETPGTSESAT PESGPGSEPA  480
TSGSETPGTS ESATPESGPG TSTEPSEGSA PGTSESATPE SGPGSPAGSP TSTEEGSPAG  540
```

-continued

```
SPTSTEEGSP AGSPTSTEEG TSESATPESG PGTSTEPSEG SAPGTSESAT PESGPGSEPA  600
TSGSETPGTS ESATPESGPG SEPATSGSET PGTSESATPE SGPGTSTEPS EGSAPGSPAG  660
SPTSTEEGTS ESATPESGPG SEPATSGSET PGTSESATPE SGPGSPAGSP TSTEEGSPAG  720
SPTSTEEGTS TEPSEGSAPG TSESATPESG PGTSESATPE SGPGTSESAT PESGPGSEPA  780
TSGSETPGSE PATSGSETPG SPAGSPTSTE EGTSTEPSEG SAPGTSTEPS EGSAPGSEPA  840
TSGSETPGTS ESATPESGPG TSTEPSEGSA PLSGRSDNHV PLSLKMGGTA EAASASGEVQ  900
LLESGGGLVQ PGGSLKLSCA ASGFTFNTYA MNWVRQAPGK GLEWVARIRS KYNNYATYYA  960
DSVKDRFTIS RDDSKNTAYL QMNNLKTEDT AVYYCVRHGN FGNSYVSWFA YWGQGTLVTV  1020
SSGATPPETG AETESPGETT GGSAESEPPG EGELVVTQEP SLTVSPGGTV TLTCRSSTGA  1080
VTTSNYANWV QQKPGQAPRG LIGGTNKRAP GTPARFSGSL LGGKAALTLS GVQPEDEAEY  1140
YCALWYSNLW VFGGGTKLTV L                                           1161

SEQ ID NO: 446         moltype = DNA  length = 3471
FEATURE                Location/Qualifiers
misc_feature           1..3471
                       note = Description of Artificial Sequence: Synthetic
                        polynucleotide
source                 1..3471
                       mol_type = other DNA
                       organism = synthetic construct
SEQUENCE: 446
gacatccaaa tgacccagag cccgagcagc ctgagcgcga gcgtgggcga ccgtgttacc  60
atcacctgcc gtgcgagcca agacatccgt aactacctga actggtatca gcaaaagccg  120
ggtaaagcgc cgaagctgct gatctactat accagccgtc tggagagcgg cgtgccgagc  180
cgtttcagcg gtagcggtag cggtaccgac tacaccctga ccattagcag cctgcagccg  240
gaagatttcg cgacctacta ttgccagcag ggtaacaccc tgccgtggac ctttggtcaa  300
ggcaccaaag ttgagattaa aggcgccacg cctccggaaa ctggtgctga gacggaatcc  360
cctggtgaaa ccactggcgg ttctgccgaa tctgaaccgc ctggtgaagg cgaggtgcag  420
ctggttgaaa gcggtggcgg tctggtgcaa ccaggcggta gcctgcgtct gagctgcgcg  480
gcgagcggtt acagctttac cggttatacc atgaactggg ttcgtcaagc gccaggtaaa  540
ggtctggagt gggtggcgct gatcaacccg tacaagggtg ttagcaccta taaccagaag  600
ttcaaagacc gttttaccat tagcgtggat aagagcaaaa acaccgcgta cctgcaaatg  660
aacagcctgc gtgcggagga caccgctgtg tactattgcg cgcgtagcgg ttactatggc  720
gacagcgact ggtattttga tgtgtggggc caaggcaccc tggttaccgt gagctccggc  780
accgccgaag cagctagcgc ctctggcctg tcaggtcgtt ctgataacca ttccccactg  840
ggtctggctg ggtctccagg tagcccagct ggtagcccaa cctctaccga agaaggtacc  900
tctgaatccg ctactccaga atccggtcct ggtactagca ctgagccaag cgaaggttct  960
gctccaggct ccccggcagg tagccctacc tctaccgaag agggcactag caccgaacca  1020
tctgagggtt ccgctcctgg cacctccact gaaccgtccg aaggcagtgc tccgggtact  1080
tccgaaagcg caactccgga atccggccct ggttctgagc ctgctacttc cggctctgaa  1140
actccaggta gcgagccagc gacttctggt tctgaaactc caggttcacc ggcgggtagc  1200
ccgacgagca cggaggaagg tacctctgag tcggccactc ctgagtccgg tccgggcacg  1260
agcaccgagc cgagcgaggg ttcagccccg ggtaccagca cggagccgtc cgagggtagc  1320
gcaccgggtt ctccggcggg ctcccctacg tctacggaag agggtacgtc cactgaacct  1380
agcgagggca gcgcgccagg caccagcact gaaccgagcg aaggcagcgc acctggcact  1440
agcgagtctg cgactccgga gagcggtccg ggtacgagca cggaaccaag cgaaggcagc  1500
gccccaggta cctctgaatc tgctacccca gaatctggcc cgggttccga gccagctacc  1560
tctggttctg aaaccccagg tacttccact gaaccaagcg aaggtagcgc tcctggcact  1620
tctactgaac catccgaagg ttccgctcct ggtacgtctg aaagcgctac cctgaaagc  1680
ggcccaggca cctctgaaag cgctactcct gagagcggtc caggctctcc agcaggttct  1740
ccaacctcca ctgaagaagg cacctctgag tctgctaccc ctgaatctgg tcctggctcc  1800
gaacctgcta cctctggttc cgaaactcca ggtacctcgg aatctgcgac tccggaatct  1860
ggcccgggca cgagcacgga gccgtctgag ggtagcgcac caggtaccag cactgagcct  1920
tctgagggct ctgcaccggg tacctccacg gaaccttcgg aaggttctgc gccgggtacc  1980
tccactgagc catccgaggg ttcagcacca ggtactagca cggaaccgtc cgagggctct  2040
gcaccaggta cgagcaccga accgtcggag ggtagcgctc caggtagccc agcgggctct  2100
ccgacaagca ccgaagaagg caccagcacc gagccgtccg aaggttccgc accaggtaca  2160
agcgagagcg cgactcctga atctggtccg ggtagcgagc ctgcaaccag cggttctgag  2220
acgccgggca cttccgaatc tgcgaccccg gagtccggtc caggttcaga gccggcgacg  2280
agcggttcgg aaacgccggg tacgtctgaa tcagccacgc cggagtctgg tccgggtacc  2340
tcgaccgaac caagcgaagg ttcggcaccg ggtactagcg agagcgcaac ccctgaaagc  2400
ggtccgggca gcccggcagg ttctccaacc agcaccgaag aaggttcccc tgctggtagc  2460
ccgacctcta cggaggaagg tagccctgca ggttccccaa cttctactga ggaaggtact  2520
tctgagtccg ctaccccaga aagcggtcct ggtacctcca ctgaaccgtc tgaaggctct  2580
gcaccaggca cttctgagtc tgctactcca gaaagcggcc caggttctga accagcaact  2640
tctggctctg agactccagg cacttctgag tccgcaacgc ctgaatccgg tcctggttct  2700
gaaccagcta cttccggcag cgaaacccca ggtacctctg agtctgcgac tccagagtct  2760
ggtcctggta cttccactga gcctagcgag ggttccgcac caggttctcc ggctggtagc  2820
ccgaccagca cggaggaggg tacgtctgaa tctgcaacgc cggaatcggg cccaggttcg  2880
gagcctgcaa cgtctggcag cgaaaccccg ggtacctccg aatctgctac accggaaagc  2940
ggtcctggca gccctgctgg ttctccaacc tctaccgagg agggttcacc ggcaggtagc  3000
ccgactagca ctgaagaagg tactagcacg gagccgagcg agggtagtgc tccgggtacg  3060
agcgagagcg caacgccaga gagcggtcca ggcaccagcg aatcggccac ccctgagagc  3120
ggcccaggta cttctgagag cgccactcct gaatccggcc ctggtagcga gccggcaacc  3180
tccggctcag aaactcctgg ttcggaacca gcgaccagcg gttctgaaac tccgggtagc  3240
ccggcaggca gcccaacgag caccgaagag ggtaccagca cggaaccgag cgagggttct  3300
gccccgggta cttccaccga accatcggag ggctctgcac ctggtagcga acctgcgacg  3360
tctggttctg aaacgccggg taccagcgaa agcgctaccc cagaatccgg tccgggcact  3420
agcaccgagc catcggaggg ctccgcacca ggtcaccatc atcaccatca c           3471
```

```
SEQ ID NO: 447          moltype = DNA  length = 3471
FEATURE                 Location/Qualifiers
misc_feature            1..3471
                        note = Description of Artificial Sequence: Synthetic
                         polynucleotide
source                  1..3471
                        mol_type = other DNA
                        organism = synthetic construct
SEQUENCE: 447
gacatccaaa tgacccagag cccgagcagc ctgagcgcga gcgtgggcga ccgtgttacc  60
atcacctgcc gtgcgagcca agacatccgt aactacctga actggtatca gcaaaagccg  120
ggtaaagcgc cgaagctgct gatctactat accagccgtc tggagagcgg cgtgccgagc  180
cgtttcagcg gtagcggtag cggtaccgac tacaccctga ccattagcag cctgcagccg  240
gaagatttcg cgacctacta ttgccagcag ggtaacaccc tgccgtggac ctttggtcaa  300
ggcaccaaag ttgagattaa aggcgccacg cctccggaaa ctggtgctga gacggaatcc  360
cctggtgaaa ccactggcgg ttctgccgaa tctgaaccgc ctggtgaagg cgaggtgcag  420
ctggttgaaa gcggtggcgg tctggtgcaa ccaggcggta gcctgcgtct gagctgcgcg  480
gcgagcggtt acagctttac cggttatacc atgaactggg ttcgtcaagc gccaggtaaa  540
ggtctggagt gggtggcgct gatcaacccg tacaagggtg ttagcaccta taaccagaag  600
ttcaaagacc gttttaccat tagcgtggat aagagcaaaa acaccgcgta cctgcaaatg  660
aacagcctgc gtgcggagga caccgctgtg tactattgcg cgcgtagcgg ttactatggc  720
gacagcgact ggtattttga tgtgtggggc caaggcaccc tggttaccgt gagctccggc  780
accgccgaag cagctagcgc ctctggcctg tcaggtcgtt ctgataacca tgttccactg  840
tctctgaaaa tgggtccagg tagcccagct ggtagcccaa cctctaccga agaaggtacc  900
tctgaatccg ctactccaga atccggtcct ggtactagca ctgagccaag cgaaggttct  960
gctccaggct ccccggcagg tagccctacc tctaccgaag agggcactag caccgaacca  1020
tctgagggtt ccgctcctgg cacctccact gaaccgtccg aaggcagtgc tccgggtact  1080
tccgaaagcg caactccgga atccggccct ggttctgagc ctgctacttc cggctctgaa  1140
actccaggta gcgagccagc gacttctggt tctgaaactc caggttcacc ggcgggtagc  1200
ccgacgagca cggaggaagg tacctctgag tcggccactc ctgagtccgg tccgggcacg  1260
agcaccgagc cgagcgaggg ttcagccccg ggtaccagca cggagccgtc cgagggtagc  1320
gcaccgggtt ctccggcggg ctcccctacg tctacggaag agggtacgtc cactgaacct  1380
agcgagggca gcgcgccagg caccagcact gaaccgagcg aaggcagcgc acctggcact  1440
agcgagtctg cgactccgga gagcggtccg ggtacgagca cggaaccaag cgaaggcagc  1500
gccccaggta cctctgaatc tgctacccca gaatctggcc cgggttccga gccagctacc  1560
tctggttctg aaaccccagg tacttccact gaaccaagcg aaggtagcgc tcctggcact  1620
tctactgaac catccgaagg ttccgctcct ggtacgtctg aaagcgctac ccctgaaagc  1680
ggcccaggca cctctgaaag cgctactcct gagagcggtc caggctctcc agcaggttct  1740
ccaacctcca ctgaagaagg cacctctggg tctgctaccc ctgaatctgg tcctggctcc  1800
gaacctgcta cctctggttc cgaaactcca ggtacctcgg aatctgcgac tccggaatct  1860
ggcccgggca cgagcacgga gccgtctgag ggtagcgcac caggtaccag cactgagcct  1920
tctgagggct ctgcaccggg tacctccacg gaaccttcgg aaggttctgc gccgggtacc  1980
tccactgagc catccgaggg ttcagcacca ggtactagca cggaaccgtc cgagggctct  2040
gcaccaggta cgagcaccga accgtcggag ggtagcgctc caggtagccc agcgggctct  2100
ccgacaagca ccgaagaagg caccagcacc gagccgtccg aaggttccgc accaggtaca  2160
agcgagagcg cgactcctga atctggtccg ggtagcgagc ctgcaaccag cggttctgag  2220
acgccgggca cttccgaatc tgcgaccccg gagtccggtc caggttcaga gccggcgacg  2280
agcggttcgg aaacgccggg tacgtctgaa tcagccacgc cggagtctgg tccgggtacc  2340
tcgaccgaac caagcgaagg ttcggcaccg ggtactagcg agagcgcaac ccctgaaagc  2400
ggtccgggca gcccggcagg ttctccaacc agcaccgaag aaggttcccc tgctggtagc  2460
ccgacctcta cggaggaagg tagccctgca ggttccccaa cttctactga ggaaggtact  2520
tctgagtccg ctaccccaga aagcggtcct ggtacctcca ctgaaccgtc tgaaggctct  2580
gcaccaggca cttctgagtc tgctactcca gaaagcggcc caggttctga accagcaact  2640
tctggctctg agactccagg cacttctgag tccgcaacgc ctgaatccgg tcctggttct  2700
gaaccagcta cttccggcag cgaaacccca ggtacctctg agtctgcgac tccagagtct  2760
ggtcctggta cttccactga gcctagcgag ggttccgcac caggttctcc ggctggtagc  2820
ccgaccagca cggaggaggg tacgtctgaa tctgcaacgc cggaatcggg cccaggttcg  2880
gagcctgcaa cgtctggcag cgaaaccccg ggtacctccg aatctgctac accggaaagc  2940
ggtcctggca gccctgctgg ttctccaacc tctaccgagg agggttcacc ggcaggtagc  3000
ccgactagca ctgaagaagg tactagcacg gagccgagcg agggtagtgc tccgggtacg  3060
agcgagagcg caacgccaga gagcggtcca ggcaccagcg aatcggccac ccctgagagc  3120
ggcccaggta cttctgagag cgccactcct gaatccggcc ctggtagcga gccggcaacc  3180
tccggctcag aaactcctgg ttcggaacca gcgaccagcg gttctgaaac tccgggtagc  3240
ccggcaggca gcccaacgag caccgaagag ggtaccagca cggaaccgag cgagggttct  3300
gccccgggta cttccaccga accatcggag ggctctgcac ctggtagcga acctgcgacg  3360
tctggttctg aaacgccggg taccagcgaa agcgctaccc cagaatccgg tccgggcact  3420
agcaccgagc catcggaggg ctccgcacca ggtcaccatc atcaccatca c           3471

SEQ ID NO: 448          moltype = DNA  length = 3471
FEATURE                 Location/Qualifiers
misc_feature            1..3471
                        note = Description of Artificial Sequence: Synthetic
                         polynucleotide
source                  1..3471
                        mol_type = other DNA
                        organism = synthetic construct
SEQUENCE: 448
gaggtgcagc tggttgaaag cggtggcggt ctggtgcaac caggcggtag cctgcgtctg  60
```

```
agctgcgcgg cgagcggtta cagctttacc ggttatacca tgaactgggt tcgtcaagcg  120
ccaggtaaag gtctggagtg ggtggcgctg atcaacccgt acaagggtgt tagcacctat  180
aaccagaagt tcaaagaccg ttttaccatt agcgtggata agagcaaaaa caccgcgtac  240
ctgcaaatga acagcctgcg tgcggaggac accgctgtgt actattgcgc gcgtagcggt  300
tactatggcg acagcgactg gtattttgat gtgtggggcc aaggcaccct ggttaccgtg  360
agctccggcg ccacgcctcc ggaaactggt gctgagacgg aatcccctgg tgaaaccact  420
ggcggttctg ccgaatctga accgcctggt gaaggcgaca tccaaatgac ccagagcccg  480
agcagcctga gcgcgagcgt gggcgaccgt gttaccatca cctgccgtgc gagccaagac  540
atccgtaact acctgaactg gtatcagcaa aagccgggta aagcgccgaa gctgctgatc  600
tactatacca gccgtctgga gagcggcgtg ccgagccgtt tcagcggtag cggtagcggt  660
accgactaca ccctgaccat tagcagcctg cagccggaag atttcgcgac ctactattgc  720
cagcagggta acaccctgcc gtggaccttt ggtcaaggca ccaaagttga gattaaaggc  780
accgccgaag cagctagcgc ctctggcctg tcaggtcgtt ctgataacca ttccccactg  840
ggtctggctg ggtctccagg tagcccagct ggtagcccaa cctctaccga agaaggtacc  900
tctgaatccg ctactccaga atccggtcct ggtactagca ctgagccaag cgaaggttct  960
gctccaggct ccccggcagg tagccctacc tctaccgaag agggcactag caccgaacca  1020
tctgagggtt ccgctcctgg cacctccacc gaaccgtccg aaggcagtgc tccgggtact  1080
tccgaaagcg caactccgga atccggccct ggttctgagc ctgctacttc cggctctgaa  1140
actccaggta gcgagccagc gacttctggt tctgaaactc caggttcacc ggcgggtagc  1200
ccgacgagca cggaggaagg tacctctgag tcggccactc ctgagtccgg tccgggcacg  1260
agcaccgagc cgagcgaggg ttcagccccg ggtaccagca cggagccgtc cgagggtagc  1320
gcaccgggtt ctccggcggg ctcccctacg tctacggaag agggtacgtc cactgaacct  1380
agcgagggca gcgcgccagg caccagcact gaaccgagcg aaggcagcgc acctggcact  1440
agcgagtctg cgactccgga gagcggtccg ggtacgagca cggaaccaag cgaaggcagc  1500
gccccaggta cctctgaatc tgctacccca gaatctggcc cgggttccga gccagctacc  1560
tctggttctg aaaccccagg tacttccact gaaccaagcg aaggtagcgc tcctggcact  1620
tctactgaac catccgaagg ttccgctcct ggtacgtctg aaagcgctac ccctgaaagc  1680
ggcccaggca cctctgaaag cgctactcct gagagcggtc caggctctcc agcaggttct  1740
ccaacctcca ctgaagaagg cacctctgag tctgctaccc ctgaatctgg tcctggctcc  1800
gaacctgcta cctctggttc cgaaactcca ggtacctcgg aatctgcgac tccggaatct  1860
ggcccgggca cgagcacgga gccgtctgag ggtagcgcac caggtaccag cactgagcct  1920
tctgagggct ctgcaccggg tacctccacg gaaccttcgg aaggttctgc gccgggtacc  1980
tccactgagc catccgaggg ttcagcacca ggtactagca cggaaccgtc cgagggctct  2040
gcaccaggta cgagcaccga accgtcggag ggtagcgctc caggtagccc agcgggctct  2100
ccgacaagca ccgaagaagg caccagcacc gagccgtccg aaggttccgc accaggtaca  2160
agcgagagcg cgactcctga atctggtccg ggtagcgagc ctgcaaccag cggttctgag  2220
acgccgggca cttccgaatc tgcgaccccg gagtccggtc caggttcaga gccggcgacg  2280
agcggttcgg aaacgccggg tacgtctgaa tcagccacgc cggagtctgg tccgggtacc  2340
tcgaccgaac caagcgaagg ttcggcaccg ggtactagcg agagcgcaac ccctgaaagc  2400
ggtccgggca gcccggcagg ttctccaacc agcaccgaag aaggttcccc tgctggtagc  2460
ccgacctcta cggaggaagg tagccctgca ggttccccaa cttctactga ggaaggtact  2520
tctgagtccg ctaccccaga aagcggtcct ggtacctcca ctgaaccgtc tgaaggctct  2580
gcaccaggca cttctgagtc tgctactcca gaaagcggcc caggttctga accagcaact  2640
tctggctctg agactccagg cacttctgag tccgcaacgc ctgaatccgg tcctggttct  2700
gaaccagcta cttccggcag cgaaacccca ggtacctctg agtctgcgac tccagagtct  2760
ggtcctggta cttccactga gcctagcgag ggttccgcac caggttctcc ggctggtagc  2820
ccgaccagca cggaggaggg tacgtctgaa tctgcaacgc cggaatcggg cccaggttcg  2880
gagcctgcaa cgtctggcag cgaaaccccg ggtacctccg aatctgctac accggaaagc  2940
ggtcctggca gccctgctgg ttctccaacc tctaccgagg agggttcacc ggcaggtagc  3000
ccgactagca ctgaagaagg tactagcacg gagccgagcg agggtagtgc tccgggtacg  3060
agcgagagcg caacgccaga gagcggtcca ggcaccagcg aatcggccac ccctgagagc  3120
ggcccaggta cttctgagag cgccactcct gaatccggcc ctggtagcga gccggcaacc  3180
tccggctcag aaactcctgg ttcggaacca gcgaccagcg gttctgaaac tccgggtagc  3240
ccggcaggca gcccaacgag caccgaagag ggtaccagca cggaaccgag cgagggttct  3300
gccccgggta cttccaccga accatcggag ggctctgcac ctggtagcga acctgcgacg  3360
tctggttctg aaacgccggg taccagcgaa agcgctaccc cagaatccgg tccgggcact  3420
agcaccgagc catcggaggg ctccgcacca ggtcaccatc atcaccatca c           3471

SEQ ID NO: 449         moltype = DNA  length = 3471
FEATURE                Location/Qualifiers
misc_feature           1..3471
                       note = Description of Artificial Sequence: Synthetic
                        polynucleotide
source                 1..3471
                       mol_type = other DNA
                       organism = synthetic construct
SEQUENCE: 449
gaggtgcagc tggttgaaag cggtggcggt ctggtgcaac caggcggtag cctgcgtctg  60
agctgcgcgg cgagcggtta cagctttacc ggttatacca tgaactgggt tcgtcaagcg  120
ccaggtaaag gtctggagtg ggtggcgctg atcaacccgt acaagggtgt tagcacctat  180
aaccagaagt tcaaagaccg ttttaccatt agcgtggata agagcaaaaa caccgcgtac  240
ctgcaaatga acagcctgcg tgcggaggac accgctgtgt actattgcgc gcgtagcggt  300
tactatggcg acagcgactg gtattttgat gtgtggggcc aaggcaccct ggttaccgtg  360
agctccggcg ccacgcctcc ggaaactggt gctgagacgg aatcccctgg tgaaaccact  420
ggcggttctg ccgaatctga accgcctggt gaaggcgaca tccaaatgac ccagagcccg  480
agcagcctga gcgcgagcgt gggcgaccgt gttaccatca cctgccgtgc gagccaagac  540
atccgtaact acctgaactg gtatcagcaa aagccgggta aagcgccgaa gctgctgatc  600
tactatacca gccgtctgga gagcggcgtg ccgagccgtt tcagcggtag cggtagcggt  660
accgactaca ccctgaccat tagcagcctg cagccggaag atttcgcgac ctactattgc  720
```

```
cagcagggta acaccctgcc gtggaccttt ggtcaaggca ccaaagttga gattaaaggc  780
accgccgaag cagctagcgc ctctggcctg tcaggtcgtt ctgataacca tgttccactg  840
tctctgaaaa tgggtccagg tagcccagct ggtagcccaa cctctaccga agaaggtacc  900
tctgaatccg ctactccaga atccggtcct ggtactagca ctgagccaag cgaaggttct  960
gctccaggct ccccggcagg tagccctacc tctaccgaag agggcactag caccgaacca  1020
tctgagggtt ccgctcctgg cacctccact gaaccgtccg aaggcagtgc tccgggtact  1080
tccgaaagcg caactccgga atccggccct ggttctgagc ctgctacttc cggctctgaa  1140
actccaggta gcgagccagc gacttctggt tctgaaactc caggttcacc ggcgggtagc  1200
ccgacgagca cggaggaagg tacctctgag tcggccactc ctgagtccgg tccgggcacg  1260
agcaccgagc cgagcgaggg ttcagccccg ggtaccagca cggagccgtc cgagggtagc  1320
gcaccgggtt ctccggcggg ctcccctacg tctacggaag agggtacgtc cactgaacct  1380
agcgagggca gcgcgccagg caccagcact gaaccgagcg aaggcagcgc acctggcact  1440
agcgagtctg cgactccgga gagcggtccg ggtacgagca cggaaccaag cgaaggcagc  1500
gccccaggta cctctgaatc tgctacccca gaatctggcc cgggttccga gccagctacc  1560
tctggttctg aaaccccagg tacttccact gaaccaagcg aaggtagcgc tcctggcact  1620
tctactgaac catccgaagg ttccgctcct ggtacgtctg aaagcgctac ccctgaaagc  1680
ggcccaggca cctctgaaag cgctactcct gagagcggtc caggctctcc agcaggttct  1740
ccaacctcca ctgaagaagg cacctctgag tctgctaccc ctgaatctgg tcctggctcc  1800
gaacctgcta cctctggttc cgaaactcca ggtacctcgg aatctgcgac tccggaatct  1860
ggcccgggca cgagcacgga gccgtctgag ggtagcgcac caggtaccag cactgagcct  1920
tctgagggct ctgcaccggg tacctccacg gaaccttcgg aaggttctgc gccgggtacc  1980
tccactgagc catccgaggg ttcagcacca ggtactagca cggaaccgtc cgagggctct  2040
gcaccaggta cgagcaccga accgtcggag ggtagcgctc caggtagccc agcgggctct  2100
ccgacaagca ccgaagaagg caccagcacc gagccgtccg aaggttccgc accaggtaca  2160
agcgagagcg cgactcctga atctggtccg ggtagcgagc ctgcaaccag cggttctgag  2220
acgccgggca cttccgaatc tgcgaccccg gagtccggtc caggttcaga gccggcgacg  2280
agcggttcgg aaacgccggg tacgtctgaa tcagccacgc cggagtctgg tccgggtacc  2340
tcgaccgaac caagcgaagg ttcggcaccg ggtactagcg agagcgcaac ccctgaaagc  2400
ggtccgggca gcccggcagg ttctccaacc agcaccgaag aaggttcccc tgctggtagc  2460
ccgacctcta cggaggaagg tagccctgca ggttccccaa cttctactga ggaaggtact  2520
tctgagtccg ctaccccaga aagcggtcct ggtacctcca ctgaaccgtc tgaaggctct  2580
gcaccaggca cttctgagtc tgctactcca gaaagcggcc caggttctga accagcaact  2640
tctggctctg agactccagg cacttctgag tccgcaacgc ctgaatccgg tcctggttct  2700
gaaccagcta cttccggcag cgaaacccca ggtacctctg agtctgcgac tccagagtct  2760
ggtcctggta cttccactga gcctagcgag ggttccgcac caggttctcc ggctggtagc  2820
ccgaccagca cggaggaggg tacgtctgaa tctgcaacgc cggaatcggg cccaggttcg  2880
gagcctgcaa cgtctggcag cgaaaccccg ggtacctccg aatctgctac accggaaagc  2940
ggtcctggca gccctgctgg ttctccaacc tctaccgagg agggttcacc ggcaggtagc  3000
ccgactagca ctgaagaagg tactagcacg gagccgagcg agggtagtgc tccgggtacg  3060
agcgagagcg caacgccaga gagcggtcca ggcaccagcg aatcggccac ccctgagagc  3120
ggcccaggta cttctgagag cgccactcct gaatccggcc ctggtagcga gccggcaacc  3180
tccggctcag aaactcctgg ttcggaacca gcgaccagcg gttctgaaac tccgggtagc  3240
ccggcaggca gcccaacgag caccgaagag ggtaccagca cggaaccgag cgagggttct  3300
gccccgggta cttccaccga accatcggag ggctctgcac ctggtagcga acctgcgacg  3360
tctggttctg aaacgccggg taccagcgaa agcgctaccc cagaatccgg tccgggcact  3420
agcaccgagc catcggaggg ctccgcacca ggtcaccatc atcaccatca c           3471

SEQ ID NO: 450          moltype = DNA  length = 3486
FEATURE                 Location/Qualifiers
misc_feature            1..3486
                        note = Description of Artificial Sequence: Synthetic
                         polynucleotide
source                  1..3486
                        mol_type = other DNA
                        organism = synthetic construct
SEQUENCE: 450
gaactggtcg tcacgcagga gccgtccctt accgtttcac caggtggaac agtgactctg  60
acgtgtcgct cctccactgg ggcggttaca acttccaatt atgctaattg ggtccagcag  120
aagccgggcc aagcccctcg cgggttgatt ggcggcacca acaaacgtgc tccagggaca  180
cctgcccgtt tttcgggctc cttattgggg ggcaaagctg cactgacgtt gtctggagtt  240
cagccggagg atgaggcaga gtattactgc gcattgtggt attctaattt atgggttttt  300
ggaggcggca caaagctgac cgtcctgggt gcgacccccgc cggaaaccgg tgcggaaacc  360
gaaagcccgg gtgaaaccac cggtggcagc gcggagagcg aaccgccggg tgaaggtgag  420
gttcagttgt tggaaagcgg gggcgggctt gtccaacctg gaggttcatt aaaattgagc  480
tgtgcagcct ccggattcac ctttaacacg tatgcaatga actgggtccg tcaagcgccc  540
ggtaaggggc tggagtgggt agctcgcatc cgctcgaagt ataataatta cgcaacctac  600
tacgcagaca gtgtcaaaga tcgcttcact atctcacgcg acgacagtaa gaacacggcc  660
tacttacaga tgaacaatct taaaacggag gacaccgctg tctactactg cgtgcgccac  720
gggaatttcg gtaactctta tgtaagttgg ttcgcatatt ggggacaagg tacgttggta  780
accgtatcca gcggcaccgc cgaagcagct agcgcctctg gcctgtcagg tcgttctgat  840
aaccattccc cactgggtct ggctgggtct ccaggtagcc cagctggtag cccaacctct  900
accgaagaag gtacctctga atccgctact ccagaatccg gtcctggtac tagcactgag  960
ccaagcgaag gttctgctcc aggctccccg gcaggtagcc ctacctctac cgaagagggc  1020
actagcaccg aaccatctga gggttccgct cctggcacct ccactgaacc gtccgaaggc  1080
agtgctccgg gtacttccga aagcgcaact ccggaatccg gccctggttc tgagcctgct  1140
acttccggct ctgaaactcc aggtagcgag ccagcgactt ctggttctga aactccaggt  1200
tcaccggcgg gtagcccgac gagcacggag gaaggtacct ctgagtcggc cactcctgag  1260
tccggtccgg gcacgagcac cgagccgagc gagggttcag ccccgggtac cagcacggag  1320
ccgtccgagg gtagcgcacc gggttctccg gcgggctccc ctacgtctac ggaagagggt  1380
```

```
acgtccactg aacctagcga gggcagcgcg ccaggcacca gcactgaacc gagcgaaggc  1440
agcgcacctg gcactagcga gtctgcgact ccggagagcg gtccgggtac gagcacggaa  1500
ccaagcgaag gcagcgcccc aggtacctct gaatctgcta ccccagaatc tggcccgggt  1560
tccgagccag ctacctctgg ttctgaaacc ccaggtactt ccactgaacc aagcgaaggt  1620
agcgctcctg gcacttctac tgaaccatcc gaaggttccg ctcctggtac gtctgaaagc  1680
gctacccctg aaagcggccc aggcacctct gaaagcgcta ctcctgagag cggtccaggc  1740
tctccagcag gttctccaac ctccactgaa gaaggcacct ctgagtctgc taccccctgaa  1800
tctggtcctg gctccgaacc tgctacctct ggttccgaaa ctccaggtac ctcggaatct  1860
gcgactccgg aatctggccc gggcacgagc acggagccgt ctgagggtag cgcaccaggt  1920
accagcactg agccttctga gggctctgca ccgggtacct ccacggaacc ttcggaaggt  1980
tctgcgccgg gtacctccac tgagccatcc gagggttcag caccaggtac tagcacggaa  2040
ccgtccgagg gctctgcacc aggtacgagc accgaaccgt cggagggtag cgctccaggt  2100
agcccagcgg gctctccgac aagcaccgaa gaaggcacca gcaccgagcc gtccgaaggt  2160
tccgcaccag gtacaagcga gagcgcgact cctgaatctg gtccgggtag cgagcctgca  2220
accagcggtt ctgagacgcc gggcacttcc gaatctgcga ccccggagtc cggtccaggt  2280
tcagagccgg cgacgagcgg ttcggaaacg ccgggtacgt ctgaatcagc cacgccggag  2340
tctggtccgg gtacctcgac cgaaccaagc gaaggttcgg caccgggtac tagcgagagc  2400
gcaacccctg aaagcggtcc gggcagcccg gcaggttctc caaccagcac cgaagaaggt  2460
tcccctgctg gtagcccgac ctctacggag gaaggtagcc ctgcaggttc cccaacttct  2520
actgaggaag gtacttctga gtccgctacc ccagaaagcg gtcctggtac ctccactgaa  2580
ccgtctgaag gctctgcacc aggcacttct gagtctgcta ctccagaaag cggcccaggt  2640
tctgaaccag caacttctgg ctctgagact ccaggcactt ctgagtccgc aacgcctgaa  2700
tccggtcctg gttctgaacc agctacttcc ggcagcgaaa ccccaggtac ctctgagtct  2760
gcgactccag agtctggtcc tggtacttcc actgagccta gcgagggttc cgcaccaggt  2820
tctccggctg gtagcccgac cagcacggag gagggtacgt ctgaatctgc aacgccggaa  2880
tcgggcccag gttcggagcc tgcaacgtct ggcagcgaaa ccccgggtac ctccgaatct  2940
gctacaccgg aaagcggtcc tggcagccct gctggttctc caacctctac cgaggagggt  3000
tcaccggcag gtagcccgac tagcactgaa gaaggtacta gcacggagcc gagcgagggt  3060
agtgctccgg gtacgagcga gagcgcaacg ccagagagcg gtccaggcac cagcgaatcg  3120
gccacccctg agagcggccc aggtacttct gagagcgcca ctcctgaatc cggccctggt  3180
agcgagccgg caacctccgg ctcagaaact cctggttcgg aaccagcgac cagcggttct  3240
gaaactccgg gtagcccggc aggcagccca acgagcaccg aagagggtac cagcacggaa  3300
ccgagcgagg gttctgcccc gggtacttcc accgaaccat cggagggctc tgcacctggt  3360
agcgaacctg cgacgtctgg ttctgaaacg ccgggtacca gcgaaagcgc taccccagaa  3420
tccggtccgg gcactagcac cgagccatcg gagggctccg caccaggtca ccatcatcac  3480
catcac                                                             3486
```

```
SEQ ID NO: 451         moltype = DNA  length = 3486
FEATURE                Location/Qualifiers
misc_feature           1..3486
                       note = Description of Artificial Sequence: Synthetic
                        polynucleotide
source                 1..3486
                       mol_type = other DNA
                       organism = synthetic construct
SEQUENCE: 451
gaactggtcg tcacgcagga gccgtccctt accgtttcac caggtggaac agtgactctg  60
acgtgtcgct cctccactgg ggcggttaca acttccaatt atgctaattg ggtccagcag  120
aagccgggcc aagcccctcg cgggttgatt ggcggcacca acaaacgtgc tccagggaca  180
cctgcccgtt tttcgggctc cttattgggg ggcaaagctg cactgacgtt gtctggagtt  240
cagccggagg atgaggcaga gtattactgc gcattgtggt attctaattt atgggttttt  300
ggaggcggca caaagctgac cgtcctgggt gcgacccgc cggaaaccgg tgcggaaacc  360
gaaagcccgg gtgaaaccac cggtggcagc gcggagagcg aaccgccggg tgaaggtgag  420
gttcagttgt tggaaagcgg gggcgggctt gtccaacctg gaggttcatt aaaattgagc  480
tgtgcagcct ccggattcac ctttaacacg tatgcaatga actgggtccg tcaagcgccc  540
ggtaaggggc tggagtgggt agctcgcatc cgctcgaagt ataataatta cgcaacctac  600
tacgcagaca gtgtcaaaga tcgcttcact atctcacgcg acgacagtaa gaacacggcc  660
tacttacaga tgaacaatct taaaacggag gacaccgctg tctactactg cgtgcgccac  720
gggaatttcg gtaactctta tgtaagttgg ttcgcatatt ggggacaagg tacgttggta  780
accgtatcca gcggcaccgc cgaagcagct agcgcctctg gcctgtcagg tcgttctgat  840
aaccatgttc cactgtctct gaaaatgggt ccaggtagcc cagctggtag cccaacctct  900
accgaagaag gtacctctga atccgctact ccagaatccg gtcctggtac tagcactgag  960
ccaagcgaag gttctgctcc aggctccccg gcaggtagcc ctacctctac cgaagagggc  1020
actagcaccg aaccatctga gggttccgct cctggcacct ccactgaacc gtccgaaggc  1080
agtgctccgg gtacttccga aagcgcaact ccggaatccg gccctggttc tgagcctgct  1140
acttccggct ctgaaactcc aggtagcgag ccagcgactt ctggttctga aactccaggt  1200
tcaccggcgg gtagcccgac gagcacggag gaaggtacct ctgagtcggc cactcctgag  1260
tccggtccgg gcacgagcac cgagccgagc gagggttcag ccccgggtac cagcacggag  1320
ccgtccgagg gtagcgcacc gggttctccg gcgggctccc ctacgtctac ggaagagggt  1380
acgtccactg aacctagcga gggcagcgcg ccaggcacca gcactgaacc gagcgaaggc  1440
agcgcacctg gcactagcga gtctgcgact ccggagagcg gtccgggtac gagcacggaa  1500
ccaagcgaag gcagcgcccc aggtacctct gaatctgcta ccccagaatc tggcccgggt  1560
tccgagccag ctacctctgg ttctgaaacc ccaggtactt ccactgaacc aagcgaaggt  1620
agcgctcctg gcacttctac tgaaccatcc gaaggttccg ctcctggtac gtctgaaagc  1680
gctacccctg aaagcggccc aggcacctct gaaagcgcta ctcctgagag cggtccaggc  1740
tctccagcag gttctccaac ctccactgaa gaaggcacct ctgagtctgc taccccctgaa  1800
tctggtcctg gctccgaacc tgctacctct ggttccgaaa ctccaggtac ctcggaatct  1860
gcgactccgg aatctggccc gggcacgagc acggagccgt ctgagggtag cgcaccaggt  1920
accagcactg agccttctga gggctctgca ccgggtacct ccacggaacc ttcggaaggt  1980
```

```
tctgcgccgg gtacctccac tgagccatcc gagggttcag caccaggtac tagcacggaa  2040
ccgtccgagg gctctgcacc aggtacgagc accgaaccgt cggagggtag cgctccaggt  2100
agcccagcgg gctctccgac aagcaccgaa gaaggcacca gcaccgagcc gtccgaaggt  2160
tccgcaccag gtacaagcga gagcgcgact cctgaatctg gtccgggtag cgagcctgca  2220
accagcggtt ctgagacgcc gggcacttcc gaatctgcga ccccggagtc cggtccaggt  2280
tcagagccgg cgacgagcgg ttcggaaacg ccgggtacgt ctgaatcagc cacgccggag  2340
tctggtccgg gtacctcgac cgaaccaagc gaaggttcgg caccgggtac tagcgagagc  2400
gcaacccctg aaagcggtcc gggcagcccg gcaggttctc caaccagcac cgaagaaggt  2460
tcccctgctg gtagcccgac ctctacggag gaaggtagcc ctgcaggttc cccaacttct  2520
actgaggaag gtacttctga gtccgctacc ccagaaagcg gtcctggtac ctccactgaa  2580
ccgtctgaag gctctgcacc aggcacttct gagtctgcta ctccagaaag cggcccaggt  2640
tctgaaccag caacttctgg ctctgagact ccaggcactt ctgagtccgc aacgcctgaa  2700
tccggtcctg gttctgaacc agctacttcc ggcagcgaaa ccccaggtac ctctgagtct  2760
gcgactccag agtctggtcc tggtacttcc actgagccta gcgagggttc cgcaccaggt  2820
tctccggctg gtagcccgac cagcacggag gagggtacgt ctgaatctgc aacgccggaa  2880
tcgggcccag gttcggagcc tgcaacgtct ggcagcgaaa ccccgggtac ctccgaatct  2940
gctacaccgg aaagcggtcc tggcagccct gctggttctc caacctctac cgaggagggt  3000
tcaccggcag gtagcccgac tagcactgaa gaaggtacta gcacggagcc gagcgagggt  3060
agtgctccgg gtacgagcga gagcgcaacg ccagagagcg gtccaggcac cagcgaatcg  3120
gccacccctg agagcggccc aggtacttct gagagcgcca ctcctgaatc cggccctggt  3180
agcgagccgg caacctccgg ctcagaaact cctggttcgg aaccagcgac cagcggttct  3240
gaaactccgg gtagcccggc aggcagccca acgagcaccg aagagggtac cagcacggaa  3300
ccgagcgagg gttctgcccc gggtacttcc accgaaccat cggagggctc tgcacctggt  3360
agcgaacctg cgacgtctgg ttctgaaacg ccgggtacca gcgaaagcgc taccccagaa  3420
tccggtccgg gcactagcac cgagccatcg gagggctccg caccaggtca ccatcatcac  3480
catcac                                                             3486
```

```
SEQ ID NO: 452         moltype = DNA  length = 3486
FEATURE                Location/Qualifiers
misc_feature           1..3486
                       note = Description of Artificial Sequence: Synthetic
                        polynucleotide
source                 1..3486
                       mol_type = other DNA
                       organism = synthetic construct
SEQUENCE: 452
gaggttcagt tgttggaaag cgggggcggg cttgtccaac ctggaggttc attaaaattg  60
agctgtgcag cctccggatt cacctttaac acgtatgcaa tgaactgggt ccgtcaagcg  120
cccggtaagg ggctggagtg ggtagctcgc atccgctcga agtataataa ttacgcaacc  180
tactacgcag acagtgtcaa agatcgcttc actatctcac gcgacgacag taagaacacg  240
gcctacttac agatgaacaa tcttaaaacg gaggacaccg ctgtctacta ctgcgtgcgc  300
cacgggaatt tcggtaactc ttatgtaagt tggttcgcat attggggaca aggtacgttg  360
gtaaccgtat ccagcggtgc gaccccgccg gaaaccggtg cggaaaccga aagcccgggt  420
gaaaccaccg gtggcagcgc ggagagcgaa ccgccgggtg aaggtgaact ggtcgtcacg  480
caggagccgt cccttaccgt ttcaccaggt ggaacagtga ctctgacgtg tcgctcctcc  540
actggggcgg ttacaacttc caattatgct aattgggtcc agcagaagcc gggccaagcc  600
cctcgcgggt tgattggcgg caccaacaaa cgtgctccag ggacacctgc ccgtttttcg  660
ggctccttat tggggggcaa agctgcactg acgttgtctg gagttcagcc ggaggatgag  720
gcagagtatt actgcgcatt gtggtattct aatttatggg tttttggagg cggcacaaag  780
ctgaccgtcc tgggcaccgc cgaagcagct agcgcctctg gcctgtcagg tcgttctgat  840
aaccattccc cactgggtct ggctgggtct ccaggtagcc cagctggtag cccaacctct  900
accgaagaag gtacctctga atccgctact ccagaatccg gtcctggtac tagcactgag  960
ccaagcgaag gttctgctcc aggctccccg gcaggtagcc ctacctctac cgaagagggc  1020
actagcaccg aaccatctga gggttccgct cctggcacct ccactgaacc gtccgaaggc  1080
agtgctccgg gtacttccga aagcgcaact ccggaatccg gccctggttc tgagcctgct  1140
acttccggct ctgaaactcc aggtagcgag ccagcgactt ctggttctga aactccaggt  1200
tcaccggcgg gtagcccgac gagcacggag gaaggtacct ctgagtcggc cactcctgag  1260
tccggtccgg gcacgagcac cgagccgagc gagggttcag ccccgggtac cagcacggag  1320
ccgtccgagg gtagcgcacc gggttctccg gcgggctccc ctacgtctac ggaagagggt  1380
acgtccactg aacctagcga gggcagcgcg ccaggcacca gcactgaacc gagcgaaggc  1440
agcgcacctg gcactagcga gtctgcgact ccggagagcg gtccgggtac gagcacggaa  1500
ccaagcgaag gcagcgcccc aggtacctct gaatctgcta ccccagaatc tggcccgggt  1560
tccgagccag ctacctctgg ttctgaaacc ccaggtactt ccactgaacc aagcgaaggt  1620
agcgctcctg gcacttctac tgaaccatcc gaaggttccg ctcctggtac gtctgaaagc  1680
gctacccctg aaagcggccc aggcacctct gaaagcgcta ctcctgagag cggtccaggc  1740
tctccagcag gttctccaac ctccactgaa gaaggcacct ctgagtctgc tacccctgaa  1800
tctggtcctg gctccgaacc tgctacctct ggttccgaaa ctccaggtac ctcggaatct  1860
gcgactccgg aatctggccc gggcacgagc acggagccgt ctgagggtag cgcaccaggt  1920
accagcactg agccttctga gggctctgca ccgggtacct ccacggaacc ttcggaaggt  1980
tctgcgccgg gtacctccac tgagccatcc gagggttcag caccaggtac tagcacggaa  2040
ccgtccgagg gctctgcacc aggtacgagc accgaaccgt cggagggtag cgctccaggt  2100
agcccagcgg gctctccgac aagcaccgaa gaaggcacca gcaccgagcc gtccgaaggt  2160
tccgcaccag gtacaagcga gagcgcgact cctgaatctg gtccgggtag cgagcctgca  2220
accagcggtt ctgagacgcc gggcacttcc gaatctgcga ccccggagtc cggtccaggt  2280
tcagagccgg cgacgagcgg ttcggaaacg ccgggtacgt ctgaatcagc cacgccggag  2340
tctggtccgg gtacctcgac cgaaccaagc gaaggttcgg caccgggtac tagcgagagc  2400
gcaacccctg aaagcggtcc gggcagcccg gcaggttctc caaccagcac cgaagaaggt  2460
tcccctgctg gtagcccgac ctctacggag gaaggtagcc ctgcaggttc cccaacttct  2520
actgaggaag gtacttctga gtccgctacc ccagaaagcg gtcctggtac ctccactgaa  2580
```

```
ccgtctgaag gctctgcacc aggcacttct gagtctgcta ctccagaaag cggcccaggt  2640
tctgaaccag caacttctgg ctctgagact ccaggcactt ctgagtccgc aacgcctgaa  2700
tccggtcctg gttctgaacc agctacttcc ggcagcgaaa ccccaggtac ctctgagtct  2760
gcgactccag agtctggtcc tggtacttcc actgagccta gcgagggttc cgcaccaggt  2820
tctccggctg gtagcccgac cagcacggag gagggtacgt ctgaatctgc aacgccggaa  2880
tcgggcccag gttcggagcc tgcaacgtct ggcagcgaaa ccccgggtac ctccgaatct  2940
gctacaccgg aaagcggtcc tggcagccct gctggttctc caacctctac cgaggagggt  3000
tcaccggcag gtagcccgac tagcactgaa gaaggtacta gcacggagcc gagcgagggt  3060
agtgctccgg gtacgagcga gagcgcaacg ccagagagcg gtccaggcac cagcgaatcg  3120
gccacccctg agagcggccc aggtacttct gagagcgcca ctcctgaatc cggccctggt  3180
agcgagccgg caacctccgg ctcagaaact cctggttcgg aaccagcgac cagcggttct  3240
gaaactccgg gtagcccggc aggcagccca acgagcaccg aagagggtac cagcacggaa  3300
ccgagcgagg gttctgcccc gggtacttcc accgaaccat cggagggctc tgcacctggt  3360
agcgaacctg cgacgtctgg ttctgaaacg ccgggtacca gcgaaagcgc taccccagaa  3420
tccggtccgg gcactagcac cgagccatcg gagggctccg caccaggtca ccatcatcac  3480
catcac                                                             3486
```

```
SEQ ID NO: 453         moltype = DNA  length = 3486
FEATURE                Location/Qualifiers
misc_feature           1..3486
                       note = Description of Artificial Sequence: Synthetic
                        polynucleotide
source                 1..3486
                       mol_type = other DNA
                       organism = synthetic construct
SEQUENCE: 453
gaggttcagt tgttggaaag cgggggcggg cttgtccaac ctggaggttc attaaaattg  60
agctgtgcag cctccggatt caccttttaac acgtatgcaa tgaactgggt ccgtcaagcg  120
cccggtaagg ggctggagtg ggtagctcgc atccgctcga agtataataa ttacgcaacc  180
tactacgcag acagtgtcaa agatcgcttc actatctcac gcgacgacag taagaacacg  240
gcctacttac agatgaacaa tcttaaaacg gaggacaccg ctgtctacta ctgcgtgcgc  300
cacgggaatt tcggtaactc ttatgtaagt tggttcgcat attggggaca aggtacgttg  360
gtaaccgtat ccagcggtgc gaccccgccg gaaaccggtg cggaaaccga aagcccgggt  420
gaaaccaccg gtggcagcgc ggagagcgaa ccgccgggtg aaggtgaact ggtcgtcacg  480
caggagccgt cccttaccgt ttcaccaggt ggaacagtga ctctgacgtg tcgctcctcc  540
actggggcgg ttacaacttc caattatgct aattgggtcc agcagaagcc gggccaagcc  600
cctcgcgggt tgattggcgg caccaacaaa cgtgctccag ggacacctgc ccgtttttcg  660
ggctccttat tggggggcaa agctgcactg acgttgtctg gagttcagcc ggaggatgag  720
gcagagtatt actgcgcatt gtggtattct aatttatggg tttttggagg cggcacaaag  780
ctgaccgtcc tgggcaccgc cgaagcagct agcgcctctg gcctgtcagg tcgttctgat  840
aaccatgttc cactgtctct gaaaatgggt ccaggtagcc cagctggtag cccaacctct  900
accgaagaag gtacctctga atccgctact ccagaatccg gtcctggtac tagcactgag  960
ccaagcgaag gttctgctcc aggctccccg gcaggtagcc ctacctctac cgaagagggc  1020
actagcaccg aaccatctga gggttccgct cctggcacct ccactgaacc gtccgaaggc  1080
agtgctccgg gtacttccga aagcgcaact ccggaatccg gccctggttc tgagcctgct  1140
acttccggct ctgaaactcc aggtagcgag ccagcgactt ctggttctga aactccaggt  1200
tcaccggcgg gtagcccgac gagcacggag gaaggtacct ctgagtcggc cactcctgag  1260
tccggtccgg gcacgagcac cgagccgagc gagggttcag ccccgggtac cagcacggag  1320
ccgtccgagg gtagcgcacc gggttctccg gcgggctccc ctacgtctac ggaagagggt  1380
acgtccactg aacctagcga gggcagcgcg ccaggcacca gcactgaacc gagcgaaggc  1440
agcgcacctg gcactagcga gtctgcgact ccggagagcg gtccgggtac gagcacggaa  1500
ccaagcgaag gcagcgcccc aggtacctct gaatctgcta ccccagaatc tggcccgggt  1560
tccgagccag ctacctctgg ttctgaaacc ccaggtactt ccactgaacc aagcgaaggt  1620
agcgctcctg gcacttctac tgaaccatcc gaaggttccg ctcctggtac gtctgaaagc  1680
gctacccctg aaagcggccc aggcacctct gaaagcgcta ctcctgagag cggtccaggc  1740
tctccagcag gttctccaac ctccactgaa gaaggcacct ctgagtctgc taccccctgaa  1800
tctggtcctg gctccgaacc tgctacctct ggttccgaaa ctccaggtac ctcggaatct  1860
gcgactccgg aatctggccc gggcacgagc acggagccgt ctgagggtag cgcaccaggt  1920
accagcactg agccttctga gggctctgca ccgggtacct ccacggaacc ttcggaaggt  1980
tctgcgccgg gtacctccac tgagccatcc gagggttcag caccaggtac tagcacggaa  2040
ccgtccgagg gctctgcacc aggtacgagc accgaaccgt cggagggtag cgctccaggt  2100
agcccagcgg gctctccgac aagcaccgaa gaaggcacca gcaccgagcc gtccgaaggt  2160
tccgcaccag gtacaagcga gagcgcgact cctgaatctg gtccgggtag cgagcctgca  2220
accagcggtt ctgagacgcc gggcacttcc gaatctgcga ccccggagtc cggtccaggt  2280
tcagagccgg cgacgagcgg ttcggaaacg ccgggtacgt ctgaatcagc cacgccggag  2340
tctggtccgg gtacctcgac cgaaccaagc gaaggttcgg caccgggtac tagcgagagc  2400
gcaaccccctg aaagcggtcc gggcagcccg gcaggttctc caaccagcac cgaagaaggt  2460
tcccctgctg gtagcccgac ctctacggag gaaggtagcc ctgcaggttc cccaacttct  2520
actgaggaag gtacttctga gtccgctacc ccagaaagcg gtcctggtac ctccactgaa  2580
ccgtctgaag gctctgcacc aggcacttct gagtctgcta ctccagaaag cggcccaggt  2640
tctgaaccag caacttctgg ctctgagact ccaggcactt ctgagtccgc aacgcctgaa  2700
tccggtcctg gttctgaacc agctacttcc ggcagcgaaa ccccaggtac ctctgagtct  2760
gcgactccag agtctggtcc tggtacttcc actgagccta gcgagggttc cgcaccaggt  2820
tctccggctg gtagcccgac cagcacggag gagggtacgt ctgaatctgc aacgccggaa  2880
tcgggcccag gttcggagcc tgcaacgtct ggcagcgaaa ccccgggtac ctccgaatct  2940
gctacaccgg aaagcggtcc tggcagccct gctggttctc caacctctac cgaggagggt  3000
tcaccggcag gtagcccgac tagcactgaa gaaggtacta gcacggagcc gagcgagggt  3060
agtgctccgg gtacgagcga gagcgcaacg ccagagagcg gtccaggcac cagcgaatcg  3120
gccacccctg agagcggccc aggtacttct gagagcgcca ctcctgaatc cggccctggt  3180
```

```
agcgagccgg caacctccgg ctcagaaact cctggttcgg aaccagcgac cagcggttct  3240
gaaactccgg gtagcccggc aggcagccca acgagcaccg aagagggtac cagcacggaa  3300
ccgagcgagg gttctgcccc gggtacttcc accgaaccat cggagggctc tgcacctggt  3360
agcgaacctg cgacgtctgg ttctgaaacg ccgggtacca gcgaaagcgc taccccagaa  3420
tccggtccgg gcactagcac cgagccatcg gagggctccg caccaggtca ccatcatcac  3480
catcac                                                             3486
```

```
SEQ ID NO: 454         moltype = DNA  length = 3468
FEATURE                Location/Qualifiers
misc_feature           1..3468
                       note = Description of Artificial Sequence: Synthetic
                        polynucleotide
source                 1..3468
                       mol_type = other DNA
                       organism = synthetic construct
SEQUENCE: 454
catcaccacc atcatcacgg aggtagccca gctggtagcc caacctctac cgaagaaggt  60
acctctgaat ccgctactcc agaatccggt cctggtacta gcactgagcc aagcgaaggt  120
tctgctccag gctccccggc aggtagccct acctctaccg aagagggcac tagcaccgaa  180
ccatctgagg gttccgctcc tggcacctcc actgaaccgt ccgaaggcag tgctccgggt  240
acttccgaaa gcgcaactcc ggaatccggc cctggttctg agcctgctac ttccggctct  300
gaaactccag gtagcgagcc agcgacttct ggttctgaaa ctccaggttc accggcgggt  360
agcccgacga gcacggagga aggtacctct gagtcggcca ctcctgagtc cggtccgggc  420
acgagcaccg agccgagcga gggttcagcc ccgggtacca gcacggagcc gtccgagggt  480
agcgcaccgg gttctccggc gggctcccct acgtctacgg aagagggtac gtccactgaa  540
cctagcgagg gcagcgcgcc aggcaccagc actgaaccga gcgaaggcag cgcacctggc  600
actagcgagt ctgcgactcc ggagagcggt ccgggtacga gcacggaacc aagcgaaggc  660
agcgccccag gtacctctga atctgctacc ccagaatctg gcccgggttc cgagccagct  720
acctctggtt ctgaaacccc aggtacttcc actgaaccaa gcgaaggtag cgctcctggc  780
acttctactg aaccatccga aggttccgct cctggtacgt ctgaaagcgc tacccctgaa  840
agcggcccag gcacctctga aagcgctact cctgagagcg gtccaggctc tccagcaggt  900
tctccaacct ccactgaaga aggcacctct gagtctgcta cccctgaatc tggtcctggc  960
tccgaacctg ctacctctgg ttccgaaact ccaggtacct cggaatctgc gactccggaa  1020
tctggcccgg gcacgagcac ggagccgtct gagggtagcg caccaggtac cagcactgag  1080
ccttctgagg gctctgcacc gggtacctcc acggaacctt cggaaggttc tgcgccgggt  1140
acctccactg agccatccga gggttcagca ccaggtacta gcacggaacc gtccgagggc  1200
tctgcaccag gtacgagcac cgaaccgtcg gagggtagcg ctccaggtag cccagcgggc  1260
tctccgacaa gcaccgaaga aggcaccagc accgagccgt ccgaaggttc cgcaccaggt  1320
acaagcgaga gcgcgactcc tgaatctggt ccgggtagcg agcctgcaac cagcggttct  1380
gagacgccgg gcacttccga atctgcgacc ccggagtccg gtccaggttc agagccggcg  1440
acgagcggtt cggaaacgcc gggtacgtct gaatcagcca cgccggagtc tggtccgggt  1500
acctcgaccg aaccaagcga aggttcggca ccgggtacta gcgagagcgc aacccctgaa  1560
agcggtccgg gcagcccggc aggttctcca accagcaccg aagaaggttc ccctgctggt  1620
agcccgacct ctacggagga aggtagccct gcaggttccc caacttctac tgaggaaggt  1680
acttctgagt ccgctacccc agaaagcggt cctggtacct ccactgaacc gtctgaaggc  1740
tctgcaccag gcacttctga gtctgctact ccagaaagcg gcccaggttc tgaaccagca  1800
acttctggct ctgagactcc aggcacttct gagtccgcaa cgcctgaatc cggtcctggt  1860
tctgaaccag ctacttccgg cagcgaaacc ccaggtacct ctgagtctgc gactccagag  1920
tctggtcctg gtacttccac tgagcctagc gagggttccg caccaggttc tccggctggt  1980
agcccgacca gcacggagga gggtacgtct gaatctgcaa cgccggaatc gggcccaggt  2040
tcggagcctg caacgtctgg cagcgaaacc ccgggtacct ccgaatctgc tacaccggaa  2100
agcggtcctg gcagccctgc tggttctcca acctctaccg aggagggttc accggcaggt  2160
agcccgacta gcactgaaga aggtactagc acggagccga gcgagggtag tgctccgggt  2220
acgagcgaga gcgcaacgcc agagagcggt ccaggcacca gcgaatcggc caccccctgag  2280
agcggcccag gtacttctga gagcgccact cctgaatccg gccctggtag cgagccggca  2340
acctccggct cagaaactcc tggttcggaa ccagcgacca gcggttctga aactccgggt  2400
agcccggcag gcagcccaac gagcaccgaa gagggtacca gcacggaacc gagcgagggt  2460
tctgccccgg gtacttccac cgaaccatcg gagggctctg cacctggtag cgaacctgcg  2520
acgtctggtt ctgaaacgcc gggtaccagc gaaagcgcta ccccagaatc cggtccgggc  2580
actagcaccg agccatcgga gggctccgca ccactgtcag gtcgttctga taaccattcc  2640
ccactgggtc tggctgggtc tggcaccgcc gaagcagcta gcgcctctgg cgacatccaa  2700
atgacccaat caccgtcatc cctgagcgcc tctgttggag atcgtgtaac aattacctgc  2760
cgcgcctccc aagacatccg caattactta aactggtatc agcaaaaacc cggtaaggca  2820
ccgaaattgc tgatttatta tacttcacgc ttagagagtg gggtgccgtc gcgcttcagt  2880
ggctcgggta gtgggaccga ttacacattg acaatttcat cactgcagcc agaggatttt  2940
gcgacttatt actgtcaaca gggtaacacg cttccctgga ccttcgggca aggcacgaaa  3000
gttgagatca agggcgctac tccccctgag acaggagcgg aaacggaatc ccctggcgag  3060
acgacgggtg gttccgcaga gtcggaacct cctggtgagg gcgaggtgca gctggttgaa  3120
agcggtggcg gtctggtgca accaggcggt agcctgcgtc tgagctgcgc ggcgagcggt  3180
tacagcttta ccggttatac catgaactgg gttcgtcaag cgccaggtaa aggtctggag  3240
tgggtggcgc tgatcaaccc gtacaagggt gttagcacct ataaccagaa gttcaaagac  3300
cgttttacca ttagcgtgga taagagcaaa aacaccgcgt acctgcaaat gaacagcctg  3360
cgtgcggagg acaccgctgt gtactattgc gcgcgtagcg gttactatgg cgacagcgac  3420
tggtattttg atgtgtgggg ccaaggcacc ctggttaccg tgagctcc              3468
```

```
SEQ ID NO: 455         moltype = DNA  length = 3468
FEATURE                Location/Qualifiers
misc_feature           1..3468
                       note = Description of Artificial Sequence: Synthetic
```

```
                         polynucleotide
source                  1..3468
                        mol_type = other DNA
                        organism = synthetic construct
SEQUENCE: 455
catcaccacc atcatcacgg aggtagccca gctggtagcc caacctctac cgaagaaggt  60
acctctgaat ccgctactcc agaatccggt cctggtacta gcactgagcc aagcgaaggt  120
tctgctccag gctccccggc aggtagccct acctctaccg aagagggcac tagcaccgaa  180
ccatctgagg gttccgctcc tggcacctcc actgaaccgt ccgaaggcag tgctccgggt  240
acttccgaaa gcgcaactcc ggaatccggc cctggttctg agcctgctac ttccggctct  300
gaaactccag gtagcgagcc agcgacttct ggttctgaaa ctccaggttc accggcgggt  360
agcccgacga gcacggagga aggtacctct gagtcggcca ctcctgagtc cggtccgggc  420
acgagcaccg agccgagcga gggttcagcc ccgggtacca gcacggagcc gtccgagggt  480
agcgcaccgg gttctccggc gggctcccct acgtctacgg aagagggtac gtccactgaa  540
cctagcgagg gcagcgcgcc aggcaccagc actgaaccga gcgaaggcag cgcacctggc  600
actagcgagt ctgcgactcc ggagagcggt ccgggtacga gcacggaacc aagcgaaggc  660
agcgccccag gtacctctga atctgctacc ccagaatctg gcccgggttc cgagccagct  720
acctctggtt ctgaaacccc aggtacttcc actgaaccaa gcgaaggtag cgctcctggc  780
acttctactg aaccatccga aggttccgct cctggtacgt ctgaaagcgc tacccctgaa  840
agcggcccag gcacctctga aagcgctact cctgagagcg gtccaggctc tccagcaggt  900
tctccaacct ccactgaaga aggcacctct gagtctgcta cccctgaatc tggtcctggc  960
tccgaacctg ctacctctgg ttccgaaact ccaggtacct cggaatctgc gactccggaa  1020
tctggcccgg gcacgagcac ggagccgtct gagggtagcg caccaggtac cagcactgag  1080
ccttctgagg gctctgcacc gggtacctcc acggaacctt cggaaggttc tgcgccgggt  1140
acctccactg agccatccga gggttcagca ccaggtacta gcacggaacc gtccgagggc  1200
tctgcaccag gtacgagcac cgaaccgtcg gagggtagcg ctccaggtag cccagcgggc  1260
tctccgacaa gcaccgaaga aggcaccagc accgagccgt ccgaaggttc cgcaccaggt  1320
acaagcgaga gcgcgactcc tgaatctggt ccgggtagcg agcctgcaac cagcggttct  1380
gagacgccgg gcacttccga atctgcgacc ccggagtccg gtccaggttc agagccggcg  1440
acgagcggtt cggaaacgcc gggtacgtct gaatcagcca cgccggagtc tggtccgggt  1500
acctcgaccg aaccaagcga aggttcggca ccgggtacta gcgagagcgc aacccctgaa  1560
agcggtccgg gcagcccggc aggttctcca accagcaccg aagaaggttc ccctgctggt  1620
agcccgacct ctacggagga aggtagccct gcaggttccc caacttctac tgaggaaggt  1680
acttctgagt ccgctacccc agaaagcggt cctggtacct ccactgaacc gtctgaaggc  1740
tctgcaccag gcacttctga gtctgctact ccagaaagcg gcccaggttc tgaaccagca  1800
acttctggct ctgagactcc aggcacttct gagtccgcaa cgcctgaatc cggtcctggt  1860
tctgaaccag ctacttccgg cagcgaaacc ccaggtacct ctgagtctgc gactccagag  1920
tctggtcctg gtacttccac tgagcctagc gagggttccg caccaggttc tccggctggt  1980
agcccgacca gcacggagga gggtacgtct gaatctgcaa cgccggaatc gggcccaggt  2040
tcggagcctg caacgtctgg cagcgaaacc ccgggtacct ccgaatctgc tacaccggaa  2100
agcggtcctg gcagccctgc tggttctcca acctctaccg aggagggttc accggcaggt  2160
agcccgacta gcactgaaga aggtactagc acggagccga gcgagggtag tgctccgggt  2220
acgagcgaga gcgcaacgcc agagagcggt ccaggcacca gcgaatcggc cacccctgag  2280
agcggcccag gtacttctga gagcgccact cctgaatccg gccctggtag cgagccggca  2340
acctccggct cagaaactcc tggttcggaa ccagcgacca gcggttctga aactccgggt  2400
agcccggcag gcagcccaac gagcaccgaa gagggtacca gcacggaacc gagcgagggt  2460
tctgccccgg gtacttccac cgaaccatcg gagggctctg cacctggtag cgaacctgcg  2520
acgtctggtt ctgaaacgcc gggtaccagc gaaagcgcta ccccagaatc cggtccgggc  2580
actagcaccg agccatcgga gggctccgca ccactgtcag gtcgttctga taaccatgtt  2640
ccactgtctc tgaaaatggg tggcaccgcc gaagcagcta gcgcctctgg cgacatccaa  2700
atgacccaat caccgtcatc cctgagcgcc tctgttggag atcgtgtaac aattacctgc  2760
cgcgcctccc aagacatccg caattactta aactggtatc agcaaaaacc cggtaaggca  2820
ccgaaattgc tgatttatta tacttcacgc ttagagagtg ggtgccgtc gcgcttcagt  2880
ggctcgggta gtgggaccga ttacacattg acaatttcat cactgcagcc agaggatttt  2940
gcgacttatt actgtcaaca gggtaacacg cttccctgga ccttcgggca aggcacgaaa  3000
gttgagatca agggcgctac tccccctgag acaggagcgg aaacggaatc ccctggcgag  3060
acgacgggtg gttccgcaga gtcggaacct cctggtgagg gcgaggtgca gctggttgaa  3120
agcggtggcg gtctggtgca accaggcggt agcctgcgtc tgagctgcgc ggcgagcggt  3180
tacagcttta ccggttatac catgaactgg gttcgtcaag cgccaggtaa aggtctggag  3240
tgggtggcgc tgatcaaccc gtacaagggt gttagcacct ataaccagaa gttcaaagac  3300
cgttttacca ttagcgtgga taagagcaaa aacaccgcgt acctgcaaat gaacagcctg  3360
cgtgcggagg acaccgctgt gtactattgc gcgcgtagcg gttactatgg cgacagcgac  3420
tggtattttg atgtgtgggg ccaaggcacc ctggttaccg tgagctcc              3468

SEQ ID NO: 456          moltype = DNA  length = 3468
FEATURE                 Location/Qualifiers
misc_feature            1..3468
                        note = Description of Artificial Sequence: Synthetic
                         polynucleotide
source                  1..3468
                        mol_type = other DNA
                        organism = synthetic construct
SEQUENCE: 456
catcaccacc atcatcacgg aggtagccca gctggtagcc caacctctac cgaagaaggt  60
acctctgaat ccgctactcc agaatccggt cctggtacta gcactgagcc aagcgaaggt  120
tctgctccag gctccccggc aggtagccct acctctaccg aagagggcac tagcaccgaa  180
ccatctgagg gttccgctcc tggcacctcc actgaaccgt ccgaaggcag tgctccgggt  240
acttccgaaa gcgcaactcc ggaatccggc cctggttctg agcctgctac ttccggctct  300
gaaactccag gtagcgagcc agcgacttct ggttctgaaa ctccaggttc accggcgggt  360
```

```
agcccgacga gcacggagga aggtacctct gagtcggcca ctcctgagtc cggtccgggc  420
acgagcaccg agccgagcga gggttcagcc ccgggtacca gcacggagcc gtccgagggt  480
agcgcaccgg gttctccggc gggctcccct acgtctacgg aagagggtac gtccactgaa  540
cctagcgagg gcagcgcgcc aggcaccagc actgaaccga gcgaaggcag cgcacctggc  600
actagcgagt ctgcgactcc ggagagcggt ccgggtacga gcacggaacc aagcgaaggc  660
agcgccccag gtacctctga atctgctacc ccagaatctg gcccgggttc cgagccagct  720
acctctggtt ctgaaacccc aggtacttcc actgaaccaa gcgaaggtag cgctcctggc  780
acttctactg aaccatccga aggttccgct cctggtacgt ctgaaagcgc tacccctgaa  840
agcggcccag gcacctctga aagcgctact cctgagagcg gtccaggctc tccagcaggt  900
tctccaacct ccactgaaga aggcacctct gagtctgcta cccctgaatc tggtcctggc  960
tccgaacctg ctacctctgg ttccgaaact ccaggtacct cggaatctgc gactccggaa  1020
tctggcccgg gcacgagcac ggagccgtct gagggtagcg caccaggtac cagcactgag  1080
ccttctgagg gctctgcacc gggtacctcc acggaacctt cggaaggttc tgcgccgggt  1140
acctccactg agccatccga gggttcagca ccaggtacta gcacggaacc gtccgagggc  1200
tctgcaccag gtacgagcac cgaaccgtcg gagggtagcg ctccaggtag cccagcgggc  1260
tctccgacaa gcaccgaaga aggcaccagc accgagccgt ccgaaggttc cgcaccaggt  1320
acaagcgaga gcgcgactcc tgaatctggt ccgggtagcg agcctgcaac cagcggttct  1380
gagacgccgg gcacttccga atctgcgacc ccggagtccg gtccaggttc agagccggcg  1440
acgagcggtt cggaaacgcc gggtacgtct gaatcagcca cgccggagtc tggtccgggt  1500
acctcgaccg aaccaagcga aggttcggca ccgggtacta gcgagagcgc aacccctgaa  1560
agcggtccgg gcagcccggc aggttctcca accagcaccg aagaaggttc ccctgctggt  1620
agcccgacct ctacggagga aggtagccct gcaggttccc caacttctac tgaggaaggt  1680
acttctgagt ccgctacccc agaaagcggt cctggtacct ccactgaacc gtctgaaggc  1740
tctgcaccag gcacttctga gtctgctact ccagaaagcg gcccaggttc tgaaccagca  1800
acttctggct ctgagactcc aggcacttct gagtccgcaa cgcctgaatc cggtcctggt  1860
tctgaaccag ctacttccgg cagcgaaacc ccaggtacct ctgagtctgc gactccagag  1920
tctggtcctg gtacttccac tgagcctagc gagggttccg caccaggttc tccggctggt  1980
agcccgacca gcacggagga gggtacgtct gaatctgcaa cgccggaatc gggcccaggt  2040
tcggagcctg caacgtctgg cagcgaaacc ccgggtacct ccgaatctgc tacaccggaa  2100
agcggtcctg gcagccctgc tggttctcca acctctaccg aggagggttc accggcaggt  2160
agcccgacta gcactgaaga aggtactagc acggagccga gcgagggtag tgctccgggt  2220
acgagcgaga gcgcaacgcc agagagcggt ccaggcacca gcgaatcggc cacccctgag  2280
agcggcccag gtacttctga gagcgccact cctgaatccg gccctggtag cgagccggca  2340
acctccggct cagaaactcc tggttcggaa ccagcgacca gcggttctga aactccgggt  2400
agcccggcag gcagcccaac gagcaccgaa gagggtacca gcacggaacc gagcgagggt  2460
tctgccccgg gtacttccac cgaaccatcg gagggctctg cacctggtag cgaacctgcg  2520
acgtctggtt ctgaaacgcc gggtaccagc gaaagcgcta ccccagaatc cggtccgggc  2580
actagcaccg agccatcgga gggctccgca ccactgtcag gtcgttctga taaccattcc  2640
ccactgggtc tggctgggtc tggcaccgcc gaagcagcta gcgcctctgg cgaggtgcag  2700
ctggttgaaa gcggtggcgg tctggtgcaa ccaggcggta gcctgcgtct gagctgcgcg  2760
gcgagcggtt acagctttac cggttatacc atgaactggg ttcgtcaagc gccaggtaaa  2820
ggtctggagt gggtggcgct gatcaacccg tacaagggtg ttagcaccta taaccagaag  2880
ttcaaagacc gttttaccat tagcgtggat aagagcaaaa acaccgcgta cctgcaaatg  2940
aacagcctgc gtgcggagga caccgctgtg tactattgcg cgcgtagcgg ttactatggc  3000
gacagcgact ggtattttga tgtgtggggc caaggcaccc tggttaccgt gagctccggc  3060
gctactcccc ctgagacagg agcggaaacg gaatcccctg gcgagacgac gggtggttcc  3120
gcagagtcgg aacctcctgg tgagggcgac atccaaatga cccaatcacc gtcatccctg  3180
agcgcctctg ttggagatcg tgtaacaatt acctgccgcg cctcccaaga catccgcaat  3240
tacttaaact ggtatcagca aaaacccggt aaggcaccga aattgctgat ttattatact  3300
tcacgcttag agagtggggt gccgtcgcgc ttcagtggct cgggtagtgg gaccgattac  3360
acattgacaa tttcatcact gcagccagag gattttgcga cttattactg tcaacagggt  3420
aacacgcttc cctggacctt cggcaaggc acgaaagttg agatcaag             3468
```

```
SEQ ID NO: 457         moltype = DNA  length = 3468
FEATURE                Location/Qualifiers
misc_feature           1..3468
                       note = Description of Artificial Sequence: Synthetic
                        polynucleotide
source                 1..3468
                       mol_type = other DNA
                       organism = synthetic construct
SEQUENCE: 457
catcaccacc atcatcacgg aggtagccca gctggtagcc caacctctac cgaagaaggt  60
acctctgaat ccgctactcc agaatccggt cctggtacta gcactgagcc aagcgaaggt  120
tctgctccag gctccccggc aggtagccct acctctaccg aagagggcac tagcaccgaa  180
ccatctgagg gttccgctcc tggcacctcc actgaaccgt ccgaaggcag tgctccgggt  240
acttccgaaa gcgcaactcc ggaatccggc cctggttctg agcctgctac ttccggctct  300
gaaactccag gtagcgagcc agcgacttct ggttctgaaa ctccaggttc accggcgggt  360
agcccgacga gcacggagga aggtacctct gagtcggcca ctcctgagtc cggtccgggc  420
acgagcaccg agccgagcga gggttcagcc ccgggtacca gcacggagcc gtccgagggt  480
agcgcaccgg gttctccggc gggctcccct acgtctacgg aagagggtac gtccactgaa  540
cctagcgagg gcagcgcgcc aggcaccagc actgaaccga gcgaaggcag cgcacctggc  600
actagcgagt ctgcgactcc ggagagcggt ccgggtacga gcacggaacc aagcgaaggc  660
agcgccccag gtacctctga atctgctacc ccagaatctg gcccgggttc cgagccagct  720
acctctggtt ctgaaacccc aggtacttcc actgaaccaa gcgaaggtag cgctcctggc  780
acttctactg aaccatccga aggttccgct cctggtacgt ctgaaagcgc tacccctgaa  840
agcggcccag gcacctctga aagcgctact cctgagagcg gtccaggctc tccagcaggt  900
tctccaacct ccactgaaga aggcacctct gagtctgcta cccctgaatc tggtcctggc  960
tccgaacctg ctacctctgg ttccgaaact ccaggtacct cggaatctgc gactccggaa  1020
```

```
tctggcccgg gcacgagcac ggagccgtct gagggtagcg caccaggtac cagcactgag  1080
ccttctgagg gctctgcacc gggtacctcc acggaacctt cggaaggttc tgcgccgggt  1140
acctccactg agccatccga gggttcagca ccaggtacta gcacggaacc gtccgagggc  1200
tctgcaccag gtacgagcac cgaaccgtcg gagggtagcg ctccaggtag cccagcgggc  1260
tctccgacaa gcaccgaaga aggcaccagc accgagccgt ccgaaggttc cgcaccaggt  1320
acaagcgaga gcgcgactcc tgaatctggt ccgggtagcg agcctgcaac cagcggttct  1380
gagacgccgg gcacttccga atctgcgacc ccggagtccg gtccaggttc agagccggcg  1440
acgagcggtt cggaaacgcc gggtacgtct gaatcagcca cgccggagtc tggtccgggt  1500
acctcgaccg aaccaagcga aggttcggca ccgggtacta gcgagagcgc aacccctgaa  1560
agcggtccgg gcagcccggc aggttctcca accagcaccg aagaaggttc ccctgctggt  1620
agcccgacct ctacggagga aggtagccct gcaggttccc caacttctac tgaggaaggt  1680
acttctgagt ccgctacccc agaaagcggt cctggtacct ccactgaacc gtctgaaggc  1740
tctgcaccag gcacttctga gtctgctact ccagaaagcg gcccaggttc tgaaccagca  1800
acttctggct ctgagactcc aggcacttct gagtccgcaa cgcctgaatc cggtcctggt  1860
tctgaaccag ctacttccgg cagcgaaacc ccaggtacct ctgagtctgc gactccagag  1920
tctggtcctg gtacttccac tgagcctagc gagggttccg caccaggttc tccggctggt  1980
agcccgacca gcacggagga gggtacgtct gaatctgcaa cgccggaatc gggcccaggt  2040
tcggagcctg caacgtctgg cagcgaaacc ccgggtacct ccgaatctgc tacaccggaa  2100
agcggtcctg gcagccctgc tggttctcca acctctaccg aggagggttc accggcaggt  2160
agcccgacta gcactgaaga aggtactagc acggagccga gcgagggtag tgctccgggt  2220
acgagcgaga gcgcaacgcc agagagcggt ccaggcacca gcgaatcggc cacccctgag  2280
agcggcccag gtacttctga gagcgccact cctgaatccg gccctggtag cgagccggca  2340
acctccggct cagaaactcc tggttcggaa ccagcgacca gcggttctga aactccgggt  2400
agcccggcag gcagcccaac gagcaccgaa gagggtacca gcacggaacc gagcgagggt  2460
tctgccccgg gtacttccac cgaaccatcg gagggctctg cacctggtag cgaacctgcg  2520
acgtctggtt ctgaaacgcc gggtaccagc gaaagcgcta ccccagaatc cggtccgggc  2580
actagcaccg agccatcgga gggctccgca ccactgtcag gtcgttctga taaccatgtt  2640
ccactgtctc tgaaaatggg tggcaccgcc gaagcagcta gcgcctctgg cgaggtgcag  2700
ctggttgaaa gcggtggcgg tctggtgcaa ccaggcggta gcctgcgtct gagctgcgcg  2760
gcgagcggtt acagctttac cggttatacc atgaactggg ttcgtcaagc gccaggtaaa  2820
ggtctggagt gggtggcgct gatcaacccg tacaagggtg ttagcaccta taaccagaag  2880
ttcaaagacc gttttaccat tagcgtggat aagagcaaaa acaccgcgta cctgcaaatg  2940
aacagcctgc gtgcggagga caccgctgtg tactattgcg cgcgtagcgg ttactatggc  3000
gacagcgact ggtattttga tgtgtggggc caaggcaccc tggttaccgt gagctccggc  3060
gctactcccc ctgagacagg agcggaaacg gaatcccctg gcgagacgac gggtggttcc  3120
gcagagtcgg aacctcctgg tgagggcgac atccaaatga cccaatcacc gtcatccctg  3180
agcgcctctg ttggagatcg tgtaacaatt acctgccgcg cctcccaaga catccgcaat  3240
tacttaaact ggtatcagca aaaacccggt aaggcaccga aattgctgat ttattatact  3300
tcacgcttag agagtggggt gccgtcgcgc ttcagtggct cgggtagtgg gaccgattac  3360
acattgacaa tttcatcact gcagccagag gattttgcga cttattactg tcaacagggt  3420
aacacgcttc cctggacctt cgggcaaggc acgaaagttg agatcaag              3468
```

```
SEQ ID NO: 458          moltype = DNA  length = 3483
FEATURE                 Location/Qualifiers
misc_feature            1..3483
                        note = Description of Artificial Sequence: Synthetic
                         polynucleotide
source                  1..3483
                        mol_type = other DNA
                        organism = synthetic construct
SEQUENCE: 458
catcaccacc atcatcacgg aggtagccca gctggtagcc caacctctac cgaagaaggt  60
acctctgaat ccgctactcc agaatccggt cctggtacta gcactgagcc aagcgaaggt  120
tctgctccag gctccccggc aggtagccct acctctaccg aagagggcac tagcaccgaa  180
ccatctgagg gttccgctcc tggcacctcc actgaaccgt ccgaaggcag tgctccgggt  240
acttccgaaa gcgcaactcc ggaatccggc cctggttctg agcctgctac ttccggctct  300
gaaactccag gtagcgagcc agcgacttct ggttctgaaa ctccaggttc accggcgggt  360
agcccgacga gcacggagga aggtacctct gagtcggcca ctcctgagtc cggtccgggc  420
acgagcaccg agccgagcga gggttcagcc ccgggtacca gcacggagcc gtccgagggt  480
agcgcaccgg gttctccggc gggctcccct acgtctacgg aagagggtac gtccactgaa  540
cctagcgagg gcagcgcgcc aggcaccagc actgaaccga gcgaaggcag cgcacctggc  600
actagcgagt ctgcgactcc ggagagcggt ccgggtacga gcacggaacc aagcgaaggc  660
agcgccccag gtacctctga atctgctacc ccagaatctg gcccgggttc cgagccagct  720
acctctggtt ctgaaacccc aggtacttcc actgaaccaa gcgaaggtag cgctcctggc  780
acttctactg aaccatccga aggttccgct cctggtacgt ctgaaagcgc tacccctgaa  840
agcggcccag gcacctctga aagcgctact cctgagagcg gtccaggctc tccagcaggt  900
tctccaacct ccactgaaga aggcacctct gagtctgcta cccctgaatc tggtcctggc  960
tccgaacctg ctacctctgg ttccgaaact ccaggtacct cggaatctgc gactccggaa  1020
tctggcccgg gcacgagcac ggagccgtct gagggtagcg caccaggtac cagcactgag  1080
ccttctgagg gctctgcacc gggtacctcc acggaacctt cggaaggttc tgcgccgggt  1140
acctccactg agccatccga gggttcagca ccaggtacta gcacggaacc gtccgagggc  1200
tctgcaccag gtacgagcac cgaaccgtcg gagggtagcg ctccaggtag cccagcgggc  1260
tctccgacaa gcaccgaaga aggcaccagc accgagccgt ccgaaggttc cgcaccaggt  1320
acaagcgaga gcgcgactcc tgaatctggt ccgggtagcg agcctgcaac cagcggttct  1380
gagacgccgg gcacttccga atctgcgacc ccggagtccg gtccaggttc agagccggcg  1440
acgagcggtt cggaaacgcc gggtacgtct gaatcagcca cgccggagtc tggtccgggt  1500
acctcgaccg aaccaagcga aggttcggca ccgggtacta gcgagagcgc aacccctgaa  1560
agcggtccgg gcagcccggc aggttctcca accagcaccg aagaaggttc ccctgctggt  1620
agcccgacct ctacggagga aggtagccct gcaggttccc caacttctac tgaggaaggt  1680
```

```
acttctgagt ccgctacccc agaaagcggt cctggtacct ccactgaacc gtctgaaggc  1740
tctgcaccag gcacttctga gtctgctact ccagaaagcg gcccaggttc tgaaccagca  1800
acttctggct ctgagactcc aggcacttct gagtccgcaa cgcctgaatc cggtcctggt  1860
tctgaaccag ctacttccgg cagcgaaacc ccaggtacct ctgagtctgc gactccagag  1920
tctggtcctg gtacttccac tgagcctagc gagggttccg caccaggttc tccggctggt  1980
agcccgacca gcacggagga gggtacgtct gaatctgcaa cgccggaatc gggcccaggt  2040
tcggagcctg caacgtctgg cagcgaaacc ccgggtacct ccgaatctgc tacaccggaa  2100
agcggtcctg gcagccctgc tggttctcca acctctaccg aggagggttc accggcaggt  2160
agcccgacta gcactgaaga aggtactagc acggagccga gcgagggtag tgctccgggt  2220
acgagcgaga gcgcaacgcc agagagcggt ccaggcacca gcgaatcggc cacccctgag  2280
agcggcccag gtacttctga gagcgccact cctgaatccg gccctggtag cgagccggca  2340
acctccggct cagaaactcc tggttcggaa ccagcgacca gcggttctga aactccgggt  2400
agcccggcag gcagcccaac gagcaccgaa gagggtacca gcacggaacc gagcgagggt  2460
tctgccccgg gtacttccac cgaaccatcg gagggctctg cacctggtag cgaacctgcg  2520
acgtctggtt ctgaaacgcc gggtaccagc gaaagcgcta ccccagaatc cggtccgggc  2580
actagcaccg agccatcgga gggctccgca ccactgtcag gtcgttctga taaccattcc  2640
ccactgggtc tggctgggtc tggcaccgcc gaagcagcta gcgcctctgg cgaactggtc  2700
gtcacgcagg agccgtccct taccgtttca ccaggtggaa cagtgactct gacgtgtcgc  2760
tcctccactg gggcggttac aacttccaat tatgctaatt gggtccagca gaagccgggc  2820
caagcccctc gcgggttgat tggcggcacc aacaaacgtg ctccagggac acctgcccgt  2880
ttttcgggct ccttattggg gggcaaagct gcactgacgt tgtctggagt tcagccggag  2940
gatgaggcag agtattactg cgcattgtgg tattctaatt tatgggtttt tggaggcggc  3000
acaaagctga ccgtcctggg tgcgaccccg ccggaaaccg gtgcggaaac cgaaagcccg  3060
ggtgaaacca ccggtggcag cgcggagagc gaaccgccgg gtgaaggtga ggttcagttg  3120
ttggaaagcg gggggcggct tgtccaacct ggaggttcat taaaattgag ctgtgcagcc  3180
tccggattca cctttaacac gtatgcaatg aactgggtcc gtcaagcgcc cggtaagggg  3240
ctggagtggg tagctcgcat ccgctcgaag tataataatt acgcaaccta ctacgcagac  3300
agtgtcaaag atcgcttcac tatctcacgc gacgacagta agaacacggc ctacttacag  3360
atgaacaatc ttaaaacgga ggacaccgct gtctactact gcgtgcgcca cgggaatttc  3420
ggtaactctt atgtaagttg gttcgcatat tggggacaag gtacgttggt aaccgtatcc  3480
agc                                                                3483

SEQ ID NO: 459         moltype = DNA  length = 3483
FEATURE                Location/Qualifiers
misc_feature           1..3483
                       note = Description of Artificial Sequence: Synthetic
                        polynucleotide
source                 1..3483
                       mol_type = other DNA
                       organism = synthetic construct
SEQUENCE: 459
catcaccacc atcatcacgg aggtagccca gctggtagcc caacctctac cgaagaaggt  60
acctctgaat ccgctactcc agaatccggt cctggtacta gcactgagcc aagcgaaggt  120
tctgctccag gctccccggc aggtagccct acctctaccg aagagggcac tagcaccgaa  180
ccatctgagg gttccgctcc tggcacctcc actgaaccgt ccgaaggcag tgctccgggt  240
acttccgaaa gcgcaactcc ggaatccggc cctggttctg agcctgctac ttccggctct  300
gaaactccag gtagcgagcc agcgacttct ggttctgaaa ctccaggttc accggcgggt  360
agcccgacga gcacggagga aggtacctct gagtcggcca ctcctgagtc cggtccgggc  420
acgagcaccg agccgagcga gggttcagcc ccgggtacca gcacggagcc gtccgagggt  480
agcgcaccgg gttctccggc gggctcccct acgtctacgg aagagggtac gtccactgaa  540
cctagcgagg gcagcgcgcc aggcaccagc actgaaccga gcgaaggcag cgcacctggc  600
actagcgagt ctgcgactcc ggagagcggt ccgggtacga gcacggaacc aagcgaaggc  660
agcgccccag gtacctctga atctgctacc ccagaatctg gcccgggttc cgagccagct  720
acctctggtt ctgaaacccc aggtacttcc actgaaccaa gcgaaggtag cgctcctggc  780
acttctactg aaccatccga aggttccgct cctggtacgt ctgaaagcgc tacccctgaa  840
agcggcccag gcacctctga aagcgctact cctgagagcg gtccaggctc tccagcaggt  900
tctccaacct ccactgaaga aggcacctct gagtctgcta cccctgaatc tggtcctggc  960
tccgaacctg ctacctctgg ttccgaaact ccaggtacct cggaatctgc gactccggaa  1020
tctggcccgg gcacgagcac ggagccgtct gagggtagcg caccaggtac cagcactgag  1080
ccttctgagg gctctgcacc gggtacctcc acggaacctt cggaaggttc tgcgccgggt  1140
acctccactg agccatccga gggttcagca ccaggtacta gcacggaacc gtccgagggc  1200
tctgcaccag gtacgagcac cgaaccgtcg gagggtagcg ctccaggtag cccagcgggc  1260
tctccgacaa gcaccgaaga aggcaccagc accgagccgt ccgaaggttc cgcaccaggt  1320
acaagcgaga gcgcgactcc tgaatctggt ccgggtagcg agcctgcaac cagcggttct  1380
gagacgccgg gcacttccga atctgcgacc ccggagtccg gtccaggttc agagccggcg  1440
acgagcggtt cggaaacgcc gggtacgtct gaatcagcca cgccggagtc tggtccgggt  1500
acctcgaccg aaccaagcga aggttcggca ccgggtacta gcgagagcgc aacccctgaa  1560
agcggtccgg gcagcccggc aggttctcca accagcaccg aagaaggttc ccctgctggt  1620
agcccgacct ctacggagga aggtagccct gcaggttccc caacttctac tgaggaaggt  1680
acttctgagt ccgctacccc agaaagcggt cctggtacct ccactgaacc gtctgaaggc  1740
tctgcaccag gcacttctga gtctgctact ccagaaagcg gcccaggttc tgaaccagca  1800
acttctggct ctgagactcc aggcacttct gagtccgcaa cgcctgaatc cggtcctggt  1860
tctgaaccag ctacttccgg cagcgaaacc ccaggtacct ctgagtctgc gactccagag  1920
tctggtcctg gtacttccac tgagcctagc gagggttccg caccaggttc tccggctggt  1980
agcccgacca gcacggagga gggtacgtct gaatctgcaa cgccggaatc gggcccaggt  2040
tcggagcctg caacgtctgg cagcgaaacc ccgggtacct ccgaatctgc tacaccggaa  2100
agcggtcctg gcagccctgc tggttctcca acctctaccg aggagggttc accggcaggt  2160
agcccgacta gcactgaaga aggtactagc acggagccga gcgagggtag tgctccgggt  2220
acgagcgaga gcgcaacgcc agagagcggt ccaggcacca gcgaatcggc cacccctgag  2280
```

```
agcggcccag gtacttctga gagcgccact cctgaatccg gccctggtag cgagccggca  2340
acctccggct cagaaactcc tggttcggaa ccagcgacca gcggttctga aactccgggt  2400
agcccggcag gcagcccaac gagcaccgaa gagggtacca gcacggaacc gagcgagggt  2460
tctgccccgg gtacttccac cgaaccatcg gagggctctg cacctggtag cgaacctgcg  2520
acgtctggtt ctgaaacgcc gggtaccagc gaaagcgcta ccccagaatc cggtccgggc  2580
actagcaccg agccatcgga gggctccgca ccactgtcag gtcgttctga taaccatgtt  2640
ccactgtctc tgaaaatggg tggcaccgcc gaagcagcta gcgcctctgg cgaactggtc  2700
gtcacgcagg agccgtccct taccgtttca ccaggtggaa cagtgactct gacgtgtcgc  2760
tcctccactg gggcggttac aacttccaat tatgctaatt gggtccagca gaagccgggc  2820
caagccccctc gcgggttgat tggcggcacc aacaaacgtg ctccagggac acctgcccgt  2880
ttttcgggct ccttattggg gggcaaagct gcactgacgt tgtctggagt tcagccggag  2940
gatgaggcag agtattactg cgcattgtgg tattctaatt tatgggtttt tggaggcggc  3000
acaaagctga ccgtcctggg tgcgaccccg ccggaaaccg gtgcggaaac cgaaagcccg  3060
ggtgaaacca ccggtggcag cgcggagagc gaaccgccgg gtgaaggtga ggttcagttg  3120
ttggaaagcg gggggcgggct tgtccaacct ggaggttcat taaaattgag ctgtgcagcc  3180
tccggattca cctttaacac gtatgcaatg aactgggtcc gtcaagcgcc cggtaagggg  3240
ctggagtggg tagctcgcat ccgctcgaag tataataatt acgcaaccta ctacgcagac  3300
agtgtcaaag atcgcttcac tatctcacgc gacgacagta agaacacggc ctacttacag  3360
atgaacaatc ttaaaacgga ggacaccgct gtctactact gcgtgcgcca cgggaatttc  3420
ggtaactctt atgtaagttg gttcgcatat tggggacaag gtacgttggt aaccgtatcc  3480
agc                                                                3483
```

```
SEQ ID NO: 460         moltype = DNA  length = 3483
FEATURE                Location/Qualifiers
misc_feature           1..3483
                       note = Description of Artificial Sequence: Synthetic
                        polynucleotide
source                 1..3483
                       mol_type = other DNA
                       organism = synthetic construct
SEQUENCE: 460
catcaccacc atcatcacgg aggtagccca gctggtagcc caacctctac cgaagaaggt  60
acctctgaat ccgctactcc agaatccggt cctggtacta gcactgagcc aagcgaaggt  120
tctgctccag gctccccggc aggtagccct acctctaccg aagagggcac tagcaccgaa  180
ccatctgagg gttccgctcc tggcacctcc actgaaccgt ccgaaggcag tgctccgggt  240
acttccgaaa gcgcaactcc ggaatccggc cctggttctg agcctgctac ttccggctct  300
gaaactccag gtagcgagcc agcgacttct ggttctgaaa ctccaggttc accggcgggt  360
agcccgacga gcacggagga aggtacctct gagtcggcca ctcctgagtc cggtccgggc  420
acgagcaccg agccgagcga gggttcagcc ccgggtacca gcacggagcc gtccgagggt  480
agcgcaccgg gttctccggc gggctcccct acgtctacgg aagagggtac gtccactgaa  540
cctagcgagg gcagcgcgcc aggcaccagc actgaaccga gcgaaggcag cgcacctggc  600
actagcgagt ctgcgactcc ggagagcggt ccgggtacga gcacggaacc aagcgaaggc  660
agcgccccag gtacctctga atctgctacc ccagaatctg gcccgggttc cgagccagct  720
acctctggtt ctgaaacccc aggtacttcc actgaaccaa gcgaaggtag cgctcctggc  780
acttctactg aaccatccga aggttccgct cctggtacgt ctgaaagcgc taccccctgaa  840
agcggcccag gcacctctga aagcgctact cctgagagcg gtccaggctc tccagcaggt  900
tctccaacct ccactgaaga aggcacctct gagtctgcta cccctgaatc tggtcctggc  960
tccgaacctg ctacctctgg ttccgaaact ccaggtacct cggaatctgc gactccggaa  1020
tctggcccgg gcacgagcac ggagccgtct gagggtagcg caccaggtac cagcactgag  1080
ccttctgagg gctctgcacc gggtacctcc acggaacctt cggaaggttc tgcgccgggt  1140
acctccactg agccatccga gggttcagca ccaggtacta gcacggaacc gtccgagggc  1200
tctgcaccag gtacgagcac cgaaccgtcg gagggtagcg ctccaggtag cccagcgggc  1260
tctccgacaa gcaccgaaga aggcaccagc accgagccgt ccgaaggttc cgcaccaggt  1320
acaagcgaga gcgcgactcc tgaatctggt ccgggtagcg agcctgcaac cagcggttct  1380
gagacgccgg gcacttccga atctgcgacc ccggagtccg gtccaggttc agagccggcg  1440
acgagcggtt cggaaacgcc gggtacgtct gaatcagcca cgccggagtc tggtccgggt  1500
acctcgaccg aaccaagcga aggttcggca ccgggtacta gcgagagcgc aaccccctgaa  1560
agcggtccgg gcagcccggc aggttctcca accagcaccg aagaaggttc ccctgctggt  1620
agcccgacct ctacggagga aggtagccct gcaggttccc caacttctac tgaggaaggt  1680
acttctgagt ccgctacccc agaaagcggt cctggtacct ccactgaacc gtctgaaggc  1740
tctgcaccag gcacttctga gtctgctact ccagaaagcg gcccaggttc tgaaccagca  1800
acttctggct ctgagactcc aggcacttct gagtccgcaa cgcctgaatc cggtcctggt  1860
tctgaaccag ctacttccgg cagcgaaacc ccaggtacct ctgagtctgc gactccagag  1920
tctggtcctg gtacttccac tgagcctagc gagggttccg caccaggttc tccggctggt  1980
agcccgacca gcacggagga gggtacgtct gaatctgcaa cgccggaatc gggcccaggt  2040
tcggagcctg caacgtctgg cagcgaaacc ccgggtacct ccgaatctgc tacaccggaa  2100
agcggtcctg gcagccctgc tggttctcca acctctaccg aggagggttc accggcaggt  2160
agcccgacta gcactgaaga aggtactagc acggagccga gcgagggtag tgctccgggt  2220
acgagcgaga gcgcaacgcc agagagcggt ccaggcacca gcgaatcggc cacccctgag  2280
agcggcccag gtacttctga gagcgccact cctgaatccg gccctggtag cgagccggca  2340
acctccggct cagaaactcc tggttcggaa ccagcgacca gcggttctga aactccgggt  2400
agcccggcag gcagcccaac gagcaccgaa gagggtacca gcacggaacc gagcgagggt  2460
tctgccccgg gtacttccac cgaaccatcg gagggctctg cacctggtag cgaacctgcg  2520
acgtctggtt ctgaaacgcc gggtaccagc gaaagcgcta ccccagaatc cggtccgggc  2580
actagcaccg agccatcgga gggctccgca ccactgtcag gtcgttctga taaccattcc  2640
ccactgggtc tggctgggtc tggcaccgcc gaagcagcta gcgcctctgg cgaggttcag  2700
ttgttggaaa gcgggggcgg gcttgtccaa cctggaggtt cattaaaatt gagctgtgca  2760
gcctccggat tcacctttaa cacgtatgca atgaactggg tccgtcaagc gcccggtaag  2820
gggctggagt gggtagctcg catccgctcg aagtataata attacgcaac ctactacgca  2880
```

-continued

```
gacagtgtca aagatcgctt cactatctca cgcgacgaca gtaagaacac ggcctactta  2940
cagatgaaca atcttaaaac ggaggacacc gctgtctact actgcgtgcg ccacgggaat  3000
ttcggtaact cttatgtaag ttggttcgca tattggggac aaggtacgtt ggtaaccgta  3060
tccagcggtg cgaccccgcc ggaaaccggt gcggaaaccg aaagcccggg tgaaaccacc  3120
ggtggcagcg cggagagcga accgccgggt gaaggtgaac tggtcgtcac gcaggagccg  3180
tcccttaccg tttcaccagg tggaacagtg actctgacgt gtcgctcctc cactggggcg  3240
gttacaactt ccaattatgc taattgggtc cagcagaagc cgggccaagc ccctcgcggg  3300
ttgattggcg gcaccaacaa acgtgctcca gggacacctg cccgtttttc gggctcctta  3360
ttgggggggca aagctgcact gacgttgtct ggagttcagc cggaggatga ggcagagtat  3420
tactgcgcat tgtggtattc taatttatgg gtttttggag gcggcacaaa gctgaccgtc  3480
ctg                                                                3483

SEQ ID NO: 461          moltype = DNA  length = 3483
FEATURE                 Location/Qualifiers
misc_feature            1..3483
                        note = Description of Artificial Sequence: Synthetic
                         polynucleotide
source                  1..3483
                        mol_type = other DNA
                        organism = synthetic construct
SEQUENCE: 461
catcaccacc atcatcacgg aggtagccca gctggtagcc caacctctac cgaagaaggt  60
acctctgaat ccgctactcc agaatccggt cctggtacta gcactgagcc aagcgaaggt  120
tctgctccag gctccccggc aggtagccct acctctaccg aagagggcac tagcaccgaa  180
ccatctgagg gttccgctcc tggcacctcc actgaaccgt ccgaaggcag tgctccgggt  240
acttccgaaa gcgcaactcc ggaatccggc cctggttctg agcctgctac ttccggctct  300
gaaactccag gtagcgagcc agcgacttct ggttctgaaa ctccaggttc accggcgggt  360
agcccgacga gcacggagga aggtacctct gagtcggcca ctcctgagtc cggtccgggc  420
acgagcaccg agccgagcga gggttcagcc ccgggtacca gcacggagcc gtccgagggt  480
agcgcaccgg gttctccggc gggctcccct acgtctacgg aagagggtac gtccactgaa  540
cctagcgagg gcagcgcgcc aggcaccagc actgaaccga gcgaaggcag cgcacctggc  600
actagcgagt ctgcgactcc ggagagcggt ccgggtacga gcacggaacc aagcgaaggc  660
agcgccccag gtacctctga atctgctacc ccagaatctg gcccgggttc cgagccagct  720
acctctggtt ctgaaacccc aggtacttcc actgaaccaa gcgaaggtag cgctcctggc  780
acttctactg aaccatccga aggttccgct cctggtacgt ctgaaagcgc taccccctgaa  840
agcggcccag gcacctctga aagcgctact cctgagagcg gtccaggctc tccagcaggt  900
tctccaacct ccactgaaga aggcacctct gagtctgcta cccctgaatc tggtcctggc  960
tccgaacctg ctacctctgg ttccgaaact ccaggtacct cggaatctgc gactccggaa  1020
tctggcccgg gcacgagcac ggagccgtct gagggtagcg caccaggtac cagcactgag  1080
ccttctgagg gctctgcacc gggtacctcc acggaacctt cggaaggttc tgcgccgggt  1140
acctccactg agccatccga gggttcagca ccaggtacta gcacggaacc gtccgagggc  1200
tctgcaccag gtacgagcac cgaaccgtcg gagggtagcg ctccaggtag cccagcgggc  1260
tctccgacaa gcaccgaaga aggcaccagc accgagccgt ccgaaggttc cgcaccaggt  1320
acaagcgaga gcgcgactcc tgaatctggt ccgggtagcg agcctgcaac cagcggttct  1380
gagacgccgg gcacttccga atctgcgacc ccggagtccg gtccaggttc agagccggcg  1440
acgagcggtt cggaaacgcc gggtacgtct gaatcagcca cgccggagtc tggtccgggt  1500
acctcgaccg aaccaagcga aggttcggca ccgggtacta gcgagagcgc aacccctgaa  1560
agcggtccgg gcagcccggc aggttctcca accagcaccg aagaaggttc ccctgctggt  1620
agcccgacct ctacggagga aggtagccct gcaggttccc caacttctac tgaggaaggt  1680
acttctgagt ccgctacccc agaaagcggt cctggtacct ccactgaacc gtctgaaggc  1740
tctgcaccag gcacttctga gtctgctact ccagaaagcg gcccaggttc tgaaccagca  1800
acttctggct ctgagactcc aggcacttct gagtccgcaa cgcctgaatc cggtcctggt  1860
tctgaaccag ctacttccgg cagcgaaacc ccaggtacct ctgagtctgc gactccagag  1920
tctggtcctg gtacttccac tgagcctagc gagggttccg caccaggttc tccggctggt  1980
agcccgacca gcacggagga gggtacgtct gaatctgcaa cgccggaatc gggcccaggt  2040
tcggagcctg caacgtctgg cagcgaaacc ccgggtacct ccgaatctgc tacaccggaa  2100
agcggtcctg gcagccctgc tggttctcca acctctaccg aggagggttc accggcaggt  2160
agcccgacta gcactgaaga aggtactagc acggagccga gcgagggtag tgctccgggt  2220
acgagcgaga gcgcaacgcc agagagcggt ccaggcacca gcgaatcggc cacccctgag  2280
agcggcccag gtacttctga gagcgccact cctgaatccg gccctggtag cgagccggca  2340
acctccggct cagaaactcc tggttcggaa ccagcgacca gcggttctga aactccgggt  2400
agcccggcag gcagcccaac gagcaccgaa gagggtacca gcacggaacc gagcgagggt  2460
tctgccccgg gtacttccac cgaaccatcg gagggctctg cacctggtag cgaacctgcg  2520
acgtctggtt ctgaaacgcc gggtaccagc gaaagcgcta ccccagaatc cggtccgggc  2580
actagcaccg agccatcgga gggctccgca ccactgtcag gtcgttctga taaccatgtt  2640
ccactgtctc tgaaaatggg tggcaccgcc gaagcagcta gcgcctctgg cgaggttcag  2700
ttgttggaaa gcgggggcgg gcttgtccaa cctggaggtt cattaaaatt gagctgtgca  2760
gcctccggat tcacctttaa cacgtatgca atgaactggg tccgtcaagc gcccggtaag  2820
gggctggagt gggtagctcg catccgctcg aagtataata attacgcaac ctactacgca  2880
gacagtgtca aagatcgctt cactatctca cgcgacgaca gtaagaacac ggcctactta  2940
cagatgaaca atcttaaaac ggaggacacc gctgtctact actgcgtgcg ccacgggaat  3000
ttcggtaact cttatgtaag ttggttcgca tattggggac aaggtacgtt ggtaaccgta  3060
tccagcggtg cgaccccgcc ggaaaccggt gcggaaaccg aaagcccggg tgaaaccacc  3120
ggtggcagcg cggagagcga accgccgggt gaaggtgaac tggtcgtcac gcaggagccg  3180
tcccttaccg tttcaccagg tggaacagtg actctgacgt gtcgctcctc cactggggcg  3240
gttacaactt ccaattatgc taattgggtc cagcagaagc cgggccaagc ccctcgcggg  3300
ttgattggcg gcaccaacaa acgtgctcca gggacacctg cccgtttttc gggctcctta  3360
ttggggggca aagctgcact gacgttgtct ggagttcagc cggaggatga ggcagagtat  3420
tactgcgcat tgtggtattc taatttatgg gtttttggag gcggcacaaa gctgaccgtc  3480
```

```
ctg                                                               3483

SEQ ID NO: 462          moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 462
GGGGSGGGGS GGGGS                                                  15

SEQ ID NO: 463          moltype = AA  length = 18
FEATURE                 Location/Qualifiers
REGION                  1..18
                        note = Description of Artificial Sequence: Synthetic peptide
source                  1..18
                        mol_type = protein
                        organism = synthetic construct
SEQUENCE: 463
GEGTSTGSGG SGGSGGAD                                               18

SEQ ID NO: 464          moltype = AA  length = 18
FEATURE                 Location/Qualifiers
REGION                  1..18
                        note = Description of Artificial Sequence: Synthetic peptide
source                  1..18
                        mol_type = protein
                        organism = synthetic construct
SEQUENCE: 464
VEGGSGGSGG SGGSGGVD                                               18

SEQ ID NO: 465          moltype = AA  length = 29
FEATURE                 Location/Qualifiers
REGION                  1..29
                        note = Description of Artificial Sequence: Synthetic peptide
source                  1..29
                        mol_type = protein
                        organism = synthetic construct
SEQUENCE: 465
RTSGPGDGGK GGPGKGPGGE GTKGTGPGG                                   29

SEQ ID NO: 466          moltype = AA  length = 30
FEATURE                 Location/Qualifiers
REGION                  1..30
                        note = Description of Artificial Sequence: Synthetic
                         polypeptide
source                  1..30
                        mol_type = protein
                        organism = synthetic construct
SEQUENCE: 466
GSGEGSEGEG GGEGSEGEGS GEGGEGEGSG                                  30

SEQ ID NO: 467          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 467
TGSGEGSEGE GGGEGSEGEG SGEGGEGEGS GT                               32

SEQ ID NO: 468          moltype = AA  length = 30
FEATURE                 Location/Qualifiers
REGION                  1..30
                        note = Description of Artificial Sequence: Synthetic
                         polypeptide
source                  1..30
                        mol_type = protein
                        organism = synthetic construct
SEQUENCE: 468
GATPPETGAE TESPGETTGG SAESEPPGEG                                  30

SEQ ID NO: 469          moltype = AA  length = 30
FEATURE                 Location/Qualifiers
REGION                  1..30
                        note = Description of Artificial Sequence: Synthetic
```

```
                         polypeptide
source                  1..30
                        mol_type = protein
                        organism = synthetic construct
SEQUENCE: 469
GSAAPTAGTT PSASPAPPTG GSSAAGSPST                                      30

SEQ ID NO: 470          moltype = AA  length = 30
FEATURE                 Location/Qualifiers
REGION                  1..30
                        note = Description of Artificial Sequence: Synthetic
                         polypeptide
source                  1..30
                        mol_type = protein
                        organism = synthetic construct
SEQUENCE: 470
GEGGESGGSE GEGSGEGEGG SGGEGESEGG                                      30

SEQ ID NO: 471          moltype = AA  length = 30
FEATURE                 Location/Qualifiers
REGION                  1..30
                        note = Description of Artificial Sequence: Synthetic
                         polypeptide
source                  1..30
                        mol_type = protein
                        organism = synthetic construct
SEQUENCE: 471
STETSPSTPT ESPEAGSGSG SPESPSGTEA                                      30

SEQ ID NO: 472          moltype = AA  length = 30
FEATURE                 Location/Qualifiers
REGION                  1..30
                        note = Description of Artificial Sequence: Synthetic
                         polypeptide
source                  1..30
                        mol_type = protein
                        organism = synthetic construct
SEQUENCE: 472
PTGTTGEPSG EGSEPEGSAP TSSTSEATPS                                      30

SEQ ID NO: 473          moltype = AA  length = 30
FEATURE                 Location/Qualifiers
REGION                  1..30
                        note = Description of Artificial Sequence: Synthetic
                         polypeptide
source                  1..30
                        mol_type = protein
                        organism = synthetic construct
SEQUENCE: 473
SESESEGEAP TGPGASTTPE PSESPTPETS                                      30

SEQ ID NO: 474          moltype = AA  length = 30
FEATURE                 Location/Qualifiers
REGION                  1..30
                        note = Description of Artificial Sequence: Synthetic
                         polypeptide
source                  1..30
                        mol_type = protein
                        organism = synthetic construct
SEQUENCE: 474
PEGGESGEGT GPGTGGEPEG EGGPGGEGGT                                      30

SEQ ID NO: 475          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 475
SGGGGS                                                                6

SEQ ID NO: 476          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
```

SEQUENCE: 476
GGGGS 5

SEQ ID NO: 477 moltype = DNA length = 4257
FEATURE Location/Qualifiers
misc_feature 1..4257
note = Description of Artificial Sequence: Synthetic polynucleotide
source 1..4257
mol_type = other DNA
organism = synthetic construct
SEQUENCE: 477
atgaagaaaa acatcgcttt tcttcttgca tctatgttcg ttttttctat tgctacaaac 60
gcgtacgctc atcaccacca tcatcaccat cacgaactgg ttatgaccca aagcccgagc 120
agcctgaccg ttaccgcggg cgaaaaggtt accatgagct gcaaaagcag ccaaagcctg 180
ctgaacagcg gcaaccaaaa gaactacctg acctggtacc aacagaagcc gggtcagccg 240
ccgaaactgc tgatctactg ggcgagcacc cgtgagagcg gcgttccgga ccgttttacc 300
ggcagcggca gcggtaccga ctttaccctg accattagca gcgtgcaggc ggaagatctg 360
gcggtgtact attgccaaaa cgactacagc tacccgctga cctttggtgc gggcaccaaa 420
ctggagatca agggtggcgg tggcagcggc ggtggtggca gcggcggcgg tggcagcgag 480
gttcagctgc tggaacagag cggcgcggag ctggtgcgtc cgggtaccag cgttaagatc 540
agctgcaagg cgagcggtta tgcgttcacc aactactggc tgggttgggt gaagcaacgt 600
ccgggtcacg gtctggagtg gatcggcgac attttcccgg gcagcggtaa catccactac 660
aacgagaaat tcaagggtaa agcgaccctg accgcggata aaagcagcag caccgcgtat 720
atgcagctga gcagcctgac cttcgaagat agcgcggttt acttctgcgc gcgtctgcgt 780
aactgggatg aaccgatgga ttactggggt cagggcacca ccgtgaccgt tagcagcggt 840
ggtggcggca gcgatgttca gctggtgcaa agcggtgcgg aagtgaaaaa gccgggtgcg 900
agcgtgaaag ttagctgcaa agcgagcggc tataccttca cccgttacac catgcactgg 960
gttcgtcagg cgccgggtca gggcctggaa tggatcggct acatcaaccc gagccgtggc 1020
tataccaact acgcggatag cgtgaaaggt cgtttcacca ttaccaccga caaaagcacc 1080
agcaccgcgt acatggaact gagcagcctg cgtagcgagg ataccgcgac ctactattgc 1140
gcgcgttact atgatgacca ctactgcctg gactattggg gccaaggtac caccgttacc 1200
gtgagcagcg gtgaaggcac cagcaccggc agcggtggta gcggtggtag cggcggtgcg 1260
gatgacatcg ttctgaccca aagcccggcg accctgagcc tgagcccggg cgagcgtgcg 1320
accctgagct gccgtgcgag ccagagcgtt agctacatga actggtacca gcaaaagccg 1380
ggcaaagcgc cgaagcgttg gatttatgat accagcaagg ttgcgagcgg tgttccggcg 1440
cgtttcagcg gtagcggtag cggcaccgat tatagcctga ccattaacag cctggaggcg 1500
gaagatgcgg cgacctacta ctgccaacaa tggagcagca atccgctgac cttcggtggt 1560
ggtaccaaag ttgaaattaa gggcaccgcc gaagcagcta gcgcctctgg cctgtcaggt 1620
cgttctgata accattcccc actgggtctg gctgggtctc caggtagccc agctggtagc 1680
ccaacctcta ccgaagaagg tacctctgaa tccgctactc cagaatccgg tcctggtact 1740
agcactgagc caagcgaagg ttctgctcca ggctccccgg caggtagccc tacctctacc 1800
gaagagggca ctagcaccga accatctgag ggttccgctc ctggcacctc cactgaaccg 1860
tccgaaggca gtgctccggg tacttccgaa agcgcaactc cggaatccgg ccctggttct 1920
gagcctgcta cttccggctc tgaaactcca ggtagcgagc cagcgacttc tggttctgaa 1980
actccaggtt caccggcggg tagcccgacg agcacggagg aaggtacctc tgagtcggcc 2040
actcctgagt ccggtccggg cacgagcacc gagccgagcg agggttcagc cccgggtacc 2100
agcacggagc cgtccgaggg tagcgcaccg ggttctccgg cgggctcccc tacgtctacg 2160
gaagagggta cgtccactga acctagcgag ggcagcgcgc caggcaccag cactgaaccg 2220
agcgaaggca gcgcacctgg cactagcgag tctgcgactc cggagagcgg tccgggtacg 2280
agcacggaac caagcgaagg cagcgcccca ggtacctctg aatctgctac cccagaatct 2340
ggcccgggtt ccgagccagc tacctctggt tctgaaaccc caggtacttc cactgaacca 2400
agcgaaggta gcgctcctgg cacttctact gaaccatccg aaggttccgc tcctggtacg 2460
tctgaaagcg ctacccctga aagcggccca ggcacctctg aaagcgctac tcctgagagc 2520
ggtccaggct ctccagcagg ttctccaacc tccactgaag aaggcacctc tgagtctgct 2580
accccctgaat ctggtcctgg ctccgaacct gctacctctg gttccgaaac tccaggtacc 2640
tcggaatctg cgactccgga atctggcccg ggcacgagca cggagccgtc tgagggtagc 2700
gcaccaggta ccagcactga gccttctgag ggctctgcac cgggtacctc cacggaacct 2760
tcggaaggtt ctgcgccggg tacctccact gagccatccg agggttcagc accaggtact 2820
agcacggaac cgtccgaggg ctctgcacca ggtacgagca ccgaaccgtc ggagggtagc 2880
gctccaggta gcccagcggg ctctccgaca agcaccgaag aaggcaccag caccgagccg 2940
tccgaaggtt ccgcaccagg tacaagcgag agcgcgactc ctgaatctgg tccgggtagc 3000
gagcctgcaa ccagcggttc tgagacgccg ggcacttccg aatctgcgac cccggagtcc 3060
ggtccaggtt cagagccggc gacgagcggt tcggaaacgc cgggtacgtc tgaatcagcc 3120
acgccggagt ctggtccggg tacctcgacc gaaccaagcg aaggttcggc accgggtact 3180
agcgagagcg caacccctga aagcggtccg ggcagcccgg caggttctcc aaccagcacc 3240
gaagaaggtt cccctgctgg tagcccgacc tctacggagg aaggtagccc tgcaggttcc 3300
ccaacttcta ctgaggaagg tacttctgag tccgctaccc cagaaagcgg tcctggtacc 3360
tccactgaac cgtctgaagg ctctgcacca ggcacttctg agtctgctac tccagaaagc 3420
ggcccaggtt ctgaaccagc aacttctggc tctgagactc caggcacttc tgagtccgca 3480
acgcctgaat ccggtcctgg ttctgaacca gctacttccg gcagcgaaac cccaggtacc 3540
tctgagtctg cgactccaga gtctggtcct ggtacttcca ctgagcctag cgagggttcc 3600
gcaccaggtt ctccggctgg tagcccgacc agcacggagg agggtacgtc tgaatctgca 3660
acgccggaat cgggcccagg ttcggagcct gcaacgtctg gcagcgaaac cccgggtacc 3720
tccgaatctg ctacaccgga aagcggtcct ggcagccctg ctggttctcc aacctctacc 3780
gaggagggtt caccggcagg tagcccgact agcactgaag aaggtactag cacggagccg 3840
agcgagggta gtgctccggg tacgagcgag agcgcaacgc cagagagcgg tccaggcacc 3900
agcgaatcgg ccacccctga gagcggccca ggtacttctg agagcgccac tcctgaatcc 3960
ggccctggta gcgagccggc aacctccggc tcagaaactc ctggttcgga accagcgacc 4020

-continued

```
agcggttctg aaactccggg tagcccggca ggcagcccaa cgagcaccga agagggtacc  4080
agcacggaac cgagcgaggg ttctgccccg ggtacttcca ccgaaccatc ggagggctct  4140
gcacctggta gcgaacctgc gacgtctggt tctgaaacgc cgggtaccag cgaaagcgct  4200
accccagaat ccggtccggg cactagcacc gagccatcgg agggctccgc accaggt     4257

SEQ ID NO: 478          moltype = DNA  length = 4329
FEATURE                 Location/Qualifiers
misc_feature            1..4329
                        note = Description of Artificial Sequence: Synthetic
                         polynucleotide
source                  1..4329
                        mol_type = other DNA
                        organism = synthetic construct
SEQUENCE: 478
atgaagaaaa acatcgcttt tcttcttgca tctatgttcg tttttctat tgctacaaac  60
gcgtacgctg atattcagat gacccaatcg ccgtcgtccc tgtcagcttc agtcggtgat  120
cgtgttacca ttacctgtcg ctcaacgaaa tccctgctgc attcaaacgg tattacctat  180
ctgtactggt atcagcaaaa accgggcaaa gcgccgaaac tgctgatcta ccagatgtcg  240
aatctggcca gcggtgttcc gtctcgtttt agctctagtg gttctggcac cgatttcacc  300
ctgacgattt cctcactgca accggaagac tttgcaacgt attactgcgc tcagaacctg  360
gaaatcccgc gtaccttcgg tcaaggcacg aaagtcgaaa ttaaaggtgc aacgcctccg  420
gagactggtg ctgaaactga gtccccgggc gagacgaccg gtggctctgc tgaatccgaa  480
ccaccgggcg aaggccaagt gcaactggtt cagagcggtc cgggtctggt ccaaccgggt  540
ggcagtgtgc gtatttcctg cgcggcctca ggttacacct ttacgaacta tggcatgaat  600
tgggtgaaac aggccccggg taaaggcctg gaatggatgg gttggatcaa cacctacacg  660
ggcgaatcta cctatgcaga tagtttcaaa ggccgcttta ccttcagcct ggacacgtct  720
gctagtgcag cttatctgca gattaatagc ctgcgtgcgg aagatacggc cgtttattac  780
tgtgcgcgct ttgcaatcaa aggcgactac tggggccaag gcaccctgct gaccgtgtcc  840
tccggtggtg gcggcagcga catccaaatg acccagagcc cgagcagcct gagcgcgagc  900
gtgggcgacc gtgttaccat cacctgccgt gcgagccaag acatccgtaa ctacctgaac  960
tggtatcagc aaaagccggg taaagcgccg aagctgctga tctactatac cagccgtctg  1020
gagagcggcg tgccgagccg tttcagcggt agcggtagcg gtaccgacta caccctgacc  1080
attagcagcc tgcagccgga agatttcgcg acctactatt gccagcaggg taacaccctg  1140
ccgtggacct ttggtcaagg caccaaagtt gagattaaag gcgccacgcc tccggaaact  1200
ggtgctgaga cggaatcccc tggtgaaacc actggcggtt ctgccgaatc tgaaccgcct  1260
ggtgaaggcg aggtgcagct ggttgaaagc ggtggcggtc tggtgcaacc aggcggtagc  1320
ctgcgtctga gctgcgcggc gagcggttac agctttaccg gttataccat gaactgggtt  1380
cgtcaagcgc caggtaaagg tctggagtgg gtggcgctga tcaacccgta caagggtgtt  1440
agcacctata accagaagtt caaagaccgt tttaccatta gcgtggataa gagcaaaaac  1500
accgcgtacc tgcaaatgaa cagcctgcgt gcggaggaca ccgctgtgta ctattgcgcg  1560
cgtagcggtt actatggcga cagcgactgg tattttgatg tgtggggcca aggcaccctg  1620
gttaccgtga gctccggcac cgccgaagca gctagcgcct ctggcctgtc aggtcgttct  1680
gataaccatt ccccactggg tctggctggg tctccaggta gcccagctgg tagcccaacc  1740
tctaccgaag aaggtacctc tgaatccgct actccagaat ccggtcctgg tactagcact  1800
gagccaagcg aaggttctgc tccaggctcc ccggcaggta gccctacctc taccgaagag  1860
ggcactagca ccgaaccatc tgagggttcc gctcctggca cctccactga accgtccgaa  1920
ggcagtgctc cgggtacttc cgaaagcgca actccggaat ccggccctgg ttctgagcct  1980
gctacttccg gctctgaaac tccaggtagc gagccagcga cttctggttc tgaaactcca  2040
ggttcaccgg cgggtagccc gacgagcacg gaggaaggta cctctgagtc ggccactcct  2100
gagtccggtc cgggcacgag caccgagccg agcgagggtt cagccccggg taccagcacg  2160
gagccgtccg agggtagcgc accgggttct ccggcgggct cccctacgtc tacggaagag  2220
ggtacgtcca ctgaacctag cgagggcagc gcgccaggca ccagcactga accgagcgaa  2280
ggcagcgcac ctggcactag cgagtctgcg actccggaga gcggtccggg tacgagcacg  2340
gaaccaagcg aaggcagcgc cccaggtacc tctgaatctg ctaccccaga atctggcccg  2400
ggttccgagc cagctacctc tggttctgaa accccaggta cttccactga accaagcgaa  2460
ggtagcgctc ctggcacttc tactgaacca tccgaaggtt ccgctcctgg tacgtctgaa  2520
agcgctaccc ctgaaagcgg cccaggcacc tctgaaagcg ctactcctga gagcggtcca  2580
ggctctccag caggttctcc aacctccact gaagaaggca cctctgagtc tgctacccct  2640
gaatctggtc ctggctccga acctgctacc tctggttccg aaactccagg tacctcggaa  2700
tctgcgactc cggaatctgg cccgggcacg agcacggagc cgtctgaggg tagcgcacca  2760
ggtaccagca ctgagccttc tgagggctct gcaccgggta cctccacgga accttcggaa  2820
ggttctgcgc cgggtacctc cactgagcca tccgagggtt cagcaccagg tactagcacg  2880
gaaccgtccg agggctctgc accaggtacg agcaccgaac cgtcggaggg tagcgctcca  2940
ggtagcccag cgggctctcc gacaagcacc gaagaaggca ccagcaccga gccgtccgaa  3000
ggttccgcac caggtacaag cgagagcgcg actcctgaat ctggtccggg tagcgagcct  3060
gcaaccagcg gttctgagac gccgggcact tccgaatctg cgaccccgga gtccggtcca  3120
ggttcagagc cggcgacgag cggttcggaa acgccgggta cgtctgaatc agccacgccg  3180
gagtctggtc cgggtacctc gaccgaacca agcgaaggtt cggcaccggg tactagcgag  3240
agcgcaaccc ctgaaagcgg tccgggcagc ccggcaggtt ctccaaccag caccgaagaa  3300
ggttcccctg ctggtagccc gacctctacg gaggaaggta gccctgcagg ttccccaact  3360
tctactgagg aaggtacttc tgagtccgct accccagaaa gcggtcctgg tacctccact  3420
gaaccgtctg aaggctctgc accaggcact tctgagtctg ctactccaga aagcggccca  3480
ggttctgaac cagcaacttc tggctctgag actccaggca cttctgagtc cgcaacgcct  3540
gaatccggtc ctggttctga accagctact tccggcagcg aaaccccagg tacctctgag  3600
tctgcgactc cagagtctgg tcctggtact tccactgagc ctagcgaggg ttccgcacca  3660
ggttctccgg ctggtagccc gaccagcacg gaggagggta cgtctgaatc tgcaacgccg  3720
gaatcgggcc caggttcgga gcctgcaacg tctggcagcg aaaccccggg tacctccgaa  3780
tctgctacac cggaaagcgg tcctggcagc cctgctggtt ctccaacctc taccgaggag  3840
ggttcaccgg caggtagccc gactagcact gaagaaggta ctagcacgga gccgagcgag  3900
```

```
ggtagtgctc cgggtacgag cgagagcgca acgccagaga gcggtccagg caccagcgaa  3960
tcggccaccc ctgagagcgg cccaggtact tctgagagcg ccactcctga atccggccct  4020
ggtagcgagc cggcaacctc cggctcagaa actcctggtt cggaaccagc gaccagcggt  4080
tctgaaactc cgggtagccc ggcaggcagc ccaacgagca ccgaagaggg taccagcacg  4140
gaaccgagcg agggttctgc cccgggtact tccaccgaac catcggaggg ctctgcacct  4200
ggtagcgaac ctgcgacgtc tggttctgaa acgccgggta ccagcgaaag cgctacccca  4260
gaatccggtc cgggcactag caccgagcca tcggagggct ccgcaccagg tcaccatcat  4320
caccatcac                                                         4329

SEQ ID NO: 479         moltype = AA  length = 1419
FEATURE                Location/Qualifiers
REGION                 1..1419
                       note = Description of Artificial Sequence: Synthetic
                        polypeptide
source                 1..1419
                       mol_type = protein
                       organism = synthetic construct
SEQUENCE: 479
MKKNIAFLLA SMFVFSIATN AYAHHHHHHH HELVMTQSPS SLTVTAGEKV TMSCKSSQSL  60
LNSGNQKNYL TWYQQKPGQP PKLLIYWAST RESGVPDRFT GSGSGTDFTL TISSVQAEDL  120
AVYYCQNDYS YPLTFGAGTK LEIKGGGGSG GGGSGGGGSE VQLLEQSGAE LVRPGTSVKI  180
SCKASGYAFT NYWLGWVKQR PGHGLEWIGD IFPGSGNIHY NEKFKGKATL TADKSSSTAY  240
MQLSSLTFED SAVYFCARLR NWDEPMDYWG QGTTVTVSSG GGGSDVQLVQ SGAEVKKPGA  300
SVKVSCKASG YTFTRYTMHW VRQAPGQGLE WIGYINPSRG YTNYADSVKG RFTITTDKST  360
STAYMELSSL RSEDTATYYC ARYYDDHYCL DYWGQGTTVT VSSGEGTSTG SGGSGGSGGA  420
DDIVLTQSPA TLSLSPGERA TLSCRASQSV SYMNWYQQKP GKAPKRWIYD TSKVASGVPA  480
RFSGSGSGTD YSLTINSLEA EDAATYYCQQ WSSNPLTFGG GTKVEIKGTA EAASASGLSG  540
RSDNHSPLGL AGSPGSPAGS PTSTEEGTSE SATPESGPGT STEPSEGSAP GSPAGSPTST  600
EEGTSTEPSE GSAPGTSTEP SEGSAPGTSE SATPESGPGS EPATSGSETP GSEPATSGSE  660
TPGSPAGSPT STEEGTSESA TPESGPGTST EPSEGSAPGT STEPSEGSAP GSPAGSPTST  720
EEGTSTEPSE GSAPGTSTEP SEGSAPGTSE SATPESGPGT STEPSEGSAP GTSESATPES  780
GPGSEPATSG SETPGTSTEP SEGSAPGTST EPSEGSAPGT SESATPESGP GTSESATPES  840
GPGSPAGSPT STEEGTSESA TPESGPGSEP ATSGSETPGT SESATPESGP GTSTEPSEGS  900
APGTSTEPSE GSAPGTSTEP SEGSAPGTST EPSEGSAPGT STEPSEGSAP GTSTEPSEGS  960
APGSPAGSPT STEEGTSTEP SEGSAPGTSE SATPESGPGS EPATSGSETP GTSESATPES  1020
GPGSEPATSG SETPGTSESA TPESGPGTST EPSEGSAPGT SESATPESGP GSPAGSPTST  1080
EEGSPAGSPT STEEGSPAGS PTSTEEGTSE SATPESGPGT STEPSEGSAP GTSESATPES  1140
GPGSEPATSG SETPGTSESA TPESGPGSEP ATSGSETPGT SESATPESGP GTSTEPSEGS  1200
APGSPAGSPT STEEGTSESA TPESGPGSEP ATSGSETPGT SESATPESGP GSPAGSPTST  1260
EEGSPAGSPT STEEGTSTEP SEGSAPGTSE SATPESGPGT SESATPESGP GTSESATPES  1320
GPGSEPATSG SETPGSEPAT SGSETPGSPA GSPTSTEEGT STEPSEGSAP GTSTEPSEGS  1380
APGSEPATSG SETPGTSESA TPESGPGTST EPSEGSAPG                        1419

SEQ ID NO: 480         moltype = AA  length = 1443
FEATURE                Location/Qualifiers
REGION                 1..1443
                       note = Description of Artificial Sequence: Synthetic
                        polypeptide
source                 1..1443
                       mol_type = protein
                       organism = synthetic construct
SEQUENCE: 480
MKKNIAFLLA SMFVFSIATN AYADIQMTQS PSSLSASVGD RVTITCRSTK SLLHSNGITY  60
LYWYQQKPGK APKLLIYQMS NLASGVPSRF SSSGSGTDFT LTISSLQPED FATYYCAQNL  120
EIPRTFGQGT KVEIKGATPP ETGAETESPG ETTGGSAESE PPGEGQVQLV QSGPGLVQPG  180
GSVRISCAAS GYTFTNYGMN WVKQAPGKGL EWMGWINTYT GESTYADSFK GRFTFSLDTS  240
ASAAYLQINS LRAEDTAVYY CARFAIKGDY WGQGTLLTVS SGGGGSDIQM TQSPSSLSAS  300
VGDRVTITCR ASQDIRNYLN WYQQKPGKAP KLLIYYTSRL ESGVPSRFSG SGSGTDYTLT  360
ISSLQPEDFA TYYCQQGNTL PWTFGQGTKV EIKGATPPET GAETESPGET TGGSAESEPP  420
GEGEVQLVES GGGLVQPGGS LRLSCAASGY SFTGYTMNWV RQAPGKGLEW VALINPYKGV  480
STYNQKFKDR FTISVDKSKN TAYLQMNSLR AEDTAVYYCA RSGYYGDSDW YFDVWGQGTL  540
VTVSSGTAEA ASASGLSGRS DNHSPLGLAG SPGSPAGSPT STEEGTSESA TPESGPGTST  600
EPSEGSAPGS PAGSPTSTEE GTSTEPSEGS APGTSTEPSE GSAPGTSESA TPESGPGSEP  660
ATSGSETPGS EPATSGSETP GSPAGSPTST EEGTSESATP ESGPGTSTEP SEGSAPGTST  720
EPSEGSAPGS PAGSPTSTEE GTSTEPSEGS APGTSTEPSE GSAPGTSESA TPESGPGTST  780
EPSEGSAPGT SESATPESGP GSEPATSGSE TPGTSTEPSE GSAPGTSTEP SEGSAPGTSE  840
SATPESGPGT SESATPESGP GSPAGSPTST EEGTSESATP ESGPGSEPAT SGSETPGTSE  900
SATPESGPGT STEPSEGSAP GTSTEPSEGS APGTSTEPSE GSAPGTSTEP SEGSAPGTST  960
EPSEGSAPGT STEPSEGSAP GSPAGSPTST EEGTSTEPSE GSAPGTSESA TPESGPGSEP  1020
ATSGSETPGT SESATPESGP GSEPATSGSE TPGTSESATP ESGPGTSTEP SEGSAPGTSE  1080
SATPESGPGS PAGSPTSTEE GSPAGSPTST EEGSPAGSPT STEEGTSESA TPESGPGTST  1140
EPSEGSAPGT SESATPESGP GSEPATSGSE TPGTSESATP ESGPGSEPAT SGSETPGTSE  1200
SATPESGPGT STEPSEGSAP GSPAGSPTST EEGTSESATP ESGPGSEPAT SGSETPGTSE  1260
SATPESGPGS PAGSPTSTEE GSPAGSPTST EEGTSTEPSE GSAPGTSESA TPESGPGTSE  1320
SATPESGPGT SESATPESGP GSEPATSGSE TPGSEPATSG SETPGSPAGS PTSTEEGTST  1380
EPSEGSAPGT STEPSEGSAP GSEPATSGSE TPGTSESATP ESGPGTSTEP SEGSAPGHHH  1440
HHH                                                               1443

SEQ ID NO: 481         moltype = AA  length = 8
```

```
FEATURE                Location/Qualifiers
REGION                 1..8
                       note = Description of Artificial Sequence: Synthetic 8xHis
                        tag
source                 1..8
                       mol_type = protein
                       organism = synthetic construct
SEQUENCE: 481
HHHHHHHH                                                          8

SEQ ID NO: 482         moltype = AA  length = 31
FEATURE                Location/Qualifiers
REGION                 1..31
                       note = Description of Artificial Sequence: Synthetic
                        polypeptide
source                 1..31
                       mol_type = protein
                       organism = synthetic construct
SEQUENCE: 482
MKKNIAFLLA SMFVFSIATN AYAHHHHHHH H                                31

SEQ ID NO: 483         moltype = AA  length = 6
FEATURE                Location/Qualifiers
REGION                 1..6
                       note = Description of Artificial Sequence: Synthetic 6xHis
                        tag
source                 1..6
                       mol_type = protein
                       organism = synthetic construct
SEQUENCE: 483
HHHHHH                                                            6

SEQ ID NO: 484         moltype = AA  length = 23
FEATURE                Location/Qualifiers
REGION                 1..23
                       note = Description of Artificial Sequence: Synthetic peptide
source                 1..23
                       mol_type = protein
                       organism = synthetic construct
SEQUENCE: 484
MKKNIAFLLA SMFVFSIATN AYA                                         23

SEQ ID NO: 485         moltype = AA  length = 1398
FEATURE                Location/Qualifiers
REGION                 1..1398
                       note = Description of Artificial Sequence: Synthetic
                        polypeptide
source                 1..1398
                       mol_type = protein
                       organism = synthetic construct
SEQUENCE: 485
HHHHHHHHDI QLTQSPASLA VSLGQRATIS CKASQSVDYD GDSYLNWYQQ IPGQPPKLLI  60
YDASNLVSGI PPRFSGSGSG TDFTLNIHPV EKVDAATYHC QQSTEDPWTF GGGTKLEIKG  120
GGGSGGGGSG GGGSQVQLQQ SGAELVRPGS SVKISCKASG YAFSSYWMNW VKQRPGQGLE  180
WIGQIWPGDG DTNYNGKFKG KATLTADESS STAYMQLSSL ASEDSAVYFC ARRETTTVGR  240
YYYAMDYWGQ GTTVTVSSGG GGSDIKLQQS GAELARPGAS VKMSCKTSGY TFTRYTMHWV  300
KQRPGQGLEW IGYINPSRGY TNYNQKFKDK ATLTTDKSSS TAYMQLSSLT SEDSAVYYCA  360
RYYDDHYCLD YWGQGTTLTV SSVEGGSGGS GGSGGSGGVD DIQLTQSPAI MSASPGEKVT  420
MTCRASSSVS YMNWYQQKSG TSPKRWIYDT SKVASGVPYR FSGSGSGTSY SLTISSMEAE  480
DAATYYCQQW SSNPLTFGAG TKLELKGTAE AASASGLSGR SDNHSPLGLA GSPGSPAGSP  540
TSTEEGTSES ATPESGPGTS TEPSEGSAPG SPAGSPTSTE EGTSTEPSEG SAPGTSTEPS  600
EGSAPGTSES ATPESGPGSE PATSGSETPG SEPATSGSET PGSPAGSPTS TEEGTSESAT  660
PESGPGTSTE PSEGSAPGTS TEPSEGSAPG SPAGSPTSTE EGTSTEPSEG SAPGTSTEPS  720
EGSAPGTSES ATPESGPGTS TEPSEGSAPG TSESATPESG PGSEPATSGS ETPGTSTEPS  780
EGSAPGTSTE PSEGSAPGTS ESATPESGPG TSESATPESG PGSPAGSPTS TEEGTSESAT  840
PESGPGSEPA TSGSETPGTS ESATPESGPG TSTEPSEGSA PGTSTEPSEG SAPGTSTEPS  900
EGSAPGTSTE PSEGSAPGTS TEPSEGSAPG TSTEPSEGSA PGSPAGSPTS TEEGTSTEPS  960
EGSAPGTSES ATPESGPGSE PATSGSETPG TSESATPESG PGSEPATSGS ETPGTSESAT  1020
PESGPGTSTE PSEGSAPGTS ESATPESGPG SPAGSPTSTE EGSPAGSPTS TEEGSPAGSP  1080
TSTEEGTSES ATPESGPGTS TEPSEGSAPG TSESATPESG PGSEPATSGS ETPGTSESAT  1140
PESGPGSEPA TSGSETPGTS ESATPESGPG TSTEPSEGSA PGSPAGSPTS TEEGTSESAT  1200
PESGPGSEPA TSGSETPGTS ESATPESGPG SPAGSPTSTE EGSPAGSPTS TEEGTSTEPS  1260
EGSAPGTSES ATPESGPGTS ESATPESGPG TSESATPESG PGSEPATSGS ETPGSEPATS  1320
GSETPGSPAG SPTSTEEGTS TEPSEGSAPG TSTEPSEGSA PGSEPATSGS ETPGTSESAT  1380
PESGPGTSTE PSEGSAPG                                               1398

SEQ ID NO: 486         moltype = AA  length = 1396
FEATURE                Location/Qualifiers
REGION                 1..1396
```

```
                         note = Description of Artificial Sequence: Synthetic
                          polypeptide
source                   1..1396
                         mol_type = protein
                         organism = synthetic construct
SEQUENCE: 486
HHHHHHHHEL VMTQSPSSLT VTAGEKVTMS CKSSQSLLNS GNQKNYLTWY QQKPGQPPKL  60
LIYWASTRES GVPDRFTGSG SGTDFTLTIS SVQAEDLAVY YCQNDYSYPL TFGAGTKLEI  120
KGGGGSGGGG SGGGGSEVQL LEQSGAELVR PGTSVKISCK ASGYAFTNYW LGWVKQRPGH  180
GLEWIGDIFP GSGNIHYNEK FKGKATLTAD KSSSTAYMQL SSLTFEDSAV YFCARLRNWD  240
EPMDYWGQGT TVTVSSGGGG SDVQLVQSGA EVKKPGASVK VSCKASGYTF TRYTMHWVRQ  300
APGQGLEWIG YINPSRGYTN YADSVKGRFT ITTDKSTSTA YMELSSLRSE DTATYYCARY  360
YDDHYCLDYW GQGTTVTVSS GEGTSTGSGG SGGSGGADDI VLTQSPATLS LSPGERATLS  420
CRASQSVSYM NWYQQKPGKA PKRWIYDTSK VASGVPARFS GSGSGTDYSL TINSLEAEDA  480
ATYYCQQWSS NPLTFGGGTK VEIKGTAEAA SASGLSGRSD NHSPLGLAGS PGSPAGSPTS  540
TEEGTSESAT PESGPGTSTE PSEGSAPGSP AGSPTSTEEG TSTEPSEGSA PGTSTEPSEG  600
SAPGTSESAT PESGPGSEPA TSGSETPGSE PATSGSETPG SPAGSPTSTE EGTSESATPE  660
SGPGTSTEPS EGSAPGTSTE PSEGSAPGSP AGSPTSTEEG TSTEPSEGSA PGTSTEPSEG  720
SAPGTSESAT PESGPGTSTE PSEGSAPGTS ESATPESGPG SEPATSGSET PGTSTEPSEG  780
SAPGTSTEPS EGSAPGTSES ATPESGPGTS ESATPESGPG SPAGSPTSTE EGTSESATPE  840
SGPGSEPATS GSETPGTSES ATPESGPGTS TEPSEGSAPG TSTEPSEGSA PGTSTEPSEG  900
SAPGTSTEPS EGSAPGTSTE PSEGSAPGTS TEPSEGSAPG SPAGSPTSTE EGTSTEPSEG  960
SAPGTSESAT PESGPGSEPA TSGSETPGTS ESATPESGPG SEPATSGSET PGTSESATPE  1020
SGPGTSTEPS EGSAPGTSES ATPESGPGSP AGSPTSTEEG SPAGSPTSTE EGSPAGSPTS  1080
TEEGTSESAT PESGPGTSTE PSEGSAPGTS ESATPESGPG SEPATSGSET PGTSESATPE  1140
SGPGSEPATS GSETPGTSES ATPESGPGTS TEPSEGSAPG SPAGSPTSTE EGTSESATPE  1200
SGPGSEPATS GSETPGTSES ATPESGPGSP AGSPTSTEEG SPAGSPTSTE EGTSTEPSEG  1260
SAPGTSESAT PESGPGTSES ATPESGPGTS ESATPESGPG SEPATSGSET PGSEPATSGS  1320
ETPGSPAGSP TSTEEGTSTE PSEGSAPGTS TEPSEGSAPG SEPATSGSET PGTSESATPE  1380
SGPGTSTEPS EGSAPG                                                 1396

SEQ ID NO: 487           moltype = AA  length = 1386
FEATURE                  Location/Qualifiers
REGION                   1..1386
                         note = Description of Artificial Sequence: Synthetic
                          polypeptide
source                   1..1386
                         mol_type = protein
                         organism = synthetic construct
SEQUENCE: 487
HHHHHHHHEV QLLEQSGAEL VRPGTSVKIS CKASGYAFTN YWLGWVKQRP GHGLEWIGDI  60
FPGSGNIHYN EKFKGKATLT ADKSSSTAYM QLSSLTFEDS AVYFCARLRN WDEPMDYWGQ  120
GTTVTVSSGG GGSDVQLVQS GAEVKKPGAS VKVSCKASGY TFTRYTMHWV RQAPGQGLEW  180
IGYINPSRGY TNYADSVKGR FTITTDKSTS TAYMELSSLR SEDTATYYCA RYYDDHYCLD  240
YWGQGTTVTV SSGEGTSTGS GGSGGSGGAD DIVLTQSPAT LSLSPGERAT LSCRASQSVS  300
YMNWYQQKPG KAPKRWIYDT SKVASGVPAR FSGSGSGTDY SLTINSLEAE DAATYYCQQW  360
SSNPLTFGGG TKVEIKGGGG SELVMTQSPS SLTVTAGEKV TMSCKSSQSL LNSGNQKNYL  420
TWYQQKPGQP PKLLIYWAST RESGVPDRFT GSGSGTDFTL TISSVQAEDL AVYYCQNDYS  480
YPLTFGAGTK LEIKGTAEAA SASGLSGRSD NHSPLGLAGS PGSPAGSPTS TEEGTSESAT  540
PESGPGTSTE PSEGSAPGSP AGSPTSTEEG TSTEPSEGSA PGTSTEPSEG SAPGTSESAT  600
PESGPGSEPA TSGSETPGSE PATSGSETPG SPAGSPTSTE EGTSESATPE SGPGTSTEPS  660
EGSAPGTSTE PSEGSAPGSP AGSPTSTEEG TSTEPSEGSA PGTSTEPSEG SAPGTSESAT  720
PESGPGTSTE PSEGSAPGTS ESATPESGPG SEPATSGSET PGTSTEPSEG SAPGTSTEPS  780
EGSAPGTSES ATPESGPGTS ESATPESGPG SPAGSPTSTE EGTSESATPE SGPGSEPATS  840
GSETPGTSES ATPESGPGTS TEPSEGSAPG TSTEPSEGSA PGTSTEPSEG SAPGTSTEPS  900
EGSAPGTSTE PSEGSAPGTS TEPSEGSAPG SPAGSPTSTE EGTSTEPSEG SAPGTSESAT  960
PESGPGSEPA TSGSETPGTS ESATPESGPG SEPATSGSET PGTSESATPE SGPGTSTEPS  1020
EGSAPGTSES ATPESGPGSP AGSPTSTEEG SPAGSPTSTE EGSPAGSPTS TEEGTSESAT  1080
PESGPGTSTE PSEGSAPGTS ESATPESGPG SEPATSGSET PGTSESATPE SGPGSEPATS  1140
GSETPGTSES ATPESGPGTS TEPSEGSAPG SPAGSPTSTE EGTSESATPE SGPGSEPATS  1200
GSETPGTSES ATPESGPGSP AGSPTSTEEG SPAGSPTSTE EGTSTEPSEG SAPGTSESAT  1260
PESGPGTSES ATPESGPGTS ESATPESGPG SEPATSGSET PGSEPATSGS ETPGSPAGSP  1320
TSTEEGTSTE PSEGSAPGTS TEPSEGSAPG SEPATSGSET PGTSESATPE SGPGTSTEPS  1380
EGSAPG                                                            1386

SEQ ID NO: 488           moltype = AA  length = 1380
FEATURE                  Location/Qualifiers
REGION                   1..1380
                         note = Description of Artificial Sequence: Synthetic
                          polypeptide
source                   1..1380
                         mol_type = protein
                         organism = synthetic construct
SEQUENCE: 488
HHHHHHHHDV QLVQSGAEVK KPGASVKVSC KASGYTFTRY TMHWVRQAPG QGLEWIGYIN  60
PSRGYTNYAD SVKGRFTITT DKSTSTAYME LSSLRSEDTA TYYCARYYDD HYCLDYWGQG  120
TTVTVSSGGS ELVMTQSPSS LTVTAGEKVT MSCKSSQSLL NSGNQKNYLT WYQQKPGQPP  180
KLLIYWASTR ESGVPDRFTG SGSGTDFTLT ISSVQAEDLA VYYCQNDYSY PLTFGAGTKL  240
EIKGGGGSGG GGSGGGGSEV QLLEQSGAEL VRPGTSVKIS CKASGYAFTN YWLGWVKQRP  300
```

-continued

```
GHGLEWIGDI FPGSGNIHYN EKFKGKATLT ADKSSSTAYM QLSSLTFEDS AVYFCARLRN  360
WDEPMDYWGQ GTTVTVSSGG GSDIVLTQSP ATLSLSPGER ATLSCRASQS VSYMNWYQQK  420
PGKAPKRWIY DTSKVASGVP ARFSGSGSGT DYSLTINSLE AEDAATYYCQ QWSSNPLTFG  480
GGTKVEIKGT AEAASASGLS GRSDNHSPLG LAGSPGSPAG SPTSTEEGTS ESATPESGPG  540
TSTEPSEGSA PGSPAGSPTS TEEGTSTEPS EGSAPGTSTE PSEGSAPGTS ESATPESGPG  600
SEPATSGSET PGSEPATSGS ETPGSPAGSP TSTEEGTSES ATPESGPGTS TEPSEGSAPG  660
TSTEPSEGSA PGSPAGSPTS TEEGTSTEPS EGSAPGTSTE PSEGSAPGTS ESATPESGPG  720
TSTEPSEGSA PGTSESATPE SGPGSEPATS GSETPGTSTE PSEGSAPGTS TEPSEGSAPG  780
TSESATPESG PGTSESATPE SGPGSPAGSP TSTEEGTSES ATPESGPGSE PATSGSETPG  840
TSESATPESG PGTSTEPSEG SAPGTSTEPS EGSAPGTSTE PSEGSAPGTS TEPSEGSAPG  900
TSTEPSEGSA PGTSTEPSEG SAPGSPAGSP TSTEEGTSTE PSEGSAPGTS ESATPESGPG  960
SEPATSGSET PGTSESATPE SGPGSEPATS GSETPGTSES ATPESGPGTS TEPSEGSAPG  1020
TSESATPESG PGSPAGSPTS TEEGSPAGSP TSTEEGSPAG SPTSTEEGTS ESATPESGPG  1080
TSTEPSEGSA PGTSESATPE SGPGSEPATS GSETPGTSES ATPESGPGSE PATSGSETPG  1140
TSESATPESG PGTSTEPSEG SAPGSPAGSP TSTEEGTSES ATPESGPGSE PATSGSETPG  1200
TSESATPESG PGSPAGSPTS TEEGSPAGSP TSTEEGTSTE PSEGSAPGTS ESATPESGPG  1260
TSESATPESG PGTSESATPE SGPGSEPATS GSETPGSEPA TSGSETPGSP AGSPTSTEEG  1320
TSTEPSEGSA PGTSTEPSEG SAPGSEPATS GSETPGTSES ATPESGPGTS TEPSEGSAPG  1380

SEQ ID NO: 489          moltype = AA  length = 1372
FEATURE                 Location/Qualifiers
REGION                  1..1372
                        note = Description of Artificial Sequence: Synthetic
                         polypeptide
source                  1..1372
                        mol_type = protein
                        organism = synthetic construct
SEQUENCE: 489
HHHHHHHHEL VMTQSPSSLT VTAGEKVTMS CKSSQSLLNS GNQKNYLTWY QQKPGQPPKL  60
LIYWASTRES GVPDRFTGSG SGTDFTLTIS SVQAEDLAVY YCQNDYSYPL TFGAGTKLEI  120
KGGGGSGGGG SGGGGSEVQL LEQSGAELVR PGTSVKISCK ASGYAFTNYW LGWVKQRPGH  180
GLEWIGDIFP GSGNIHYNEK FKGKATLTAD KSSSTAYMQL SSLTFEDSAV YFCARLRNWD  240
EPMDYWGQGT TVTVSSGGGG SDVQLVQSGA EVKKPGASVK VSCKASGYTF TRYTMHWVRQ  300
APGQGLEWIG YINPSRGYTN YADSVKGRFT ITTDKSTSTA YMELSSLRSE DTATYYCARY  360
YDDHYCLDYW GQGTTVTVSS GEGTSTGSGG SGGSGGADDI VLTQSPATLS LSPGERATLS  420
CRASQSVSYM NWYQQKPGKA PKRWIYDTSK VASGVPARFS GSGSGTDYSL TINSLEAEDA  480
ATYYCQQWSS NPLTFGGGTK VEIKGSPGSP AGSPTSTEEG TSESATPESG PGTSTEPSEG  540
SAPGSPAGSP TSTEEGTSTE PSEGSAPGTS TEPSEGSAPG TSESATPESG PGSEPATSGS  600
ETPGSEPATS GSETPGSPAG SPTSTEEGTS ESATPESGPG TSTEPSEGSA PGTSTEPSEG  660
SAPGSPAGSP TSTEEGTSTE PSEGSAPGTS TEPSEGSAPG TSESATPESG PGTSTEPSEG  720
SAPGTSESAT PESGPGSEPA TSGSETPGTS TEPSEGSAPG TSTEPSEGSA PGTSESATPE  780
SGPGTSESAT PESGPGSPAG SPTSTEEGTS ESATPESGPG SEPATSGSET PGTSESATPE  840
SGPGTSTEPS EGSAPGTSTE PSEGSAPGTS TEPSEGSAPG TSTEPSEGSA PGTSTEPSEG  900
SAPGTSTEPS EGSAPGSPAG SPTSTEEGTS TEPSEGSAPG TSESATPESG PGSEPATSGS  960
ETPGTSESAT PESGPGSEPA TSGSETPGTS ESATPESGPG TSTEPSEGSA PGTSESATPE  1020
SGPGSPAGSP TSTEEGSPAG SPTSTEEGSP AGSPTSTEEG TSESATPESG PGTSTEPSEG  1080
SAPGTSESAT PESGPGSEPA TSGSETPGTS ESATPESGPG SEPATSGSET PGTSESATPE  1140
SGPGTSTEPS EGSAPGSPAG SPTSTEEGTS ESATPESGPG SEPATSGSET PGTSESATPE  1200
SGPGSPAGSP TSTEEGSPAG SPTSTEEGTS TEPSEGSAPG TSESATPESG PGTSESATPE  1260
SGPGTSESAT PESGPGSEPA TSGSETPGSE PATSGSETPG SPAGSPTSTE EGTSTEPSEG  1320
SAPGTSTEPS EGSAPGSEPA TSGSETPGTS ESATPESGPG TSTEPSEGSA PG          1372

SEQ ID NO: 490          moltype = AA  length = 1411
FEATURE                 Location/Qualifiers
REGION                  1..1411
                        note = Description of Artificial Sequence: Synthetic
                         polypeptide
source                  1..1411
                        mol_type = protein
                        organism = synthetic construct
SEQUENCE: 490
HHHHHHHHEL VMTQSPSSLT VTAGEKVTMS CKSSQSLLNS GNQKNYLTWY QQKPGQPPKL  60
LIYWASTRES GVPDRFTGSG SGTDFTLTIS SVQAEDLAVY YCQNDYSYPL TFGAGTKLEI  120
KGGGGSGGGG SGGGGSEVQL LEQSGAELVR PGTSVKISCK ASGYAFTNYW LGWVKQRPGH  180
GLEWIGDIFP GSGNIHYNEK FKGKATLTAD KSSSTAYMQL SSLTFEDSAV YFCARLRNWD  240
EPMDYWGQGT TVTVSSGGGG SDIQMTQSPS SLSASVGDRV TITCRASQDI RNYLNWYQQK  300
PGKAPKLLIY YTSRLESGVP SRFSGSGSGT DYTLTISSLQ PEDFATYYCQ QGNTLPWTFG  360
QGTKVEIKRT SGPGDGGKGG PGKGPGGEGT KGTGPGGEVQ LVESGGGLVQ PGGSLRLSCA  420
ASGYSFTGYT MNWVRQAPGK GLEWVALINP YKGVSTYNQK FKDRFTISVD KSKNTAYLQM  480
NSLRAEDTAV YYCARSGYYG DSDWYFDVWG QGTLVTVSSG TAEAASASGL SGRSDNHSPL  540
GLAGSPGSPA GSPTSTEEGT SESATPESGP GTSTEPSEGS APGSPAGSPT STEEGTSTEP  600
SEGSAPGTST EPSEGSAPGT SESATPESGP GSEPATSGSE TPGSEPATSG SETPGSPAGS  660
PTSTEEGTSE SATPESGPGT STEPSEGSAP GTSTEPSEGS APGSPAGSPT STEEGTSTEP  720
SEGSAPGTST EPSEGSAPGT SESATPESGP GTSTEPSEGS APGTSESATP ESGPGSEPAT  780
SGSETPGTST EPSEGSAPGT STEPSEGSAP GTSESATPES GPGTSESATP ESGPGSPAGS  840
PTSTEEGTSE SATPESGPGS EPATSGSETP GTSESATPES GPGTSTEPSE GSAPGTSTEP  900
SEGSAPGTST EPSEGSAPGT STEPSEGSAP GTSTEPSEGS APGTSTEPSE GSAPGSPAGS  960
PTSTEEGTST EPSEGSAPGT SESATPESGP GSEPATSGSE TPGTSESATP ESGPGSEPAT  1020
SGSETPGTSE SATPESGPGT STEPSEGSAP GTSESATPES GPGSPAGSPT STEEGSPAGS  1080
```

-continued

```
PTSTEEGSPA GSPTSTEEGT SESATPESGP GTSTEPSEGS APGTSESATP ESGPGSEPAT  1140
SGSETPGTSE SATPESGPGS EPATSGSETP GTSESATPES GPGTSTEPSE GSAPGSPAGS  1200
PTSTEEGTSE SATPESGPGS EPATSGSETP GTSESATPES GPGSPAGSPT STEEGSPAGS  1260
PTSTEEGTST EPSEGSAPGT SESATPESGP GTSESATPES GPGTSESATP ESGPGSEPAT  1320
SGSETPGSEP ATSGSETPGS PAGSPTSTEE GTSTEPSEGS APGTSTEPSE GSAPGSEPAT  1380
SGSETPGTSE SATPESGPGT STEPSEGSAP G                                 1411

SEQ ID NO: 491         moltype = AA  length = 1411
FEATURE                Location/Qualifiers
REGION                 1..1411
                       note = Description of Artificial Sequence: Synthetic
                        polypeptide
source                 1..1411
                       mol_type = protein
                       organism = synthetic construct
SEQUENCE: 491
HHHHHHHHEL VMTQSPSSLT VTAGEKVTMS CKSSQSLLNS GNQKNYLTWY QQKPGQPPKL  60
LIYWASTRES GVPDRFTGSG SGTDFTLTIS SVQAEDLAVY YCQNDYSYPL TFGAGTKLEI  120
KGGGGSGGGG SGGGGSEVQL LEQSGAELVR PGTSVKISCK ASGYAFTNYW LGWVKQRPGH  180
GLEWIGDIFP GSGNIHYNEK FKGKATLTAD KSSSTAYMQL SSLTFEDSAV YFCARLRNWD  240
EPMDYWGQGT TVTVSSGGGG SEVQLVESGG GLVQPGGSLR LSCAASGYSF TGYTMNWVRQ  300
APGKGLEWVA LINPYKGVST YNQKFKDRFT ISVDKSKNTA YLQMNSLRAE DTAVYYCARS  360
GYYGDSDWYF DVWGQGTLVT VSSRTSGPGD GGKGGPGKGP GGEGTKGTGP GGDIQMTQSP  420
SSLSASVGDR VTITCRASQD IRNYLNWYQQ KPGKAPKLLI YYTSRLESGV PSRFSGSGSG  480
TDYTLTISSL QPEDFATYYC QQGNTLPWTF GQGTKVEIKG TAEAASASGL SGRSDNHSPL  540
GLAGSPGSPA GSPTSTEEGT SESATPESGP GTSTEPSEGS APGSPAGSPT STEEGTSTEP  600
SEGSAPGTST EPSEGSAPGT SESATPESGP GSEPATSGSE TPGSEPATSG SETPGSPAGS  660
PTSTEEGTSE SATPESGPGT STEPSEGSAP GTSTEPSEGS APGSPAGSPT STEEGTSTEP  720
SEGSAPGTST EPSEGSAPGT SESATPESGP GTSTEPSEGS APGTSESATP ESGPGSEPAT  780
SGSETPGTST EPSEGSAPGT STEPSEGSAP GTSESATPES GPGTSESATP ESGPGSPAGS  840
PTSTEEGTSE SATPESGPGS EPATSGSETP GTSESATPES GPGTSTEPSE GSAPGTSTEP  900
SEGSAPGTST EPSEGSAPGT STEPSEGSAP GTSTEPSEGS APGTSTEPSE GSAPGSPAGS  960
PTSTEEGTST EPSEGSAPGT SESATPESGP GSEPATSGSE TPGTSESATP ESGPGSEPAT  1020
SGSETPGTSE SATPESGPGT STEPSEGSAP GTSESATPES GPGSPAGSPT STEEGSPAGS  1080
PTSTEEGSPA GSPTSTEEGT SESATPESGP GTSTEPSEGS APGTSESATP ESGPGSEPAT  1140
SGSETPGTSE SATPESGPGS EPATSGSETP GTSESATPES GPGTSTEPSE GSAPGSPAGS  1200
PTSTEEGTSE SATPESGPGS EPATSGSETP GTSESATPES GPGSPAGSPT STEEGSPAGS  1260
PTSTEEGTST EPSEGSAPGT SESATPESGP GTSESATPES GPGTSESATP ESGPGSEPAT  1320
SGSETPGSEP ATSGSETPGS PAGSPTSTEE GTSTEPSEGS APGTSTEPSE GSAPGSEPAT  1380
SGSETPGTSE SATPESGPGT STEPSEGSAP G                                 1411

SEQ ID NO: 492         moltype = AA  length = 1423
FEATURE                Location/Qualifiers
REGION                 1..1423
                       note = Description of Artificial Sequence: Synthetic
                        polypeptide
source                 1..1423
                       mol_type = protein
                       organism = synthetic construct
SEQUENCE: 492
HHHHHHHHGT SESATPESGP GSEPATSGSE TPGTSESATP ESGPGSEPAT SGSETPGTSE  60
SATPESGPGT STEPSEGSAP GSPAGSPTST EEGTSESATP ESGPGSEPAT SGSETPGTSE  120
SATPESGPGS PAGSPTSTEE GSPAGSPTST EEGTSTEPSE GSAPGTSESA TPESGPGTSE  180
SATPESGPGT SESATPESGP GSEPATSGSE TPGSEPATSG SETPGSPAGS PTSTEEGTST  240
EPSEGSAPGT STEPSEGSAP GSEPATSGSE TPGTSESATP ESGPGTSTEP SEGSAPGLSG  300
RSDNHSPLGL AGSGTAEAAS ASGELVMTQS PSSLTVTAGE KVTMSCKSSQ SLLNSGNQKN  360
YLTWYQQKPG QPPKLLIYWA STRESGVPDR FTGSGSGTDF TLTISSVQAE DLAVYYCQND  420
YSYPLTFGAG TKLEIKGGGG SGGGGSGGGG SEVQLLEQSG AELVRPGTSV KISCKASGYA  480
FTNYWLGWVK QRPGHGLEWI GDIFPGSGNI HYNEKFKGKA TLTADKSSST AYMQLSSLTF  540
EDSAVYFCAR LRNWDEPMDY WGQGTTVTVS SGGGGSDVQL VQSGAEVKKP GASVKVSCKA  600
SGYTFTRYTM HWVRQAPGQG LEWIGYINPS RGYTNYADSV KGRFTITTDK STSTAYMELS  660
SLRSEDTATY YCARYYDDHY CLDYWGQGTT VTVSSGEGTS TGSGGSGGSG GADDIVLTQS  720
PATLSLSPGE RATLSCRASQ SVSYMNWYQQ KPGKAPKRWI YDTSKVASGV PARFSGSGSG  780
TDYSLTINSL EAEDAATYYC QQWSSNPLTF GGGTKVEIKG TAEAASASGL SGRSDNHSPL  840
GLAGSPGSPA GSPTSTEEGT SESATPESGP GTSTEPSEGS APGSPAGSPT STEEGTSTEP  900
SEGSAPGTST EPSEGSAPGT SESATPESGP GSEPATSGSE TPGSEPATSG SETPGSPAGS  960
PTSTEEGTSE SATPESGPGT STEPSEGSAP GTSTEPSEGS APGSPAGSPT STEEGTSTEP  1020
SEGSAPGTST EPSEGSAPGT SESATPESGP GTSTEPSEGS APGTSESATP ESGPGSEPAT  1080
SGSETPGTST EPSEGSAPGT STEPSEGSAP GTSESATPES GPGTSESATP ESGPGSPAGS  1140
PTSTEEGTSE SATPESGPGS EPATSGSETP GTSESATPES GPGTSTEPSE GSAPGTSTEP  1200
SEGSAPGTST EPSEGSAPGT STEPSEGSAP GTSTEPSEGS APGTSTEPSE GSAPGSPAGS  1260
PTSTEEGTST EPSEGSAPGT SESATPESGP GSEPATSGSE TPGTSESATP ESGPGSEPAT  1320
SGSETPGTSE SATPESGPGT STEPSEGSAP GTSESATPES GPGSPAGSPT STEEGSPAGS  1380
PTSTEEGSPA GSPTSTEEGT SESATPESGP GTSTEPSEGS APG                    1423

SEQ ID NO: 493         moltype = AA  length = 1398
FEATURE                Location/Qualifiers
REGION                 1..1398
                       note = Description of Artificial Sequence: Synthetic
```

```
                         polypeptide
source                  1..1398
                        mol_type = protein
                        organism = synthetic construct
SEQUENCE: 493
GSPGSPAGSP TSTEEGTSES ATPESGPGTS TEPSEGSAPG SPAGSPTSTE EGTSTEPSEG  60
SAPGTSTEPS EGSAPGTSES ATPESGPGSE PATSGSETPG SEPATSGSET PGSPAGSPTS  120
TEEGTSESAT PESGPGTSTE PSEGSAPGTS TEPSEGSAPG SPAGSPTSTE EGTSTEPSEG  180
SAPGTSTEPS EGSAPGTSES ATPESGPGTS TEPSEGSAPG TSESATPESG PGSEPATSGS  240
ETPGTSTEPS EGSAPGTSTE PSEGSAPGTS ESATPESGPG TSESATPESG PGSPAGSPTS  300
TEEGTSESAT PESGPGSEPA TSGSETPGTS ESATPESGPG TSTEPSEGSA PGTSTEPSEG  360
SAPGTSTEPS EGSAPGTSTE PSEGSAPGTS TEPSEGSAPG TSTEPSEGSA PGSPAGSPTS  420
TEEGTSTEPS EGSAPGTSES ATPESGPGSE PATSGSETPG TSESATPESG PGSEPATSGS  480
ETPGTSESAT PESGPGTSTE PSEGSAPGTS ESATPESGPG SPAGSPTSTE EGSPAGSPTS  540
TEEGSPAGSP TSTEEGTSES ATPESGPGTS TEPSEGSAPG TSESATPESG PGSEPATSGS  600
ETPGTSESAT PESGPGSEPA TSGSETPGTS ESATPESGPG TSTEPSEGSA PGSPAGSPTS  660
TEEGTSESAT PESGPGSEPA TSGSETPGTS ESATPESGPG SPAGSPTSTE EGSPAGSPTS  720
TEEGTSTEPS EGSAPGTSES ATPESGPGTS ESATPESGPG TSESATPESG PGSEPATSGS  780
ETPGSEPATS GSETPGSPAG SPTSTEEGTS TEPSEGSAPG TSTEPSEGSA PGSEPATSGS  840
ETPGTSESAT PESGPGTSTE PSEGSAPGLS GRSDNHSPLG LAGSGTAEAA SASGELVMTQ  900
SPSSLTVTAG EKVTMSCKSS QSLLNSGNQK NYLTWYQQKP GQPPKLLIYW ASTRESGVPD  960
RFTGSGSGTD FTLTISSVQA EDLAVYYCQN DYSYPLTFGA GTKLEIKGGG GSGGGGSGGG  1020
GSEVQLLEQS GAELVRPGTS VKISCKASGY AFTNYWLGWV KQRPGHGLEW IGDIFPGSGN  1080
IHYNEKFKGK ATLTADKSSS TAYMQLSSLT FEDSAVYFCA RLRNWDEPMD YWGQGTTVTV  1140
SSGGGGSDVQ LVQSGAEVKK PGASVKVSCK ASGYTFTRYT MHWVRQAPGQ GLEWIGYINP  1200
SRGYTNYADS VKGRFTITTD KSTSTAYMEL SSLRSEDTAT YYCARYYDDH YCLDYWGQGT  1260
TVTVSSGEGT STGSGGSGGS GGADDIVLTQ SPATLSLSPG ERATLSCRAS QSVSYMNWYQ  1320
QKPGKAPKRW IYDTSKVASG VPARFSGSGS GTDYSLTINS LEAEDAATYY CQQWSSNPLT  1380
FGGGTKVEIK HHHHHHHH                                              1398

SEQ ID NO: 494          moltype = AA  length = 1396
FEATURE                 Location/Qualifiers
REGION                  1..1396
                        note = Description of Artificial Sequence: Synthetic
                         polypeptide
source                  1..1396
                        mol_type = protein
                        organism = synthetic construct
SEQUENCE: 494
HHHHHHHHEL VMTQSPSSLT VTAGEKVTMS CKSSQSLLNS GNQKNYLTWY QQKPGQPPKL  60
LIYWASTRES GVPDRFTGSG SGTDFTLTIS SVQAEDLAVY YCQNDYSYPL TFGAGTKLEI  120
KGGGGSGGGG SGGGGSEVQL LEQSGAELVR PGTSVKISCK ASGYAFTNYW LGWVKQRPGH  180
GLEWIGDIFP GSGNIHYNEK FKGKATLTAD KSSSTAYMQL SSLTFEDSAV YFCARLRNWD  240
EPMDYWGQGT TVTVSSGGGG SDIVLTQSPA TLSLSPGERA TLSCRASQSV SYMNWYQQKP  300
GKAPKRWIYD TSKVASGVPA RFSGSGSGTD YSLTINSLEA EDAATYYCQQ WSSNPLTFGG  360
GTKVEIKGEG TSTGSGGSGG SGGADDVQLV QSGAEVKKPG ASVKVSCKAS GYTFTRYTMH  420
WVRQAPGQGL EWIGYINPSR GYTNYADSVK GRFTITTDKS TSTAYMELSS LRSEDTATYY  480
CARYYDDHYC LDYWGQGTTV TVSSGTAEAA SASGLSGRSD NHSPLGLAGS PGSPAGSPTS  540
TEEGTSESAT PESGPGTSTE PSEGSAPGSP AGSPTSTEEG TSTEPSEGSA PGTSTEPSEG  600
SAPGTSESAT PESGPGSEPA TSGSETPGSE PATSGSETPG SPAGSPTSTE EGTSESATPE  660
SGPGTSTEPS EGSAPGTSTE PSEGSAPGSP AGSPTSTEEG TSTEPSEGSA PGTSTEPSEG  720
SAPGTSESAT PESGPGTSTE PSEGSAPGTS ESATPESGPG SEPATSGSET PGTSTEPSEG  780
SAPGTSTEPS EGSAPGTSES ATPESGPGTS ESATPESGPG SPAGSPTSTE EGTSESATPE  840
SGPGSEPATS GSETPGTSES ATPESGPGTS TEPSEGSAPG TSTEPSEGSA PGTSTEPSEG  900
SAPGTSTEPS EGSAPGTSTE PSEGSAPGTS TEPSEGSAPG SPAGSPTSTE EGTSTEPSEG  960
SAPGTSESAT PESGPGSEPA TSGSETPGTS ESATPESGPG SEPATSGSET PGTSESATPE  1020
SGPGTSTEPS EGSAPGTSES ATPESGPGSP AGSPTSTEEG SPAGSPTSTE EGSPAGSPTS  1080
TEEGTSESAT PESGPGTSTE PSEGSAPGTS ESATPESGPG SEPATSGSET PGTSESATPE  1140
SGPGSEPATS GSETPGTSES ATPESGPGTS TEPSEGSAPG SPAGSPTSTE EGTSESATPE  1200
SGPGSEPATS GSETPGTSES ATPESGPGSP AGSPTSTEEG SPAGSPTSTE EGTSTEPSEG  1260
SAPGTSESAT PESGPGTSES ATPESGPGTS ESATPESGPG SEPATSGSET PGSEPATSGS  1320
ETPGSPAGSP TSTEEGTSTE PSEGSAPGTS TEPSEGSAPG SEPATSGSET PGTSESATPE  1380
SGPGTSTEPS EGSAPG                                                1396

SEQ ID NO: 495          moltype = AA  length = 1396
FEATURE                 Location/Qualifiers
REGION                  1..1396
                        note = Description of Artificial Sequence: Synthetic
                         polypeptide
source                  1..1396
                        mol_type = protein
                        organism = synthetic construct
SEQUENCE: 495
HHHHHHHHEV QLLEQSGAEL VRPGTSVKIS CKASGYAFTN YWLGWVKQRP GHGLEWIGDI  60
FPGSGNIHYN EKFKGKATLT ADKSSSTAYM QLSSLTFEDS AVYFCARLRN WDEPMDYWGQ  120
GTTVTVSSGG GGSGGGGSGG GGSELVMTQS PSSLTVTAGE KVTMSCKSSQ SLLNSGNQKN  180
YLTWYQQKPG QPPKLLIYWA STRESGVPDR FTGSGSGTDF TLTISSVQAE DLAVYYCQND  240
YSYPLTFGAG TKLEIKGGGG SDVQLVQSGA EVKKPGASVK VSCKASGYTF TRYTMHWVRQ  300
APGQGLEWIG YINPSRGYTN YADSVKGRFT ITTDKSTSTA YMELSSLRSE DTATYYCARY  360
```

```
YDDHYCLDYW GQGTTVTVSS GEGTSTGSGG SGGSGGADDI VLTQSPATLS LSPGERATLS  420
CRASQSVSYM NWYQQKPGKA PKRWIYDTSK VASGVPARFS GSGSGTDYSL TINSLEAEDA  480
ATYYCQQWSS NPLTFGGGTK VEIKGTAEAA SASGLSGRSD NHSPLGLAGS PGSPAGSPTS  540
TEEGTSESAT PESGPGTSTE PSEGSAPGSP AGSPTSTEEG TSTEPSEGSA PGTSTEPSEG  600
SAPGTSESAT PESGPGSEPA TSGSETPGSE PATSGSETPG SPAGSPTSTE EGTSESATPE  660
SGPGTSTEPS EGSAPGTSTE PSEGSAPGSP AGSPTSTEEG TSTEPSEGSA PGTSTEPSEG  720
SAPGTSESAT PESGPGTSTE PSEGSAPGTS ESATPESGPG SEPATSGSET PGTSTEPSEG  780
SAPGTSTEPS EGSAPGTSES ATPESGPGTS ESATPESGPG SPAGSPTSTE EGTSESATPE  840
SGPGSEPATS GSETPGTSES ATPESGPGTS TEPSEGSAPG TSTEPSEGSA PGTSTEPSEG  900
SAPGTSTEPS EGSAPGTSTE PSEGSAPGTS TEPSEGSAPG SPAGSPTSTE EGTSTEPSEG  960
SAPGTSESAT PESGPGSEPA TSGSETPGTS ESATPESGPG SEPATSGSET PGTSESATPE  1020
SGPGTSTEPS EGSAPGTSES ATPESGPGSP AGSPTSTEEG SPAGSPTSTE EGSPAGSPTS  1080
TEEGTSESAT PESGPGTSTE PSEGSAPGTS ESATPESGPG SEPATSGSET PGTSESATPE  1140
SGPGSEPATS GSETPGTSES ATPESGPGTS TEPSEGSAPG SPAGSPTSTE EGTSESATPE  1200
SGPGSEPATS GSETPGTSES ATPESGPGSP AGSPTSTEEG SPAGSPTSTE EGTSTEPSEG  1260
SAPGTSESAT PESGPGTSES ATPESGPGTS ESATPESGPG SEPATSGSET PGSEPATSGS  1320
ETPGSPAGSP TSTEEGTSTE PSEGSAPGTS TEPSEGSAPG SEPATSGSET PGTSESATPE  1380
SGPGTSTEPS EGSAPG                                                  1396

SEQ ID NO: 496         moltype = AA  length = 1396
FEATURE                Location/Qualifiers
REGION                 1..1396
                       note = Description of Artificial Sequence: Synthetic
                        polypeptide
source                 1..1396
                       mol_type = protein
                       organism = synthetic construct
SEQUENCE: 496
HHHHHHHHDV QLVQSGAEVK KPGASVKVSC KASGYTFTRY TMHWVRQAPG QGLEWIGYIN  60
PSRGYTNYAD SVKGRFTITT DKSTSTAYME LSSLRSEDTA TYYCARYYDD HYCLDYWGQG  120
TTVTVSSGEG TSTGSGGSGG SGGADDIVLT QSPATLSLSP GERATLSCRA SQSVSYMNWY  180
QQKPGKAPKR WIYDTSKVAS GVPARFSGSG SGTDYSLTIN SLEAEDAATY YCQQWSSNPL  240
TFGGGTKVEI KGGGGSELVM TQSPSSLTVT AGEKVTMSCK SSQSLLNSGN QKNYLTWYQQ  300
KPGQPPKLLI YWASTRESGV PDRFTGSGSG TDFTLTISSV QAEDLAVYYC QNDYSYPLTF  360
GAGTKLEIKG GGGSGGGGSG GGGSEVQLLE QSGAELVRPG TSVKISCKAS GYAFTNYWLG  420
WVKQRPGHGL EWIGDIFPGS GNIHYNEKFK GKATLTADKS SSTAYMQLSS LTFEDSAVYF  480
CARLRNWDEP MDYWGQGTTV TVSSGTAEAA SASGLSGRSD NHSPLGLAGS PGSPAGSPTS  540
TEEGTSESAT PESGPGTSTE PSEGSAPGSP AGSPTSTEEG TSTEPSEGSA PGTSTEPSEG  600
SAPGTSESAT PESGPGSEPA TSGSETPGSE PATSGSETPG SPAGSPTSTE EGTSESATPE  660
SGPGTSTEPS EGSAPGTSTE PSEGSAPGSP AGSPTSTEEG TSTEPSEGSA PGTSTEPSEG  720
SAPGTSESAT PESGPGTSTE PSEGSAPGTS ESATPESGPG SEPATSGSET PGTSTEPSEG  780
SAPGTSTEPS EGSAPGTSES ATPESGPGTS ESATPESGPG SPAGSPTSTE EGTSESATPE  840
SGPGSEPATS GSETPGTSES ATPESGPGTS TEPSEGSAPG TSTEPSEGSA PGTSTEPSEG  900
SAPGTSTEPS EGSAPGTSTE PSEGSAPGTS TEPSEGSAPG SPAGSPTSTE EGTSTEPSEG  960
SAPGTSESAT PESGPGSEPA TSGSETPGTS ESATPESGPG SEPATSGSET PGTSESATPE  1020
SGPGTSTEPS EGSAPGTSES ATPESGPGSP AGSPTSTEEG SPAGSPTSTE EGSPAGSPTS  1080
TEEGTSESAT PESGPGTSTE PSEGSAPGTS ESATPESGPG SEPATSGSET PGTSESATPE  1140
SGPGSEPATS GSETPGTSES ATPESGPGTS TEPSEGSAPG SPAGSPTSTE EGTSESATPE  1200
SGPGSEPATS GSETPGTSES ATPESGPGSP AGSPTSTEEG SPAGSPTSTE EGTSTEPSEG  1260
SAPGTSESAT PESGPGTSES ATPESGPGTS ESATPESGPG SEPATSGSET PGSEPATSGS  1320
ETPGSPAGSP TSTEEGTSTE PSEGSAPGTS TEPSEGSAPG SEPATSGSET PGTSESATPE  1380
SGPGTSTEPS EGSAPG                                                  1396

SEQ ID NO: 497         moltype = AA  length = 1396
FEATURE                Location/Qualifiers
REGION                 1..1396
                       note = Description of Artificial Sequence: Synthetic
                        polypeptide
source                 1..1396
                       mol_type = protein
                       organism = synthetic construct
SEQUENCE: 497
HHHHHHHHDI VLTQSPATLS LSPGERATLS CRASQSVSYM NWYQQKPGKA PKRWIYDTSK  60
VASGVPARFS GSGSGTDYSL TINSLEAEDA ATYYCQQWSS NPLTFGGGTK VEIKGEGTST  120
GSGGSGGSGG ADDVQLVQSG AEVKKPGASV KVSCKASGYT FTRYTMHWVR QAPGQGLEWI  180
GYINPSRGYT NYADSVKGRF TITTDKSTST AYMELSSLRS EDTATYYCAR YYDDHYCLDY  240
WGQGTTVTVS SGGGGSELVM TQSPSSLTVT AGEKVTMSCK SSQSLLNSGN QKNYLTWYQQ  300
KPGQPPKLLI YWASTRESGV PDRFTGSGSG TDFTLTISSV QAEDLAVYYC QNDYSYPLTF  360
GAGTKLEIKG GGGSGGGGSG GGGSEVQLLE QSGAELVRPG TSVKISCKAS GYAFTNYWLG  420
WVKQRPGHGL EWIGDIFPGS GNIHYNEKFK GKATLTADKS SSTAYMQLSS LTFEDSAVYF  480
CARLRNWDEP MDYWGQGTTV TVSSGTAEAA SASGLSGRSD NHSPLGLAGS PGSPAGSPTS  540
TEEGTSESAT PESGPGTSTE PSEGSAPGSP AGSPTSTEEG TSTEPSEGSA PGTSTEPSEG  600
SAPGTSESAT PESGPGSEPA TSGSETPGSE PATSGSETPG SPAGSPTSTE EGTSESATPE  660
SGPGTSTEPS EGSAPGTSTE PSEGSAPGSP AGSPTSTEEG TSTEPSEGSA PGTSTEPSEG  720
SAPGTSESAT PESGPGTSTE PSEGSAPGTS ESATPESGPG SEPATSGSET PGTSTEPSEG  780
SAPGTSTEPS EGSAPGTSES ATPESGPGTS ESATPESGPG SPAGSPTSTE EGTSESATPE  840
SGPGSEPATS GSETPGTSES ATPESGPGTS TEPSEGSAPG TSTEPSEGSA PGTSTEPSEG  900
SAPGTSTEPS EGSAPGTSTE PSEGSAPGTS TEPSEGSAPG SPAGSPTSTE EGTSTEPSEG  960
SAPGTSESAT PESGPGSEPA TSGSETPGTS ESATPESGPG SEPATSGSET PGTSESATPE  1020
```

```
SGPGTSTEPS EGSAPGTSES ATPESGPGSP AGSPTSTEEG SPAGSPTSTE EGSPAGSPTS  1080
TEEGTSESAT PESGPGTSTE PSEGSAPGTS ESATPESGPG SEPATSGSET PGTSESATPE  1140
SGPGSEPATS GSETPGTSES ATPESGPGTS TEPSEGSAPG SPAGSPTSTE EGTSESATPE  1200
SGPGSEPATS GSETPGTSES ATPESGPGSP AGSPTSTEEG SPAGSPTSTE EGTSTEPSEG  1260
SAPGTSESAT PESGPGTSES ATPESGPGTS ESATPESGPG SEPATSGSET PGSEPATSGS  1320
ETPGSPAGSP TSTEEGTSTE PSEGSAPGTS TEPSEGSAPG SEPATSGSET PGTSESATPE  1380
SGPGTSTEPS EGSAPG                                                 1396

SEQ ID NO: 498         moltype = AA  length = 1420
FEATURE                Location/Qualifiers
REGION                 1..1420
                       note = Description of Artificial Sequence: Synthetic
                        polypeptide
source                 1..1420
                       mol_type = protein
                       organism = synthetic construct
SEQUENCE: 498
DIQMTQSPSS LSASVGDRVT ITCRSTKSLL HSNGITYLYW YQQKPGKAPK LLIYQMSNLA  60
SGVPSRFSSS GSGTDFTLTI SSLQPEDFAT YYCAQNLEIP RTFGQGTKVE IKGATPPETG  120
AETESPGETT GGSAESEPPG EGQVQLVQSG PGLVQPGGSV RISCAASGYT FTNYGMNWVK  180
QAPGKGLEWM GWINTYTGES TYADSFKGRF TFSLDTSASA AYLQINSLRA EDTAVYYCAR  240
FAIKGDYWGQ GTLLTVSSGG GGSDIQMTQS PSSLSASVGD RVTITCRASQ DIRNYLNWYQ  300
QKPGKAPKLL IYYTSRLESG VPSRFSGSGS GTDYTLTISS LQPEDFATYY CQQGNTLPWT  360
FGQGTKVEIK GATPPETGAE TESPGETTGG SAESEPPGEG EVQLVESGGG LVQPGGSLRL  420
SCAASGYSFT GYTMNWVRQA PGKGLEWVAL INPYKGVSTY NQKFKDRFTI SVDKSKNTAY  480
LQMNSLRAED TAVYYCARSG YYGDSDWYFD VWGQGTLVTV SSGTAEAASA SGLSGRSDNH  540
SPLGLAGSPG SPAGSPTSTE EGTSESATPE SGPGTSTEPS EGSAPGSPAG SPTSTEEGTS  600
TEPSEGSAPG TSTEPSEGSA PGTSESATPE SGPGSEPATS GSETPGSEPA TSGSETPGSP  660
AGSPTSTEEG TSESATPESG PGTSTEPSEG SAPGTSTEPS EGSAPGSPAG SPTSTEEGTS  720
TEPSEGSAPG TSTEPSEGSA PGTSESATPE SGPGTSTEPS EGSAPGTSES ATPESGPGSE  780
PATSGSETPG TSTEPSEGSA PGTSTEPSEG SAPGTSESAT PESGPGTSES ATPESGPGSP  840
AGSPTSTEEG TSESATPESG PGSEPATSGS ETPGTSESAT PESGPGTSTE PSEGSAPGTS  900
TEPSEGSAPG TSTEPSEGSA PGTSTEPSEG SAPGTSTEPS EGSAPGTSTE PSEGSAPGSP  960
AGSPTSTEEG TSTEPSEGSA PGTSESATPE SGPGSEPATS GSETPGTSES ATPESGPGSE  1020
PATSGSETPG TSESATPESG PGTSTEPSEG SAPGTSESAT PESGPGSPAG SPTSTEEGSP  1080
AGSPTSTEEG SPAGSPTSTE EGTSESATPE SGPGTSTEPS EGSAPGTSES ATPESGPGSE  1140
PATSGSETPG TSESATPESG PGSEPATSGS ETPGTSESAT PESGPGTSTE PSEGSAPGSP  1200
AGSPTSTEEG TSESATPESG PGSEPATSGS ETPGTSESAT PESGPGSPAG SPTSTEEGSP  1260
AGSPTSTEEG TSTEPSEGSA PGTSESATPE SGPGTSESAT PESGPGTSES ATPESGPGSE  1320
PATSGSETPG SEPATSGSET PGSPAGSPTS TEEGTSTEPS EGSAPGTSTE PSEGSAPGSE  1380
PATSGSETPG TSESATPESG PGTSTEPSEG SAPGHHHHHH                       1420

SEQ ID NO: 499         moltype = AA  length = 1396
FEATURE                Location/Qualifiers
REGION                 1..1396
                       note = Description of Artificial Sequence: Synthetic
                        polypeptide
source                 1..1396
                       mol_type = protein
                       organism = synthetic construct
SEQUENCE: 499
DIQMTQSPSS LSASVGDRVT ITCRSTKSLL HSNGITYLYW YQQKPGKAPK LLIYQMSNLA  60
SGVPSRFSSS GSGTDFTLTI SSLQPEDFAT YYCAQNLEIP RTFGQGTKVE IKGATPPETG  120
AETESPGETT GGSAESEPPG EGQVQLVQSG PGLVQPGGSV RISCAASGYT FTNYGMNWVK  180
QAPGKGLEWM GWINTYTGES TYADSFKGRF TFSLDTSASA AYLQINSLRA EDTAVYYCAR  240
FAIKGDYWGQ GTLLTVSSGG GGSDIQMTQS PSSLSASVGD RVTITCRASQ DIRNYLNWYQ  300
QKPGKAPKLL IYYTSRLESG VPSRFSGSGS GTDYTLTISS LQPEDFATYY CQQGNTLPWT  360
FGQGTKVEIK GATPPETGAE TESPGETTGG SAESEPPGEG EVQLVESGGG LVQPGGSLRL  420
SCAASGYSFT GYTMNWVRQA PGKGLEWVAL INPYKGVSTY NQKFKDRFTI SVDKSKNTAY  480
LQMNSLRAED TAVYYCARSG YYGDSDWYFD VWGQGTLVTV SSGSPGSPAG SPTSTEEGTS  540
ESATPESGPG TSTEPSEGSA PGSPAGSPTS TEEGTSTEPS EGSAPGTSTE PSEGSAPGTS  600
ESATPESGPG SEPATSGSET PGSEPATSGS ETPGSPAGSP TSTEEGTSES ATPESGPGTS  660
TEPSEGSAPG TSTEPSEGSA PGSPAGSPTS TEEGTSTEPS EGSAPGTSTE PSEGSAPGTS  720
ESATPESGPG TSTEPSEGSA PGTSESATPE SGPGSEPATS GSETPGTSTE PSEGSAPGTS  780
TEPSEGSAPG TSESATPESG PGTSESATPE SGPGSPAGSP TSTEEGTSES ATPESGPGSE  840
PATSGSETPG TSESATPESG PGTSTEPSEG SAPGTSTEPS EGSAPGTSTE PSEGSAPGTS  900
TEPSEGSAPG TSTEPSEGSA PGTSTEPSEG SAPGSPAGSP TSTEEGTSTE PSEGSAPGTS  960
ESATPESGPG SEPATSGSET PGTSESATPE SGPGSEPATS GSETPGTSES ATPESGPGTS  1020
TEPSEGSAPG TSESATPESG PGSPAGSPTS TEEGSPAGSP TSTEEGSPAG SPTSTEEGTS  1080
ESATPESGPG TSTEPSEGSA PGTSESATPE SGPGSEPATS GSETPGTSES ATPESGPGSE  1140
PATSGSETPG TSESATPESG PGTSTEPSEG SAPGSPAGSP TSTEEGTSES ATPESGPGSE  1200
PATSGSETPG TSESATPESG PGSPAGSPTS TEEGSPAGSP TSTEEGTSTE PSEGSAPGTS  1260
ESATPESGPG TSESATPESG PGTSESATPE SGPGSEPATS GSETPGSEPA TSGSETPGSP  1320
AGSPTSTEEG TSTEPSEGSA PGTSTEPSEG SAPGSEPATS GSETPGTSES ATPESGPGTS  1380
TEPSEGSAPG HHHHHH                                                 1396

SEQ ID NO: 500         moltype = AA  length = 1425
FEATURE                Location/Qualifiers
REGION                 1..1425
```

```
                       note = Description of Artificial Sequence: Synthetic
                        polypeptide
source                 1..1425
                       mol_type = protein
                       organism = synthetic construct
SEQUENCE: 500
DIVMTQSPLS LPVTPGEPAS ISCRSSKNLL HSNGITYLYW YLQKPGQSPQ LLIYQMSNLA  60
SGVPDRFSSS GSGTDFTLKI SRVEAEDVGV YYCAQNLEIP RTFGQGTKVE IKGATPPETG  120
AETESPGETT GGSAESEPPG EGQVQLVQSG PEVKKPGASV KVSCKASGYT FTNYGMNWVR  180
QAPGQGLEWM GWINTYTGEP TYGEDFKGRF AFSLDTSAST AYMELSSLRS EDTAVYFCAR  240
FGNYVDYWGQ GSLVTVSSGG GGSELVVTQE PSLTVSPGGT VTLTCRSSTG AVTTSNYANW  300
VQQKPGQAPR GLIGGTNKRA PGTPARFSGS LLGGKAALTL SGVQPEDEAE YYCALWYSNL  360
WVFGGGTKLT VLGATPPETG AETESPGETT GGSAESEPPG EGEVQLLESG GGLVQPGGSL  420
KLSCAASGFT FNTYAMNWVR QAPGKGLEWV ARIRSKYNNY ATYYADSVKD RFTISRDDSK  480
NTAYLQMNNL KTEDTAVYYC VRHGNFGNSY VSWFAYWGQG TLVTVSSGTA EAASASGLSG  540
RSDNHSPLGL AGSPGSPAGS PTSTEEGTSE SATPESGPGT STEPSEGSAP GSPAGSPTST  600
EEGTSTEPSE GSAPGTSTEP SEGSAPGTSE SATPESGPGS EPATSGSETP GSEPATSGSE  660
TPGSPAGSPT STEEGTSESA TPESGPGTST EPSEGSAPGT STEPSEGSAP GSPAGSPTST  720
EEGTSTEPSE GSAPGTSTEP SEGSAPGTSE SATPESGPGT STEPSEGSAP GTSESATPES  780
GPGSEPATSG SETPGTSTEP SEGSAPGTST EPSEGSAPGT SESATPESGP GTSESATPES  840
GPGSPAGSPT STEEGTSESA TPESGPGSEP ATSGSETPGT SESATPESGP GTSTEPSEGS  900
APGTSTEPSE GSAPGTSTEP SEGSAPGTST EPSEGSAPGT STEPSEGSAP GTSTEPSEGS  960
APGSPAGSPT STEEGTSTEP SEGSAPGTSE SATPESGPGS EPATSGSETP GTSESATPES  1020
GPGSEPATSG SETPGTSESA TPESGPGTST EPSEGSAPGT SESATPESGP GSPAGSPTST  1080
EEGSPAGSPT STEEGSPAGS PTSTEEGTSE SATPESGPGT STEPSEGSAP GTSESATPES  1140
GPGSEPATSG SETPGTSESA TPESGPGSEP ATSGSETPGT SESATPESGP GTSTEPSEGS  1200
APGSPAGSPT STEEGTSESA TPESGPGSEP ATSGSETPGT SESATPESGP GSPAGSPTST  1260
EEGSPAGSPT STEEGTSTEP SEGSAPGTSE SATPESGPGT SESATPESGP GTSESATPES  1320
GPGSEPATSG SETPGSEPAT SGSETPGSPA GSPTSTEEGT STEPSEGSAP GTSTEPSEGS  1380
APGSEPATSG SETPGTSESA TPESGPGTST EPSEGSAPGH HHHHH                 1425

SEQ ID NO: 501         moltype = AA  length = 1401
FEATURE                Location/Qualifiers
REGION                 1..1401
                       note = Description of Artificial Sequence: Synthetic
                        polypeptide
source                 1..1401
                       mol_type = protein
                       organism = synthetic construct
SEQUENCE: 501
DIVMTQSPLS LPVTPGEPAS ISCRSSKNLL HSNGITYLYW YLQKPGQSPQ LLIYQMSNLA  60
SGVPDRFSSS GSGTDFTLKI SRVEAEDVGV YYCAQNLEIP RTFGQGTKVE IKGATPPETG  120
AETESPGETT GGSAESEPPG EGQVQLVQSG PEVKKPGASV KVSCKASGYT FTNYGMNWVR  180
QAPGQGLEWM GWINTYTGEP TYGEDFKGRF AFSLDTSAST AYMELSSLRS EDTAVYFCAR  240
FGNYVDYWGQ GSLVTVSSGG GGSELVVTQE PSLTVSPGGT VTLTCRSSTG AVTTSNYANW  300
VQQKPGQAPR GLIGGTNKRA PGTPARFSGS LLGGKAALTL SGVQPEDEAE YYCALWYSNL  360
WVFGGGTKLT VLGATPPETG AETESPGETT GGSAESEPPG EGEVQLLESG GGLVQPGGSL  420
KLSCAASGFT FNTYAMNWVR QAPGKGLEWV ARIRSKYNNY ATYYADSVKD RFTISRDDSK  480
NTAYLQMNNL KTEDTAVYYC VRHGNFGNSY VSWFAYWGQG TLVTVSSGSP GSPAGSPTST  540
EEGTSESATP ESGPGTSTEP SEGSAPGSPA GSPTSTEEGT STEPSEGSAP GTSTEPSEGS  600
APGTSESATP ESGPGSEPAT SGSETPGSEP ATSGSETPGS PAGSPTSTEE GTSESATPES  660
GPGTSTEPSE GSAPGTSTEP SEGSAPGSPA GSPTSTEEGT STEPSEGSAP GTSTEPSEGS  720
APGTSESATP ESGPGTSTEP SEGSAPGTSE SATPESGPGS EPATSGSETP GTSTEPSEGS  780
APGTSTEPSE GSAPGTSESA TPESGPGTSE SATPESGPGS PAGSPTSTEE GTSESATPES  840
GPGSEPATSG SETPGTSESA TPESGPGTST EPSEGSAPGT STEPSEGSAP GTSTEPSEGS  900
APGTSTEPSE GSAPGTSTEP SEGSAPGTST EPSEGSAPGS PAGSPTSTEE GTSTEPSEGS  960
APGTSESATP ESGPGSEPAT SGSETPGTSE SATPESGPGS EPATSGSETP GTSESATPES  1020
GPGTSTEPSE GSAPGTSESA TPESGPGSPA GSPTSTEEGS PAGSPTSTEE GSPAGSPTST  1080
EEGTSESATP ESGPGTSTEP SEGSAPGTSE SATPESGPGS EPATSGSETP GTSESATPES  1140
GPGSEPATSG SETPGTSESA TPESGPGTST EPSEGSAPGS PAGSPTSTEE GTSESATPES  1200
GPGSEPATSG SETPGTSESA TPESGPGSPA GSPTSTEEGS PAGSPTSTEE GTSTEPSEGS  1260
APGTSESATP ESGPGTSESA TPESGPGTSE SATPESGPGS EPATSGSETP GSEPATSGSE  1320
TPGSPAGSPT STEEGTSTEP SEGSAPGTST EPSEGSAPGS EPATSGSETP GTSESATPES  1380
GPGTSTEPSE GSAPGHHHHH H                                          1401

SEQ ID NO: 502         moltype = AA  length = 1419
FEATURE                Location/Qualifiers
REGION                 1..1419
                       note = Description of Artificial Sequence: Synthetic
                        polypeptide
source                 1..1419
                       mol_type = protein
                       organism = synthetic construct
SEQUENCE: 502
HHHHHHGGSP AGSPTSTEEG TSESATPESG PGTSTEPSEG SAPGSPAGSP TSTEEGTSTE  60
PSEGSAPGTS TEPSEGSAPG TSESATPESG PGSEPATSGS ETPGSEPATS GSETPGSPAG  120
SPTSTEEGTS ESATPESGPG TSTEPSEGSA PGTSTEPSEG SAPGSPAGSP TSTEEGTSTE  180
PSEGSAPGTS TEPSEGSAPG TSESATPESG PGTSTEPSEG SAPGTSESAT PESGPGSEPA  240
TSGSETPGTS TEPSEGSAPG TSTEPSEGSA PGTSESATPE SGPGTSESAT PESGPGSPAG  300
```

-continued

```
SPTSTEEGTS ESATPESGPG SEPATSGSET PGTSESATPE SGPGTSTEPS EGSAPGTSTE  360
PSEGSAPGTS TEPSEGSAPG TSTEPSEGSA PGTSTEPSEG SAPGTSTEPS EGSAPGSPAG  420
SPTSTEEGTS TEPSEGSAPG TSESATPESG PGSEPATSGS ETPGTSESAT PESGPGSEPA  480
TSGSETPGTS ESATPESGPG TSTEPSEGSA PGTSESATPE SGPGSPAGSP TSTEEGSPAG  540
SPTSTEEGSP AGSPTSTEEG TSESATPESG PGTSTEPSEG SAPGTSESAT PESGPGSEPA  600
TSGSETPGTS ESATPESGPG SEPATSGSET PGTSESATPE SGPGTSTEPS EGSAPGSPAG  660
SPTSTEEGTS ESATPESGPG SEPATSGSET PGTSESATPE SGPGSPAGSP TSTEEGSPAG  720
SPTSTEEGTS TEPSEGSAPG TSESATPESG PGTSESATPE SGPGTSESAT PESGPGSEPA  780
TSGSETPGSE PATSGSETPG SPAGSPTSTE EGTSTEPSEG SAPGTSTEPS EGSAPGSEPA  840
TSGSETPGTS ESATPESGPG TSTEPSEGSA PLSGRSDNHS PLGLAGSGTA EAASASGDIQ  900
MTQSPSSLSA SVGDRVTITC RASQDIRNYL NWYQQKPGKA PKLLIYYTSR LESGVPSRFS  960
GSGSGTDYTL TISSLQPEDF ATYYCQQGNT LPWTFGQGTK VEIKGATPPE TGAETESPGE  1020
TTGGSAESEP PGEGEVQLVE SGGGLVQPGG SLRLSCAASG YSFTGYTMNW VRQAPGKGLE  1080
WVALINPYKG VSTYNQKFKD RFTISVDKSK NTAYLQMNSL RAEDTAVYYC ARSGYYGDSD  1140
WYFDVWGQGT LVTVSSGGGG SDIQMTQSPS SLSASVGDRV TITCRSTKSL LHSNGITYLY  1200
WYQQKPGKAP KLLIYQMSNL ASGVPSRFSS SGSGTDFTLT ISSLQPEDFA TYYCAQNLEI  1260
PRTFGQGTKV EIKGATPPET GAETESPGET TGGSAESEPP GEGQVQLVQS GPGLVQPGGS  1320
VRISCAASGY TFTNYGMNWV KQAPGKGLEW MGWINTYTGE STYADSFKGR FTFSLDTSAS  1380
AAYLQINSLR AEDTAVYYCA RFAIKGDYWG QGTLLTVSS                         1419

SEQ ID NO: 503         moltype = AA  length = 1396
FEATURE                Location/Qualifiers
REGION                 1..1396
                       note = Description of Artificial Sequence: Synthetic
                        polypeptide
source                 1..1396
                       mol_type = protein
                       organism = synthetic construct
SEQUENCE: 503
HHHHHHGGSP AGSPTSTEEG TSESATPESG PGTSTEPSEG SAPGSPAGSP TSTEEGTSTE  60
PSEGSAPGTS TEPSEGSAPG TSESATPESG PGSEPATSGS ETPGSEPATS GSETPGSPAG  120
SPTSTEEGTS ESATPESGPG TSTEPSEGSA PGTSTEPSEG SAPGSPAGSP TSTEEGTSTE  180
PSEGSAPGTS TEPSEGSAPG TSESATPESG PGTSTEPSEG SAPGTSESAT PESGPGSEPA  240
TSGSETPGTS TEPSEGSAPG TSTEPSEGSA PGTSESATPE SGPGTSESAT PESGPGSPAG  300
SPTSTEEGTS ESATPESGPG SEPATSGSET PGTSESATPE SGPGTSTEPS EGSAPGTSTE  360
PSEGSAPGTS TEPSEGSAPG TSTEPSEGSA PGTSTEPSEG SAPGTSTEPS EGSAPGSPAG  420
SPTSTEEGTS TEPSEGSAPG TSESATPESG PGSEPATSGS ETPGTSESAT PESGPGSEPA  480
TSGSETPGTS ESATPESGPG TSTEPSEGSA PGTSESATPE SGPGSPAGSP TSTEEGSPAG  540
SPTSTEEGSP AGSPTSTEEG TSESATPESG PGTSTEPSEG SAPGTSESAT PESGPGSEPA  600
TSGSETPGTS ESATPESGPG SEPATSGSET PGTSESATPE SGPGTSTEPS EGSAPGSPAG  660
SPTSTEEGTS ESATPESGPG SEPATSGSET PGTSESATPE SGPGSPAGSP TSTEEGSPAG  720
SPTSTEEGTS TEPSEGSAPG TSESATPESG PGTSESATPE SGPGTSESAT PESGPGSEPA  780
TSGSETPGSE PATSGSETPG SPAGSPTSTE EGTSTEPSEG SAPGTSTEPS EGSAPGSEPA  840
TSGSETPGTS ESATPESGPG TSTEPSEGSA PGSPDIQMTQ SPSSLSASVG DRVTITCRAS  900
QDIRNYLNWY QQKPGKAPKL LIYYTSRLES GVPSRFSGSG SGTDYTLTIS SLQPEDFATY  960
YCQQGNTLPW TFGQGTKVEI KGATPPETGA ETESPGETTG GSAESEPPGE GEVQLVESGG  1020
GLVQPGGSLR LSCAASGYSF TGYTMNWVRQ APGKGLEWVA LINPYKGVST YNQKFKDRFT  1080
ISVDKSKNTA YLQMNSLRAE DTAVYYCARS GYYGDSDWYF DVWGQGTLVT VSSGGGGSDI  1140
QMTQSPSSLS ASVGDRVTIT CRSTKSLLHS NGITYLYWYQ QKPGKAPKLL IYQMSNLASG  1200
VPSRFSSSGS GTDFTLTISS LQPEDFATYY CAQNLEIPRT FGQGTKVEIK GATPPETGAE  1260
TESPGETTGG SAESEPPGEG QVQLVQSGPG LVQPGGSVRI SCAASGYTFT NYGMNWVKQA  1320
PGKGLEWMGW INTYTGESTY ADSFKGRFTF SLDTSASAAY LQINSLRAED TAVYYCARFA  1380
IKGDYWGQGT LLTVSS                                                  1396

SEQ ID NO: 504         moltype = AA  length = 1419
FEATURE                Location/Qualifiers
REGION                 1..1419
                       note = Description of Artificial Sequence: Synthetic
                        polypeptide
source                 1..1419
                       mol_type = protein
                       organism = synthetic construct
SEQUENCE: 504
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ HYTTPPTFGQ GTKVEIKGAT PPETGAETES  120
PGETTGGSAE SEPPGEGEVQ LVESGGGLVQ PGGSLRLSCA ASGFNIKDTY IHWVRQAPGK  180
GLEWVARIYP TNGYTRYADS VKGRFTISAD TSKNTAYLQM NSLRAEDTAV YYCSRWGGDG  240
FYAMDYWGQG TLVTVSSGGG GSDIQMTQSP SSLSASVGDR VTITCRASQD IRNYLNWYQQ  300
KPGKAPKLLI YYTSRLESGV PSRFSGSGSG TDYTLTISSL QPEDFATYYC QQGNTLPWTF  360
GQGTKVEIKG ATPPETGAET ESPGETTGGS AESEPPGEGE VQLVESGGGL VQPGGSLRLS  420
CAASGYSFTG YTMNWVRQAP GKGLEWVALI NPYKGVSTYN QKFKDRFTIS VDKSKNTAYL  480
QMNSLRAEDT AVYYCARSGY YGDSDWYFDV WGQGTLVTVS SGTAEAASAS GLSGRSDNHS  540
PLGLAGSPGS PAGSPTSTEE GTSESATPES GPGTSTEPSE GSAPGSPAGS PTSTEEGTST  600
EPSEGSAPGT STEPSEGSAP GTSESATPES GPGSEPATSG SETPGSEPAT SGSETPGSPA  660
GSPTSTEEGT SESATPESGP GTSTEPSEGS APGTSTEPSE GSAPGSPAGS PTSTEEGTST  720
EPSEGSAPGT STEPSEGSAP GTSESATPES GPGTSTEPSE GSAPGTSESA TPESGPGSEP  780
ATSGSETPGT STEPSEGSAP GTSTEPSEGS APGTSESATP ESGPGTSESA TPESGPGSPA  840
GSPTSTEEGT SESATPESGP GSEPATSGSE TPGTSESATP ESGPGTSTEP SEGSAPGTST  900
EPSEGSAPGT STEPSEGSAP GTSTEPSEGS APGTSTEPSE GSAPGTSTEP SEGSAPGSPA  960
```

```
GSPTSTEEGT STEPSEGSAP GTSESATPES GPGSEPATSG SETPGTSESA TPESGPGSEP  1020
ATSGSETPGT SESATPESGP GTSTEPSEGS APGTSESATP ESGPGSPAGS PTSTEEGSPA  1080
GSPTSTEEGS PAGSPTSTEE GTSESATPES GPGTSTEPSE GSAPGTSESA TPESGPGSEP  1140
ATSGSETPGT SESATPESGP GSEPATSGSE TPGTSESATP ESGPGTSTEP SEGSAPGSPA  1200
GSPTSTEEGT SESATPESGP GSEPATSGSE TPGTSESATP ESGPGSPAGS PTSTEEGSPA  1260
GSPTSTEEGT STEPSEGSAP GTSESATPES GPGTSESATP ESGPGTSESA TPESGPGSEP  1320
ATSGSETPGS EPATSGSETP GSPAGSPTST EEGTSTEPSE GSAPGTSTEP SEGSAPGSEP  1380
ATSGSETPGT SESATPESGP GTSTEPSEGS APGHHHHHH                         1419

SEQ ID NO: 505         moltype = AA  length = 1395
FEATURE                Location/Qualifiers
REGION                 1..1395
                       note = Description of Artificial Sequence: Synthetic
                        polypeptide
source                 1..1395
                       mol_type = protein
                       organism = synthetic construct
SEQUENCE: 505
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ HYTTPPTFGQ GTKVEIKGAT PPETGAETES  120
PGETTGGSAE SEPPGEGEVQ LVESGGGLVQ PGGSLRLSCA ASGFNIKDTY IHWVRQAPGK  180
GLEWVARIYP TNGYTRYADS VKGRFTISAD TSKNTAYLQM NSLRAEDTAV YYCSRWGGDG  240
FYAMDYWGQG TLVTVSSGGG GSDIQMTQSP SSLSASVGDR VTITCRASQD IRNYLNWYQQ  300
KPGKAPKLLI YYTSRLESGV PSRFSGSGSG TDYTLTISSL QPEDFATYYC QQGNTLPWTF  360
GQGTKVEIKG ATPPETGAET ESPGETTGGS AESEPPGEGE VQLVESGGGL VQPGGSLRLS  420
CAASGYSFTG YTMNWVRQAP GKGLEWVALI NPYKGVSTYN QKFKDRFTIS VDKSKNTAYL  480
QMNSLRAEDT AVYYCARSGY YGDSDWYFDV WGQGTLVTVS SGSPGSPAGS PTSTEEGTSE  540
SATPESGPGT STEPSEGSAP GSPAGSPTST EEGTSTEPSE GSAPGTSTEP SEGSAPGTSE  600
SATPESGPGS EPATSGSETP GSEPATSGSE TPGSPAGSPT STEEGTSESA TPESGPGTST  660
EPSEGSAPGT STEPSEGSAP GSPAGSPTST EEGTSTEPSE GSAPGTSTEP SEGSAPGTSE  720
SATPESGPGT STEPSEGSAP GTSESATPES GPGSEPATSG SETPGTSTEP SEGSAPGTST  780
EPSEGSAPGT SESATPESGP GTSESATPES GPGSPAGSPT STEEGTSESA TPESGPGSEP  840
ATSGSETPGT SESATPESGP GTSTEPSEGS APGTSTEPSE GSAPGTSTEP SEGSAPGTST  900
EPSEGSAPGT STEPSEGSAP GTSTEPSEGS APGSPAGSPT STEEGTSTEP SEGSAPGTSE  960
SATPESGPGS EPATSGSETP GTSESATPES GPGSEPATSG SETPGTSESA TPESGPGTST  1020
EPSEGSAPGT SESATPESGP GSPAGSPTST EEGSPAGSPT STEEGSPAGS PTSTEEGTSE  1080
SATPESGPGT STEPSEGSAP GTSESATPES GPGSEPATSG SETPGTSESA TPESGPGSEP  1140
ATSGSETPGT SESATPESGP GTSTEPSEGS APGSPAGSPT STEEGTSESA TPESGPGSEP  1200
ATSGSETPGT SESATPESGP GSPAGSPTST EEGSPAGSPT STEEGTSTEP SEGSAPGTSE  1260
SATPESGPGT SESATPESGP GTSESATPES GPGSEPATSG SETPGSEPAT SGSETPGSPA  1320
GSPTSTEEGT STEPSEGSAP GTSTEPSEGS APGSEPATSG SETPGTSESA TPESGPGTST  1380
EPSEGSAPGH HHHHH                                                   1395

SEQ ID NO: 506         moltype = AA  length = 1424
FEATURE                Location/Qualifiers
REGION                 1..1424
                       note = Description of Artificial Sequence: Synthetic
                        polypeptide
source                 1..1424
                       mol_type = protein
                       organism = synthetic construct
SEQUENCE: 506
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ HYTTPPTFGQ GTKVEIKGAT PPETGAETES  120
PGETTGGSAE SEPPGEGEVQ LVESGGGLVQ PGGSLRLSCA ASGFNIKDTY IHWVRQAPGK  180
GLEWVARIYP TNGYTRYADS VKGRFTISAD TSKNTAYLQM NSLRAEDTAV YYCSRWGGDG  240
FYAMDYWGQG TLVTVSSGGG GSELVVTQEP SLTVSPGGTV TLTCRSSTGA VTTSNYANWV  300
QQKPGQAPRG LIGGTNKRAP GTPARFSGSL LGGKAALTLS GVQPEDEAEY YCALWYSNLW  360
VFGGGTKLTV LGATPPETGA ETESPGETTG GSAESEPPGE GEVQLLESGG GLVQPGGSLK  420
LSCAASGFTF NTYAMNWVRQ APGKGLEWVA RIRSKYNNYA TYYADSVKDR FTISRDDSKN  480
TAYLQMNNLK TEDTAVYYCV RHGNFGNSYV SWFAYWGQGT LVTVSSGTAE AASASGLSGR  540
SDNHSPLGLA GSPGSPAGSP TSTEEGTSES ATPESGPGTS TEPSEGSAPG SPAGSPTSTE  600
EGTSTEPSEG SAPGTSTEPS EGSAPGTSES ATPESGPGSE PATSGSETPG SEPATSGSET  660
PGSPAGSPTS TEEGTSESAT PESGPGTSTE PSEGSAPGTS TEPSEGSAPG SPAGSPTSTE  720
EGTSTEPSEG SAPGTSTEPS EGSAPGTSES ATPESGPGTS TEPSEGSAPG TSESATPESG  780
PGSEPATSGS ETPGTSTEPS EGSAPGTSTE PSEGSAPGTS ESATPESGPG TSESATPESG  840
PGSPAGSPTS TEEGTSESAT PESGPGSEPA TSGSETPGTS ESATPESGPG TSTEPSEGSA  900
PGTSTEPSEG SAPGTSTEPS EGSAPGTSTE PSEGSAPGTS TEPSEGSAPG TSTEPSEGSA  960
PGSPAGSPTS TEEGTSTEPS EGSAPGTSES ATPESGPGSE PATSGSETPG TSESATPESG  1020
PGSEPATSGS ETPGTSESAT PESGPGTSTE PSEGSAPGTS ESATPESGPG SPAGSPTSTE  1080
EGSPAGSPTS TEEGSPAGSP TSTEEGTSES ATPESGPGTS TEPSEGSAPG TSESATPESG  1140
PGSEPATSGS ETPGTSESAT PESGPGSEPA TSGSETPGTS ESATPESGPG TSTEPSEGSA  1200
PGSPAGSPTS TEEGTSESAT PESGPGSEPA TSGSETPGTS ESATPESGPG SPAGSPTSTE  1260
EGSPAGSPTS TEEGTSTEPS EGSAPGTSES ATPESGPGTS ESATPESGPG TSESATPESG  1320
PGSEPATSGS ETPGSEPATS GSETPGSPAG SPTSTEEGTS TEPSEGSAPG TSTEPSEGSA  1380
PGSEPATSGS ETPGTSESAT PESGPGTSTE PSEGSAPGHH HHHH                   1424

SEQ ID NO: 507         moltype = AA  length = 1400
FEATURE                Location/Qualifiers
```

```
REGION                  1..1400
                        note = Description of Artificial Sequence: Synthetic
                         polypeptide
source                  1..1400
                        mol_type = protein
                        organism = synthetic construct
SEQUENCE: 507
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ HYTTPPTFGQ GTKVEIKGAT PPETGAETES  120
PGETTGGSAE SEPPGEGEVQ LVESGGGLVQ PGGSLRLSCA ASGFNIKDTY IHWVRQAPGK  180
GLEWVARIYP TNGYTRYADS VKGRFTISAD TSKNTAYLQM NSLRAEDTAV YYCSRWGGDG  240
FYAMDYWGQG TLVTVSSGGG GSELVVTQEP SLTVSPGGTV TLTCRSSTGA VTTSNYANWV  300
QQKPGQAPRG LIGGTNKRAP GTPARFSGSL LGGKAALTLS GVQPEDEAEY YCALWYSNLW  360
VFGGGTKLTV LGATPPETGA ETESPGETTG GSAESEPPGE GEVQLLESGG GLVQPGGSLK  420
LSCAASGFTF NTYAMNWVRQ APGKGLEWVA RIRSKYNNYA TYYADSVKDR FTISRDDSKN  480
TAYLQMNNLK TEDTAVYYCV RHGNFGNSYV SWFAYWGQGT LVTVSSGSPG SPAGSPTSTE  540
EGTSESATPE SGPGTSTEPS EGSAPGSPAG SPTSTEEGTS TEPSEGSAPG TSTEPSEGSA  600
PGTSESATPE SGPGSEPATS GSETPGSEPA TSGSETPGSP AGSPTSTEEG TSESATPESG  660
PGTSTEPSEG SAPGTSTEPS EGSAPGSPAG SPTSTEEGTS TEPSEGSAPG TSTEPSEGSA  720
PGTSESATPE SGPGTSTEPS EGSAPGTSES ATPESGPGSE PATSGSETPG TSTEPSEGSA  780
PGTSTEPSEG SAPGTSESAT PESGPGTSES ATPESGPGSP AGSPTSTEEG TSESATPESG  840
PGSEPATSGS ETPGTSESAT PESGPGTSTE PSEGSAPGTS TEPSEGSAPG TSTEPSEGSA  900
PGTSTEPSEG SAPGTSTEPS EGSAPGTSTE PSEGSAPGSP AGSPTSTEEG TSTEPSEGSA  960
PGTSESATPE SGPGSEPATS GSETPGTSES ATPESGPGSE PATSGSETPG TSESATPESG  1020
PGTSTEPSEG SAPGTSESAT PESGPGSPAG SPTSTEEGSP AGSPTSTEEG SPAGSPTSTE  1080
EGTSESATPE SGPGTSTEPS EGSAPGTSES ATPESGPGSE PATSGSETPG TSESATPESG  1140
PGSEPATSGS ETPGTSESAT PESGPGTSTE PSEGSAPGSP AGSPTSTEEG TSESATPESG  1200
PGSEPATSGS ETPGTSESAT PESGPGSPAG SPTSTEEGSP AGSPTSTEEG TSTEPSEGSA  1260
PGTSESATPE SGPGTSESAT PESGPGTSES ATPESGPGSE PATSGSETPG SEPATSGSET  1320
PGSPAGSPTS TEEGTSTEPS EGSAPGTSTE PSEGSAPGSE PATSGSETPG TSESATPESG  1380
PGTSTEPSEG SAPGHHHHHH                                              1400

SEQ ID NO: 508          moltype = AA  length = 1418
FEATURE                 Location/Qualifiers
REGION                  1..1418
                        note = Description of Artificial Sequence: Synthetic
                         polypeptide
source                  1..1418
                        mol_type = protein
                        organism = synthetic construct
SEQUENCE: 508
DIQMTQSPSS LSASVGDRVT ITCKASQDVS IGVAWYQQKP GKAPKLLIYS ASYRYTGVPS  60
RFSGSGSGTD FTLTISSLQP EDFATYYCQQ YYIYPYTFGQ GTKVEIKGAT PPETGAETES  120
PGETTGGSAE SEPPGEGEVQ LVESGGGLVQ PGGSLRLSCA ASGFTFTDYT MDWVRQAPGK  180
GLEWVADVNP NSGGSIYNQR FKGRFTLSVD RSKNTLYLQM NSLRAEDTAV YYCARNLGPS  240
FYFDYWGQGT LVTVSSGGGG SDIQMTQSPS SLSASVGDRV TITCRASQDI RNYLNWYQQK  300
PGKAPKLLIY YTSRLESGVP SRFSGSGSGT DYTLTISSLQ PEDFATYYCQ QGNTLPWTFG  360
QGTKVEIKGA TPPETGAETE SPGETTGGSA ESEPPGEGEV QLVESGGGLV QPGGSLRLSC  420
AASGYSFTGY TMNWVRQAPG KGLEWVALIN PYKGVSTYNQ KFKDRFTISV DKSKNTAYLQ  480
MNSLRAEDTA VYYCARSGYY GDSDWYFDVW GQGTLVTVSS GTAEAASASG LSGRSDNHSP  540
LGLAGSPGSP AGSPTSTEEG TSESATPESG PGTSTEPSEG SAPGSPAGSP TSTEEGTSTE  600
PSEGSAPGTS TEPSEGSAPG TSESATPESG PGSEPATSGS ETPGSEPATS GSETPGSPAG  660
SPTSTEEGTS ESATPESGPG TSTEPSEGSA PGTSTEPSEG SAPGSPAGSP TSTEEGTSTE  720
PSEGSAPGTS TEPSEGSAPG TSESATPESG PGTSTEPSEG SAPGTSESAT PESGPGSEPA  780
TSGSETPGTS TEPSEGSAPG TSTEPSEGSA PGTSESATPE SGPGTSESAT PESGPGSPAG  840
SPTSTEEGTS ESATPESGPG SEPATSGSET PGTSESATPE SGPGTSTEPS EGSAPGTSTE  900
PSEGSAPGTS TEPSEGSAPG TSTEPSEGSA PGTSTEPSEG SAPGTSTEPS EGSAPGSPAG  960
SPTSTEEGTS TEPSEGSAPG TSESATPESG PGSEPATSGS ETPGTSESAT PESGPGSEPA  1020
TSGSETPGTS ESATPESGPG TSTEPSEGSA PGTSESATPE SGPGSPAGSP TSTEEGSPAG  1080
SPTSTEEGSP AGSPTSTEEG TSESATPESG PGTSTEPSEG SAPGTSESAT PESGPGSEPA  1140
TSGSETPGTS ESATPESGPG SEPATSGSET PGTSESATPE SGPGTSTEPS EGSAPGSPAG  1200
SPTSTEEGTS ESATPESGPG SEPATSGSET PGTSESATPE SGPGSPAGSP TSTEEGSPAG  1260
SPTSTEEGTS TEPSEGSAPG TSESATPESG PGTSESATPE SGPGTSESAT PESGPGSEPA  1320
TSGSETPGSE PATSGSETPG SPAGSPTSTE EGTSTEPSEG SAPGTSTEPS EGSAPGSEPA  1380
TSGSETPGTS ESATPESGPG TSTEPSEGSA PGHHHHHH                          1418

SEQ ID NO: 509          moltype = AA  length = 1394
FEATURE                 Location/Qualifiers
REGION                  1..1394
                        note = Description of Artificial Sequence: Synthetic
                         polypeptide
source                  1..1394
                        mol_type = protein
                        organism = synthetic construct
SEQUENCE: 509
DIQMTQSPSS LSASVGDRVT ITCKASQDVS IGVAWYQQKP GKAPKLLIYS ASYRYTGVPS  60
RFSGSGSGTD FTLTISSLQP EDFATYYCQQ YYIYPYTFGQ GTKVEIKGAT PPETGAETES  120
PGETTGGSAE SEPPGEGEVQ LVESGGGLVQ PGGSLRLSCA ASGFTFTDYT MDWVRQAPGK  180
GLEWVADVNP NSGGSIYNQR FKGRFTLSVD RSKNTLYLQM NSLRAEDTAV YYCARNLGPS  240
```

-continued

```
FYFDYWGQGT LVTVSSGGGG SDIQMTQSPS SLSASVGDRV TITCRASQDI RNYLNWYQQK  300
PGKAPKLLIY YTSRLESGVP SRFSGSGSGT DYTLTISSLQ PEDFATYYCQ QGNTLPWTFG  360
QGTKVEIKGA TPPETGAETE SPGETTGGSA ESEPPGEGEV QLVESGGGLV QPGGSLRLSC  420
AASGYSFTGY TMNWVRQAPG KGLEWVALIN PYKGVSTYNQ KFKDRFTISV DKSKNTAYLQ  480
MNSLRAEDTA VYYCARSGYY GDSDWYFDVW GQGTLVTVSS GSPGSPAGSP TSTEEGTSES  540
ATPESGPGTS TEPSEGSAPG SPAGSPTSTE EGTSTEPSEG SAPGTSTEPS EGSAPGTSES  600
ATPESGPGSE PATSGSETPG SEPATSGSET PGSPAGSPTS TEEGTSESAT PESGPGTSTE  660
PSEGSAPGTS TEPSEGSAPG SPAGSPTSTE EGTSTEPSEG SAPGTSTEPS EGSAPGTSES  720
ATPESGPGTS TEPSEGSAPG TSESATPESG PGSEPATSGS ETPGTSTEPS EGSAPGTSTE  780
PSEGSAPGTS ESATPESGPG TSESATPESG PGSPAGSPTS TEEGTSESAT PESGPGSEPA  840
TSGSETPGTS ESATPESGPG TSTEPSEGSA PGTSTEPSEG SAPGTSTEPS EGSAPGTSTE  900
PSEGSAPGTS TEPSEGSAPG TSTEPSEGSA PGSPAGSPTS TEEGTSTEPS EGSAPGTSES  960
ATPESGPGSE PATSGSETPG TSESATPESG PGSEPATSGS ETPGTSESAT PESGPGTSTE  1020
PSEGSAPGTS ESATPESGPG SPAGSPTSTE EGSPAGSPTS TEEGSPAGSP TSTEEGTSES  1080
ATPESGPGTS TEPSEGSAPG TSESATPESG PGSEPATSGS ETPGTSESAT PESGPGSEPA  1140
TSGSETPGTS ESATPESGPG TSTEPSEGSA PGSPAGSPTS TEEGTSESAT PESGPGSEPA  1200
TSGSETPGTS ESATPESGPG SPAGSPTSTE EGSPAGSPTS TEEGTSTEPS EGSAPGTSES  1260
ATPESGPGTS ESATPESGPG TSESATPESG PGSEPATSGS ETPGSEPATS GSETPGSPAG  1320
SPTSTEEGTS TEPSEGSAPG TSTEPSEGSA PGSEPATSGS ETPGTSESAT PESGPGTSTE  1380
PSEGSAPGHH HHHH                                                    1394

SEQ ID NO: 510          moltype = AA  length = 528
FEATURE                 Location/Qualifiers
REGION                  1..528
                        note = Description of Artificial Sequence: Synthetic
                         polypeptide
source                  1..528
                        mol_type = protein
                        organism = synthetic construct
SEQUENCE: 510
HHHHHHHHDI QLTQSPASLA VSLGQRATIS CKASQSVDYD GDSYLNWYQQ IPGQPPKLLI  60
YDASNLVSGI PPRFSGSGSG TDFTLNIHPV EKVDAATYHC QQSTEDPWTF GGGTKLEIKG  120
GGGSGGGGSG GGGSQVQLQQ SGAELVRPGS SVKISCKASG YAFSSYWMNW VKQRPGQGLE  180
WIGQIWPGDG DTNYNGKFKG KATLTADESS STAYMQLSSL ASEDSAVYFC ARRETTTVGR  240
YYYAMDYWGQ GTTVTVSSGG GGSDIKLQQS GAELARPGAS VKMSCKTSGY TFTRYTMHWV  300
KQRPGQGLEW IGYINPSRGY TNYNQKFKDK ATLTTDKSSS TAYMQLSSLT SEDSAVYYCA  360
RYYDDHYCLD YWGQGTTLTV SSVEGGSGGS GGSGGSGGVD DIQLTQSPAI MSASPGEKVT  420
MTCRASSSVS YMNWYQQKSG TSPKRWIYDT SKVASGVPYR FSGSGSGTSY SLTISSMEAE  480
DAATYYCQQW SSNPLTFGAG TKLELKGTAE AASASGLSGR SDNHSPLG               528

SEQ ID NO: 511          moltype = AA  length = 526
FEATURE                 Location/Qualifiers
REGION                  1..526
                        note = Description of Artificial Sequence: Synthetic
                         polypeptide
source                  1..526
                        mol_type = protein
                        organism = synthetic construct
SEQUENCE: 511
HHHHHHHHEL VMTQSPSSLT VTAGEKVTMS CKSSQSLLNS GNQKNYLTWY QQKPGQPPKL  60
LIYWASTRES GVPDRFTGSG SGTDFTLTIS SVQAEDLAVY YCQNDYSYPL TFGAGTKLEI  120
KGGGGSGGGG SGGGGSEVQL LEQSGAELVR PGTSVKISCK ASGYAFTNYW LGWVKQRPGH  180
GLEWIGDIFP GSGNIHYNEK FKGKATLTAD KSSSTAYMQL SSLTFEDSAV YFCARLRNWD  240
EPMDYWGQGT TVTVSSGGGG SDVQLVQSGA EVKKPGASVK VSCKASGYTF TRYTMHWVRQ  300
APGQGLEWIG YINPSRGYTN YADSVKGRFT ITTDKSTSTA YMELSSLRSE DTATYYCARY  360
YDDHYCLDYW GQGTTVTVSS GEGTSTGSGG SGGSGGADDI VLTQSPATLS LSPGERATLS  420
CRASQSVSYM NWYQQKPGKA PKRWIYDTSK VASGVPARFS GSGSGTDYSL TINSLEAEDA  480
ATYYCQQWSS NPLTFGGGTK VEIKGTAEAA SASGLSGRSD NHSPLG                 526

SEQ ID NO: 512          moltype = AA  length = 516
FEATURE                 Location/Qualifiers
REGION                  1..516
                        note = Description of Artificial Sequence: Synthetic
                         polypeptide
source                  1..516
                        mol_type = protein
                        organism = synthetic construct
SEQUENCE: 512
HHHHHHHHEV QLLEQSGAEL VRPGTSVKIS CKASGYAFTN YWLGWVKQRP GHGLEWIGDI  60
FPGSGNIHYN EKFKGKATLT ADKSSSTAYM QLSSLTFEDS AVYFCARLRN WDEPMDYWGQ  120
GTTVTVSSGG GGSDVQLVQS GAEVKKPGAS VKVSCKASGY TFTRYTMHWV RQAPGQGLEW  180
IGYINPSRGY TNYADSVKGR FTITTDKSTS TAYMELSSLR SEDTATYYCA RYYDDHYCLD  240
YWGQGTTVTV SSGEGTSTGS GGSGGSGGAD DIVLTQSPAT LSLSPGERAT LSCRASQSVS  300
YMNWYQQKPG KAPKRWIYDT SKVASGVPAR FSGSGSGTDY SLTINSLEAE DAATYYCQQW  360
SSNPLTFGGG TKVEIKGGGG SELVMTQSPS SLTVTAGEKV TMSCKSSQSL LNSGNQKNYL  420
TWYQQKPGQP PKLLIYWAST RESGVPDRFT GSGSGTDFTL TISSVQAEDL AVYYCQNDYS  480
YPLTFGAGTK LEIKGTAEAA SASGLSGRSD NHSPLG                            516

SEQ ID NO: 513          moltype = AA  length = 510
```

```
FEATURE                Location/Qualifiers
REGION                 1..510
                       note = Description of Artificial Sequence: Synthetic
                        polypeptide
source                 1..510
                       mol_type = protein
                       organism = synthetic construct
SEQUENCE: 513
HHHHHHHHDV QLVQSGAEVK KPGASVKVSC KASGYTFTRY TMHWVRQAPG QGLEWIGYIN  60
PSRGYTNYAD SVKGRFTITT DKSTSTAYME LSSLRSEDTA TYYCARYYDD HYCLDYWGQG  120
TTVTVSSGGS ELVMTQSPSS LTVTAGEKVT MSCKSSQSLL NSGNQKNYLT WYQQKPGQPP  180
KLLIYWASTR ESGVPDRFTG SGSGTDFTLT ISSVQAEDLA VYYCQNDYSY PLTFGAGTKL  240
EIKGGGGSGG GGSGGGGSEV QLLEQSGAEL VRPGTSVKIS CKASGYAFTN YWLGWVKQRP  300
GHGLEWIGDI FPGSGNIHYN EKFKGKATLT ADKSSSTAYM QLSSLTFEDS AVYFCARLRN  360
WDEPMDYWGQ GTTVTVSSGG GSDIVLTQSP ATLSLSPGER ATLSCRASQS VSYMNWYQQK  420
PGKAPKRWIY DTSKVASGVP ARFSGSGSGT DYSLTINSLE AEDAATYYCQ QWSSNPLTFG  480
GGTKVEIKGT AEAASASGLS GRSDNHSPLG                                  510

SEQ ID NO: 514         moltype = AA  length = 541
FEATURE                Location/Qualifiers
REGION                 1..541
                       note = Description of Artificial Sequence: Synthetic
                        polypeptide
source                 1..541
                       mol_type = protein
                       organism = synthetic construct
SEQUENCE: 514
HHHHHHHHEL VMTQSPSSLT VTAGEKVTMS CKSSQSLLNS GNQKNYLTWY QQKPGQPPKL  60
LIYWASTRES GVPDRFTGSG SGTDFTLTIS SVQAEDLAVY YCQNDYSYPL TFGAGTKLEI  120
KGGGGSGGGG SGGGGSEVQL LEQSGAELVR PGTSVKISCK ASGYAFTNYW LGWVKQRPGH  180
GLEWIGDIFP GSGNIHYNEK FKGKATLTAD KSSSTAYMQL SSLTFEDSAV YFCARLRNWD  240
EPMDYWGQGT TVTVSSGGGG SDIQMTQSPS SLSASVGDRV TITCRASQDI RNYLNWYQQK  300
PGKAPKLLIY YTSRLESGVP SRFSGSGSGT DYTLTISSLQ PEDFATYYCQ QGNTLPWTFG  360
QGTKVEIKRT SGPGDGGKGG PGKGPGGEGT KGTGPGGEVQ LVESGGGLVQ PGGSLRLSCA  420
ASGYSFTGYT MNWVRQAPGK GLEWVALINP YKGVSTYNQK FKDRFTISVD KSKNTAYLQM  480
NSLRAEDTAV YYCARSGYYG DSDWYFDVWG QGTLVTVSSG TAEAASASGL SGRSDNHSPL  540
G                                                                 541

SEQ ID NO: 515         moltype = AA  length = 541
FEATURE                Location/Qualifiers
REGION                 1..541
                       note = Description of Artificial Sequence: Synthetic
                        polypeptide
source                 1..541
                       mol_type = protein
                       organism = synthetic construct
SEQUENCE: 515
HHHHHHHHEL VMTQSPSSLT VTAGEKVTMS CKSSQSLLNS GNQKNYLTWY QQKPGQPPKL  60
LIYWASTRES GVPDRFTGSG SGTDFTLTIS SVQAEDLAVY YCQNDYSYPL TFGAGTKLEI  120
KGGGGSGGGG SGGGGSEVQL LEQSGAELVR PGTSVKISCK ASGYAFTNYW LGWVKQRPGH  180
GLEWIGDIFP GSGNIHYNEK FKGKATLTAD KSSSTAYMQL SSLTFEDSAV YFCARLRNWD  240
EPMDYWGQGT TVTVSSGGGG SEVQLVESGG GLVQPGGSLR LSCAASGYSF TGYTMNWVRQ  300
APGKGLEWVA LINPYKGVST YNQKFKDRFT ISVDKSKNTA YLQMNSLRAE DTAVYYCARS  360
GYYGDSDWYF DVWGQGTLVT VSSRTSGPGD GGKGGPGKGP GGEGTKGTGP GGDIQMTQSP  420
SSLSASVGDR VTITCRASQD IRNYLNWYQQ KPGKAPKLLI YYTSRLESGV PSRFSGSGSG  480
TDYTLTISSL QPEDFATYYC QQGNTLPWTF GQGTKVEIKG TAEAASASGL SGRSDNHSPL  540
G                                                                 541

SEQ ID NO: 516         moltype = AA  length = 532
FEATURE                Location/Qualifiers
REGION                 1..532
                       note = Description of Artificial Sequence: Synthetic
                        polypeptide
source                 1..532
                       mol_type = protein
                       organism = synthetic construct
SEQUENCE: 516
LAGSGTAEAA SASGELVMTQ SPSSLTVTAG EKVTMSCKSS QSLLNSGNQK NYLTWYQQKP  60
GQPPKLLIYW ASTRESGVPD RFTGSGSGTD FTLTISSVQA EDLAVYYCQN DYSYPLTFGA  120
GTKLEIKGGG GSGGGGSGGG GSEVQLLEQS GAELVRPGTS VKISCKASGY AFTNYWLGWV  180
KQRPGHGLEW IGDIFPGSGN IHYNEKFKGK ATLTADKSSS TAYMQLSSLT FEDSAVYFCA  240
RLRNWDEPMD YWGQGTTVTV SSGGGGSDVQ LVQSGAEVKK PGASVKVSCK ASGYTFTRYT  300
MHWVRQAPGQ GLEWIGYINP SRGYTNYADS VKGRFTITTD KSTSTAYMEL SSLRSEDTAT  360
YYCARYYDDH YCLDYWGQGT TVTVSSGEGT STGSGGSGGS GGADDIVLTQ SPATLSLSPG  420
ERATLSCRAS QSVSYMNWYQ QKPGKAPKRW IYDTSKVASG VPARFSGSGS GTDYSLTINS  480
LEAEDAATYY CQQWSSNPLT FGGGTKVEIK GTAEAASASG LSGRSDNHSP LG          532

SEQ ID NO: 517         moltype = AA  length = 518
FEATURE                Location/Qualifiers
```

```
REGION                  1..518
                        note = Description of Artificial Sequence: Synthetic
                         polypeptide
source                  1..518
                        mol_type = protein
                        organism = synthetic construct
SEQUENCE: 517
LAGSGTAEAA SASGELVMTQ SPSSLTVTAG EKVTMSCKSS QSLLNSGNQK NYLTWYQQKP  60
GQPPKLLIYW ASTRESGVPD RFTGSGSGTD FTLTISSVQA EDLAVYYCQN DYSYPLTFGA  120
GTKLEIKGGG GSGGGGSGGG GSEVQLLEQS GAELVRPGTS VKISCKASGY AFTNYWLGWV  180
KQRPGHGLEW IGDIFPGSGN IHYNEKFKGK ATLTADKSSS TAYMQLSSLT FEDSAVYFCA  240
RLRNWDEPMD YWGQGTTVTV SSGGGGSDVQ LVQSGAEVKK PGASVKVSCK ASGYTFTRYT  300
MHWVRQAPGQ GLEWIGYINP SRGYTNYADS VKGRFTITTD KSTSTAYMEL SSLRSEDTAT  360
YYCARYYDDH YCLDYWGQGT TVTVSSGEGT STGSGGSGGS GGADDIVLTQ SPATLSLSPG  420
ERATLSCRAS QSVSYMNWYQ QKPGKAPKRW IYDTSKVASG VPARFSGSGS GTDYSLTINS  480
LEAEDAATYY CQQWSSNPLT FGGGTKVEIK HHHHHHHH                         518

SEQ ID NO: 518          moltype = AA  length = 526
FEATURE                 Location/Qualifiers
REGION                  1..526
                        note = Description of Artificial Sequence: Synthetic
                         polypeptide
source                  1..526
                        mol_type = protein
                        organism = synthetic construct
SEQUENCE: 518
HHHHHHHHEL VMTQSPSSLT VTAGEKVTMS CKSSQSLLNS GNQKNYLTWY QQKPGQPPKL  60
LIYWASTRES GVPDRFTGSG SGTDFTLTIS SVQAEDLAVY YCQNDYSYPL TFGAGTKLEI  120
KGGGGSGGGG SGGGGSEVQL LEQSGAELVR PGTSVKISCK ASGYAFTNYW LGWVKQRPGH  180
GLEWIGDIFP GSGNIHYNEK FKGKATLTAD KSSSTAYMQL SSLTFEDSAV YFCARLRNWD  240
EPMDYWGQGT TVTVSSGGGG SDIVLTQSPA TLSLSPGERA TLSCRASQSV SYMNWYQQKP  300
GKAPKRWIYD TSKVASGVPA RFSGSGSGTD YSLTINSLEA EDAATYYCQQ WSSNPLTFGG  360
GTKVEIKGEG TSTGSGGSGG SGGADDVQLV QSGAEVKKPG ASVKVSCKAS GYTFTRYTMH  420
WVRQAPGQGL EWIGYINPSR GYTNYADSVK GRFTITTDKS TSTAYMELSS LRSEDTATYY  480
CARYYDDHYC LDYWGQGTTV TVSSGTAEAA SASGLSGRSD NHSPLG                526

SEQ ID NO: 519          moltype = AA  length = 526
FEATURE                 Location/Qualifiers
REGION                  1..526
                        note = Description of Artificial Sequence: Synthetic
                         polypeptide
source                  1..526
                        mol_type = protein
                        organism = synthetic construct
SEQUENCE: 519
HHHHHHHHEV QLLEQSGAEL VRPGTSVKIS CKASGYAFTN YWLGWVKQRP GHGLEWIGDI  60
FPGSGNIHYN EKFKGKATLT ADKSSSTAYM QLSSLTFEDS AVYFCARLRN WDEPMDYWGQ  120
GTTVTVSSGG GGSGGGGSGG GGSELVMTQS PSSLTVTAGE KVTMSCKSSQ SLLNSGNQKN  180
YLTWYQQKPG QPPKLLIYWA STRESGVPDR FTGSGSGTDF TLTISSVQAE DLAVYYCQND  240
YSYPLTFGAG TKLEIKGGGG SDVQLVQSGA EVKKPGASVK VSCKASGYTF TRYTMHWVRQ  300
APGQGLEWIG YINPSRGYTN YADSVKGRFT ITTDKSTSTA YMELSSLRSE DTATYYCARY  360
YDDHYCLDYW GQGTTVTVSS GEGTSTGSGG SGGSGGADDI VLTQSPATLS LSPGERATLS  420
CRASQSVSYM NWYQQKPGKA PKRWIYDTSK VASGVPARFS GSGSGTDYSL TINSLEAEDA  480
ATYYCQQWSS NPLTFGGGTK VEIKGTAEAA SASGLSGRSD NHSPLG                526

SEQ ID NO: 520          moltype = AA  length = 526
FEATURE                 Location/Qualifiers
REGION                  1..526
                        note = Description of Artificial Sequence: Synthetic
                         polypeptide
source                  1..526
                        mol_type = protein
                        organism = synthetic construct
SEQUENCE: 520
HHHHHHHHDV QLVQSGAEVK KPGASVKVSC KASGYTFTRY TMHWVRQAPG QGLEWIGYIN  60
PSRGYTNYAD SVKGRFTITT DKSTSTAYME LSSLRSEDTA TYYCARYYDD HYCLDYWGQG  120
TTVTVSSGEG TSTGSGGSGG SGGADDIVLT QSPATLSLSP GERATLSCRA SQSVSYMNWY  180
QQKPGKAPKR WIYDTSKVAS GVPARFSGSG SGTDYSLTIN SLEAEDAATY YCQQWSSNPL  240
TFGGGTKVEI KGGGGSELVM TQSPSSLTVT AGEKVTMSCK SSQSLLNSGN QKNYLTWYQQ  300
KPGQPPKLLI YWASTRESGV PDRFTGSGSG TDFTLTISSV QAEDLAVYYC QNDYSYPLTF  360
GAGTKLEIKG GGGSGGGGSG GGGSEVQLLE QSGAELVRPG TSVKISCKAS GYAFTNYWLG  420
WVKQRPGHGL EWIGDIFPGS GNIHYNEKFK GKATLTADKS SSTAYMQLSS LTFEDSAVYF  480
CARLRNWDEP MDYWGQGTTV TVSSGTAEAA SASGLSGRSD NHSPLG                526

SEQ ID NO: 521          moltype = AA  length = 526
FEATURE                 Location/Qualifiers
REGION                  1..526
                        note = Description of Artificial Sequence: Synthetic
                         polypeptide
```

```
source                  1..526
                        mol_type = protein
                        organism = synthetic construct
SEQUENCE: 521
HHHHHHHHDI VLTQSPATLS LSPGERATLS CRASQSVSYM NWYQQKPGKA PKRWIYDTSK  60
VASGVPARFS GSGSGTDYSL TINSLEAEDA ATYYCQQWSS NPLTFGGGTK VEIKGEGTST  120
GSGGSGGSGG ADDVQLVQSG AEVKKPGASV KVSCKASGYT FTRYTMHWVR QAPGQGLEWI  180
GYINPSRGYT NYADSVKGRF TITTDKSTST AYMELSSLRS EDTATYYCAR YYDDHYCLDY  240
WGQGTTVTVS SGGGGSELVM TQSPSSLTVT AGEKVTMSCK SSQSLLNSGN QKNYLTWYQQ  300
KPGQPPKLLI YWASTRESGV PDRFTGSGSG TDFTLTISSV QAEDLAVYYC QNDYSYPLTF  360
GAGTKLEIKG GGGSGGGGSG GGGSEVQLLE QSGAELVRPG TSVKISCKAS GYAFTNYWLG  420
WVKQRPGHGL EWIGDIFPGS GNIHYNEKFK GKATLTADKS SSTAYMQLSS LTFEDSAVYF  480
CARLRNWDEP MDYWGQGTTV TVSSGTAEAA SASGLSGRSD NHSPLG                526

SEQ ID NO: 522          moltype = AA  length = 544
FEATURE                 Location/Qualifiers
REGION                  1..544
                        note = Description of Artificial Sequence: Synthetic
                         polypeptide
source                  1..544
                        mol_type = protein
                        organism = synthetic construct
SEQUENCE: 522
DIQMTQSPSS LSASVGDRVT ITCRSTKSLL HSNGITYLYW YQQKPGKAPK LLIYQMSNLA  60
SGVPSRFSSS GSGTDFTLTI SSLQPEDFAT YYCAQNLEIP RTFGQGTKVE IKGATPPETG  120
AETESPGETT GGSAESEPPG EGQVQLVQSG PGLVQPGGSV RISCAASGYT FTNYGMNWVK  180
QAPGKGLEWM GWINTYTGES TYADSFKGRF TFSLDTSASA AYLQINSLRA EDTAVYYCAR  240
FAIKGDYWGQ GTLLTVSSGG GGSDIQMTQS PSSLSASVGD RVTITCRASQ DIRNYLNWYQ  300
QKPGKAPKLL IYYTSRLESG VPSRFSGSGS GTDYTLTISS LQPEDFATYY CQQGNTLPWT  360
FGQGTKVEIK GATPPETGAE TESPGETTGG SAESEPPGEG EVQLVESGGG LVQPGGSLRL  420
SCAASGYSFT GYTMNWVRQA PGKGLEWVAL INPYKGVSTY NQKFKDRFTI SVDKSKNTAY  480
LQMNSLRAED TAVYYCARSG YYGDSDWYFD VWGQGTLVTV SSGTAEAASA SGLSGRSDNH  540
SPLG                                                              544

SEQ ID NO: 523          moltype = AA  length = 549
FEATURE                 Location/Qualifiers
REGION                  1..549
                        note = Description of Artificial Sequence: Synthetic
                         polypeptide
source                  1..549
                        mol_type = protein
                        organism = synthetic construct
SEQUENCE: 523
DIVMTQSPLS LPVTPGEPAS ISCRSSKNLL HSNGITYLYW YLQKPGQSPQ LLIYQMSNLA  60
SGVPDRFSSS GSGTDFTLKI SRVEAEDVGV YYCAQNLEIP RTFGQGTKVE IKGATPPETG  120
AETESPGETT GGSAESEPPG EGQVQLVQSG PEVKKPGASV KVSCKASGYT FTNYGMNWVR  180
QAPGQGLEWM GWINTYTGEP TYGEDFKGRF AFSLDTSAST AYMELSSLRS EDTAVYFCAR  240
FGNYVDYWGQ GSLVTVSSGG GGSELVVTQE PSLTVSPGGT VTLTCRSSTG AVTTSNYANW  300
VQQKPGQAPR GLIGGTNKRA PGTPARFSGS LLGGKAALTL SGVQPEDEAE YYCALWYSNL  360
WVFGGGTKLT VLGATPPETG AETESPGETT GGSAESEPPG EGEVQLLESG GGLVQPGGSL  420
KLSCAASGFT FNTYAMNWVR QAPGKGLEWV ARIRSKYNNY ATYYADSVKD RFTISRDDSK  480
NTAYLQMNNL KTEDTAVYYC VRHGNFGNSY VSWFAYWGQG TLVTVSSGTA EAASASGLSG  540
RSDNHSPLG                                                         549

SEQ ID NO: 524          moltype = AA  length = 536
FEATURE                 Location/Qualifiers
REGION                  1..536
                        note = Description of Artificial Sequence: Synthetic
                         polypeptide
source                  1..536
                        mol_type = protein
                        organism = synthetic construct
SEQUENCE: 524
LAGSGTAEAA SASGDIQMTQ SPSSLSASVG DRVTITCRAS QDIRNYLNWY QQKPGKAPKL  60
LIYYTSRLES GVPSRFSGSG SGTDYTLTIS SLQPEDFATY YCQQGNTLPW TFGQGTKVEI  120
KGATPPETGA ETESPGETTG GSAESEPPGE GEVQLVESGG GLVQPGGSLR LSCAASGYSF  180
TGYTMNWVRQ APGKGLEWVA LINPYKGVST YNQKFKDRFT ISVDKSKNTA YLQMNSLRAE  240
DTAVYYCARS GYYGDSDWYF DVWGQGTLVT VSSGGGGSDI QMTQSPSSLS ASVGDRVTIT  300
CRSTKSLLHS NGITYLYWYQ QKPGKAPKLL IYQMSNLASG VPSRFSSSGS GTDFTLTISS  360
LQPEDFATYY CAQNLEIPRT FGQGTKVEIK GATPPETGAE TESPGETTGG SAESEPPGEG  420
QVQLVQSGPG LVQPGGSVRI SCAASGYTFT NYGMNWVKQA PGKGLEWMGW INTYTGESTY  480
ADSFKGRFTF SLDTSASAAY LQINSLRAED TAVYYCARFA IKGDYWGQGT LLTVSS      536

SEQ ID NO: 525          moltype = AA  length = 543
FEATURE                 Location/Qualifiers
REGION                  1..543
                        note = Description of Artificial Sequence: Synthetic
                         polypeptide
source                  1..543
```

```
                         mol_type = protein
                         organism = synthetic construct
SEQUENCE: 525
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ HYTTPPTFGQ GTKVEIKGAT PPETGAETES  120
PGETTGGSAE SEPPGEGEVQ LVESGGGLVQ PGGSLRLSCA ASGFNIKDTY IHWVRQAPGK  180
GLEWVARIYP TNGYTRYADS VKGRFTISAD TSKNTAYLQM NSLRAEDTAV YYCSRWGGDG  240
FYAMDYWGQG TLVTVSSGGG GSDIQMTQSP SSLSASVGDR VTITCRASQD IRNYLNWYQQ  300
KPGKAPKLLI YYTSRLESGV PSRFSGSGSG TDYTLTISSL QPEDFATYYC QQGNTLPWTF  360
GQGTKVEIKG ATPPETGAET ESPGETTGGS AESEPPGEGE VQLVESGGGL VQPGGSLRLS  420
CAASGYSFTG YTMNWVRQAP GKGLEWVALI NPYKGVSTYN QKFKDRFTIS VDKSKNTAYL  480
QMNSLRAEDT AVYYCARSGY YGDSDWYFDV WGQGTLVTVS SGTAEAASAS GLSGRSDNHS  540
PLG                                                               543

SEQ ID NO: 526           moltype = AA  length = 548
FEATURE                  Location/Qualifiers
REGION                   1..548
                         note = Description of Artificial Sequence: Synthetic
                          polypeptide
source                   1..548
                         mol_type = protein
                         organism = synthetic construct
SEQUENCE: 526
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ HYTTPPTFGQ GTKVEIKGAT PPETGAETES  120
PGETTGGSAE SEPPGEGEVQ LVESGGGLVQ PGGSLRLSCA ASGFNIKDTY IHWVRQAPGK  180
GLEWVARIYP TNGYTRYADS VKGRFTISAD TSKNTAYLQM NSLRAEDTAV YYCSRWGGDG  240
FYAMDYWGQG TLVTVSSGGG GSELVVTQEP SLTVSPGGTV TLTCRSSTGA VTTSNYANWV  300
QQKPGQAPRG LIGGTNKRAP GTPARFSGSL LGGKAALTLS GVQPEDEAEY YCALWYSNLW  360
VFGGGTKLTV LGATPPETGA ETESPGETTG GSAESEPPGE GEVQLLESGG GLVQPGGSLK  420
LSCAASGFTF NTYAMNWVRQ APGKGLEWVA RIRSKYNNYA TYYADSVKDR FTISRDDSKN  480
TAYLQMNNLK TEDTAVYYCV RHGNFGNSYV SWFAYWGQGT LVTVSSGTAE AASASGLSGR  540
SDNHSPLG                                                          548

SEQ ID NO: 527           moltype = AA  length = 542
FEATURE                  Location/Qualifiers
REGION                   1..542
                         note = Description of Artificial Sequence: Synthetic
                          polypeptide
source                   1..542
                         mol_type = protein
                         organism = synthetic construct
SEQUENCE: 527
DIQMTQSPSS LSASVGDRVT ITCKASQDVS IGVAWYQQKP GKAPKLLIYS ASYRYTGVPS  60
RFSGSGSGTD FTLTISSLQP EDFATYYCQQ YYIYPYTFGQ GTKVEIKGAT PPETGAETES  120
PGETTGGSAE SEPPGEGEVQ LVESGGGLVQ PGGSLRLSCA ASGFTFTDYT MDWVRQAPGK  180
GLEWVADVNP NSGGSIYNQR FKGRFTLSVD RSKNTLYLQM NSLRAEDTAV YYCARNLGPS  240
FYFDYWGQGT LVTVSSGGGG SDIQMTQSPS SLSASVGDRV TITCRASQDI RNYLNWYQQK  300
PGKAPKLLIY YTSRLESGVP SRFSGSGSGT DYTLTISSLQ PEDFATYYCQ QGNTLPWTFG  360
QGTKVEIKGA TPPETGAETE SPGETTGGSA ESEPPGEGEV QLVESGGGLV QPGGSLRLSC  420
AASGYSFTGY TMNWVRQAPG KGLEWVALIN PYKGVSTYNQ KFKDRFTISV DKSKNTAYLQ  480
MNSLRAEDTA VYYCARSGYY GDSDWYFDVW GQGTLVTVSS GTAEAASASG LSGRSDNHSP  540
LG                                                                542

SEQ ID NO: 528           moltype = AA  length = 547
FEATURE                  Location/Qualifiers
REGION                   1..547
                         note = Description of Artificial Sequence: Synthetic
                          polypeptide
source                   1..547
                         mol_type = protein
                         organism = synthetic construct
SEQUENCE: 528
DIQMTQSPSS LSASVGDRVT ITCKASQDVS IGVAWYQQKP GKAPKLLIYS ASYRYTGVPS  60
RFSGSGSGTD FTLTISSLQP EDFATYYCQQ YYIYPYTFGQ GTKVEIKGAT PPETGAETES  120
PGETTGGSAE SEPPGEGEVQ LVESGGGLVQ PGGSLRLSCA ASGFTFTDYT MDWVRQAPGK  180
GLEWVADVNP NSGGSIYNQR FKGRFTLSVD RSKNTLYLQM NSLRAEDTAV YYCARNLGPS  240
FYFDYWGQGT LVTVSSGGGG SELVVTQEPS LTVSPGGTVT LTCRSSTGAV TTSNYANWVQ  300
QKPGQAPRGL IGGTNKRAPG TPARFSGSLL GGKAALTLSG VQPEDEAEYY CALWYSNLWV  360
FGGGTKLTVL GATPPETGAE TESPGETTGG SAESEPPGEG EVQLLESGGG LVQPGGSLKL  420
SCAASGFTFN TYAMNWVRQA PGKGLEWVAR IRSKYNNYAT YYADSVKDRF TISRDDSKNT  480
AYLQMNNLKT EDTAVYYCVR HGNFGNSYVS WFAYWGQGTL VTVSSGTAEA ASASGLSGRS  540
DNHSPLG                                                           547

SEQ ID NO: 529           moltype = AA  length = 541
FEATURE                  Location/Qualifiers
REGION                   1..541
                         note = Description of Artificial Sequence: Synthetic
                          polypeptide
```

```
source                  1..541
                        mol_type = protein
                        organism = synthetic construct
SEQUENCE: 529
DIQLTQSPSS LSASVGDRVT ITCKASQDVG TSVAWYQQKP GKAPKLLIYW TSTRHTGVPS  60
RFSGSGSGTD FTFTISSLQP EDIATYYCQQ YSLYRSFGQG TKVEIKGATP PETGAETESP  120
GETTGGSAES EPPGEGEVQL VESGGGVVQP GRSLRLSCSA SGFDFTTYWM SWVRQAPGKG  180
LEWIGEIHPD SSTINYAPSL KDRFTISRDN AKNTLFLQMD SLRPEDTGVY FCASLYFGFP  240
WFAYWGQGTP VTVSSGGGGS DIQMTQSPSS LSASVGDRVT ITCRASQDIR NYLNWYQQKP  300
GKAPKLLIYY TSRLESGVPS RFSGSGSGTD YTLTISSLQP EDFATYYCQQ GNTLPWTFGQ  360
GTKVEIKGAT PPETGAETES PGETTGGSAE SEPPGEGEVQ LVESGGGLVQ PGGSLRLSCA  420
ASGYSFTGYT MNWVRQAPGK GLEWVALINP YKGVSTYNQK FKDRFTISVD KSKNTAYLQM  480
NSLRAEDTAV YYCARSGYYG DSDWYFDVWG QGTLVTVSSG TAEAASASGL SGRSDNHSPL  540
G                                                                 541

SEQ ID NO: 530          moltype = AA  length = 538
FEATURE                 Location/Qualifiers
REGION                  1..538
                        note = Description of Artificial Sequence: Synthetic
                         polypeptide
source                  1..538
                        mol_type = protein
                        organism = synthetic construct
SEQUENCE: 530
DIQMTQSPSS LSTSVGDRVT LTCKASQDVG TAVDWYQQKP GPSPKLLIYW ASTRHTGIPS  60
RFSGSGSGTD FTLTISSLQP EDFADYYCQQ YNSYPLTFGP GTKVDIKGAT PPETGAETES  120
PGETTGGSAE SEPPGEGEVQ LVQSGPEVKK PGATVKISCK TSGYTFTEYT IHWVKQAPGK  180
GLEWIGNINP NNGGTTYNQK FEDKATLTVD KSTDTAYMEL SSLRSEDTAV YYCAAGWNFD  240
YWGQGTLLTV SSGGGGSDIQ MTQSPSSLSA SVGDRVTITC RASQDIRNYL NWYQQKPGKA  300
PKLLIYYTSR LESGVPSRFS GSGSGTDYTL TISSLQPEDF ATYYCQQGNT LPWTFGQGTK  360
VEIKGATPPE TGAETESPGE TTGGSAESEP PGEGEVQLVE SGGGLVQPGG SLRLSCAASG  420
YSFTGYTMNW VRQAPGKGLE WVALINPYKG VSTYNQKFKD RFTISVDKSK NTAYLQMNSL  480
RAEDTAVYYC ARSGYYGDSD WYFDVWGQGT LVTVSSGTAE AASASGLSGR SDNHSPLG    538

SEQ ID NO: 531          moltype = DNA  length = 4260
FEATURE                 Location/Qualifiers
misc_feature            1..4260
                        note = Description of Artificial Sequence: Synthetic
                         polynucleotide
source                  1..4260
                        mol_type = other DNA
                        organism = synthetic construct
SEQUENCE: 531
gatattcaga tgacccaatc gccgtcgtcc ctgtcagctt cagtcggtga tcgtgttacc  60
attacctgtc gctcaacgaa atccctgctg cattcaaacg gtattaccta tctgtactgg  120
tatcagcaaa aaccgggcaa agcgccgaaa ctgctgatct accagatgtc gaatctggcc  180
agcggtgttc cgtctcgttt tagctctagt ggttctggca ccgatttcac cctgacgatt  240
tcctcactgc aaccggaaga ctttgcaacg tattactgcg ctcagaacct ggaaatcccg  300
cgtaccttcg gtcaaggcac gaaagtcgaa attaaaggtg caacgcctcc ggagactggt  360
gctgaaactg agtccccggg cgagacgacc ggtggctctg ctgaatccga accaccgggc  420
gaaggccaag tgcaactggt tcagagcggt ccgggtctgg tccaaccggg tggcagtgtg  480
cgtatttcct gcgcggcctc aggttacacc tttacgaact atggcatgaa ttgggtgaaa  540
caggccccgg gtaaaggcct ggaatggatg ggttggatca acacctacac gggcgaatct  600
acctatgcag atagtttcaa aggccgcttt accttcagcc tggacacgtc tgctagtgca  660
gcttatctgc agattaatag cctgcgtgcg gaagatacgg ccgtttatta ctgtgcgcgc  720
tttgcaatca aaggcgacta ctggggccaa ggcaccctgc tgaccgtgtc ctccggtggt  780
ggcggcagcg acatccaaat gacccagagc ccgagcagcc tgagcgcgag cgtgggcgac  840
cgtgttacca tcacctgccg tgcgagccaa gacatccgta actacctgaa ctggtatcag  900
caaaagccgg gtaaagcgcc gaagctgctg atctactata ccagccgtct ggagagcggc  960
gtgccgagcc gtttcagcgg tagcggtagc ggtaccgact acaccctgac cattagcagc  1020
ctgcagccgg aagatttcgc gacctactat tgccagcagg gtaacaccct gccgtggacc  1080
tttggtcaag gcaccaaagt tgagattaaa ggcgccacgc ctccggaaac tggtgctgag  1140
acggaatccc ctggtgaaac cactggcggt tctgccgaat ctgaaccgcc tggtgaaggc  1200
gaggtgcagc tggttgaaag cggtggcggt ctggtgcaac caggcggtag cctgcgtctg  1260
agctgcgcgg cgagcggtta cagctttacc ggttatacca tgaactgggt tcgtcaagcg  1320
ccaggtaaag gtctggagtg ggtggcgctg atcaacccgt acaagggtgt tagcacctat  1380
aaccagaagt tcaaagaccg ttttaccatt agcgtggata agagcaaaaa caccgcgtac  1440
ctgcaaatga acagcctgcg tgcggaggac accgctgtgt actattgcgc gcgtagcggt  1500
tactatggcg acagcgactg gtattttgat gtgtggggcc aaggcaccct ggttaccgtg  1560
agctccggca ccgccgaagc agctagcgcc tctggcctgt caggtcgttc tgataaccat  1620
tccccactgg gtctggctgg gtctccaggt agcccagctg gtagcccaac ctctaccgaa  1680
gaaggtacct ctgaatccgc tactccagaa tccggtcctg gtactagcac tgagccaagc  1740
gaaggttctg ctccaggctc ccccggcaggt agccctacct ctaccgaaga gggcactagc  1800
accgaaccat ctgagggttc cgctcctggc acctccactg aaccgtccga aggcagtgct  1860
ccgggtactt ccgaaagcgc aactccggaa tccggccctg gttctgagcc tgctacttcc  1920
ggctctgaaa ctccaggtag cgagccagcg acttctggtt ctgaaactcc aggttcaccg  1980
gcgggtagcc cgacgagcac ggaggaaggt acctctgagt cggccactcc tgagtccggt  2040
ccgggcacga gcaccgagcc gagcgagggt tcagccccgg gtaccagcac ggagccgtcc  2100
gagggtagcg caccgggttc tccggcgggc tcccctacgt ctacggaaga gggtacgtcc  2160
```

-continued

```
actgaaccta gcgagggcag cgcgccaggc accagcactg aaccgagcga aggcagcgca  2220
cctggcacta gcgagtctgc gactccggag agcggtccgg gtacgagcac ggaaccaagc  2280
gaaggcagcg ccccaggtac ctctgaatct gctaccccag aatctggccc gggttccgag  2340
ccagctacct ctggttctga aaccccaggt acttccactg aaccaagcga aggtagcgct  2400
cctggcactt ctactgaacc atccgaaggt tccgctcctg gtacgtctga aagcgctacc  2460
cctgaaagcg gcccaggcac ctctgaaagc gctactcctg agagcggtcc aggctctcca  2520
gcaggttctc caacctccac tgaagaaggc acctctgagt ctgctacccc tgaatctggt  2580
cctggctccg aacctgctac ctctggttcc gaaactccag gtacctcgga atctgcgact  2640
ccggaatctg gcccgggcac gagcacggag ccgtctgagg gtagcgcacc aggtaccagc  2700
actgagcctt ctgagggctc tgcaccgggt acctccacgg aaccttcgga aggttctgcg  2760
ccgggtacct ccactgagcc atccgagggt tcagcaccag gtactagcac ggaaccgtcc  2820
gagggctctg caccaggtac gagcaccgaa ccgtcggagg gtagcgctcc aggtagccca  2880
gcgggctctc cgacaagcac cgaagaaggc accagcaccg agccgtccga aggttccgca  2940
ccaggtacaa gcgagagcgc gactcctgaa tctggtccgg gtagcgagcc tgcaaccagc  3000
ggttctgaga cgccgggcac ttccgaatct gcgaccccgg agtccggtcc aggttcagag  3060
ccggcgacga gcggttcgga aacgccgggt acgtctgaat cagccacgcc ggagtctggt  3120
ccgggtacct cgaccgaacc aagcgaaggt tcggcaccgg gtactagcga gagcgcaacc  3180
cctgaaagcg gtccgggcag cccggcaggt tctccaacca gcaccgaaga aggttcccct  3240
gctggtagcc cgacctctac ggaggaaggt agccctgcag gttccccaac ttctactgag  3300
gaaggtactt ctgagtccgc taccccagaa agcggtcctg gtacctccac tgaaccgtct  3360
gaaggctctg caccaggcac ttctgagtct gctactccag aaagcggccc aggttctgaa  3420
ccagcaactt ctggctctga gactccaggc acttctgagt ccgcaacgcc tgaatccggt  3480
cctggttctg aaccagctac ttccggcagc gaaaccccag gtacctctga gtctgcgact  3540
ccagagtctg gtcctggtac ttccactgag cctagcgagg gttccgcacc aggttctccg  3600
gctggtagcc cgaccagcac ggaggagggt acgtctgaat ctgcaacgcc ggaatcgggc  3660
ccaggttcgg agcctgcaac gtctggcagc gaaaccccgg gtacctccga atctgctaca  3720
ccggaaagcg gtcctggcag ccctgctggt tctccaacct ctaccgagga gggttcaccg  3780
gcaggtagcc cgactagcac tgaagaaggt actagcacgg agccgagcga gggtagtgct  3840
ccgggtacga gcgagagcgc aacgccagag agcggtccag gcaccagcga atcggccacc  3900
cctgagagcg gcccaggtac ttctgagagc gccactcctg aatccggccc tggtagcgag  3960
ccggcaacct ccggctcaga aactcctggt tcggaaccag cgaccagcgg ttctgaaact  4020
ccgggtagcc cggcaggcag cccaacgagc accgaagagg gtaccagcac ggaaccgagc  4080
gagggttctg ccccgggtac ttccaccgaa ccatcggagg gctctgcacc tggtagcgaa  4140
cctgcgacgt ctggttctga aacgccgggt accagcgaaa gcgctacccc agaatccggt  4200
ccgggcacta gcaccgagcc atcggagggc tccgcaccag gtcaccatca tcaccatcac  4260
```

```
SEQ ID NO: 532          moltype = DNA  length = 4260
FEATURE                 Location/Qualifiers
misc_feature            1..4260
                        note = Description of Artificial Sequence: Synthetic
                         polynucleotide
source                  1..4260
                        mol_type = other DNA
                        organism = synthetic construct
SEQUENCE: 532
gatatccaga tgacccagag cccttcttcc ctgtccgcat ccgtcggcga tcgtgtcacg  60
attacctgtc gcagcactaa gagcctgctg cactcaaacg gtatcacgta cctgtactgg  120
taccagcaga agccgggcaa agcgccgaag ctgctgattt atcagatgag caacctggca  180
tcgggcgtgc cgagccgttt cagcagcagc ggtagcggta ccgacttcac gctgaccatc  240
agctcgttgc agccagagga ctttgcgacg tactattgtg cgcaaaactt ggaaattccg  300
cgcaccttcg gccagggtac gaaagttgag attaaaggtg ccaccccacc ggagactggt  360
gcagaaaccg agtctccggg cgaaaccacg ggcggtagcg cggagagcga accgcctggt  420
gagggtcaag ttcaattggt tcagagcggt ccgggtctgg ttcaaccggg cggcagcgtg  480
cgcatttctt gtgcggccag cggttacacc tttacgaact acggtatgaa ttgggtgaaa  540
caagctccgg gcaaaggtct ggagtggatg ggttggatca atacctatac cggtgaatcc  600
acttacgcgg attcctttaa gggccgtttc accttcagcc tggacacgag cgcgagcgct  660
gcatatctgc aaatcaatag cctgcgtgcc gaagataccg cggtgtacta ttgcgcgcgt  720
tttgcaatca agggcgacta ttggggtcaa ggcacgctgc tgaccgtgag cagcggtggt  780
ggcggcagcg atatccaaat gacccaatcc ccatcctccc tgtctgcaag cgttggtgat  840
cgtgtgacga ttacgtgccg tgcctcccaa gatatccgta actacctgaa ttggtatcag  900
cagaaaccgg gcaaggctcc gaaattgctg atctactaca ccagccgcct ggagtcgggt  960
gtgcctagcc gcttcagcgg cagcggttcg ggtaccgact ataccttgac cattagcagc  1020
ctgcagccgg aagatttcgc gacgtattac tgccaacagg gtaacacgct gccgtggacc  1080
tttggccaag gtaccaaagt cgagattaag ggtgcgaccc cgccggaaac cggtgcggaa  1140
accgagagcc cgggtgaaac gactggcggc tctgcagaga gcgagccgcc aggtgagggc  1200
gaagtccaac tggtcgagtc tggtggcggc ctggtgcaac cgggtggcag cctgcgtctg  1260
agctgcgctg cgagcggcta tagctttacc ggttatacca tgaactgggt tcgccaggca  1320
ccgggtaagg gtctggaatg ggtggcgctg atcaatccgt acaaaggtgt gagcacttac  1380
aatcagaaat tcaaagaccg tttcaccatt agcgttgaca agagcaagaa taccgcgtat  1440
ctgcagatga acagcttgcg cgccgaggat acggccgttt actactgtgc acgtagcggc  1500
tattacggtg acagcgactg gtactttgac gtctggggtc agggcacgct ggtcaccgtt  1560
agcagcggca ccgccgaagc agctagcgcc tctggcctgt caggtcgttc tgataaccat  1620
tccccactgg gtctggctgg gtctccaggt agcccagctg gtagcccaac ctctaccgaa  1680
gaaggtacct ctgaatccgc tactccagaa tccggtcctg gtactagcac tgagccaagc  1740
gaaggttctg ctccaggctc cccggcaggt agccctacct ctaccgaaga gggcactagc  1800
accgaaccat ctgagggttc cgctcctggc acctccactg aaccgtccga aggcagtgct  1860
ccgggtactt ccgaaagcgc aactccggaa tccggccctg gttctgagcc tgctacttcc  1920
ggctctgaaa ctccaggtag cgagccagcg acttctggtt ctgaaactcc aggttcaccg  1980
gcgggtagcc cgacgagcac ggaggaaggt acctctgagt cggccactcc tgagtccggt  2040
```

-continued

```
ccgggcacga gcaccgagcc gagcgagggt tcagccccgg gtaccagcac ggagccgtcc  2100
gagggtagcg caccgggttc tccggcgggc tcccctacgt ctacggaaga gggtacgtcc  2160
actgaaccta gcgagggcag cgcgccaggc accagcactg aaccgagcga aggcagcgca  2220
cctggcacta gcgagtctgc gactccggag agcggtccgg gtacgagcac ggaaccaagc  2280
gaaggcagcg ccccaggtac ctctgaatct gctaccccag aatctggccc gggttccgag  2340
ccagctacct ctggttctga aaccccaggt acttccactg aaccaagcga aggtagcgct  2400
cctggcactt ctactgaacc atccgaaggt tccgctcctg gtacgtctga aagcgctacc  2460
cctgaaagcg gcccaggcac ctctgaaagc gctactcctg agagcggtcc aggctctcca  2520
gcaggttctc caacctccac tgaagaaggc acctctgagt ctgctacccc tgaatctggt  2580
cctggctccg aacctgctac ctctggttcc gaaactccag gtacctcgga atctgcgact  2640
ccggaatctg gcccgggcac gagcacggag ccgtctgagg gtagcgcacc aggtaccagc  2700
actgagcctt ctgagggctc tgcaccgggt acctccacgg aaccttcgga aggttctgcg  2760
ccgggtacct ccactgagcc atccgagggt tcagcaccag gtactagcac ggaaccgtcc  2820
gagggctctg caccaggtac gagcaccgaa ccgtcggagg gtagcgctcc aggtagccca  2880
gcgggctctc cgacaagcac cgaagaaggc accagcaccg agccgtccga aggttccgca  2940
ccaggtacaa gcgagagcgc gactcctgaa tctggtccgg gtagcgagcc tgcaaccagc  3000
ggttctgaga cgccgggcac ttccgaatct gcgaccccgg agtccggtcc aggttcagag  3060
ccggcgacga gcggttcgga aacgccgggt acgtctgaat cagccacgcc ggagtctggt  3120
ccgggtacct cgaccgaacc aagcgaaggt tcggcaccgg gtactagcga gagcgcaacc  3180
cctgaaagcg gtccgggcag cccggcaggt tctccaacca gcaccgaaga aggttcccct  3240
gctggtagcc cgacctctac ggaggaaggt agccctgcag gttccccaac ttctactgag  3300
gaaggtactt ctgagtccgc taccccagaa agcggtcctg gtacctccac tgaaccgtct  3360
gaaggctctg caccaggcac ttctgagtct gctactccag aaagcggccc aggttctgaa  3420
ccagcaactt ctggctctga gactccaggc acttctgagt ccgcaacgcc tgaatccggt  3480
cctggttctg aaccagctac ttccggcagc gaaaccccag gtacctctga gtctgcgact  3540
ccagagtctg gtcctggtac ttccactgag cctagcgagg gttccgcacc aggttctccg  3600
gctggtagcc cgaccagcac ggaggagggt acgtctgaat ctgcaacgcc ggaatcgggc  3660
ccaggttcgg agcctgcaac gtctggcagc gaaaccccgg gtacctccga atctgctaca  3720
ccggaaagcg gtcctggcag ccctgctggt tctccaacct ctaccgagga gggttcaccg  3780
gcaggtagcc cgactagcac tgaagaaggt actagcacgg agccgagcga gggtagtgct  3840
ccgggtacga gcgagagcgc aacgccagag agcggtccag gcaccagcga atcggccacc  3900
cctgagagcg gcccaggtac ttctgagagc gccactcctg aatccggccc tggtagcgag  3960
ccggcaacct ccggctcaga aactcctggt tcggaaccag cgaccagcgg ttctgaaact  4020
ccgggtagcc cggcaggcag cccaacgagc accgaagagg gtaccagcac ggaaccgagc  4080
gagggttctg ccccgggtac ttccaccgaa ccatcggagg gctctgcacc tggtagcgaa  4140
cctgcgacgt ctggttctga aacgccgggt accagcgaaa gcgctacccc agaatccggt  4200
ccgggcacta gcaccgagcc atcggagggc tccgcaccag gtcaccatca tcaccatcac  4260
```

```
SEQ ID NO: 533          moltype = AA  length = 1420
FEATURE                 Location/Qualifiers
REGION                  1..1420
                        note = Description of Artificial Sequence: Synthetic
                         polypeptide
source                  1..1420
                        mol_type = protein
                        organism = synthetic construct
SEQUENCE: 533
DIQMTQSPSS LSASVGDRVT ITCRSTKSLL HSNGITYLYW YQQKPGKAPK LLIYQMSNLA  60
SGVPSRFSSS GSGTDFTLTI SSLQPEDFAT YYCAQNLEIP RTFGQGTKVE IKGATPPETG  120
AETESPGETT GGSAESEPPG EGQVQLVQSG PGLVQPGGSV RISCAASGYT FTNYGMNWVK  180
QAPGKGLEWM GWINTYTGES TYADSFKGRF TFSLDTSASA AYLQINSLRA EDTAVYYCAR  240
FAIKGDYWGQ GTLLTVSSGG GGSDIQMTQS PSSLSASVGD RVTITCRASQ DIRNYLNWYQ  300
QKPGKAPKLL IYYTSRLESG VPSRFSGSGS GTDYTLTISS LQPEDFATYY CQQGNTLPWT  360
FGQGTKVEIK GATPPETGAE TESPGETTGG SAESEPPGEG EVQLVESGGG LVQPGGSLRL  420
SCAASGYSFT GYTMNWVRQA PGKGLEWVAL INPYKGVSTY NQKFKDRFTI SVDKSKNTAY  480
LQMNSLRAED TAVYYCARSG YYGDSDWYFD VWGQGTLVTV SSGTAEAASA SGLSGRSDNH  540
SPLGLAGSPG SPAGSPTSTE EGTSESATPE SGPGTSTEPS EGSAPGSPAG SPTSTEEGTS  600
TEPSEGSAPG TSTEPSEGSA PGTSESATPE SGPGSEPATS GSETPGSEPA TSGSETPGSP  660
AGSPTSTEEG TSESATPESG PGTSTEPSEG SAPGTSTEPS EGSAPGSPAG SPTSTEEGTS  720
TEPSEGSAPG TSTEPSEGSA PGTSESATPE SGPGTSTEPS EGSAPGTSES ATPESGPGSE  780
PATSGSETPG TSTEPSEGSA PGTSTEPSEG SAPGTSESAT PESGPGTSES ATPESGPGSP  840
AGSPTSTEEG TSESATPESG PGSEPATSGS ETPGTSESAT PESGPGTSTE PSEGSAPGTS  900
TEPSEGSAPG TSTEPSEGSA PGTSTEPSEG SAPGTSTEPS EGSAPGTSTE PSEGSAPGSP  960
AGSPTSTEEG TSTEPSEGSA PGTSESATPE SGPGSEPATS GSETPGTSES ATPESGPGSE  1020
PATSGSETPG TSESATPESG PGTSTEPSEG SAPGTSESAT PESGPGSPAG SPTSTEEGSP  1080
AGSPTSTEEG SPAGSPTSTE EGTSESATPE SGPGTSTEPS EGSAPGTSES ATPESGPGSE  1140
PATSGSETPG TSESATPESG PGSEPATSGS ETPGTSESAT PESGPGTSTE PSEGSAPGSP  1200
AGSPTSTEEG TSESATPESG PGSEPATSGS ETPGTSESAT PESGPGSPAG SPTSTEEGSP  1260
AGSPTSTEEG TSTEPSEGSA PGTSESATPE SGPGTSESAT PESGPGTSES ATPESGPGSE  1320
PATSGSETPG SEPATSGSET PGSPAGSPTS TEEGTSTEPS EGSAPGTSTE PSEGSAPGSE  1380
PATSGSETPG TSESATPESG PGTSTEPSEG SAPGHHHHHH                        1420
```

```
SEQ ID NO: 534          moltype = AA  length = 1425
FEATURE                 Location/Qualifiers
REGION                  1..1425
                        note = Description of Artificial Sequence: Synthetic
                         polypeptide
source                  1..1425
                        mol_type = protein
```

-continued

```
                          organism = synthetic construct
SEQUENCE: 534
DIVMTQSPLS LPVTPGEPAS ISCRSSKNLL HSNGITYLYW YLQKPGQSPQ LLIYQMSNLA  60
SGVPDRFSSS GSGTDFTLKI SRVEAEDVGV YYCAQNLEIP RTFGQGTKVE IKGATPPETG  120
AETESPGETT GGSAESEPPG EGQVQLVQSG PEVKKPGASV KVSCKASGYT FTNYGMNWVR  180
QAPGQGLEWM GWINTYTGEP TYGEDFKGRF AFSLDTSAST AYMELSSLRS EDTAVYFCAR  240
FGNYVDYWGQ GSLVTVSSGG GGSELVVTQE PSLTVSPGGT VTLTCRSSTG AVTTSNYANW  300
VQQKPGQAPR GLIGGTNKRA PGTPARFSGS LLGGKAALTL SGVQPEDEAE YYCALWYSNL  360
WVFGGGTKLT VLGATPPETG AETESPGETT GGSAESEPPG EGEVQLLESG GGLVQPGGSL  420
KLSCAASGFT FNTYAMNWVR QAPGKGLEWV ARIRSKYNNY ATYYADSVKD RFTISRDDSK  480
NTAYLQMNNL KTEDTAVYYC VRHGNFGNSY VSWFAYWGQG TLVTVSSGTA EAASASGLSG  540
RSDNHSPLGL AGSPGSPAGS PTSTEEGTSE SATPESGPGT STEPSEGSAP GSPAGSPTST  600
EEGTSTEPSE GSAPGTSTEP SEGSAPGTSE SATPESGPGS EPATSGSETP GSEPATSGSE  660
TPGSPAGSPT STEEGTSESA TPESGPGTST EPSEGSAPGT STEPSEGSAP GSPAGSPTST  720
EEGTSTEPSE GSAPGTSTEP SEGSAPGTSE SATPESGPGT STEPSEGSAP GTSESATPES  780
GPGSEPATSG SETPGTSTEP SEGSAPGTST EPSEGSAPGT SESATPESGP GTSESATPES  840
GPGSPAGSPT STEEGTSESA TPESGPGSEP ATSGSETPGT SESATPESGP GTSTEPSEGS  900
APGTSTEPSE GSAPGTSTEP SEGSAPGTST EPSEGSAPGT STEPSEGSAP GTSTEPSEGS  960
APGSPAGSPT STEEGTSTEP SEGSAPGTSE SATPESGPGS EPATSGSETP GTSESATPES  1020
GPGSEPATSG SETPGTSESA TPESGPGTST EPSEGSAPGT SESATPESGP GSPAGSPTST  1080
EEGSPAGSPT STEEGSPAGS PTSTEEGTSE SATPESGPGT STEPSEGSAP GTSESATPES  1140
GPGSEPATSG SETPGTSESA TPESGPGSEP ATSGSETPGT SESATPESGP GTSTEPSEGS  1200
APGSPAGSPT STEEGTSESA TPESGPGSEP ATSGSETPGT SESATPESGP GSPAGSPTST  1260
EEGSPAGSPT STEEGTSTEP SEGSAPGTSE SATPESGPGT SESATPESGP GTSESATPES  1320
GPGSEPATSG SETPGSEPAT SGSETPGSPA GSPTSTEEGT STEPSEGSAP GTSTEPSEGS  1380
APGSEPATSG SETPGTSESA TPESGPGTST EPSEGSAPGH HHHHH                 1425
```